US011897871B1

(12) United States Patent
St. Jean, Jr.

(10) Patent No.: US 11,897,871 B1
(45) Date of Patent: Feb. 13, 2024

(54) METHODS FOR TREATING CANCER

(71) Applicant: Scorpion Therapeutics, Inc., Boston, MA (US)

(72) Inventor: David St. Jean, Jr., Natick, MA (US)

(73) Assignee: Scorpion Therapeutics, Inc., Boston, MA (US)

( * ) Notice: Subject to any disclaimer, the term of this patent is extended or adjusted under 35 U.S.C. 154(b) by 0 days.

(21) Appl. No.: 18/450,586

(22) Filed: Aug. 16, 2023

Related U.S. Application Data

(63) Continuation of application No. PCT/US2022/033255, filed on Jun. 13, 2022.

(60) Provisional application No. 63/348,261, filed on Jun. 2, 2022, provisional application No. 63/319,236, filed on Mar. 11, 2022, provisional application No. 63/316,017, filed on Mar. 3, 2022, provisional application No. 63/288,909, filed on Dec. 13, 2021, provisional application No. 63/228,351, filed on Aug. 2, 2021, provisional application No. 63/210,370, filed on Jun. 14, 2021.

(51) Int. Cl.
*C07D 405/12* (2006.01)

(52) U.S. Cl.
CPC ................. *C07D 405/12* (2013.01)

(58) Field of Classification Search
CPC .................................................. C07D 405/12
USPC ........................................................ 544/297
See application file for complete search history.

(56) References Cited

U.S. PATENT DOCUMENTS

| | | | |
|---|---|---|---|
| 4,735,941 A | 4/1988 | Freidinger et al. | |
| 5,041,453 A | 8/1991 | Huang et al. | |
| 5,166,151 A | 11/1992 | Freidinger et al. | |
| 5,324,726 A | 6/1994 | Bock et al. | |
| 5,459,150 A | 10/1995 | Brooks et al. | |
| 5,559,127 A | 9/1996 | Hartman et al. | |
| 5,821,261 A | 10/1998 | Durette et al. | |
| 6,545,152 B1 | 4/2003 | Uckun et al. | |
| 2005/0026916 A1 | 2/2005 | Shum et al. | |
| 2007/0072892 A1 | 3/2007 | Schrimpf et al. | |
| 2013/0018079 A1 | 1/2013 | Weibel et al. | |
| 2014/0200215 A1 | 7/2014 | Buckman et al. | |

FOREIGN PATENT DOCUMENTS

| | | |
|---|---|---|
| CA | 2068500 | 11/1992 |
| CN | 101412692 | 4/2009 |
| CN | 111039942 | 4/2020 |
| DE | 102012103405 | 10/2013 |
| EP | 284256 | 9/1988 |
| EP | 304223 | 2/1989 |
| EP | 431944 | 6/1991 |
| EP | 434360 | 6/1991 |
| EP | 434369 | 6/1991 |
| EP | 490590 | 6/1992 |
| EP | 514125 | 11/1992 |
| EP | 514126 | 11/1992 |
| EP | 514131 | 11/1992 |
| EP | 523845 | 1/1993 |
| EP | 523846 | 1/1993 |
| EP | 519678 | 3/1993 |
| EP | 532456 | 3/1995 |
| EP | 708099 | 4/1996 |
| EP | 745583 | 12/1996 |
| EP | 974363 | 1/2000 |
| GB | 2259013 | 3/1993 |
| JP | 2000053572 | 2/2000 |
| JP | 2001163784 | 6/2001 |
| JP | 2004083511 | 3/2004 |
| KR | 20150136294 | 12/2015 |
| WO | WO 1992/03132 | 3/1992 |
| WO | WO 1993/15081 | 8/1993 |
| WO | WO 1993/24458 | 12/1993 |
| WO | WO 1994/08962 | 4/1994 |
| WO | WO 1995/03308 | 2/1995 |
| WO | WO 1995/09159 | 4/1995 |
| WO | WO 1995/29907 | 11/1995 |
| WO | WO 1997/14418 | 4/1997 |
| WO | WO 1998/23290 | 6/1998 |
| WO | WO 1998/49150 | 11/1998 |
| WO | WO 1999/02158 | 1/1999 |
| WO | WO 1999/05146 | 2/1999 |
| WO | WO 1999/11289 | 3/1999 |
| WO | WO 1999/58495 | 11/1999 |
| WO | WO 1999/59586 | 11/1999 |
| WO | WO 2000/014097 | 3/2000 |
| WO | WO 2000/018738 | 4/2000 |

(Continued)

OTHER PUBLICATIONS

CAS Registry No. 1311882-44-6 "Urea, N-[1-(5-fluoro-3-methyl-2-benzofuranyl)ethyl]-N'-(4-hydroxycyclohexyl)" dated Jul. 7, 2011, Chemical Library; Supplier: Enamine, 1 page.
CAS Registry No. 1370846-42-6 "Benzamide, 4-[[[[1-(2-benzofuranyl)ethyl]amino]carbonyl]amino]-N,N-diethyl-" dated Apr. 29, 2012, Chemical Library; Supplier: Interchim, 1 page.
CAS Registry No. 1424597-14-7 "Urea, N-[3-(1,3-dithian-2-yl)phenyl]-N'-[1-(3-methyl-2-benzofuranyl)ethyl]-" dated Mar. 16, 2013, Chemical Library; Supplier: Enamine, 1 page.
CAS Registry No. 1623108-98-4 "Urea, N-[(1R,2S)-2,3-dihydro-2-hydroxy-1H-inden-1-yl]-N'-[1-(3-methyl-2-benzofuranyl)ethyl]-, rel-" dated Sep. 17, 2014, Chemical Library; Supplier: Ukrorgsyntez Ltd., 1 page.

(Continued)

*Primary Examiner* — Taylor V Oh
(74) *Attorney, Agent, or Firm* — Fish & Richardson P.C.

(57) ABSTRACT

This disclosure provides compounds of Formula (I), Formula (II), and pharmaceutically acceptable salts thereof, that inhibit phosphatidylinositol 4,5-bisphosphate 3-kinase (PI3K) isoform alpha (PI3Kα). These chemical entities are useful, e.g., for treating a condition, disease or disorder in which increased (e.g., excessive) PI3Kα activation contributes to the pathology and/or symptoms and/or progression of the condition, disease or disorder (e.g., cancer) in a subject (e.g., a human). This disclosure also provides compositions containing the same as well as methods of using and making the same.

12 Claims, No Drawings
Specification includes a Sequence Listing.

(56) References Cited

FOREIGN PATENT DOCUMENTS

| | | |
|---|---|---|
| WO | WO 2000/035452 | 6/2000 |
| WO | WO 2000/039108 | 7/2000 |
| WO | WO 2000/064888 | 11/2000 |
| WO | WO 2001/014383 | 3/2001 |
| WO | WO 2001/051456 | 7/2001 |
| WO | WO 2002/000651 | 1/2002 |
| WO | WO 2002/078744 | 10/2002 |
| WO | WO 2002/089845 | 11/2002 |
| WO | WO 2002/096863 | 12/2002 |
| WO | WO 2003/037916 | 5/2003 |
| WO | WO 2003/091224 | 11/2003 |
| WO | WO 2004/007459 | 1/2004 |
| WO | WO 2004/022535 | 3/2004 |
| WO | WO 2004/108709 | 12/2004 |
| WO | WO 2005/004810 | 1/2005 |
| WO | WO 2005/019190 | 3/2005 |
| WO | WO 2005/034838 | 4/2005 |
| WO | WO 2005/040157 | 5/2005 |
| WO | WO 2005/042497 | 5/2005 |
| WO | WO 2005/051938 | 6/2005 |
| WO | WO 2005/054179 | 6/2005 |
| WO | WO 2005/087700 | 9/2005 |
| WO | WO 2005/105780 | 11/2005 |
| WO | WO 2006/100204 | 9/2006 |
| WO | WO 2006/099379 | 12/2006 |
| WO | WO 2006/133459 | 12/2006 |
| WO | WO 2007/026720 | 3/2007 |
| WO | WO 2007/047474 | 4/2007 |
| WO | WO 2007/075895 | 7/2007 |
| WO | WO 2007/109330 | 9/2007 |
| WO | WO 2007/126362 | 11/2007 |
| WO | WO 2008/013963 | 1/2008 |
| WO | WO 2008/027483 | 3/2008 |
| WO | WO 2008/048991 | 4/2008 |
| WO | WO 2008/133297 | 11/2008 |
| WO | WO 2008/133330 | 11/2008 |
| WO | WO 2008/154642 | 12/2008 |
| WO | WO 2008/156573 | 12/2008 |
| WO | WO 2009/044883 | 4/2009 |
| WO | WO 2009/089508 | 7/2009 |
| WO | WO 2009/112445 | 9/2009 |
| WO | WO 2009/126691 | 10/2009 |
| WO | WO 2009/137404 | 11/2009 |
| WO | WO 2010/025295 | 3/2010 |
| WO | WO 2010/040272 | 4/2010 |
| WO | WO 2010/047381 | 4/2010 |
| WO | WO 2010/050445 | 5/2010 |
| WO | WO 2010/063996 | 6/2010 |
| WO | WO 2010/065668 | 6/2010 |
| WO | WO 2010/088574 | 8/2010 |
| WO | WO 2010/111534 | 9/2010 |
| WO | WO 2011/023081 | 3/2011 |
| WO | WO 2011/088181 | 7/2011 |
| WO | WO 2011/093441 | 8/2011 |
| WO | WO 2012/028106 | 3/2012 |
| WO | WO 2012/050918 | 4/2012 |
| WO | WO 2012/107475 | 8/2012 |
| WO | WO 2012/105475 | 9/2012 |
| WO | WO 2013/009810 | 1/2013 |
| WO | WO 2013/009830 | 1/2013 |
| WO | WO 2013/096055 | 6/2013 |
| WO | WO 2013/105608 | 7/2013 |
| WO | WO 2015/095701 | 6/2015 |
| WO | WO 2016/172255 | 10/2016 |
| WO | WO 2017/039318 | 3/2017 |
| WO | WO 2017/117447 | 7/2017 |
| WO | WO 2017/191297 | 11/2017 |
| WO | WO 2018/165501 | 9/2018 |
| WO | WO 2018/208985 | 11/2018 |
| WO | WO 2019/111225 | 6/2019 |
| WO | WO 2019/229464 | 12/2019 |
| WO | WO 2020/028515 | 2/2020 |
| WO | WO 2020/033782 | 2/2020 |
| WO | WO 2020/050253 | 3/2020 |
| WO | WO 2020/210785 | 10/2020 |
| WO | WO 2020/228649 | 11/2020 |
| WO | WO 2022/265993 | 12/2022 |
| WO | WO 2016/038045 | 3/2023 |

OTHER PUBLICATIONS

CAS Registry No. 1624160-83-3 "Urea, N-(3,4-dihydro-3-oxo-2H-1,4-benzoxazin-7-yl)-N'-[1-(3-methyl-2-benzofuranyl)ethyl]-" dated Sep. 22, 2014, Chemical Library; Supplier: Ukrorgsyntez Ltd., 1 page.

CAS Registry No. 1624561-09-6 "Benzamide, N-ethyl-4-methyl-3-[[[[1-(3-methyl-2-benzofuranyl)ethyl]amino]carbonyl]amino]-" dated Sep. 23, 2014, Chemical Library; Supplier: Ukrorgsyntez Ltd., 1 page.

CAS Registry No. 1624775-76-3 "Cyclohexanecarboxamide, 3-[[[[1-(5-fluoro-3-methyl-2-benzofuranyl)ethyl]amino]carbonyl]amino]-N-(1-methylethyl)-" dated Sep. 23, 2014, Chemical Library; Supplier: Ukrorgsyntez Ltd., 1 page.

CAS Registry No. 1625022-71-0 "Urea, N-[1-(2-ethyl-1-oxobutyl)-4-piperidinyl]-N'-[1-(5-fluoro-3-methyl-2-benzofuranyl)ethyl]-" dated Sep. 24, 2014, Chemical Library; Supplier: Ukrorgsyntez Ltd., 1 page.

CAS Registry No. 1625023-70-2 "Urea, N-[1-(5-fluoro-3-methyl-2-benzofuranyl)ethyl]-N'-[4-(2-oxo-1-pyrrolidinyl)phenyl]-" dated Sep. 24, 2014, Chemical Library; Supplier: Ukrorgsyntez Ltd., 1 page.

CAS Registry No. 1625032-76-9 "Urea, N-(2,3-dihydro-3-benzofuranyl)-N'-[1-(5-fluoro-3-methyl-2-benzofuranyl)ethyl]-" dated Sep. 24, 2014, Chemical Library; Supplier: Ukrorgsyntez Ltd., 1 page.

CAS Registry No. 1626154-71-9 "Benzamide, N-ethyl-3-methyl-4-[[[[1-(3-methyl-2-benzofuranyl)ethyl]amino]carbonyl]amino]-" dated Sep. 25, 2014, Chemical Library; Supplier: Ukrorgsyntez Ltd., 1 page.

CAS Registry No. 1626196-04-0 "Benzamide, N,2-dimethyl-3-[[[[1-(3-methyl-2-benzofuranyl)ethyl]amino]carbonyl]amino]-" dated Sep. 25, 2014, Chemical Library; Supplier: Ukrorgsyntez Ltd., 1 page.

CAS Registry No. 1626196-29-9 "Urea, N-(2,3-dihydro-5-benzofuranyl)-N'-[1-(3-methyl-2-benzofuranyl)ethyl]-" dated Sep. 25, 2014, Chemical Library; Supplier: Ukrorgsyntez Ltd., 1 page.

CAS Registry No. 1626914-96-2 "Urea, N-[4-(dimethylamino)-2-methylphenyl]-N'-[1-(5-fluoro-3-methyl-2-benzofuranyl)ethyl]-" dated Sep. 26, 2014, Chemical Library; Supplier: Ukrorgsyntez Ltd., 1 page.

CAS Registry No. 1646339-79-8 "Urea, N-(2-ethyl-5-benzoxazolyl)-N'-[1-(3-methyl-2-benzofuranyl)ethyl]-" dated Feb. 10, 2015, Chemical Library; Supplier: Ukrorgsyntez Ltd., 1 page.

CAS Registry No. 1647237-54-4 "Urea, N-[1-(3-methyl-2-benzofuranyl)ethyl]-N'-(2-methyl-5-benzoxazolyl)-" dated Feb. 14, 2015, Chemical Library; Supplier: Ukrorgsyntez Ltd., 1 page.

CAS Registry No. 1647327-15-8 "Urea, N-[1-(3-methyl-2-benzofuranyl)ethyl]-N'-[1-(1-methylethyl)-1H-indazol-6-yl]-" dated Feb. 14, 2015, Chemical Library; Supplier: Ukrorgsyntez Ltd., 1 page.

CAS Registry No. 1647611-05-9 "Urea, N-(1-ethyl-1H-indazol-6-yl)-N'-[1-(3-methyl-2-benzofuranyl)ethyl]-" dated Feb. 14, 2015, Chemical Library; Supplier: Ukrorgsyntez Ltd., 1 page.

CAS Registry No. 1648340-68-4 "Urea, N-[1-(3-methyl-2-benzofuranyl)ethyl]-N'-(5-methyl-2-thiazolyl)-" dated Feb. 16, 2015, Chemical Library; Supplier: Ukrorgsyntez Ltd., 1 page.

CAS Registry No. 1797831-62-9 "Urea, N-[1-(3-methyl-2-benzofuranyl)ethyl]-N'-[6-(1-pyrrolidinyl)-3-pyridinyl]-" dated Jul. 9, 2015, Chemical Library; Supplier: Aurora Fine Chemicals, 1 page.

CAS Registry No. 1808609-32-6 "2-Pyridinecarboxamide, 5-[[[[(1S)-1-(3-methyl-2-benzofuranyl)ethyl]amino]carbonyl]amino]-" dated Sep. 29, 2015, Chemical Library; Supplier: Enamine LLC, 1 page.

CAS Registry No. 1808818-00-9 "Urea, N-(1-acetyl-4-piperidinyl)-N'-[(1S)-1-(3-methyl-2-benzofuranyl)ethyl]-" dated Sep. 29, 2015, Chemical Library; Supplier: Enamine LLC, 1 page.

CAS Registry No. 1808831-39-1 "Urea, N-[(1R)-1-(3-methyl-2-benzofuranyl)ethyl]-N'-[6-(methylsulfonyl)-3-pyridinyl]-" dated Sep. 29, 2015, Chemical Library; Supplier: Enamine LLC, 1 page.

(56) References Cited

OTHER PUBLICATIONS

CAS Registry No. 1808878-16-1 "Urea, N-[(1R)-1-(3-methyl-2-benzofuranyl)ethyl]-N'-[2-methyl-6-(4-morpholinyl)-3-pyridinyl]-" dated Sep. 29, 2015, Chemical Library; Supplier: Enamine LLC, 1 page.
CAS Registry No. 1824919-54-1 "Urea, N-[(1S)-1-(3-methyl-2-benzofuranyl)ethyl]-N'-(1-methyl-1H-pyrazol-4-yl)-" dated Dec. 8, 2015, Chemical Library; Supplier: Ukrorgsyntez Ltd., 1 page.
CAS Registry No. 1942992-12-2 "No CA Index Name" dated Jul. 1, 2016, Chemical Library; Supplier: Ukrorgsyntez Ltd., 1 page.
CAS Registry No. 1943007-05-3 "Urea, N-[(1R)-1-(3-methyl-2-benzofuranyl)ethyl]-N'-6-oxaspiro[4.5]dec-9-yl-" dated Jul. 1, 2016, Chemical Library; Supplier: Ukrorgsyntez Ltd., 1 page.
CAS Registry No. 1943008-49-8 "Urea, N-[(1R)-1-(3-methyl-2-benzofuranyl)ethyl]-N'-[5,6,7,8-tetrahydro-2-(1-methylethyl)[1,2,4]triazolo[1,5-a]pyridin-6-yl]-" dated Jul. 1, 2016, Chemical Library; Supplier: Ukrorgsyntez Ltd., 1 page.
CAS Registry No. 1943064-93-4 "Urea, N-[(1S)-1-(3-methyl-2-benzofuranyl)ethyl]-N'-[5,6,7,8-tetrahydro-3-(1-methylethyl)-1,2,4-triazolo[4,3-a]pyridin-6-yl]-" dated Jul. 1, 2016, Chemical Library; Supplier: Ukrorgsyntez Ltd., 1 page.
CAS Registry No. 1943083-31-5 "Urea, N-(3-ethoxy-7-oxaspiro[3.5]non-1-yl)-N'-[(1R)-1-(3-methyl-2-benzofuranyl)ethyl]-" dated Jul. 1, 2016, Chemical Library; Supplier: Ukrorgsyntez Ltd., 1 page.
CAS Registry No. 1943375-82-3 "Urea, N-[(1R)-1-(3-methyl-2-benzofuranyl)ethyl]-N'-(octahydro-4-benzofuranyl)-" dated Jul. 1, 2016, Chemical Library; Supplier: Ukrorgsyntez Ltd., 1 page.
CAS Registry No. 1943513-12-9 "Urea, N-(2-ethyl-5,6,7,8-tetrahydro[1,2,4]triazolo[1,5-a]pyridin-6-yl)-N'-[(1S)-1-(3-methyl-2-benzofuranyl)ethyl]-" dated Jul. 1, 2016, Chemical Library; Supplier: Ukrorgsyntez Ltd., 1 page.
CAS Registry No. 1943613-85-1 "Urea, N-[(1S)-1-(3-methyl-2-benzofuranyl)ethyl]-N'-(5,6,7,8-tetrahydro-2-methyl[1,2,4]triazolo[1,5-a]pyridin-6-yl)-" dated Jul. 1, 2016, Chemical Library; Supplier: Ukrorgsyntez Ltd., 1 page.
CAS Registry No. 1943825-30-6 "Urea, N-(9-methyl-9-azabicyclo[3.3.1]non-3-yl)-N'-[(1R)-1-(3-methyl-2-benzofuranyl)ethyl]-" dated Jul. 2, 2016, Chemical Library; Supplier: Ukrorgsyntez Ltd., 1 page.
CAS Registry No. 1944509-79-8 "Urea, N-[1-(3-methyl-2-benzofuranyl)ethyl]-N'-spiro[cyclobutane-1,7'-[2]oxabicyclo[3.2.0]heptan]-6'-yl-" dated Jul. 4, 2016, Chemical Library; Supplier: Ukrorgsyntez Ltd., 1 page.
CAS Registry No. 1944642-24-3 "Urea, N-[2-methyl-1-(3-methyl-2-benzofuranyl)propyl]-N'-(tetrahydro-1-oxido-3-thienyl)-" dated Jul. 4, 2016, Chemical Library; Supplier: Ukrorgsyntez Ltd., 1 page.
CAS Registry No. 1945498-05-4 "Urea, N-[1-(3-methyl-2-benzofuranyl)ethyl]-N'-(tetrahydro-1-oxido-3-thienyl)-" dated Jul. 5, 2016, Chemical Library; Supplier: Ukrorgsyntez Ltd., 1 page.
CAS Registry No. 1946388-30-2 "Urea, N-[2-methyl-1-(3-methyl-2-benzofuranyl)propyl]-N'-4-oxepanyl-" dated Jul. 6, 2016, Chemical Library; Supplier: Ukrorgsyntez Ltd., 1 page.
CAS Registry No. 1946939-38-3 "Urea, N-[1-(3-methyl-2-benzofuranyl)ethyl]-N'-(4,5,6,7-tetrahydro-1H-indazol-6-yl)-" dated Jul. 7, 2016, Chemical Library; Supplier: Ukrorgsyntez Ltd., 1 page.
CAS Registry No. 1947228-91-2 "Urea, N-[1-(3-methyl-2-benzofuranyl)ethyl]-N'-(5,6,7,8-tetrahydro[1,2,4]triazolo[1,5-a]pyridin-6-yl)-" dated Jul. 7, 2016, Chemical Library; Supplier: Ukrorgsyntez Ltd., 1 page.
CAS Registry No. 1947339-35-6 "Urea, N-[2-methyl-1-(3-methyl-2-benzofuranyl)propyl]-N'-(5,6,7,8-tetrahydro[1,2,4]triazolo[1,5-a]pyridin-6-yl)-" dated Jul. 7, 2016, Chemical Library; Supplier: Ukrorgsyntez Ltd., 1 page.
CAS Registry No. 1948652-11-6 "Urea, N-[1-(3-methyl-2-benzofuranyl)ethyl]-N'-[1-methyl-3-(tetrahydro-2-furanyl)-1H-pyrazol-5-yl]-" dated Jul. 9, 2016, Chemical Library; Supplier: Ukrorgsyntez Ltd., 1 page.
CAS Registry No. 1951735-17-3 "Urea, N-2,6-dioxaspiro[4.5]dec-9-yl-N'-[1-(3-methyl-2-benzofuranyl)ethyl]-" dated Jul. 14, 2016, Chemical Library; Supplier: Ukrorgsyntez Ltd., 1 page.

CAS Registry No. 1951892-73-1 "Urea, N-[2-methyl-1-(3-methyl-2-benzofuranyl)propyl]-N'-(4,5,6,7-tetrahydro-1H-indazol-6-yl)-" dated Jul. 14, 2016, Chemical Library; Supplier: Ukrorgsyntez Ltd., 1 page.
CAS Registry No. 1953088-71-5 "Urea, N-[2-methyl-1-(3-methyl-2-benzofuranyl)propyl]-N'-(4,5,6,7-tetrahydro-1H-indazol-7-yl)-" dated Jul. 15, 2016, Chemical Library; Supplier: Ukrorgsyntez Ltd., 1 page.
CAS Registry No. 1957794-34-1 "Urea, N-[2-methyl-1-(3-methyl-2-benzofuranyl)propyl]-N'-(4,5,6,7-tetrahydro-2-methyl-2H-indazol-4-yl)-" dated Jul. 22, 2016, Chemical Library; Supplier: Ukrorgsyntez Ltd., 1 page.
CAS Registry No. 2058073-81-5 "Urea, N-(trans-4-hydroxycyclohexyl)-N'-[2-methyl-1-(3-methyl-2-benzofuranyl)propyl]-" dated Jan. 23, 2017, Chemical Library; Supplier: Aurora Fine Chemicals, 1 page.
CAS Registry No. 2069134-97-8 "Urea, N-(2-hydroxycyclohexyl)-N'-[1-(3-methyl-2-benzofuranyl)ethyl]-" dated Feb. 10, 2017, Chemical Library; Supplier: Aurora Fine Chemicals, 1 page.
CAS Registry No. 2071247-53-3 "Urea, N-(4-hydroxycyclohexyl)-N'-[1-(3-methyl-2-benzofuranyl)ethyl]-" dated Feb. 15, 2017, Chemical Library; Supplier: Aurora Fine Chemicals, 1 page.
CAS Registry No. 2119166-46-8 "Urea, N-[1-(3-methyl-2-benzofuranyl)ethyl]-N'-(6-oxo-5-azaspiro[3.5]non-9-yl)-" dated Aug. 24, 2017, Chemical Catalog; Supplier: Aurora Fine Chemicals, 1 page.
CAS Registry No. 2119741-66-9 "Urea, N-[(1R)-1-(3-methyl-2-benzofuranyl)ethyl]-N'-(5,6,7,8-tetrahydro-2-methyl[1,2,4]triazolo[1,5-a]pyridin-6-yl)-" dated Aug. 24, 2017, Chemical Catalog; Supplier: Aurora Fine Chemicals, 1 page.
CAS Registry No. 2119743-05-2 "No CA Index Name" dated Aug. 24, 2017, Chemical Catalog; Supplier: Aurora Fine Chemicals, 1 page.
CAS Registry No. 2119806-81-2 "Urea, N-[(1S)-1-(3-methyl-2-benzofuranyl)ethyl]-N'-(octahydro-4-benzofuranyl)-" dated Aug. 25, 2017, Chemical Catalog; Supplier: Aurora Fine Chemicals, 1 page.
CAS Registry No. 2119841-80-2 "Urea, N-[(1S)-1-(3-methyl-2-benzofuranyl)ethyl]-N'-6-oxaspiro[4.5]dec-9-yl-" dated Aug. 25, 2017, Chemical Catalog; Supplier: Aurora Fine Chemicals, 1 page.
CAS Registry No. 2119874-86-9 "Urea, N-(2-ethyl-5,6,7,8-tetrahydro[1,2,4]triazolo[1,5-a]pyridin-6-yl)-N'-[(1R)-1-(3-methyl-2-benzofuranyl)ethyl]-" dated Aug. 25, 2017, Chemical Catalog; Supplier: Aurora Fine Chemicals, 1 page.
CAS Registry No. 2120275-98-9 "Urea, N-[1-(3-methyl-2-benzofuranyl)ethyl]-N'-6-oxa-2-thiaspiro[4.5]dec-9-yl-" dated Aug. 25, 2017, Chemical Catalog; Supplier: Aurora Fine Chemicals, 1 page.
CAS Registry No. 2121771-45-5 "Urea, N-[1-(3-methyl-2-benzofuranyl)ethyl]-N'-8-oxaspiro[4.5]dec-1-yl-" dated Aug. 29, 2017, Chemical Catalog; Supplier: Aurora Fine Chemicals, 1 page.
CAS Registry No. 2122659-22-5 "Urea, N-[1-(3-methyl-2-benzofuranyl)ethyl]-N'-(4,5,6,7-tetrahydro-1H-indazol-7-yl)-" dated Aug. 30, 2017, Chemical Catalog; Supplier: Aurora Fine Chemicals, 1 page.
CAS Registry No. 2173642-11-8 "Urea, N-[(1S)-1-(3-methyl-2-benzofuranyl)ethyl]-N'-[1-(1-methylethyl)-2-oxo-3-pyrrolidinyl]-" dated Feb. 15, 2018, Chemical Library; Supplier: Aurora Fine Chemicals, 1 page.
CAS Registry No. 2173660-82-5 "Urea, N-[(1R)-1-(3-methyl-2-benzofuranyl)ethyl]-N'-(4-methyl-2-oxo-3-piperidinyl)-" dated Feb. 15, 2018, Chemical Library; Supplier: Aurora Fine Chemicals, 1 page.
CAS Registry No. 2173679-33-7 "Urea, N-[(1R)-1-(3-methyl-2-benzofuranyl)ethyl]-N'-[1-(1-methylethyl)-5-oxo-3-pyrrolidinyl]-" dated Feb. 15, 2018, Chemical Library; Supplier: Aurora Fine Chemicals, 1 page.
CAS Registry No. 2173683-02-6 "Urea, N-[(1R)-1-(3-methyl-2-benzofuranyl)ethyl]-N'-(tetrahydro-1,1-dioxido-2H-thiopyran-3-yl)-" dated Feb. 15, 2018, Chemical Library; Supplier: Aurora Fine Chemicals, 1 page.
CAS Registry No. 2173711-86-7 "Urea, N-[(1R)-1-(3-methyl-2-benzofuranyl)ethyl]-N'-(tetrahydro-2H-thiopyran-3-yl)-" dated Feb. 15, 2018, Chemical Library; Supplier: Aurora Fine Chemicals, 1 page.

(56) References Cited

OTHER PUBLICATIONS

CAS Registry No. 2173731-95-6 "Urea, N-[(1S)-1-(3-methyl-2-benzofuranyl)ethyl]-N'-[1-(methylsulfonyl)-3-piperidinyl]-" dated Feb. 15, 2018, Chemical Library; Supplier: Aurora Fine Chemicals, 1 page.
CAS Registry No. 2173736-03-1 "1-Pyrrolidinecarboxamide, N-ethyl-3-[[[[(1S)-1-(3-methyl-2-benzofuranyl)ethyl]amino]carbonyl]amino]-" dated Feb. 15, 2018, Chemical Library; Supplier: Aurora Fine Chemicals, 1 page.
CAS Registry No. 2173925-60-3 "Urea, N-(1-acetyl-3-pyrrolidinyl)-N'-[(1R)-1-(3-methyl-2-benzofuranyl)ethyl]-" dated Feb. 15, 2018, Chemical Library; Supplier: Aurora Fine Chemicals, 1 page.
CAS Registry No. 2173967-89-8 "Urea, N-(2,2-dimethyl-6-oxo-3-piperidinyl)-N'-[(1S)-1-(3-methyl-2-benzofuranyl)ethyl]-" dated Feb. 15, 2018, Chemical Library; Supplier: Aurora Fine Chemicals, 1 page.
CAS Registry No. 2174231-48-0 "Urea, N-[1-(1-methylethyl)-2-oxo-3-pyrrolidinyl]-N'-[2-methyl-1-(3-methyl-2-benzofuranyl)propyl]-" dated Feb. 16, 2018, Chemical Library; Supplier: Aurora Fine Chemicals, 1 page.
CAS Registry No. 2174549-44-9 "Urea, N-[2-methyl-1-(3-methyl-2-benzofuranyl)propyl]-N'-(1-methyl-2-oxo-3-pyrrolidinyl)-" dated Feb. 16, 2018, Chemical Library; Supplier: Aurora Fine Chemicals, 1 page.
CAS Registry No. 2174601-06-8 "Urea, N-[1-(3-methyl-2-benzofuranyl)ethyl]-N'-(1-methyl-2-oxo-3-pyrrolidinyl)-" dated Feb. 16, 2018, Chemical Library; Supplier: Aurora Fine Chemicals, 1 page.
CAS Registry No. 2174885-91-5 "Urea, N-[1-(3-methyl-2-benzofuranyl)ethyl]-N'-(2-oxo-3-piperidinyl)-" dated Feb. 16, 2018, Chemical Library; Supplier: Aurora Fine Chemicals, 1 page.
CAS Registry No. 2175207-31-3 "Urea, N-[2-methyl-1-(3-methyl-2-benzofuranyl)propyl]-N'-(2-oxo-3-piperidinyl)-" dated Feb. 17, 2018, Chemical Library; Supplier: Aurora Fine Chemicals, 1 page.
CAS Registry No. 2175748-28-2 "Urea, N-[(1R)-1-(3-methyl-2-benzofuranyl)ethyl]-N'-(1-propyl-4-piperidinyl)-" dated Feb. 19, 2018, Chemical Library; Supplier: Aurora Fine Chemicals, 1 page.
CAS Registry No. 2175995-85-2 "Cyclohexanecarboxamide, N-methyl-4-[[[[(1R)-1-(3-methyl-2-benzofuranyl)ethyl]amino]carbonyl]amino]-" dated Feb. 19, 2018, Chemical Library; Supplier: Aurora Fine Chemicals, 1 page.
CAS Registry No. 2175996-19-5 "Urea, N-[(1S)-1-(3-methyl-2-benzofuranyl)ethyl]-N'-[1-(3-methyl-1-oxobutyl)-4-piperidinyl]-" dated Feb. 19, 2018, Chemical Library; Supplier: Aurora Fine Chemicals, 1 page.
CAS Registry No. 2176054-50-3 "Urea, N-[1-(3-methyl-2-benzofuranyl)ethyl]-N'-(1-methyl-5-oxo-3-pyrrolidinyl)-" dated Feb. 19, 2018, Chemical Library; Supplier: Aurora Fine Chemicals, 1 page.
CAS Registry No. 2176306-20-8 "Urea, N-[2-methyl-1-(3-methyl-2-benzofuranyl)propyl]-N'-(1-methyl-4-piperidinyl)-" dated Feb. 19, 2018, Chemical Library; Supplier: Aurora Fine Chemicals, 1 page.
CAS Registry No. 2176424-60-3 "Urea, N-(1-acetyl-3-pyrrolidinyl)-N'-[2-methyl-1-(3-methyl-2-benzofuranyl)propyl]-" dated Feb. 19, 2018, Chemical Library; Supplier: Aurora Fine Chemicals, 1 page.
CAS Registry No. 2177001-80-6 "Urea, N-[2-methyl-1-(3-methyl-2-benzofuranyl)propyl]-N'-(1-methyl-5-oxo-3-pyrrolidinyl)-" dated Feb. 20, 2018, Chemical Library; Supplier: Aurora Fine Chemicals, 1 page.
CAS Registry No. 2178297-36-2 "Urea, N-[1-(ethylsulfonyl)-4-piperidinyl]-N'-[(1R)-1-(3-methyl-2-benzofuranyl)ethyl]-" dated Feb. 22, 2018, Chemical Library; Supplier: Aurora Fine Chemicals, 1 page.
CAS Registry No. 2178423-70-4 "Urea, N-[1-(3-methyl-2-benzofuranyl)ethyl]-N'-(tetrahydro-1,1-dioxido-3-thienyl)-" dated Feb. 22, 2018, Chemical Library; Supplier: Aurora Fine Chemicals, 1 page.
CAS Registry No. 2178424-01-4 "Urea, N-[1-(3-methyl-2-benzofuranyl)ethyl]-N'-[1-(1-methylethyl)-4-piperidinyl]-" dated Feb. 22, 2018, Chemical Library; Supplier: Aurora Fine Chemicals, 1 page.
CAS Registry No. 2178424-03-6 "Urea, N-[1-(3-methyl-2-benzofuranyl)ethyl]-N'-(1-methyl-4-piperidinyl)-" dated Feb. 22, 2018, Chemical Library; Supplier: Aurora Fine Chemicals, 1 page.
CAS Registry No. 2178627-09-1 "No CA Index Name" dated Feb. 22, 2018, Chemical Library; Supplier: Aurora Fine Chemicals, 1 page.
CAS Registry No. 2179767-57-6 "Urea, N-(3-methoxycyclopentyl)-N'-[1-(3-methyl-2-benzofuranyl)ethyl]-" dated Feb. 26, 2018, Chemical Library; Supplier: Aurora Fine Chemicals, 1 page.
CAS Registry No. 2186280-72-6 "Urea, N-[1-(1,1-dimethylethyl)-4-piperidinyl]-N'-[1-(3-methyl-2-benzofuranyl)ethyl]-" dated Mar. 7, 2018, Chemical Library; Supplier: Aurora Fine Chemicals, 1 page.
CAS Registry No. 2189848-84-6 "Urea, N-[1-(3-methyl-2-benzofuranyl)ethyl]-N'-(tetrahydro-2,2-dimethyl-2H-pyran-4-yl)-" dated Mar. 13, 2018, Chemical Library; Supplier: Aurora Fine Chemicals, 1 page.
CAS Registry No. 2190747-26-1 "Cyclohexanecarboxamide, 3-[[[[1-(3-methyl-2-benzofuranyl)ethyl]amino]carbonyl]amino]-" dated Mar. 14, 2018, Chemical Library; Supplier: Aurora Fine Chemicals, 1 page.
CAS Registry No. 2191106-25-7 "Urea, N-[1-(3-methyl-2-benzofuranyl)ethyl]-N'-[1-(methylsulfonyl)-4-piperidinyl]-" dated Mar. 14, 2018, Chemical Library; Supplier: Aurora Fine Chemicals, 1 page.
CAS Registry No. 2191565-44-1 "Cyclohexanecarboxamide, 3-[[[[2-methyl-1-(3-methyl-2-benzofuranyl)propyl]amino]carbonyl]amino]-" dated Mar. 15, 2018, Chemical Library; Supplier: Aurora Fine Chemicals, 1 page.
CAS Registry No. 2193295-09-7 "Urea, N-[1-(3-methyl-2-benzofuranyl)ethyl]-N'-[4-(methylsulfonyl)cyclohexyl]-" dated Mar. 17, 2018, Chemical Library; Supplier: Aurora Fine Chemicals, 1 page.
CAS Registry No. 2193493-17-1 "Urea, N-[1-(3-methyl-2-benzofuranyl)ethyl]-N'-(tetrahydro-2-methyl-2H-pyran-4-yl)-" dated Mar. 17, 2018, Chemical Library; Supplier: Aurora Fine Chemicals, 1 page.
CAS Registry No. 2193654-89-4 "Urea, N-(1-ethyl-4-piperidinyl)-N'-[1-(3-methyl-2-benzofuranyl)ethyl]-" dated Mar. 17, 2018, Chemical Library; Supplier: Aurora Fine Chemicals, 1 page.
CAS Registry No. 2193720-74-8 "Urea, N-[1-(3-methyl-2-benzofuranyl)ethyl]-N'-(tetrahydro-2H-pyran-4-yl)-" dated Mar. 17, 2018, Chemical Library; Supplier: Aurora Fine Chemicals, 1 page.
CAS Registry No. 2194252-63-4 "Cyclopentanecarboxamide, N-methyl-2-[[[[1-(3-methyl-2-benzofuranyl)ethyl]amino]carbonyl]amino]-" dated Mar. 19, 2018, Chemical Library; Supplier: Aurora Fine Chemicals, 1 page.
CAS Registry No. 2194265-11-5 "Urea, N-[(1S)-1-(3-methyl-2-benzofuranyl)ethyl]-N'-(tetrahydro-2H-thiopyran-4-yl)-" dated Mar. 19, 2018, Chemical Library; Supplier: Aurora Fine Chemicals, 1 page.
CAS Registry No. 2194408-61-0 "Urea, N-(4,4-difluorocyclohexyl)-N'-[(1R)-1-(3-methyl-2-benzofuranyl)ethyl]-" dated Mar. 19, 2018, Chemical Library; Supplier: Aurora Fine Chemicals, 1 page.
CAS Registry No. 2195576-58-8 "Urea, N-[1-(3-methyl-2-benzofuranyl)ethyl]-N'-(tetrahydro-2H-pyran-3-yl)-" dated Mar. 21, 2018, Chemical Library; Supplier: Aurora Fine Chemicals, 1 page.
CAS Registry No. 2195946-35-9 "Urea, N-[1-(3-methyl-2-benzofuranyl)ethyl]-N'-(1-methyl-6-oxo-3-piperidinyl)-" dated Mar. 21, 2018, Chemical Library; Supplier: Aurora Fine Chemicals, 1 page.
CAS Registry No. 2196116-64-8 "Urea, N-[2-methyl-1-(3-methyl-2-benzofuranyl)propyl]-N'-(tetrahydro-2H-pyran-3-yl)-" dated Mar. 21, 2018, Chemical Library; Supplier: Aurora Fine Chemicals, 1 page.
CAS Registry No. 2196373-03-0 "Cyclohexanecarboxamide, 3-[[[[1-(3-methyl-2-benzofuranyl)ethyl]amino]carbonyl]amino]-N-(1-methylethyl)-" dated Mar. 22, 2018, Chemical Library; Supplier: Aurora Fine Chemicals, 1 page.

(56) References Cited

OTHER PUBLICATIONS

CAS Registry No. 2263104-40-9 "Urea, N-(2,4-dioxo-1,3-diazaspiro[4.5]dec-8-yl)-N'-[1-(3-methyl-2-benzofuranyl)ethyl]-" dated Jan. 31, 2019, Chemical Library; Supplier: Ukrorgsyntez Ltd., 1 page.
CAS Registry No. 2395556-55-3 "Urea, N-[1-(3-methyl-2-benzofuranyl)ethyl]-N'-(3-methyl-4-isothiazolyl)-" dated Dec. 20, 2019, Chemical Library; Supplier: FCH Group, 1 page.
CAS Registry No. 2397033-02-0 "Urea, N-[(1R)-1-(3-methyl-2-benzofuranyl)ethyl]-N'-[(3S)-tetrahydro-2-oxo-3-furanyl]-" dated Dec. 31, 2019, Chemical Library; Supplier: Ukrorgsyntez Ltd., 1 page.
CAS Registry No. 2397238-39-8 "No CA Index Name" dated Dec. 31, 2019, Chemical Library; Supplier: Ukrorgsyntez Ltd., 1 page.
CAS Registry No. 2397958-96-0 "Urea, N-[(1S)-1-(3-methyl-2-benzofuranyl)ethyl]-N'-[(3S)-tetrahydro-2-oxo-3-furanyl]-" dated Jan. 1, 2020, Chemical Library; Supplier: Ukrorgsyntez Ltd., 1 page.
CAS Registry No. 2420670-07-9 "Urea, N-[1-(3-methyl-2-benzofuranyl)ethyl]-N'-[(3R,4R)-tetrahydro-4-methoxy-3-furanyl]-, rel-" dated Jun. 9, 2020, Chemical Library; Supplier: Aurora Fine Chemicals, 1 page.
CAS Registry No. 2420683-70-9 "Urea, N-[1-(3-methyl-2-benzofuranyl)ethyl]-N'-[(3R,4S)-tetrahydro-4-methoxy-3-furanyl]-, rel-" dated Jun. 9, 2020, Chemical Library; Supplier: Aurora Fine Chemicals, 1 page.
CAS Registry No. 2420860-97-3 "Urea, N-[1-(3-methyl-2-benzofuranyl)ethyl]-N'- (1R,2S,4S)-7-oxabicyclo[2.2.1]hept-2-yl-, rel-" dated Jun. 9, 2020, Chemical Library; Supplier: Aurora Fine Chemicals, 1 page.
CAS Registry No. 2425614-90-8 "Urea, N-[1-(3-methyl-2-benzofuranyl)ethyl]-N'-4-oxepanyl-" dated Jun. 15, 2020, Chemical Library; Supplier: Aurora Fine Chemicals, 1 page.
CAS Registry No. 2433660-24-1 "Urea, N-(trans-3-methoxycyclobutyl)-N'-[(1S)-1-(3-methyl-2-benzofuranyl)ethyl]-, rel-" dated Jun. 24, 2020, Chemical Library; Supplier: Aurora Fine Chemicals, 1 page.
CAS Registry No. 2448979-37-9 "Urea, N-[(1R)-1-(3-methyl-2-benzofuranyl)ethyl]-N'-[(3S,4R)-tetrahydro-4-methoxy-3-furanyl]-, rel-" dated Jul. 24, 2020, Chemical Library; Supplier: Aurora Fine Chemicals, 1 page.
CAS Registry No. 2450113-37-6 "Urea, N-[(1R)-1-(3-methyl-2-benzofuranyl)ethyl]-N'-[(3R,4S)-tetrahydro-4-methoxy-3-furanyl]-, rel-" dated Jul. 27, 2020, Chemical Library; Supplier: Aurora Fine Chemicals, 1 page.
CAS Registry No. 2451400-38-5 "Urea, N-[(1R)-1-(3-methyl-2-benzofuranyl)ethyl]-N'-(1R,2S,4S)-7-oxabicyclo[2.2.1]hept-2-yl-, rel-" dated Jul. 30, 2020, Chemical Library; Supplier: Aurora Fine Chemicals, 1 page.
CAS Registry No. 2462178-07-8 "Urea, N-[1-(3-methyl-2-benzofuranyl)ethyl]-N'-6-oxaspiro[2.5]oct-1-yl-" dated Aug. 26, 2020, Chemical Library; Supplier: Aurora Fine Chemicals, 1 page.
CAS Registry No. 2464101-94-6 "Urea, N-[(1R)-1-(3-methyl-2-benzofuranyl)ethyl]-N'-[(3R,4R)-tetrahydro-4-methoxy-3-furanyl]-, rel-" dated Aug. 27, 2020, Chemical Library; Supplier: Aurora Fine Chemicals, 1 page.
CAS Registry No. 2464140-95-0 "No CA Index Name" dated Aug. 27, 2020, Chemical Library; Supplier: Aurora Fine Chemicals, 1 page.
CAS Registry No. 2464723-82-6 "No CA Index Name" dated Aug. 27, 2020, Chemical Library; Supplier: Aurora Fine Chemicals, 1 page.
CAS Registry No. 2466812-87-1 "Urea, N-[1-(3-methyl-2-benzofuranyl)ethyl]-N'-(3-methyl-3-oxetanyl)-" dated Aug. 28, 2020, Chemical Library; Supplier: Aurora Fine Chemicals, 1 page.
CAS Registry No. 2467887-81-4 "No CA Index Name" dated Aug. 28, 2020, Chemical Library; Supplier: Aurora Fine Chemicals, 1 page.
André et al., "Alpelisib for PIK3CA-Mutated, Hormone Receptor-Positive Advanced Breast Cancer," N Engl J Med, May 16, 2019, 380(20): 1929-1940.
Arafeh et al., "PIK3CA in cancer: the past 30 years," InSeminars in cancer biology, Dec. 1, 2019, 59:36-49.
Bauer et al., "Targeting PI3 kinase in cancer," Pharmacology & therapeutics, Feb. 1, 2015, 146:53-60.
Bedard et al., "Long-term safety of inavolisib (GDC-0077) in an ongoing phase 1/1b study evaluating monotherapy and in combination (combo) with palbociclib and/or endocrine therapy in patients (pts) with PIK3CA-mutated, hormone receptor-positive/HER2-negative (HR+/HER2−) metastatic breast cancer (BC)," J. Clin. Oncol., Jun. 1, 2022, 40:1052.
Belli et al., "The emerging role of PI3K inhibitors for solid tumour treatment and beyond," British journal of cancer, Mar. 2023, 13:1-3.
Bello et al., "Alpelisib and fulvestrant in PIK3CA-mutated hormone receptor-positive HER2-negative advanced breast cancer included in the French early access program," Oncogene, Jun. 6, 2023, 42(23): 1951-1956.
Burke et al., "Oncogenic mutations mimic and enhance dynamic events in the natural activation of phosphoinositide 3-kinase p110α (PIK3CA)," Proceedings of the National Academy of Sciences, Sep. 18, 2012, 109(38): 15259-15264.
Castel et al., "The present and future of PI3K inhibitors for cancer therapy," Nature cancer, Jun. 2021, 2(6):587-597.
Cerami et al., "The cBio cancer genomics portal: an open platform for exploring multidimensional cancer genomics data," Cancer discovery, May 1, 2012, 2(5):401- 4044.
Chandarlapaty et al., "AKT inhibition relieves feedback suppression of receptor tyrosine kinase expression and activity," Cancer cell, Jan. 18, 2011, 19(1):58-71.
Cheung et al., "Factors leading to alpelisib discontinuation in patients with hormone receptor positive, human epidermal growth factor receptor-2 negative breast cancer," Breast Cancer Research and Treatment, Apr. 1, 2022, 192(2):303-311.
Croessmann et al., "PIK3CA C2 domain deletions hyperactivate phosphoinositide 3- kinase (PI3K), generate oncogene dependence, and are exquisitely sensitive to PI3K α inhibitors, " Clinical Cancer Research, Mar. 15, 2018, 24(6):1426-1435.
Di Veroli et al., "Combenefit: an interactive platform for the analysis and visualization of drug combinations," Bioinformatics, Sep. 15, 2016, 32(18):2866-2868.
Dockx et al., "Early Changes in [18F] FDG Uptake as a Readout for PI3K/Akt/mTOR Targeted Drugs in HER-2-Positive Cancer Xenografts," Molecular imaging, May 25, 2021, 2021:1-14.
Elkabets et al., "mTORC1 inhibition is required for sensitivity to PI3K p110α inhibitors in PIK3CA-mutant breast cancer," Science translational medicine, Jul. 31, 2013, 5(196): 28 pages.
El-Khouly et al., "Synthesis, anticancer and antimicrobial evaluation of new benzofuran based derivatives: PI3K inhibition, quorum sensing and molecular modeling study," Bioorganic & medicinal chemistry, Feb. 1, 2021, 31:115976, 45 pages.
Emsley et al., "Features and development of Coot," Acta Crystallographica Section D: Biological Crystallography, Apr. 1, 2010, 66(4):486-501.
Evans, "Scaling and assessment of data quality," Acta Crystallographica Section D: Biological Crystallography, Jan. 1, 2006, 62(1):72-82.
Filipski et al., "Intestinal targeting of drugs: rational design approaches and challenges," Current Topics in Medicinal Chemistry, Apr. 1, 2013, 13(7):776-802.
Fritsch et al., "Characterization of the novel and specific PI3Kα inhibitor NVP-BYL719 and development of the patient stratification strategy for clinical trials," Molecular cancer therapeutics, May 1, 2014, 13(5):1117-1129.
Fruman et al., "The PI3K pathway in human disease," Cell, Aug. 10, 2017, 170(4):605-635.
Gao et al., "Integrative analysis of complex cancer genomics and clinical profiles using the cBioPortal," Science signaling, Apr. 2, 2013, 6(269): 34 pages.
García-Aranda et al., "Tetramic acids and indole derivatives from amino acid β-keto esters. Fine-tuning the conditions of the key Cu-catalyzed reaction," Tetrahedron Letters, Mar. 26, 2014, 55(13):2142-2145.
Gkeka et al., "Exploring a non-ATP pocket for potential allosteric modulation of PI3Kα.," The Journal of Physical Chemistry B, Jan. 22, 2015, 119(3):1002-1016.

(56) References Cited

OTHER PUBLICATIONS

Hanker et al., "Challenges for the clinical development of PI3K inhibitors: strategies to improve their impact in solid tumors," Cancer discovery, Apr. 1, 2019, 9(4):482-491.
Hauner et al., "Development of insulin-responsive glucose uptake and GLUT4 expression in differentiating human adipocyte precursor cells," International journal of obesity, May 1998, 22(5):448-453.
Hopkins et al., "Suppression of insulin feedback enhances the efficacy of PI3K inhibitors," Nature, Aug. 23, 2018, 560(7719):499-503.
International Search Report and Written Opinion in International Appln. No. PCT/US2022/033255, dated Aug. 26, 2022, 16 pages.
James et al., "The aetiology and molecular landscape of insulin resistance," Nature Reviews Molecular Cell Biology, Nov. 2021, 22(11):751-771.
Janku et al., "Targeting the PI3K pathway in cancer: are we making headway?" Nature reviews Clinical oncology, May 2018, 15(5):273-291.
Juric et al., "Alpelisib plus fulvestrant in PIK3CA-altered and PIK3CA-wild-type estrogen receptor-positive advanced breast cancer: a phase 1b clinical trial," JAMA oncology, Feb. 1, 2019, 5(2):e184475, 9pages.
Juric et al., "Phosphatidylinositol 3-kinase α-selective inhibition with alpelisib (BYL719) in PIK3CA-altered solid tumors: results from the first-in-human study," Journal of Clinical Oncology, May 5, 2018, 36(13): 12 pages.
Kabsch, "Integration, scaling, space-group assignment and post-refinement," Acta Crystallographica Section D: Biological Crystallography, Feb. 1, 2010, 66(2): 133-144.
Karachaliou et al., "Real-time liquid biopsies become a reality in cancer treatment," Annals of translational medicine, Mar. 2015, 3(3): 3 pages.
Karakas et al., "Mutation of the PIK3CA oncogene in human cancers," British journal of cancer, Feb. 2006, 94(4):455-459.
Lammers et al., "Effect of intratumoral injection on the biodistribution, the therapeutic potential of HPMA copolymer-based drug delivery systems," Neoplasia, Oct. 1, 2006, 8(10):788-795.
Lopes et al., "Metabolomics atlas of oral 13C-glucose tolerance test in mice," Cell Reports, Oct. 12, 2021, 37(2): 16 pages.
Madsen et al., "Cancer-associated PIK3CA mutations in overgrowth disorders," Trends in molecular medicine, Oct. 1, 2018, 24(10):856-870.
Mandelker et al., "A frequent kinase domain mutation that changes the interaction between PI3Kα and the membrane," Proceedings of the National Academy of Sciences, Oct. 6, 2009, 106(40): 16996-17001.
Marin-Acevedo et al., "Next generation of immune checkpoint therapy in cancer: new developments and challenges," Journal of hematology & oncology, Dec. 2018, 11(39):1-20.
Martínez-Sáez et al., "Frequency and spectrum of PIK3CA somatic mutations in breast cancer," Breast Cancer Research, Dec. 2020, 22(1): 1-9.
Martini et al., "PI3K/AKT signaling pathway and cancer: an updated review," Annals of medicine, Sep. 1, 2014, 46(6):372-383.
Mayer et al., "The PI3K/AKT pathway as a target for cancer treatment," Annual review of medicine, Jan. 14, 2016, 67:11-28.
Mishra et al., "PI3K inhibitors in cancer: clinical implications and adverse effects," International Journal of Molecular Sciences, Mar. 27, 2021, 22(7):3464, 77 pages.
O'Brien et al., "Targeting activated PI3K/mTOR signaling overcomes acquired resistance to CDK4/6-based therapies in preclinical models of hormone receptor-positive breast cancer," Breast Cancer Research, Dec. 2020, 22(1): 1-17.

Peairs et al., "Diabetes mellitus and breast cancer outcomes: a systematic review and meta-analysis," Journal of Clinical Oncology, Jan. 1, 2011, 29(1):40-46.
Razavi et al., "Alterations in PTEN and ESR1 promote clinical resistance to alpelisib plus aromatase inhibitors," Nature Cancer, Apr. 2020, 1(4): 33 pages.
Rosfjord et al., "Advances in patient-derived tumor xenografts: from target identification to predicting clinical response rates in oncology," Biochemical pharmacology, Sep. 15, 2014, 91(2):135-143.
Rugo et al., "A multidisciplinary approach to optimizing care of patients treated with alpelisib," The Breast, Feb. 2022, 61:156-167.
Rugo et al., "Time course and management of key adverse events during the randomized phase III SOLAR-1 study of PI3K inhibitor alpelisib plus fulvestrant in patients with HR-positive advanced breast cancer," Annals of Oncology, Aug. 1, 2020, 31(8):1001-1010.
Samuels et al., "High frequency of mutations of the PIK3CA gene in human cancers," Science, Apr. 23, 2004, 304(5670):554.
Sarker et al., "First-in-human phase I study of pictilisib (GDC-0941), a potent pan-class I phosphatidylinositol-3-kinase (PI3K) inhibitor, in patients with advanced solid tumors," Clinical cancer research, Jan. 1, 2015, 21(1):77-86.
Savas et al., "Alpelisib monotherapy for PI3K-altered, pretreated advanced breast cancer: A phase II study," Cancer Discovery, Sep. 2, 2022, 12(9):2058-2073.
Serra et al., "PI3K inhibition results in enhanced HER signaling and acquired ERK dependency in HER2-overexpressing breast cancer," Oncogene, Jun. 2011, 30(22):2547-2557.
Sivakumar et al., "Genetic heterogeneity and tissue-specific patterns of tumors with multiple PIK3CA mutations," Clinical Cancer Research, Mar. 14, 2023, 29(6):1125-1136.
Smirnov et al., "PharmacoGx: an R package for analysis of large pharmacogenomic datasets," Bioinformatics, Apr. 15, 2016, 32(8):1244-1246.
Tolaney et al., "Phase Ib study of ribociclib plus fulvestrant and ribociclib plus fulvestrant plus PI3K inhibitor (Alpelisib or Buparlisib) for HR+ advanced breast cancer," Clinical Cancer Research, Jan. 15, 2021, 27(2):418-428.
Vanhaesebroeck et al., "PI3K inhibitors are finally coming of age," Nature Reviews Drug Discovery, Oct. 2021, 20(10): 71 pages.
Vasan et al., "At a crossroads: how to translate the roles of PI3K in oncogenic and metabolic signalling into improvements in cancer therapy," Nature Reviews Clinical Oncology, Jul. 2022, 19(7):471-485.
Velho et al., "The prevalence of PIK3CA mutations in gastric and colon cancer," European journal of cancer, Jul. 1, 2005, 41(11):1649-1654.
Venot et al., "Targeted therapy in patients with PIK3CA-related overgrowth syndrome," Nature, Jun. 28, 2018, 558(7711): 39 pages.
Vonrhein et al., "Data processing and analysis with the autoPROC toolbox," Acta Crystallographica Section D: Biological Crystallography, Apr. 1, 2011, 67(4):293-302.
Wang et al., "Dermatologic adverse events related to the PI3Kα inhibitor alpelisib (BYL719) in patients with breast cancer," Breast cancer research and treatment, Aug. 2020, 183: 20 pages.
Zegzouti et al., "ADP-Glo: A Bioluminescent and homogeneous ADP monitoring assay for kinases," Assay and drug development technologies, Dec. 1, 2009, 7(6):560-572.
Zhang et al., "A pan-cancer proteogenomic atlas of PI3K/AKT/mTOR pathway alterations," Cancer cell, Jun. 12, 2017, 31(6):820-832.
Zhao et al., "Class I PI3K in oncogenic cellular transformation," Oncogene, Sep. 2008, 27(41): 21 pages.
Di Grandi et al., "Thiourea inhibitors of herpesviruses. Part 3: Inhibitors of varicella zoster virus," Bioorganic & medicinal chemistry letters, Aug. 16, 2004, 14(16):4157-4160.

METHODS FOR TREATING CANCER

CROSS-REFERENCE TO RELATED APPLICATIONS

This application is a continuation of International Application No. PCT/US2022/033255, filed on Jun. 13, 2022, which claims the benefit of priority to U.S. Application No. 63/210,370, filed on Jun. 14, 2021, U.S. Application No. 63/228,351, filed on Aug. 2, 2021, U.S. Application No. 63/288,909, filed on Dec. 13, 2021, U.S. Application No. 63/316,017, filed on Mar. 3, 2022, U.S. Application No. 63/319,236, filed on Mar. 11, 2022, and U.S. Application No. 63/348,261, filed on Jun. 2, 2022, the contents of which are hereby incorporated by reference.

SEQUENCE LISTING

This application contains a Sequence Listing that has been submitted electronically as an XML file named 50006-0084001_ST26_SL.XML." The XML file, created on Aug. 14, 2023, is 2,934 bytes in size. The material in the XML file is hereby incorporated by reference in its entirety.

TECHNICAL FIELD

This disclosure provides compounds of Formula (I), Formula (II), and pharmaceutically acceptable salts thereof, that inhibit phosphatidylinositol 4,5-bisphosphate 3-kinase (PI3K) isoform alpha (PI3Kα). These chemical entities are useful, e.g., for treating a condition, disease or disorder in which increased (e.g., excessive) PI3Kα activation contributes to the pathology and/or symptoms and/or progression of the condition, disease or disorder (e.g., cancer) in a subject (e.g., a human). This disclosure also provides compositions containing the same as well as methods of using and making the same.

BACKGROUND

Phosphatidylinositol 4,5-bisphosphate 3-kinase (PI3K) isoform alpha (PI3Kα), encoded by the PIK3CA gene is a part of the PI3K/AKT/TOR signaling network and is altered in several human cancers. Several investigators have demonstrated the role of PI3K/AKT signaling is involved in physiological and pathophysiological functions that drive tumor progression such as metabolism, cell growth, proliferation, angiogenesis and metastasis. (See, Fruman, D. A. *The PI3K Pathway in Human Disease.* Cell 2017, 170, 605-635 and Janku, F. et al., *Targeting the PI3K pathway in cancer: Are we making headway?* Nat. Rev. Clin. Oncol. 2018, 15, 273-291.) Suppression (e.g., pharmacological or genetic) of PI3K/AKT/TOR signaling may cause cancer cell death and regression of tumor growth.

The PI3K pathway can be activated via, for example, point mutation(s) of the PIK3CA gene or via inactivation of the phosphatase and tensin homolog (PTEN) gene. Activation of this pathway occurs in approximately 30-50% human cancers and contributes to resistance to various anti-cancer therapies. (See, Martini, M. et al., *PI3K/AKT signaling pathway and cancer: An updated review.* Ann. Med. 2014, 46, 372-383 and Bauer, T. M. et al., *Targeting PI3 kinase in cancer.* Pharmacol. Ther. 2015, 146, 53-60.) PI3K consists of three subunits: p85 regulatory subunit, p55 regulatory subunit, and p110 catalytic subunit. According to their different structures and specific substrates, PI3K is divided into 3 classes: classes I, II, and III. Class I PI3Ks include class IA and class IB PI3Ks. Class IA PI3K, a heterodimer of p85 regulatory subunit and p¹10 catalytic subunit, is the type most clearly implicated in human cancer. Class IA PI3K includes p110a, p110ß and p110δ catalytic subunits produced from different genes (PIK3CA, PIK3CB and PIK3CD, respectively), while p110γ produced by PIK3CG represents the only catalytic subunit in class IB PI3K. PIK3CA, the gene encoding the p110α subunit, is frequently mutated or amplified in many human cancers, such as breast cancer, colon cancer, gastric cancer, cervical cancer, prostate cancer, and lung cancer. (See, Samuels Y, et al. High frequency of mutations of the PIK3CA gene in human cancers. Science. 2004; 304:554.)

However, the development of PI3K inhibitors has been problematic for several reasons including (i) adaptive molecular mechanisms upon therapeutic inhibition of PI3K, (ii) inability to specifically inhibit signaling by PIK3CA mutations while sparing endogenous p110α, (iii) the limited use of these therapies in rational combinations, including those informed with strong mechanistic support, and (iv) dose-limiting toxicities that prevent sustained PI3K pathway suppression. (See, Hanker et al., *Challenges for the Clinical Development of PI3K Inhibitors: strategies to Improve Their Impact in solid Tumors,* Cancer Discovery, April 2019; 9: 482-491.) For example, alpelisib is an alpha-selective PI3K inhibitor that is equipotent against wild-type and mutant forms of PI3Kα. However, the therapeutic benefit of alpelisib is limited by wild-type PI3Kα inhibition in normal tissues, resulting in dose-limiting toxicities including hyperglycemia.

Additionally, there are other factors and compensatory pathways derived from both clinical and in vitro lab studies, which affect PI3K signaling, such as HRAS and KRAS mutations, which reduce susceptibility to PI3K inhibitors (and knockdown of these has shown to improve sensitivity to PI3K inhibitors). (See, Misrha, R.; PI3K *Inhibitors in Cancer: Clinical Implications and Adverse Effects.* Int. J. Mol. Sci. 2021, 22, 3464.) Domain deletions in PIK3CA can activate PI3K signaling significantly and also enhance the sensitivity to PI3K inhibitors. (See, Croessmann, S. et al., Clin. Cancer Res. 2018, 24, 1426-1435.) Thus, targeting PI3Kα represents an approach for the treatment of proliferative disorders such as cancer.

SUMMARY

Some embodiments provide a compound of Formula (I):

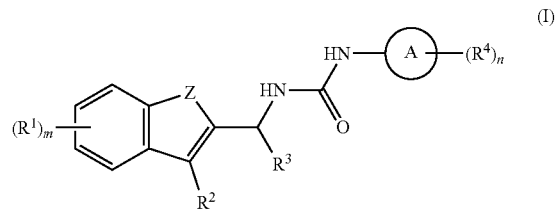

or a pharmaceutically acceptable salt thereof, wherein:

Z is O or $NR^x$;

$R^x$ is hydrogen, C1-C6 alkyl, or C3-C6 cycloalkyl;

each $R^1$ is independently selected from halogen, hydroxyl, cyano, C1-C6 alkyl optionally substituted with hydroxyl, and C3-C6 cycloalkyl;

m is 0, 1, 2, or 3;

$R^2$ is halogen, hydroxyl, C1-C6 alkyl optionally substituted with hydroxyl, C1-C6 haloalkyl, C3-C6 cycloalkyl optionally substituted with 1 or 2 fluoro;

$R^3$ is a C1-C6 alkyl, a C1-C6 haloalkyl, or a C3-C6 cycloalkyl optionally substituted with 1 or 2 substituents independently selected from fluoro and C1-C6 alkyl;

Ring A is a 6-10 membered aryl, a C3-C8 cycloalkyl, a 5-10 membered heteroaryl, or a 4-10 membered heterocyclyl;

each $R^4$ is independently selected from the group consisting of:
(i) halogen,
(ii) C1-C6 alkyl optionally substituted with 1 or 2 hydroxyl or $-NR^AR^B$,
(iii) C1-C6 alkoxy optionally substituted with 1-2 substituents independently selected from hydroxyl and C3-C6 cycloalkyl,
(iv) C1-C6 haloalkyl,
(v) hydroxyl,
(vi) cyano,
(vii) $-CO_2H$,
(viii) $-NR^AR^B$,
(ix) $=NR^{A2}$,
(x) $-C(=O)NR^CR^D$,
(xi) $-SO_2(NR^ER^F)$,
(xii) $-SO_2(C1-C6 \text{ alkyl})$,
(xiii) $-S(=O)(=NH)(C1-C6 \text{ alkyl})$,
(xiv) $-C(=O)(C1-C6 \text{ alkyl})$,
(xv) $-CO_2(C1-C6 \text{ alkyl})$,
(xvi) 5-6 membered heteroaryl optionally substituted with C1-C6 alkyl,
(xvii) 3-9 membered heterocyclyl optionally substituted with 1 or 2 independently selected $R^G$, and
(xviii) 3-6 membered cycloalkyl optionally substituted with 1 or 2 independently selected $R^G$;

n is 0, 1, or 2;

each $R^A$, $R^{A1}$, $R^B$, $R^{B1}$, $R^C$, $R^{C1}$, $R^D$, $R^{D1}$, $R^E$, and $R^F$ is independently
(i) hydrogen,
(ii) hydroxyl,
(iii) 4-6 membered heterocyclyl,
(iv) C1-C6 haloalkyl,
(v) $-C(=O)(C1-C6 \text{ alkyl})$,
(vi) $-C(=O)O(C1-C6 \text{ alkyl})$,
(vii) $-SO_2(C1-C6 \text{ alkyl})$,
(viii) 3-6 membered cycloalkyl optionally substituted with hydroxyl, or
(ix) C1-C6 alkyl optionally substituted with 1-2 substituents independently selected from hydroxyl, $-C(=O)NR^{B2}R^{C2}$, 5-6 membered heteroaryl, 3-6 membered cycloalkyl, $-SO_2(C1-C6 \text{ alkyl})$, $-CO_2H$, and $-SO_2(NH_2)$; or $R^C$ and $R^D$, together with the nitrogen atom to which they are attached form a 4-10 membered heterocyclyl optionally substituted with 1-2 substituents independently selected from hydroxyl, halogen, $-C(=O)NR^{B1}R^{C1}$, $-SO_2(C1-C6 \text{ alkyl})$, $-CO_2H$, C1-C6 alkyl optionally substituted with hydroxyl, C1-C6 alkoxy, and C1-C6 haloalkoxy;

each $R^{A2}$, $R^{B2}$, and $R^{C2}$ is independently hydrogen or C1-C6 alkyl;

each $R^G$ is independently selected from the group consisting of: fluoro, cyano, hydroxyl, C1-C6 alkyl optionally substituted with hydroxyl, C1-C6 alkoxy, $-NR^{A1}R^{B1}$, $=NR^{A2}$, $-C(=O)NR^{C1}R^{D1}$, $-CO_2$(C1-C6 alkyl), C1-C6 haloalkyl, C3-C6 cycloalkyl, C1-C6 haloalkoxy, $-SO_2(C1-C6 \text{ alkyl})$, and $-CO_2H$; and wherein the compound is not a compound selected from the group consisting of:

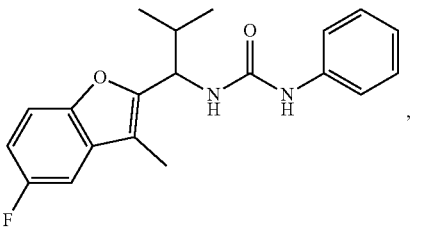

,

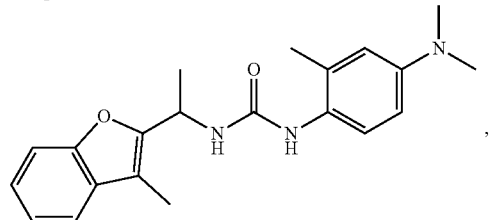

,

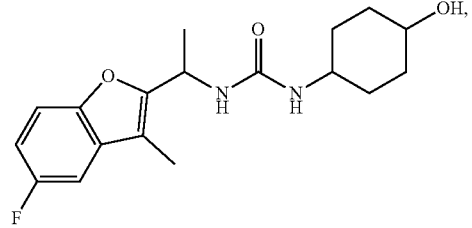

,

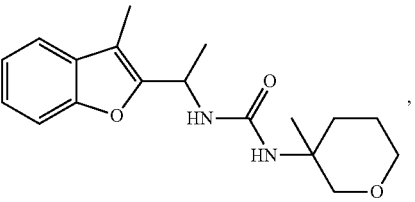

,

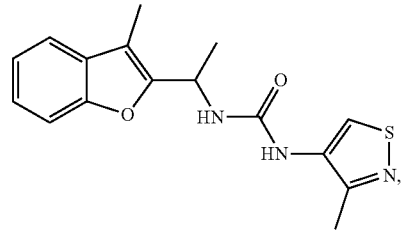

,

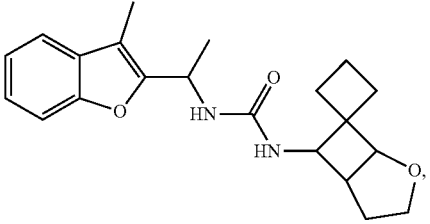

,

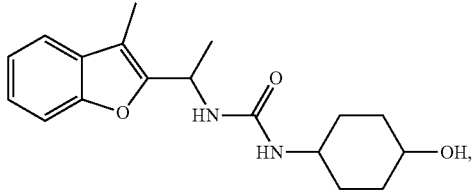

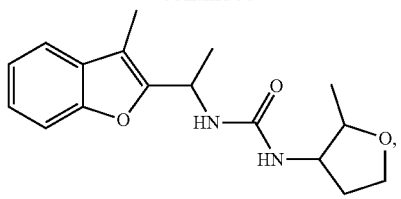
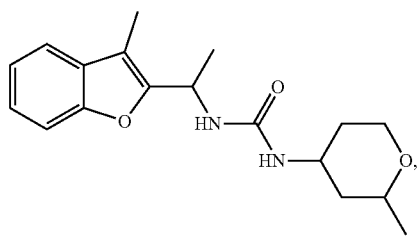
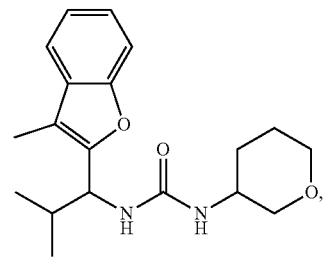
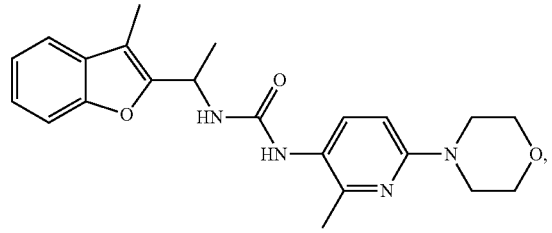
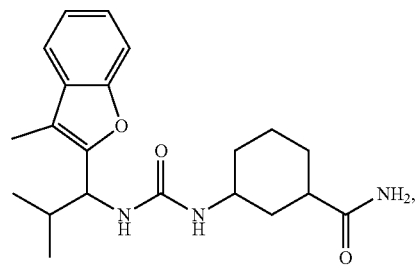
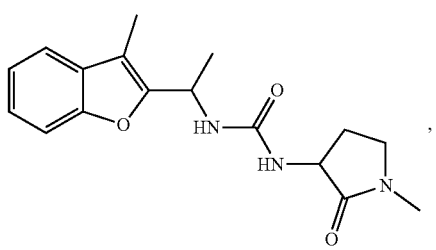
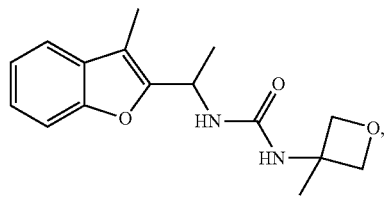
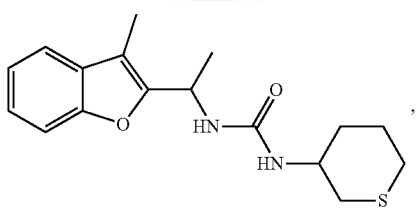
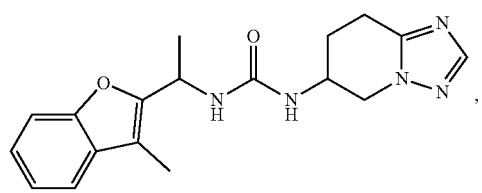
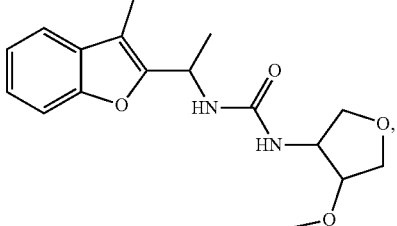
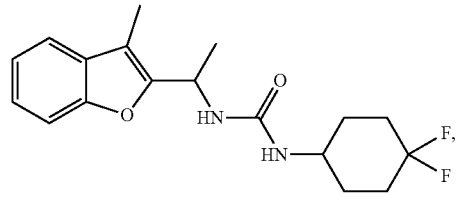
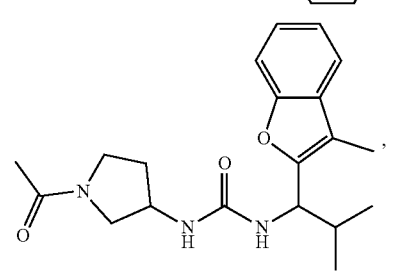
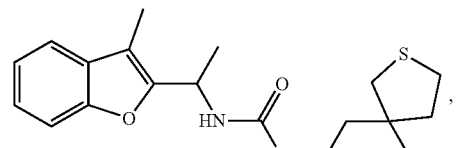
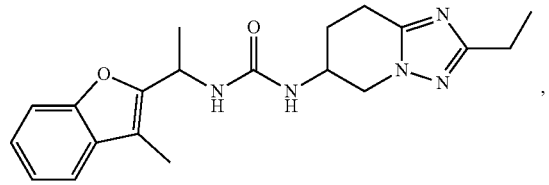
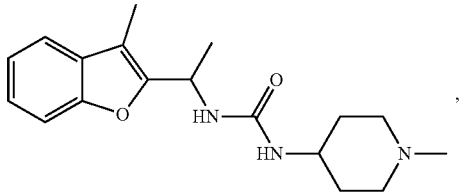

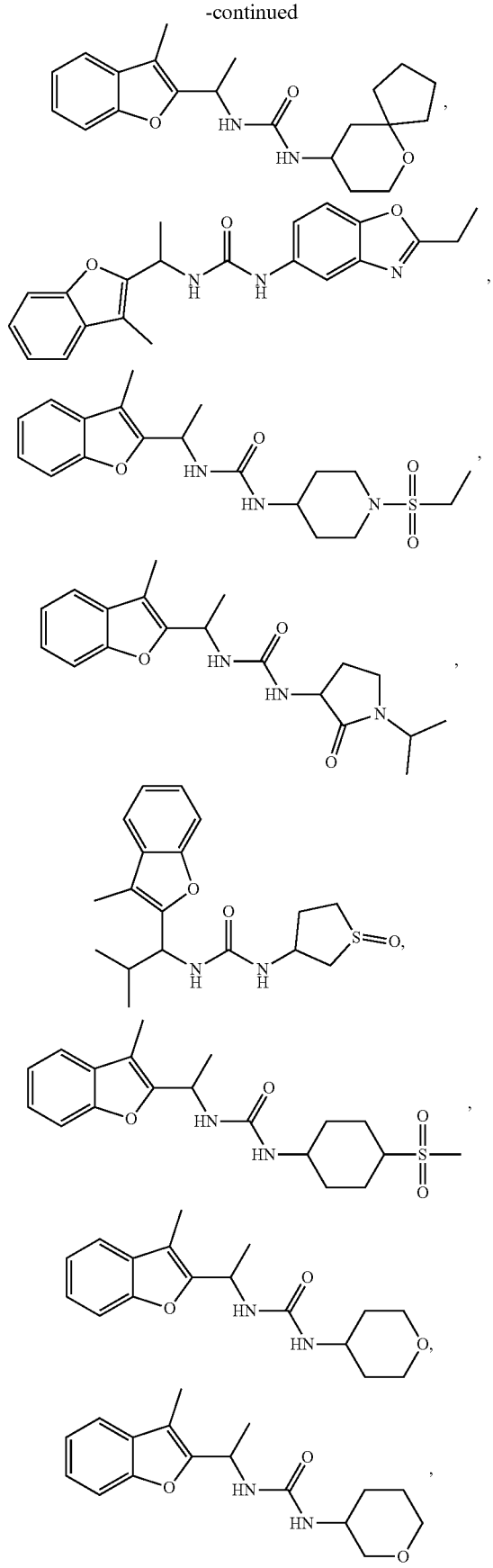
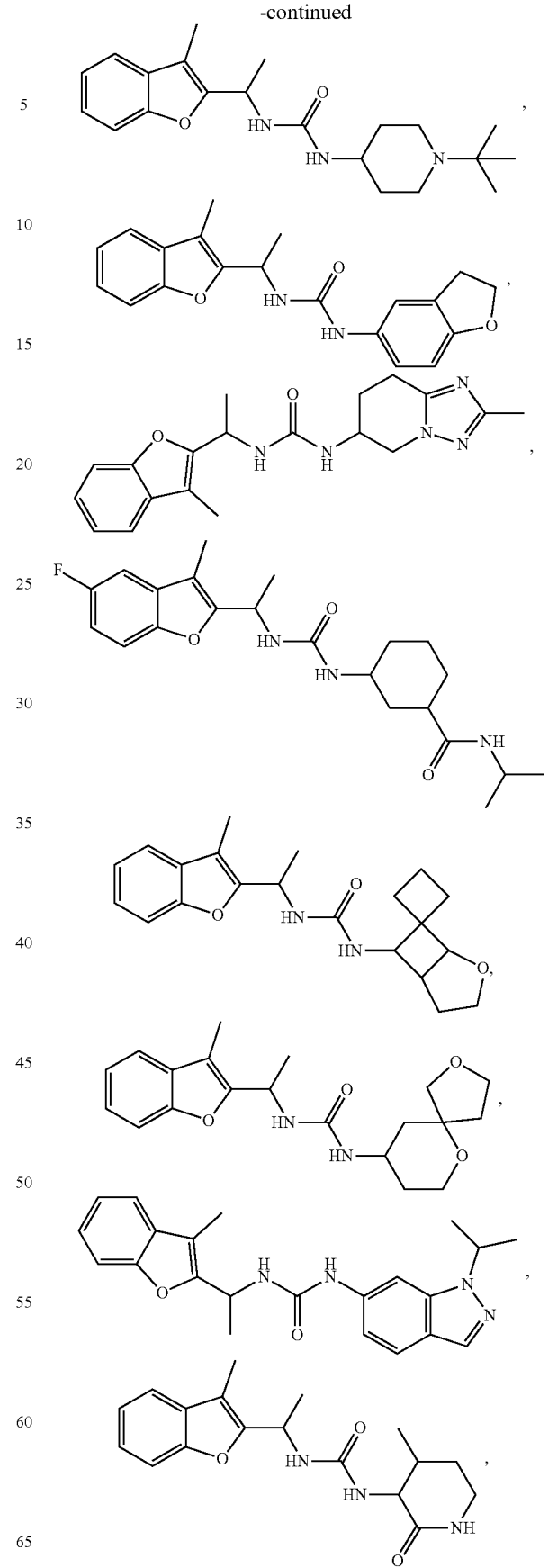

-continued
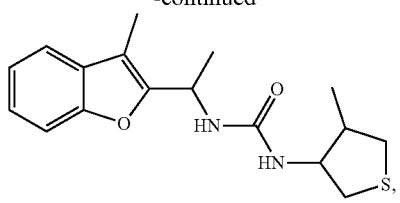
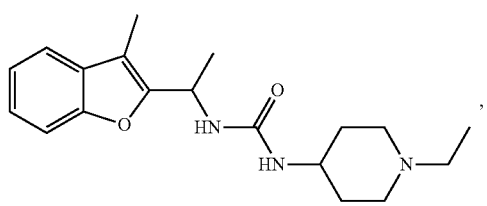
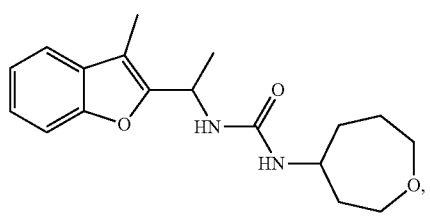
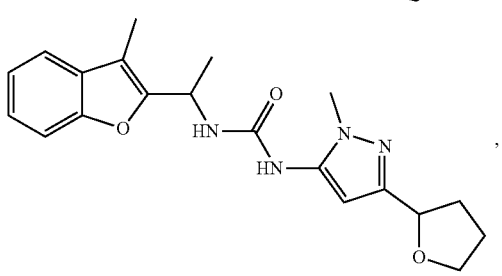
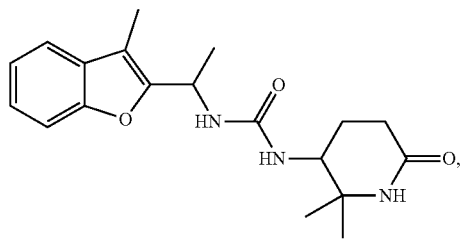
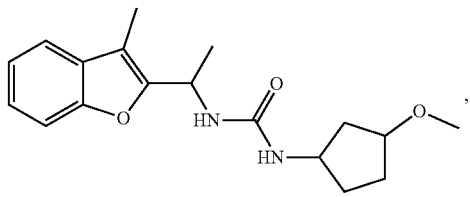
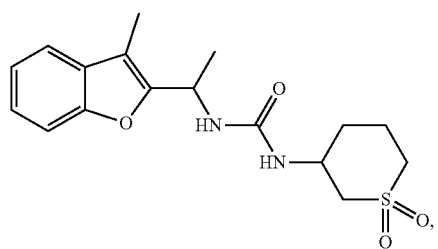
-continued
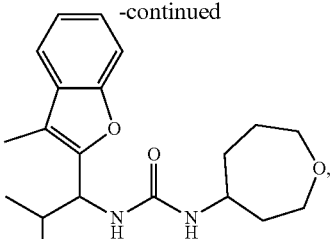
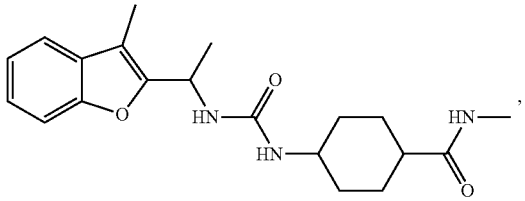
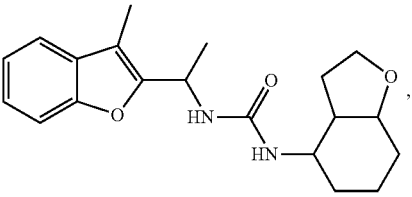
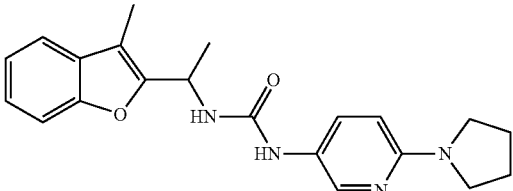
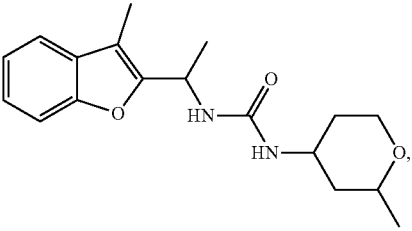
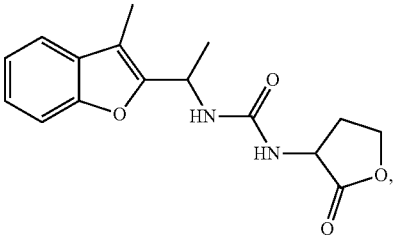
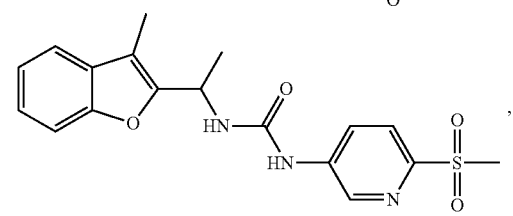
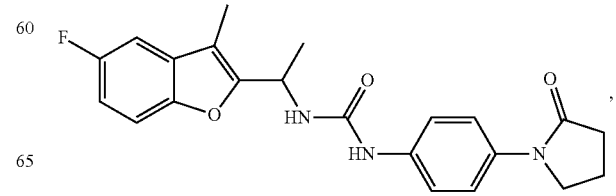

-continued
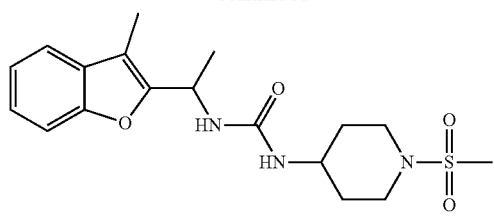
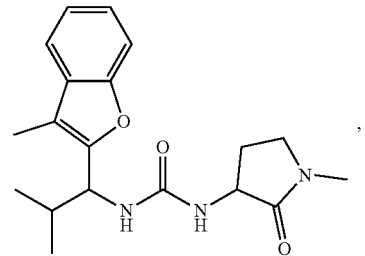
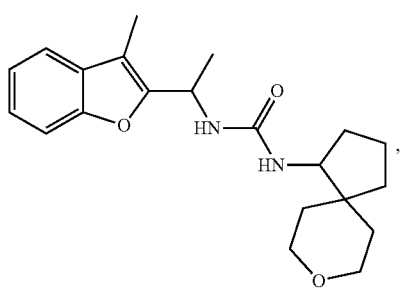
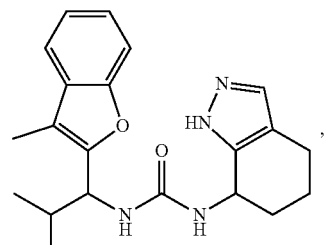
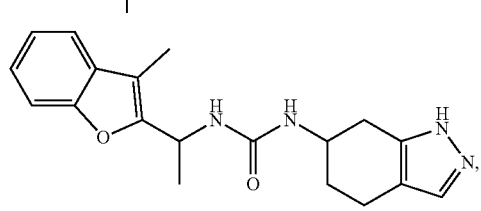
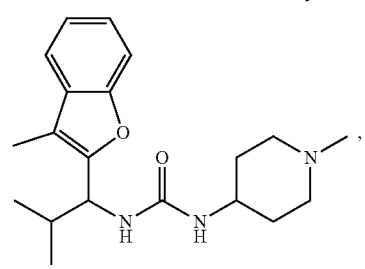
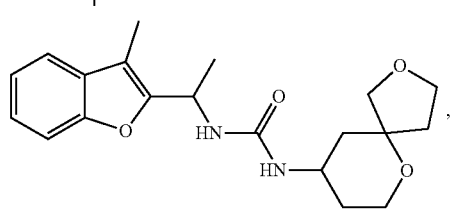
-continued
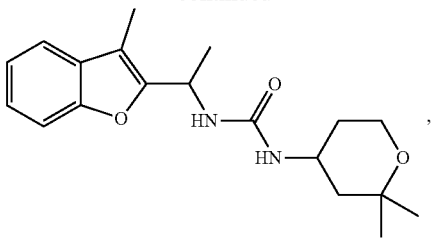
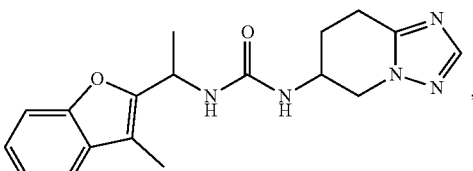
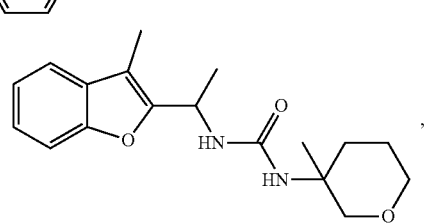
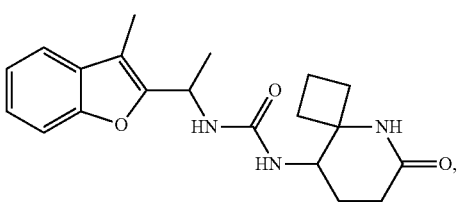
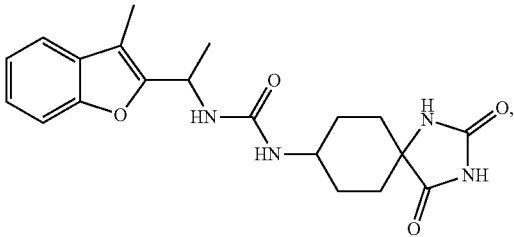
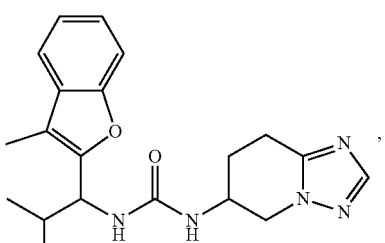
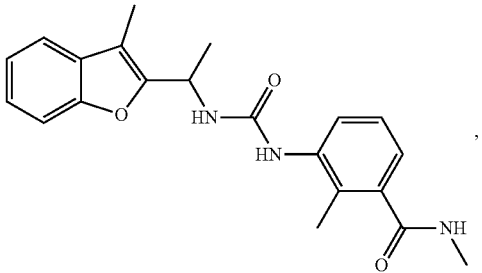

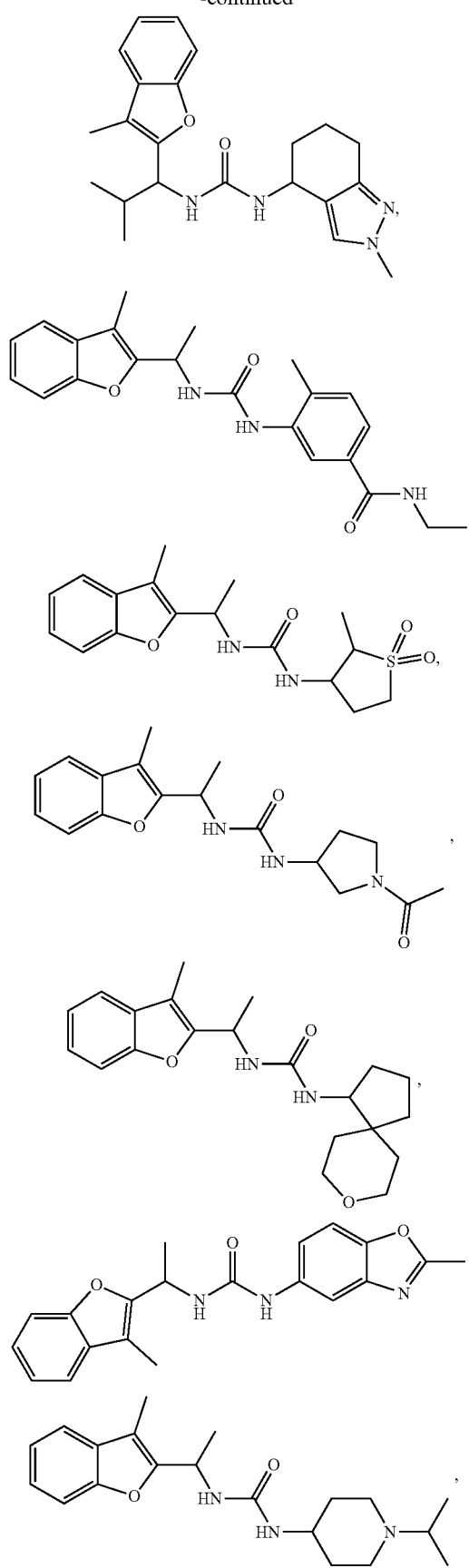
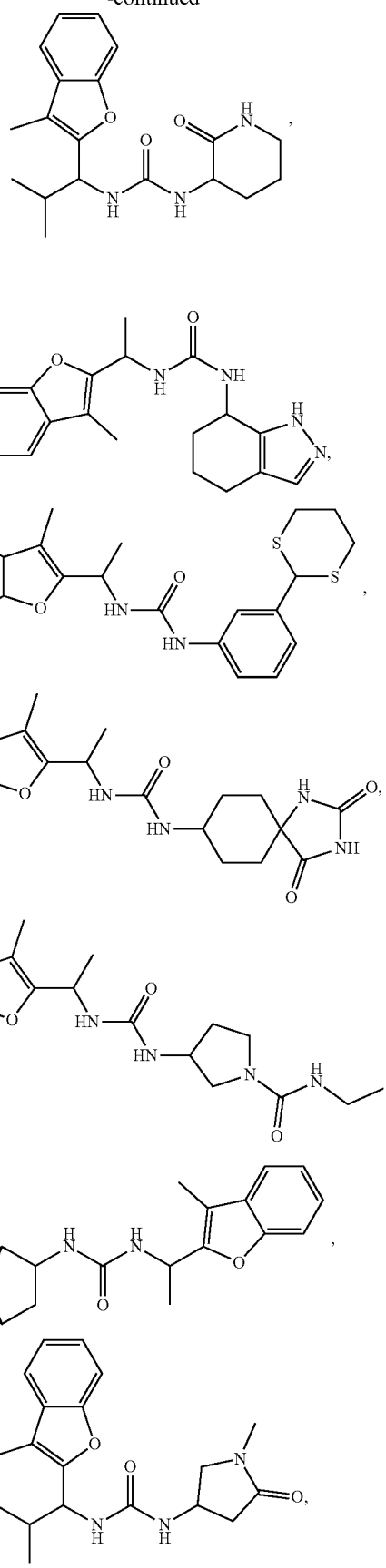

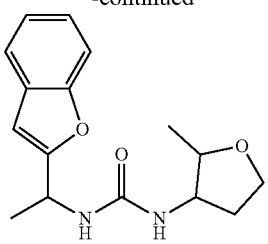, 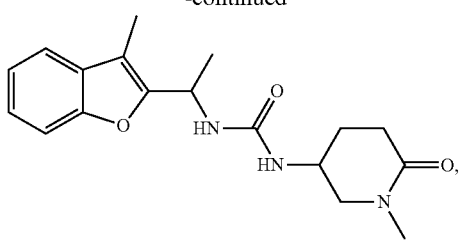
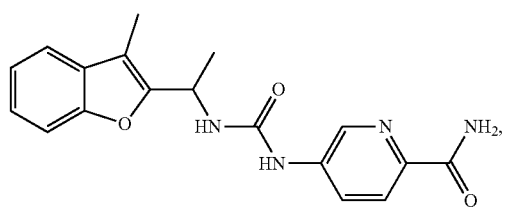, 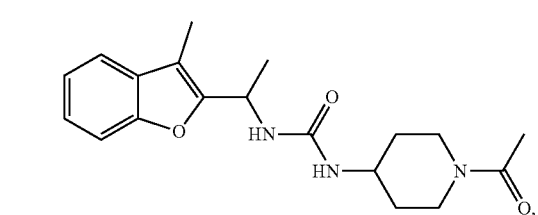
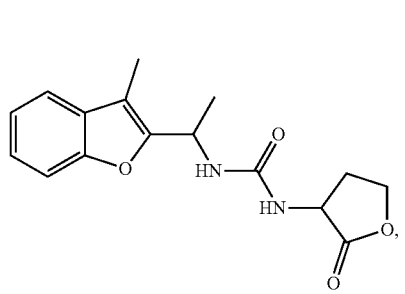, 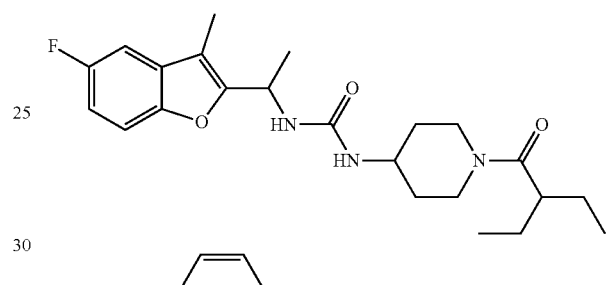
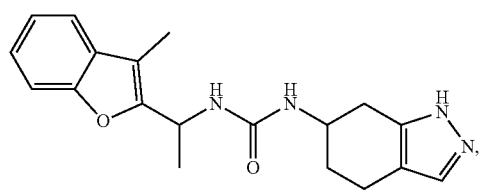, 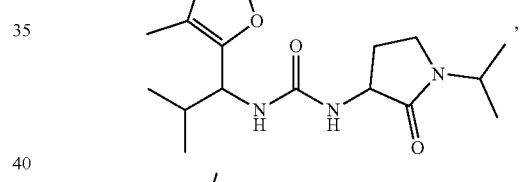
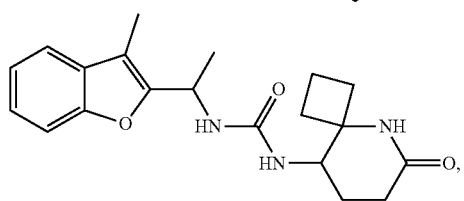, 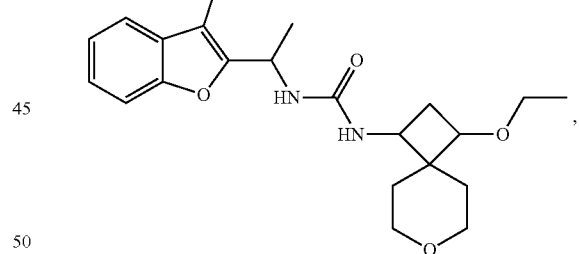
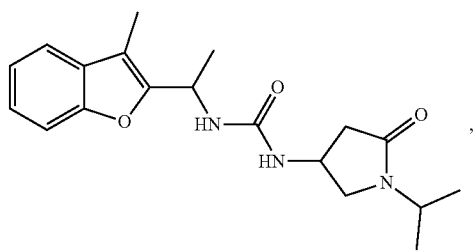, 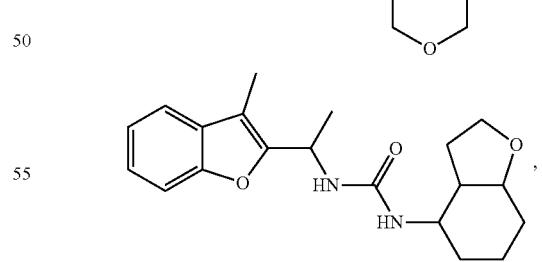
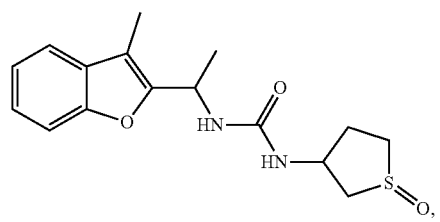, 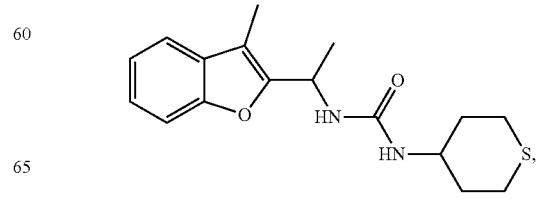

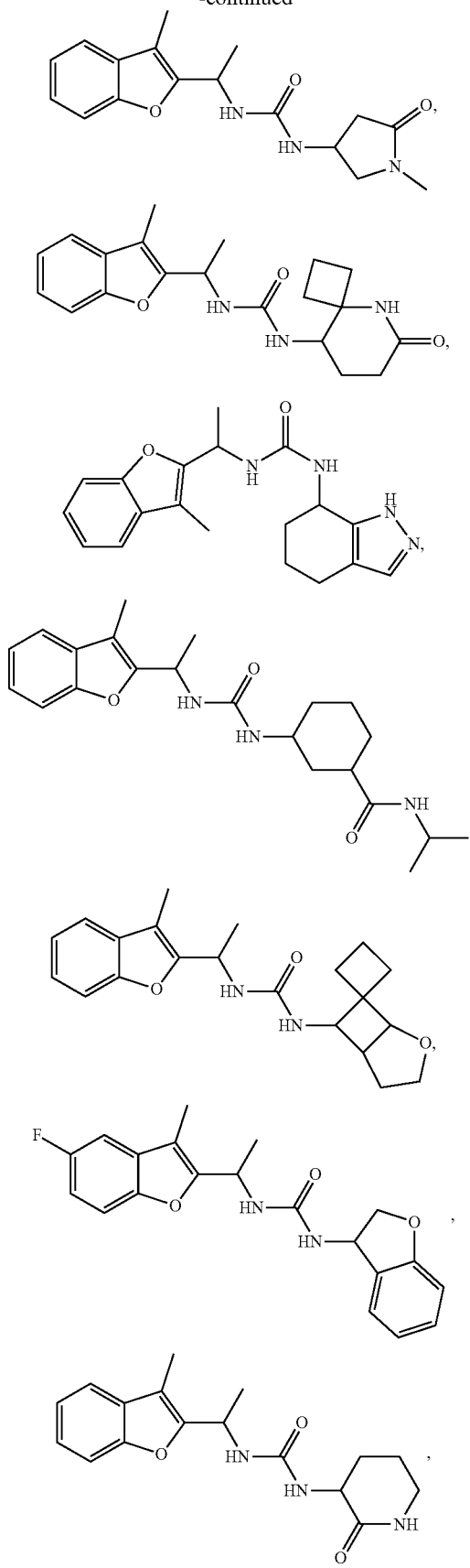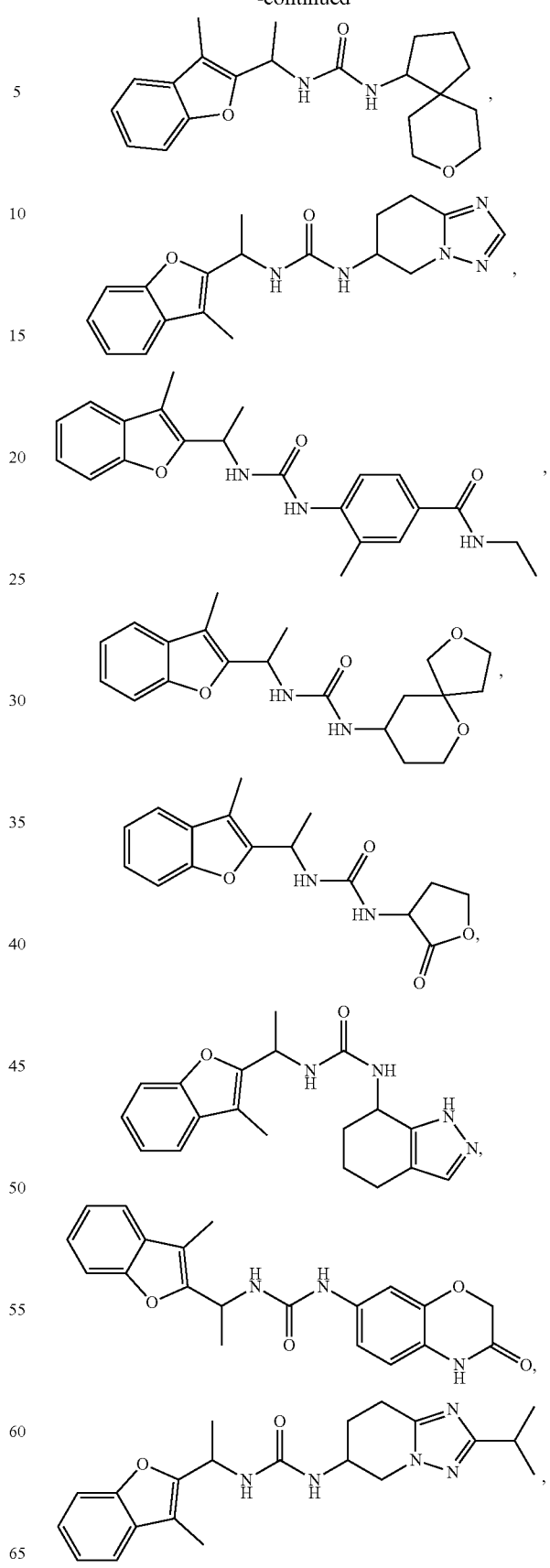

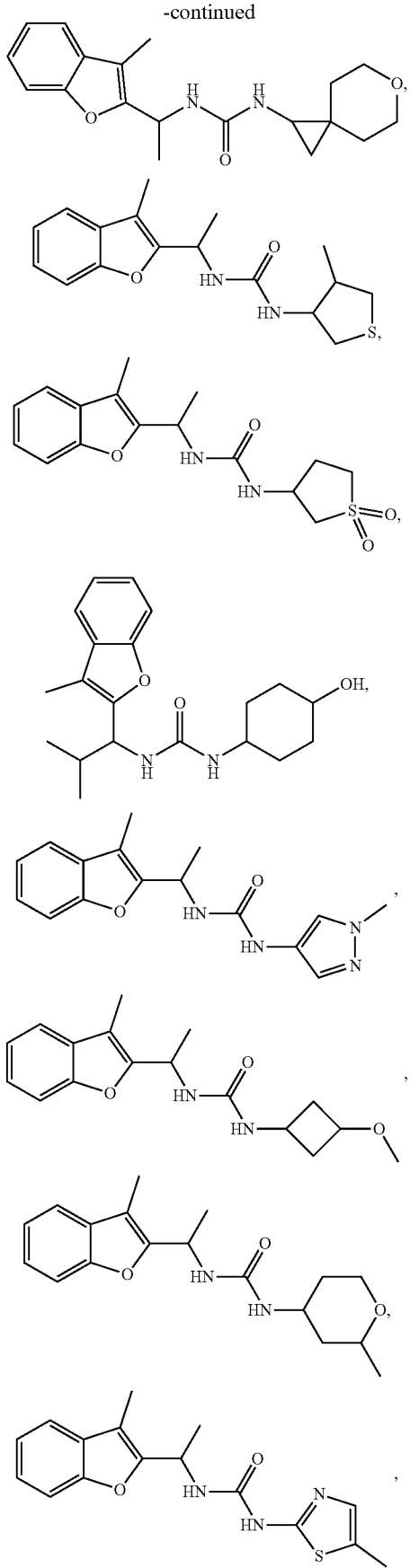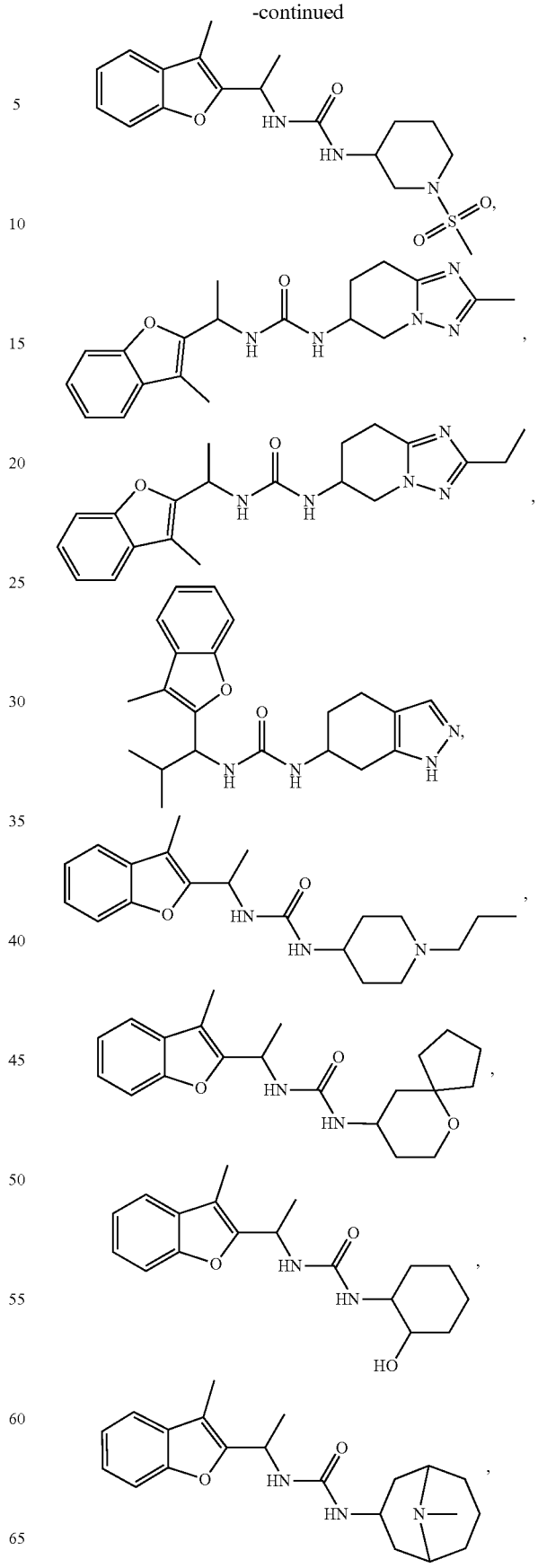

-continued
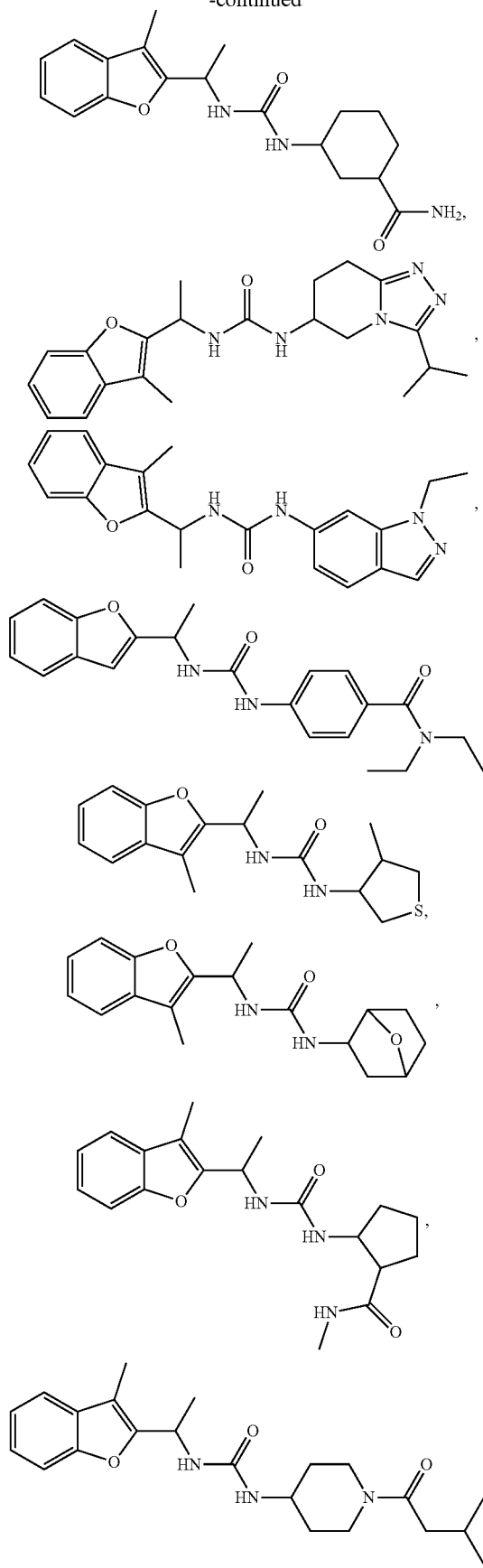
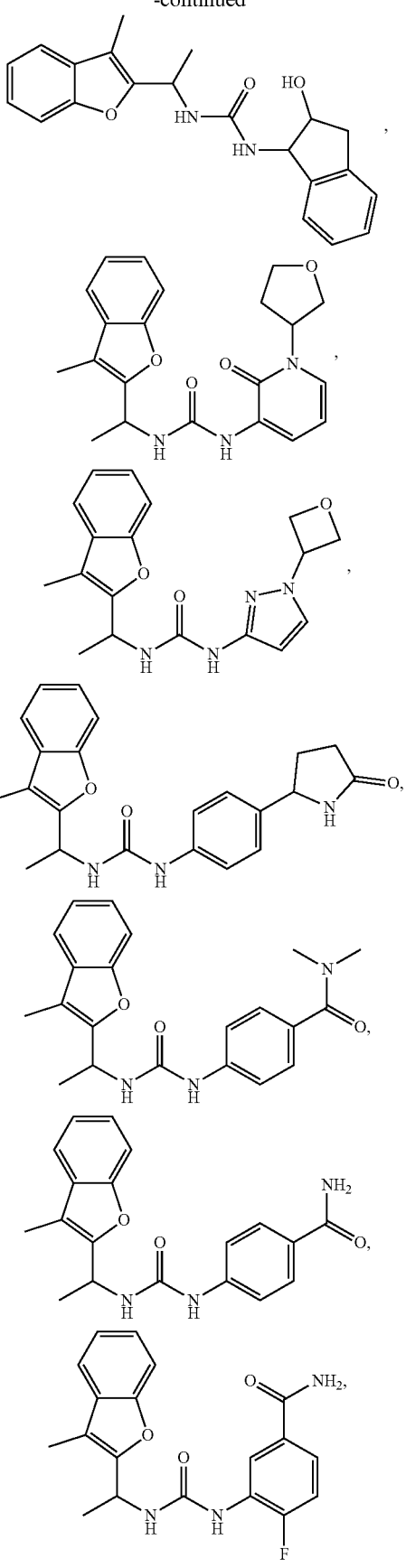

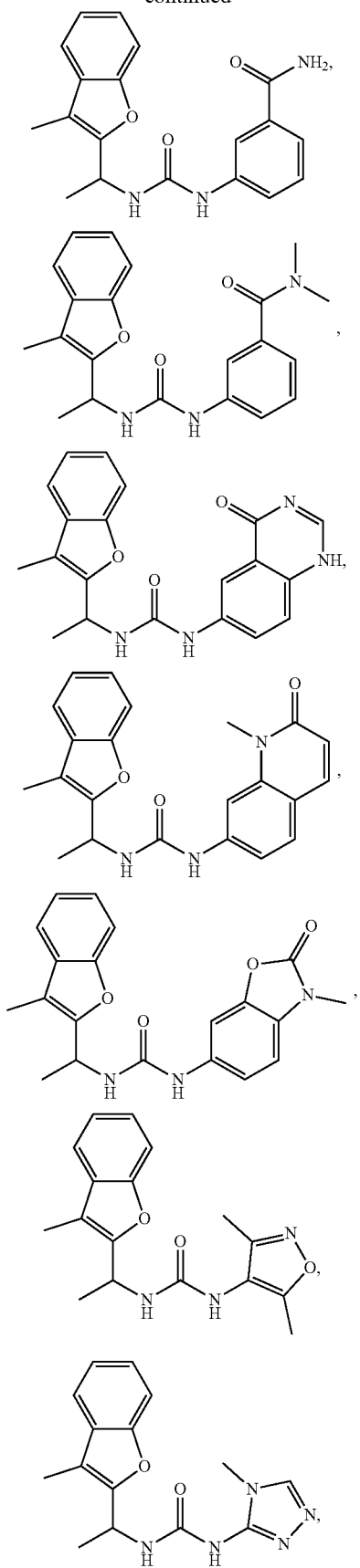

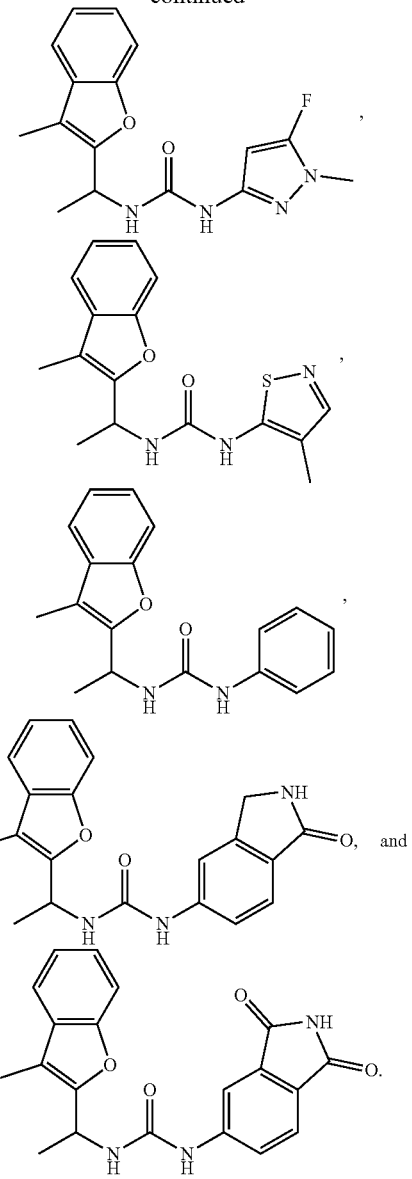

Some embodiments provide a compound of Formula (I):

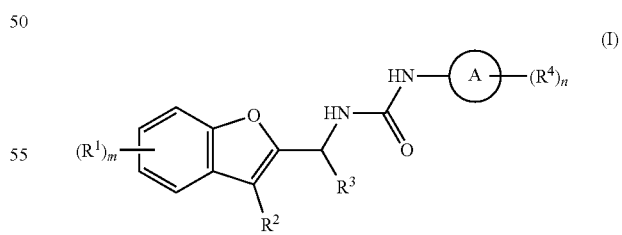

or a pharmaceutically acceptable salt thereof, wherein:
each $R^1$ is independently selected from halogen, hydroxyl, cyano, C1-C6 alkyl optionally substituted with hydroxyl, and C3-C6 cycloalkyl;
m is 0, 1, 2, or 3;
$R^2$ is halogen, hydroxyl, C1-C6 alkyl optionally substituted with hydroxyl, C1-C6 haloalkyl, C3-C6 cycloalkyl optionally substituted with 1 or 2 fluoro;

R³ is a C1-C6 alkyl, a C1-C6 haloalkyl, or a C3-C6 cycloalkyl optionally substituted with 1 or 2 substituents independently selected from fluoro and C1-C6 alkyl;

Ring A is a 6-10 membered aryl, a C3-C8 cycloalkyl, a 5-10 membered heteroaryl, or a 4-10 membered heterocyclyl;

each R⁴ is independently selected from the group consisting of:
(i) halogen,
(ii) C1-C6 alkyl optionally substituted with 1 or 2 hydroxyl or —NR^A R^B,
(iii) C1-C6 alkoxy optionally substituted with 1-2 substituents independently selected from hydroxyl and C3-C6 cycloalkyl,
(iv) C1-C6 haloalkyl,
(v) hydroxyl,
(vi) cyano,
(vii) —CO₂H,
(viii) —NR^A R^B,
(ix) =NR^{A2},
(x) —C(=O)NR^C R^D,
(xi) —SO₂(NR^E R^F),
(xii) —SO₂(C1-C6 alkyl),
(xiii) —S(=O)(=NH)(C1-C6 alkyl),
(xiv) —C(=O)(C1-C6 alkyl),
(xv) —CO₂(C1-C6 alkyl),
(xvi) 5-6 membered heteroaryl optionally substituted with C1-C6 alkyl,
(xvii) 3-9 membered heterocyclyl optionally substituted with 1 or 2 independently selected R^G, and
(xviii) 3-6 membered cycloalkyl optionally substituted with 1 or 2 independently selected R^G;

n is 0, 1, or 2;

each R^A, R^{A1}, R^B, R^{B1}, R^C, R^{C1}, R^D, R^{D1}, R^E, and R^F is independently
(i) hydrogen,
(ii) hydroxyl,
(iii) 4-6 membered heterocyclyl,
(iv) C1-C6 haloalkyl,
(v) —C(=O)(C1-C6 alkyl),
(vi) —C(=O)O(C1-C6 alkyl),
(vii) —SO₂(C1-C6 alkyl),
(viii) 3-6 membered cycloalkyl optionally substituted with hydroxyl, or
(ix) C1-C6 alkyl optionally substituted with 1-2 substituents independently selected from hydroxyl, —C(=O)NR^{B2}R^{C2}, 5-6 membered heteroaryl, 3-6 membered cycloalkyl, —SO₂(C1-C6 alkyl), —CO₂H, and —SO₂(NH₂); or R^C and R^D, together with the nitrogen atom to which they are attached form a 4-10 membered heterocyclyl optionally substituted with 1-2 substituents independently selected from hydroxyl, halogen, —C(=O)NR^{B1}R^{C1}, —SO₂(C1-C6 alkyl), —CO₂H, C1-C6 alkyl optionally substituted with hydroxyl, C1-C6 alkoxy, and C1-C6 haloalkoxy;

each R^{A2}, R^{B2}, and R^{C2} is independently hydrogen or C1-C6 alkyl;

each R^G is independently selected from the group consisting of: fluoro, cyano, hydroxyl, C1-C6 alkyl optionally substituted with hydroxyl, C1-C6 alkoxy, —NR^{A1}R^{B1}, =NR^{A2}, —C(=O)NR^{C1}R^{D1}, —CO₂(C1-C6 haloalkyl), C3-C6 cycloalkyl, C1-C6 haloalkoxy, —SO₂(C1-C6 alkyl), and —CO₂H; and wherein the compound is not a compound selected from the group consisting of:

-continued
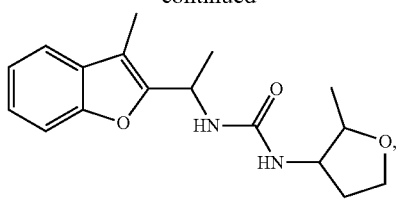
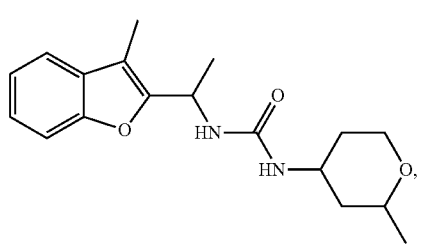
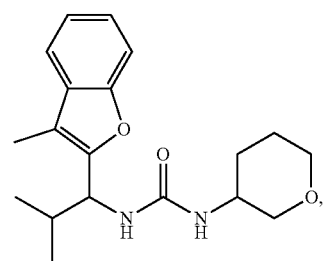
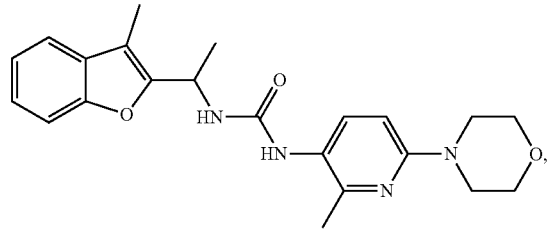
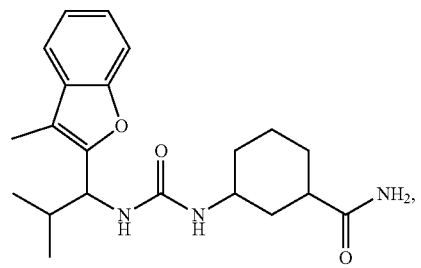
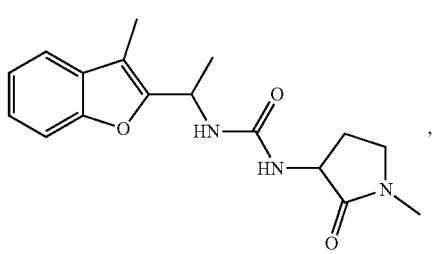
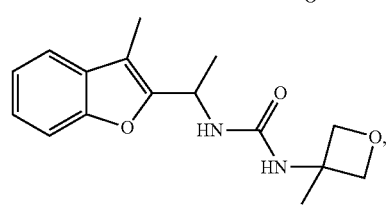
-continued
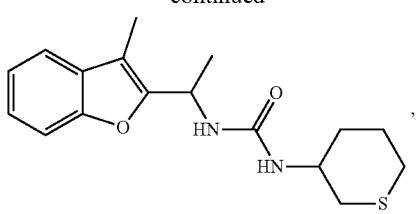
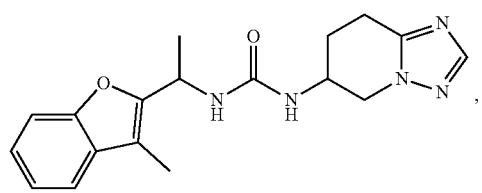
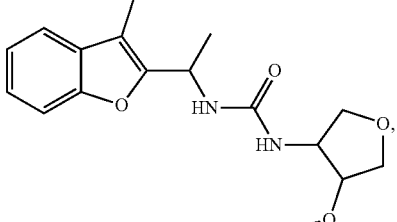
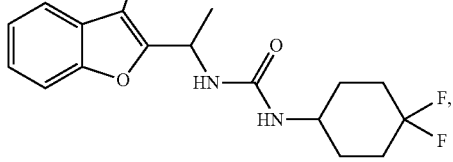
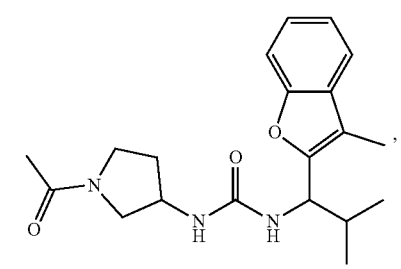
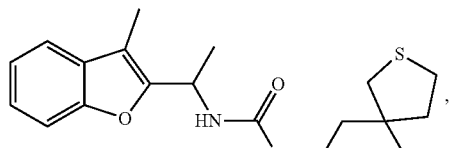
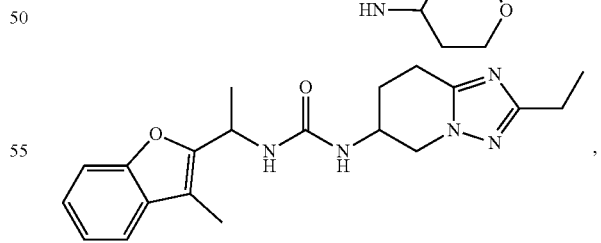
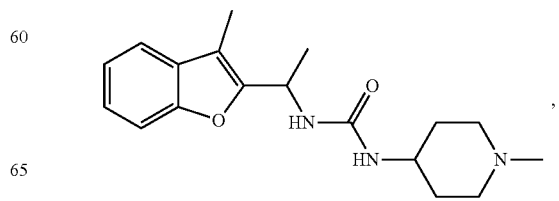

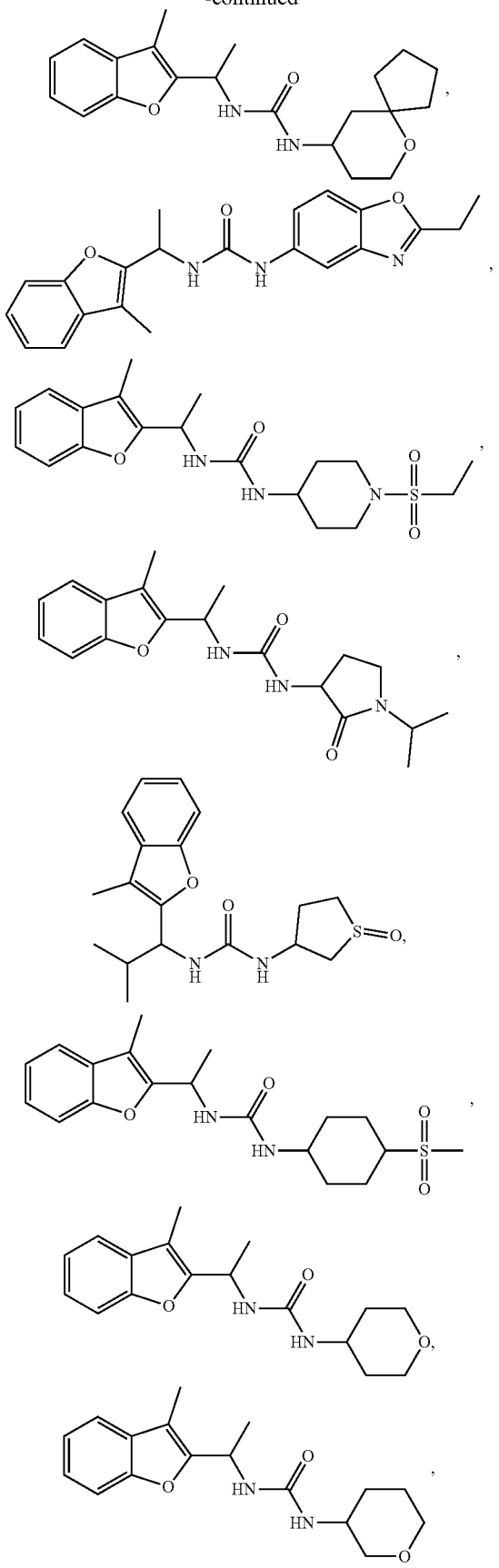
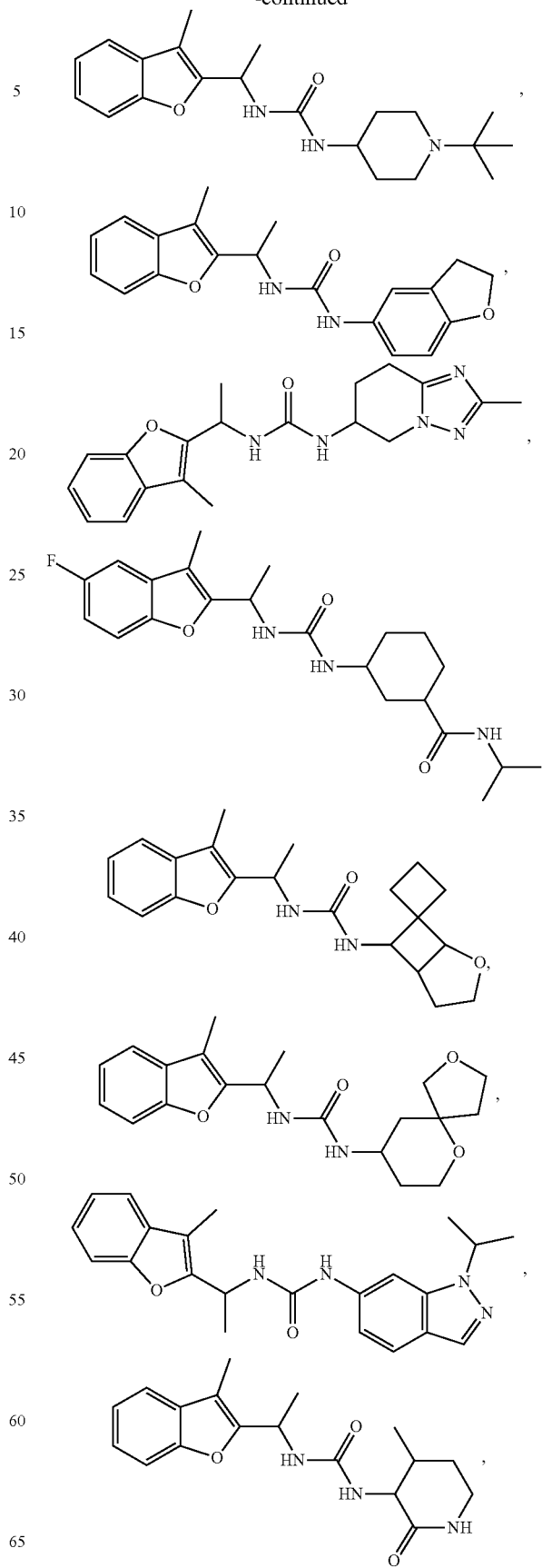

31
-continued
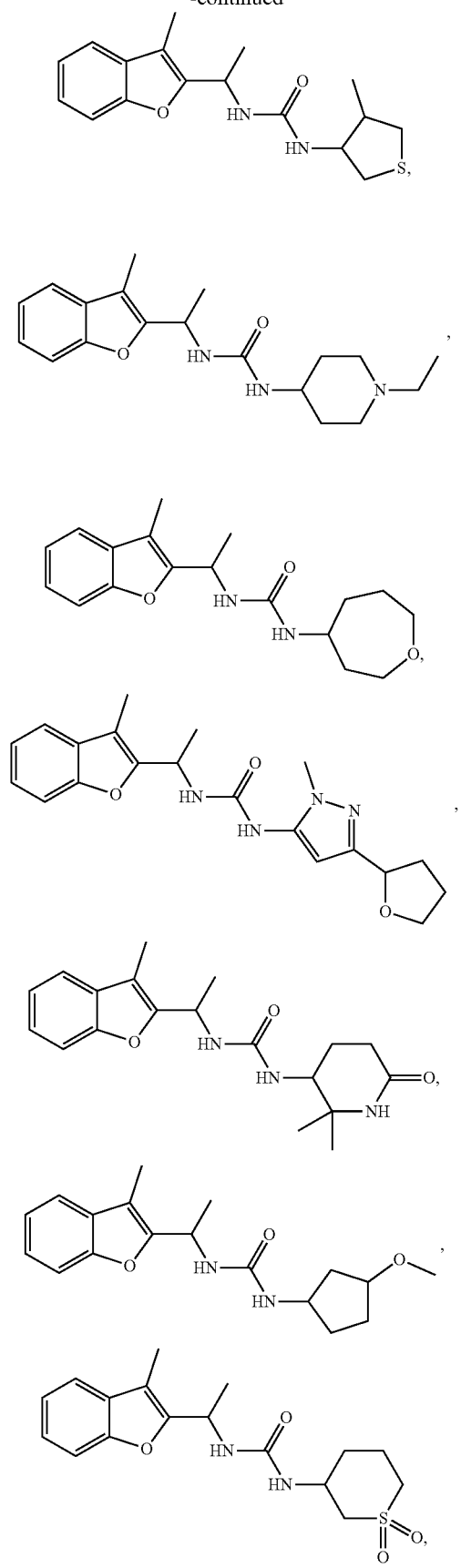
32
-continued
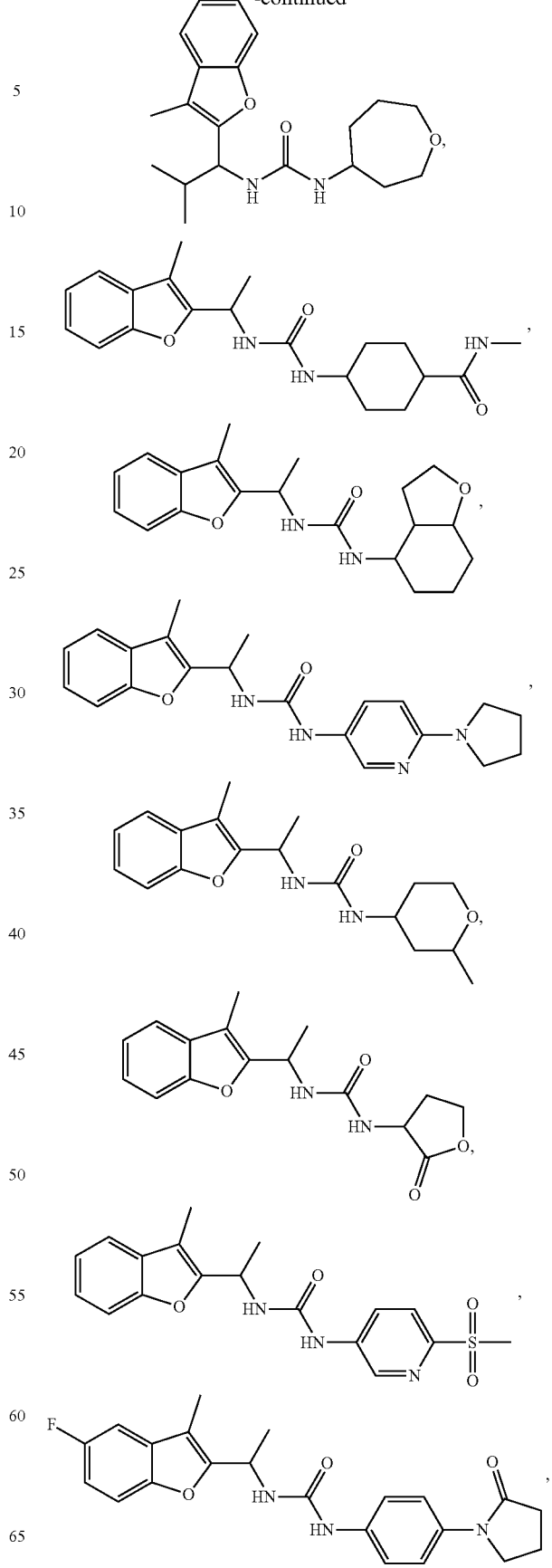

-continued
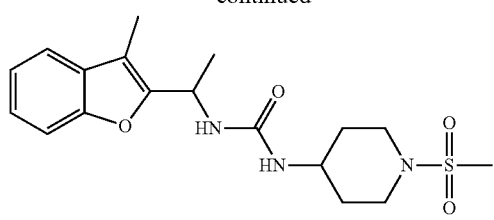
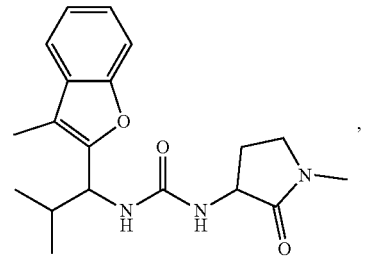
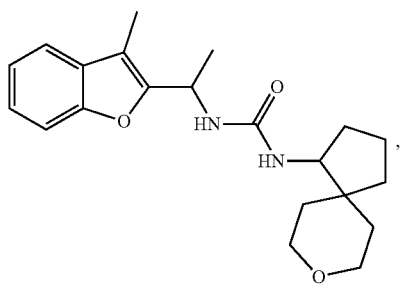
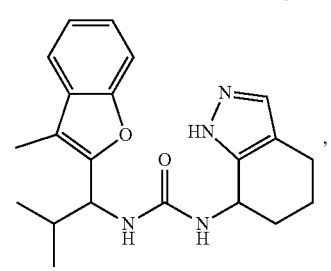
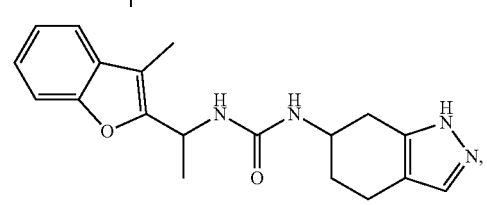
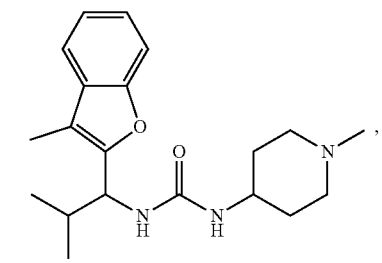
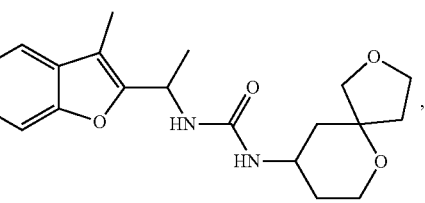
-continued
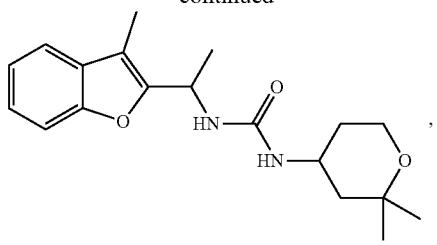
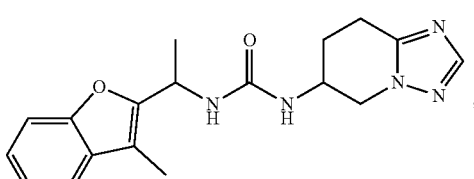
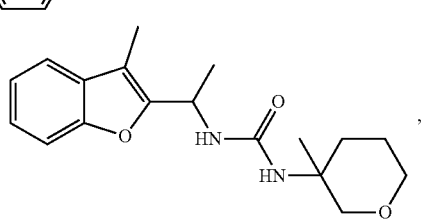
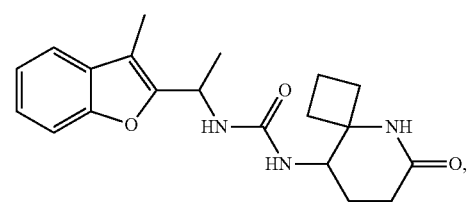
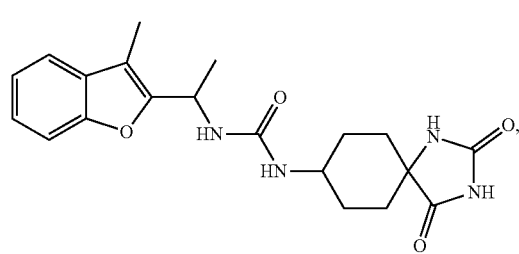
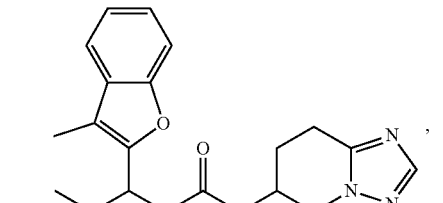
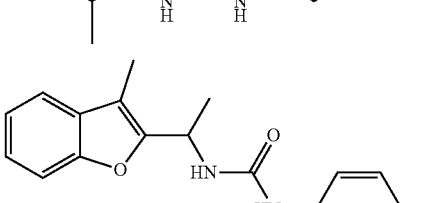

35
-continued
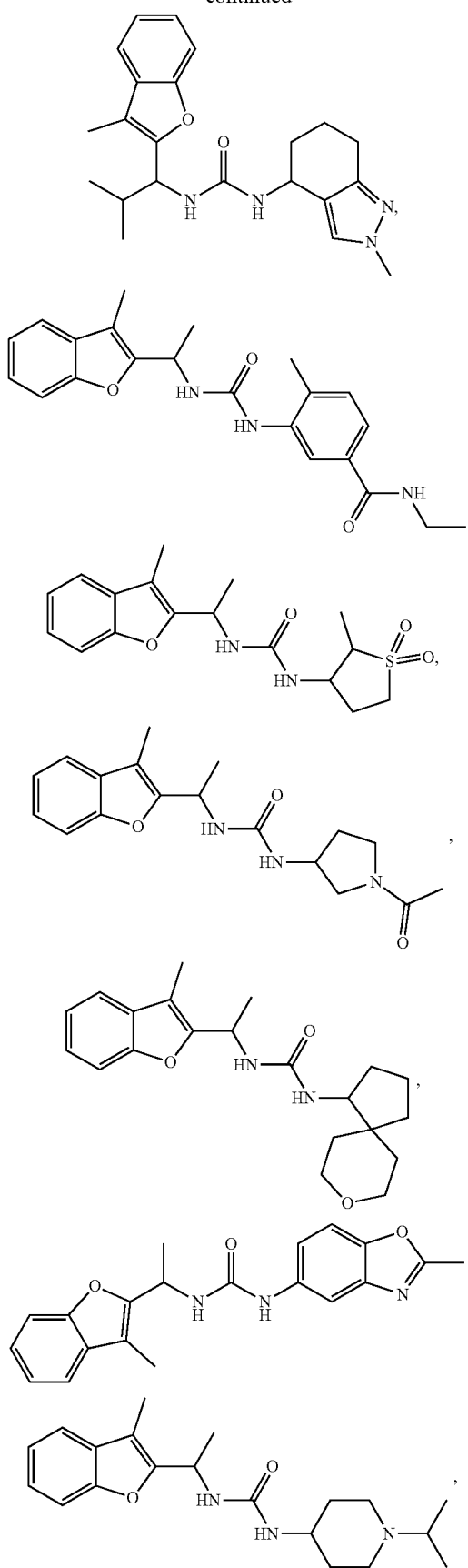
36
-continued
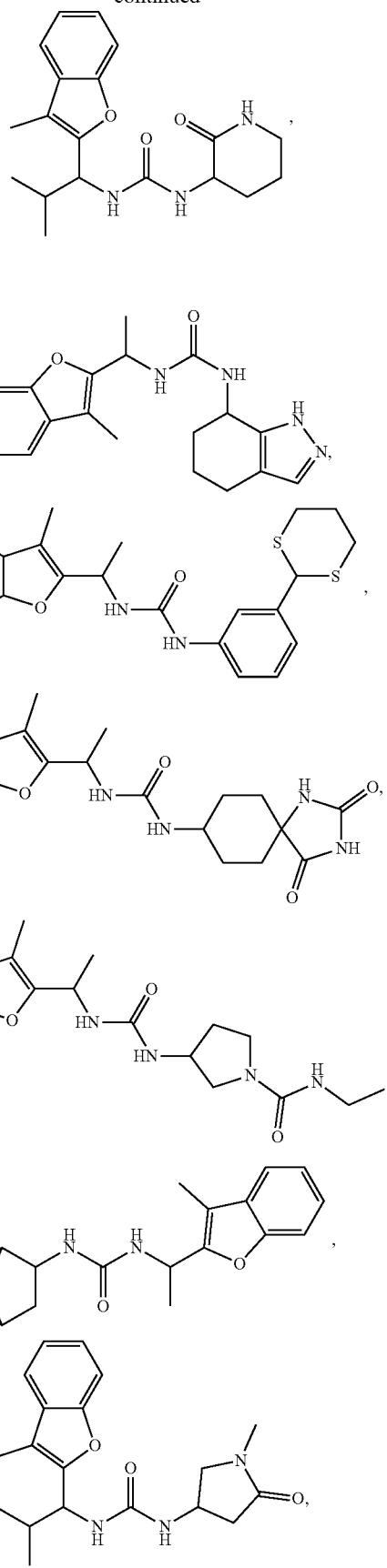

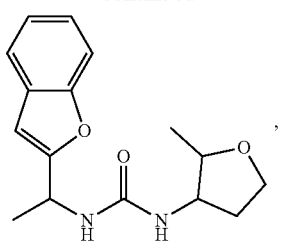
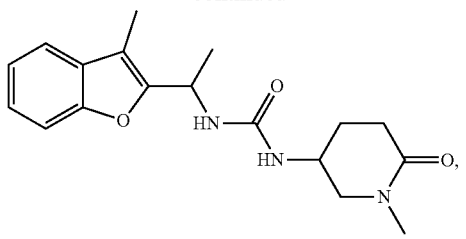
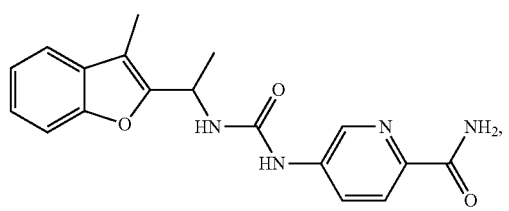
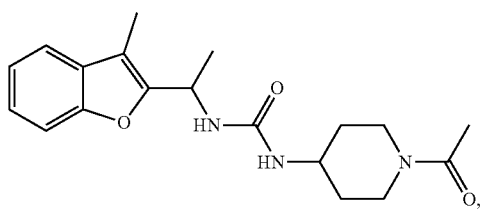
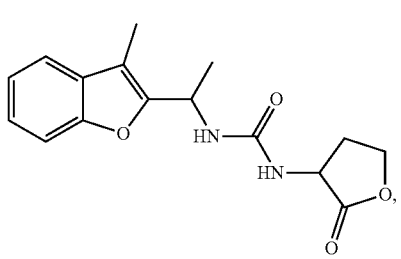
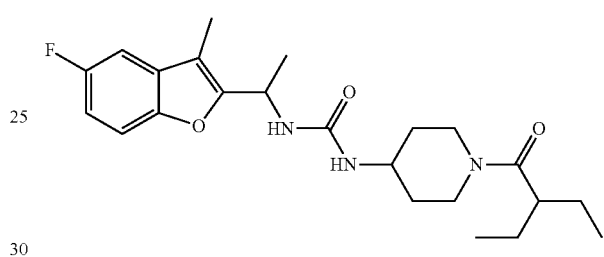
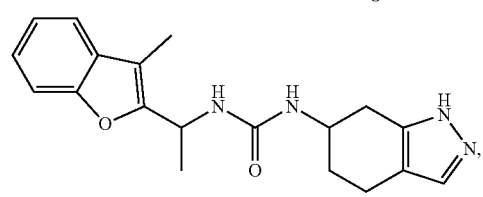
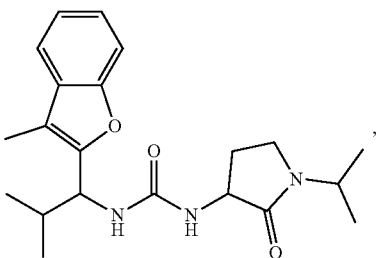
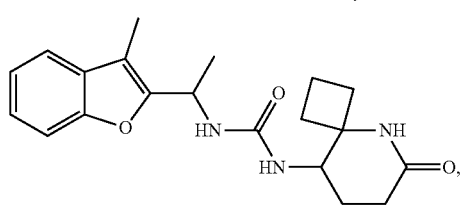
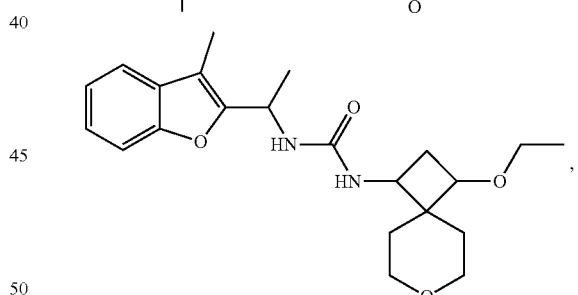
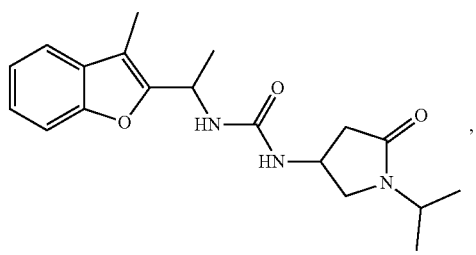
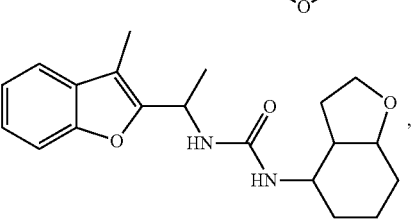
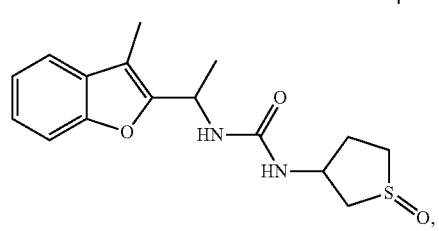
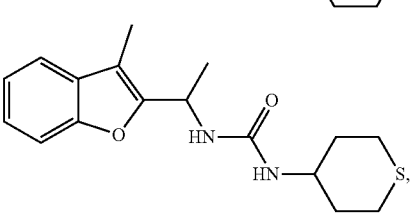

-continued
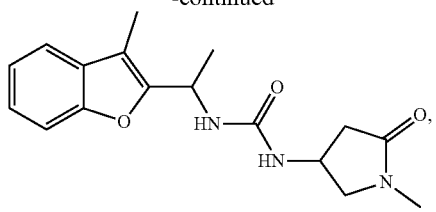
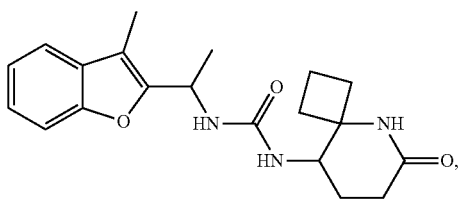
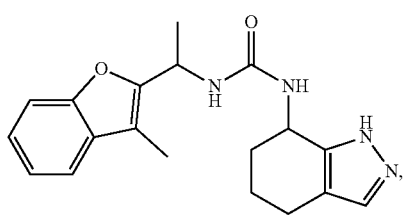
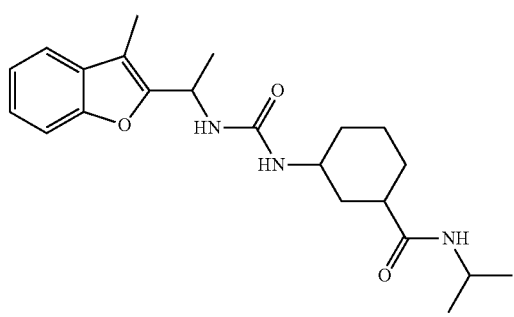
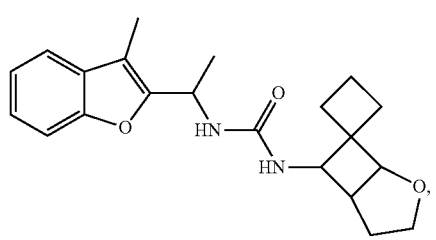
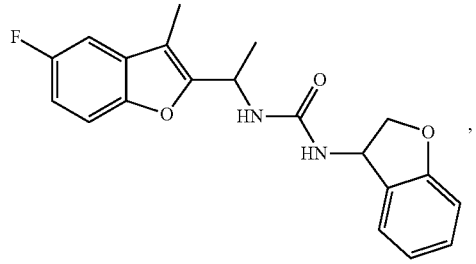
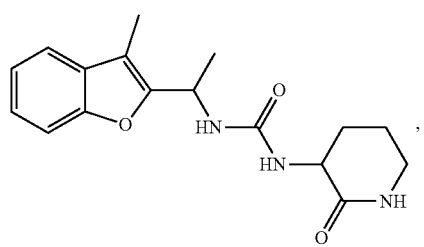
-continued
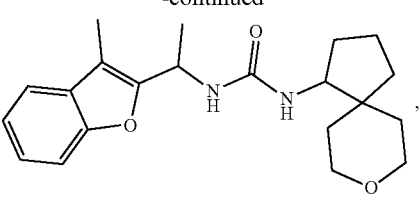
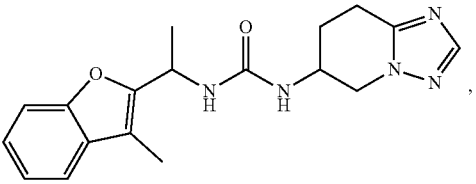
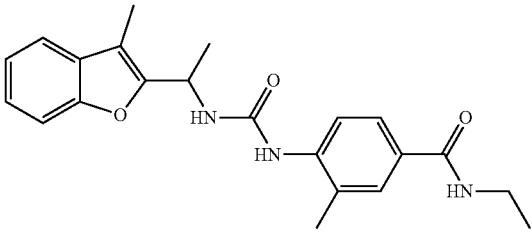
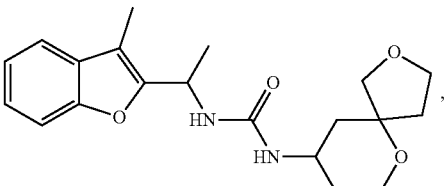
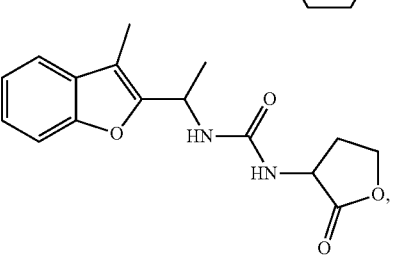
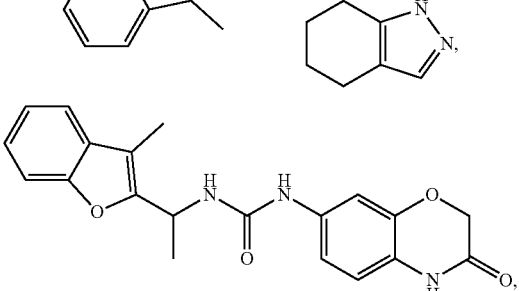
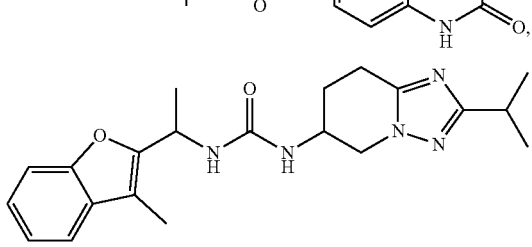

-continued
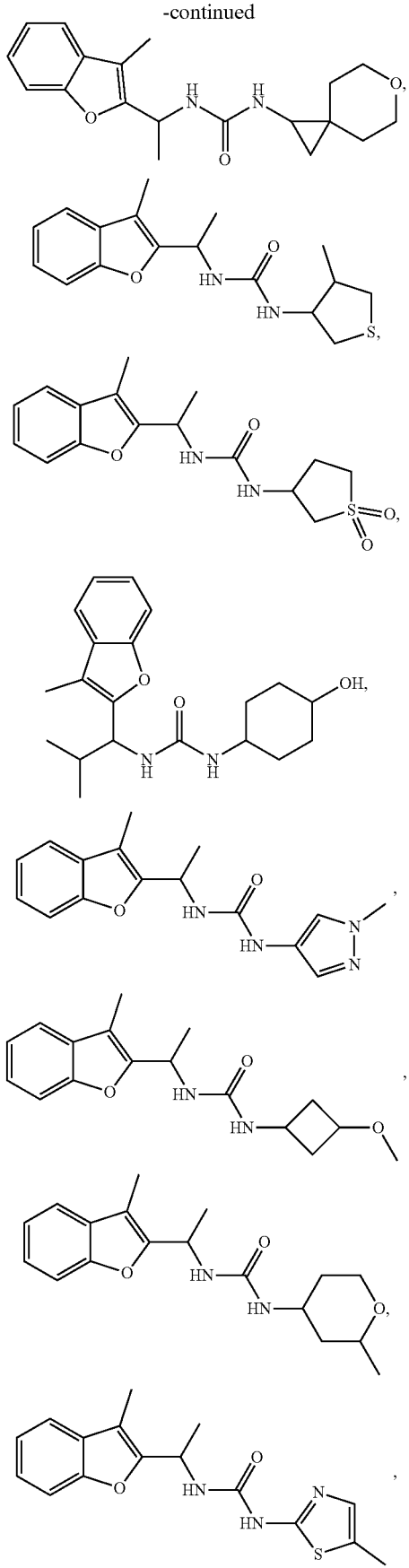
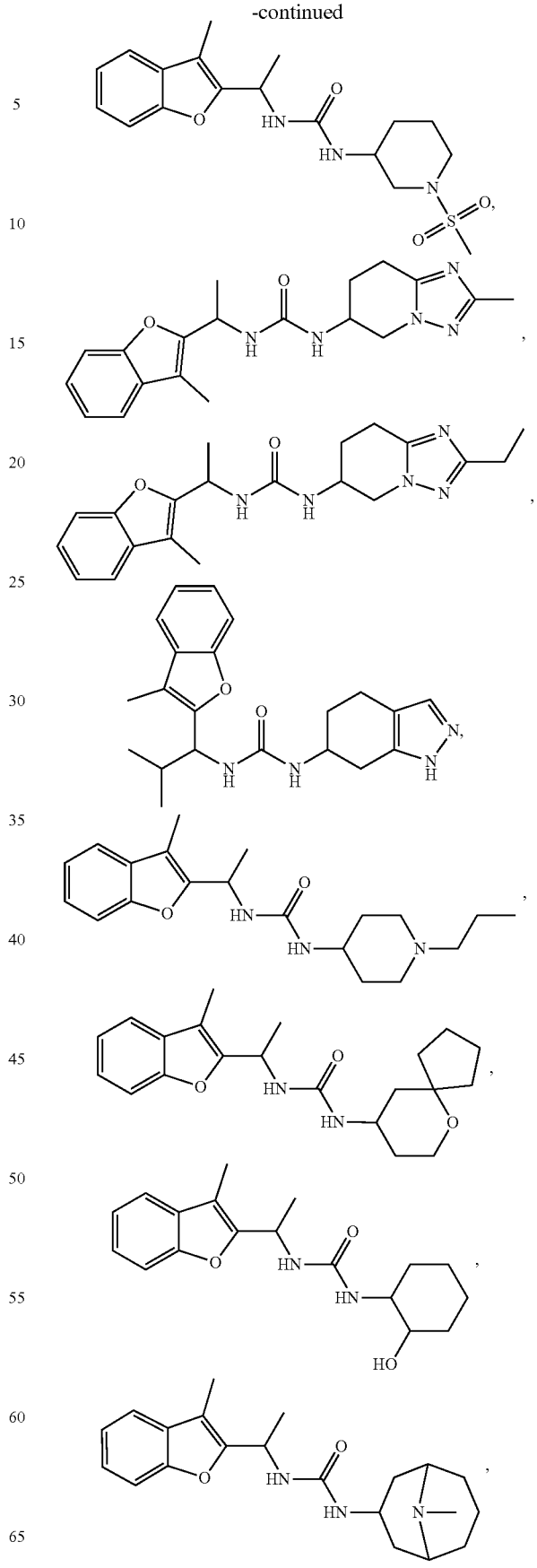

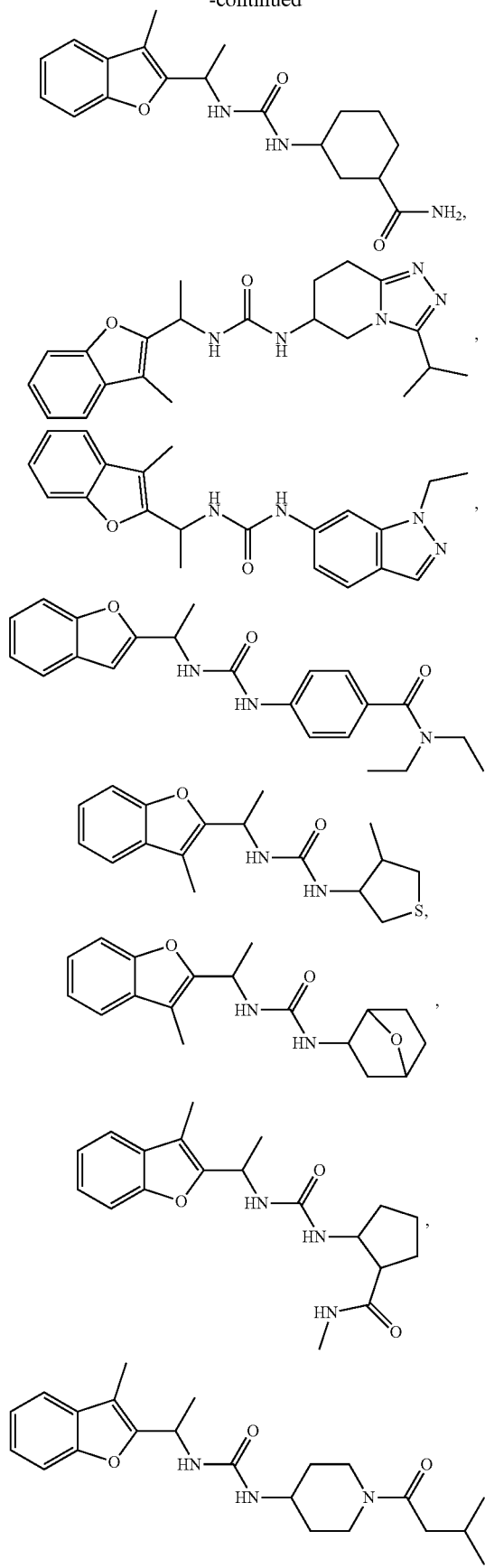
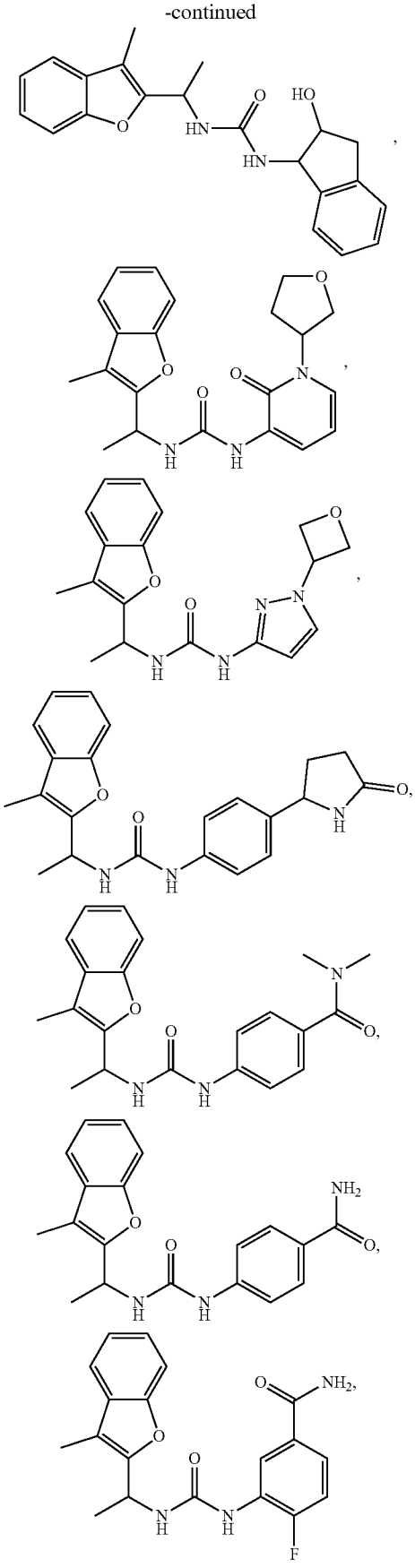

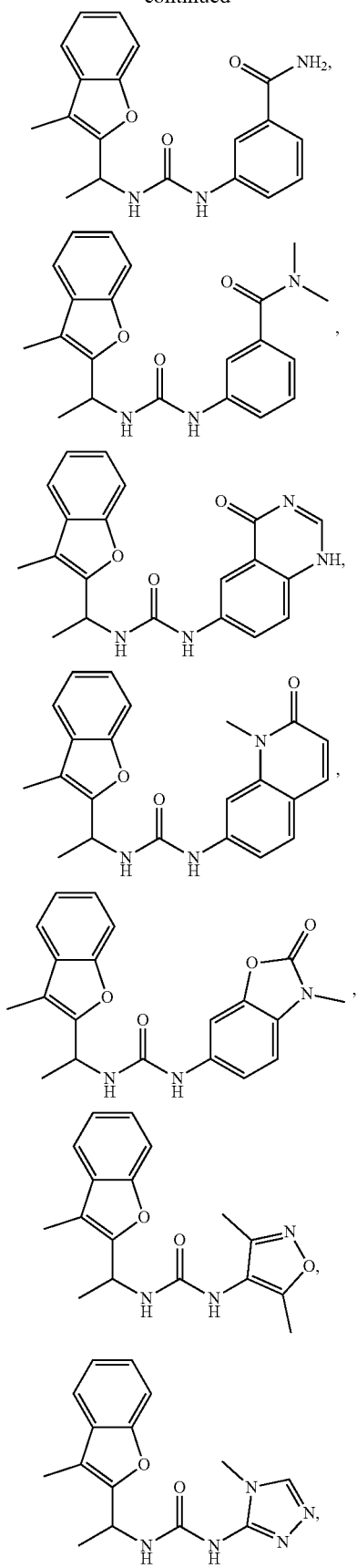

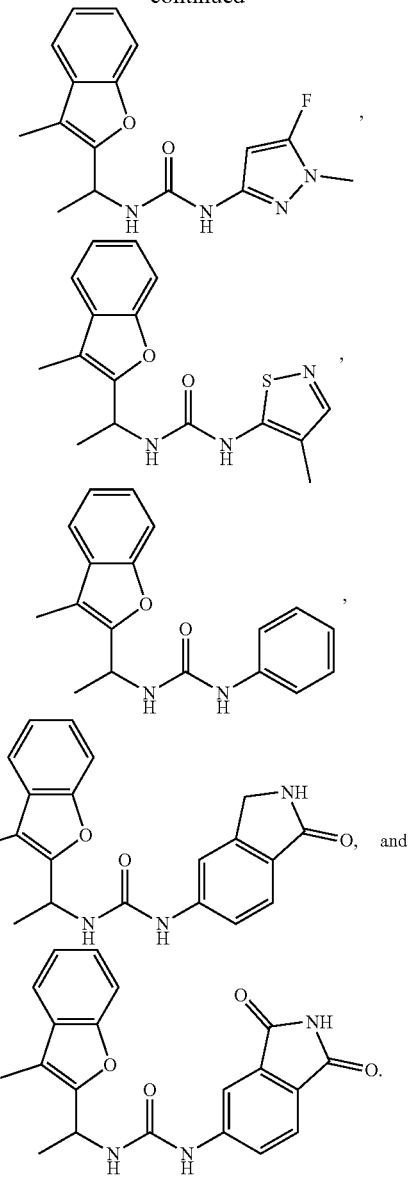

Some embodiments provide a compound of Formula (I):

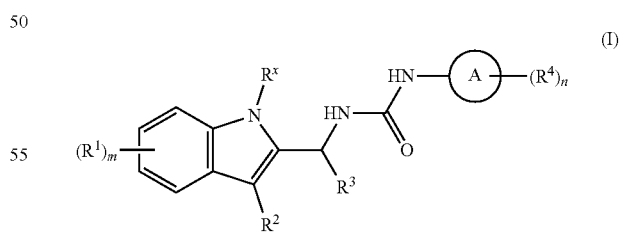

or a pharmaceutically acceptable salt thereof, wherein:
each $R^1$ is independently selected from halogen, hydroxyl, cyano, C1-C6 alkyl optionally substituted with hydroxyl, and C3-C6 cycloalkyl;
m is 0, 1, 2, or 3;
$R^2$ is halogen, hydroxyl, C1-C6 alkyl optionally substituted with hydroxyl, C1-C6 haloalkyl, C3-C6 cycloalkyl optionally substituted with 1 or 2 fluoro;

R³ is a C1-C6 alkyl, a C1-C6 haloalkyl, or a C3-C6 cycloalkyl optionally substituted with 1 or 2 substituents independently selected from fluoro and C1-C6 alkyl;

Ring A is a 6-10 membered aryl, a C3-C8 cycloalkyl, a 5-10 membered heteroaryl, or a 4-10 membered heterocyclyl;

each R⁴ is independently selected from the group consisting of:
(i) halogen,
(ii) C1-C6 alkyl optionally substituted with 1 or 2 hydroxyl or —NR$^A$R$^B$,
(iii) C1-C6 alkoxy optionally substituted with 1-2 substituents independently selected from hydroxyl and C3-C6 cycloalkyl,
(iv) C1-C6 haloalkyl,
(v) hydroxyl,
(vi) cyano,
(vii) —CO₂H,
(viii) —NR$^A$R$^B$,
(ix) =NR$^{A2}$,
(x) —C(=O)NR$^C$R$^D$,
(xi) —SO₂(NR$^E$R$^F$),
(xii) —SO₂(C1-C6 alkyl),
(xiii) —S(=O)(=NH)(C1-C6 alkyl),
(xiv) —C(=O)(C1-C6 alkyl),
(xv) —CO₂(C1-C6 alkyl),
(xvi) 5-6 membered heteroaryl optionally substituted with C1-C6 alkyl,
(xvii) 3-9 membered heterocyclyl optionally substituted with 1 or 2 independently selected R$^G$, and
(xviii) 3-6 membered cycloalkyl optionally substituted with 1 or 2 independently selected R$^G$;

n is 0, 1, or 2;

each R$^A$, R$^{A1}$, R$^B$, R$^{B1}$, R$^C$, R$^{C1}$, R$^D$, R$^{D1}$, R$^E$, and R$^F$ is independently
(i) hydrogen,
(ii) hydroxyl,
(iii) 4-6 membered heterocyclyl,
(iv) C1-C6 haloalkyl,
(v) —C(=O)(C1-C6 alkyl),
(vi) —C(=O)O(C1-C6 alkyl),
(vii) —SO₂(C1-C6 alkyl),
(viii) 3-6 membered cycloalkyl optionally substituted with hydroxyl, or
(ix) C1-C6 alkyl optionally substituted with 1-2 substituents independently selected from hydroxyl, —C(=O)NR$^{B2}$R$^{C2}$, 5-6 membered heteroaryl, 3-6 membered cycloalkyl, —SO₂(C1-C6 alkyl), —CO₂H, and —SO₂(NH₂); or R$^C$ and R$^D$, together with the nitrogen atom to which they are attached form a 4-10 membered heterocyclyl optionally substituted with 1-2 substituents independently selected from hydroxyl, halogen, —C(=O)NR$^{B1}$R$^{C1}$, —SO₂(C1-C6 alkyl), —CO₂H, C1-C6 alkyl optionally substituted with hydroxyl, C1-C6 alkoxy, and C1-C6 haloalkoxy;

each R$^{A2}$, R$^{B2}$, and R$^{C2}$ is independently hydrogen or C1-C6 alkyl;

each R$^G$ is independently selected from the group consisting of: fluoro, cyano, hydroxyl, C1-C6 alkyl optionally substituted with hydroxyl, C1-C6 alkoxy, —NR$^{A1}$R$^{B1}$, =NR$^{A2}$, —C(=O)NR$^{C1}$R$^{D1}$, —CO₂(C1-C6 alkyl), C1-C6 haloalkyl, C3-C6 cycloalkyl, C1-C6 haloalkoxy, —SO₂(C1-C6 alkyl), and —CO₂H.

Some embodiments provide compounds of Formula (I), having Formula (X):

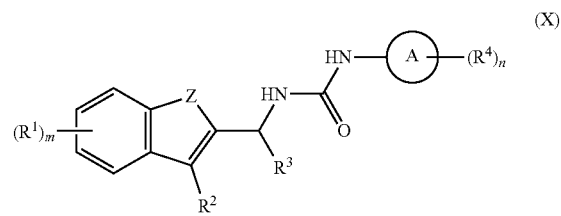

or a pharmaceutically acceptable salt thereof, wherein:

Z is O or NR$^x$;

R$^x$ is hydrogen, C1-C6 alkyl, or C3-C6 cycloalkyl;

each R¹ is an independently selected halogen;

m is 0, 1, 2, or 3;

R² is halogen, C1-C6 alkyl, C1-C6 haloalkyl, C3-C6 cycloalkyl optionally substituted with 1 or 2 fluoro;

R³ is a C1-C6 alkyl, a C1-C6 haloalkyl, or a C3-C6 cycloalkyl optionally substituted with 1 or 2 fluoro;

Ring A is a 6-10 membered aryl, a C3-C8 cycloalkyl, a 5-10 membered heteroaryl, or a 4-10 membered heterocyclyl;

each R⁴ is independently selected from the group consisting of: halogen, C1-C6 alkyl optionally substituted with 1 or 2 hydroxyl or —NR$^A$R$^B$, C1-C6 alkoxy, C1-C6 haloalkyl, hydroxyl, cyano, —CO₂H, —NR$^A$R$^B$, —C(=O)NR$^C$R$^D$, —SO₂(NR$^E$R$^F$), —SO₂(C1-C6 alkyl), —S(=O)(=NH)(C1-C6 alkyl), —C(=O)(C1-C6 alkyl), —CO₂(C1-C6 alkyl), 5-6 membered heteroaryl, and a 3-6 membered heterocyclyl or 3-6 membered cycloalkyl each optionally substituted with 1 or 2 independently selected R$^G$;

n is 0, 1, or 2;

each R$^A$, R$^{A1}$, R$^B$, R$^{B1}$, R$^C$, R$^{C1}$, R$^D$, R$^{D1}$, R$^E$, and R$^F$ is independently hydrogen, 4-6 membered heterocyclyl, C1-C6 haloalkyl, —C(=O)(C1-C6 alkyl), —SO₂(C1-C6 alkyl), 3-6 membered cycloalkyl optionally substituted with hydroxyl, or C1-C6 alkyl optionally substituted with 1-2 substituents independently selected from hydroxyl, —C(=O)NR$^{B2}$R$^{C2}$, 5-6 membered heteroaryl, 3-6 membered cycloalkyl, SO₂(C1-C6 alkyl), —SO₂(NH₂); or R$^C$ and R$^D$, together with the nitrogen atom to which they are attached form a 4-6 membered heterocyclyl;

each R$^G$ is independently selected from the group consisting of: fluoro, hydroxyl, cyano, C1-C6 alkyl, C1-C6 alkoxy, —NR$^{A1}$R$^{B1}$, —C(=O)NR$^{C1}$R$^{D1}$, —CO₂(C1-C6 alkyl), C1-C6 haloalkyl, C3-C6 cycloalkyl, and —CO₂H; and wherein the compound is not a compound selected from the group consisting of:

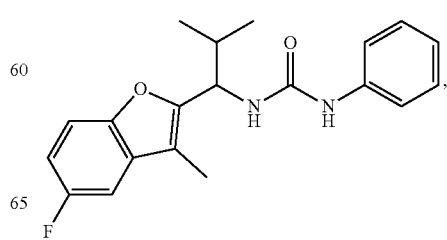

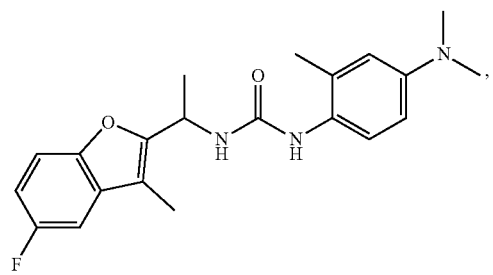
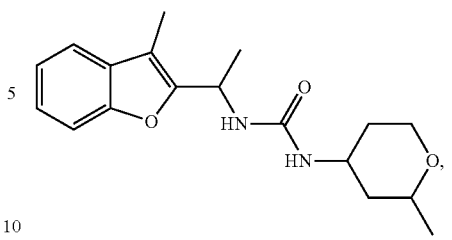
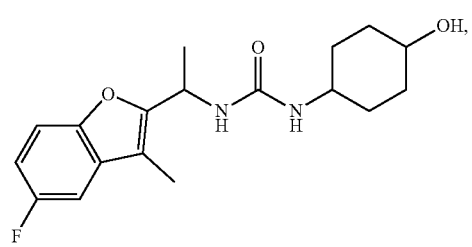
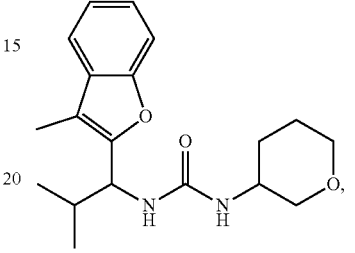
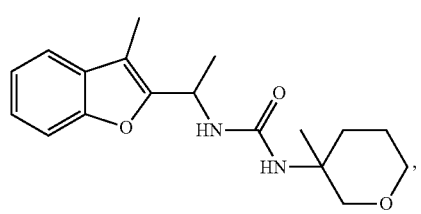
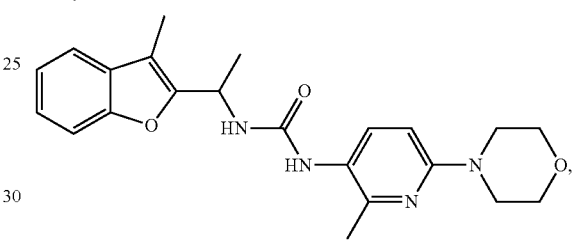
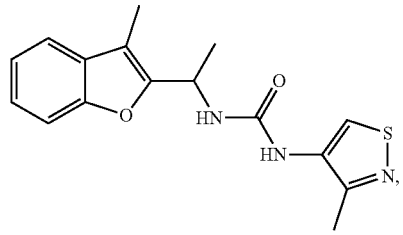
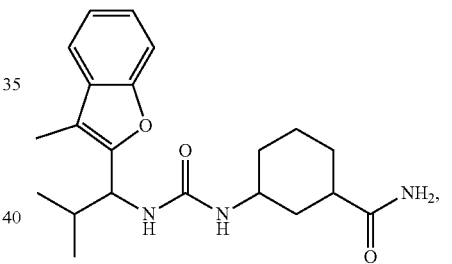
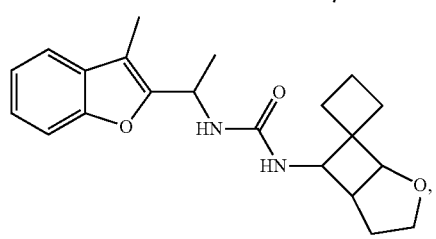
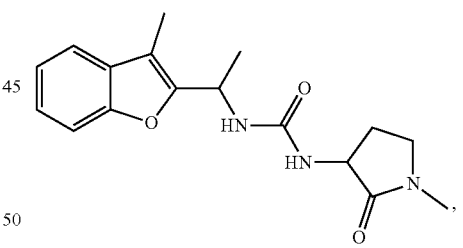
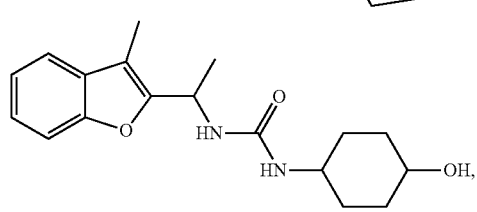
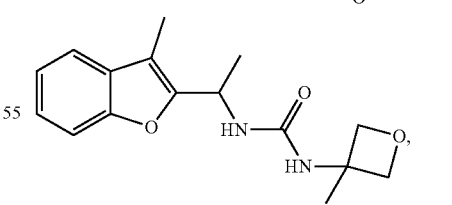
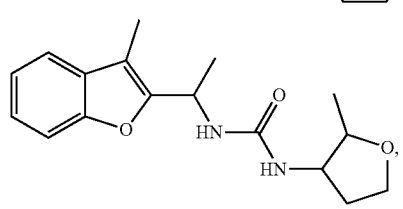
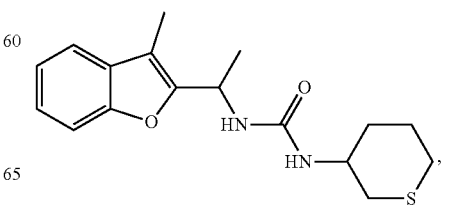

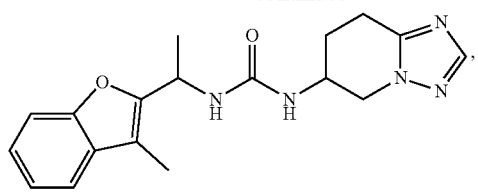
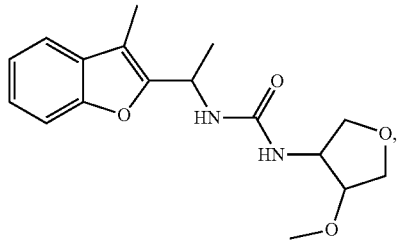
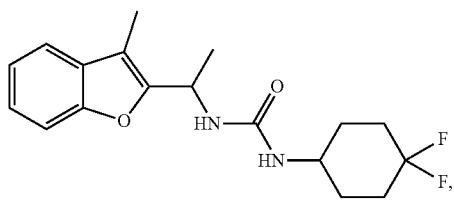
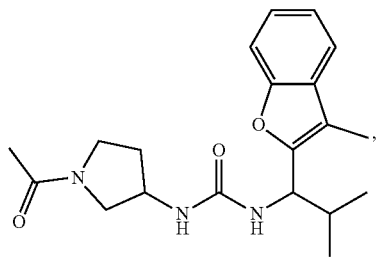
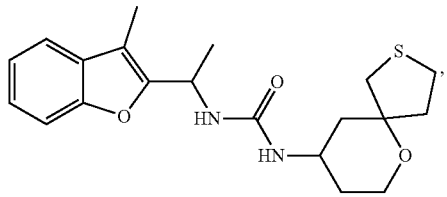
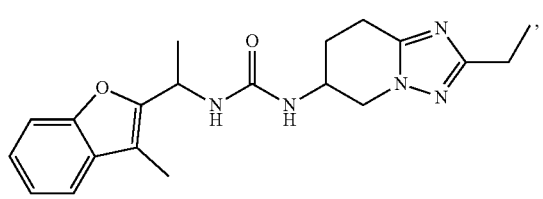
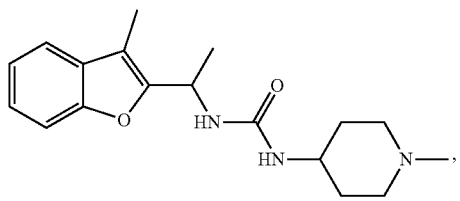
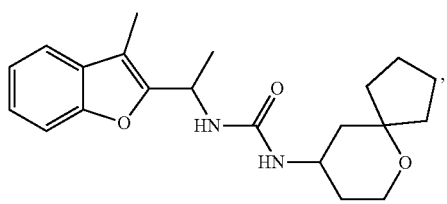
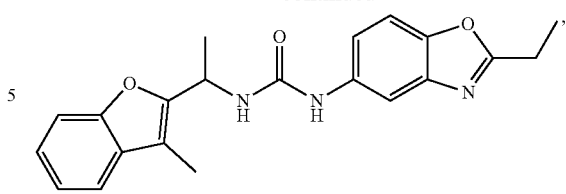
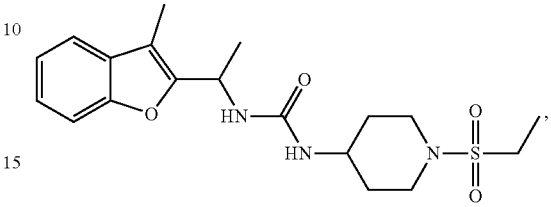
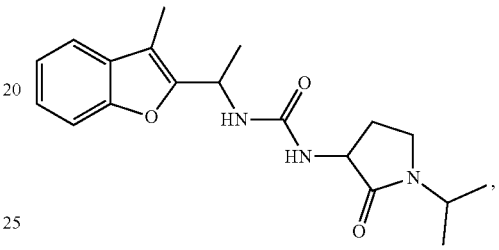
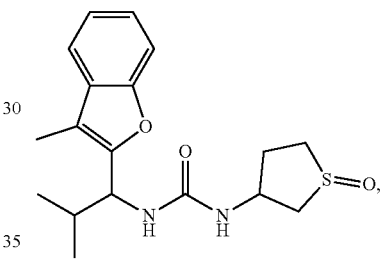
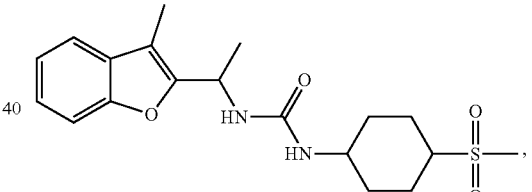

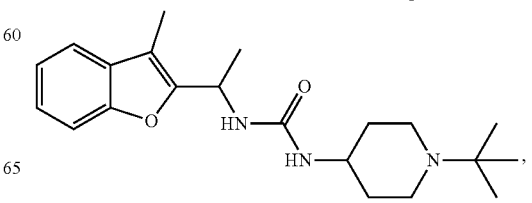

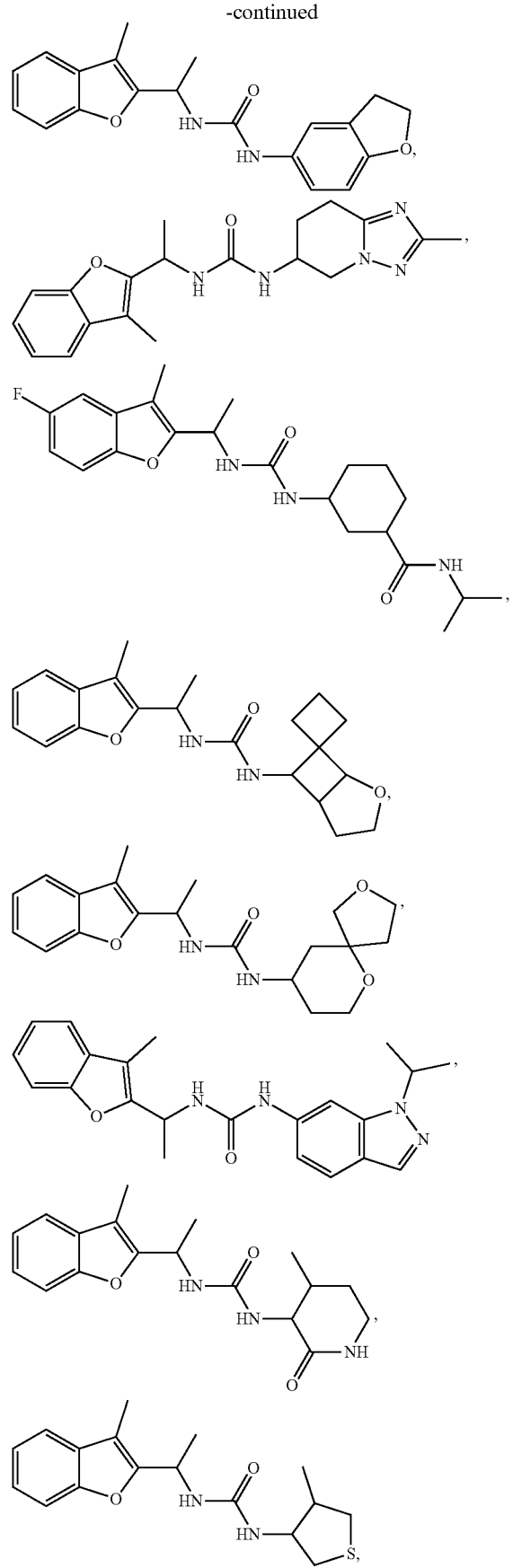
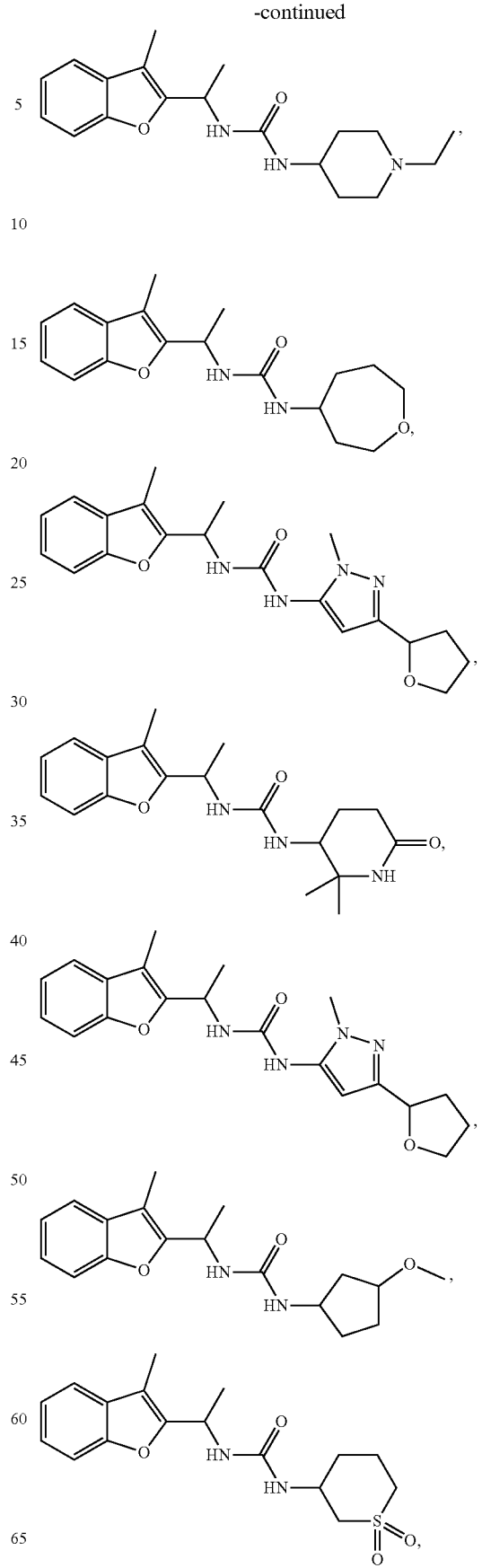

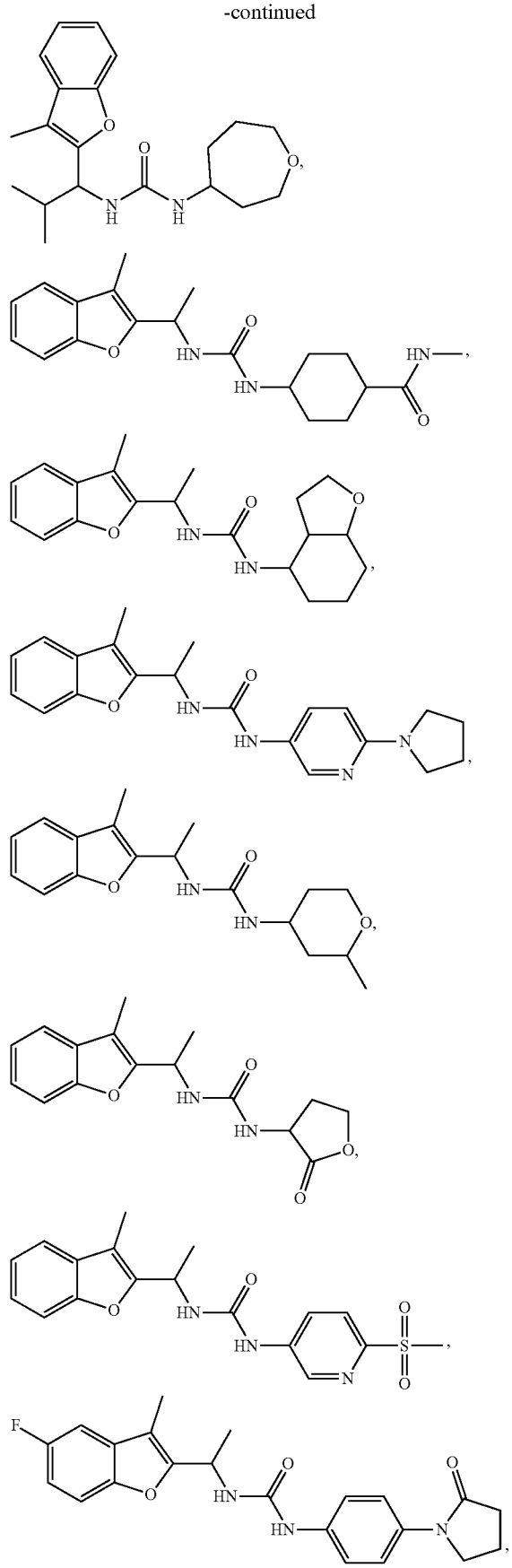
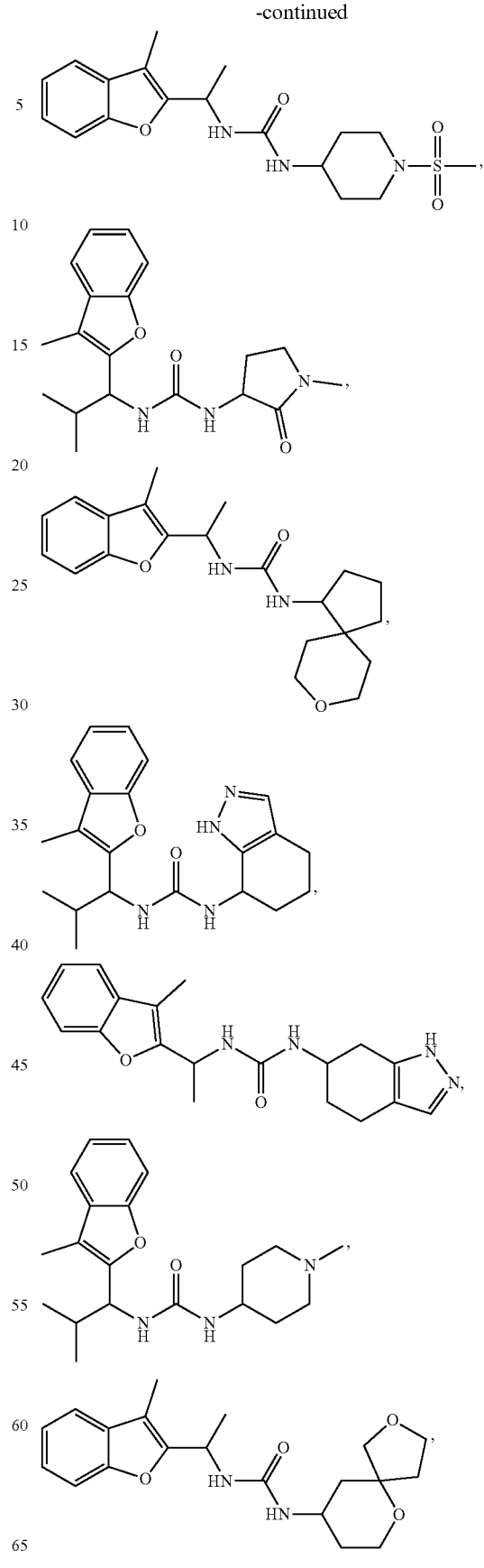

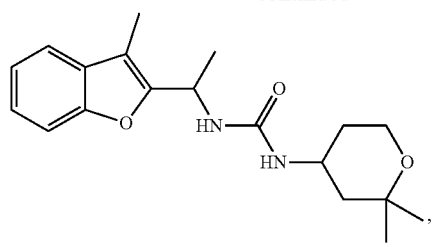
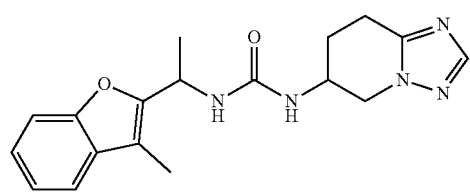
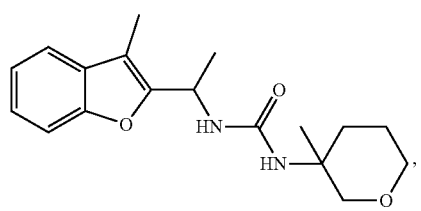
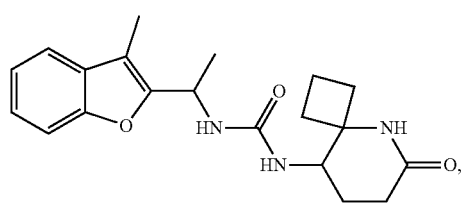
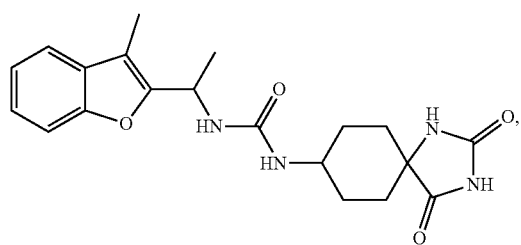
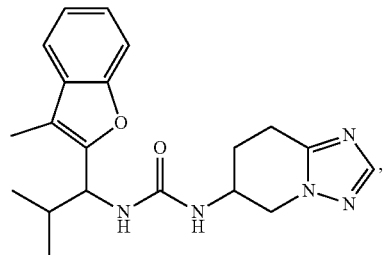
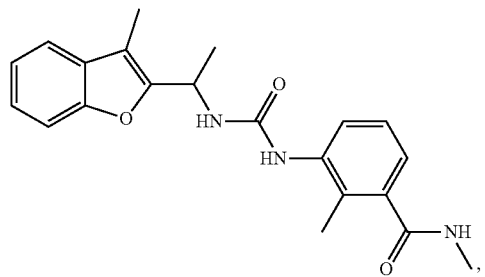
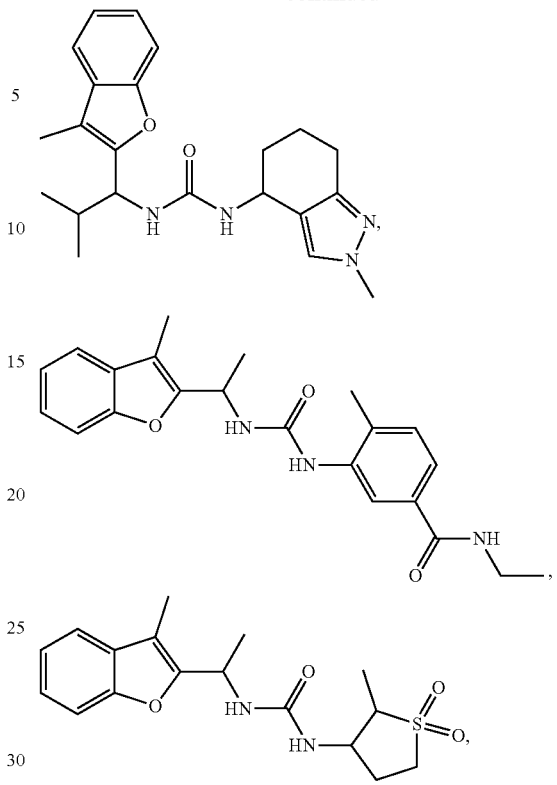
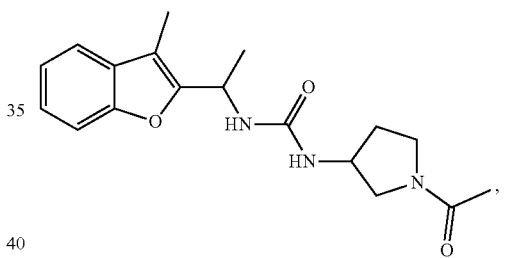
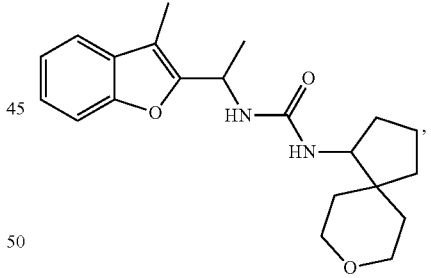
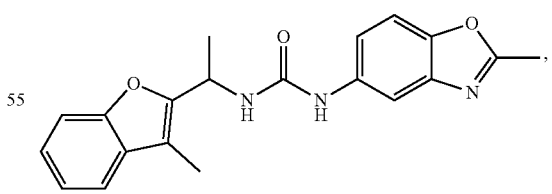
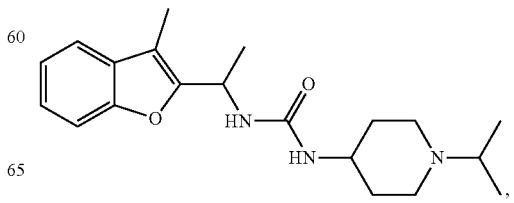

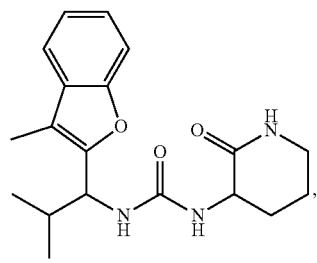
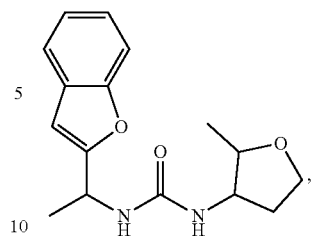
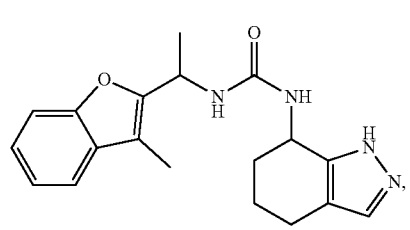
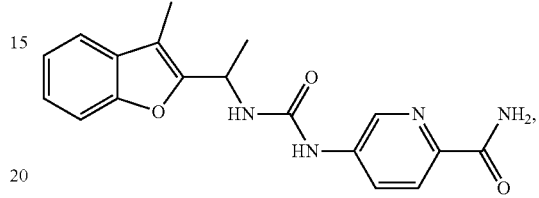
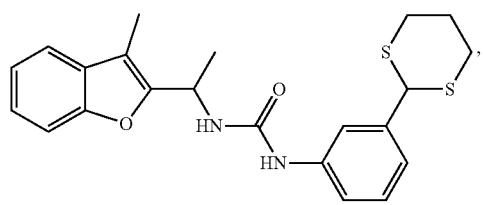
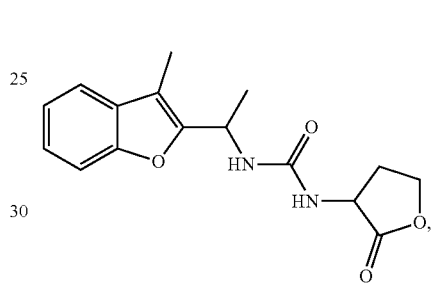
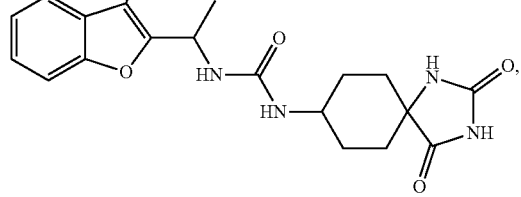
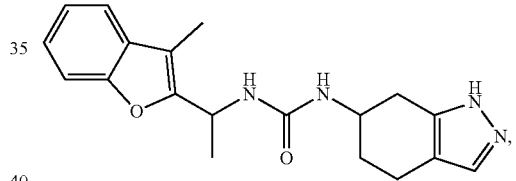
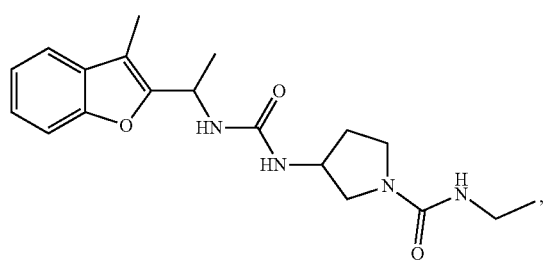
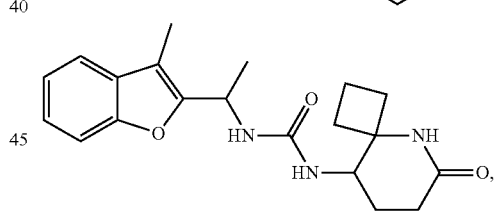
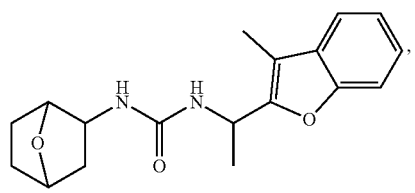
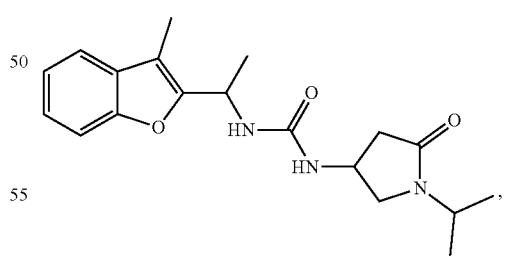
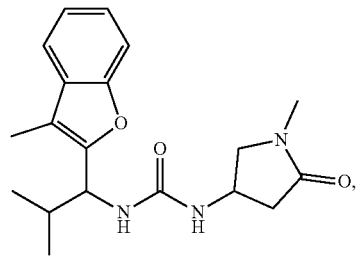
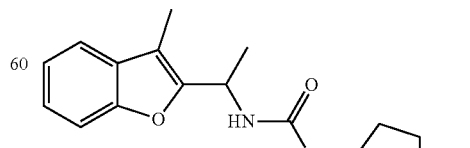

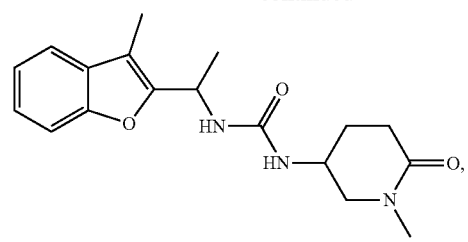
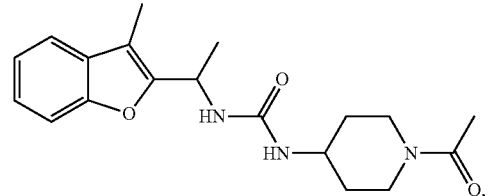
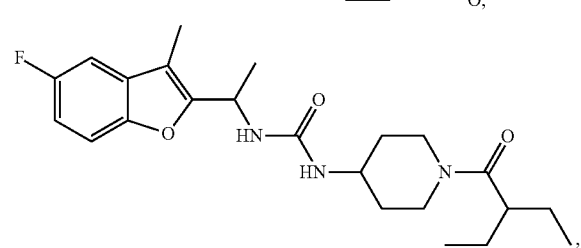
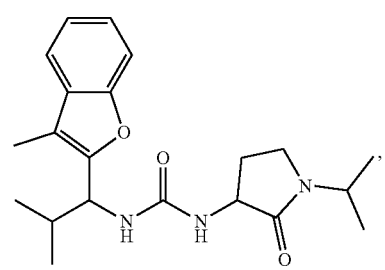
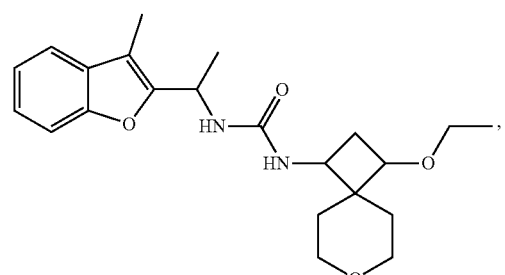
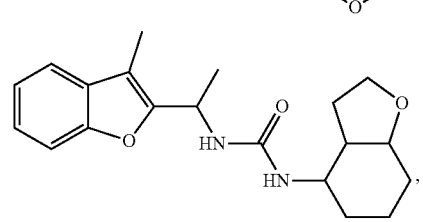
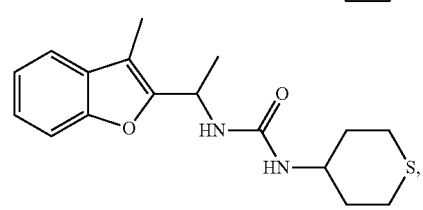
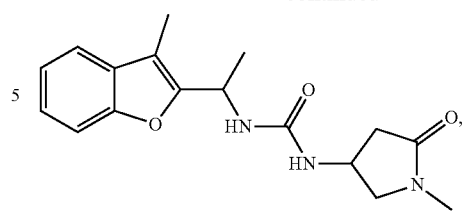
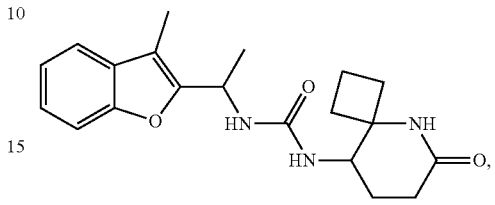
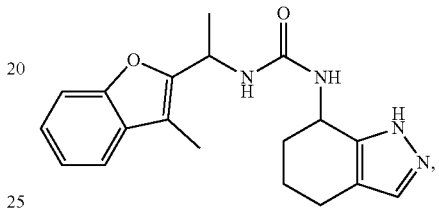
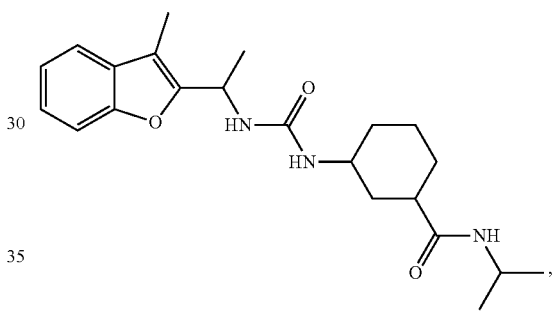
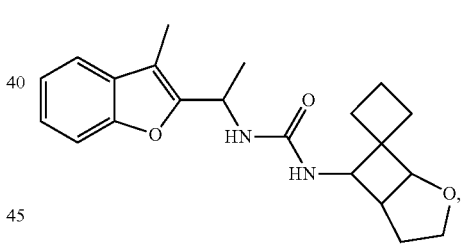
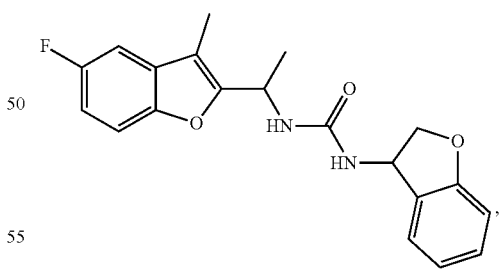
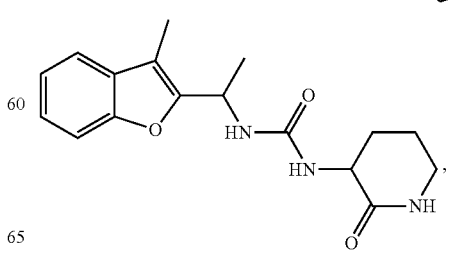

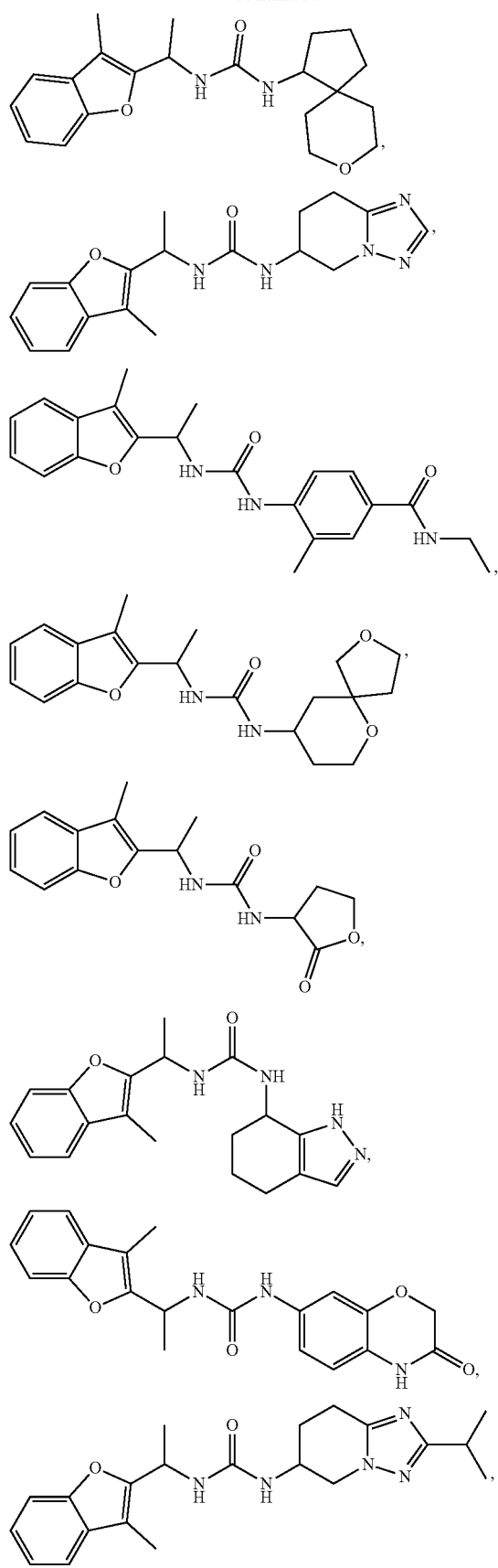
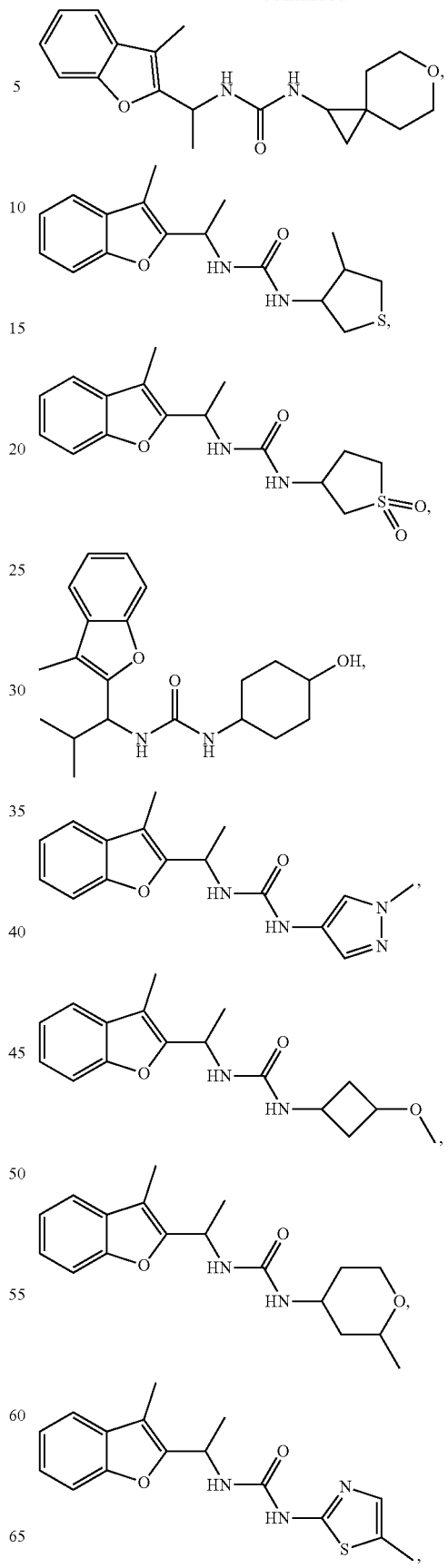

65
-continued
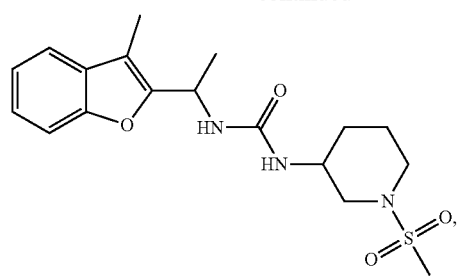
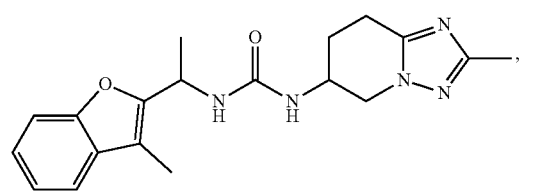
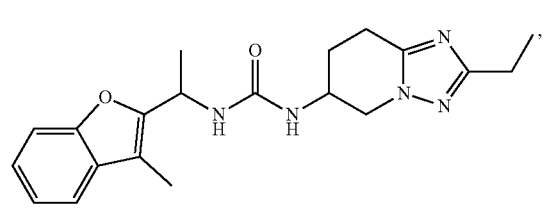
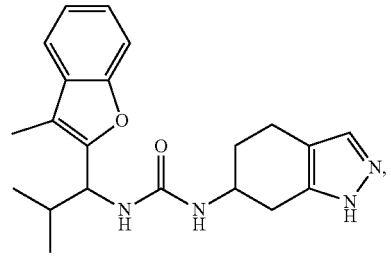
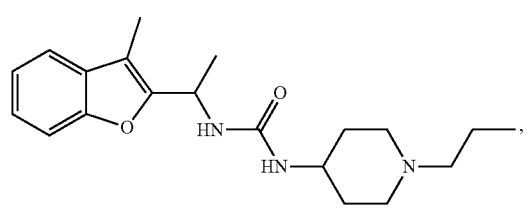
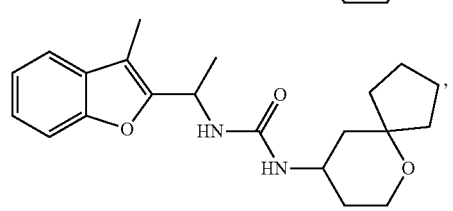
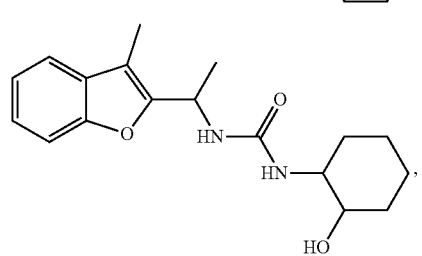
66
-continued
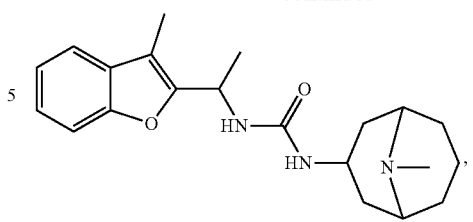
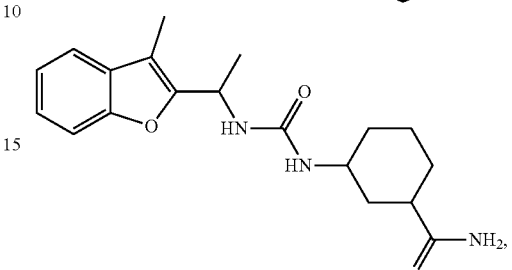
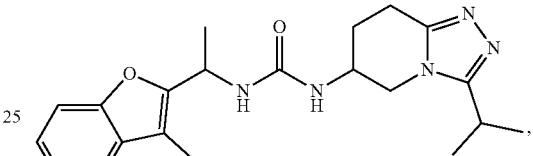
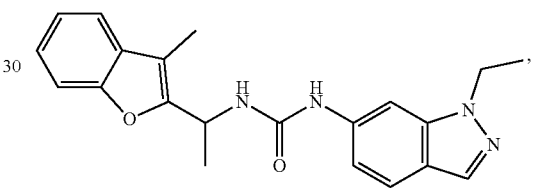
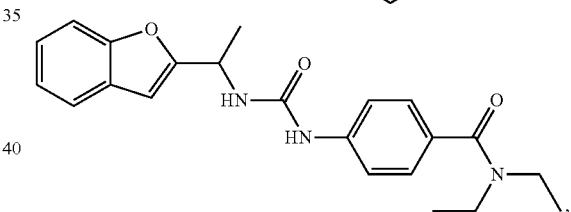
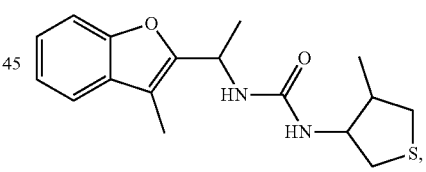
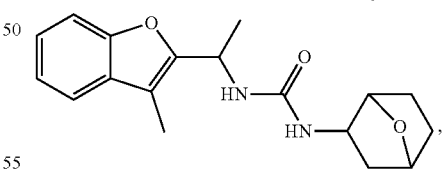
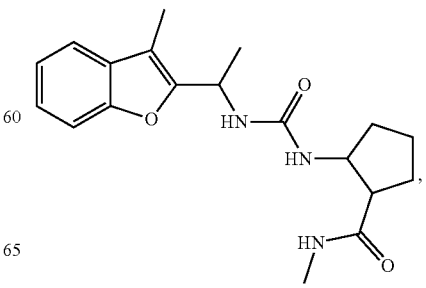

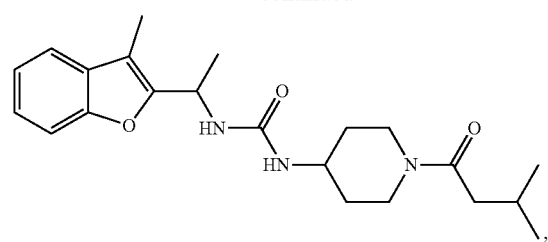
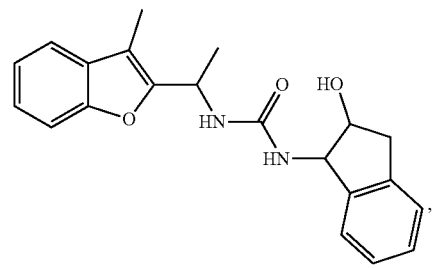
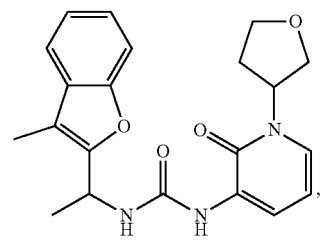
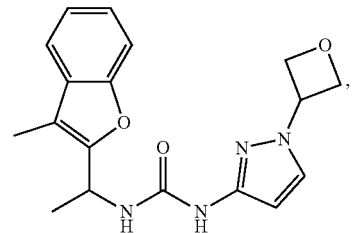
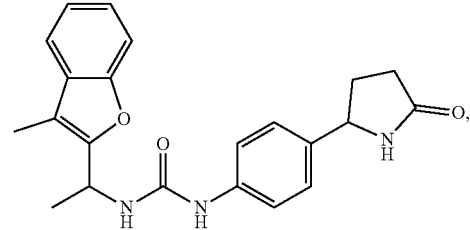
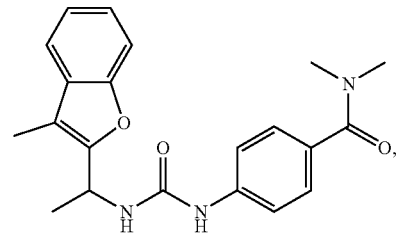
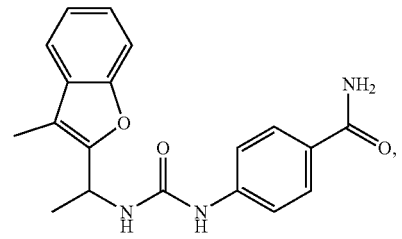
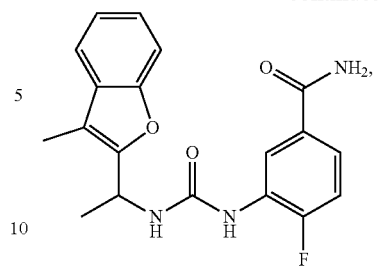
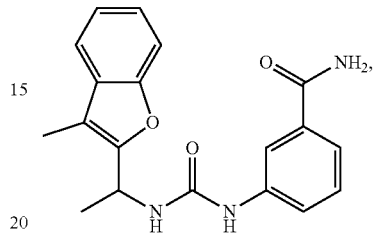
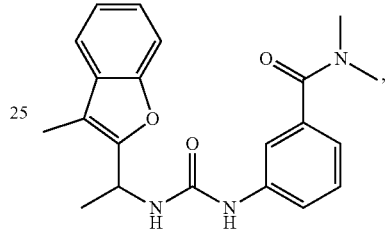
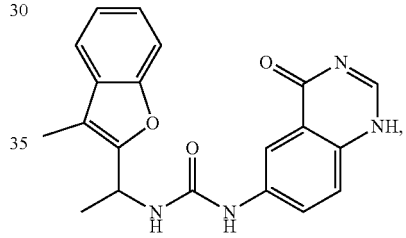
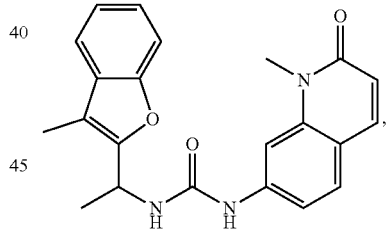
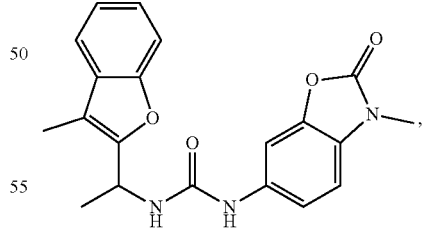
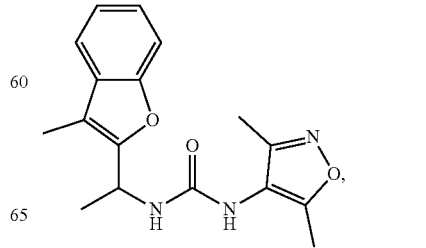

-continued

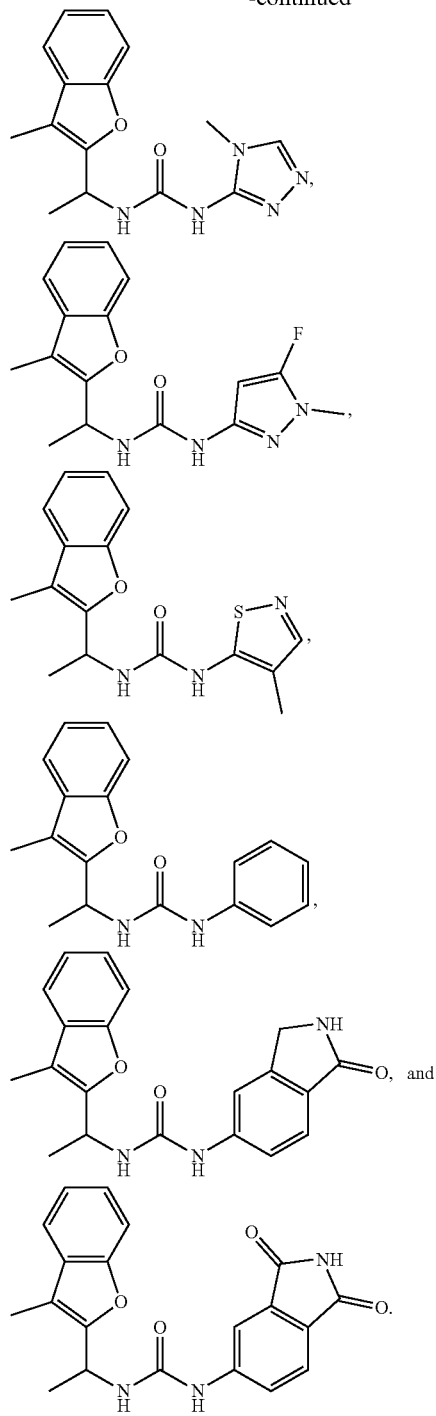

Also provided herein is a pharmaceutical composition comprising a compound of Formula (I), or a pharmaceutically acceptable salt thereof, and one or more pharmaceutically acceptable excipients.

Provided herein is a method for treating cancer in a subject in need thereof, the method comprising administering to the subject a therapeutically effective amount of a compound of Formula (I), or a pharmaceutically acceptable salt thereof, or a pharmaceutical composition as provided herein.

Also provided herein is a method for treating cancer in a subject in need thereof, the method comprising (a) determining that the cancer is associated with a dysregulation of a PIK3CA gene, a PI3Kα protein, or expression or activity or level of any of the same; and (b) administering to the subject a therapeutically effective amount of a compound of Formula (I), or a pharmaceutically acceptable salt thereof, or a pharmaceutical composition as provided herein.

Provided herein is a method of treating a PI3Kα-associated disease or disorder in a subject, the method comprising administering to a subject identified or diagnosed as having a PI3Kα-associated disease or disorder a therapeutically effective amount of a compound of Formula (I), or a pharmaceutically acceptable salt thereof, or a pharmaceutical composition as provided herein.

This disclosure also provides a method of treating a PI3Kα-associated disease or disorder in a subject, the method comprising: determining that the cancer in the subject is a PI3Kα-associated disease or disorder; and administering to the subject a therapeutically effective amount of a compound of Formula (I), or a pharmaceutically acceptable salt thereof, or a pharmaceutical composition as provided herein.

Further provided herein is a method of treating a PI3Kα-associated cancer in a subject, the method comprising administering to a subject identified or diagnosed as having a PI3Kα-associated cancer a therapeutically effective amount of a compound of Formula (I), or a pharmaceutically acceptable salt thereof, or a pharmaceutical composition as provided herein.

This disclosure also provides a method of treating a PI3Kα-associated cancer in a subject, the method comprising: determining that the cancer in the subject is a PI3Kα-associated cancer; and administering to the subject a therapeutically effective amount of a compound of Formula (I), or a pharmaceutically acceptable salt thereof, or a pharmaceutical composition as provided herein.

Provided herein is a method of treating a subject, the method comprising administering a therapeutically effective amount of a compound of Formula (I), or a pharmaceutically acceptable salt thereof, or a pharmaceutical composition as provided herein, to a subject having a clinical record that indicates that the subject has a dysregulation of a PIK3CA gene, a PI3Kα protein, or expression or activity or level of any of the same.

This disclosure also provides a method for inhibiting PI3Kα in a mammalian cell, the method comprising contacting the mammalian cell with an effective amount of a compound of Formula (I), or a pharmaceutically acceptable salt thereof.

Some embodiments of the methods and composition described herein include compounds of Formula (II):

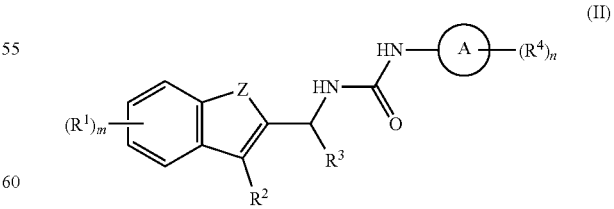

or a pharmaceutically acceptable salt thereof, wherein:
Z is O or NR$^x$;
R$^x$ is hydrogen, C1-C6 alkyl, or C3-C6 cycloalkyl;
each R$^1$ is an independently selected halogen;
m is 0, 1, 2, or 3;

$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
Ring A is a 6-10 membered aryl, a C3-C8 cycloalkyl, a 5-10 membered heteroaryl, or a 4-10 membered heterocyclyl;
each $R^4$ is independently selected from the group consisting of: C1-C6 alkyl optionally substituted with 1 or 2 hydroxyl or —$NR^A R^B$, C1-C6 alkoxy, C1-C6 haloalkyl, hydroxyl, cyano, —$NR^A R^B$, —C(=O)$NR^C R^D$, —$SO_2(NR^E R^F)$, —$SO_2$(C1-C6 alkyl), —S(=O)(=NH)(C1-C6 alkyl), —C(=O)(C1-C6 alkyl), —$CO_2$(C1-C6 alkyl), 5-6 membered heteroaryl, and 3-6 membered heterocyclyl optionally substituted with 1 or 2 independently selected $R^G$;
n is 0, 1, or 2;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, —C(=O)(C1-C6 alkyl), C(=O)O(C1-C6 alkyl), —$SO_2$(C1-C6 alkyl), 3-6 membered cycloalkyl optionally substituted with hydroxyl, or C1-C6 alkyl optionally substituted with 1-2 substituents independently selected from hydroxyl, —C(=O)$NR^{B2}R^{C2}$, 5-6 membered heteroaryl, 3-6 membered cycloalkyl, —$SO_2$(C1-C6 alkyl), and —$SO_2(NH_2)$; or $R^C$ and $R^D$, together with the nitrogen atom to which they are attached form a 4-10 membered heterocyclyl optionally substituted with 1-2 substituents independently selected from hydroxyl, halogen, —C(=O)$NR^{B1}R^{C1}$, —$SO_2$(C1-C6 alkyl), —$CO_2H$, C1-C6 alkyl optionally substituted with hydroxyl, C1-C6 alkoxy, and C1-C6 haloalkoxy;
each $R^{A2}$, $R^{B2}$, and $R^{C2}$ is independently hydrogen or C1-C6 alkyl;
each $R^G$ is independently selected from the group consisting of: fluoro, cyano, hydroxyl, C1-C6 alkyl optionally substituted with hydroxyl, C1-C6 alkoxy, —$NR^{A1}R^{B1}$=$NR^{A2}$, —C(=O)$NR^{C1}R^{D1}$, —$CO_2$(C1-C6 alkyl), C1-C6 haloalkyl, C3-C6 cycloalkyl, C1-C6 haloalkoxy, —$SO_2$(C1-C6 alkyl), and —$CO_2H$.

Also provided herein is a pharmaceutical composition comprising a compound of Formula (II), or a pharmaceutically acceptable salt thereof, and a pharmaceutically acceptable carrier.

Provided herein is a method for treating cancer in a subject in need thereof, the method comprising administering to the subject a therapeutically effective amount of a compound of Formula (II), or a pharmaceutically acceptable salt thereof, or a pharmaceutical composition as provided herein.

Also provided herein is a method for treating cancer in a subject in need thereof, the method comprising (a) determining that the cancer is associated with a dysregulation of a PIK3CA gene, a PI3Kα protein, or expression or activity or level of any of the same; and (b) administering to the subject a therapeutically effective amount of a compound of Formula (II), or a pharmaceutically acceptable salt thereof, or a pharmaceutical composition as provided herein.

Provided herein is a method of treating a PI3Kα-associated disease or disorder in a subject, the method comprising administering to a subject identified or diagnosed as having a PI3Kα-associated disease or disorder a therapeutically effective amount of a compound of Formula (II), or a pharmaceutically acceptable salt thereof, or a pharmaceutical composition as provided herein.

This disclosure also provides a method of treating a PI3Kα-associated disease or disorder in a subject, the method comprising: determining that the cancer in the subject is a PI3Kα-associated disease or disorder; and administering to the subject a therapeutically effective amount of a compound of Formula (II), or a pharmaceutically acceptable salt thereof, or a pharmaceutical composition as provided herein.

Further provided herein is a method of treating a PI3Kα-associated cancer in a subject, the method comprising administering to a subject identified or diagnosed as having a PI3Kα-associated cancer a therapeutically effective amount of a compound of Formula (II), or a pharmaceutically acceptable salt thereof, or a pharmaceutical composition as provided herein.

This disclosure also provides a method of treating a PI3Kα-associated cancer in a subject, the method comprising: determining that the cancer in the subject is a PI3Kα-associated cancer; and administering to the subject a therapeutically effective amount of a compound of Formula (II), or a pharmaceutically acceptable salt thereof, or a pharmaceutical composition as provided herein.

Provided herein is a method of treating a subject, the method comprising administering a therapeutically effective amount of a compound of Formula (II), or a pharmaceutically acceptable salt thereof, or a pharmaceutical composition as provided herein, to a subject having a clinical record that indicates that the subject has a dysregulation of a PIK3CA gene, a PI3Kα protein, or expression or activity or level of any of the same.

This disclosure also provides a method for inhibiting PI3Kα in a mammalian cell, the method comprising contacting the mammalian cell with an effective amount of a compound of Formula (II), or a pharmaceutically acceptable salt thereof.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "about" when referring to a number or a numerical range means that the number or numerical range referred to is an approximation, for example, within experimental variability and/or statistical experimental error, and thus the number or numerical range may vary up to ±10% of the stated number or numerical range.

The term "acceptable" with respect to a formulation, composition or ingredient, as used herein, means having no persistent detrimental effect on the general health of the subject being treated.

The term "inhibit" or "inhibition of" means to reduce by a measurable amount, or to prevent entirely (e.g., 100% inhibition).

"API" refers to an active pharmaceutical ingredient.

The terms "effective amount" or "therapeutically effective amount," as used herein, refer to a sufficient amount of a chemical entity being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.*; Lippincott Williams & Wilkins: Philadelphia, P A, 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, F L, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "pharmaceutically acceptable excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

As used herein, the terms "subject," "individual," or "patient," are used interchangeably, refers to any animal, including mammals such as primates (e.g., humans), mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

The term "halo" refers to fluoro (F), chloro (Cl), bromo (Br), or iodo (I).

The term "oxo" refers to a divalent doubly bonded oxygen atom (i.e., "=O"). As used herein, oxo groups are attached to carbon atoms to form carbonyls.

The term "hydroxyl" refers to an —OH radical.

The term "cyano" refers to a —CN radical.

The term "alkyl" refers to a saturated acyclic hydrocarbon radical that may be a straight chain or branched chain, containing the indicated number of carbon atoms. For example, $C_{1-10}$ indicates that the group may have from 1 to 10 (inclusive) carbon atoms in it. Alkyl groups can either be unsubstituted or substituted with one or more substituents. Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

The term "cycloalkyl" as used herein refers to cyclic saturated hydrocarbon groups having, e.g., 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0] hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like. The term "saturated" as used in this context means only single bonds present between constituent carbon atoms.

The term "heteroaryl", as used herein, means a mono-, bi-, tri- or polycyclic group having 5 to 20 ring atoms, alternatively 5, 6, 9, 10, or 14 ring atoms; wherein at least one ring in the system contains one or more heteroatoms independently selected from the group consisting of N, O, and S and at least one ring in the system is aromatic (but does not have to be a ring which contains a heteroatom, e.g. tetrahydroisoquinolinyl, e.g., tetrahydroquinolinyl). Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl. For purposes of clarification, heteroaryl also includes aromatic lactams, aromatic cyclic ureas, or vinylogous analogs thereof, in which each ring nitrogen adjacent to a carbonyl is tertiary (i.e., all three valences are occupied by non-hydrogen substituents), such as one or more of pyridone (e.g., 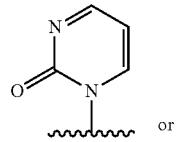, 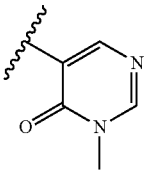,

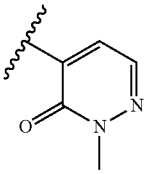, or 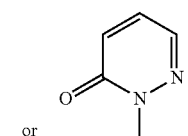), pyrimodone (e.g.,

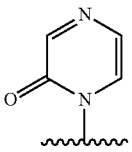 or 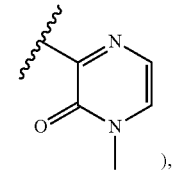), pyridazinone (e.g.,

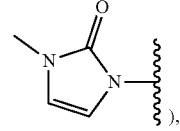), pyrazinone (e.g.,

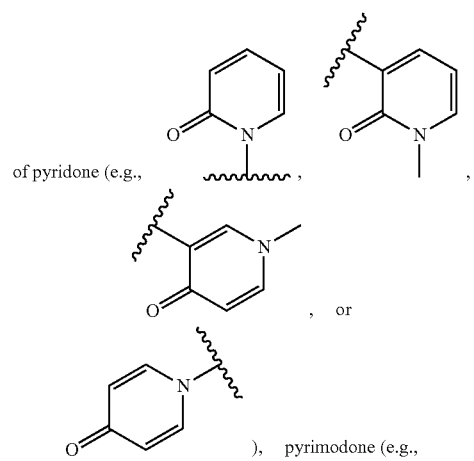

wherein each ring nitrogen adjacent to a carbonyl is tertiary (i.e., the oxo group (i.e., "=O") herein is a constituent part of the heteroaryl ring).

The term "heterocyclyl" refers to a mono-, bi-, tri-, or polycyclic saturated or partially unsaturated ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein one or more ring atoms may be substituted by 1-3 oxo (forming, e.g., a lactam) and one or more N or S atoms may be substituted by 1-2 oxido (forming, e.g., an N-oxide, an S-oxide, or an S,S-dioxide), valence permitting; and wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, tetrahydropyridyl, dihydropyrazinyl, dihydropyridyl, dihydropyrrolyl, dihydrofuranyl, dihydrothiophenyl, and the like. Heterocyclyl may include multiple fused and bridged rings. Non-limiting examples of fused/bridged heterocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, examples of aromatic rings include: benzene, pyridine, pyrimidine, pyrazine, pyridazine, pyridone, pyrrole, pyrazole, oxazole, thioazole, isoxazole, isothiazole, and the like.

As used herein, when a ring is described as being "partially unsaturated", it means said ring has one or more additional degrees of unsaturation (in addition to the degree of unsaturation attributed to the ring itself; e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

For the avoidance of doubt, and unless otherwise specified, for rings and cyclic groups (e.g., aryl, heteroaryl, heterocyclyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g.,

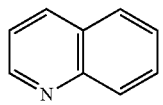

)); (ii) a single ring atom (spiro-fused ring systems) (e.g.,

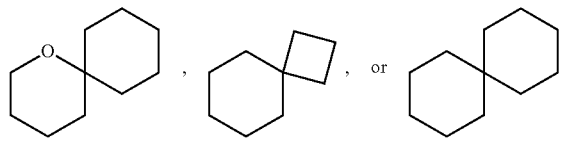

), or (iii) a contiguous array of ring atoms (bridged ring systems having all bridge lengths >0) (e.g.,

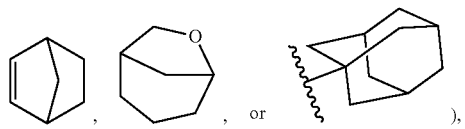

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In addition, the compounds generically or specifically disclosed herein are intended to include all tautomeric forms. Thus, by way of example, a compound containing the moiety:

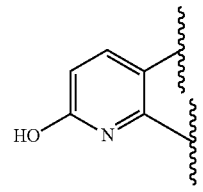 [SMILES: *c1ccc(O)nc1*]

encompasses the tautomeric form containing the moiety:

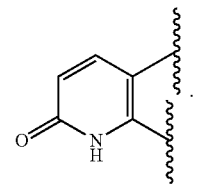 [SMILES: *c1ccc(=O)[nH]c1* ; "."]

Similarly, a pyridinyl or pyrimidinyl moiety that is described to be optionally substituted with hydroxyl encompasses pyridone or pyrimidone tautomeric forms.

The compounds provided herein may encompass various stereochemical forms. The compounds also encompass enantiomers (e.g., R and S isomers), diastereomers, as well as mixtures of enantiomers (e.g., R and S isomers) including racemic mixtures and mixtures of diastereomers, as well as individual enantiomers and diastereomers, which arise as a consequence of structural asymmetry in certain compounds. Unless otherwise indicated, when a disclosed compound is named or depicted by a structure without specifying the stereochemistry (e.g., a "flat" structure) and has one or more chiral centers, it is understood to represent all possible stereoisomers of the compound. Likewise, unless otherwise indicated, when a disclosed compound is named or depicted by a structure that specifies the stereochemistry (e.g., a structure with "wedge" and/or "dashed" bonds) and has one or more chiral centers, it is understood to represent the indicated stereoisomer of the compound.

The details of one or more embodiments of this disclosure are set forth in the accompanying drawings and the description below. Other features and advantages of the present disclosure will be apparent from the description and drawings, and from the claims.

DETAILED DESCRIPTION

This disclosure provides compounds of Formula (I), Formula (II), and pharmaceutically acceptable salts thereof, that inhibit phosphatidylinositol 4,5-bisphosphate 3-kinase (PI3K) isoform alpha (PI3Kα). These chemical entities are useful, e.g., for treating a condition, disease or disorder in which increased (e.g., excessive) PI3Kα activation contributes to the pathology and/or symptoms and/or progression of the condition, disease or disorder (e.g., cancer) in a subject (e.g., a human). This disclosure also provides compositions containing the same as well as methods of using and making the same.

Formulae (I) Compounds
Some embodiments provide a compound of Formula (I):

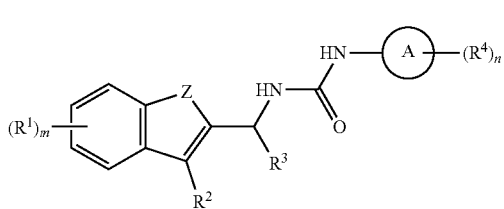

or a pharmaceutically acceptable salt thereof, wherein:
Z is O or NR$^x$;
R$^x$ is hydrogen, C1-C6 alkyl, or C3-C6 cycloalkyl;
each R$^1$ is independently selected from halogen, hydroxyl, cyano, C1-C6 alkyl optionally substituted with hydroxyl, and C3-C6 cycloalkyl;
m is 0, 1, 2, or 3;
R$^2$ is halogen, hydroxyl, C1-C6 alkyl optionally substituted with hydroxyl, C1-C6 haloalkyl, C3-C6 cycloalkyl optionally substituted with 1 or 2 fluoro;
R$^3$ is a C1-C6 alkyl, a C1-C6 haloalkyl, or a C3-C6 cycloalkyl optionally substituted with 1 or 2 substituents independently selected from fluoro and C1-C6 alkyl;
Ring A is a 6-10 membered aryl, a C3-C8 cycloalkyl, a 5-10 membered heteroaryl, or a 4-10 membered heterocyclyl;
each R$^4$ is independently selected from the group consisting of:
(i) halogen,
(ii) C1-C6 alkyl optionally substituted with 1 or 2 hydroxyl or —NR$^A$R$^B$,
(iii) C1-C6 alkoxy optionally substituted with 1-2 substituents independently selected from hydroxyl and C3-C6 cycloalkyl,
(iv) C1-C6 haloalkyl,
(v) hydroxyl,
(vi) cyano,
(vii) —CO$_2$H,
(viii) —NR$^A$R$^B$,
(ix) =NR$^{A2}$,
(x) —C(=O)NR$^C$R$^D$,
(xi) —SO$_2$(NR$^E$R$^F$),
(xii) —SO$_2$(C1-C6 alkyl),
(xiii) —S(=O)(=NH)(C1-C6 alkyl),
(xiv) —C(=O)(C1-C6 alkyl),
(xv) —CO$_2$(C1-C6 alkyl),
(xvi) 5-6 membered heteroaryl optionally substituted with C1-C6 alkyl,
(xvii) 3-9 membered heterocyclyl optionally substituted with 1 or 2 independently selected R$^G$, and
(xviii) 3-6 membered cycloalkyl optionally substituted with 1 or 2 independently selected R$^G$.
n is 0, 1, or 2;
each R$^A$, R$^{A1}$, R$^B$, R$^{B1}$, R$^C$, R$^{C1}$, R$^D$, R$^{D1}$, R$^E$, and R$^F$ is independently
(i) hydrogen,
(ii) hydroxyl,
(iii) 4-6 membered heterocyclyl,
(iv) C1-C6 haloalkyl,
(v) —C(=O)(C1-C6 alkyl),
(vi) —C(=O)O(C1-C6 alkyl),
(vii) —SO$_2$(C1-C6 alkyl),
(viii) 3-6 membered cycloalkyl optionally substituted with hydroxyl, or
(ix) C1-C6 alkyl optionally substituted with 1-2 substituents independently selected from hydroxyl, —C(=O)NR$^{B2}$R$^{C2}$, 5-6 membered heteroaryl, 3-6 membered cycloalkyl, SO$_2$(C1-C6 alkyl), —CO$_2$H, and —SO$_2$(NH$_2$); or R$^C$ and R$^D$, together with the nitrogen atom to which they are attached form a 4-10 membered heterocyclyl optionally substituted with 1-2 substituents independently selected from hydroxyl, halogen, —C(=O)NR$^{B1}$R$^{C1}$, —SO$_2$(C1-C6 alkyl), —CO$_2$H, C1-C6 alkyl optionally substituted with hydroxyl, C1-C6 alkoxy, and C1-C6 haloalkoxy;

each R$^{A2}$, R$^{B2}$, and R$^{C2}$ is independently hydrogen or C1-C6 alkyl;

each R$^G$ is independently selected from the group consisting of: fluoro, cyano, hydroxyl, C1-C6 alkyl optionally substituted with hydroxyl, C1-C6 alkoxy, —NR$^{A1}$R$^{B1}$, =NR$^{A2}$, —C(=O)NR$^{C1}$R$^{D1}$, —CO$_2$(C1-C6 alkyl), C1-C6 haloalkyl, C3-C6 cycloalkyl, C1-C6 haloalkoxy, —SO$_2$(C1-C6 alkyl), and —CO$_2$H; and wherein the compound is not a compound selected from the group consisting of:

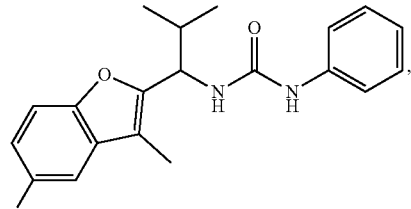

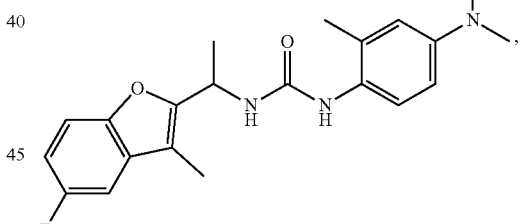

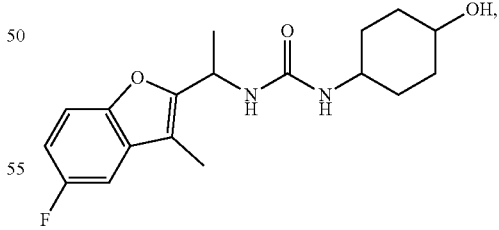

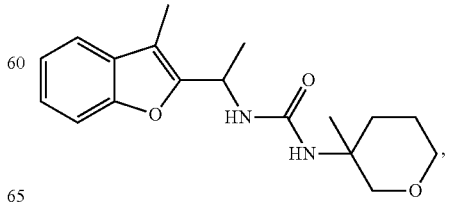

-continued
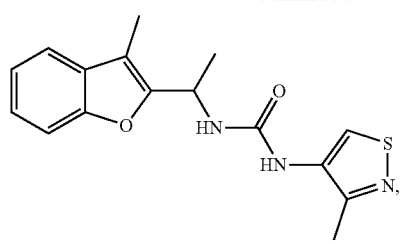
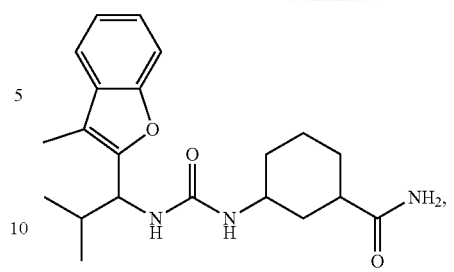
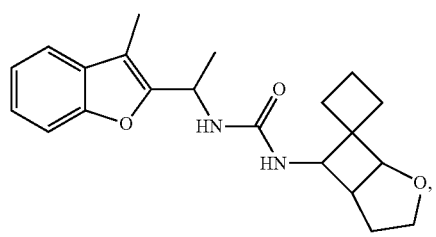
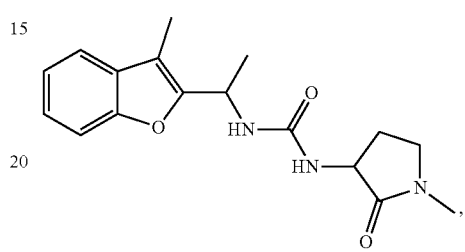
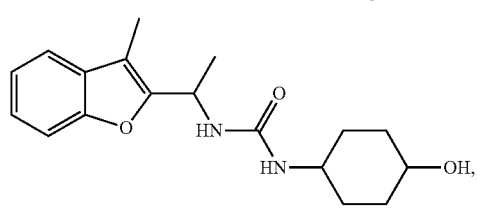
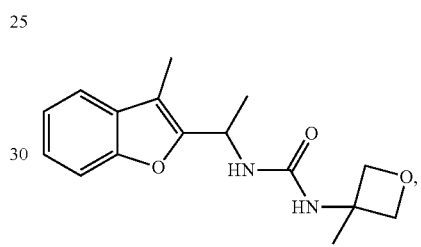
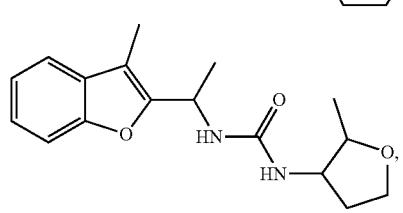
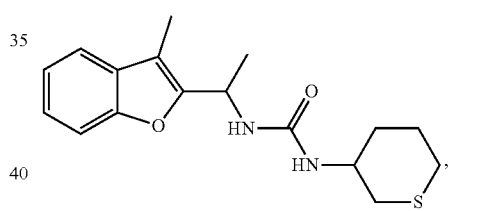
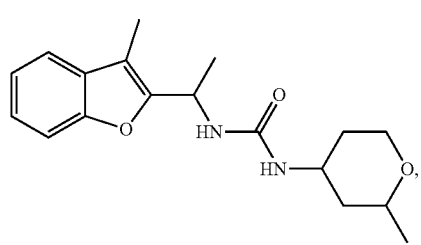
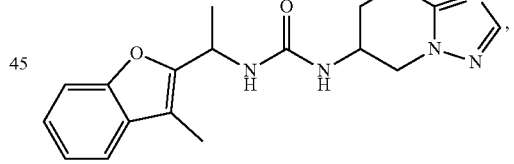
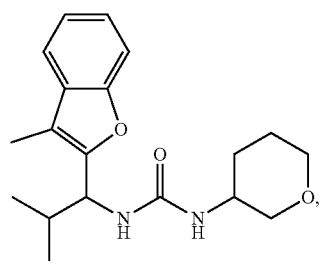
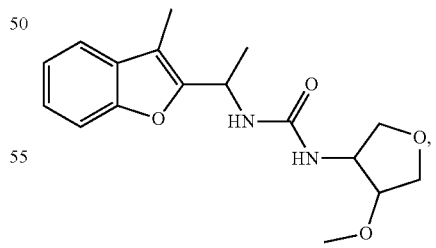
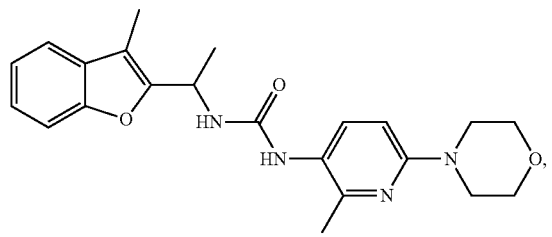
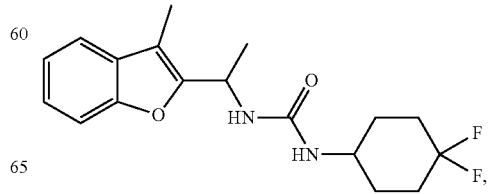

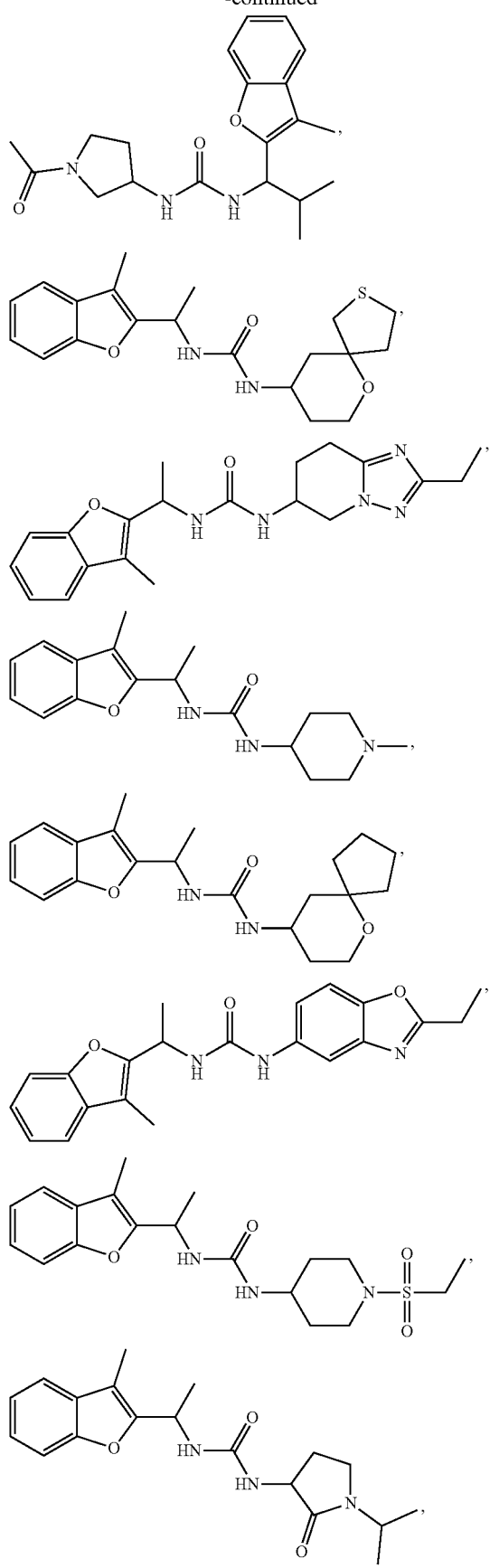
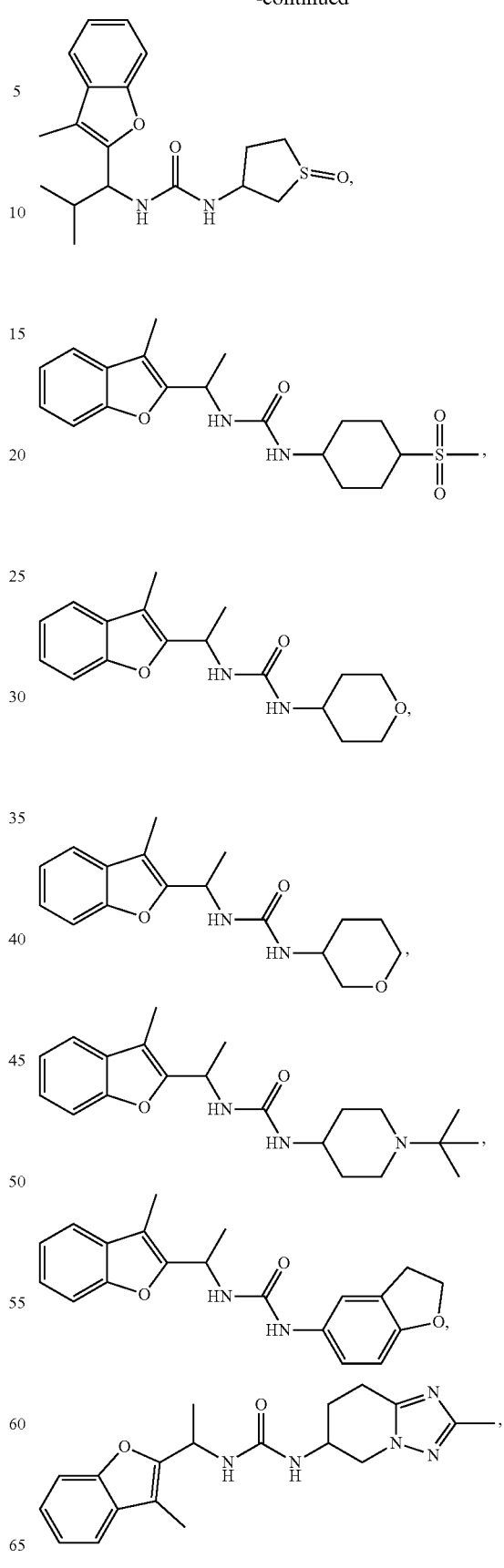

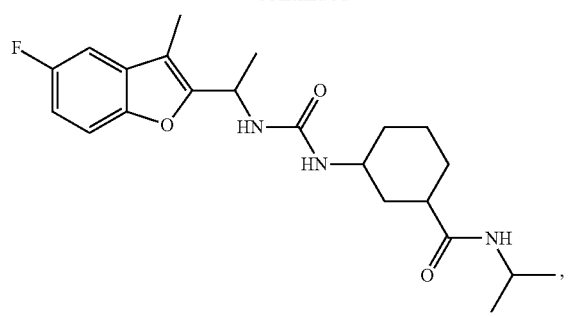
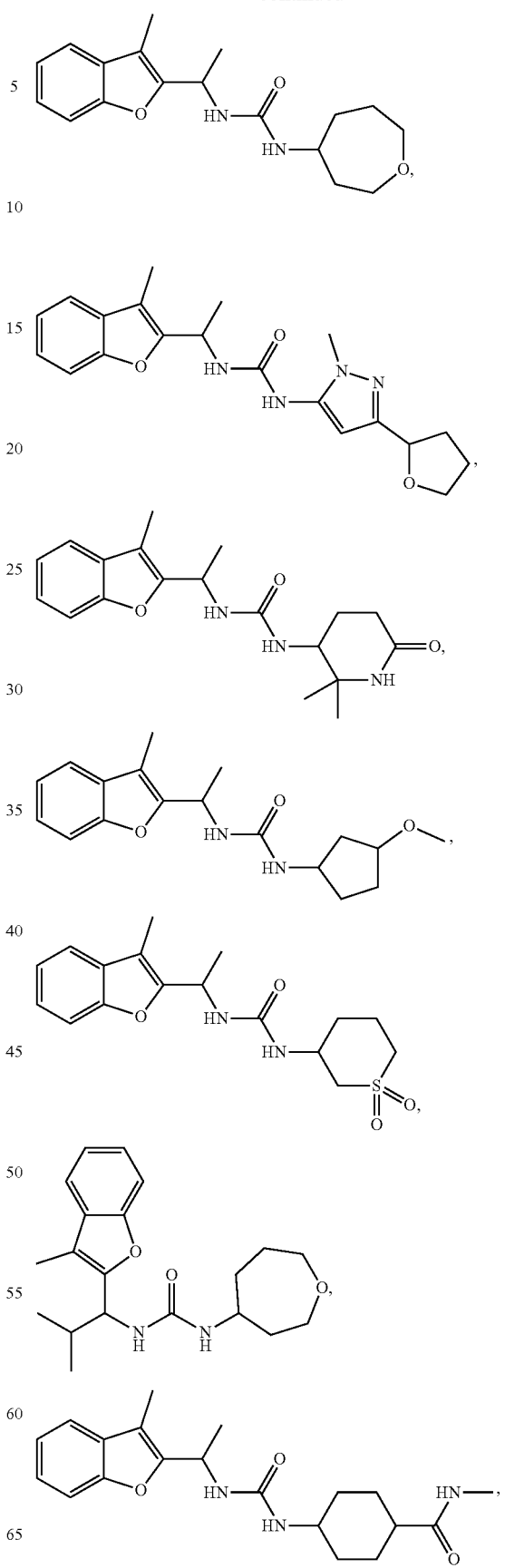

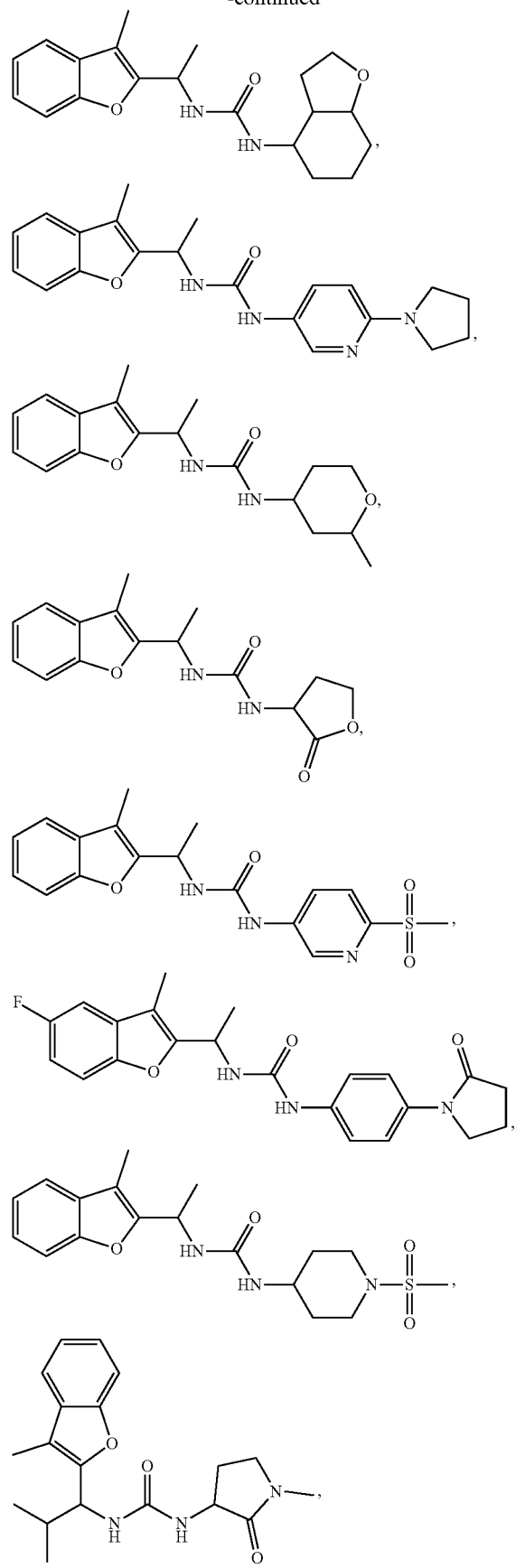
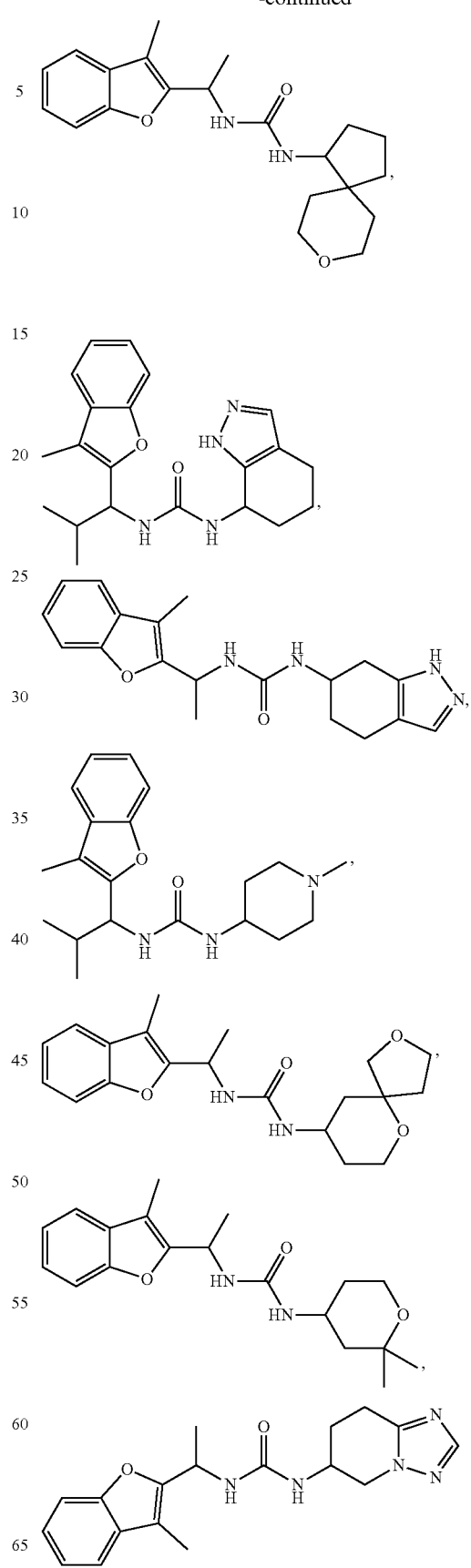

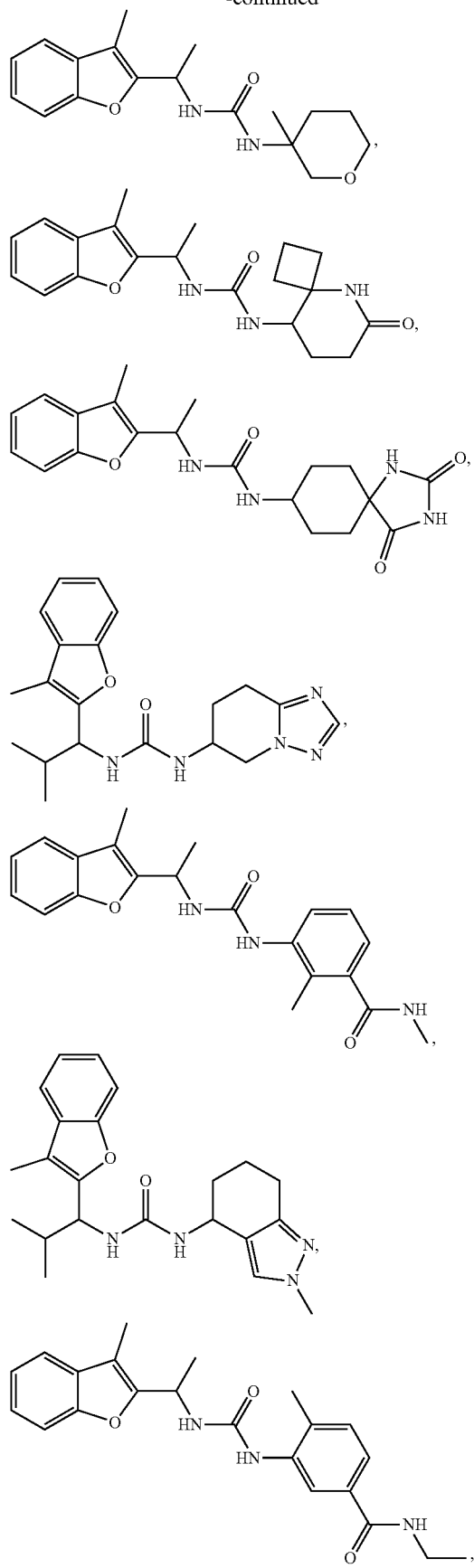
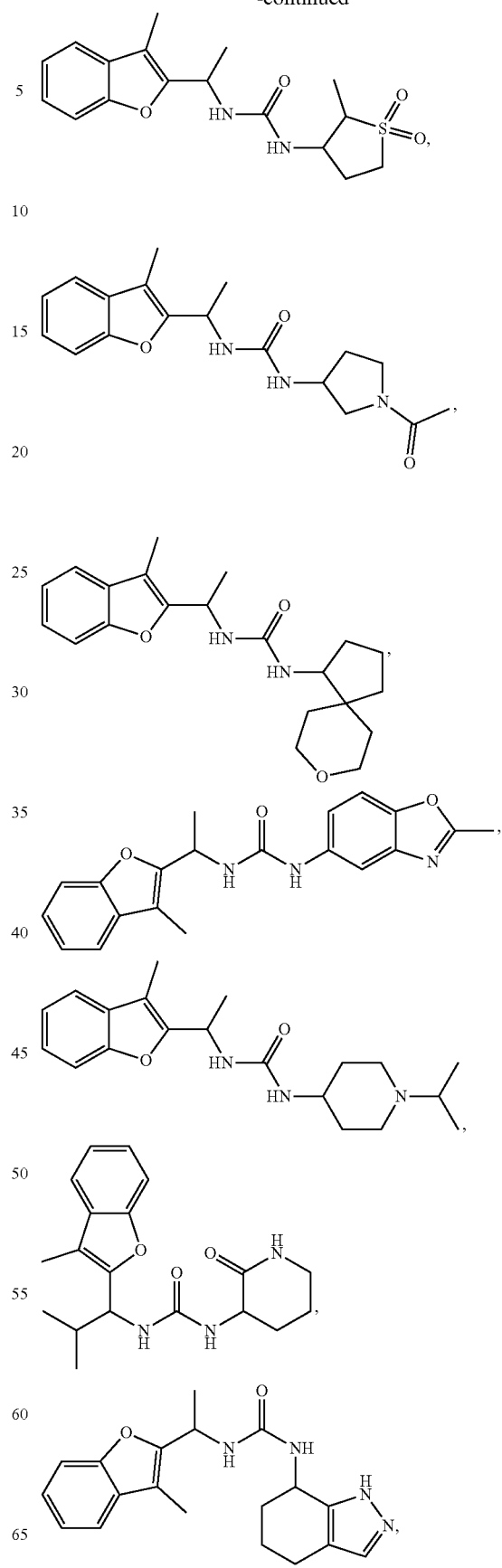

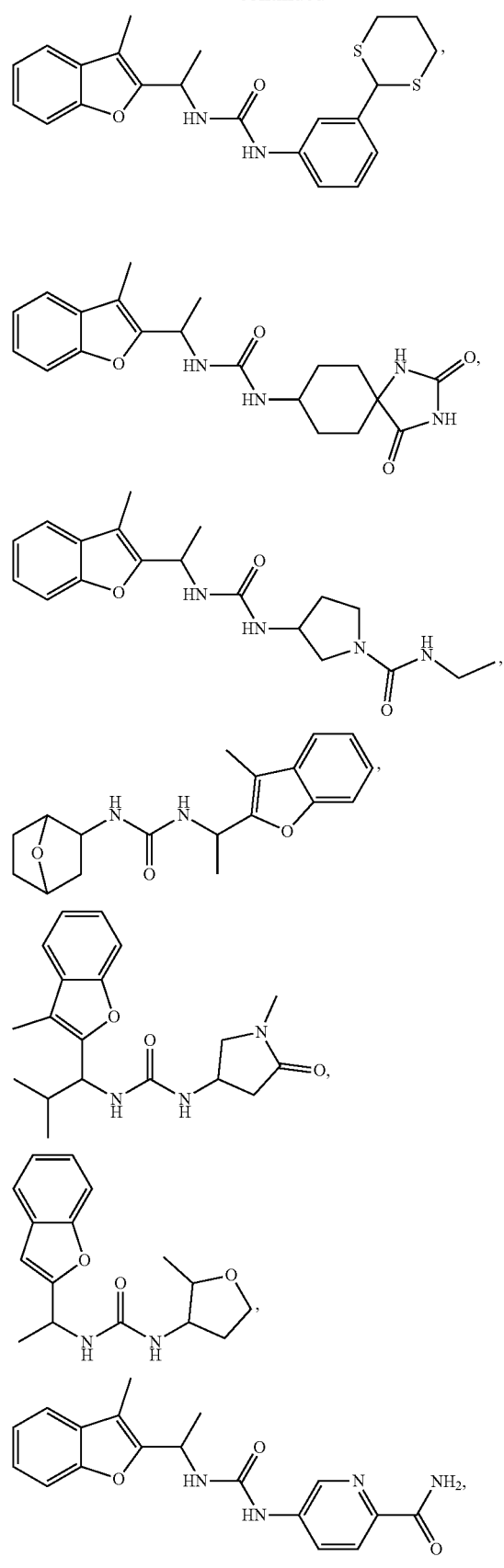
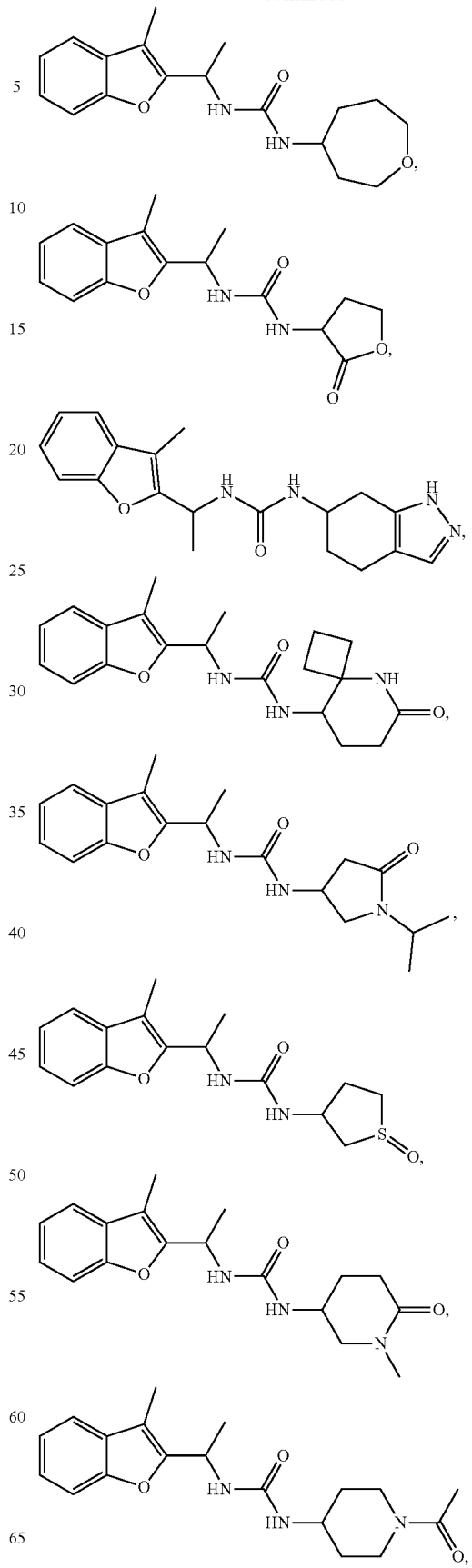

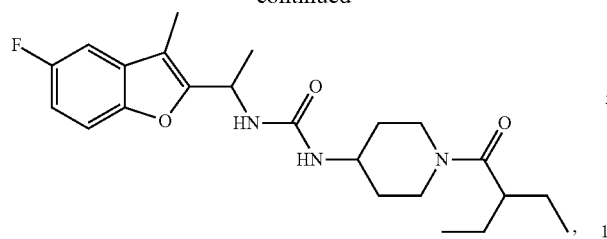
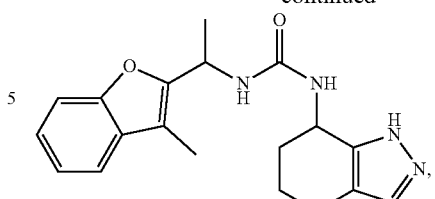
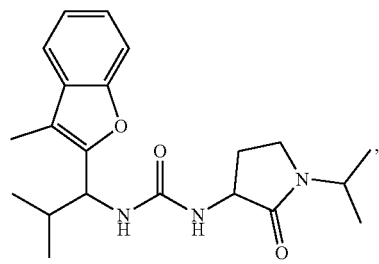
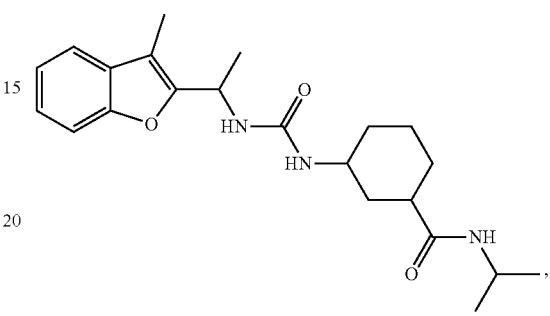
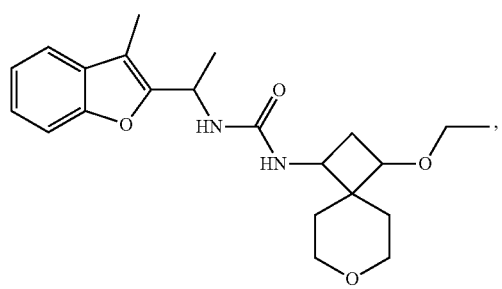
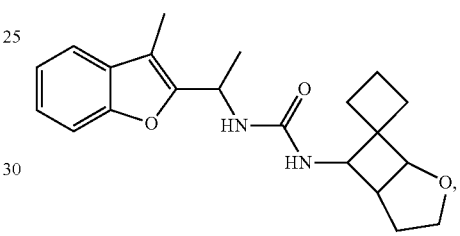
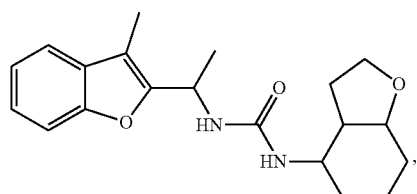
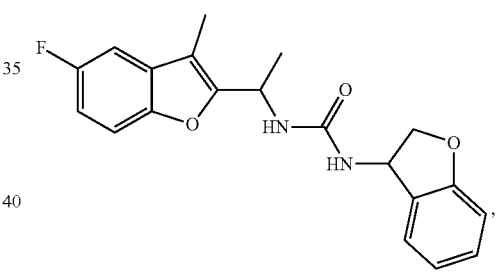
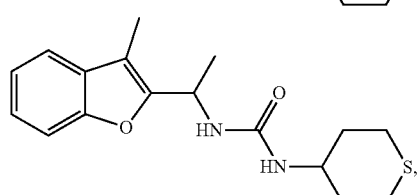
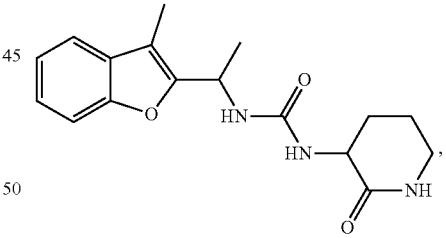
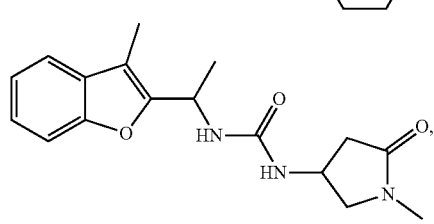
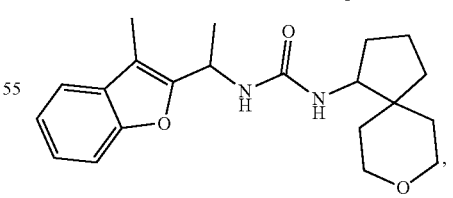
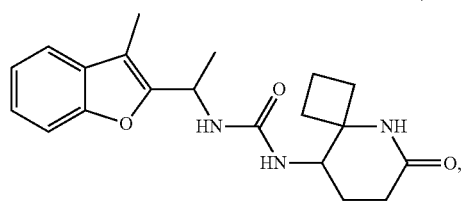
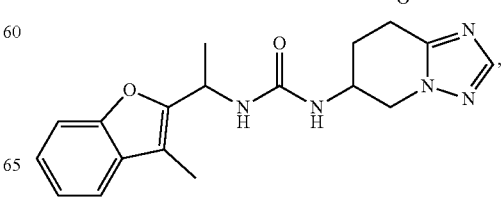

95
-continued
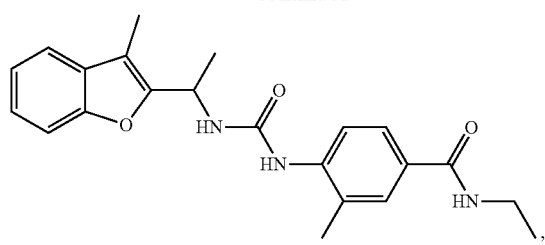
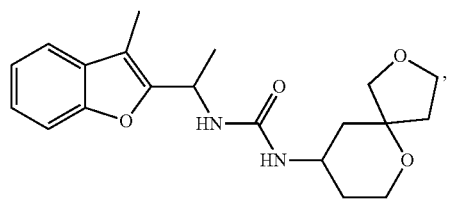
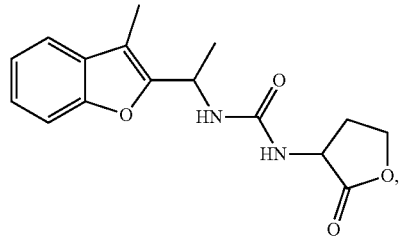
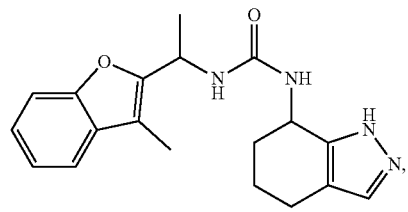
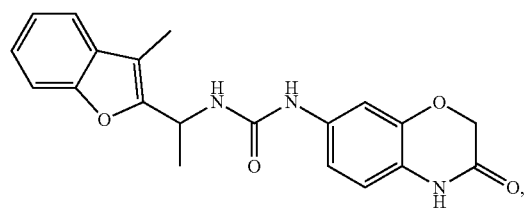
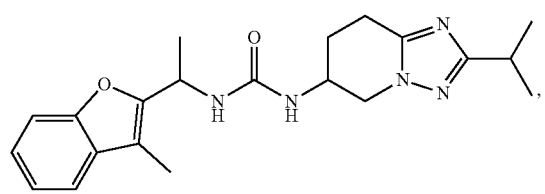
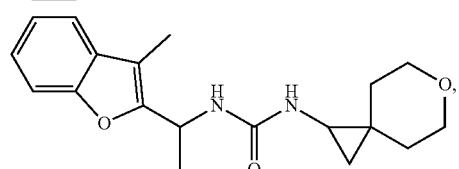
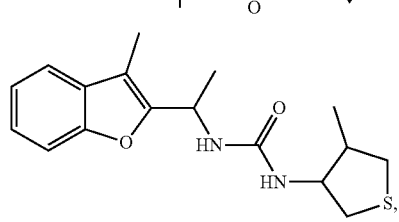
96
-continued
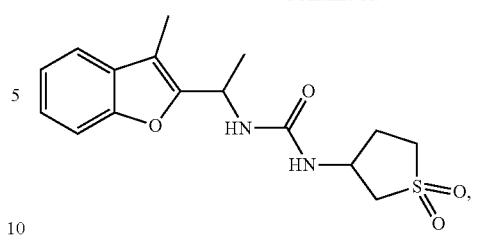
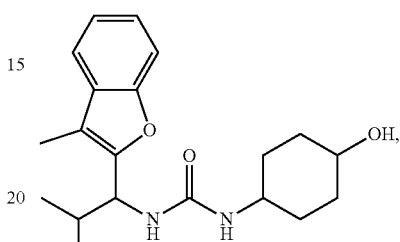
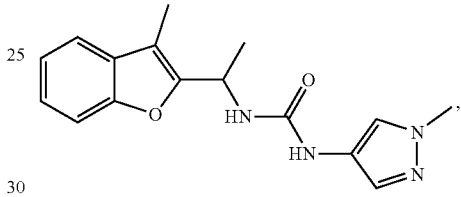
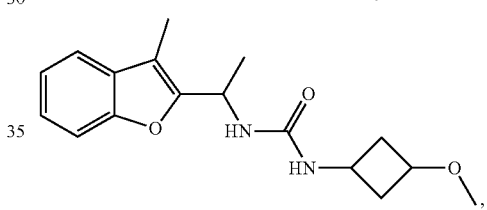
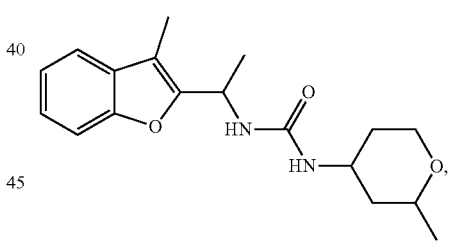
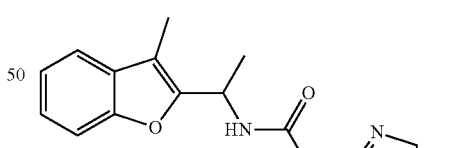
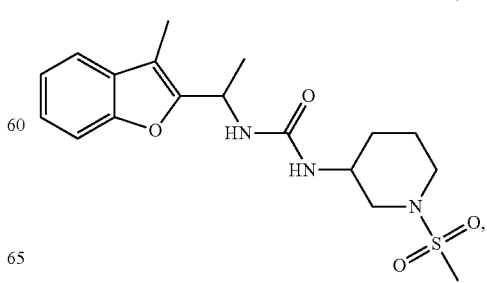

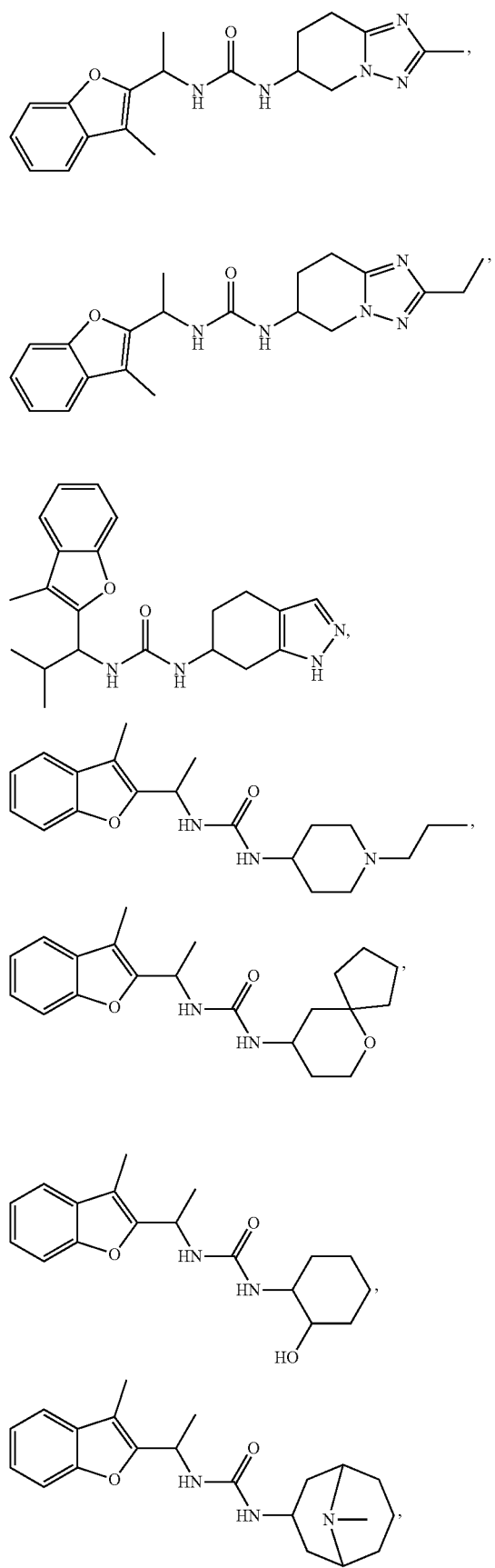
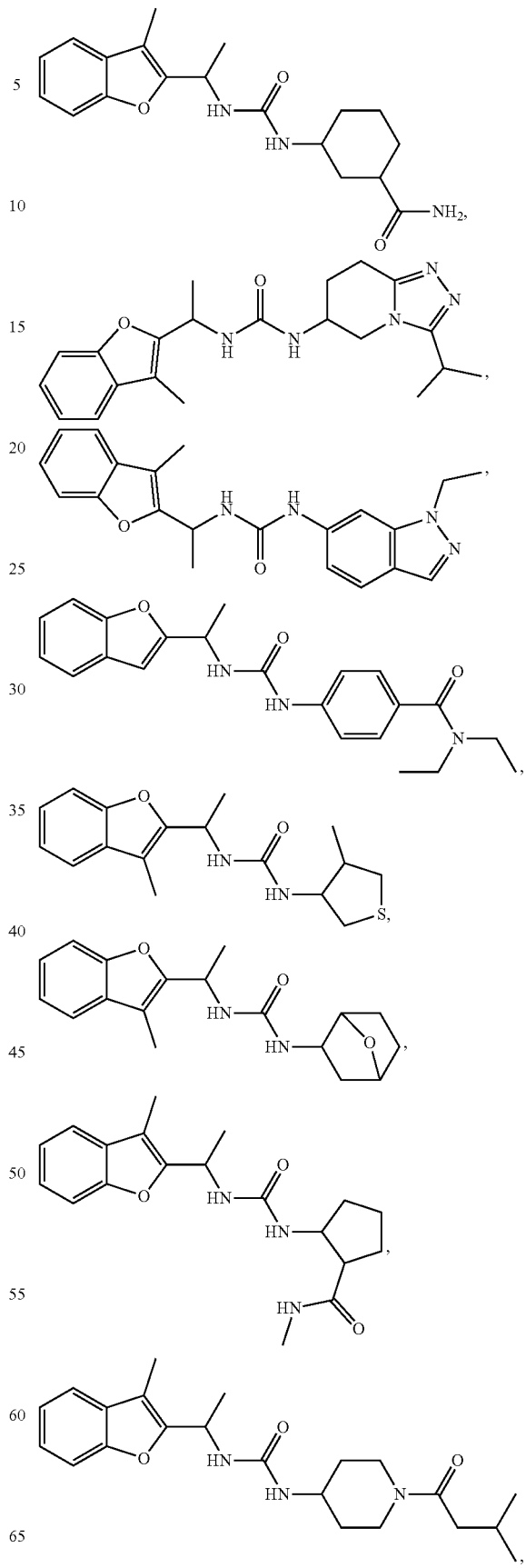

99
-continued
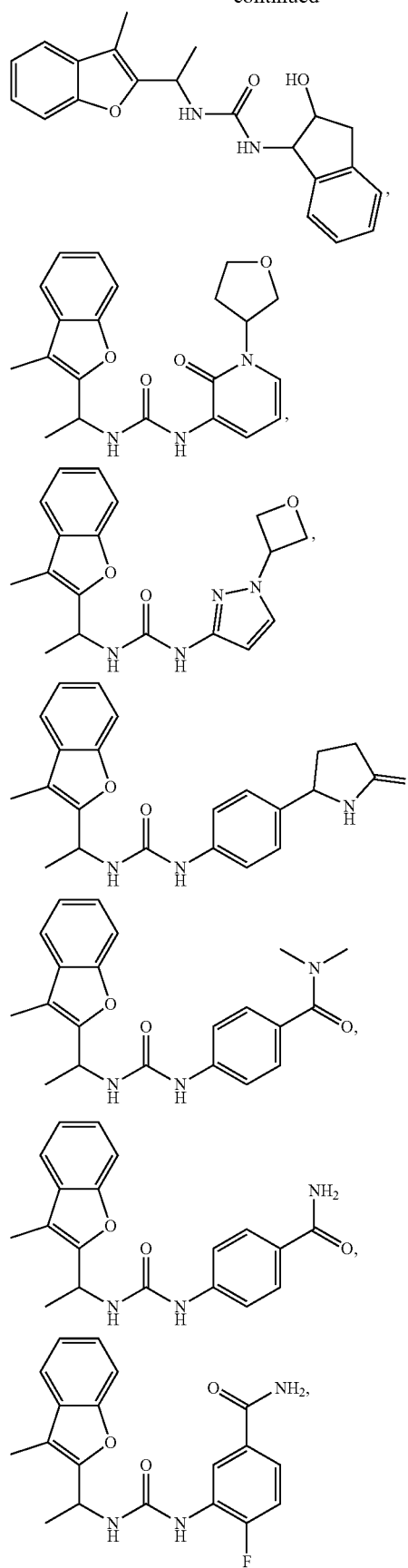
100
-continued
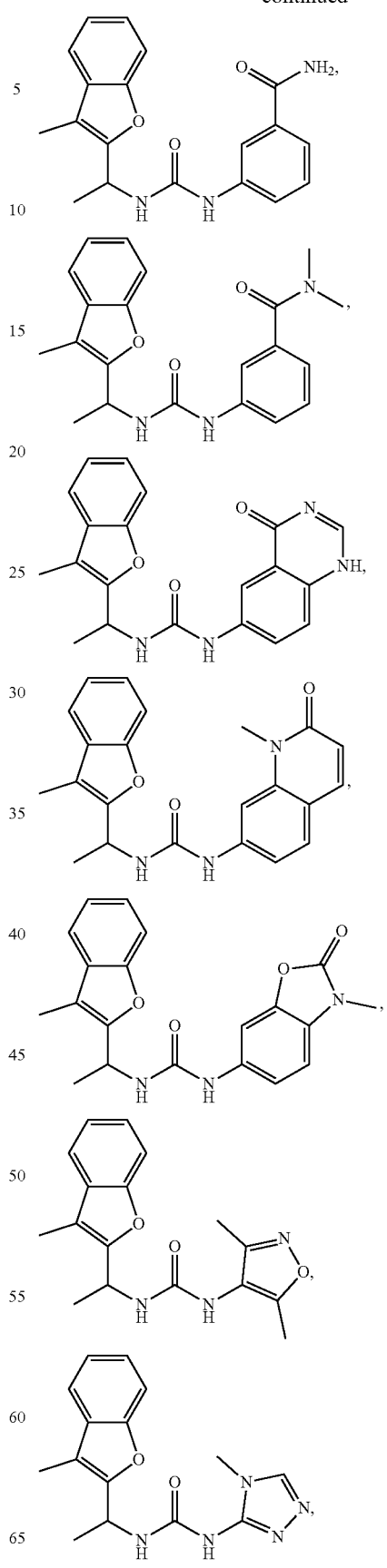

101
-continued
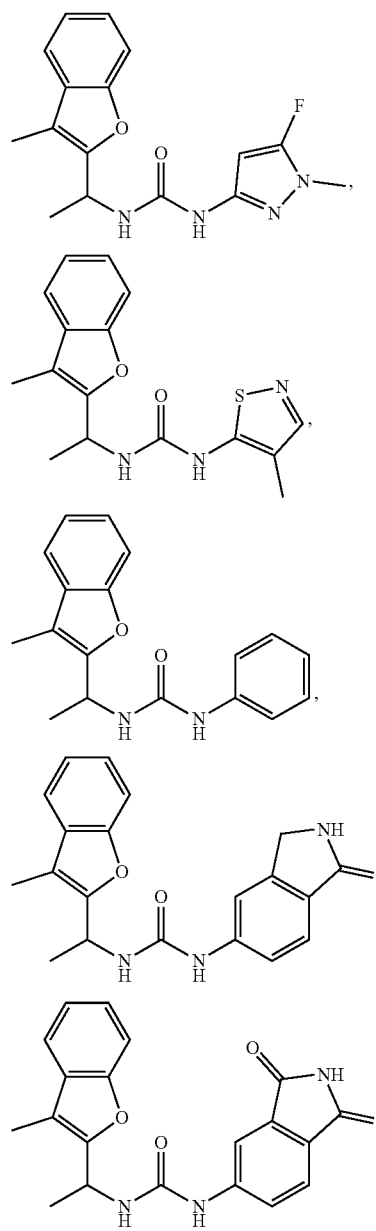
In some embodiments, when Z is $NR^x$ and $R^3$ is methyl, Ring A is not phenyl.
Some embodiments provide a compound of Formula (I), or a pharmaceutically acceptable salt thereof, as described herein, wherein the compound is not a compound selected from the group consisting of:
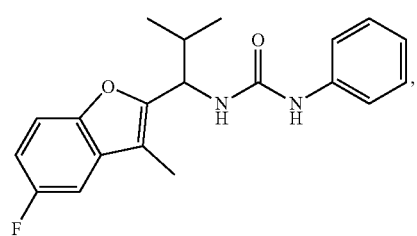
102
-continued
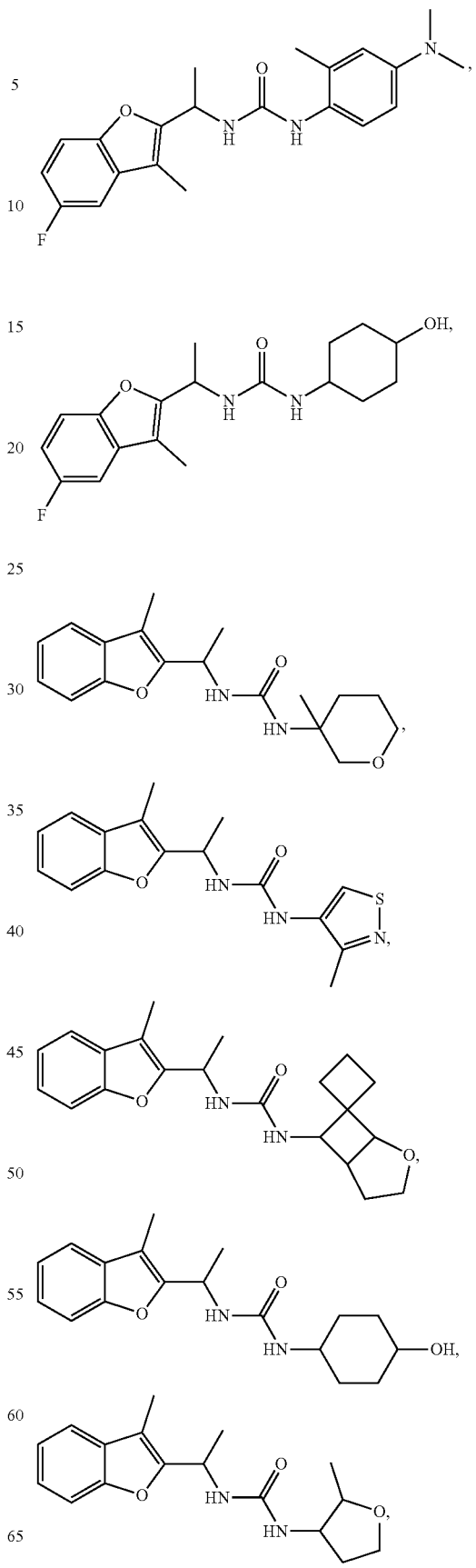

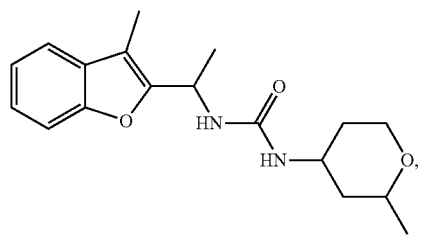
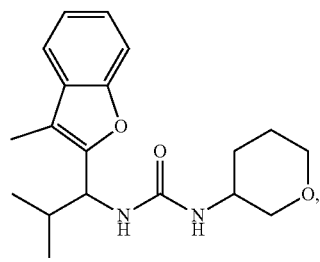
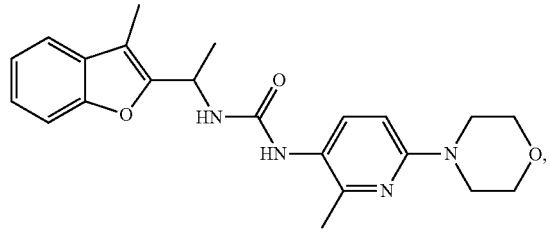
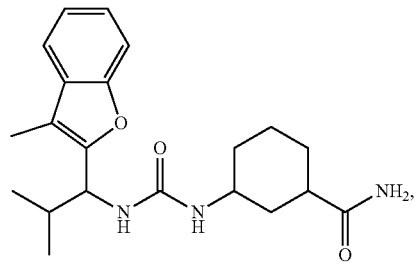
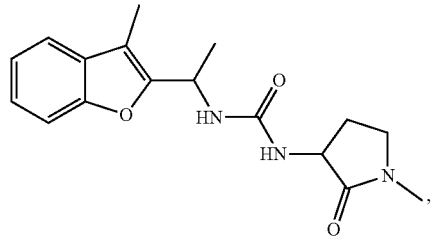
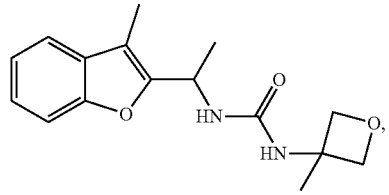
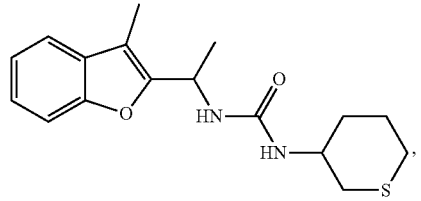
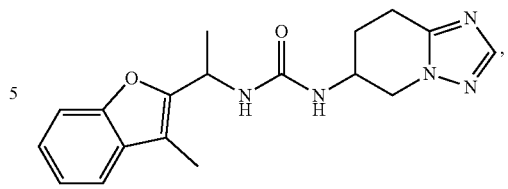
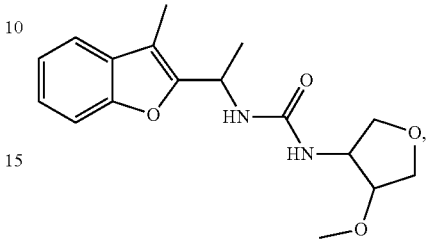
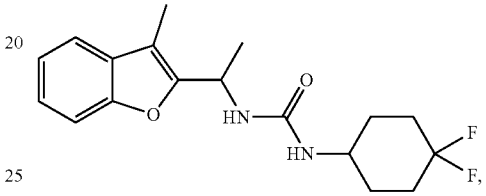
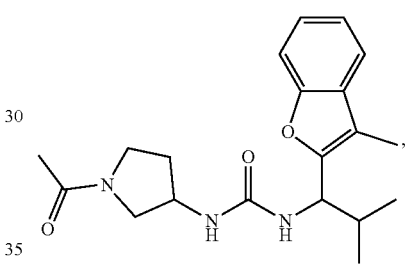
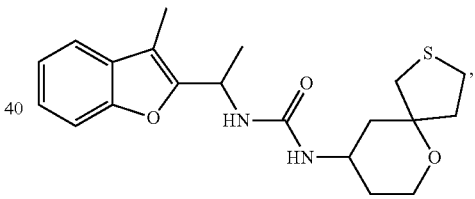
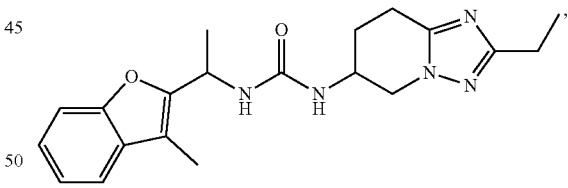
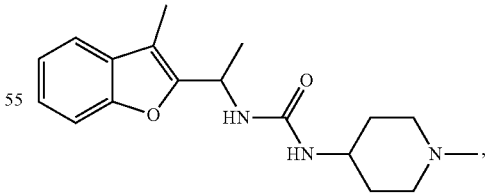
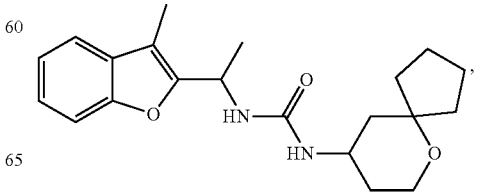

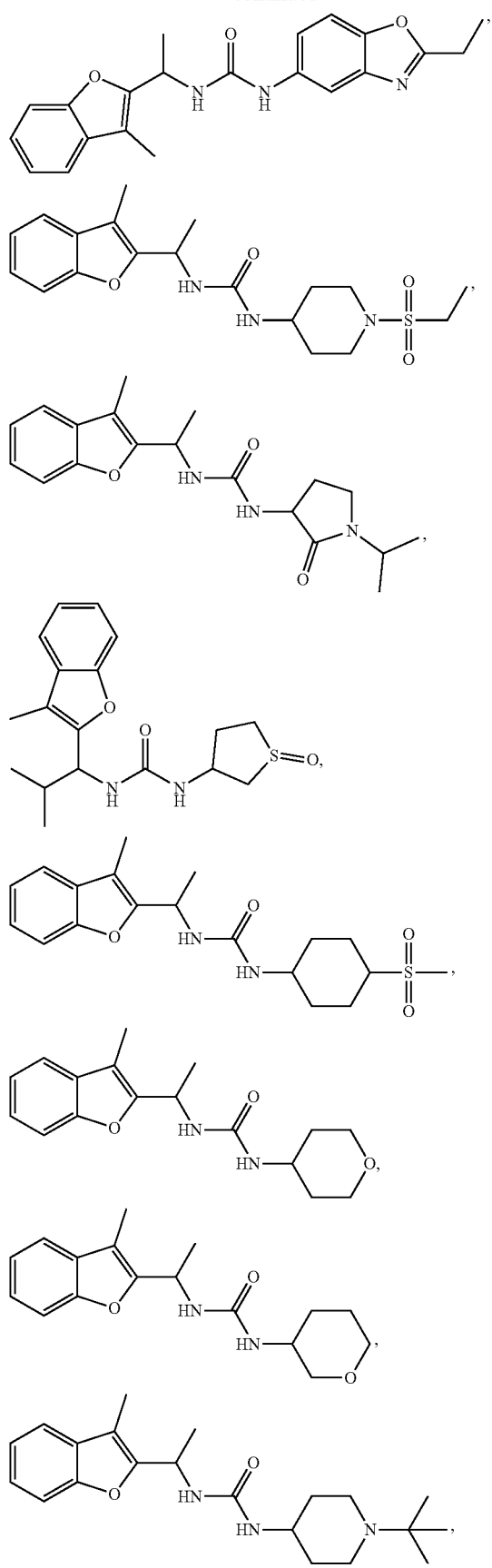
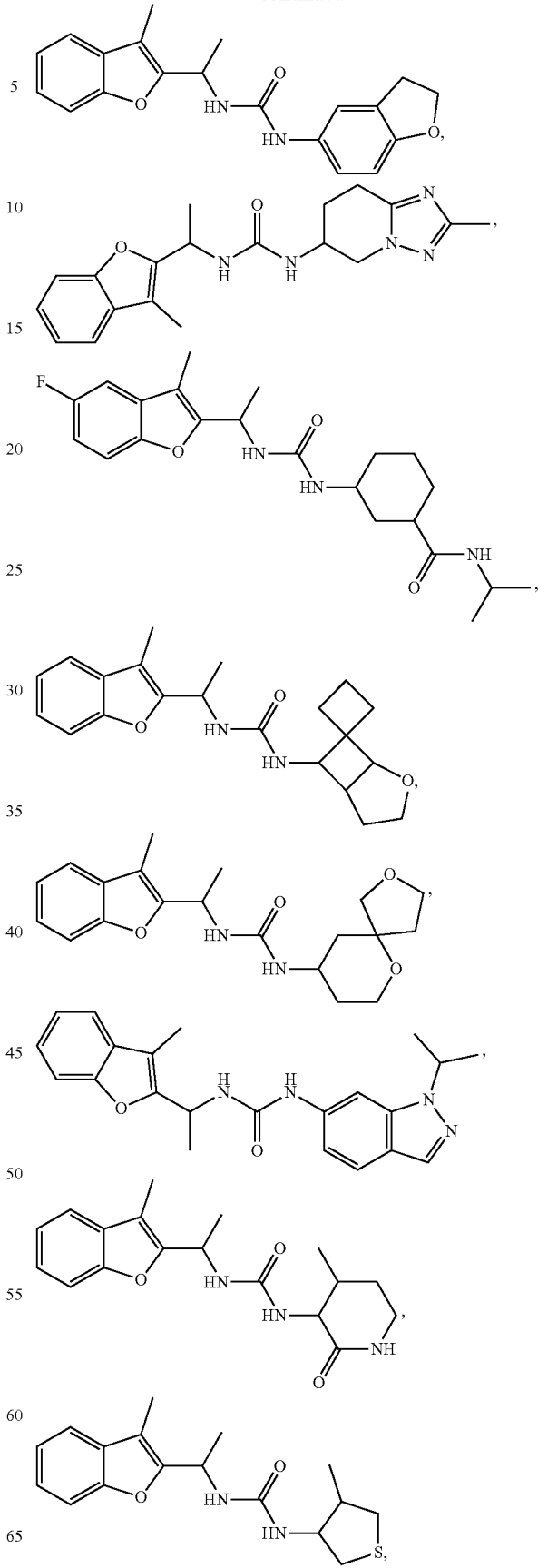

107
-continued
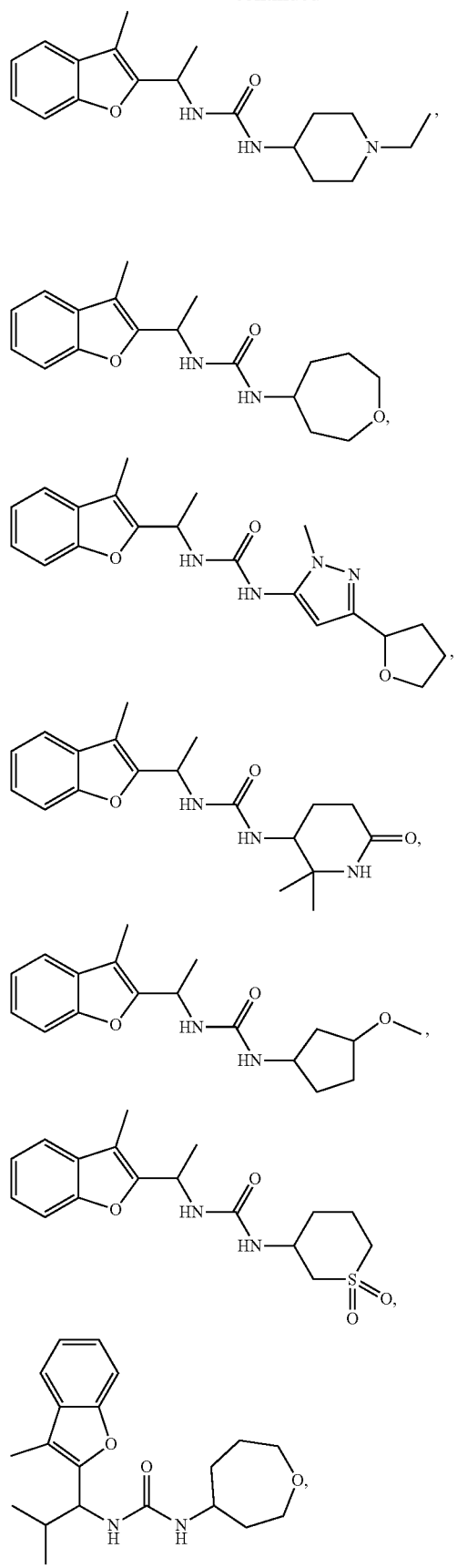
108
-continued
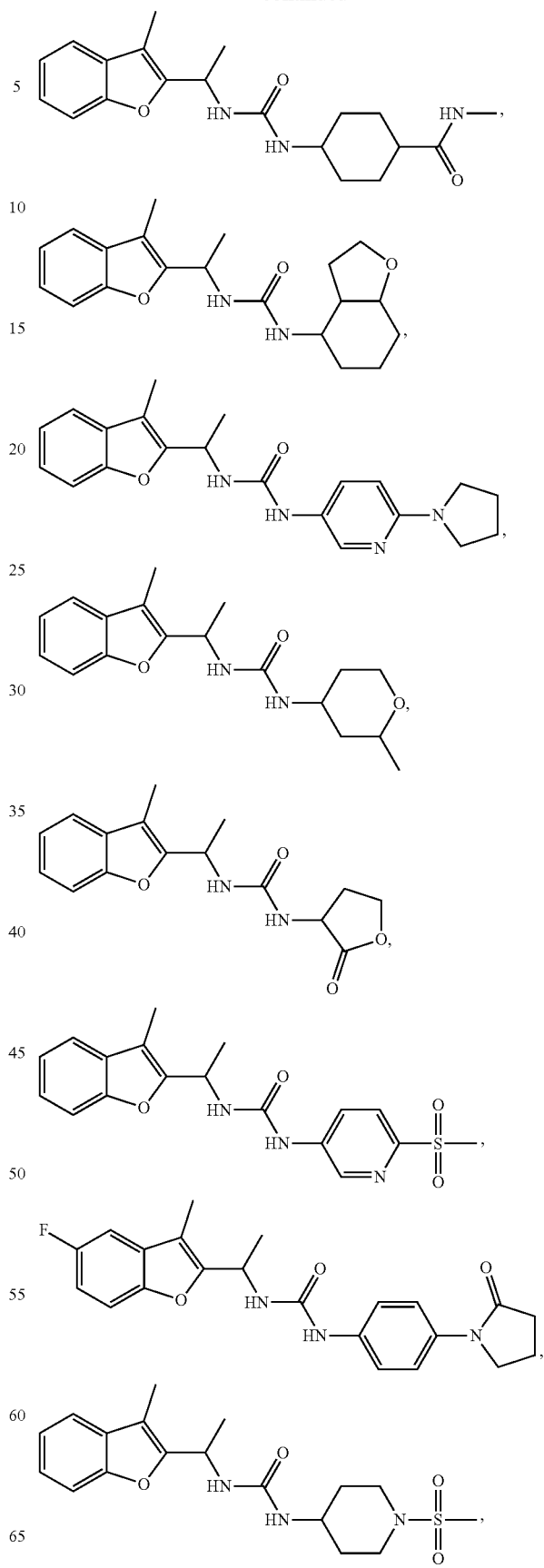

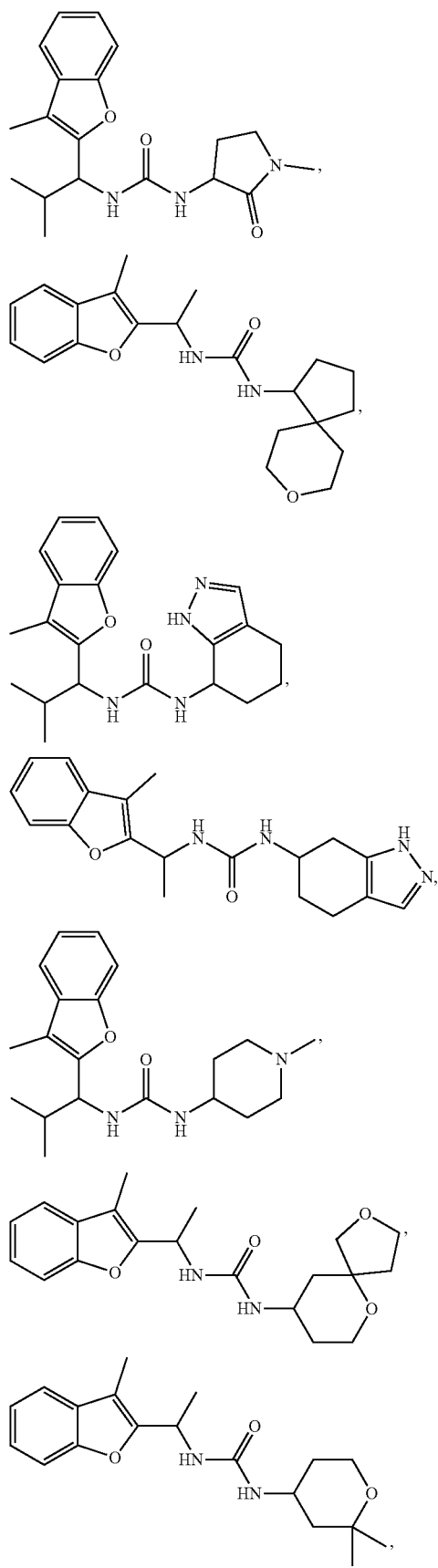
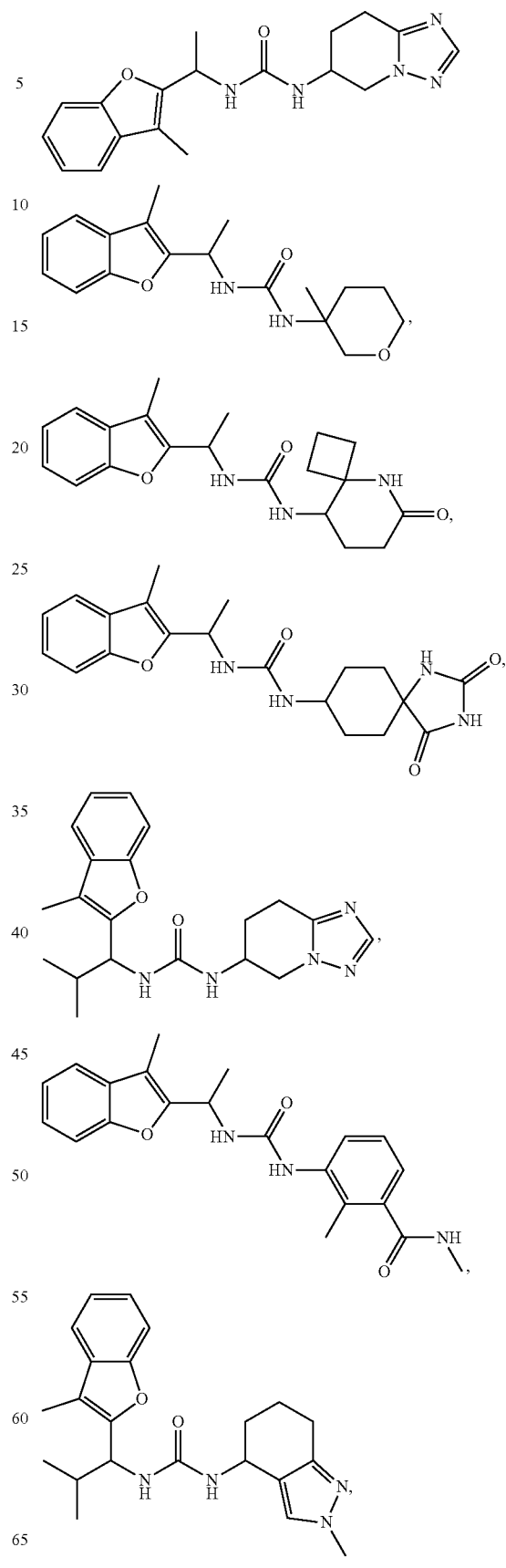

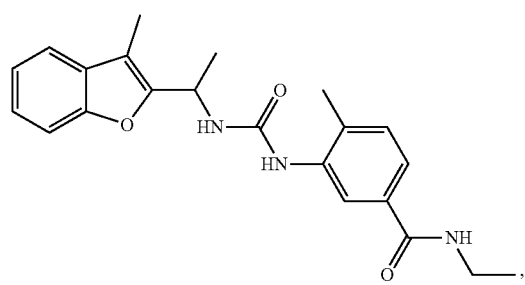
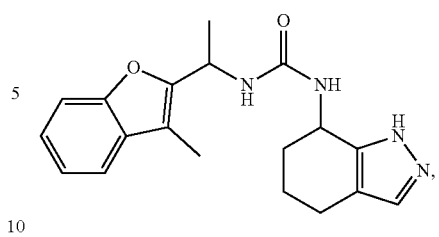
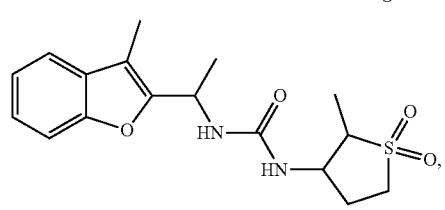
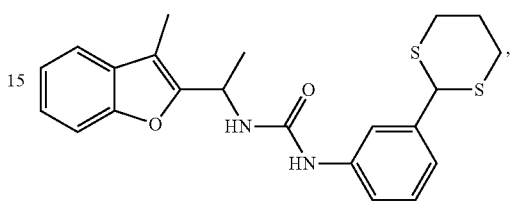
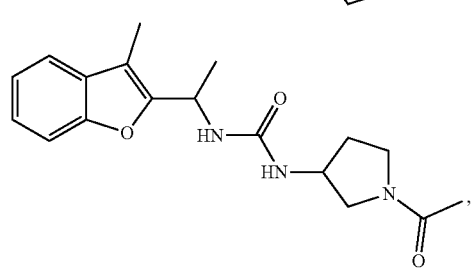
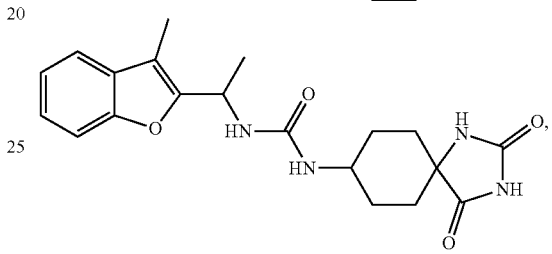
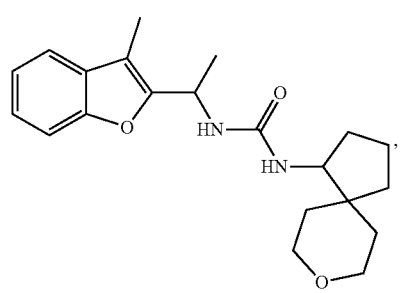
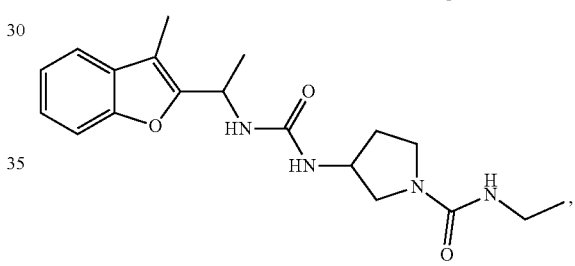
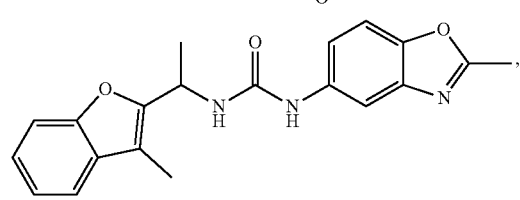
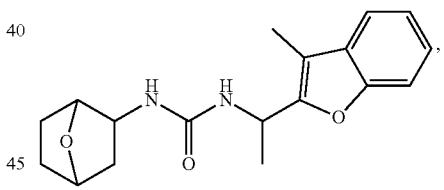
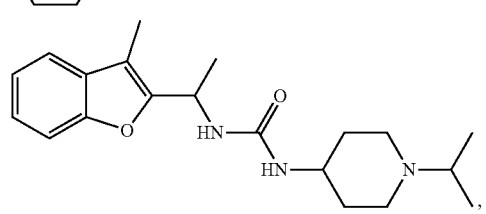
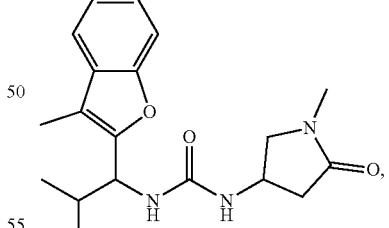
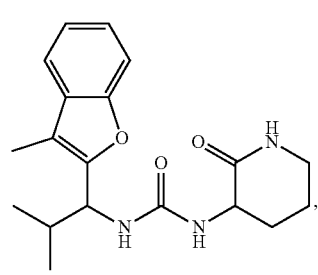
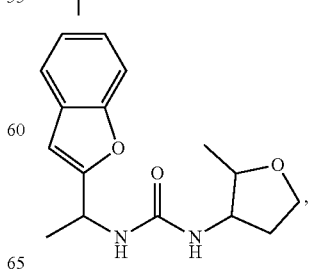

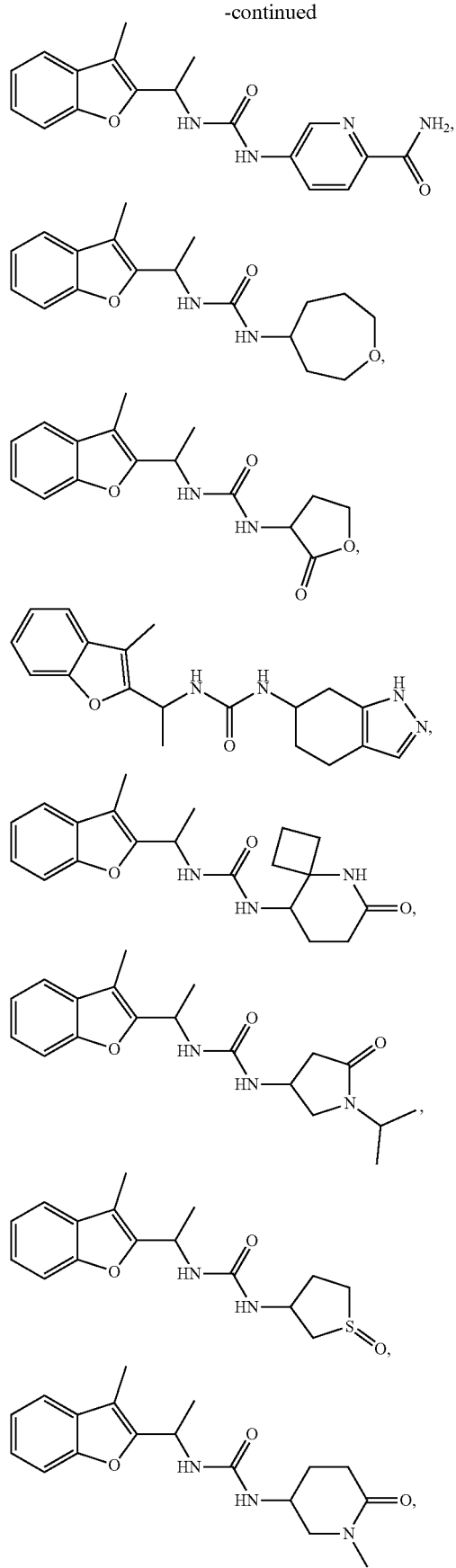
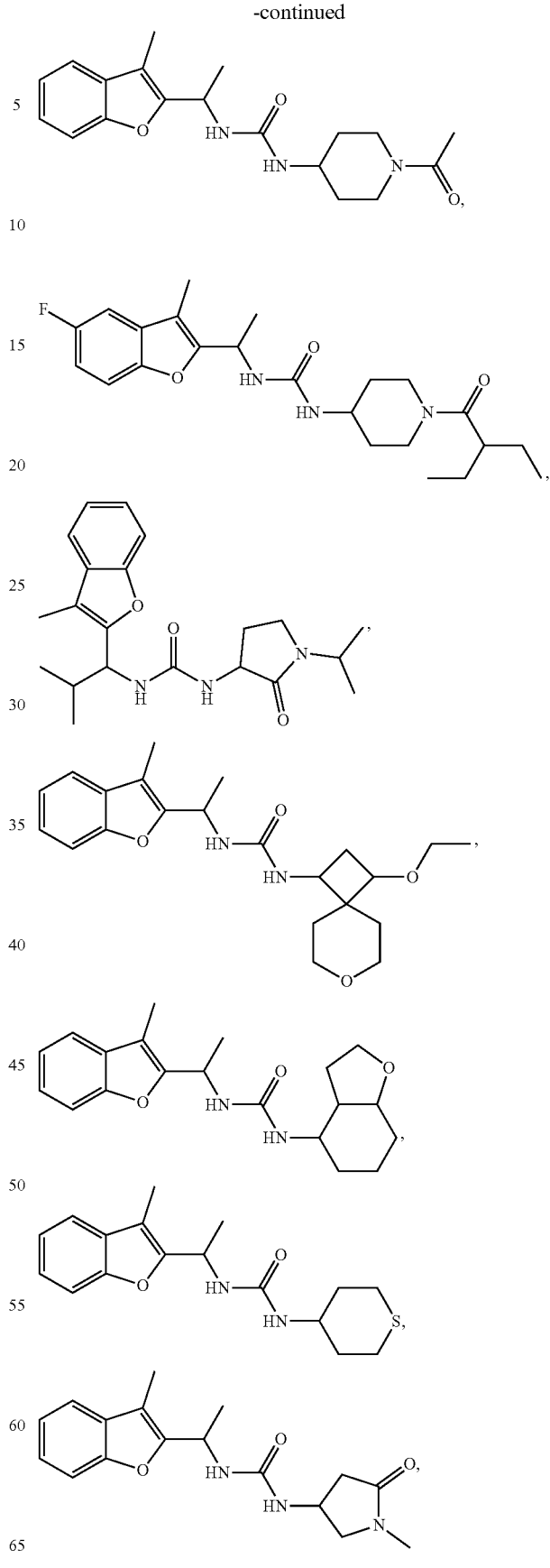

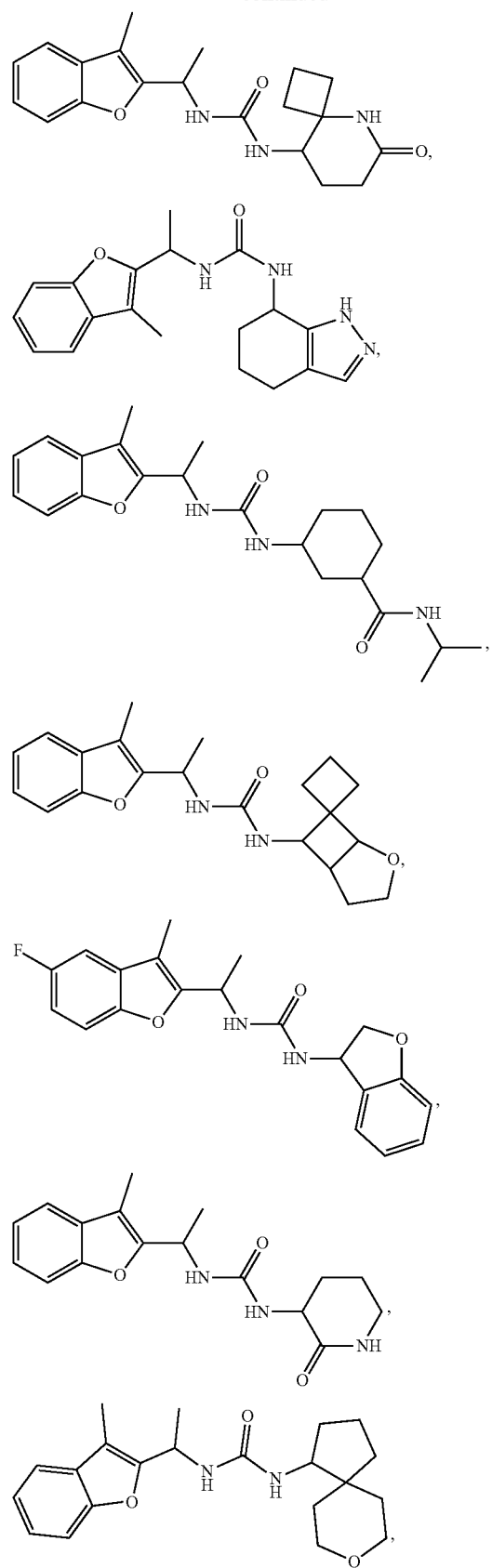
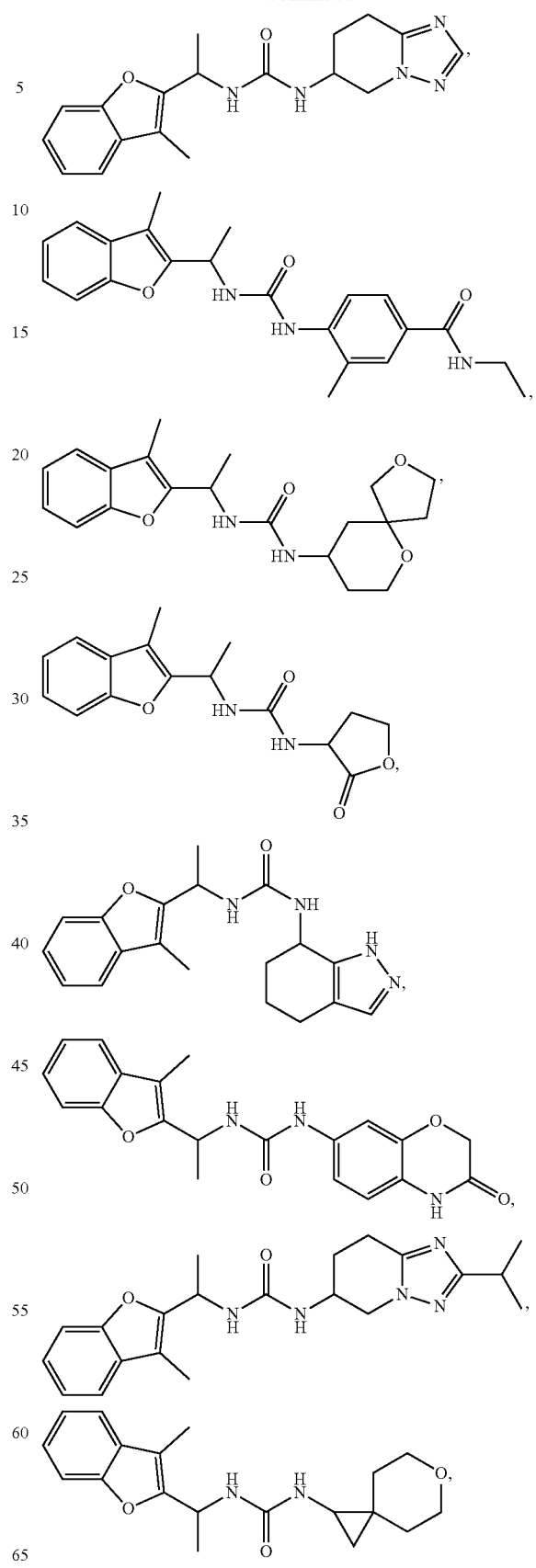

117
-continued
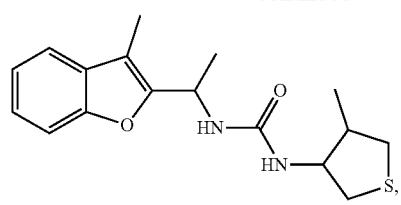
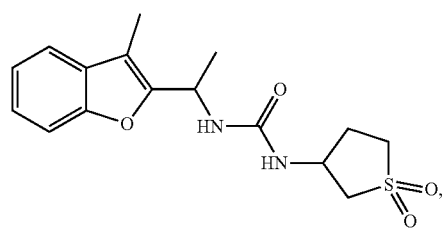
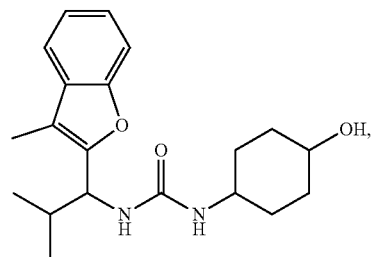
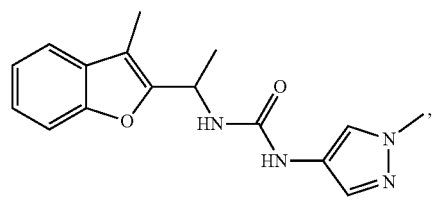
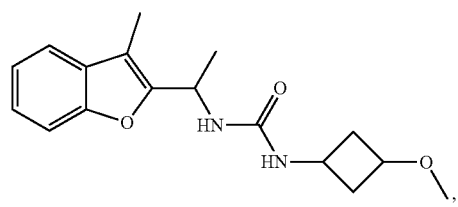
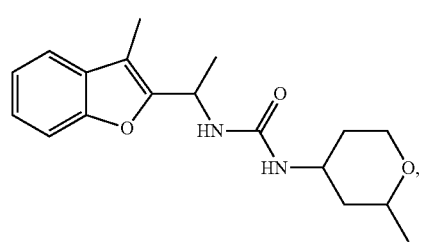
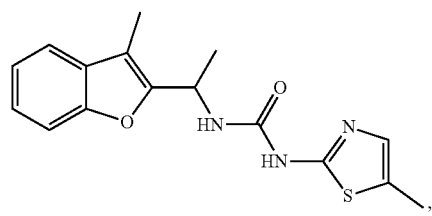
118
-continued
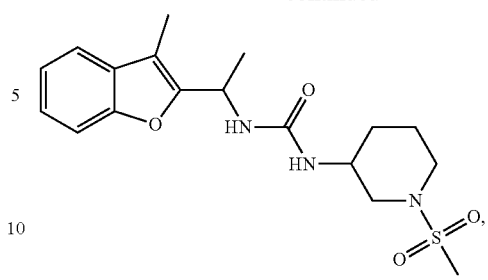
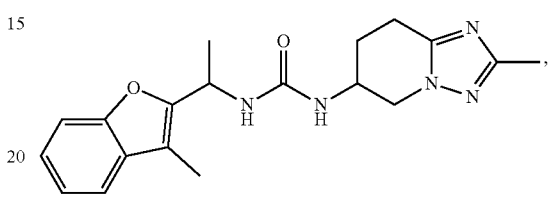
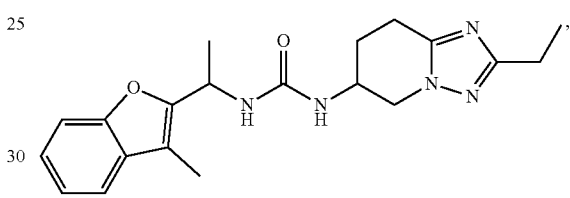
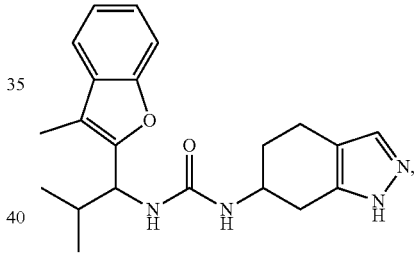
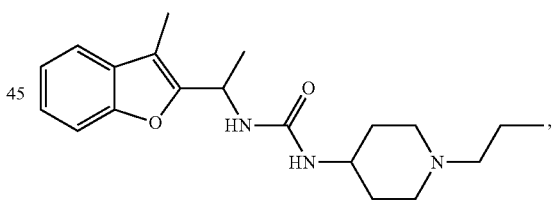
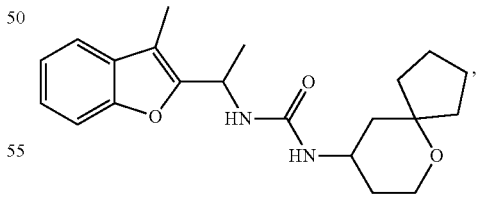
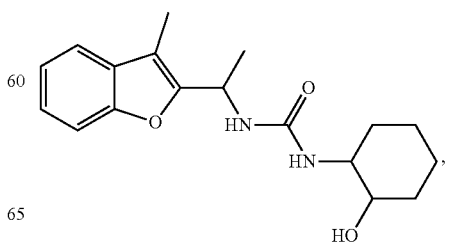

119
-continued
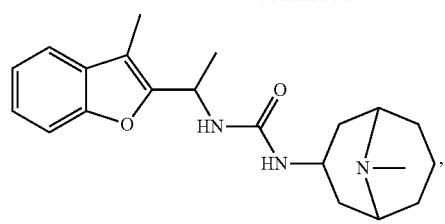
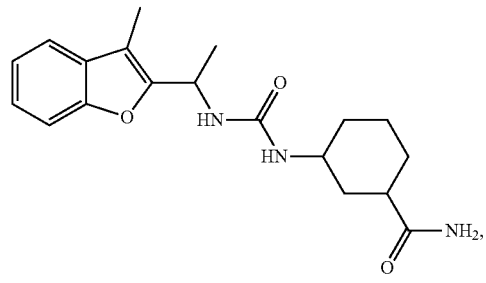
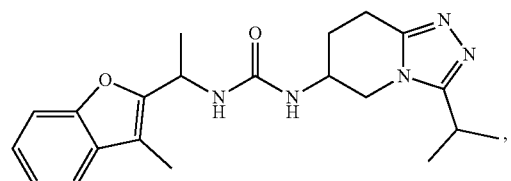
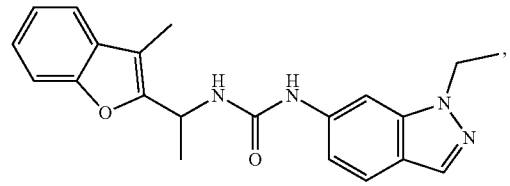
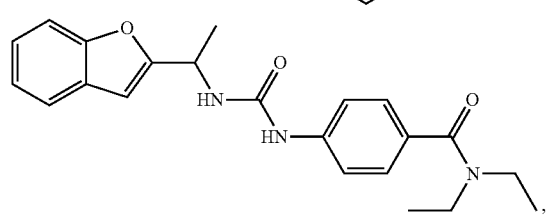
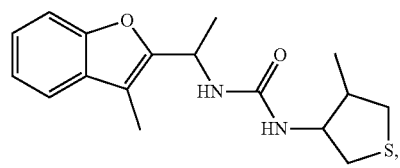
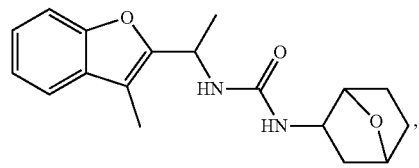
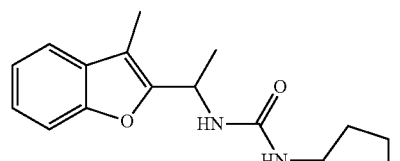
120
-continued
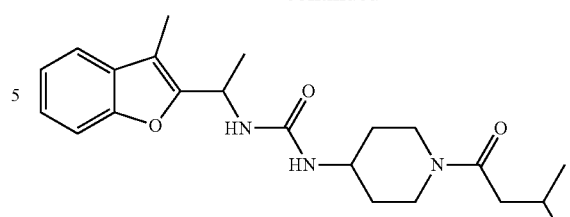
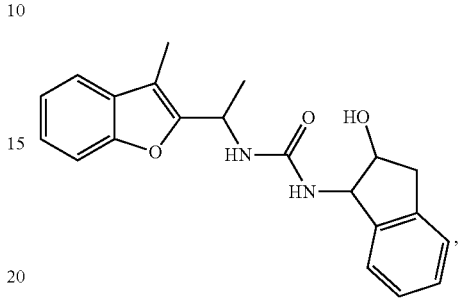
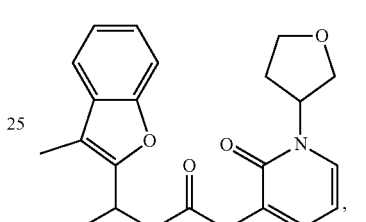
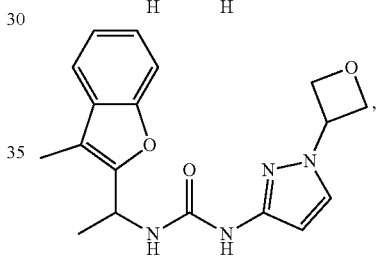
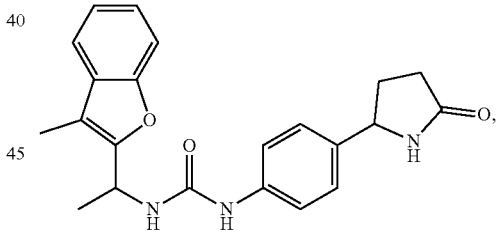
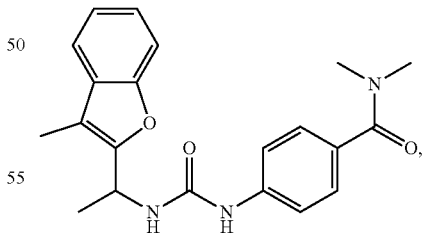
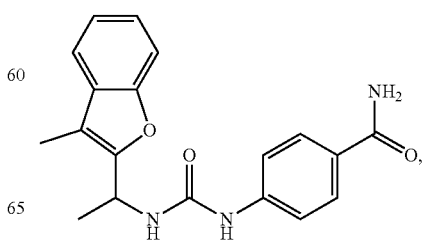

121
-continued
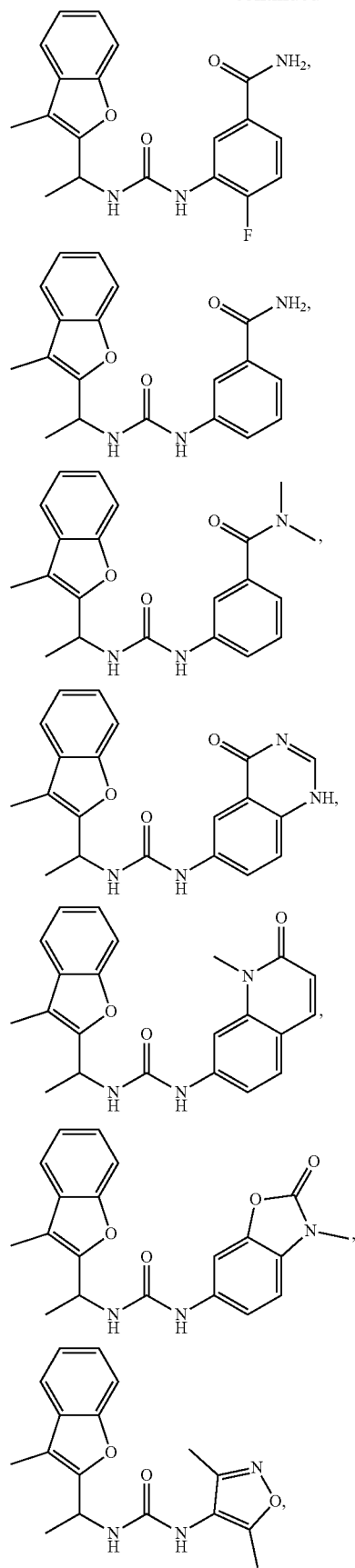
122
-continued
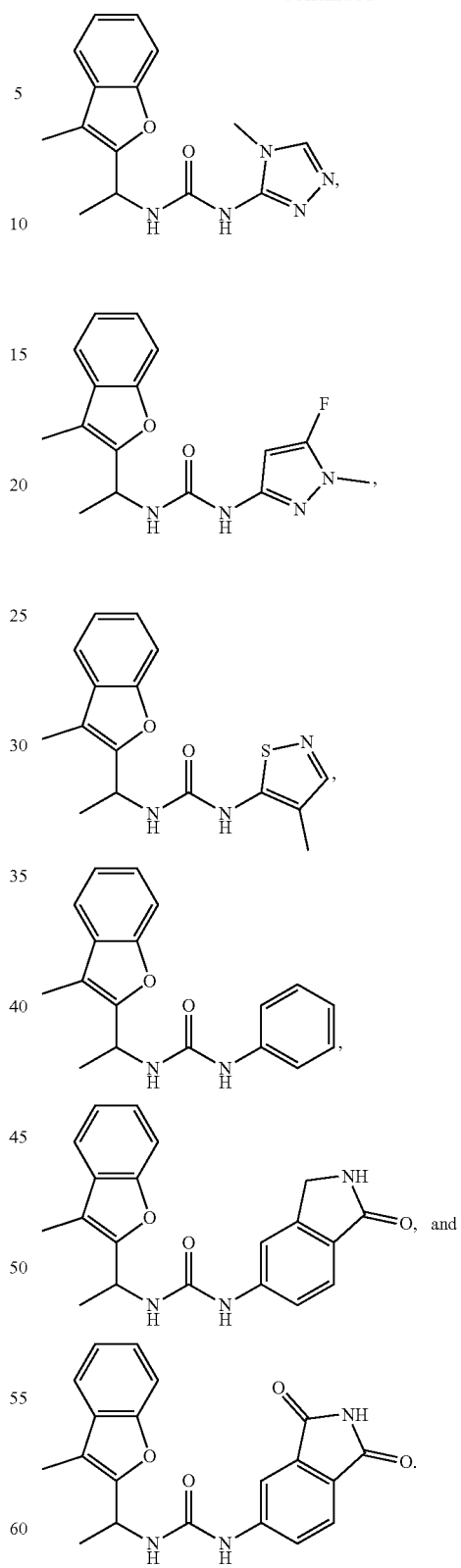
Some embodiments provide a compound of Formula (I), or a pharmaceutically acceptable salt thereof, as described herein, wherein the compound is not a compound selected from the group consisting of:

123
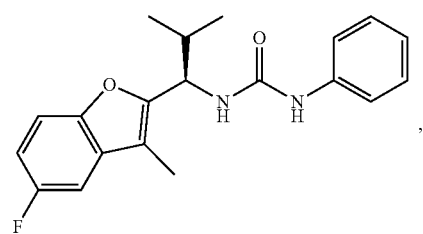
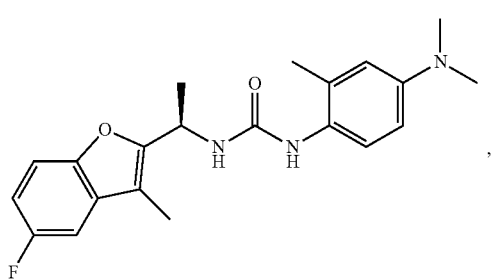
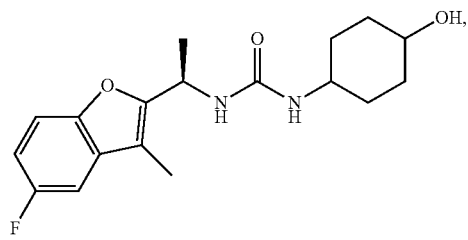
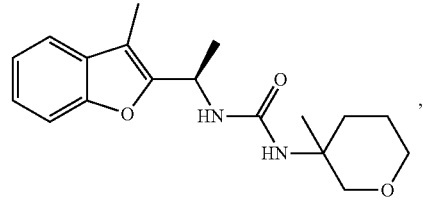
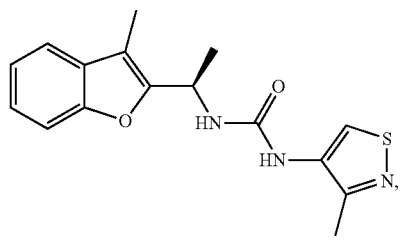
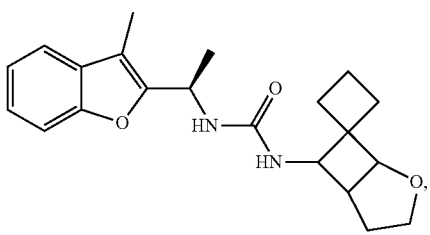
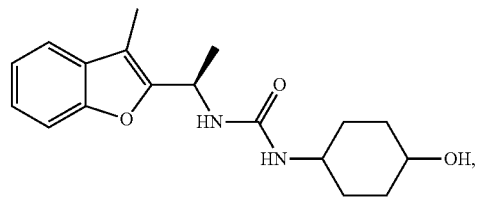
124
-continued
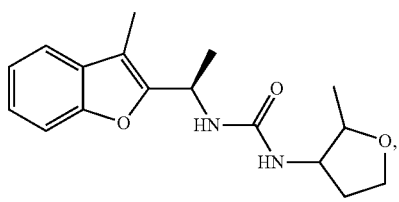
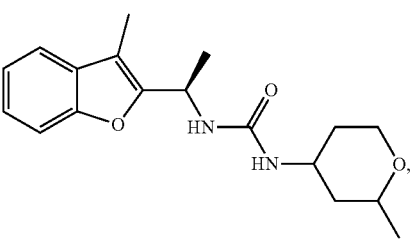
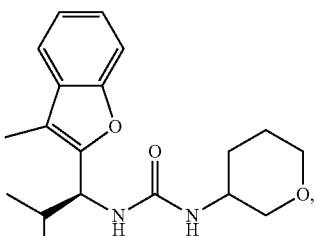
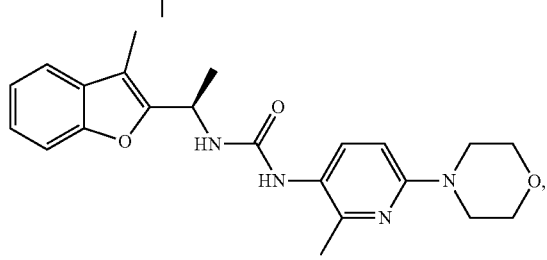
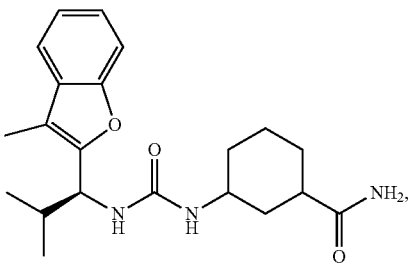
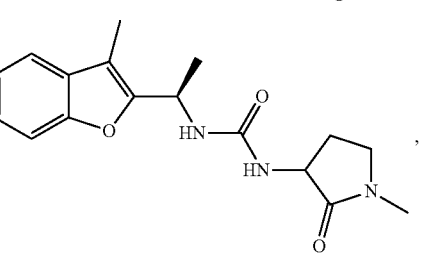
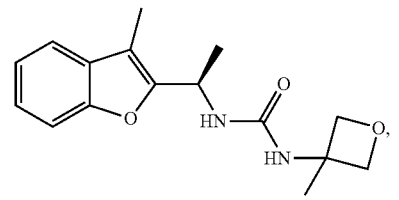

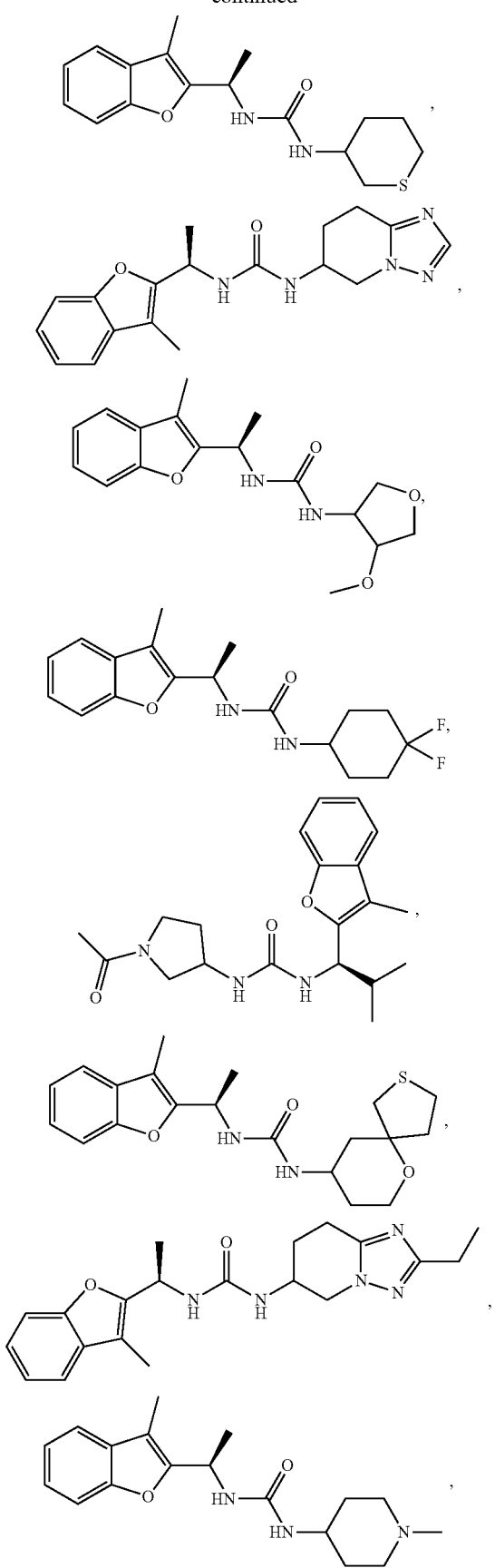
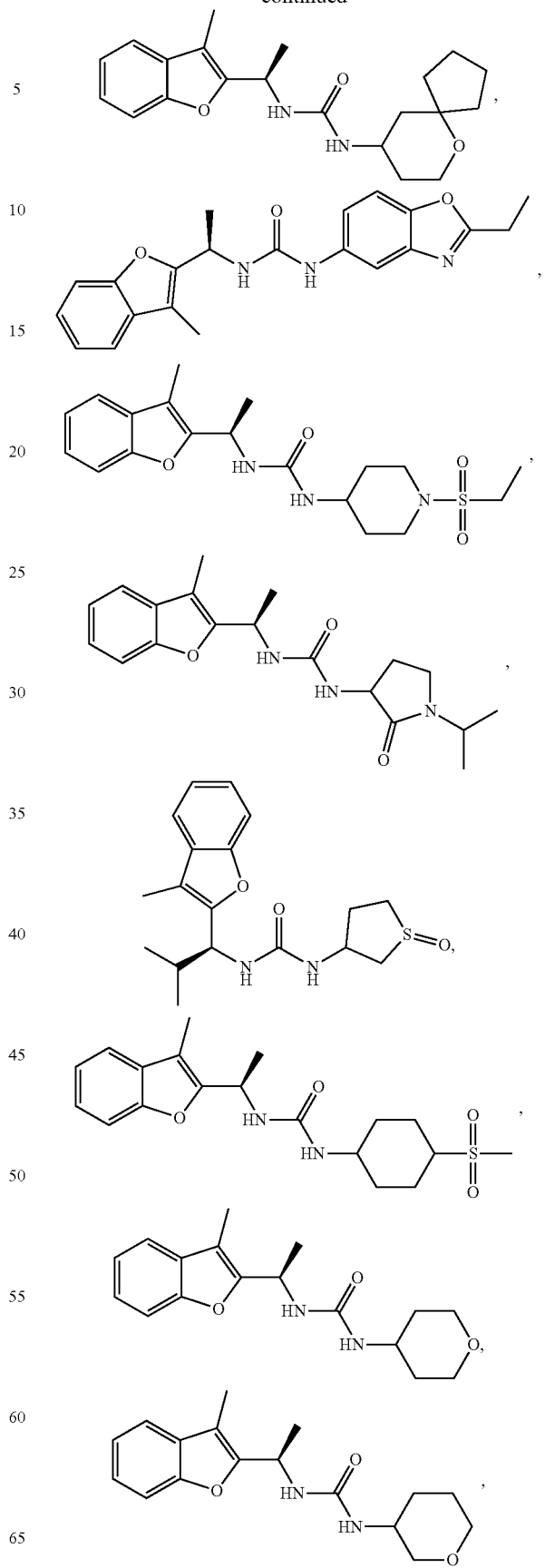

127
-continued
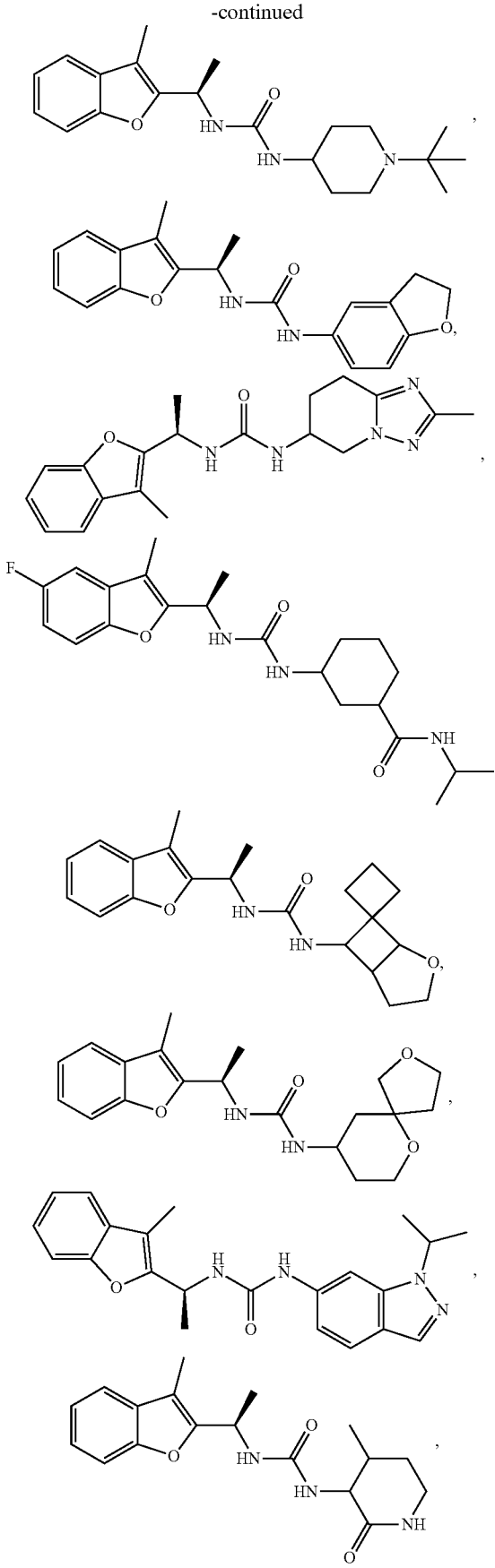
128
-continued
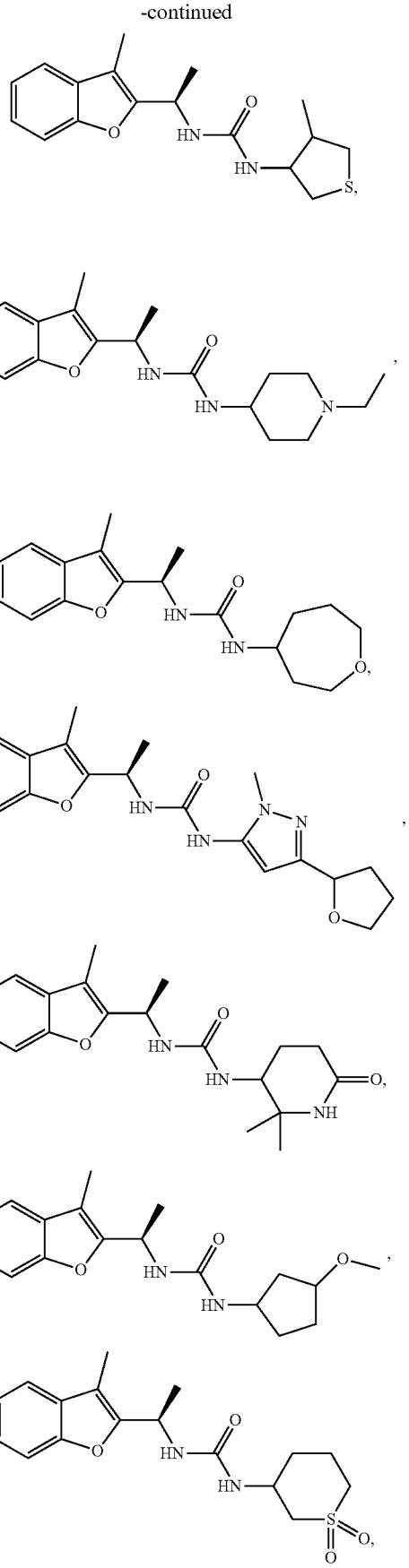

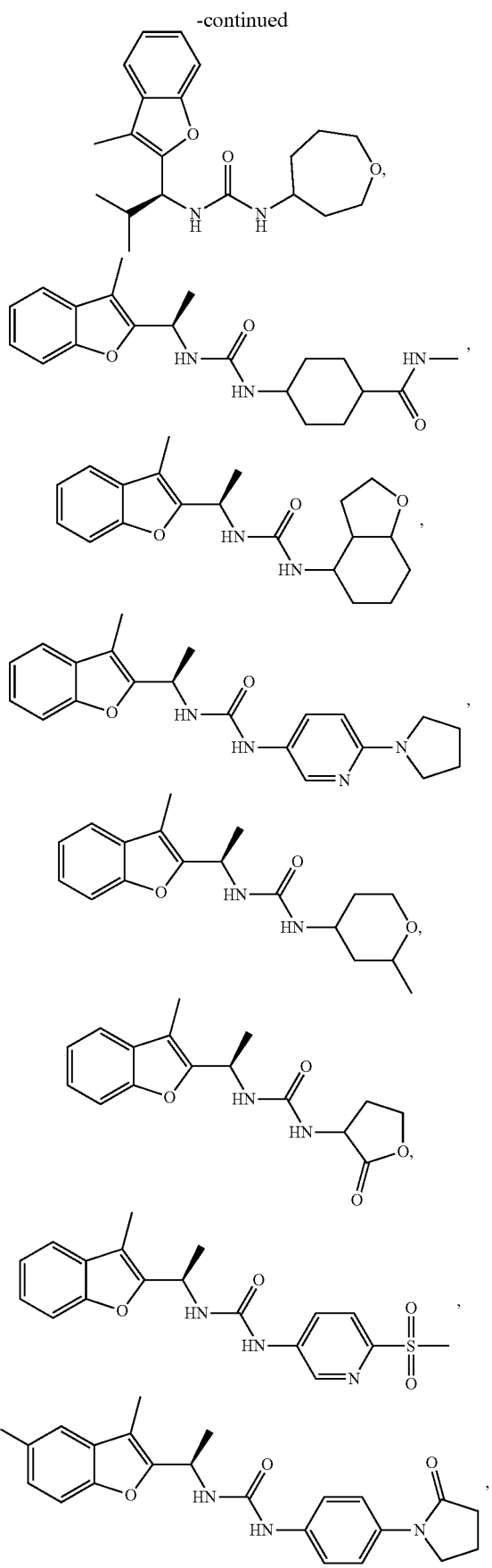
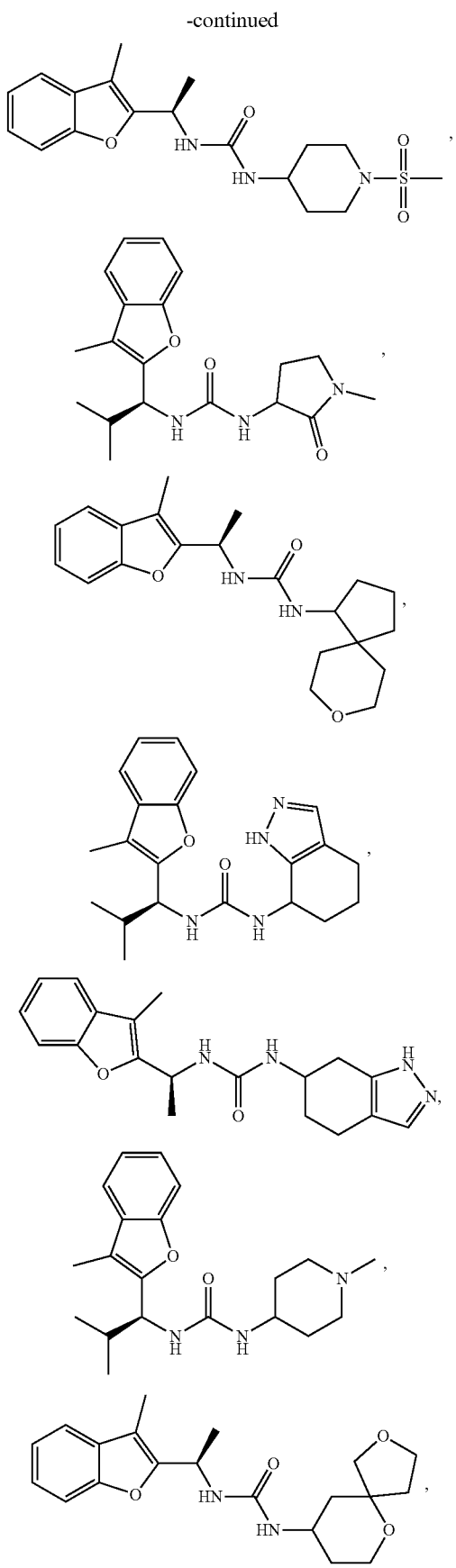

-continued
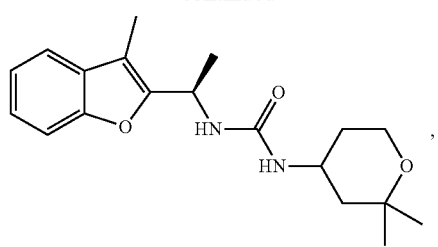
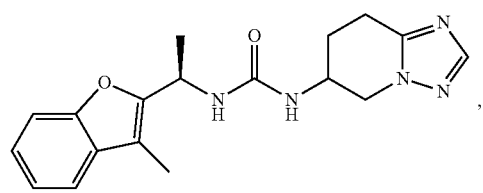
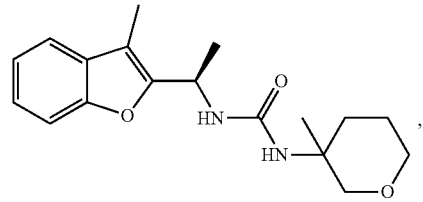
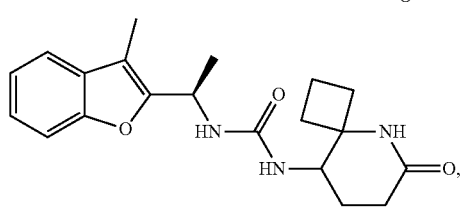
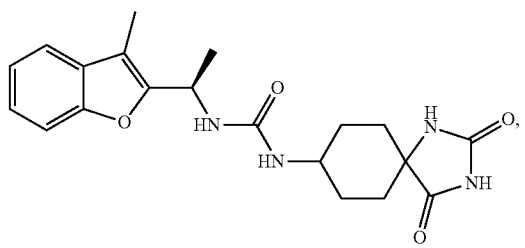
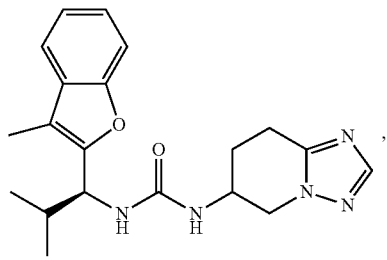
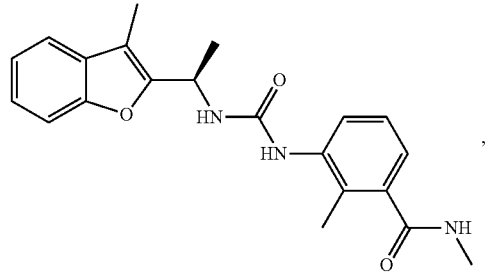
-continued
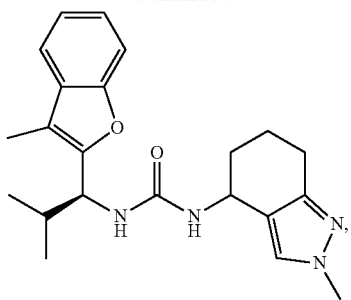
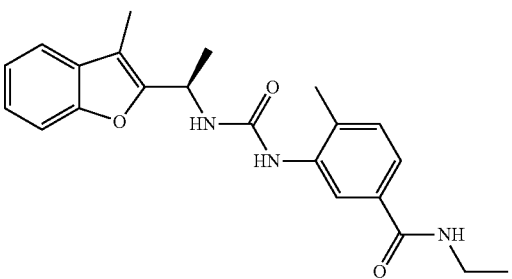
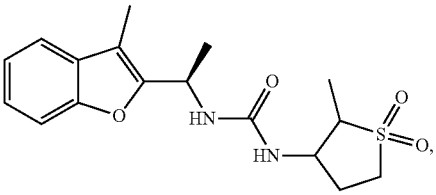
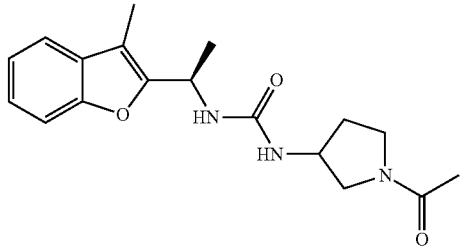
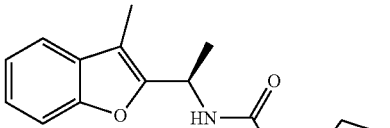
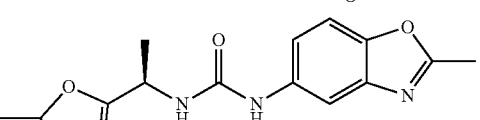
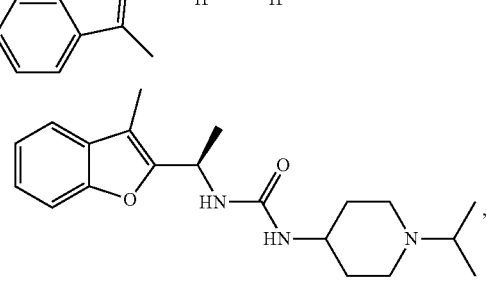

133
-continued
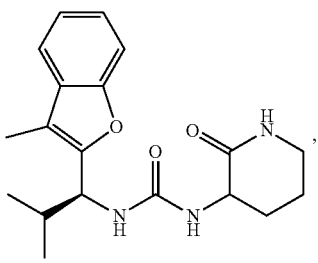
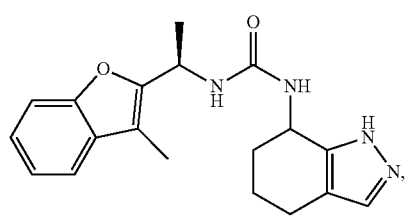
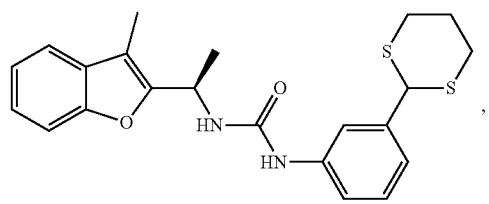
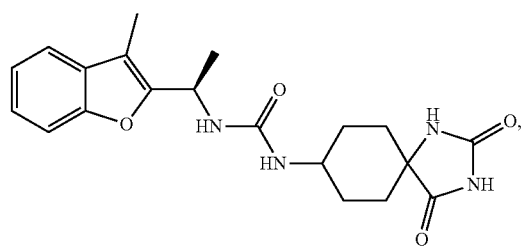
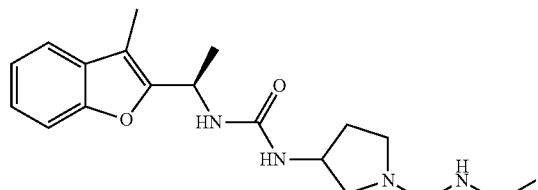
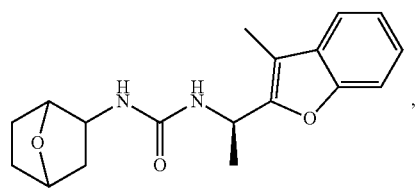
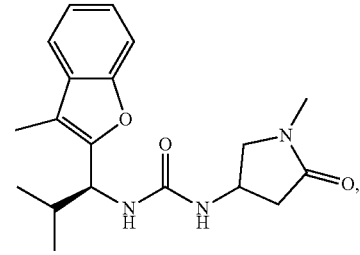
134
-continued
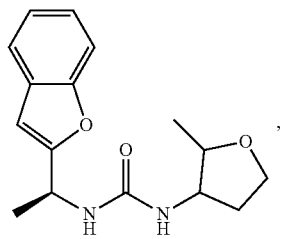
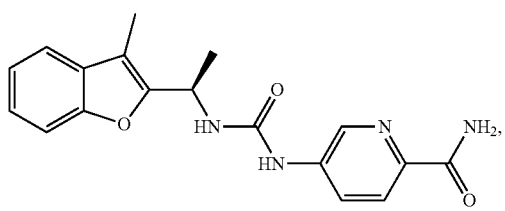
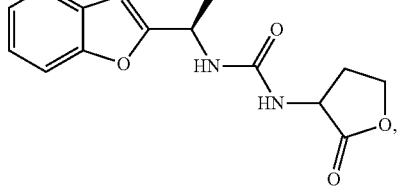
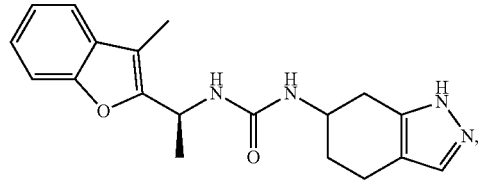
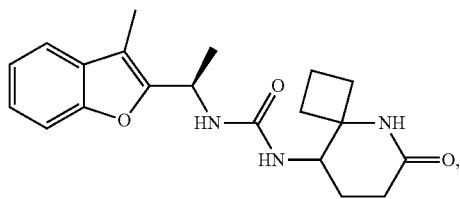
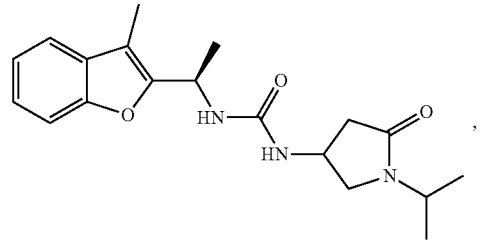
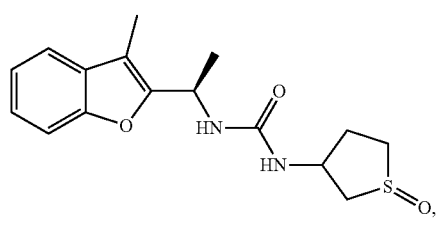

135
-continued
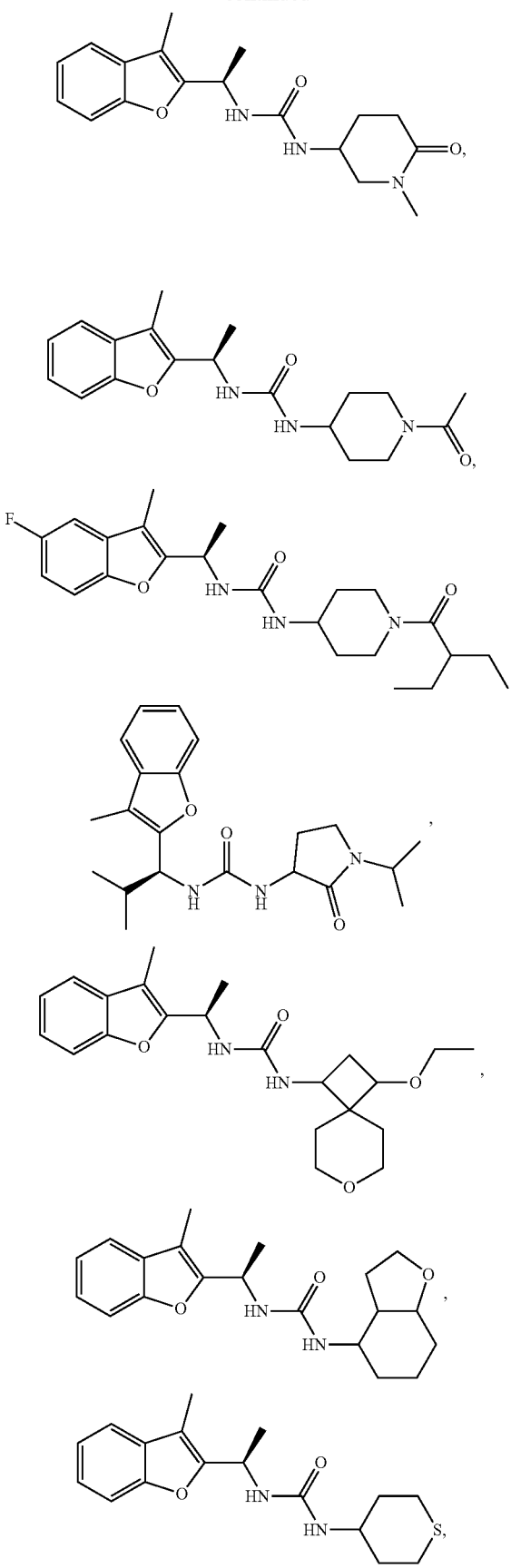
136
-continued
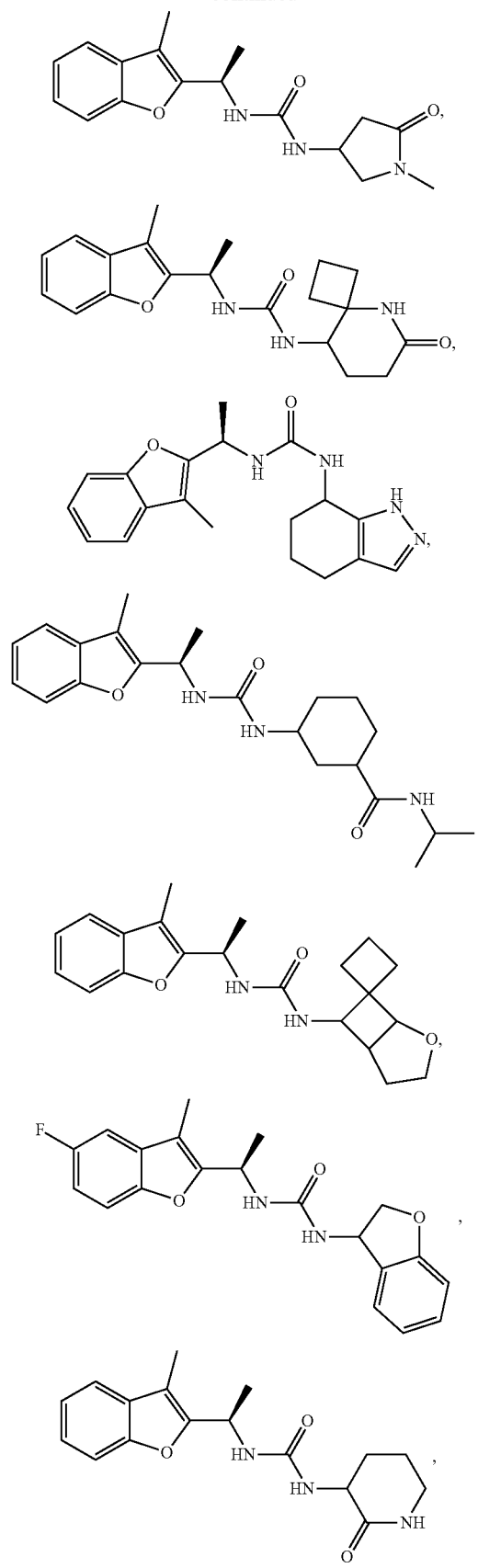

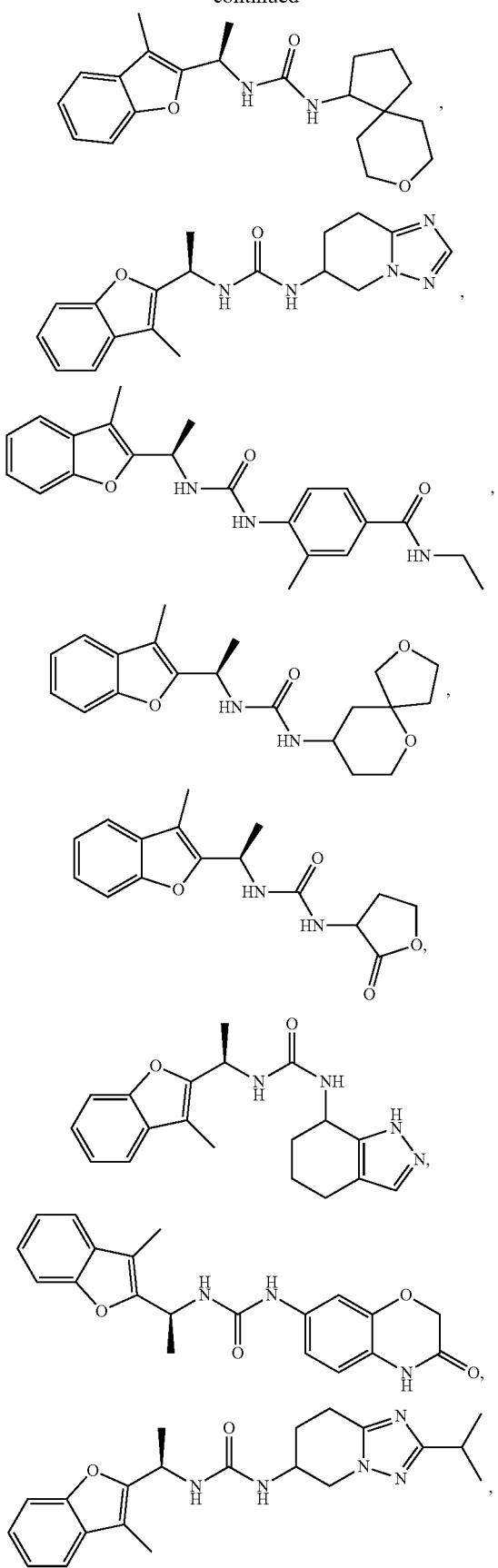
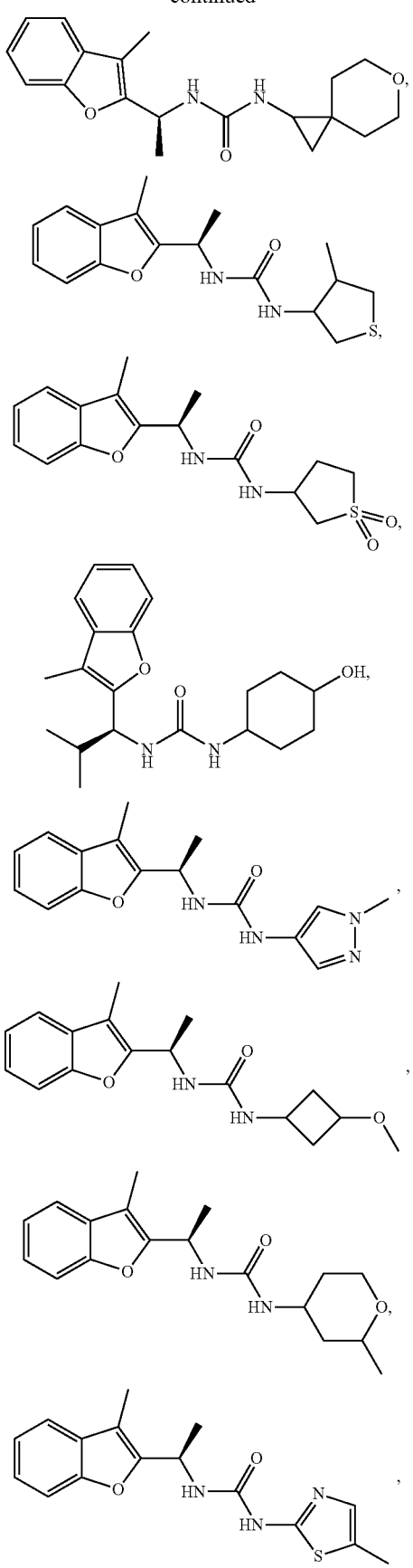

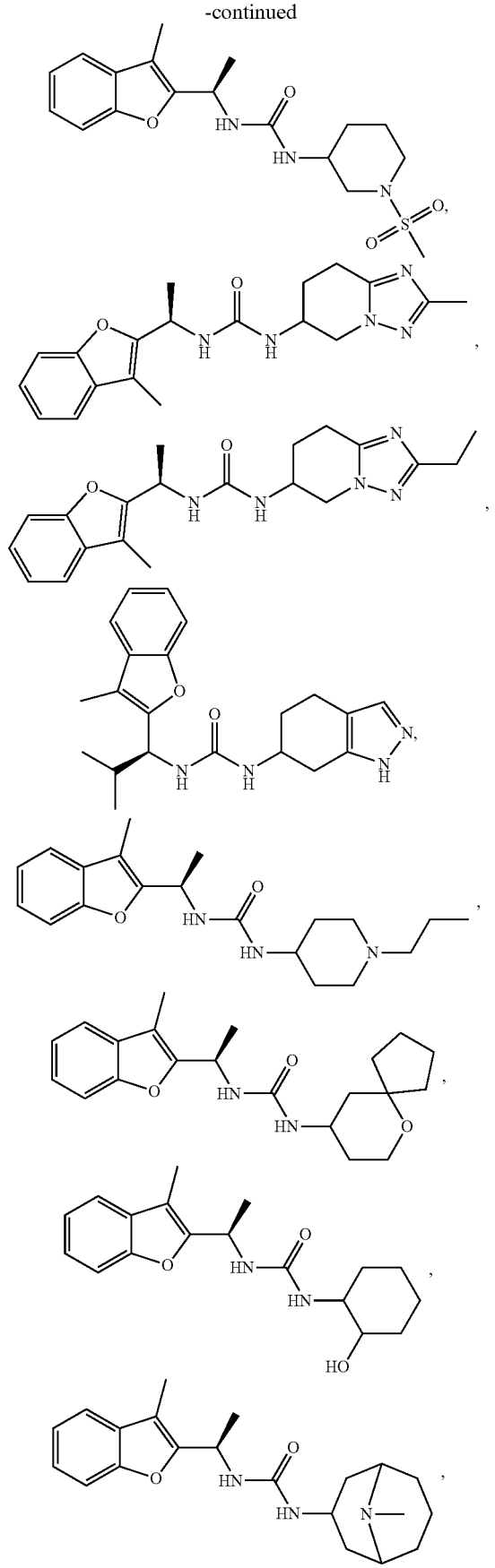
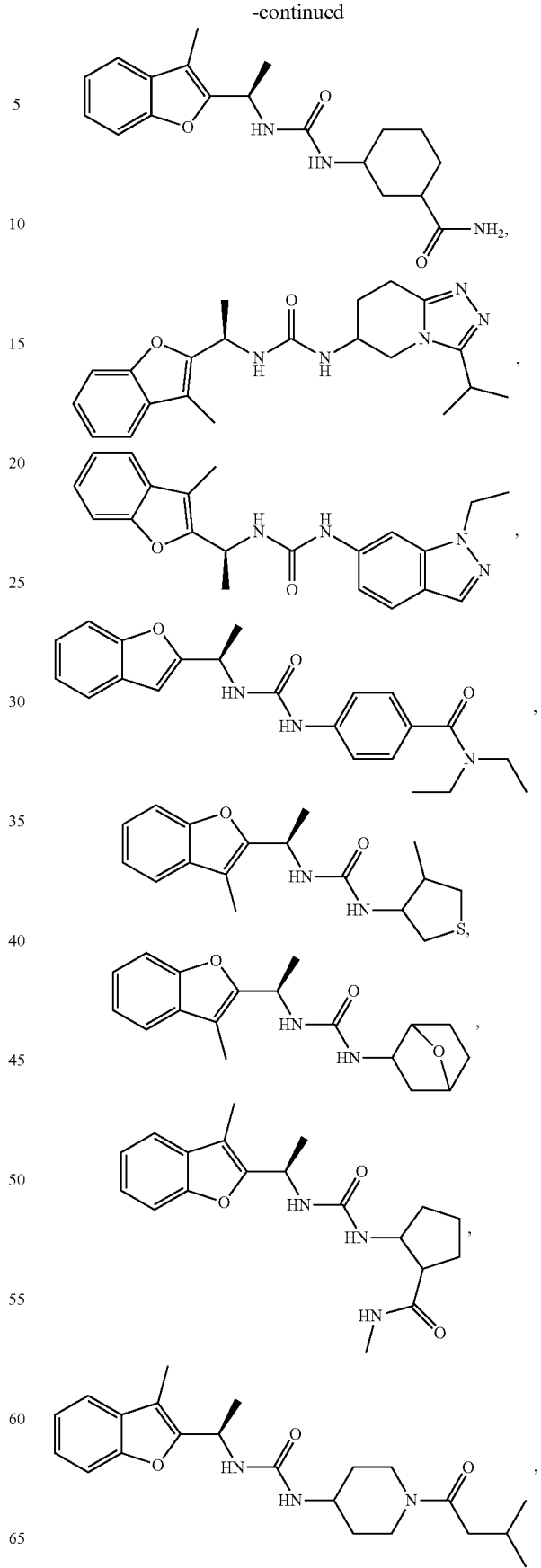

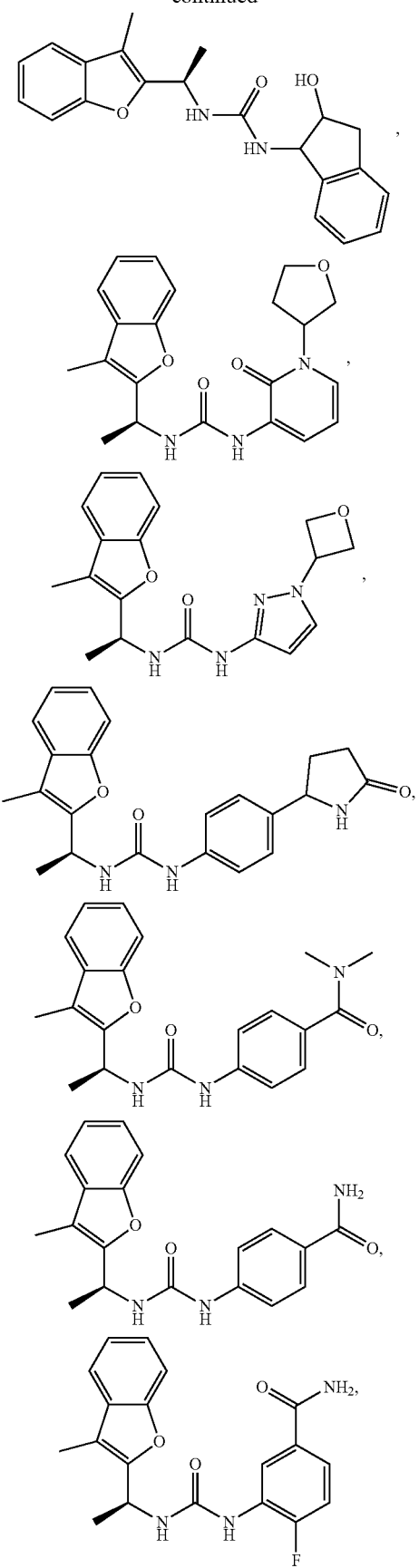
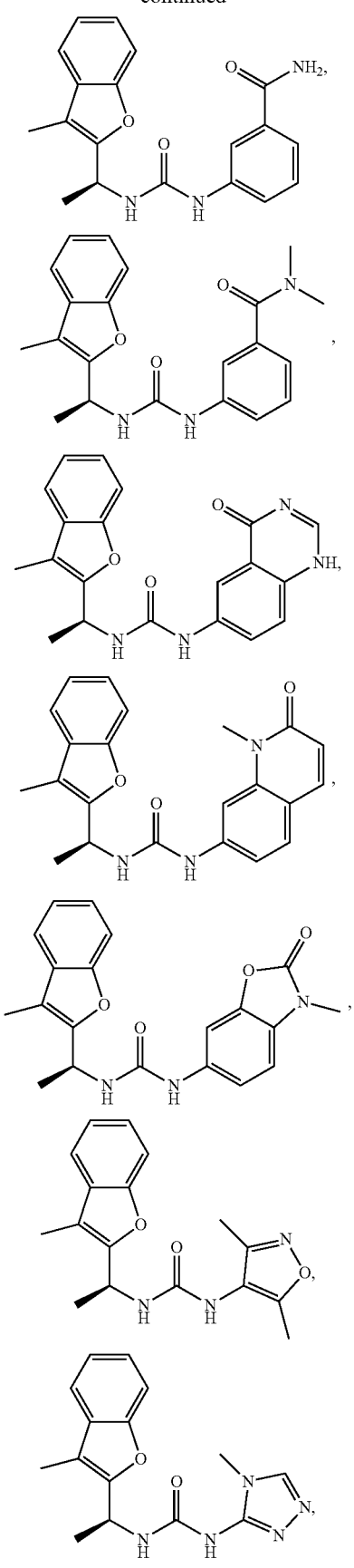

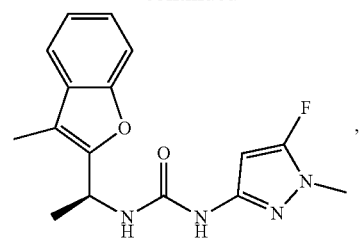
,
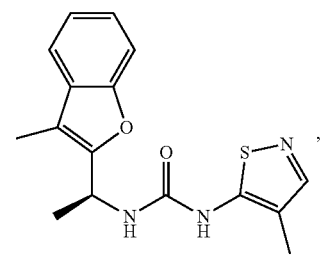
,
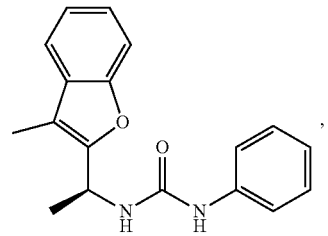
,
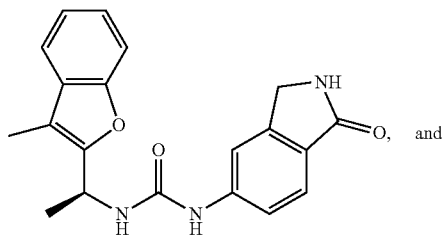
,
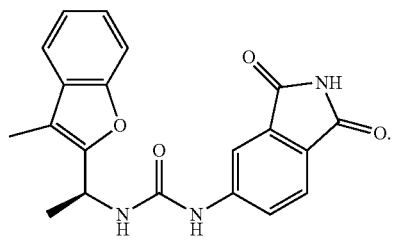 [SMILES: Cc1c(C(C)NC(=O)Nc2ccc3c(c2)C(=O)NC3=O)oc2ccccc12]
, and
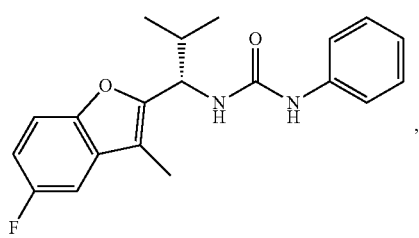
.
Some embodiments provide a compound of Formula (I), or a pharmaceutically acceptable salt thereof, as described herein, wherein the compound is not a compound selected from the group consisting of:
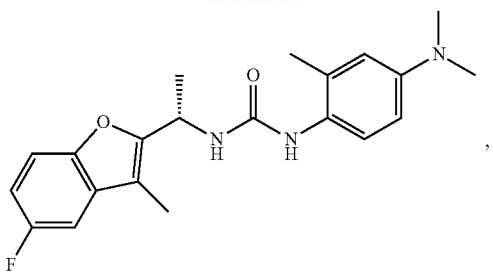
,
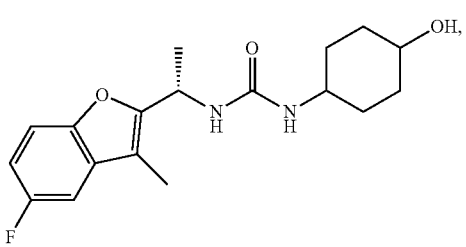
,
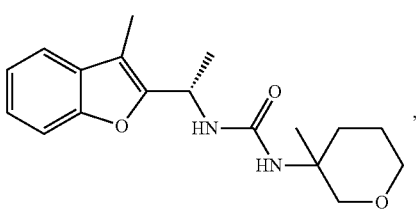
,
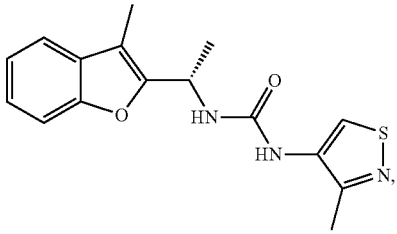
,
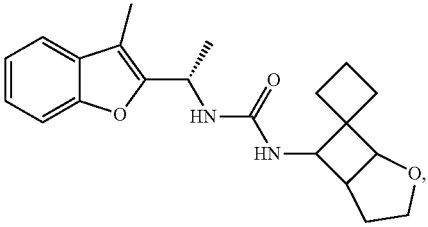
,
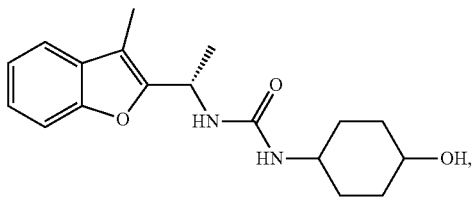
,
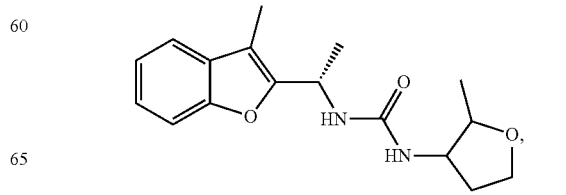
,

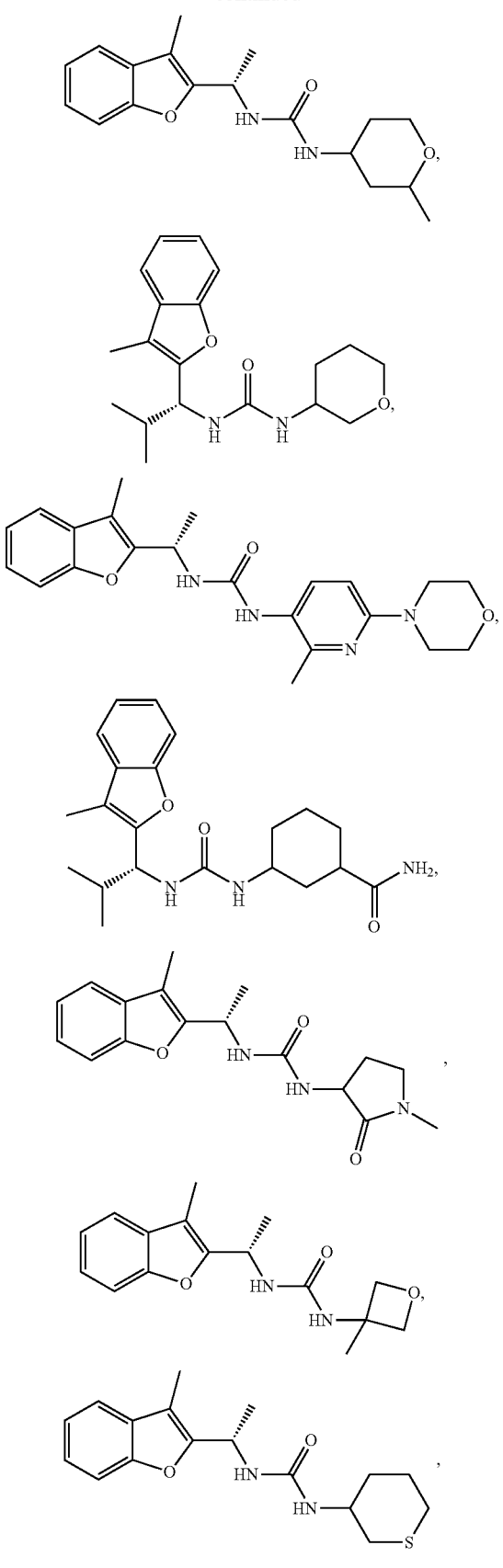
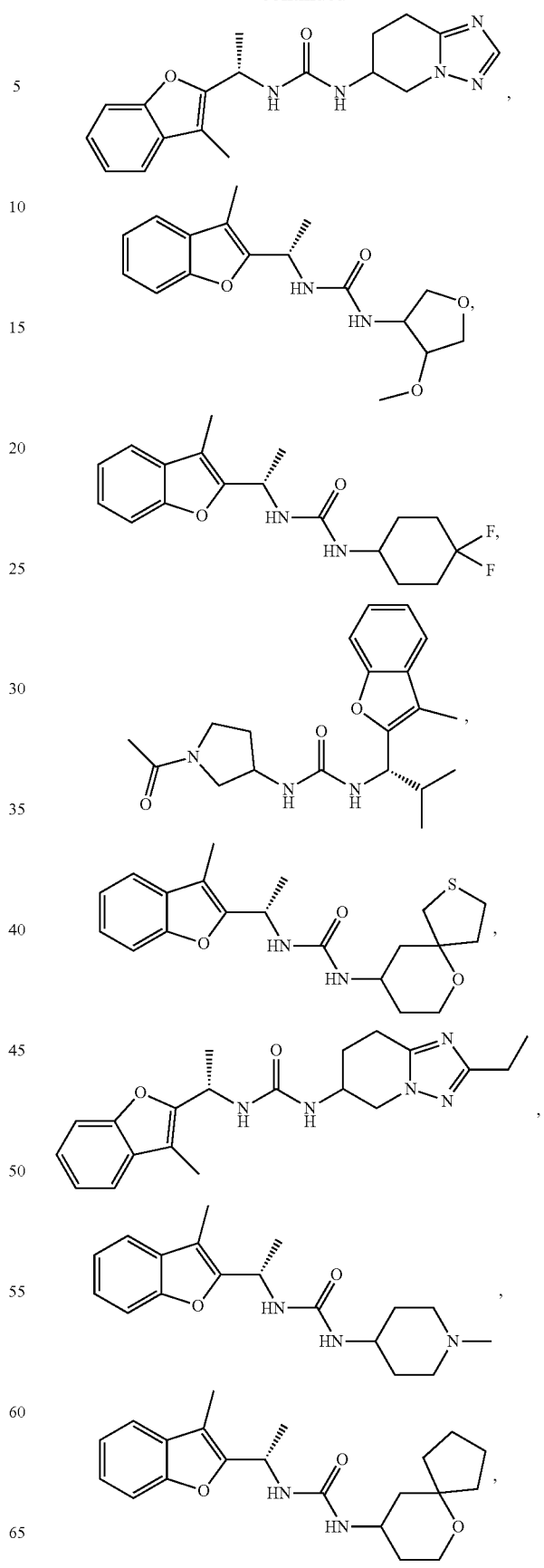

147
-continued
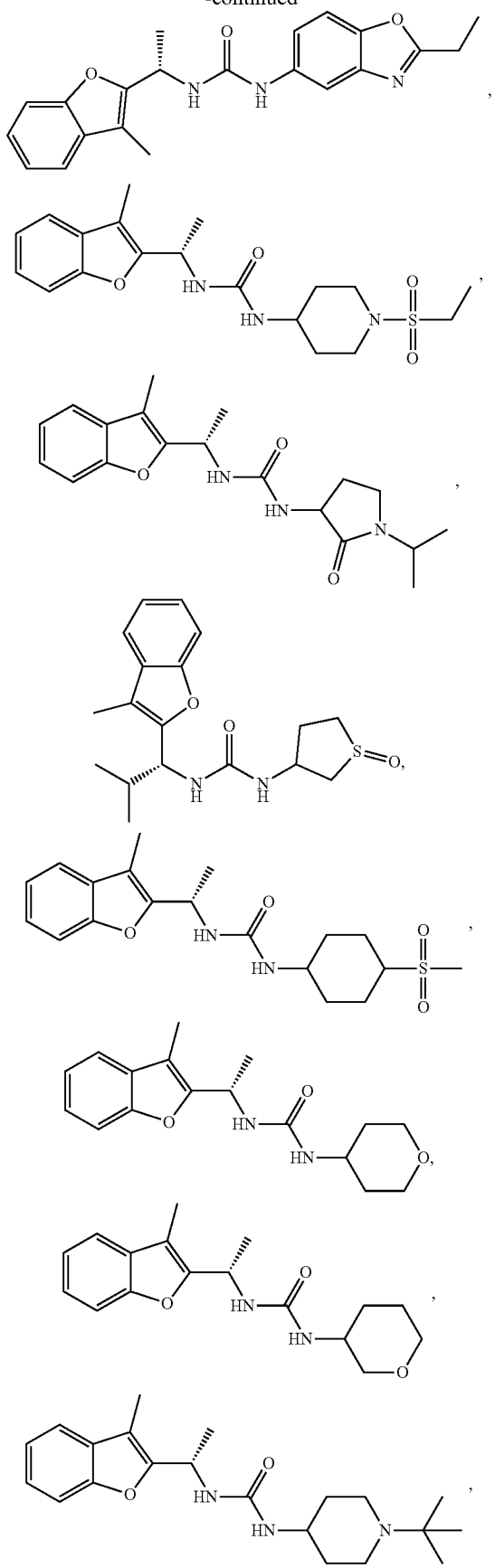
148
-continued
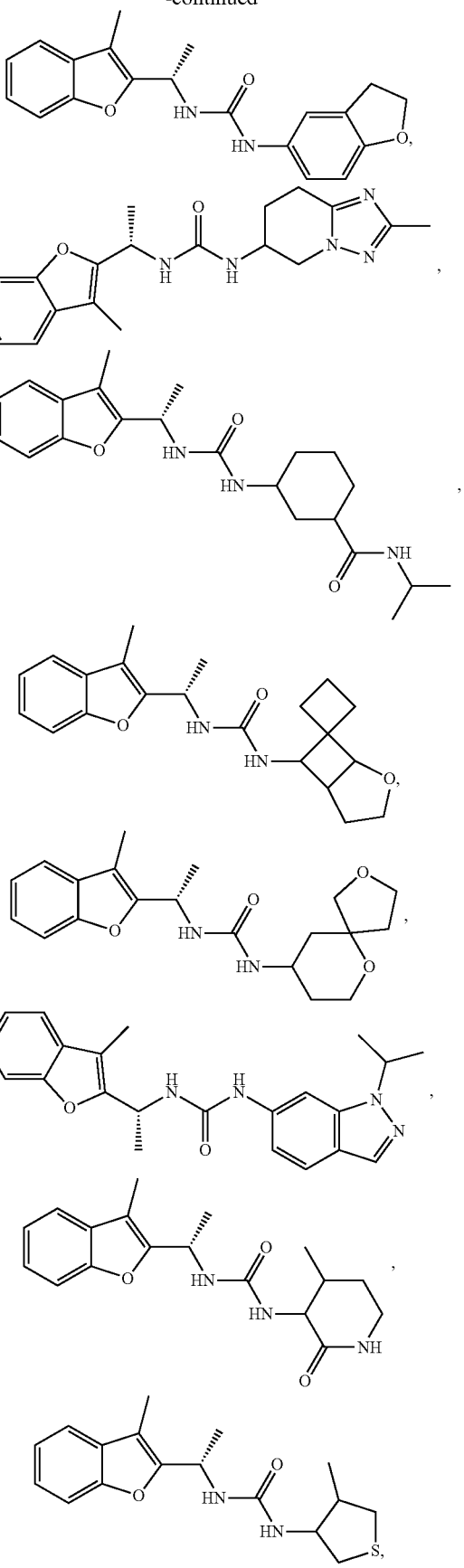

149
-continued
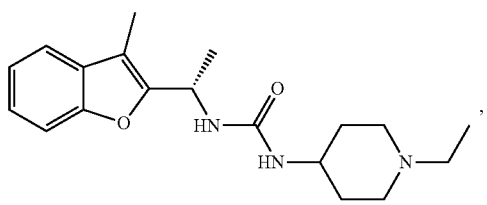
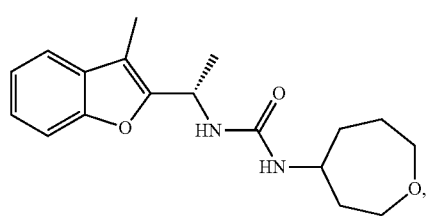
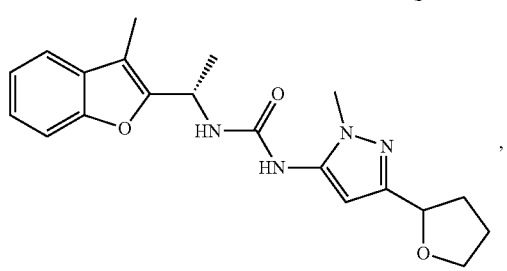
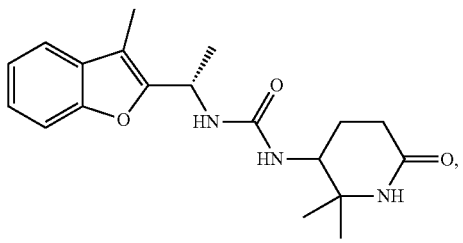
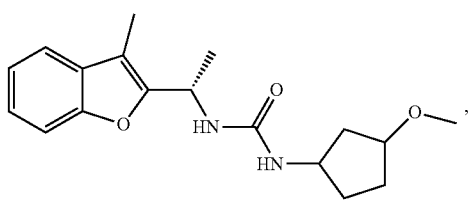
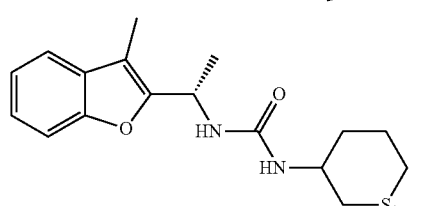
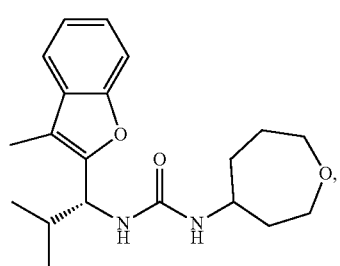
150
-continued
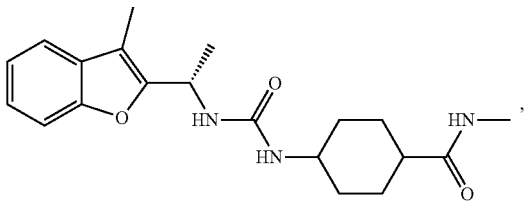
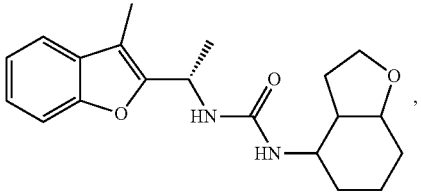
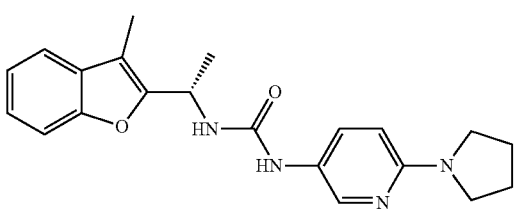
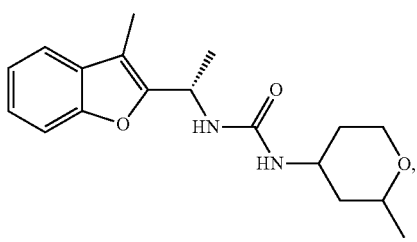
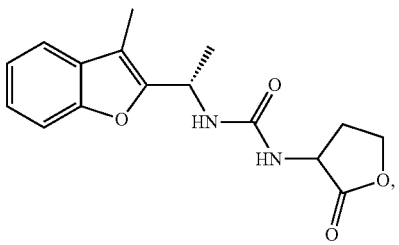
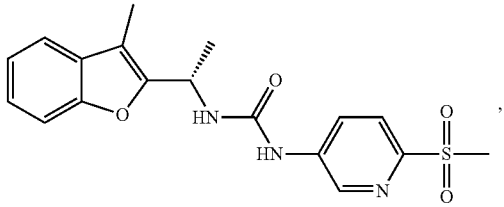
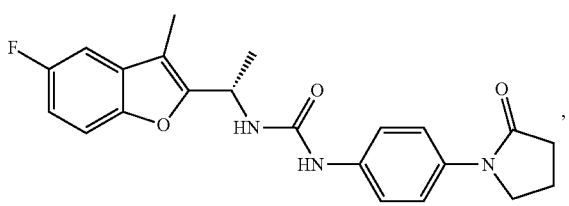
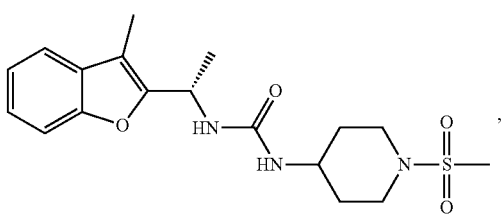

151
-continued
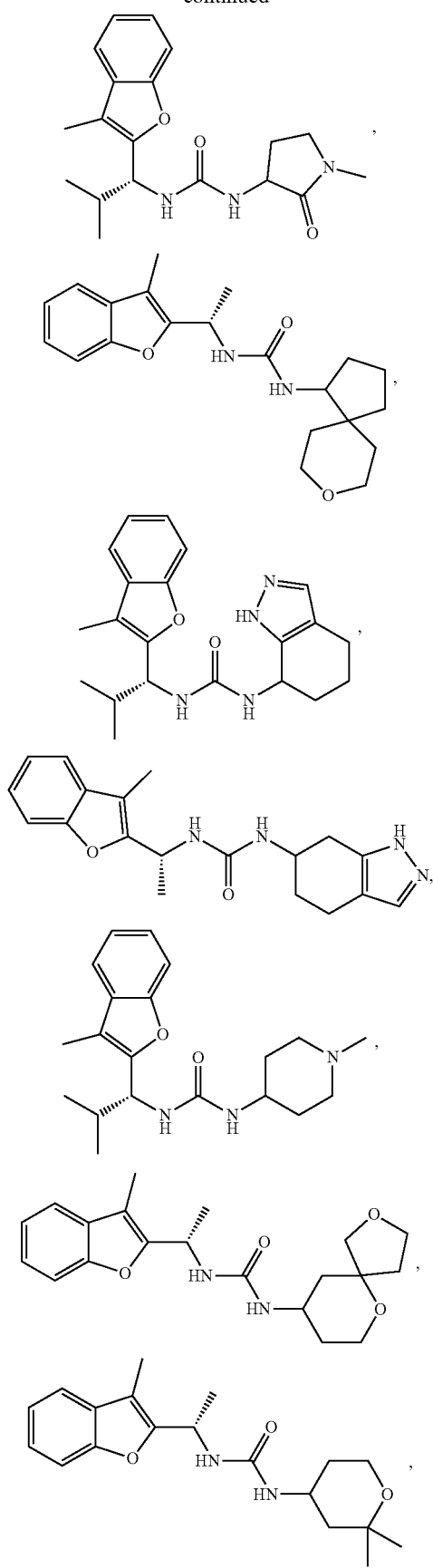
152
-continued
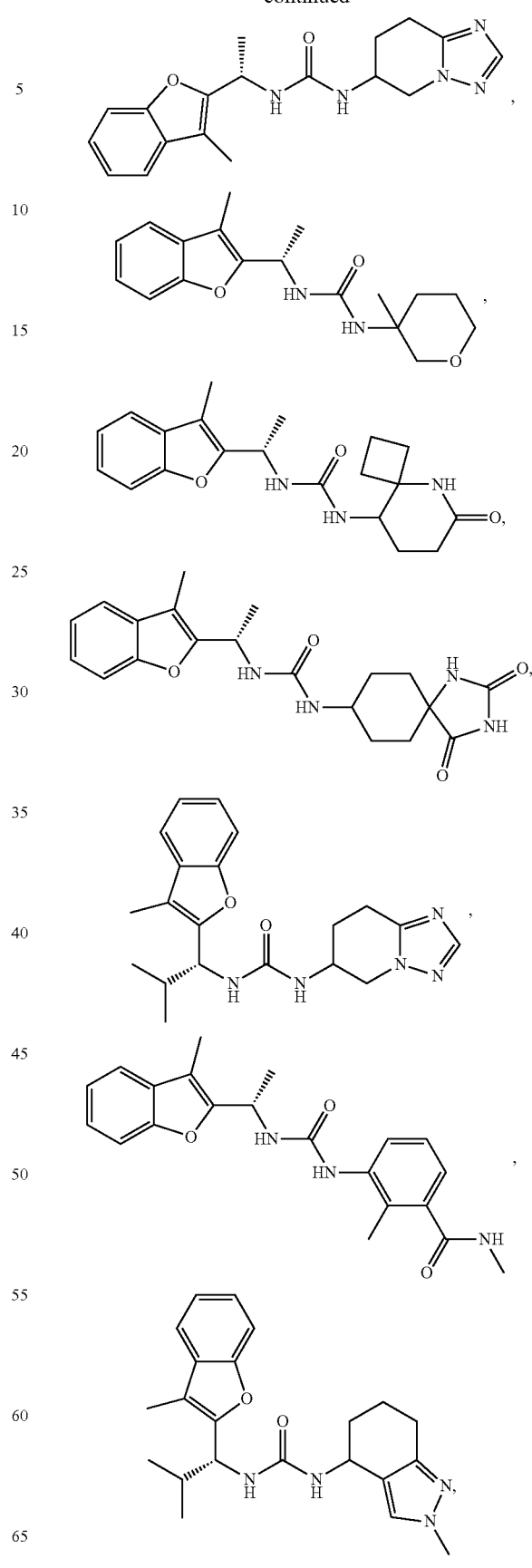

153
-continued
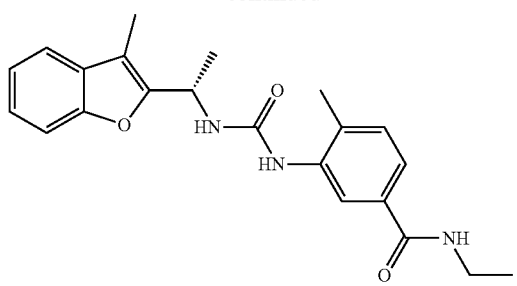
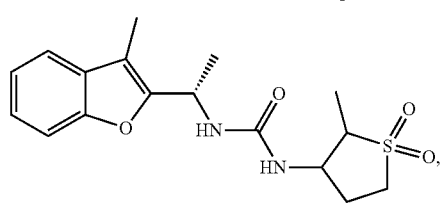
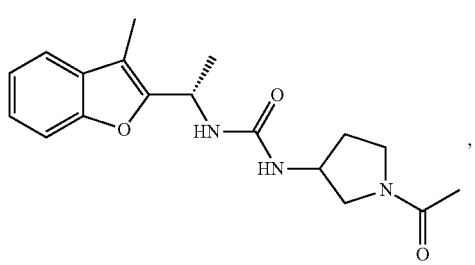
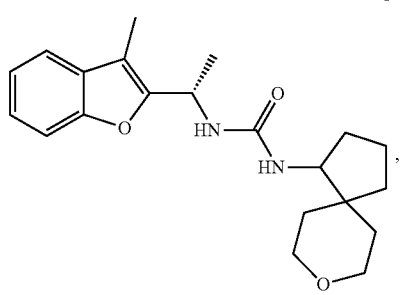
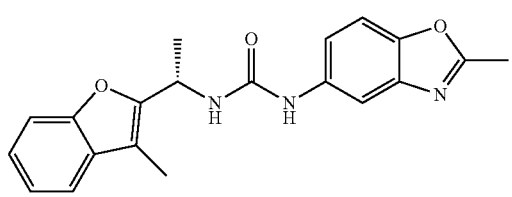
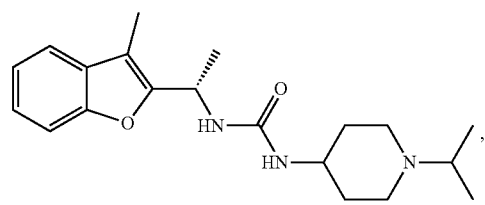
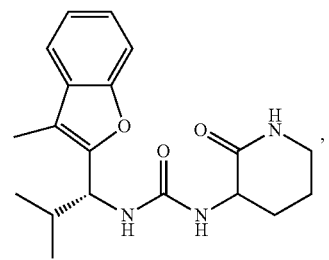
154
-continued
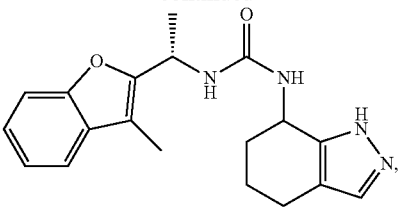
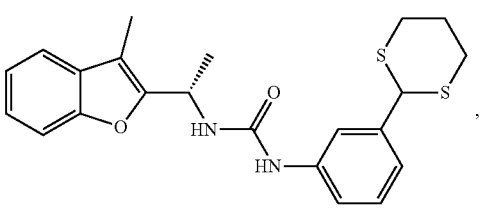
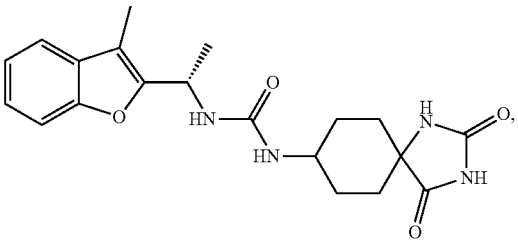
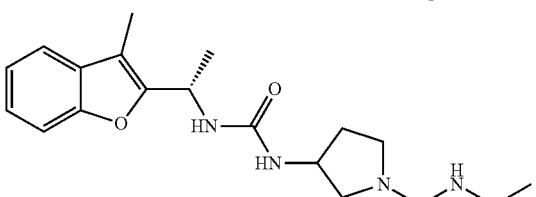
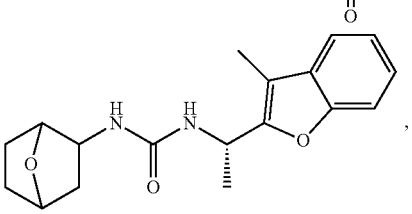
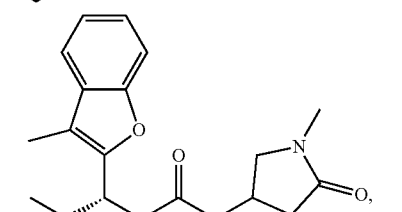
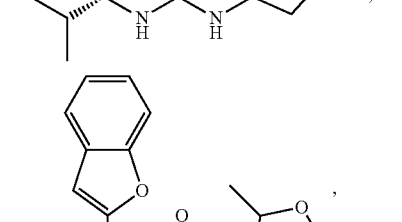

155
-continued
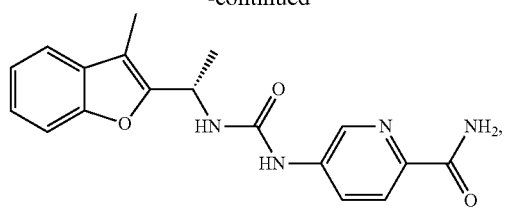
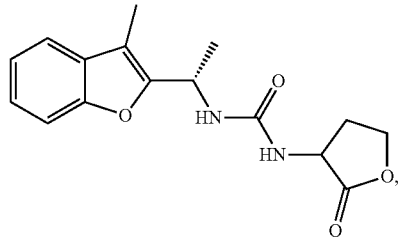
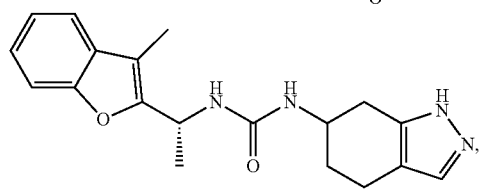
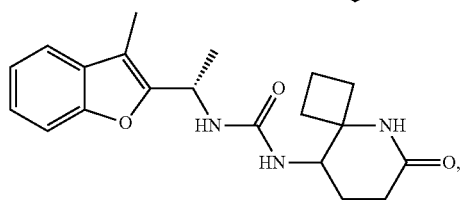
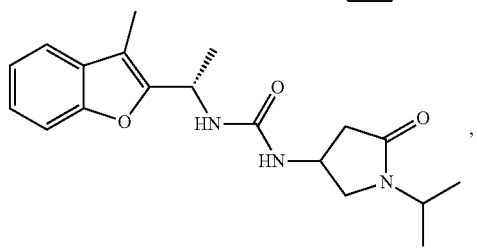
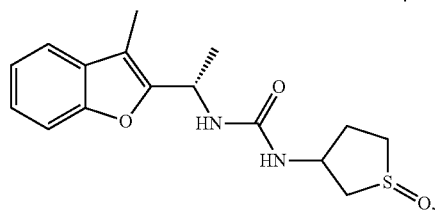
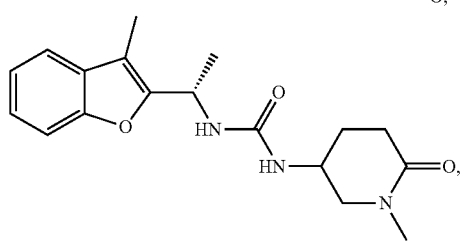
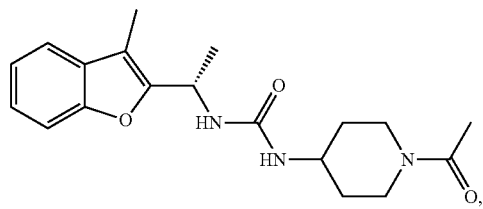
156
-continued
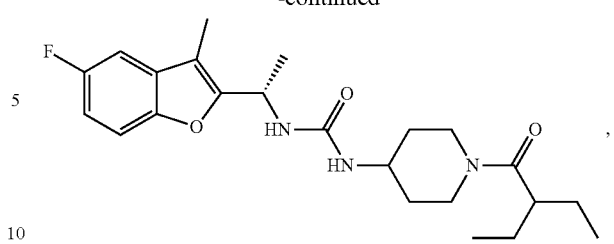
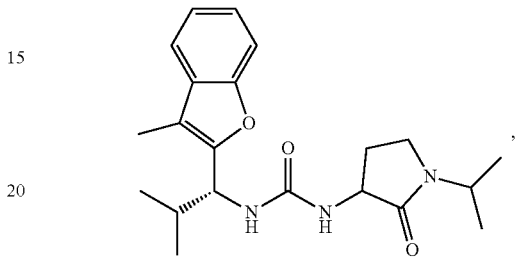
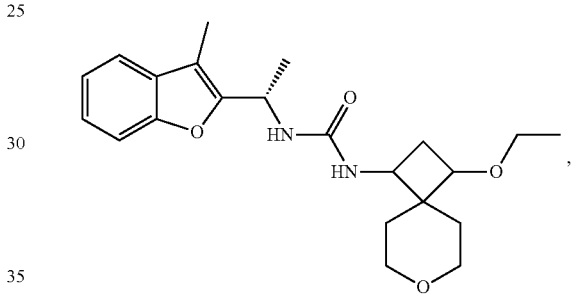
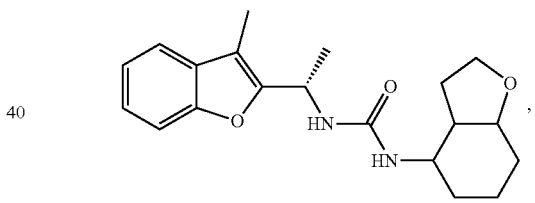
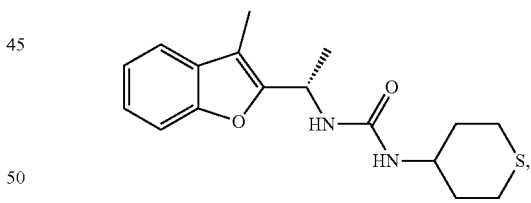
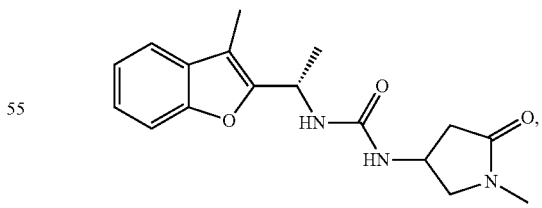
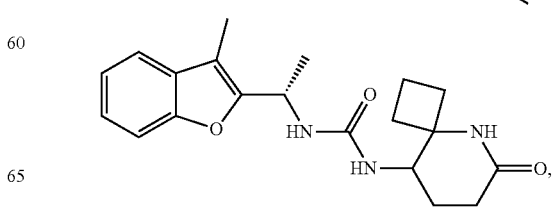

-continued
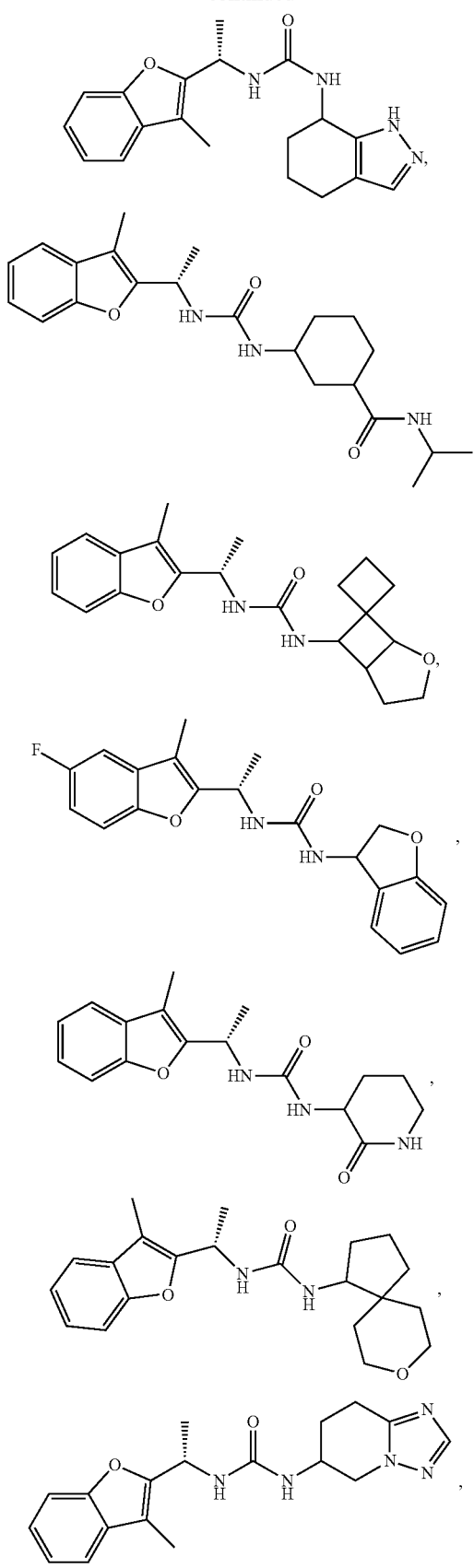
-continued
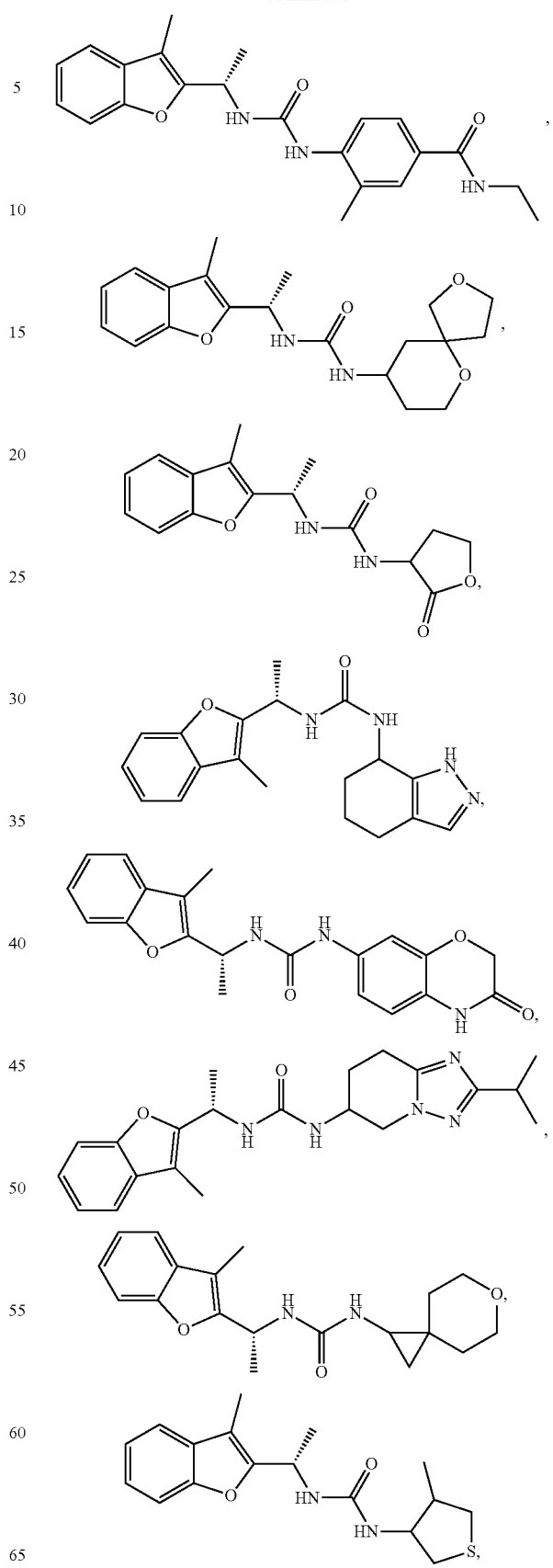

159
-continued
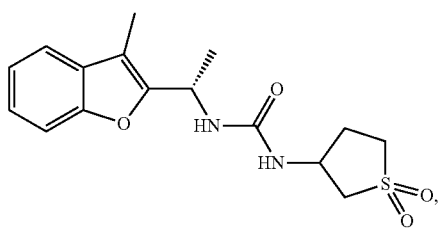
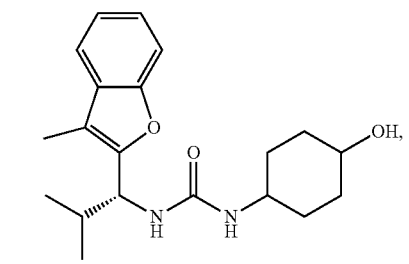
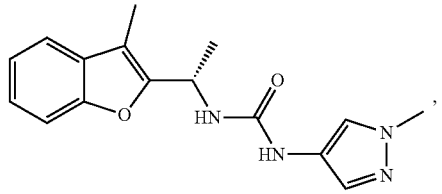
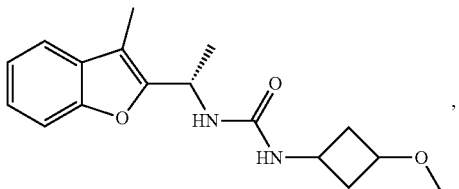
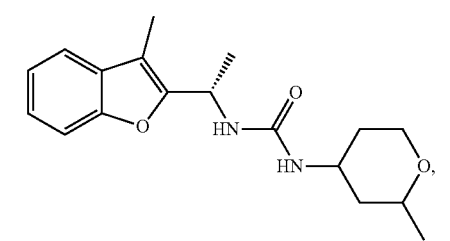
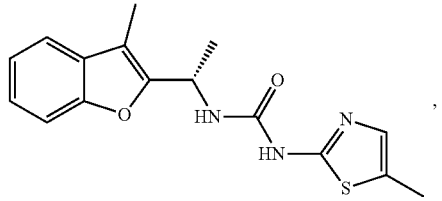
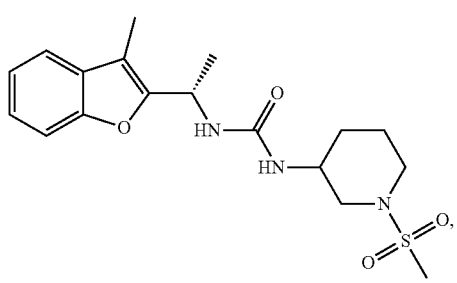
160
-continued
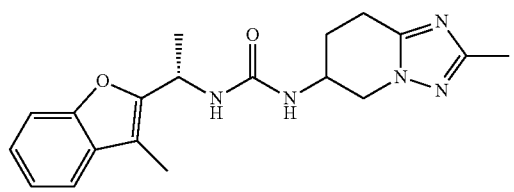
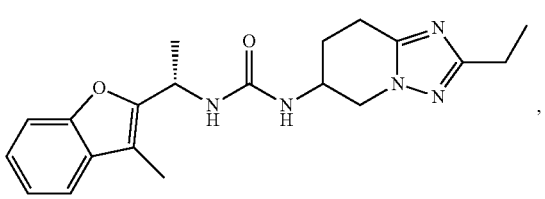
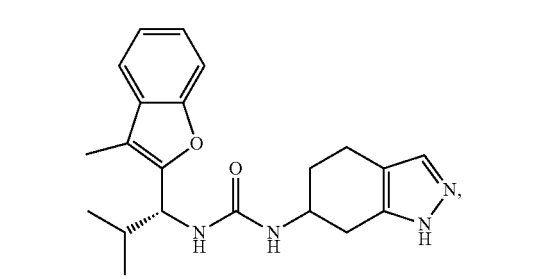
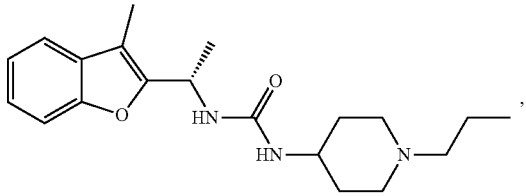
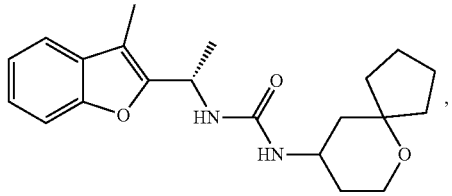
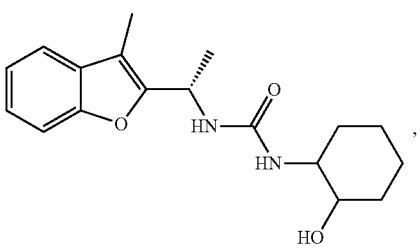
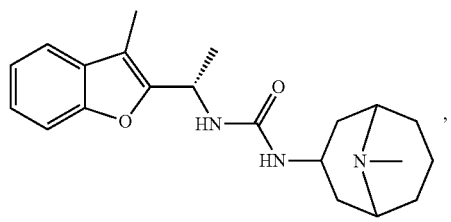

161
-continued
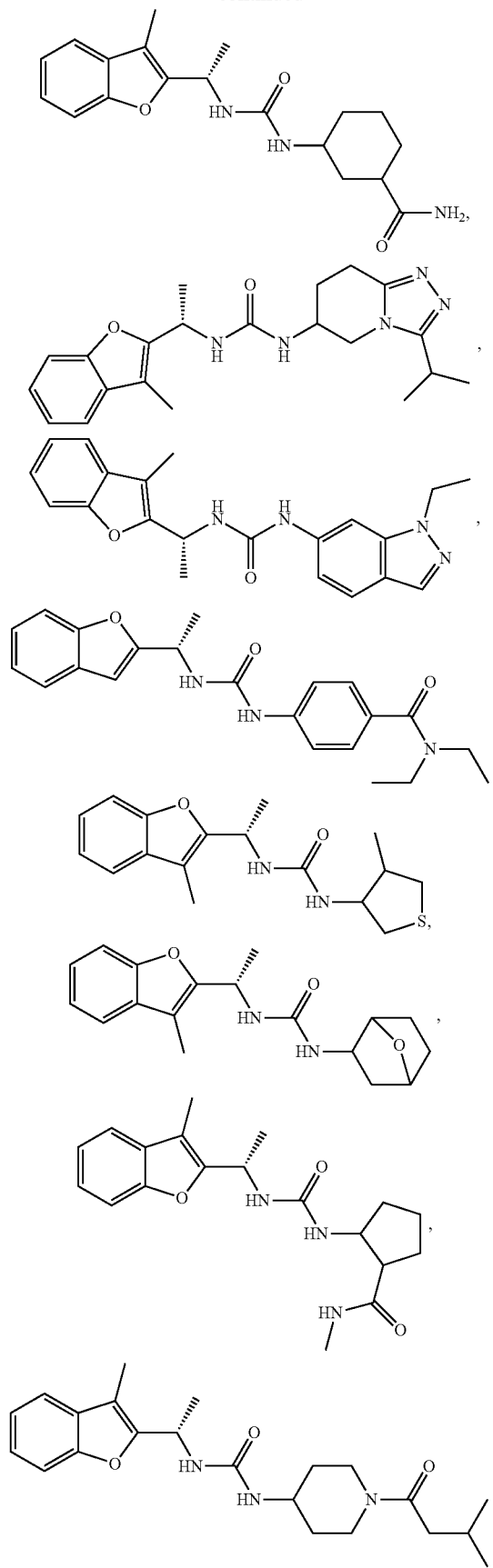
162
-continued
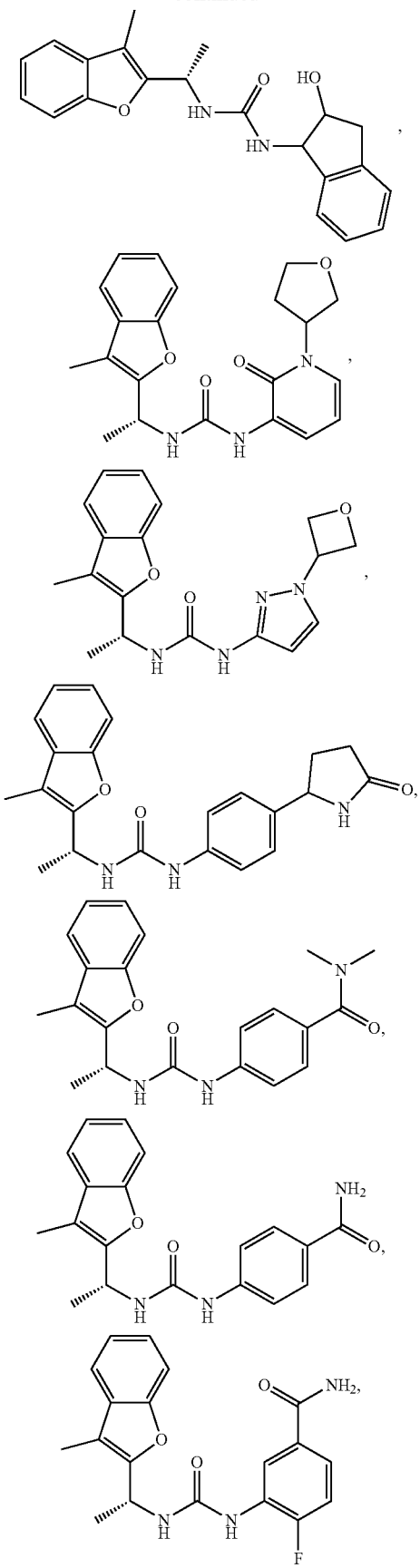

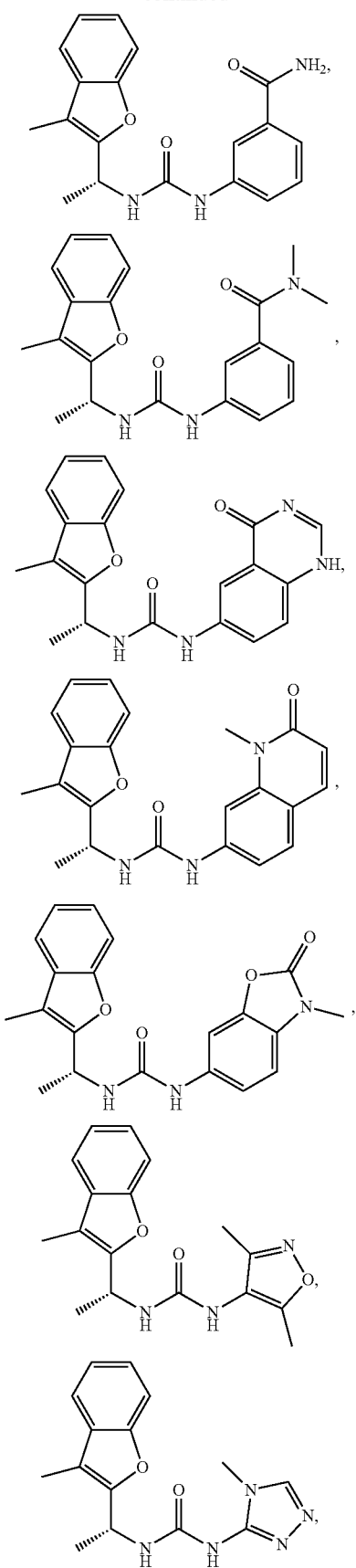
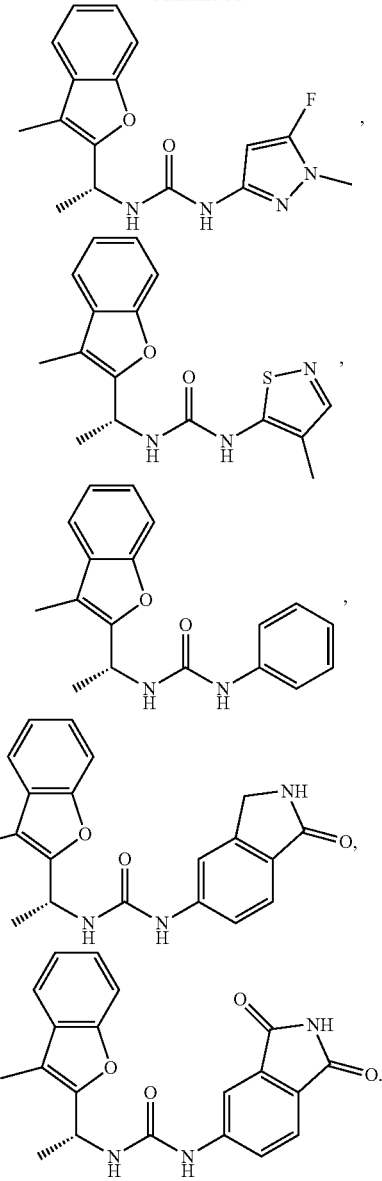
Some embodiments provide a compound of Formula (I), having Formula (X):
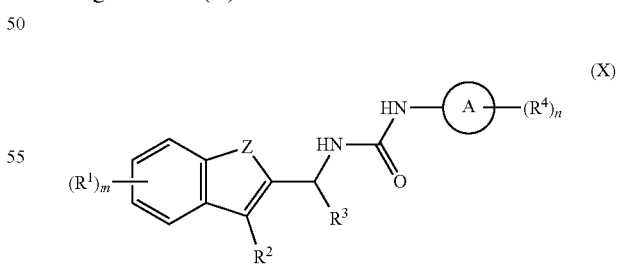
or a pharmaceutically acceptable salt thereof, wherein:
Z is O or NR$^x$;
R$^x$ is hydrogen, C1-C6 alkyl, or C3-C6 cycloalkyl;
each R$^1$ is an independently selected halogen;
m is 0, 1, 2, or 3;
R$^2$ is halogen, C1-C6 alkyl, C1-C6 haloalkyl, C3-C6 cycloalkyl optionally substituted with 1 or 2 fluoro;

R³ is a C1-C6 alkyl, a C1-C6 haloalkyl, or a C3-C6 cycloalkyl optionally substituted with 1 or 2 substituents independently selected from fluoro and C1-C6 alkyl;

Ring A is a 6-10 membered aryl, a C3-C8 cycloalkyl, a 5-10 membered heteroaryl, or a 4-10 membered heterocyclyl;

each R⁴ is independently selected from the group consisting of: halogen, C1-C6 alkyl optionally substituted with 1 or 2 hydroxyl or —NR^A R^B, C1-C6 alkoxy, C1-C6 haloalkyl, hydroxyl, cyano, —CO₂H, —NR^A R^B, —C(=O)NR^C R^D, —SO₂(NR^E R^F), —SO₂(C1-C6 alkyl), —S(=O)(=NH)(C1-C6 alkyl), —C(=O)(C1-C6 alkyl), —CO₂(C1-C6 alkyl), 5-6 membered heteroaryl optionally substituted with C1-C6 alkyl, and a 3-6 membered heterocyclyl or 3-6 membered cycloalkyl each optionally substituted with 1 or 2 independently selected R^G;

n is 0, 1, or 2;

each R^A, R^A1, R^B, R^B1, R^C, R^C1, R^D, R^D1, R^E, and R^F is independently hydrogen, 4-6 membered heterocyclyl, C1-C6 haloalkyl, —C(=O)(C1-C6 alkyl), —SO₂(C1-C6 alkyl), 3-6 membered cycloalkyl optionally substituted with hydroxyl, or C1-C6 alkyl optionally substituted with 1-2 substituents independently selected from hydroxyl, —C(=O)NR^B2 R^C2, 5-6 membered heteroaryl, 3-6 membered cycloalkyl, SO₂(C1-C6 alkyl), —SO₂(NH₂); or R^C and R^D, together with the nitrogen atom to which they are attached form a 4-6 membered heterocyclyl;

each R^G is independently selected from the group consisting of: fluoro, cyano, hydroxyl, C1-C6 alkyl, C1-C6 alkoxy, —NR^A1 R^B, —C(=O)NR^C1 R^D1, —CO₂(C1-C6 alkyl), C1-C6 haloalkyl, C3-C6 cycloalkyl, and —CO₂H; and wherein the compound is not a compound selected from the group consisting of:

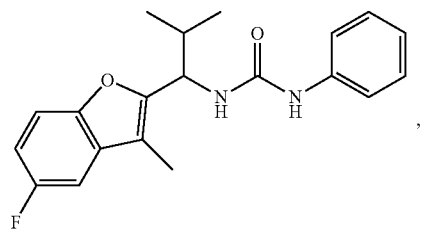

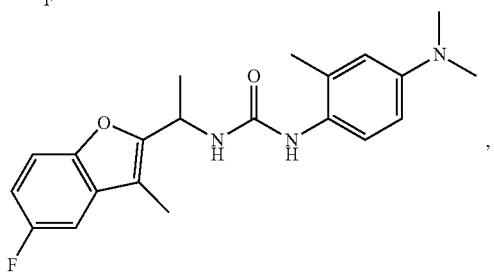

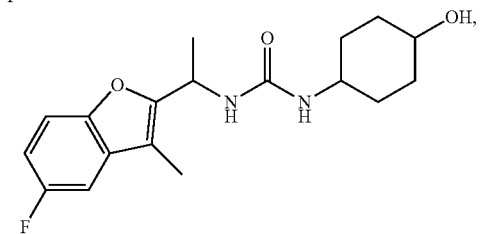

-continued

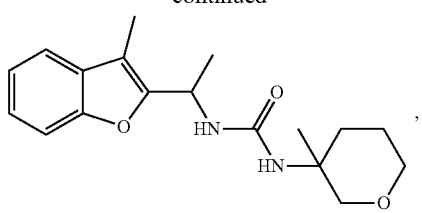

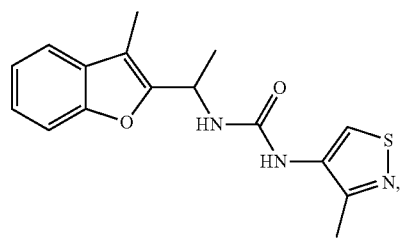

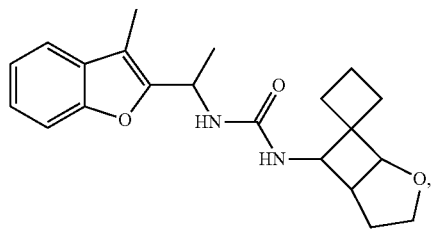

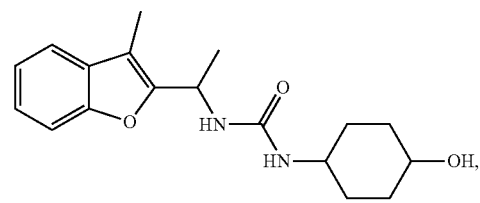

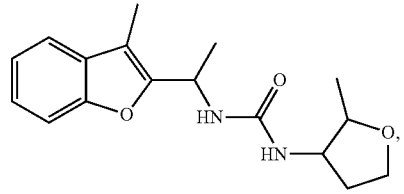

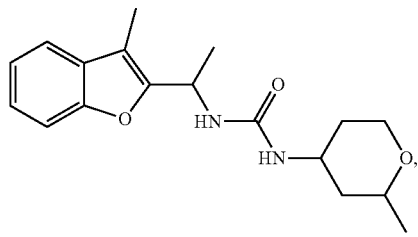

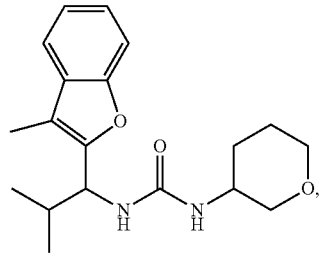

167
-continued
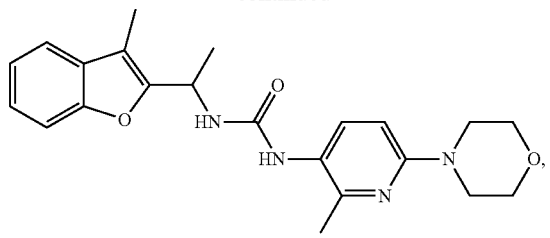
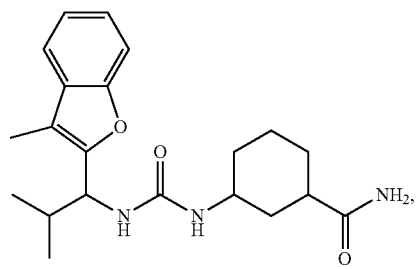
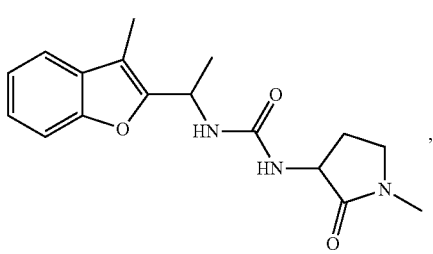
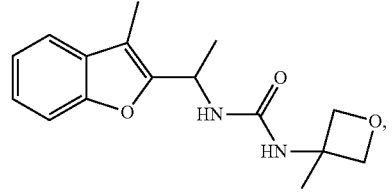
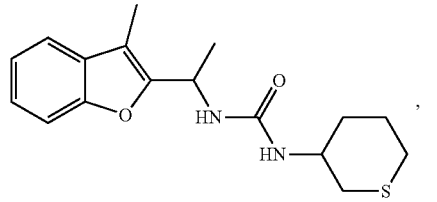
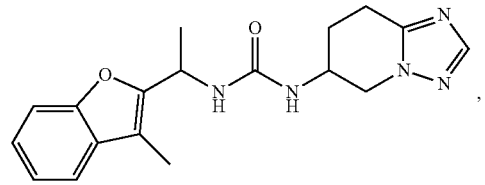
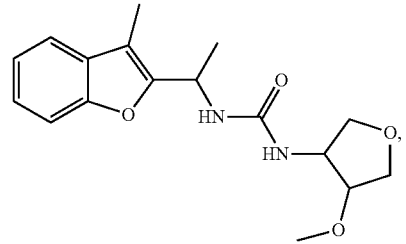
168
-continued
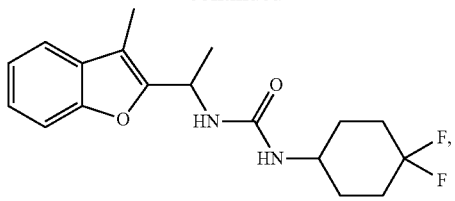
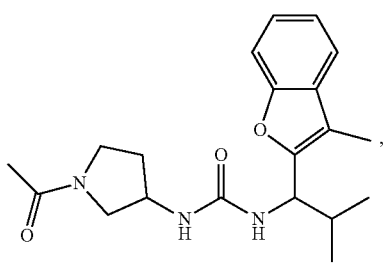
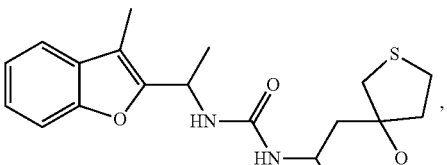
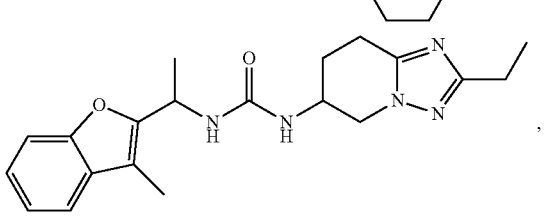
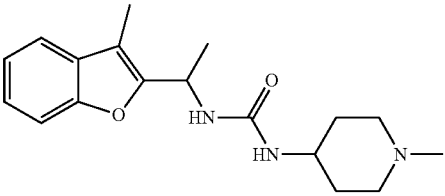
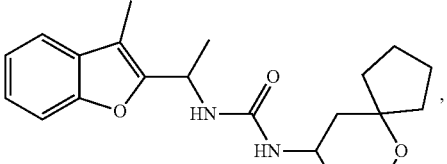
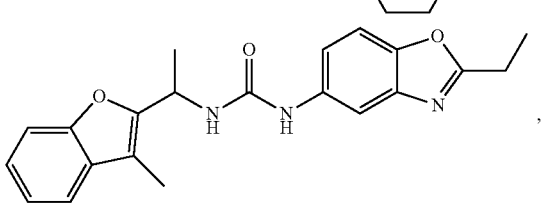
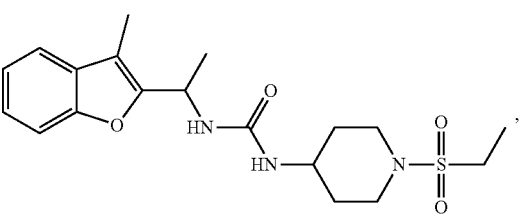

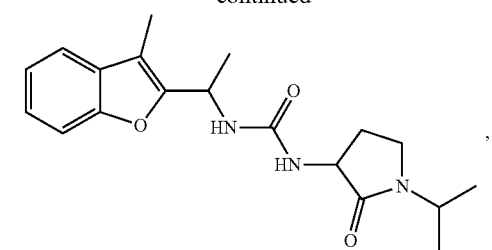,
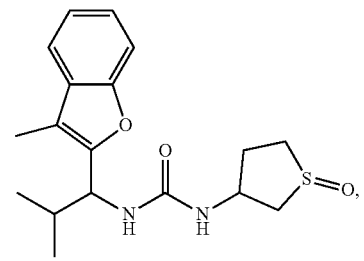,
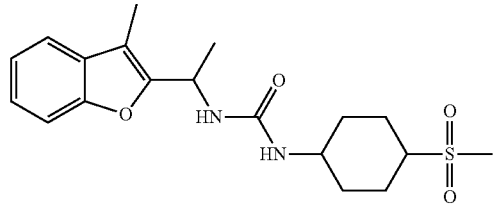,
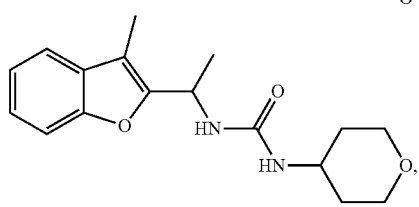,
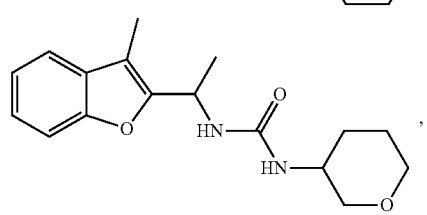,
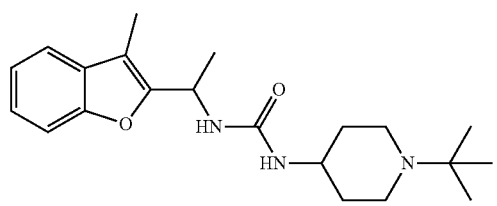,
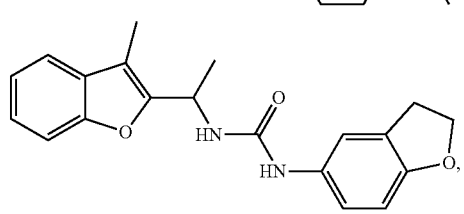,
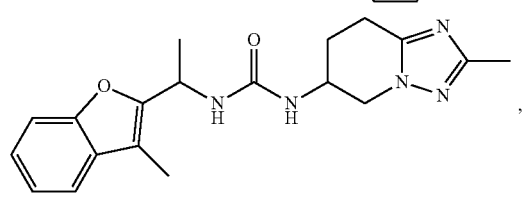,
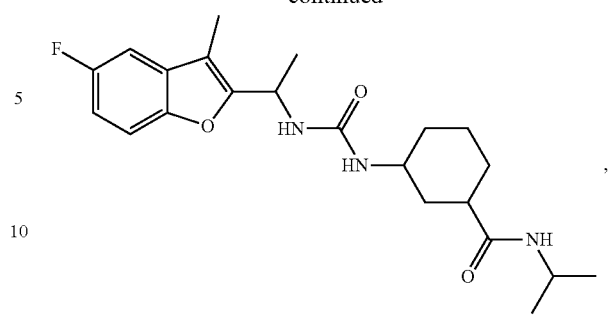,
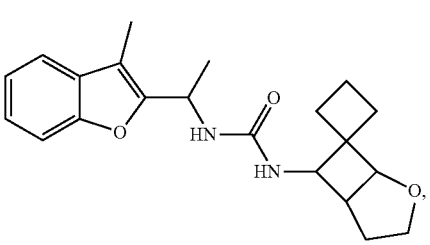,
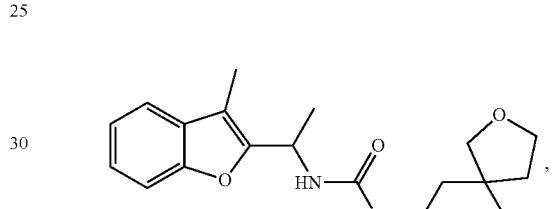,
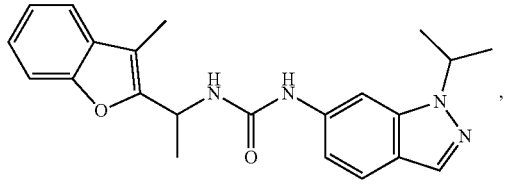,
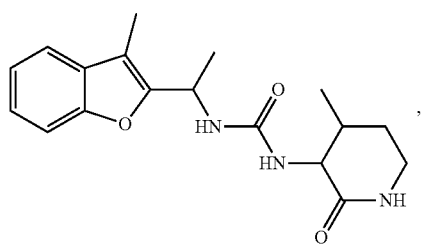,
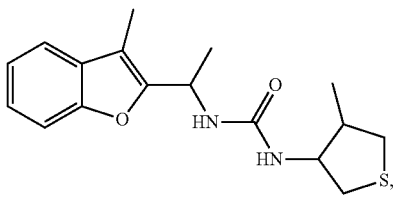,
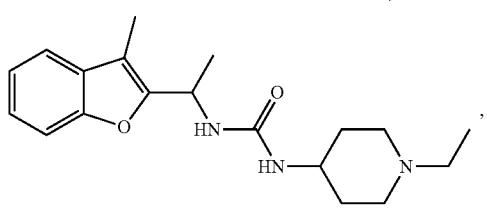, 171
-continued
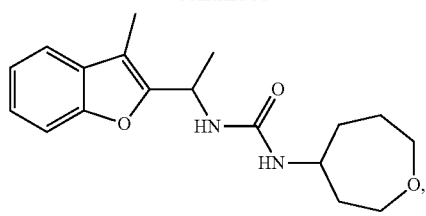
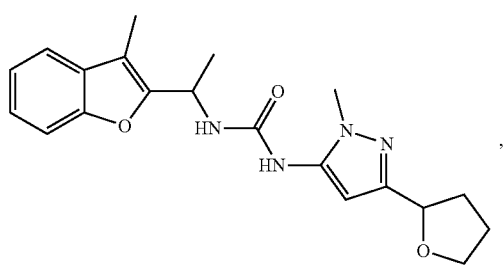
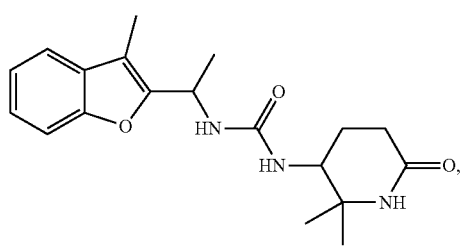
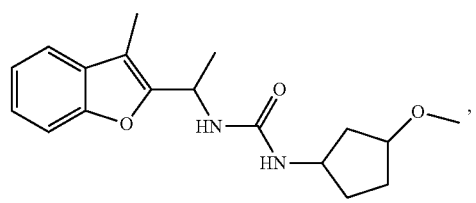
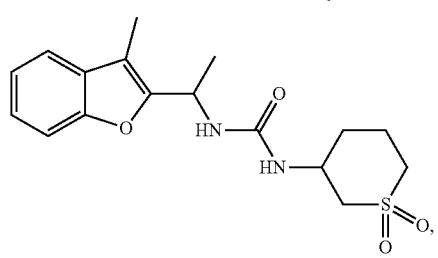
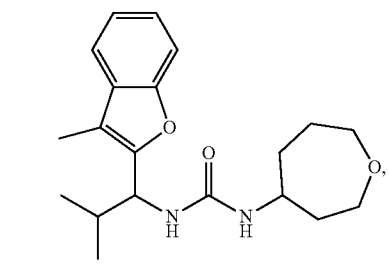
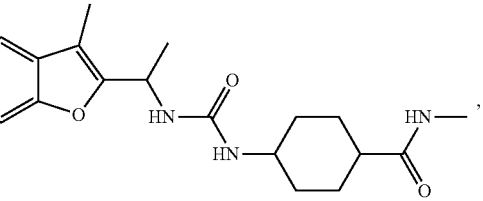
172
-continued
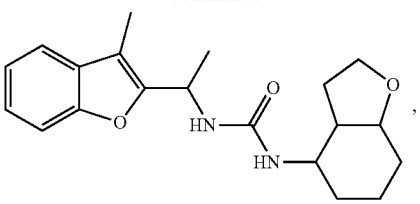
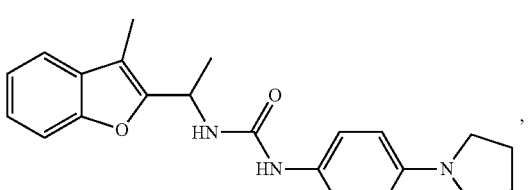
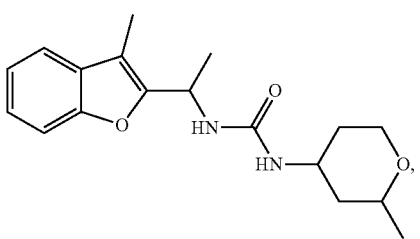
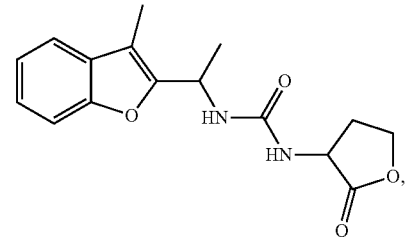
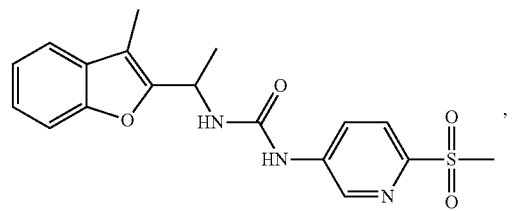
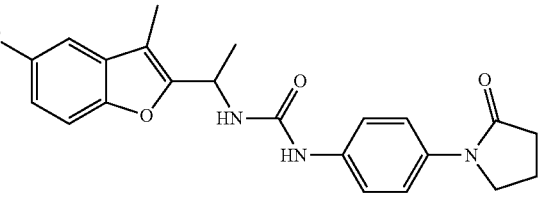
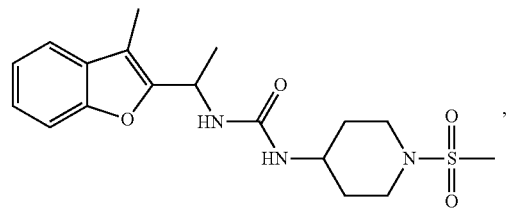

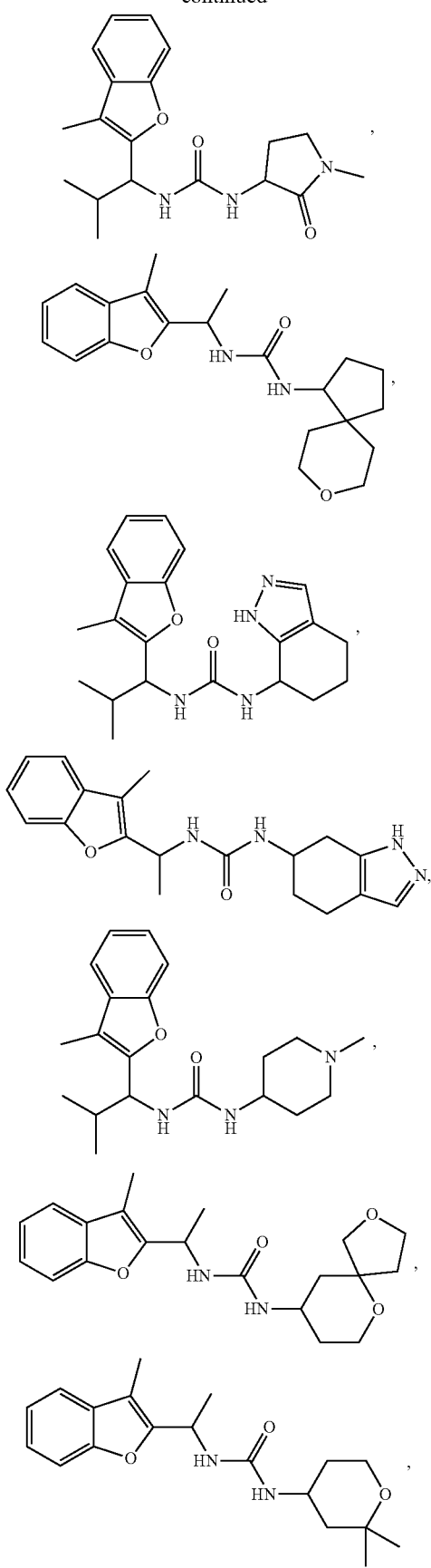
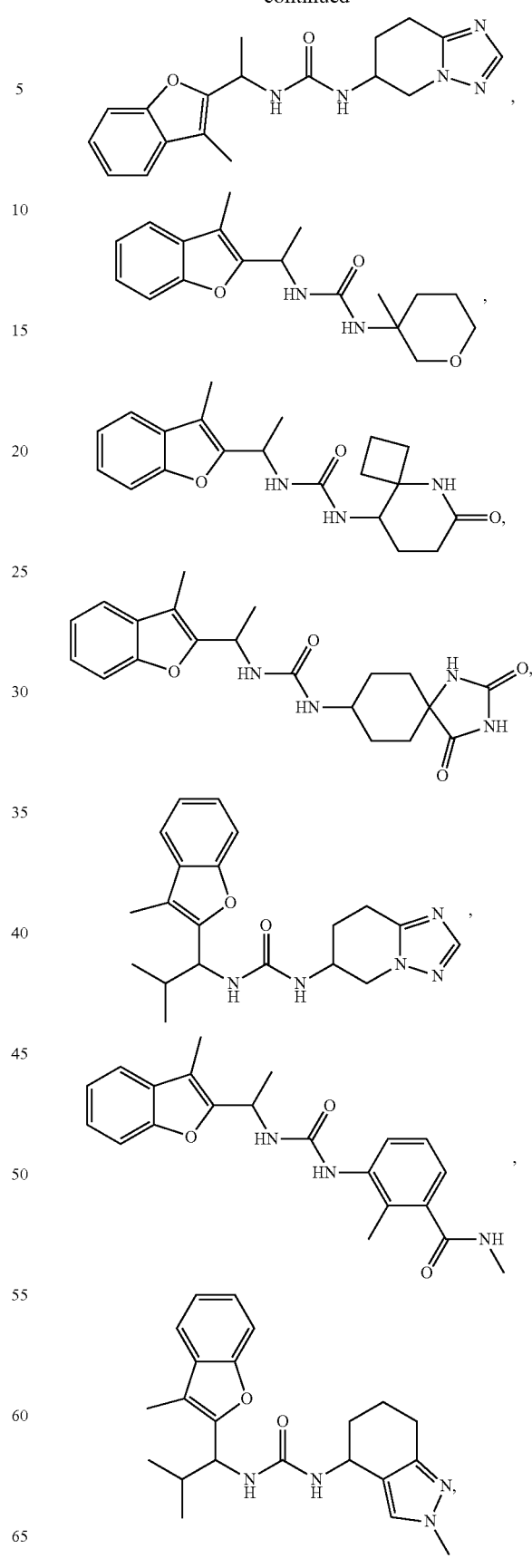

175
-continued
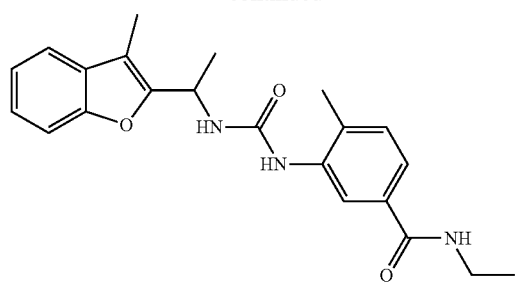
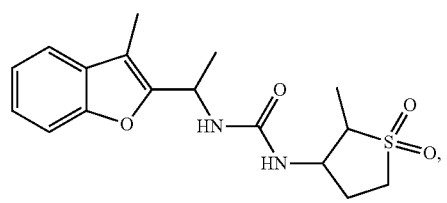
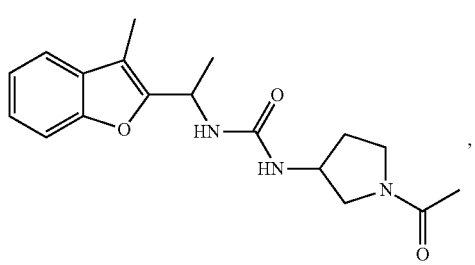
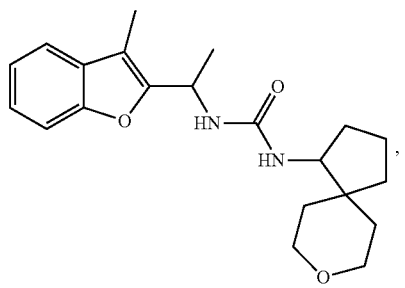
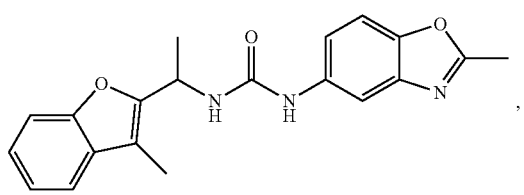
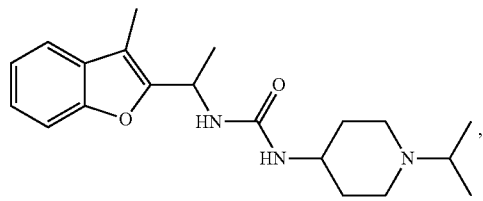
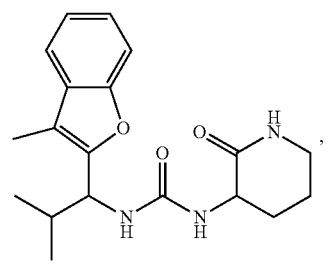
176
-continued
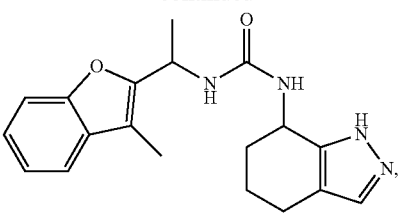
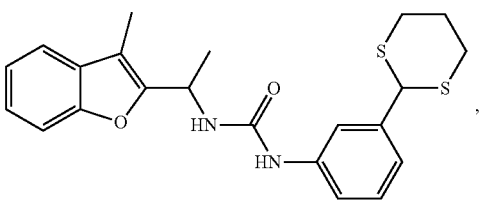
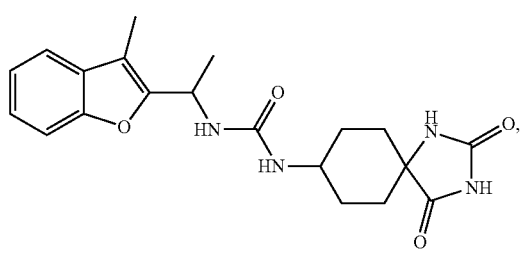
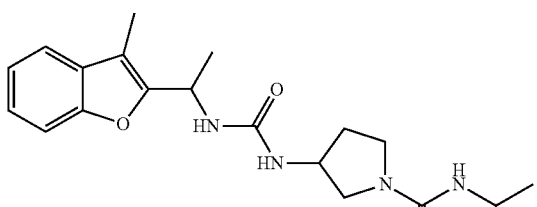
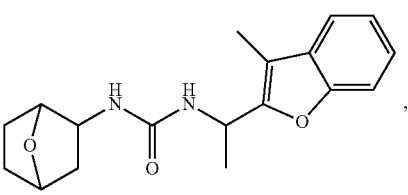
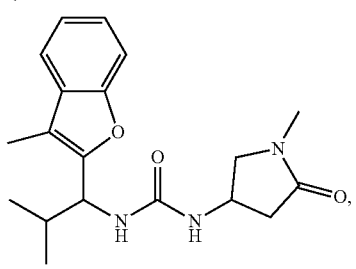
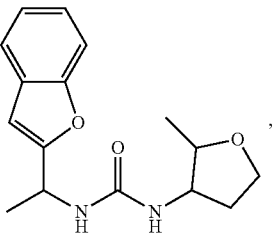

177
-continued
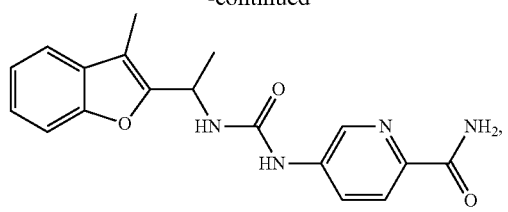
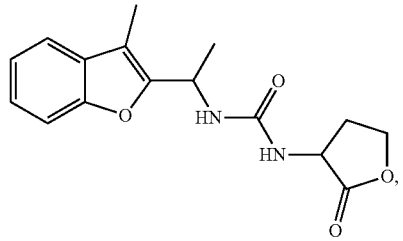
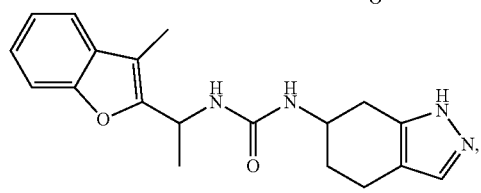
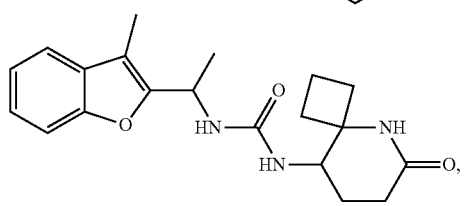
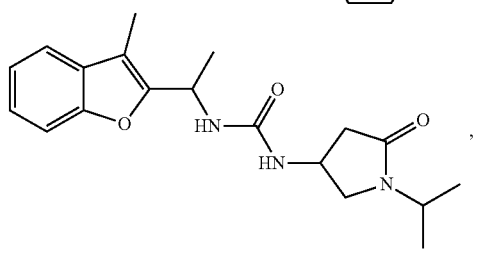
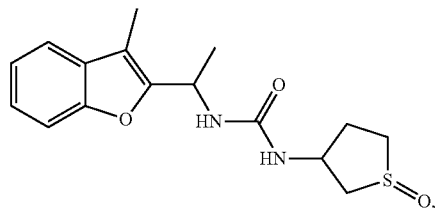
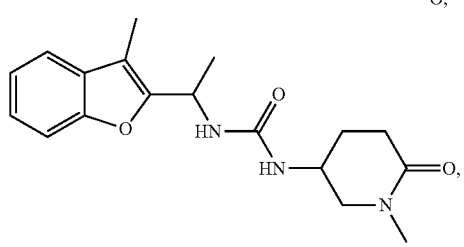
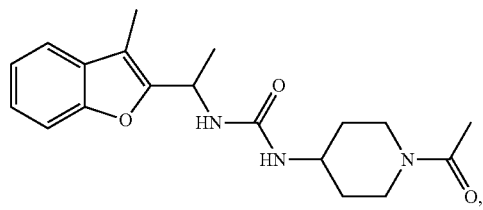
178
-continued
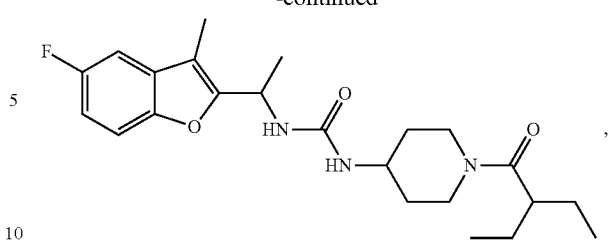
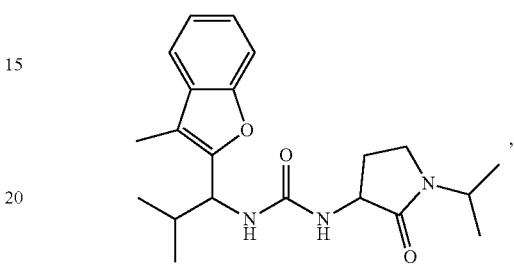
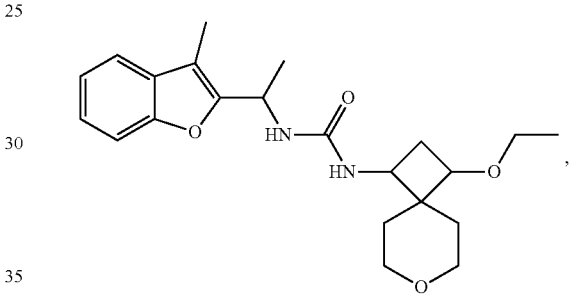
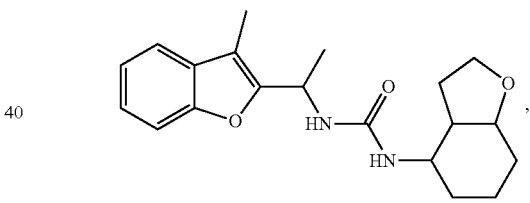
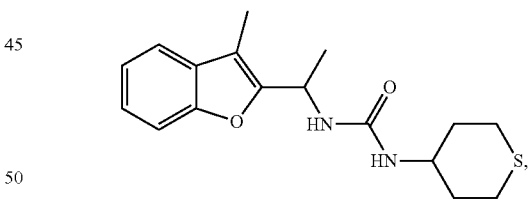
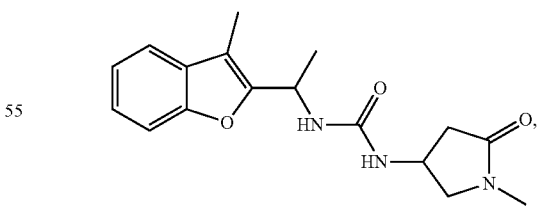
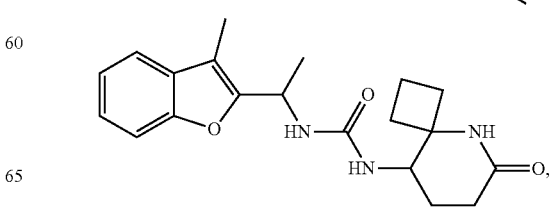

179
-continued
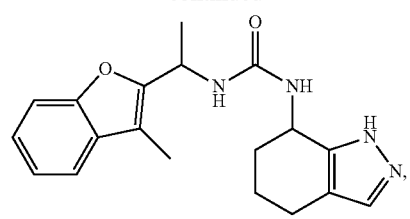
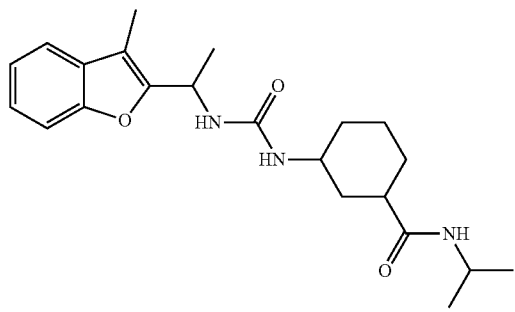
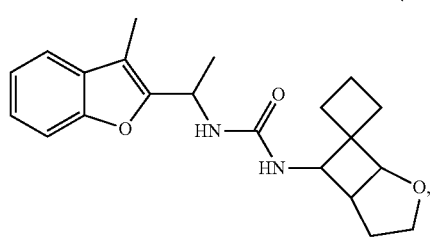
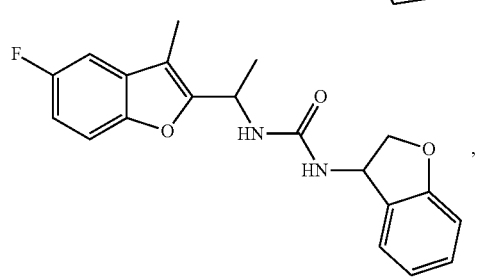
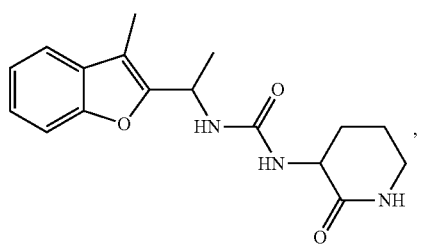
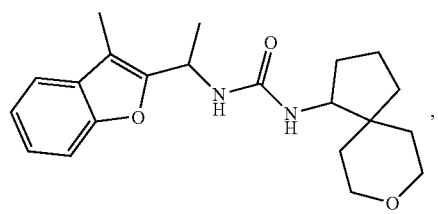
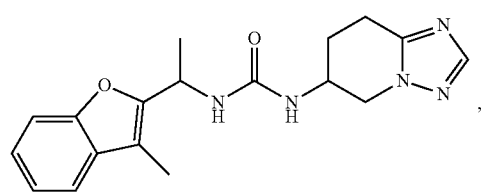
180
-continued
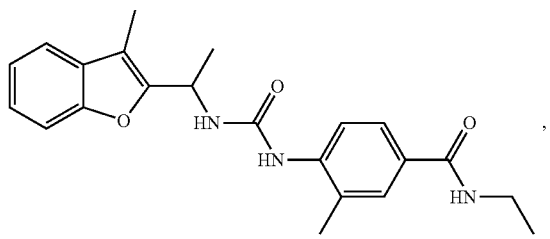
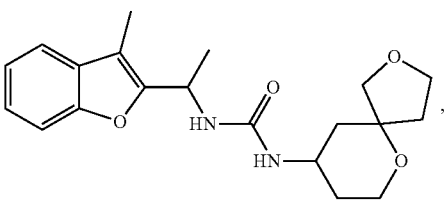
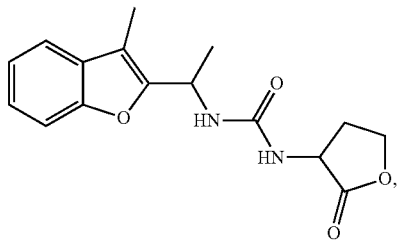
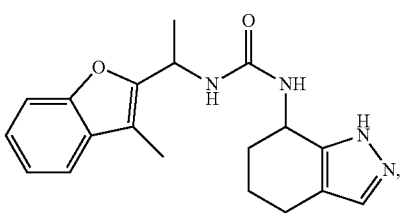
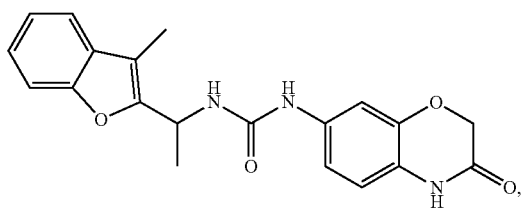
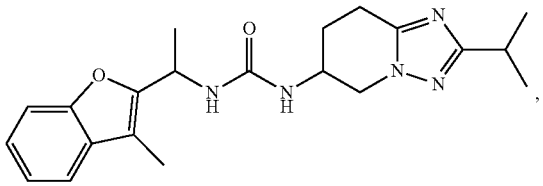
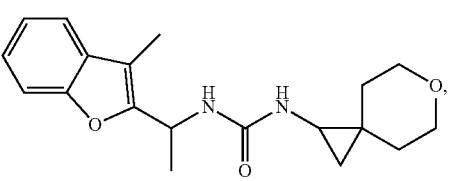
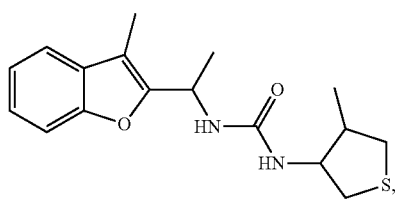

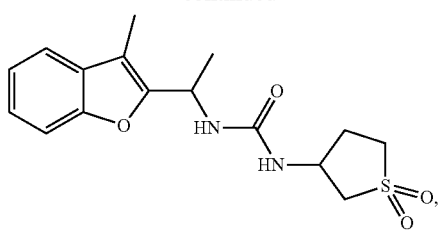
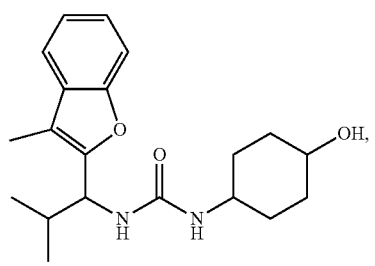
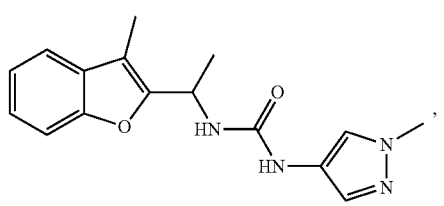
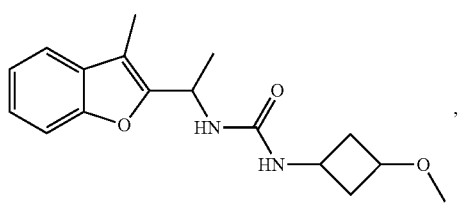
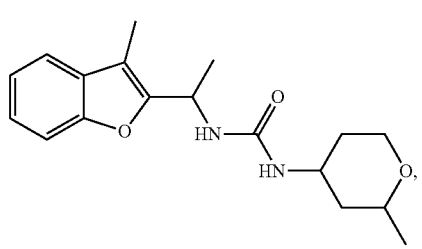
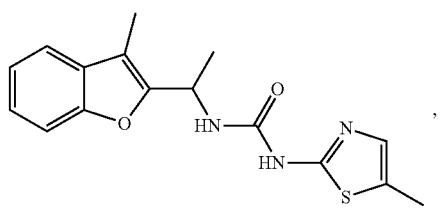
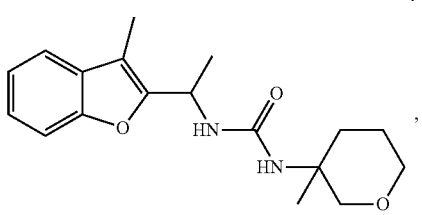
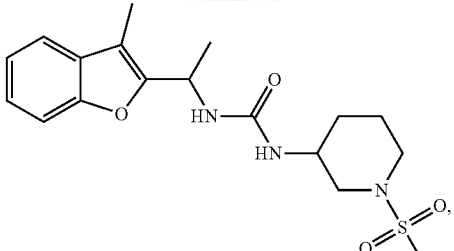
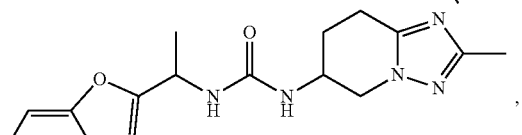
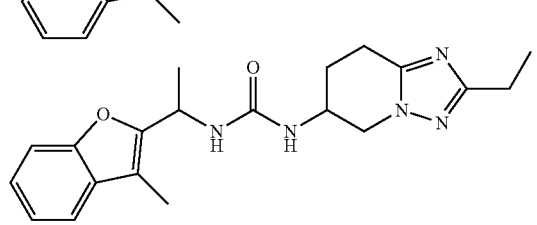
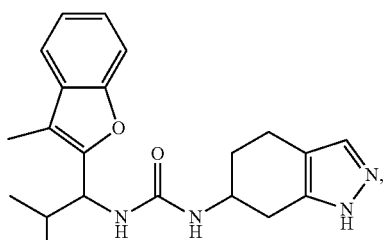
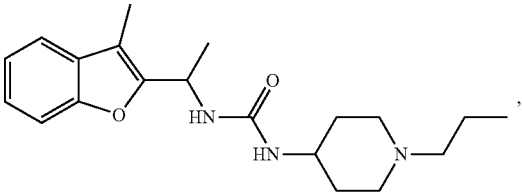
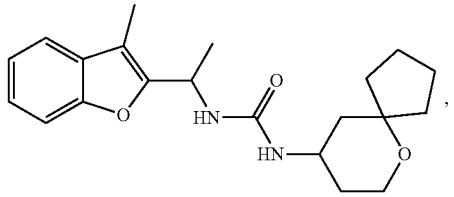
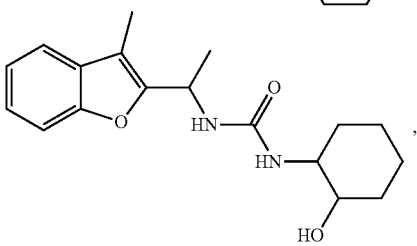
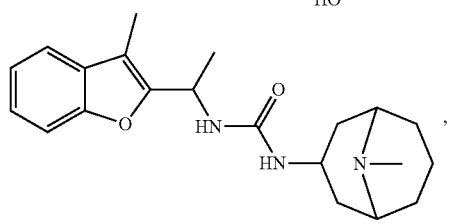

183
-continued
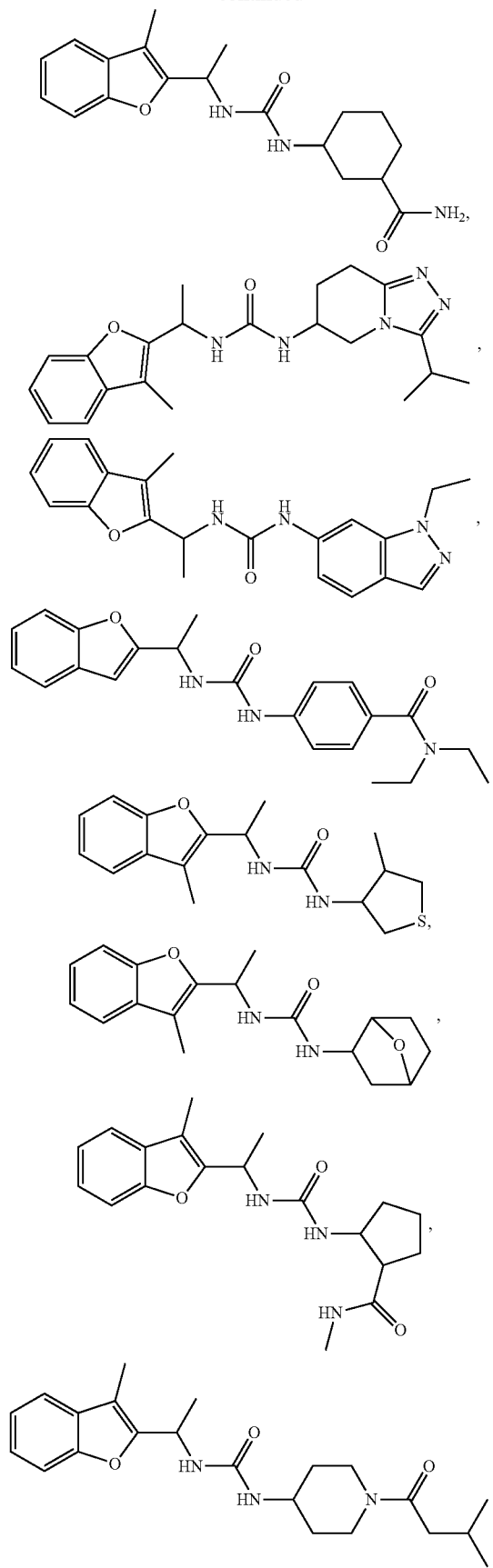
184
-continued
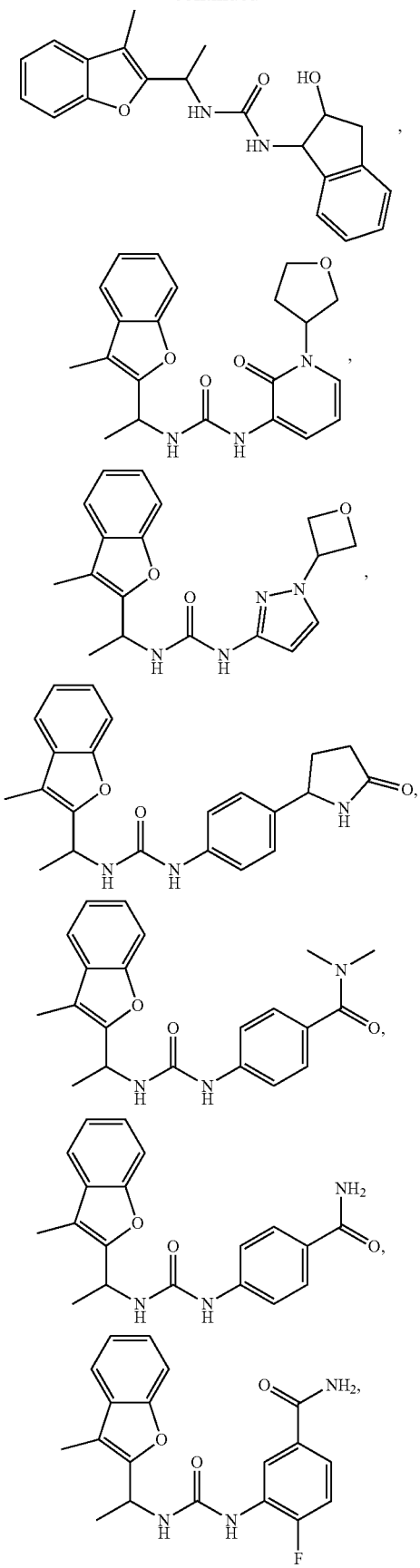

185
-continued
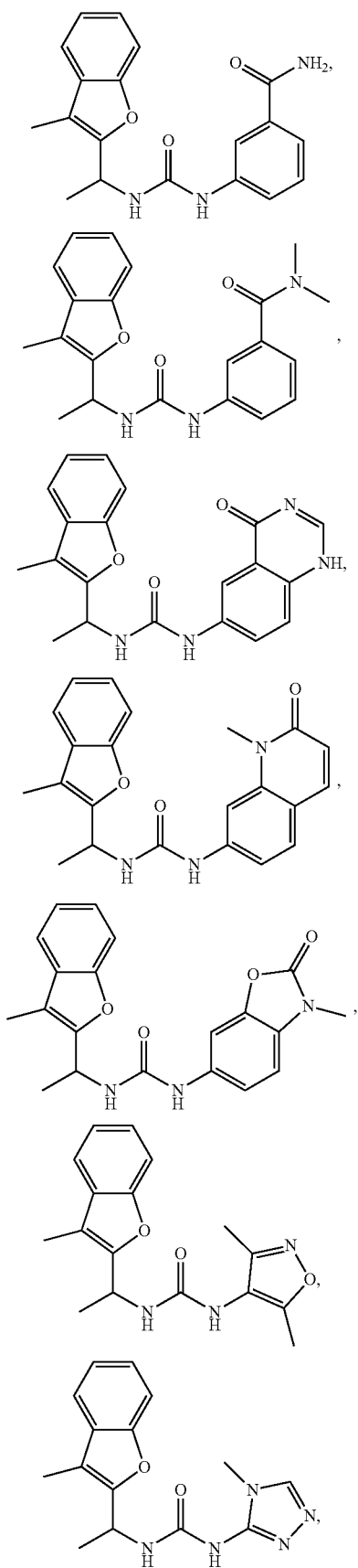
186
-continued
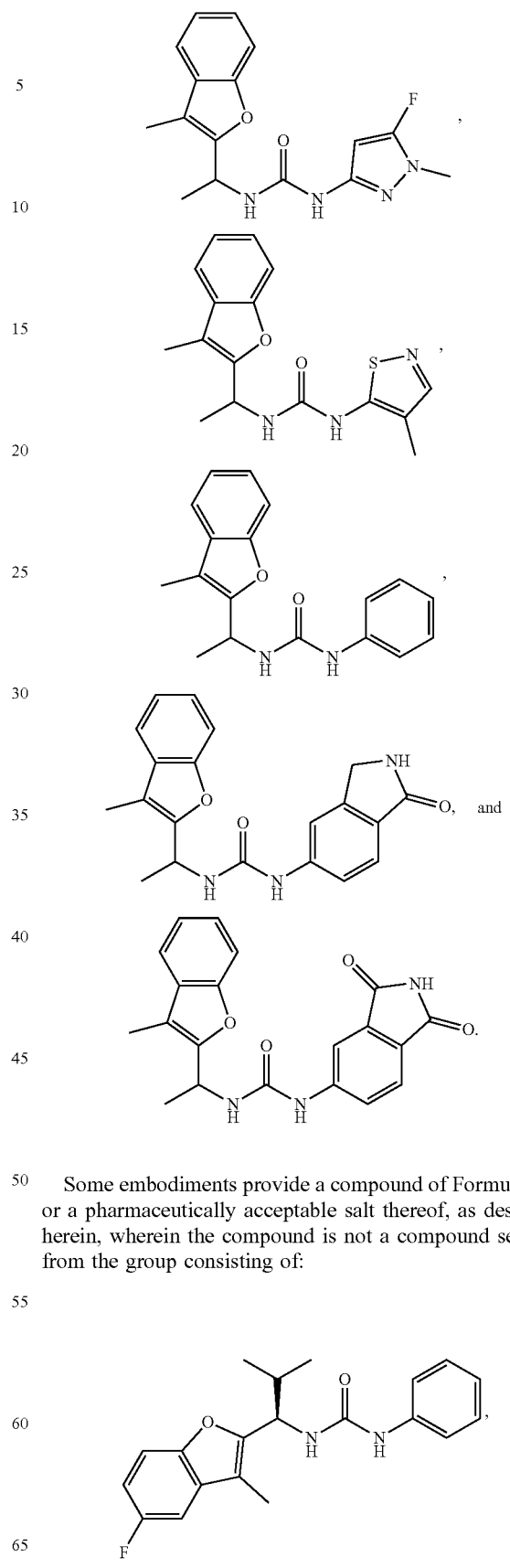
Some embodiments provide a compound of Formula (X), or a pharmaceutically acceptable salt thereof, as described herein, wherein the compound is not a compound selected from the group consisting of:
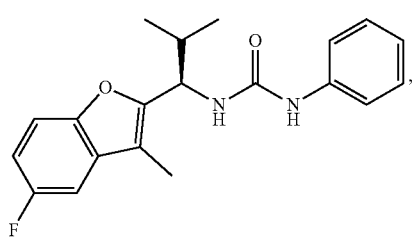

187
-continued
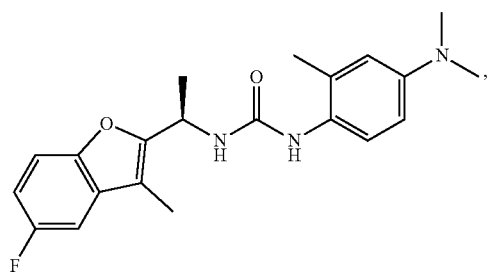
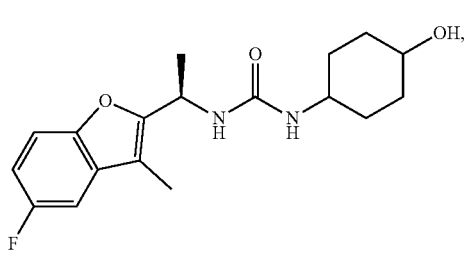
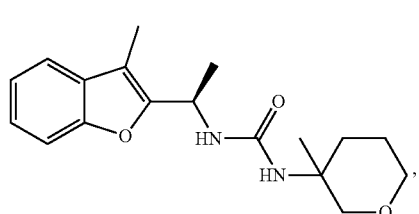
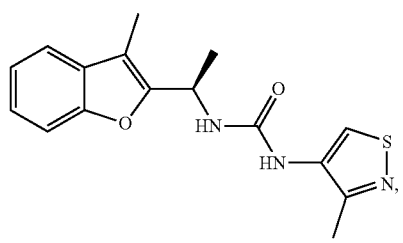
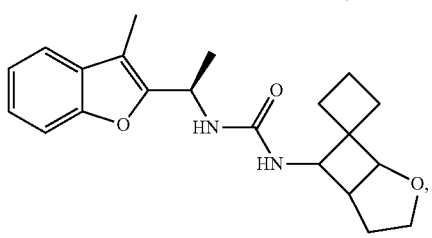
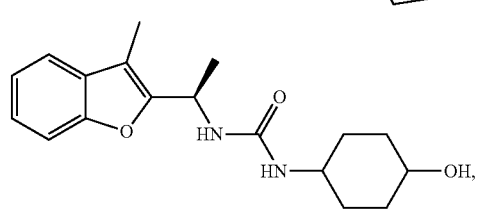
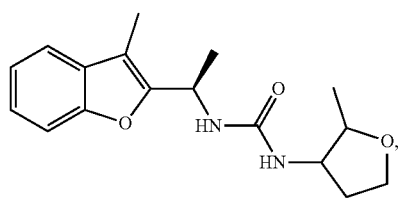
188
-continued
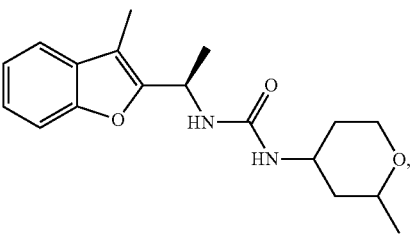
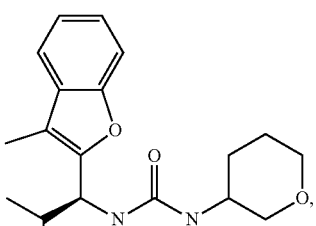
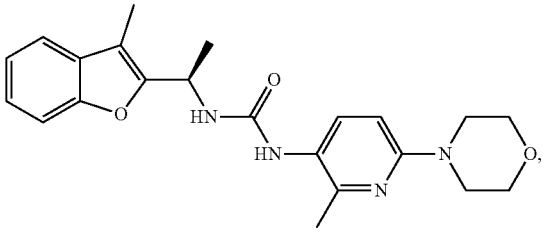
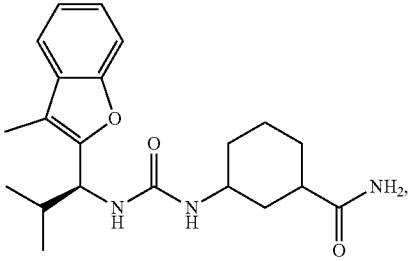
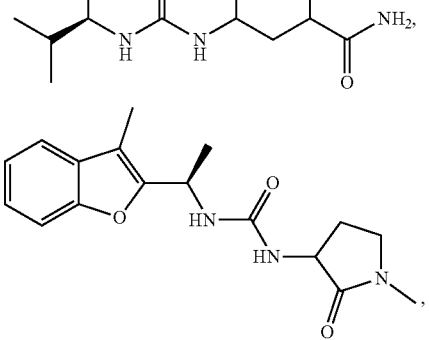
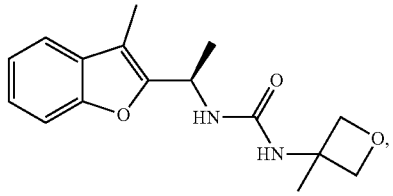
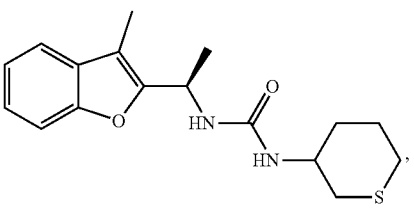

189
-continued
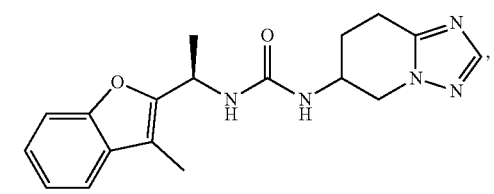
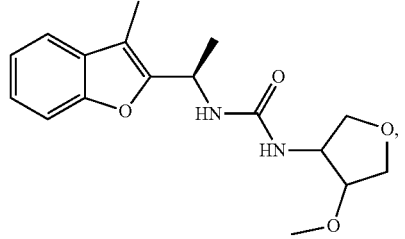
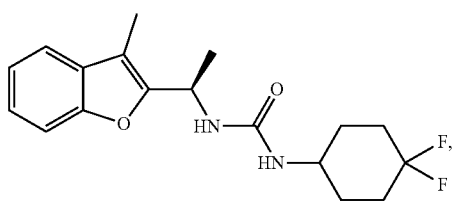
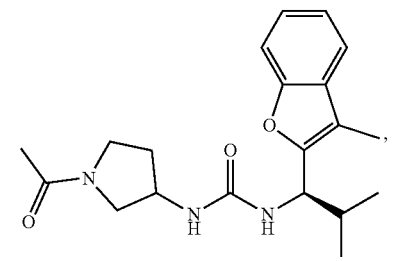
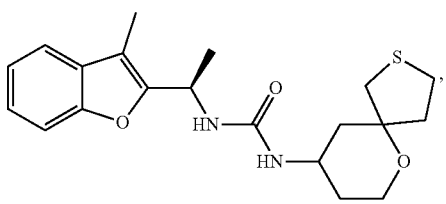
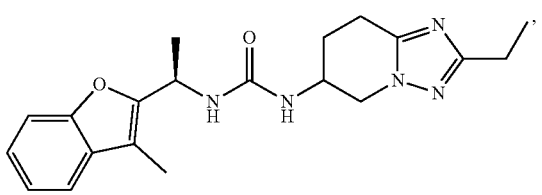
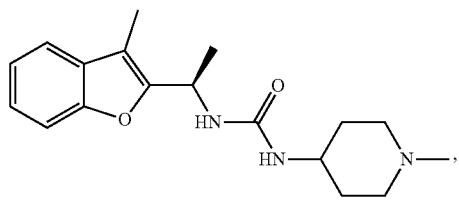
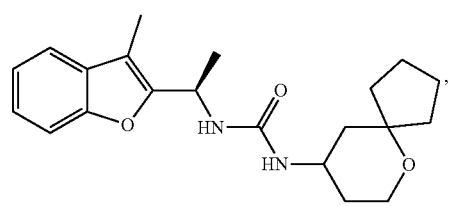
190
-continued
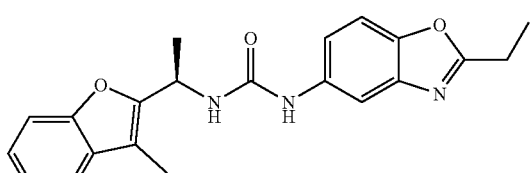
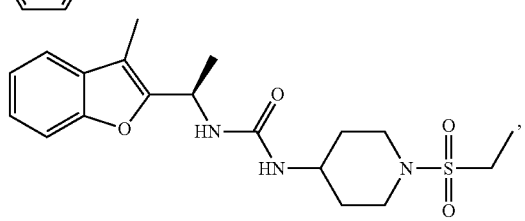
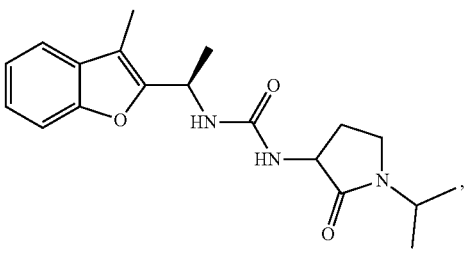
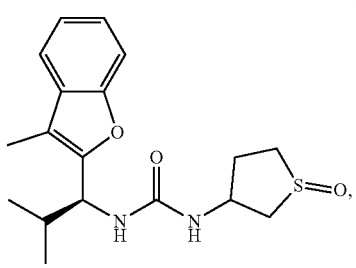
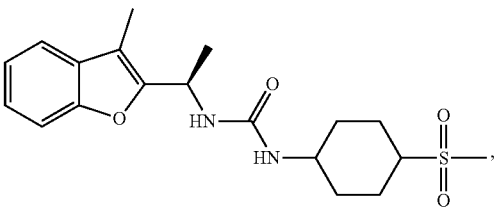
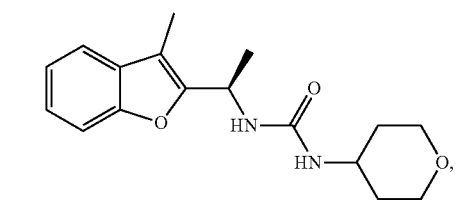
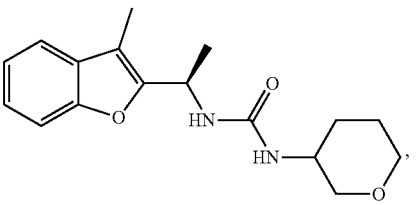
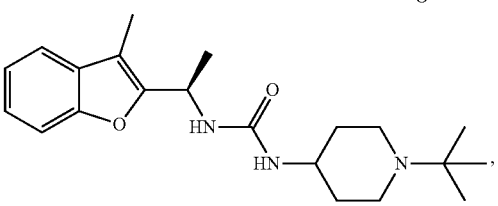

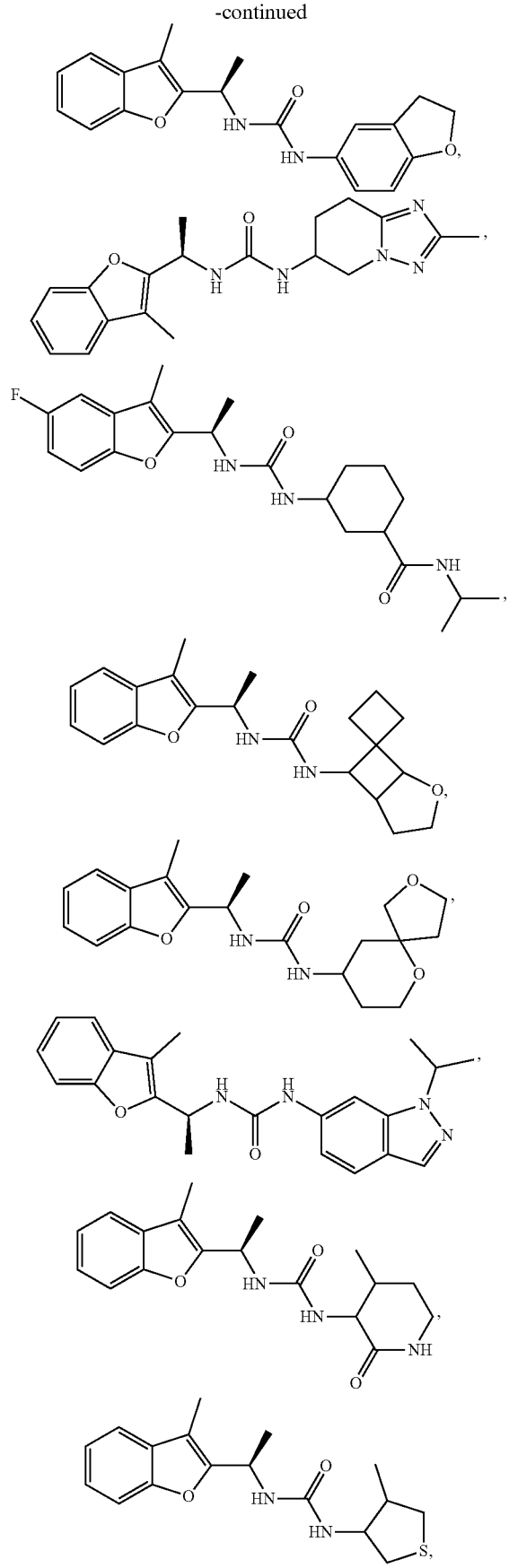
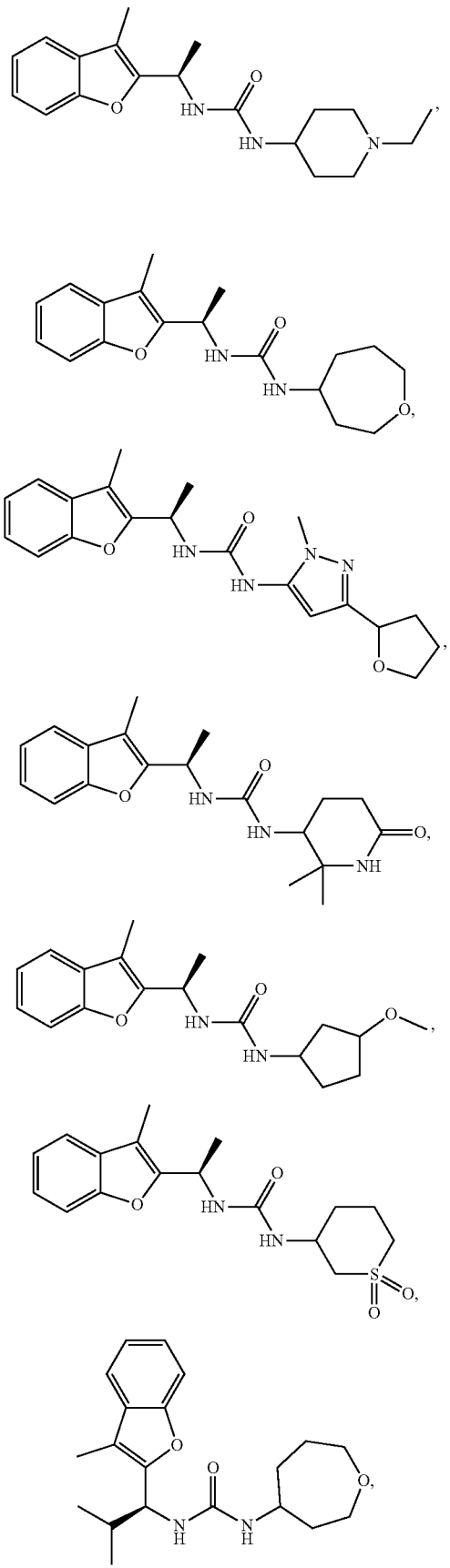

193
-continued
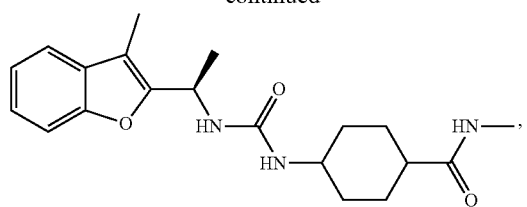
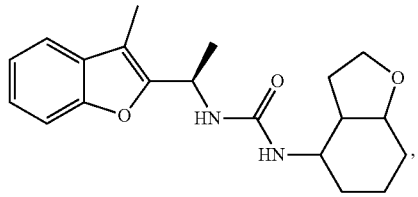
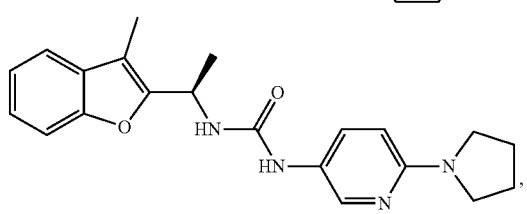
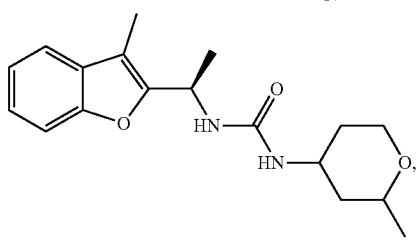
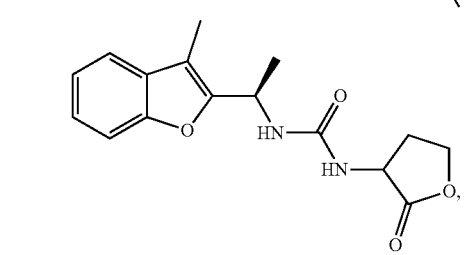
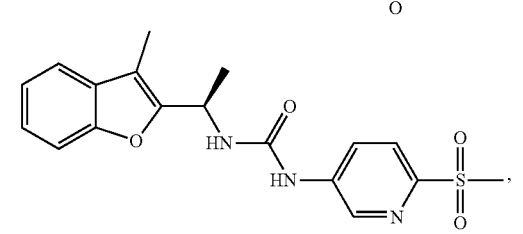
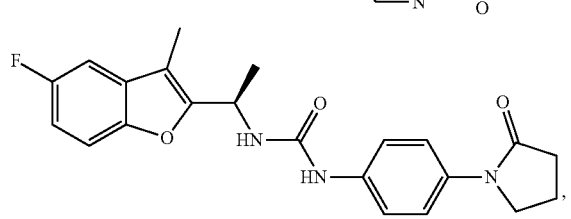
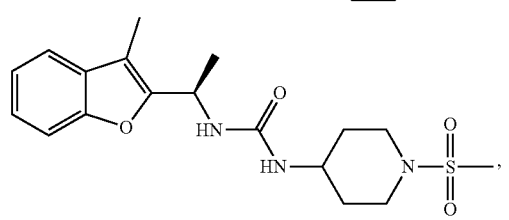
194
-continued
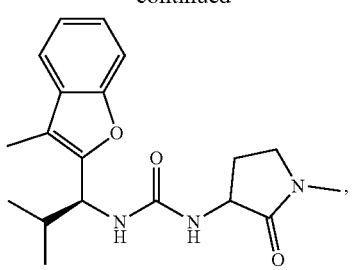
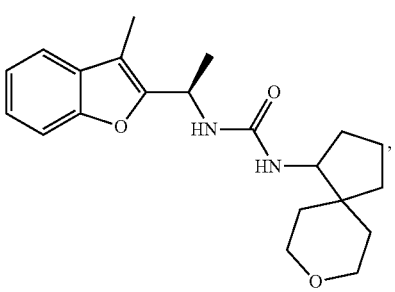
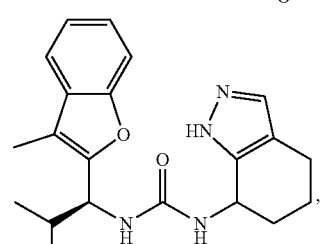
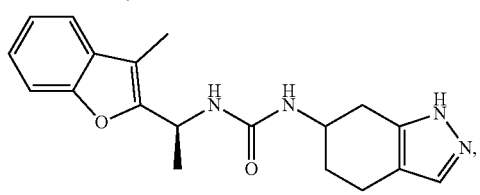
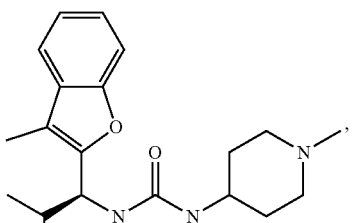
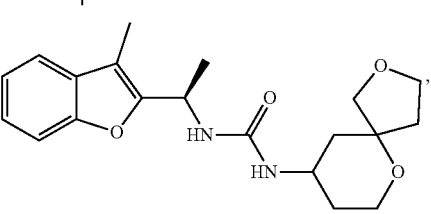
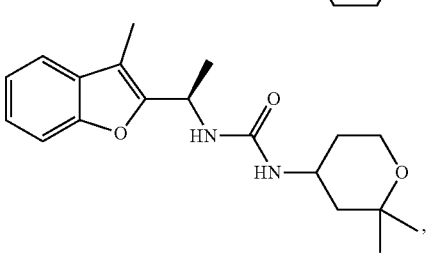

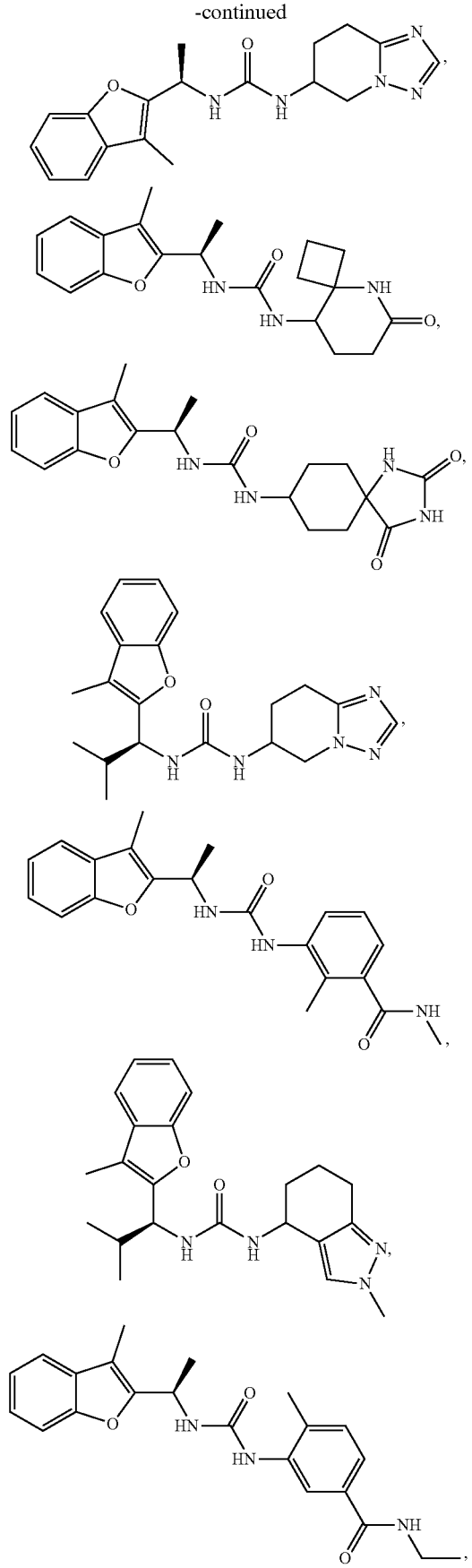
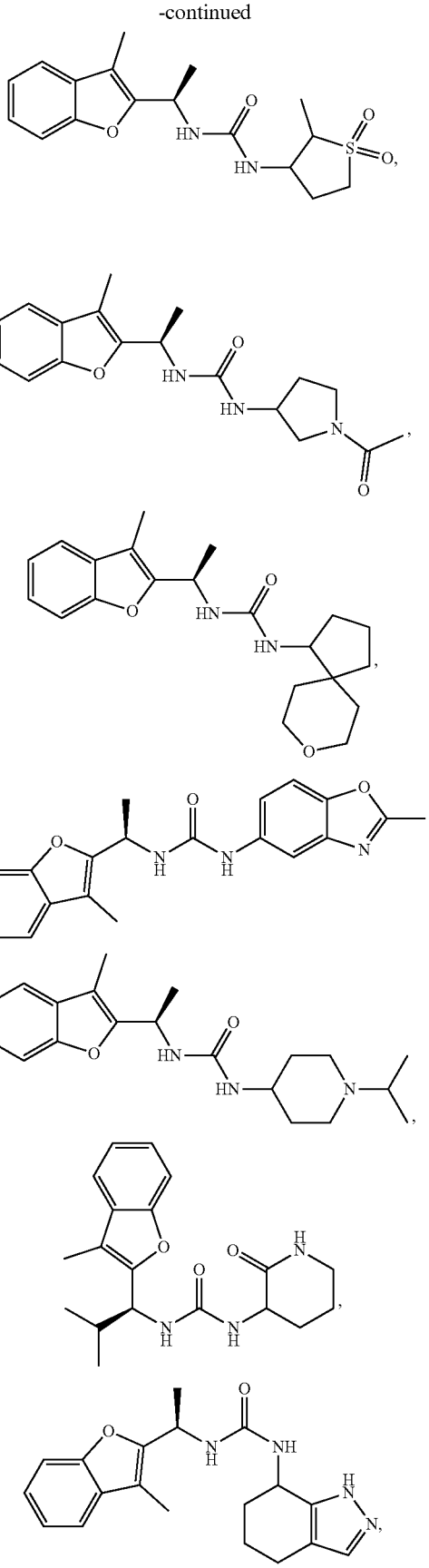

197
-continued
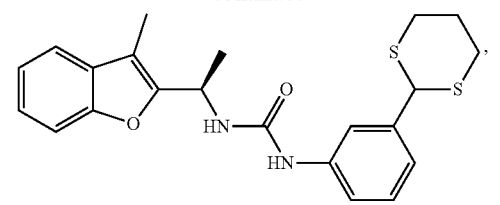
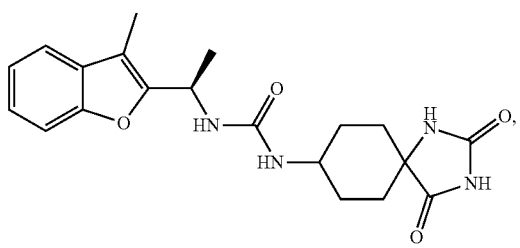
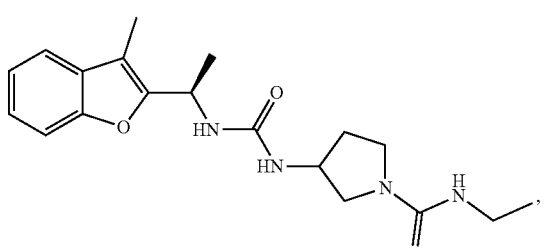
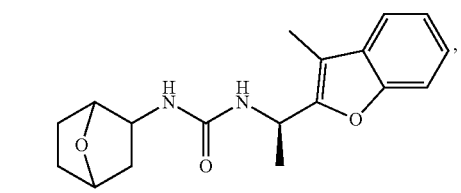
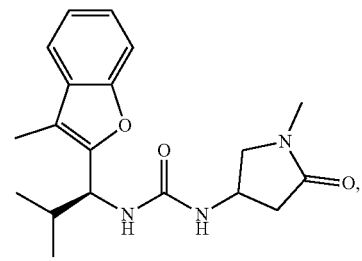
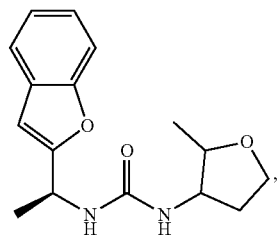
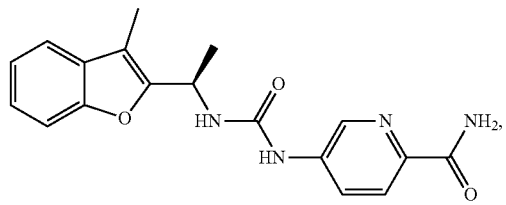
198
-continued
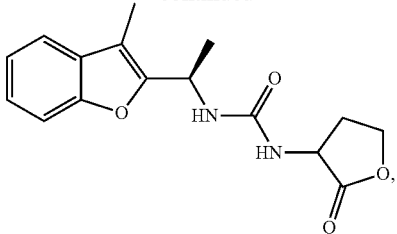
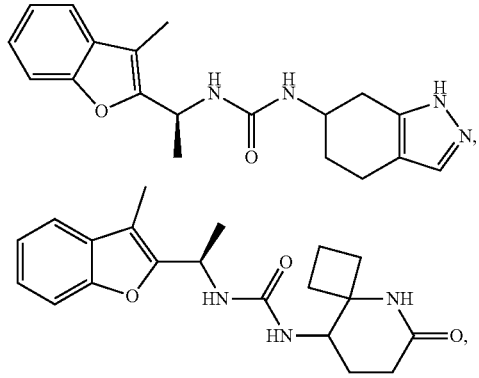
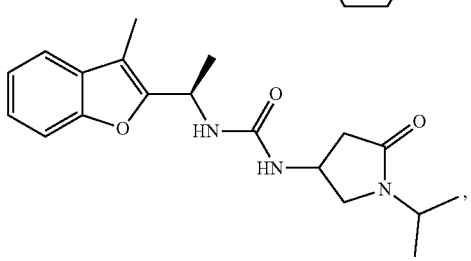
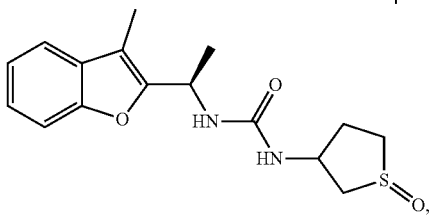
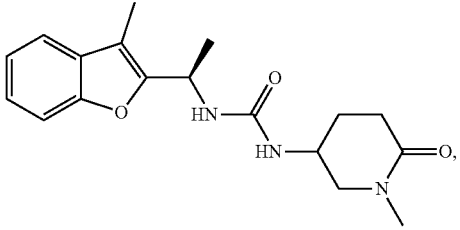
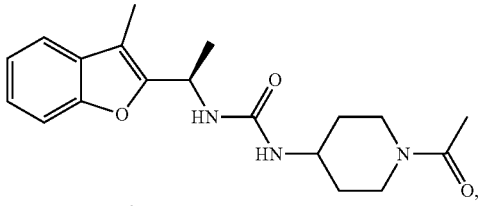
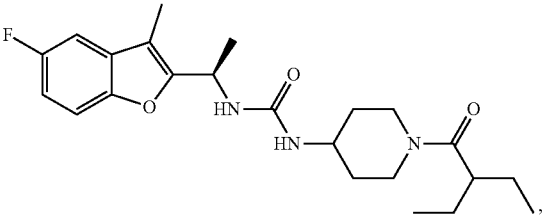

199
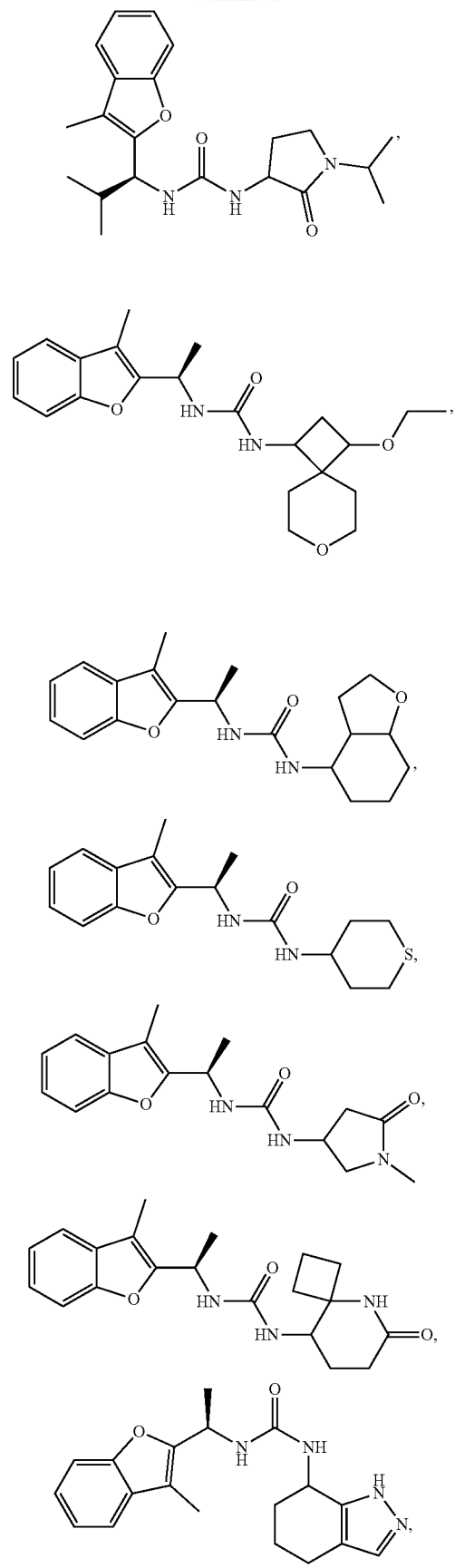
200
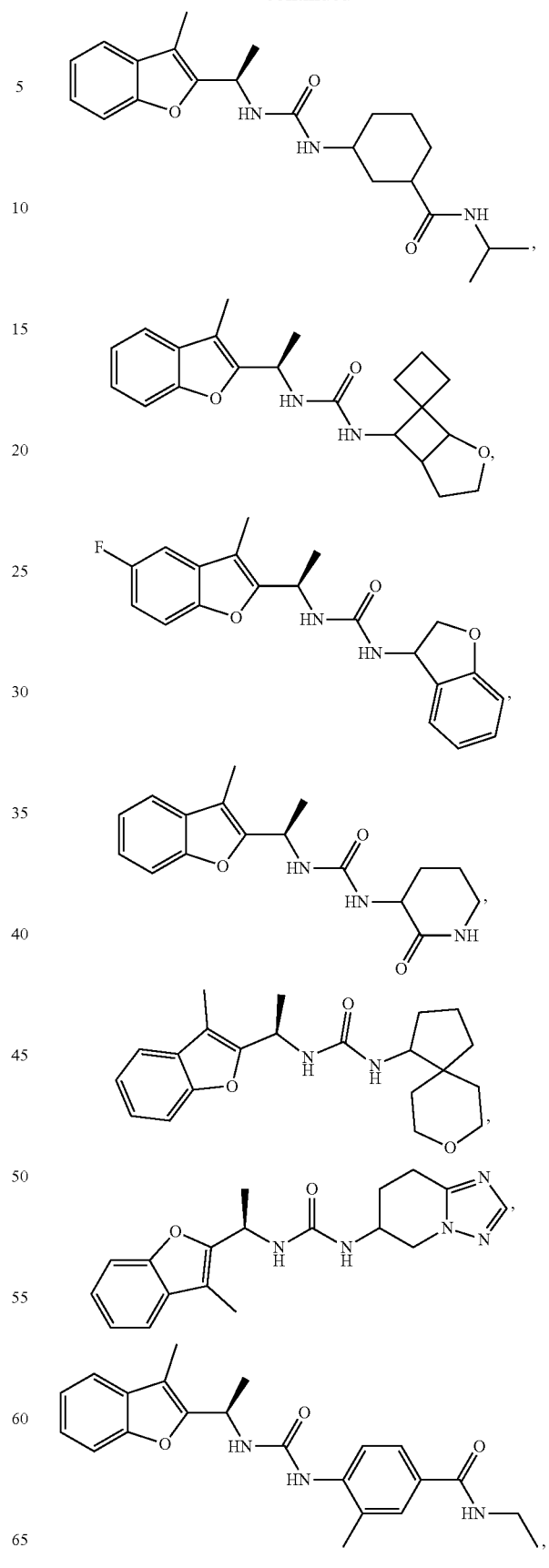

-continued
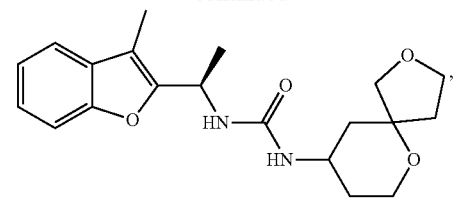
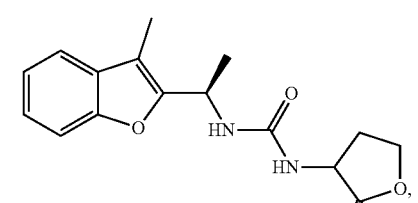
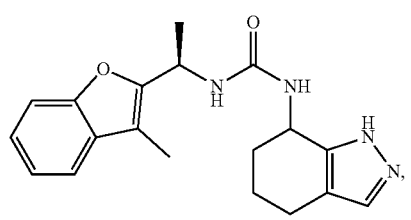
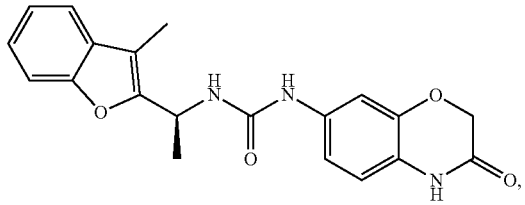
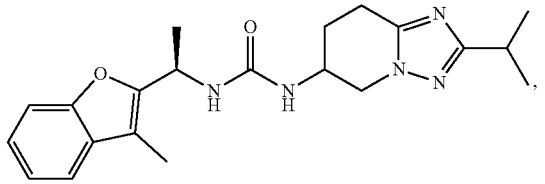
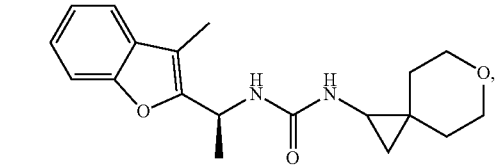
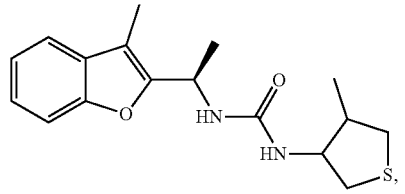
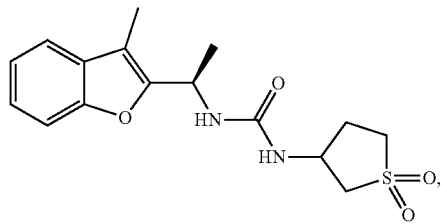
-continued
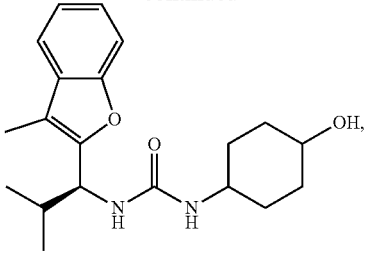
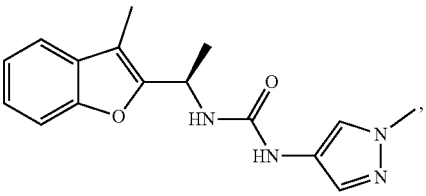
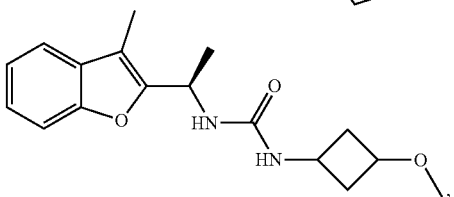
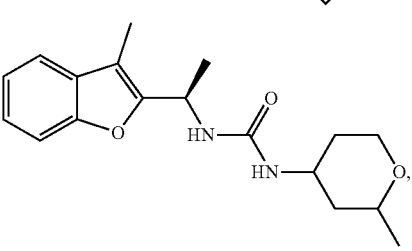
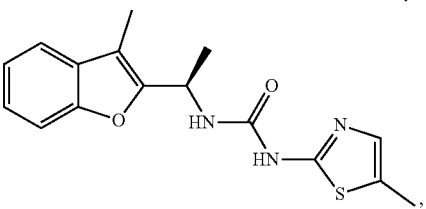
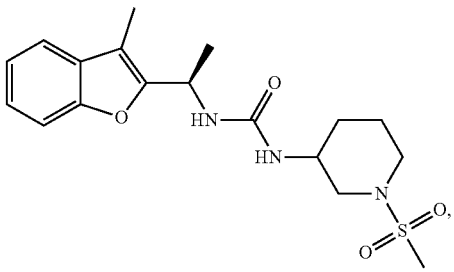
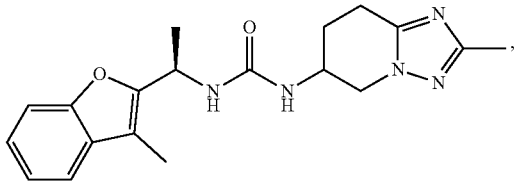
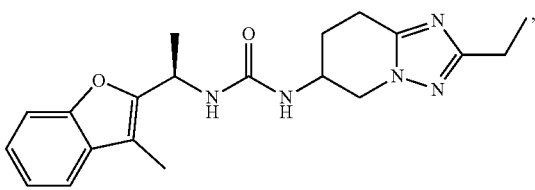

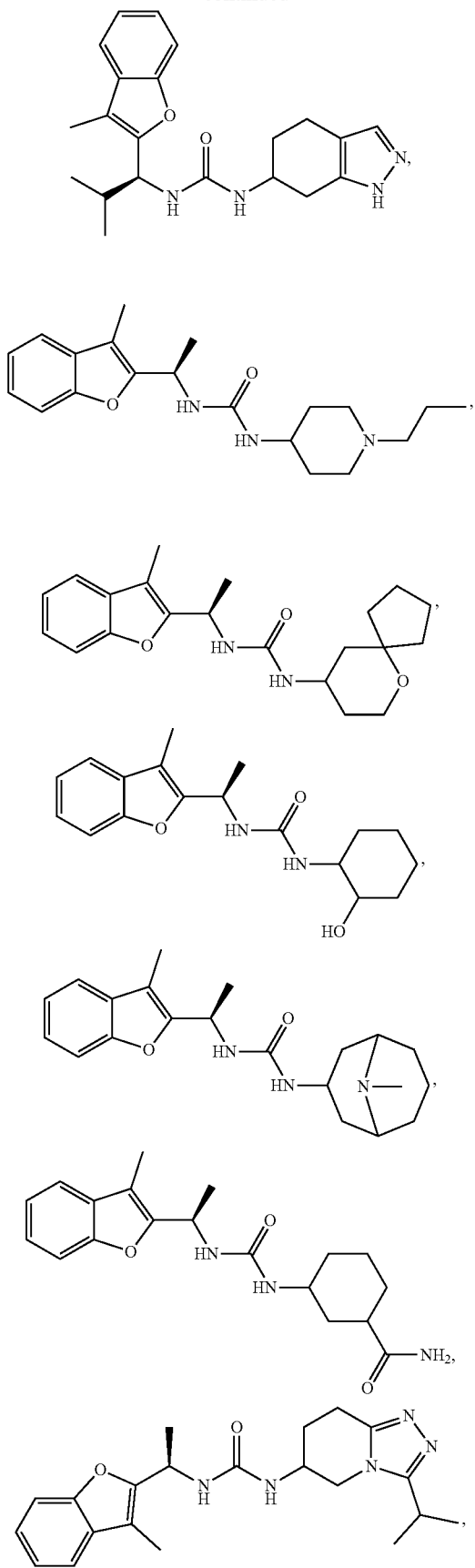
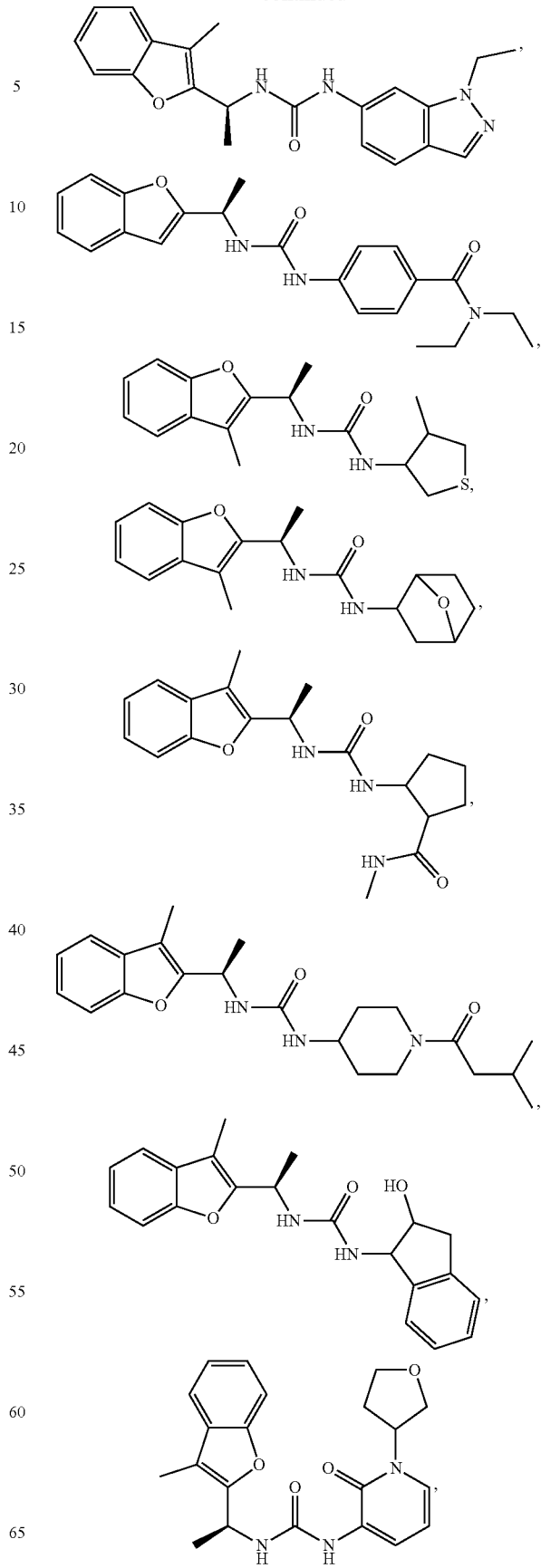

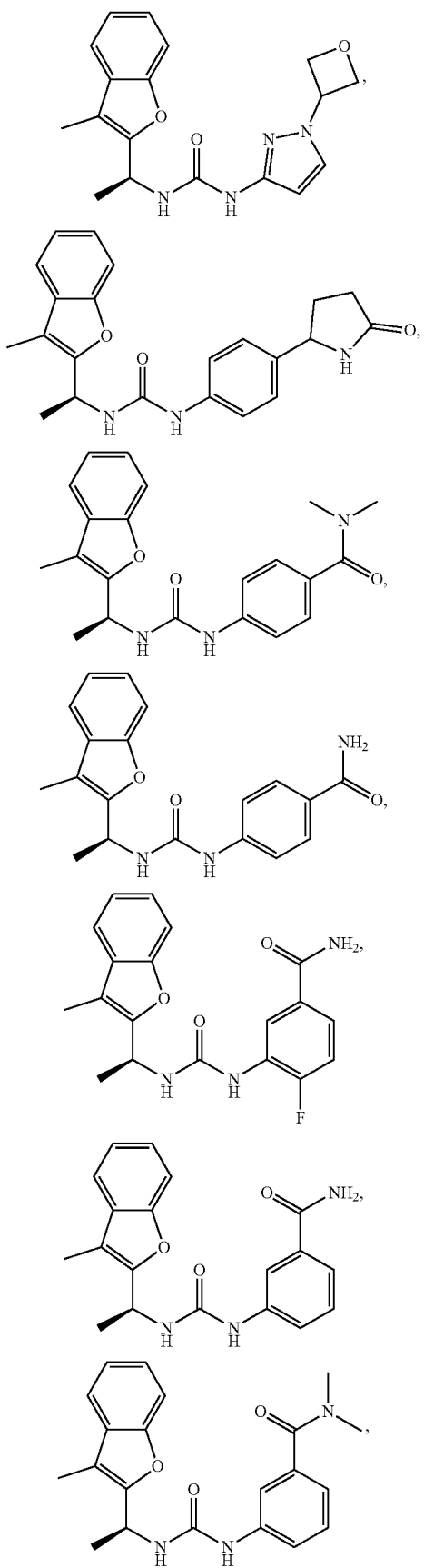
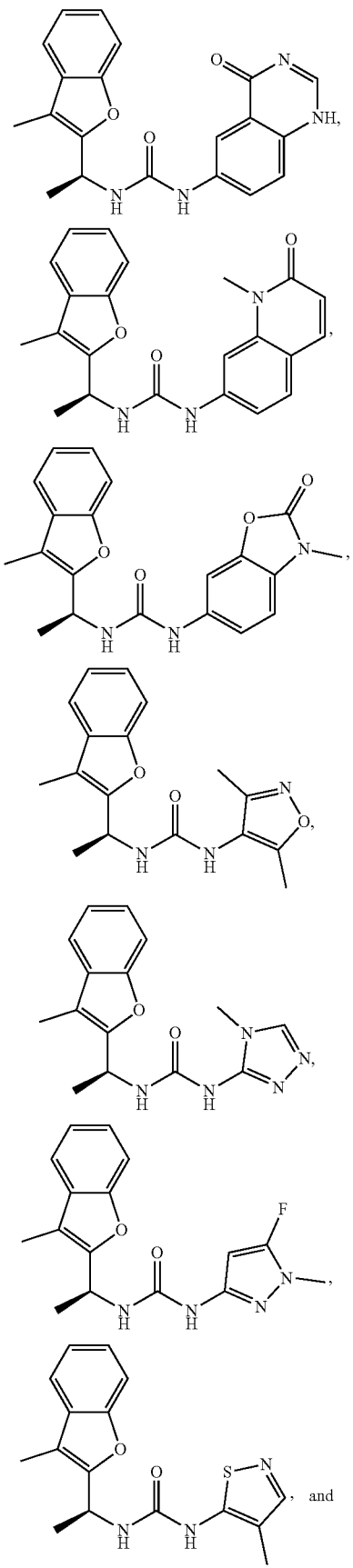

207
-continued
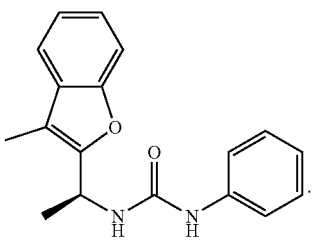
Some embodiments provide a compound of Formula (X), or a pharmaceutically acceptable salt thereof, as described herein, wherein the compound is not a compound selected from the group consisting of:
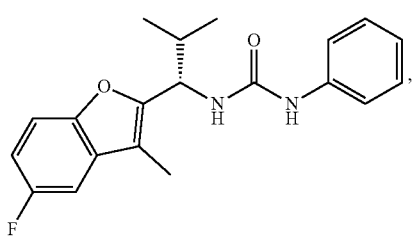
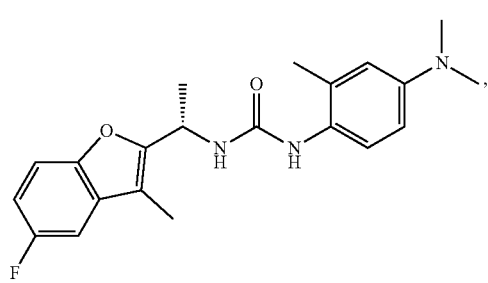
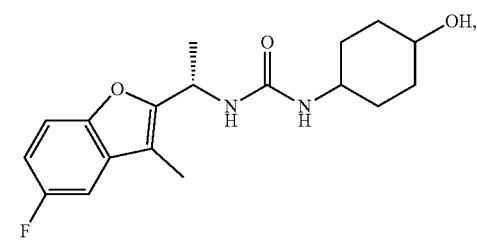
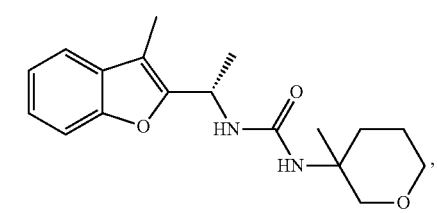
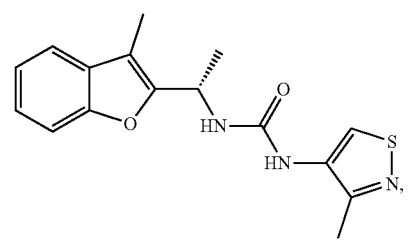
208
-continued
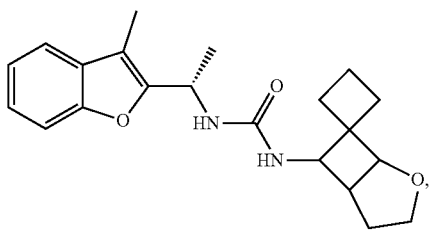
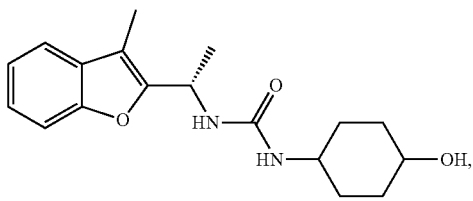
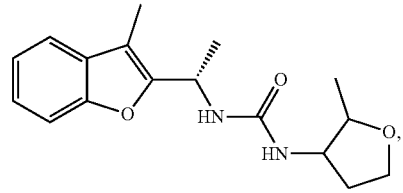
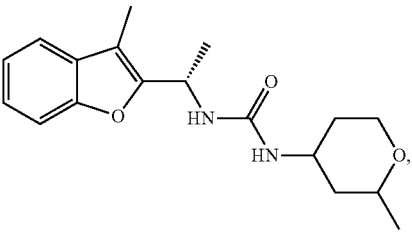
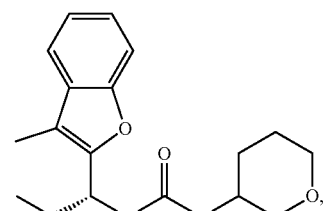
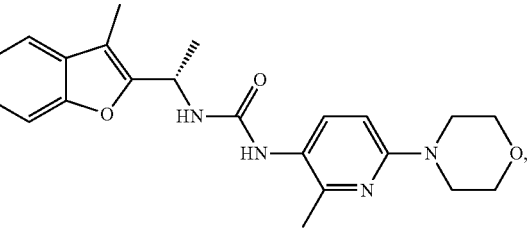
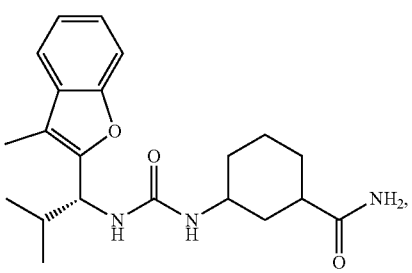

-continued
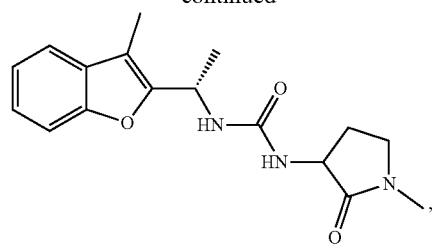
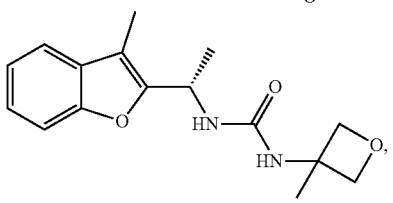
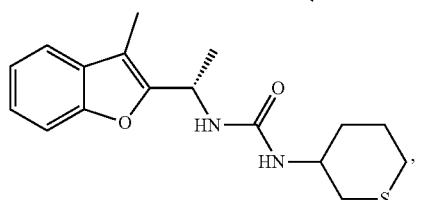
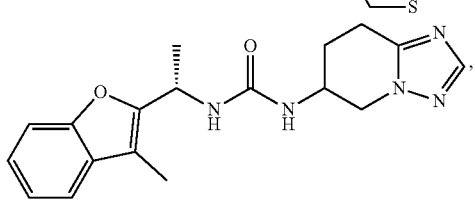
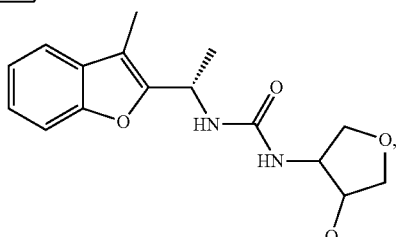
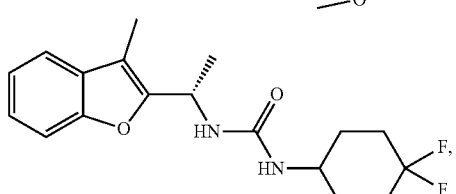
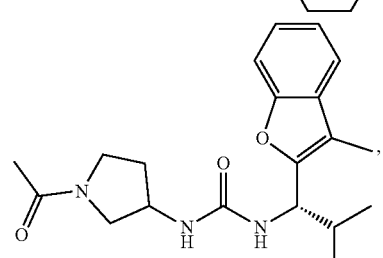
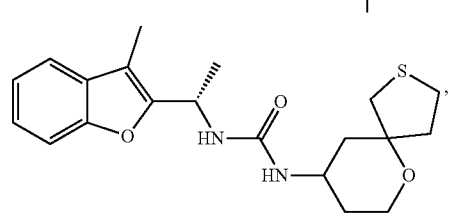
-continued
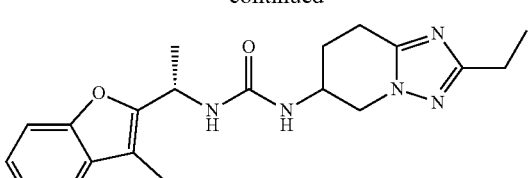
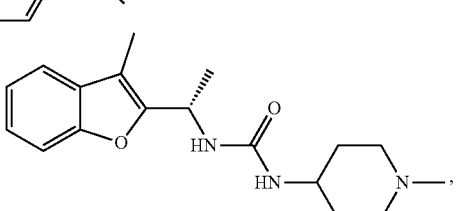
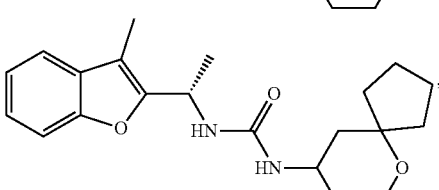
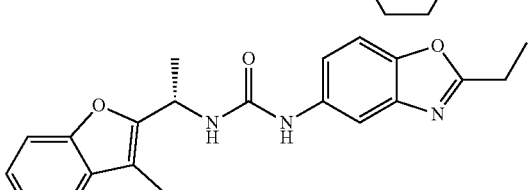
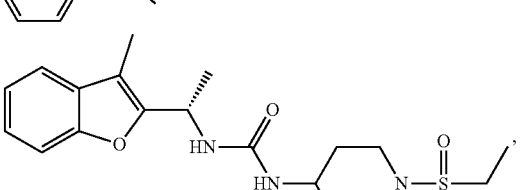
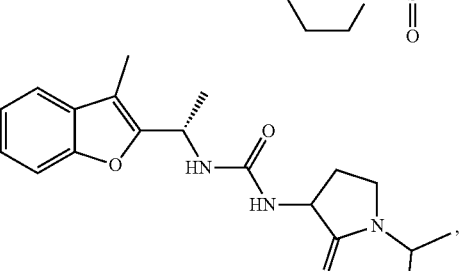
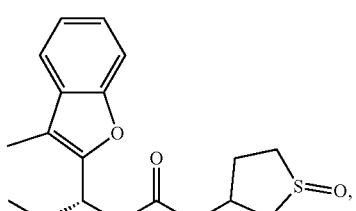
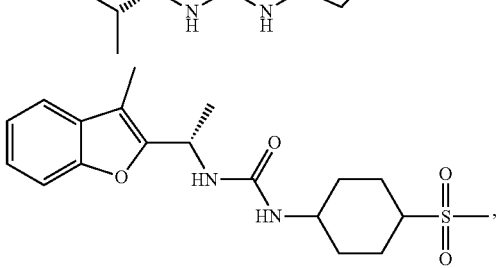

-continued

213
-continued
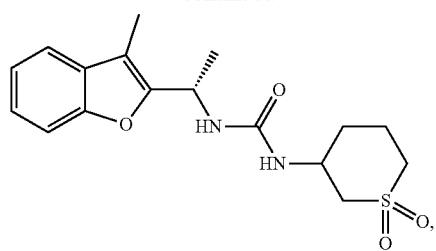
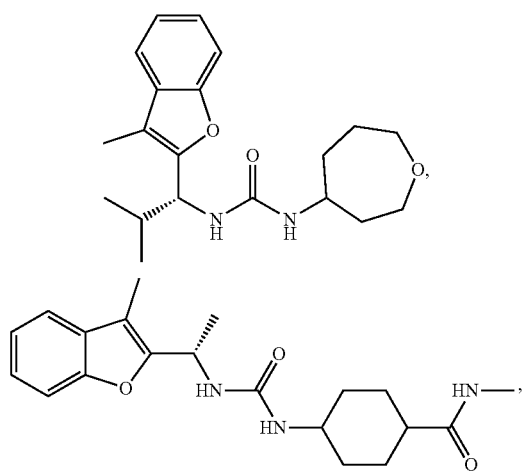
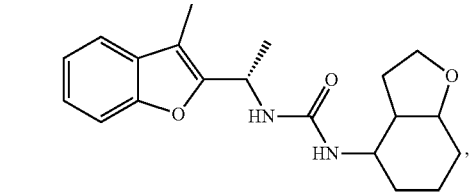
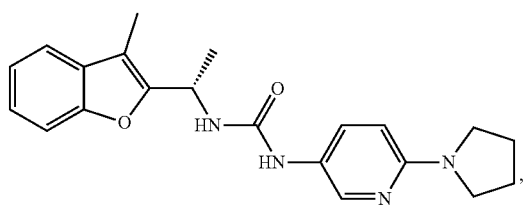
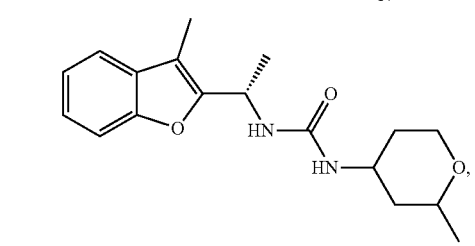
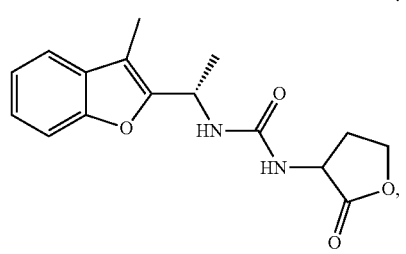
214
-continued
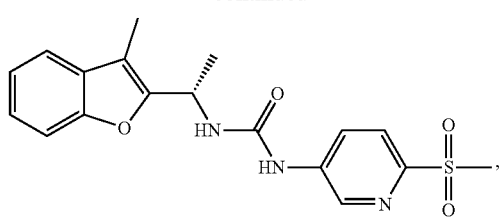
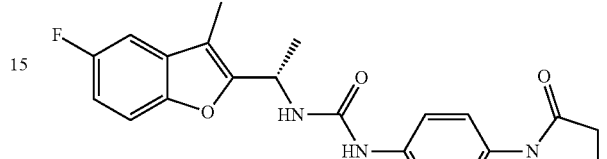
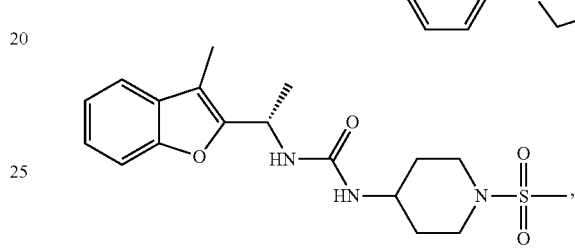
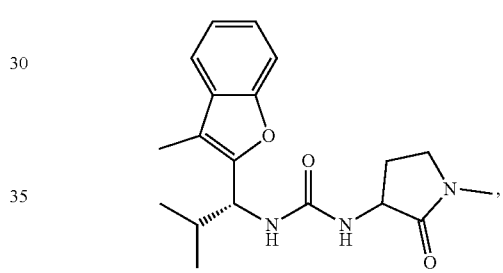
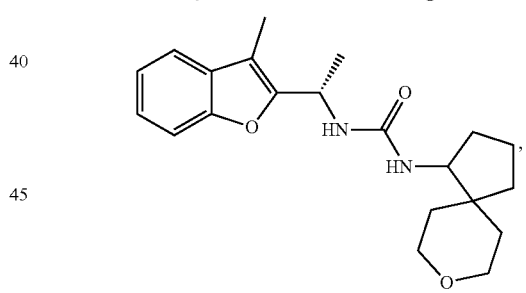
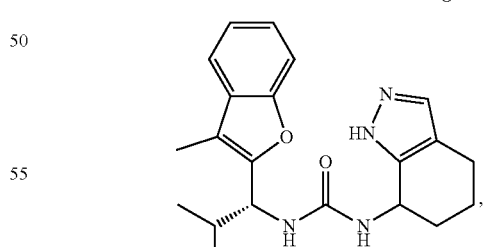
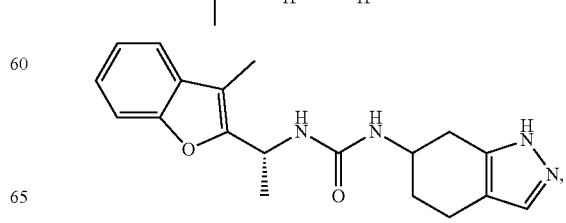

215
-continued
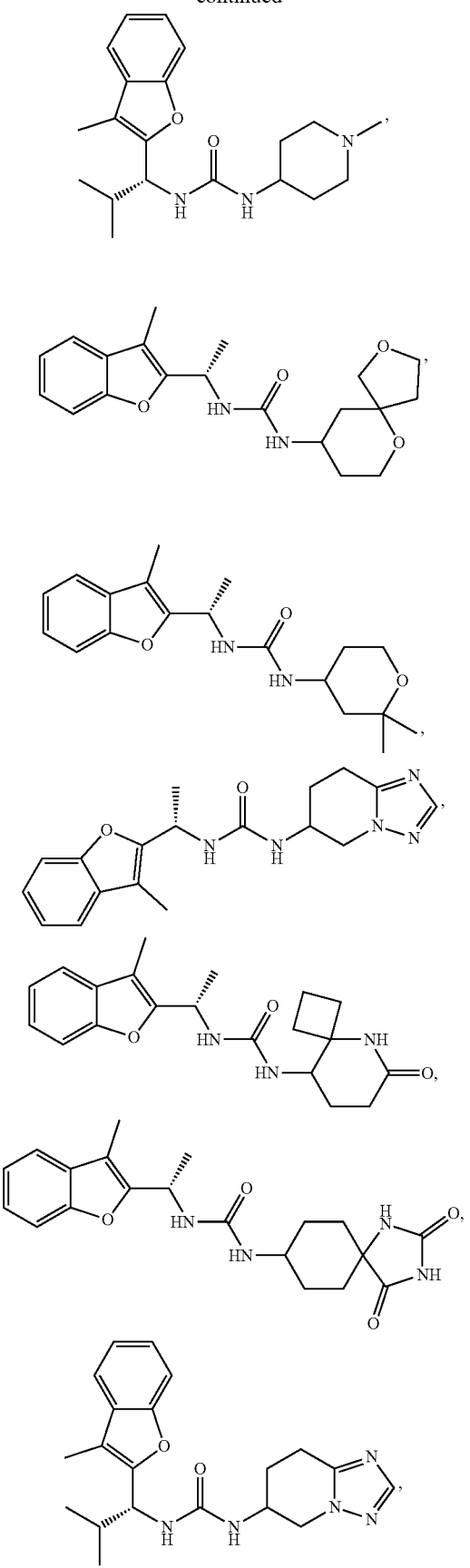
216
-continued
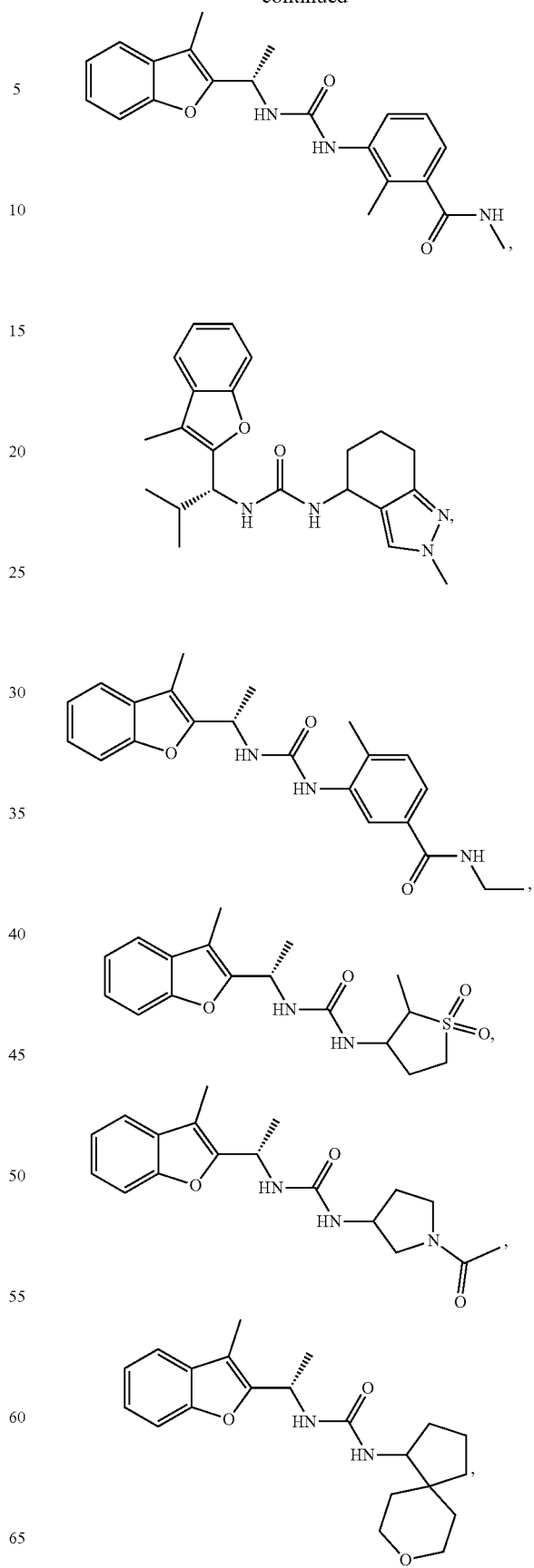

217
-continued
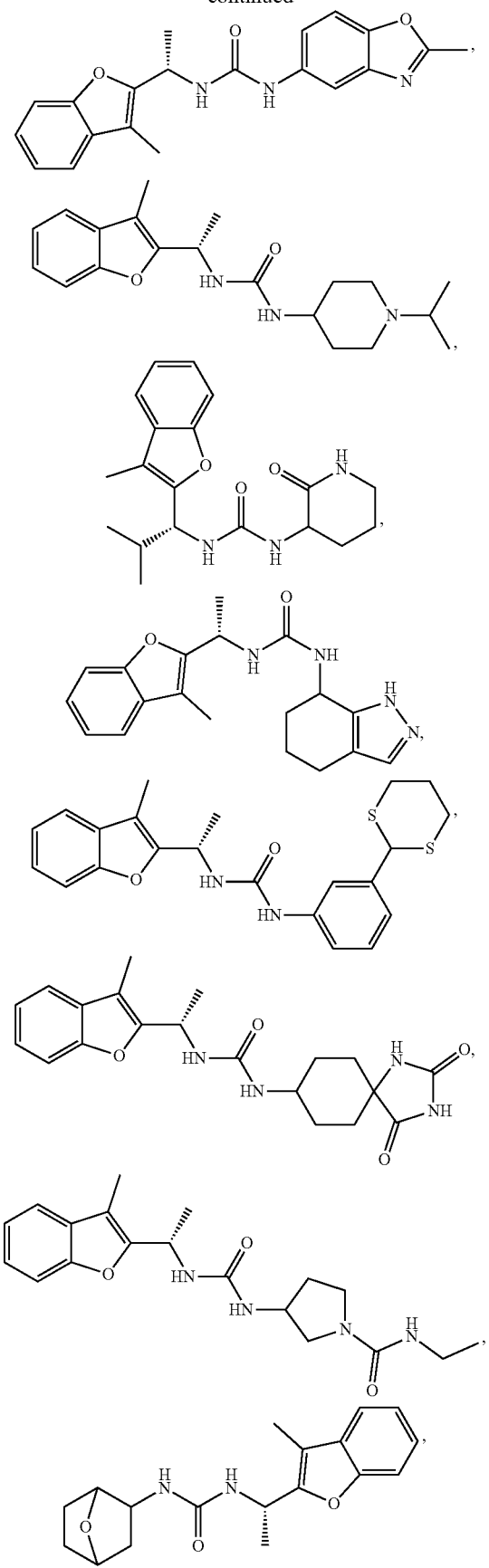
218
-continued
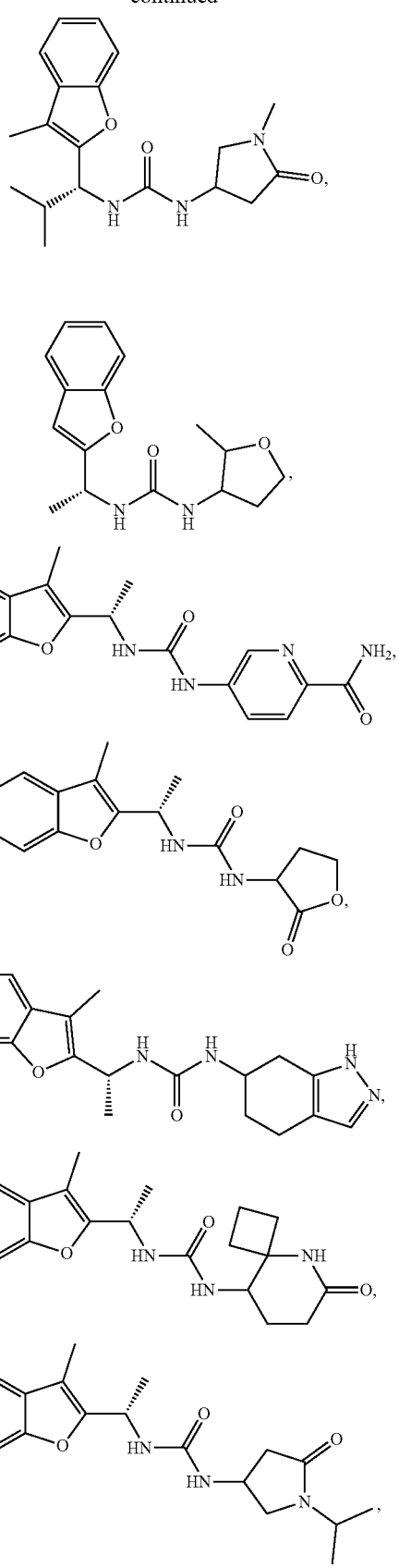

219
-continued
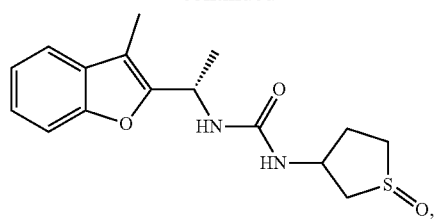
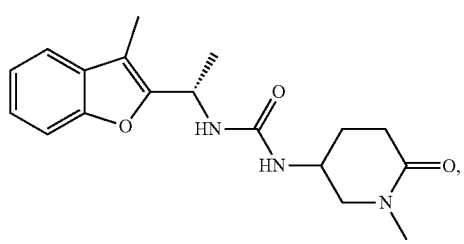
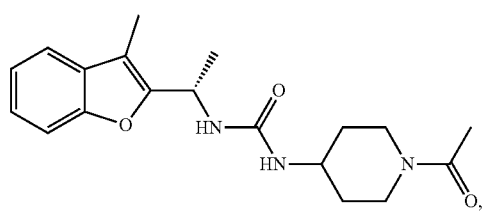
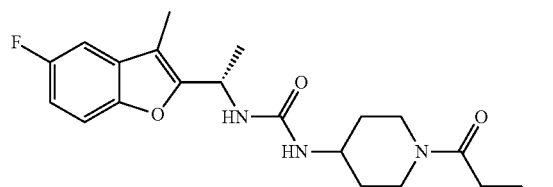
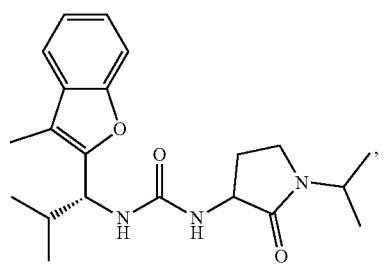
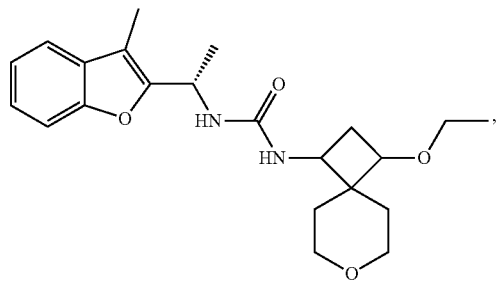
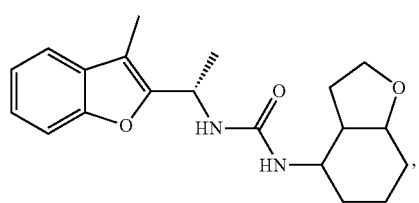
220
-continued
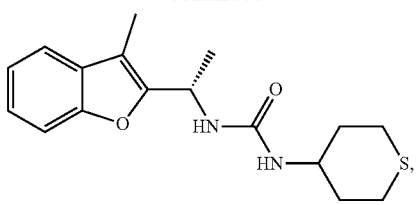
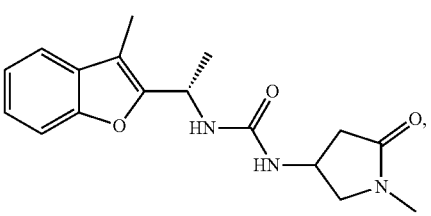
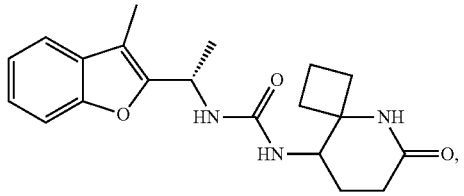
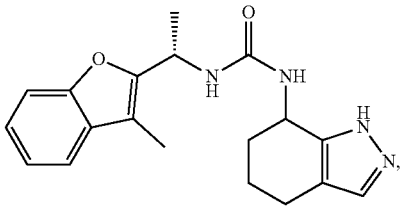
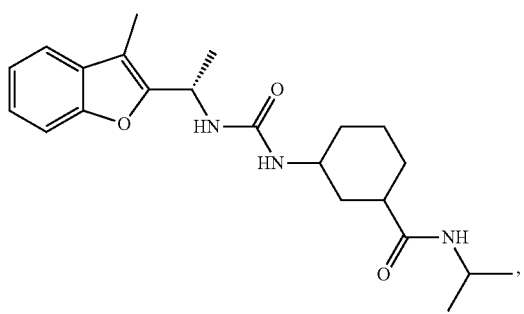
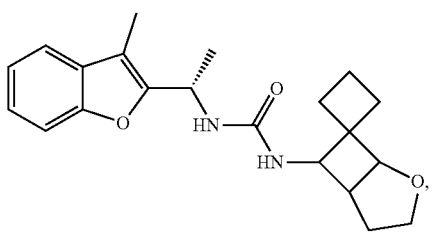
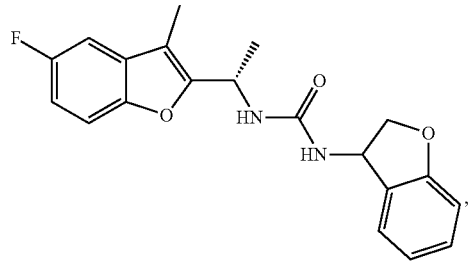

221
-continued
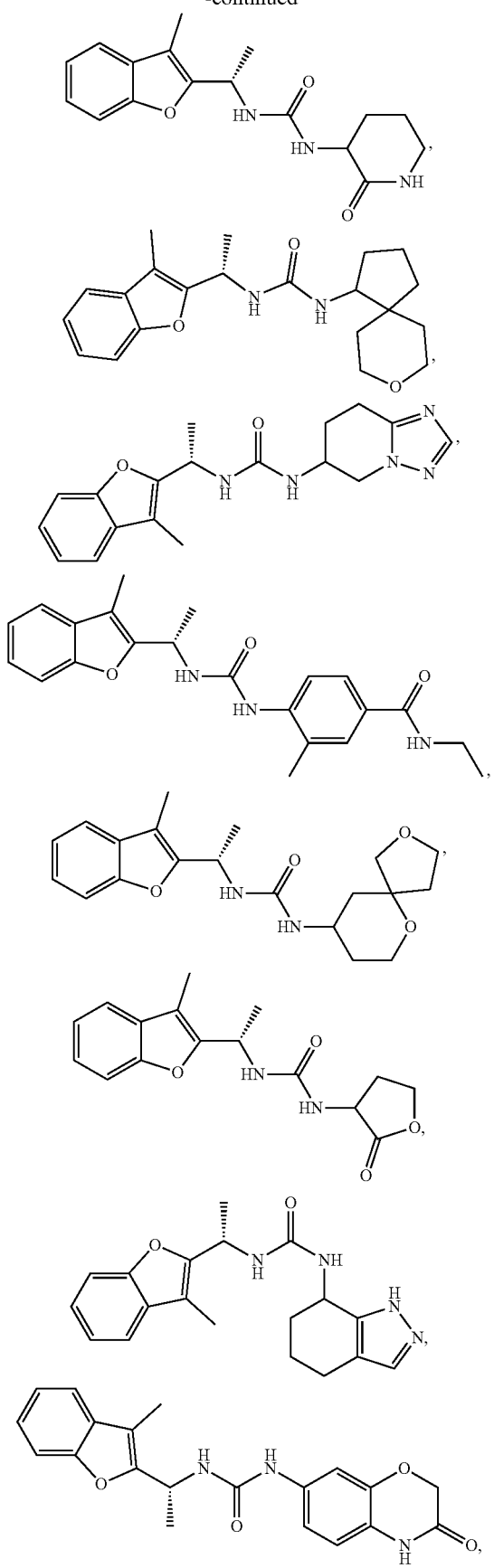
222
-continued
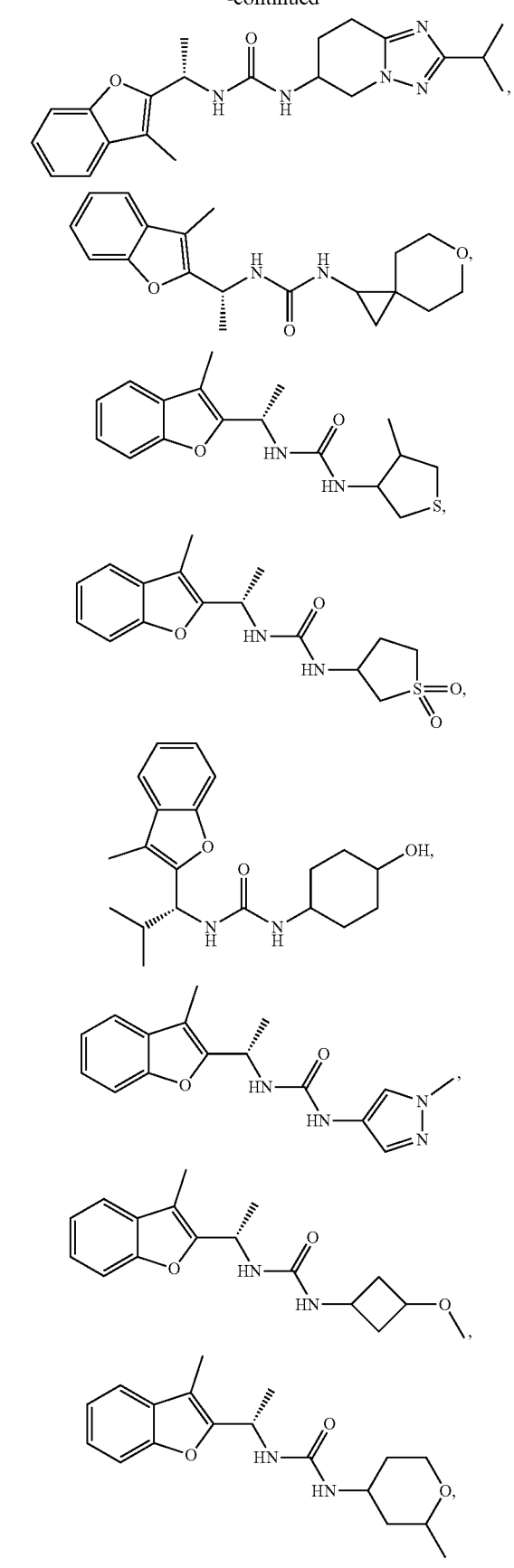

223
-continued
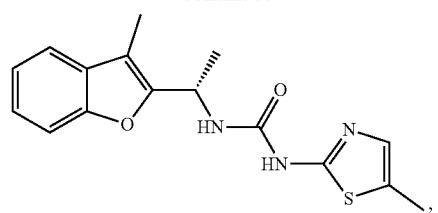
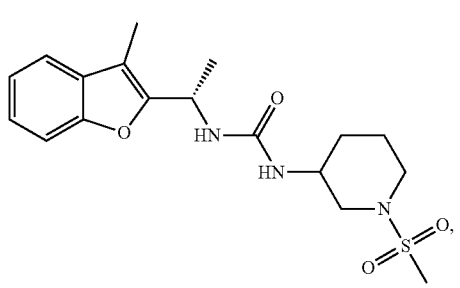
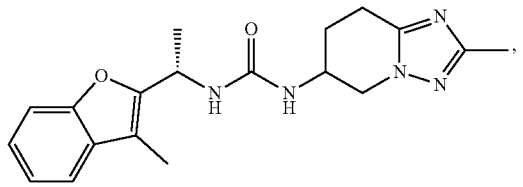
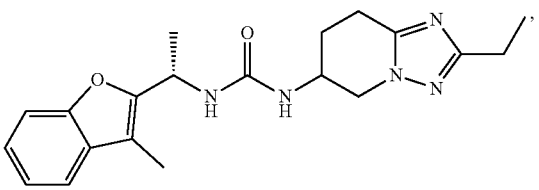
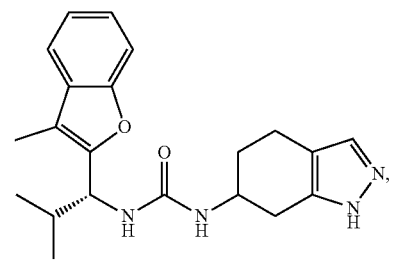
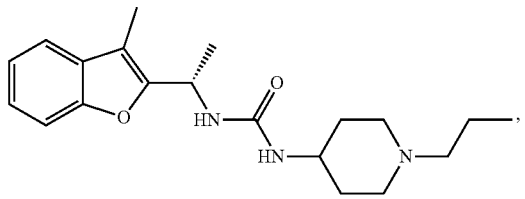
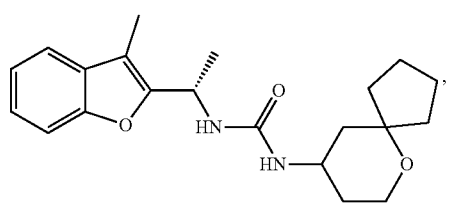
224
-continued
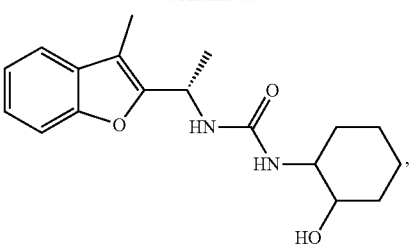
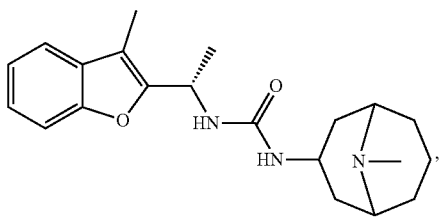
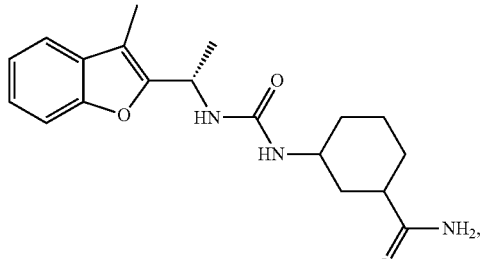
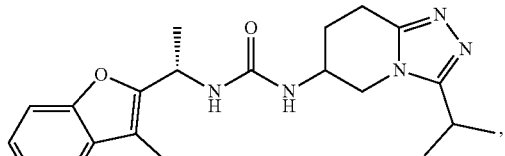
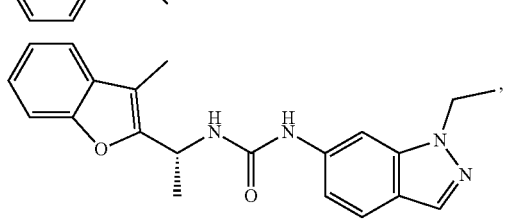
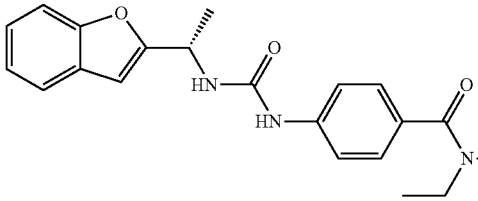
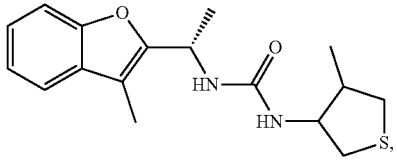
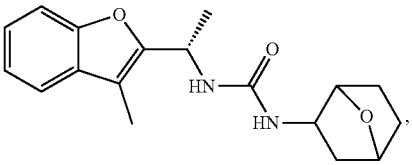

-continued
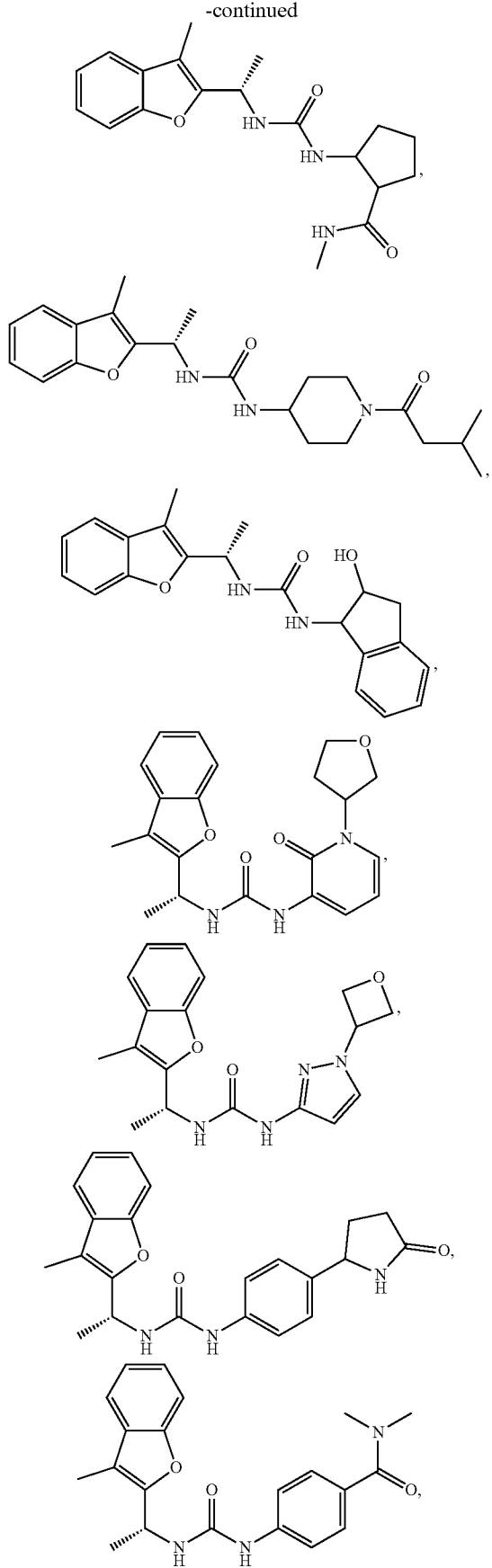
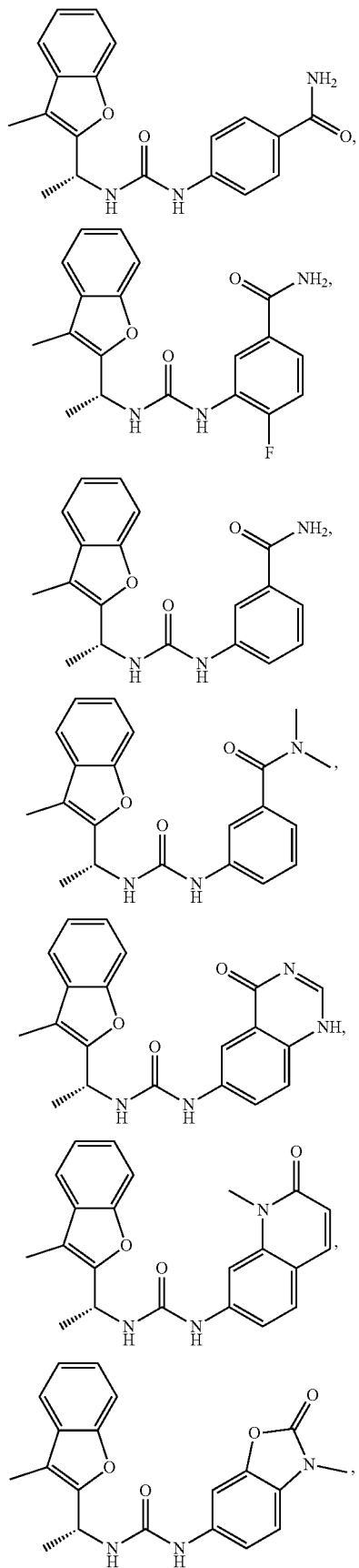

-continued

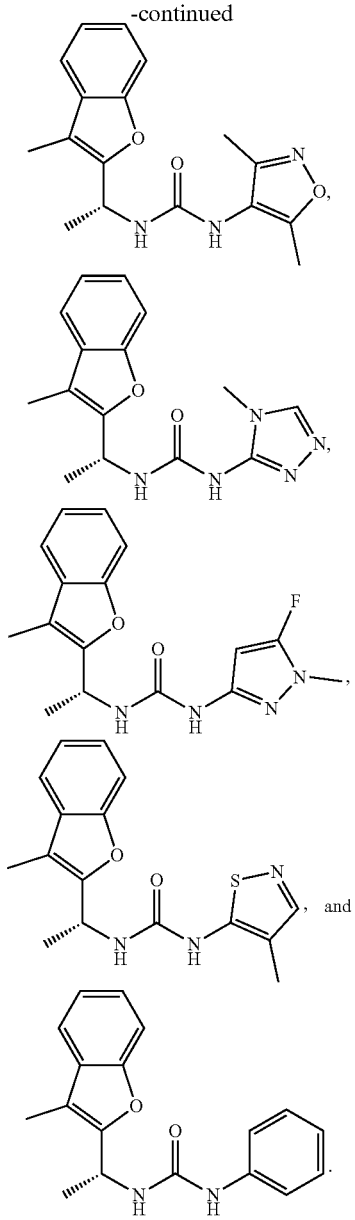

In some embodiments, the compounds described herein are not compounds that are selected from the group described above (i.e., the "excluded compounds"). In some embodiments, the excluded compounds are flat structures, as indicated above. In some embodiments, the excluded compounds are specific stereoisomers, e.g. specific enantiomers or diastereomers. In some embodiments, the excluded compounds are R isomers. In some embodiments, the excluded compounds are S isomers. In some embodiments, one or more of the excluded compounds are R isomers, and the remaining excluded compounds are S isomers. In some embodiments, the excluded compounds are R isomers. In some embodiments, one or more of the excluded compounds are S isomers, and the remaining excluded compounds are S isomers.

In some embodiments, m is 0. In some embodiments, m is 1. In some embodiments, m is 2. In some embodiments, m is 3.

In some embodiments,

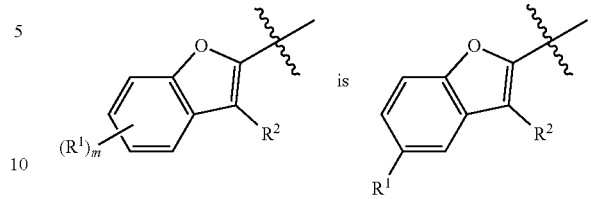

In some embodiments,

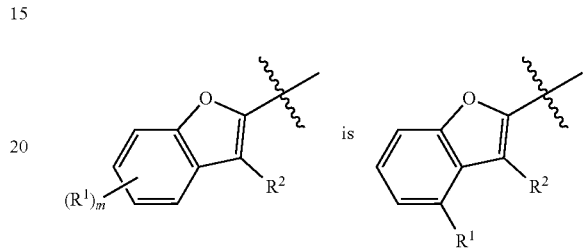

In some embodiments,

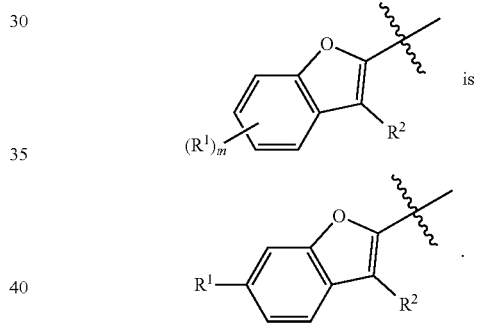

In some embodiments,

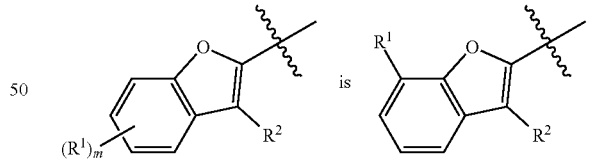

In some embodiments,

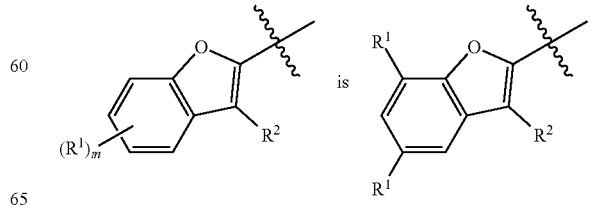

In some embodiments,

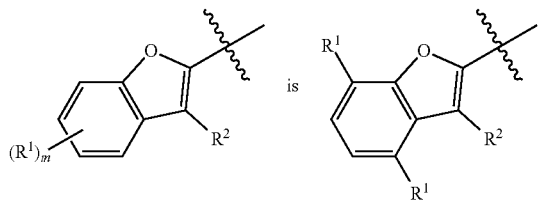 is 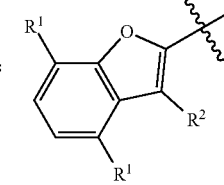.

In some embodiments,

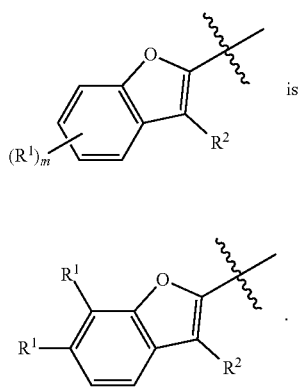

In some embodiments,

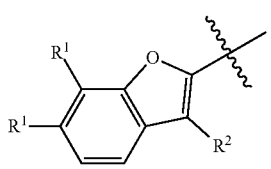 is

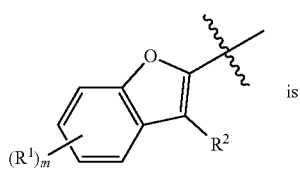.

In some embodiments,

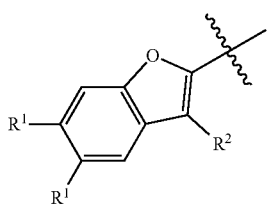

In some embodiments,

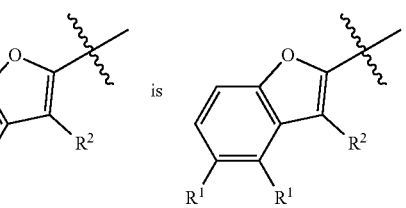

In some embodiments,

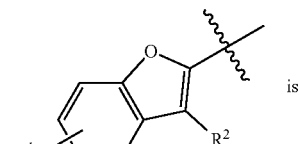 is

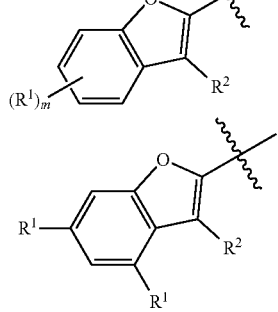.

In some embodiments,

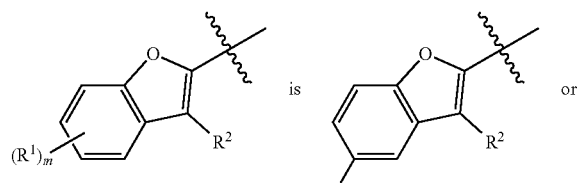 is 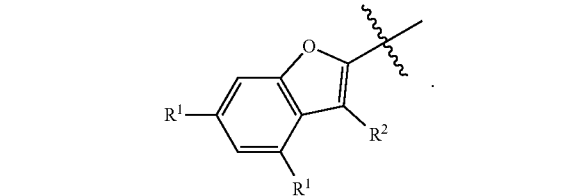 or

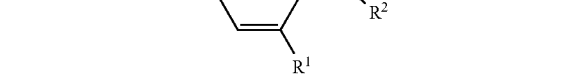.

In some embodiments, each $R^1$ is an independently selected halogen. In some embodiments, each $R^1$ is independently selected from fluoro and chloro. In some embodiments, each $R^1$ is independently selected from fluoro and bromo. In some embodiments, each $R^1$ is fluoro. In some embodiments, at least one $R^1$ is an independently selected halogen. In some embodiments, at least one $R^1$ is independently selected from fluoro and chloro. In some embodiments, at least one $R^1$ is fluoro.

In some embodiments, at least one $R^1$ is cyano. In some embodiments, at least one $R^1$ is hydroxyl. In some embodiments, at least one $R^1$ is C1-C6 alkyl optionally substituted with hydroxyl. In some embodiments, at least one $R^1$ is C1-C6 alkyl substituted with hydroxyl. In some embodiments, at least one $R^1$ is C1-C3 alkyl substituted with hydroxyl. In some embodiments, at least one $R^1$ is hydroxymethyl. In some embodiments, at least one $R^1$ is unsubstituted C1-C6 alkyl. In some embodiments, at least one $R^1$ is methyl. In some embodiments, at least one $R^1$ is C3-C6 cycloalkyl. In some embodiments, at least one $R^1$ is cyclopropyl.

In some embodiments, m is 2; one $R^1$ is halogen; and the other $R^1$ is C1-C6 alkyl. In some embodiments, m is 2; one $R^1$ is fluoro; and the other $R^1$ is methyl In some embodiments, m is 2; one $R^1$ is halogen; and the other $R^1$ is C3-C6 cycloalkyl. In some embodiments, m is 2; one $R^1$ is halogen; and the other $R^1$ is cyclopropyl. In some embodiments, m is 2; one $R^1$ is fluoro; and the other $R^1$ is cyano. In some embodiments, m is 2; one $R^1$ is halogen; and the other $R^1$ is halogen. In some embodiments, m is 2; one $R^1$ is fluoro; and the other $R^1$ is fluoro.

In some embodiments, R² is hydroxyl. In some embodiments, R² is C1-C6 alkyl optionally substituted with hydroxyl. In some embodiments, R² is C1-C6 alkyl substituted with hydroxyl. In some embodiments, R² is C1-C3 alkyl substituted with hydroxyl. In some embodiments, R² is hydroxymethyl. In some embodiments, R² is an unsubstituted C1-C6 alkyl. In some embodiments, R² is unsubstituted C1-C3 alkyl. In some embodiments, R² is methyl.

In some embodiments, R² is a C1-C6 haloalkyl. In some embodiments, R² is a C1-C3 haloalkyl. In some embodiments, R² is difluoromethyl. In some embodiments, R² is trifluoromethyl.

In some embodiments, R² is halogen. In some embodiments, R² is fluoro. In some embodiments, R² is chloro.

In some embodiments, R² is C3-C6 cycloalkyl optionally substituted with 1 or 2 fluoro. In some embodiments, R² is C3-C6 cycloalkyl substituted with 1 or 2 fluoro. In some embodiments, R² is C3-C6 cycloalkyl substituted with 1 fluoro. In some embodiments, R² is C3-C6 cycloalkyl substituted with 2 fluoro. In some embodiments, R² is C3-C4 cycloalkyl substituted with 1 fluoro. In some embodiments, R² is C3-C4 cycloalkyl substituted with 2 fluoro. In some embodiments, R² is an unsubstituted C3-C6 cycloalkyl.

In some embodiments, R³ is a C1-C6 alkyl. In some embodiments, R³ is a C1-C3 alkyl. In some embodiments, R³ is methyl, ethyl, t-butyl, or isopropyl. In some embodiments, R³ is methyl, ethyl, or isopropyl. In some embodiments, R³ is methyl. In some embodiments, R³ is ethyl. In some embodiments, R³ is isopropyl.

In some embodiments, R³ is a C1-C6 haloalkyl. In some embodiments, R³ is a C1-C3 haloalkyl. In some embodiments, R³ is difluoromethyl. In some embodiments, R³ is trifluoromethyl.

In some embodiments, R³ is C3-C6 cycloalkyl optionally substituted with 1 or 2 substituents independently selected from fluoro and C1-C6 alkyl. In some embodiments, R³ is C3—C6 cycloalkyl optionally substituted with 1 or 2 fluoro. In some embodiments, R³ is C3-C6 cycloalkyl substituted with 1 or 2 fluoro. In some embodiments, R³ is C3-C6 cycloalkyl substituted with 1 fluoro. In some embodiments, R³ is C3-C6 cycloalkyl substituted with 1 fluoro at the position of the C3-C6 cycloalkyl that is bonded to the methine of Formula (I). In some embodiments, R³ is 2,2-difluorocyclopropyl or 3,3-difluorocyclopropyl. In some embodiments, R³ is C3-C6 cycloalkyl optionally substituted with 1 or 2 methyl. In some embodiments, R³ is C3-C6 cycloalkyl substituted with 1 or 2 methyl. In some embodiments, R³ is C3-C6 cycloalkyl substituted with 1 methyl. In some embodiments, R³ is C3-C6 cycloalkyl substituted with 1 methyl at the position of the C3-C6 cycloalkyl that is bonded to the methine of Formula (I). In some embodiments, R³ is an unsubstituted C3-C6 cycloalkyl. In some embodiments, the R³ C3-C6 cycloalkyl is cyclopropyl. In some embodiments, R³ is cyclopropyl. In some embodiments, R³ is cyclobutyl. In some embodiments, R³ is cyclopentyl. In some embodiments, R³ is cyclohexyl.

In some embodiments, Ring A is a 6-10 membered aryl. In some embodiments, Ring A is phenyl, naphthyl, or tetrahydronaphthyl. In some embodiments, Ring A is phenyl.

In some embodiments, Ring A is a C3-C8 cycloalkyl. In some embodiments, Ring A is a C5-C6 cycloalkyl. In some embodiments, Ring A is cyclohexyl.

In some embodiments, Ring A is a 5-10 membered heteroaryl. In some embodiments, Ring A is a 9-10 membered heteroaryl. In some embodiments, Ring A is a 9 membered heteroaryl. In some embodiments, Ring A is a 9 membered heteroaryl, wherein the point of attachment to the urea nitrogen atom in Formula (I) is on a 6-membered ring of Ring A. In some embodiments, Ring A is a 9 membered heteroaryl, wherein the point of attachment to the urea nitrogen atom in Formula (I) is on a 5-membered ring of Ring A.

In some embodiments, Ring A is benzimidazolyl, indazolyl, indolyl, quinazolone, isobenzofuranonyl, isoindolinonyl, imidazo[1,2-a]pyridinyl, or imidazo[1,2-a]pyrimidinyl. In some embodiments, Ring A is benzimidazolyl, indazolyl, indolyl, quinazolone, isobenzofuranonyl, isoindolinonyl, 5,6,7,8-tetrahydroimidazo[1,5-a]pyridin-6-yl, or imidazo[1,2-a]pyridinyl. In some embodiments, Ring A is benzimidazolyl, indazolyl, indolyl, or imidazo[1,2-a]pyridinyl. In some embodiments, Ring A is 2-benzimidazolyl, 5-indazolyl, 2-indolyl, 7-imidazo[1,2-a]pyridinyl,

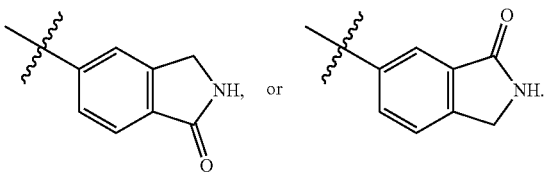 [SMILES: *c1ccc2c(c1)CNC2=O ; "or" ; *c1ccc2c(c1)C(=O)NC2]

In some embodiments, Ring A is selected from the group consisting of

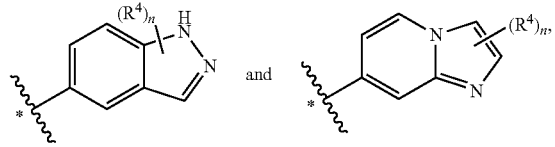

wherein "*" indicates the attachment point to the urea nitrogen atom in Formula (I).

In some embodiments, Ring A is a 5-6 membered heteroaryl. In some embodiments, Ring A is selected from the group consisting of pyrrolyl, pyrazolyl, imidazolyl, triazolyl, tetrazolyl, furanyl, thiophenyl, oxazolyl, isoxazolyl, isothiazolyl, thiazolyl, furzanyl, oxadiazolyl, thiadiazolyl, oxatriazolyl, and thiatriazolyl. In some embodiments, Ring A is selected from the groups consisting of pyridinyl, pyrimidinyl, pyrazinyl, pyridazinyl, and triazinyl. In some embodiments, Ring A is pyrimidinyl, pyridyl, thiazolyl, thiophenyl, or pyrazolyl. In some embodiments, Ring A is pyrimidinyl, pyridyl, or pyrazolyl. In some embodiments, Ring A is 5-pyrimidinyl, 3-pyridyl, or 4-pyrazolyl. In some embodiments, Ring A is selected from the group consisting of

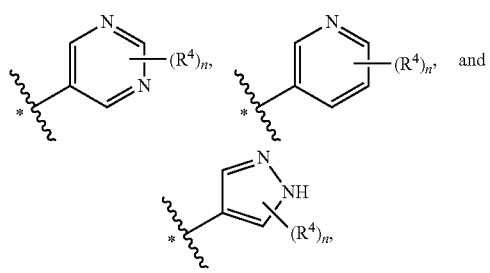

wherein "*" indicates the attachment point to the urea nitrogen atom in Formula (I). In some embodiments, Ring A is pyrimidinyl. In some embodiments, Ring A is 5-pyrimidinyl. In some embodiments, Ring A is

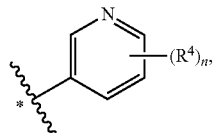

wherein "*" indicates the attachment point to the urea nitrogen atom in Formula (I). In some embodiments, Ring A is a 4-10 membered heterocyclyl. In some embodiments, Ring A is a 6-9 membered heterocyclyl. In some embodiments, Ring A is piperidinyl, isoindolinone, or tetrahydro-2H-thiopyranyl-1,1-dioxide.

In some embodiments, Ring A is 2-benzimidazolyl, 5-indazolyl, 2-indolyl, 7-imidazo[1,2-a]pyridinyl,

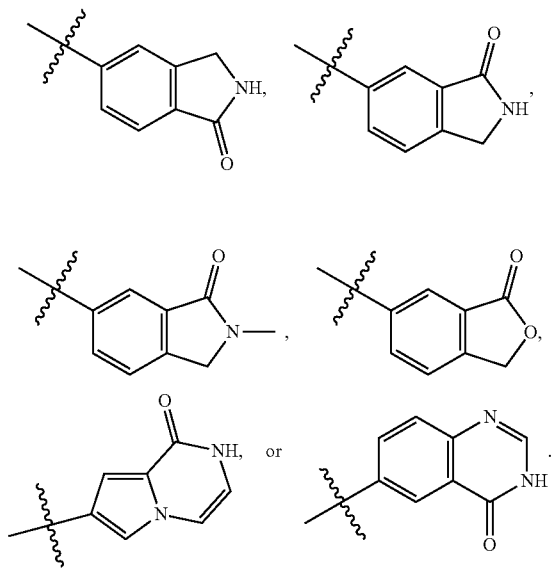

In some embodiments, Ring A is 2-benzimidazolyl, 5-indazolyl, 2-indolyl, 7-imidazo[1,2-a]pyridinyl,

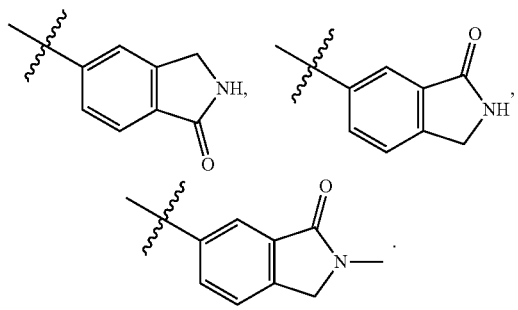

In some embodiments, Ring A is selected from the group consisting of 3-piperidinyl,

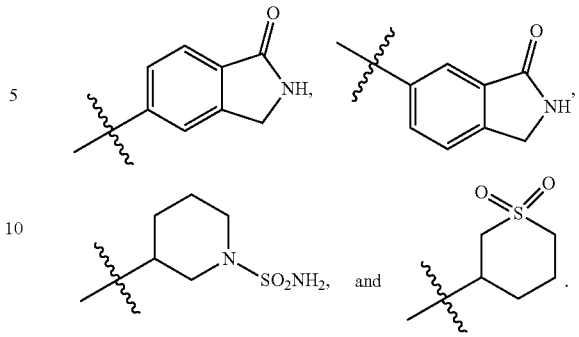

In some embodiments, n is 0. In some embodiments, n is 1. In some embodiments, n is 2.

In some embodiments, one $R^4$ is C1-C6 alkyl. In some embodiments, one $R^4$ is unsubstituted C1-C6 alkyl. In some embodiments, one $R^4$ is C1-C4 alkyl. In some embodiments, one $R^4$ is t-butyl. In some embodiments, one $R^4$ is methyl.

In some embodiments, one $R^4$ is C1-C6 alkoxy optionally substituted with 1-2 substituents independently selected from hydroxyl and C3-C6 cycloalkyl. In some embodiments, one $R^4$ is C1-C6 alkoxy substituted with 1-2 substituents independently selected from hydroxyl and C3-C6 cycloalkyl. In some embodiments, one $R^4$ is C1-C6 alkoxy substituted with 1-2 substituents independently selected from hydroxyl and cyclopropyl. In some embodiments, one $R^4$ is C1-C6 alkoxy substituted with hydroxyl. In some embodiments, one $R^4$ is C1-C6 alkoxy substituted with C3-C6 cycloalkyl. In some embodiments, one $R^4$ is C1-C6 alkoxy substituted with cyclopropyl. In some embodiments, $R^4$ is C1-C6 alkoxy. In some embodiments, $R^4$ is C1-C3 alkoxy. In some embodiments, one $R^4$ is methoxy.

In some embodiments, one $R^4$ is C1-C6 haloalkyl. In some embodiments, one $R^4$ is C1-C3 haloalkyl. In some embodiments, one $R^4$ is difluoromethyl. In some embodiments, one $R^4$ is trifluoromethyl.

In some embodiments, one $R^4$ is hydroxyl. In some embodiments, one $R^4$ is cyano. In some embodiments, one $R^4$ is —$CO_2H$. In some embodiments, one $R^4$ is halogen. In some embodiments, one $R^4$ is fluoro. In some embodiments, one $R^4$ is chloro.

In some embodiments, one $R^4$ is C1-C6 alkyl optionally substituted with 1-2 hydroxyl. In some embodiments, one $R^4$ is C1-C6 alkyl substituted with 1-2 hydroxyl. In some embodiments, one $R^4$ is C1-C6 alkyl substituted with 1 hydroxyl. In some embodiments, one $R^4$ is C1-C6 alkyl substituted with 2 hydroxyl. In some embodiments, one $R^4$ is C1-C3 alkyl substituted with 2 hydroxyl. In some embodiments, one $R^4$ is C1-C6 alkyl optionally substituted with —$NR^A R^B$. In some embodiments, one $R^4$ is C1-C6 alkyl substituted with —$NR^A R^B$. In some embodiments, one $R^4$ is methyl or ethyl substituted with —$NR^A R^B$. In some embodiments, one $R^4$ is an unsubstituted C1-C6 alkyl. In some embodiments, one $R^4$ is methyl.

In some embodiments, one $R^4$ is —$NR^A R^B$.

In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl or —$C(=O)NR^{B2}R^{C2}$. In some embodiments, one of $R^A$ and $R^B$ is hydrogen and the other of $R^A$ and $R^B$ is C1-C6 alkyl optionally substituted with hydroxyl or —$C(=O)NH_2$. In some embodiments, one of $R^A$ and $R^B$ is hydrogen and the other of $R^A$ and $R^B$ is —$C(=O)O(C1-C6$ alkyl). In some embodiments, one of $R^A$ and $R^B$ is hydrogen and the other of $R^A$ and $R^B$ is —C(=O)OCH$_3$. In some embodiments, one of $R^A$ and $R^B$ is hydrogen and the other of $R^A$ and $R^B$ is 4-6 membered heterocyclyl (e.g., oxetanyl), In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl). In some embodiments, one of $R^A$ and $R^B$ is hydrogen and the other of $R^A$ and $R^B$ is propyl substituted with hydroxyl (e.g., 3-hydroxy-1-propyl, 2-hydroxy-1-propyl or 1-hydroxy-2-propyl). In some embodiments, one of $R^A$ and $R^B$ is hydrogen and the other of $R^A$ and $R^B$ is butyl substituted with hydroxyl (e.g., 2-hydroxy-2-methyl-1-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, both of $R^{B2}$ and $R^{C2}$ are hydrogen. In some embodiments, one of $R^{B2}$ and $R^{C2}$ is hydrogen and the other of $R^{B2}$ and $R^{C2}$ is C1-C6 alkyl. In some embodiments, one of $R^{B2}$ and $R^{C2}$ is hydrogen and the other of $R^{B2}$ and $R^{C2}$ is methyl. In some embodiments, both of $R^{B2}$ and $R^{C2}$ are methyl.

In some embodiments, one of $R^A$ and $R^B$ is hydrogen and the other of $R^A$ and $R^B$ is C1-C6 haloalkyl. In some embodiments, one of $R^A$ and $R^B$ is hydrogen and the other of $R^A$ and $R^B$ is C1-C3 haloalkyl. In some embodiments, $R^A$ and $R^B$ are each C1-C6 haloalkyl. In some embodiments, $R^A$ and $R^B$ are each C1-C3 haloalkyl.

In some embodiments, one of $R^A$ and $R^B$ is C1-C6 alkyl and the other of one of $R^A$ and $R^B$ is C1-C6 haloalkyl.

In some embodiments, one $R^4$ is —C(=O)NR$^C$R$^D$.

In some embodiments, $R^C$ and $R^D$ are each hydrogen. In some embodiments, one of $R^C$ and $R^D$ is hydrogen and the other of $R^C$ and $R^D$ is C1-C6 alkyl. In some embodiments, one of $R^C$ and $R^D$ is hydrogen and the other of $R^C$ and $R^D$ is C1-C3 alkyl. In some embodiments, one of $R^C$ and $R^D$ is hydrogen and the other of $R^C$ and $R^D$ is methyl. In some embodiments, $R^C$ and $R^D$ are each C1-C6 alkyl. In some embodiments, $R^C$ and $R^D$ are each C1-C3 alkyl. In some embodiments, $R^C$ and $R^D$ are each methyl. In some embodiments, one of $R^C$ and $R^D$ is C1-C6 alkyl and the other of $R^C$ and $R^D$ is C1-C3 alkyl.

In some embodiments, one of $R^C$ and $R^D$ is hydrogen and the other of $R^C$ and $R^D$ is C1-C6 haloalkyl. In some embodiments, one of $R^C$ and $R^D$ is hydrogen and the other of $R^C$ and $R^D$ is C1-C3 haloalkyl. In some embodiments, $R^C$ and $R^D$ are each is C1-C6 haloalkyl. In some embodiments, one of $R^C$ and $R^D$ is C1-C6 alkyl and the other of $R^C$ and $R^D$ is C1-C6 haloalkyl.

In some embodiments, $R^C$ and $R^D$, together with the nitrogen atom to which they are attached form a 4-10 membered heterocyclyl optionally substituted with 1-2 substituents independently selected from hydroxyl, halogen, —C(=O)NR$^{B1}$R$^{C1}$, —SO$_2$(C1-C6 alkyl), —CO$_2$H, C1-C6 alkyl optionally substituted with hydroxyl, C1-C6 alkoxy, and C1-C6 haloalkoxy. In some embodiments, $R^C$ and $R^D$, together with the nitrogen atom to which they are attached form a 4-10 membered heterocyclyl substituted with 1-2 substituents independently selected from hydroxyl, halogen, —C(=O)NR$^{B1}$R$^{C1}$, —SO$_2$(C1-C6 alkyl), —CO$_2$H, C1-C6 alkyl optionally substituted with hydroxyl, C1-C6 alkoxy, and C1-C6 haloalkoxy.

In some embodiments, $R^{B1}$ and $R^{C1}$ are each hydrogen. In some embodiments, one of $R^{B1}$ and $R^{C1}$ is hydrogen and the other of $R^{B1}$ and $R^{C1}$ is C1-C6 alkyl. In some embodiments, one of $R^{B1}$ and $R^{C1}$ is hydrogen and the other of $R^{B1}$ and $R^{C1}$ is methyl. In some embodiments, $R^{B1}$ and $R^{C1}$ are each independently selected C1-C6 alkyl. In some embodiments, $R^{B1}$ and $R^{C1}$ are each methyl.

In some embodiments, $R^C$ and $R^D$, together with the nitrogen atom to which they are attached form a 4-6 membered heterocyclyl. In some embodiments, $R^C$ and $R^D$, together with the nitrogen atom to which they are attached form azetidine or piperazine.

In some embodiments, one $R^4$ is —SO$_2$(NR$^E$R$^F$). In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is C1-C3 alkyl. In some embodiments, one of $R^E$ and $R^F$ is hydrogen and the other of $R^E$ and $R^F$ is methyl. In some embodiments, $R^E$ and $R^F$ are each is C1-C6 alkyl. In some embodiments, $R^E$ and $R^F$ are each is C1-C3 alkyl. In some embodiments, $R^E$ and $R^F$ are each methyl.

In some embodiments, one of $R^E$ and $R^F$ is hydrogen and the other of $R^E$ and $R^F$ is C1-C6 haloalkyl. In some embodiments, one of $R^E$ and $R^F$ is hydrogen and the other of $R^E$ and $R^F$ is C1-C3 haloalkyl. In some embodiments, $R^E$ and $R^F$ are each C1-C6 haloalkyl. In some embodiments, one of $R^E$ and $R^F$ is C1-C6 alkyl and the other of $R^E$ and $R^F$ is C1-C6 haloalkyl.

In some embodiments, one $R^4$ is —SO$_2$(C1-C6 alkyl). In some embodiments, one $R^4$ is —SO$_2$(C1-C3 alkyl). In some embodiments, one $R^4$ is —SO$_2$Et. In some embodiments, one $R^4$ is —SO$_2$Me.

In some embodiments, one $R^4$ is —S(=O)(=NH)(C1-C6 alkyl). In some embodiments, one $R^4$ is —S(=O)(=NH)(C1-C3 alkyl). In some embodiments, one $R^4$ is —S(=O)(=NH)Me.

In some embodiments, one $R^4$ is —C(=O)(C1-C6 alkyl). In some embodiments, one $R^4$ is —C(=O)(C1-C3 alkyl). In some embodiments, one $R^4$ is —C(=O)Me.

In some embodiments, one $R^4$ is —CO$_2$(C1-C6 alkyl). In some embodiments, one $R^4$ is —CO$_2$(C1-C3 alkyl). In some embodiments, one $R^4$ is —CO$_2$Me.

In some embodiments, one $R^4$ is 5-6 membered heteroaryl optionally substituted with C1-C6 alkyl. In some embodiments, one $R^4$ is 5-6 membered heteroaryl substituted with C1-C6 alkyl. In some embodiments, one $R^4$ is 5-6 membered heteroaryl. In some embodiments, one $R^4$ is selected from the group consisting of pyrrolyl, pyrazolyl, imidazolyl, triazolyl, tetrazolyl, furanyl, thiophenyl, oxazolyl, isoxazolyl, isothiazolyl, thiazolyl, furanyl, oxadiazolyl, thiadiazolyl, oxatriazolyl, and thiatriazolyl, pyridinyl, pyrimidinyl, pyrazinyl, pyridazinyl, and triazinyl. In some embodiments, one $R^4$ is tetrazolyl substituted with methyl. In some embodiments, one $R^4$ is pyrazolyl. In some embodiments, one $R^4$ is unsubstituted pyrazolyl. In some embodiments, one $R^4$ is 1-pyrazolyl.

In some embodiments, one $R^4$ is 3-9 membered heterocyclyl optionally substituted with 1 or 2 independently selected $R^G$. In some embodiments, one $R^4$ is 3 membered heterocyclyl optionally substituted with 1 or 2 independently selected $R^G$. In some embodiments, one $R^4$ is 4 membered heterocyclyl optionally substituted with 1 or 2 independently selected $R^G$. In some embodiments, one $R^4$ is 5 membered heterocyclyl optionally substituted with 1 or 2 independently selected $R^G$. In some embodiments, one $R^4$ is 7-9 membered heterocyclyl optionally substituted with 1 or 2 independently selected $R^G$. In some embodiments, the $R^4$ heterocyclyl is a spirocycle. In some embodiments, one $R^4$ is 3-6 membered heterocyclyl optionally substituted with 1 or 2 independently selected $R^G$. In some embodiments, one $R^4$ is 3-6 membered heterocyclyl substituted with 1 or 2 independently selected $R^G$. In some embodiments, one $R^4$ is 3-6 membered heterocyclyl substituted with 1 $R^G$. In some embodiments, one $R^4$ is 3-6 membered heterocyclyl substituted with 2 independently selected $R^G$. In some embodiments, one $R^4$ is an unsubstituted 3-6 membered heterocyclyl.

In some embodiments, one $R^4$ is a 3-6 membered cycloalkyl optionally substituted with 1 or 2 independently selected $R^G$. In some embodiments, one $R^4$ is 3-6 membered cycloalkyl substituted with 1 or 2 independently selected $R^G$. In some embodiments, one $R^4$ is 3-6 membered cycloalkyl substituted with 1 $R^G$. In some embodiments, one $R^4$ is 3-6 membered cycloalkyl substituted with 2 independently selected $R^G$. In some embodiments, one $R^4$ is an unsubstituted 3-6 membered cycloalkyl.

In some embodiments, the 1 or 2 independently selected $R^G$ is 1 $R^G$. In some embodiments, the 1 or 2 independently selected $R^G$ are 2 independently selected $R^G$. In some embodiments, when 2 $R^G$ are present, they are bonded to the same atom, valency permitting. In some embodiments, when 2 $R^G$ are present, they are bonded to adjacent atoms, valency permitting. In some embodiments, when 2 $R^G$ are present, the 2 $R^G$ are different. In some embodiments, when 2 $R^G$ are present, the 2 $R^G$ are the same. In some embodiments, one $R^G$ is fluoro. In some embodiments, one $R^G$ is cyano. In some embodiments, one $R^G$ is hydroxyl. In some embodiments, one $R^G$ is C1-C6 alkyl optionally substituted with hydroxyl. In some embodiments, one $R^G$ is 2-hydroxy-2-propyl. In some embodiments, one $R^G$ is C1-C6 alkyl. In some embodiments, one $R^G$ is C1-C3 alkyl. In some embodiments, one $R^G$ is methyl. In some embodiments, one $R^G$ is ethyl.

In some embodiments, one $R^G$ is C1-C6 alkoxy. In some embodiments, one $R^G$ is C1-C3 alkoxy. In some embodiments, one $R^G$ is methoxy.

In some embodiments, one $R^G$ is —$NR^{A1}R^{B1}$. In some embodiments, $R^{A1}$ and $R^{B1}$ are each hydrogen. In some embodiments, one of $R^{A1}$ and $R^{B1}$ is hydrogen and the other of $R^{A1}$ and $R^{B1}$ is C1-C6 alkyl. In some embodiments, one of $R^{A1}$ and $R^{B1}$ is hydrogen and the other of $R^{A1}$ and $R^{B1}$ is C1-C3 alkyl. In some embodiments, one of $R^{A1}$ and $R^{B1}$ is hydrogen and the other of $R^{A1}$ and $R^{B1}$ is methyl. In some embodiments, $R^{A1}$ and $R^{B1}$ are each C1-C6 alkyl. In some embodiments, $R^{A1}$ and $R^{B1}$ are each methyl.

In some embodiments, one of $R^{A1}$ and $R^{B1}$ is hydrogen and the other of $R^{A1}$ and $R^{B1}$ is C1-C6 haloalkyl. In some embodiments, one of $R^{A1}$ and $R^{B1}$ is hydrogen and the other of $R^{A1}$ and $R^{B1}$ is C1-C3 haloalkyl. In some embodiments, $R^{A1}$ and $R^{B1}$ are each C1-C6 haloalkyl. In some embodiments, one of $R^{A1}$ and $R^{B1}$ is C1-C6 alkyl and the other of $R^{A1}$ and $R^{B1}$ is C1-C6 haloalkyl.

In some embodiments, one $R^G$ is =$NR^{A2}$. In some embodiments, one $R^G$ is =NH. In some embodiments, $R^{A2}$ is hydrogen. In some embodiments, $R^{A2}$ is C1-C6 alkyl. In some embodiments, $R^{A2}$ is methyl.

In some embodiments, one $R^G$ is —$C(=O)NR^{C1}R^{D1}$. In some embodiments, one $R^G$ is —$CO_2NH_2$. In some embodiments, one $R^G$ is —$CO_2NHCH_3$. In some embodiments, $R^{C1}$ and $R^{D1}$ are each is hydrogen. In some embodiments, one of $R^{C1}$ and $R^{D1}$ is hydrogen and the other of $R^{C1}$ and $R^{D1}$ is C1-C6 alkyl. In some embodiments, one of $R^{C1}$ and $R^{D1}$ is hydrogen and the other of $R^{C1}$ and $R^{D1}$ is C1-C3 alkyl. In some embodiments, one of $R^{C1}$ and $R^{D1}$ is hydrogen and the other of $R^{C1}$ and $R^{D1}$ is methyl. In some embodiments, $R^{C1}$ and $R^{D1}$ are each is C1-C6 alkyl. In some embodiments, $R^{C1}$ and $R^{D1}$ are each is C1-C3 alkyl. In some embodiments, $R^{C1}$ and $R^{D1}$ are each is methyl.

In some embodiments, one of $R^{C1}$ and $R^{D1}$ is hydrogen and the other of $R^{C1}$ and $R^{D1}$ is C1-C6 haloalkyl. In some embodiments, one of $R^{C1}$ and $R^{D1}$ is hydrogen and the other of $R^{C1}$ and $R^{D1}$ is C1-C3 haloalkyl. In some embodiments, $R^{C1}$ and $R^{D1}$ are each is C1-C6 haloalkyl. In some embodiments, one of $R^{C1}$ and $R^{D1}$ is C1-C6 alkyl and the other of $R^{C1}$ and $R^{D1}$ is C1-C6 haloalkyl.

In some embodiments, one $R^G$ is —$CO_2$(C1-C6 alkyl). In some embodiments, one $R^G$ is —$CO_2CH_3$. In some embodiments, one $R^G$ is C1-C6 haloalkyl. In some embodiments, one $R^G$ is trifluoromethyl. In some embodiments, one $R^G$ is difluoromethyl. In some embodiments, one $R^G$ is C3-C6 cycloalkyl. In some embodiments, one $R^G$ is cyclopropyl. In some embodiments, one $R^G$ is —$CO_2H$.

In some embodiments, one $R^G$ is C1-C6 haloalkoxy. In some embodiments, one $R^G$ is C1-C3 haloalkoxy. In some embodiments, one $R^G$ is difluoromethoxy. In some embodiments, one $R^G$ is trifluoromethoxy.

In some embodiments, one $R^G$ is —$SO_2$(C1-C6 alkyl). In some embodiments, one $R^G$ is —$SO_2CH_3$.

In some embodiments, the $R^4$ 3-9 membered heterocyclyl is a 3-6 membered heterocyclyl. In some embodiments, the $R^4$ 3-6 membered heterocyclyl is a 5-6 membered heterocyclyl. In some embodiments, the $R^4$ 3-6 membered heterocyclyl is azetidinyl, azetidin-2-onyl, morpholinyl, piperazinyl, or tetrahydropyranyl. In some embodiments, the $R^4$ 3-6 membered heterocyclyl is 1-azetidinyl, 1-azetidin-2-onyl, 1-piperazinyl, 1-morpholinyl, or 4-tetrahydropyranyl. In some embodiments, the $R^4$ 3-9 membered heterocyclyl is selected from the group consisting of

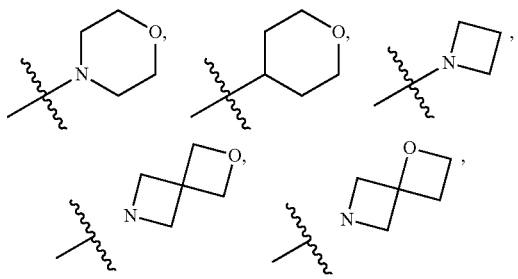

-continued

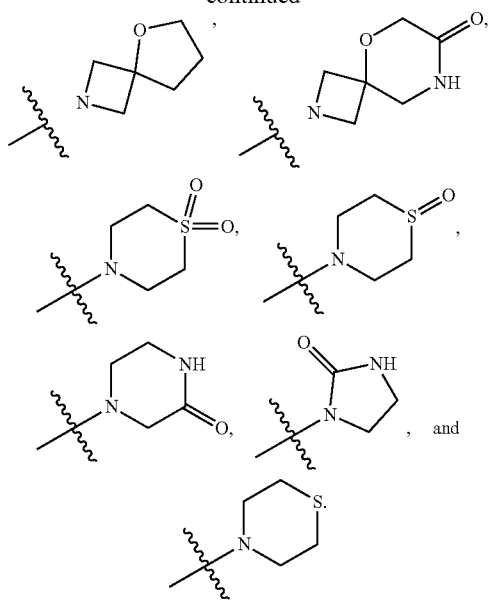

In some embodiments, the $R^4$ 3-9 membered heterocyclyl (e.g., the $R^4$ 3-6 membered heterocyclyl) is

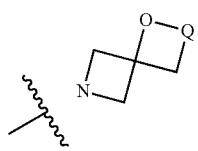

wherein Q is a C1-C3 alkylene in which one or more carbons is optionally replaced by —C(=O)—, NH, O, or S. In some embodiments, Q is a C1-C3 alkylene in which one or more carbons is optionally replaced by —C(=O)— or NH. In some embodiments, Q is a C1-C2 alkylene in which one or more carbons is optionally replaced by —C(=O)— or NH. In some embodiments, the $R^4$ 3-9 membered heterocyclyl is selected from the group consisting of

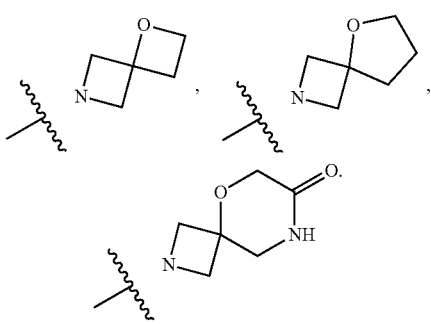

In some embodiments, one $R^4$ is unsubstituted 3-6 membered heterocyclyl. In some embodiments, $R^4$ 3-6 membered heterocyclyl is a 5-6 membered heterocyclyl. In some embodiments, $R^4$ is azetidinyl, morpholinyl, or tetrahydropyranyl. In some embodiments, $R^4$ is selected from the group consisting of

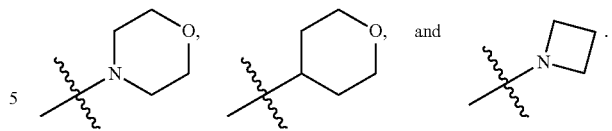

In some embodiments,


wherein: X is selected from N and $CR^{4A2}$; $R^{4A1}$ and $R^{4A2}$ are independently selected from hydrogen, C1-C3 alkyl optionally substituted with —$NR^A R^B$, methoxy, C1-C3 haloalkyl, hydroxyl, cyano, —$CO_2H$, —$NR^A R^B$, —$C(=O)NR^C R^D$, —$SO_2(NR^E R^F)$, —$SO_2(C1-C6\ alkyl)$, and 3-6 membered heterocyclyl optionally substituted with 1 or 2 independently selected $R^G$, and 3-6 membered cycloalkyl optionally substituted with 1 or 2 independently selected $R^G$. In some embodiments, X is N. In some embodiments, X is $CR^{4A2}$. In some embodiments, $R^{4A1}$ and, when present, $R^{4A2}$ are independently selected from hydrogen, methyl, ethyl, isopropyl, difluoromethyl, trifluoromethyl, cyano, hydroxyl, methoxy, amino, —$C(=O)NH_2$, —$C(=O)NHMe$, —$SO_2NH_2$, —$SO_2Me$, and azetidinyl optionally substituted with 1-2 independently selected fluoro, hydroxyl, or methyl. In some embodiments, $R^C$ and $R^D$, together with the nitrogen atom to which they are attached form a 4-6 membered heterocyclyl. In some embodiments, X is N and $R^{4A1}$ is 3-6 membered heterocyclyl optionally substituted with 1 or 2 independently selected $R^G$. In some embodiments, $R^C$ and $R^D$, together with the nitrogen atom to which they are attached form azetidine or piperazine.

In some embodiments, X is N; and $R^{4A1}$ is selected from amino or an azetidinyl optionally substituted with 1-2 independently selected fluoro, hydroxyl, or methyl.

In some embodiments,

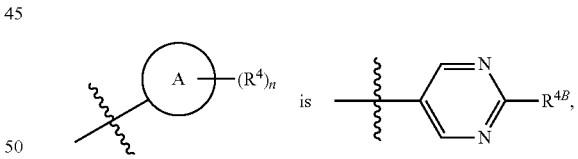

wherein: $R^{4B}$ is selected from —$NR^A R^B$ and 4-6 membered heterocyclyl comprising one nitrogen ring member and optionally substituted with 1-2 independently selected $R^{G1}$; wherein $R^{G1}$ is selected from fluoro, hydroxyl, C1-C6 haloalkyl, and C1-C6 alkyl. In some embodiments, $R^{G1}$ is selected from fluoro, hydroxyl, and C1-C6 alkyl.

In some embodiments,

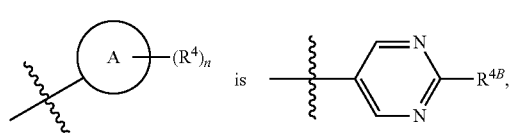

wherein: $R^{4B}$ is selected from $-NR^AR^B$ and 4-6 membered heterocyclyl comprising one nitrogen ring member and optionally substituted with 1-2 independently selected $R^{G1}$; wherein $R^{G1}$ is selected from fluoro, hydroxyl, methoxy, methyl, ethyl, amino, hydroxymethyl, 2-hydroxy-2-propyl, —C(O)Me, —C(O)NH$_2$, =NH, difluoromethoxy, —S(O)$_2$Me, —CO$_2$H, C1-C6 haloalkyl, and C1-C6 alkyl. In some embodiments, $R^{G1}$ is selected from fluoro, hydroxyl, methoxy, methyl, ethyl, hydroxymethyl, 2-hydroxy-2-propyl, —C(O)Me, —C(O)NH$_2$, =NH, difluoromethoxy, —S(O)$_2$Me, —CO$_2$H, C1-C6 haloalkyl, and C1-C6 alkyl. In some embodiments, $R^{G1}$ is selected from fluoro, hydroxyl, and C1-C6 alkyl.

In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl. In some embodiments, one of $R^A$ and $R^B$ is hydrogen and the other of $R^A$ and $R^B$ is propyl substituted with hydroxyl (e.g., 2-hydroxyl-propyl or 1-hydroxy-2-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, $R^{4B}$ is amino or a 4-6 membered heterocyclyl having one nitrogen atom and optionally substituted with 1-2 independently selected $R^G$; wherein $R^G$ is selected from fluoro, hydroxyl, and C1-C6 alkyl.

In some embodiments, $R^{4B}$ is

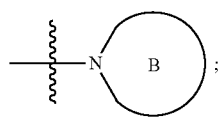

wherein Ring B is azetidinyl, pyrrolidinyl, piperidinyl, piperazinyl, morpholinyl, thiomorpholinyl, each optionally containing 1-2 =O, and each optionally substituted with 1-2 $R^G$ independently selected from fluoro, hydroxyl, trifluoromethyl, amino, cyclopropyl, —CO$_2$CH$_3$, and C1-C6 alkyl. In some embodiments, $R^{4B}$ is

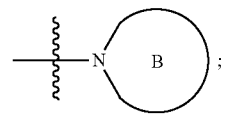

wherein Ring B is azetidinyl, pyrrolidinyl, piperidinyl, piperazinyl, or morpholinyl, each optionally substituted with 1-2 $R^G$ independently selected from fluoro, hydroxyl, trifluoromethyl, amino, cyclopropyl, —CO$_2$CH$_3$, and C1-C6 alkyl. In some embodiments, $R^{4B}$ is N K D

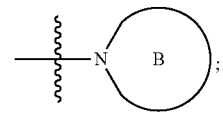

wherein Ring B is azetidinyl, pyrrolidinyl, piperidinyl, piperazinyl, or morpholinyl, each optionally substituted with 1-2 $R^G$ independently selected from fluoro, hydroxyl, trifluoromethyl, and C1-C6 alkyl. In some embodiments, $R^{4B}$ is

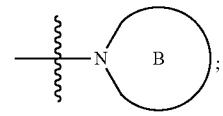

wherein Ring B is azetidinyl, pyrrolidinyl, or piperidinyl, each optionally substituted with 1-2 $R^G$ independently selected from fluoro, hydroxyl, and C1-C6 alkyl. In some embodiments, Ring B is azetidinyl.

In some embodiments, Ring B is unsubstituted.

In some embodiments, Ring B is substituted with 1 $R^G$. In some embodiments, $R^G$ is fluoro. In some embodiments, $R^G$ is cyano. In some embodiments, $R^G$ is amino, In some embodiments, $R^G$ is hydroxyl. In some embodiments, $R^G$ is C1-C3 alkyl. In some embodiments, $R^G$ is methyl. In some embodiments, $R^G$ is ethyl. In some embodiments, $R^G$ is —CO$_2$CH$_3$. In some embodiments, $R^G$ is methoxy. In some embodiments, $R^G$ is methoxy.

In some embodiments, Ring B is substituted with 2 $R^G$. In some embodiments, each $R^G$ is fluoro. In some embodiments, each $R^G$ is C1-C3 alkyl. In some embodiments, each $R^G$ is methyl. In some embodiments, one $R^G$ is hydroxyl and the other $R^G$ is methyl. In some embodiments, one $R^G$ is hydroxyl and the other $R^G$ is ethyl. In some embodiments, one $R^G$ is amino and the other $R^G$ is methyl. In some embodiments, one $R^G$ is hydroxyl and the other $R^G$ is cyclopropyl. In some embodiments, one $R^G$ is fluoro and the other $R^{G1}$ is methyl. In some embodiments, one $R^G$ is hydroxyl and the other $R^G$ is fluoro. In some embodiments, one $R^G$ is hydroxyl and the other $R^G$ is trifluoromethyl. In some embodiments, each $R^G$ is bonded to the position of Ring B para to the nitrogen that is bonded to Ring A.

In some embodiments,

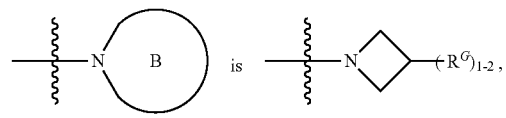

wherein 1 or 2 independently selected $R^G$ attach at the 3-position of the azetidine. In some embodiments,

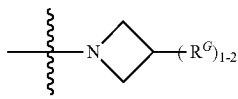

selected from the group consisting of

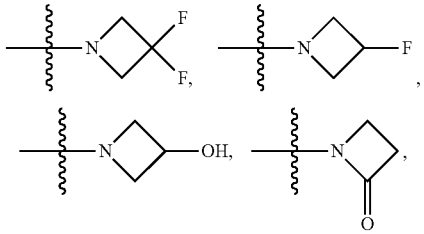

and

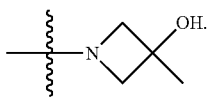

In some embodiments,

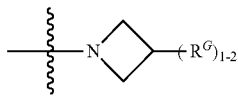

is selected from the group consisting of

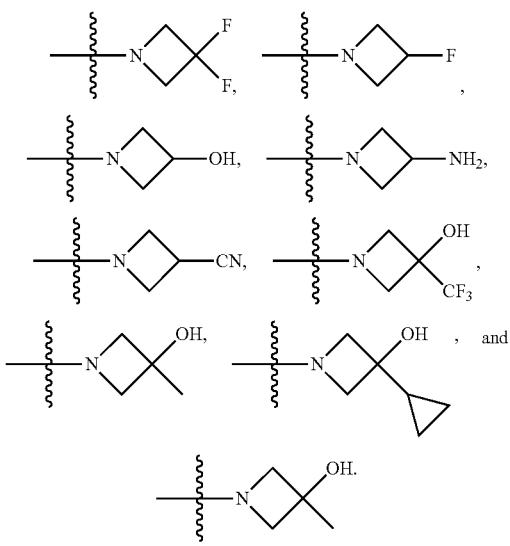

In some embodiments,

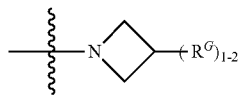

is selected from the group consisting of

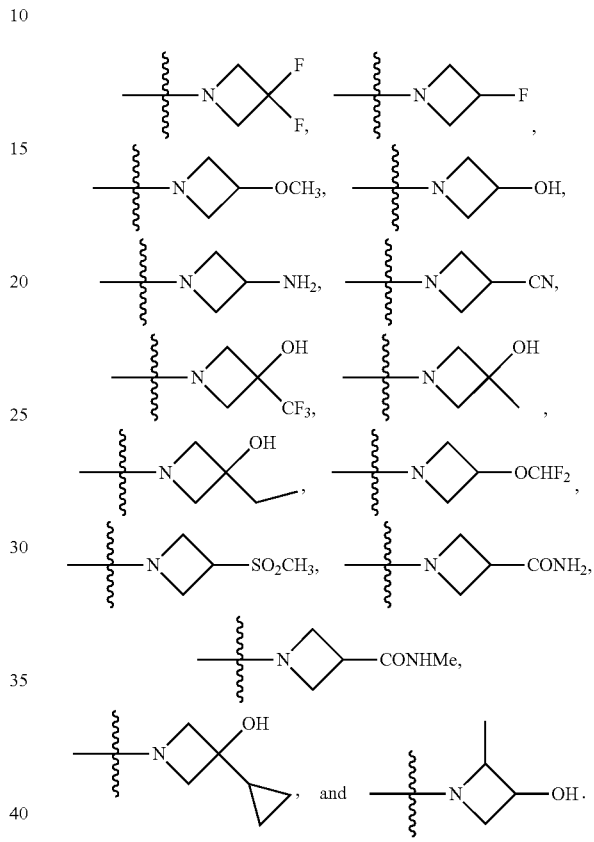

In some embodiments, Z is O.
In some embodiments, Z is $NR^x$.
In some embodiments, $R^x$ is hydrogen.
In some embodiments, $R^x$ is C1-C6 alkyl. In some embodiments, $R^x$ is C1-C3 alkyl. In some embodiments, $R^x$ is methyl. In some embodiments, $R^x$ is ethyl. In some embodiments, $R^x$ is n-propyl. In some embodiments, $R^x$ is isopropyl.
In some embodiments, $R^x$ is C3-C6 cycloalkyl. In some embodiments, $R^x$ is C3-C4 cycloalkyl. In some embodiments, $R^x$ is cyclopropyl. In some embodiments, $R^x$ is cyclobutyl.
In some embodiments, each $R^1$ is fluoro; m is 1 or 2; $R^2$ is a C1-C6 alkyl; and $R^3$ is a C1-C6 alkyl. In some embodiments, each $R^1$ is fluoro; m is 1 or 2; $R^2$ is methyl; and $R^3$ is selected from methyl, ethyl, isopropyl, or tert-butyl.
In some embodiments, each $R^1$ is fluoro; m is 1 or 2; $R^2$ is a C1-C6 alkyl; and $R^3$ is a C1-C6 haloalkyl. In some embodiments, each $R^1$ is fluoro; m is 1 or 2; $R^2$ is methyl; and $R^3$ is trifluoromethyl.
In some embodiments, m is 2, one $R^4$ is halogen, and the other $R^4$ is $-SO_2$(C1-C6 alkyl). In some embodiments, m is 2, one $R^4$ is chloro, and the other $R^4$ is $-SO_2CH_3$.
In some embodiments, m is 2, one $R^4$ is C1-C6 alkoxy, and the other $R^4$ is $-C(=O)NR^CR^D$.

In some embodiments, m is 2, one $R^4$ is methoxy, and the other $R^4$ is —C(O)NHCH$_3$. In some embodiments, Ring A is a phenyl or a 5-6 membered heteroaryl;

each $R^4$ is independently selected from the group consisting of: C1-C3 alkyl, C1-C3 alkoxy, C1-C3 haloalkyl, hydroxyl, cyano, —CO$_2$H, —NH$_2$, —C(=O)NH$_2$, —C(=O)NHMe, —SO$_2$NH$_2$, —SO$_2$NHMe, —SO$_2$Me, —S(=O)(=NH)Me, —C(=O)Me, 5-6 membered heteroaryl, and unsubstituted 3-6 membered heterocyclyl; and n is 1 or 2.

In some embodiments, each $R^1$ is fluoro;
m is 1 or 2;
$R^2$ is a C1-C6 alkyl;
$R^3$ is a C1-C6 alkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and unsubstituted 3-6 membered heterocyclyl; and
n is 1 or 2.

In some embodiments, each $R^1$ is fluoro;
m is 1 or 2;
$R^2$ is a C1-C6 alkyl;
$R^3$ is a C1-C6 alkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and 3-6 membered heterocyclyl optionally substituted with 1 or 2 independently selected $R^G$; and
n is 1 or 2.

In some embodiments, each $R^1$ is fluoro, cyano, or methyl;
m is 1 or 2;
$R^2$ is a C1-C3 alkyl;
$R^3$ is a C1-C3 alkyl or C1-C3 haloalkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and unsubstituted 3-6 membered heterocyclyl; and
n is 1 or 2.

In some embodiments, each $R^1$ is fluoro, cyano, or methyl;
m is 1 or 2;
$R^2$ is a C1-C3 alkyl;
$R^3$ is a C1-C3 alkyl or C1-C3 haloalkyl;
Ring A is a phenyl or a 5-6 membered heteroaryl;
each $R^4$ is independently selected from the group consisting of: —NHR$^B$, and 4-6 membered heterocyclyl optionally substituted with 1-2 $R^G$; and
n is 1 or 2.

In some embodiments, Z is O; each $R^1$ is fluoro; m is 1 or 2; $R^2$ is a C1-C6 alkyl; and $R^3$ is a C1-C6 alkyl. In some embodiments, Z is O; each $R^1$ is fluoro; m is 1 or 2; $R^2$ is methyl; and $R^3$ is selected from methyl, ethyl, isopropyl, or tert-butyl.

In some embodiments, Z is O; each $R^1$ is fluoro; m is 1 or 2; $R^2$ is a C1-C6 alkyl; and $R^3$ is a C1-C6 haloalkyl. In some embodiments, Z is O; each $R^1$ is fluoro; m is 1 or 2; $R^2$ is methyl; and $R^3$ is trifluoromethyl.

In some embodiments, Z is O; m is 2, one $R^4$ is halogen, and the other $R^4$ is —SO$_2$(C1-C6 alkyl). In some embodiments, m is 2, one $R^4$ is chloro, and the other $R^4$ is —SO$_2$CH$_3$.

In some embodiments, Z is O; m is 2, one $R^4$ is C1-C6 alkoxy, and the other $R^4$ is —C(=O)NR$^C$R$^D$.

In some embodiments, Z is O; m is 2, one $R^4$ is methoxy, and the other $R^4$ is —C(O)NHCH$_3$. In some embodiments, Ring A is a phenyl or a 5-6 membered heteroaryl;

each $R^4$ is independently selected from the group consisting of: C1-C3 alkyl, C1-C3 alkoxy, C1-C3 haloalkyl, hydroxyl, cyano, —CO$_2$H, —NH$_2$, —C(=O)NH$_2$, —C(=O)NHMe, —SO$_2$NH$_2$, —SO$_2$NHMe, —SO$_2$Me, —S(=O)(=NH)Me, —C(=O)Me, 5-6 membered heteroaryl, and unsubstituted 3-6 membered heterocyclyl; and n is 1 or 2.

In some embodiments, Z is O;
each $R^1$ is fluoro;
m is 1 or 2;
$R^2$ is a C1-C6 alkyl;
$R^3$ is a C1-C6 alkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and unsubstituted 3-6 membered heterocyclyl; and
n is 1 or 2.

In some embodiments, Z is O;
each $R^1$ is fluoro;
m is 1 or 2;
$R^2$ is a C1-C6 alkyl;
$R^3$ is a C1-C6 alkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and 3-6 membered heterocyclyl optionally substituted with 1 or 2 independently selected $R^G$; and
n is 1 or 2.

In some embodiments, Z is O;
each $R^1$ is fluoro, cyano, or methyl;
m is 1 or 2;
$R^2$ is a C1-C3 alkyl;
$R^3$ is a C1-C3 alkyl or C1-C3 haloalkyl;
Ring A is a phenyl or a 5-6 membered heteroaryl;
each $R^4$ is independently selected from the group consisting of: C1-C3 alkyl, C1-C3 alkoxy, C1-C3 haloalkyl, hydroxyl, cyano, —NH$_2$, —C(=O)NH$_2$, —C(=O)NHMe, —SO$_2$NH$_2$, —SO$_2$NHMe, —SO$_2$Me, —S(=O)(=NH)Me, —C(=O) Me, 5-6 membered heteroaryl, and unsubstituted 3-6 membered heterocyclyl; and
n is 1 or 2.

In some embodiments, Z is O;
each $R^1$ is fluoro, cyano, or methyl;
m is 1 or 2;
$R^2$ is a C1-C3 alkyl;

R³ is a C1-C3 alkyl or C1-C3 haloalkyl;
Ring A is a phenyl or a 5-6 membered heteroaryl;
each R⁴ is independently selected from the group consisting of: —NHR^B, and 4-6 membered heterocyclyl optionally substituted with 1-2 R^G; and
n is 1 or 2.

In some embodiments, Z is NR^x; each R¹ is fluoro; m is 1 or 2; R² is a C1-C6 alkyl; and R³ is a C1-C6 alkyl. In some embodiments, Z is NR^x; each R¹ is fluoro; m is 1 or 2; R² is methyl; and R³ is selected from methyl, ethyl, isopropyl, or tert-butyl.

In some embodiments, Z is NR^x; each R¹ is fluoro; m is 1 or 2; R² is a C1-C6 alkyl; and R³ is a C1-C6 haloalkyl. In some embodiments, Z is O; each R¹ is fluoro; m is 1 or 2; R² is methyl; and R³ is trifluoromethyl.

In some embodiments, Z is NR^x; m is 2, one R⁴ is halogen, and the other R⁴ is —SO₂(C1-C6 alkyl). In some embodiments, m is 2, one R⁴ is chloro, and the other R⁴ is —SO₂CH₃.

In some embodiments, Z is NR^x; m is 2, one R⁴ is C1-C6 alkoxy, and the other R⁴ is —C(=O)NR^C R^D.

In some embodiments, Z is NR^x; m is 2, one R⁴ is methoxy, and the other R⁴ is —C(O)NHCH₃. In some embodiments, Ring A is a phenyl or a 5-6 membered heteroaryl;
each R⁴ is independently selected from the group consisting of: C1-C3 alkyl, C1-C3 alkoxy, C1-C3 haloalkyl, hydroxyl, cyano, —CO₂H, —NH₂, —C(=O)NH₂, —C(=O)NHMe, —SO₂NH₂, —SO₂NHMe, —SO₂Me, —S(=O)(=NH)Me, —C(=O)Me, 5-6 membered heteroaryl, and unsubstituted 3-6 membered heterocyclyl; and
n is 1 or 2.

In some embodiments, Z is NR^x;
each R¹ is fluoro;
m is 1 or 2;
R² is a C1-C6 alkyl;
R³ is a C1-C6 alkyl;
Ring A is a phenyl or a 5-6 membered heteroaryl;
each R⁴ is independently selected from the group consisting of: C1-C3 alkyl, C1-C3 alkoxy, C1-C3 haloalkyl, hydroxyl, cyano, —NH₂, —C(=O)NH₂, —C(=O)NHMe, —SO₂NH₂, —SO₂NHMe, —SO₂Me, —S(=O)(=NH)Me, —C(=O) Me, 5-6 membered heteroaryl, and unsubstituted 3-6 membered heterocyclyl; and
n is 1 or 2.

In some embodiments, Z is NR^x;
each R¹ is fluoro;
m is 1 or 2;
R² is a C1-C6 alkyl;
R³ is a C1-C6 alkyl;
Ring A is a phenyl or a 5-6 membered heteroaryl;
each R⁴ is independently selected from the group consisting of: C1-C3 alkyl, C1-C3 alkoxy, C1-C3 haloalkyl, hydroxyl, cyano, —NH₂, —C(=O)NH₂, —C(=O)NHMe, —SO₂NH₂, —SO₂NHMe, —SO₂Me, —S(=O)(=NH)Me, —C(=O) Me, 5-6 membered heteroaryl, and 3-6 membered heterocyclyl optionally substituted with 1 or 2 independently selected R^G; and
n is 1 or 2.

In some embodiments, Z is NR^x;
each R¹ is fluoro, cyano, or methyl;
m is 1 or 2;
R² is a C1-C3 alkyl;
R³ is a C1-C3 alkyl or C1-C3 haloalkyl;
Ring A is a phenyl or a 5-6 membered heteroaryl;
each R⁴ is independently selected from the group consisting of: C1-C3 alkyl, C1-C3 alkoxy, C1-C3 haloalkyl, hydroxyl, cyano, —NH₂, —C(=O)NH₂, —C(=O)NHMe, —SO₂NH₂, —SO₂NHMe, —SO₂Me, —S(=O)(=NH)Me, —C(=O) Me, 5-6 membered heteroaryl, and unsubstituted 3-6 membered heterocyclyl; and
n is 1 or 2.

In some embodiments, Z is NR^x;
each R¹ is fluoro, cyano, or methyl;
m is 1 or 2;
R² is a C1-C3 alkyl;
R³ is a C1-C3 alkyl or C1-C3 haloalkyl;
Ring A is a phenyl or a 5-6 membered heteroaryl;
each R⁴ is independently selected from the group consisting of: —NHR^B, and 4-6 membered heterocyclyl optionally substituted with 1-2 R^G; and
n is 1 or 2.

In some embodiments, the compound of Formula (I) is Formula (I-A):

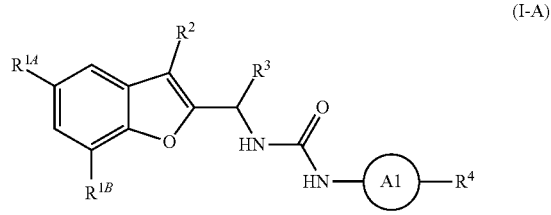

(I-A)

or a pharmaceutically acceptable salt thereof, wherein:
R^{1A} is halogen;
R^{1B} is halogen or absent (the phenyl ring is monosubstituted with R^{1A});
R² is a C1-C6 alkyl or a C1-C6 haloalkyl;
R³ is a C1-C6 alkyl, a C1-C6 haloalkyl, or a C3-C6 cycloalkyl optionally substituted with 1 or 2 substituents independently selected from fluoro and C1-C6 alkyl;
Ring A1 is a 6 membered heteroaryl;
R⁴ is independently selected from the group consisting of: C1-C6 alkyl optionally substituted with —NR^A R^B, C1-C6 alkoxy, C1-C6 haloalkyl, hydroxyl, cyano, —CO₂H, —NR^A R^B, —C(=O)NR^C R^D, —SO₂(NR^E R^F), —SO₂(C1-C6 alkyl), —S(=O)(=NH)(C1-C6 alkyl), —C(=O)(C1-C6 alkyl), —CO₂(C1-C6 alkyl), 5-6 membered heteroaryl optionally substituted with C1-C6 alkyl, 3-6 membered heterocyclyl optionally substituted with 1 or 2 independently selected R^G, and 3-6 membered cycloalkyl optionally substituted with 1 or 2 independently selected R^G;
wherein R⁴ is bonded to the position of Ring A1 that is para to the N atom of the urea moiety;
each R^A, R^{A1}, R^B, R^{B1}, R^C, R^{C1}, R^D, R^{D1}, R^E, and R^F is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —SO₂(C1-C6 alkyl), and —SO₂(NH₂); or
R^C and R^D, together with the nitrogen atom to which they are attached form a 4-6 membered heterocyclyl;
each R^G is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H.

In some embodiments, Ring A1 is pyrimidinyl, pyridyl, or pyrazolyl. In some embodiments, Ring A1 is pyrimidinyl. In some embodiments, Ring A1 is pyridyl. In some embodiments, Ring A1 is pyrazolyl.

In some embodiments, Ring A1 is 5-pyrimidinyl, 3-pyridyl, or 4-pyrazolyl. In some embodiments, Ring A1 is 5-pyrimidinyl. In some embodiments, Ring A1 is 3-pyridyl. In some embodiments, Ring A1 is 4-pyrazolyl.

In some embodiments of Formula (I-A),

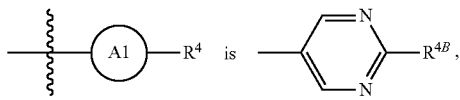

wherein: R$^{4B}$ is selected from —NR$^A$R$^B$ and 4-6 membered heterocyclyl comprising one nitrogen ring member and optionally substituted with 1-2 independently selected R$^{G1}$; wherein R$^{G1}$ is selected from fluoro, hydroxyl, and C1-C6 alkyl.

In some embodiments of Formula (I-A), R$^A$ and R$^B$ are each hydrogen.

In some embodiments of Formula (I-A), R$^A$ and R$^B$ are each 4-6 membered heterocyclyl. In some embodiments of Formula (I-A), one of R$^A$ and R$^B$ is hydrogen and the other of R$^A$ and R$^B$ is 4-6 membered heterocyclyl. In some embodiments of Formula (I-A), one of R$^A$ and R$^B$ is hydrogen and the other of R$^A$ and R$^B$ is 4 membered heterocyclyl. In some embodiments of Formula (I-A), one of R$^A$ and R$^B$ is hydrogen and the other of R$^A$ and R$^B$ is 5 membered heterocyclyl. In some embodiments of Formula (I-A), one of R$^A$ and R$^B$ is hydrogen and the other of R$^A$ and R$^B$ is 1,1-dioxidotetrahydrothiophen-3-yl. In some embodiments of Formula (I-A), one of R$^A$ and R$^B$ is hydrogen and the other of R$^A$ and R$^B$ is 6 membered heterocyclyl. In some embodiments of Formula (I-A), R$^A$ and R$^B$ are each C1-C6 haloalkyl. In some embodiments of Formula (I-A), one of R$^A$ and R$^B$ is hydrogen and the other of R$^A$ and R$^B$ is C1-C6 haloalkyl. In some embodiments of Formula (I-A), one of R$^A$ and R$^B$ is hydrogen and the other of R$^A$ and R$^B$ is C1-C3 haloalkyl. In some embodiments of Formula (I-A), one of R$^A$ and R$^B$ is C1-C6 alkyl and the other of R$^A$ and R$^B$ is C1-C6 haloalkyl.

In some embodiments of Formula (I-A), R$^A$ and R$^B$ are each 3-6 membered cycloalkyl optionally substituted with hydroxyl. In some embodiments of Formula (I-A), one of R$^A$ and R$^B$ is hydrogen and the other of R$^A$ and R$^B$ is 3-6 membered cycloalkyl optionally substituted with hydroxyl. In some embodiments of Formula (I-A), one of R$^A$ and R$^B$ is hydrogen and the other of R$^A$ and R$^B$ is 3-6 membered cycloalkyl substituted with hydroxyl. In some embodiments of Formula (I-A), one of R$^A$ and R$^B$ is hydrogen and the other of R$^A$ and R$^B$ is unsubstituted 3-6 membered cycloalkyl. In some embodiments of Formula (I-A), one of R$^A$ and R$^B$ is hydrogen and the other of R$^A$ and R$^B$ is 3 membered cycloalkyl optionally substituted with hydroxyl. In some embodiments of Formula (I-A), one of R$^A$ and R$^B$ is hydrogen and the other of R$^A$ and R$^B$ is 4 membered cycloalkyl optionally substituted with hydroxyl. In some embodiments of Formula (I-A), one of R$^A$ and R$^B$ is hydrogen and the other of R$^A$ and R$^B$ is cis- or trans-3-hydroxycyclobutyl. In some embodiments of Formula (I-A), one of R$^A$ and R$^B$ is hydrogen and the other of R$^A$ and R$^B$ is 5 membered cycloalkyl optionally substituted with hydroxyl. In some embodiments of Formula (I-A), one of R$^A$ and R$^B$ is hydrogen and the other of R$^A$ and R$^B$ is 6 membered cycloalkyl optionally substituted with hydroxyl. In some embodiments of Formula (I-A), one of R$^A$ and R$^B$ is C1-C6 alkyl and the other of R$^A$ and R$^B$ is 3-6 membered cycloalkyl substituted with hydroxyl.

In some embodiments of Formula (I-A), one of R$^A$ and R$^B$ is hydrogen and the other of R$^A$ and R$^B$ is C1-C6 alkyl optionally substituted with 1-2 substituents independently selected from hydroxyl, 3-6 membered cycloalkyl, —SO$_2$(C1-C6 alkyl), and —SO$_2$(NH$_2$). In some embodiments of Formula (I-A), one of R$^A$ and R$^B$ is hydrogen and the other of R$^A$ and R$^B$ is C1-C6 alkyl optionally substituted with hydroxyl In some embodiments of Formula (I-A), one of R$^A$ and R$^B$ is hydrogen and the other of R$^A$ and R$^B$ is C1-C6 alkyl substituted with hydroxyl. In some embodiments of Formula (I-A), one of R$^A$ and R$^B$ is hydrogen and the other of R$^A$ and R$^B$ is C1-C6 alkyl. In some embodiments of Formula (I-A), one of R$^A$ and R$^B$ is hydrogen and the other of R$^A$ and R$^B$ is C1-C3 alkyl optionally substituted with hydroxyl. In some embodiments of Formula (I-A), one of R$^A$ and R$^B$ is hydrogen and the other of R$^A$ and R$^B$ is C1-C3 alkyl substituted with hydroxyl. In some embodiments of Formula (I-A), one of R$^A$ and R$^B$ is hydrogen and the other of R$^A$ and R$^B$ is ethyl substituted with hydroxyl (e.g., 2-hydroxy-1-propyl. In some embodiments of Formula (I-A), one of R$^A$ and R$^B$ is hydrogen and the other of R$^A$ and R$^B$ is propyl substituted with hydroxyl (e.g., 2-hydroxyl-propyl or 1-hydroxy-2-propyl). In some embodiments of Formula (I-A), one of R$^A$ and R$^B$ is hydrogen and the other of R$^A$ and R$^B$ is C1-C3 alkyl. In some embodiments of Formula (I-A), one of R$^A$ and R$^B$ is hydrogen and the other of R$^A$ and R$^B$ is methyl.

In some embodiments of Formula (I-A), R$^A$ and R$^B$ are each C1-C6 alkyl optionally substituted with hydroxyl. In some embodiments of Formula (I-A), R$^A$ and R$^B$ are each C1-C6 alkyl substituted with hydroxyl. In some embodiments of Formula (I-A), one of R$^A$ and R$^B$ is C1-C3 alkyl and the other of R$^A$ and R$^B$ is C1-C3 alkyl substituted with hydroxyl. In some embodiments of Formula (I-A), one of R$^A$ and R$^B$ is methyl and the other of R$^A$ and R$^B$ is C1-C3 alkyl substituted with hydroxyl. In some embodiments of Formula (I-A), one of R$^A$ and R$^B$ is methyl and the other of R$^A$ and R$^B$ is ethyl substituted with hydroxyl (e.g., 2-hydroxy-1-propyl). In some embodiments of Formula (I-A), R$^A$ and R$^B$ are each C1-C6 alkyl. In some embodiments of Formula (I-A), R$^A$ and R$^B$ are each C1-C3 alkyl. In some embodiments of Formula (I-A), R$^A$ and R$^B$ are each methyl.

In some embodiments of Formula (I-A), one of R$^A$ and R$^B$ is hydrogen and the other of R$^A$ and R$^B$ is C1-C6 alkyl substituted with 3-6 membered cycloalkyl. In some embodiments of Formula (I-A), one of R$^A$ and R$^B$ is hydrogen and the other of R$^A$ and R$^B$ is C1-C3 alkyl substituted with 3-6 membered cycloalkyl. In some embodiments of Formula (I-A), one of R$^A$ and R$^B$ is hydrogen and the other of R$^A$ and R$^B$ is C1-C3 alkyl substituted with 3-4 membered cycloalkyl. In some embodiments of Formula (I-A), one of R$^A$ and R$^B$ is hydrogen and the other of R$^A$ and R$^B$ is C1-C3 alkyl substituted with 3-4 membered cycloalkyl and hydroxyl. In some embodiments of Formula (I-A), one of R$^A$ and R$^B$ is hydrogen and the other of R$^A$ and R$^B$ is C1-C3 alkyl substituted with cyclopropyl and hydroxyl. In some embodiments of Formula (I-A), one of R$^A$ and R$^B$ is hydrogen and the other of R$^A$ and R$^B$ is ethyl substituted with cyclopropyl and hydroxyl, e.g., 1-cyclopropyl-2-hydroxyethyl. In some embodiments of Formula (I-A), one of R$^A$ and R$^B$ is C1-C6 alkyl and the other of R$^A$ and R$^B$ is C1-C6 alkyl substituted with 3-6 membered cycloalkyl. In some embodiments of Formula (I-A), R$^A$ and R$^B$ are both C1-C6 alkyl substituted with 3-6 membered cycloalkyl.

In some embodiments of Formula (I-A), one of R$^A$ and R$^B$ is hydrogen and the other of R$^A$ and R$^B$ is C1-C6 alkyl substituted with —SO$_2$(C1-C6 alkyl). In some embodiments of Formula (I-A), one of R$^A$ and R$^B$ is hydrogen and the other of R$^A$ and R$^B$ is C1-C3 alkyl substituted with —SO$_2$(C1-C6 alkyl). In some embodiments of Formula (I-A), one of R$^A$ and R$^B$ is hydrogen and the other of R$^A$ and R$^B$ is C1-C3 alkyl substituted with —SO$_2$(C1-C3 alkyl). In some embodiments of Formula (I-A), one of R$^A$ and R$^B$ is hydrogen and the other of R$^A$ and R$^B$ is C1-C3 alkyl substituted with —SO$_2$CH$_3$, e.g., 1-(methylsulfonyl)propan-2-yl. In some embodiments of Formula (I-A), one of R$^A$ and R$^B$ is C1-C6 alkyl and the other of R$^A$ and R$^B$ is C1-C6 alkyl substituted with —SO$_2$(C1-C6 alkyl). In some embodiments of Formula (I-A), R$^A$ and R$^B$ are both C1-C6 alkyl substituted with —SO$_2$(C1-C6 alkyl).

In some embodiments of Formula (I-A), one of R$^A$ and R$^B$ is hydrogen and the other of R$^A$ and R$^B$ is C1-C6 alkyl substituted with —SO$_2$(NH$_2$). In some embodiments of Formula (I-A), one of R$^A$ and R$^B$ is hydrogen and the other of R$^A$ and R$^B$ is C1-C3 alkyl substituted with —SO$_2$(NH$_2$), e.g., 1-sulfamoylpropan-2-yl. In some embodiments of Formula (I-A), one of R$^A$ and R$^B$ is C1-C6 alkyl hydrogen and the other of R$^A$ and R$^B$ is C1-C6 alkyl substituted with —SO$_2$(NH$_2$). In some embodiments of Formula (I-A), R$^A$ and R$^B$ are both C1-C6 alkyl substituted with —SO$_2$(NH$_2$).

In some embodiments of Formula (I-A), R$^{4B}$ is 4-6 membered heterocyclyl comprising one nitrogen ring member and optionally substituted with 1-2 independently selected R$^G$; wherein R$^G$ is selected from fluoro, hydroxyl, and C1-C6 alkyl.

In some embodiments of Formula (I-A), R$^{4B}$ is

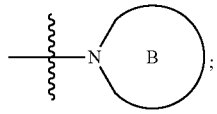

wherein Ring B is azetidinyl, pyrrolidinyl, or piperidinyl, each optionally substituted with 1-2 R$^G$ independently selected from fluoro, hydroxyl, and C1-C6 alkyl. In some embodiments of Formula (I-A), Ring B is azetidinyl.

In some embodiments of Formula (I-A), Ring B is unsubstituted.

In some embodiments of Formula (I-A), Ring B is substituted with 1 R$^G$. In some embodiments of Formula (I-A), R$^G$ is fluoro. In some embodiments of Formula (I-A), R$^G$ is cyano. In some embodiments of Formula (I-A), R$^G$ is hydroxyl. In some embodiments of Formula (I-A), R$^G$ is C1-C3 alkyl. In some embodiments of Formula (I-A), R$^G$ is methyl. In some embodiments of Formula (I-A), R$^G$ is —CO$_2$CH$_3$.

In some embodiments of Formula (I-A), Ring B is substituted with 2 independently selected R$^G$. In some embodiments of Formula (I-A), each R$^G$ is fluoro. In some embodiments of Formula (I-A), each R$^G$ is C1-C3 alkyl. In some embodiments of Formula (I-A), each R$^G$ is methyl. In some embodiments of Formula (I-A), one R$^G$ is hydroxyl and the other R$^G$ is C1-C3 alkyl. In some embodiments of Formula (I-A), one R$^G$ is hydroxyl and the other R$^G$ is methyl. In some embodiments of Formula (I-A), one R$^G$ is fluoro and the other R$^G$ is C1-C3 alkyl. In some embodiments of Formula (I-A), one R$^G$ is fluoro and the other R$^G$ is methyl. In some embodiments of Formula (I-A), one R$^G$ is hydroxyl and the other R$^G$ is fluoro. In some embodiments of Formula (I-A), one R$^G$ is hydroxyl and the other R$^G$ is trifluoromethyl.

In some embodiments of Formula (I-A),

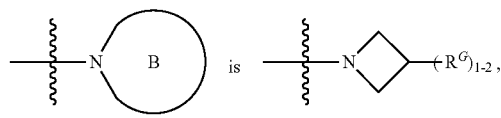

wherein 1 or 2 independently selected R$^G$ is at the 3-position of the azetidine. In some embodiments of Formula (I-A),

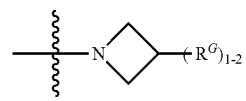

is selected from the group consisting of

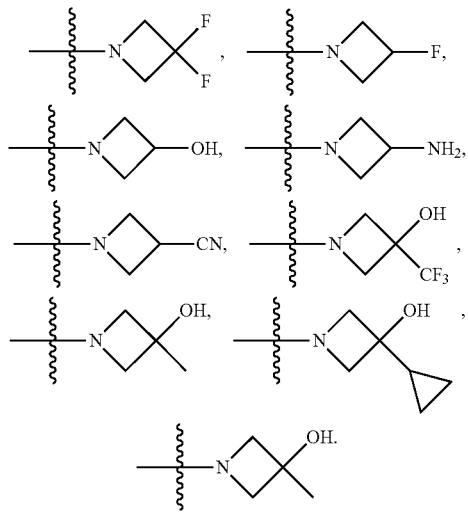

and

In some embodiments of Formula (I-A),

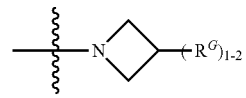

is selected from the groups consisting of

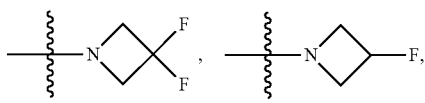

-continued

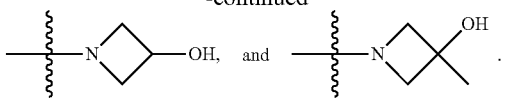

In some embodiments, the compound of Formula (I) is Formula (I-B).

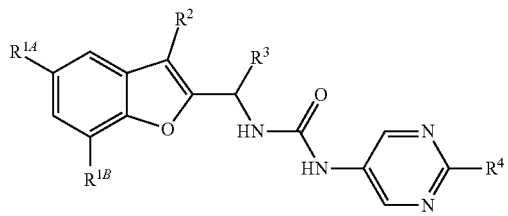

(I-B)

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 substituents independently selected from fluoro and C1-C6 alkyl;
$R^4$ is independently selected from the group consisting of: C1-C6 alkyl optionally substituted with —$NR^A R^B$, C1-C6 alkoxy, C1-C6 haloalkyl, hydroxyl, cyano, —$CO_2H$, —$NR^A R^B$, —$C(=O)NR^C R^D$, —$SO_2(NR^E R^F)$, —$SO_2$(C1-C6 alkyl), —$S(=O)(=NH)$(C1-C6 alkyl), —$C(=O)$(C1-C6 alkyl), —$CO_2$(C1-C6 alkyl), 5-6 membered heteroaryl optionally substituted with C1-C6 alkyl, 3-6 membered heterocyclyl optionally substituted with 1 or 2 independently selected $R^G$, and 3-6 membered cycloalkyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —$SO_2$(C1-C6 alkyl), and —$SO_2(NH_2)$; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —$NR^{A1}R^{B1}$, —$C(=O)NR^{C1}R^{D1}$, —$CO_2$(C1-C6 alkyl), C1-C6 haloalkyl, C3-C6 cycloalkyl, and —$CO_2H$.

In some embodiments, $R^{1A}$ and $R^{1B}$ are each fluoro; In some embodiments, $R^2$ is a C1-C6 alkyl. In some embodiments, $R^2$ is a C1-C3 alkyl. In some embodiments, $R^2$ is methyl.

In some embodiments, $R^2$ is a C1-C6 haloalkyl. In some embodiments, $R^2$ is a C1-C3 haloalkyl. In some embodiments, $R^2$ is trifluoromethyl.

In some embodiments, $R^3$ is a C1-C6 alkyl. In some embodiments, $R^3$ is a C1-C3 alkyl. In some embodiments, $R^3$ is methyl, ethyl, or isopropyl. In some embodiments, $R^3$ is methyl. In some embodiments, $R^3$ is ethyl. In some embodiments, $R^3$ is isopropyl.

In some embodiments, $R^3$ is a C1-C6 haloalkyl. In some embodiments, $R^3$ is a C1-C3 haloalkyl. In some embodiments, $R^3$ is a trifluoromethyl.

In some embodiments, $R^3$ is C3-C6 cycloalkyl optionally substituted with 1 or 2 substituents independently selected from fluoro and C1-C6 alkyl. In some embodiments, $R^3$ is C3-C6 cycloalkyl optionally substituted with 1 or 2 fluoro. In some embodiments, $R^3$ is C3-C6 cycloalkyl substituted with 1 or 2 fluoro. In some embodiments, $R^3$ is unsubstituted C3-C6 cycloalkyl. In some embodiments, the $R^3$ C3-C6 cycloalkyl is cyclopropyl. In some embodiments, $R^3$ is cyclopropyl.

In some embodiments, $R^4$ is C1-C6 alkyl optionally substituted with —$NR^A R^B$. In some embodiments, $R^4$ is C1-C3 alkyl optionally substituted with —$NR^A R^B$. In some embodiments, $R^4$ is methyl optionally substituted with —$NR^A R^B$. In some embodiments, $R^4$ is C1-C4 alkyl. In some embodiments, $R^4$ is methyl.

In some embodiments, $R^4$ is C1-C6 alkoxy. In some embodiments, $R^4$ is C1-C3 alkoxy. In some embodiments, $R^4$ is methoxy.

In some embodiments, $R^4$ is C1-C6 haloalkyl. In some embodiments, $R^4$ is C1-C3 haloalkyl. In some embodiments, $R^4$ is trifluoromethyl.

In some embodiments, $R^4$ is hydroxyl. In some embodiments, $R^4$ is cyano. In some embodiments, $R^4$ is —$CO_2H$. In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl. In some embodiments, one of $R^A$ and $R^B$ is hydrogen and the other of $R^A$ and $R^B$ is propyl substituted with hydroxyl (e.g., 2-hydroxyl-propyl or 1-hydroxy-2-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, one of $R^A$ and $R^B$ is hydrogen and the other of $R^A$ and $R^B$ is C1-C6 haloalkyl. In some embodiments, $R^A$ and $R^B$ are each C1-C6 haloalkyl. In some embodiments, one of $R^A$ and $R^B$ is C1-C6 alkyl and the other of one of $R^A$ and $R^B$ is C1-C6 haloalkyl. In some embodiments, one of $R^A$ and $R^B$ is hydrogen and the other of $R^A$ and $R^B$ is C1-C3 haloalkyl. In some embodiments, one of $R^A$ and $R^B$ is C1-C6 alkyl and the other of $R^A$ and $R^B$ is C1-C6 haloalkyl.

In some embodiments, $R^A$ and $R^B$ are each 4-6 membered heterocyclyl. In some embodiments, one of $R^A$ and $R^B$ is hydrogen and the other of $R^A$ and $R^B$ is 4-6 membered heterocyclyl. In some embodiments, one of $R^A$ and $R^B$ is hydrogen and the other of $R^A$ and $R^B$ is 4 membered heterocyclyl. In some embodiments, one of $R^A$ and $R^B$ is hydrogen and the other of $R^A$ and $R^B$ is 5 membered heterocyclyl. In some embodiments of Formula (I-A), one of $R^A$ and $R^B$ is hydrogen and the other of $R^A$ and $R^B$ is 1,1-dioxidotetrahydrothiophen-3-yl. In some embodiments, one of $R^A$ and $R^B$ is hydrogen and the other of $R^A$ and $R^B$ is 6 membered heterocyclyl.

In some embodiments, $R^A$ and $R^B$ are each 3-6 membered cycloalkyl optionally substituted with hydroxyl. In some embodiments, one of $R^A$ and $R^B$ is hydrogen and the other of $R^A$ and $R^B$ is 3-6 membered cycloalkyl optionally substituted with hydroxyl. In some embodiments, one of $R^A$ and $R^B$ is hydrogen and the other of $R^A$ and $R^B$ is 3-6 membered cycloalkyl substituted with hydroxyl. In some embodiments, one of $R^A$ and $R^B$ is hydrogen and the other of $R^A$ and $R^B$ is unsubstituted 3-6 membered cycloalkyl. In some embodiments, one of $R^A$ and $R^B$ is hydrogen and the other of $R^A$ and $R^B$ is 3 membered cycloalkyl optionally substituted with hydroxyl. In some embodiments, one of $R^A$ and $R^B$ is hydrogen and the other of $R^A$ and $R^B$ is 4 membered cycloalkyl optionally substituted with hydroxyl. In some embodiments, one of $R^A$ and $R^B$ is hydrogen and the other of $R^A$ and $R^B$ is cis- or trans-3-hydroxycyclobutyl. In some embodiments, one of $R^A$ and $R^B$ is hydrogen and the other of $R^A$ and $R^B$ is 5 membered cycloalkyl optionally substituted with hydroxyl. In some embodiments, one of $R^A$ and $R^B$ is hydrogen and the other of $R^A$ and $R^B$ is 6 membered cycloalkyl optionally substituted with hydroxyl. In some embodiments, one of $R^A$ and $R^B$ is C1-C6 alkyl and the other of $R^A$ and $R^B$ is 3-6 membered cycloalkyl substituted with hydroxyl.

In some embodiments, one of $R^A$ and $R^B$ is hydrogen and the other of $R^A$ and $R^B$ is C1-C6 alkyl optionally substituted with 1-2 substituents independently selected from hydroxyl, 3-6 membered cycloalkyl, —SO$_2$(C1-C6 alkyl), and —SO$_2$(NH$_2$).

In some embodiments, one of $R^A$ and $R^B$ is hydrogen and the other of $R^A$ and $R^B$ is C1-C6 alkyl substituted with 3-6 membered cycloalkyl. In some embodiments, one of $R^A$ and $R^B$ is hydrogen and the other of $R^A$ and $R^B$ is C1-C3 alkyl substituted with 3-6 membered cycloalkyl. In some embodiments, one of $R^A$ and $R^B$ is hydrogen and the other of $R^A$ and $R^B$ is C1-C3 alkyl substituted with 3-4 membered cycloalkyl. In some embodiments, one of $R^A$ and $R^B$ is hydrogen and the other of $R^A$ and $R^B$ is C1-C3 alkyl substituted with 3-4 membered cycloalkyl and hydroxyl. In some embodiments, one of $R^A$ and $R^B$ is hydrogen and the other of $R^A$ and $R^B$ is C1-C3 alkyl substituted with cyclopropyl and hydroxyl. In some embodiments, one of $R^A$ and $R^B$ is hydrogen and the other of $R^A$ and $R^B$ is ethyl substituted with cyclopropyl and hydroxyl, e.g., 1-cyclopropyl-2-hydroxyethyl. In some embodiments, one of $R^A$ and $R^B$ is C1-C6 alkyl and the other of $R^A$ and $R^B$ is C1-C6 alkyl substituted with 3-6 membered cycloalkyl. In some embodiments, $R^A$ and $R^B$ are both C1-C6 alkyl substituted with 3-6 membered cycloalkyl.

In some embodiments, one of $R^A$ and $R^B$ is hydrogen and the other of $R^A$ and $R^B$ is C1-C6 alkyl substituted with —SO$_2$(C1-C6 alkyl). In some embodiments, one of $R^A$ and $R^B$ is hydrogen and the other of $R^A$ and $R^B$ is C1-C3 alkyl substituted with —SO$_2$(C1-C6 alkyl). In some embodiments, one of $R^A$ and $R^B$ is hydrogen and the other of $R^A$ and $R^B$ is C1-C3 alkyl substituted with —SO$_2$(C1-C3 alkyl). In some embodiments, one of $R^A$ and $R^B$ is hydrogen and the other of $R^A$ and $R^B$ is C1-C3 alkyl substituted with —SO$_2$CH$_3$, e.g., 1-(methylsulfonyl)propan-2-yl. In some embodiments, one of $R^A$ and $R^B$ is C1-C6 alkyl and the other of $R^A$ and $R^B$ is C1-C6 alkyl substituted with —SO$_2$(C1-C6 alkyl). In some embodiments, $R^A$ and $R^B$ are both C1-C6 alkyl substituted with —SO$_2$(C1-C6 alkyl). In some embodiments, one of $R^A$ and $R^B$ is hydrogen and the other of $R^A$ and $R^B$ is C1-C6 alkyl substituted with —SO$_2$(NH$_2$). In some embodiments, one of $R^A$ and $R^B$ is hydrogen and the other of $R^A$ and $R^B$ is C1-C3 alkyl substituted with —SO$_2$(NH$_2$), e.g., 1-sulfamoylpropan-2-yl. In some embodiments, one of $R^A$ and $R^B$ is C1-C6 alkyl hydrogen and the other of $R^A$ and $R^B$ is C1-C6 alkyl substituted with —SO$_2$(NH$_2$). In some embodiments, $R^A$ and $R^B$ are both C1-C6 alkyl substituted with —SO$_2$(NH$_2$).

In some embodiments, one $R^4$ is —C(=O)NR$^C$R$^D$. In some embodiments, $R^C$ and $R^D$ are each hydrogen. In some embodiments, one of $R^C$ and $R^D$ is hydrogen and the other of $R^C$ and $R^D$ is C1-C6 alkyl. In some embodiments, one of $R^C$ and $R^D$ is hydrogen and the other of $R^C$ and $R^D$ is C1-C3 alkyl. In some embodiments, one of $R^C$ and $R^D$ is hydrogen and the other of $R^C$ and $R^D$ is methyl. In some embodiments, $R^C$ and $R^D$ are each C1-C6 alkyl. In some embodiments, $R^C$ and $R^D$ are each C1-C3 alkyl. In some embodiments, $R^C$ and $R^D$ are each methyl. In some embodiments, one of $R^C$ and $R^D$ is hydrogen and the other of $R^C$ and $R^D$ is C1-C6 haloalkyl. In some embodiments, $R^C$ and $R^D$ are each is C1-C6 haloalkyl. In some embodiments, one of $R^C$ and $R^D$ is C1-C6 alkyl and the other of $R^C$ and $R^D$ is C1-C6 haloalkyl. In some embodiments, $R^C$ and $R^D$, together with the nitrogen atom to which they are attached form a 4-6 membered heterocyclyl. In some embodiments, $R^C$ and $R^D$, together with the nitrogen atom to which they are attached form azetidine or piperazine.

In some embodiments, one $R^4$ is —SO$_2$(NR$^E$R$^F$). In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is methyl. In some embodiments, $R^E$ and $R^F$ are each is C1-C6 alkyl. In some embodiments, $R^E$ and $R^F$ are each is C1-C3 alkyl. In some embodiments, $R^E$ and $R^F$ are each methyl. In some embodiments, one of $R^E$ and $R^F$ is hydrogen and the other of $R^E$ and $R^F$ is C1-C6 haloalkyl. In some embodiments, $R^E$ and $R^F$ are each C1-C6 haloalkyl. In some embodiments, one of $R^E$ and $R^F$ is C1-C6 alkyl and the other of $R^E$ and $R^F$ is C1-C6 haloalkyl.

In some embodiments, $R^4$ is —SO$_2$(C1-C6 alkyl). In some embodiments, $R^4$ is —SO$_2$(C1-C3 alkyl). In some embodiments, $R^4$ is —SO$_2$Me. In some embodiments, $R^4$ is —SO$_2$Et.

In some embodiments, $R^4$ is —S(=O)(=NH)(C1-C6 alkyl). In some embodiments, $R^4$ is —S(=O)(=NH)(C1-C4 alkyl). In some embodiments, $R^4$ is —S(=O)(=NH)Me.

In some embodiments, $R^4$ is —C(=O)(C1-C6 alkyl). In some embodiments, $R^4$ is —C(=O)(C1-C3 alkyl). In some embodiments, $R^4$ is —C(=O)Me.

In some embodiments, $R^4$ is —CO$_2$(C1-C6 alkyl). In some embodiments, $R^4$ is —CO$_2$(C1-C3 alkyl). In some embodiments, $R^4$ is —CO$_2$Me.

In some embodiments, one $R^4$ is 5-6 membered heteroaryl optionally substituted with C1-C6 alkyl. In some embodiments, one $R^4$ is 5-6 membered heteroaryl substituted with C1-C6 alkyl. In some embodiments, $R^4$ is 5-6 membered heteroaryl. In some embodiments, $R^4$ is selected from the group consisting of pyrrolyl, pyrazolyl, imidazolyl, triazolyl, tetrazolyl, furanyl, thiophenyl, oxazolyl, isoxazolyl, isothiazolyl, thiazolyl, furanyl, oxadiazolyl, thiadiazolyl, oxatriazolyl, and thiatriazolyl, pyridinyl, pyrimidinyl, pyrazinyl, pyridazinyl, and triazinyl. In some embodiments, $R^4$ is pyrazolyl. In some embodiments, one $R^4$ is tetrazolyl substituted with methyl. In some embodiments, one $R^4$ is pyrazolyl. In some embodiments, one $R^4$ is unsubstituted pyrazolyl. In some embodiments, one $R^4$ is 1-pyrazolyl.

In some embodiments, $R^4$ is 3-6 membered heterocyclyl optionally substituted with 1 or 2 independently selected $R^G$. In some embodiments, $R^4$ is 3-6 membered heterocyclyl substituted with 1 or 2 independently selected $R^G$. In some embodiments, $R^4$ is 3-6 membered heterocyclyl substituted with 1 $R^G$. In some embodiments, $R^4$ is 3-6 membered heterocyclyl substituted with 2 independently selected $R^G$.

In some embodiments, $R^G$ is fluoro. In some embodiments, $R^G$ is cyano. In some embodiments, $R^G$ is hydroxyl. In some embodiments, $R^G$ is C1-C6 alkyl. In some embodiments, $R^G$ is C1-C3 alkyl. In some embodiments, $R^G$ is methyl.

In some embodiments, $R^G$ is C1-C6 alkoxy. In some embodiments, $R^G$ is C1-C3 alkoxy. In some embodiments, $R^G$ is methoxy.

In some embodiments, one $R^G$ is —$NR^{A1}R^{B1}$. In some embodiments, $R^{A1}$ and $R^{B1}$ are each hydrogen. In some embodiments, one of $R^{A1}$ and $R^{B1}$ is hydrogen and the other of $R^{A1}$ and $R^{B1}$ is C1-C6 alkyl. In some embodiments, one of $R^{A1}$ and $R^{B1}$ is hydrogen and the other of $R^{A1}$ and $R^{B1}$ is C1-C3 alkyl. In some embodiments, one of $R^{A1}$ and $R^{B1}$ is hydrogen and the other of $R^{A1}$ and $R^{B1}$ is methyl. In some embodiments, $R^{A1}$ and $R^{B1}$ are each C1-C6 alkyl. In some embodiments, $R^{A1}$ and $R^{B1}$ are each C1-C3 alkyl. In some embodiments, $R^{A1}$ and $R^{B1}$ are each methyl.

In some embodiments, one of $R^{A1}$ and $R^{B1}$ is hydrogen and the other of $R^{A1}$ and $R^{B1}$ is C1-C6 haloalkyl. In some embodiments, $R^{A1}$ and $R^{B1}$ are each C1-C6 haloalkyl. In some embodiments, one of $R^{A1}$ and $R^{B1}$ is C1-C6 alkyl and the other of $R^{A1}$ and $R^{B1}$ is C1-C6 haloalkyl.

In some embodiments, one $R^G$ is —C(=O)$NR^{C1}R^{D1}$. In some embodiments, $R^{C1}$ and $R^{D1}$ are each is hydrogen. In some embodiments, one of $R^{C1}$ and $R^{D1}$ is hydrogen and the other of $R^{C1}$ and $R^{D1}$ is C1-C6 alkyl. In some embodiments, one of $R^{C1}$ and $R^{D1}$ is hydrogen and the other of $R^{C1}$ and $R^{D1}$ is C1-C3 alkyl. In some embodiments, one of $R^{C1}$ and $R^{D1}$ is hydrogen and the other of $R^{C1}$ and $R^{D1}$ is methyl. In some embodiments, $R^{C1}$ and $R^{D1}$ are each is C1-C6 alkyl. In some embodiments, $R^{C1}$ and $R^{D1}$ are each is methyl. In some embodiments, one of $R^{C1}$ and $R^{D1}$ is hydrogen and the other of $R^{C1}$ and $R^{D1}$ is C1-C6 haloalkyl. In some embodiments, $R^{C1}$ and $R^{D1}$ are each is C1-C6 haloalkyl. In some embodiments, one of $R^{C1}$ and $R^{D1}$ is C1-C6 alkyl and the other of $R^{C1}$ and $R^{D1}$ is C1-C6 haloalkyl.

In some embodiments, one $R^G$ is —$CO_2$(C1-C6 alkyl). In some embodiments, one $R^G$ is —$CO_2CH_3$.

In some embodiments, one $R^G$ is C1-C6 haloalkyl. In some embodiments, one $R^G$ is trifluoromethyl.

In some embodiments, one $R^G$ is C3-C6 cycloalkyl. In some embodiments, one $R^G$ is cyclopropyl.

In some embodiments, $R^G$ is —$CO_2H$.

In some embodiments, the $R^4$ 3-6 membered heterocyclyl is a 5-6 membered heterocyclyl. In some embodiments, the $R^4$ 3-6 membered heterocyclyl is azetidinyl, azetidin-2-onyl, morpholinyl, piperazinyl, or tetrahydropyranyl. In some embodiments, the $R^4$ 3-6 membered heterocyclyl is 1-azetidinyl, 1-azetidin-2-onyl, 1-piperazinyl, 1-morpholinyl, or 4-tetrahydropyranyl.

In some embodiments, $R^4$ is unsubstituted 3-6 membered heterocyclyl. In some embodiments, $R^4$ is a 5-6 membered heterocyclyl. In some embodiments, $R^4$ is azetidinyl, morpholinyl, or tetrahydropyranyl.

In some embodiments, $R^4$ is selected from the group consisting of

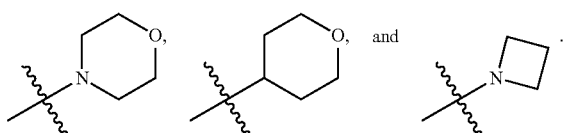 [SMILES: *N1CCOCC1 ; *C1CCOCC1 ; "and" ; *N1CCC1 ; "."]

In some embodiments, $R^4$ is selected from —$NR^AR^B$ and 4-6 membered heterocyclyl comprising one nitrogen ring member and optionally substituted with 1-2 independently selected $R^{G1}$; wherein $R^{G1}$ is selected from fluoro, hydroxyl, and C1-C6 alkyl.

In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl. In some embodiments, one of $R^A$ and $R^B$ is hydrogen and the other of $R^A$ and $R^B$ is propyl substituted with hydroxyl (e.g., 2-hydroxy-propyl or 1-hydroxy-2-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, $R^4$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

In some embodiments, the compound of Formula (I) is Formula (I-C):

(I-C)

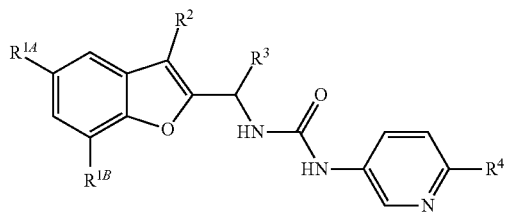

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(═O)NR$^C$R$^D$, —SO$_2$(NR$^E$R$^F$), —SO$_2$(C1-C6 alkyl), —S(═O)(═NH)(C1-C6 alkyl), —C(═O)(C1-C6 alkyl), —CO$_2$(C1-C6 alkyl), 5-6 membered heteroaryl, and 3-6 membered heterocyclyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
$R^C$ and $R^D$, together with the nitrogen atom to which they are attached form a 4-6 membered heterocyclyl;
each $R^G$ is independently selected from the group consisting of: fluoro, hydroxyl, C1-C6 alkyl, C1-C6 alkoxy, —NR$^{A1}$R$^{B1}$, —C(═O)NR$^{C1}$R$^{D1}$ and —CO$_2$H.

In some embodiments, the compound of Formula (I) is Formula (I-D):

(I-D)

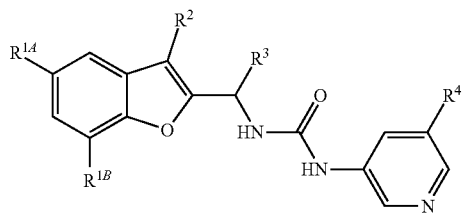

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(═O)NR$^C$R$^D$, —SO$_2$(NR$^E$R$^F$), —SO$_2$(C1-C6 alkyl), —S(═O)(═NH)(C1-C6 alkyl), —C(═O)(C1-C6 alkyl), —CO$_2$(C1-C6 alkyl), 5-6 membered heteroaryl, and 3-6 membered heterocyclyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl, C1-C6 haloalkyl; or $R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —NR$^{A1}$R$^{B1}$, —C(═O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-E):

(I-E)

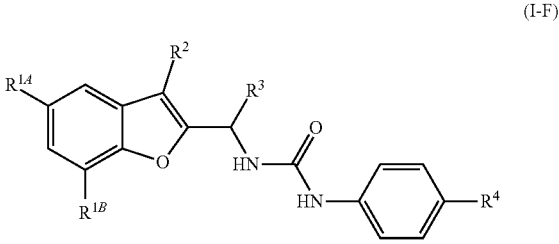

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(═O)NR$^C$R$^D$, —SO$_2$(NR$^E$R$^F$), —SO$_2$(C1-C6 alkyl), —S(═O)(═NH)(C1-C6 alkyl), —C(═O)(C1-C6 alkyl), —CO$_2$(C1-C6 alkyl), 5-6 membered heteroaryl, and 3-6 membered heterocyclyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —NR$^{A1}$R$^{B1}$, —C(═O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-F):

(I-F)

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;

$R^3$ is a C1-C6 alkyl, a C1-C6 haloalkyl, or a C3-C6 cycloalkyl optionally substituted with 1 or 2 fluoro;

$R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(=O)NR$^C$R$^D$, —SO$_2$(NR$^E$R$^F$), —SO$_2$(C1-C6 alkyl), —S(=O)(=NH)(C1-C6 alkyl), —C(=O)(C1-C6 alkyl), —CO$_2$(C1-C6 alkyl), 5-6 membered heteroaryl, and 3-6 membered heterocyclyl optionally substituted with 1 or 2 independently selected R$^G$;

each R$^A$, R$^{A1}$, R$^B$, R$^{B1}$, R$^C$, R$^{C1}$, R$^D$, R$^{D1}$, R$^E$, and R$^F$ is independently hydrogen or C1-C6 alkyl optionally substituted with hydroxyl, C1-C6 haloalkyl; or R$^C$ and R$^D$, together with the nitrogen atom to which they are attached form a 4-6 membered heterocyclyl;

each R$^G$ is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H; and wherein the compound is not

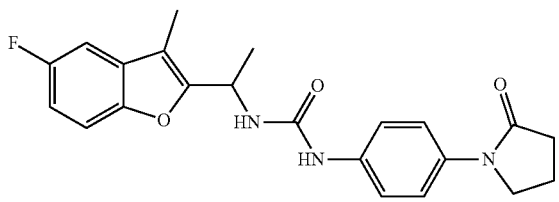

Some embodiments provide a compound of Formula (I-F), wherein the compound is not a compound selected from the group consisting of:

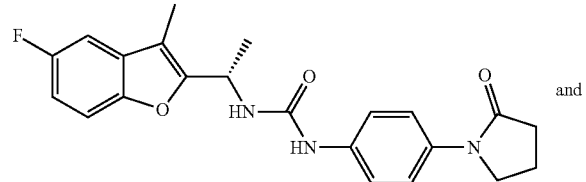

and

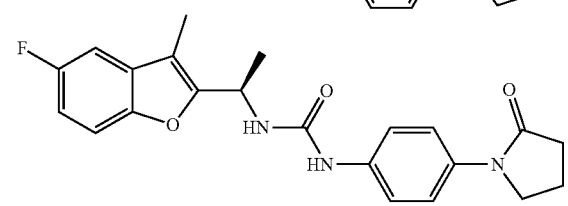

In some embodiments, the compound of Formula (I) is Formula (I-G):

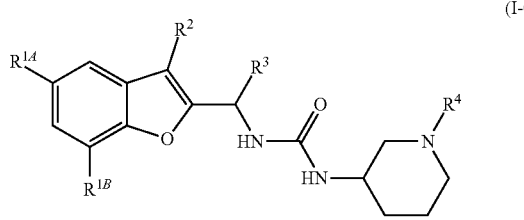

(I-G)

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(=O)NR$^C$R$^D$, —SO$_2$(NR$^E$R$^F$), —SO$_2$(C1-C6 alkyl), —S(=O)(=NH)(C1-C6 alkyl), —C(=O)(C1-C6 alkyl), —CO$_2$(C1-C6 alkyl), 5-6 membered heteroaryl, and 3-6 membered heterocyclyl optionally substituted with 1 or 2 independently selected R$^G$;

each R$^A$, R$^{A1}$, R$^B$, R$^{B1}$, R$^C$, R$^{C1}$, R$^D$, R$^{D1}$, R$^E$, and R$^F$ is independently hydrogen or C1-C6 alkyl optionally substituted with hydroxyl, C1-C6 haloalkyl; or R$^C$ and R$^D$, together with the nitrogen atom to which they are attached form a 4-6 membered heterocyclyl;

each R$^G$ is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-H):

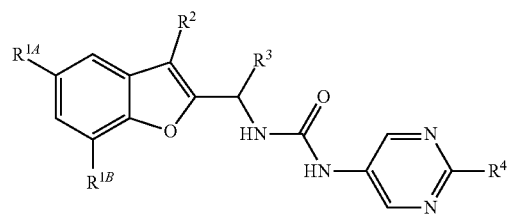

(I-H)

or a pharmaceutically acceptable salt thereof, wherein:
$R^{1A}$ is halogen;
$R^{1B}$ is halogen, cyano, cyclopropyl, or absent (the phenyl ring is monosubstituted with $R^{1A}$);
$R^2$ is a C1-C6 alkyl or C1-C6 haloalkyl;
$R^3$ is a C1-C6 alkyl or a C1-C6 haloalkyl;
$R^4$ is independently selected from the group consisting of: C1-C6 alkyl, C1-C6 alkoxy optionally substituted with 1-2 substituents independently selected from hydroxyl and C3-C6 cycloalkyl, C1-C6 haloalkyl, —NR$^A$R$^B$, and 3-9 membered heterocyclyl optionally substituted with 1 or 2 independently selected R$^G$;

each R$^A$, R$^B$, R$^{C1}$, and R$^{D1}$ is independently hydrogen, 4-6 membered heterocyclyl, C1-C6 alkyl optionally substituted with hydroxyl or —C(=O)NR$^{B2}$R$^{C2}$, —C(=O)O(C1-C6 alkyl), or C1-C6 haloalkyl;

each R$^{A2}$, R$^{B2}$, and R$^{C2}$ is independently hydrogen or C1-C6 alkyl;

each R$^G$ is independently selected from the group consisting of: fluoro, hydroxyl, C1-C6 alkyl optionally substituted with hydroxyl, C1-C6 alkoxy, =NR$^{A2}$, —C(=O)NR$^{C1}$R$^{D1}$, C1-C6 haloalkoxy, —SO$_2$(C1-C6 alkyl), and —CO$_2$H.

In some embodiments, the compound of Formula (I) is Formula (I-J):

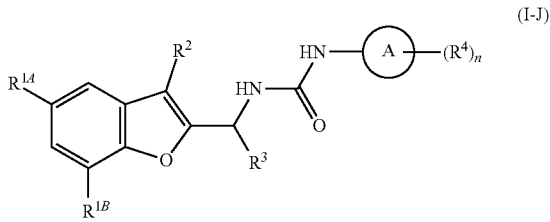

(I-J)

or a pharmaceutically acceptable salt thereof, wherein:
$R^x$ is hydrogen, C1-C6 alkyl, or C3-C6 cycloalkyl;
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 substituents independently selected from fluoro and C1-C6 alkyl;
Ring A1 is a 6 membered heteroaryl;
$R^4$ is independently selected from the group consisting of: C1-C6 alkyl optionally substituted with —$NR^A R^B$, C1-C6 alkoxy, C1-C6 haloalkyl, hydroxyl, cyano, —$CO_2H$, —$NR^A R^B$, —$C(=O)NR^C R^D$, —$SO_2(NR^E R^F)$, —$SO_2$(C1-C6 alkyl), —$S(=O)(=NH)$(C1-C6 alkyl), —$C(=O)$(C1-C6 alkyl), —$CO_2$(C1-C6 alkyl), 5-6 membered heteroaryl optionally substituted with C1-C6 alkyl, 3-6 membered heterocyclyl optionally substituted with 1 or 2 independently selected $R^G$, and 3-6 membered cycloalkyl optionally substituted with 1 or 2 independently selected $R^G$;
wherein $R^4$ is bonded to the position of Ring A1 that is para to the N atom of the urea moiety;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —$SO_2$(C1-C6 alkyl), and —$SO_2(NH_2)$; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —$NR^{A1} R^{B1}$, —$C(=O)NR^{C1} R^{D1}$, —$CO_2$(C1-C6 alkyl), C1-C6 haloalkyl, C3-C6 cycloalkyl, and —$CO_2H$.

In some embodiments, Ring A1 is pyrimidinyl, pyridyl, or pyrazolyl. In some embodiments, Ring A1 is pyrimidinyl. In some embodiments, Ring A1 is pyridyl. In some embodiments, Ring A1 is pyrazolyl.

In some embodiments, Ring A1 is 5-pyrimidinyl, 3-pyridyl, or 4-pyrazolyl. In some embodiments, Ring A1 is 5-pyrimidinyl. In some embodiments, Ring A1 is 3-pyridyl. In some embodiments, Ring A1 is 4-pyrazolyl.

In some embodiments of Formula (I-A),

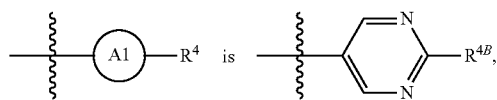

wherein: $R^{4B}$ is selected from —$NR^A R^B$ and 4-6 membered heterocyclyl comprising one nitrogen ring member and optionally substituted with 1-2 independently selected $R^{G1}$; wherein $R^{G1}$ is selected from fluoro, hydroxyl, and C1-C6 alkyl.

In some embodiments of Formula (I-A), $R^A$ and $R^B$ are each hydrogen.

In some embodiments of Formula (I-A), $R^A$ and $R^B$ are each 4-6 membered heterocyclyl. In some embodiments of Formula (I-A), one of $R^A$ and $R^B$ is hydrogen and the other of $R^A$ and $R^B$ is 4-6 membered heterocyclyl. In some embodiments of Formula (I-A), one of $R^A$ and $R^B$ is hydrogen and the other of $R^A$ and $R^B$ is 4 membered heterocyclyl. In some embodiments of Formula (I-A), one of $R^A$ and $R^B$ is hydrogen and the other of $R^A$ and $R^B$ is 5 membered heterocyclyl. In some embodiments of Formula (I-A), one of $R^A$ and $R^B$ is hydrogen and the other of $R^A$ and $R^B$ is 1,1-dioxidotetrahydrothiophen-3-yl. In some embodiments of Formula (I-A), one of $R^A$ and $R^B$ is hydrogen and the other of $R^A$ and $R^B$ is 6 membered heterocyclyl.

In some embodiments of Formula (I-A), $R^A$ and $R^B$ are each C1-C6 haloalkyl. In some embodiments of Formula (I-A), one of $R^A$ and $R^B$ is hydrogen and the other of $R^A$ and $R^B$ is C1-C6 haloalkyl. In some embodiments of Formula (I-A), one of $R^A$ and $R^B$ is hydrogen and the other of $R^A$ and $R^B$ is C1-C3 haloalkyl. In some embodiments of Formula (I-A), one of $R^A$ and $R^B$ is C1-C6 alkyl and the other of $R^A$ and $R^B$ is C1-C6 haloalkyl.

In some embodiments of Formula (I-A), $R^A$ and $R^B$ are each 3-6 membered cycloalkyl optionally substituted with hydroxyl. In some embodiments of Formula (I-A), one of $R^A$ and $R^B$ is hydrogen and the other of $R^A$ and $R^B$ is 3-6 membered cycloalkyl optionally substituted with hydroxyl. In some embodiments of Formula (I-A), one of $R^A$ and $R^B$ is hydrogen and the other of $R^A$ and $R^B$ is 3-6 membered cycloalkyl substituted with hydroxyl. In some embodiments of Formula (I-A), one of $R^A$ and $R^B$ is hydrogen and the other of $R^A$ and $R^B$ is unsubstituted 3-6 membered cycloalkyl. In some embodiments of Formula (I-A), one of $R^A$ and $R^B$ is hydrogen and the other of $R^A$ and $R^B$ is 3 membered cycloalkyl optionally substituted with hydroxyl. In some embodiments of Formula (I-A), one of $R^A$ and $R^B$ is hydrogen and the other of $R^A$ and $R^B$ is 4 membered cycloalkyl optionally substituted with hydroxyl. In some embodiments of Formula (I-A), one of $R^A$ and $R^B$ is hydrogen and the other of $R^A$ and $R^B$ is cis- or trans-3-hydroxycyclobutyl. In some embodiments of Formula (I-A), one of $R^A$ and $R^B$ is hydrogen and the other of $R^A$ and $R^B$ is 5 membered cycloalkyl optionally substituted with hydroxyl. In some embodiments of Formula (I-A), one of $R^A$ and $R^B$ is hydrogen and the other of $R^A$ and $R^B$ is 6 membered cycloalkyl optionally substituted with hydroxyl. In some embodiments of Formula (I-A), one of $R^A$ and $R^B$ is C1-C6 alkyl and the other of $R^A$ and $R^B$ is 3-6 membered cycloalkyl substituted with hydroxyl.

In some embodiments of Formula (I-A), one of $R^A$ and $R^B$ is hydrogen and the other of $R^A$ and $R^B$ is C1-C6 alkyl optionally substituted with 1-2 substituents independently selected from hydroxyl, 3-6 membered cycloalkyl, —$SO_2$(C1-C6 alkyl), and —$SO_2(NH_2)$. In some embodiments of Formula (I-A), one of $R^A$ and $R^B$ is hydrogen and the other of $R^A$ and $R^B$ is C1-C6 alkyl optionally substituted with hydroxyl In some embodiments of Formula (I-A), one of $R^A$ and $R^B$ is hydrogen and the other of $R^A$ and $R^B$ is C1-C6 alkyl substituted with hydroxyl. In some embodiments of Formula (I-A), one of $R^A$ and $R^B$ is hydrogen and the other of $R^A$ and $R^B$ is C1-C6 alkyl. In some embodiments of Formula (I-A), one of $R^A$ and $R^B$ is hydrogen and the other of $R^A$ and $R^B$ is C1-C3 alkyl optionally substituted with hydroxyl. In some embodiments of Formula (I-A), one of $R^A$ and $R^B$ is hydrogen and the other of $R^A$ and $R^B$ is C1-C3 alkyl substituted with hydroxyl. In some embodiments of Formula (I-A), one of $R^A$ and $R^B$ is hydrogen and the other of $R^A$ and $R^B$ is ethyl substituted with hydroxyl (e.g., 2-hydroxy-1-propyl. In some embodiments of Formula (I-A), one of $R^A$ and $R^B$ is hydrogen and the other of $R^A$ and $R^B$ is propyl substituted with hydroxyl (e.g., 2-hydroxylpropyl or 1-hydroxy-2-propyl). In some embodiments of Formula (I-A), one of $R^A$ and $R^B$ is hydrogen and the other of $R^A$ and $R^B$ is C1-C3 alkyl. In some embodiments of Formula (I-A), one of $R^A$ and $R^B$ is hydrogen and the other of $R^A$ and $R^B$ is methyl.

In some embodiments of Formula (I-A), $R^A$ and $R^B$ are each C1-C6 alkyl optionally substituted with hydroxyl. In some embodiments of Formula (I-A), $R^A$ and $R^B$ are each C1-C6 alkyl substituted with hydroxyl. In some embodiments of Formula (I-A), one of $R^A$ and $R^B$ is C1-C3 alkyl and the other of $R^A$ and $R^B$ is C1-C3 alkyl substituted with hydroxyl. In some embodiments of Formula (I-A), one of $R^A$ and $R^B$ is methyl and the other of $R^A$ and $R^B$ is C1-C3 alkyl substituted with hydroxyl. In some embodiments of Formula (I-A), one of $R^A$ and $R^B$ is methyl and the other of $R^A$ and $R^B$ is ethyl substituted with hydroxyl (e.g., 2-hydroxy-1-propyl). In some embodiments of Formula (I-A), $R^A$ and $R^B$ are each C1-C6 alkyl. In some embodiments of Formula (I-A), $R^A$ and $R^B$ are each C1-C3 alkyl. In some embodiments of Formula (I-A), $R^A$ and $R^B$ are each methyl.

In some embodiments of Formula (I-A), one of $R^A$ and $R^B$ is hydrogen and the other of $R^A$ and $R^B$ is C1-C6 alkyl substituted with 3-6 membered cycloalkyl. In some embodiments of Formula (I-A), one of $R^A$ and $R^B$ is hydrogen and the other of $R^A$ and $R^B$ is C1-C3 alkyl substituted with 3-6 membered cycloalkyl. In some embodiments of Formula (I-A), one of $R^A$ and $R^B$ is hydrogen and the other of $R^A$ and $R^B$ is C1-C3 alkyl substituted with 3-4 membered cycloalkyl. In some embodiments of Formula (I-A), one of $R^A$ and $R^B$ is hydrogen and the other of $R^A$ and $R^B$ is C1-C3 alkyl substituted with 3-4 membered cycloalkyl and hydroxyl. In some embodiments of Formula (I-A), one of $R^A$ and $R^B$ is hydrogen and the other of $R^A$ and $R^B$ is C1-C3 alkyl substituted with cyclopropyl and hydroxyl. In some embodiments of Formula (I-A), one of $R^A$ and $R^B$ is hydrogen and the other of $R^A$ and $R^B$ is ethyl substituted with cyclopropyl and hydroxyl, e.g., 1-cyclopropyl-2-hydroxyethyl. In some embodiments of Formula (I-A), one of $R^A$ and $R^B$ is C1-C6 alkyl and the other of $R^A$ and $R^B$ is C1-C6 alkyl substituted with 3-6 membered cycloalkyl. In some embodiments of Formula (I-A), $R^A$ and $R^B$ are both C1-C6 alkyl substituted with 3-6 membered cycloalkyl.

In some embodiments of Formula (I-A), one of $R^A$ and $R^B$ is hydrogen and the other of $R^A$ and $R^B$ is C1-C6 alkyl substituted with —SO$_2$(C1-C6 alkyl). In some embodiments of Formula (I-A), one of $R^A$ and $R^B$ is hydrogen and the other of $R^A$ and $R^B$ is C1-C3 alkyl substituted with —SO$_2$(C1-C6 alkyl). In some embodiments of Formula (I-A), one of $R^A$ and $R^B$ is hydrogen and the other of $R^A$ and $R^B$ is C1-C3 alkyl substituted with —SO$_2$(C1-C3 alkyl). In some embodiments of Formula (I-A), one of $R^A$ and $R^B$ is hydrogen and the other of $R^A$ and $R^B$ is C1-C3 alkyl substituted with —SO$_2$CH$_3$, e.g., 1-(methylsulfonyl)propan-2-yl. In some embodiments of Formula (I-A), one of $R^A$ and $R^B$ is C1-C6 alkyl and the other of $R^A$ and $R^B$ is C1-C6 alkyl substituted with —SO$_2$(C1-C6 alkyl). In some embodiments of Formula (I-A), $R^A$ and $R^B$ are both C1-C6 alkyl substituted with —SO$_2$(C1-C6 alkyl).

In some embodiments of Formula (I-A), one of $R^A$ and $R^B$ is hydrogen and the other of $R^A$ and $R^B$ is C1-C6 alkyl substituted with —SO$_2$(NH$_2$). In some embodiments of Formula (I-A), one of $R^A$ and $R^B$ is hydrogen and the other of $R^A$ and $R^B$ is C1-C3 alkyl substituted with —SO$_2$(NH$_2$), e.g., 1-sulfamoylpropan-2-yl. In some embodiments of Formula (I-A), one of $R^A$ and $R^B$ is C1-C6 alkyl hydrogen and the other of $R^A$ and $R^B$ is C1-C6 alkyl substituted with —SO$_2$(NH$_2$). In some embodiments of Formula (I-A), $R^A$ and $R^B$ are both C1-C6 alkyl substituted with —SO$_2$(NH$_2$).

In some embodiments of Formula (I-A), $R^{4B}$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

In some embodiments of Formula (I-A), $R^{4B}$ is

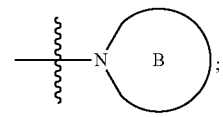

wherein Ring B is azetidinyl, pyrrolidinyl, or piperidinyl, each optionally substituted with 1-2 $R^G$ independently selected from fluoro, hydroxyl, and C1-C6 alkyl. In some embodiments of Formula (I-A), Ring B is azetidinyl.

In some embodiments of Formula (I-A), Ring B is unsubstituted.

In some embodiments of Formula (I-A), Ring B is substituted with 1 $R^G$. In some embodiments of Formula (I-A), $R^G$ is fluoro. In some embodiments of Formula (I-A), $R^G$ is cyano. In some embodiments of Formula (I-A), $R^G$ is hydroxyl. In some embodiments of Formula (I-A), $R^G$ is C1-C3 alkyl. In some embodiments of Formula (I-A), $R^G$ is methyl. In some embodiments of Formula (I-A), $R^G$ is —CO$_2$CH$_3$.

In some embodiments of Formula (I-A), Ring B is substituted with 2 independently selected $R^G$. In some embodiments of Formula (I-A), each $R^G$ is fluoro. In some embodiments of Formula (I-A), each $R^G$ is C1-C3 alkyl. In some embodiments of Formula (I-A), each $R^G$ is methyl. In some embodiments of Formula (I-A), one $R^G$ is hydroxyl and the other $R^G$ is C1-C3 alkyl. In some embodiments of Formula (I-A), one $R^G$ is hydroxyl and the other $R^G$ is methyl. In some embodiments of Formula (I-A), one $R^G$ is fluoro and the other $R^G$ is C1-C3 alkyl. In some embodiments of Formula (I-A), one $R^G$ is fluoro and the other $R^G$ is methyl. In some embodiments of Formula (I-A), one $R^G$ is hydroxyl and the other $R^G$ is fluoro. In some embodiments of Formula (I-A), one $R^G$ is hydroxyl and the other $R^G$ is trifluoromethyl.

In some embodiments of Formula (I-A),

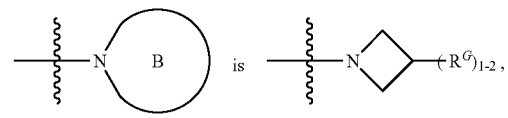

wherein 1 or 2 independently selected $R^G$ is at the 3-position of the azetidine. In some embodiments of Formula (I-A),

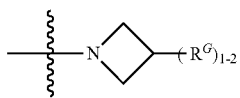

is selected from the group consisting of

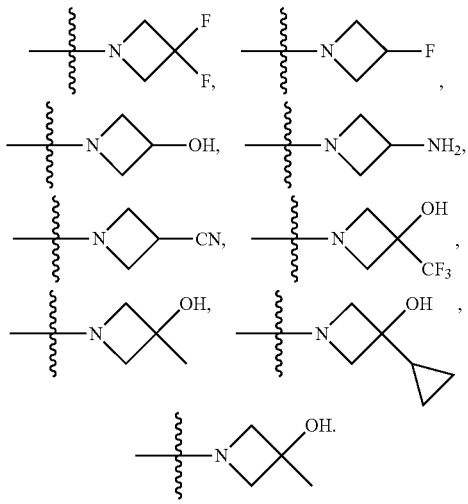

and
In some embodiments of Formula (I-A),

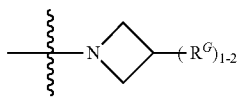

is selected from the groups consisting of

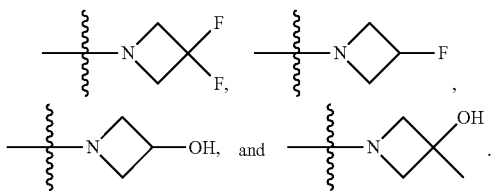

In some embodiments, the compound of Formula (I) is Formula (I-K):

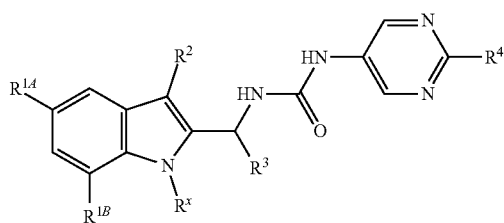

(I-K)

or a pharmaceutically acceptable salt thereof, wherein:
$R^x$ is hydrogen, C1-C6 alkyl, or C3-C6 cycloalkyl;
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 substituents independently selected from fluoro and C1-C6 alkyl;
$R^4$ is independently selected from the group consisting of: C1-C6 alkyl optionally substituted with $-NR^A R^B$, C1-C6 alkoxy, C1-C6 haloalkyl, hydroxyl, cyano, $-CO_2H$, $-NR^A R^B$, $-C(=O)NR^C R^D$, $-SO_2(NR^E R^F)$, $-SO_2(C1-C6\ alkyl)$, $-S(=O)(=NH)(C1-C6\ alkyl)$, $-C(=O)(C1-C6\ alkyl)$, $-CO_2(C1-C6\ alkyl)$, 5-6 membered heteroaryl optionally substituted with C1-C6 alkyl, 3-6 membered heterocyclyl optionally substituted with 1 or 2 independently selected $R^G$, and 3-6 membered cycloalkyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, $-SO_2(C1-C6\ alkyl)$, and $-SO_2(NH_2)$; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, $-NR^{A1}R^{B1}$, $-C(=O)NR^{C1}R^{D1}$, $-CO_2(C1-C6\ alkyl)$, C1-C6 haloalkyl, C3-C6 cycloalkyl, and $-CO_2H$.

In some embodiments, $R^{1A}$ and $R^{1B}$ are each fluoro; In some embodiments, $R^2$ is a C1-C6 alkyl. In some embodiments, $R^2$ is a C1-C3 alkyl. In some embodiments, $R^2$ is methyl.

In some embodiments, $R^2$ is a C1-C6 haloalkyl. In some embodiments, $R^2$ is a C1-C3 haloalkyl. In some embodiments, $R^2$ is a trifluoromethyl.

In some embodiments, $R^3$ is a C1-C6 alkyl. In some embodiments, $R^3$ is a C1-C3 alkyl. In some embodiments, $R^3$ is methyl, ethyl, or isopropyl. In some embodiments, $R^3$ is methyl. In some embodiments, $R^3$ is ethyl. In some embodiments, $R^3$ is isopropyl.

In some embodiments, $R^3$ is a C1-C6 haloalkyl. In some embodiments, $R^3$ is a C1-C3 haloalkyl. In some embodiments, $R^3$ is a trifluoromethyl.

In some embodiments, $R^3$ is C3-C6 cycloalkyl optionally substituted with 1 or 2 substituents independently selected from fluoro and C1-C6 alkyl. In some embodiments, $R^3$ is C3-C6 cycloalkyl optionally substituted with 1 or 2 fluoro. In some embodiments, $R^3$ is C3-C6 cycloalkyl substituted with 1 or 2 fluoro. In some embodiments, $R^3$ is unsubstituted C3-C6 cycloalkyl. In some embodiments, the $R^3$ C3-C6 cycloalkyl is cyclopropyl. In some embodiments, $R^3$ is cyclopropyl.

In some embodiments, $R^4$ is C1-C6 alkyl optionally substituted with $-NR^A R^B$. In some embodiments, $R^4$ is C1-C3 alkyl optionally substituted with $-NR^A R^B$. In some embodiments, $R^4$ is methyl optionally substituted with $-NR^A R^B$. In some embodiments, $R^4$ is C1-C4 alkyl. In some embodiments, $R^4$ is methyl.

In some embodiments, $R^4$ is C1-C6 alkoxy. In some embodiments, $R^4$ is C1-C3 alkoxy. In some embodiments, $R^4$ is methoxy.

In some embodiments, $R^4$ is C1-C6 haloalkyl. In some embodiments, $R^4$ is C1-C3 haloalkyl. In some embodiments, $R^4$ is trifluoromethyl.

In some embodiments, $R^4$ is hydroxyl. In some embodiments, $R^4$ is cyano. In some embodiments, $R^4$ is —CO$_2$H. In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl. In some embodiments, one of $R^A$ and $R^B$ is hydrogen and the other of $R^A$ and $R^B$ is propyl substituted with hydroxyl (e.g., 2-hydroxyl-propyl or 1-hydroxy-2-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, one of $R^A$ and $R^B$ is hydrogen and the other of $R^A$ and $R^B$ is C1-C6 haloalkyl. In some embodiments, $R^A$ and $R^B$ are each C1-C6 haloalkyl. In some embodiments, one of $R^A$ and $R^B$ is C1-C6 alkyl and the other of one of $R^A$ and $R^B$ is C1-C6 haloalkyl. In some embodiments, one of $R^A$ and $R^B$ is hydrogen and the other of $R^A$ and $R^B$ is C1-C3 haloalkyl. In some embodiments, one of $R^A$ and $R^B$ is C1-C6 alkyl and the other of $R^A$ and $R^B$ is C1-C6 haloalkyl.

In some embodiments, $R^A$ and $R^B$ are each 4-6 membered heterocyclyl. In some embodiments, one of $R^A$ and $R^B$ is hydrogen and the other of $R^A$ and $R^B$ is 4-6 membered heterocyclyl. In some embodiments, one of $R^A$ and $R^B$ is hydrogen and the other of $R^A$ and $R^B$ is 4 membered heterocyclyl. In some embodiments, one of $R^A$ and $R^B$ is hydrogen and the other of $R^A$ and $R^B$ is 5 membered heterocyclyl. In some embodiments of Formula (I-A), one of $R^A$ and $R^B$ is hydrogen and the other of $R^A$ and $R^B$ is 1,1-dioxidotetrahydrothiophen-3-yl. In some embodiments, one of $R^A$ and $R^B$ is hydrogen and the other of $R^A$ and $R^B$ is 6 membered heterocyclyl.

In some embodiments, $R^A$ and $R^B$ are each 3-6 membered cycloalkyl optionally substituted with hydroxyl. In some embodiments, one of $R^A$ and $R^B$ is hydrogen and the other of $R^A$ and $R^B$ is 3-6 membered cycloalkyl optionally substituted with hydroxyl. In some embodiments, one of $R^A$ and $R^B$ is hydrogen and the other of $R^A$ and $R^B$ is 3-6 membered cycloalkyl substituted with hydroxyl. In some embodiments, one of $R^A$ and $R^B$ is hydrogen and the other of $R^A$ and $R^B$ is unsubstituted 3-6 membered cycloalkyl. In some embodiments, one of $R^A$ and $R^B$ is hydrogen and the other of $R^A$ and $R^B$ is 3 membered cycloalkyl optionally substituted with hydroxyl. In some embodiments, one of $R^A$ and $R^B$ is hydrogen and the other of $R^A$ and $R^B$ is 4 membered cycloalkyl optionally substituted with hydroxyl. In some embodiments, one of $R^A$ and $R^B$ is hydrogen and the other of $R^A$ and $R^B$ is cis- or trans-3-hydroxycyclobutyl. In some embodiments, one of $R^A$ and $R^B$ is hydrogen and the other of $R^A$ and $R^B$ is 5 membered cycloalkyl optionally substituted with hydroxyl. In some embodiments, one of $R^A$ and $R^B$ is hydrogen and the other of $R^A$ and $R^B$ is 6 membered cycloalkyl optionally substituted with hydroxyl. In some embodiments, one of $R^A$ and $R^B$ is C1-C6 alkyl and the other of $R^A$ and $R^B$ is 3-6 membered cycloalkyl substituted with hydroxyl.

In some embodiments, one of $R^A$ and $R^B$ is hydrogen and the other of $R^A$ and $R^B$ is C1-C6 alkyl optionally substituted with 1-2 substituents independently selected from hydroxyl, 3-6 membered cycloalkyl, —SO$_2$(C1-C6 alkyl), and —SO$_2$(NH$_2$).

In some embodiments, one of $R^A$ and $R^B$ is hydrogen and the other of $R^A$ and $R^B$ is C1-C6 alkyl substituted with 3-6 membered cycloalkyl. In some embodiments, one of $R^A$ and $R^B$ is hydrogen and the other of $R^A$ and $R^B$ is C1-C3 alkyl substituted with 3-6 membered cycloalkyl. In some embodiments, one of $R^A$ and $R^B$ is hydrogen and the other of $R^A$ and $R^B$ is C1-C3 alkyl substituted with 3-4 membered cycloalkyl. In some embodiments, one of $R^A$ and $R^B$ is hydrogen and the other of $R^A$ and $R^B$ is C1-C3 alkyl substituted with 3-4 membered cycloalkyl and hydroxyl. In some embodiments, one of $R^A$ and $R^B$ is hydrogen and the other of $R^A$ and $R^B$ is C1-C3 alkyl substituted with cyclopropyl and hydroxyl. In some embodiments, one of $R^A$ and $R^B$ is hydrogen and the other of $R^A$ and $R^B$ is ethyl substituted with cyclopropyl and hydroxyl, e.g., 1-cyclopropyl-2-hydroxyethyl. In some embodiments, one of $R^A$ and $R^B$ is C1-C6 alkyl and the other of $R^A$ and $R^B$ is C1-C6 alkyl substituted with 3-6 membered cycloalkyl. In some embodiments, $R^A$ and $R^B$ are both C1-C6 alkyl substituted with 3-6 membered cycloalkyl.

In some embodiments, one of $R^A$ and $R^B$ is hydrogen and the other of $R^A$ and $R^B$ is C1-C6 alkyl substituted with —SO$_2$(C1-C6 alkyl). In some embodiments, one of $R^A$ and $R^B$ is hydrogen and the other of $R^A$ and $R^B$ is C1-C3 alkyl substituted with —SO$_2$(C1-C6 alkyl). In some embodiments, one of $R^A$ and $R^B$ is hydrogen and the other of $R^A$ and $R^B$ is C1-C3 alkyl substituted with —SO$_2$(C1-C3 alkyl). In some embodiments, one of $R^A$ and $R^B$ is hydrogen and the other of $R^A$ and $R^B$ is C1-C3 alkyl substituted with —SO$_2$CH$_3$, e.g., 1-(methylsulfonyl)propan-2-yl. In some embodiments, one of $R^A$ and $R^B$ is C1-C6 alkyl and the other of $R^A$ and $R^B$ is C1-C6 alkyl substituted with —SO$_2$(C1-C6 alkyl). In some embodiments, $R^A$ and $R^B$ are both C1-C6 alkyl substituted with —SO$_2$(C1-C6 alkyl). In some embodiments, one of $R^A$ and $R^B$ is hydrogen and the other of $R^A$ and $R^B$ is C1-C6 alkyl substituted with —SO$_2$(NH$_2$). In some embodiments, one of $R^A$ and $R^B$ is hydrogen and the other of $R^A$ and $R^B$ is C1-C3 alkyl substituted with —SO$_2$(NH$_2$), e.g., 1-sulfamoylpropan-2-yl. In some embodiments, one of $R^A$ and $R^B$ is C1-C6 alkyl hydrogen and the other of $R^A$ and $R^B$ is C1-C6 alkyl substituted with —SO$_2$(NH$_2$). In some embodiments, $R^A$ and $R^B$ are both C1-C6 alkyl substituted with —SO$_2$(NH$_2$).

In some embodiments, one $R^4$ is —C(=O)NR$^C$R$^D$. In some embodiments, $R^C$ and $R^D$ are each hydrogen. In some embodiments, one of $R^C$ and $R^D$ is hydrogen and the other of $R^C$ and $R^D$ is C1-C6 alkyl. In some embodiments, one of $R^C$ and $R^D$ is hydrogen and the other of $R^C$ and $R^D$ is C1-C3 alkyl. In some embodiments, one of $R^C$ and $R^D$ is hydrogen and the other of $R^C$ and $R^D$ is methyl. In some embodiments, $R^C$ and $R^D$ are each C1-C6 alkyl. In some embodiments, $R^C$ and $R^D$ are each C1-C3 alkyl. In some embodiments, $R^C$ and $R^D$ are each methyl. In some embodiments, one of $R^C$ and $R^D$ is hydrogen and the other of $R^C$ and $R^D$ is C1-C6 haloalkyl. In some embodiments, $R^C$ and $R^D$ are each is C1-C6 haloalkyl. In some embodiments, one of $R^C$ and $R^D$ is C1-C6 alkyl and the other of $R^C$ and $R^D$ is C1-C6 haloalkyl. In some embodiments, $R^C$ and $R^D$, together with the nitrogen atom to which they are attached form a 4-6 membered heterocyclyl. In some embodiments, $R^C$ and $R^D$, together with the nitrogen atom to which they are attached form azetidine or piperazine.

In some embodiments, one $R^4$ is —SO$_2$(NR$^E$R$^F$). In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is methyl. In some embodiments, $R^E$ and $R^F$ are each is C1-C6 alkyl. In some embodiments, $R^E$ and $R^F$ are each is C1-C3 alkyl. In some embodiments, $R^E$ and $R^F$ are each methyl. In some embodiments, one of $R^E$ and $R^F$ is hydrogen and the other of $R^E$ and $R^F$ is C1-C6 haloalkyl. In some embodiments, $R^E$ and $R^F$ are each C1-C6 haloalkyl. In some embodiments, one of $R^E$ and $R^F$ is C1-C6 alkyl and the other of $R^E$ and $R^F$ is C1-C6 haloalkyl.

In some embodiments, $R^4$ is —SO$_2$(C1-C6 alkyl). In some embodiments, $R^4$ is —SO$_2$(C1-C3 alkyl). In some embodiments, $R^4$ is —SO$_2$Me. In some embodiments, $R^4$ is —SO$_2$Et.

In some embodiments, $R^4$ is —S(=O)(=NH)(C1-C6 alkyl). In some embodiments, $R^4$ is —S(=O)(=NH)(C1-C4 alkyl). In some embodiments, $R^4$ is —S(=O)(=NH)Me.

In some embodiments, $R^4$ is —C(=O)(C1-C6 alkyl). In some embodiments, $R^4$ is —C(=O)(C1-C3 alkyl). In some embodiments, $R^4$ is —C(=O)Me.

In some embodiments, $R^4$ is —CO$_2$(C1-C6 alkyl). In some embodiments, $R^4$ is —CO$_2$(C1-C3 alkyl). In some embodiments, $R^4$ is —CO$_2$H.

In some embodiments, one $R^4$ is 5-6 membered heteroaryl optionally substituted with C1-C6 alkyl. In some embodiments, one $R^4$ is 5-6 membered heteroaryl substituted with C1-C6 alkyl. In some embodiments, $R^4$ is 5-6 membered heteroaryl. In some embodiments, $R^4$ is selected from the group consisting of pyrrolyl, pyrazolyl, imidazolyl, triazolyl, tetrazolyl, furanyl, thiophenyl, oxazolyl, isoxazolyl, isothiazolyl, thiazolyl, furanyl, oxadiazolyl, thiadiazolyl, oxatriazolyl, and thiatriazolyl, pyridinyl, pyrimidinyl, pyrazinyl, pyridazinyl, and triazinyl. In some embodiments, $R^4$ is pyrazolyl. In some embodiments, one $R^4$ is tetrazolyl substituted with methyl. In some embodiments, one $R^4$ is pyrazolyl. In some embodiments, one $R^4$ is unsubstituted pyrazolyl. In some embodiments, one $R^4$ is 1-pyrazolyl.

In some embodiments, $R^4$ is 3-6 membered heterocyclyl optionally substituted with 1 or 2 independently selected $R^G$. In some embodiments, $R^4$ is 3-6 membered heterocyclyl substituted with 1 or 2 independently selected $R^G$. In some embodiments, $R^4$ is 3-6 membered heterocyclyl substituted with 1 $R^G$. In some embodiments, $R^4$ is 3-6 membered heterocyclyl substituted with 2 independently selected $R^G$.

In some embodiments, $R^G$ is fluoro. In some embodiments, $R^G$ is cyano. In some embodiments, $R^G$ is hydroxyl.

In some embodiments, $R^G$ is C1-C6 alkyl. In some embodiments, $R^G$ is C1-C3 alkyl. In some embodiments, $R^G$ is methyl.

In some embodiments, $R^G$ is C1-C6 alkoxy. In some embodiments, $R^G$ is C1-C3 alkoxy. In some embodiments, $R^G$ is methoxy.

In some embodiments, one $R^G$ is —NR$^{A1}$R$^{B1}$. In some embodiments, $R^{A1}$ and $R^{B1}$ are each hydrogen. In some embodiments, one of $R^{A1}$ and $R^{B1}$ is hydrogen and the other of $R^{A1}$ and $R^{B1}$ is C1-C6 alkyl. In some embodiments, one of $R^{A1}$ and $R^{B1}$ is hydrogen and the other of $R^{A1}$ and $R^{B1}$ is C1-C3 alkyl. In some embodiments, one of $R^{A1}$ and $R^{B1}$ is hydrogen and the other of $R^{A1}$ and $R^{B1}$ is methyl. In some embodiments, $R^{A1}$ and $R^{B1}$ are each C1-C6 alkyl. In some embodiments, $R^{A1}$ and $R^{B1}$ are each C1-C3 alkyl. In some embodiments, $R^{A1}$ and $R^{B1}$ are each methyl.

In some embodiments, one of $R^{A1}$ and $R^{B1}$ is hydrogen and the other of $R^{A1}$ and $R^{B1}$ is C1-C6 haloalkyl. In some embodiments, $R^{A1}$ and $R^{B1}$ are each C1-C6 haloalkyl. In some embodiments, one of $R^{A1}$ and $R^{B1}$ is C1-C6 alkyl and the other of $R^{A1}$ and $R^{B1}$ is C1-C6 haloalkyl.

In some embodiments, one $R^G$ is —C(=O)NR$^{C1}$R$^{D1}$. In some embodiments, $R^{C1}$ and $R^{D1}$ are each is hydrogen. In some embodiments, one of $R^{C1}$ and $R^{D1}$ is hydrogen and the other of $R^{C1}$ and $R^{D1}$ is C1-C6 alkyl. In some embodiments, one of $R^{C1}$ and $R^{D1}$ is hydrogen and the other of $R^{C1}$ and $R^{D1}$ is C1-C3 alkyl. In some embodiments, one of $R^{C1}$ and $R^{D1}$ is hydrogen and the other of $R^{C1}$ and $R^{D1}$ is methyl. In some embodiments, $R^{C1}$ and $R^{D1}$ are each is C1-C6 alkyl. In some embodiments, $R^{C1}$ and $R^{D1}$ are each is methyl. In some embodiments, one of $R^{C1}$ and $R^{D1}$ is hydrogen and the other of $R^{C1}$ and $R^{D1}$ is C1-C6 haloalkyl. In some embodiments, $R^{C1}$ and $R^{D1}$ are each is C1-C6 haloalkyl. In some embodiments, one of $R^{C1}$ and $R^{D1}$ is C1-C6 alkyl and the other of $R^{C1}$ and $R^{D1}$ is C1-C6 haloalkyl.

In some embodiments, one $R^G$ is —CO$_2$(C1-C6 alkyl). In some embodiments, one $R^G$ is —CO$_2$CH$_3$.

In some embodiments, one $R^G$ is C1-C6 haloalkyl. In some embodiments, one $R^G$ is trifluoromethyl.

In some embodiments, one $R^G$ is C3-C6 cycloalkyl. In some embodiments, one $R^G$ is cyclopropyl.

In some embodiments, $R^G$ is —CO$_2$H.

In some embodiments, the $R^4$ 3-6 membered heterocyclyl is a 5-6 membered heterocyclyl. In some embodiments, the $R^4$ 3-6 membered heterocyclyl is azetidinyl, azetidin-2-onyl, morpholinyl, piperazinyl, or tetrahydropyranyl. In some embodiments, the $R^4$ 3-6 membered heterocyclyl is 1-azetidinyl, 1-azetidin-2-onyl, 1-piperazinyl, 1-morpholinyl, or 4-tetrahydropyranyl.

In some embodiments, $R^4$ is unsubstituted 3-6 membered heterocyclyl. In some embodiments, $R^4$ is a 5-6 membered heterocyclyl. In some embodiments, $R^4$ is azetidinyl, morpholinyl, or tetrahydropyranyl. In some embodiments, $R^4$ is selected from the group consisting of

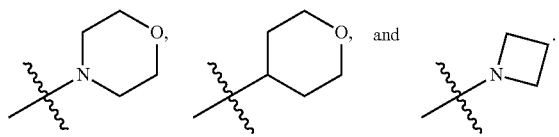 [SMILES: *N1CCOCC1 ; *C1CCOCC1 ; *N1CCC1]

In some embodiments, $R^4$ is selected from —NR$^A$R$^B$ and 4-6 membered heterocyclyl comprising one nitrogen ring member and optionally substituted with 1-2 independently selected $R^{G1}$; wherein $R^{G1}$ is selected from fluoro, hydroxyl, and C1-C6 alkyl.

In some embodiments, $R^A$ and $R^B$ are each hydrogen. In some embodiments, one of $R^A$ and $R^B$ is hydrogen and the other of $R^A$ and $R^B$ is C1-C6 alkyl optionally substituted with hydroxyl. In some embodiments, one of $R^A$ and $R^B$ is hydrogen and the other of $R^A$ and $R^B$ is C1-C6 alkyl substituted with hydroxyl. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is C1-C3 alkyl optionally substituted with hydroxyl. In some embodiments, one of $R^A$ and $R^B$ is hydrogen and the other of $R^A$ and $R^B$ is C1-C3 alkyl substituted with hydroxyl. In some embodiments, one of $R^A$ and $R^B$ is hydrogen and the other of $R^A$ and $R^B$ is ethyl substituted with hydroxyl (e.g., 2-hydroxy-1-propyl. In some embodiments, one of $R^A$ and $R^B$ is hydrogen and the other of $R^A$ and $R^B$ is propyl substituted with hydroxyl (e.g., 2-hydroxyl-propyl or 1-hydroxy-2-propyl). In some embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, $R^A$ and $R^B$ are each C1-C6 alkyl optionally substituted with hydroxyl. In some embodiments, $R^A$ and $R^B$ are each C1-C6 alkyl substituted with hydroxyl. In some embodiments, one of $R^A$ and $R^B$ is C1-C3 alkyl and the other of $R^A$ and $R^B$ is C1-C3 alkyl substituted with hydroxyl. In some embodiments, one of $R^A$ and $R^B$ is methyl and the other of $R^A$ and $R^B$ is C1-C3 alkyl substituted with hydroxyl. In some embodiments, one of $R^A$ and $R^B$ is methyl and the other of $R^A$ and $R^B$ is ethyl substituted with hydroxyl (e.g., 2-hydroxy-1-propyl). In some embodiments, $R^A$ and $R^B$ are each C1-C6 alkyl. In some embodiments, $R^A$ and $R^B$ are each C1-C3 alkyl. In some embodiments, $R^A$ and $R^B$ are each methyl.

In some embodiments, $R^4$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

In some embodiments, the compound of Formula (I) is Formula (I-L):

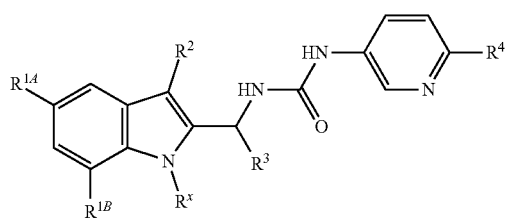

(I-L)

or a pharmaceutically acceptable salt thereof, wherein:
$R^x$ is hydrogen, C1-C6 alkyl, or C3-C6 cycloalkyl;
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —$CO_2H$, —$NR^AR^B$, —C(═O)$NR^C R^D$, —$SO_2(NR^ER^F)$, —$SO_2$(C1-C6 alkyl), —S(═O)(═NH)(C1-C6 alkyl), —C(═O)(C1-C6 alkyl), —$CO_2$(C1-C6 alkyl), 5-6 membered heteroaryl, and 3-6 membered heterocyclyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
$R^C$ and $R^D$, together with the nitrogen atom to which they are attached form a 4-6 membered heterocyclyl;
each $R^G$ is independently selected from the group consisting of: fluoro, hydroxyl, C1-C6 alkyl, C1-C6 alkoxy, —$NR^{A1}R^{B1}$, —C(═O)$NR^{C1}R^{D1}$ and —$CO_2H$.

In some embodiments, the compound of Formula (I) is Formula (I-M):

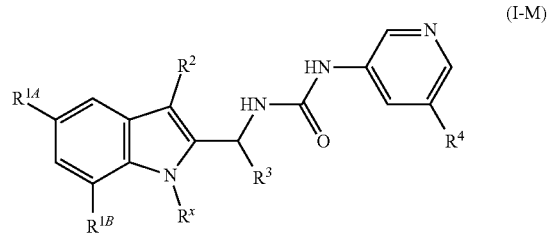

(I-M)

or a pharmaceutically acceptable salt thereof, wherein:
$R^x$ is hydrogen, C1-C6 alkyl, or C3-C6 cycloalkyl;
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 fluoro;
$R^4$ is independently selected from the group consisting of: C1-C6 alkyl, C1-C6 alkoxy, C1-C6 haloalkyl, hydroxyl, cyano, —$CO_2H$, —$NR^AR^B$, —C(═O)$NR^C R^D$, —$SO_2(NR^ER^F)$, —$SO_2$(C1-C6 alkyl), —S(═O)(═NH)(C1-C6 alkyl), —C(═O)(C1-C6 alkyl), —$CO_2$(C1-C6 alkyl), 5-6 membered heteroaryl, and 3-6 membered heterocyclyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl, C1-C6 haloalkyl; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —$NR^{A1}R^{B1}$, —C(═O)$NR^{C1}R^{D1}$, —$CO_2$(C1-C6 alkyl), C1-C6 haloalkyl, C3-C6 cycloalkyl, and —$CO_2H$.

In some embodiments, the compound of Formula (I) is Formula (I-N):

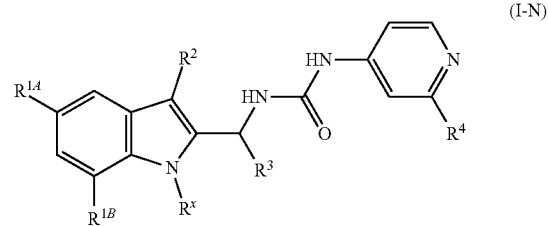

(I-N)

or a pharmaceutically acceptable salt thereof, wherein:
  $R^x$ is hydrogen, C1-C6 alkyl, or C3-C6 cycloalkyl;
  $R^{1A}$ is halogen;
  $R^{1B}$ is halogen or absent (the phenyl ring is monosubstituted with $R^{1A}$);
  $R^2$ is a C1-C6 alkyl or a C1-C6 haloalkyl;
  $R^3$ is a C1-C6 alkyl, a C1-C6 haloalkyl, or a C3-C6 cycloalkyl optionally substituted with 1 or 2 fluoro;
  $R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(=O)NR$^C$R$^D$, —SO$_2$(NR$^E$R$^F$), —SO$_2$(C1-C6 alkyl), —S(=O)(=NH)(C1-C6 alkyl), —C(=O)(C1-C6 alkyl), —CO$_2$(C1-C6 alkyl), 5-6 membered heteroaryl, and 3-6 membered heterocyclyl optionally substituted with 1 or 2 independently selected $R^G$;
  each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
  $R^C$ and $R^D$, together with the nitrogen atom to which they are attached form a 4-6 membered heterocyclyl;
  each $R^G$ is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-O):

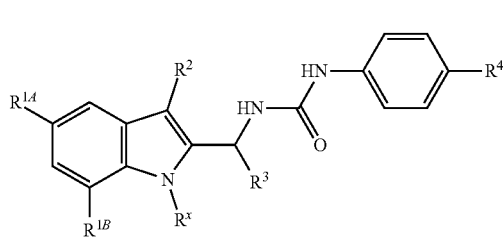

(I-O)

or a pharmaceutically acceptable salt thereof, wherein:
  $R^x$ is hydrogen, C1-C6 alkyl, or C3-C6 cycloalkyl;
  $R^{1A}$ is halogen;
  $R^{1B}$ is halogen or absent (the phenyl ring is monosubstituted with $R^{1A}$);
  $R^2$ is a C1-C6 alkyl or a C1-C6 haloalkyl;
  $R^3$ is a C1-C6 alkyl, a C1-C6 haloalkyl, or a C3-C6 cycloalkyl optionally substituted with 1 or 2 fluoro;
  $R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(=O)NR$^C$R$^D$, —SO$_2$(NR$^E$R$^F$), —SO$_2$(C1-C6 alkyl), —S(=O)(=NH)(C1-C6 alkyl), —C(=O)(C1-C6 alkyl), —CO$_2$(C1-C6 alkyl), 5-6 membered heteroaryl, and 3-6 membered heterocyclyl optionally substituted with 1 or 2 independently selected $R^G$;
  each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
  $R^C$ and $R^D$, together with the nitrogen atom to which they are attached form a 4-6 membered heterocyclyl;
  each $R^G$ is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-P):

(I-P)

or a pharmaceutically acceptable salt thereof, wherein:
  $R^x$ is hydrogen, C1-C6 alkyl, or C3-C6 cycloalkyl;
  $R^{1A}$ is halogen;
  $R^{1B}$ is halogen or absent (the phenyl ring is monosubstituted with $R^{1A}$);
  $R^2$ is a C1-C6 alkyl or a C1-C6 haloalkyl;
  $R^3$ is a C1-C6 alkyl, a C1-C6 haloalkyl, or a C3-C6 cycloalkyl optionally substituted with 1 or 2 fluoro;
  $R^4$ is independently selected from the group consisting of: C1-C6 alkyl, C1-C6 alkoxy, C1-C6 haloalkyl, hydroxyl, cyano, —CO$_2$H, —NR$^A$R$^B$, —C(=O)NR$^C$R$^D$, —SO$_2$(NR$^E$R$^F$), —SO$_2$(C1-C6 alkyl), —S(=O)(=NH)(C1-C6 alkyl), —C(=O)(C1-C6 alkyl), —CO$_2$(C1-C6 alkyl), 5-6 membered heteroaryl, and 3-6 membered heterocyclyl optionally substituted with 1 or 2 independently selected $R^G$;
  each $R^A$, $R^{A1}$, $R^B$, $R^{B1}$, $R^C$, $R^{C1}$, $R^D$, $R^{D1}$, $R^E$, and $R^F$ is independently hydrogen or C1-C6 alkyl optionally substituted with hydroxyl, C1-C6 haloalkyl; or
  $R^C$ and $R^D$, together with the nitrogen atom to which they are attached form a 4-6 membered heterocyclyl;
  each $R^G$ is independently selected from the group consisting of: fluoro, cyano, hydroxyl, C1-C6 alkyl, C1-C6 alkoxy, —NR$^{A1}$R$^{B1}$, —C(=O)NR$^{C1}$R$^{D1}$, —CO$_2$(C1-C6 alkyl), C1-C6 haloalkyl, C3-C6 cycloalkyl, and —CO$_2$H.

In some embodiments, the compound of Formula (I) is Formula (I-Q):

(I-Q)

or a pharmaceutically acceptable salt thereof, wherein:
  $R^x$ is hydrogen, C1-C6 alkyl, or C3-C6 cycloalkyl;
  $R^{1A}$ is halogen;
  $R^{1B}$ is halogen, cyano, cyclopropyl, or absent (the phenyl ring is monosubstituted with RIA);
  $R^2$ is a C1-C6 alkyl or C1-C6 haloalkyl;
  $R^3$ is a C1-C6 alkyl or a C1-C6 haloalkyl;
  $R^4$ is independently selected from the group consisting of: C1-C6 alkyl, C1-C6 alkoxy optionally substituted with 1-2 substituents independently selected from hydroxyl and C3-C6 cycloalkyl, C1-C6 haloalkyl, —NR$^A$R$^B$, and 3-9 membered heterocyclyl optionally substituted with 1 or 2 independently selected $R^G$;

each $R^A$, $R^B$, $R^{C1}$, and $R^{D1}$ is independently hydrogen, 4-6 membered heterocyclyl, C1-C6 alkyl optionally substituted with hydroxyl or —C(=O)NR$^{B2}$R$^{C2}$, —C(=O)O(C1-C6 alkyl), or C1-C6 haloalkyl;

each $R^{A2}$, $R^{B2}$, and $R^{C2}$ is independently hydrogen or C1-C6 alkyl;

each $R^G$ is independently selected from the group consisting of: fluoro, hydroxyl, C1-C6 alkyl optionally substituted with hydroxyl, C1-C6 alkoxy, =NR$^{A2}$, —C(=O)NR$^{C1}$R$^{D1}$, C1-C6 haloalkoxy, —SO$_2$(C1-C6 alkyl), and —CO$_2$H.

In some embodiments, the compound of Formula (I) is

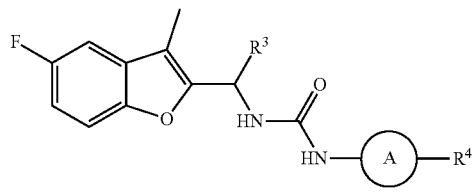

or a pharmaceutically acceptable salt thereof, wherein $R^3$, $R^4$, and Ring A are as described herein; and wherein the compound is not a compound selected from the group consisting of:

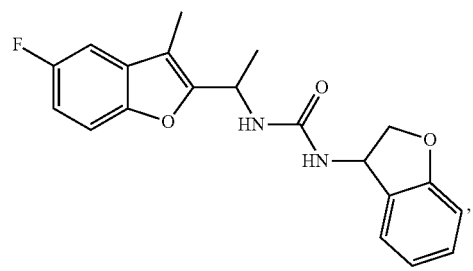

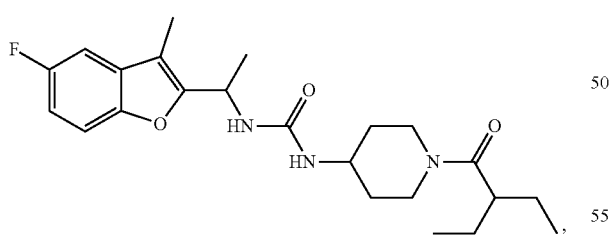

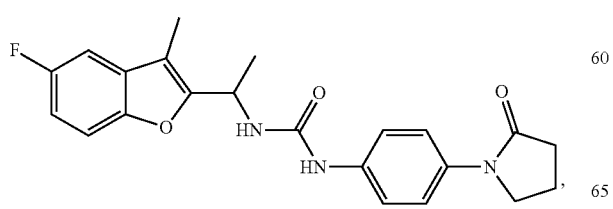

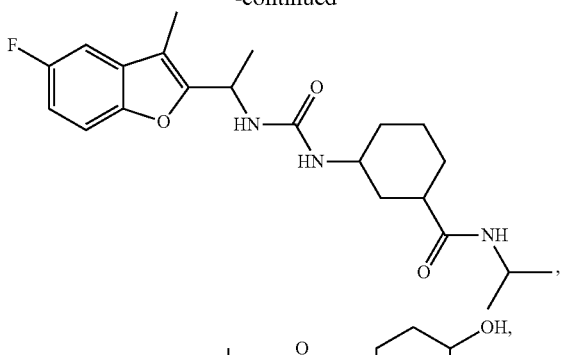

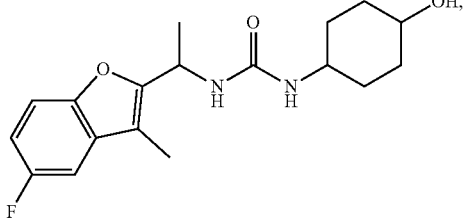

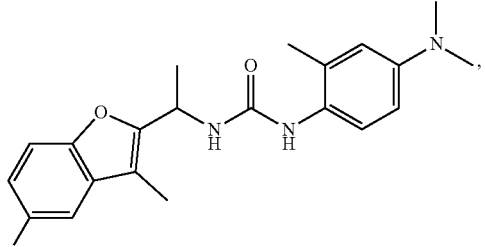

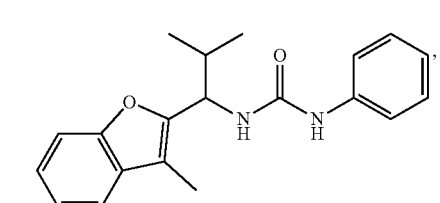

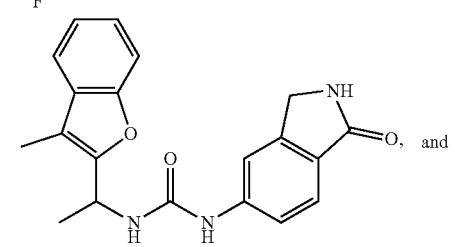

and

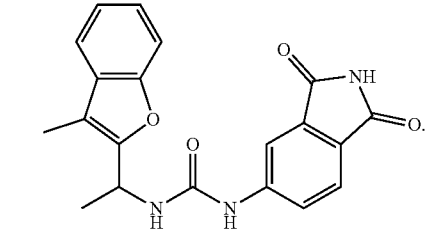

In some embodiments, the compound of Formula (I) is

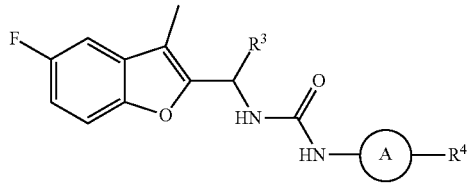

or a pharmaceutically acceptable salt thereof, wherein R³, R⁴, and Ring A are as described herein; and wherein the compound is not a compound selected from the group consisting of:

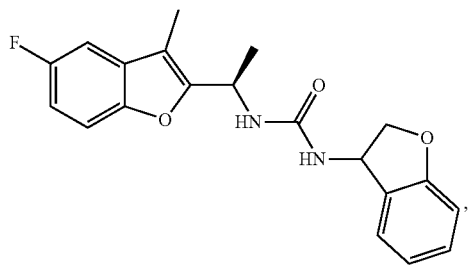

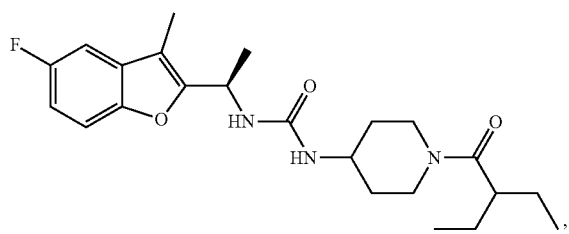

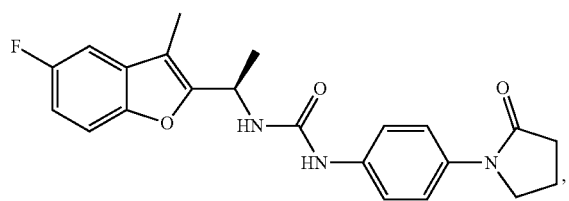

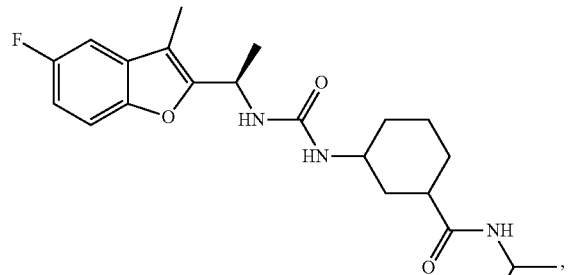

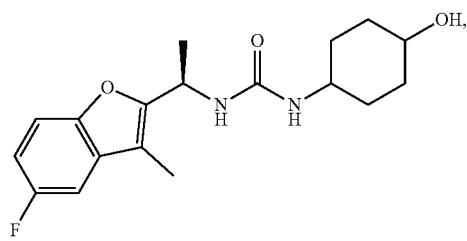

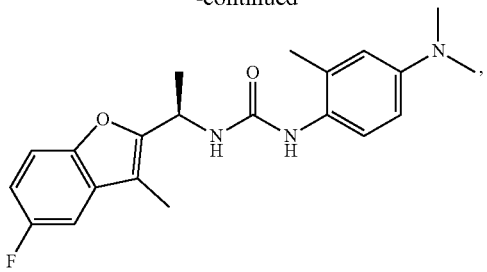

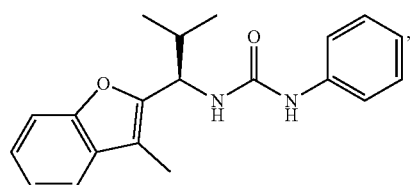

and

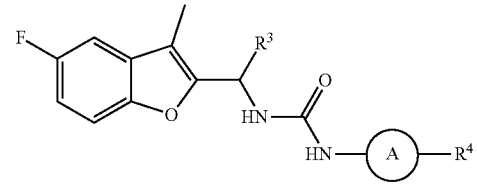

In some embodiments, the compound of Formula (I) is

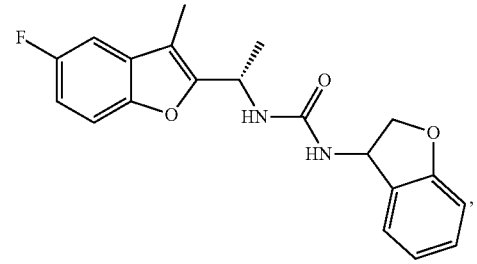

or a pharmaceutically acceptable salt thereof, wherein R³, R⁴, and Ring A are as described herein; and wherein the compound is not a compound selected from the group consisting of:

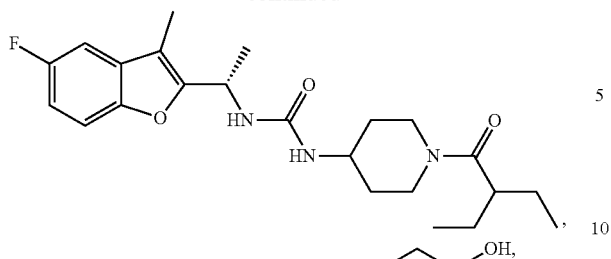

In some embodiments, the compound of Formula (I) is or a pharmaceutically acceptable salt thereof, wherein $R^3$, $R^4$, and Ring A are as described herein.

In some embodiments, the compound of Formula (I) is or a pharmaceutically acceptable salt thereof, wherein $R^3$, $R^4$, and Ring A are as described herein.

In some embodiments, the compound of Formula (I) is or a pharmaceutically acceptable salt thereof, wherein $R^3$, $R^4$, and Ring A are as described herein.

Non-Limiting Exemplary Compounds

In some embodiments, the compound is selected from the group consisting of the compounds in Examples 1-195 (e.g., Compounds 1-276), or a pharmaceutically acceptable salt thereof.

In some embodiments, the compound is selected from the group consisting of the compounds delineated in Table A, or a pharmaceutically acceptable salt thereof.

TABLE A
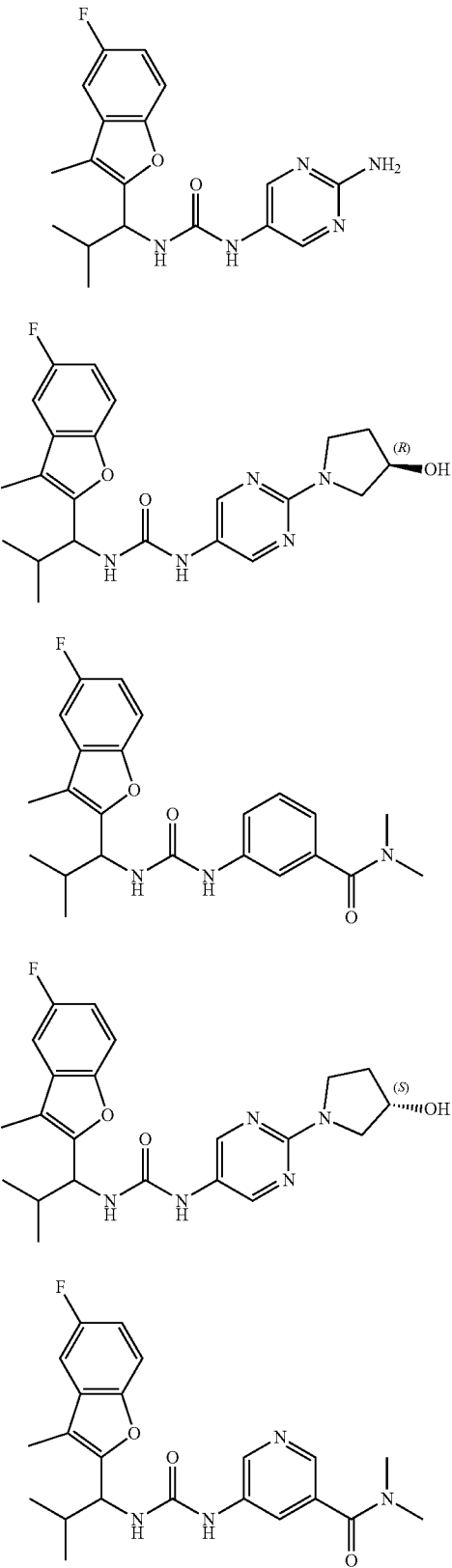
TABLE A-continued
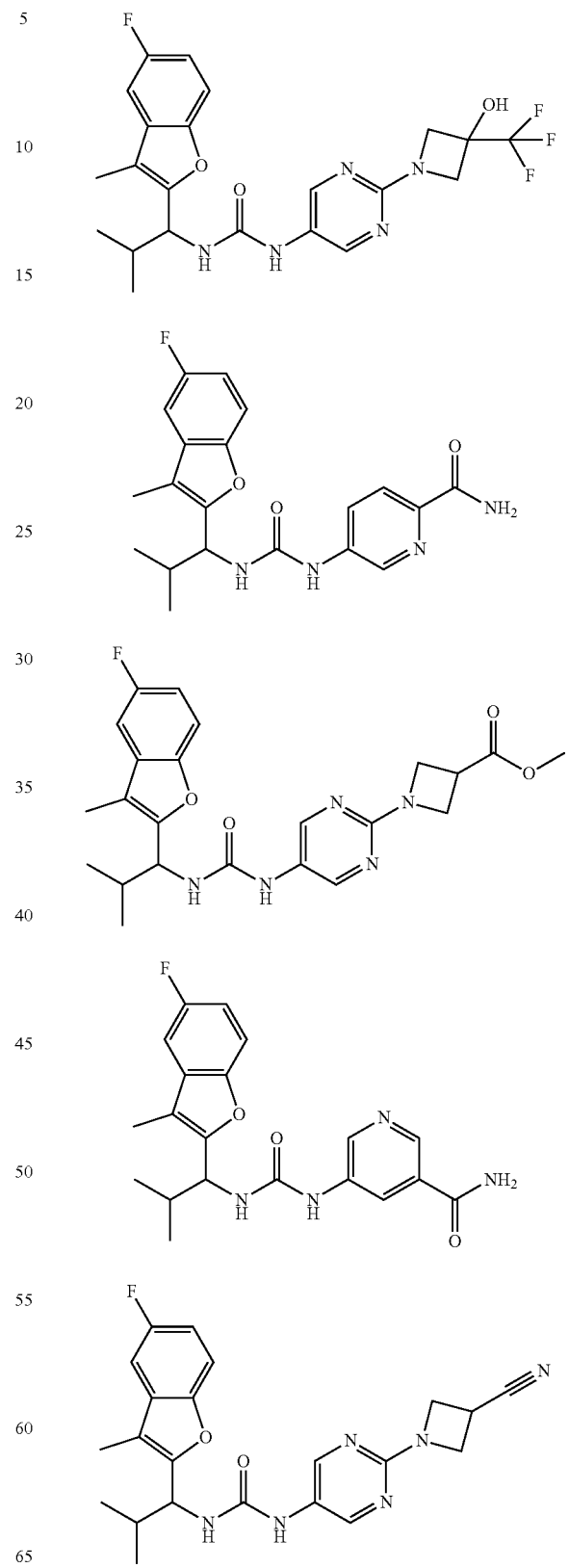

TABLE A-continued

Structure

TABLE A-continued

| Structure |
|---|
| (chemical structures) |

TABLE A-continued

Structure

TABLE A-continued

Structure

TABLE A-continued

Structure

TABLE A-continued

Structure

TABLE A-continued

Structure

TABLE A-continued

Structure

TABLE A-continued
Structure
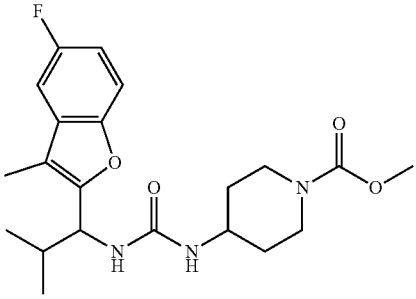
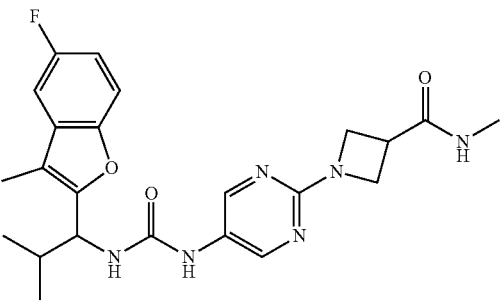
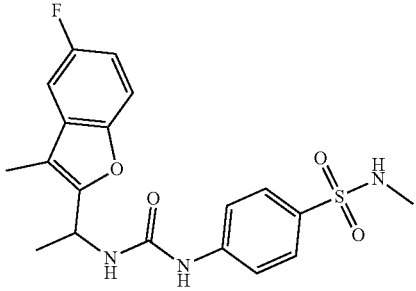
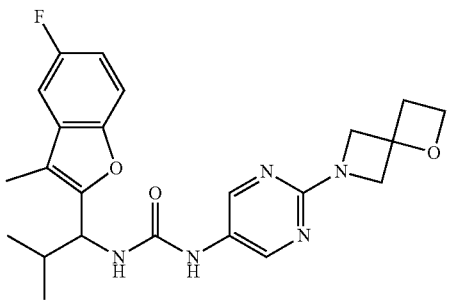 [SMILES: Cc1c(C(NC(=O)Nc2cnc(N3CC4(CCO4)C3)nc2)C(C)C)oc2ccc(F)cc12]
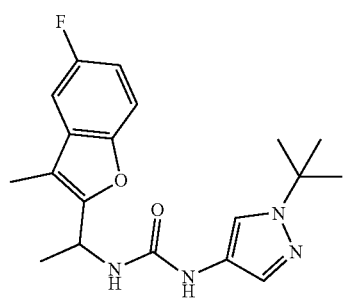 [SMILES: Cc1c(C(C)NC(=O)Nc2cnn(C(C)(C)C)c2)oc2ccc(F)cc12]
TABLE A-continued
Structure
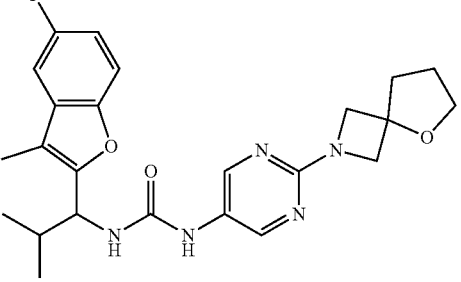
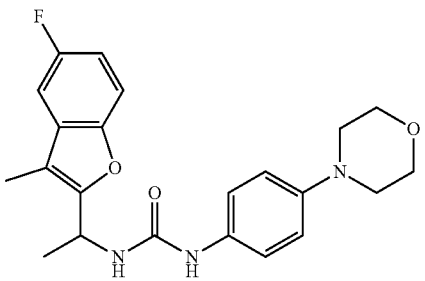 [SMILES: Cc1c(C(C)NC(=O)Nc2ccc(N3CCOCC3)cc2)oc2ccc(F)cc12]
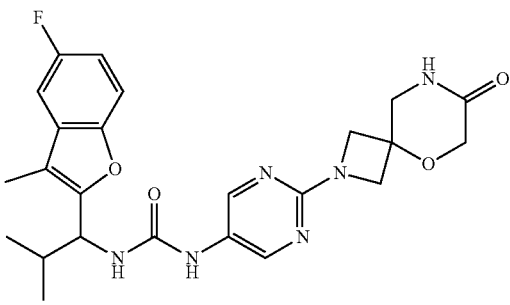 [SMILES: Cc1c(C(NC(=O)Nc2cnc(N3CC4(CNC(=O)CO4)C3)nc2)C(C)C)oc2ccc(F)cc12]
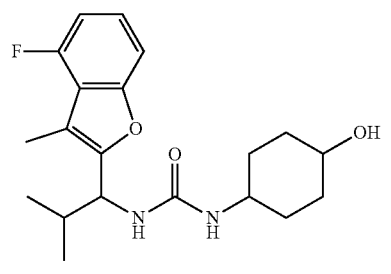 [SMILES: Cc1c(C(NC(=O)NC2CCC(O)CC2)C(C)C)oc2cccc(F)c12]
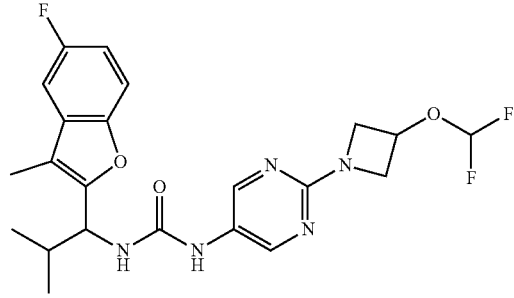 [SMILES: Cc1c(C(NC(=O)Nc2cnc(N3CC(OC(F)F)C3)nc2)C(C)C)oc2ccc(F)cc12]

TABLE A-continued
| Structure |
|---|
| 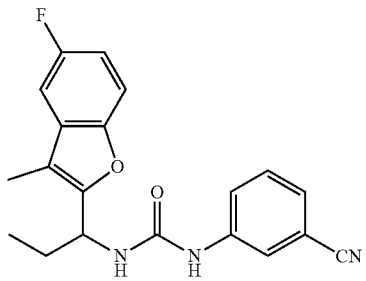 [SMILES: CCC(NC(=O)Nc1cccc(C#N)c1)c1oc2ccc(F)cc2c1C] |
| 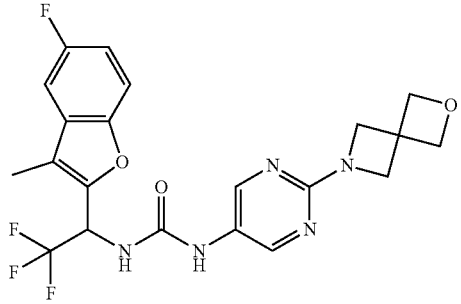 |
| 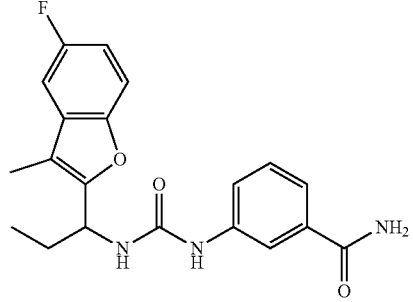 [SMILES: CCC(NC(=O)Nc1cccc(C(N)=O)c1)c1oc2ccc(F)cc2c1C] |
| 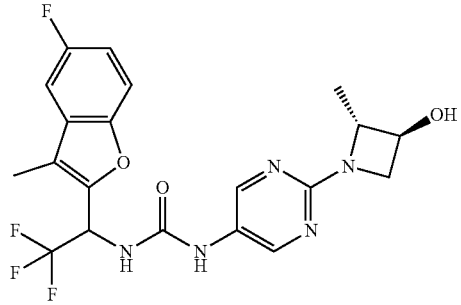 [SMILES: Cc1c(C(NC(=O)Nc2cnc(N3C[C@H](O)[C@H]3C)nc2)C(F)(F)F)oc2ccc(F)cc12] |
| 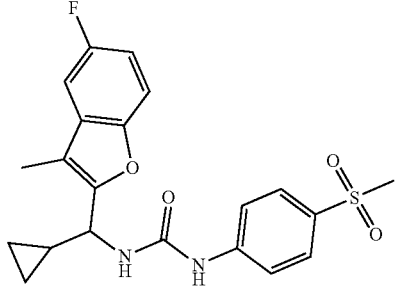 [SMILES: Cc1c(C(NC(=O)Nc2ccc(S(C)(=O)=O)cc2)C2CC2)oc2ccc(F)cc12] |
TABLE A-continued
| Structure |
|---|
| 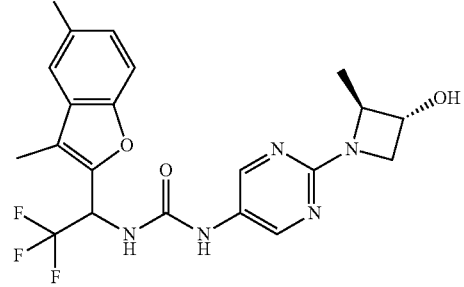 |
| 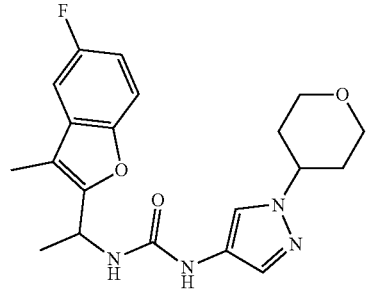 [SMILES: Cc1c(C(C)NC(=O)Nc2cnn(C3CCOCC3)c2)oc2ccc(F)cc12] |
| 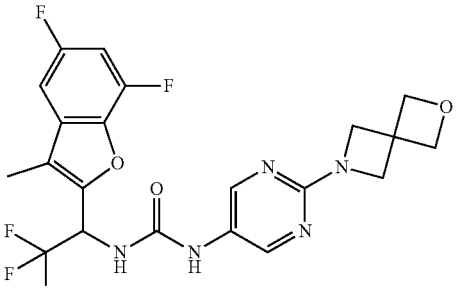 |
| 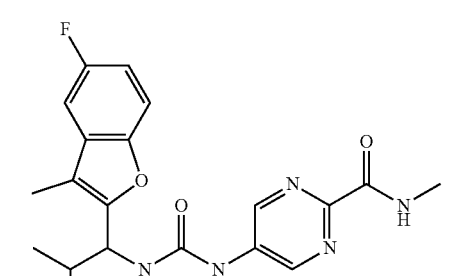 |
| 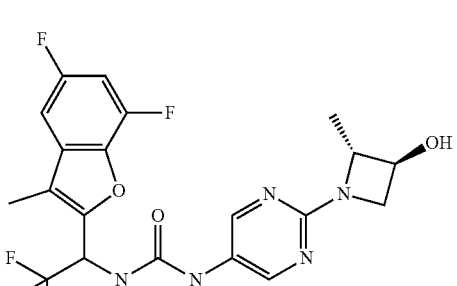 |

TABLE A-continued
Structure
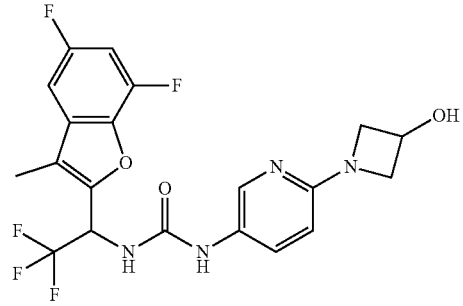 [SMILES: Cc1c(C(NC(=O)Nc2ccc(N3CC(O)C3)nc2)C(F)(F)F)oc2c(F)cc(F)cc12]

TABLE A-continued
| Structure |
|---|
| 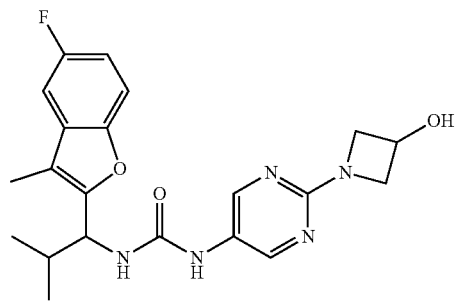 [SMILES: Cc1c(C(NC(=O)Nc2cnc(N3CC(O)C3)nc2)C(C)C)oc2ccc(F)cc12] |
| 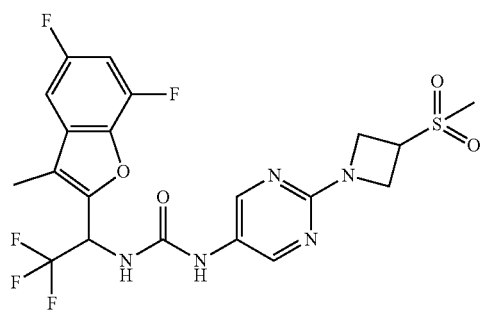 |
| 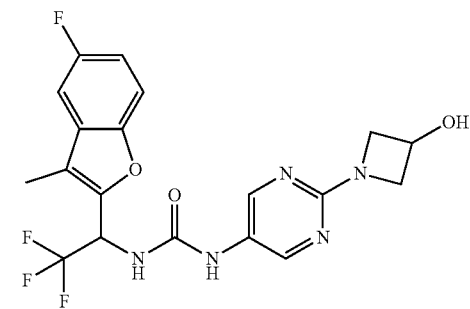 [SMILES: Cc1c(C(NC(=O)Nc2cnc(N3CC(O)C3)nc2)C(F)(F)F)oc2ccc(F)cc12] |
| 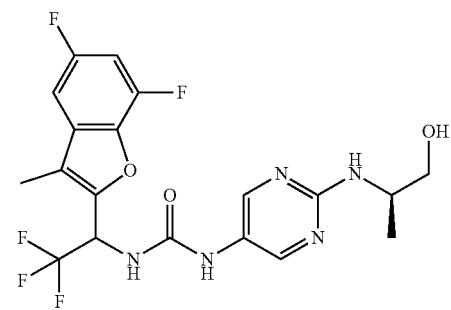 [SMILES: Cc1c(C(NC(=O)Nc2cnc(N[C@H](C)CO)nc2)C(F)(F)F)oc2c(F)cc(F)cc12] |
| 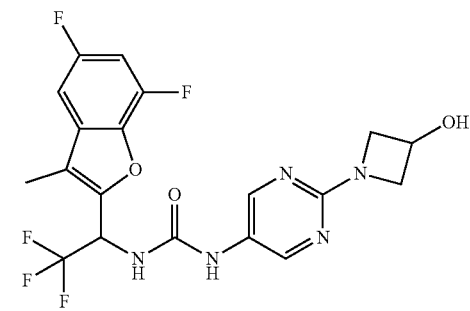 [SMILES: Cc1c(C(NC(=O)Nc2cnc(N3CC(O)C3)nc2)C(F)(F)F)oc2c(F)cc(F)cc12] |
TABLE A-continued
| Structure |
|---|
| 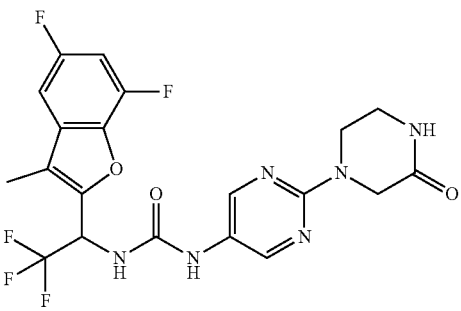 [SMILES: Cc1c(C(NC(=O)Nc2cnc(N3CCNC(=O)C3)nc2)C(F)(F)F)oc2c(F)cc(F)cc12] |
| 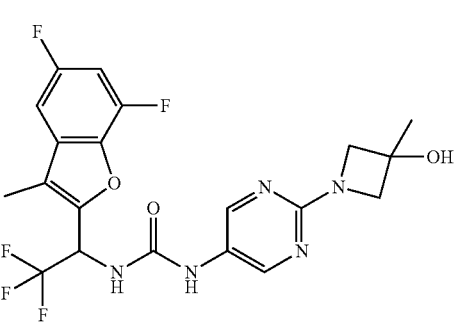 [SMILES: Cc1c(C(NC(=O)Nc2cnc(N3CC(C)(O)C3)nc2)C(F)(F)F)oc2c(F)cc(F)cc12] |
| 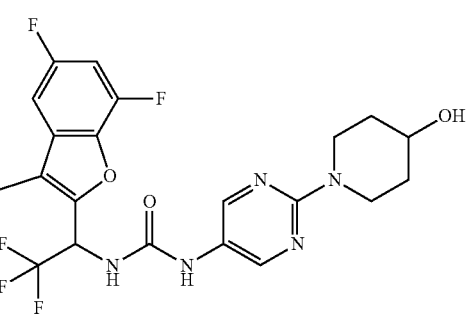 [SMILES: Cc1c(C(NC(=O)Nc2cnc(N3CCC(O)CC3)nc2)C(F)(F)F)oc2c(F)cc(F)cc12] |
| 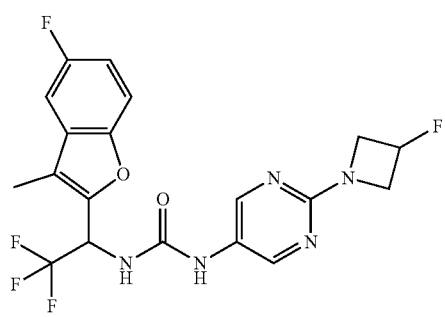 [SMILES: Cc1c(C(NC(=O)Nc2cnc(N3CC(F)C3)nc2)C(F)(F)F)oc2ccc(F)cc12] |
| 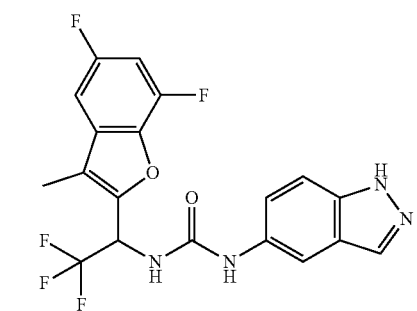 [SMILES: Cc1c(C(NC(=O)Nc2ccc3[nH]ncc3c2)C(F)(F)F)oc2c(F)cc(F)cc12] |

TABLE A-continued

Structure

311
TABLE A-continued
Structure
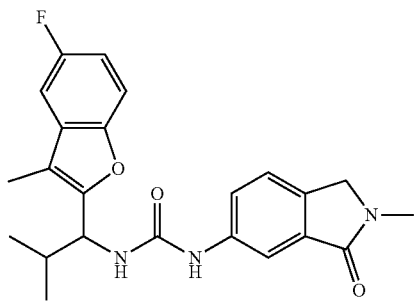
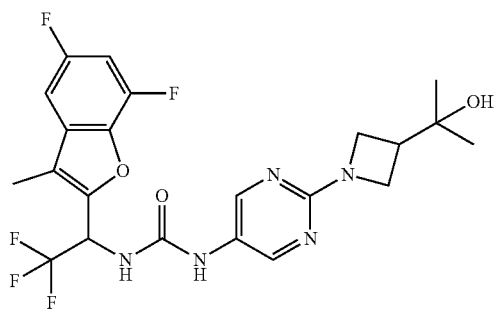 [SMILES: Cc1c(C(NC(=O)Nc2cnc(N3CC(C(C)(C)O)C3)nc2)C(F)(F)F)oc2c(F)cc(F)cc12]
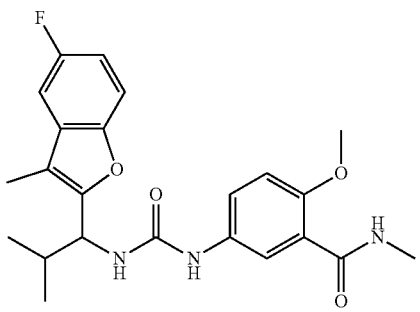
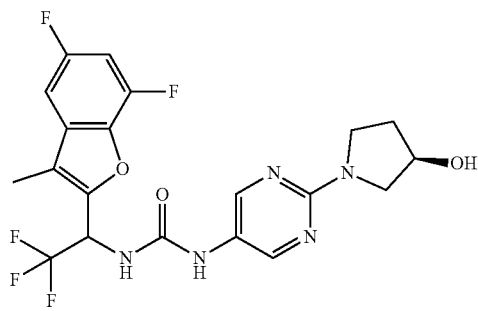 [SMILES: Cc1c(C(NC(=O)Nc2cnc(N3CC[C@@H](O)C3)nc2)C(F)(F)F)oc2c(F)cc(F)cc12]
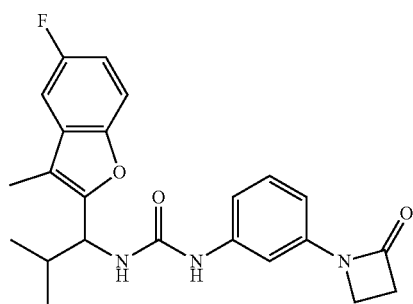 [SMILES: Cc1c(C(NC(=O)Nc2cccc(N3CCC3=O)c2)C(C)C)oc2ccc(F)cc12]
312
TABLE A-continued
Structure
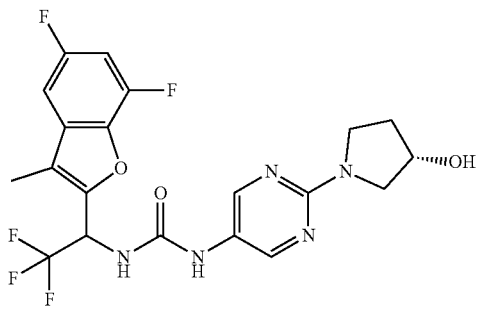 [SMILES: Cc1c(C(NC(=O)Nc2cnc(N3CC[C@H](O)C3)nc2)C(F)(F)F)oc2c(F)cc(F)cc12]
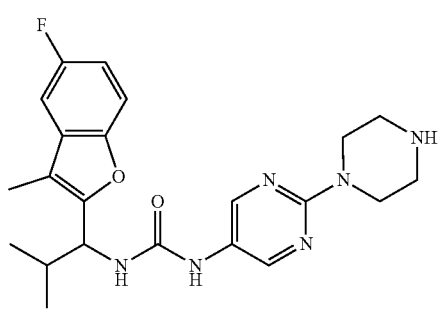 [SMILES: Cc1c(C(NC(=O)Nc2cnc(N3CCNCC3)nc2)C(C)C)oc2ccc(F)cc12]
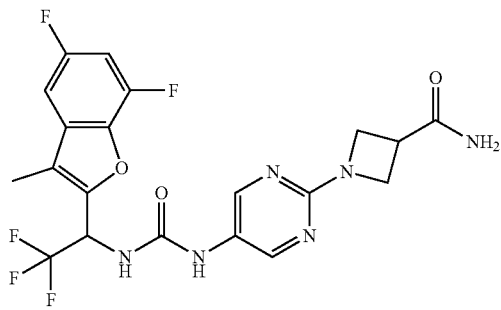
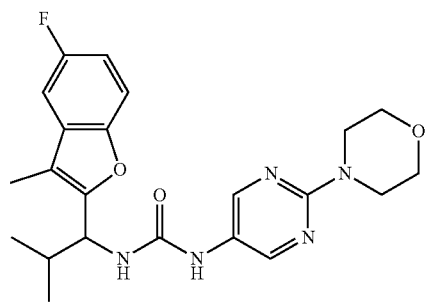 [SMILES: Cc1c(C(NC(=O)Nc2cnc(N3CCOCC3)nc2)C(C)C)oc2ccc(F)cc12]
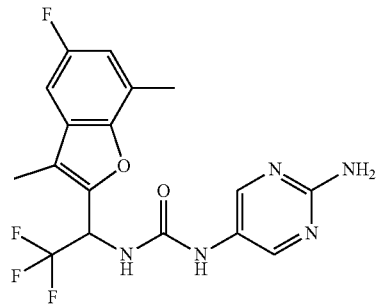 [SMILES: Cc1c(C(NC(=O)Nc2cnc(N)nc2)C(F)(F)F)oc2c(C)cc(F)cc12]

TABLE A-continued
Structure
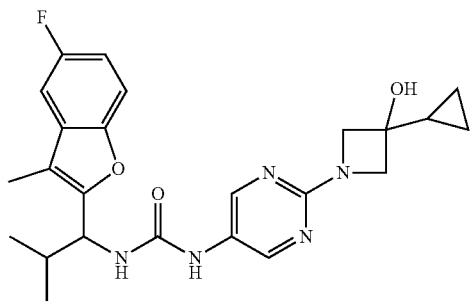 [SMILES: Cc1c(C(NC(=O)Nc2cnc(N3CC(O)(C4CC4)C3)nc2)C(C)C)oc2ccc(F)cc12]
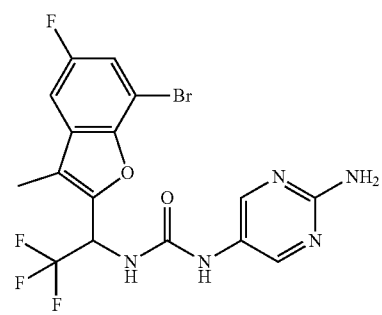
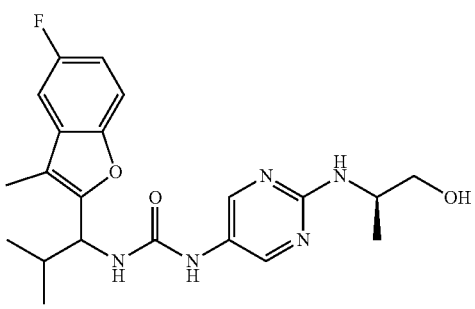 [SMILES: Cc1c(C(NC(=O)Nc2cnc(N[C@H](C)CO)nc2)C(C)C)oc2ccc(F)cc12]
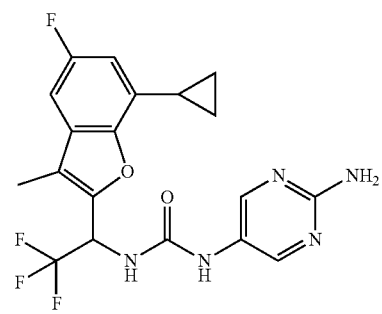 [SMILES: Cc1c(C(NC(=O)Nc2cnc(N)nc2)C(F)(F)F)oc2c(C3CC3)cc(F)cc12]
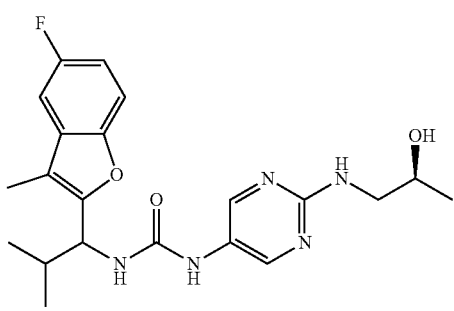 [SMILES: Cc1c(C(NC(=O)Nc2cnc(NC[C@H](C)O)nc2)C(C)C)oc2ccc(F)cc12]
TABLE A-continued
Structure
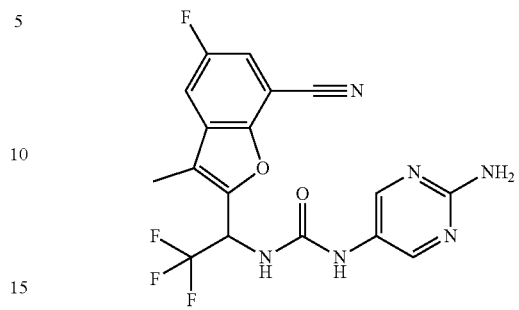
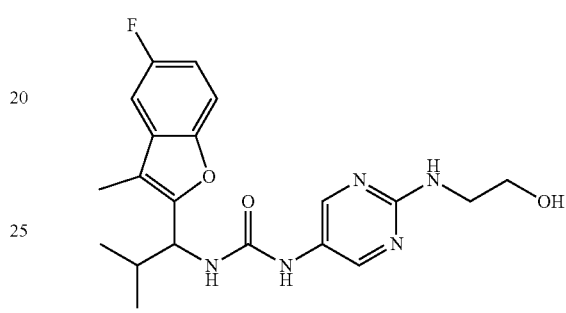
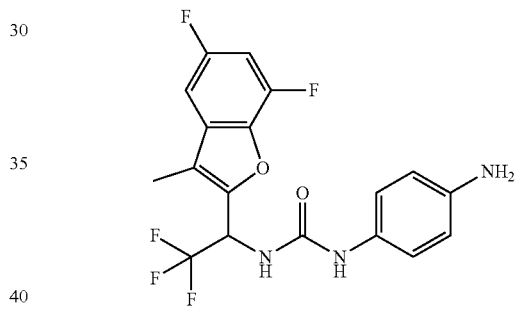
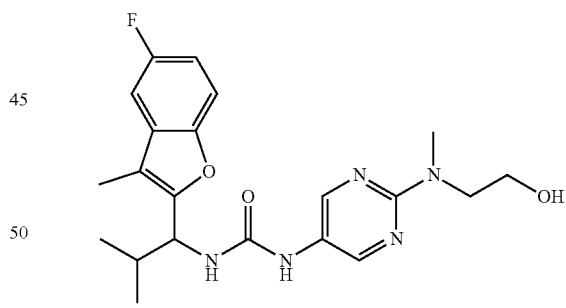
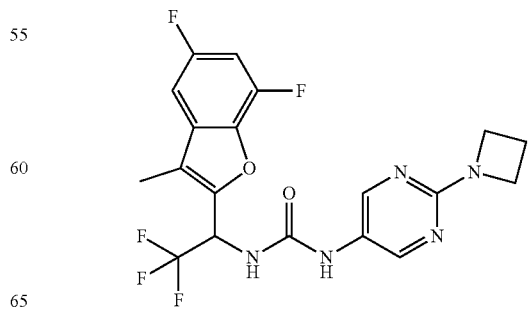

TABLE A-continued

Structure

TABLE A-continued
Structure
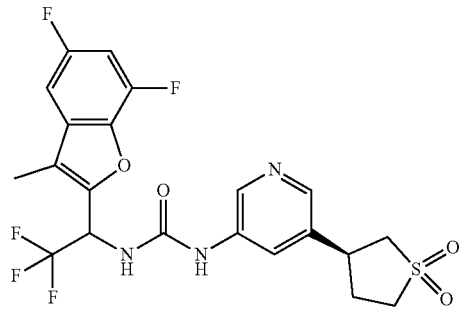 [SMILES: Cc1c(C(NC(=O)Nc2cncc([C@@H]3CCS(=O)(=O)C3)c2)C(F)(F)F)oc2c(F)cc(F)cc12]
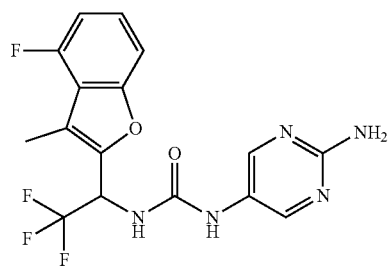 [SMILES: Cc1c(C(NC(=O)Nc2cnc(N)nc2)C(F)(F)F)oc2cccc(F)c12]
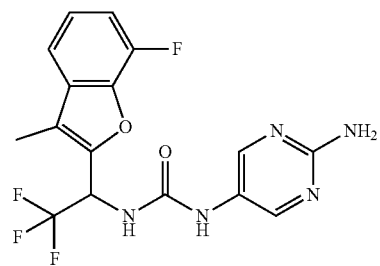 [SMILES: Cc1c(C(NC(=O)Nc2cnc(N)nc2)C(F)(F)F)oc2c(F)cccc12]
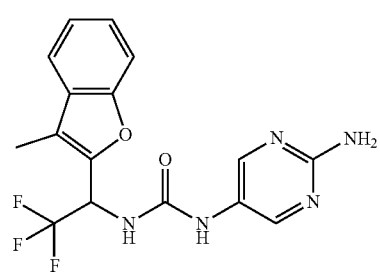
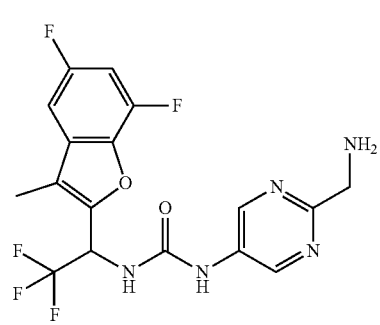 [SMILES: Cc1c(C(NC(=O)Nc2cnc(CN)nc2)C(F)(F)F)oc2c(F)cc(F)cc12]

TABLE A-continued
Structure
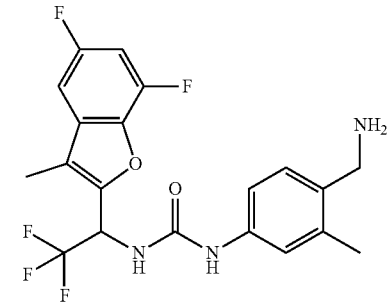 [SMILES: Cc1cc(NC(=O)NC(c2oc3c(F)cc(F)cc3c2C)C(F)(F)F)ccc1CN]
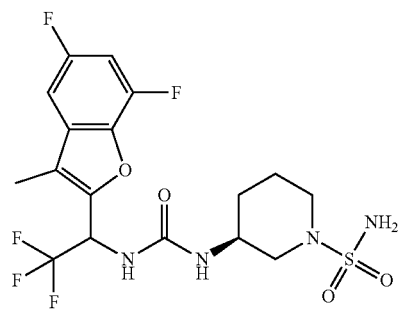
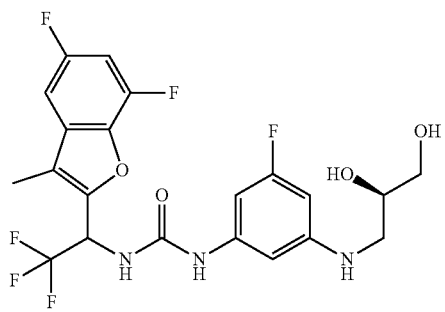 [SMILES: Cc1c(C(NC(=O)Nc2cc(F)cc(NC[C@@H](O)CO)c2)C(F)(F)F)oc2c(F)cc(F)cc12]
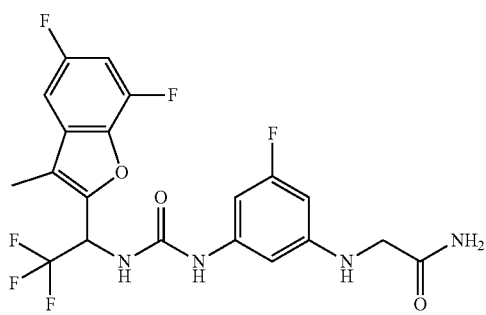
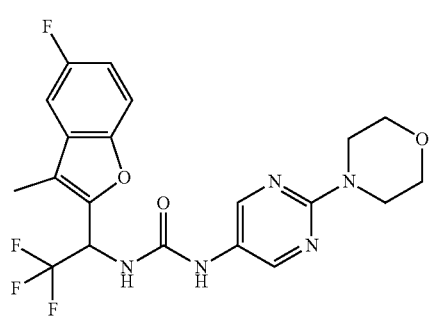 [SMILES: Cc1c(C(NC(=O)Nc2cnc(N3CCOCC3)nc2)C(F)(F)F)oc2ccc(F)cc12]
TABLE A-continued
Structure
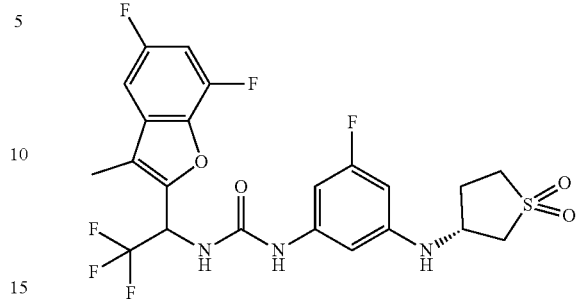
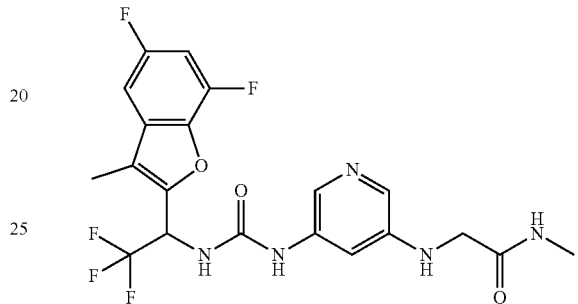
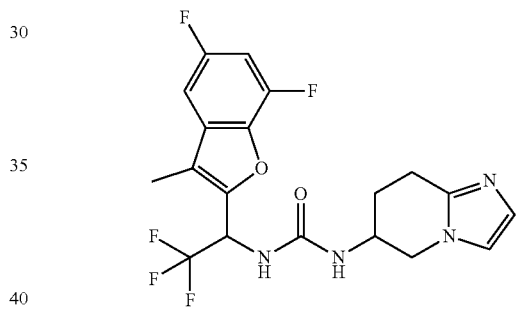
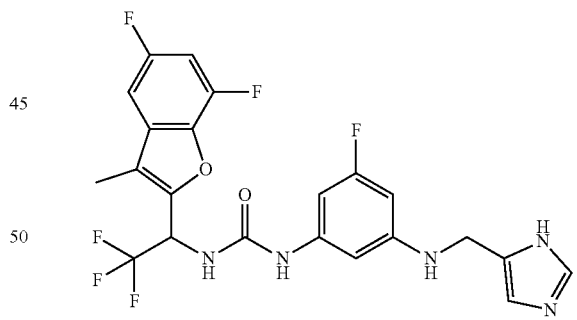
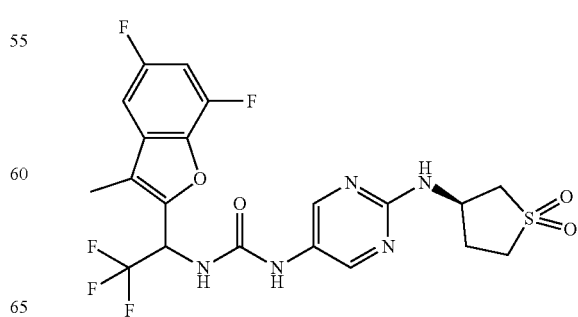

TABLE A-continued

Structure

TABLE A-continued
Structure
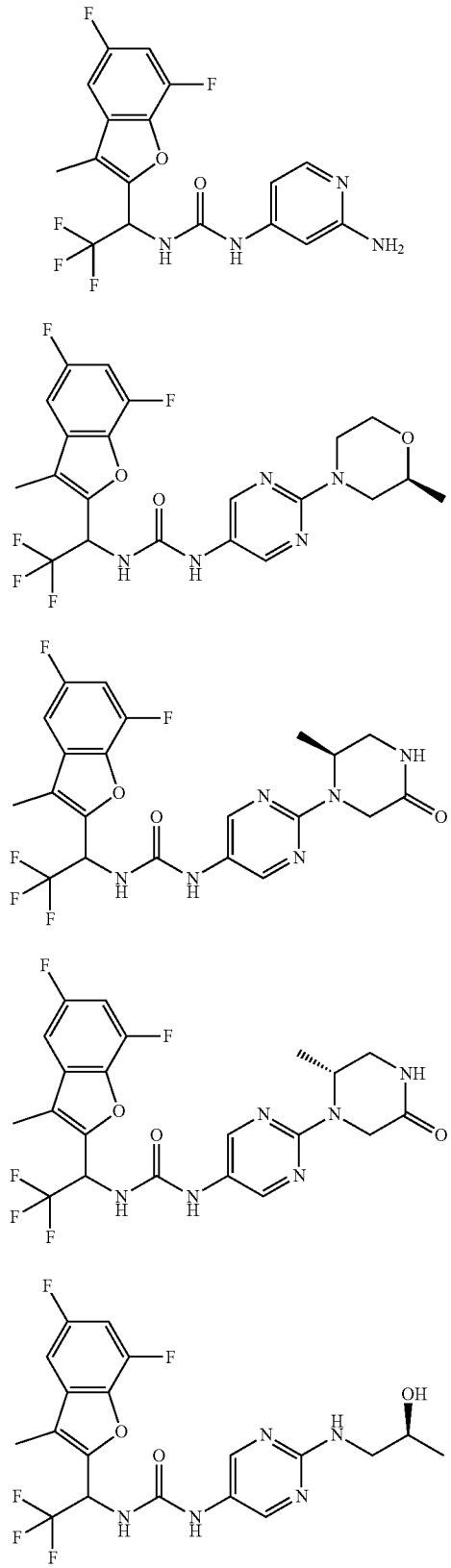
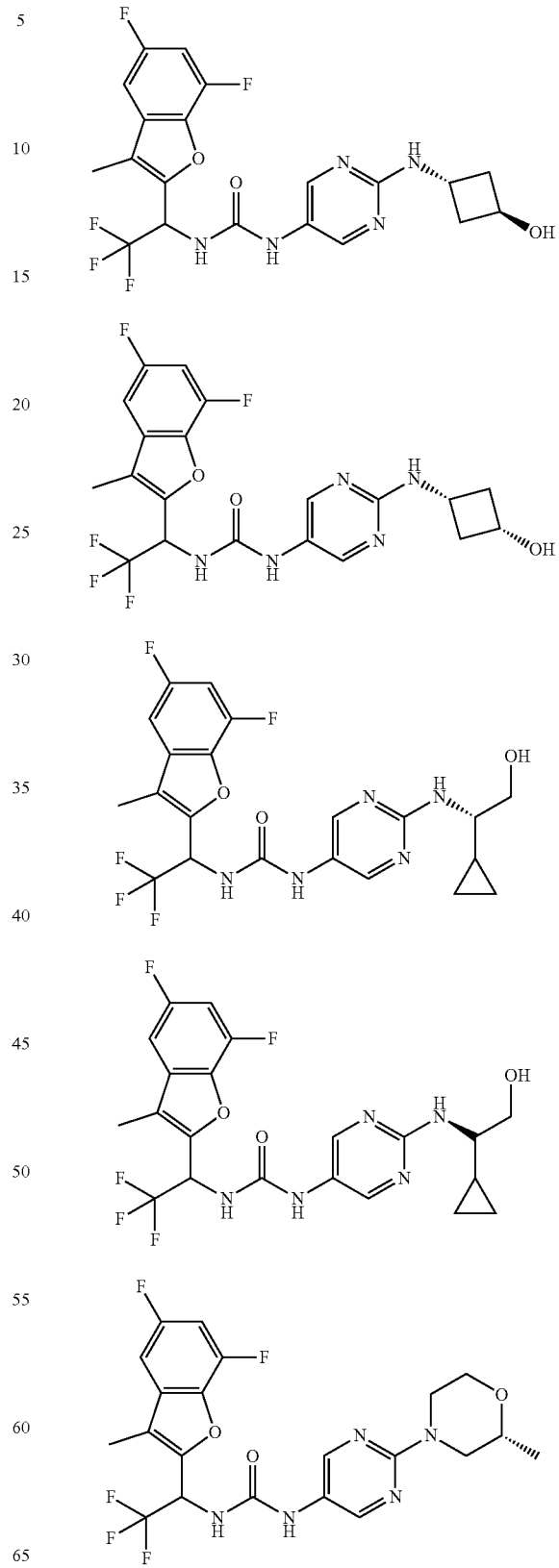

TABLE A-continued
Structure
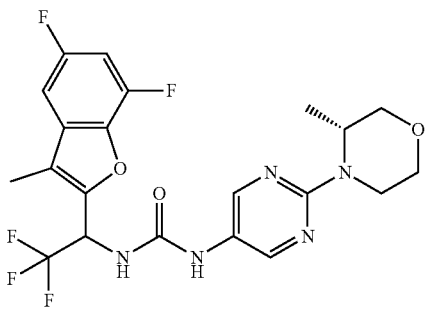
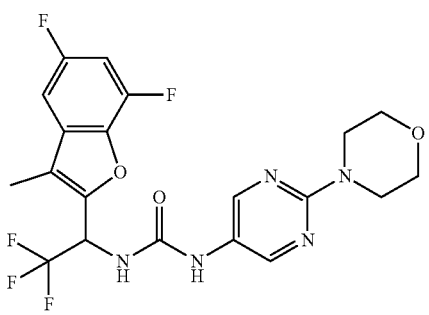
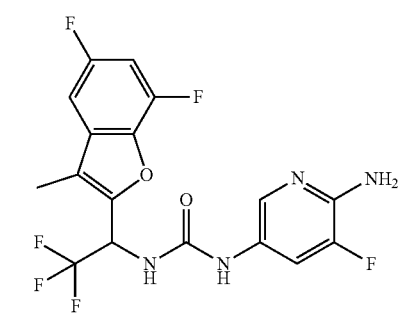 [SMILES: Cc1c(C(NC(=O)Nc2cnc(N)c(F)c2)C(F)(F)F)oc2c(F)cc(F)cc12]
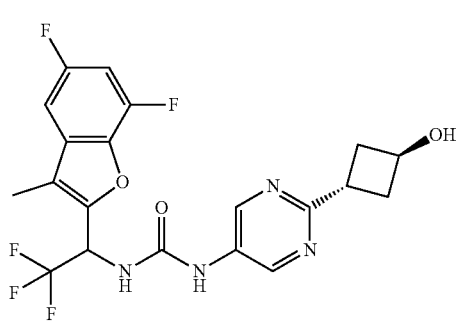
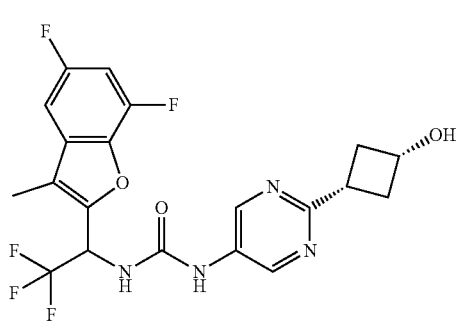
TABLE A-continued
Structure
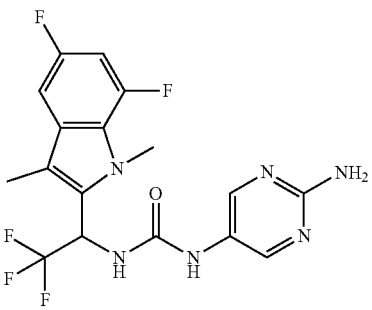
In some embodiments, the compound is selected from the group consisting of the compounds delineated in Table B, or a pharmaceutically acceptable salt thereof.
TABLE B
Structure
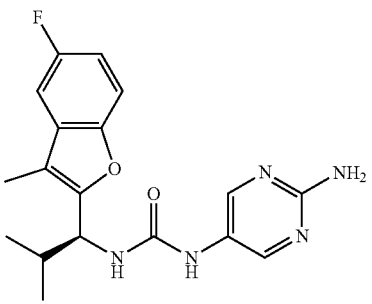 [SMILES: Cc1c([C@@H](NC(=O)Nc2cnc(N)nc2)C(C)C)oc2ccc(F)cc12]
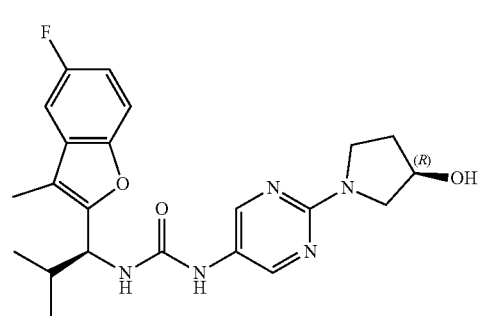
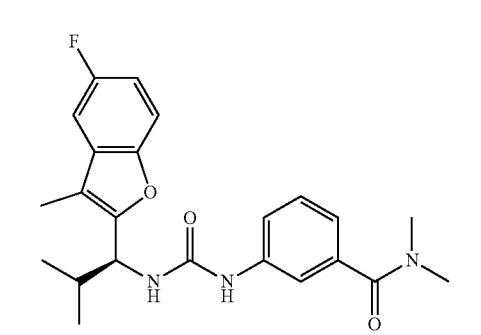

TABLE B-continued
| Structure |
|---|
| 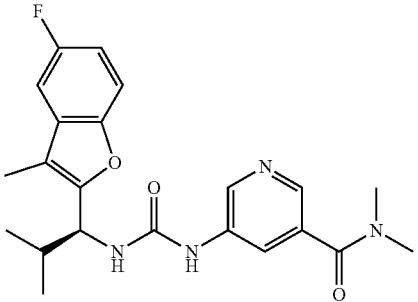 |
| 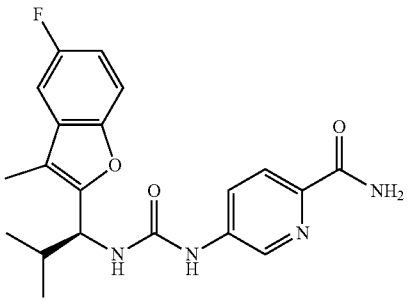 |
| 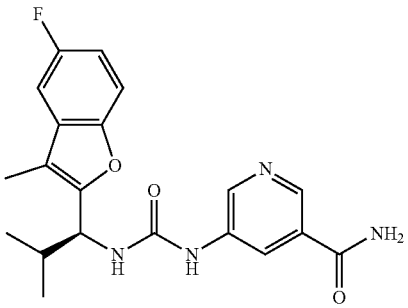 |
| 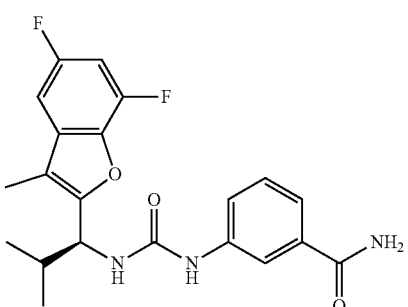 |
| 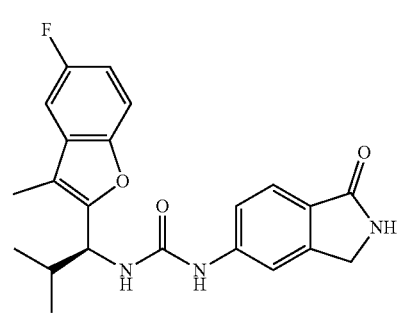 [SMILES: Cc1c([C@@H](NC(=O)Nc2ccc3c(c2)CNC3=O)C(C)C)oc2ccc(F)cc12] |
TABLE B-continued
| Structure |
|---|
| 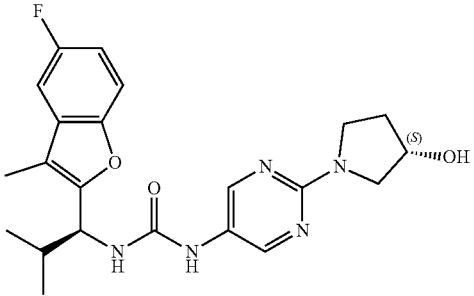 |
| 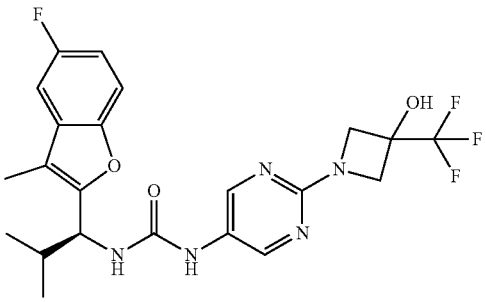 [SMILES: Cc1c([C@@H](NC(=O)Nc2cnc(N3CC(O)(C(F)(F)F)C3)nc2)C(C)C)oc2ccc(F)cc12] |
| 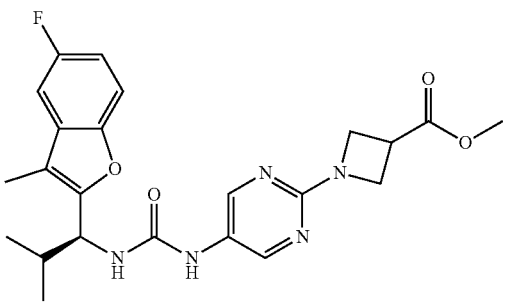 |
| 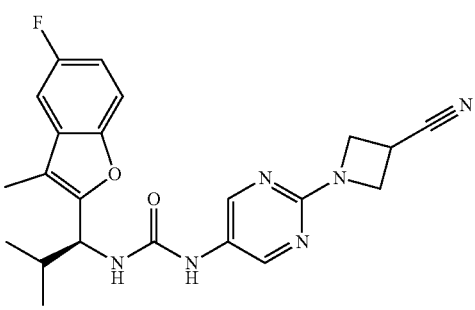 [SMILES: Cc1c([C@@H](NC(=O)Nc2cnc(N3CC(C#N)C3)nc2)C(C)C)oc2ccc(F)cc12] |
| 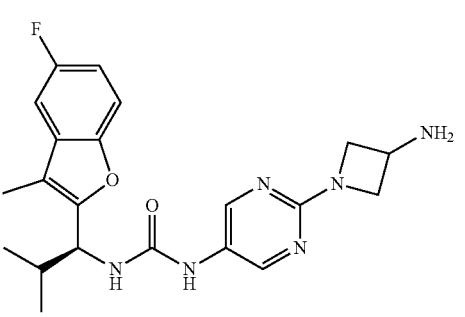 [SMILES: Cc1c([C@@H](NC(=O)Nc2cnc(N3CC(N)C3)nc2)C(C)C)oc2ccc(F)cc12] |

TABLE B-continued

Structure

TABLE B-continued
Structure
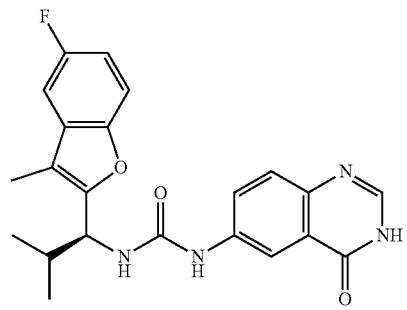 [SMILES: Cc1c([C@@H](NC(=O)Nc2ccc3nc[nH]c(=O)c3c2)C(C)C)oc2ccc(F)cc12]
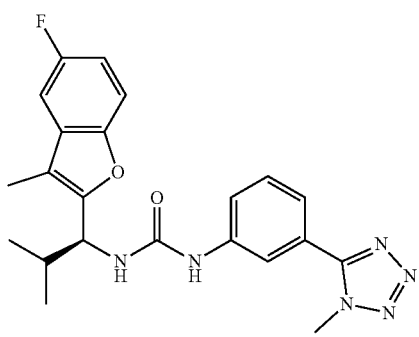 [SMILES: Cc1c([C@@H](NC(=O)Nc2cccc(-c3nnnn3C)c2)C(C)C)oc2ccc(F)cc12]
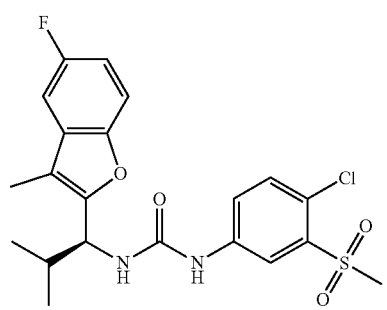
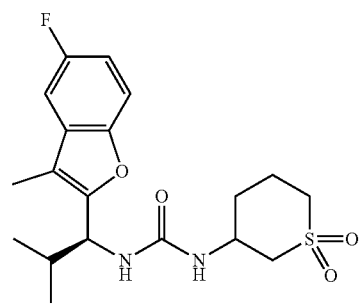 [SMILES: Cc1c([C@@H](NC(=O)NC2CCCS(=O)(=O)C2)C(C)C)oc2ccc(F)cc12]
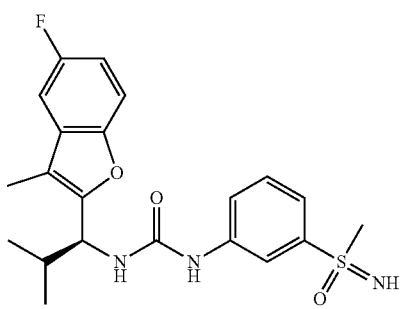 [SMILES: Cc1c([C@@H](NC(=O)Nc2cccc(S(C)(=N)=O)c2)C(C)C)oc2ccc(F)cc12]
TABLE B-continued
Structure
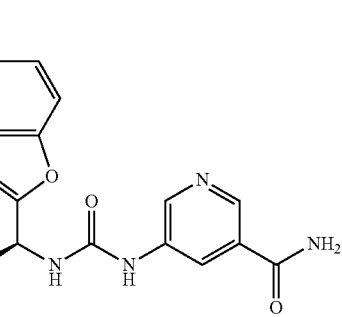
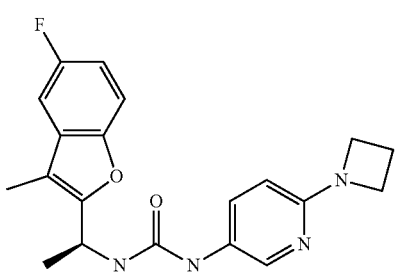
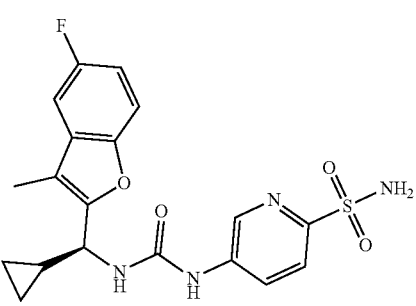 [SMILES: Cc1c([C@@H](NC(=O)Nc2ccc(S(N)(=O)=O)nc2)C2CC2)oc2ccc(F)cc12]
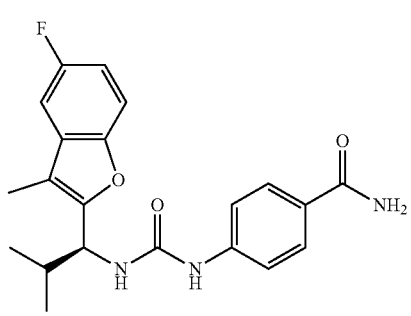 [SMILES: Cc1c([C@@H](NC(=O)Nc2ccc(C(N)=O)cc2)C(C)C)oc2ccc(F)cc12]
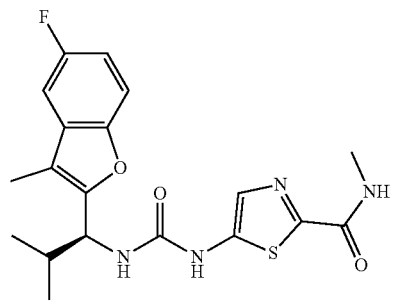 [SMILES: CNC(=O)c1ncc(NC(=O)N[C@H](c2oc3ccc(F)cc3c2C)C(C)C)s1]

TABLE B-continued

Structure

TABLE B-continued

Structure

TABLE B-continued

Structure

339

TABLE B-continued

Structure

340

TABLE B-continued

Structure

TABLE B-continued

Structure

TABLE B-continued

| Structure |
|---|

TABLE B-continued
Structure
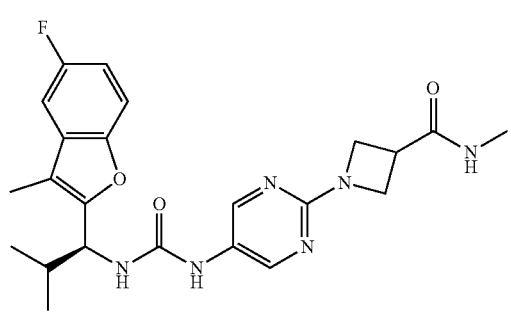
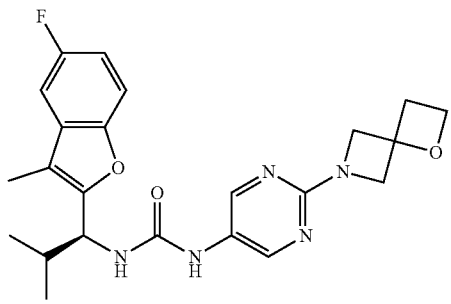 [SMILES: Cc1c([C@@H](NC(=O)Nc2cnc(N3CC4(CCO4)C3)nc2)C(C)C)oc2ccc(F)cc12]
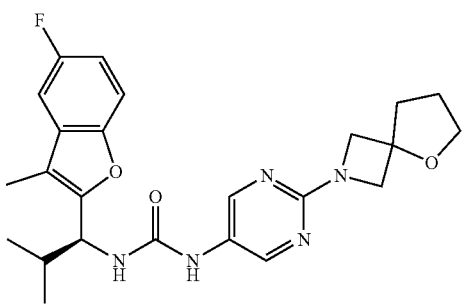
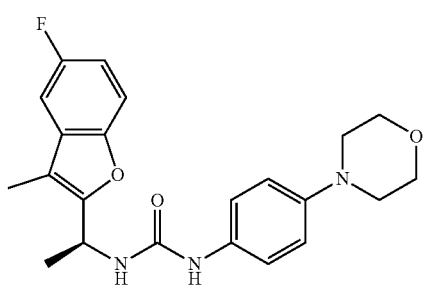 [SMILES: Cc1c([C@H](C)NC(=O)Nc2ccc(N3CCOCC3)cc2)oc2ccc(F)cc12]
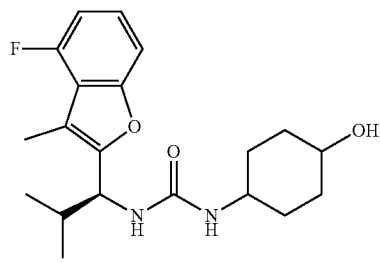 [SMILES: Cc1c([C@@H](NC(=O)NC2CCC(O)CC2)C(C)C)oc2cccc(F)c12]
TABLE B-continued
Structure
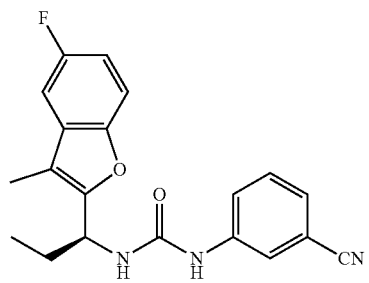 [SMILES: CC[C@H](NC(=O)Nc1cccc(C#N)c1)c1oc2ccc(F)cc2c1C]
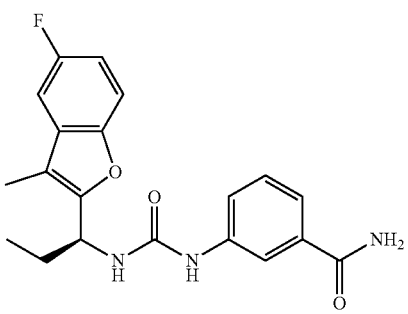 [SMILES: CC[C@H](NC(=O)Nc1cccc(C(N)=O)c1)c1oc2ccc(F)cc2c1C]
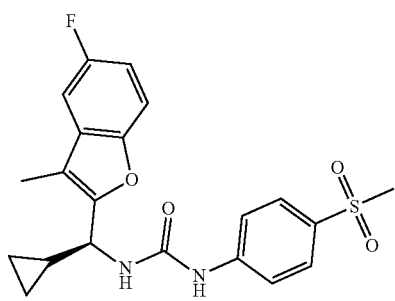 [SMILES: Cc1c([C@@H](NC(=O)Nc2ccc(S(C)(=O)=O)cc2)C2CC2)oc2ccc(F)cc12]
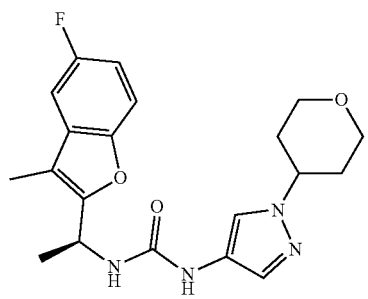 [SMILES: Cc1c([C@H](C)NC(=O)Nc2cnn(C3CCOCC3)c2)oc2ccc(F)cc12]
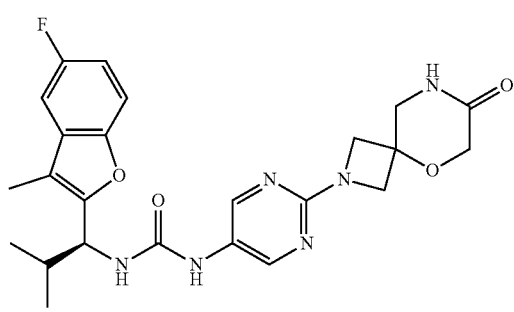 [SMILES: Cc1c([C@@H](NC(=O)Nc2cnc(N3CC4(CNC(=O)CO4)C3)nc2)C(C)C)oc2ccc(F)cc12]

TABLE B-continued

Structure

TABLE B-continued
Structure
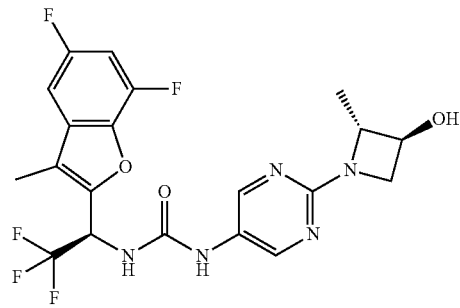 [SMILES: Cc1c([C@@H](NC(=O)Nc2cnc(N3C[C@H](O)[C@H]3C)nc2)C(F)(F)F)oc2c(F)cc(F)cc12]
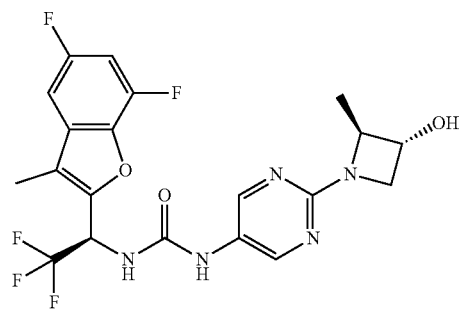 [SMILES: Cc1c([C@@H](NC(=O)Nc2cnc(N3C[C@@H](O)[C@@H]3C)nc2)C(F)(F)F)oc2c(F)cc(F)cc12]
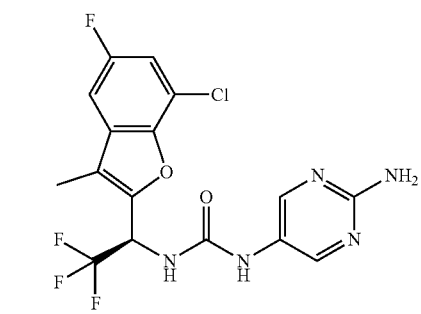 [SMILES: Cc1c([C@@H](NC(=O)Nc2cnc(N)nc2)C(F)(F)F)oc2c(Cl)cc(F)cc12]
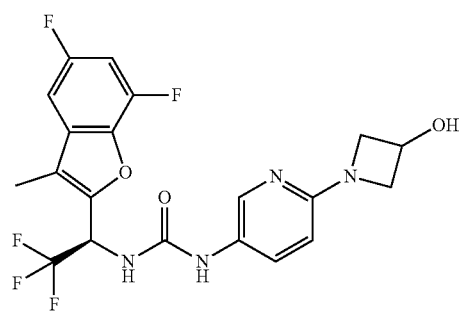
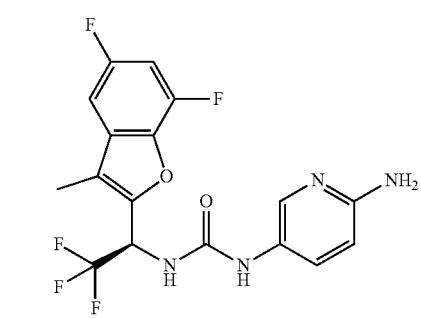
TABLE B-continued
Structure
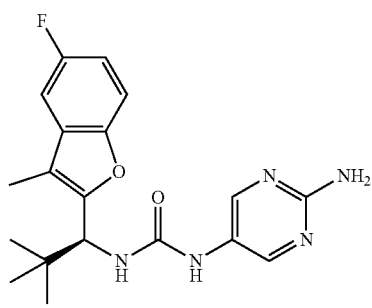 [SMILES: Cc1c([C@@H](NC(=O)Nc2cnc(N)nc2)C(C)(C)C)oc2ccc(F)cc12]
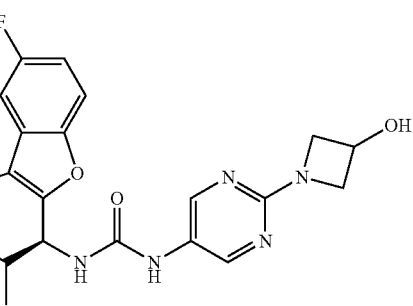
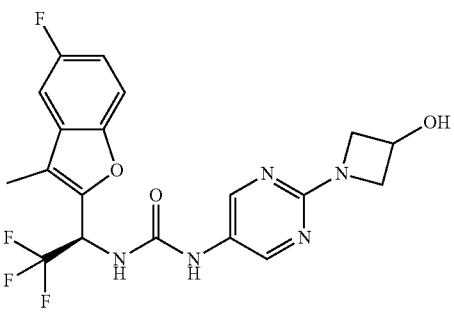 [SMILES: Cc1c([C@@H](NC(=O)Nc2cnc(N3CC(O)C3)nc2)C(F)(F)F)oc2ccc(F)cc12]
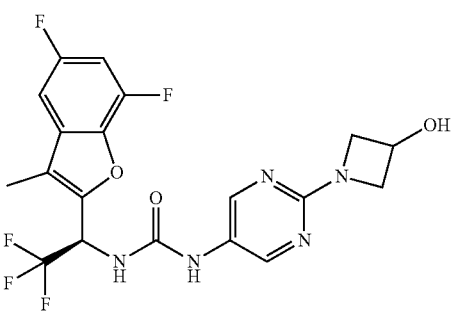 [SMILES: Cc1c([C@@H](NC(=O)Nc2cnc(N3CC(O)C3)nc2)C(F)(F)F)oc2c(F)cc(F)cc12]
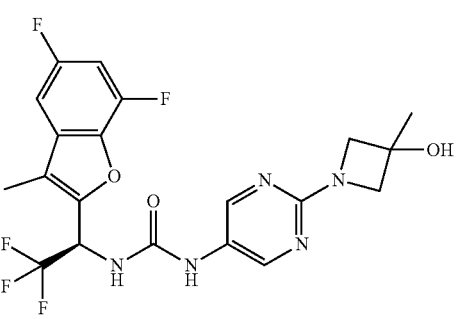 [SMILES: Cc1c([C@@H](NC(=O)Nc2cnc(N3CC(C)(O)C3)nc2)C(F)(F)F)oc2c(F)cc(F)cc12]

TABLE B-continued

Structure (Chemical structures for entries 351 and 352, showing various fluorinated benzofuran-pyrimidine urea derivatives)

TABLE B-continued

| Structure |
|---|

355

TABLE B-continued

Structure

356

TABLE B-continued

Structure

TABLE B-continued
| Structure | Structure |
|---|---|
| 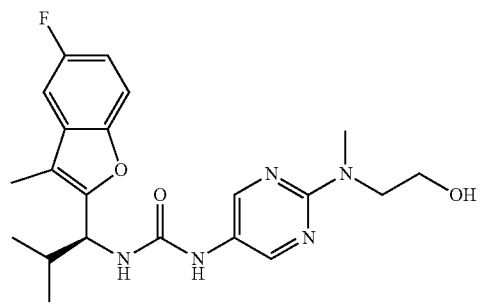 [SMILES: Cc1c([C@@H](NC(=O)Nc2cnc(N(C)CCO)nc2)C(C)C)oc2ccc(F)cc12] | 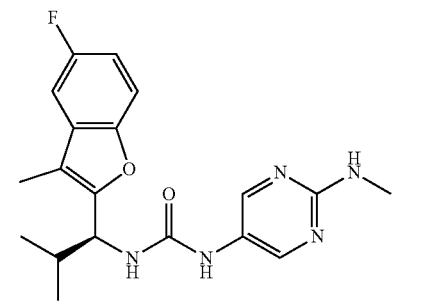 |

TABLE B-continued
| Structure |
|---|
|  |
TABLE B-continued
| Structure |
|---|
| 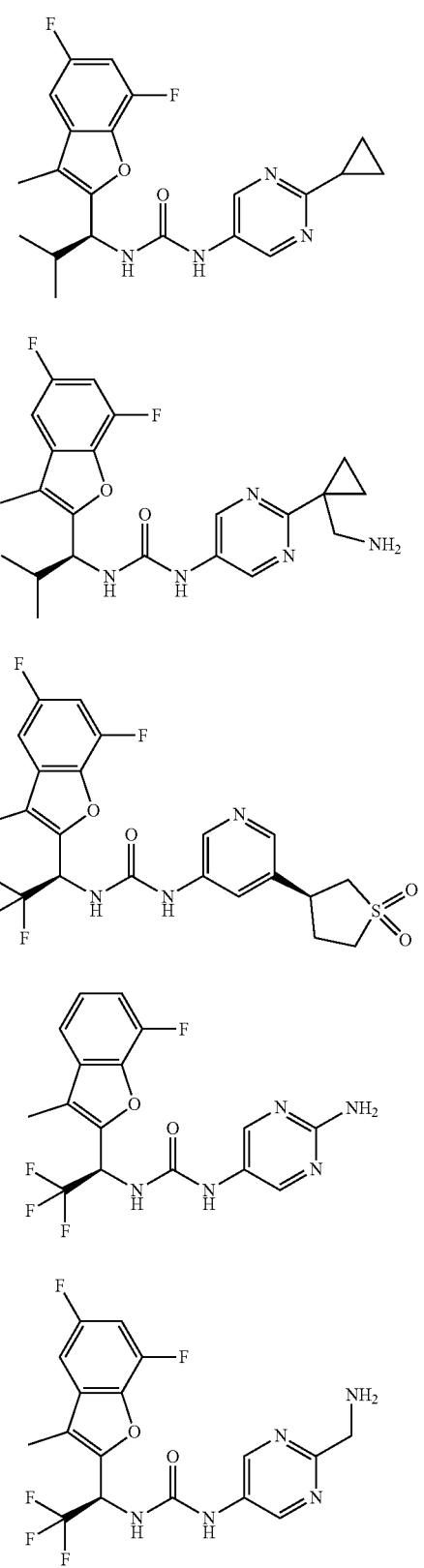 |

TABLE B-continued
Structure
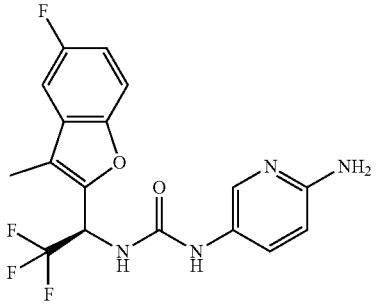 [SMILES: Cc1c([C@@H](NC(=O)Nc2ccc(N)nc2)C(F)(F)F)oc2ccc(F)cc12]
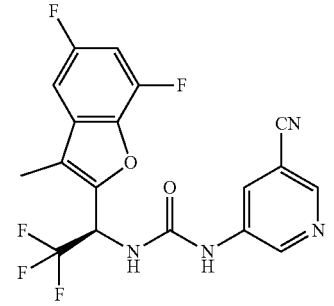 [SMILES: Cc1c([C@@H](NC(=O)Nc2cncc(C#N)c2)C(F)(F)F)oc2c(F)cc(F)cc12]
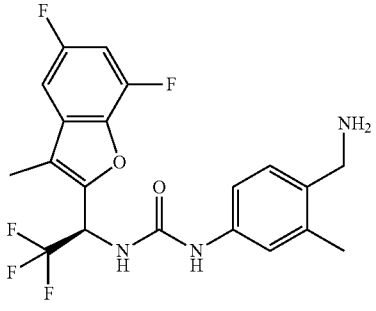
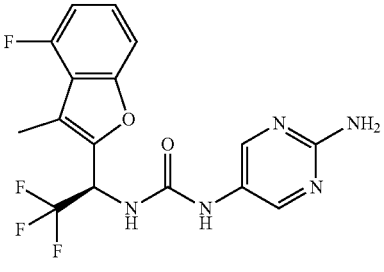 [SMILES: Cc1c([C@@H](NC(=O)Nc2cnc(N)nc2)C(F)(F)F)oc2cccc(F)c12]
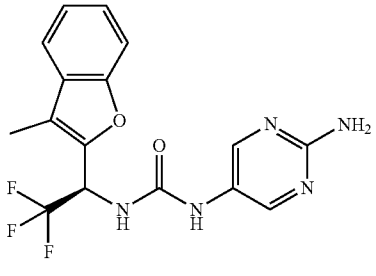 [SMILES: Cc1c([C@@H](NC(=O)Nc2cnc(N)nc2)C(F)(F)F)oc2ccccc12]
TABLE B-continued
Structure
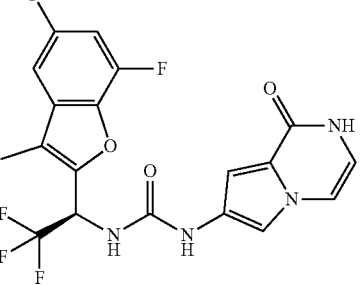
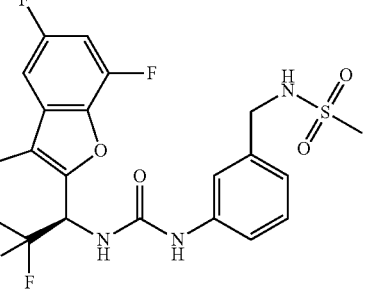
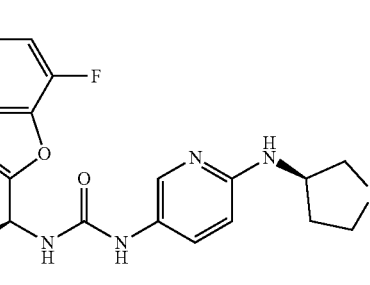
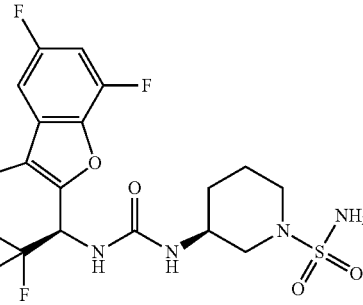
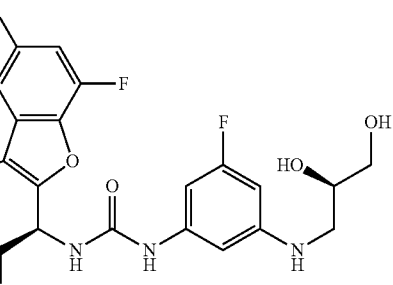

TABLE B-continued
Structure
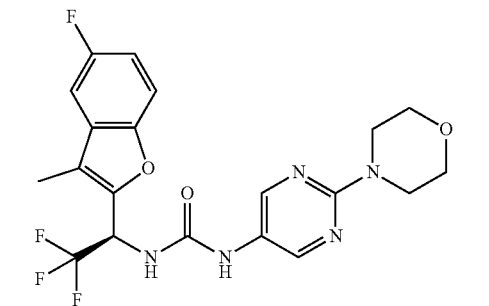 [SMILES: Cc1c([C@@H](NC(=O)Nc2cnc(N3CCOCC3)nc2)C(F)(F)F)oc2ccc(F)cc12]
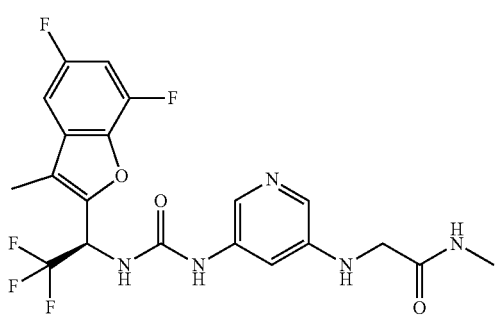
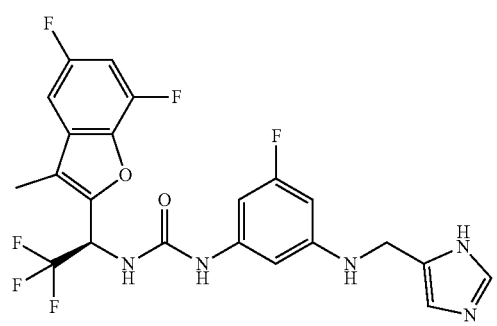 [SMILES: Cc1c([C@@H](NC(=O)Nc2cc(F)cc(NCc3cnc[nH]3)c2)C(F)(F)F)oc2c(F)cc(F)cc12]
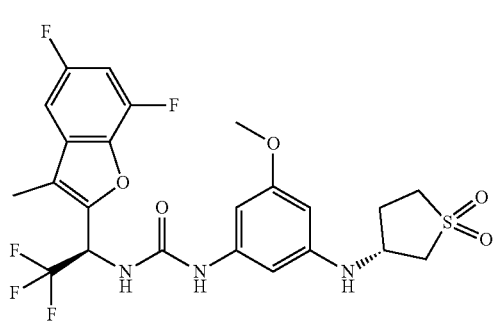 [SMILES: COc1cc(NC(=O)N[C@H](c2oc3c(F)cc(F)cc3c2C)C(F)(F)F)cc(N[C@@H]2CCS(=O)(=O)C2)c1]
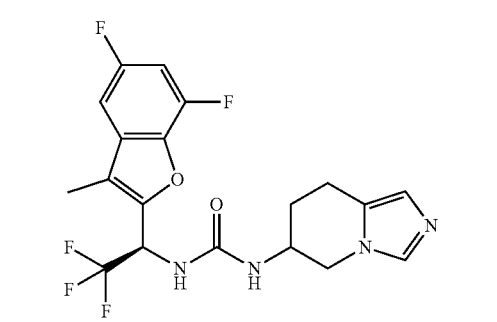
TABLE B-continued
Structure
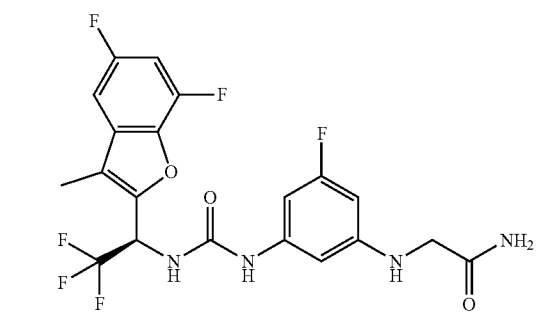 [SMILES: Cc1c([C@@H](NC(=O)Nc2cc(F)cc(NCC(N)=O)c2)C(F)(F)F)oc2c(F)cc(F)cc12]
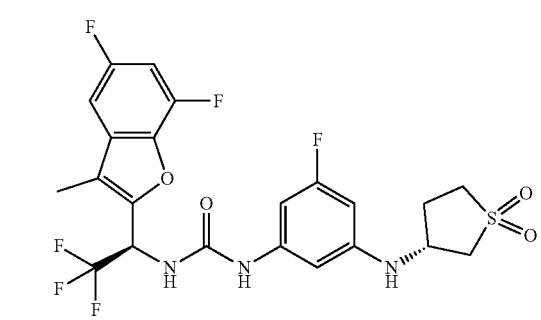 [SMILES: Cc1c([C@@H](NC(=O)Nc2cc(F)cc(N[C@@H]3CCS(=O)(=O)C3)c2)C(F)(F)F)oc2c(F)cc(F)cc12]
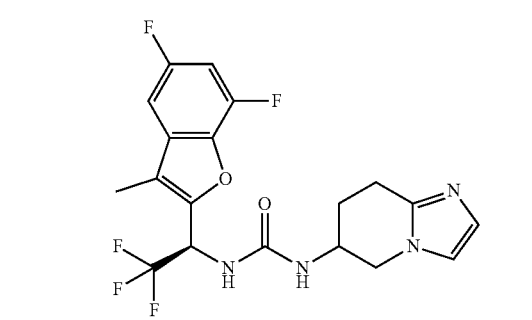 [SMILES: Cc1c([C@@H](NC(=O)NC2CCc3nccn3C2)C(F)(F)F)oc2c(F)cc(F)cc12]
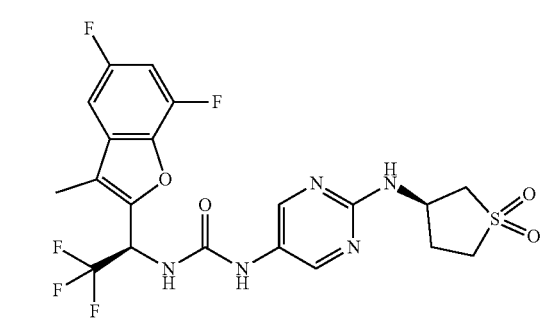 [SMILES: Cc1c([C@@H](NC(=O)Nc2cnc(N[C@@H]3CCS(=O)(=O)C3)nc2)C(F)(F)F)oc2c(F)cc(F)cc12]
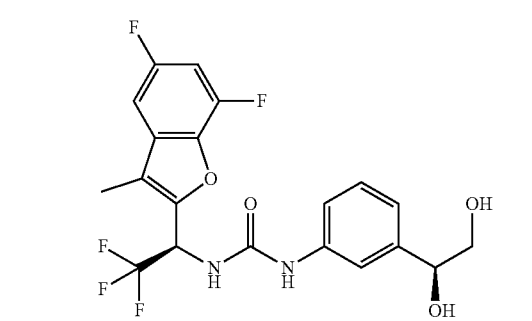 [SMILES: Cc1c([C@@H](NC(=O)Nc2cccc([C@H](O)CO)c2)C(F)(F)F)oc2c(F)cc(F)cc12]

TABLE B-continued

Structure

TABLE B-continued

Structure

TABLE B-continued
Structure
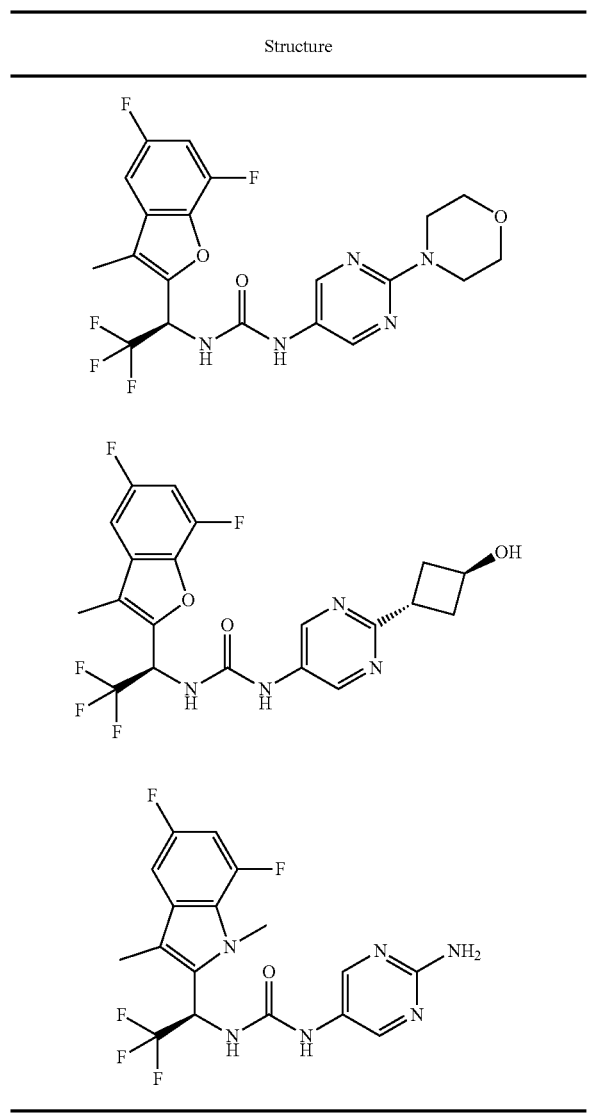
In some embodiments, the compound is selected from the group consisting of the compounds delineated in Table C, or a pharmaceutically acceptable salt thereof.
TABLE C
Structure
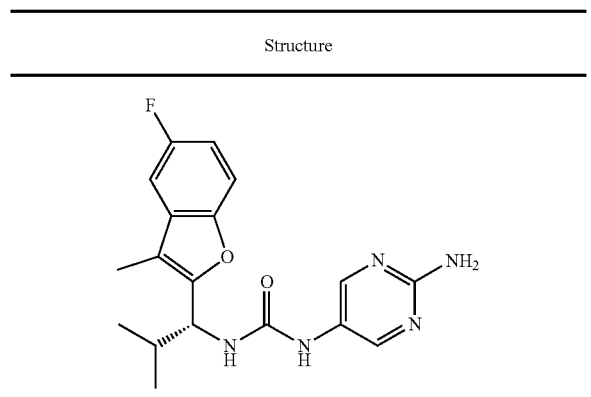
TABLE C-continued
Structure
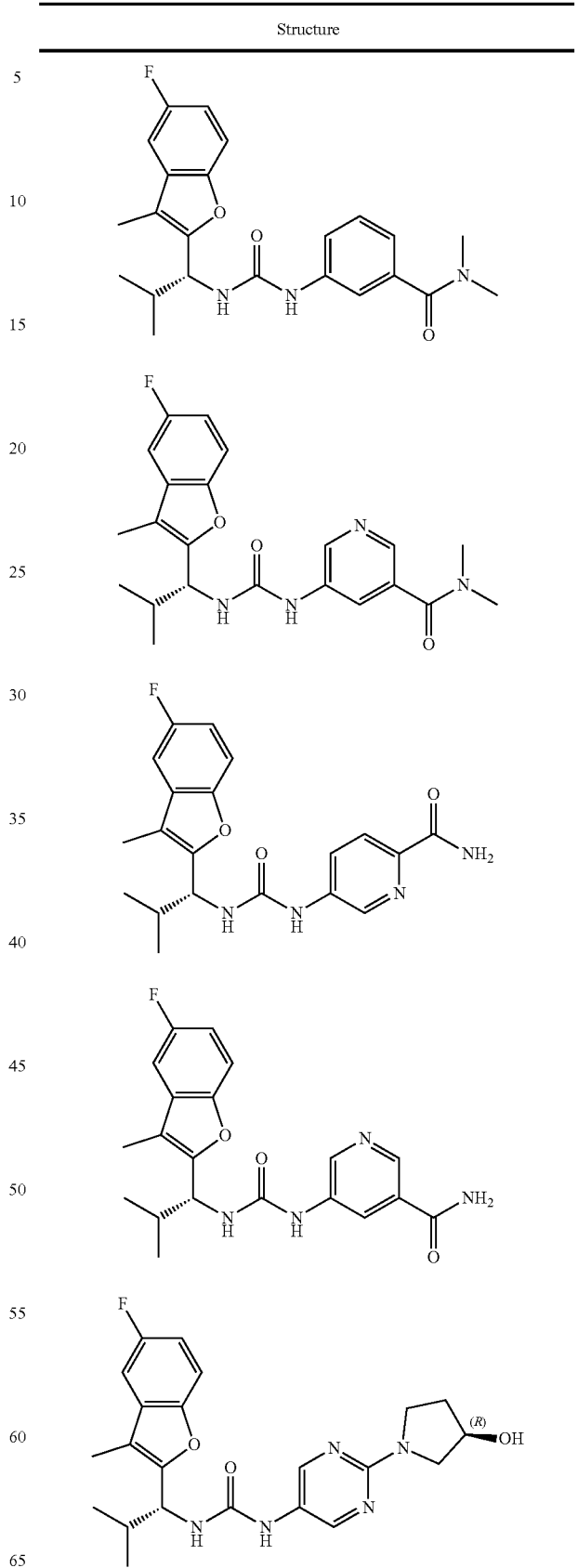

TABLE C-continued
Structure
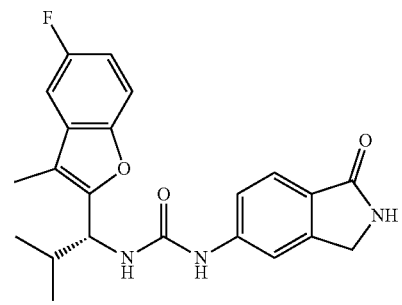

TABLE C-continued

| Structure |
|---|
| (chemical structures on pages 373 and 374) |

TABLE C-continued
Structure
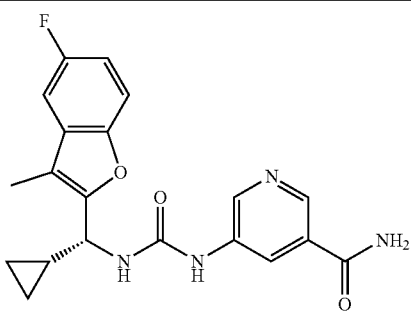
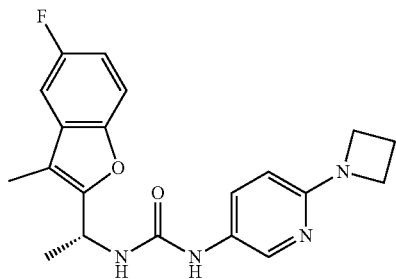 [SMILES: Cc1c([C@@H](C)NC(=O)Nc2ccc(N3CCC3)nc2)oc2ccc(F)cc12]

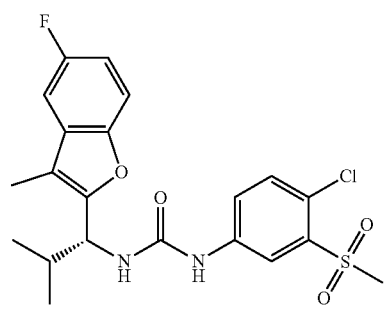
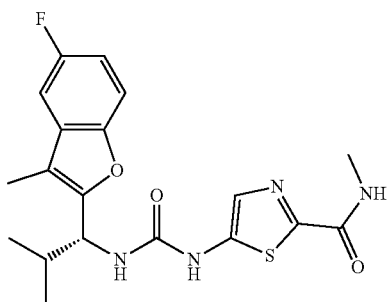 [SMILES: CNC(=O)c1ncc(NC(=O)N[C@@H](c2oc3ccc(F)cc3c2C)C(C)C)s1]
TABLE C-continued
Structure
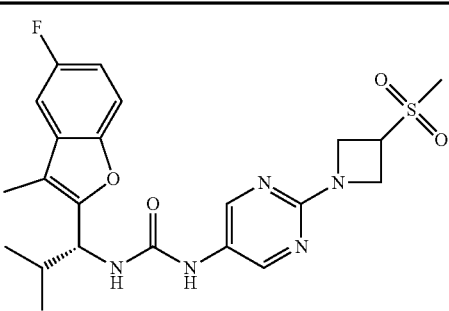
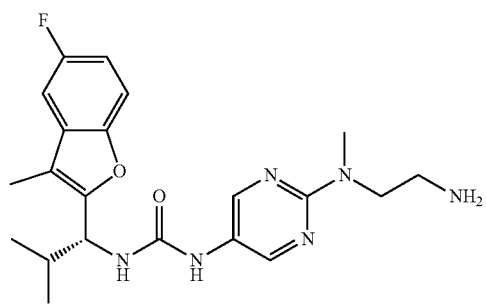 [SMILES: Cc1c([C@H](NC(=O)Nc2cnc(N(C)CCN)nc2)C(C)C)oc2ccc(F)cc12]
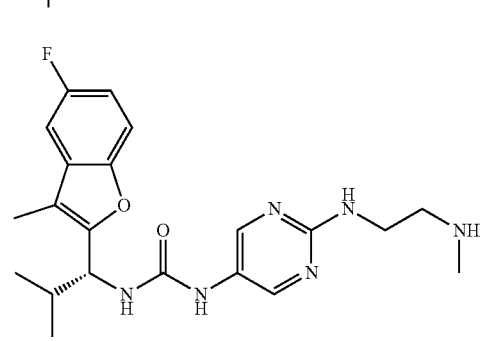
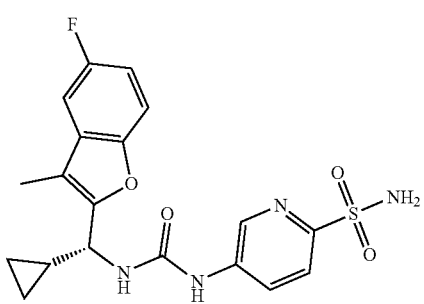 [SMILES: Cc1c([C@H](NC(=O)Nc2ccc(S(N)(=O)=O)nc2)C2CC2)oc2ccc(F)cc12]
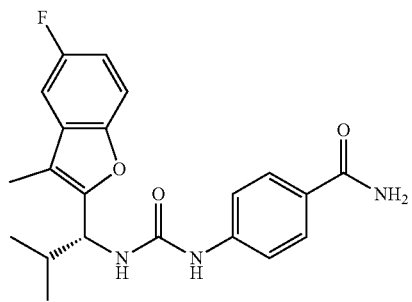 [SMILES: Cc1c([C@H](NC(=O)Nc2ccc(C(N)=O)cc2)C(C)C)oc2ccc(F)cc12]

TABLE C-continued

Structure

TABLE C-continued
Structure
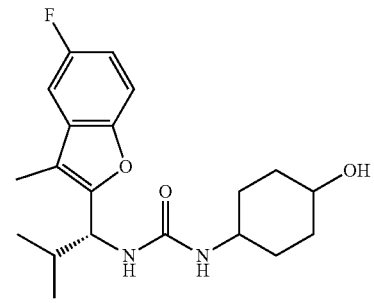 [SMILES: Cc1c([C@H](NC(=O)NC2CCC(O)CC2)C(C)C)oc2ccc(F)cc12]

TABLE C-continued
| Structure |
|---|
| 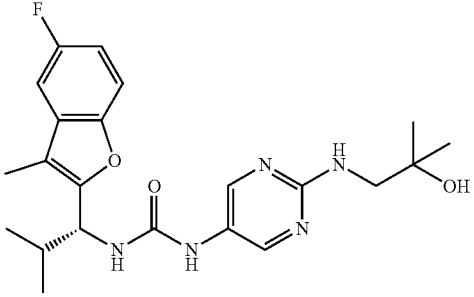 [SMILES: Cc1c([C@H](NC(=O)Nc2cnc(NCC(C)(C)O)nc2)C(C)C)oc2ccc(F)cc12] |
| 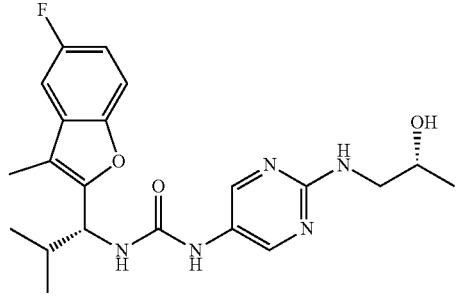 [SMILES: Cc1c([C@H](NC(=O)Nc2cnc(NC[C@@H](C)O)nc2)C(C)C)oc2ccc(F)cc12] |
| 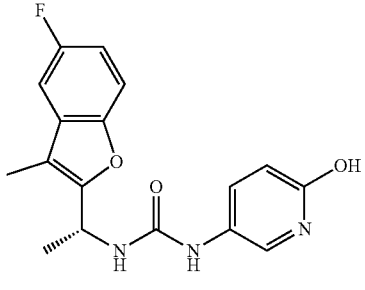 [SMILES: Cc1c([C@@H](C)NC(=O)Nc2ccc(O)nc2)oc2ccc(F)cc12] |
| 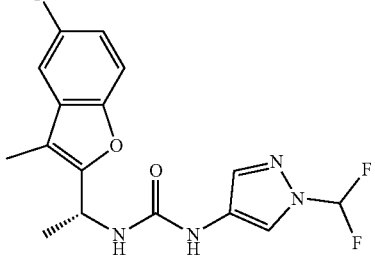 |
| 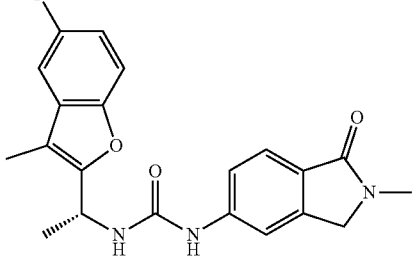 |
TABLE C-continued
| Structure |
|---|
| 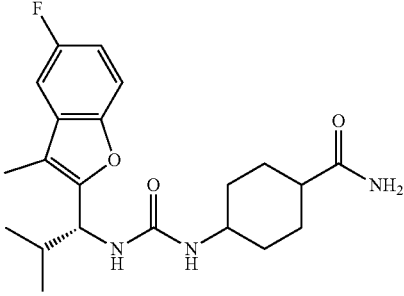 [SMILES: Cc1c([C@H](NC(=O)NC2CCC(C(N)=O)CC2)C(C)C)oc2ccc(F)cc12] |
| 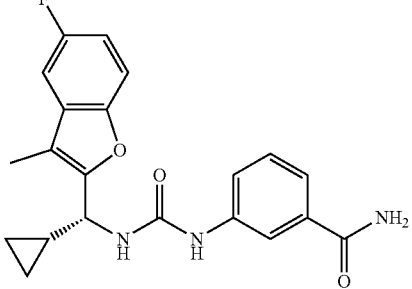 |
| 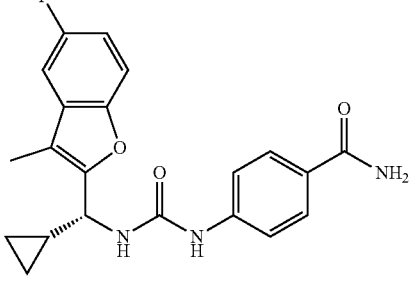 |
| 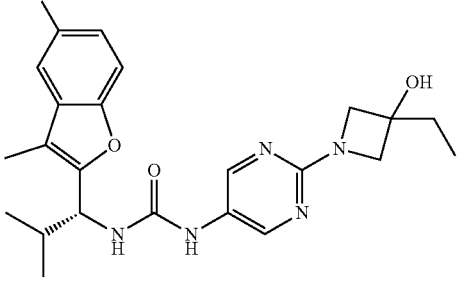 |
| 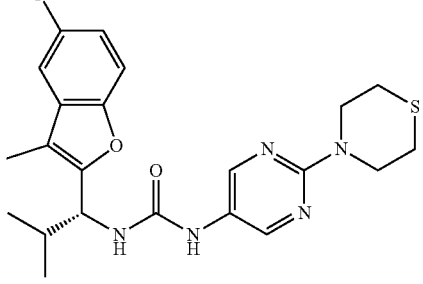 |

TABLE C-continued

Structure

385
TABLE C-continued
Structure
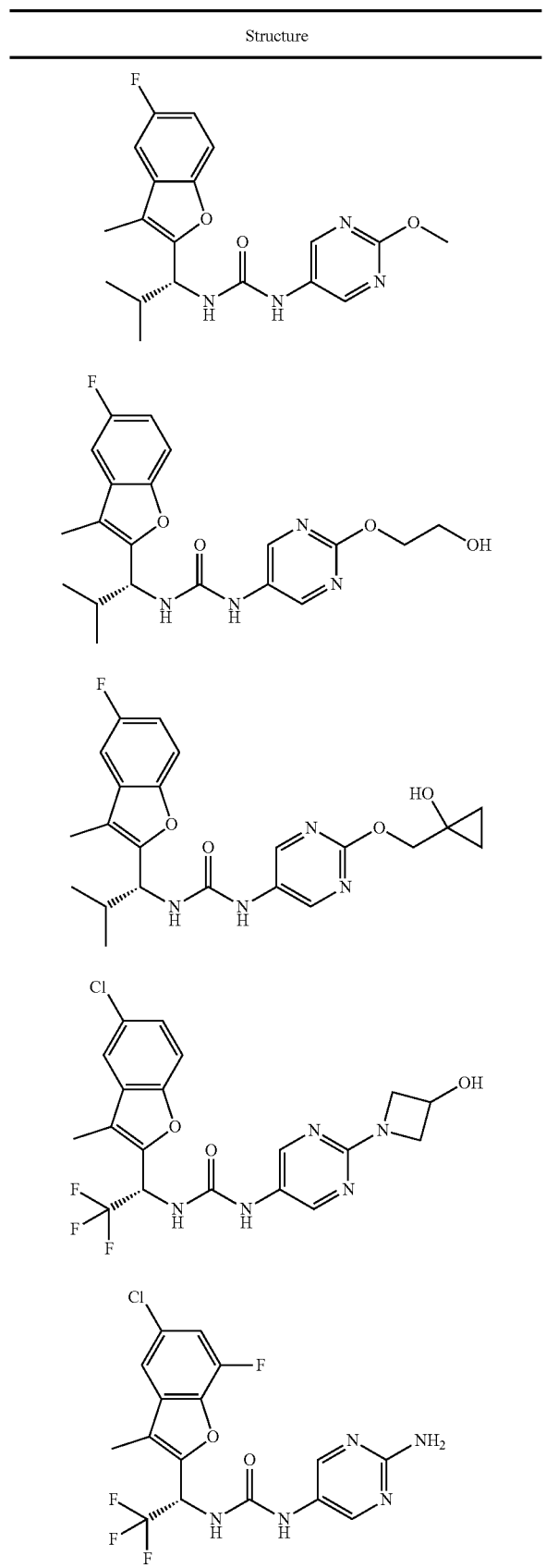
386
TABLE C-continued
Structure
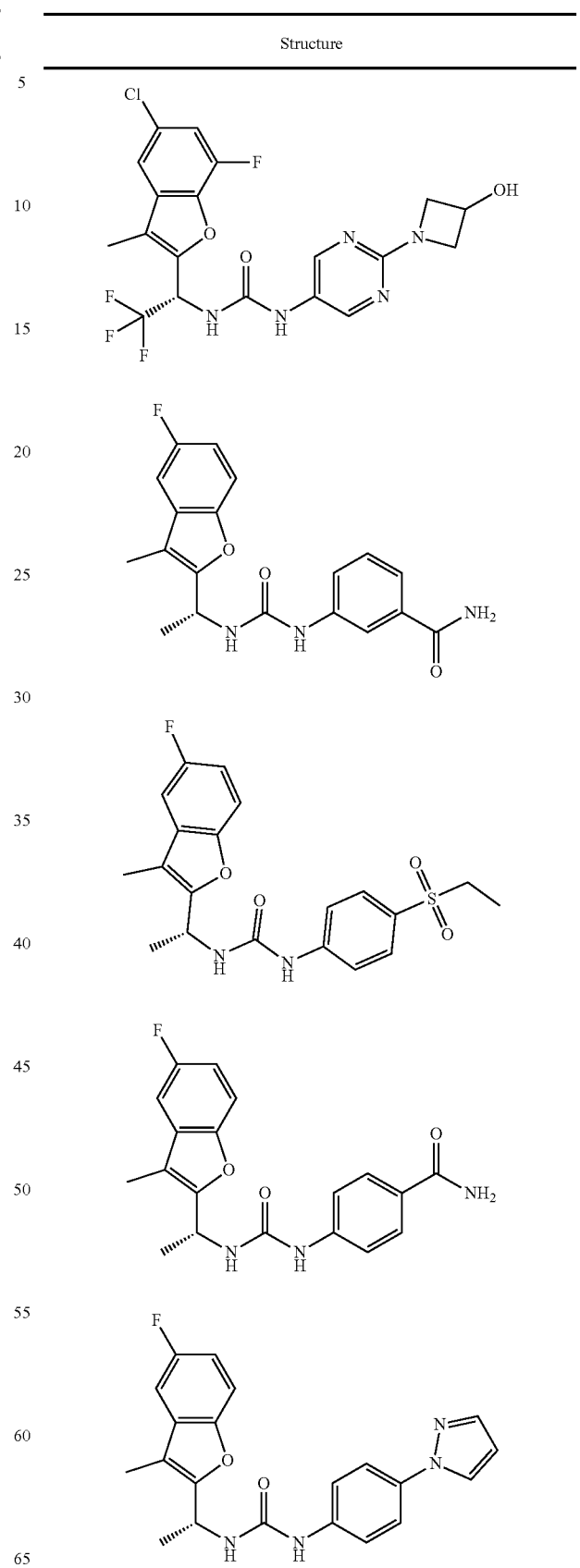

TABLE C-continued

Structure

TABLE C-continued
Structure
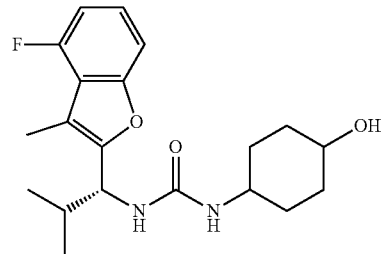
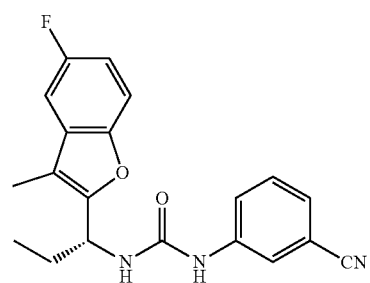
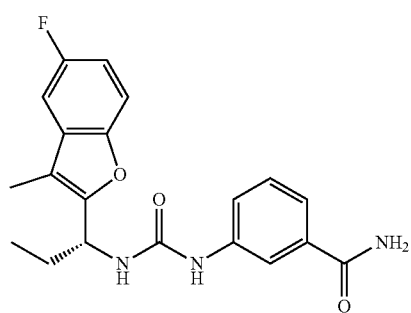 [SMILES: CC[C@@H](NC(=O)Nc1cccc(C(N)=O)c1)c1oc2ccc(F)cc2c1C]
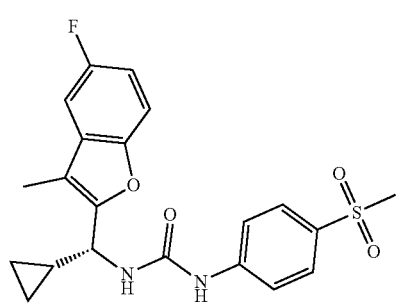 [SMILES: Cc1c([C@H](NC(=O)Nc2ccc(S(C)(=O)=O)cc2)C2CC2)oc2ccc(F)cc12]
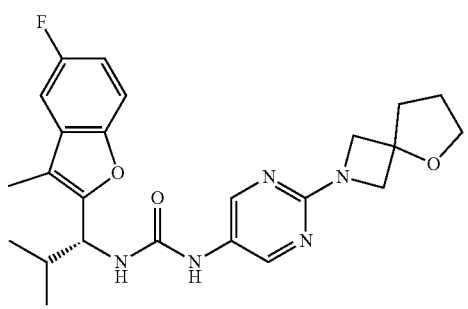
TABLE C-continued
Structure
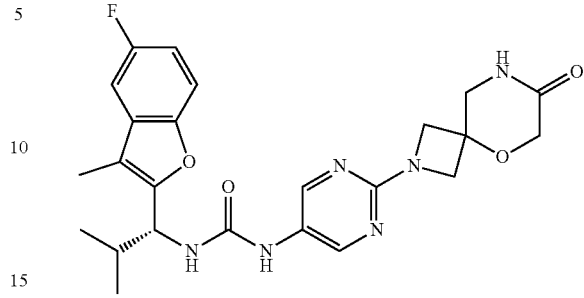
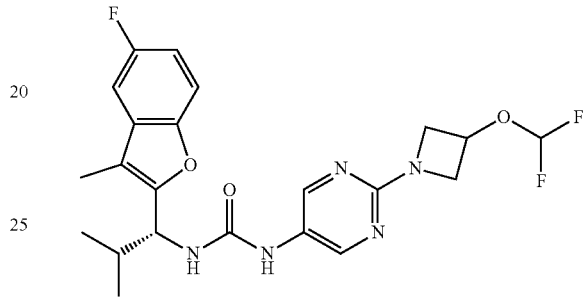
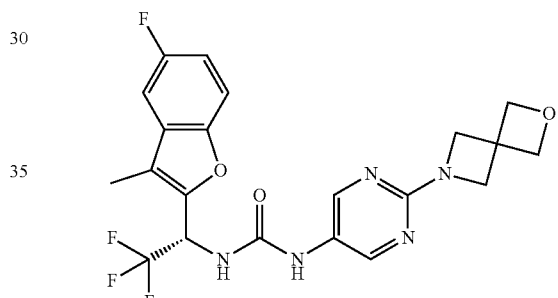
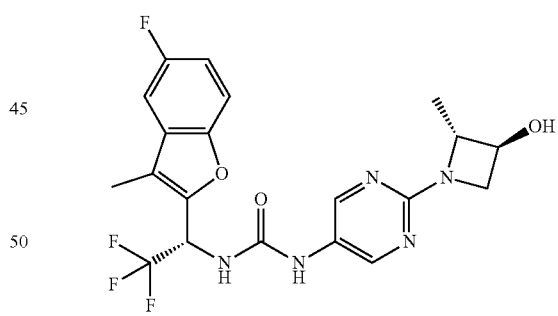
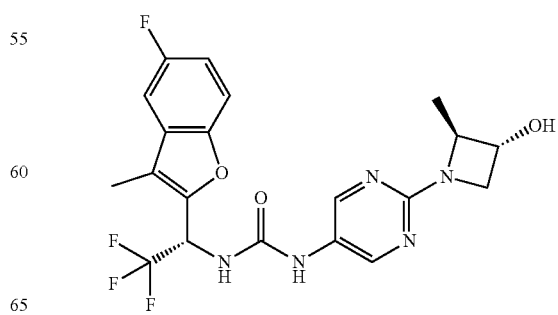

TABLE C-continued

| 391 | 392 |
|---|---|
| Structure | Structure |

TABLE C-continued
Structure
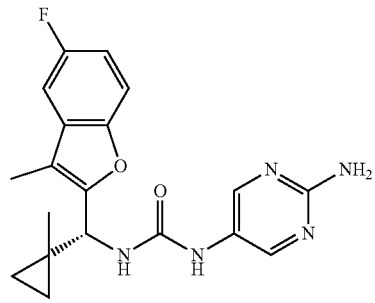
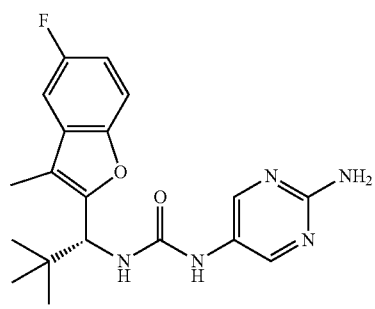
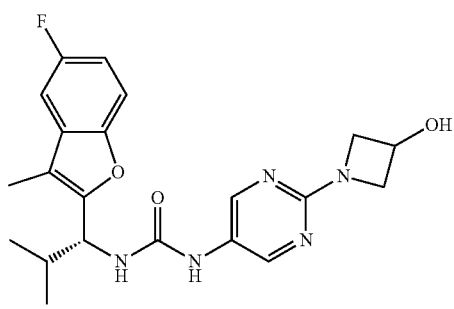 [SMILES: Cc1c([C@H](NC(=O)Nc2cnc(N3CC(O)C3)nc2)C(C)C)oc2ccc(F)cc12]
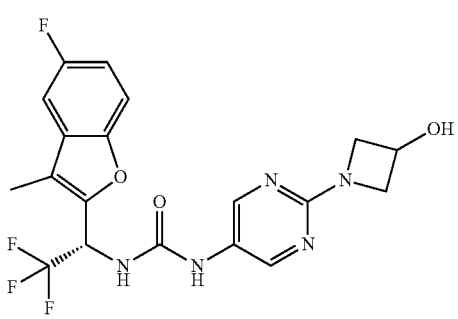
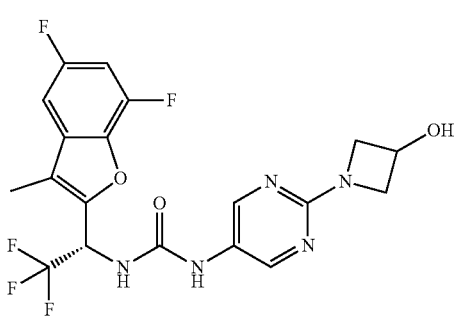
TABLE C-continued
Structure
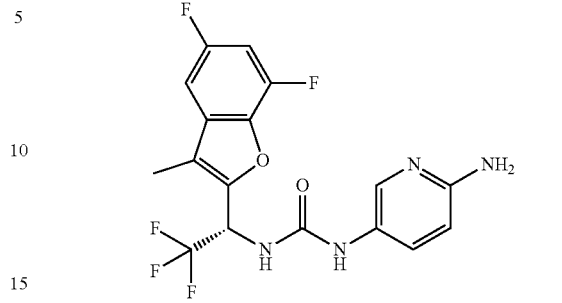
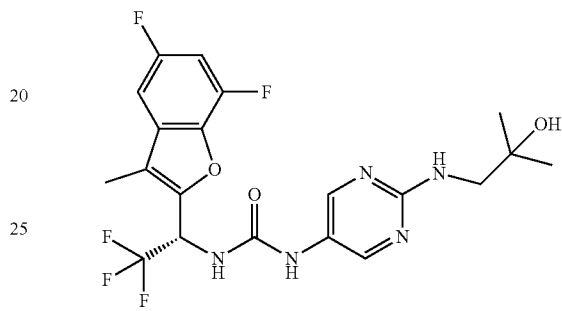
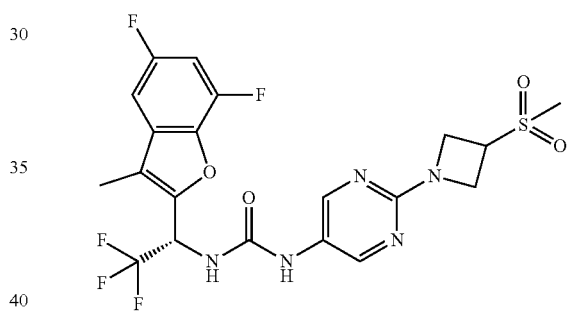
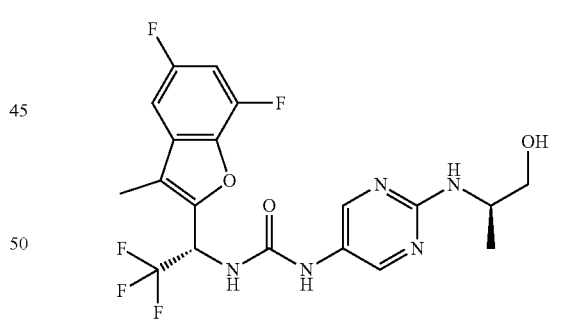
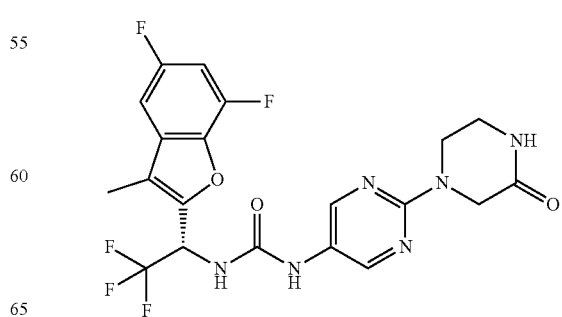

TABLE C-continued

Structure

TABLE C-continued
Structure
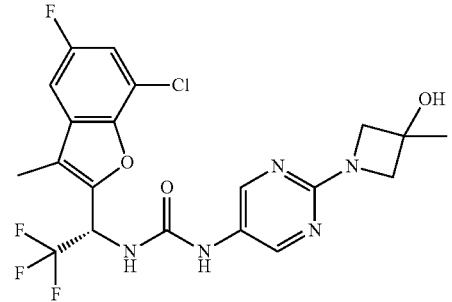
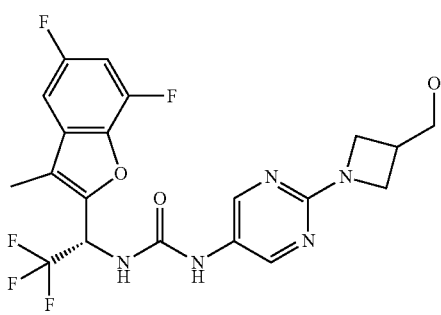
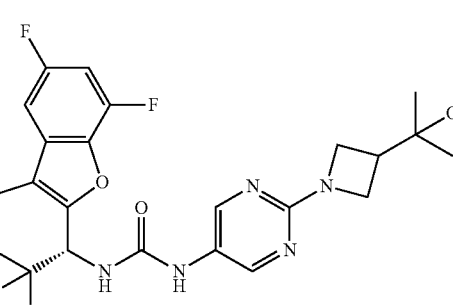
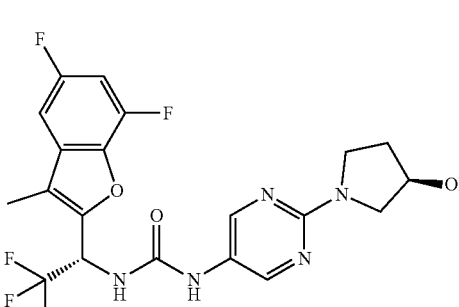
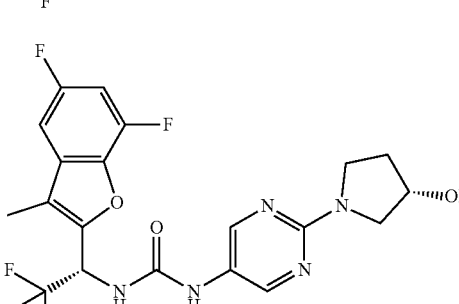
TABLE C-continued
Structure
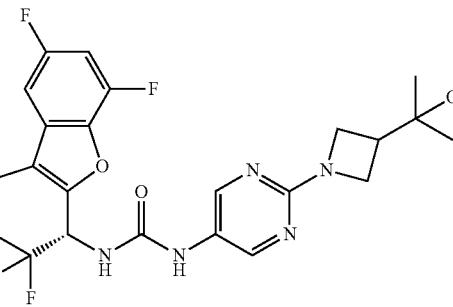
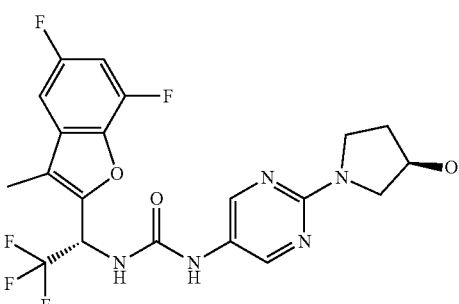
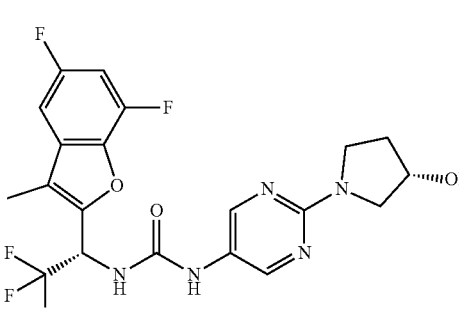
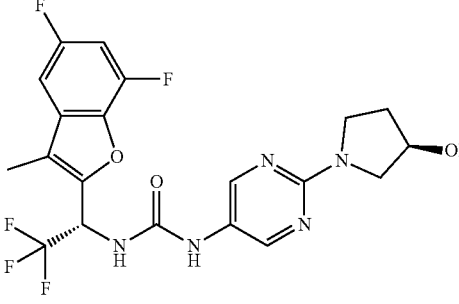
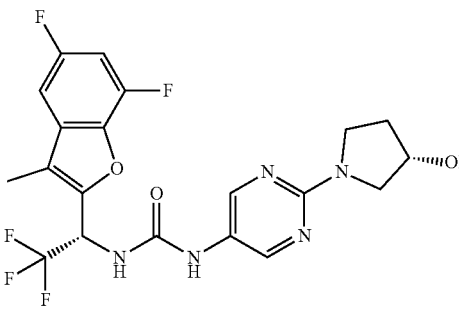

TABLE C-continued

Structure

TABLE C-continued
Structure
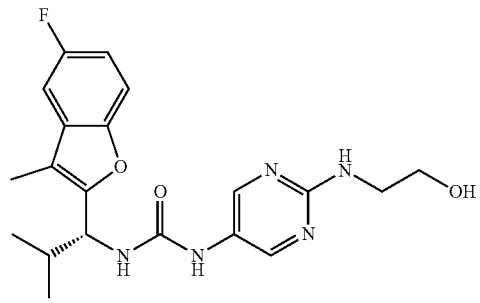
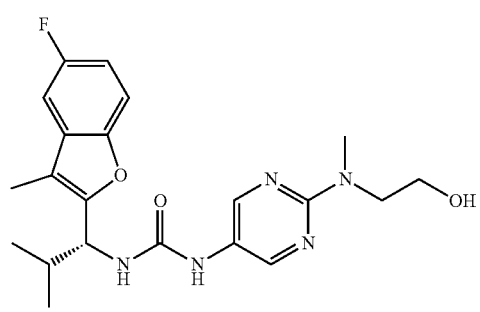 [SMILES: Cc1c([C@H](NC(=O)Nc2cnc(N(C)CCO)nc2)C(C)C)oc2ccc(F)cc12]
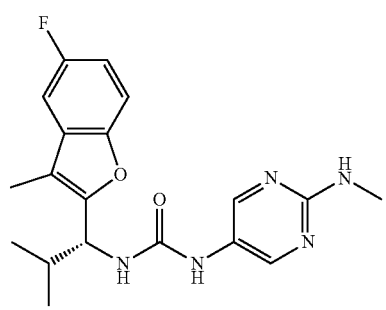
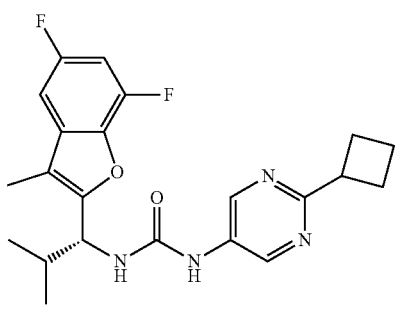
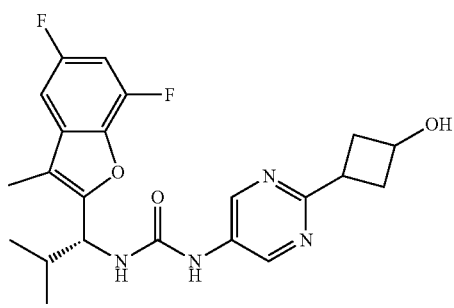
TABLE C-continued
Structure
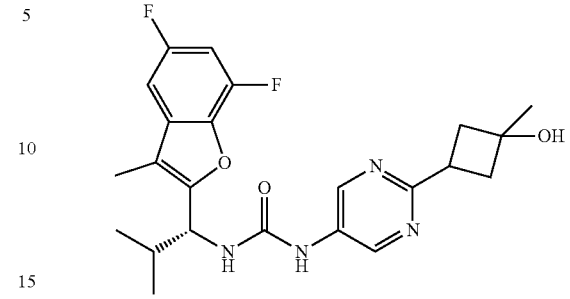
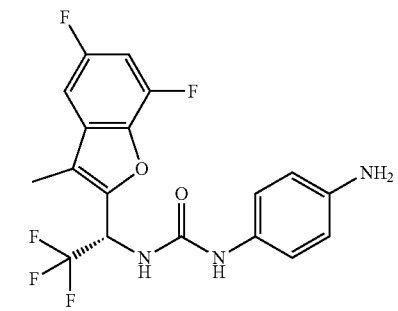
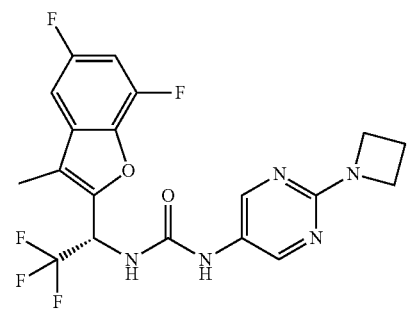 [SMILES: Cc1c([C@H](NC(=O)Nc2cnc(N3CCC3)nc2)C(F)(F)F)oc2c(F)cc(F)cc12]
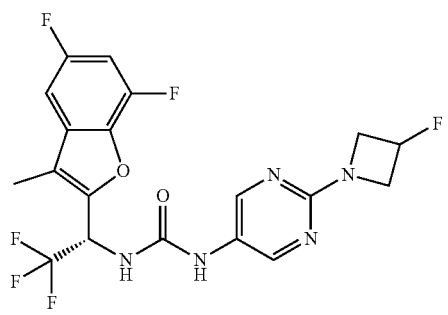
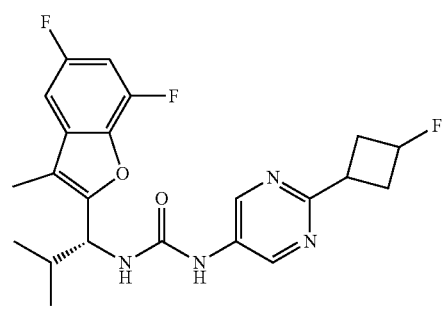

TABLE C-continued

Structure

TABLE C-continued
Structure
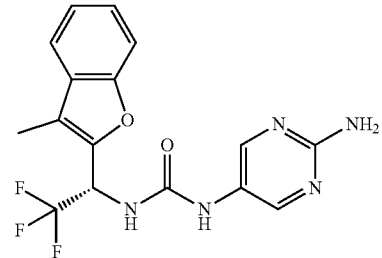 [SMILES: Cc1c([C@H](NC(=O)Nc2cnc(N)nc2)C(F)(F)F)oc2ccccc12]
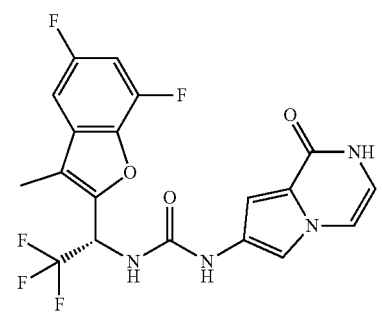 [SMILES: Cc1c([C@H](NC(=O)Nc2cc3c(=O)[nH]ccn3c2)C(F)(F)F)oc2c(F)cc(F)cc12]
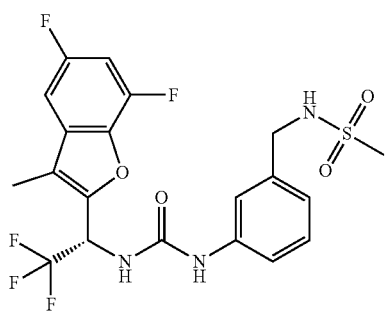
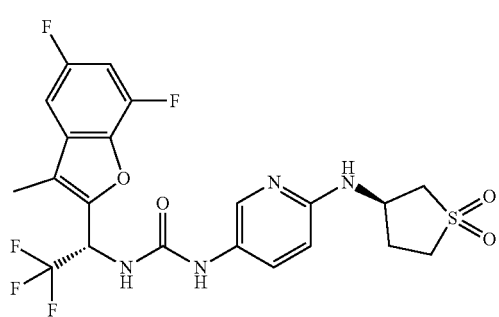
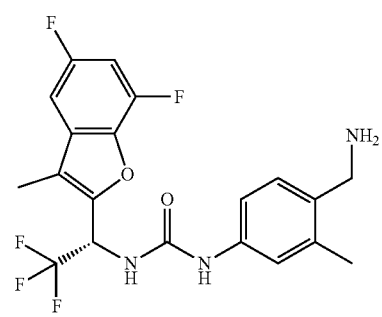
TABLE C-continued
Structure
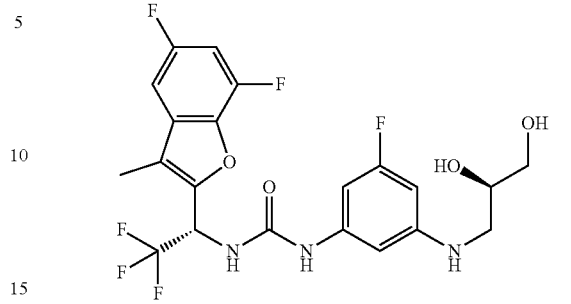
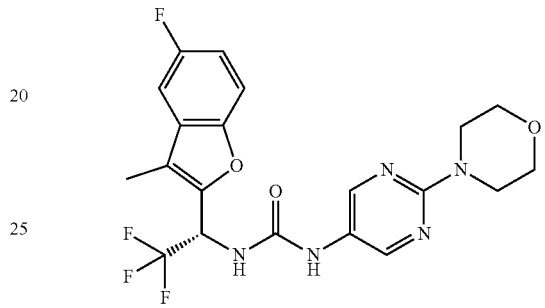
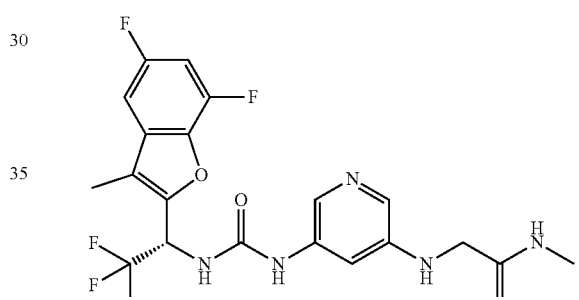
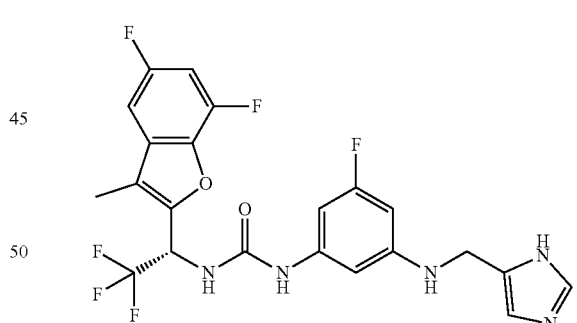
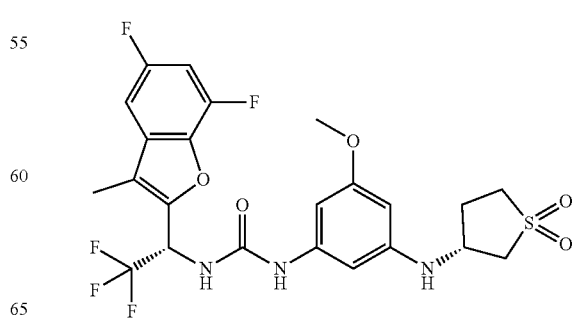

TABLE C-continued
Structure
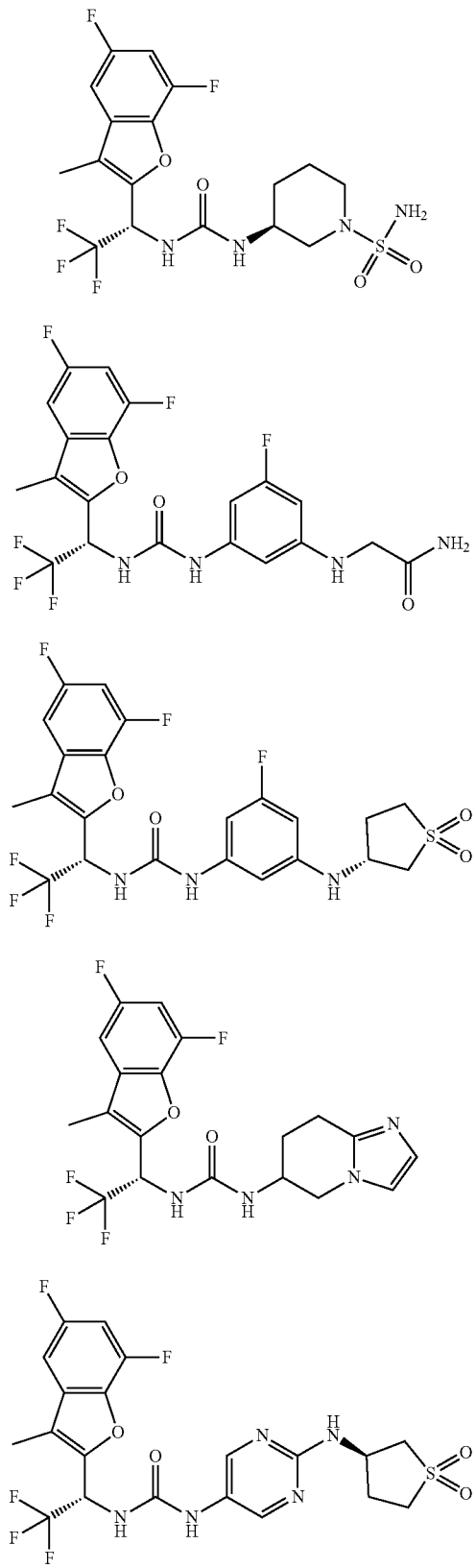
TABLE C-continued
Structure
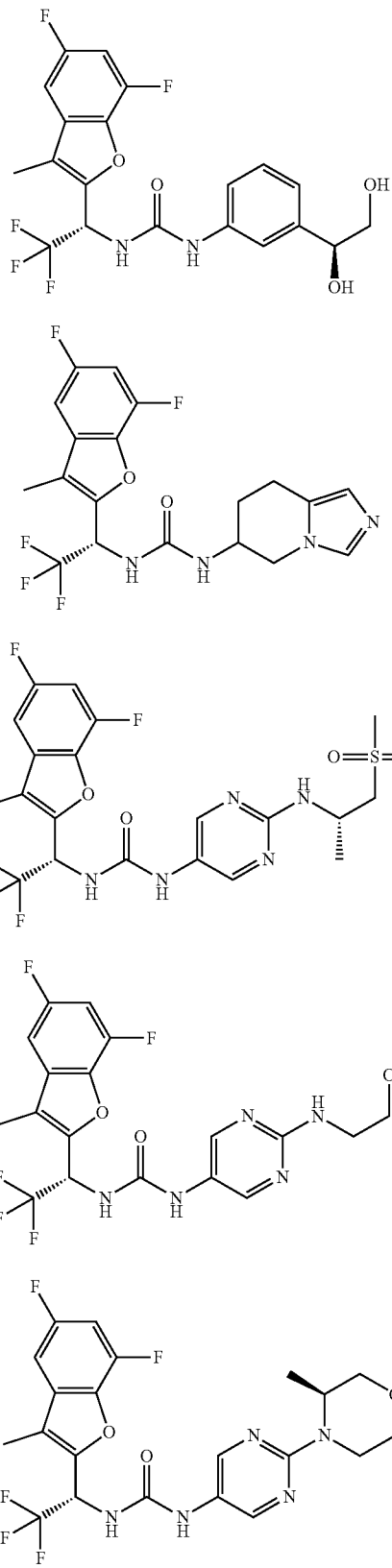

TABLE C-continued

Structure

| 411 | 412 |
|---|---|
| TABLE C-continued | TABLE C-continued |
| Structure | Structure |
| 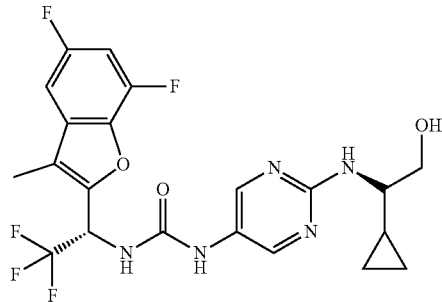 | 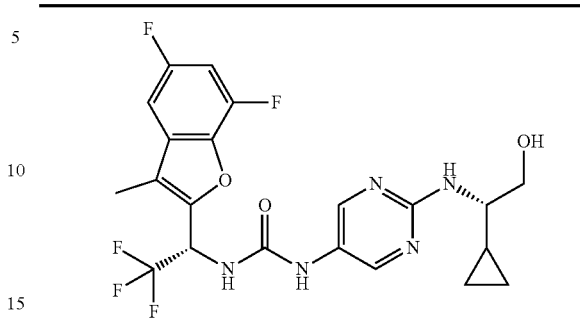 |
| 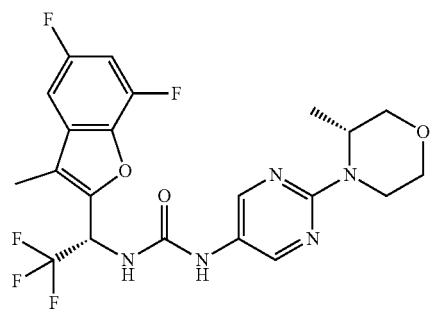 [SMILES: Cc1c([C@H](NC(=O)Nc2cnc(N3CCOC[C@H]3C)nc2)C(F)(F)F)oc2c(F)cc(F)cc12] | 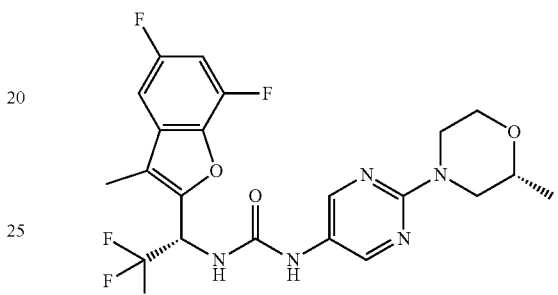 |
| 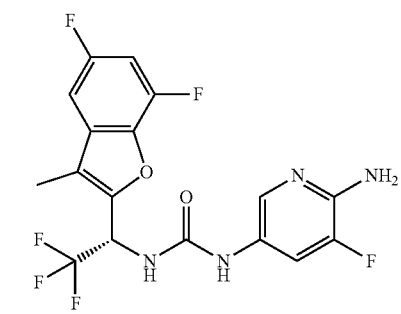 [SMILES: Cc1c([C@H](NC(=O)Nc2cnc(N)c(F)c2)C(F)(F)F)oc2c(F)cc(F)cc12] | 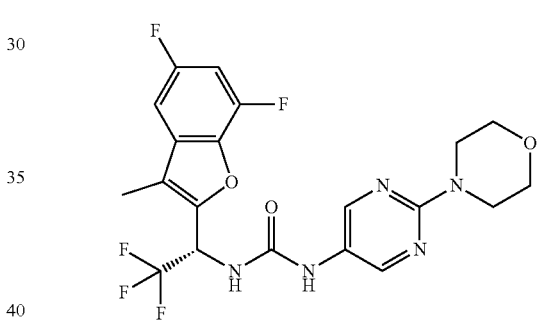 |
| 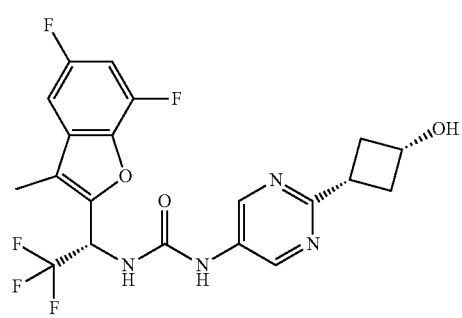 [SMILES: Cc1c([C@H](NC(=O)Nc2cnc([C@H]3C[C@@H](O)C3)nc2)C(F)(F)F)oc2c(F)cc(F)cc12] | 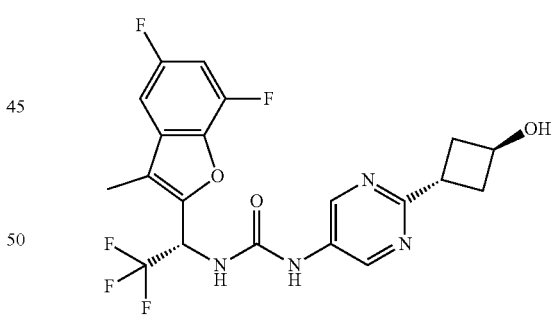 |
| 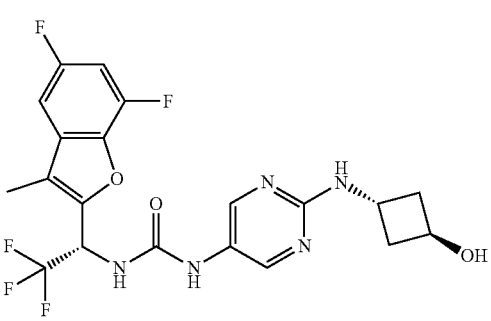 [SMILES: Cc1c([C@H](NC(=O)Nc2cnc(N[C@H]3C[C@H](O)C3)nc2)C(F)(F)F)oc2c(F)cc(F)cc12] | 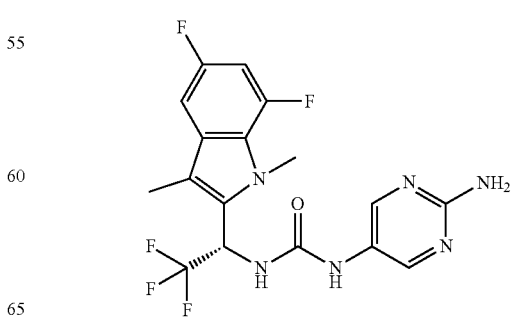 |

In some embodiments, the compound is selected from the group consisting of the compounds delineated in Table D, or a pharmaceutically acceptable salt thereof.
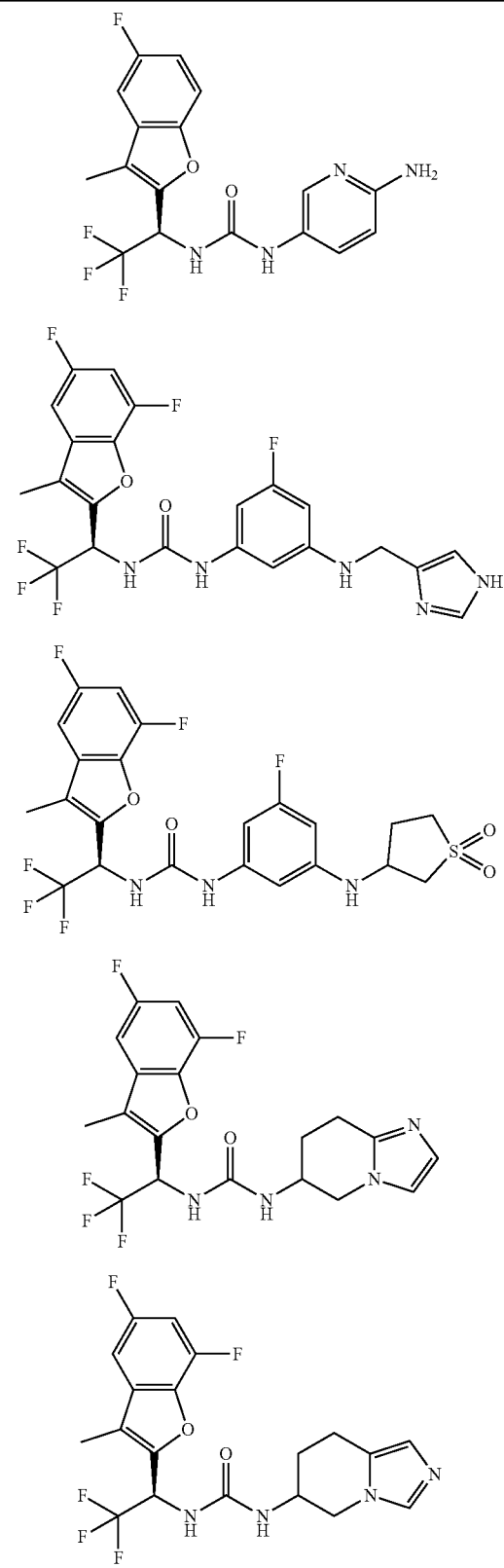
-continued
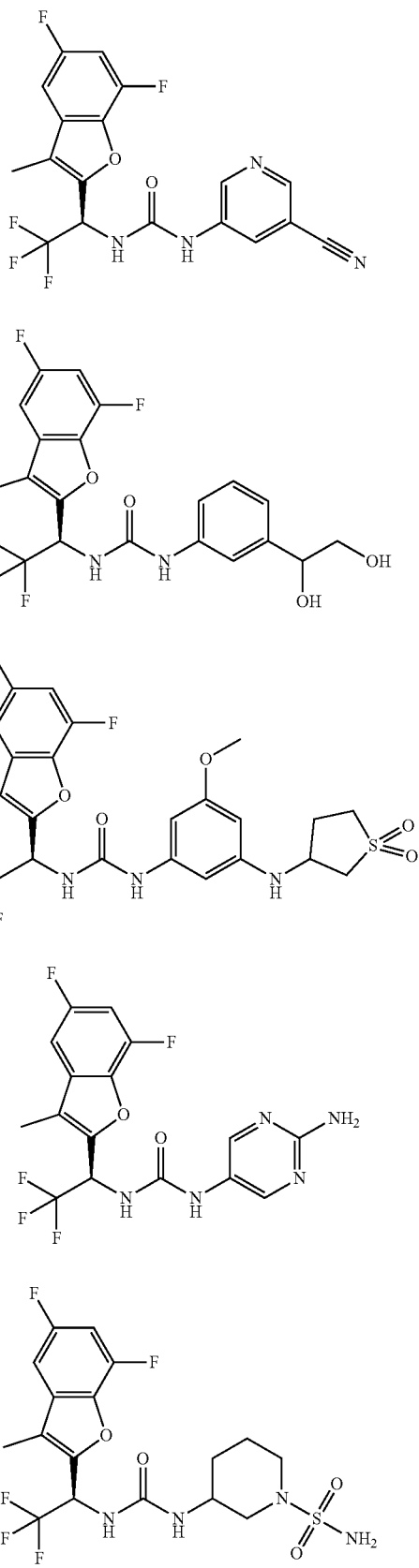

415
-continued
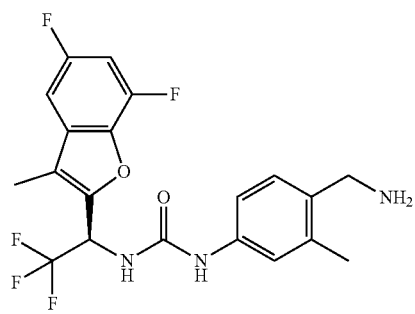 [SMILES: Cc1cc(NC(=O)N[C@H](c2oc3c(F)cc(F)cc3c2C)C(F)(F)F)ccc1CN]
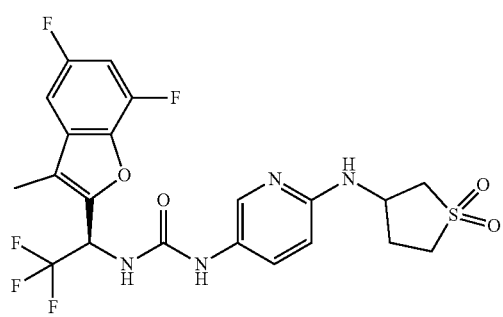 [SMILES: Cc1c([C@@H](NC(=O)Nc2ccc(NC3CCS(=O)(=O)C3)nc2)C(F)(F)F)oc2c(F)cc(F)cc12]
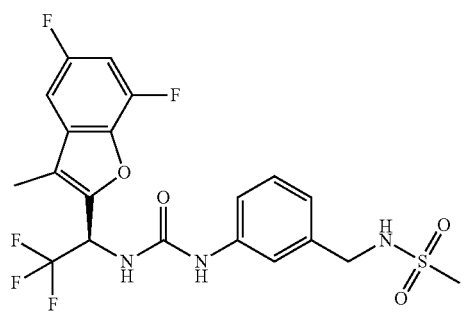
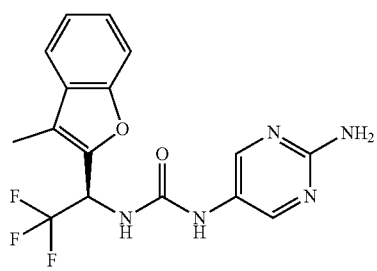 [SMILES: Cc1c([C@@H](NC(=O)Nc2cnc(N)nc2)C(F)(F)F)oc2ccccc12]
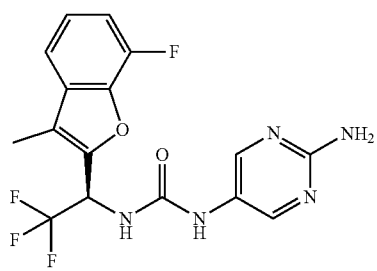 [SMILES: Cc1c([C@@H](NC(=O)Nc2cnc(N)nc2)C(F)(F)F)oc2c(F)cccc12]
416
-continued
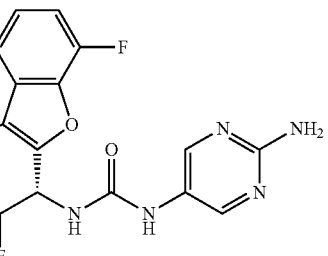
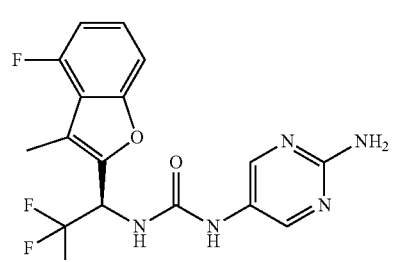
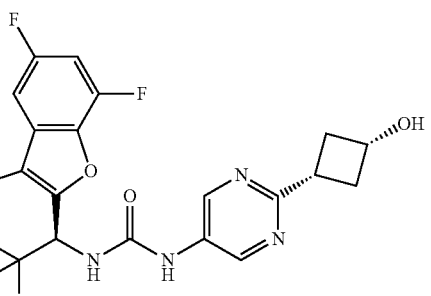
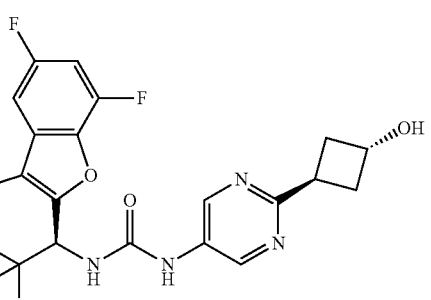
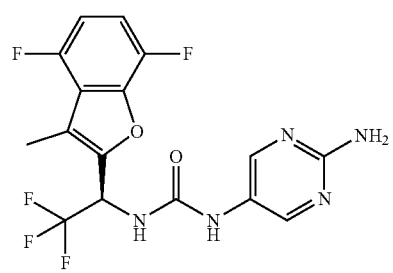 [SMILES: Cc1c([C@@H](NC(=O)Nc2cnc(N)nc2)C(F)(F)F)oc2c(F)ccc(F)c12]

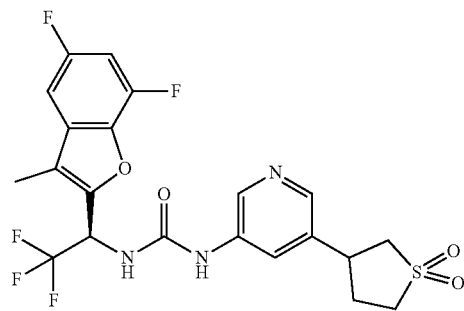 [SMILES: Cc1c([C@@H](NC(=O)Nc2cncc(C3CCS(=O)(=O)C3)c2)C(F)(F)F)oc2c(F)cc(F)cc12]
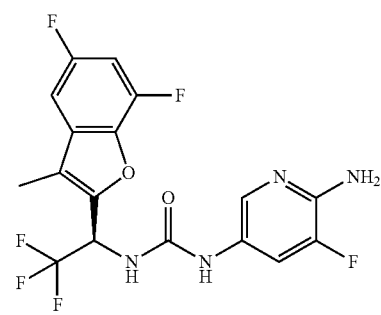 [SMILES: Cc1c([C@@H](NC(=O)Nc2cnc(N)c(F)c2)C(F)(F)F)oc2c(F)cc(F)cc12]
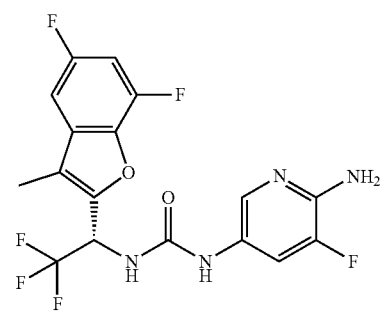
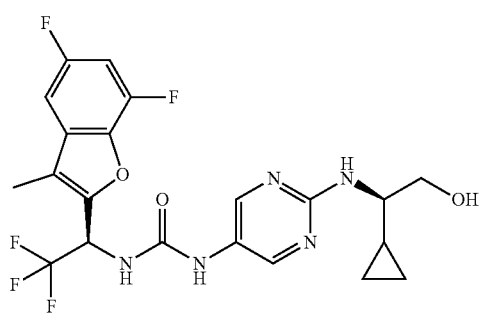 [SMILES: Cc1c([C@@H](NC(=O)Nc2cnc(N[C@@H](CO)C3CC3)nc2)C(F)(F)F)oc2c(F)cc(F)cc12]
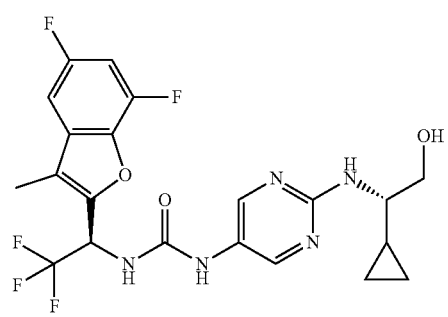 [SMILES: Cc1c([C@@H](NC(=O)Nc2cnc(N[C@H](CO)C3CC3)nc2)C(F)(F)F)oc2c(F)cc(F)cc12]
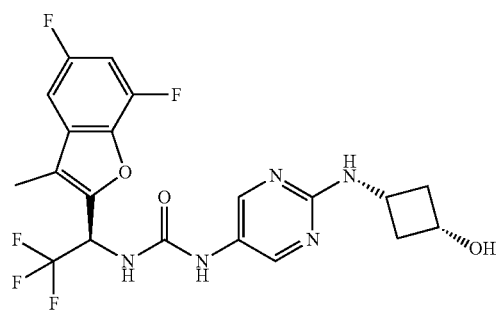
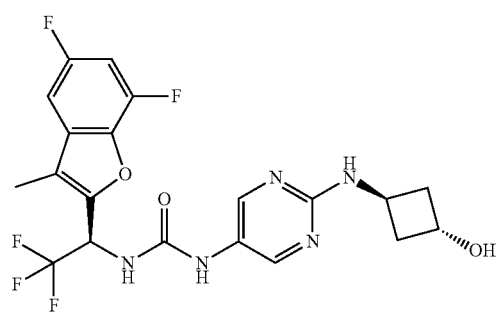 [SMILES: Cc1c([C@@H](NC(=O)Nc2cnc(N[C@H]3C[C@H](O)C3)nc2)C(F)(F)F)oc2c(F)cc(F)cc12]
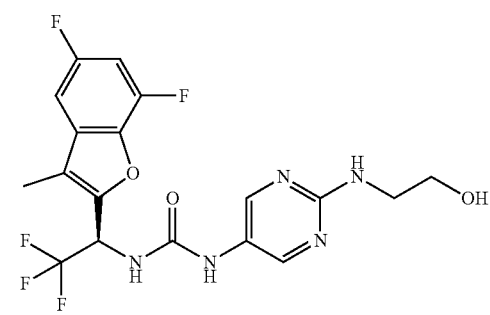 [SMILES: Cc1c([C@@H](NC(=O)Nc2cnc(NCCO)nc2)C(F)(F)F)oc2c(F)cc(F)cc12]
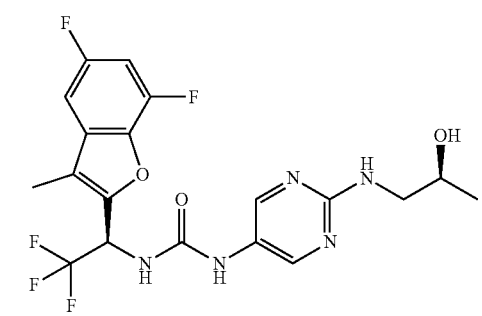 [SMILES: Cc1c([C@@H](NC(=O)Nc2cnc(NC[C@H](C)O)nc2)C(F)(F)F)oc2c(F)cc(F)cc12]
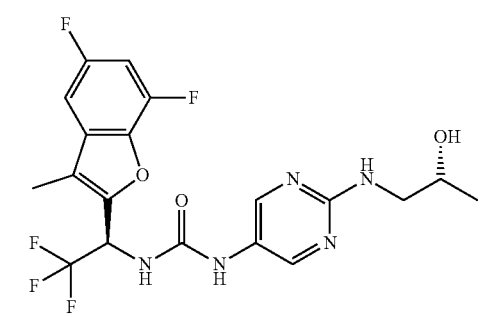

419
-continued
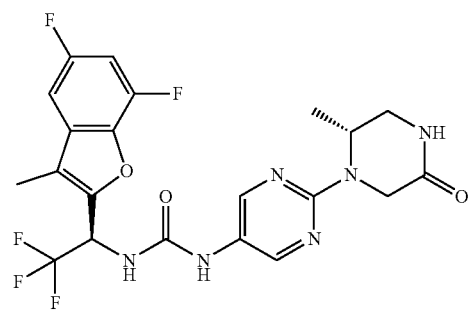 [SMILES: Cc1c([C@@H](NC(=O)Nc2cnc(N3CC(=O)NC[C@H]3C)nc2)C(F)(F)F)oc2c(F)cc(F)cc12]
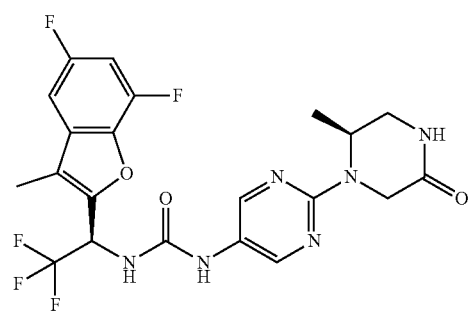 [SMILES: Cc1c([C@@H](NC(=O)Nc2cnc(N3CC(=O)NC[C@@H]3C)nc2)C(F)(F)F)oc2c(F)cc(F)cc12]
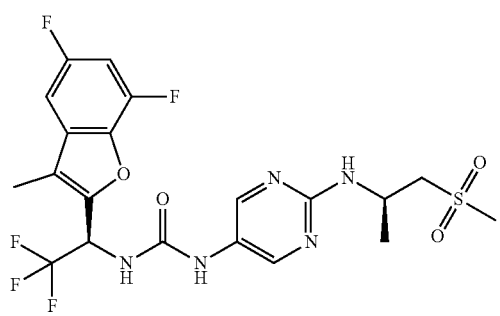
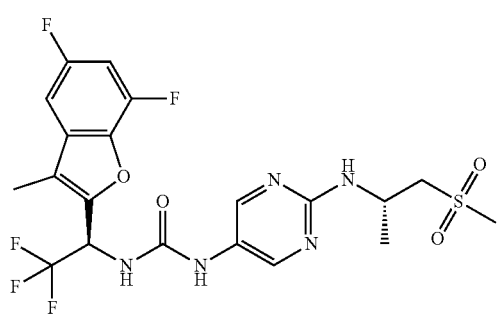
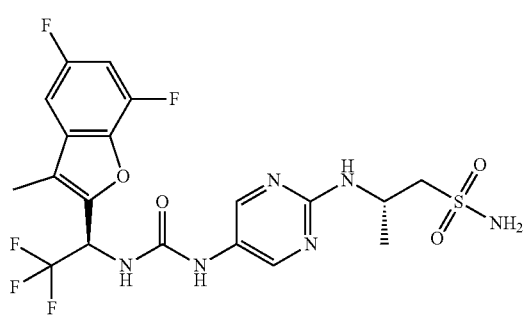 [SMILES: Cc1c([C@@H](NC(=O)Nc2cnc(N[C@@H](C)CS(N)(=O)=O)nc2)C(F)(F)F)oc2c(F)cc(F)cc12]
420
-continued
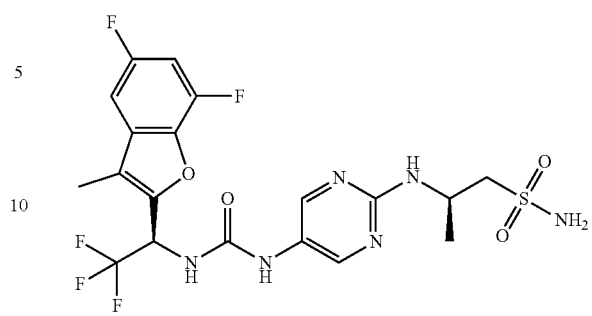
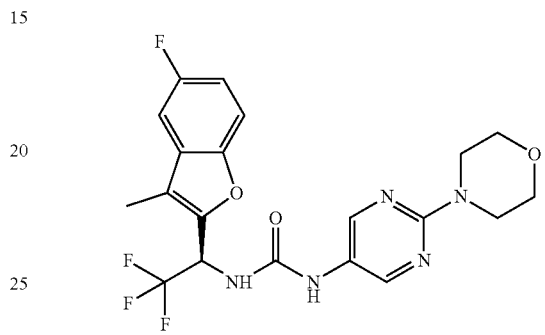
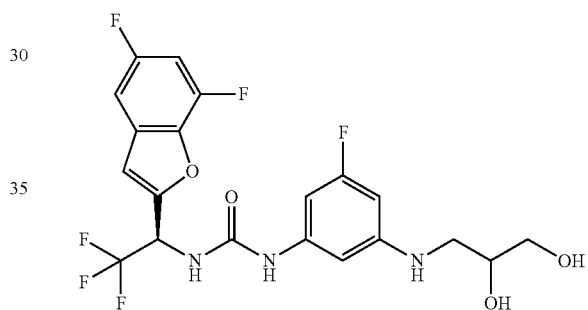
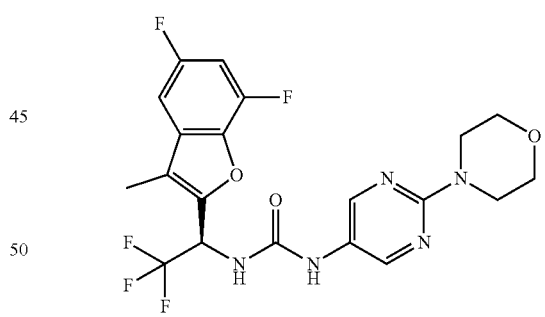
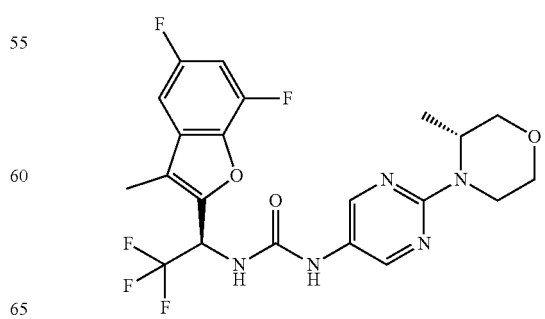

421
-continued
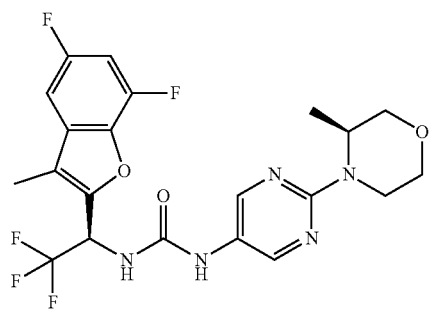 [SMILES: Cc1c([C@@H](NC(=O)Nc2cnc(N3CCOC[C@@H]3C)nc2)C(F)(F)F)oc2c(F)cc(F)cc12]
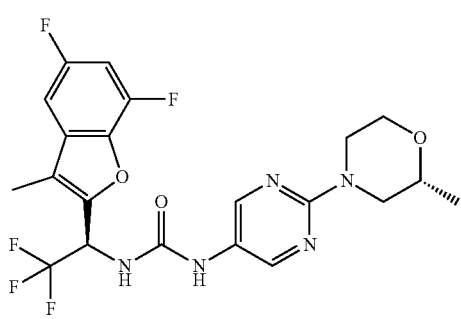
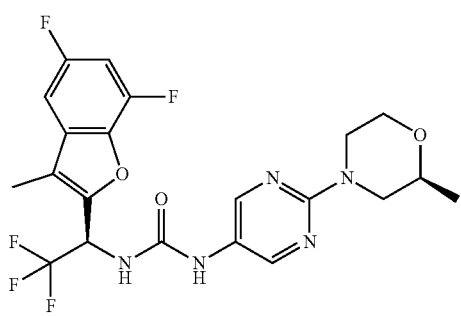
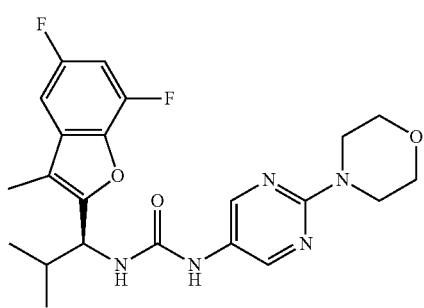 [SMILES: Cc1c([C@@H](NC(=O)Nc2cnc(N3CCOCC3)nc2)C(C)C)oc2c(F)cc(F)cc12]
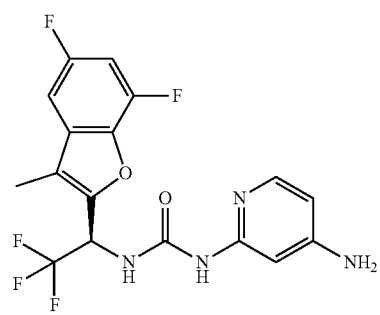 [SMILES: Cc1c([C@@H](NC(=O)Nc2cc(N)ccn2)C(F)(F)F)oc2c(F)cc(F)cc12]
422
-continued
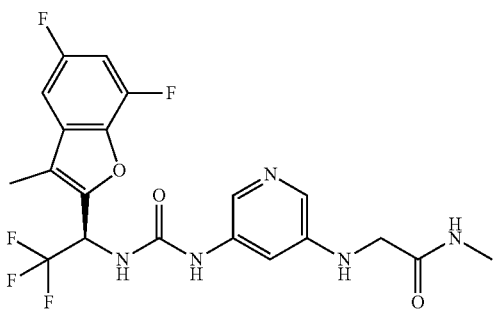
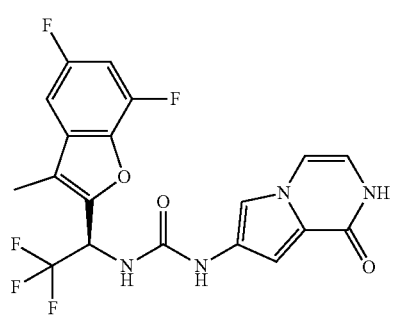 [SMILES: Cc1c([C@@H](NC(=O)Nc2cc3c(=O)[nH]ccn3c2)C(F)(F)F)oc2c(F)cc(F)cc12]
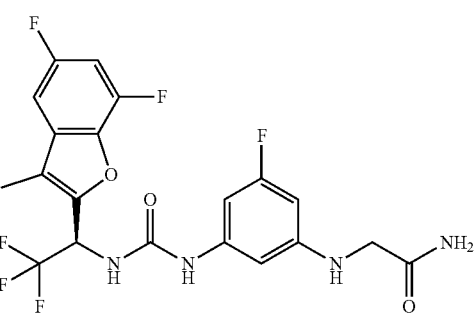 [SMILES: Cc1c([C@@H](NC(=O)Nc2cc(F)cc(NCC(N)=O)c2)C(F)(F)F)oc2c(F)cc(F)cc12]
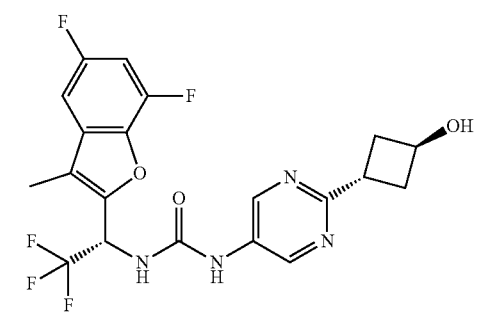 [SMILES: Cc1c([C@H](NC(=O)Nc2cnc([C@H]3C[C@H](O)C3)nc2)C(F)(F)F)oc2c(F)cc(F)cc12]
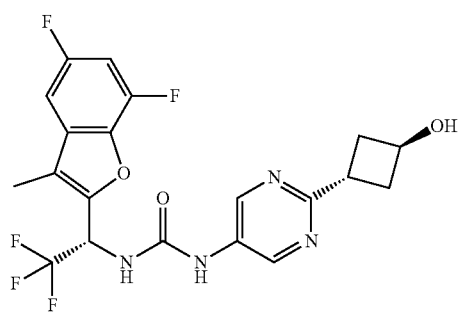

423
-continued
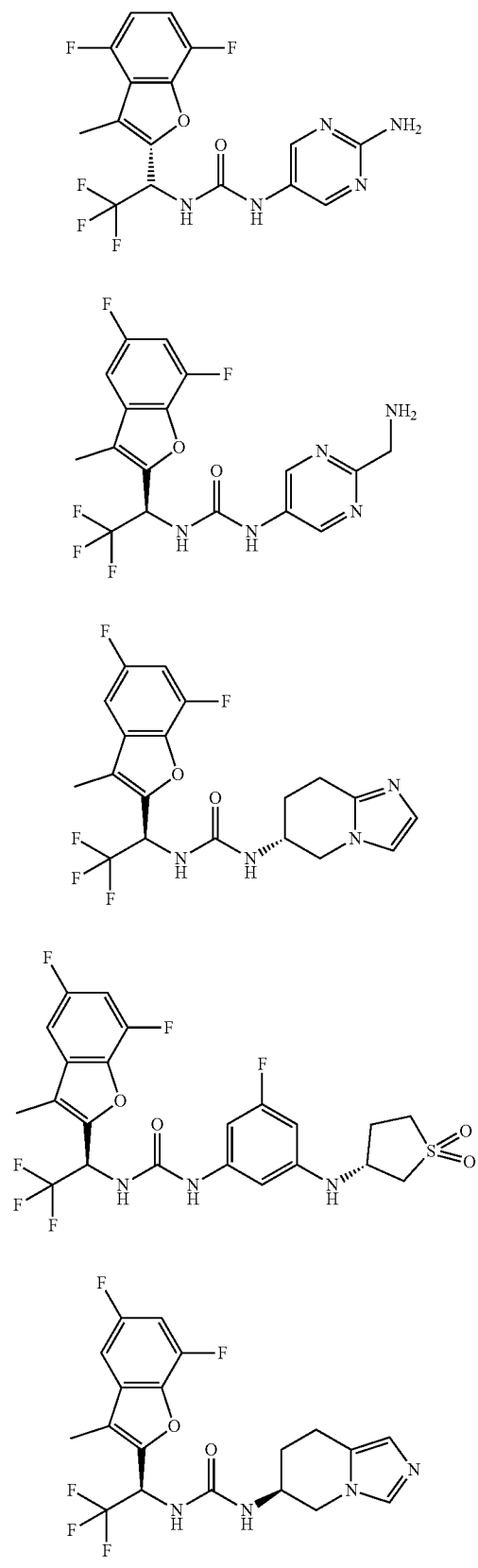
424
-continued
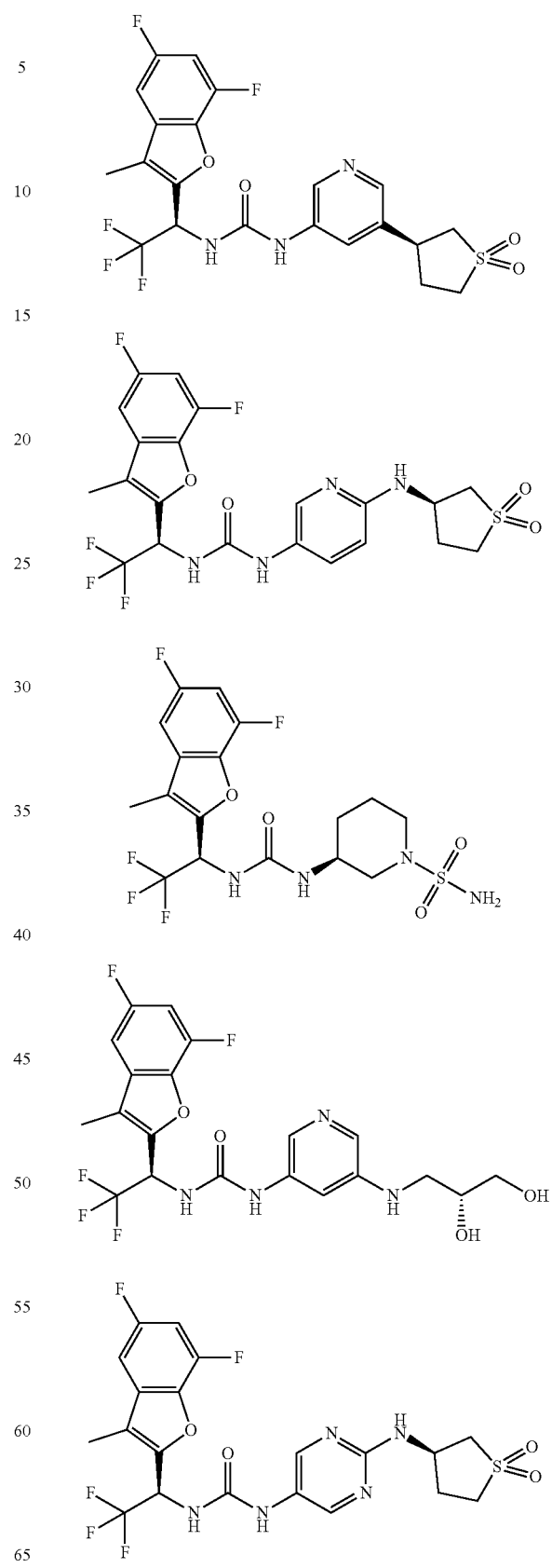

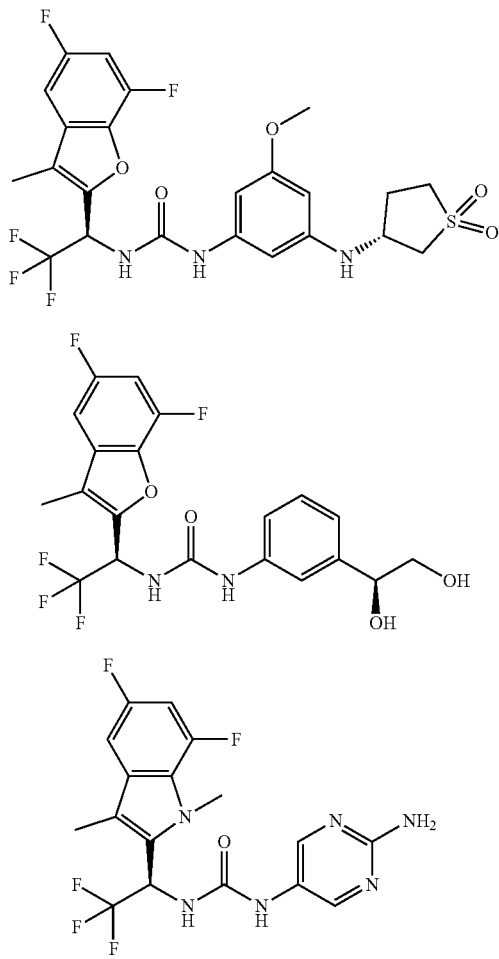

Pharmaceutical Compositions and Administration

General

In some embodiments, a chemical entity (e.g., a compound that inhibits PI3Kα, or a pharmaceutically acceptable salt thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from pharmaceutically acceptable excipients may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22d Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmaceutically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating pharmaceutically acceptable excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such pharmaceutically acceptable excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments, the pharmaceutically acceptable excipients are sterile and generally free of undesirable matter. These compositions can be sterilized by conventional, well-known sterilization techniques. For various oral dosage forms, pharmaceutically acceptable excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and pharmaceutically acceptable excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

Indications

Provided herein are methods for inhibiting phosphatidylinositol 4,5-bisphosphate 3-kinase isoform alpha (PI3Kα), encoded by PIK3CA gene. For example, provided herein are inhibitors of PI3Kα useful for treating or preventing diseases or disorders associated with dysregulation of a PIK3CA gene, a PI3Kα protein, or the expression or activity or level of any of the same (i.e., a PI3Kα-associated disease or disorder), such as PIK3CA-related overgrowth syndromes ((PROS), see, e.g., Venot, et al., Nature, 558, 540-546 (2018)), brain disorders (e.g., as macrocephaly-capillary malformation (MCAP) and hemimegalencephaly), congenital lipomatous (e.g., overgrowth of vascular malformations), epidermal nevi and skeletal/spinal anomalies (e.g., CLOVES syndrome) and fibroadipose hyperplasia (FH), or cancer (e.g., PI3Kα-associated cancer).

A "PI3Kα inhibitor" as used herein includes any compound exhibiting PI3Kα inactivation activity (e.g., inhibiting or decreasing). In some embodiments, a PI3Kα inhibitor can be selective for a PI3Kα having one or more mutations.

The ability of test compounds to act as inhibitors of PI3Kα may be demonstrated by assays known in the art. The activity of the compounds and compositions provided herein as PI3Kα inhibitors can be assayed in vitro, in vivo, or in a cell line. In vitro assays include assays that determine inhibition of the kinase. Alternate in vitro assays quantitate the ability of the inhibitor to bind to the protein kinase and can be measured either by radio labeling the compound prior to binding, isolating the compound/kinase complex and determining the amount of radio label bound, or by running a competition experiment where new compounds are incubated with the kinase bound to known radio ligands.

Potency of a PI3Kα inhibitor as provided herein can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining a PI3Kα-dependent phosphorylation level, in vitro or in vivo (e.g., in tumor cells, A594 cells, U2OS cells, A431 cells, Ba/F3 cells, or 3T3 cells expressing a wild type PI3Kα, a mutant PI3Kα, or a fragment of any thereof).

Potency of a PI3Kα inhibitor as provided herein can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a PI3Kα-dependent phosphorylation level, in vitro or in vivo (e.g., in tumor cells, SKOV3, T47D, CAL33, BT20, HSC2, OAW42, NCI, HCC1954, NCIH1048, Detroit562, A594 cells, U2OS cells, A431 cells, A594 cells, U2OS cells, Ba/F3 cells, or 3T3 cells expressing a wild type PI3Kα, a mutant PI3Kα, or a fragment of any thereof).

The selectivity between wild type PI3Kα and PI3Kα containing one or more mutations as described herein can also be measured using in vitro assays such as surface plasmon resonance and fluorence-based binding assays, and cellular assays such as the levels of pAKT, abiomarker of PI3Kα activity, or proliferation assays where cell proliferation is dependent on mutant PI3Kα kinase activity.

In some embodiments, the compounds provided herein can exhibit potent and selective inhibition of PI3Kα. For example, the compounds provided herein can bind to the helical phosphatidylinositol kinase homology domain catalytic domain of PI3Kα. In some embodiments, the compounds provided herein can exhibit nanomolar potency against a PI3Kα kinase including one or more mutations, for example, the mutations in Tables 1 and 2.

In some embodiments, the compounds provided herein can exhibit potent and selective inhibition of mutant PI3Kα. For example, the compounds provided herein can bind to an allosteric site in the kinase domain. In some embodiments, the compounds provided herein can exhibit nanomolar potency against a PI3Kα protein including an activating mutation, with minimal activity against related kinases (e.g., wild type PI3Kα). Inhibition of wild type PI3Kα can cause undesirable side effects (e.g., hyperglycemia and skin rashes) that can impact quality of life and compliance. In some cases, the inhibition of wild type PI3Kα can lead to dose limiting toxicities. See, e.g., Hanker, et al., Cancer Disc. 2019, 9, 4, 482-491. Mutant-selective inhibitors may reduce the risk of such dose limiting toxicities, including hyperglycemia, observed with inhibitors of wild type PI3Kα.

In some embodiments, the compounds of Formula (I), or a pharmaceutically acceptable salt thereof, can selectively target PI3Kα. For example, a compound of Formula (I), or a pharmaceutically acceptable salt thereof, can selectively target PI3Kα over another kinase or non-kinase target.

In some embodiments, a compound of Formula (I), or a pharmaceutically acceptable salt thereof, can exhibit greater inhibition of PI3Kα containing one or more mutations as described herein (e.g., one or more mutations as described in Table 1 or Table 2) relative to inhibition of wild type PI3Kα. In some embodiments, a compound of Formula (I), or a pharmaceutically acceptable salt thereof can exhibit at least 2-fold, 3-fold, 5-fold, 10-fold, 25-fold, 50-fold or 100-fold greater inhibition of PI3Kα containing one or more mutations as described herein relative to inhibition of wild type PI3Kα. In some embodiments, a compound of Formula (I), or a pharmaceutically acceptable salt thereof, can exhibit up to 1000-fold greater inhibition of PI3Kα containing one or more mutations as described herein relative to inhibition of wild type PI3Kα. In some embodiments, a compound of Formula (I), or a pharmaceutically acceptable salt thereof, can exhibit up to 10000-fold greater inhibition of PI3Kα having a combination of mutations described herein relative to inhibition of wild type PI3Kα.

In some embodiments, a compound of Formula (I), or a pharmaceutically acceptable salt thereof, can exhibit from about 2-fold to about 10-fold greater inhibition of PI3Kα containing one or more mutations as described herein relative to inhibition of wild type PI3Kα. In some embodiments, a compound of Formula (I), or a pharmaceutically acceptable salt thereof, can exhibit from about 10-fold to about 100-fold greater inhibition of PI3Kα containing one or more mutations as described herein relative to inhibition of wild type PI3Kα. In some embodiments, a compound of Formula (I), or a pharmaceutically acceptable salt thereof, can exhibit from about 100-fold to about 1000-fold greater inhibition of PI3Kα containing one or more mutations as described herein relative to inhibition of wild type PI3Kα. In some embodiments, a compound of Formula (I), or a pharmaceutically acceptable salt thereof, can exhibit from about 1000-fold to about 10000-fold greater inhibition of PI3Kα containing one or more mutations as described herein relative to inhibition of wild type PI3Kα.

Compounds of Formula (I), or pharmaceutically acceptable salts thereof, are useful for treating diseases and disorders which can be treated with a PI3Kα inhibitor, such as PI3Kα-associated diseases and disorders, e.g., PIK3CA-related overgrowth syndromes (PROS) and proliferative disorders such as cancers, including hematological cancers and solid tumors (e.g., advanced or metastatic solid tumors).

In some embodiments, the subject has been identified or diagnosed as having a cancer with a dysregulation of a PIK3CA gene, a PI3Kα protein, or expression or activity, or level of any of the same (a PI3Kα-associated cancer) (e.g., as determined using a regulatory agency-approved, e.g., FDA-approved, assay or kit). In some embodiments, the subject has a tumor that is positive for a dysregulation of a PIK3CA gene, a PI3Kα protein, or expression or activity, or level of any of the same (e.g., as determined using a regulatory agency-approved assay or kit). For example, the subject has a tumor that is positive for a mutation as described in Table 1 or Table 2. The subject can be a subject with a tumor(s) that is positive for a dysregulation of a PIK3CA gene, a PI3Kα protein, or expression or activity, or level of any of the same (e.g., identified as positive using a regulatory agency-approved, e.g., FDA-approved, assay or kit). The subject can be a subject whose tumors have a dysregulation of a PIK3CA gene, a PI3Kα protein, or expression or activity, or a level of the same (e.g., where the tumor is identified as such using a regulatory agency-approved, e.g., FDA-approved, kit or assay). In some embodiments, the subject is suspected of having a PI3Kα-associated cancer. In some embodiments, the subject has a clinical record indicating that the subject has a tumor that has a dysregulation of a PIK3CA gene, a PI3Kα protein, or expression or activity, or level of any of the same (and optionally the clinical record indicates that the subject should be treated with any of the compositions provided herein).

In some embodiments, the subject is a pediatric subject. The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula (I), or pharmaceutically acceptable salts thereof, are useful for preventing diseases and disorders as defined herein (for example, PIK3CA-related overgrowth syndromes (PROS) and cancer). The term "preventing" as used herein means to delay the onset, recurrence or spread, in whole or in part, of the disease or condition as described herein, or a symptom thereof.

The term "PI3Kα-associated disease or disorder" as used herein refers to diseases or disorders associated with or having a dysregulation of a PIK3CA gene, a PI3Kα protein, or the expression or activity or level of any (e.g., one or more) of the same (e.g., any of the types of dysregulation of a PIK3CA gene, or a PI3Kα protein, or the expression or activity or level of any of the same described herein). Non-limiting examples of a PI3Kα-associated disease or disorder include, for example, PIK3CA-related overgrowth syndromes (PROS), brain disorders (e.g., as macrocephaly-capillary malformation (MCAP) and hemimegalencephaly), congenital lipomatous (e.g., overgrowth of vascular malformations), epidermal nevi and skeletal/spinal anomalies (e.g., CLOVES syndrome) and fibroadipose hyperplasia (FH), or cancer (e.g., PI3Kα-associated cancer).

The term "PI3Kα-associated cancer" as used herein refers to cancers associated with or having a dysregulation of a PIK3CA gene, a PI3Kα protein, or expression or activity, or level of any of the same. Non-limiting examples of PI3Kα-associated cancer are described herein.

The phrase "dysregulation of a PIK3CA gene, a PI3Kα protein, or the expression or activity or level of any of the same" refers to a genetic mutation (e.g., a mutation in a PIK3CA gene that results in the expression of a PI3Kα that includes a deletion of at least one amino acid as compared to a wild type PI3Kα, a mutation in a PIK3CA gene that results in the expression of PI3Kα with one or more point mutations as compared to a wild type PI3Kα, a mutation in a PIK3CA gene that results in the expression of PI3Kα with at least one inserted amino acid as compared to a wild type PI3Kα, a gene duplication that results in an increased level of PI3Kα in a cell, or a mutation in a regulatory sequence (e.g., a promoter and/or enhancer) that results in an increased level of PI3Kα in a cell), an alternative spliced version of PI3Kα mRNA that results in PI3Kα having a deletion of at least one amino acid in the PI3Kα as compared to the wild type PI3Kα), or increased expression (e.g., increased levels) of a wild type PI3Kα in a mammalian cell due to aberrant cell signaling and/or dysregulated autocrine/paracrine signaling (e.g., as compared to a control non-cancerous cell). As another example, a dysregulation of a PIK3CA gene, a PI3Kα protein, or expression or activity, or level of any of the same, can be a mutation in a PIK3CA gene that encodes a PI3Kα that is constitutively active or has increased activity as compared to a protein encoded by a PIK3CA gene that does not include the mutation. Non-limiting examples of PI3Kα point mutations/substitutions/insertions/deletions are described in Table 1 and Table 2.

The term "activating mutation" in reference to PI3Kα describes a mutation in a PIK3CA gene that results in the expression of PI3Kα that has an increased kinase activity, e.g., as compared to a wild type PI3Kα, e.g., when assayed under identical conditions. For example, an activating mutation can be a mutation in a PIK3CA gene that results in the expression of a PI3Kα that has one or more (e.g., two, three, four, five, six, seven, eight, nine, or ten) amino acid substitutions (e.g., any combination of any of the amino acid substitutions described herein) that has increased kinase activity, e.g., as compared to a wild type a PI3Kα, e.g., when assayed under identical conditions. In another example, an activating mutation can be a mutation in a PIK3CA that results in the expression of a PI3Kα that has one or more (e.g., two, three, four, five, six, seven, eight, nine, or ten) amino acids deleted, e.g., as compared to a wild type PI3Kα, e.g., when assayed under identical conditions. In another example, an activating mutation can be a mutation in a PIK3CA gene that results in the expression of a PI3Kα that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wild type PI3Kα, e.g., the exemplary wild type PI3Kα described herein, e.g., when assayed under identical conditions. Additional examples of activating mutations are known in the art.

The term "wild type" or "wild-type" describes a nucleic acid (e.g., a PIK3CA gene or a PI3Kα mRNA) or protein (e.g., a PI3Kα) sequence that is typically found in a subject that does not have a disease or disorder related to the reference nucleic acid or protein.

The term "wild type PI3Kα" or "wild-type PI3Kα" describes a normal PI3Kα nucleic acid (e.g., a PIK3CA or PI3Kα mRNA) or protein that is found in a subject that does not have a PI3Kα-associated disease, e.g., a PI3Kα-associated cancer (and optionally also does not have an increased risk of developing a PI3Kα-associated disease and/or is not suspected of having a PI3Kα-associated disease), or is found in a cell or tissue from a subject that does not have a PI3Kα-associated disease, e.g., a PI3Kα-associated cancer (and optionally also does not have an increased risk of developing a PI3Kα-associated disease and/or is not suspected of having a PI3Kα-associated disease).

Provided herein is a method of treating cancer (e.g., a PI3Kα-associated cancer) in a subject in need of such treatment, the method comprising administering to the subject a therapeutically effective amount of a compound of Formula (I), or a pharmaceutically acceptable salt thereof, or a pharmaceutical composition thereof. For example, provided herein are methods for treating PI3Kα-associated cancer in a subject in need of such treatment, the method comprising a) detecting a dysregulation of PIK3CA gene, a PI3Kα protein, or the expression or activity or level of any of the same in a sample from the subject; and b) administering a therapeutically effective amount of a compound of Formula (I), or a pharmaceutically acceptable salt thereof. In some embodiments, the dysregulation of a PIK3CA gene, a PI3Kα protein, or the expression or activity or level of any of the same includes one or more a PI3Kα protein substitutions/point mutations/insertions. Non-limiting examples of PI3Kα protein substitutions/insertions/deletions are described in Table 1 and Table 2.

In some embodiments, the PI3Kα protein substitution/insertion/deletion is selected from the group consisting of E542A, E542G, E542K, E542Q, E542V, E545A, E545D, E545G, E545K, E545Q, M1043I, M1043L, M1043T, M1043V, H1047L, H1047Q, H1047R, H1047Y, G1049R, and combinations thereof. In some embodiments, the PI3Kα protein substitution/insertion/deletion is H1047X, where X is any amino acid.

In some embodiments of any of the methods or uses described herein, the cancer (e.g., PI3Kα-associated cancer) is selected from a hematological cancer and a solid tumor.

In some embodiments of any of the methods or uses described herein, the cancer (e.g., PI3Kα-associated cancer) is selected from breast cancer (including both HER2$^+$ and HER2$^-$ breast cancer, ER$^+$ breast cancer, and triple negative breast cancer), endometrial cancer, lung cancer (including adenocarcinoma lung cancer and squamous cell lung carcinoma), esophageal squamous cell carcinoma, ovarian cancer, colorectal cancer, esophagastric adenocarcinoma, bladder cancer, head and neck cancer (including head and neck squamous cell cancers such as oropharyngeal squamous cell carcinoma), thyroid cancer, glioma, cervical cancer, lymphangioma, meningioma, melanoma (including uveal melanoma), kidney cancer, pancreatic neuroendocine neoplasms (pNETs), stomach cancer, esophageal cancer, acute myeloid leukemia, relapsed and refractory multiple myeloma, and pancreatic cancer.

In some embodiments of any of the methods or uses described herein, the cancer (e.g., PI3Kα-associated cancer) is selected from breast cancer (including both HER2$^+$ and HER2$^-$ breast cancer, ER$^+$ breast cancer, and triple negative breast cancer), colon cancer, rectal cancer, colorectal cancer, ovarian cancer, lymphangioma, meningioma, head and neck squamous cell cancer (including oropharyngeal squamous cell carcinoma), melanoma (including uveal melanoma), kidney cancer, pancreatic neuroendocine neoplasms (pNETs), stomach cancer, esophageal cancer, acute myeloid leukemia, relapsed and refractory multiple myeloma, pancreatic cancer, lung cancer (including adenocarcinoma lung cancer and squamous cell lung carcinoma), and endometrial cancer.

In some embodiments of any of the methods or uses described herein, the cancer (e.g., PI3Kα-associated cancer) is selected from breast cancer, lung cancer, endometrial cancer, esophageal squamous cell carcinoma, ovarian cancer, colorectal cancer, esophagastric adenocarcinoma, bladder cancer, head and neck cancer, thyroid cancer, glioma, and cervical cancer.

In some embodiments of any of the methods or uses described herein, the PI3Kα-associated cancer is breast cancer. In some embodiments of any of the methods or uses described herein, the PI3Kα-associated cancer is colorectal cancer. In some embodiments of any of the methods or uses described herein, the PI3Kα-associated cancer is endometrial cancer. In some embodiments of any of the methods or uses described herein, the PI3Kα-associated cancer is lung cancer.

In some embodiments of any of the methods or uses described herein, the PI3Kα-associated cancer is selected from the cancers described in Table 1 and Table 2.

TABLE 1

PI3Kα Protein Amino Acid Substitutions/Insertions/Deletions[A]

| Amino Acid Position | Non-Limiting Exemplary Mutations | Non-Limiting Exemplary PI3Kα Associated Cancer(s) |
|---|---|---|
| 1 | M1 (Translation Start Site) | Astrocytoma<br>Glioblastoma Multiforme |
| 4 | R4* (Nonsense Mutation) | Glioblastoma Multiforme |
| 9 | E9G | Stomach Adenocarcinoma |
| 10 | L10_M16del | Glioblastoma Multiforme |
| 11 | W11L, W11S, W11_P18del (In Frame Deletion) | Lung Adenocarcinoma, Oligodendroglioma, Uterine Endometrioid Carcinoma |
| 12 | G12D | Uterine Endometrioid Carcinoma |
| 13 | I13T | Colon Adenocarcinoma |
| 19 | R19I | Uterine Endometrioid Carcinoma |
| 27 | P27T | Hepatocellular Carcinoma |
| 36 | C36Y | Uterine Endometrioid Carcinoma |
| 38 | R38C, R38H, R38L, R38S | Uterine Endometrioid Carcinoma<br>Papillary Renal Cell Carcinoma<br>Papillary Stomach Adenocarcinoma<br>Mucinous Adenocarcinoma of the Colon and Rectum<br>Glioblastoma Multiforme<br>Cervical Squamous Cell Carcinoma<br>Hepatocellular Carcinoma<br>Uterine Endometrioid Carcinoma<br>Diffuse Type Stomach Adenocarcinoma<br>Lung Squamous Cell Carcinoma<br>Uterine Endometrioid Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| 39 | E39G, E39K | Uterine Endometrioid Carcinoma Glioblastoma Multiforme |
| 57 | P57L | Cutaneous Melanoma |
| 65 | E65K | Lung Squamous Cell Carcinoma |
| 66 | S66C | Bladder Urothelial Carcinoma |
| 69 | I69N | Colon Adenocarcinoma |
| 71 | V71I | Head and Neck Squamous Cell Carcinoma |
| 75 | Q75E | Bladder Urothelial Carcinoma Cervical Squamous Cell Carcinoma Head and Neck Squamous Cell Carcinoma |
| 78 | E78* (nonsense mutation) | Lung Squamous Cell Carcinoma |
| 80 | E80K | Uterine Mixed Endometrial Carcinoma |
| 81 | E81* (nonsense mutation), E81del (in frame deletion), E81K | Colon Adenocarcinoma Glioblastoma Multiforme Colon Adenocarcinoma Uterine Serous Carcinoma/Uterine Papillary Serous Carcinoma Glioblastoma Multiforme Uterine Endometrioid Carcinoma Lung Squamous Cell Carcinoma Mucinous Adenocarcinoma of the Colon and Rectum Breast Invasive Ductal Carcinoma Cervical Squamous Cell Carcinoma Head and Neck Squamous Cell Carcinoma |
| 83 | F83L, F83S | Breast Invasive Lobular Carcinoma |
| 84 | D84H | Lung Adenocarcinoma |
| 86 | T86S | Hepatocellular Carcinoma |
| 87 | R87T | Lung Adenocarcinoma |
| 88 | R88Q | Breast Invasive Ductal Carcinoma Rectal Adenocarcinoma Colon Adenocarcinoma Prostate Adenocarcinoma Cervical Squamous Cell Carcinoma Uterine Carcinosarcoma/Uterine Malignant Mixed Mullerian Tumor Tubular Stomach Adenocarcinoma Oligodendroglioma Mucinous Stomach Adenocarcinoma Glioblastoma Multiforme Stomach Adenocarcinoma Uterine Endometrioid Carcinoma Uterine Mixed Endometrial Carcinoma Head and Neck Squamous Cell Carcinoma Mucinous Adenocarcinoma of the Colon and Rectum Breast Invasive Lobular Carcinoma Intestinal Type Stomach Adenocarcinoma Bladder Urothelial Carcinoma |
| 90 | C90G, C90R, C90Y | Glioblastoma Multiforme Cervical Squamous Cell Carcinoma |
| 93 | R93P, R93Q, R93W | Mucinous Adenocarcinoma of the Colon and Rectum Stomach Adenocarcinoma Glioblastoma Multiforme Uterine Endometrioid Carcinoma Tubular Stomach Adenocarcinoma Mucinous Stomach Adenocarcinoma Bladder Urothelial Carcinoma Cervical Squamous Cell Carcinoma Colon Adenocarcinoma |
| 102 | I102del | Uterine Endometrioid Carcinoma |
| 103 | E103G, E103_G106delinsD (In Frame Deletion), E103_P104del (In Frame Deletion) | Glioblastoma Multiforme Breast Invasive Ductal Carcinoma |
| 104 | P104L, P104R, P104T | Breast Invasive Ductal Carcinoma Head and Neck Squamous Cell Carcinoma Lung Adenocarcinoma Colon Adenocarcinoma Uterine Serous Carcinoma/Uterine Papillary Serous Carcinoma |
| 105 | V105del, V105_R108del | Uterine Endometrioid Carcinoma Breast Invasive Ductal Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| 106 | G106D, G106R, G106S, G106V, G106_R108del (In Frame Deletion), G106_N107del (In Frame Deletion) | Uterine Mixed Endometrial Carcinoma<br>Breast Invasive Ductal Carcinoma<br>Mucinous Adenocarcinoma of the Colon and Rectum<br>Mucinous Carcinoma<br>Oligodendroglioma<br>Uterine Carcinosarcoma/Uterine Malignant Mixed Mullerian Tumor<br>Uterine Serous Carcinoma/Uterine Papillary Serous Carcinoma<br>Uterine Endometrioid Carcinoma<br>Rectal Adenocarcinoma<br>Lung Squamous Cell Carcinoma<br>Cervical Squamous Cell Carcinoma<br>Tubular Stomach Adenocarcinoma<br>Uterine Endometrioid Carcinoma |
| 107 | N107S | Uterine Endometrioid Carcinoma<br>Lung Adenocarcinoma |
| 108 | R108C, R108H, R108L | Prostate Adenocarcinoma<br>Uterine Endometrioid Carcinoma<br>Glioblastoma Multiforme<br>Uterine Carcinosarcoma/Uterine Malignant Mixed Mullerian Tumor<br>Mucinous Adenocarcinoma of the Colon and Rectum<br>Tubular Stomach Adenocarcinoma<br>Colon Adenocarcinoma<br>Uterine Serous Carcinoma/Uterine Papillary Serous Carcinoma<br>Uterine Mixed Endometrial Carcinoma<br>Breast Invasive Ductal Carcinoma<br>Lung Squamous Cell Carcinoma |
| 109 | E109_I112delinsD (In Frame Deletion) | Breast Invasive Ductal Carcinoma |
| 110 | E110del | Uterine Endometrioid Carcinoma<br>Oligodendroglioma<br>Breast Invasive Lobular Carcinoma<br>Breast Invasive Ductal Carcinoma<br>Uterine Mixed Endometrial Carcinoma<br>Colon Adenocarcinoma<br>Head and Neck Squamous Cell Carcinoma<br>Lung Adenocarcinoma<br>Papillary Thyroid Cancer |
| 111 | K111del, K111E, K111N, K111R, K111_L113del (In Frame Deletion) | Uterine Endometrioid Carcinoma<br>Breast Invasive Ductal Carcinoma<br>Oligodendroglioma<br>Head and Neck Squamous Cell Carcinoma<br>Colon Adenocarcinoma<br>Intestinal Type Stomach Adenocarcinoma<br>Stomach Adenocarcinoma<br>Uterine Endometrioid Carcinoma<br>Lung Adenocarcinoma<br>Esophageal Adenocarcinoma<br>Lung Squamous Cell Carcinoma<br>Glioblastoma Multiforme |
| 113 | L113del | Uterine Endometrioid Carcinoma |
| 115 | R115L, R115P | Serous Ovarian Cancer<br>Bladder Urothelial Carcinoma<br>Uterine Carcinosarcoma/Uterine Malignant Mixed Mullerian Tumor<br>Uterine Endometrioid Carcinoma<br>Uterine Serous Carcinoma/Uterine Papillary Serous Carcinoma<br>Rectal Adenocarcinoma<br>Cervical Squamous Cell Carcinoma |
| 116 | E116K | Rectal Adenocarcinoma |
| 118 | G118D | Glioblastoma Multiforme<br>Breast Invasive Ductal Carcinoma<br>Uterine Endometrioid Carcinoma<br>Bladder Urothelial Carcinoma<br>Oligodendroglioma<br>Esophageal Adenocarcinoma<br>Astrocytoma<br>Lung Squamous Cell Carcinoma<br>Breast Invasive Lobular Carcinoma<br>Uterine Serous Carcinoma/Uterine Papillary Serous |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| | | Carcinoma |
| | | Mucinous Carcinoma |
| | | Uterine Mixed Endometrial Carcinoma |
| | | Stomach Adenocarcinoma |
| | | Pancreatic Adenocarcinoma |
| | | Papillary Thyroid Cancer |
| | | Rectal Adenocarcinoma |
| 123 | M123I | Lung Adenocarcinoma |
| 124 | P124A | Lung Adenocarcinoma |
| 151 | V151M | Bladder Urothelial Carcinoma |
| | | Astrocytoma |
| 165 | Y165H | Uterine Mixed Endometrial Carcinoma |
| 170 | N170S | Uterine Endometrioid Carcinoma |
| 182 | Y182H | Stomach Adenocarcinoma |
| 213 | H213N | Cutaneous Melanoma |
| 224 | A224S | Colon Adenocarcinoma |
| 239 | L239R | Colon Adenocarcinoma |
| 258 | D258N | Rectal Adenocarcinoma |
| 262 | L262I | Cutaneous Melanoma |
| 266 | P266T | Uterine Endometrioid Carcinoma |
| 267 | L267M | Cutaneous Melanoma |
| 272 | Y272* (Nonsense Mutation) | Renal Clear Cell Carcinoma |
| 274 | R274K | Bladder Urothelial Carcinoma |
| 279 | L279I | Uterine Endometrioid Carcinoma |
| 282 | M282V | Uterine Endometrioid Carcinoma |
| 292 | S292I | Glioblastoma Multiforme |
| 296 | Q296E | Lung Adenocarcinoma |
| 300 | D300V | Lung Squamous Cell Carcinoma |
| 310 | R310C | Uterine Endometrioid Carcinoma |
| 322 | T322A | Uterine Endometrioid Carcinoma |
| 335 | R335G | Head and Neck Squamous Cell Carcinoma |
| 337 | K337N | Rectal Adenocarcinoma |
| 339 | L339I | Cervical Squamous Cell Carcinoma |
| | | Uterine Endometrioid Carcinoma |
| 342 | T342S | Lung Adenocarcinoma |
| 344 | V344A, V344G, V344M | Uterine Endometrioid Carcinoma |
| | | Mucinous Adenocarcinoma of the Colon and Rectum |
| | | Colon Adenocarcinoma |
| | | Cervical Squamous Cell Carcinoma |
| | | Rectal Adenocarcinoma |
| | | Head and Neck Squamous Cell Carcinoma |
| | | Breast Invasive Carcinoma (NOS) |
| | | Uterine Mixed Endometrial Carcinoma |
| | | Glioblastoma Multiforme |
| 345 | N345H, N345I, N345K, N345T, N345Y | Breast Invasive Lobular Carcinoma |
| | | Uterine Carcinosarcoma/Uterine Malignant Mixed Mullerian Tumor |
| | | Uterine Serous Carcinoma/Uterine Papillary Serous Carcinoma |
| | | Uterine Endometrioid Carcinoma |
| | | Breast Invasive Carcinoma (NOS) |
| | | Lung Adenocarcinoma |
| | | Mucinous Adenocarcinoma of the Colon and Rectum |
| | | Bladder Urothelial Carcinoma |
| | | Colon Adenocarcinoma |
| | | Leiomyosarcoma |
| | | Glioblastoma Multiforme |
| | | Uterine Endometrioid Carcinoma |
| | | Seminoma |
| | | Tubular Stomach Adenocarcinoma |
| | | Breast Invasive Ductal Carcinoma |
| | | Head and Neck Squamous Cell Carcinoma |
| | | Stomach Adenocarcinoma |
| | | Diffuse Type Stomach Adenocarcinoma |
| | | Prostate Adenocarcinoma |
| | | Breast Invasive Ductal Carcinoma |
| | | Oligodendroglioma |
| 350 | D350G, D350N | Lung Squamous Cell Carcinoma |
| | | Breast Invasive Ductal Carcinoma |
| | | Uterine Endometrioid Carcinoma |
| | | Colon Adenocarcinoma |
| | | Uterine Endometrioid Carcinoma |
| | | Mucinous Stomach Adenocarcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| | | Lung Adenocarcinoma |
| | | Breast Invasive Lobular Carcinoma |
| 351 | I351T | Uterine Endometrioid Carcinoma |
| 357 | R357Q | Uterine Endometrioid Carcinoma |
| | | Mucinous Adenocarcinoma of the Colon and Rectum |
| | | Colon Adenocarcinoma |
| 359 | G359R | Uterine Endometrioid Carcinoma |
| 363 | G363A | Head and Neck Squamous Cell Carcinoma |
| 364 | G364R | Uterine Mixed Endometrial Carcinoma |
| | | Intestinal Type Stomach Adenocarcinoma |
| | | Colon Adenocarcinoma |
| 365 | E365K, E365V | Uterine Endometrioid Carcinoma |
| | | Bladder Urothelial Carcinoma |
| | | Mucinous Adenocarcinoma of the Colon and Rectum |
| | | Diffuse Type Stomach Adenocarcinoma |
| | | Breast Invasive Ductal Carcinoma |
| | | Head and Neck Squamous Cell Carcinoma |
| 366 | P366R | Breast Invasive Ductal Carcinoma |
| 378 | C378F, C378R, C378Y | Uterine Serous Carcinoma/Uterine Papillary Serous Carcinoma |
| | | Uterine Endometrioid Carcinoma |
| | | Oligodendroglioma |
| 379 | S379T | Cutaneous Melanoma |
| 380 | N380S | Diffuse Type Stomach Adenocarcinoma |
| 390 | D390N | Lung Adenocarcinoma |
| 392 | Y392H | Uterine Endometrioid Carcinoma |
| 398 | R398H | Breast Invasive Ductal Carcinoma |
| 399 | A399T | Cervical Squamous Cell Carcinoma |
| 401 | R401Q | Uterine Endometrioid Carcinoma |
| 405 | S405F | Intestinal Type Stomach Adenocarcinoma |
| 406 | I406V | Uterine Mixed Endometrial Carcinoma |
| 412 | R412Q | Stomach Adenocarcinoma |
| 417 | E417K | Bladder Urothelial Carcinoma |
| 418 | E418K | Uterine Endometrioid Carcinoma |
| | | Rectal Adenocarcinoma |
| | | Mucinous Carcinoma |
| | | Head and Neck Squamous Cell Carcinoma |
| | | Bladder Urothelial Carcinoma |
| 420 | C420R | Uterine Endometrioid Carcinoma |
| | | Tubular Stomach Adenocarcinoma |
| | | Lung Squamous Cell Carcinoma |
| | | Breast Invasive Ductal Carcinoma |
| | | Uterine Serous Carcinoma/Uterine Papillary Serous Carcinoma |
| | | Colon Adenocarcinoma |
| | | Intestinal Type Stomach Adenocarcinoma |
| | | Stomach Adenocarcinoma |
| | | Head and Neck Squamous Cell Carcinoma |
| | | Breast Invasive Carcinoma (NOS) |
| | | Astrocytoma |
| | | Cervical Squamous Cell Carcinoma |
| 432 | Y432C | Cervical Squamous Cell Carcinoma |
| 447 | P447_L455del (In frame Deletion) | Breast Invasive Ductal Carcinoma |
| 449 | P449L, P449S | Uterine Endometrioid Carcinoma |
| 450 | H450_P458del (In Frame Deletion) | Breast Invasive Ductal Carcinoma |
| 451 | G451R, G451V, G451_D454del (In Frame Deletion) | Head and Neck Squamous Cell Carcinoma |
| | | Bladder Urothelial Carcinoma |
| | | Colon Adenocarcinoma |
| 452 | L452_G460del (In Frame Deletion) | Breast Invasive Ductal Carcinoma |
| 453 | E453del, E453K, E453Q, E453_G460delins DDF (in Frame Deletion), E453_L455del | Oligodendroglioma |
| | | Uterine Mixed Endometrial Carcinoma |
| | | Intestinal Type Stomach Adenocarcinoma |
| | | Breast Invasive Ductal Carcinoma |
| | | Breast Invasive Lobular Carcinoma |
| | | Head and Neck Squamous Cell Carcinoma |
| | | Astrocytoma |
| | | Stomach Adenocarcinoma |
| | | Bladder Urothelial Carcinoma |
| | | Lung Squamous Cell Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| | | Cervical Squamous Cell Carcinoma |
| | | Lung Adenocarcinoma |
| | | Mucinous Carcinoma |
| | | Uterine Endometrioid Carcinoma |
| | | Uterine Serous Carcinoma/Uterine Papillary Serous Carcinoma |
| | | Glioblastoma Multiforme |
| | | Colon Adenocarcinoma |
| 454 | D454Y | Uterine Endometrioid Carcinoma |
| 455 | L455_G463del (In Frame Deletion) | Glioblastoma Multiforme |
| 463 | G463_N465delinsD (In Frame Deletion) | Uterine Endometrioid Carcinoma |
| 469 | E469A, E469delinsDK (In Frame Insertion) | Rectal Adenocarcinoma Breast Invasive Ductal Carcinoma |
| 471 | P471A, P471L | Bladder Urothelial Carcinoma |
| | | Rectal Adenocarcinoma |
| | | Uterine Endometrioid Carcinoma |
| | | Oligoastrocytoma |
| | | Hepatocellular Carcinoma |
| 474 | E474A | Prostate Adenocarcinoma |
| 475 | L475F | Cutaneous Melanoma |
| 479 | W479* | Uterine Endometrioid Carcinoma |
| 495 | H495L, H495Y | Lung Squamous Cell Carcinoma |
| | | Uterine Endometrioid Carcinoma |
| 499 | S499F | Bladder Urothelial Carcinoma |
| 519 | R519G | Head and Neck Squamous Cell Carcinoma |
| 520 | D520V | Breast Invasive Lobular Carcinoma |
| 522 | E522A | Uterine Endometrioid Carcinoma |
| 531 | L531V | Breast Invasive Ductal Carcinoma |
| 539 | P539R, P539S | Breast Invasive Ductal Carcinoma |
| | | Pancreatic Adenocarcinoma |
| | | Uterine Endometrioid Carcinoma |
| | | Lung Squamous Cell Carcinoma |
| 542 | E542A, E542G, E542K, E542Q, E542V | Uterine Serous Carcinoma/Uterine Papillary Serous Carcinoma |
| | | Uterine Endometrioid Carcinoma |
| | | Colon Adenocarcinoma |
| | | Prostate Adenocarcinoma |
| | | Breast Invasive Ductal Carcinoma |
| | | Breast Invasive Lobular Carcinoma |
| | | Endocervical Adenocarcinoma |
| | | Intestinal Type Stomach Adenocarcinoma |
| | | Prostate Adenocarcinoma |
| | | Papillary Renal Cell Carcinoma |
| | | Oligoastrocytoma |
| | | Hepatocellular Carcinoma |
| | | Bladder Urothelial Carcinoma |
| | | Mucinous Adenocarcinoma of the Colon and Rectum |
| | | Diffuse Type Stomach Adenocarcinoma |
| | | Lung Squamous Cell Carcinoma |
| | | Signet Ring Cell Carcinoma of the Stomach |
| | | Head and Neck Squamous Cell Carcinoma |
| | | Breast Invasive Carcinoma (NOS) |
| | | Mucinous Carcinoma |
| | | Breast Invasive Ductal Carcinoma |
| | | Cervical Squamous Cell Carcinoma |
| | | Glioblastoma Multiforme |
| | | Lung Adenocarcinoma |
| 545 | E545A, E545D, E545G, E545K, E545Q | Uterine Serous Carcinoma/Uterine Papillary Serous Carcinoma |
| | | Uterine Endometrioid Carcinoma |
| | | Colon Adenocarcinoma |
| | | Prostate Adenocarcinoma |
| | | Breast Invasive Ductal Carcinoma |
| | | Breast Invasive Lobular Carcinoma |
| | | Endocervical Adenocarcinoma |
| | | Intestinal Type Stomach Adenocarcinoma |
| | | Papillary Renal Cell Carcinoma |
| | | Oligoastrocytoma |
| | | Hepatocellular Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| | | Bladder Urothelial Carcinoma |
| | | Mucinous Adenocarcinoma of the Colon and Rectum |
| | | Diffuse Type Stomach Adenocarcinoma |
| | | Lung Squamous Cell Carcinoma |
| | | Signet Ring Cell Carcinoma of the Stomach |
| | | Head and Neck Squamous Cell Carcinoma |
| | | Breast Invasive Carcinoma (NOS) |
| | | Mucinous Carcinoma |
| | | Cervical Squamous Cell Carcinoma |
| | | Glioblastoma Multiforme |
| | | Oligodendroglioma |
| | | Lung Adenocarcinoma |
| | | Serous Ovarian Cancer |
| | | Uterine Carcinosarcoma/Uterine Malignant Mixed Mullerian Tumor |
| | | Astrocytoma |
| | | Rectal Adenocarcinoma |
| | | Stomach Adenocarcinoma |
| | | Cutaneous Melanoma |
| | | Esophageal Squamous Cell Carcinoma |
| | | Breast Invasive Mixed Mucinous Carcinoma |
| | | Intrahepatic Cholangiocarcinoma |
| | | Renal Clear Cell Carcinoma |
| | | Seminoma |
| | | Esophageal Adenocarcinoma |
| | | Tubular Stomach Adenocarcinoma |
| | | Uterine Mixed Endometrial Carcinoma |
| 546 | Q546E, Q546H, Q546K, Q546P, Q546R | Uterine Endometrioid Carcinoma |
| | | Rectal Adenocarcinoma |
| | | Oligodendroglioma |
| | | Stomach Adenocarcinoma |
| | | Esophageal Adenocarcinoma |
| | | Bladder Urothelial Carcinoma |
| | | Breast Invasive Carcinoma (NOS) |
| | | Breast Invasive Ductal Carcinoma |
| | | Colon Adenocarcinoma |
| | | Glioblastoma Multiforme |
| | | Uterine Serous Carcinoma/Uterine Papillary Serous Carcinoma |
| | | Undifferentiated Pleomorphic Sarcoma/Malignant Fibrous Histiocytoma/High-Grade Spindle Cell Sarcoma |
| | | Astrocytoma |
| | | Uterine Carcinosarcoma/Uterine Malignant Mixed Mullerian Tumor |
| | | Oligoastrocytoma |
| | | Breast Invasive Lobular Carcinoma |
| | | Tubular Stomach Adenocarcinoma |
| | | Head and Neck Squamous Cell Carcinoma |
| | | Cervical Squamous Cell Carcinoma |
| | | Intestinal Type Stomach Adenocarcinoma |
| 547 | E547D, E547K | Lung Squamous Cell Carcinoma |
| | | Stomach Adenocarcinoma |
| 552 | W552C | Bladder Urothelial Carcinoma |
| 569 | L569I | Uterine Serous Carcinoma/Uterine Papillary Serous Carcinoma |
| | | Prostate Adenocarcinoma |
| 576 | S576Y | Uterine Endometrioid Carcinoma |
| 581 | A581S | Cutaneous Melanoma |
| 589 | D589N | Cervical Squamous Cell Carcinoma |
| 600 | E600K, E600V | Uterine Endometrioid Carcinoma |
| | | Bladder Urothelial Carcinoma |
| | | Lung Adenocarcinoma |
| | | Breast Invasive Lobular Carcinoma |
| | | Papillary Stomach Adenocarcinoma |
| 603 | D603H | Breast Invasive Ductal Carcinoma |
| 604 | C604R | Uterine Endometrioid Carcinoma |
| | | Uterine Carcinosarcoma/Uterine Malignant Mixed Mullerian Tumor |
| | | Uterine Serous Carcinoma/Uterine Papillary Serous Carcinoma |
| | | Head and Neck Squamous Cell Carcinoma |
| 606 | Y606C | Head and Neck Squamous Cell Carcinoma |
| 607 | P607Q | Cutaneous Melanoma |
| 609 | P609H | Colon Adenocarcinoma |
| 614 | F614I | Breast Invasive Ductal Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| 617 | R617Q, R617W | Uterine Endometrioid Carcinoma |
| 617 | R617W | Uterine Endometrioid Carcinoma |
| 629 | S629C | Breast Invasive Ductal Carcinoma |
| 636 | V636L | Bladder Urothelial Carcinoma |
| 642 | E642K | Uterine Serous Carcinoma/Uterine Papillary Serous Carcinoma |
| 643 | Q643H | Uterine Endometrioid Carcinoma |
| 658 | L658F | Colon Adenocarcinoma |
| 667 | F667L | Uterine Endometrioid Carcinoma |
|  |  | Lung Squamous Cell Carcinoma |
|  |  | Uterine Serous Carcinoma/Uterine Papillary Serous Carcinoma |
| 673 | S673T | Breast Invasive Ductal Carcinoma |
| 674 | E674* (Nonsense mutation), E674D, E674Q | Papillary Thyroid Cancer |
|  |  | Cutaneous Melanoma |
|  |  | Bladder Urothelial Carcinoma |
| 682 | Q682K, Q682Rfs*18 (Frame Shift Deletion) | Cutaneous Melanoma |
|  |  | Glioblastoma Multiforme |
| 683 | R683M | Cutaneous Melanoma |
| 684 | F684L | Uterine Endometrioid Carcinoma |
| 693 | R693H | Cervical Squamous Cell Carcinoma |
| 710 | E710Q | Bladder Urothelial Carcinoma |
| 711 | K711N | Astrocytoma |
| 722 | E722K | Colon Adenocarcinoma |
| 725 | D725G, D725N | Colon Adenocarcinoma |
|  |  | Uterine Endometrioid Carcinoma |
| 726 | E726K | Cervical Squamous Cell Carcinoma |
|  |  | Uterine Endometrioid Carcinoma |
|  |  | Breast Invasive Ductal Carcinoma |
|  |  | Hepatocellular Carcinoma |
|  |  | Lung Adenocarcinoma |
|  |  | Esophageal Squamous Cell Carcinoma |
|  |  | Esophageal Adenocarcinoma |
|  |  | Rectal Adenocarcinoma |
|  |  | Head and Neck Squamous Cell Carcinoma |
|  |  | Lung Squamous Cell Carcinoma |
|  |  | Breast Invasive Lobular Carcinoma |
|  |  | Bladder Urothelial Carcinoma |
|  |  | Colon Adenocarcinoma |
| 729 | K729N | Cutaneous Melanoma |
| 732 | M732I | Colon Adenocarcinoma |
| 737 | E737K | Cutaneous Melanoma |
| 741 | R741Q | Serous Ovarian Cancer |
| 744 | F744I | Stomach Adenocarcinoma |
| 746 | D746Y | Cutaneous Melanoma |
| 749 | Q749H | Cutaneous Melanoma |
| 752 | L752V | Bladder Urothelial Carcinoma |
| 766 | L766F | Breast Invasive Ductal Carcinoma |
| 770 | R770Q | Uterine Endometrioid Carcinoma |
| 773 | S773F | Cutaneous Melanoma |
| 777 | R777M, R777K | Cutaneous Melanoma |
|  |  | Colon Adenocarcinoma |
| 791 | E791Q | Bladder Urothelial Carcinoma |
| 811 | M811I | Uterine Endometrioid Carcinoma |
| 816 | I816S | Uterine Endometrioid Carcinoma |
| 818 | R818C, R818H | Cutaneous Melanoma |
|  |  | Uterine Endometrioid Carcinoma |
| 849 | E849K | Serous Ovarian Cancer |
| 852 | R852Q | Leiomyosarcoma |
|  |  | Uterine Serous Carcinoma/Uterine Papillary Serous Carcinoma |
| 865 | G865D | Cutaneous Melanoma |
| 866 | L866F, L866W | Cervical Squamous Cell Carcinoma |
|  |  | Uterine Endometrioid Carcinoma |
| 879 | Q879R | Stomach Adenocarcinoma |
| 886 | K886E | Undifferentiated Pleomorphic Sarcoma/Malignant Fibrous Histiocytoma/High-Grade Spindle Cell Sarcoma |
| 901 | C901F | Uterine Endometrioid Carcinoma |
|  |  | Astrocytoma |
|  |  | Breast Invasive Ductal Carcinoma |
|  |  | Head and Neck Squamous Cell Carcinoma |
| 903 | G903E | Uterine Serous Carcinoma/Uterine Papillary Serous Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| 905 | C905S | Head and Neck Squamous Cell Carcinoma |
| 909 | F909C | Esophageal Adenocarcinoma |
| 914 | G914R | Uterine Serous Carcinoma/Uterine Papillary Serous Carcinoma |
| | | Astrocytoma |
| 929 | L929M | Uterine Endometrioid Carcinoma |
| 930 | F930V | Uterine Endometrioid Carcinoma |
| 939 | D939G | Breast Invasive Carcinoma (NOS) |
| | | Uterine Endometrioid Carcinoma |
| | | Breast Invasive Ductal Carcinoma |
| 948 | K948E | Intestinal Type Stomach Adenocarcinoma |
| 951 | R951C | Rectal Adenocarcinoma |
| 953 | P953S | Uterine Endometrioid Carcinoma |
| 956 | L956F | Bladder Urothelial Carcinoma |
| 958 | Q958R | Uterine Mixed Endometrial Carcinoma |
| 970 | E970K | Esophageal Squamous Cell Carcinoma |
| | | Head and Neck Squamous Cell Carcinoma |
| | | Mucinous Adenocarcinoma of the Colon and Rectum |
| | | Colon Adenocarcinoma |
| 971 | C971R | Head and Neck Squamous Cell Carcinoma |
| 978 | E978K | Bladder Urothelial Carcinoma |
| 979 | R979G | Pancreatic Adenocarcinoma |
| 985 | Y985* | Pleural Mesothelioma, Biphasic Type |
| 989 | L989V | Breast Invasive Ductal Carcinoma |
| 992 | R992L, R992P | Bladder Urothelial Carcinoma |
| | | Uterine Serous Carcinoma/Uterine Papillary Serous Carcinoma |
| | | Mucinous Carcinoma |
| 997 | L997I | Uterine Endometrioid Carcinoma |
| 1002 | F1002L | Uterine Endometrioid Carcinoma |
| 1004 | M1004I, M1004R, M1004V | Uterine Endometrioid Carcinoma |
| | | Breast Invasive Ductal Carcinoma |
| | | Bladder Urothelial Carcinoma |
| | | Lung Squamous Cell Carcinoma |
| 1005 | M1005V | Oligodendroglioma |
| 1006 | L1006R | Uterine Endometrioid Carcinoma |
| 1007 | G1007R | Uterine Endometrioid Carcinoma |
| | | Breast Invasive Ductal Carcinoma |
| | | Head and Neck Squamous Cell Carcinoma |
| | | Colon Adenocarcinoma |
| | | Endocervical Adenocarcinoma |
| 1012 | E1012Q | Bladder Urothelial Carcinoma |
| 1015 | S1015Y | Mucinous Adenocarcinoma of the Colon and Rectum |
| 1016 | F1016C | Uterine Endometrioid Carcinoma |
| 1017 | D1017N | Pancreatic Adenocarcinoma |
| 1020 | A1020T | Uterine Endometrioid Carcinoma |
| 1021 | Y1021C, Y1021H | Uterine Carcinosarcoma/Uterine Malignant Mixed Mullerian Tumor |
| | | Colon Adenocarcinoma |
| | | Breast Invasive Ductal Carcinoma |
| | | Uterine Serous Carcinoma/Uterine Papillary Serous Carcinoma |
| | | Uterine Endometrioid Carcinoma |
| | | Stomach Adenocarcinoma |
| | | Mucinous Adenocarcinoma of the Colon and Rectum |
| | | Tubular Stomach Adenocarcinoma |
| 1025 | T1025A, T1025S | Uterine Endometrioid Carcinoma |
| | | Breast Invasive Ductal Carcinoma |
| | | Mucinous Adenocarcinoma of the Colon and Rectum |
| | | Uterine Mixed Endometrial Carcinoma |
| 1023 | R1023Q[†] | Colorectal Cancer |
| 1026 | L1026I | Cutaneous Melanoma |
| 1029 | D1029H | Uterine Serous Carcinoma/Uterine Papillary Serous Carcinoma |
| 1037 | E1037K | Breast Invasive Ductal Carcinoma |
| 1040 | M1040I, M1040V | Head and Neck Squamous Cell Carcinoma |
| | | Breast Invasive Ductal Carcinoma |
| 1043 | M1043I, M1043L, M1043T, M1043V | Breast Invasive Lobular Carcinoma |
| | | Tubular Stomach Adenocarcinoma |
| | | Uterine Endometrioid Carcinoma |
| | | Mucinous Adenocarcinoma of the Colon and Rectum |
| | | Papillary Thyroid Cancer |
| | | Esophageal Squamous Cell Carcinoma |
| | | Colon Adenocarcinoma |
| | | Breast Invasive Ductal Carcinoma |

TABLE 1-continued

PI3Kα Protein Amino Acid Substitutions/Insertions/Deletions[4]

| Amino Acid Position | Non-Limiting Exemplary Mutations | Non-Limiting Exemplary PI3Kα Associated Cancer(s) |
|---|---|---|
| | | Bladder Urothelial Carcinoma |
| | | Pancreatic Adenocarcinoma |
| | | Oligodendroglioma |
| | | Uterine Serous Carcinoma/Uterine Papillary Serous Carcinoma |
| | | Glioblastoma Multiforme |
| | | Head and Neck Squamous Cell Carcinoma |
| 1044 | N1044I, N1044K, N1044Y | Uterine Endometrioid Carcinoma |
| | | Breast Invasive Ductal Carcinoma |
| 1045 | D1045A, D1045V | Uterine Endometrioid Carcinoma |
| | | Lung Squamous Cell Carcinoma |
| 1047 | H1047L, H1047Q, H1047R, H1047Y | Esophageal Squamous Cell Carcinoma |
| | | Uterine Endometrioid Carcinoma |
| | | Hepatocellular Carcinoma |
| | | Cutaneous Melanoma |
| | | Mucinous Adenocarcinoma of the Colon and Rectum |
| | | Bladder Urothelial Carcinoma |
| | | Cervical Squamous Cell Carcinoma |
| | | Intrahepatic Cholangiocarcinoma |
| | | Uterine Mixed Endometrial Carcinoma |
| | | Breast Invasive Ductal Carcinoma |
| | | Renal Clear Cell Carcinoma |
| | | Uterine Serous Carcinoma/Uterine Papillary Serous Carcinoma |
| | | Head and Neck Squamous Cell Carcinoma |
| | | Lung Squamous Cell Carcinoma |
| | | Breast Invasive Lobular Carcinoma |
| | | Breast Invasive Carcinoma (NOS) |
| | | Astrocytoma |
| | | Colon Adenocarcinoma |
| | | Leiomyosarcoma |
| | | Uterine Carcinosarcoma/Uterine Malignant Mixed Mullerian Tumor |
| | | Oligodendroglioma |
| | | Serous Ovarian Cancer |
| | | Mucinous Stomach Adenocarcinoma |
| | | Rectal Adenocarcinoma |
| | | Intestinal Type Stomach Adenocarcinoma |
| | | Diffuse Type Stomach Adenocarcinoma |
| | | Prostate Adenocarcinoma |
| | | Lung Adenocarcinoma |
| | | Stomach Adenocarcinoma |
| | | Tubular Stomach Adenocarcinoma |
| | | Adrenocortical Carcinoma |
| | | Undifferentiated Pleomorphic Sarcoma/Malignant Fibrous Histiocytoma/High-Grade Spindle Cell Sarcoma |
| | | Glioblastoma Multiforme |
| | | Oligoastrocytoma |
| 1048 | H1048R | Colon Adenocarcinoma |
| | | Renal Clear Cell Carcinoma |
| 1049 | G1049R | Intestinal Type Stomach Adenocarcinoma |
| | | Bladder Urothelial Carcinoma |
| | | Renal Clear Cell Carcinoma |
| | | Breast Invasive Ductal Carcinoma |
| | | Breast Invasive Lobular Carcinoma |
| | | Uterine Endometrioid Carcinoma |
| | | Colon Adenocarcinoma |
| 1052 | T1052K | Hepatocellular Carcinoma |
| | | Colon Adenocarcinoma |
| 1055 | M1055I | Uterine Mixed Endometrial Carcinoma |
| 1058 | I1058M | Uterine Carcinosarcoma/Uterine Malignant Mixed Mullerian Tumor |
| 1065 | H1065L | Breast Invasive Lobular Carcinoma |
| 1066 | A1066V | Uterine Mixed Endometrial Carcinoma |
| 1068 | N1068Y, N1068fs*5 (Frame Shift Insertion) | Pleural Mesothelioma, Epithelioid Type |
| | | Dedifferentiated Liposarcoma |
| | | Head and Neck Squamous Cell Carcinoma |

TABLE 1-continued

PI3Kα Protein Amino Acid Substitutions/Insertions/Deletions[A]

| Amino Acid Position | Non-Limiting Exemplary Mutations | Non-Limiting Exemplary PI3Kα Associated Cancer(s) |
|---|---|---|
| 1069 | *1069Wext*4 (nonstop Mutation) | Glioblastoma Multiforme |

[A]Unless noted otherwise, the mutations of Table 1 are found in cBioPortal database derived from Cerami et al. *The cBio Cancer Genomics Portal: An Open Platform for Exploring Multidimensional Cancer Genomics Data.* Cancer Discovery. May 2012 2; 401; and Gao et al. *Integrative analysis of complex cancer genomics and clinical profiles using the cBioPortal.* Sci. Signal. 6, pl1 (2013).
†Velho S, Oliveira C, Ferreira A, Ferreira AC, Suriano G, Schwartz S Jr, Duval A, Carneiro F, Machado JC, Hamelin R, Seruca R. The prevalence of PIK3CA mutations in gastric and colon cancer. Eur J Cancer. 2005 Jul;41(11):1649-54. doi: 10.1016/j.ejca.2005.04.022. PMID: 15994075.

TABLE 2

Additional PI3Kα Protein Amino Acid Substitutions/Insertions/DeletionsA

| Amino Acid Position | Non-Limiting Exemplary Mutations | Non-Limiting Exemplary PI3Kα Associated Cancer(s) |
|---|---|---|
| 1043 | M1043I, M1043L, M1043T, M1043V | Breast Invasive Lobular Carcinoma<br>Tubular Stomach Adenocarcinoma<br>Uterine Endometrioid Carcinoma<br>Mucinous Adenocarcinoma of the Colon and Rectum<br>Papillary Thyroid Cancer<br>Esophageal Squamous Cell Carcinoma<br>Colon Adenocarcinoma<br>Breast Invasive Ductal Carcinoma<br>Bladder Urothelial Carcinoma<br>Pancreatic Adenocarcinoma<br>Oligodendroglioma<br>Uterine Serous Carcinoma/Uterine Papillary Serous Carcinoma<br>Glioblastoma Multiforme<br>Head and Neck Squamous Cell Carcinoma |
| 1044 | N1044I, N1044K, N1044Y | Uterine Endometrioid Carcinoma<br>Breast Invasive Ductal Carcinoma |
| 1045 | D1045A, D1045V | Uterine Endometrioid Carcinoma<br>Lung Squamous Cell Carcinoma |
| 1047 | H1047L, H1047Q, H1047R, H1047Y | Esophageal Squamous Cell Carcinoma<br>Uterine Endometrioid Carcinoma<br>Hepatocellular Carcinoma<br>Cutaneous Melanoma<br>Mucinous Adenocarcinoma of the Colon and Rectum<br>Bladder Urothelial Carcinoma<br>Cervical Squamous Cell Carcinoma<br>Intrahepatic Cholangiocarcinoma<br>Uterine Mixed Endometrial Carcinoma<br>Breast Invasive Ductal Carcinoma<br>Renal Clear Cell Carcinoma<br>Uterine Serous Carcinoma/Uterine Papillary Serous Carcinoma<br>Head and Neck Squamous Cell Carcinoma<br>Lung Squamous Cell Carcinoma<br>Breast Invasive Lobular Carcinoma<br>Breast Invasive Carcinoma (NOS)<br>Astrocytoma<br>Colon Adenocarcinoma<br>Leiomyosarcoma<br>Uterine Carcinosarcoma/Uterine Malignant Mixed Mullerian Tumor<br>Oligodendroglioma<br>Serous Ovarian Cancer<br>Mucinous Stomach Adenocarcinoma<br>Rectal Adenocarcinoma<br>Intestinal Type Stomach Adenocarcinoma<br>Diffuse Type Stomach Adenocarcinoma<br>Prostate Adenocarcinoma<br>Lung Adenocarcinoma<br>Stomach Adenocarcinoma<br>Tubular Stomach Adenocarcinoma<br>Adrenocortical Carcinoma<br>Undifferentiated Pleomorphic Sarcoma/Malignant Fibrous Histiocytoma/High-Grade Spindle Cell Sarcoma<br>Glioblastoma Multiforme<br>Oligoastrocytoma |

TABLE 2-continued

Additional PI3Kα Protein Amino Acid Substitutions/Insertions/DeletionsA

| Amino Acid Position | Non-Limiting Exemplary Mutations | Non-Limiting Exemplary PI3Kα Associated Cancer(s) |
|---|---|---|
| 1048 | H1048R | Colon Adenocarcinoma |
|  |  | Renal Clear Cell Carcinoma |
| 1049 | G1049R | Intestinal Type Stomach Adenocarcinoma |
|  |  | Bladder Urothelial Carcinoma |
|  |  | Renal Clear Cell Carcinoma |
|  |  | Breast Invasive Ductal Carcinoma |
|  |  | Breast Invasive Lobular Carcinoma |
|  |  | Uterine Endometrioid Carcinoma |
|  |  | Colon Adenocarcinoma |
| 1052 | T1052K | Hepatocellular Carcinoma |
|  |  | Colon Adenocarcinoma |
| 1055 | M1055I | Uterine Mixed Endometrial Carcinoma |
| 1058 | I1058M | Uterine Carcinosarcoma/Uterine Malignant Mixed Mullerian Tumor |
| 1065 | H1065L | Breast Invasive Lobular Carcinoma |
| 1066 | A1066V | Uterine Mixed Endometrial Carcinoma |
| 1068 | N1068Y, N1068fs*5 (Frame Shift Insertion) | Pleural Mesothelioma, Epithelioid Type Dedifferentiated Liposarcoma Head and Neck Squamous Cell Carcinoma |

[A]Unless noted otherwise, the mutations of Table 2 are found in cBioPortal database derived from Cerami et al. *The cBio Cancer Genomics Portal: An Open Platform for Exploring Multidimensional Cancer Genomics Data.* Cancer Discovery. May 2012 2; 401; and Gao et al. *Integrative analysis of complex cancer genomics and clinical profiles using the cBioPortal.* Sci. Signal. 6, pl1 (2013).
[†]Velho S, Oliveira C, Ferreira A, Ferreira AC, Suriano G, Schwartz S Jr, Duval A, Carneiro F, Machado JC, Hamelin R, Seruca R. The prevalence of PIK3CA mutations in gastric and colon cancer. Eur J Cancer. 2005 Jul;41(11):1649-54. doi: 10.1016/j.ejca.2005.04.022. PMID: 15994075.

In some embodiments, the dysregulation of a PIK3CA gene, a PI3Kα protein, or expression or activity or level of any of the same, includes a splice variation in a PI3Kα mRNA which results in an expressed protein that is an alternatively spliced variant of PI3Kα having at least one residue deleted (as compared to the wild type PI3Kα protein) resulting in a constitutive activity of a PI3Kα protein domain.

In some embodiments, the dysregulation of a PIK3CA gene, a PI3Kα protein, or expression or activity or level of any of the same, includes at least one point mutation in a PIK3CA gene that results in the production of a PI3Kα protein that has one or more amino acid substitutions or insertions or deletions in a PIK3CA gene that results in the production of a PI3Kα protein that has one or more amino acids inserted or removed, as compared to the wild type PI3Kα protein. In some cases, the resulting mutant PI3Kα protein has increased activity, as compared to a wild type PI3Kα protein or a PI3Kα protein not including the same mutation. In some embodiments, the compounds described herein selectively inhibit the resulting mutant PI3Kα protein relative to a wild type PI3Kα protein or a PI3Kα protein not including the same mutation.

Exemplary Sequence of Human Phosphatidylinositol 4,5-bisphosphate 3-kinase isoform alpha (UniProtKB entry P42336) (SEQ ID NO: 1)
MPPRPSSGEL WGIHLMPPRI LVECLLPNGM IVTLECLREA TLITIKHELF KEARKYPLHQ LLQDESSYIF VSVTQEAERE EFFDETRRLC DLRLFQPFLK
VIEPVGNREE KILNREIGFA IGMPVCEFDM VKDPEVQDFR RNILNVCKEA
VDLRDLNSPH SRAMYVYPPN VESSPELPKH IYNKLDKGQI IVVIWVIVSP
NNDKQKYTLK INHDCVPEQV IAEAIRKKTR SMLLSSEQLK LCVLEYQGKY
ILKVCGCDEY FLEKYPLSQY KYIRSCIMLG RMPNLMLMAK ESLYSQLPMD
CFTMPSYSRR ISTATPYMNG ETSTKSLWVI NSALRIKILC ATYVNVNIRD
IDKIYVRTGI YHGGEPLCDN VNTQRVPCSN PRWNEWLNYD IYIPDLPRAA
RLCLSICSVK GRKGAKEEHC PLAWGNINLF DYTDTLVSGK MALNLWPVPH
GLEDLLNPIG VTGSNPNKET PCLELEFDWF SSVVKFPDMS VIEEHANWSV
SREAGFSYSH AGLSNRLARD NELRENDKEQ LKAISTRDPL SEITEQEKDF
LWSHRHYCVT IPEILPKLLL SVKWNSRDEV AQMYCLVKDW PPIKPEQAME
LLDCNYPDPM VRGFAVRCLE KYLTDDKLSQ YLIQLVQVLK YEQYLDNLLV
RFLLKKALTN QRIGHFFFWH LKSEMHNKTV SQRFGLLLES YCRACGMYLK
HLNRQVEAME KLINLTDILK QEKKDETQKV QMKFLVEQMR RPDFMDALQG
FLSPLNPAHQ LGNLRLEECR IMSSAKRPLW LNWENPDIMS ELLFQNNEII
FKNGDDLRQD MLTLQIIRIM ENIWQNQGLD LRMLPYGCLS IGDCVGLIEV
VRNSHTIMQI QCKGGLKGAL QFNSHTLHQW LKDKNKGEIY DAAIDLFTRS
CAGYCVATFI LGIGDRHNSN IMVKDDGQLF HIDFGHFLDH KKKKFGYKRE
RVPFVLTQDF LIVISKGAQE CTKTREFERF QEMCYKAYLA IRQHANLFIN
LFSMMLGSGM PELQSFDDIA YIRKTLALDK TEQEALEYFM KQMNDAHHGG
WTTKMDWIFH TIKQHALN In some embodiments, compounds of Formula (I), or pharmaceutically acceptable thereof, are useful for treating a cancer that has been identified as having one or more PI3Kα mutations. Accordingly, provided herein are methods for treating a subject diagnosed with (or identified as having) a cancer that include administering to the subject a therapeutically effective amount of a compound of Formula (I), or a pharmaceutically acceptable salt thereof.

Also provided herein are methods for treating a subject identified or diagnosed as having a PI3Kα-associated cancer that include administering to the subject a therapeutically effective amount of a compound of Formula (I), or a pharmaceutically acceptable salt thereof, or a pharmaceutical composition thereof. In some embodiments, the subject that has been identified or diagnosed as having a PI3Kα-associated cancer through the use of a regulatory agency-approved, e.g., FDA-approved test or assay for identifying dysregulation of a PIK3CA gene, a PI3Kα protein, or expression or activity or level of any of the same, in a subject or a biopsy sample from the subject or by performing any of the non-limiting examples of assays described herein. In some embodiments, the test or assay is provided as a kit. In some embodiments, the cancer is an PI3Kα-associated cancer.

The term "regulatory agency" refers to a country's agency for the approval of the medical use of pharmaceutical agents with the country. For example, a non-limiting example of a regulatory agency is the U.S. Food and Drug Administration (FDA).

Also provided are methods for treating cancer in a subject in need thereof, the method comprising: (a) detecting a PI3Kα-associated cancer in the subject; and (b) administering to the subject a therapeutically effective amount of a compound of Formula (I), or a pharmaceutically acceptable salt thereof, or a pharmaceutical composition thereof. Some embodiments of these methods further include administering to the subject another anticancer agent (e.g., an immunotherapy). In some embodiments, the subject was previously treated with another anticancer treatment, e.g., at least partial resection of the tumor or radiation therapy. In some embodiments, the subject is determined to have a PI3Kα-associated cancer through the use of a regulatory agency-approved, e.g., FDA-approved test or assay for identifying dysregulation of a PIK3CA gene, a PI3Kα protein, or expression or activity or level of any of the same, in a subject or a biopsy sample from the subject or by performing any of the non-limiting examples of assays described herein. In some embodiments, the test or assay is provided as a kit. In some embodiments, the cancer is an PI3Kα-associated cancer.

Also provided are methods of treating a subject that include performing an assay on a sample obtained from the subject to determine whether the subject has a dysregulation of a PIK3CA gene, a PI3Kα protein, or expression or activity or level of any of the same, and administering (e.g., specifically or selectively administering) a therapeutically effective amount of a compound of Formula (I), or a pharmaceutically acceptable salt thereof, or a pharmaceutical composition thereof, to the subject determined to have a dysregulation of a PIK3CA gene, a PI3Kα protein, or expression or activity or level of any of the same. Some embodiments of these methods further include administering to the subject another anticancer agent (e.g., an immunotherapy). In some embodiments of these methods, the subject was previously treated with another anticancer treatment, e.g., at least partial resection of a tumor or radiation therapy. In some embodiments, the subject is a subject suspected of having a PI3Kα-associated cancer, a subject presenting with one or more symptoms of a PI3Kα-associated cancer, or a subject having an elevated risk of developing a PI3Kα-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided is a compound of Formula (I), or a pharmaceutically acceptable salt thereof, or a pharmaceutical composition thereof, for use in treating a PI3Kα-associated cancer in a subject identified or diagnosed as having a PI3Kα-associated cancer through a step of performing an assay (e.g., an in vitro assay) on a sample obtained from the subject to determine whether the subject has a dysregulation of a PIK3CA gene, a PI3Kα protein, or expression or activity or level of any of the same, where the presence of a dysregulation of a PIK3CA gene, a PI3Kα protein, or expression or activity or level of any of the same, identifies that the subject has a PI3Kα-associated cancer. Also provided is the use of a compound of Formula (I), or a pharmaceutically acceptable salt thereof, for the manufacture of a medicament for treating a PI3Kα-associated cancer in a subject identified or diagnosed as having a PI3Kα-associated cancer through a step of performing an assay on a sample obtained from the subject to determine whether the subject has a dysregulation of a PIK3CA gene, a PI3Kα protein, or expression or activity or level of any of the same where the presence of dysregulation of a PIK3CA gene, a PI3Kα protein, or expression or activity or level of any of the same, identifies that the subject has a PI3Kα-associated cancer. Some embodiments of any of the methods or uses described herein further include recording in the subject's clinical record (e.g., a computer readable medium) that the subject is determined to have a dysregulation of a PIK3CA gene, a PI3Kα protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, for use in the treatment of a cancer in a subject in need thereof, or a subject identified or diagnosed as having a PI3Kα-associated cancer. Also provided is the use of a compound of Formula (I), or a pharmaceutically acceptable salt thereof, for the manufacture of a medicament for treating a cancer in a subject identified or diagnosed as having a PI3Kα-associated cancer. In some embodiments, a subject is identified or diagnosed as having a PI3Kα-associated cancer through the use of a regulatory agency-approved, e.g., FDA-approved, kit for identifying dysregulation of a PIK3CA gene, a PI3Kα protein, or expression or activity or level of any of the same, in a subject or a biopsy sample from the subject. As provided herein, a PI3Kα-associated cancer includes those described herein and known in the art.

In some embodiments of any of the methods or uses described herein, the subject has been identified or diagnosed as having a cancer with a dysregulation of a PIK3CA gene, a PI3Kα protein, or expression or activity or level of any of the same. In some embodiments of any of the methods or uses described herein, the subject has a tumor that is positive for a dysregulation of a PIK3CA gene, a PI3Kα protein, or expression or activity or level of any of the same. In some embodiments of any of the methods or uses described herein, the subject can be a subject with a tumor(s) that is positive for a dysregulation of a PIK3CA gene, a PI3Kα protein, or expression or activity or level of any of the same. In some embodiments of any of the methods or uses described herein, the subject can be a subject whose tumors have a dysregulation of a PIK3CA gene, a PI3Kα protein, or expression or activity or level of any of the same. In some embodiments of any of the methods or uses described herein, the subject is suspected of having a PI3Kα-associated cancer. In some embodiments, provided herein are methods for treating a PI3Kα-associated cancer in a subject in need of such treatment, the method comprising a) detecting a dysregulation of a PIK3CA gene, a PI3Kα protein, or the expression or activity or level of any of the same in a sample from the subject; and b) administering a therapeutically effective amount of a compound of Formula (I), or a pharmaceutically acceptable salt thereof. In some embodiments, the dysregulation of a PIK3CA gene, a PI3Kα protein, or the expression or activity or level of any of the same includes one or more PI3Kα protein point mutations/insertions/deletions. Non-limiting examples of PI3Kα protein point mutations/insertions/deletions are described in Table 1 and Table 2. In some embodiments, the PI3Kα protein point mutation/insertion/deletion is H1047X, where X is any amino acid. In some embodiments, the PI3Kα protein point mutations/insertions/deletions are selected from the group consisting of E542A, E542G, E542K, E542Q, E542V, E545A, E545D, E545G, E545K, E545Q, M1043I, M1043L, M1043T, M1043V, H1047L, H1047Q, H1047R, H1047Y, and G1049R. In some embodiments, the cancer with a dysregulation of a PIK3CA gene, a PI3Kα protein, or expression or activity or level of any of the same is determined using a regulatory agency-approved, e.g., FDA-approved, assay or kit. In some embodiments, the tumor with a dysregulation of a PIK3CA gene, a PI3Kα protein, or expression or activity or level of any of the same is determined using a regulatory agency-approved, e.g., FDA-approved, assay or kit.

In some embodiments of any of the methods or uses described herein, the subject has a clinical record indicating that the subject has a tumor that has a dysregulation of a PIK3CA gene, a PI3Kα protein, or expression or activity or level of any of the same. Also provided are methods of treating a subject that include administering a therapeutically effective amount of a compound of Formula (I), or a pharmaceutically acceptable salt thereof, to a subject having a clinical record that indicates that the subject has a dysregulation of a PIK3CA gene, a PI3Kα protein, or expression or activity or level of any of the same.

In some embodiments, the methods provided herein include performing an assay on a sample obtained from the subject to determine whether the subject has a dysregulation of a PIK3CA gene, a PI3Kα protein, or expression or level of any of the same. In some such embodiments, the method also includes administering to a subject determined to have a dysregulation of a PIK3CA gene, a PI3Kα protein, or expression or activity, or level of any of the same a therapeutically effective amount of a compound of Formula (I), or a pharmaceutically acceptable salt thereof. In some embodiments, the method includes determining that a subject has a dysregulation of a PIK3CA gene, a PI3Kα protein, or expression or level of any of the same via an assay performed on a sample obtained from the subject. In such embodiments, the method also includes administering to a subject a therapeutically effective amount of a compound of Formula (I), or a pharmaceutically acceptable salt thereof. In some embodiments, the dysregulation in a PIK3CA gene, a PI3Kα protein, or expression or activity or level of any of the same is one or more point mutation in the PIK3CA gene (e.g., any of the one or more of the PI3Kα point mutations described herein). The one or more point mutations in a PIK3CA gene can result, e.g., in the translation of a PI3Kα protein having one or more of the following amino acid substitutions, deletions, and insertions: E542A, E542G, E542K, E542Q, E542V, E545A, E545D, E545G, E545K, E545Q, M1043I, M1043L, M1043T, M1043V, H1047L, H1047Q, H1047R, H1047Y, and G1049R. The one or more mutations in a PIK3CA gene can result, e.g., in the translation of an PI3Kα protein having one or more of the following amino acids: 542, 545, 1043, and 1047 and 1049. In some embodiments, the dysregulation in a PIK3CA gene, a PI3Kα protein, or expression or activity or level of any of the same is one or more PI3Kα amino acid substitutions (e.g., any of the PI3Kα amino acid substitution described herein). Some embodiments of these methods further include administering to the subject another anticancer agent (e.g., an immunotherapy).

In some embodiments of any of the methods or uses described herein, an assay used to determine whether the subject has a dysregulation of a PIK3CA gene, or a PI3Kα protein, or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labeled nucleic acid probe or at least one labeled antibody or antigen-binding fragment thereof. Assays can utilize other detection methods known in the art for detecting dysregulation of a PIK3CA gene, a PI3Kα protein, or expression or activity or levels of any of the same (see, e.g., the references cited herein). In some embodiments, the sample is a biological sample or a biopsy sample (e.g., a paraffin-embedded biopsy sample) from the subject. In some embodiments, the subject is a subject suspected of having a PI3Kα-associated cancer, a subject having one or more symptoms of a PI3Kα-associated cancer, and/or a subject that has an increased risk of developing a PI3Kα-associated cancer).

In some embodiments, dysregulation of a PIK3CA gene, a PI3Kα protein, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.*, 3(3):36, 2016. Liquid biopsy methods can be used to detect total tumor burden and/or the dysregulation of a PIK3CA gene, a PI3Kα protein, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a PIK3CA gene, a PI3Kα protein, or the expression or activity or level of any of the same. In some embodiments, liquid biopsies can be used to detect the presence of dysregulation of a PIK3CA gene, a PI3Kα protein, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a PIK3CA gene, a PI3Kα protein, or the expression or activity or level of any of the same.

Also provided is a method for inhibiting PI3Kα activity in a cell, comprising contacting the cell with a compound of Formula (I), or a pharmaceutically acceptable salt thereof. In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof, to a subject having a cell having aberrant PI3Kα activity. In some embodiments, the cell is a cancer cell. In some embodiments, the cancer cell is any cancer as described herein. In some embodiments, the cancer cell is a PI3Kα-associated cancer cell. As used herein, the term "contacting" refers to the bringing together of indicated moieties in an in vitro system or an in vivo system. For example, "contacting" a PI3Kα protein with a compound provided herein includes the administration of a compound provided herein to an individual or subject, such as a human, having a PI3Kα protein, as well as, for example, introducing a compound provided herein into a sample containing a cellular or purified preparation containing the PI3Kα protein.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Further provided herein is a method of increase cell death, in vitro or in vivo, the method comprising contacting a cell with an effective amount of a compound of Formula (I), or a pharmaceutically acceptable salt thereof, or a pharmaceutical composition thereof as defined herein. Also provided herein is a method of increasing tumor cell death in a subject. The method comprises administering to the subject an effective compound of Formula (I), or a pharmaceutically acceptable salt thereof, in an amount effective to increase tumor cell death.

The phrase "therapeutically effective amount" means an amount of compound that, when administered to a subject in need of such treatment, is sufficient to (i) treat a PI3Kα protein-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula (I), or a pharmaceutically acceptable salt thereof, that will correspond to such an amount will vary depending upon factors such as the particular compound, disease condition and its severity, the identity (e.g., weight) of the subject in need of treatment, but can nevertheless be routinely determined by one skilled in the art.

When employed as pharmaceuticals, the compounds of Formula (I), including pharmaceutically acceptable salts thereof, can be administered in the form of pharmaceutical compositions as described herein.

Combinations

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula (I), or pharmaceutically acceptable salts thereof, therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I), or a pharmaceutically acceptable salt thereof, can be used prior to administration of an additional therapeutic agent or additional therapy. For example, a subject in need thereof can be administered one or more doses of a compound of Formula (I), or a pharmaceutically acceptable salt thereof, for a period of time and then undergo at least partial resection of the tumor. In some embodiments, the treatment with one or more doses of a compound of Formula (I), or a pharmaceutically acceptable salt thereof, reduces the size of the tumor (e.g., the tumor burden) prior to the at least partial resection of the tumor. In some embodiments, a subject in need thereof can be administered one or more doses of a compound of Formula (I), or a pharmaceutically acceptable salt thereof, for a period of time and under one or more rounds of radiation therapy. In some embodiments, the treatment with one or more doses of a compound of Formula (I), or a pharmaceutically acceptable salt thereof, reduces the size of the tumor (e.g., the tumor burden) prior to the one or more rounds of radiation therapy.

In some embodiments, a subject has a cancer (e.g., a locally advanced or metastatic tumor) that is refractory or intolerant to standard therapy (e.g., administration of a chemotherapeutic agent, such as a multi-kinase inhibitor, immunotherapy, or radiation (e.g., radioactive iodine)). In some embodiments, a subject has a cancer (e.g., a locally advanced or metastatic tumor) that is refractory or intolerant to prior therapy (e.g., administration of a chemotherapeutic agent, such as a multi-kinase inhibitor, immunotherapy, or radiation (e.g., radioactive iodine)). In some embodiments, a subject has a cancer (e.g., a locally advanced or metastatic tumor) that has no standard therapy. In some embodiments, a subject is PI3Kα inhibitor naïve. For example, the subject is naïve to treatment with a selective PI3Kα inhibitor. In some embodiments, a subject is not PI3Kα inhibitor naïve. In some embodiments, a subject is kinase inhibitor naïve. In some embodiments, a subject is not kinase inhibitor naïve. In some embodiments, a subject has undergone prior therapy. For example, treatment with a multi-kinase inhibitor (MKI) or another PI3K inhibitor, such as buparlisib (BKM120), alpelisib (BYL719), WX-037, copanlisib (AL-IQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, or GSK2636771.

In some embodiments of any the methods described herein, the compound of Formula (I) (or a pharmaceutically acceptable salt thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other PI3Kα-targeted therapeutic agents (i.e., other PI3Kα inhibitors), EGFR inhibitors, HER2 inhibitors, RAS pathway targeted therapeutic agents (including mTOR inhibitors, as described herein), PARP inhibitors, other kinase inhibitors (e.g., receptor tyrosine kinase-targeted therapeutic agents (e.g., Trk inhibitors or multi-kinase inhibitors)), farnesyl transferase inhibitors, signal transduction pathway inhibitors, aromatase inhibitors, selective estrogen receptor modulators or degraders (SERMs/SERDs), checkpoint inhibitors, modulators of the apoptosis pathway (e.g., obataclax); cytotoxic chemotherapeutics, angiogenesis-targeted therapies, immune-targeted agents, including immunotherapy, and radiotherapy.

In some embodiments, the EGFR inhibitor is osimertinib (AZD9291, merelectinib, TAGRISSO™), erlotinib (TARCEVA®), gefitinib (IRESSA®), cetuximab (ERBITUX®), necitumumab (PORTRAZZA™, IMC-11F8), neratinib (HKI-272, NERLYNX®), lapatinib (TYKERB®), panitumumab (ABX-EGF, VECTIBIX®), vandetanib (CAPRELSA®), rociletinib (CO-1686), olmutinib (OLITA™, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC00010), AC0010MA EAI045, matuzumab (EMD-7200), nimotuzumab (h-R3, BIOMAb EGFR®), zalutumumab, MDX447, depatuxizumab (humanized mAb 806, ABT-806), depatuxizumab mafodotin (ABT-414), ABT-806, mAb 806, canertinib (CI-1033), shikonin, shikonin derivatives (e.g., deoxyshikonin, isobutyryl-shikonin, acetylshikonin, β,β-dimethylacrylshikonin and acetylalkannin), poziotinib (NOV120101, HM781-36B), AV-412, ibrutinib, WZ4002, brigatinib (AP26113, ALUNBRIG®), pelitinib (EKB-569), tarloxotinib (TH-4000, PR610), BPI-15086, Hemay022, ZN-e4, tesevatinib (KD019, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, avitinib, GW572016, pyrotinib (SHR1258), SCT200, CPGJ602, Sym004, MAb-425, Modotuximab (TAB-H49), futuximab (992 DS), zalutumumab, KL-140, RO5083945, IMGN289, JNJ-61186372, LY3164530, Sym013, AMG 595, BDTX-189, avatinib, Disruptin, CL-387785, EGFRBi-Armed Autologous T Cells, and EGFR CAR-T Therapy. In some embodiments, the EGFR-targeted therapeutic agent is selected from osimertinib, gefitinib, erlotinib, afatinib, lapatinib, neratinib, AZD-9291, CL-387785, CO-1686, or WZ4002.

Exemplary HER2 inhibitors include trastuzumab (e.g., TRAZIMERA™, HERCEPTIN®), pertuzumab (e.g., PERJETA®), trastuzumab emtansine (T-DM1 or ado-trastuzumab emtansine, e.g., KADCYLA®), lapatinib, KU004, neratinib (e.g., NERLYNX®), dacomitinib (e.g., VIZIMPRO®), afatinib (GILOTRIF®), tucatinib (e.g., TUKYSA™), erlotinib (e.g., TARCEVA®), pyrotinib, poziotinib, CP-724714, CUDC-101, sapitinib (AZD8931), tanespimycin (17-AAG), IPI-504, PF299, pelitinib, S-222611, and AEE-788.

A "RAS pathway targeted therapeutic agent" as used herein includes any compound exhibiting inactivation activity of any protein in a RAS pathway (e.g., kinase inhibition, allosteric inhibition, inhibition of dimerization, and induction of degradation). Non-limiting examples of a protein in a RAS pathway include any one of the proteins in the RAS-RAF-MAPK pathway or PI3K/AKT pathway such as RAS (e.g., KRAS, HRAS, and NRAS), RAF (ARAF, BRAF, CRAF), MEK, ERK, PI3K, AKT, and mTOR. In some embodiments, a RAS pathway modulator can be selective for a protein in a RAS pathway, e.g., the RAS pathway modulator can be selective for RAS (also referred to as a RAS modulator). In some embodiments, a RAS modulator is a covalent inhibitor. In some embodiments, a RAS pathway targeted therapeutic agent is a "KRAS pathway modulator." A KRAS pathway modulator includes any compound exhibiting inactivation activity of any protein in a KRAS pathway (e.g., kinase inhibition, allosteric inhibition, inhibition of dimerization, and induction of degradation). Non-limiting examples of a protein in a KRAS pathway include any one of the proteins in the KRAS-RAF-MAPK pathway or PI3K/AKT pathway such as KRAS, RAF, BRAF, MEK, ERK, PI3K (i.e., other PI3K inhibitors, as described herein), AKT, and mTOR. In some embodiments, a KRAS pathway modulator can be selective for a protein in a RAS pathway, e.g., the KRAS pathway modulator can be selective for KRAS (also referred to as a KRAS modulator). In some embodiments, a KRAS modulator is a covalent inhibitor.

Non-limiting examples of a KRAS-targeted therapeutic agents (e.g., KRAS inhibitors) include BI 1701963, AMG 510, ARS-3248, ARS1620, AZD4785, SML-8-73-1, SML-10-70-1, VSA9, AA12, and MRTX-849.

Further non-limiting examples of RAS-targeted therapeutic agents include BRAF inhibitors, MEK inhibitors, ERK inhibitors, PI3K inhibitors, AKT inhibitors, and mTOR inhibitors. In some embodiments, the BRAF inhibitor is vemurafenib (ZELBORAF®), dabrafenib (TAFINLAR®), and encorafenib (BRAFTOVI®), BMS-908662 (XL281), sorafenib, PLX3603, RAF265, RO5185426, GSK2118436, ARQ 736, GDC-0879, PLX-4720, AZ304, PLX-8394, HM95573, RO5126766, LXH254, or a combination thereof.

In some embodiments, the MEK inhibitor is trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, R05126766, CS3006, WX-554, PD98059, CI1040 (PD184352), hypothemycin, or a combination thereof.

In some embodiments, the ERK inhibitor is FRI-20 (ON-01060), VTX-11e, 25-OH-D3-3-BE (B3CD, bromoacetoxy-calcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, ONC201, or a combination thereof.

In some embodiments, the other PI3K inhibitor is another PI3Kα inhibitor. In some embodiments, the other PI3K inhibitor is a pan-PI3K inhibitor. In some embodiments, the other PI3K inhibitor is selected from buparlisib (BKM120), alpelisib (BYL719), WX-037, copanlisib (ALIQOPA™, BAY80-6946), dactolisib (NVP-BEZ235, BEZ-235), taselisib (GDC-0032, R⁷7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084

(RG7666), VS-5584 (SB2343), PKI-402, wortmannin, LY294002, PI-103, rigosertib, XL-765, LY2023414, SAR260301, KIN-193 (AZD-6428), GS-9820, AMG319, GSK2636771, or a combination thereof.

In some embodiments, the AKT inhibitor is selected from miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b] pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, ONC201, or a combination thereof.

In some embodiments, the mTOR inhibitor is selected from MLN0128, vistusertib (AZD-2014), onatasertib (CC-223), CC-115, everolimus (RAD001), temsirolimus (CCI-779), ridaforolimus (AP-23573), sirolimus (rapamycin), ridaforolimus (MK-8669), or a combination thereof.

Non-limiting examples of farnesyl transferase inhibitors include lonafarnib, tipifarnib, BMS-214662, L778123, L744832, and FTI-277.

In some embodiments, a chemotherapeutic agent includes an anthracycline, cyclophosphamide, a taxane, a platinum-based agent, mitomycin, gemcitabine, eribulin (HALAVEN™), or combinations thereof.

Non-limiting examples of a taxane include paclitaxel, docetaxel, abraxane, and taxotere.

In some embodiments, the anthracycline is selected from daunorubicin, doxorubicin, epirubicin, idarubicin, and combinations thereof.

In some embodiments, the platinum-based agent is selected from carboplatin, cisplatin, oxaliplatin, nedplatin, triplatin tetranitrate, phenanthriplatin, picoplatin, satraplatin and combinations thereof.

Non-limiting examples of PARP inhibitors include olaparib (LYNPARZA®), talazoparib, rucaparib, niraparib, veliparib, BGB-290 (pamiparib), CEP 9722, E7016, iniparib, IMP4297, NOV1401, 2X-121, ABT-767, RBN-2397, BMN 673, KU-0059436 (AZD2281), BSI-201, PF-01367338, INO-1001, and JPI-289.

Non-limiting examples of aromatase inhibitors include aminoglutethimide, testolactone, anastrozole, letrozole, exemestane, vorozole, formestane, and fadrozole.

Non-limiting examples of selective estrogen receptor modulators or degraders (SERMs/SERDs) include tamoxifen, fulvestrant, brilanestrant, elacestrant, giredestrant, amcenestrant (SAR439859), AZD9833, rintodestrant, LSZ102, LY3484356, ZN-c5, D-0502, and SHR9549.

Non-limiting examples of immunotherapy include immune checkpoint therapies, atezolizumab (TECENTRIQ®), albumin-bound paclitaxel. Non-limiting examples of immune checkpoint therapies include inhibitors that target CTLA-4, PD-1, PD-L1, BTLA, LAG-3, A2AR, TIM-3, B7-H3, VISTA, IDO, and combinations thereof. In some embodiments the CTLA-4 inhibitor is ipilimumab (YERVOY®). In some embodiments, the PD-1 inhibitor is selected from pembrolizumab (KEYTRUDA®), nivolumab (OPDIVO®), cemiplimab (LIBTAYO®), or combinations thereof. In some embodiments, the PD-L1 inhibitor is selected from atezolizumab (TECENTRIQ®), avelumab (BAVENCIO®), durvalumab (IMFINZI®), or combinations thereof. In some embodiments, the LAG-3 inhibitor is IMP701 (LAG525). In some embodiments, the A2AR inhibitor is CPI-444. In some embodiments, the TIM-3 inhibitor is MBG453. In some embodiments, the B7-H3 inhibitor is enoblituzumab. In some embodiments, the VISTA inhibitor is JNJ-61610588. In some embodiments, the IDO inhibitor is indoximod. See, for example, Marin-Acevedo, et al., *J Hematol Oncol.* 11: 39 (2018).

In some embodiments, the additional therapy or therapeutic agent is selected from fulvestrant, capecitabine, trastuzumab, ado-trastuzumab emtansine, pertuzumab, paclitaxel, nab-paclitaxel, enzalutamide, olaparib, pegylated liposomal doxorubicin (PLD), trametinib, ribociclib, palbociclib, buparlisib, AEB071, everolimus, exemestane, cisplatin, letrozole, AMG479, LSZ102, LEE011, cetuximab, AUY922, BGJ398, MEK162, LJM716, LGH447, imatinib, gemcitabine, LGX818, amcenestrant, and combinations thereof.

In some embodiments, additional therapeutic agents may also be administered to treat potential side-effects for particular anticancer therapies and/or as palliative therapy, for example, opioids and corticosteroids. In some embodiments, the additional therapy or therapeutic agent described herein is selected from the group consisting of a glucagon-like peptide-1 (GLP-1) receptor agonist, a sodium-glucose transport protein 2 (SGLT-2) inhibitor, a dipeptidyl peptidase 4 (DPP-4) inhibitor, metformin, and combinations thereof.

Non-limiting examples of GLP-1 receptor agonists include liraglutide (VICTOZA®, NN2211), dulaglutide (LY2189265, TRULICITY®), exenatide (BYETTA®, BYDUREON®, Exendin-4), taspoglutide, lixisenatide (LYXUMIA®), albiglutide (TANZEUM®), semaglutide (OZEMPIC®), ZP2929, NNC0113-0987, BPI-3016, and TT401.

Non-limiting examples of SGLT-2 inhibitors include bexagliflozin, canagliflozin (INVOKANA®), dapagliflozin (FARXIGA®), empagliflozin (JARDIANCE®), ertugliflozin (STEGLATRO™), ipragliflozin (SUGLAT®), luseogliflozin (LUSEFI®), remogliflozin, serfliflozin, licofliglozin, sotagliflozin (ZYNQUISTA™), and tofogliflozin.

Non-limiting examples of DPP-4 inhibitors include, sitagliptin (JANUVIA®), vildagliptin, saxagliptin (ONGLYZA®), linagliptin (TRADJENDA®), gemigliptin, anagliptin, teneligliptin, alogliptin, trelagliptin (NESINA®), omarigliptin, evogliptin, and dutogliptin.

In some embodiments, the subject is also instructed to maintain a particular diet and/or exercise regimen to control blood sugar levels.

Accordingly, also provided herein is a method of treating cancer, comprising administering to a subject in need thereof a pharmaceutical combination for treating cancer which comprises (a) a compound of Formula (I), or a pharmaceutically acceptable salt thereof, (b) an additional therapeutic agent, and (c) optionally at least one pharmaceutically acceptable carrier for simultaneous, separate or sequential use for the treatment of cancer, wherein the amounts of the compound of Formula (I), or a pharmaceutically acceptable salt thereof, and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a PIK3CA gene, a PI3Kα protein, or expression or activity, or level of any of the same.

These additional therapeutic agents may be administered with one or more doses of the compound of Formula (I), or a pharmaceutically acceptable salt thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a subject in need thereof, which comprises (a) a compound of Formula (I), or a pharmaceutically acceptable salt thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula (I), or pharmaceutically acceptable salt thereof, and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a subject in need thereof. In some embodiments, the cancer is a PI3Kα-associated cancer.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula (I), or a pharmaceutically acceptable salt thereof, and at least one additional therapeutic agent (e.g., a chemotherapeutic agent), are both administered to a subject simultaneously in the form of a single composition or dosage. The term "non-fixed combination" means that a compound of Formula (I), or a pharmaceutically acceptable salt thereof, and at least one additional therapeutic agent (e.g., chemotherapeutic agent) are formulated as separate compositions or dosages such that they may be administered to a subject in need thereof simultaneously, concurrently or sequentially with variable intervening time limits, wherein such administration provides effective levels of the two or more compounds in the body of the subject. These also apply to cocktail therapies, e.g., the administration of three or more active ingredients Accordingly, also provided herein is a method of treating a cancer, comprising administering to a subject in need thereof a pharmaceutical combination for treating cancer which comprises (a) a compound of Formula (I), or pharmaceutically acceptable salt thereof, and (b) an additional therapeutic agent, wherein the compound of Formula (I) and the additional therapeutic agent are administered simultaneously, separately or sequentially, wherein the amounts of the compound of Formula (I), or pharmaceutically acceptable salt thereof, and the additional therapeutic agent are together effective in treating the cancer. In some embodiments, the compound of Formula (I), or pharmaceutically acceptable salt thereof, and the additional therapeutic agent are administered simultaneously as separate dosages. In some embodiments, the compound of Formula (I), or pharmaceutically acceptable salt thereof, and the additional therapeutic agent are administered as separate dosages sequentially in any order, in jointly therapeutically effective amounts, e.g., in daily or intermittently dosages. In some embodiments, the compound of Formula (I), or pharmaceutically acceptable salt thereof, and the additional therapeutic agent are administered simultaneously as a combined dosage.

EMBODIMENTS

Embodiment 1: A compound of Formula (I):

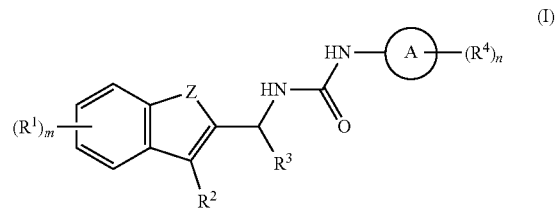

or a pharmaceutically acceptable salt thereof, wherein:
Z is O or $NR^x$;
$R^x$ is hydrogen, C1-C6 alkyl, or C3-C6 cycloalkyl;
each $R^1$ is independently selected from halogen, hydroxyl, cyano, C1-C6 alkyl optionally substituted with hydroxyl, and C3-C6 cycloalkyl;
m is 0, 1, 2, or 3;
$R^2$ is halogen, hydroxyl, C1-C6 alkyl alkyl optionally substituted with hydroxyl, C1-C6 haloalkyl, C3-C6 cycloalkyl optionally substituted with 1 or 2 fluoro;
$R^3$ is a C1-C6 alkyl, a C1-C6 haloalkyl, or a C3-C6 cycloalkyl optionally substituted with 1 or 2 substituents independently selected from fluoro and C1-C6 alkyl;
Ring A is a 6-10 membered aryl, a C3-C8 cycloalkyl, a 5-10 membered heteroaryl, or a 4-10 membered heterocyclyl;
each $R^4$ is independently selected from the group consisting of:
(i) halogen,
(ii) C1-C6 alkyl optionally substituted with 1 or 2 hydroxyl or $-NR^A R^B$
(iii) C1-C6 alkoxy optionally substituted with 1-2 substituents independently selected from hydroxyl and C3-C6 cycloalkyl,
(iv) C1-C6 haloalkyl,
(v) hydroxyl,
(vi) cyano,
(vii) $-CO_2H$,
(viii) $-NR^A R^B$,
(ix) $=NR^{A2}$,
(x) $-C(=O)NR^C R^D$,
(xi) $-SO_2(NR^E R^F)$,
(xii) $-SO_2(C1-C6\ alkyl)$,
(xiii) $-S(=O)(=NH)(C1-C6\ alkyl)$,
(xiv) $-C(=O)(C1-C6\ alkyl)$,
(xv) $-CO_2(C1-C6\ alkyl)$,
(xvi) 5-6 membered heteroaryl optionally substituted with C1-C6 alkyl,
(xvii) 3-9 membered heterocyclyl optionally substituted with 1 or 2 independently selected $R^G$, and
(xviii) 3-6 membered cycloalkyl optionally substituted with 1 or 2 independently selected $R^G$;
n is 0, 1, or 2;
each $R^A$, $R^{A1}$, $R^B$, $R^{B1}$, $R^C$, $R^{C1}$, $R^D$, $R^{D1}$, $R^E$, and $R^F$ is independently
(i) hydrogen,
(ii) hydroxyl,
(iii) 4-6 membered heterocyclyl, (iv) C1-C6 haloalkyl,
(v) —C(=O)(C1-C6 alkyl),
(vi) —C(=O)O(C1-C6 alkyl),
(vii) —SO₂(C1-C6 alkyl),
(viii) 3-6 membered cycloalkyl optionally substituted with hydroxyl, or
(ix) C1-C6 alkyl optionally substituted with 1-2 substituents independently selected from hydroxyl, —C(=O)NR$^{B2}$R$^{C2}$, 5-6 membered heteroaryl, 3-6 membered cycloalkyl, —SO₂(C1-C6 alkyl), —CO₂H, and —SO₂(NH₂); or R$^C$ and R$^D$, together with the nitrogen atom to which they are attached form a 4-10 membered heterocyclyl optionally substituted with 1-2 substituents independently selected from hydroxyl, halogen, —C(=O)NR$^{B1}$R$^{C1}$, —SO₂(C1-C6 alkyl), —CO₂H, C1-C6 alkyl optionally substituted with hydroxyl, C1-C6 alkoxy, and C1-C6 haloalkoxy;

each R$^{A2}$, R$^{B2}$, and R$^{C2}$ is independently hydrogen or C1-C6 alkyl;

each R$^G$ is independently selected from the group consisting of: fluoro, cyano, hydroxyl, C1-C6 alkyl optionally substituted with hydroxyl, C1-C6 alkoxy, —NR$^{A1}$R$^{B1}$, =NR$^{A2}$, —C(=O)NR$^{C1}$R$^{D1}$, —CO₂(C1-C6 alkyl), C1-C6 haloalkyl, C3-C6 cycloalkyl, C1-C6 haloalkoxy, —SO₂(C1-C6 alkyl), and —CO₂H; and wherein the compound is not a compound selected from the group consisting of:

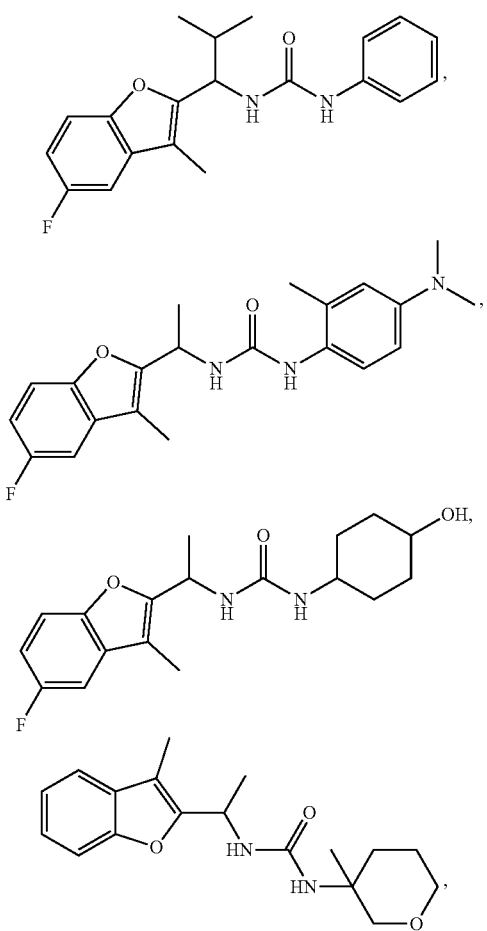

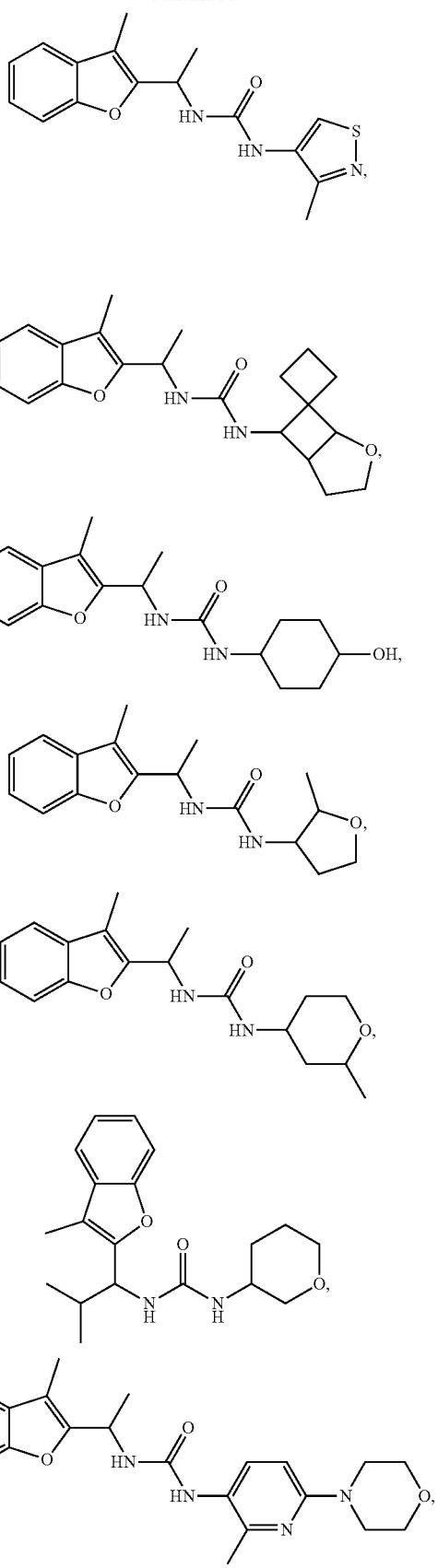

-continued
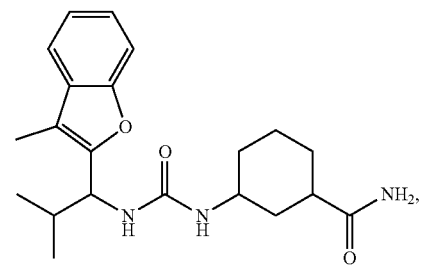
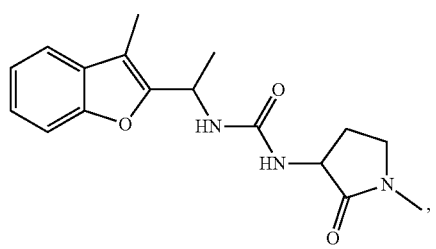
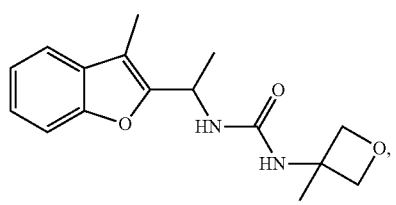
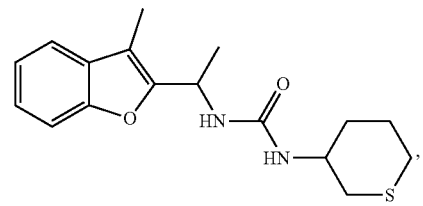
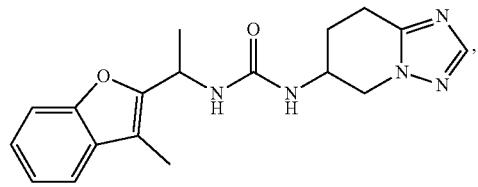
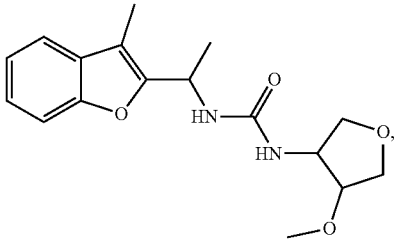
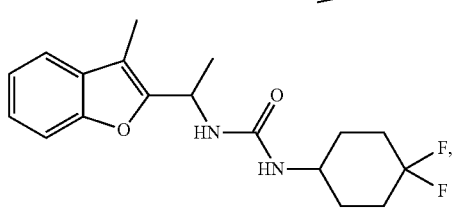
-continued
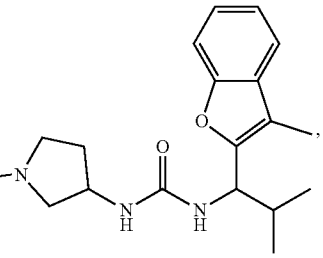
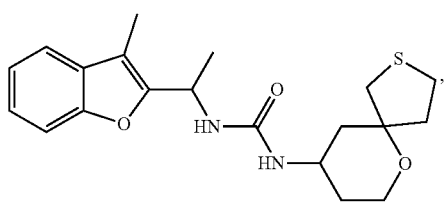
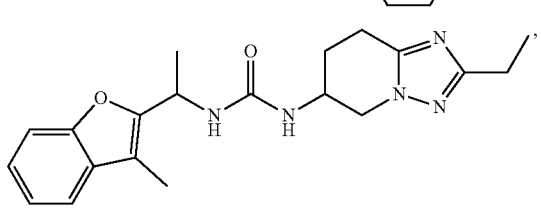
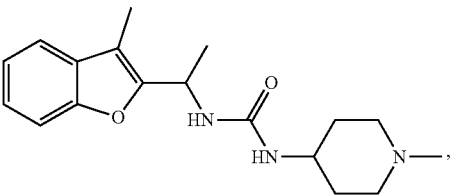
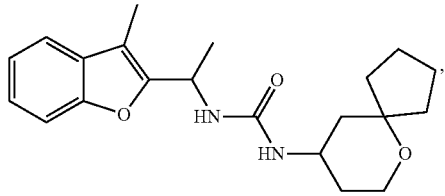
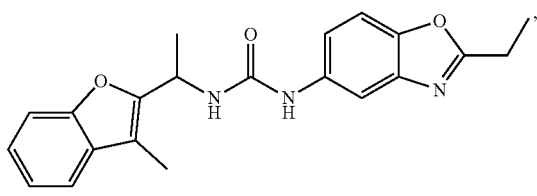
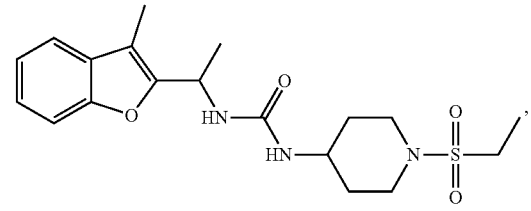
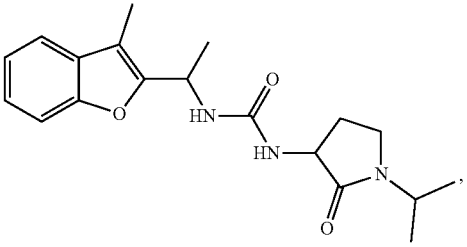

475
-continued
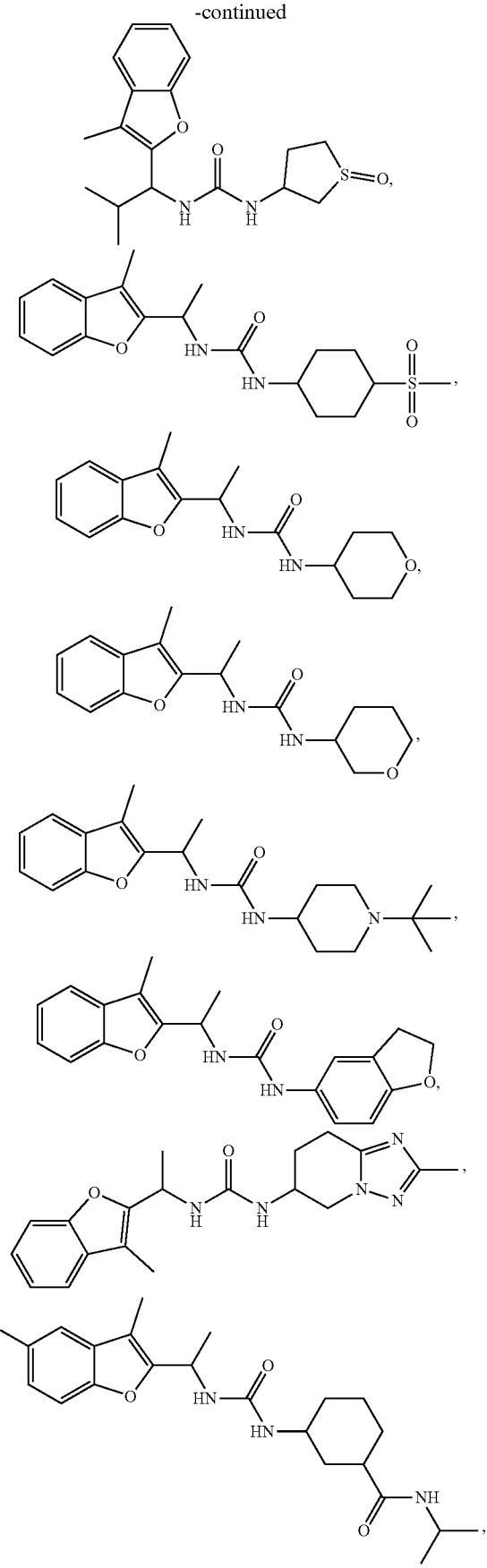
476
-continued
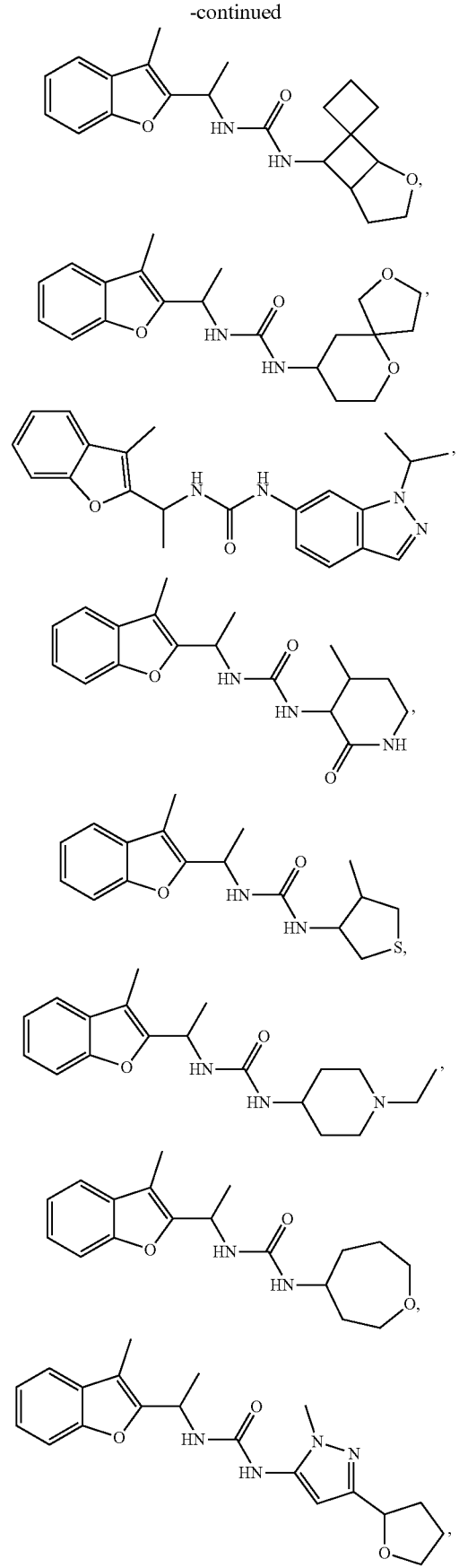

477
-continued
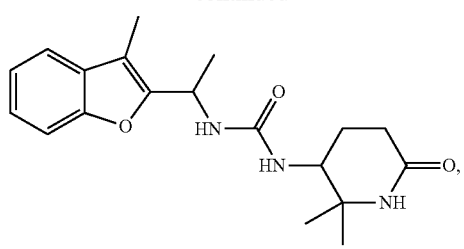
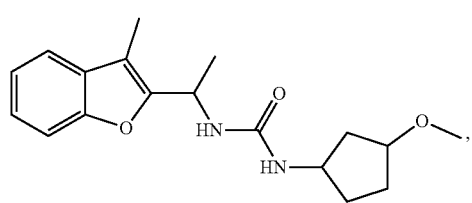
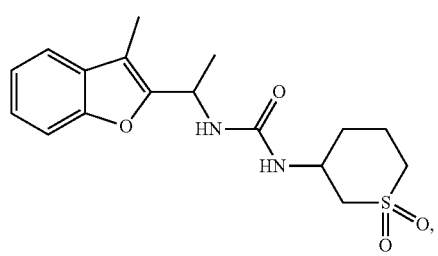
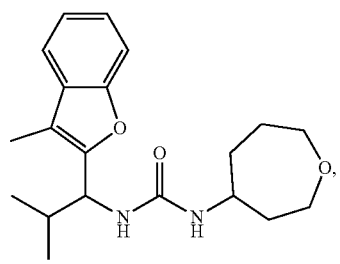
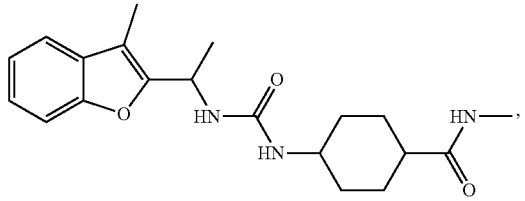
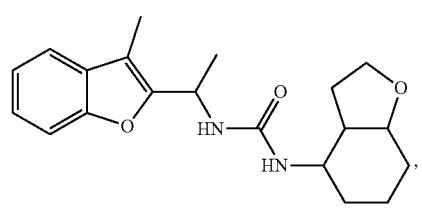
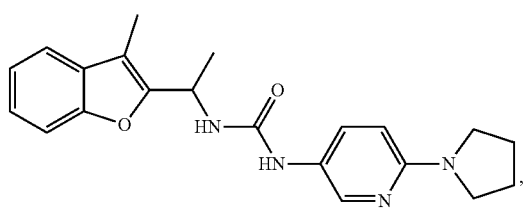
478
-continued
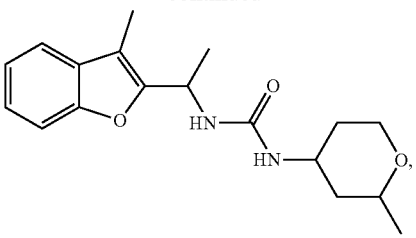
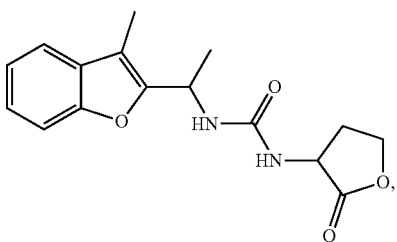
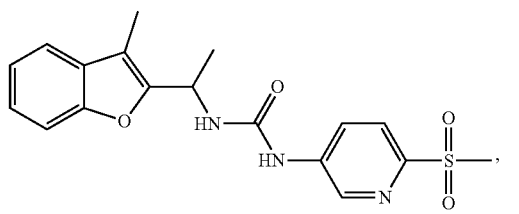
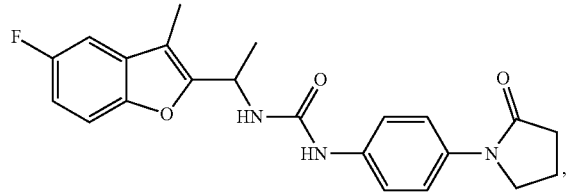
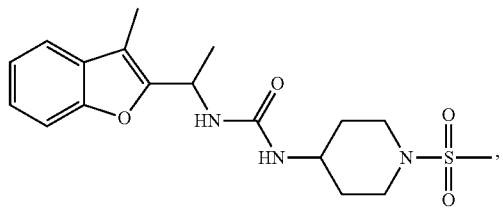
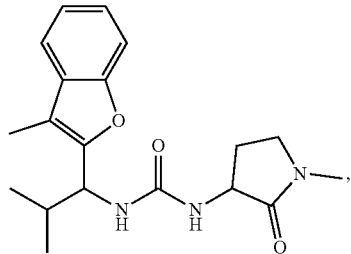
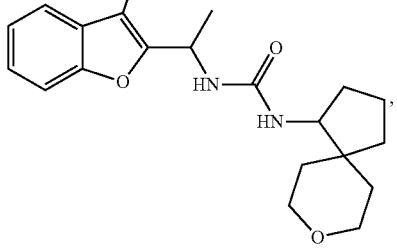

479
-continued
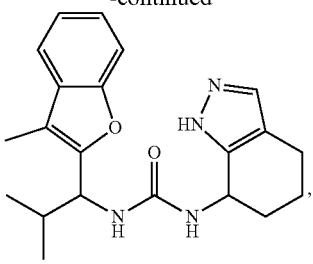
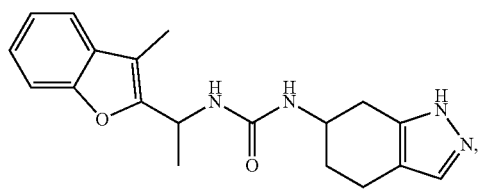
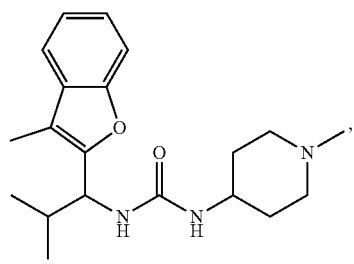
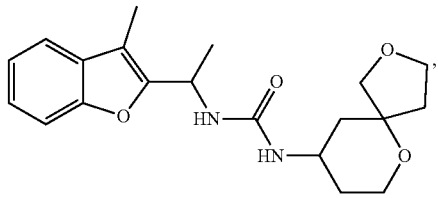
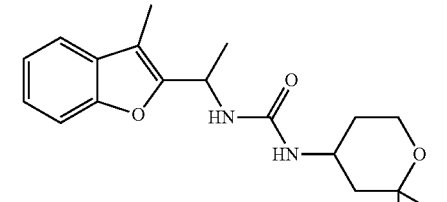
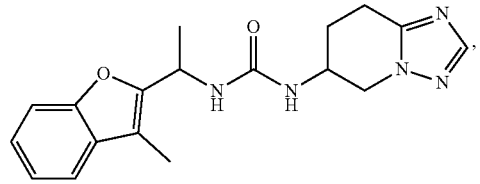
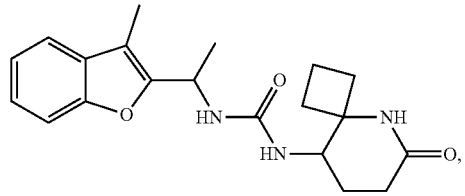
480
-continued
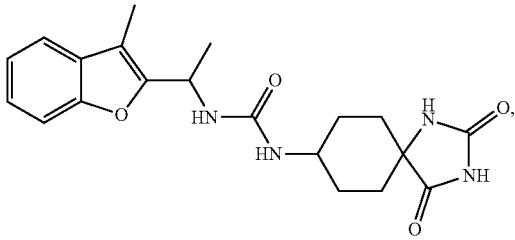
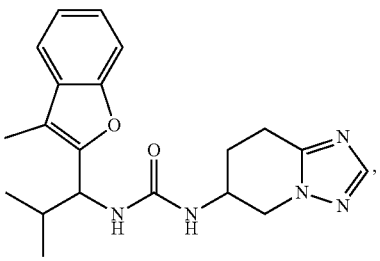
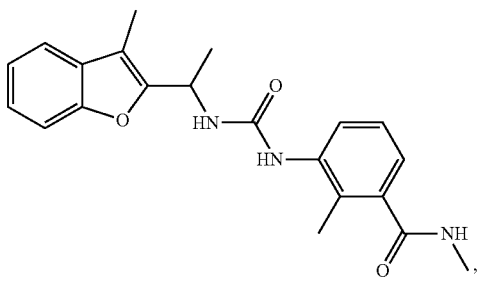
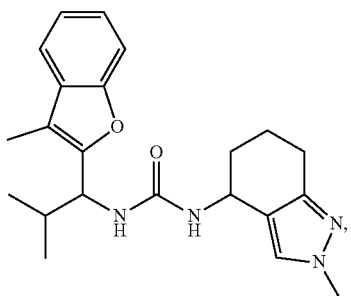
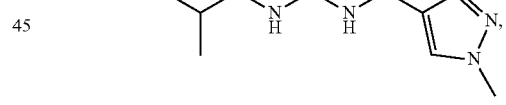
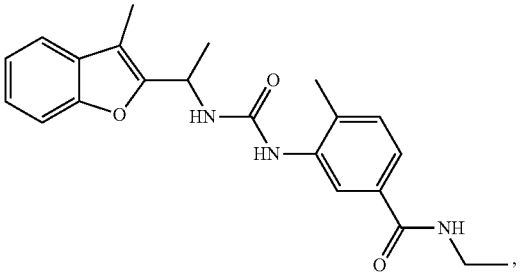

481
-continued
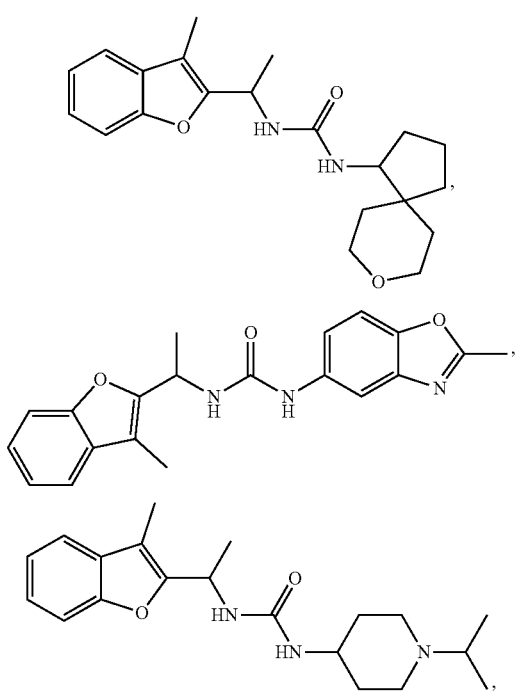
482
-continued
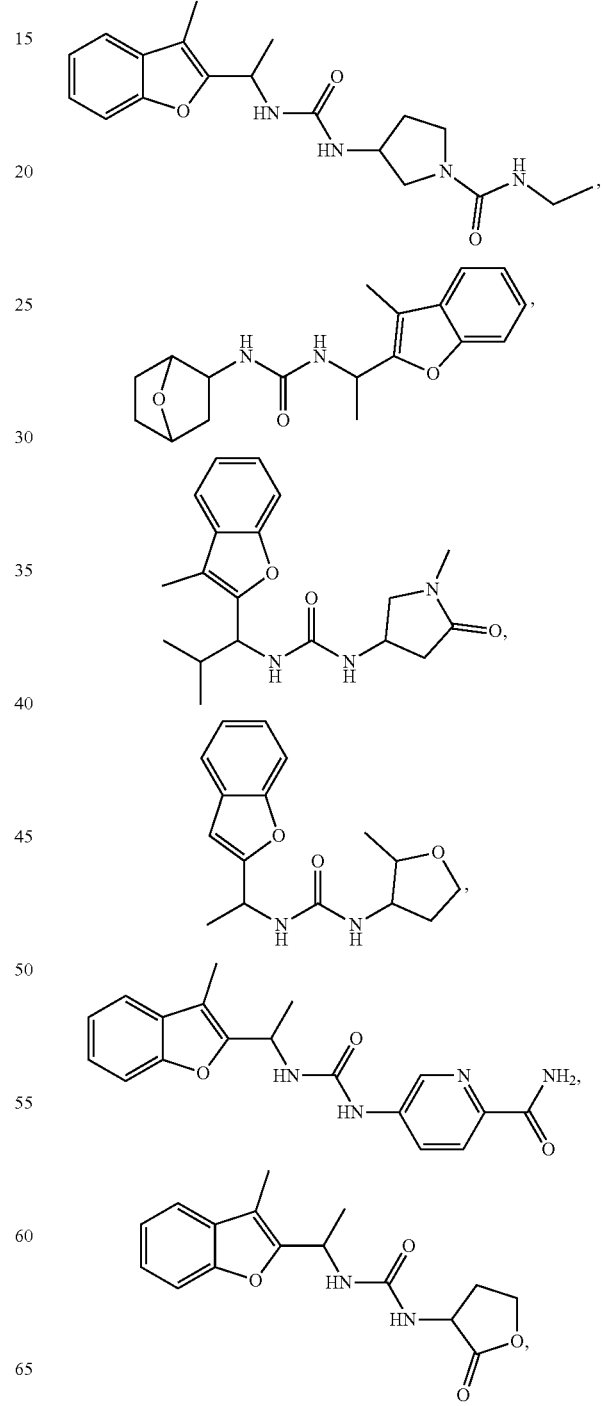

483
-continued
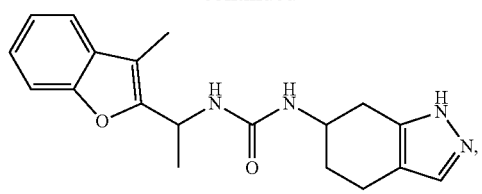
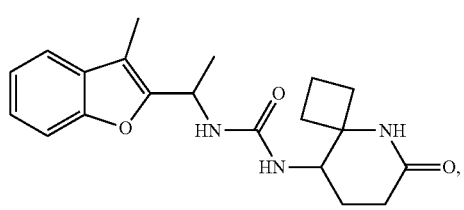
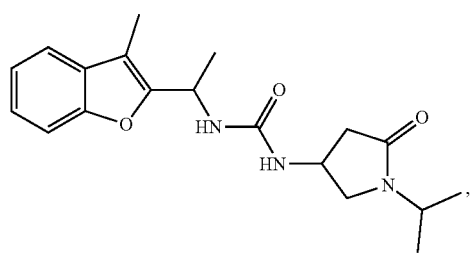
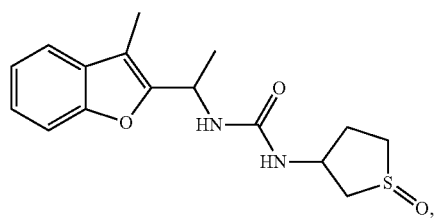
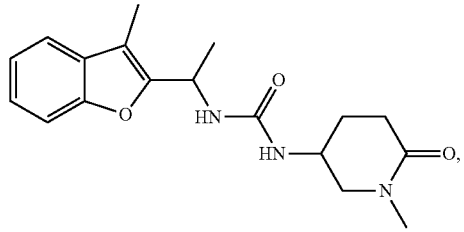
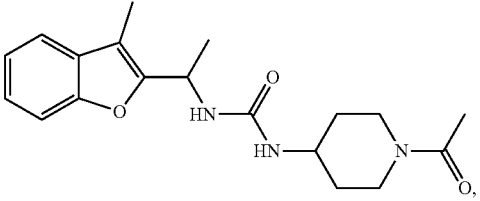
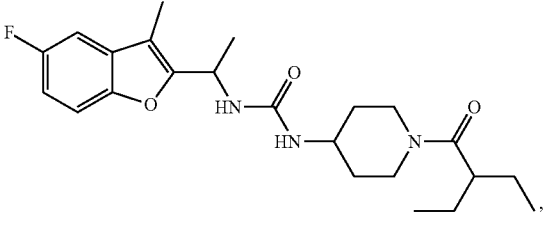
484
-continued
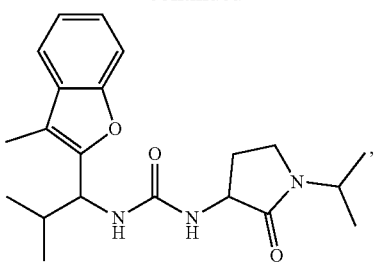
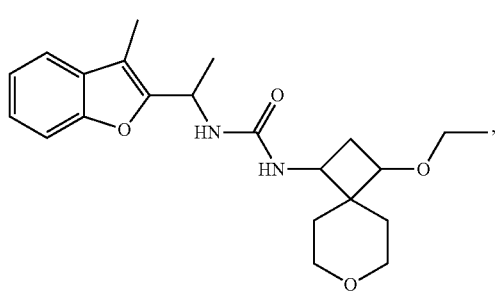
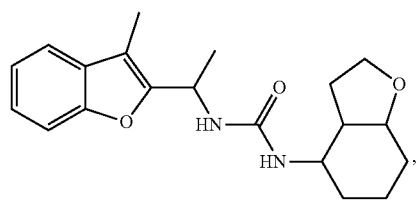
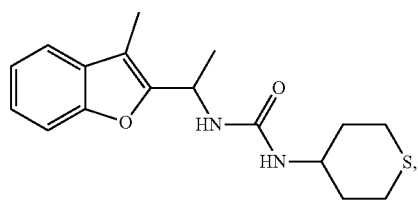
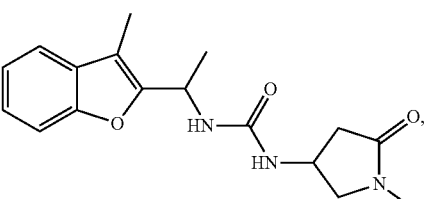
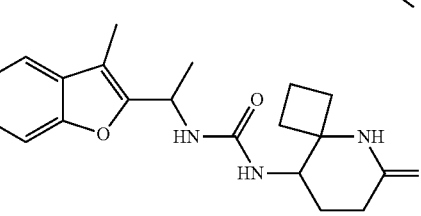
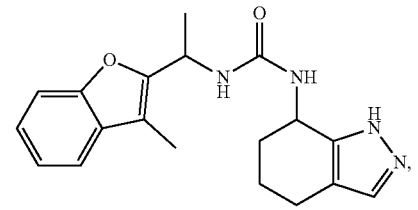

485
-continued
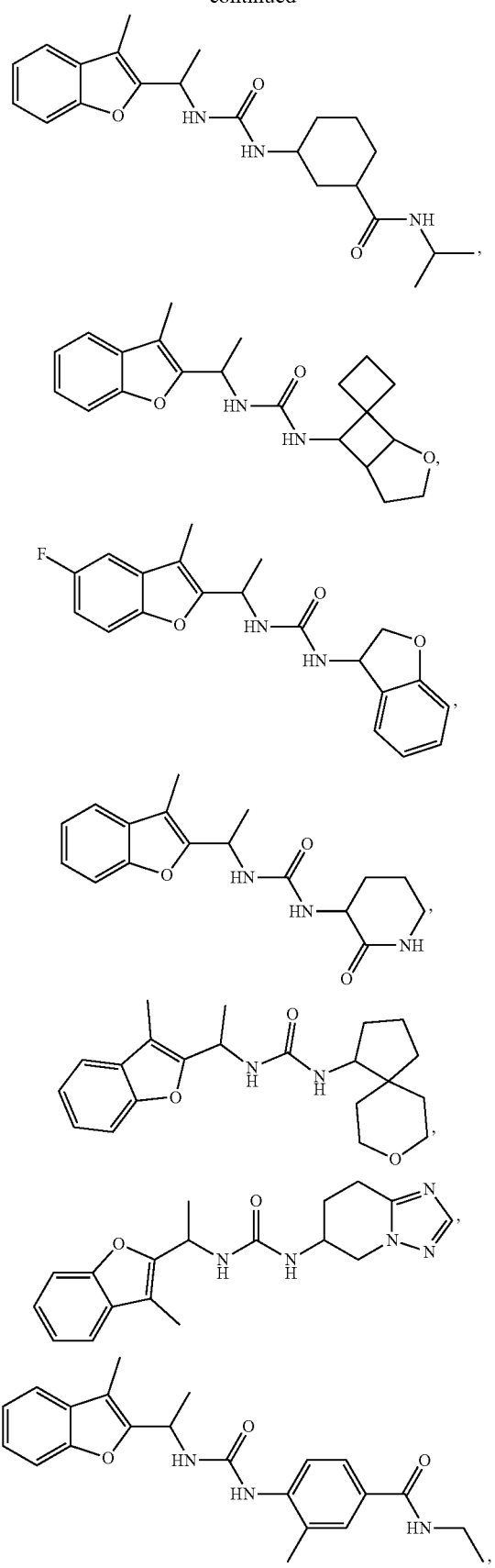
486
-continued
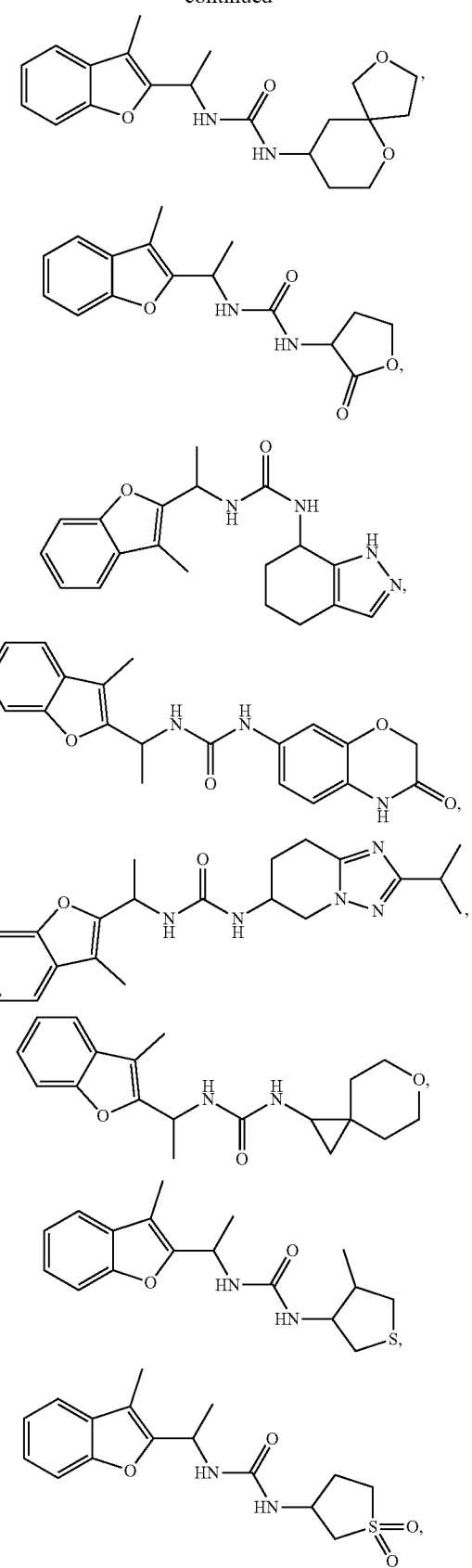

487
-continued
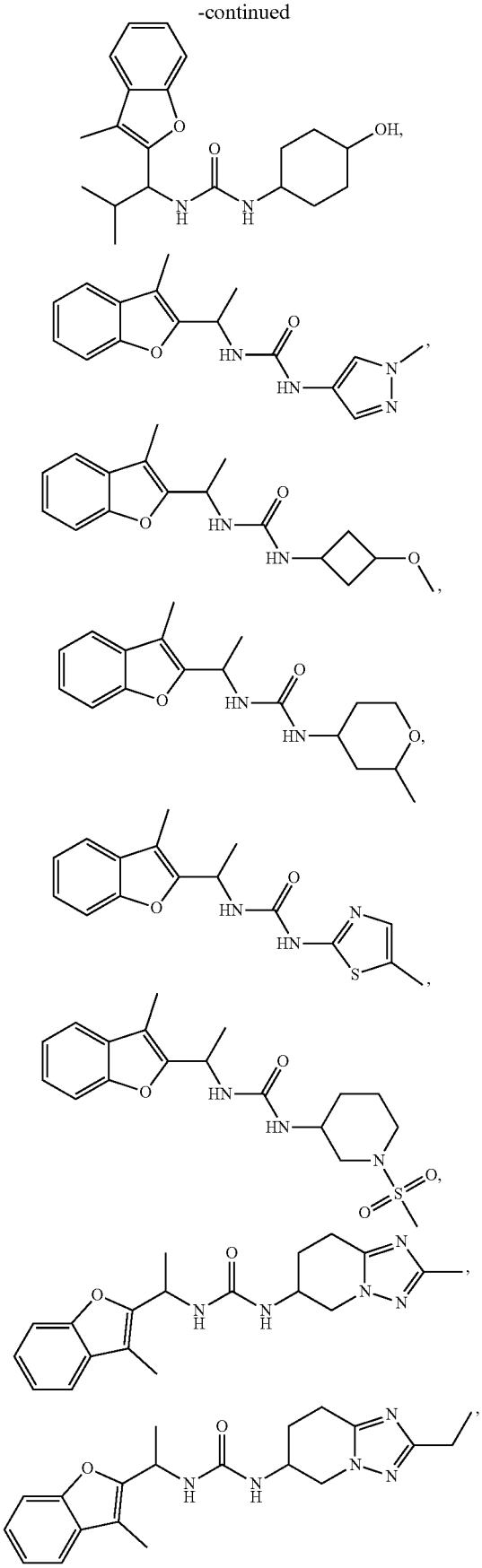
488
-continued
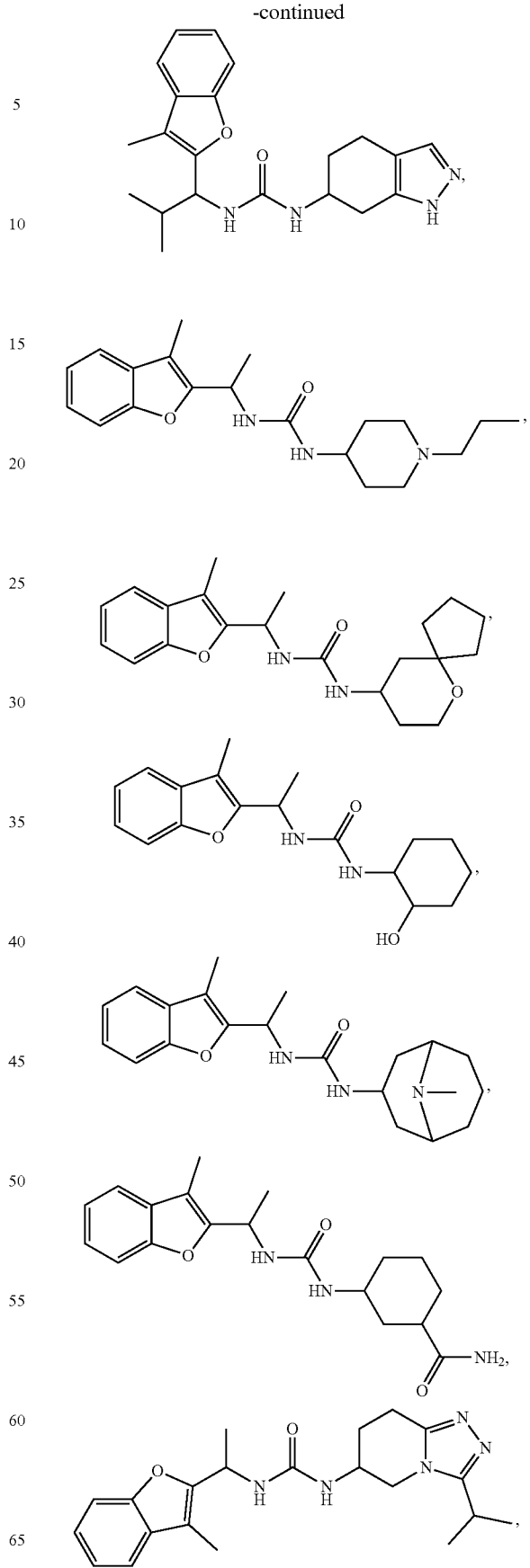

489
-continued
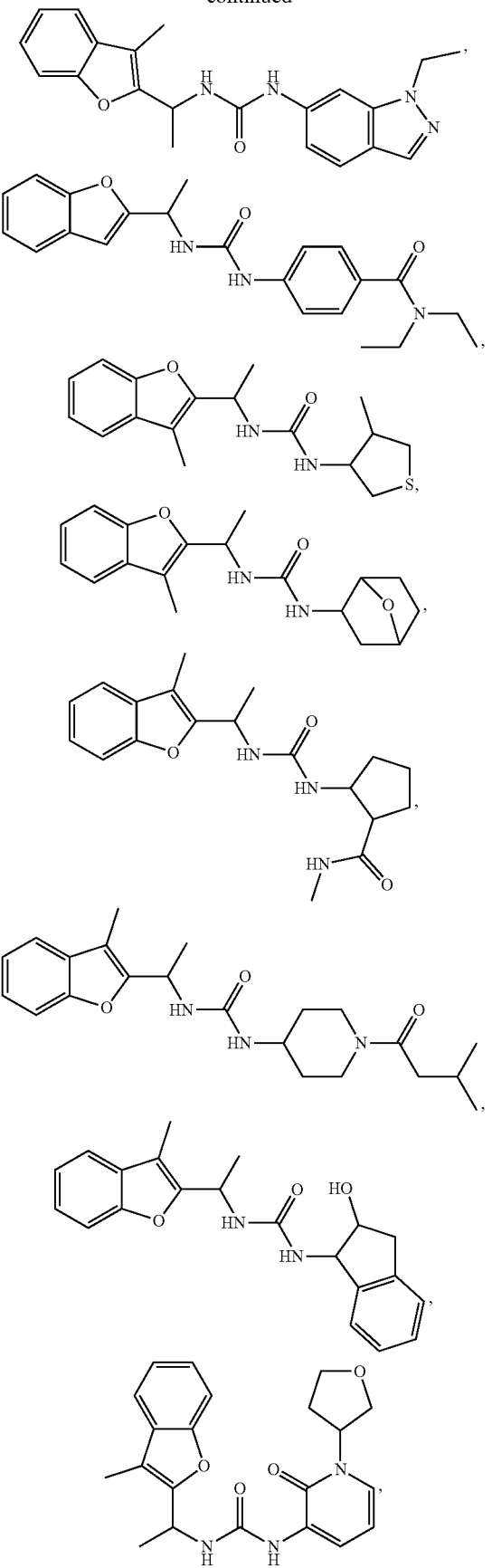
490
-continued
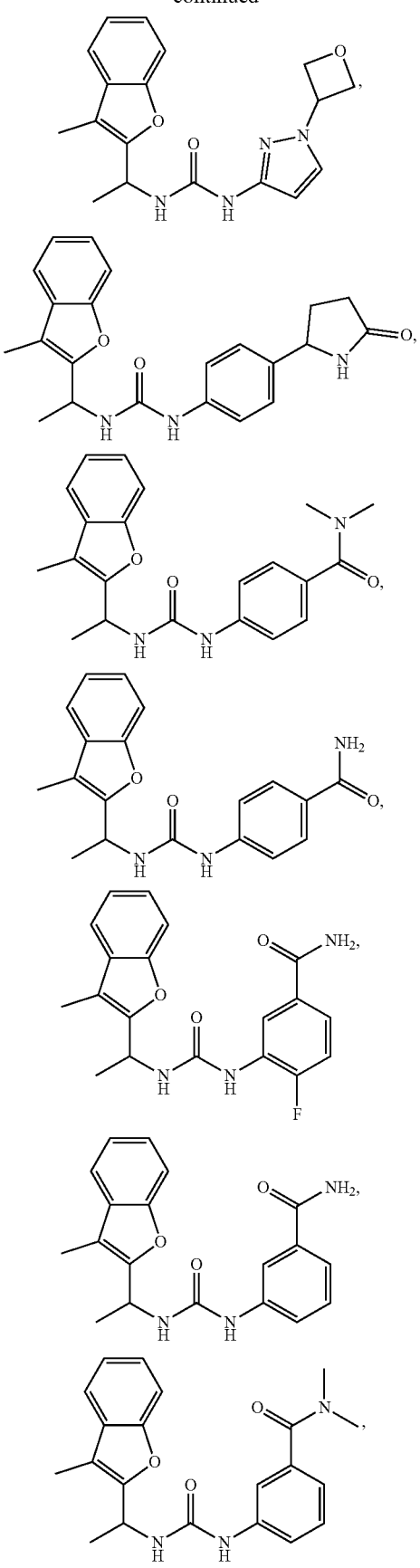

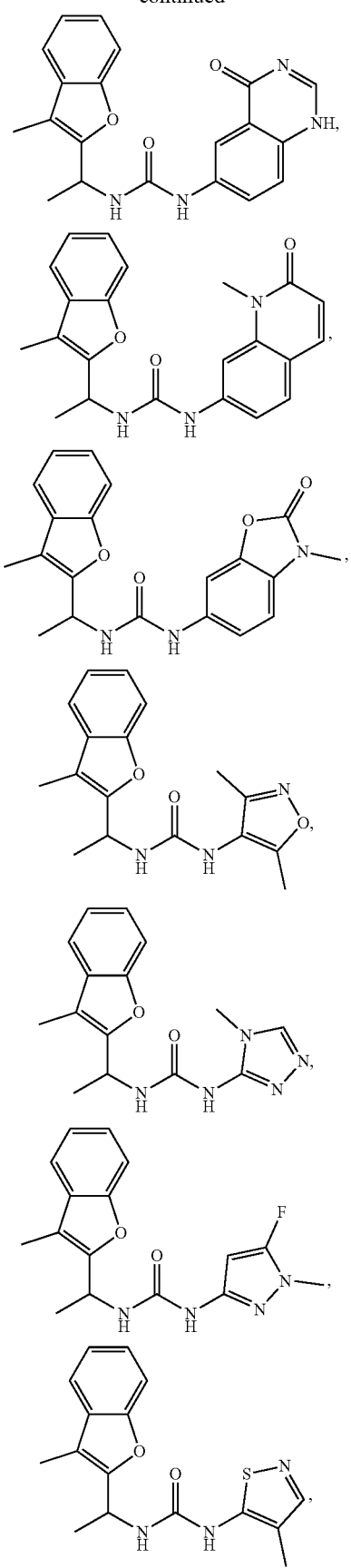
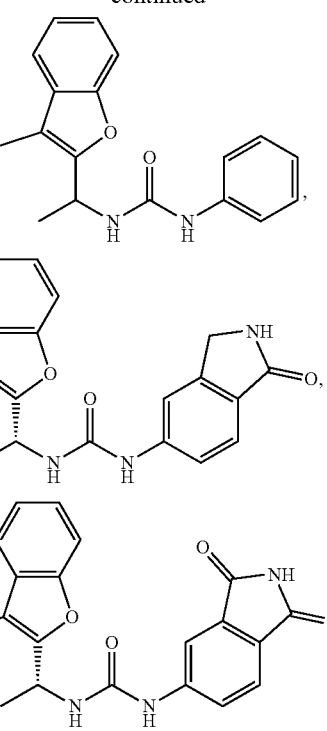
Embodiment 2: The compound of embodiment 1, wherein m is 1.
Embodiment 3: The compound of embodiment 1, wherein m is 2.
Embodiment 4: The compound of embodiments 1 or 2, wherein
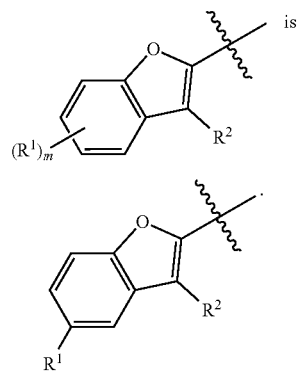
Embodiment 5: The compound of embodiments 1 or 2, wherein
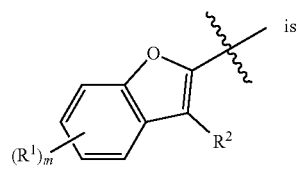

-continued

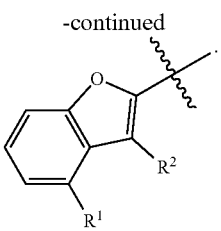

Embodiment 6: The compound of embodiments 1 or 3, wherein

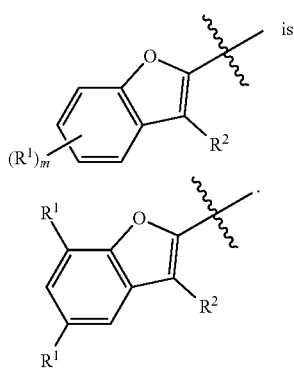

is

Embodiment 7: The compound of any one of embodiments 1-6, wherein each $R^1$ is halogen.

Embodiment 8: The compound of any one of embodiments 1-7, wherein each $R^1$ is selected from fluoro and chloro.

Embodiment 9: The compound of any one of embodiments 1-8, wherein each $R^1$ is fluoro.

Embodiment 10: The compound of any one of embodiments 1-6, wherein one $R^1$ is cyano.

Embodiment 11: The compound of any one of embodiments 1-6, wherein one $R^1$ is C1-C6 alkyl.

Embodiment 12: The compound of any one of embodiments 1-6, wherein one $R^1$ is C3-C6 cycloalkyl.

Embodiment 13: The compound of embodiment 1, wherein m is 0.

Embodiment 14: The compound of any one of embodiments 1-13, wherein $R^2$ is a C1-C6 alkyl.

Embodiment 15: The compound of embodiment 14, wherein $R^2$ is methyl.

Embodiment 16: The compound of any one of embodiments 1-13, wherein $R^2$ is a C1-C6 haloalkyl.

Embodiment 17: The compound of embodiment 16, wherein $R^2$ is difluoromethyl.

Embodiment 18: The compound of embodiment 16, wherein $R^2$ is trifluoromethyl.

Embodiment 19: The compound of any one of embodiments 1-13, wherein $R^2$ is halogen.

Embodiment 20: The compound of any one of embodiments 1-13, wherein $R^2$ is C3-C6 cycloalkyl optionally substituted with 1 or 2 fluoro.

Embodiment 21: The compound of any one of embodiments 1-13 or 20, wherein $R^2$ is C3-C6 cycloalkyl substituted with 1 or 2 fluoro.

Embodiment 22: The compound of any one of embodiments 1-13 or 21, wherein $R^2$ is an unsubstituted C3-C6 cycloalkyl.

Embodiment 23: The compound of any one of embodiments 1-22, wherein $R^3$ is a C1-C6 alkyl.

Embodiment 24: The compound of any one of embodiments 1-23, wherein $R^3$ is methyl, ethyl, or isopropyl.

Embodiment 25: The compound of any one of embodiments 1-23, wherein $R^3$ is methyl.

Embodiment 26: The compound of any one of embodiments 1-23, wherein $R^3$ is ethyl.

Embodiment 27: The compound of any one of embodiments 1-23, wherein $R^3$ is isopropyl.

Embodiment 28: The compound of any one of embodiments 1-22, wherein $R^3$ is a C1-C6 haloalkyl.

Embodiment 29: The compound of any one of embodiments 1-22 and 28, wherein $R^3$ is trifluoromethyl.

Embodiment 30: The compound of any one of embodiments 1-22, wherein $R^3$ is C3-C6 cycloalkyl optionally substituted with 1 or 2 substituents independently selected from fluoro and C1-C6 alkyl.

Embodiment 31: The compound of any one of embodiments 1-22 and 30, wherein $R^3$ is C3-C6 cycloalkyl substituted with 1 or 2 fluoro.

Embodiment 32: The compound of any one of embodiments 1-22 and 30, wherein $R^3$ is an unsubstituted C3-C6 cycloalkyl.

Embodiment 33: The compound of any one of embodiments 1-22, 30, and 31, wherein the $R^3$ C3-C6 cycloalkyl is cyclopropyl.

Embodiment 34: The compound of any one of embodiments 1-33, wherein Ring A is a 6-10 membered aryl.

Embodiment 35: The compound of any one of embodiments 1-34, wherein Ring A is phenyl.

Embodiment 36: The compound of any one of embodiments 1-33, wherein Ring A is a C3-C8 cycloalkyl.

Embodiment 37: The compound of any one of embodiments 1-33 and 36, wherein Ring A is a C5-C6 cycloalkyl.

Embodiment 38: The compound of any one of embodiments 1-33 and 36-37, wherein Ring A is a cyclohexyl.

Embodiment 39: The compound of any one of embodiments 1-33, wherein Ring A is a 5-10 membered heteroaryl.

Embodiment 40: The compound of any one of embodiments 1-33 and 39, wherein Ring A is a 5-6 membered heteroaryl.

Embodiment 41: The compound of any one of embodiments 1-33 and 39-40, wherein Ring A is pyrimidinyl, pyridyl, thiazolyl, thiophenyl, or pyrazolyl.

Embodiment 42: The compound of any one of embodiments 1-33 and 39-41, wherein Ring A is pyrimidinyl.

Embodiment 43: The compound of any one of embodiments 1-33 and 39-41, wherein Ring A is pyridyl.

Embodiment 44: The compound of any one of embodiments 1-33 and 39-41, wherein Ring A is thiazolyl.

Embodiment 45: The compound of any one of embodiments 1-33 and 39-41, wherein Ring A is thiophenyl.

Embodiment 46: The compound of any one of embodiments 1-33 and 39-41, wherein Ring A is pyrazolyl.

Embodiment 47: The compound of any one of embodiments 1-33 and 39-41, wherein Ring A is 5-pyrimidinyl, 3-pyridyl, or 4-pyrazolyl.

Embodiment 48: The compound of any one of embodiments 1-33, 39-41, and 47, wherein Ring A is 5-pyrimidinyl.

Embodiment 49: The compound of any one of embodiments 1-33, 39-41, and 47, wherein Ring A is 3-pyridyl.

Embodiment 50: The compound of any one of embodiments 1-33, 39-41, and 47, wherein Ring A is 4-pyrazolyl.

Embodiment 51: The compound of any one of embodiments 1-33 and 39, wherein Ring A is a 9-10 membered heteroaryl.

Embodiment 52: The compound of any one of embodiments 1-33, 39, and 51, wherein Ring A is benzimidazolyl, indazolyl, indolyl, quinazolone, isobenzofuranonyl, isoindolinonyl, or imidazo[1,2-a]pyridinyl.

Embodiment 53: The compound of any one of embodiments 1-33, 39, and 51-52, wherein Ring A is benzimidazolyl.

Embodiment 54: The compound of any one of embodiments 1-33, 39, and 51-52, wherein Ring A is indazolyl.

Embodiment 55: The compound of any one of embodiments 1-33, 39, and 51-52, wherein Ring A is indolyl.

Embodiment 56: The compound of any one of embodiments 1-33, 39, and 51-52, wherein Ring A is indolyl.

Embodiment 57: The compound of any one of embodiments 1-33, 39, and 51-52, wherein Ring A is quinazolone.

Embodiment 58: The compound of any one of embodiments 1-33, 39, and 51-52, wherein Ring A is isobenzofuranonyl.

Embodiment 59: The compound of any one of embodiments 1-33, 39, and 51-52, wherein Ring A is isoindolinonyl.

Embodiment 60: The compound of any one of embodiments 1-33, 39, and 51-52, wherein Ring A is imidazo[1,2-a]pyridinyl.

Embodiment 61: The compound of any one of embodiments 1-33, 39, and 51-52, wherein Ring A is 2-benzimidazolyl, 5-indazolyl, 2-indolyl, 7-imidazo[1,2-a]pyridinyl,

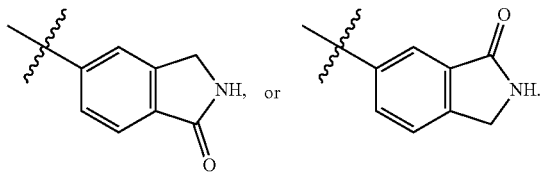 [SMILES: *c1ccc2c(c1)CNC2=O ; *c1ccc2c(c1)C(=O)NC2]

Embodiment 62: The compound of any one of embodiments 1-33, 39, and 61, wherein Ring A is 2-benzimidazolyl.

Embodiment 63: The compound of any one of embodiments 1-33, 39, and 61, wherein Ring A is 5-indazolyl.

Embodiment 64: The compound of any one of embodiments 1-33, 39, and 61, wherein Ring A is 2-indolyl.

Embodiment 65: The compound of any one of embodiments 1-33, 39, and 61, wherein Ring A is 7-imidazo[1,2-a]pyridinyl.

Embodiment 66: The compound of any one of embodiments 1-33, 39, and 61, wherein Ring A is

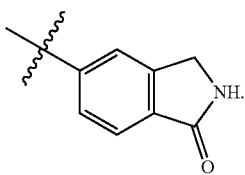 [SMILES: *c1ccc2c(c1)CNC2=O]

Embodiment 67: The compound of any one of embodiments 1-33, 39, and 61, wherein Ring A is

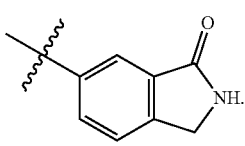 [SMILES: *c1ccc2c(c1)C(=O)NC2]

Embodiment 68: The compound of any one of embodiments 1-33, wherein Ring A is a 4-10 membered heterocyclyl.

Embodiment 69: The compound of any one of embodiments 1-33 and 68, wherein Ring A is a 6-9 membered heterocyclyl.

Embodiment 70: The compound of any one of embodiments 1-33 and 68-69, wherein Ring A is piperidinyl or 3-methyltetrahydro-2H-thiopyranyl-1,1-dioxide.

Embodiment 71: The compound of any one of embodiments 1-33 and 68-70, wherein Ring A is piperidinyl.

Embodiment 72: The compound of any one of embodiments 1-33 and 68-70, wherein Ring A is 3-methyltetrahydro-2H-thiopyranyl-1,1-dioxide.

Embodiment 73: The compound of any one of embodiments 1-33 and 68-70, wherein Ring A is 3-piperidinyl, 4-piperidinyl, or

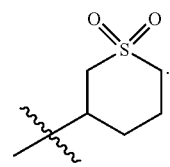

Embodiment 73: The compound of any one of embodiments 1-33 and 68-70, wherein Ring A is 3-piperidinyl.

Embodiment 74: The compound of any one of embodiments 1-33 and 68-70, wherein Ring A is 4-piperidinyl.

Embodiment 75: The compound of any one of embodiments 1-33 and 68-70, wherein Ring A is

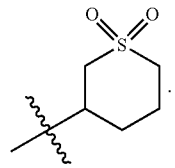 [SMILES: *C1CCCS(=O)(=O)C1]

Embodiment 76: The compound of any one of embodiments 1-75, wherein n is 1.

Embodiment 77: The compound of any one of embodiments 1-75, wherein n is 2.

Embodiment 78: The compound of any one of embodiments 1-77, wherein one $R^4$ is an unsubstituted C1-C6 alkyl.

Embodiment 79: The compound of any one of embodiments 1-78, wherein one $R^4$ is methyl.

Embodiment 80: The compound of any one of embodiments 1-77, wherein one $R^4$ is C1-C6 alkoxy optionally substituted with 1-2 substituents independently selected from hydroxyl and C3-C6 cycloalkyl.

Embodiment 81: The compound of any one of embodiments 1-77, wherein one $R^4$ is C1-C6 alkoxy substituted with 1-2 substituents independently selected from hydroxyl and C3-C6 cycloalkyl.

Embodiment 82: The compound of any one of embodiments 1-77, wherein one $R^4$ is C1-C6 alkoxy substituted with hydroxyl or C3-C6 cycloalkyl.

Embodiment 83: The compound of any one of embodiments 1-77, wherein one $R^4$ is C1-C6 alkoxy substituted with 2 substituents independently selected from hydroxyl and C3-C6 cycloalkyl.

Embodiment 84: The compound of any one of embodiments 1-77, wherein one $R^4$ is C1-C6 alkoxy.

Embodiment 85: The compound of any one of embodiments 1-77 and 84, wherein one R4 is methoxy.

Embodiment 86: The compound of any one of embodiments 1-77, wherein one $R^4$ is C1-C6 haloalkyl.

Embodiment 87: The compound of any one of embodiments 1-77 and 86, wherein one R4 is trifluoromethyl.

Embodiment 88: The compound of any one of embodiments 1-77, wherein one $R^4$ is hydroxyl.

Embodiment 89: The compound of any one of embodiments 1-77, wherein one $R^4$ is cyano.

Embodiment 90: The compound of any one of embodiments 1-77, wherein one $R^4$ is —CO$_2$H.

Embodiment 91: The compound of any one of embodiments 1-77, wherein one $R^4$ is halogen.

Embodiment 92: The compound of any one of embodiments 1-77, wherein one $R^4$ is C1-C6 alkyl substituted with 1-2 hydroxyl.

Embodiment 93: The compound of any one of embodiments 1-77 and 92, wherein one R4 is C1-C6 alkyl substituted with hydroxyl.

Embodiment 94: The compound of any one of embodiments 1-77 and 92, wherein one R4 is C1-C6 alkyl substituted with 2 hydroxyl.

Embodiment 95: The compound of any one of embodiments 1-77, wherein one $R^4$ is C1-C6 alkyl substituted with —NR$^A$R$^B$.

Embodiment 96: The compound of any one of embodiments 1-77, wherein one $R^4$ is —NR$^A$R$^B$.

Embodiment 97: The compound of any one of embodiments 1-77 and 95-96, wherein $R^A$ and $R^B$ are each hydrogen.

Embodiment 98: The compound of any one of embodiments 1-77 and 95-96, wherein $R^A$ and $R^B$ are each C1-C6 alkyl.

Embodiment 99: The compound of any one of embodiments 1-52, 95-96, and 98, wherein $R^A$ and $R^B$ are each methyl.

Embodiment 100: The compound of any one of embodiments 1-77 and 95-96, wherein one of $R^A$ and $R^B$ is hydrogen and the other of $R^A$ and $R^B$ is C1-C6 haloalkyl.

Embodiment 101: The compound of any one of embodiments 1-77, wherein one $R^4$ is —C(=O)NR$^C$R$^D$.

Embodiment 102: The compound of any one of embodiments 1-77 and 101, wherein $R^C$ and $R^D$ are each hydrogen.

Embodiment 103: The compound of any one of embodiments 1-77 and 101, wherein $R^C$ and $R^D$ are each C1-C6 alkyl.

Embodiment 104: The compound of any one of embodiments 1-77 and 101, wherein $R^C$ and $R^D$, together with the nitrogen atom to which they are attached form a 4-10 membered heterocyclyl optionally substituted with 1-2 substituents independently selected from hydroxyl, halogen, —C(=O)NR$^{B1}$R$^{C1}$, —SO$_2$(C1-C6 alkyl), —CO$_2$H, C1-C6 alkyl optionally substituted with hydroxyl, C1-C6 alkoxy, and C1-C6 haloalkoxy.

Embodiment 105: The compound of any one of embodiments 1-77 and 101, wherein $R^C$ and $R^D$, together with the nitrogen atom to which they are attached form a 4-10 membered heterocyclyl substituted with 1-2 substituents independently selected from hydroxyl, halogen, —C(=O)NR$^{B1}$R$^{C1}$, —SO$_2$(C1-C6 alkyl), —CO$_2$H, C1-C6 alkyl optionally substituted with hydroxyl, C1-C6 alkoxy, and C1-C6 haloalkoxy.

Embodiment 106: The compound of any one of embodiments 1-77 and 101, wherein $R^C$ and $R^D$, together with the nitrogen atom to which they are attached form a 4-6 membered heterocyclyl.

Embodiment 107: The compound of any one of embodiments 1-77, 101, and 76, wherein $R^C$ and $R^D$, together with the nitrogen atom to which they are attached form azetidine or piperazine.

Embodiment 108: The compound of any one of embodiments 1-77, wherein one $R^4$ is —SO$_2$(NR$^E$R$^F$).

Embodiment 109: The compound of any one of embodiments 1-77 and 108, wherein $R^E$ and $R^F$ are each hydrogen.

Embodiment 110: The compound of any one of embodiments 1-77 and 208, wherein $R^E$ and $R^F$ are each is C1-C6 alkyl.

Embodiment 111: The compound of any one of embodiments 1-77, wherein one $R^4$ is —SO$_2$(C1-C6 alkyl).

Embodiment 112: The compound of any one of embodiments 1-77 and 111, wherein one $R^4$ is —SO$_2$Me.

Embodiment 113: The compound of any one of embodiments 1-77 and 111, wherein one $R^4$ is —SO$_2$Et.

Embodiment 114: The compound of any one of embodiments 1-77, wherein one $R^4$ is —S(=O)(=NH)(C1-C6 alkyl).

Embodiment 115: The compound of any one of embodiments 1-77 and 84, wherein one R4 is —S(=O)(=NH)Me.

Embodiment 116: The compound of any one of embodiments 1-77, wherein one $R^4$ is —C(=O)(C1-C6 alkyl).

Embodiment 117: The compound of any one of embodiments 1-77 and 106, wherein one $R^4$ is —C(=O)Me.

Embodiment 118: The compound of any one of embodiments 1-77, wherein one $R^4$ is —CO$_2$(C1-C6 alkyl).

Embodiment 119: The compound of any one of embodiments 1-77 and 118, wherein one $R^4$ is —CO$_2$Me.

Embodiment 120: The compound of any one of embodiments 1-77, wherein one $R^4$ is 5-6 membered heteroaryl optionally substituted with C1-C6 alkyl.

Embodiment 121: The compound of any one of embodiments 1-77 and 120, wherein one $R^4$ is 5-6 membered heteroaryl substituted with C1-C6 alkyl.

Embodiment 122: The compound of any one of embodiments 1-77 and 120-121, wherein one $R^4$ is tetrazolyl substituted with methyl.

Embodiment 123: The compound of any one of embodiments 1-77 and 90, wherein one $R^4$ is unsubstituted 5-6 membered heteroaryl.

Embodiment 124: The compound of any one of embodiments 1-77, 90, and 93, wherein one $R^4$ is unsubstituted pyrazolyl.

Embodiment 125: The compound of any one of embodiments 1-77, wherein one $R^4$ is 3-9 membered heterocyclyl optionally substituted with 1 or 2 independently selected $R^G$.

Embodiment 126: The compound of any one of embodiments 1-77, wherein one $R^4$ is 3-6 membered heterocyclyl optionally substituted with 1 or 2 independently selected $R^G$.

Embodiment 127: The compound of any one of embodiments 1-77 and 96, wherein one R4 is 3-6 membered heterocyclyl substituted with 1 or 2 independently selected $R^G$.

Embodiment 128: The compound of any one of embodiments 1-77 and 126-127, wherein one $R^4$ is 3-6 membered heterocyclyl substituted with 1 $R^G$.

Embodiment 129: The compound of any one of embodiments 1-77 and 126-127, wherein one $R^4$ is 3-6 membered heterocyclyl substituted with 2 independently selected $R^G$.

Embodiment 130: The compound of any one of embodiments 1-77, wherein one $R^4$ is 3-6 membered cycloalkyl optionally substituted with 1 or 2 independently selected $R^G$.

Embodiment 131: The compound of any one of embodiments 1-77 and 130, wherein one $R^4$ is 3-6 membered cycloalkyl substituted with 1 or 2 independently selected $R^G$.

Embodiment 132: The compound of any one of embodiments 1-77 and 130-131, wherein one $R^4$ is 3-6 membered cycloalkyl substituted with 1 $R^G$.

Embodiment 133: The compound of any one of embodiments 1-77 and 130-131, wherein one $R^4$ is 3-6 membered cycloalkyl substituted with 2 independently selected $R^G$.

Embodiment 134: The compound of any one of embodiments 1-77 and 125-133, wherein one $R^G$ is fluoro.

Embodiment 135: The compound of any one of embodiments 1-77 and 125-133, wherein one $R^G$ is cyano.

Embodiment 136: The compound of any one of embodiments 1-77 and 125-133, wherein one $R^G$ is hydroxyl.

Embodiment 137: The compound of any one of embodiments 1-77 and 125-133, wherein one $R^G$ is C1-C6 alkyl.

Embodiment 138: The compound of any one of embodiments 1-77, 125-133, and 137, wherein one $R^G$ is methyl.

Embodiment 139: The compound of any one of embodiments 1-77 and 125-133, wherein one $R^G$ is C1-C6 alkoxy.

Embodiment 140: The compound of any one of embodiments 1-77, 125-133, and 139, wherein one $R^G$ is methoxy.

Embodiment 141: The compound of any one of embodiments 1-77 and 125-133, wherein one $R^G$ is —$NR^{A1}R^{B1}$.

Embodiment 142: The compound of any one of embodiments 1-77 and 125-133, wherein one $R^G$ is =$NR^{A2}$.

Embodiment 143: The compound of any one of embodiments 1-77, 125-133, and 142, wherein $R^{A2}$ is hydrogen.

Embodiment 144: The compound of any one of embodiments 1-77, 125-133, and 142, wherein $R^{A2}$ is C1-C6 alkyl.

Embodiment 145: The compound of any one of embodiments 1-77 and 125-133, wherein $R^{A1}$ and $R^{B1}$ are each hydrogen.

Embodiment 146: The compound of any one of embodiments 1-77, and 126-133, wherein one of $R^{A1}$ and $R^{B1}$ is hydrogen and the other of $R^{A1}$ and $R^{B1}$ is C1-C6 alkyl.

Embodiment 147: The compound of any one of embodiments 1-77, 126-133, and 116, wherein one of $R^{A1}$ and $R^{B1}$ is hydrogen and the other of $R^{A1}$ and $R^{B1}$ is methyl.

Embodiment 148: The compound of any one of embodiments 1-77 and 126-133, wherein $R^{A1}$ and $R^{B1}$ are each C1-C6 alkyl.

Embodiment 149: The compound of any one of embodiments 1-77, 126-133, and 118, wherein $R^{A1}$ and $R^{B1}$ are each methyl.

Embodiment 150: The compound of any one of embodiments 1-77 and 126-133, wherein one of $R^{A1}$ and $R^{B1}$ is hydrogen and the other of $R^{A1}$ and $R^{B1}$ is C1-C6 haloalkyl.

Embodiment 151: The compound of any one of embodiments 1-77 and 126-133, wherein $R^{A1}$ and $R^{B1}$ are each C1-C6 haloalkyl.

Embodiment 152: The compound of any one of embodiments 1-77 and 126-133, wherein one of $R^{A1}$ and $R^{B1}$ is C1-C6 alkyl and the other of $R^{A1}$ and $R^{B1}$ is C1-C6 haloalkyl.

Embodiment 153: The compound of any one of embodiments 1-77 and 126-133, wherein one $R^G$ is —C(=O)$NR^{C1}R^{D1}$.

Embodiment 154: The compound of any one of embodiments 1-77, 126-133, and 123, wherein $R^{C1}$ and $R^{D1}$ are each is hydrogen.

Embodiment 155: The compound of any one of embodiments 1-77, 126-133, and 123, wherein one of $R^{C1}$ and $R^{D1}$ is hydrogen and the other of $R^{C1}$ and $R^{D1}$ is C1-C6 alkyl.

Embodiment 156: The compound of any one of embodiments 1-77, 126-133, 123, and 125, wherein one of $R^{C1}$ and $R^{D1}$ is hydrogen and the other of $R^{C1}$ and $R^{D1}$ is methyl.

Embodiment 157: The compound of any one of embodiments 1-77, 126-133, and 123, wherein $R^{C1}$ and $R^{D1}$ are each is C1-C6 alkyl.

Embodiment 158: The compound of any one of embodiments 1-77, 126-133, 123, and 127, wherein $R^{C1}$ and $R^{D1}$ are each is methyl.

Embodiment 159: The compound of any one of embodiments 1-77, 126-133, and 123, wherein one of $R^{C1}$ and $R^{D1}$ is hydrogen and the other of $R^{C1}$ and $R^{D1}$ is C1-C6 haloalkyl.

Embodiment 160: The compound of any one of embodiments 1-77, 126-133, and 123, wherein $R^{C1}$ and $R^{D1}$ are each is C1-C6 haloalkyl.

Embodiment 161: The compound of any one of embodiments 1-77, 126-133, and 123, wherein one of $R^{C1}$ and $R^{D1}$ is C1-C6 alkyl and the other of $R^{C1}$ and $R^{D1}$ is C1-C6 haloalkyl.

Embodiment 162: The compound of any one of embodiments 1-77 and 126-133, wherein one $R^G$ is —$CO_2$(C1-C6 alkyl).

Embodiment 163: The compound of any one of embodiments 1-77 and 126-133, wherein one $R^G$ is —$CO_2CH_3$.

Embodiment 164: The compound of any one of embodiments 1-77 and 126-133, wherein one $R^G$ is C1-C6 haloalkyl.

Embodiment 165: The compound of any one of embodiments 1-77 and 126-133, wherein one $R^G$ is trifluoromethyl.

Embodiment 166: The compound of any one of embodiments 1-77 and 126-133, wherein one $R^G$ is C1-C6 haloalkoxy.

Embodiment 167: The compound of any one of embodiments 1-77 and 126-133, wherein one $R^G$ is —$SO_2$(C1-C6 alkyl).

Embodiment 168: The compound of any one of embodiments 1-77 and 126-133, wherein one $R^G$ is C3-C6 cycloalkyl.

Embodiment 169: The compound of any one of embodiments 1-77 and 126-133, wherein one $R^G$ is cyclopropyl.

Embodiment 170: The compound of any one of embodiments 1-77 and 126-133, wherein one $R^G$ is —$CO_2H$.

Embodiment 171: The compound of any one of embodiments 1-77 and 125, wherein one $R^4$ is unsubstituted 3-6 membered heterocyclyl.

Embodiment 172: The compound of any one of embodiments 125-129, wherein the $R^4$ 3-6 membered heterocyclyl is a 5-6 membered heterocyclyl.

Embodiment 173: The compound of any one of embodiments 125-129, wherein the $R^4$ 3-6 membered heterocyclyl is azetidinyl, azetidin-2-onyl, morpholinyl, piperazinyl, or tetrahydropyranyl.

Embodiment 174: The compound of any one of embodiments 125-129, wherein the $R^4$ 3-6 membered heterocyclyl is 1-azetidinyl, 1-azetidin-2-onyl, 1-piperazinyl, 1-morpholinyl, or 4-tetrahydropyranyl.

Embodiment 175: The compound of any one of embodiments 1-77 and 130, wherein one $R^4$ is unsubstituted 3-6 membered cycloalkyl.

Embodiment 176: The compound of any one of embodiments 130-170 and 175, wherein the $R^4$ 3-6 membered cycloalkyl is a 3-4 membered cycloalkyl.

Embodiment 177: The compound of any one of embodiments 130-170 and 175-176, wherein the $R^4$ 3-6 membered cycloalkyl is cyclobutyl.

Embodiment 178: The compound of any one of embodiments 1-77, wherein n is 0.

Embodiment 179: The compound of any one of embodiments 1-33, wherein

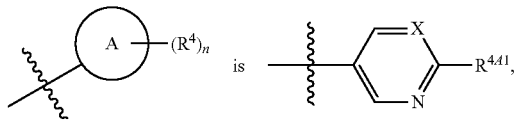

wherein: X is selected from N and $CR^{4.A2}$; $R^{4.A1}$ and $R^{4.A2}$ are independently selected from hydrogen, C1-C3 alkyl optionally substituted with —$NR^A R^B$ methoxy, C1-C3 haloalkyl, hydroxyl, cyano, —$NR^A R^B$, —C(=O)$NR^C R^D$, —$SO_2$(NR-$^E R^F$), —$SO_2$(C1-C6 alkyl), 3-6 membered heterocyclyl optionally substituted with 1 or 2 independently selected $R^G$ and 3-6 membered cycloalkyl optionally substituted with 1 or 2 independently selected $R^G$.

Embodiment 180: The compound of embodiment 179, wherein X is N.

Embodiment 181: The compound of embodiment 179, wherein X is $CR^{4.A2}$.

Embodiment 182: The compound of any one of embodiments 179-181, wherein $R^{4.A1}$ and, when present, $R^{4.A2}$ are independently selected from hydrogen, methyl, ethyl, isopropyl, difluoromethyl, trifluoromethyl, cyano, hydroxyl, methoxy, amino, —C(=O)$NH_2$, —C(=O)NHMe, —$SO_2NH_2$, —$SO_2$Me, and azetidinyl optionally substituted with 1-2 independently selected fluoro, hydroxyl, or methyl.

Embodiment 183: The compound of embodiment 179, wherein X is N and $R^{4.A1}$ is selected from amino and azetidinyl optionally substituted with 1-2 independently selected fluoro, hydroxyl, or methyl.

Embodiment 184: The compound of any one of embodiments 1-33, wherein

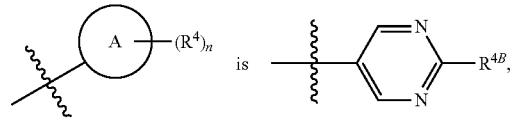

wherein: $R^{4B}$ is selected from —$NR^A R^B$ and 4-6 membered heterocyclyl comprising one nitrogen ring member and optionally substituted with 1-2 independently selected $R^{G1}$; wherein $R^{G1}$ is selected from fluoro, hydroxyl, C1-C6 haloalkyl, and C1-C6 alkyl.

Embodiment 185: The compound of embodiment 184, wherein $R^A$ and $R^B$ are both hydrogen.

Embodiment 186: The compound of embodiment 184, wherein one of $R^A$ and $R^B$ is hydrogen and the other of $R^A$ and $R^B$ is C1-C6 alkyl.

Embodiment 187: The compound of any one of embodiments 184 and 186, wherein one of $R^A$ and $R^B$ is hydrogen and the other of $R^A$ and $R^B$ is methyl.

Embodiment 188: The compound of embodiment 184, wherein $R^{4B}$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

Embodiment 189: The compound of embodiment 184, wherein $R^{4B}$ is

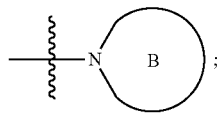

wherein Ring B is azetidinyl, pyrrolidinyl, piperidinyl, piperazinyl, or morpholinyl, each optionally substituted with 1-2 $R^G$ independently selected from fluoro, hydroxyl, trifluoromethyl, and C1-C6 alkyl.

Embodiment 190: The compound of embodiment 189, wherein Ring B is azetidinyl.

Embodiment 191: The compound of any one of embodiments 189-190, wherein Ring B is unsubstituted.

Embodiment 192: The compound of any one of embodiments 189-190, wherein Ring B is substituted with 1 $R^G$.

Embodiment 193: The compound of embodiment 192, wherein $R^G$ is fluoro.

Embodiment 194: The compound of embodiment 192, wherein $R^G$ is hydroxyl.

Embodiment 195: The compound of embodiment 192, wherein $R^G$ is methyl.

Embodiment 196: The compound of any one of embodiments 189-190, wherein Ring B is substituted with 2 $R^G$.

Embodiment 197: The compound of embodiment 196, wherein each $R^G$ is fluoro.

Embodiment 198: The compound of embodiment 196, wherein each $R^G$ is methyl.

Embodiment 199: The compound of embodiment 196, wherein one $R^G$ is hydroxyl and the other $R^G$ is methyl.

Embodiment 200: The compound of embodiment 196, wherein one $R^G$ is fluoro and the other $R^G$ is methyl.

Embodiment 201: The compound of embodiment 196, wherein one $R^G$ is hydroxyl and the other $R^G$ is fluoro.

Embodiment 202: The compound of any one of embodiments 189-201, wherein each $R^G$ is bonded to the position of Ring B para to the nitrogen that is bonded to Ring A.

Embodiment 203: The compound of embodiment 1, wherein each $R^1$ is fluoro; m is 1 or 2; $R^2$ is a C1-C6 alkyl; and $R^3$ is a C1-C6 alkyl.

Embodiment 204: The compound of embodiment 1, wherein each $R^1$ is fluoro; m is 1 or 2; $R^2$ is a C1-C6 alkyl; and $R^3$ is a C1-C6 haloalkyl.

Embodiment 205: The compound of embodiment 1, wherein: Ring A is a phenyl or a 5-6 membered heteroaryl;
 each $R^4$ is independently selected from the group consisting of: C1-C3 alkyl, C1-C3 alkoxy, C1-C3 haloalkyl, hydroxyl, cyano, —$NH_2$, —C(=O)$NH_2$, —C(=O)NHMe, —$SO_2NH_2$, —$SO_2$NHMe, —$SO_2$Me, —S(=O)(=NH)Me, —C(=O)Me, 5-6 membered heteroaryl, and unsubstituted 3-6 membered heterocyclyl; and
 n is 1 or 2.

Embodiment 206: The compound of embodiment 1, wherein:
 each $R^1$ is fluoro;
 m is 1 or 2;
 $R^2$ is a C1-C6 alkyl;
 $R^3$ is a C1-C6 alkyl;
 Ring A is a phenyl or a 5-6 membered heteroaryl;
 each $R^4$ is independently selected from the group consisting of: C1-C3 alkyl, C1-C3 alkoxy, C1-C3 haloalkyl, hydroxyl, cyano, —$NH_2$, —C(=O)$NH_2$, —C(=O)

NHMe, —SO₂NH₂, —SO₂NHMe, —SO₂Me, —S(═O)(═NH)Me, —C(═O) Me, 5-6 membered heteroaryl, and 3-6 membered heterocyclyl optionally substituted with 1 or 2 independently selected $R^G$; and n is 1 or 2.

Embodiment 207: A compound of Formula (I-A):

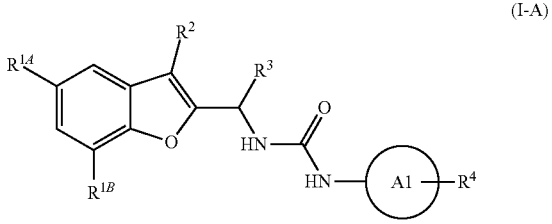

(I-A)

or a pharmaceutically acceptable salt thereof, wherein:
$R^{1A}$ is halogen;
$R^{1B}$ is halogen or absent;
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 substituents independently selected from fluoro and C1-C6 alkyl;
Ring A1 is a 6 membered heteroaryl;
$R^4$ is independently selected from the group consisting of: C1-C6 alkyl optionally substituted with —$NR^AR^B$, C1-C6 alkoxy, C1-C6 haloalkyl, hydroxyl, cyano, —CO₂H, —$NR^AR^B$, —C(═O)$NR^CR^D$, —SO₂($NR^E R^F$), —SO₂(C1-C6 alkyl), —S(═O)(═NH)(C1-C6 alkyl), —C(═O)(C1-C6 alkyl), —CO₂(C1-C6 alkyl), 5-6 membered heteroaryl optionally substituted with C1-C6 alkyl, 3-6 membered heterocyclyl optionally substituted with 1 or 2 independently selected $R^G$, and 3-6 membered cycloalkyl optionally substituted with 1 or 2 independently selected $R^G$;
wherein $R^4$ is bonded to the position of Ring A1 that is para to the N atom of the urea moiety;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —SO₂(C1-C6 alkyl), and —SO₂(NH₂); or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —$NR^{A1}R^{B1}$, —C(═O)$NR^{C1}R^{D1}$, —CO₂(C1-C6 alkyl), C1-C6 haloalkyl, C3-C6 cycloalkyl, and —CO₂H.

Embodiment 208: The compound of embodiment 207, wherein Ring A1 is pyrimidinyl.

Embodiment 209: The compound of embodiment 207, wherein Ring A1 is pyridyl.

Embodiment 210: The compound of embodiment 207, wherein Ring A1 is pyrazolyl.

Embodiment 211: The compound of embodiment 207, wherein Ring A1 is 5-pyrimidinyl, 3-pyridyl, or 4-pyrazolyl.

Embodiment 212: The compound of embodiment 207, wherein

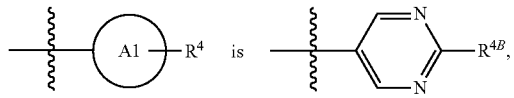

wherein: $R^{4B}$ is selected from —$NR^AR^B$ and 4-6 membered heterocyclyl comprising one nitrogen ring member and optionally substituted with 1-2 independently selected $R^{G1}$; wherein $R^{G1}$ is selected from fluoro, hydroxyl, and C1-C6 alkyl.

Embodiment 213: The compound of embodiment 212, wherein $R^A$ and $R^B$ are both hydrogen.

Embodiment 214: The compound of embodiment 212, wherein one of $R^A$ and $R^B$ is hydrogen and the other of $R^A$ and $R^B$ is 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —SO₂(C1-C6 alkyl), and —SO₂(NH₂).

Embodiment 215: The compound of any one of embodiments 212 and 214, wherein one of $R^A$ and $R^B$ is hydrogen and the other of $R^A$ and $R^B$ is 4-6 membered heterocyclyl.

Embodiment 216: The compound of any one of embodiments 212 and 214-215, wherein one of $R^A$ and $R^B$ is hydrogen and the other of $R^A$ and $R^B$ is 5 membered heterocyclyl.

Embodiment 217: The compound of any one of embodiments 212 and 214, wherein one of $R^A$ and $R^B$ is hydrogen and the other of $R^A$ and $R^B$ is C1-C6 haloalkyl.

Embodiment 218: The compound of any one of embodiments 212 and 214, wherein $R^A$ and $R^B$ are both C1-C6 haloalkyl.

Embodiment 219: The compound of any one of embodiments 212 and 214, wherein one of $R^A$ and $R^B$ is C1-C6 alkyl and the other of $R^A$ and $R^B$ is C1-C6 haloalkyl.

Embodiment 220: The compound of any one of embodiments 212 and 214, wherein one of $R^A$ and $R^B$ is hydrogen and the other of $R^A$ and $R^B$ is 3-6 membered cycloalkyl optionally substituted with hydroxyl.

Embodiment 221: The compound of any one of embodiments 212, 214, and 220, wherein one of $R^A$ and $R^B$ is hydrogen and the other of $R^A$ and $R^B$ is cyclobutanyl optionally substituted with hydroxyl.

Embodiment 222: The compound of any one of embodiments 212, 214, and 220-221, wherein one of $R^A$ and $R^B$ is hydrogen and the other of $R^A$ and $R^B$ is 3-hydroxycyclobutyl.

Embodiment 223: The compound of any one of embodiments 212 and 214, wherein one of $R^A$ and $R^B$ is hydrogen and the other of $R^A$ and $R^B$ C1-C6 alkyl optionally substituted with 1-2 substituents independently selected from hydroxyl, 3-6 membered cycloalkyl, —SO₂(C1-C6 alkyl), and —SO₂(NH₂).

Embodiment 224: The compound of any one of embodiments 212, 214, and 223, wherein one of $R^A$ and $R^B$ is hydrogen and the other of $R^A$ and $R^B$ is methyl.

Embodiment 225: The compound of any one of embodiments 212, 214, and 223, wherein one of $R^A$ and $R^B$ is hydrogen and the other of $R^A$ and $R^B$ is ethyl or propyl substituted with hydroxyl.

Embodiment 226: The compound of any one of embodiments 212, 214, and 223, wherein one of $R^A$ and $R^B$ is hydrogen and the other of $R^A$ and $R^B$ is ethyl or propyl substituted with 3-6 membered cycloalkyl and hydroxyl.

Embodiment 227: The compound of any one of embodiments 212, 214, 223, and 226, wherein one of $R^A$ and $R^B$ is hydrogen and the other of $R^A$ and $R^B$ is ethyl substituted with 3-4 membered cycloalkyl and hydroxyl.

Embodiment 228: The compound of any one of embodiments 212, 214, and 223, wherein one of $R^A$ and $R^B$ is hydrogen and the other of $R^A$ and $R^B$ is ethyl or propyl substituted with —$SO_2$(C1-C6 alkyl).

Embodiment 229: The compound of any one of embodiments 212, 214, 223, and 228, wherein one of $R^A$ and $R^B$ is hydrogen and the other of $R^A$ and $R^B$ is ethyl or propyl substituted with —$SO_2CH_3$.

Embodiment 230: The compound of any one of embodiments 212, 214, and 223, wherein one of $R^A$ and $R^B$ is hydrogen and the other of $R^A$ and $R^B$ is ethyl or propyl substituted with —$SO_2(NH_2)$.

Embodiment 231: The compound of embodiment 212, wherein $R^{4B}$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

Embodiment 232: The compound of embodiment 212 or 231, wherein $R^{4B}$ is

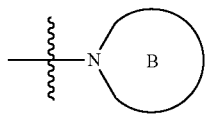

wherein Ring B is azetidinyl, pyrrolidinyl, or piperidinyl, each optionally substituted with 1-2 $R^G$ independently selected from fluoro, hydroxyl, and C1-C6 alkyl.

Embodiment 233: The compound of embodiment 232, wherein Ring B is azetidinyl.

Embodiment 234: The compound of any one of embodiments 232-233, wherein Ring B is unsubstituted.

Embodiment 235: The compound of any one of embodiments 232-233, wherein Ring B is substituted with 1 $R^G$.

Embodiment 236: The compound of embodiment 235, wherein $R^G$ is fluoro.

Embodiment 237: The compound of embodiment 235, wherein $R^G$ is cyano.

Embodiment 238: The compound of embodiment 235, wherein $R^G$ is hydroxyl.

Embodiment 239: The compound of embodiment 235, wherein $R^G$ is methyl.

Embodiment 240: The compound of embodiment 235, wherein $R^G$ is —$CO_2CH_3$.

Embodiment 241: The compound of any one of embodiments 232-233, wherein Ring B is substituted with 2 independently selected $R^G$.

Embodiment 242: The compound of embodiment 241, wherein each $R^G$ is fluoro.

Embodiment 243: The compound of embodiment 241, wherein each $R^G$ is methyl.

Embodiment 244: The compound of embodiment 241, wherein one $R^G$ is hydroxyl and the other $R^G$ is methyl.

Embodiment 245: The compound of embodiment 241, wherein one $R^G$ is fluoro and the other $R^{G1}$ is methyl.

Embodiment 246: The compound of embodiment 241, wherein one $R^G$ is hydroxyl and the other $R^{G1}$ is fluoro.

Embodiment 247: The compound of any one of embodiments 232-233 and 235-246, wherein each $R^G$ is bonded to the position of Ring B para to the nitrogen.

Embodiment 248: A compound of Formula (I-B):

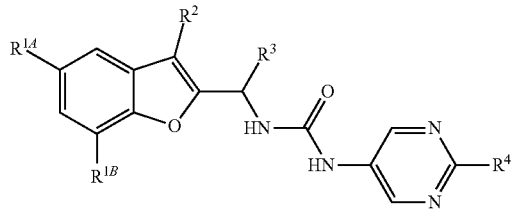

(I-B)

or a pharmaceutically acceptable salt thereof, wherein:
$R^{1A}$ is halogen;
$R^{1B}$ is halogen or absent (the phenyl ring is monosubstituted with $R^{1A}$);
$R^2$ is a C1-C6 alkyl or a C1-C6 haloalkyl;
$R^3$ is a C1-C6 alkyl, a C1-C6 haloalkyl, or a C3-C6 cycloalkyl optionally substituted with 1 or 2 substituents independently selected from fluoro and C1-C6 alkyl;
$R^4$ is independently selected from the group consisting of: C1-C6 alkyl optionally substituted with —$NR^AR^B$, C1-C6 alkoxy, C1-C6 haloalkyl, hydroxyl, cyano, —$CO_2H$, —$NR^AR^B$, —C(=O)$NR^CR^D$, —$SO_2(NR^E R^F)$, —$SO_2$(C1-C6 alkyl), —S(=O)(=NH)(C1-C6 alkyl), —C(=O)(C1-C6 alkyl), —$CO_2$(C1-C6 alkyl), 5-6 membered heteroaryl optionally substituted with C1-C6 alkyl, 3-6 membered heterocyclyl optionally substituted with 1 or 2 independently selected $R^G$, and 3-6 membered cycloalkyl optionally substituted with 1 or 2 independently selected $R^G$;
each $R^A$, $R^{A1}$, $R^B$, $R^{B1}$, $R^C$, $R^{C1}$, $R^D$, $R^{D1}$, $R^E$, and $R^F$ is independently hydrogen, 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —$SO_2$(C1-C6 alkyl), and —$SO_2(NH_2)$; or
$R^C$ and $R^D$, together with the nitrogen atom to which they are attached form a 4-6 membered heterocyclyl;
each $R^G$ is independently selected from the group consisting of: fluoro, cyano, hydroxyl, C1-C6 alkyl, C1-C6 alkoxy, —$NR^{A1}R^{B1}$, —C(=O)$NR^{C1}R^{D1}$, —$CO_2$(C1-C6 alkyl), C1-C6 haloalkyl, C3-C6 cycloalkyl, and —$CO_2H$.

Embodiment 249: The compound of any one of embodiments 207-248, wherein $R^{1A}$ and $R^{1B}$ are each fluoro.

Embodiment 250: The compound of any one of embodiments 207-249, wherein $R^2$ is a C1-C6 alkyl.

Embodiment 251: The compound of any one of embodiments 207-250, wherein $R^2$ is methyl.

Embodiment 252: The compound of any one of embodiments 207-249, wherein $R^2$ is a C1-C6 haloalkyl.

Embodiment 253: The compound of any one of embodiments 207-249 and 242, wherein $R^2$ is a trifluoromethyl.

Embodiment 254: The compound of any one of embodiments 207-253, wherein $R^3$ is a C1-C6 alkyl.

Embodiment 255: The compound of any one of embodiments 207-254, wherein $R^3$ is a C1-C3 alkyl.

Embodiment 256: The compound of any one of embodiments 207-255, wherein $R^3$ is methyl, ethyl, or isopropyl.

Embodiment 257: The compound of any one of embodiments 207-256, wherein $R^3$ is methyl.

Embodiment 258: The compound of any one of embodiments 207-256, wherein $R^3$ is ethyl.

Embodiment 259: The compound of any one of embodiments 207-256, wherein $R^3$ is isopropyl.

Embodiment 260: The compound of any one of embodiments 207-253, wherein $R^3$ is a C1-C6 haloalkyl.

Embodiment 261: The compound of any one of embodiments 207-253 and 260, wherein $R^3$ is a trifluoromethyl.

Embodiment 262: The compound of any one of embodiments 207-253, wherein $R^3$ is C3-C6 cycloalkyl optionally substituted with 1 or 2 substituents independently selected from fluoro and C1-C6 alkyl.

Embodiment 263: The compound of any one of embodiments 207-253 and 262, wherein $R^3$ is C3-C6 cycloalkyl substituted with 1 or 2 fluoro.

Embodiment 264: The compound of any one of embodiments 207-253 and 262, wherein $R^3$ is unsubstituted C3-C6 cycloalkyl.

Embodiment 265: The compound of any one of embodiments 207-253, wherein the $R^3$ C3-C6 cycloalkyl is cyclopropyl.

Embodiment 266: The compound of any one of embodiments 207-211 and 248-265, wherein, $R^4$ is C1-C6 alkyl optionally substituted with —$NR^A R^B$.

Embodiment 267: The compound of any one of embodiments 207-211 and 248-266, wherein $R^4$ is C1-C3 alkyl optionally substituted with —$NR^A R^B$.

Embodiment 268: The compound of any one of embodiments 207-211 and 248-267, wherein $R^4$ is methyl optionally substituted with —$NR^A R^B$.

Embodiment 269: The compound of any one of embodiments 207-211 and 248-265, wherein $R^4$ is C1-C6 alkyl.

Embodiment 270: The compound of any one of embodiments 207-211 and 248-265, wherein $R^4$ is methyl.

Embodiment 271: The compound of any one of embodiments 207-211 and 248-265, wherein $R^4$ is C1-C6 alkoxy.

Embodiment 272: The compound of any one of embodiments 207-211, 248-265, and 271, wherein $R^4$ is methoxy.

Embodiment 273: The compound of any one of embodiments 207-211 and 248-265, wherein $R^4$ is C1-C6 haloalkyl.

Embodiment 274: The compound of any one of embodiments 207-211, 248-265, and 273, wherein $R^4$ is trifluoromethyl.

Embodiment 275: The compound of any one of embodiments 207-211 and 248-265, wherein $R^4$ is hydroxyl.

Embodiment 276: The compound of any one of embodiments 207-211 and 248-265, wherein $R^4$ is cyano or —$CO_2H$.

Embodiment 277: The compound of any one of embodiments 207-211 and 248-265, wherein $R^4$ is —$NR^A R^B$.

Embodiment 278: The compound of any one of embodiments 207-211, 248-265, and 277, wherein $R^A$ and $R^B$ are each hydrogen.

Embodiment 279: The compound of any one of embodiments 207-211, 248-265, and 277, wherein one of $R^A$ and $R^B$ is hydrogen and the other of $R^A$ and $R^B$ is C1-C6 alkyl.

Embodiment 280: The compound of any one of embodiments 207-211, 248-265, 277, and 249, wherein one of $R^A$ and $R^B$ is hydrogen and the other of $R^A$ and $R^B$ is methyl.

Embodiment 281: The compound of any one of embodiments 207-265, and 277, wherein $R^A$ and $R^B$ are each C1-C6 alkyl.

Embodiment 282: The compound of any one of embodiments 207-211, 248-265, 277, and 251, wherein $R^A$ and $R^B$ are each methyl.

Embodiment 283: The compound of any one of embodiments 207-211, 248-265, and 277, wherein one of $R^A$ and $R^B$ is hydrogen and the other of $R^A$ and $R^B$ is 4-6 membered heterocyclyl, C1-C6 haloalkyl, 3-6 membered cycloalkyl optionally substituted with hydroxyl, or C1-C6 alkyl optionally substituted with 1-2 substituents independently selected from hydroxyl, 3-6 membered cycloalkyl, —$SO_2$(C1-C6 alkyl), and —$SO_2(NH_2)$.

Embodiment 284: The compound of any one of embodiments 207-211, 248-265, 277 and 283, wherein one of $R^A$ and $R^B$ is hydrogen and the other of $R^A$ and $R^B$ is 4-6 membered heterocyclyl.

Embodiment 285: The compound of any one of embodiments 207-211, 248-265, 277 and 283-284, wherein one of $R^A$ and $R^B$ is hydrogen and the other of $R^A$ and $R^B$ is 5 membered heterocyclyl.

Embodiment 286: The compound of any one of embodiments 207-211, 248-265, 277 and 283, wherein one of $R^A$ and $R^B$ is hydrogen and the other of $R^A$ and $R^B$ is 3-6 membered cycloalkyl optionally substituted with hydroxyl.

Embodiment 287: The compound of any one of embodiments 207-211, 248-265, 277, 283 and 286, wherein one of $R^A$ and $R^B$ is hydrogen and the other of $R^A$ and $R^B$ is cyclobutanyl optionally substituted with hydroxyl.

Embodiment 288: The compound of any one of embodiments 207-211, 248-265, 277, 283 and 286-287, wherein one of $R^A$ and $R^B$ is hydrogen and the other of $R^A$ and $R^B$ is 3-hydroxycyclobutyl.

Embodiment 289: The compound of any one of embodiments 207-211, 248-265, 277, and 283, wherein one of $R^A$ and $R^B$ is hydrogen and the other of $R^A$ and $R^B$ is C1-C6 haloalkyl.

Embodiment 290: The compound of any one of embodiments 207-211, 248-265, and 277, wherein $R^A$ and $R^B$ are each C1-C6 haloalkyl.

Embodiment 291: The compound of any one of embodiments 207-211, 248-265, and 277, wherein one of $R^A$ and $R^B$ is C1-C6 alkyl and the other of one of $R^A$ and $R^B$ is C1-C6 haloalkyl.

Embodiment 292: The compound of any one of embodiments 207-211, 248-265, 277, and 283, wherein one of $R^A$ and $R^B$ is hydrogen and the other of $R^A$ and $R^B$ C1-C6 alkyl optionally substituted with 1-2 substituents independently selected from hydroxyl, 3-6 membered cycloalkyl, —$SO_2$(C1-C6 alkyl), and —$SO_2(NH_2)$.

Embodiment 293: The compound of any one of embodiments 207-211, 248-265, 277, 283, and 292, wherein one of $R^A$ and $R^B$ is hydrogen and the other of $R^A$ and $R^B$ is ethyl or propyl substituted with hydroxyl.

Embodiment 294: The compound of any one of embodiments 207-211, 248-265, 277, 283, and 292, wherein one of $R^A$ and $R^B$ is hydrogen and the other of $R^A$ and $R^B$ is ethyl or propyl substituted with 3-6 membered cycloalkyl and hydroxyl.

Embodiment 295: The compound of any one of embodiments 207-211, 248-265, 277, 283, 292 and 294, wherein one of $R^A$ and $R^B$ is hydrogen and the other of $R^A$ and $R^B$ is ethyl substituted with 3-4 membered cycloalkyl and hydroxyl.

Embodiment 296: The compound of any one of embodiments 207-211, 248-265, 277, 283, and 292, wherein one of $R^A$ and $R^B$ is hydrogen and the other of $R^A$ and $R^B$ is ethyl or propyl substituted with —$SO_2$(C1-C6 alkyl).

Embodiment 297: The compound of any one of embodiments 207-211, 248-265, 277, 283, 292, and 296, wherein one of $R^A$ and $R^B$ is hydrogen and the other of $R^A$ and $R^B$ is ethyl or propyl substituted with —$SO_2CH_3$.

Embodiment 298: The compound of any one of embodiments 207-211, 248-265, 277, 283, and 292, wherein one of $R^A$ and $R^B$ is hydrogen and the other of $R^A$ and $R^B$ is ethyl or propyl substituted with —$SO_2(NH_2)$ Embodiment 299: The compound of any one of embodiments 207-211 and 248-265, wherein one $R^4$ is —C(=O)$NR^CR^D$.

Embodiment 300: The compound of any one of embodiments 207-211, 248-265, and 299, wherein $R^C$ and $R^D$ are each hydrogen.

Embodiment 301: The compound of any one of embodiments 207-211, 248-265, and 299, wherein one of $R^C$ and $R^D$ is hydrogen and the other of $R^C$ and $R^D$ is C1-C6 alkyl.

Embodiment 302: The compound of any one of embodiments 207-211, 248-265, and 299, wherein one of $R^C$ and $R^D$ is hydrogen and the other of $R^C$ and $R^D$ is methyl.

Embodiment 303: The compound of any one of embodiments 207-211, 248-265, and 299, wherein $R^C$ and $R^D$ are each C1-C6 alkyl.

Embodiment 304: The compound of any one of embodiments 207-211, 248-265, and 299, wherein $R^C$ and $R^D$ are each methyl.

Embodiment 305: The compound of any one of embodiments 207-211, 248-265, and 299, wherein one of $R^C$ and $R^D$ is hydrogen and the other of $R^C$ and $R^D$ is C1-C6 haloalkyl.

Embodiment 306: The compound of any one of embodiments 207-211, 248-265, and 299, wherein $R^C$ and $R^D$ are each is C1-C6 haloalkyl.

Embodiment 307: The compound of any one of embodiments 207-211, 248-265, and 299, wherein one of $R^C$ and $R^D$ is C1-C6 alkyl and the other of $R^C$ and $R^D$ is C1-C6 haloalkyl.

Embodiment 308: The compound of any one of embodiments 207-211 and 248-265, wherein one $R^4$ is —$SO_2$($NR^ER^F$).

Embodiment 309: The compound of any one of embodiments 207-211, 248-265, and 308, wherein $R^E$ and $R^F$ are each hydrogen.

Embodiment 310: The compound of any one of embodiments 207-211, 248-265, and 308, wherein one of $R^E$ and $R^F$ is hydrogen and the other of $R^E$ and $R^F$ is C1-C6 alkyl.

Embodiment 311: The compound of any one of embodiments 207-211, 248-265, and 308, wherein one of $R^E$ and $R^F$ is hydrogen and the other of $R^E$ and $R^F$ is methyl.

Embodiment 312: The compound of any one of embodiments 207-211, 248-265, and 308, wherein $R^E$ and $R^F$ are each is C1-C6 alkyl.

Embodiment 313: The compound of any one of embodiments 207-211, 248-235, and 308, wherein $R^E$ and $R^F$ are each methyl.

Embodiment 314: The compound of any one of embodiments 207-211, 248-265, and 308, wherein one of $R^E$ and $R^F$ is hydrogen and the other of $R^E$ and $R^F$ is C1-C6 haloalkyl.

Embodiment 315: The compound of any one of embodiments 207-211, 248-265, and 308, wherein $R^E$ and $R^F$ are each C1-C6 haloalkyl.

Embodiment 316: The compound of any one of embodiments 207-211, 248-265, and 308, wherein one of $R^E$ and $R^F$ is C1-C6 alkyl and the other of $R^E$ and $R^F$ is C1-C6 haloalkyl.

Embodiment 317: The compound of any one of embodiments 207-211 and 248-265, wherein $R^4$ is —$SO_2$(C1-C6 alkyl).

Embodiment 318: The compound of any one of embodiments 207-211, 248-265, and 317, wherein $R^4$ is —$SO_2$Me.

Embodiment 319: The compound of any one of embodiments 207-211, 248-265, and 317, wherein $R^4$ is —$SO_2$Et.

Embodiment 320: The compound of any one of embodiments 207-211 and 248-265, wherein $R^4$ is —S(=O)(=NH)(C1-C6 alkyl).

Embodiment 321: The compound of any one of embodiments 207-211, 248-265, and 320, wherein $R^4$ is —S(=O)(=NH)Me.

Embodiment 322: The compound of any one of embodiments 207-211 and 248-265, wherein $R^4$ is —C(=O)(C1-C6 alkyl).

Embodiment 323: The compound of any one of embodiments 207-211, 248-265, and 322, wherein $R^4$ is —C(=O)Me.

Embodiment 324: The compound of any one of embodiments 207-211 and 248-265, wherein $R^4$ is —$CO_2$(C1-C6 alkyl).

Embodiment 325: The compound of any one of embodiments 207-211, 248-265, and 324, wherein $R^4$ is —$CO_2$Me.

Embodiment 326: The compound of any one of embodiments 207-211 and 248-265, wherein $R^4$ is 5-6 membered heteroaryl optionally substituted with C1-C6 alkyl.

Embodiment 327: The compound of any one of embodiments 207-211, 248-265, and 326, wherein one $R^4$ is 5-6 membered heteroaryl substituted with C1-C6 alkyl.

Embodiment 328: The compound of any one of embodiments 207-211, 248-265, and 326-327, wherein one $R^4$ is tetrazolyl substituted with methyl.

Embodiment 329: The compound of any one of embodiments 207-211, 248-265, and 326, wherein one $R^4$ is unsubstituted 5-6 membered heteroaryl.

Embodiment 330: The compound of any one of embodiments 207-211, 248-265, 326, and 329, wherein $R^4$ is unsubstituted pyrazolyl.

Embodiment 331: The compound of any one of embodiments 207-211 and 248-265, wherein $R^4$ is 3-6 membered heterocyclyl optionally substituted with 1 or 2 independently selected $R^G$.

Embodiment 332: The compound of any one of embodiments 207-211, 248-265, and 331, wherein $R^4$ is 3-6 membered heterocyclyl substituted with 1 or 2 independently selected $R^G$.

Embodiment 333: The compound of any one of embodiments 207-211, 248-265, and 332, wherein $R^4$ is 3-6 membered heterocyclyl substituted with 1 $R^G$.

Embodiment 334: The compound of any one of embodiments 207-211, 248-265, and 332, wherein $R^4$ is 3-6 membered heterocyclyl substituted with 2 independently selected $R^G$.

Embodiment 335: The compound of any one of embodiments 207-211, 248-265, wherein $R^4$ is 3-6 membered cycloalkyl substituted with 1 or 2 independently selected $R^G$.

Embodiment 336: The compound of any one of embodiments 207-211, 248-265, and 335, wherein $R^4$ is 3-6 membered cycloalkyl substituted with 1 $R^G$.

Embodiment 337: The compound of any one of embodiments 207-211, 248-265, and 335, wherein $R^4$ is 3-6 membered cycloalkyl substituted with 2 independently selected $R^G$.

Embodiment 338: The compound of any one of embodiments 207-211, 248-265, and 336, wherein $R^4$ is cyclobutanyl substituted with 1 $R^G$.

Embodiment 339: The compound of any one of embodiments 207-211, 248-265, and 331-338, wherein one $R^G$ is halogen.

Embodiment 340: The compound of any one of embodiments 207-211, 248-265, and 331-338, wherein one $R^G$ is fluoro.

Embodiment 341: The compound of any one of embodiments 207-211, 248-265, and 331-338, wherein one $R^G$ is cyano.

Embodiment 342: The compound of any one of embodiments 207-211, 248-265, and 331-338, wherein one $R^G$ is hydroxyl.

Embodiment 343: The compound of any one of embodiments 207-211, 248-265, and 331-338, wherein one $R^G$ is C1-C6 alkyl.

Embodiment 344: The compound of any one of embodiments 207-211, 248-265, 331-338, and 343, wherein one $R^G$ is methyl.

Embodiment 345: The compound of any one of embodiments 207-211, 248-265, and 331-338, wherein one $R^G$ is C1-C6 alkoxy.

Embodiment 346: The compound of any one of embodiments 207-211, 248-265, and 331-338, and 345, wherein one $R^G$ is methoxy.

Embodiment 347: The compound of any one of embodiments 207-211, 248-265, and 331-338, wherein one $R^G$ is —$NR^{A1}R^{B1}$.

Embodiment 348: The compound of any one of embodiments 207-211, 248-265, and 331-338, and 347, wherein $R^{A1}$ and $R^{B1}$ are each hydrogen.

Embodiment 349: The compound of any one of embodiments 207-211, 248-265, and 331-338, and 347, wherein one of $R^{A1}$ and $R^{B1}$ is hydrogen and the other of $R^{A1}$ and $R^{B1}$ is C1-C6 alkyl.

Embodiment 350: The compound of any one of embodiments 207-211, 248-265, and 331-338, and 347, wherein one of $R^{A1}$ and $R^{B1}$ is hydrogen and the other of $R^{A1}$ and $R^{B1}$ is methyl.

Embodiment 351: The compound of any one of embodiments 207-211, 248-265, and 331-338, and 347, wherein $R^{A1}$ and $R^{B1}$ are each C1-C6 alkyl.

Embodiment 352: The compound of any one of embodiments 207-211, 248-265, and 331-338, and 347, wherein $R^{A1}$ and $R^{B1}$ are each methyl.

Embodiment 353: The compound of any one of embodiments 207-211, 248-265, and 331-338, and 347, wherein one of $R^{A1}$ and $R^{B1}$ is hydrogen and the other of $R^{A1}$ and $R^{B1}$ is C1-C6 haloalkyl.

Embodiment 354: The compound of any one of embodiments 207-211, 248-265, and 331-338, and 347, wherein $R^{A1}$ and $R^{B1}$ are each C1-C6 haloalkyl.

Embodiment 355: The compound of any one of embodiments 207-211, 248-265, and 331-338, and 347, wherein one of $R^{A1}$ and $R^{B1}$ is C1-C6 alkyl and the other of $R^{A1}$ and $R^{B1}$ is C1-C6 haloalkyl.

Embodiment 356: The compound of any one of embodiments 207-211, 248-265, and 331-338, wherein one $R^G$ is —C(=O)$NR^{C1}R^{D1}$.

Embodiment 357: The compound of any one of embodiments 207-211, 248-265, 331-338, and 356, wherein $R^{C1}$ and $R^{D1}$ are each is hydrogen.

Embodiment 358: The compound of any one of embodiments 207-211, 248-265, 331-338, and 356, wherein one of $R^{C1}$ and $R^{D1}$ is hydrogen and the other of $R^{C1}$ and $R^{D1}$ is C1-C6 alkyl.

Embodiment 359: The compound of any one of embodiments 207-211, 248-265, 331-338, and 356, wherein one of $R^{C1}$ and $R^{D1}$ is hydrogen and the other of $R^{C1}$ and $R^{D1}$ is methyl.

Embodiment 360: The compound of any one of embodiments 207-211, 248-265, 331-338, and 356, wherein $R^{C1}$ and $R^{D1}$ are each is C1-C6 alkyl.

Embodiment 361: The compound of any one of embodiments 207-211, 248-265, 331-338, and 356, wherein $R^{C1}$ and $R^{D1}$ are each is methyl.

Embodiment 362: The compound of any one of embodiments 207-211, 248-265, 331-338, and 356, wherein one of $R^{C1}$ and $R^{D1}$ is hydrogen and the other of $R^{C1}$ and $R^{D1}$ is C1-C6 haloalkyl.

Embodiment 363: The compound of any one of embodiments 207-211, 248-265, 331-338, and 356, wherein $R^{C1}$ and $R^{D1}$ are each is C1-C6 haloalkyl.

Embodiment 364: The compound of any one of embodiments 207-211, 248-265, 331-338, and 356, wherein one of $R^{C1}$ and $R^{D1}$ is C1-C6 alkyl and the other of $R^{C1}$ and $R^{D1}$ is C1-C6 haloalkyl.

Embodiment 365: The compound of any one of embodiments 207-211, 248-265, and 331-338, wherein one $R^G$ is —$CO_2$(C1-C6 alkyl).

Embodiment 366: The compound of any one of embodiments 207-211, 248-265, 331-338, and 365, wherein one $R^G$ is —$CO_2CH_3$.

Embodiment 367: The compound of any one of embodiments 207-211, 248-265, and 331-338, wherein one $R^G$ is C1-C6 haloalkyl.

Embodiment 368: The compound of any one of embodiments 207-211, 248-265, 331-338, and 367, wherein one $R^G$ is trifluoromethyl.

Embodiment 369: The compound of any one of embodiments 207-211, 248-265 and 331-338, wherein one $R^G$ is C3-C6 cycloalkyl.

Embodiment 370: The compound of any one of embodiments 207-211, 248-265, 331-338, and 369, wherein one $R^G$ is cyclopropyl.

Embodiment 371: The compound of any one of embodiments 207-211, 248-265 and 331-338, wherein $R^G$ is —$CO_2H$.

Embodiment 372: The compound of any one of embodiments 207-211, 248-265, and 331, wherein $R^4$ is unsubstituted 3-6 membered heterocyclyl.

Embodiment 373: The compound of any one of embodiments 331-334, wherein the $R^4$ 3-6 membered heterocyclyl is a 5-6 membered heterocyclyl.

Embodiment 374: The compound of any one of embodiments 331-334, wherein the $R^4$ 3-6 membered heterocyclyl is azetidinyl, azetidin-2-onyl, morpholinyl, piperazinyl, or tetrahydropyranyl.

Embodiment 375: The compound of any one of embodiments 331-334, wherein the $R^4$ 3-6 membered heterocyclyl is 1-azetidinyl, 1-azetidin-2-onyl, 1-piperazinyl, 1-morpholinyl, or 4-tetrahydropyranyl.

Embodiment 376: The compound of embodiment 248, wherein $R^4$ is selected from —$NR^AR^B$ and 4-6 membered heterocyclyl comprising one nitrogen ring member and optionally substituted with 1-2 independently selected $R^{G1}$; wherein $R^{G1}$ is selected from fluoro, hydroxyl, and C1-C6 alkyl.

Embodiment 377: The compound of embodiment 376, wherein $R^A$ and $R^B$ are both hydrogen.

Embodiment 378: The compound of embodiment 376, wherein one of $R^A$ and $R^B$ is hydrogen and the other of $R^A$ and $R^B$ is C1-C6 alkyl.

Embodiment 379: The compound of any one of embodiments 376 and 378, wherein one of $R^A$ and $R^B$ is hydrogen and the other of $R^A$ and $R^B$ is methyl.

Embodiment 380: The compound of embodiment 376, wherein $R^4$ is 4-6 membered heterocyclyl comprising one nitrogen ring member and optionally substituted with 1-2 independently selected $R^G$; wherein $R^G$ is selected from fluoro, hydroxyl, and C1-C6 alkyl.

Embodiment 381: The compound of embodiment 376, wherein $R^4$ is

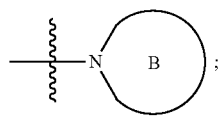

wherein Ring B is azetidinyl, pyrrolidinyl, piperidinyl, piperazinyl, or morpholinyl, each optionally substituted with 1-2 $R^G$ independently selected from fluoro, hydroxyl, and C1-C6 alkyl.

Embodiment 382: The compound of embodiment 381, wherein Ring B is azetidinyl.

Embodiment 383: The compound of any one of embodiments 381-382, wherein Ring B is unsubstituted.

Embodiment 384: The compound of any one of embodiments 381-382, wherein Ring B is substituted with 1 $R^G$.

Embodiment 385: The compound of embodiment 384, wherein $R^G$ is fluoro.

Embodiment 386: The compound of embodiment 384, wherein $R^G$ is hydroxyl.

Embodiment 387: The compound of embodiment 384, wherein $R^G$ is methyl.

Embodiment 388: The compound of embodiment 381, wherein Ring B is substituted with 2 $R^G$.

Embodiment 389: The compound of embodiment 388, wherein each $R^G$ is fluoro.

Embodiment 390: The compound of embodiment 388, wherein each $R^G$ is methyl.

Embodiment 391: The compound of embodiment 388, wherein one $R^G$ is hydroxyl and the other $R^G$ is methyl.

Embodiment 392: The compound of embodiment 388, wherein one $R^G$ is fluoro and the other $R^{G1}$ is methyl.

Embodiment 393: The compound of embodiment 388, wherein one $R^G$ is hydroxyl and the other $R^{G1}$ is fluoro.

Embodiment 394: The compound of any one of embodiment 381-393, wherein each $R^G$ is bonded to the position of Ring B para to the nitrogen that is bonded to Ring A.

Embodiment 395: A compound selected from the group consisting of the compounds in Table A, Table B, and Table C, Table D, or a pharmaceutically acceptable salt thereof.

Embodiment 396: A pharmaceutical composition comprising a compound of any one of embodiments 1-395, or a pharmaceutically acceptable salt thereof, and one or more pharmaceutically acceptable excipients.

Embodiment 397: A method for treating cancer in a subject in need thereof, the method comprising administering to the subject a therapeutically effective amount of a compound of any one of embodiments 1-395, or a pharmaceutically acceptable salt thereof, or a pharmaceutical composition of embodiment 396.

Embodiment 398: A method for treating cancer in a subject in need thereof, the method comprising:
(a) determining that the cancer is associated with a dysregulation of a PIK3CA gene, a PI3Kα protein, or expression or activity or level of any of the same; and
(b) administering to the subject a therapeutically effective amount of a compound of any one of embodiments 1-395, or a pharmaceutically acceptable salt thereof, or a pharmaceutical composition of embodiment 396.

Embodiment 399: A method of treating a PI3Kα-associated cancer in a subject, the method comprising administering to a subject identified or diagnosed as having a PI3Kα-associated cancer a therapeutically effective amount of a compound of any one of embodiments 1-395 or a pharmaceutically acceptable salt thereof, or a pharmaceutical composition of embodiment 396.

Embodiment 400: A method of treating a PI3Kα-associated cancer in a subject, the method comprising:
(a) determining that the cancer in the subject is a PI3Kα-associated cancer; and
(b) administering to the subject a therapeutically effective amount of a compound of any one of embodiments 1-395 or a pharmaceutically acceptable salt thereof, or a pharmaceutical composition of embodiment 396.

Embodiment 401: A method of treating a subject, the method comprising administering a therapeutically effective amount of a compound of any one of embodiments 1-395 or a pharmaceutically acceptable salt thereof, or a pharmaceutical composition of embodiment 366, to a subject having a clinical record that indicates that the subject has a dysregulation of a PIK3CA gene, PI3Kα protein or expression or activity or level of any of the same.

Embodiment 402: The method of any one of embodiments 398 and 400, wherein the step of determining that the cancer in the subject is a PI3Kα-associated cancer includes performing an assay to detect dysregulation in a PIK3CA gene, a PI3Kα protein, or expression or activity or level of any of the same in a sample from the subject.

Embodiment 403: The method of embodiment 402, further comprising obtaining a sample from the subject.

Embodiment 404: The method of embodiment 403, wherein the sample is a biopsy sample.

Embodiment 405: The method of any one of embodiments 402-404, wherein the assay is selected from the group consisting of sequencing, immunohistochemistry, enzyme-linked immunosorbent assay, and fluorescence in situ hybridization (FISH).

Embodiment 406: The method of embodiment 405, wherein the FISH is break apart FISH analysis.

Embodiment 407: The method of embodiment 405, wherein the sequencing is pyrosequencing or next generation sequencing.

Embodiment 408: The method of any one of embodiments 398, 401, and 402, wherein the dysregulation in a PIK3CA gene, a PI3Kα protein, or expression or activity or level of any of the same is one or more point mutations in the PIK3CA gene.

Embodiment 409: The method of embodiment 408, wherein the one or more point mutations in a PIK3CA gene results in the translation of a PI3Kα protein having one or more amino acid substitutions at one or more of the following amino acid positions exemplified in Table 1.

Embodiment 410: The method of embodiment 409, wherein the one or more point mutations in a PIK3CA gene are selected from the mutations in Table 2.

Embodiment 411: The method of embodiment 409, wherein the one or more point mutations in a PIK3CA gene include a substitution at amino acid position 1047 of a human PI3Kα protein.

Embodiment 412: The method of embodiment 411, wherein the substitution is H1047R.

Embodiment 413: The method of any one of embodiments 399, 400, and 402-412, wherein the PI3Kα-associated cancer is selected from the group consisting of breast cancer, lung cancer, endometrial cancer, esophageal squamous cell carcinoma, ovarian cancer, colorectal cancer, esophagastric adenocarcinoma, bladder cancer, head and neck cancer, thyroid cancer, glioma, and cervical cancer.

Embodiment 414: The method of any one of embodiments 399, 400, and 402-413, wherein the PI3Kα-associated cancer is breast cancer, colorectal cancer, lung cancer, or endometrial cancer.

Embodiment 415: The method of any one of embodiments 397-414, further comprising administering an additional therapy or therapeutic agent to the subject.

Embodiment 416: The method of embodiment 415, wherein the additional therapy or therapeutic agent is selected from radiotherapy, cytotoxic chemotherapeutics, kinase targeted-therapeutics, apoptosis modulators, signal transduction inhibitors, immune-targeted therapies, and angiogenesis-targeted therapies.

Embodiment 417: The method of embodiment 416, wherein the additional therapeutic agent is selected from one or more kinase targeted therapeutics.

Embodiment 418: The method of embodiment 417, wherein the additional therapeutic agent is a tyrosine kinase inhibitor.

Embodiment 419: The method of embodiment 418, wherein the additional therapeutic agent is an mTOR inhibitor.

Embodiment 420: The method of embodiment 415, wherein the additional therapeutic agent is selected from fulvestrant, capecitabine, trastuzumab, ado-trastuzumab emtansine, pertuzumab, paclitaxel, nab-paclitaxel, enzalutamide, olaparib, pegylated liposomal doxorubicin (PLD), trametinib, ribociclib, palbociclib, buparlisib, AEB071, everolimus, exemestane, cisplatin, letrozole, AMG 479, LSZ102, LEE011, cetuximab, AUY922, BGJ398, MEK162, LJM716, LGH447, imatinib, gemcitabine, LGX818, amcenestrant, and combinations thereof.

Embodiment 421: The method of embodiment 415, wherein the additional therapeutic agent is selected from the group consisting of a glucagon-like peptide-1 (GLP-1) receptor agonist, a sodium-glucose transport protein 2 (SGLT-2) inhibitor, a dipeptidyl peptidase 4 (DPP-4) inhibitor, metformin, and combinations thereof.

Embodiment 422: The method of any one of embodiments 415-421, wherein the compound of any one of embodiments 1-395 or a pharmaceutically acceptable salt thereof, or a pharmaceutical composition of embodiment 396, and the additional therapeutic agent are administered simultaneously as separate dosages.

Embodiment 423: The method of any one of embodiments 415-421, wherein the compound of any one of embodiments 1-395 or a pharmaceutically acceptable salt thereof, or a pharmaceutical composition of embodiment 396, and the additional therapeutic agent are administered as separate dosages sequentially in any order.

Embodiment 424: A method for modulating PI3Kα in a mammalian cell, the method comprising contacting the mammalian cell with an effective amount of a compound of any one of embodiments 1-395, or a pharmaceutically acceptable salt thereof.

Embodiment 425: The method of embodiment 424, wherein the contacting occurs in vivo.

Embodiment 426: The method of embodiment 424, wherein the contacting occurs in vitro.

Embodiment 427: The method of any one of embodiments 424-426, wherein the mammalian cell is a mammalian cancer cell.

Embodiment 428: The method of embodiment 427, wherein the mammalian cancer cell is a mammalian PI3Kα-associated cancer cell.

Embodiment 429: The method of any one of embodiments 424-427, wherein the cell has a dysregulation of a PIK3CA gene, a PI3Kα protein, or expression or activity or level of any of the same.

Embodiment 430: The method of embodiment 429, wherein the dysregulation in a PIK3CA gene, a PI3Kα protein, or expression or activity or level of any of the same is one or more point mutations in the PIK3CA gene.

Embodiment 431: The method of embodiment 430, wherein the one or more point mutations in a PIK3CA gene results in the translation of a PI3Kα protein having one or more amino acid substitutions at one or more of the following amino acid positions exemplified in Table 1.

Embodiment 432: The method of embodiment 431, wherein the one or more point mutations in a PIK3CA gene is selected from the mutations in Table 2.

Embodiment 433: The method of embodiment 432, wherein the one or more point mutations in a PIK3CA gene include a substitution at amino acid position 1047 of a human PI3Kα protein.

Embodiment 434: The method of embodiment 433, wherein the substitution is H1047R.

EXAMPLES

Compound Preparation

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. The synthesis of the compounds disclosed herein can be achieved by generally following the schemes provided herein, with modification for specific desired substituents.

Standard synthetic methods and procedures for the preparation of organic molecules and functional group transformations and manipulations can be obtained from the relevant scientific literature or from standard textbooks in the field. Although not limited to any one or several sources, classic texts such as R. Larock, Comprehensive Organic Transformations, VCH Publishers (1989); L. Fieser and M. Fieser, Fieser and Fieser's Reagents for Organic Synthesis, John Wiley and Sons (1994); Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, are useful and recognized reference textbooks of organic synthesis known to those in the art. The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt thereof.

Example 1: Preparation of Compound 1 and Compound 2

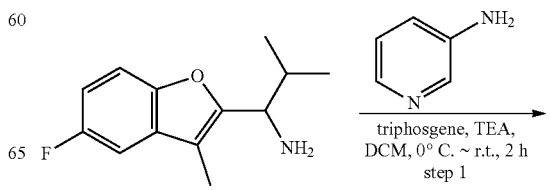

-continued

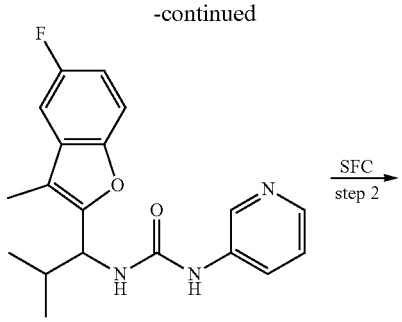

SFC
step 2 →

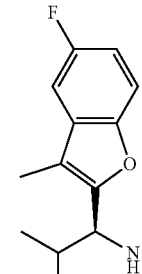

Compound 1

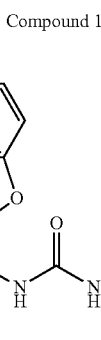

Compound 2

Step 1

To a mixture of 1-(5-fluoro-3-methylbenzofuran-2-yl)-2-methylpropan-1-amine (90 mg, 0.41 mmol), TEA (331 mg, 3.28 mmol), triphosgene (152 mg, 0.51 mmol) in DCM (7 mL) stirred at 0° C. for 1 h. then a solution of pyridin-3-amine (39 mg, 0.41 mmol) in DCM (1 mL) was added thereto at 0° C. The reaction mixture was stirred at room temperature for 1 h under $N_2$. After completion, the reaction was diluted with $H_2O$ (30 mL), extracted with EtOAc (30 mL×3). The combined organic layers were washed with brine (40 mL), dried over $Na_2SO_4$, concentrated in vacuo to give the crude, which was purified with silica gel column chromatography (eluent: DCM/MeOH from 0 to 3%) to afford 1-(1-(5-fluoro-3-methylbenzofuran-2-yl)-2-methylpropyl)-3-(pyridin-3-yl)urea (100 mg, yield: 71.4%) as a white solid. MS (ESI): mass calcd. $C_{19}H_{20}FN_3O_2$, 341.15, m/z found 342.1 [M+H]$^+$.

Step 2

1-(1-(5-fluoro-3-methylbenzofuran-2-yl)-2-methylpropyl)-3-(pyridin-3-yl)urea was separated by SFC 80 (Daicel CHIRALPAK OD-H, 250 mm, 20 mm ID, 5 m $CO_2$/MeOH [0.2% $NH_3$ (7M Solution in MeOH)]=85/15, 120 bar, 35° C.) to give two enantiomers: (S)-1-(1-(5-fluoro-3-methylbenzofuran-2-yl)-2-methylpropyl)-3-(pyridin-3-yl)urea (28 mg, yield: 28%) as a white solid and (R)-1-(1-(5-fluoro-3-methylbenzofuran-2-yl)-2-methylpropyl)-3-(pyridin-3-yl)urea (28 mg, yield: 28%) as a white solid. MS (ESI): mass calcd. $C_{19}H_{20}FN_3O_2$, 341.15, m/z found 342.1 [M+H]$^+$.

Compound 1

MS (ESI): mass calcd. $C_{19}H_{20}FN_3O_2$, 341.15, m/z found 342.1 [M+H]$^+$.

$^1$H NMR (400 MHz, dmso) δ 8.62 (s, 1H), 8.48 (d, J=2.5 Hz, 1H), 8.10 (dd, J=4.7, 1.4 Hz, 1H), 7.87-7.84 (m, 1H), 7.51 (dd, J=8.9, 4.1 Hz, 1H), 7.38 (dd, J=8.8, 2.7 Hz, 1H), 7.23 (dd, J=8.3, 4.7 Hz, 1H), 7.12-7.07 (m, 1H), 6.94 (d, J=8.7 Hz, 1H), 4.76 (t, J=8.6 Hz, 1H), 2.21 (s, 3H), 2.16-2.08 (m, 1H), 1.02 (d, J=6.7 Hz, 3H), 0.82 (d, J=6.7 Hz, 3H).

Compound 2

MS (ESI): mass calcd. $C_{19}H_{20}FN_3O_2$, 341.15, m/z found 342.1 [M+H]$^+$.

1H NMR (400 MHz, dmso) δ 8.62 (s, 1H), 8.48 (d, J=2.5 Hz, 1H), 8.10 (dd, J=4.6, 1.4 Hz, 1H), 7.88-7.84 (m, 1H), 7.51 (dd, J=8.9, 4.1 Hz, 1H), 7.38 (dd, J=8.8, 2.6 Hz, 1H), 7.23 (dd, J=8.3, 4.7 Hz, 1H), 7.12-7.07 (m, 1H), 6.95 (d, J=8.7 Hz, 1H), 4.76 (t, J=8.6 Hz, 1H), 2.20 (s, 3H), 2.16-2.08 (m, 1H), 1.02 (d, J=6.7 Hz, 3H), 0.83 (t, J=7.1 Hz, 3H).

Example 2: Preparation of Compound 3

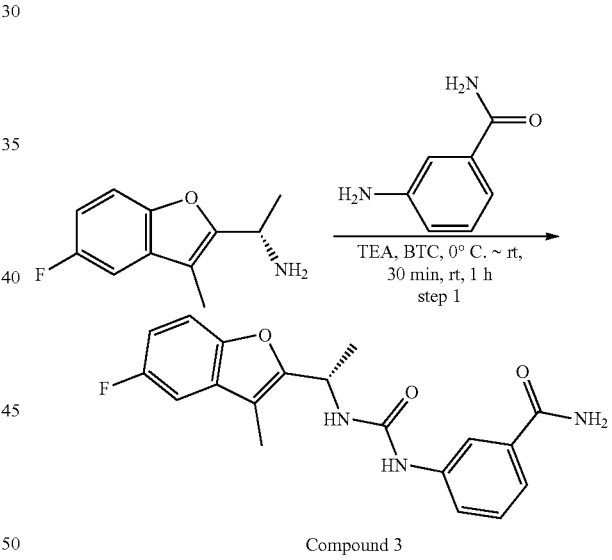

Compound 3

To a stirred solution of (S)-1-(5-fluoro-3-methylbenzofuran-2-yl)ethan-1-amine (30 mg, 0.16 mmol) in anhydrous DCM (4 mL) was added TEA (110 mg, 1.1 mmol) and triphosgene (33 mg, 0.11 mmol) at 0° C. After stirring for 0.5 h at room temperature, 3-aminobenzamide (43 mg, 0.31 mmol) was added to the reaction mixture at 0° C. The reaction mixture was stirred at room temperature for 1 h. After completion, the reaction mixture was concentrated under reduced pressure. The residue was purified by prep-HPLC to give (S)-3-(3-(1-(5-fluoro-3-methylbenzofuran-2-yl)ethyl)ureido) benzamide (26 mg, 47%) as white solid. MS (ESI): mass calcd. for $C_{19}H_{18}FN_3O_3$, 355.1, m/z found 356.1 [M+H]$^+$.

$^1$H NMR (400 MHz, DMSO) δ 8.51 (s, 1H), 7.86 (s, 1H), 7.77 (t, J=2.0 Hz, 1H), 7.54-7.51 (m, 2H), 7.39-7.36 (m,

2H), 7.29-7.25 (m, 2H), 7.13-7.07 (m, 1H), 6.80 (d, J=8.0 Hz, 1H), 5.17-5.09 (m, 1H), 2.22 (s, 3H), 1.48 (d, J=7.2 Hz, 3H).

Example 3: Preparation of Compound 4

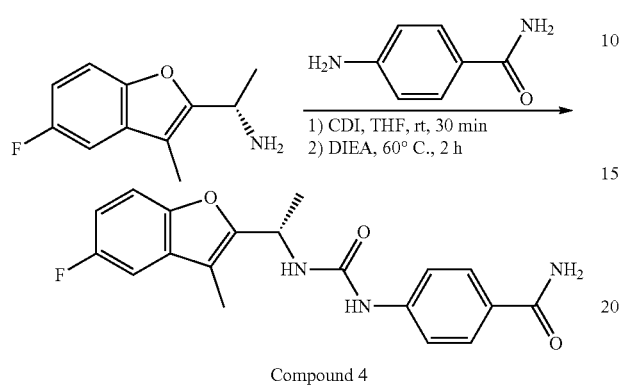

A mixture of (1S)-1-(5-fluoro-3-methyl-1-benzofuran-2-yl) ethanamine (30 mg, 0.15 mmol), CDI (28 mg, 0.17 mmol) in THF (5 mL) was stirred at room temperature for 0.5 h. 4-aminobenzamide (21 mg, 0.15 mmol) and DIEA (60 mg, 0.47 mmol) were added into the reaction mixture and the mixture was stirred at 60° C. for 2 h. After completion, the reaction mixture was concentrated under reduced pressure to give the crude product which was purified by prep-HPLC to give (R)-4-(3-(1-(5-fluoro-3-methylbenzofuran-2-yl)ethyl)ureido)benzamide (18 mg, 34%) as a white solid. MS (ESI): mass calcd. for $C_{19}H_{18}FN_3O_3$, 355.1, m/z found 356.2 $[M+H]^+$.

$^1$H NMR (400 MHz, DMSO) δ 8.67 (s, 1H), 7.76-7.73 (m, 3H), 7.54-7.51 (m, 1H), 7.41-7.36 (m, 3H), 7.13-7.07 (m, 2H), 6.88 (d, J=8.0 Hz, 1H), 5.15-5.11 (m, 1H), 2.22 (s, 3H), 1.48 (d, J=8.0 Hz, 3H).

Example 4: Preparation of Compound 5 and Compound 6

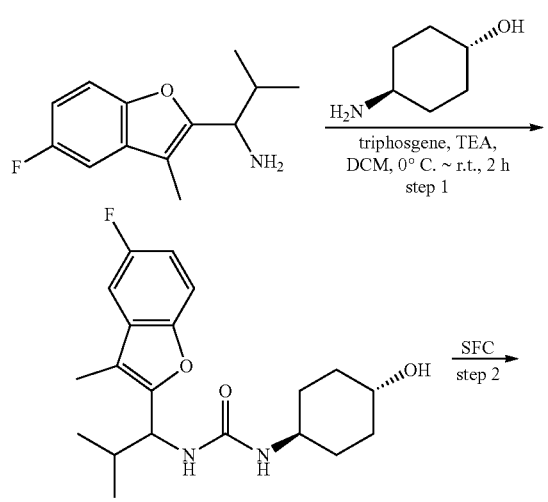

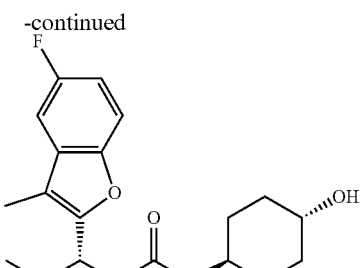

Compound 5

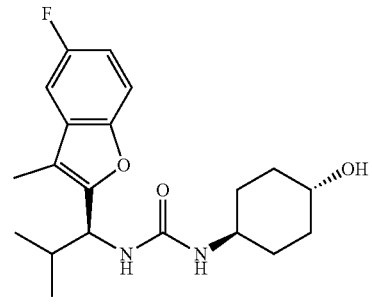

Compound 6

To a mixture of 1-(5-fluoro-3-methylbenzofuran-2-yl)-2-methylpropan-1-amine (90 mg, 0.41 mmol), TEA (331 mg, 3.28 mmol), triphosgene (152 mg, 0.51 mmol) in DCM (10 mL) stirred at 0° C. for 1 h. then a solution of (1r,4r)-4-aminocyclohexan-1-ol (39 mg, 0.41 mmol) in DCM (1 mL) was added thereto at 0° C. The reaction mixture was stirred at room temperature for 1 h under $N_2$. After completion, the reaction was diluted with $H_2O$ (30 mL), extracted with EtOAc (50 mL×3). The combined organic layers were washed with brine (40 mL), dried over $Na_2SO_4$, concentrated in vacuo to give the crude, which was purified with silica gel column chromatography (DCM/MeOH from 0 to 7%) to afford 1-(1-(5-fluoro-3-methylbenzofuran-2-yl)-2-methylpropyl)-3-((1r,4r)-4-hydroxycyclohexyl)urea (65 mg, yield: 72%) as a white solid. MS (ESI): mass calcd. $C_{20}H_{27}FN_2O_3$, 362.20, m/z found 363.1 $[M+H]^+$.

Step 2

1-(1-(5-fluoro-3-methylbenzofuran-2-yl)-2-methylpropyl)-3-((1r,4r)-4-hydroxycyclohexyl)urea was separated by SFC 80 (Daicel CHIRALPAK OD-H, 250 mm, 20 mm I.D., 5 μm $CO_2$/MeOH[0.2% $NH_3$ (7M Solution in MeOH)]=85/15, 120 bar, 35° C.) to give two enantiomers: 1-((R)-1-(5-fluoro-3-methylbenzofuran-2-yl)-2-methylpropyl)-3-((1r,4R)-4-hydroxycyclohexyl)urea (20 mg, yield: 22%) as a white solid and 1-((S)-1-(5-fluoro-3-methylbenzofuran-2-yl)-2-methylpropyl)-3-((1r,4S)-4-hydroxycyclohexyl)urea (20 mg, yield: 22%) as a white solid.

Compound 5

MS (ESI): mass calcd. $C_{20}H_{27}FN_2O_3$, 362.20, m/z found 363.1 $[M+H]^+$.

$^1$H NMR (400 MHz, dmso) δ 7.48 (dd, J=8.9, 4.1 Hz, 1H), 7.35 (dd, J=8.8, 2.6 Hz, 1H), 7.07 (t, J=9.2 Hz, 1H), 6.28 (d, J=8.9 Hz, 1H), 5.74 (d, J=7.7 Hz, 1H), 4.65 (t, J=8.6 Hz, 1H), 4.48 (d, J=4.4 Hz, 1H), 3.39-3.35 (m, 1H), 3.29-3.23

(m, 1H), 2.16 (s, 3H), 2.04-1.98 (m, 1H), 1.77-1.68 (m, 4H), 1.28-0.99 (m, 4H), 0.95 (d, J=6.8 Hz, 3H), 0.76 (d, J=6.7 Hz, 3H).

Compound 6

MS (ESI): mass calcd. $C_{20}H_{27}FN_2O_3$, 362.20, m/z found 363.1 [M+H]$^+$.

$^1$H NMR (400 MHz, dmso) δ 7.47 (dd, J=8.9, 4.1 Hz, 1H), 7.35 (dd, J=8.8, 2.6 Hz, 1H), 7.05 (t, J=9.2 Hz, 1H), 6.28 (d, J=8.9 Hz, 1H), 5.74 (d, J=7.7 Hz, 1H), 4.65 (t, J=8.6 Hz, 1H), 4.48 (d, J=4.4 Hz, 1H), 3.38-3.35 (m, 1H), 3.29-3.22 (m, 1H), 2.15 (s, 3H), 2.05-1.98 (m, 1H), 1.77-1.68 (m, 4H), 1.28-0.99 (m, 4H), 0.95 (d, J=6.8 Hz, 3H), 0.76 (d, J=6.7 Hz, 3H).

Example 5: Preparation of Compound 7

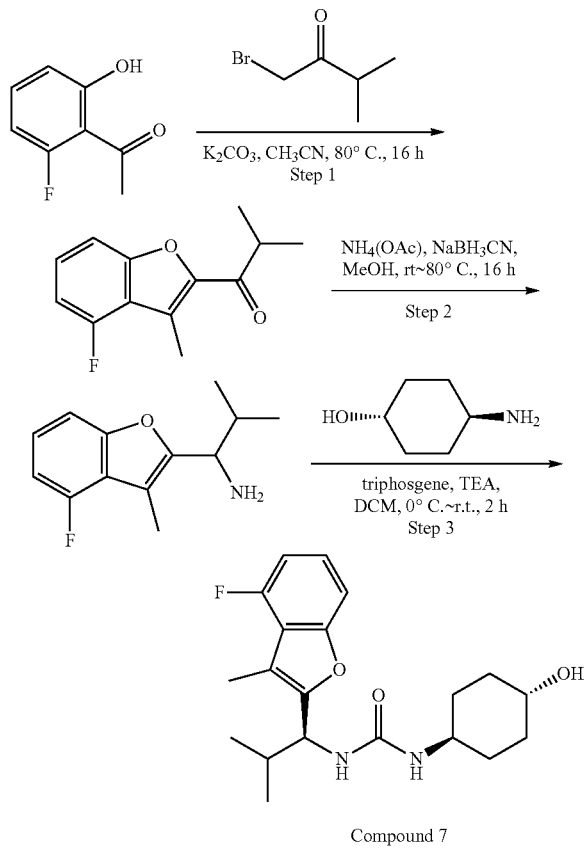

Compound 7

Step 1

To a stirred solution of 1-(2-fluoro-6-hydroxyphenyl) ethanone (1 g, 6.49 mmol) in MeCN (30 mL) was added $K_2CO_3$ (1.8 g, 13 mmol). 1-bromo-3-methylbutan-2-one (1.07 g, 6.49 mmol) was added to the reaction mixture at 0° C. The mixture was stirred at 80° C. for 16 h. After completion, the reaction mixture was cooled to room temperature and concentrated under reduced pressure. The residue was purified by silica gel chromatography column (PE/EA from 0~10%) to get 1-(4-fluoro-3-methylbenzo-furan-2-yl)-2-methylpropan-1-one (1.3 g, 90%) as white solid. MS (ESI): mass calcd. for $C_{13}H_{13}FO_2$, 220.1, m/z found 221.1 [M+H]$^+$.

Step 2

To a stirred solution of 1-(4-fluoro-3-methyl-1-benzo-furan-2-yl)-2-methylpropan-1-one (1.3 g, 5.9 mmol) in MeOH (30 mL) were added anhydrous $Na_2SO_4$ (260 mg) and $NH_4OAc$ (4.55 g, 59 mmol). The reaction mixture was stirred at room temperature for 1 h. Then NaBH$_3$CN (371 mg, 5.9 mmol) was added to the mixture. The reaction mixture was stirred at 80° C. for 24 h. After completion, the reaction mixture was cooled to room temperature and concentrated under reduced pressure. The residue was purified by flash silica gel column chromatography (DCM/MeOH from 0~10%) to give 1-(4-fluoro-3-methylbenzofuran-2-yl)-2-methylpropan-1-amine (700 mg, 50%) as a pale-yellow oil. MS (ESI): mass calcd. for, $C_{13}H_{16}FNO$, 221.1, m/z found 205.2 [M−NH$_3$$^{+1}$]$^+$.

Step 3

To a stirred solution of 1-(4-fluoro-3-methylbenzofuran-2-yl)-2-methylpropan-1-amine (170 mg, 0.769 mmol) in anhydrous DCM (25 mL) were added TEA (545 mg, 15.38 mmol), triphosgene (160 mg, 0.538 mmol) at 0° C. After stirring for 0.5 h at room temperature, (1r, 4r)-4-aminocyclohexan-1-ol (133 mg, 1.15 mmol) was added to the solution at 0° C. The reaction mixture was stirred at room temperature for 2 h. After completion, the reaction mixture was concentrated under reduced pressure. The residue was purified by flash silica gel column chromatography (DCM/MeOH from 0~10%) to give 1-((S)-1-(4-fluoro-3-methyl-benzofuran-2-yl)-2-methylpropyl)-3-((1r, 4S)-4-hydroxycyclo hexyl)urea (270 mg, 97%) as a white solid. MS (ESI): mass calcd. for $C_{20}H_{27}FN_2O_3$, 362.2, m/z found 363.2 [M+H]$^+$.

$^1$H NMR (400 MHz, DMSO) δ 7.34 (d, J=7.6 Hz, 1H), 7.27-7.21 (m, 1H), 7.03-6.99 (m, 1H), 6.30 (d, J=8.0 Hz, 1H), 5.73 (d, J=8.0 Hz, 1H), 4.64 (t, J=8.8 Hz, 1H), 4.47 (d, J=4.4 Hz, 1H), 3.38-3.34 (m, 1H), 3.29-3.21 (m, 1H), 2.28 (s, 3H), 2.05-1.96 (m, 1H), 1.80-1.67 (m, 4H), 1.20-1.01 (m, 4H), 0.96 (d, J=7.2 Hz, 3H), 0.77 (d, J=7.2 Hz, 3H).

Example 6: Preparation of Compound 8 and Compound 9

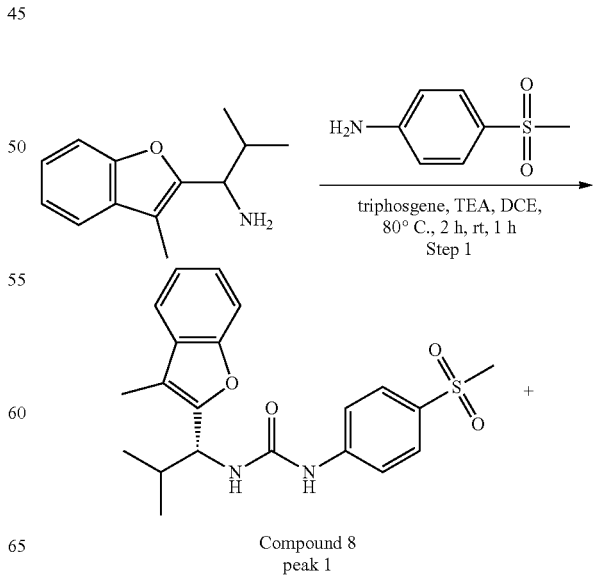

Compound 8
peak 1

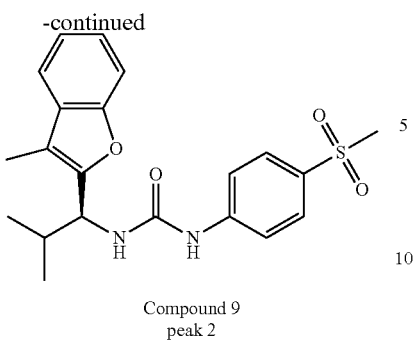

Compound 9
peak 2

To a stirred solution of 4-(methylsulfonyl) aniline (131 mg, 0.64 mmol) in DCE (10 mL) were added TEA (414 mg, 4.1 mmol), triphosgene (122 mg, 0.41 mmol) at 0° C. After stirring at 80° C. for 2 h, 2-methyl-1-(3-methylbenzofuran-2-yl) propan-1-amine (100 mg, 0.58 mmol) was added to the mixture at 0° C. The reaction mixture was stirred at room temperature for 1 h. After completion, the reaction mixture was concentrated under reduced pressure. The residue was purified by flash silica gel column chromatography (DCM/MeOH from 0~10%) to give 1-(2-methyl-1-(3-methylbenzofuran-2-yl)propyl)-3-(4-(methylsulfonyl)phenyl)urea (170 mg, 72%) as a white solid. Then the product was separated by Chiral HPLC to give (R)-1-(2-methyl-1-(3-methylbenzofuran-2-yl)propyl)-3-(4-(methylsulfonyl)phenyl)urea (Compound 8, 64 mg) and (S)-1-(2-methyl-1-(3-methylbenzofuran-2-yl)propyl)-3-(4-(methylsulfonyl) phenyl)urea (Compound 9, 64 mg) as white solids with the following conditions. MS (ESI): mass calcd. for $C_{21}H_{24}N_2O_4S$, 400.1, m/z found 401.1 [M+H]$^+$.

Chiral Separation Conditions:
Column: Daicel CHIRALPAK OJ_3, 3*150 mm, 3 um;
Mobile Phase: A/B: $CO_2$/MeOH (0.1% DEA)=85/15;
Flow rate: 2.0 ml/min; Column
Temp: 37 degrees.

Compound 8

$^1$H NMR (400 MHz, DMSO) δ 8.98 (s, 1H), 7.75-7.73 (m, 2H), 7.60-7.54 (m, 3H), 7.50-7.48 (m, 1H), 7.30-7.22 (m, 2H), 7.00 (d, J=8.8 Hz, 1H), 4.78 (t, J=8.8 Hz, 1H), 3.11 (s, 3H), 2.23 (s, 3H), 2.17-2.11 (m, 1H), 1.03 (d, J=7.2 Hz, 3H), 0.83 (d, J=7.2 Hz, 3H).

Compound 9

$^1$H NMR (400 MHz, DMSO) δ 8.99 (s, 1H), 7.75-7.73 (m, 2H), 7.60-7.54 (m, 3H), 7.50-7.48 (m, 1H), 7.30-7.22 (m, 2H), 7.00 (d, J=8.8 Hz, 1H), 4.78 (t, J=8.8 Hz, 1H), 3.11 (s, 3H), 2.23 (s, 3H), 2.18-2.10 (m, 1H), 1.03 (d, J=7.2 Hz, 3H), 0.83 (d, J=6.4 Hz, 3H).

Example 7: Preparation of Compound 10 and Compound 11

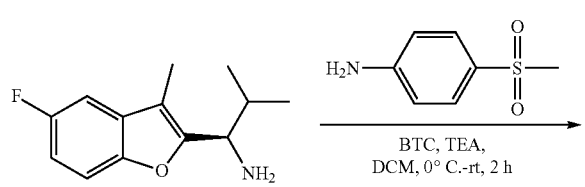

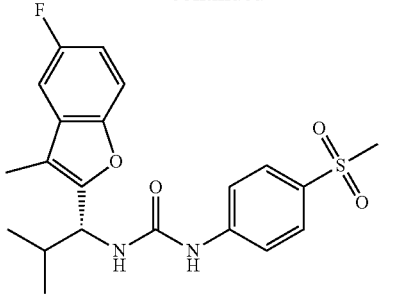

Compound 10
peak 1

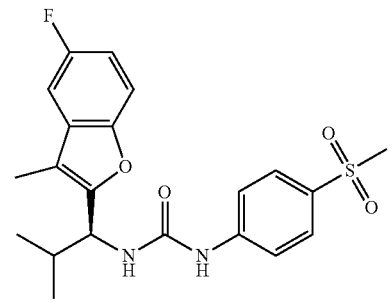

Compound 11
peak 2

To a solution of (R)-1-(5-fluoro-3-methylbenzofuran-2-yl)-2-methylpropan-1-amine (Int-1) (200 mg, 0.9 mmol) and TEA (731 mg, 7.23 mmol) in DCM (5 mL) was added BTC (220 mg, 0.74 mmol) at 0° C. The reaction mixture was stirred for 30 min at room temperature. 4-(methylsulfonyl) aniline (162 mg, 0.94 mmol) was added to the reaction mixture at 0° C. The reaction mixture was stirred at room temperature for 2 h. The reaction mixture was concentrated to give a residue which was purified by prep-HPLC to give racemic 1-(1-(5-fluoro-3-methylbenzofuran-2-yl)-2-methylpropyl)-3-(4-(methylsulfonyl)phenyl)urea (203 mg, 53%) as white solid, which was separated by SFC to give rel-(R)-1-(1-(5-fluoro-3-methylbenzofuran-2-yl)-2-methylpropyl)-3-(4-(methylsulfonyl)phenyl)urea (Peak 1, 83.07 mg, 22%) and rel-(R)-1-(1-(5-fluoro-3-methylbenzofuran-2-yl)-2-methylpropyl)-3-(4-(methylsulfonyl)phenyl)urea (Peak 2, 82.85 mg, 21%) as white solid with the following separation conditions. MS (ESI): mass calcd. for $C_{21}H_{23}FN_2O_4S$, 418.1, m/z found 419.2 [M+H]$^+$.

Separation Conditions: Apparatus: SFC 150; Column: Daicel CHIRALCEL IE, 250 mm×30 mm I.D., 10 μm; Mobile phase: $CO_2$/MeOH [0.2% NH3 (7M Solution in MeOH)]=75/25

Flow rate: 80 g/min; Wave length: UV 214 nm; Temperature: 35° C.

Compound 10

$^1$H NMR (400 MHz, DMSO-d6) δ 8.99 (s, 1H), 7.75 (d, J=8.8 Hz, 2H), 7.59 (d, J=8.8 Hz, 2H), 7.53-7.50 (m, 1H), 7.40-7.37 (m, 1H), 7.13-7.07 (m, 1H), 7.02 (d, J=8.4 Hz, 1H), 4.76 (t, J=8.4 Hz, 1H), 3.12 (s, 3H), 2.21 (s, 3H), 2.17-2.10 (m, 1H), 1.03 (d, J=6.8 Hz, 3H), 0.83 (d, J=6.8 Hz, 3H).

Compound 11

$^1$H NMR (400 MHz, DMSO-d6) δ 8.99 (s, 1H), 7.76 (s, 1H), 7.73 (s, 1H), 7.58 (d, J=8.8 Hz, 2H), 7.53-7.50 (m, 1H), 7.40-7.37 (m, 1H), 7.13-7.07 (m, 1H), 7.02 (d, J=8.4 Hz, 1H), 4.76 (t, J=8.4 Hz, 1H), 3.11 (s, 3H), 2.21 (s, 3H), 2.16-2.10 (m, 1H), 1.03 (d, J=6.8 Hz, 3H), 0.82 (d, J=6.8 Hz, 3H).

Example 8: Preparation of Compound 12

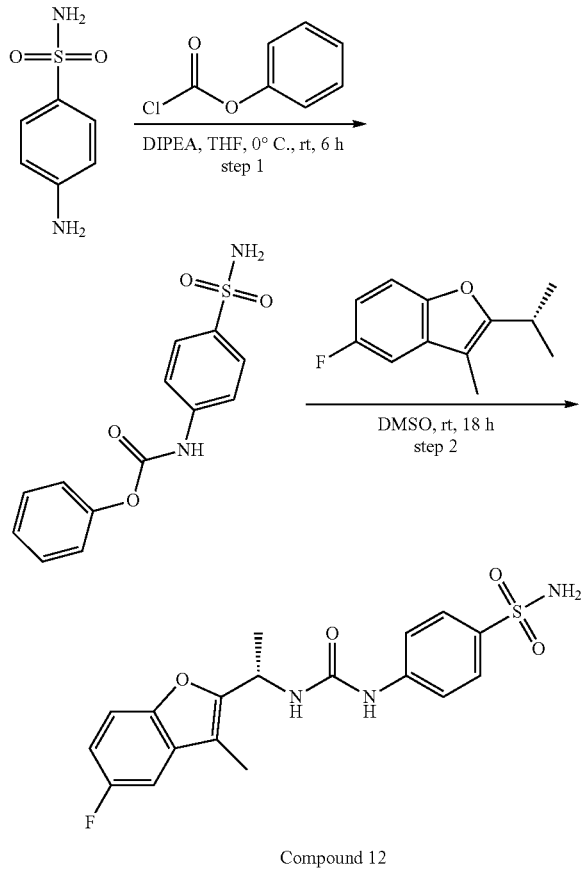

Compound 12

Step 1

To a stirred solution of 4-aminobenzenesulfonamide (1.72 g, 10 mmol) in anhydrous THF (15 mL) was added DIEA (2.1 mL, 12 mmol) at room temperature. Phenyl chloroformate (1.5 mL, 12 mmol) was added to the solution dropwise at 0° C. The reaction mixture was stirred at room temperature for 6 h. After completion, the reaction mixture was concentrated under reduced pressure and diluted with water. The precipitate was filtered. The filter cake was dried in vacuum to give phenyl (4-sulfamoylphenyl) carbamate (3.1 g, 85%) as white solid. MS (ESI): mass calcd. for $C_{13}H_{12}N_2O_4S$, 292.0, m/z found 293.1 [M+H]$^+$.

Step 2

To a stirred solution of phenyl N-(4-sulfamoylphenyl) carbamate (76 mg, 0.26 mmol) in DMSO (2 mL) was added (R)-1-(5-fluoro-3-methylbenzofuran-2-yl)ethan-1-amine (50 mg, 0.26 mmol). The reaction mixture was stirred at room temperature for 18 h. After completion, the reaction mixture was purified by prep-HPLC to give (R)-4-(3-(1-(5-fluoro-3-methylbenzofuran-2-yl) ethyl) ureido) benzenesulfonamide (66 mg, 65%) as white solid. MS (ESI): mass calcd. for $C_{18}H_{18}FN_3O_4S$, 391.1, m/z found 392.1 [M+H]$^+$.

$^1$H NMR (400 MHz, DMSO) δ 8.80 (s, 1H), 7.66 (d, J=8.8 Hz, 2H), 7.53-7.48 (m, 3H), 7.39-7.36 (m, 1H), 7.16 (s, 2H), 7.13-7.07 (m, 1H), 6.93 (d, J=7.6 Hz, 1H), 5.16-5.09 (m, 1H), 2.22 (s, 3H), 1.48 (d, J=7.2 Hz, 3H).

Example 8: Preparation of Compound 13

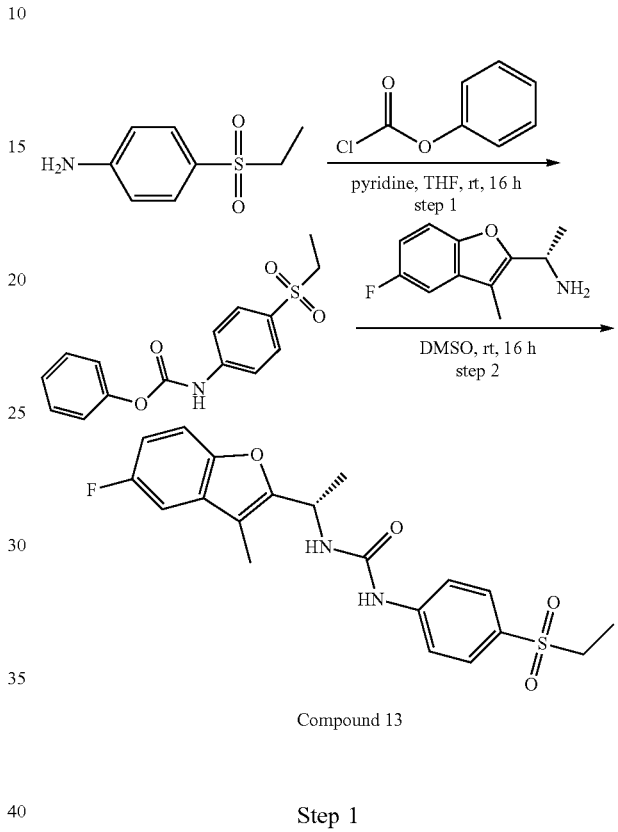

Compound 13

Step 1

To a stirred solution of 4-(ethanesulfonyl) aniline (50 mg, 0.27 mmol) in anhydrous THF (3 mL) were added pyridine (1 drop) and phenyl chloroformate (51 mg, 0.324 mmol) at room temperature. The reaction mixture was stirred at room temperature for 16 h. After completion, the reaction mixture was concentrated under reduced pressure and diluted with water. The precipitate was filtered. The filter cake was dried in vacuum to give phenyl (4-(ethylsulfonyl) phenyl) carbamate (60 mg, 72%) as a white solid. MS (ESI): mass calcd. for $C_{15}H_{15}NO_4S$, 305.1, m/z found 306.1 [M+H]$^+$.

Step 2

To a stirred solution of phenyl (4-(ethylsulfonyl)phenyl) carbamate (40 mg, 0.13 mmol) in DMSO (2 mL) was added (R)-1-(5-fluoro-3-methylbenzofuran-2-yl)ethan-1-amine (26 mg, 0.13 mmol). The reaction mixture was stirred at room temperature for 16 h. After completion, the reaction mixture was purification by prep-HPLC to give (R)-1-(4-(ethylsulfonyl)phenyl)-3-(1-(5-fluoro-3-methylbenzofuran-2-yl)ethyl)urea (42 mg, 79%) as white solid. MS (ESI): mass calcd. for $C_{20}H_{21}FN_2O_4S$, 404.1, m/z found 405.1 [M+H]$^+$.

$^1$H NMR (400 MHz, DMSO) δ 8.96 (s, 1H), 7.70 (d, J=8.8 Hz, 2H), 7.60 (d, J=8.8 Hz, 2H), 7.54-7.51 (m, 1H), 7.39-7.36 (m, 1H), 7.13-7.08 (m, 1H), 7.00 (d, J=7.6 Hz, 1H), 5.17-5.10 (m, 1H), 3.18 (q, J=7.6 Hz, 2H), 2.22 (s, 3H), 1.49 (d, J=7.6 Hz, 3H), 1.06 (t, J=7.6 Hz, 3H).

Example 9: Preparation of Compound 14

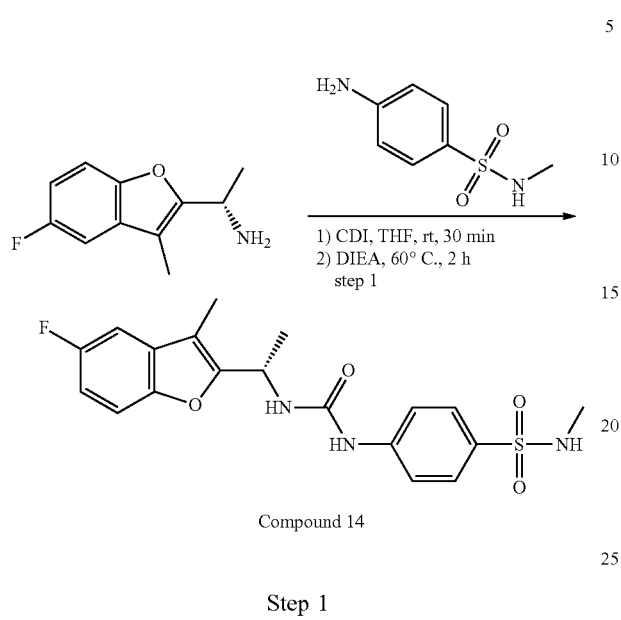

Compound 14

Step 1

A mixture of (1S)-1-(5-fluoro-3-methyl-1-benzofuran-2-yl) ethanamine (50 mg, 0.26 mmol) and CDI (46 mg, 0.28 mmol) in THF (10 mL) was stirred at 20° C. for 0.5 h. 4-amino-N-methylbenzene sulfonamide (48 mg, 0.26 mmol) and DIEA (100 mg, 0.78 mmol) were added into the above reaction mixture and the mixture was stirred at 60° C. for 2 h. After completion, the mixture was concentrated under reduced pressure to give a residue which was purified by prep-HPLC to give rel-(R)-4-(3-(1-(5-fluoro-3-methylbenzofuran-2-yl)ethyl)ureido)-N-methylbenzenesulfonamide (41 mg, 39%) as a white solid. MS (ESI): mass calcd. for $C_{19}H_{20}FN_3O_4S$, 405.1, m/z found 406.0 [M+H]$^+$.
$^1$H NMR (400 MHz, DMSO) δ 8.85 (s, 1H), 7.62-7.60 (m, 2H), 7.56-7.51 (m, 3H), 7.39-7.36 (m, 1H), 7.22-7.19 (m, 1H), 7.13-7.07 (m, 1H), 6.94 (d, J=8.0 Hz, 1H), 5.15-5.12 (m, 1H), 2.36 (d, J=4.0 Hz, 3H), 2.22 (s, 3H), 1.49 (d, J=8.0 Hz, 3H).

Example 10: Preparation of Compound 15 and Compound 16

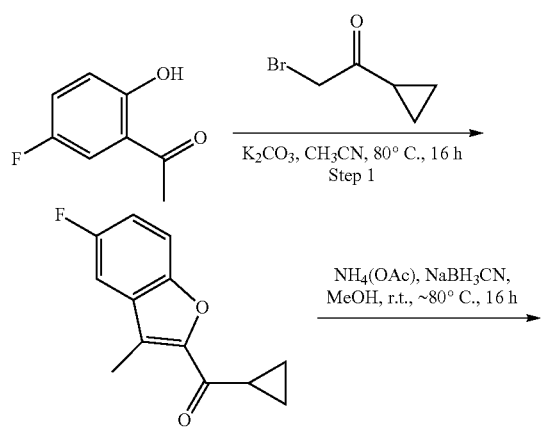

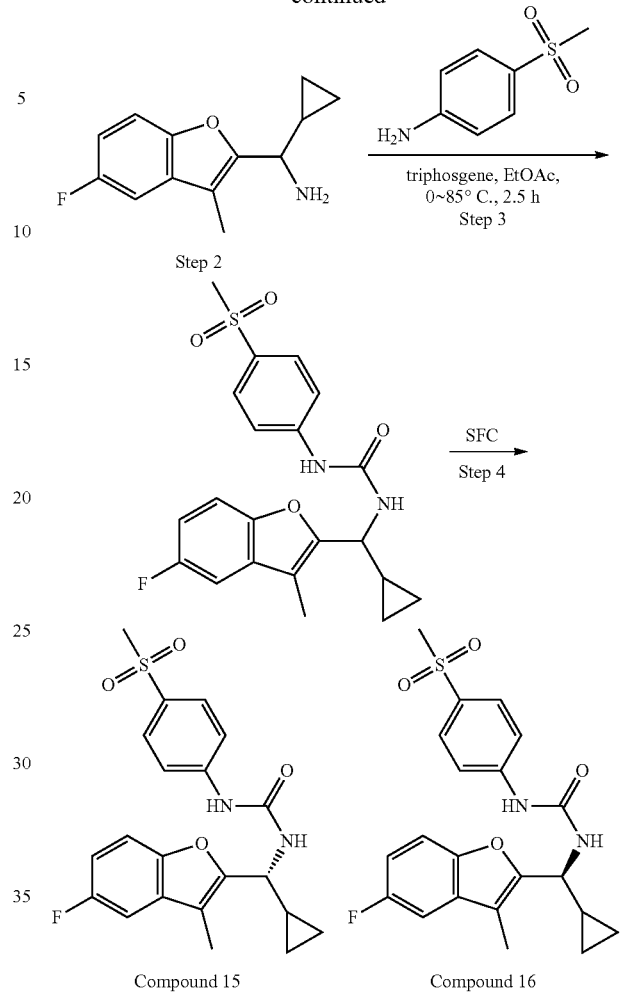

Compound 15   Compound 16

Step 1

To a mixture 1-(5-fluoro-2-hydroxyphenyl)ethan-1-one (500 mg, 3.3 mmol) and $K_2CO_3$ (911 mg, 6.6 mmol) in $CH_3CN$ (15 mL) was added 2-bromo-1-cyclopropylethan-1-one (653 mg, 4 mmol). The reaction mixture was stirred at 80° C. for 16 h under $N_2$. After completion, the reaction was quenched with $H_2O$ (35 mL), extracted with EtOAc (40 mL×3). The combined organic layers were washed with brine (40 mL), dried over $Na_2SO_4$, concentrated in vacuo to give the crude, which was purified with silica gel column chromatography (DCM/MeOH from 0 to 3%) to give the cyclopropyl(5-fluoro-3-methylbenzofuran-2-yl)methanone (245 mg, yield: 34%) as a yellow solid. MS (ESI): mass calcd. for $C_{13}H_{11}FO_2$, 218.07, m/z found 219.1 [M+H]$^+$.

Step 2

To a mixture cyclopropyl(5-fluoro-3-methylbenzofuran-2-yl)methanone (245 mg, 1.13 mmol) and $Na_2SO_4$ (49 mg, 0.34 mmol) in MeOH (5 mL) was added $NH_4OAc$ (871 mg, 11.3 mmol). The reaction mixture was stirred at room temperature for 1 h under $N_2$ and then $NaBH_3CN$ (72 mg, 1.13 mmol) was added. The reaction mixture was stirred at 80° C. for 16 h. After completion, the reaction was quenched with $H_2O$ (25 mL), extracted with EtOAc (20 mL×3). The combined organic layers were washed with brine (30 mL), dried over Na$_2$SO$_4$, concentrated in vacuo to give the crude, which was purified with silica gel column chromatography (DCM/MeOH from 0 to 6%) to give the cyclopropyl(5-fluoro-3-methylbenzofuran-2-yl)methanamine (156 mg, yield: 40.4%) as yellow oil. MS (ESI): mass calcd. for C13H14FNO, 219.11, m/z found 203.2 [M-NH$_2$]$^+$.

Step 3

To a mixture of 4-(methylsulfonyl)aniline (156 mg, 0.91 mmol) and TEA (93 mg, 0.92 mmol) in EtOAc (5 mL) was added a solution of triphosgene (271 mg, 0.91 mmol) in EtOAc (1 mL) at 0° C. The resulting reaction was stirred at 85° C. for 2 h. After cooled to room temperature, cyclopropyl(5-fluoro-3-methylbenzofuran-2-yl)methanamine (200 mg, 0.91 mmol) was added thereto and stirred at room temperature for another 30 min. After completion, the reaction mixture was concentrated in vacuo to give a residue, which was purified by Prep-TLC (DCM/MeOH=15/1) to give the 1-(cyclopropyl(5-fluoro-3-methylbenzofuran-2-yl)methyl)-3-(4-(methylsulfonyl)phenyl)urea (70 mg, 18.5%) as a white solid. MS (ESI): mass calcd. for C$_{21}$H$_{21}$FN$_2$O$_4$S, 416.12, m/z found 439.1 [M+Na]$^+$.

Step 4

Compound 3 was separated by SFC (Daicel CHIRAL-PAK OD-H, 20×250 mm, 5 μm 70/30 CO$_2$/MeOH [0.2% NH$_3$ (7M Solution in MeOH)], 50 g/min, 120 bar, 35° C.) to give two enantiomers: (R)-1-(cyclopropyl(5-fluoro-3-methylbenzofuran-2-yl)methyl)-3-(4(methylsulfonyl)phenyl)urea (Compound 15, 25 mg, 6.5%) as a white solid and (S)-1-(cyclopropyl(5-fluoro-3-methylbenzofuran-2-yl)methyl)-3-(4-(methylsulfonyl)phenyl)urea (Compound 16, 25 mg, 6.5%) as a white solid respectively.

Compound 15

MS (ESI): mass calcd. for C$_{21}$H$_{21}$FN$_2$O$_4$S, 416.12, m/z found 439.1 [M+Na]$^+$.
$^1$H NMR (400 MHz, dmso) δ 9.00 (s, 1H), 7.74 (d, J=8.9 Hz, 2H), 7.58 (d, J=8.9 Hz, 2H), 7.53 (dd, J=8.9, 4.1 Hz, 1H), 7.38 (dd, J=8.8, 2.7 Hz, 1H), 7.18-7.03 (m, 2H), 4.47 (t, J=8.3 Hz, 1H), 3.14 (s, 3H), 2.20 (s, 3H), 1.43-1.32 (m, 1H), 0.64-0.28 (m, 4H).

Compound 16

MS (ESI): mass calcd. for C$_{21}$H$_{21}$FN$_2$O$_4$S, 416.12, m/z found 439.1 [M+Na]$^+$.
$^1$H NMR (400 MHz, dmso) δ 9.04 (s, 1H), 7.74 (d, J=8.9 Hz, 2H), 7.58 (d, J=8.9 Hz, 2H), 7.53 (dd, J=8.9, 4.1 Hz, 1H), 7.38 (dd, J=8.8, 2.6 Hz, 1H), 7.17 (d, J=8.0 Hz, 1H), 7.13-7.05 (m, 1H), 4.47 (t, J=8.2 Hz, 1H), 3.10 (s, 3H), 2.20 (s, 3H), 1.39-1.32 (m, 1H), 0.60-0.31 (m, 4H).

Preparation of Int-1 and Int-2 Chiral intermediates (R)- and (S)-1-(5-fluoro-3-methylbenzofuran-2-yl)-2-methylpropan-1-amine

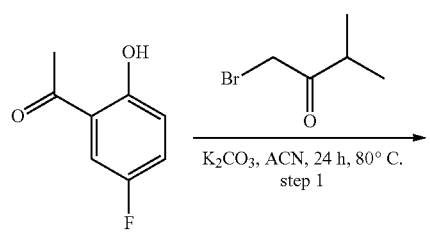

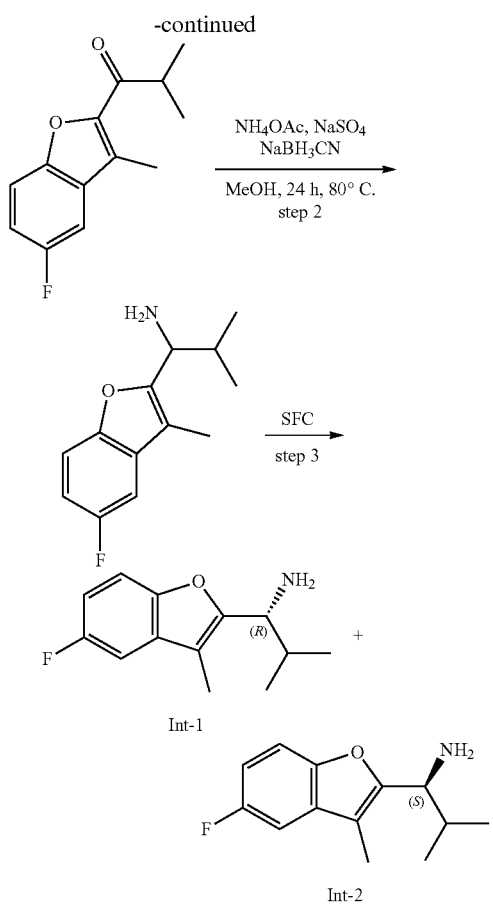

Step 1

To a mixture of 1-(5-fluoro-2-hydroxyphenyl) ethan-1-one (18.6 g, 0.12 mol) and 1-bromo-3-methylbutan-2-one (20 g, 0.12 mol) in ACN (300 mL) was added K$_2$CO$_3$ (33.4 g, 0.24 mol). The reaction mixture was stirred at 80° C. for 24 h. After reaction, the reaction mixture was diluted with water and extracted with EA (500 mL×3). The combined organic layer was washed with brine and concentrated to give a residue which was purified by silica gel chromatography column (PE/EA from 0~10%) to give 1-(5-fluoro-3-methylbenzofuran-2-yl)-2-methylpropan-1-one (24 g, 90%) as yellow oil. MS (ESI): mass calcd. for C$_{13}$H$_{13}$FO$_2$, 220.1, m/z found 221.2 [M+H]$^+$.

Step 2

A mixture of 1-(5-fluoro-3-methylbenzofuran-2-yl)-2-methylpropan-1-one (24 g, 0.11 mol), Na$_2$SO$_4$ (4.8 g) and NH$_4$OAc (83.9 g, 1.08 mol) in MeOH (400 mL) was stirred at room temperature for 1 h. NaBH$_3$CN (6.8 g, 0.10 mol) was added into the reaction mixture and the mixture was stirred at 80° C. for 24 h. After completion, the reaction mixture was filtered and the filtrate was concentrated to give a crude product which was re-dissolved in 10% NaOH aqueous solution. The aqueous solution was extracted with DCM (600 mL×3) and the combined organic layer was concentrated to give a residue which was purified by silica gel chromatography column (PE/EA from 0~50%) to give racemic 1-(5-fluoro-3-methylbenzofuran-2-yl)-2-methylpropan-1-amine (16 g, 66%) as yellow solid. MS (ESI): mass calcd. for $C_{13}H_{16}FNO$, 221.1, m/z found 205.2 $[M-NH_3+1]^+$.

Step 3

Racemic 1-(5-fluoro-3-methylbenzofuran-2-yl)-2-methylpropan-1-amine (16 g) was separated by SFC to give (R)-1-(5-fluoro-3-methylbenzofuran-2-yl)-2-methylpropan-1-amine (Int-1) (peak 1, 7.1 g, 44%) and (S)-1-(5-fluoro-3-methylbenzofuran-2-yl)-2-methylpropan-1-amine (Int-2) (peak 2, 7.2 g, 45%) as yellow oil with the following chiral separation conditions.

MS (ESI): mass calcd. for $C_{13}H_{16}FNO$, 221.1, m/z found 205.2.

Chiral Separation Conditions: Apparatus: SFC 150; Column: Daicel CHIRALCEL AS, 250 mm×30 mm I.D., 10 μm; Mobile phase: $CO_2$/MeOH [0.2% $NH_3$ (7M Solution in MeOH)]=70/30;

Flow rate: 80 g/min; Wavelength: UV 214 nm; Temperature: 35° C.

(R)-1-(5-fluoro-3-methylbenzofuran-2-yl)-2-methylpropan-1-amine (Int-1) (Peak 1)

$^1$H NMR (400 MHz, DMSO) δ 7.49-7.46 (m, 1H), 7.34-7.31 (m, 1H), 7.08-7.01 (m, 1H), 3.69 (d, J=7.6 Hz, 1H), 2.22 (s, 2H), 2.15 (s, 3H), 1.96-1.87 (m, 1H), 1.00 (d, J=6.8 Hz, 3H), 0.74 (d, J=6.8 Hz, 3H).

(S)-1-(5-fluoro-3-methylbenzofuran-2-yl)-2-methylpropan-1-amine (Int-2) (Peak 2)

$^1$H NMR (400 MHz, DMSO) δ 7.49-7.46 (m, 1H), 7.34-7.31 (m, 1H), 7.08-7.01 (m, 1H), 3.68 (d, J=7.6 Hz, 1H), 2.16 (s, 3H), 2.03-1.80 (m, 3H), 1.00 (d, J=6.8 Hz, 3H), 0.75 (d, J=6.8 Hz, 3H).

Example 11: Preparation of Compound 17 and Compound 18

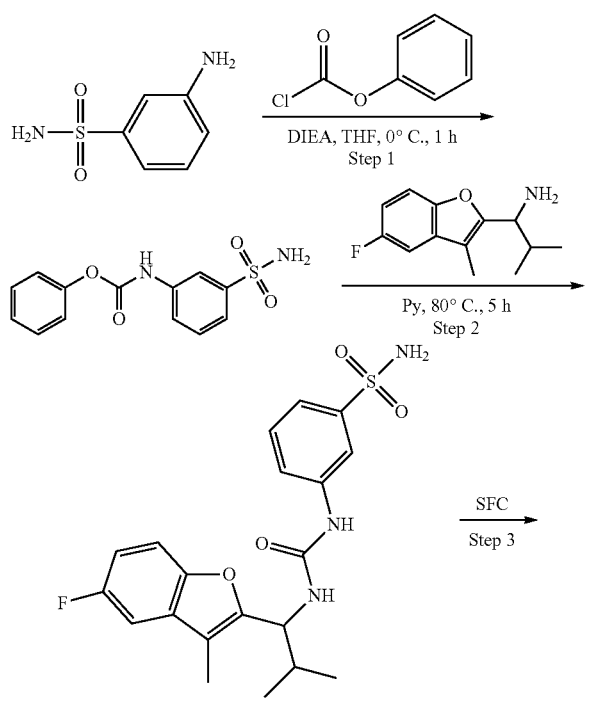

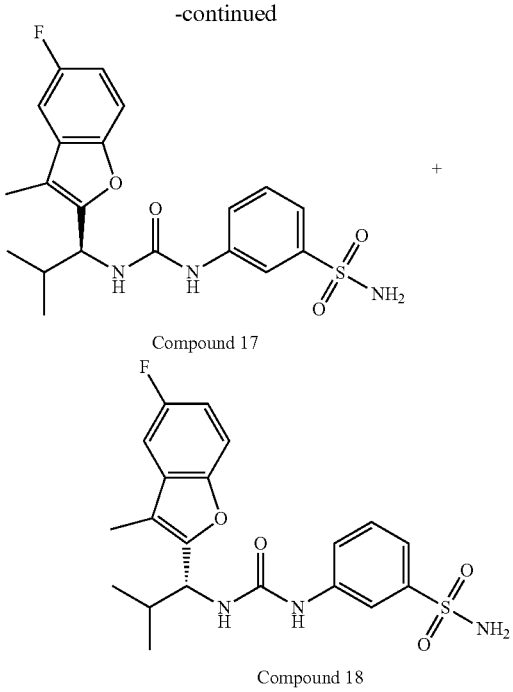

Compound 17

Compound 18

Step 1

To a solution of 3-aminobenzenesulfonamide (520 mg, 3.02 mmol) in THF (15 mL) was added DIEA (781 mg, 6.05 mmol) and was slowly added benzyl chloroformate (473 mg, 3.02 mmol) at 0° C. Then the reaction mixture was stirred at 0° C. for 1 h. After completion, the reaction was concentrated with under reduced pressure and the residue was purified by flash silica gel column chromatography (EA/PE from 0%~50%) to give phenyl (3-sulfamoylphenyl) carbamate (500 mg, 56%) as white solid. MS (ESI): mass calcd. for $C_{13}H_{14}N_2O_4S$, 292.31, m/z found 293.06 $[M+H]^+$.

Step 2

To a solution of phenyl (3-sulfamoylphenyl)carbamate (240 mg, 0.82 mmol) in pyridine (5.0 mL) was added 1-(5-fluoro-3-methylbenzofuran-2-yl)-2-methylpropan-1-amine (150 mg, 0.678 mmol). The reaction was stirred at 80° C. for 5 h. After completion, the reaction mixture was concentrated under reduced pressure. The residue was purified by prep-HPLC with the following conditions: Column: Acquity BEH 50*2.1 mm, 1.7 um; Mobile Phase A: $H_2O$ (0.05% TFA), Mobile Phase B: ACN (0.05% TFA); Flow rate: 0.5 mL/min; Gradient: 5% B to 95% B in 2.5 min; 214 nm; Rt: 1.536 min to 3-(3-(1-(5-fluoro-3-methylbenzofuran-2-yl)-2-methylpropyl)ureido)benzenesulfonamide (240 mg, 100%) as white solid. MS (ESI): mass calcd. for $C_{20}H_{22}FN_3O_4S$, 419.47, m/z found 420.13 $[M+H]^+$.

Step 3

200 mg of the 3-(3-(1-(5-fluoro-3-methylbenzofuran-2-yl)-2-methylpropyl)ureido) benzenesulfonamide was sent for SFC separation to give (S)-3-(3-(1-(5-fluoro-3-methylbenzofuran-2-yl)-2-methylpropyl)ureido)benzenesulfonamide (Compound 17) (89.7 mg) as white solid and (R)-3-

(3-(1-(5-fluoro-3-methylbenzofuran-2-yl)-2-methylpropyl) ureido)benzenesulfonamide (Compound 18) (99.2 mg) as white solid.

Separation Condition: Apparatus: SFC 150; Column: Daicel CHIRALCEL OJ, 250 mm*30 mm I.D., 10 μm; Mobile phase: $CO_2$/MeOH [0.2% $NH_3$ (7M Solution in MeOH)]= 65/35; Flow rate 80 g/min; Wave length: UV 214 nm; Temperature: 35° C.

Compound 17

MS (ESI): mass calcd. for $C_{20}H_{22}FN_3O_4S$, 419.47, m/z found 420.13 $[M+H]^+$.

$^1$H NMR (400 MHz, DMSO) δ 8.77 (s, 1H), 8.00 (d, J=1.8 Hz, 1H), 7.52-7.41 (m, 1H), 7.35-7.28 (m, 6H), 7.10-7.07 (m, 1H), 6.86 (d, J=8.8 Hz, 1H), 4.76 (t, J=8.8 Hz, 1H), 2.21 (s, 3 H), 2.10-2.05 (m, 1H), 1.03 (d, J=6.8 Hz, 3H), 0.82 (d, J=6.8 Hz, 3H).

Compound 18

MS (ESI): mass calcd. for $C_{20}H_{22}FN_3O_4S$, 419.47, m/z found 420.13 $[M+H]^+$.

$^1$H NMR (400 MHz, DMSO) δ 8.77 (s, 1H), 7.99 (d, J=1.8 Hz, 1H), 7.53-7.52 (m, 1H), 7.40-7.35 (m, 4H), 7.34-7.32 (m, 2H), 7.10-7.09 (m, 1H), 6.86 (d, J=8.8 Hz, 1H), 4.76 (t, J=8.8 Hz, 1H), 2.21 (s, 3H), 2.16-2.08 (m, 1H), 1.4 (d, J=6.8 Hz, 3H), 0.82 (d, J=6.8 Hz, 3H).

Example 12: Preparation of Compound 19 and Compound 20

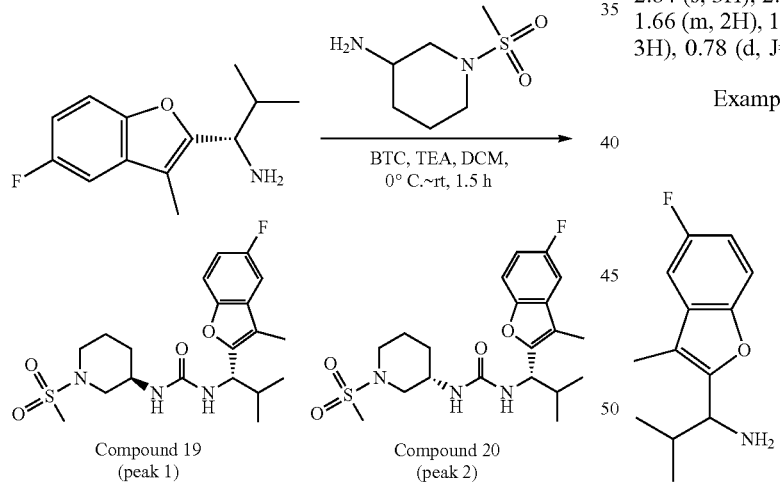

Step 1

To a stirred solution of (S)-1-(5-fluoro-3-methylbenzofuran-2-yl)-2-methylpropan-1-amine (Int-2) (100 mg, 0.45 mmol) and TEA (320 mg, 3.16 mmol) in DCM (3 mL) was added triphosgene (93 mg, 0.32 mmol) at 0° C. under $N_2$ atmosphere. The mixture was stirred at room temperature for 30 min. 1-(methylsulfonyl) piperidin-3-amine (161 mg, 0.90 mmol) was added into the reaction mixture at 0° C. and the mixture was stirred at room temperature for 1 h. After reaction, the reaction mixture was concentrated under reduced pressure to give a residue which was purified by SFC to give the racemic product and the solid was separated by chiral separation HPLC to give 1-((S)-1-(5-fluoro-3-methylbenzofuran-2-yl)-2-methylpropyl)-3-((R)-1-(methylsulfonyl) piperidin-3-yl)urea (Peak 1, 79 mg) and 1-((S)-1-(5-fluoro-3-methylbenzofuran-2-yl)-2-methylpropyl)-3-((S)-1-(methylsulfonyl)piperidin-3-yl)urea (Peak 2, 58 mg) as off-white solid with the following chiral separation conditions.

Chiral separation conditions: Apparatus: SFC 80; Column: Daicel CHIRALCEL IB-N, 250 mm×30 mm I.D., 10 μm; Mobile phase: $CO_2$/MeOH [0.2% $NH_3$ (7M Solution in MeOH)]=85/15; Flow rate: 80 g/min; Wavelength: UV 214 nm; Temperature: 35° C.

Compound 19

MS (ESI): mass calcd. for $C_{20}H_{28}FN_3O_4S$, 425.2, m/z found 426.2 $[M+H]^+$.

$^1$H NMR (400 MHz, DMSO) δ=7.49 (dd, J=8.8, 4.0, 1H), 7.36 (dd, J=8.8, 4.8, 1H), 7.08 (m, 1H), 6.55 (d, J=8.8, 1H), 6.09 (d, J=8.0, 1H), 4.68 (t, J=8.8, 1H), 3.67-3.57 (m, 1H), 3.28 (m, 1H), 3.12 (m, 1H), 2.93 (m, 1H), 2.79 (s, 3H), 2.63 (m, 1H), 2.17 (s, 3H), 2.06-1.96 (m, 1H), 1.77-1.63 (m, 2H), 1.60-1.49 (m, 1H), 1.33 (m, 1H), 0.95 (d, J=6.8, 3H), 0.78 (d, J=6.8, 3H).

Compound 20

MS (ESI): mass calcd. for $C_{20}H_{28}FN_3O_4S$, 425.2, m/z found 426.2 $[M+H]^+$.

$^1$H NMR (400 MHz, DMSO-d6) δ 7.48 (dd, J=8.8, 4.0 Hz, 1H), 7.36 (dd, J=8.8, 2.4 Hz, 1H), 7.08 (m, 1H), 6.53 (d, J=8.8 Hz, 1H), 6.09 (d, J=7.6 Hz, 1H), 4.67 (t, J=8.4 Hz, 1H), 3.56 (m, 1H), 3.22-3.09 (m, 1H), 2.96-2.87 (m, 1H), 2.84 (s, 3H), 2.67 (m, 1H), 2.16 (s, 3H), 2.09-1.95 (m, 1H), 1.66 (m, 2H), 1.50 (m, 1H), 1.27 (m, 2H), 0.96 (d, J=6.8 Hz, 3H), 0.78 (d, J=6.8 Hz, 3H).

Example 13: Preparation of Compound 21

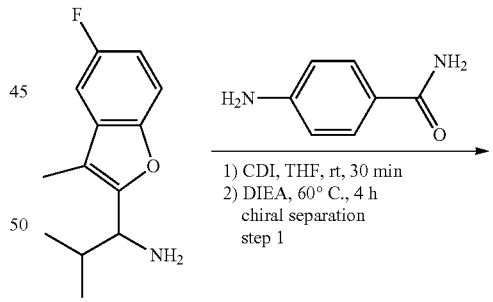

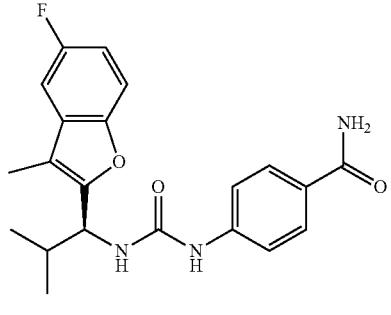

Compound 21

Step 1

A mixture of 1-(5-fluoro-3-methyl-1-benzofuran-2-yl)-2-methylpropan-1-amine (300 mg, 1.36 mmol) and CDI (242 mg, 1.49 mmol) in THF (20 mL) was stirred at 20° C. for 0.5 h. 4-aminobenzamide (185 mg, 1.36 mmol) and DIEA (526 mg, 4.07 mmol) were added and the reaction mixture was stirred at 60° C. for 4 h. The reaction mixture was concentrated to give a residue which was purified by silica gel Chromatography column (DCM/MeOH from 0~10%) to get 4-(3-(1-(5-fluoro-3-methylbenzofuran-2-yl)-2-methylpropyl)ureido)benzamide. The racemic compound was separated by SFC to give (S)-4-(3-(1-(5-fluoro-3-methylbenzofuran-2-yl)-2-methylpropyl)ureido)benzamide (peak 2, 121 mg, 23%) as a white solid with the following separation conditions.

Chiral separation conditions: Apparatus: SFC 150; Column: Daicel CHIRALCEL AZ, 250 mm×30 mm I.D., 10 μm; Mobile phase: $CO_2$/MeOH [0.2% $NH_3$ (7M Solution in MeOH)]=80/20; Flow rate: 80 g/min; Wavelength: UV 214 nm; Temperature: 35° C.

MS (ESI): mass calcd. for $C_{21}H_{24}FN_5O_2$, 383.2, m/z found 384.1 $[M+H]^+$.

$^1$H NMR (400 MHz, DMSO) δ 8.71 (s, 1H), 7.77-7.74 (m, 3H), 7.53-7.50 (m, 1H), 7.42-7.37 (m, 3H), 7.14-7.07 (m, 2H), 6.91 (d, J=8.0 Hz, 1H), 4.76 (t, J=8.0 Hz, 1H), 2.21 (s, 3H), 2.15-2.08 (m, 1H), 1.03 (d, J=8.0 Hz, 3H), 0.83 (d, J=8.0 Hz, 3H).

Example 14: Preparation of Compound 22

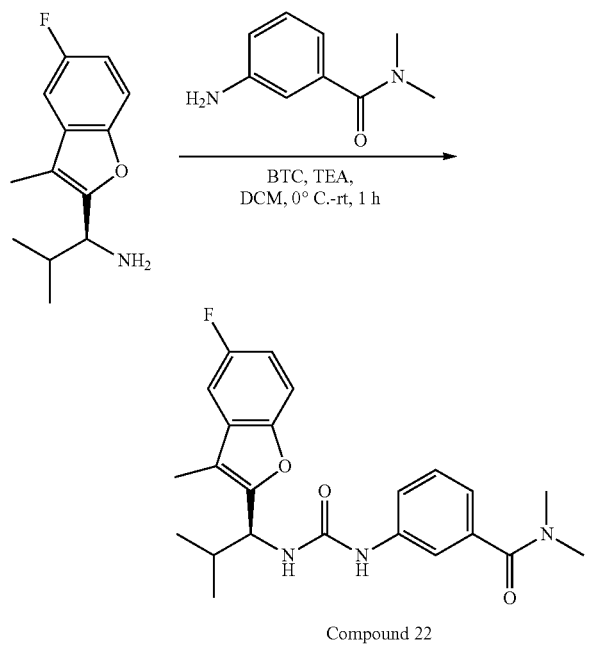

Compound 22

To a stirred solution of 3-amino-N,N-dimethylbenzamide (50 mg, 0.30 mmol) in anhydrous DCM (4 mL) were added TEA (246 mg, 2.4 mmol), triphosgene (71 mg, 0.24 mmol) at 0° C. After stirring at room temperature for 0.5 h, (S)-1-(5-fluoro-3-methylbenzofuran-2-yl)-2-methylpropan-1-amine (67 mg, 0.30 mmol) was added to the solution at 0° C. The reaction mixture was stirred at room temperature for 1 h. After completion, the reaction mixture was concentrated under reduced pressure to give a residue which was purified by prep-HPLC to give (S)-3-(3-(1-(5-fluoro-3-methylbenzofuran-2-yl)-2-methylpropyl)ureido)-N,N-dimethylbenzamide (36 mg, 26%) as white solid. MS (ESI): mass calcd. for C23H26FN3O3, 411.2, m/z found 412.2 $[M+H]^+$.

$^1$H NMR (400 MHz, DMSO) δ 8.60 (s, 1H), 7.50-7.53 (m, 1H), 7.48 (t, J=1.6 Hz, 1H), 7.37-7.38 (m, 1H), 7.32-7.22 (m, 2H), 7.06-7.12 (m, 1H), 6.85-6.90 (m, 2H), 4.75 (t, J=8.6 Hz, 1H), 2.95 (s, 3H), 2.87 (s, 3H), 2.20 (s, 3H), 2.07-2.16 (m, 1H), 1.02 (d, J=6.4 Hz, 3H), 0.82 (d, J=6.4 Hz, 3H).

Example 15: Preparation of Compound 23

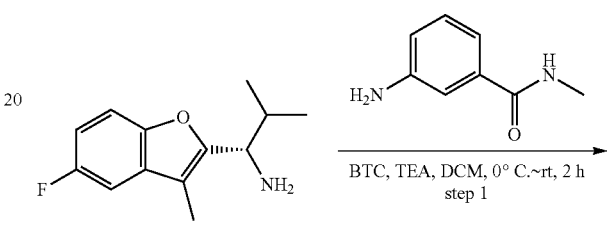

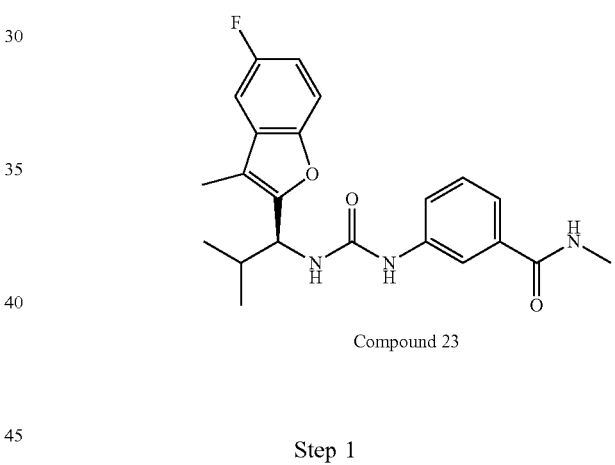

Compound 23

Step 1

To a stirred solution of (S)-1-(5-fluoro-3-methylbenzofuran-2-yl)-2-methylpropan-1-amine (Int-2) (30 mg, 0.14 mmol) and TEA (96 mg, 0.95 mmol) in DCM (3 mL) was added triphosgene (28 mg, 0.10 mmol) at 0° C. under $N_2$ atmosphere. After stirring at room temperature for 30 min, 3-amino-N-methylbenzamide (41 mg, 0.27 mmol) was added into the reaction mixture at 0° C. and the mixture was stirred at room temperature for 1 h. The mixture was concentrated under reduced pressure to give a residue which was purified by Prep-HPLC to afford (S)-3-(3-(1-(5-fluoro-3-methylbenzofuran-2-yl)-2-methylpropyl)ureido)-N-methylbenzamide (16 mg, 28%) as an off-white solid. MS (ESI): mass calcd. for $C_{22}H_{24}FN_3O_3$, 397.2, m/z found 398.1 $[M+H]^+$.

$^1$H NMR (400 MHz, DMSO) δ 8.62 (s, 1H), 8.32 (m, 1H), 7.79 (s, 1H), 7.50 (m, 2H), 7.41-7.22 (m, 3H), 7.09 (m, 1H), 6.84 (d, J=8.8 Hz, 1H), 4.76 (t, J=8.8 Hz, 1H), 2.75 (d, J=4.4 Hz, 3H), 2.21 (s, 3H), 2.12 (m, 1H), 1.03 (d, J=6.8 Hz, 3H), 0.83 (d, J=6.8 Hz, 3H).

Example 16: Preparation of Compound 24

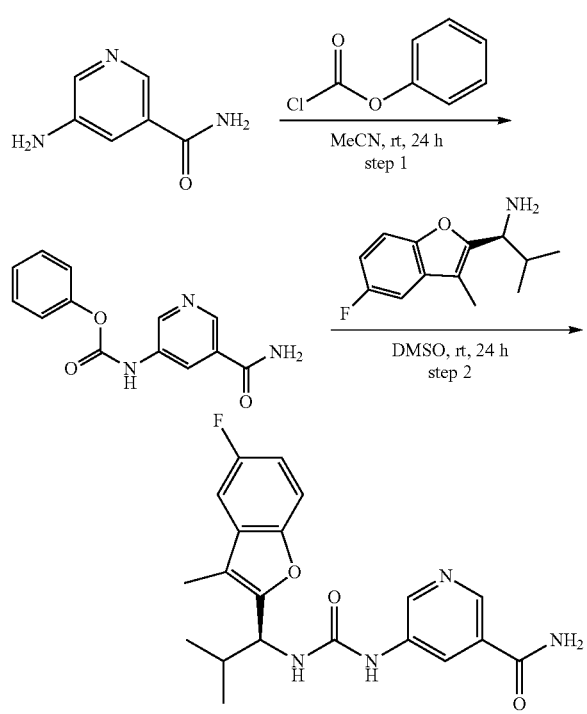

Compound 24

Step 1

To a stirred suspension of 5-aminonicotinamide (400 mg, 2.92 mmol) in anhydrous MeCN (40 mL) was added phenyl chloroformate (685 mg, 4.38 mmol). The reaction mixture was stirred at room temperature for 24 h. After completion, the reaction mixture was concentrated under reduced pressure. The residue was purified by flash silica gel column chromatography (DCM/MeOH=10/1) to give phenyl (5-carbamoylpyridin-3-yl) carbamate (230 mg, 30%) as a white solid. MS (ESI): mass calcd. for $C_{13}H_{11}N_3O_3$, 257.1, m/z found 258.1 $[M+H]^+$.

Step 2

To a stirred solution of phenyl (5-carbamoylpyridin-3-yl) carbamate (58 mg, 0.226 mmol) in DMSO (2 mL) was added (S)-1-(5-fluoro-3-methylbenzofuran-2-yl)-2-methyl-propan-1-amine (Int-1, 50 mg, 0.23 mmol). The reaction mixture was stirred at room temperature for 24 h. After completion, the reaction mixture was purification by prep-HPLC to give (S)-5-(3-(1-(5-fluoro-3-methylbenzofuran-2-yl)-2-methylpropyl)ureido) nicotinamide (10 mg, 11%) as white solid. MS (ESI): mass calcd. for $C_{20}H_{21}FN_4O_3$, 384.2, m/z found 385.2 $[M+H]^+$.

$^1$H NMR (400 MHz, DMSO) δ 8.92 (s, 1H), 8.65 (d, J=2.4 Hz, 1H), 8.59 (d, J=2.4 Hz, 1H), 8.29 (t, J=2.0 Hz, 1H), 8.11 (s, 1H), 7.57 (s, 1H), 7.53-7.50 (m, 1H), 7.39-7.36 (m, 1H), 7.12-7.07 (m, 2H), 4.76 (t, J=8.4 Hz, 1H), 2.21 (s, 3H), 2.18-2.09 (m, 1H), 1.04 (d, J=6.4 Hz, 3H), 0.83 (d, J=6.4 Hz, 3H).

Example 17: Preparation of Compound 25 and Compound 26

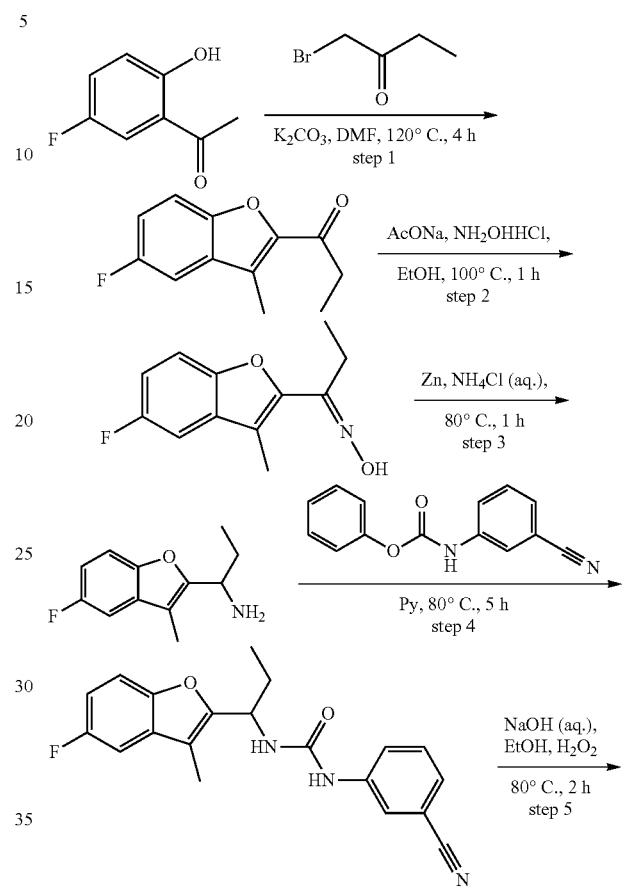

Compound 26

Compound 25

Step 1

To a solution of 1-(5-fluoro-2-hydroxyphenyl)ethanone (200 mg, 1.29 mmol) and $K_2CO_3$ (358 mg, 2.59 mmol) in DMF (10 mL) was added a solution of 1-bromobutan-2-one (215 mg, 1.42 mmol). The reaction mixture was stirred at 120° C. for 4 h with microwave. The residue was diluted with water 20 mL and extracted with EA (40 mL×3). The organic layers were collected, washed with brine, dried over $Na_2SO_4$ and evaporated to get 1-(5-fluoro-3-methylbenzofuran-2-yl)propan-1-one (300 mg, 112% crude) as a white solid. MS (ESI): mass calcd. for $C_{12}H_{11}FO_2$, 206.1, m/z found 207.1 $[M+H]^+$.

Step 2

To a solution of 1-(5-fluoro-3-methylbenzofuran-2-yl)propan-1-one (300 mg, 1.45 mmol, crude from above step), NaOAc (596 mg, 7.26 mmol) and NH$_2$OH·HCl (500 mg, 7.26 mmol) in EtOH (10 mL) was stirred at 100° C. for 2 h. The residue was concentrated, diluted with water 20 mL and extracted with EA (40 mL×3). The organic layers were collected, washed with brine, dried over Na$_2$SO$_4$ and evaporated to get 1-(5-fluoro-3-methylbenzofuran-2-yl)propan-1-one oxime (300 mg, 93%) as a yellow solid. MS (ESI): mass calcd. for C$_{12}$H$_{12}$FNO$_2$, 221.1, m/z found 222.1 [M+H]$^+$.

Step 3

To a solution of 1-(5-fluoro-3-methylbenzofuran-2-yl)propan-1-one oxime (300 mg, 1.38 mmol), NH$_4$Cl[aq.] (10 mL) and Zn (452 mg, 6.91 mmol) in EtOH (10 mL) was stirred at 80° C. for 2 h. The residue was concentrated, diluted with water (20 mL) and extracted with EA (40 mL×3). The organic layers was collected, washed with brine, dried over Na$_2$SO$_4$ and evaporated to get 1-(5-fluoro-3-methylbenzofuran-2-yl)propan-1-amine (200 mg, 71%) as yellow oil. MS (ESI): mass calcd. for C$_{12}$H$_{14}$FNO, 207.1, m/z found 191.1[M−NH]$^+$.

Step 4

To a solution of 1-(5-fluoro-3-methylbenzofuran-2-yl)propan-1-amine (200 mg, 0.97 mmol) and phenyl N-(3-cyanophenyl)carbamate (238 mg, 099 mmol) in pyridine (10 mL) was stirred at 80° C. for 4 h. The residue was purified by Prep-HPLC with condition [Column: Xbridge prep c18 Sum OBD 19*150 mm, Condition: A/water (0.1% FA) B (Acetonitrile), 10-20% B in 8 min, hold at 100% B at for 2 min, back to 5% B with 0.5 min, stop at 13 min. Flow rate: 20 ml/min, Detector: 214/254] to get 1-(3-cyanophenyl)-3-(1-(5-fluoro-3-methylbenzofuran-2-yl)propyl)urea (25.2 mg, 8%) as a white solid. MS (ESI): mass calcd. for C$_{20}$H$_{18}$FN$_3$O$_2$, 351.1, m/z found 352.1[M+H]$^+$.

$^1$H NMR (400 MHz, DMSO-d6) δ 8.76 (s, 1H), 7.90 (s, 1H), 7.52-7.50 (m, 2H), 7.40-7.32 (m, 3H), 7.10-7.08 (m, 1H), 6.95 (d, J=8.0 Hz, 1H), 4.94-4.88 (m, 1H), 2.07 (s, 3H), 1.88-1.81 (m, 2H), 0.85 (t, J=7.2 Hz, 3H)

Step 5

To a solution of 1-(3-cyanophenyl)-3-[1-(5-fluoro-3-methyl-1-benzofuran-2-yl)propyl]urea (70 mg, 0.19 mmol) and Hydrogen peroxide (27 mg, 0.79 mmol) in EtOH (5 mL) stirred at 20° C. was added a solution of NaOH (12 mg, 0.29 mmol) in H$_2$O (5 mL) dropwise. The reaction mixture was stirred at 80° C. for 2 h. The residue was evaporated, diluted with water and extracted with EA. The organic layers was evaporated and purified by Prep-HPLC with condition [Column: Xbridge prep c18 5 um OBD 19*150 mm Condition: A water (0.1% FA) B (Acetonitrile) 10-20% B in 8 min, hold at 100% B at for 2 min, back to 5% B with 0.5 min, stop at 13 min. Flow rate: 20 ml/min Detector: 214/254] to get 3-(3-(1-(5-fluoro-3-methylbenzofuran-2-yl)propyl)ureido)benzamide (12.6 mg, 17%) as a white solid. MS (ESI): mass calcd. for C$_{20}$H$_{20}$FN$_3$O$_3$, 369.4, m/z found 370.1 [M+H]$^+$.

$^1$H NMR (400 MHz, DMSO-d$_6$) δ 8.51 (s, 1H), 7.78 (s, 1H), 7.73-7.69 (t, J=2.0 Hz, 1H), 7.51 (d, J=8.0 Hz, 2H), 7.38 (d, J=8.0 Hz, 2H), 7.25-7.2 (m, 2H), 7.15-7.07 (m, 1H), 6.78 (d, J=8.0 Hz, 1H), 4.98-4.94 (m, 1H), 2.50 (s, 3H), 1.89-1.84 (m, 2H), 0.88 (t, J=7.2 Hz, 3H).

Example 18: Preparation of Compound 27

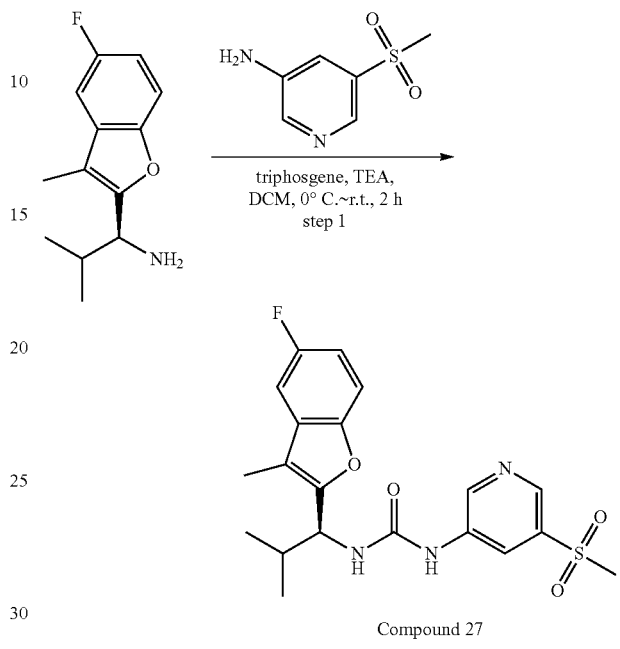

Compound 27

To a mixture of (1S)-1-(5-fluoro-3-methyl-1-benzofuran-2-yl)-2-methylpropan-1-amine (50 mg, 0.23 mmol), triethylamine (69 mg, 0.68 mmol) in DCM (10 mL) was added triphosgene (54 mg, 0.18 mmol) at 0° C. After stirring at 20° C. for 0.5 h, 5-methanesulfonylpyridin-3-amine (38.92 mg, 0.226 mmol) was added at 0° C. and the reaction mixture was stirred at 20° C. for 2 h. After completion, the reaction mixture was concentrated under reduced pressure to give the crude product which was purified by prep-HPLC to give (S)-1-(1-(5-fluoro-3-methylbenzofuran-2-yl)-2-methylpropyl)-3-(5-(methylsulfonyl)pyridin-3-yl)urea (23.2 mg, 24%) as a white solid. MS (ESI): mass calcd. for C$_{20}$H$_{22}$FN$_3$O$_4$S, 419.1, m/z found 420.1 [M+H]$^+$.

$^1$H NMR (400 MHz, DMSO) δ 9.12 (s, 1H), 8.66 (d, J=4.0 Hz, 1H), 8.60 (d, J=4.0 Hz, 1H), 8.51 (t, J=4.0 Hz, 1H), 7.54-7.50 (m, 1H), 7.40-7.37 (m, 1H), 7.20 (d, J=8.0 Hz, 1H), 7.13-7.08 (m, 1H), 4.76 (t, J=8.0 Hz, 1H), 3.27 (s, 3H), 2.22 (s, 3H), 2.18-2.12 (m, 1H), 1.04 (d, J=6.8 Hz, 3H), 0.83 (d, J=6.8 Hz, 3H).

Example 19: Preparation of Compound 28, Compound 29, and Compound 30

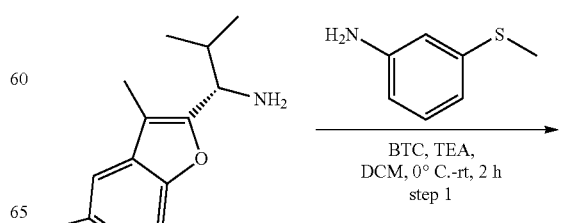

541
-continued

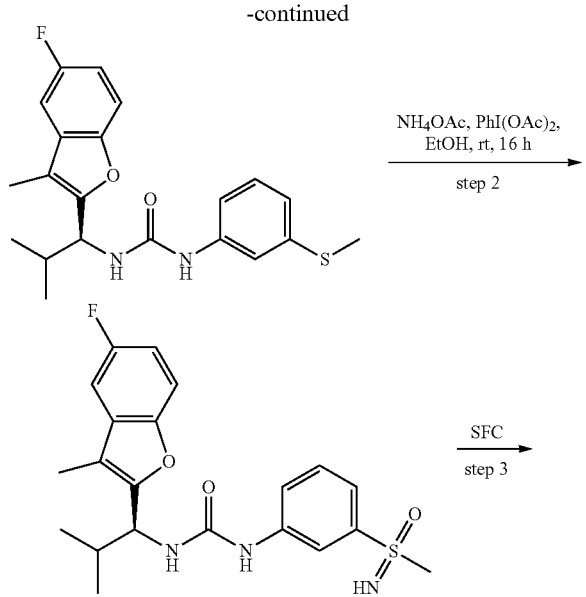

Compound 28

Compound 29
peak 1

Compound 30
peak 2

542

Step 1

To a mixture of (S)-1-(5-fluoro-3-methylbenzofuran-2-yl)-2-methylpropan-1-amine (Int-1) (159 mg, 0.72 mmol) and TEA (581 mg, 5.75 mmol) in DCM (5 mL) was added BTC (171 mg, 0.57 mmol) at 0° C. The reaction mixture was stirred for 30 min at room temperature. 3-(methylthio)aniline (100 mg, 0.72 mmol) was added to the reaction mixture at 0° C. The reaction mixture was stirred at room temperature for 2 h. The reaction mixture was concentrated to give a residue which was purified by flash silica gel column chromatography (PE:EA=3:1) to get 1-(S)-1-(1-(5-fluoro-3-methylbenzofuran-2-yl)-2-methylpropyl)-3-(3-(methylthio)phenyl)urea (250 mg, 90%) as yellow solid. MS (ESI): mass calcd. for $C_{21}H_{23}FN_2O_2S$, 386.1, m/z found 387.1 $[M+H]^+$.

Step 2

To a mixture of (S)-1-(1-(5-fluoro-3-methylbenzofuran-2-yl)-2-methylpropyl)-3-(3-(methylthio)phenyl)urea (250 mg, 0.65 mmol) and $NH_4OAc$ (150 mg, 1.94 mmol) in EtOH (10 mL). was added $PhI(OAc)_2$ (834 mg, 2.59 mmol). The reaction mixture was stirred at room temperature for 16 h. The reaction mixture was concentrated to give a residue which was purified by silica gel column chromatography (DCM:MeOH=10:1) to get 1-((S)-1-(5-fluoro-3-methylbenzofuran-2-yl)-2-methylpropyl)-3-(3-(S-methylsulfonimidoyl)phenyl)urea (120 mg, 44%) as white solid. MS (ESI): mass calcd. for $C_{21}H_{24}FN_3O_3S$, 417.1, m/z found 418.2 $[M+H]^+$.

$^1$H NMR (400 MHz, DMSO) δ 8.82 (s, 1H), 8.05 (d, J=1.6 Hz, 1H), 7.54-7.50 (m, 2H), 7.45-7.42 (m, 2H), 7.39-7.37 (m, 1H), 7.12-7.07 (m, 1H), 6.86 (d, J=8.8 Hz, 1H), 4.76 (t, J=8.8 Hz, 1H), 4.12 (s, 1H), 3.00 (s, 3H), 2.21 (s, 3H), 2.15-2.10 (m, 1H), 1.03 (d, J=6.8 Hz, 3H), 0.83 (d, J=6.8 Hz, 3H).

Example 20: Preparation of Compound 31 and Compound 32

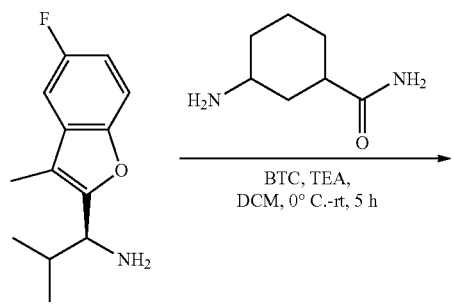

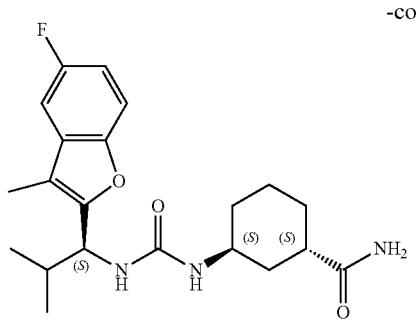

Compound 31

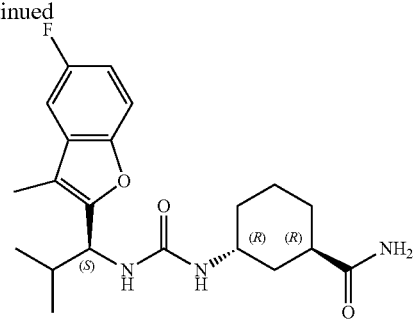

Compound 32

To a stirred solution of (S)-1-(5-fluoro-3-methylbenzofuran-2-yl)-2-methylpropan-1-amine (Int-1) (350 mg, 1.58 mmol) in anhydrous DCM (20 mL) was added TEA (1.28 g, 12.67 mmol), triphosgene (375 mg, 1.26 mmol) at 0° C. After stirring at room temperature for 0.5 h, 3-aminocyclohexane-1-carboxamide (225 mg, 1.58 mmol) was added to the solution at 0° C. The reaction mixture was stirred at room temperature for 5 h. After completion, the reaction mixture was concentrated under reduced pressure to give a residue which was purified by prep-HPLC to give 3-(3-((S)-1-(5-fluoro-3-methylbenzofuran-2-yl)-2-methylpropyl)ureido) cyclohexane-1-carboxamide (450 mg, 73%) as white solid. The obtained solid was separated by SFC with the following separation condition to give (1S,3S)-3-(3-((S)-1-(5-fluoro-3-methylbenzofuran-2-yl)-2-methylpropyl)ureido) cyclohexane-1-carboxamide (Peak 1, 180 mg, 29%) and (1R,3R)-3-(3-((S)-1-(5-fluoro-3-methylbenzofuran-2-yl)-2-methylpropyl)ureido)cyclohexane-1-carboxamide (Peak 2, 181 mg, 29%) as white solid.

Apparatus: SFC 80; Column: Daicel CHIRALCEL IE, 250 mm×30 mm I.D., 10 μm; Mobile phase: $CO_2$/MeOH [0.2% $NH_3$ (7M Solution in MeOH)]=70/30; Flow rate: 70 g/min; Wave length: UV 214 nm; Temperature: 35° C.

MS (ESI): mass calcd. For $C_{21}H_{28}FN_3O_3$, 389.2, m/z found 390.2 $[M+H]^+$.

Compound 31

$^1$H NMR (400 MHz, DMSO) δ 7.50-7.46 (m, 1H), 7.33-7.36 (m, 1H), 7.16 (s, 1H), 7.10-7.04 (m, 1H), 6.62 (s, 1H), 6.29 (d, J=8.8 Hz, 1H), 5.79 (d, J=8.0 Hz, 1H), 4.66 (t, J=8.8 Hz, 1H), 3.35-3.29 (m, 1H), 2.16 (s, 3H), 2.14-1.95 (m, 2H), 1.84-1.60 (m, 4H), 1.30-1.12 (m, 2H), 1.10-0.92 (m, 2H), 0.95 (d, J=8 Hz, 3H), 0.77 (d, J=8 Hz, 3H).

Compound 32

$^1$H NMR (400 MHz, DMSO) δ 7.50-7.47 (m, 1H), 7.37-7.34 (m, 1H), 7.20 (s, 1H), 7.10-7.05 (m, 1H), 6.66 (s, 1H), 6.29 (d, J=8.0 Hz, 1H), 5.79 (d, J=8.0 Hz, 1H), 4.66 (t, J=8.8 Hz, 1H), 3.32-3.24 (m, 1H), 2.16 (s, 3H), 2.14-1.96 (m, 2H), 1.87 (d, J=12.0 Hz, 1H), 1.70-1.62 (m, 3H), 1.23-085 (m, 4H), 0.95 (d, J=8 Hz, 3H), 0.77 (d, J=8 Hz, 3H).

Example 21: Preparation of Compound 33

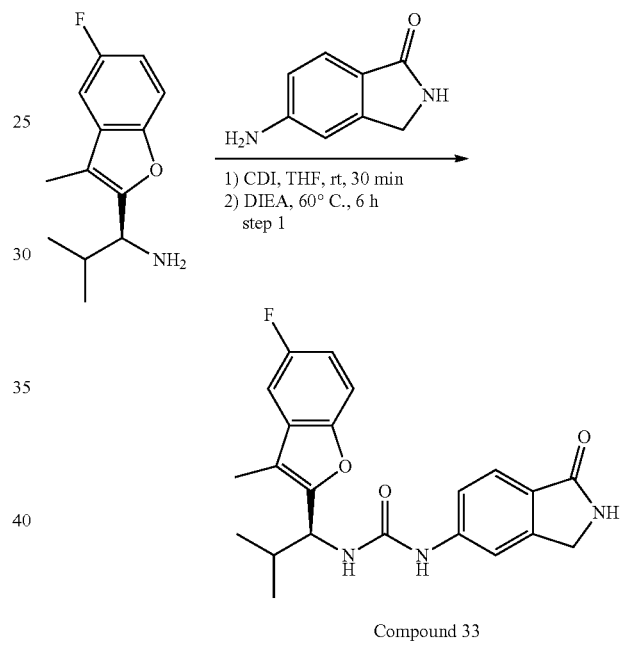

Compound 33

Step 1

A mixture of (1S)-1-(5-fluoro-3-methyl-1-benzofuran-2-yl)-2-methylpropan-1-amine (50 mg, 0.23 mmol) and CDI (40 mg, 0.25 mmol) in THF (5 mL) was stirred at 20° C. for 0.5 h. 5-amino-2,3-dihydroisoindol-1-one (33 mg, 0.23 mmol) and DIEA (88 mg, 0.68 mmol) were added into the reaction mixture and the mixture was stirred at 60° C. for 6 h and concentrated under reduced pressure to give a residue which was purified by prep-HPLC to give (S)-1-(1-(5-fluoro-3-methylbenzofuran-2-yl)-2-methylpropyl)-3-(1-oxoisoindolin-5-yl)urea (28.4 mg, 31%) as white solid. MS (ESI): mass calcd. for $C_{22}H_{22}FN_3O_3$, 395.2, m/z found 396.1 $[M+H]^+$. H NMR (400 MHz, DMSO) δ 8.88 (s, 1H), 8.25 (s, 1H), 7.73 (s, 1H), 7.53-7.48 (m, 2H), 7.39-7.36 (m, 1H), 7.30-7.27 (m, 1H), 7.12-7.07 (m, 1H), 6.99 (d, J=8.0 Hz, 1H), 4.76 (t, J=8.0 Hz, 1H), 4.27 (s, 2H), 2.21 (s, 3H), 2.16-2.08 (m, 1H), 1.03 (d, J=8.0 Hz, 3H), 0.83 (d, J=8.0 Hz, 3H).

Example 22: Preparation of Compound 34

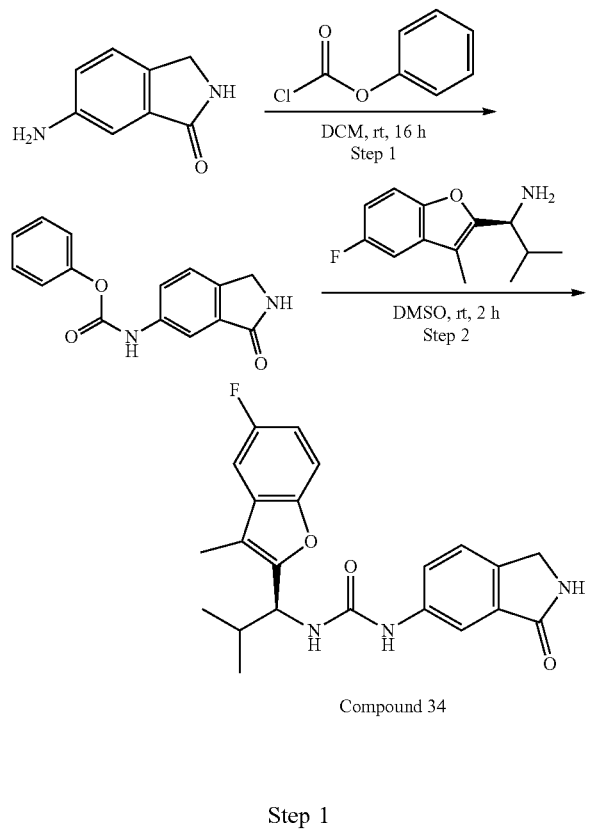

Compound 34

Step 1

To a stirred solution of 6-amino-2, 3-dihydroisoindol-1-one (300 mg, 2.02 mmol) in anhydrous DCM (30 mL) was added phenyl chloroformate (476 mg, 3.04 mmol). The reaction mixture was stirred at room temperature for 16 h. After completion, the reaction mixture was concentrated under reduced pressure and diluted with DCM (5 mL). The precipitate was filtered. The filter cake was dried in vacuum to give phenyl (3-oxoisoindolin-5-yl) carbamate (250 mg, 46%) as a white solid. MS (ESI): mass calcd. for $C_{15}H_{12}N_2O_3$, 268.1, m/z found 269.1 [M+H]+.

Step 2

To a stirred solution of phenyl (3-oxoisoindolin-5-yl) carbamate (49 mg, 0.181 mmol) in DMSO (2 mL) was added (S)-1-(5-fluoro-3-methylbenzofuran-2-yl)-2-methyl-propan-1-amine (Int-1, 40 mg, 0.18 mmol) at room temperature. The reaction mixture was stirred at room temperature for 2 h. After completion, the reaction mixture was purified by prep-HPLC to give (S)-1-(1-(5-fluoro-3-methylbenzofuran-2-yl)-2-methylpropyl)-3-(3-oxoisoindolin-5-yl)urea (40 mg, 56%) as a white solid. MS (ESI): mass calcd. for $C_{22}H_{22}FN_3O_3$, 395.2, m/z found 396.2 [M+H]+.

$^1$H NMR (400 MHz, DMSO) δ 8.68 (s, 1H), 8.47 (s, 1H), 7.81 (d, J=1.6 Hz, 1H), 7.53-7.49 (m, 1H), 7.44-7.35 (m, 3H), 7.12-7.07 (m, 1H), 6.85 (d, J=8.8 Hz, 1H), 4.77 (t, J=8.8 Hz, 1H), 4.26 (s, 2H), 2.22 (s, 3H), 2.18-2.05 (m, 1H), 1.03 (d, J=6.8 Hz, 3H), 0.83 (d, J=6.8 Hz, 3H).

Example 23: Preparation of Compound 35

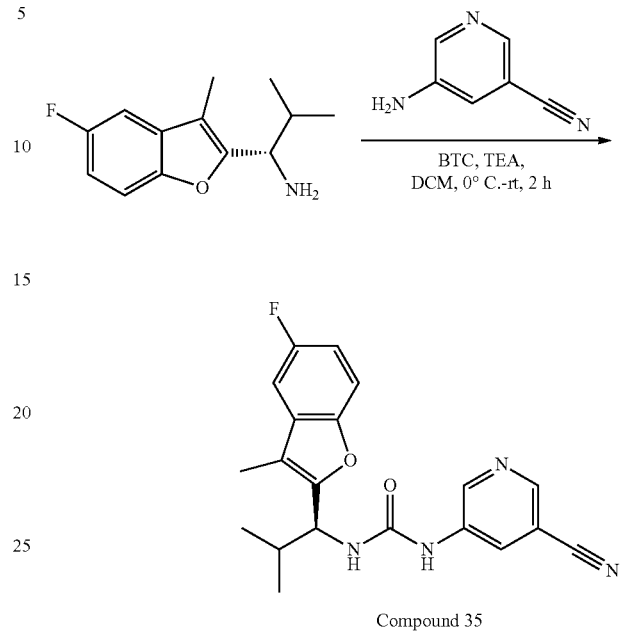

Compound 35

To a mixture of 5-aminonicotinonitrile (27 mg, 0.22 mmol) and TEA (128 mg, 1.26 mmol in DCM (5 mL) was added BTC (54 mg, 0.18 mmol) at 0° C. The reaction mixture was stirred for 1 h at room temperature. (S)-1-(5-fluoro-3-methylbenzofuran-2-yl)-2-methylpropan-1-amine (Int-2) (50 mg, 0.22 mmol) was added to the reaction mixture at 0° C. The reaction mixture was stirred for 2 h at room temperature. The reaction mixture was concentrated to give a residue which was purified by flash silica gel column chromatography (DCM:MeOH=10:1) to get (S)-1-(5-cyanopyridin-3-yl)-3-(1-(5-fluoro-3-methylbenzofuran-2-yl)-2-methylpropyl)urea (27.66 mg, 33%) as white solid. MS (ESI): mass calcd. for $C_{20}H_{19}FN_4O_2$, 366.1, m/z found 367.1 [M+H]+.

$^1$H NMR (400 MHz, DMSO) δ 8.99 (s, 1H), 8.71 (d, J=2.4 Hz, 1H), 8.53 (d, J=2.4 Hz, 1H), 8.35-8.31 (m, 1H), 7.53-7.50 (m, 1H), 7.40-7.37 (m, 1H), 7.21 (d, J=8.8 Hz, 1H), 7.13-7.07 (m, 1H), 4.75 (t, J=8.8 Hz, 1H), 2.21 (s, 3H), 2.17-2.11 (m, 1H), 1.03 (d, J=6.8 Hz, 3H), 0.82 (d, J=6.8 Hz, 3H).

Example 24: Preparation of Compound 36

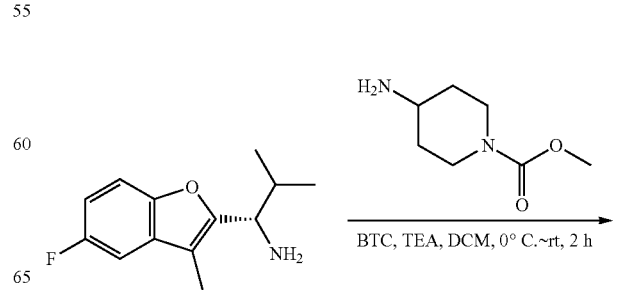

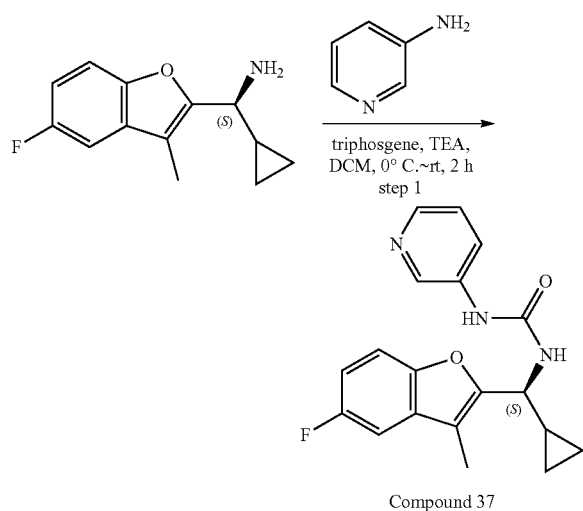

Compound 36

To a stirred solution of (S)-1-(5-fluoro-3-methylbenzofuran-2-yl)-2-methylpropan-1-amine (Int-2) (30 mg, 0.14 mmol) and TEA (96 mg, 0.95 mmol) in DCM (3 mL) was added triphosgene (28 mg, 0.10 mmol) at 0° C. under $N_2$ atmosphere. After stirring at room temperature for 30 min, methyl 4-aminopiperidine-1-carboxylate (43 mg, 0.27 mmol) was added into the reaction mixture at 0° C. and the mixture was stirred at room temperature for 1 h. After completion, the mixture was concentrated under reduced pressure to give a reside which was purified by Prep-HPLC to afford rel-methyl (S)-4-(3-(1-(5-fluoro-3-methylbenzofuran-2-yl)-2-methylpropyl)ureido)piperidine-1-carboxylate (25 mg, 45%) as off-white solid. MS (ESI): mass calcd. for $C_{21}H_{28}FN_3O_4$, 405.2, m/z found 428.1 $[M+Na]^+$.

$^1$H NMR (400 MHz, DMSO) δ=7.49 (m, 1H), 7.36 (d, J=6.8 Hz, 1H), 7.08 (m, 1H), 6.36 (d, J=7.2 Hz, 1H), 5.94 (m, 1H), 4.67 (m, 1H), 3.78 (m, 2H), 3.57 (m, 4H), 2.92 (m, 2H), 2.16 (s, 3H), 2.02 (m, 1H), 1.83-1.57 (m, 2H), 1.16 (m, 2H), 0.95 (d, J=6.8 Hz, 3H), 0.77 (6, J=6.8 Hz, 3H).

Example 25: Preparation of Compound 37

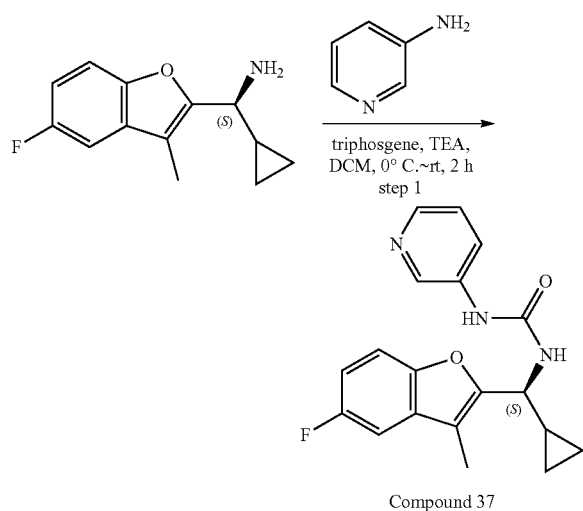

Compound 37

To a mixture of (S)-cyclopropyl(5-fluoro-3-methylbenzofuran-2-yl)methanamine (100 mg, 0.46 mmol) and TEA (373 mg, 3.68 mmol) in DCM (4 mL) was added triphosgene (110 mg, 0.37 mmol) at 0° C. and the reaction mixture was stirred for 1 h at room temperature. Then the reaction was cooled to 0° C., a solution of pyridin-3-amine (52 mg, 0.55 mmol) in DCM (1 mL) was added thereto. The reaction mixture was stirred at room temperature for another 1 h. LCMS indicated starting material consumed up and desired product was formed. The reaction mixture was concentrated to give a residue, which was purified by Prep-HPLC to give the (S)-1-(cyclopropyl(5-fluoro-3-methylbenzofuran-2-yl)methyl)-3-(pyridin-3-yl)urea (60 mg, 38.4%) as a white solid.

MS (ESI): mass calcd. for $C_{19}H_{18}FN_3O_2$, 339.14, m/z found 340.2 $[M+H]^+$.

$^1$H NMR (400 MHz, dmso) δ 8.62 (s, 1H), 8.48 (d, J=2.5 Hz, 1H), 8.10 (dd, J=4.6, 1.3 Hz, 1H), 7.88-7.79 (m, 1H), 7.59-7.47 (m, 1H), 7.38 (dd, J=8.8, 2.7 Hz, 1H), 7.28-7.17 (m, 1H), 7.14-7.03 (m, 2H), 4.47 (t, J=8.2 Hz, 1H), 2.22 (s, 3H), 1.57-1.27 (m, 1H), 0.67-0.31 (m, 4H).

Example 26: Preparation of Compound 38

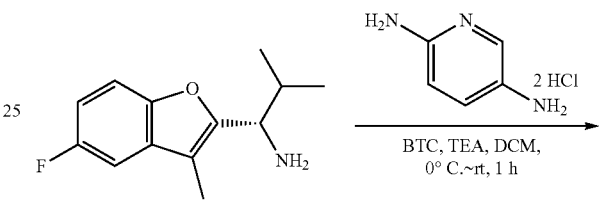

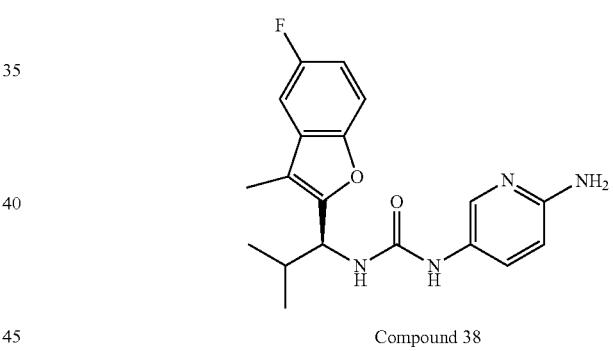

Compound 38

To a stirred solution of (S)-1-(5-fluoro-3-methylbenzofuran-2-yl)-2-methylpropan-1-amine (Int-2)(30 mg, 0.14 mmol) and TEA (96 mg, 0.95 mmol) in DCM (3 mL) was added triphosgene (28 mg, 0.10 mmol) at 0° C. under $N_2$ atmosphere. After stirring at room temperature for 30 min, 2,5-diaminopyridine dihydrochloride (49 mg, 0.27 mmol) was added into the reaction mixture at 0° C. under $N_2$ atmosphere. The mixture was stirred at room temperature for 1 h. After completion, the reaction mixture was concentrated under reduced pressure to give a residue which was purified by Prep-HPLC to afford =(S)-1-(6-aminopyridin-3-yl)-3-(1-(5-fluoro-3-methylbenzofuran-2-yl)-2-methylpropyl)urea (36 mg, 75%) as off-white solid. MS (ESI): mass calcd. for $C_{19}H_{21}FN_4O_2$, 356.2, m/z found 357.1 $[M+H]^+$.

$^1$H NMR (400 MHz, DMSO) δ 7.99 (s, 1H), 7.83 (d, J=2.4 Hz, 1H), 7.51 (dd, J=9.2, 4.4 Hz, 1H), 7.38 (m, 2H), 7.09 (m, 1H), 6.67 (d, J=8.8 Hz, 1H), 6.35 (d, J=8.8 Hz, 1H), 5.52 (s, 2H), 4.72 (t, J=8.4 Hz, 1H), 2.19 (s, 3H), 2.08 (m, 1H), 1.01 (d, J=6.8 Hz, 3H), 0.81 (d, J=6.8 Hz, 3H).

Example 27: Preparation of Compound 39

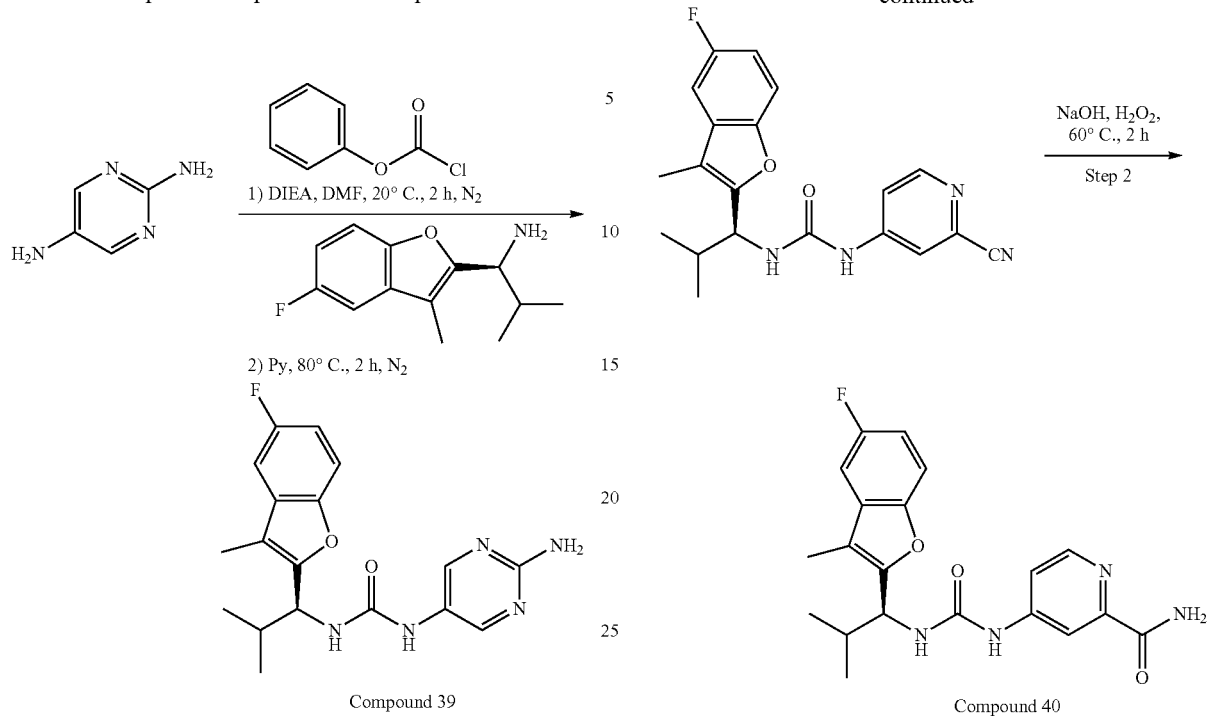

Compound 39

To a solution of pyrimidine-2,5-diamine (50 mg, 0.454 mmol) and DIEA (0.23 mL, 1.36 mmol) in DMF (10 mL) was added phenyl carbonochloridate (0.06 mL, 0.45 mmol). The reaction was stirred at 20° C. under $N_2$ for 2 h. To the above solution was added (S)-1-(5-fluoro-3-methylbenzofuran-2-yl)-2-methylpropan-1-amine (Int-2) (50 mg, 0.23 mmol) and pyridine (2 mL). The mixture was heated at 80° C. under $N_2$ for 2 h. After completion, the mixture solution was concentrated and treated with EA and $H_2O$. Collected the organic phase, dried over anhydrous $Na_2SO_4$, filtrated and concentrated. The residue was purified by Pre-HPLC to (S)-1-(2-aminopyrimidin-5-yl)-3-(1-(5-fluoro-3-methylbenzofuran-2-yl)-2-methylpropyl)urea (18.4 mg, 11.4%) as yellow solid.

HPLC condition: Column: Xbridge prep c18 5 um OBD 19*150 mm; Condition: A water (0.1% FA) B (Acetonitrile); 30-60% B in 8 min, hold at 100% B at for 2 min, back to 5% B with 0.5 min, stop at 13 min; Flow rate: 20 ml/min; Detector: 214/254.

MS (ESI): mass calcd. for $C_{20}H_{21}FN_4O_3$, 357.16, m/z found 358.2 [M+H]$^+$.

$^1$H NMR (400 MHz, DMSO) δ 8.19 (s, 2H), 8.03 (s, 1H), 7.52-7.49 (m, 1H), 7.39-7.36 (m, 1H), 7.12-7.07 (m, 1H), 6.86 (d, J=8.8 Hz, 1H), 6.27 (s, 2H), 4.72 (t, J=8.4 Hz, 1H), 2.19 (s, 3H), 2.13-2.08 (m, 1H), 1.01 (d, J=6.8 Hz, 3H), 0.81 (d, J=6.4 Hz, 3H).

Example 28: Preparation of Compound 40

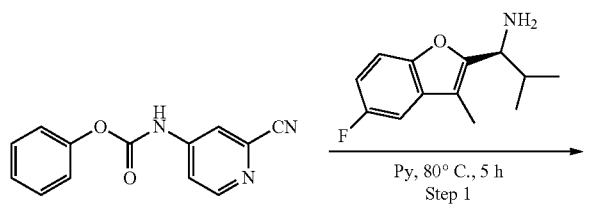

Compound 40

Step 1

To a solution of phenyl (2-cyanopyridin-4-yl)carbamate (54 mg, 0.226 mmol) in Py (5.0 mL) was added (S)-1-(5-fluoro-3-methylbenzofuran-2-yl)-2-methylpropan-1-amine (Int-2) (50 mg, 0.226 mmol). The reaction was stirred for 6 h at 80° C. After completion, the reaction mixture was concentrated under reduced pressure to give (S)-1-(2-cyanopyridin-4-yl)-3-(1-(5-fluoro-3-methylbenzofuran-2-yl)-2-methylpropyl) urea as a crude. MS (ESI): mass calcd. for $C_{20}H_{19}FN_4O_2$, 366.15, m/z found 367.2[M+H]$^+$.

Step 2

To a solution of (S)-1-(2-cyanopyridin-4-yl)-3-(1-(5-fluoro-3-methylbenzofuran-2-yl)-2-methylpropyl) urea) in EtOH (2 mL) was added NaOH (12 mg, 0.54 mmol) in $H_2O$ (0.5 ml) and $H_2O_2$ (100 mg, 30% wet). The reaction was stirred for 4 h at 60° C. The residue was purified by prep-HPLC with the following conditions: Column:AcqultyBEH 50*2.1 mm, 1.7 um; Mobile Phase A: $H_2O$ (0.05% TFA), Mobile Phase B: ACN (0.05% TFA); Flow rate: 20 mL/min; Gradient: 10-20% B in 8 min, hold at 100% B at for 2 min, back to 5% B with 0.5 min, stop at 13 min to (S)-4-(3-(1-(5-fluoro-3-methylbenzofuran-2-yl)-2-methylpropyl)ureido)picolinamide (52 mg, 50%) as white solid. MS (ESI): mass calcd. for $C_{20}H_{21}FN_4O_3$, 384.41, m/z found 385.16[M+H]$^+$.

$^1$H NMR (400 MHz, DMSO) δ 9.10 (s, 1H), 8.32 (d, J=5.6 Hz, 1H), 8.05-7.96 (m, 2H), 7.59-7.48 (m, 3H), 7.38 (d, J=8.8, 1H), 7.12-7.08 (m, 2H), 4.76 (t, J=8.6 Hz, 1H), 2.22 (s, 3H), 2.15-2.12 (m, 1H), 1.03 (d, J=6.8 Hz, 3H), 0.82 (d, J=6.8 Hz, 3H).

Example 29: Preparation of Compound 41

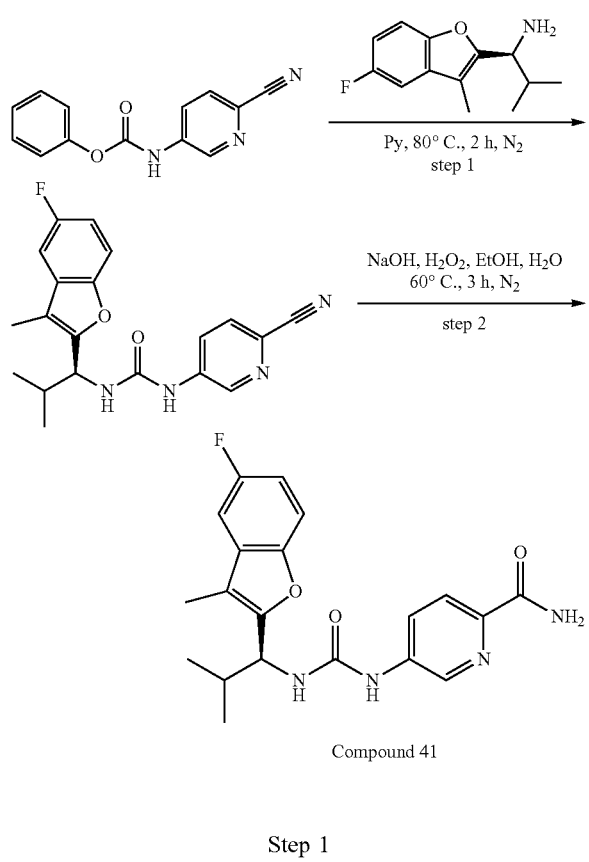

Compound 41

Step 1

A solution of phenyl (6-cyanopyridin-3-yl)carbamate (60 mg, 0.251 mmol) and (S)-1-(5-fluoro-3-methylbenzofuran-2-yl)-2-methylpropan-1-amine (Int-2) (50 mg, 0.228 mmol) in pyridine (10 mL) was stirred at 80° C. under $N_2$ atmosphere for 2 h. After completion, the mixture solution was concentrated to get (S)-1-(6-cyanopyridin-3-yl)-3-(1-(5-fluoro-3-methylbenzofuran-2-yl)-2-methylpropyl)urea (80 mg crude, 96.4%) as yellow oil without further purification. MS (ESI): mass calcd. for $C_{20}H_{19}FN_4O_2$, 366.15, m/z found 367.1 [M+H]$^+$.

Step 2

To a solution of (S)-1-(6-cyanopyridin-3-yl)-3-(1-(5-fluoro-3-methylbenzofuran-2-yl)-2-methylpropyl)urea (80 mg crude, 0.218 mmol) and NaOH (11 mg, 0.262 mmol) in EtOH (5 mL) and $H_2O$ (1 mL) was added $H_2O_2$ (30% w.t. in $H_2O$) (74 mg, 0.655 mmol). Then the reaction was stirred at 60° C. under $N_2$ atmosphere for 3 h. After completion, the mixture solution was concentrated and treated with EA and $H_2O$. Collected the organic phase, dried over anhydrous $Na_2SO_4$, filtrated and concentrated. The residue was by Pre-HPLC to (S)-5-(3-(1-(5-fluoro-3-methylbenzofuran-2-yl)-2-methylpropyl)ureido)picolinamide (23.9 mg, 28.5%) as white solid. HPLC condition: Column: Xbridge prep c18 5 um OBD 19*150 mm; Condition: A water (0.1% FA) B (Acetonitrile); 43-53% B in 8 min, hold at 100% B at for 2 min, back to 5% B with 0.5 min, stop at 13 min; Flow rate: 20 ml/min; Detector: 214/254. MS (ESI): mass calcd. for $C_{20}H_{21}FN_4O_3$, 384.16, m/z found 385.2 [M+H]$^+$.

$^1$H NMR (400 MHz, DMSO) δ 9.00 (s, 1H), 8.55 (d, J=2.0 Hz, 1H), 8.01-7.98 (m, 1H), 7.91-7.89 (d, J=8.0 Hz, 2H), 7.53-7.50 (m, 1H), 7.43-7.42 (m, 1H), 7.40-7.37 (m, 1H), 7.13-7.08 (m, 2H), 4.77 (t, J=8.4 Hz, 1H), 2.22 (s, 3H), 2.17-2.11 (m, 1H), 1.03 (d, J=6.8 Hz, 3H), 0.83 (d, J=6.4 Hz, 3H).

Example 30: Preparation of Compound 42

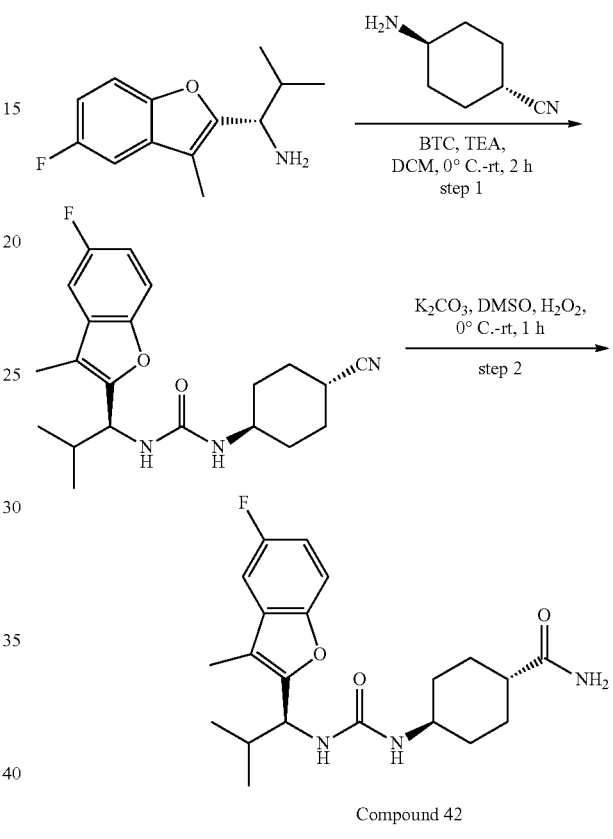

Compound 42

Step 1

To a mixture of (S)-1-(5-fluoro-3-methylbenzofuran-2-yl)-2-methylpropan-1-amine (Int-2) (108 mg, 0.49 mmol) and TEA (390 mg, 3.86 mmol) in DCM (5 mL) was added BTC (115 mg, 0.38 mmol) at 0° C. The reaction mixture was stirred at room temperature for 1 h. 4-aminocyclohexane-1-carbonitrile (60 mg, 0.48 mmol) was added to the reaction mixture at 0° C. The reaction mixture was stirred for 2 h at room temperature. The reaction mixture was diluted with water and extracted with DCM (50 mL×3). The combine organic layer was concentrated to give a residue which was purified by silica gel column chromatography (PE:EA=1:1) to get (S)-1-(4-cyanocyclohexyl)-3-(1-(5-fluoro-3-methylbenzofuran-2-yl)-2-methylpropyl)urea (160 mg, 88%) as yellow solid. MS (ESI): mass calcd. for $C_{21}H_{26}FN_3O_2$, 371.2, m/z found 372.2 [M+H]$^+$.

Step 2

To a mixture of (S)-1-(4-cyanocyclohexyl)-3-(1-(5-fluoro-3-methylbenzofuran-2-yl)-2-methylpropyl) urea (160 mg, 0.43 mmol) and $K_2CO_3$ (14 mg, 0.1 mmol) in DMSO/

H$_2$O$_2$ (5 mL, 4:1) at 0° C. The reaction mixture was stirred at room temperature for 1 h. The reaction mixture was diluted with water and extracted with EA three times. The combine organic layer was washed with brine. The organic layer was concentrated to give a residue which was purified by column chromatography (DCM:MeOH=10:1) to give (1R,4r)-4-(3-((R*)-1-(5-fluoro-3-methylbenzofuran-2-yl)-2-methylpropyl)ureido)cyclohexane-1-carboxamide (29 mg, 36%) as white solid. MS (ESI): mass calcd. for C$_{21}$H$_{28}$FN$_3$O$_3$, 389.2, m/z found 390.1 [M+H]$^+$.

$^1$H NMR (400 MHz, DMSO) δ 7.50-7.46 (m, 1H), 7.37-7.34 (m, 1H), 7.15 (s, 1H), 7.10-7.05 (m, 1H), 6.66 (s, 1H), 6.28 (d, J=8.8 Hz, 1H), 5.76 (d, J=7.6 Hz, 1H), 4.65 (t, J=8.8 Hz, 1H), 3.26-3.19 (m, 1H), 2.16 (s, 3H), 2.04-1.94 (m, 2H), 1.86 (d, J=10.8 Hz, 1H), 1.79-1.67 (m, 3H), 1.39-1.26 (m, 2H), 1.09-0.97 (m, 2H), 0.95 (d, J=6.8 Hz, 3H), 0.76 (d, J=6.8 Hz, 3H).

Example 31: Preparation of Compound 43

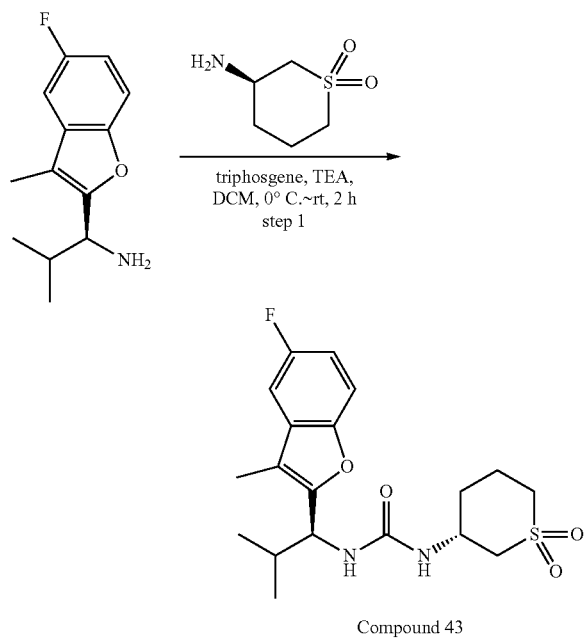

Compound 43

To a mixture of (1S)-1-(5-fluoro-3-methyl-1-benzofuran-2-yl)-2-methylpropan-1-amine (50 mg, 0.23 mmol) and triethylamine (69 mg, 0.68 mmol) in DCM (10 mL) was added triphosgene (54 mg, 0.18 mmol) at 0° C. After stirring at 20° C. for 0.5 h, (3R)-3-amino-1$1^{6}$-thiane-1,1-dione (34 mg, 0.23 mmol) was added at 0° C. and the reaction mixture was stirred at 20° C. for 2 h. After completion, the reaction mixture was concentrated under reduced pressure to give a residue which was purified by prep-HPLC to give 1-((R)-1,1-dioxidotetrahydro-2H-thiopyran-3-yl)-3-((S)-1-(5-fluoro-3-methylbenzofuran-2-yl)-2-methylpropyl)urea (61 mg, 68%) as a white solid. MS (ESI): mass calcd. for C$_{19}$H$_{25}$FN$_2$O$_4$S, 396.1, m/z found 397.1 [M+H]$^+$.

$^1$H NMR (400 MHz, DMSO) δ 7.50-7.47 (m, 1H), 7.37-7.35 (m, 1H), 7.11-7.05 (m, 1H), 6.64 (d, J=8.0 Hz, 1H), 6.14 (d, J=8.0 Hz, 1H), 4.67 (t, J=8.0 Hz, 1H), 3.95-3.93 (m, 1H), 3.16-3.13 (m, 1H), 3.00-2.93 (m, 3H), 2.16 (s, 3H), 2.04-1.99 (m, 2H), 1.82-1.73 (m, 2H), 1.44-1.41 (m, 1H), 0.95 (d, J=8.0 Hz, 3H), 0.77 (d, J=8.0 Hz, 3H).

Example 32: Preparation of Compound 44

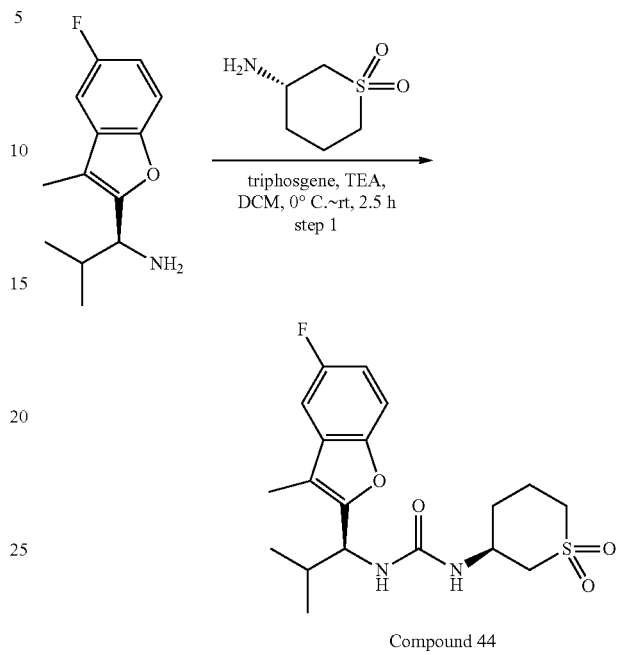

Compound 44

To a mixture of (1S)-1-(5-fluoro-3-methyl-1-benzofuran-2-yl)-2-methylpropan-1-amine (50 mg, 0.23 mmol), triethylamine (69 mg, 0.68 mmol) in DCM (10 mL) was added triphosgene (54 mg, 0.18 mmol) at 0° C. After stirring at 20° C. for 0.5 h, (S)-3-aminotetrahydro-2H-thiopyran 1,1-dioxide (34 mg, 0.23 mmol) was added into the reaction mixture at 0° C. and the mixture was stirred at 20° C. for 2 h. After completion, the reaction mixture was concentrated under reduced pressure to give the crude product which was purified by prep-HPLC to give 1-((S)-1,1-dioxidotetrahydro-2H-thiopyran-3-yl)-3-((S)-1-(5-fluoro-3-methylbenzofuran-2-yl)-2-methylpropyl)urea (10 mg, 11%) as white solid. MS (ESI): mass calcd. for C$_{19}$H$_{25}$FN$_2$O$_4$S, 396.1, m/z found 397.2 [M+H]$^+$.

$^1$H NMR (400 MHz, DMSO) δ 7.50-7.47 (m, 1H), 7.37-7.34 (m, 1H), 7.10-7.05 (m, 1H), 6.61 (d, J=8.0 Hz, 1H), 6.13 (d, J=8.0 Hz, 1H), 4.65 (t, J=8.0 Hz, 1H), 3.91-3.89 (m, 1H), 3.23-3.19 (m, 1H), 3.04-2.98 (m, 3H), 2.16 (s, 3H), 2.08-1.94 (m, 2H), 1.74-1.71 (m, 2H), 1.43-1.37 (m, 1H), 0.96 (d, J=8.0 Hz, 3H), 0.77 (d, J=8.0 Hz, 3H).

Example 33: Preparation of Compound 45

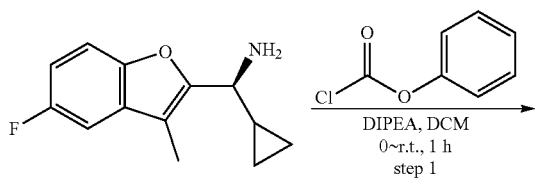

555

-continued

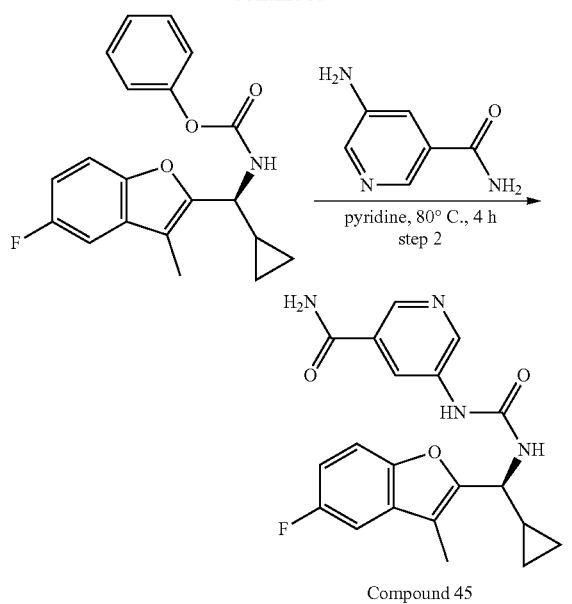

Compound 45

Step 1

To a mixture of (S)-cyclopropyl(5-fluoro-3-methylbenzofuran-2-yl)methanamine (100 mg, 0.46 mmol) and DIPEA (238 mg, 1.84 mmol) in DCM (5 mL), phenyl carbonochloridate (143 mg, 0.91 mmol) was added at 0° C. The reaction mixture was stirred at room temperature for 1 h under $N_2$. After completion, the reaction was diluted with $H_2O$ (15 mL), extracted with DCM (15 mL×3). The combined organic layers were washed with brine (20 mL), dried over $Na_2SO_4$, concentrated in vacuo to give the crude, which was purified by Prep-TLC (eluent: PE/EA=10/1) to give the phenyl (S)-(cyclopropyl(5-fluoro-3-methylbenzofuran-2-yl)methyl)carbamate (80 mg, yield: 51.3%) as a white solid. MS (ESI): mass calcd. for $C_{20}H_{18}FNO_3$, 339.13, m/z found 362.1 $[M+Na]^+$.

Step 2

A mixture of phenyl (S)-(cyclopropyl(5-fluoro-3-methylbenzofuran-2-yl)methyl)carbamate (50 mg, 0.15 mmol) and 5-aminonicotinamide (32 mg, 0.23 mmol) in pyridine (5 mL) was stirred at 80° C. for 4 h under $N_2$. After completion, the reaction was diluted with $H_2O$ (20 mL), extracted with DCM (25 mL×3). The combined organic layers were washed with brine (20 mL), dried over $Na_2SO_4$, concentrated in vacuo to give the crude, which was purified by Prep-TLC (eluent: DCM/MeOH=10/1) to give (S)-5-(3-(cyclopropyl(5-fluoro-3-methylbenzofuran-2-yl)methyl)ureido)nicotinamide (35 mg, yield: 61%) as a white solid. MS (ESI): mass calcd. $C_{20}H_{19}FN_4O_3$, 382.14, m/z found 383.2 $[M+H]^+$.

$^1$H NMR (400 MHz, dmso) δ 8.77 (s, 1H), 8.58 (dd, J=12.3, 2.2 Hz, 2H), 8.24 (t, J=2.2 Hz, 1H), 8.07 (s, 1H), 7.68-7.45 (m, 2H), 7.38 (dd, J=8.8, 2.7 Hz, 1H), 7.21-6.94 (m, 2H), 4.47 (t, J=8.2 Hz, 1H), 2.14 (s, 3H), 1.43-1.30 (m, 1H), 0.65-0.27 (m, 4H).

556

Example 34: Preparation of Compound 46

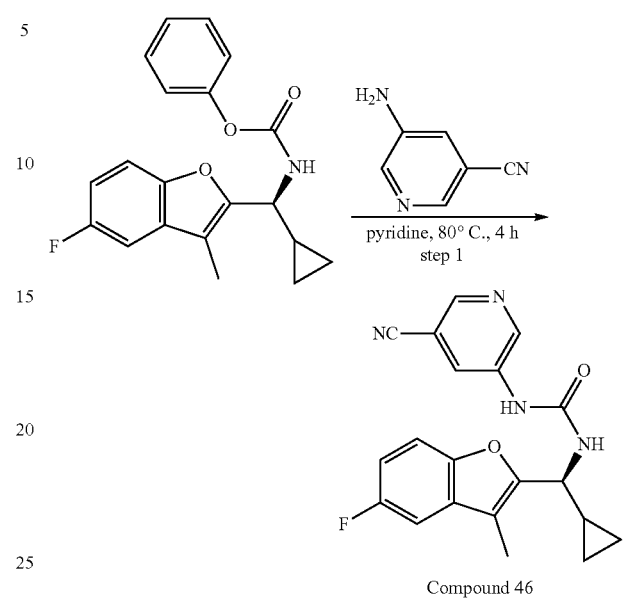

Compound 46

Step 1

A mixture of phenyl (S)-(cyclopropyl(5-fluoro-3-methylbenzofuran-2-yl)methyl)carbamate (50 mg, 0.15 mmol) and 5-aminonicotinonitrile (27 mg, 0.23 mmol) in pyridine (5 mL) was stirred at 80° C. for 4 h under $N_2$. After completion, the reaction was diluted with $H_2O$ (20 mL), extracted with DCM (25 mL×3). The combined organic layers were washed with brine (20 mL), dried over $Na_2SO_4$, concentrated in vacuo to give the crude, which was purified by Prep-TLC (eluent: DCM/MeOH=10/1) to give (S)-1-(5-cyanopyridin-3-yl)-3-(cyclopropyl(5-fluoro-3-methylbenzofuran-2-yl)methyl)urea (35 mg, yield: 61%) as a white solid. MS (ESI): mass calcd. C20H17FN4O2, 364.13, m/z found 365.1 $[M+H]^+$.

$^1$H NMR (400 MHz, dmso) δ 9.24 (s, 1H), 8.72 (d, J=2.5 Hz, 1H), 8.53 (d, J=1.8 Hz, 1H), 8.33-8.32 (m, 1H), 7.55-7.51 (m, 2H), 7.38 (dd, J=8.8, 2.7 Hz, 1H), 7.13-7.08 (m, 1H), 4.45 (t, J=8.3 Hz, 1H), 2.20 (s, 3H), 1.43-1.35 (m, 1H), 0.64-0.32 (m, 4H).

Example 35: Preparation of Compound 47

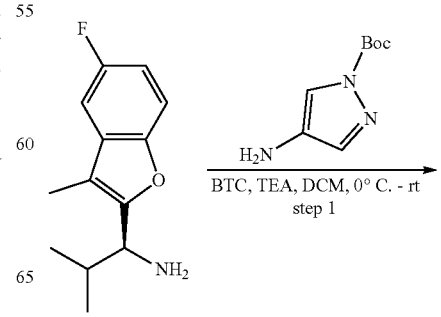

Example 36: Preparation of Compound 48

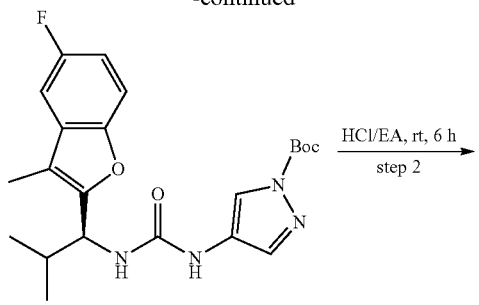

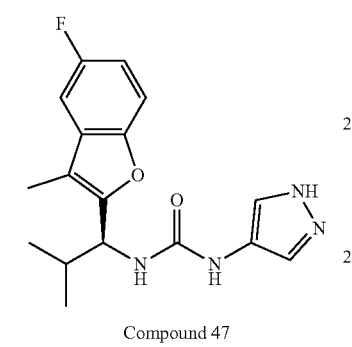

Compound 47

Step 1

To a mixture of (1S)-1-(5-fluoro-3-methyl-1-benzofuran-2-yl)-2-methylpropan-1-amine (50 mg, 0.23 mmol) and triethylamine (691 mg, 0.68 mmol) in DCM (5 mL) was added triphosgene (54 mg, 0.18 mmol) at 0° C. After stirring at 20° C. for 0.5 h, (4-aminopyrazol-1-yl) tert-butyl formate (42 mg, 0.23 mmol) was added at 0° C. and the reaction mixture was stirred at 20° C. for 2 h. After completion, the reaction mixture was diluted with water and extracted with DCM (50 mL×3). The organic layer was dried over anhydrous $Na_2SO_4$ and concentrated under reduced pressure to give a residue which was purified by Flash Chromatography to give tert-butyl (S)-4-(3-(1-(5-fluoro-3-methylbenzofuran-2-yl)-2-methylpropyl)ureido)-1H-pyrazole-1-carboxylate (50 mg, 46%) as yellow solid. MS (ESI): mass calcd. for $C_{22}H_{27}FN_4O_4$, 430.2, m/z found 431.2 $[M+H]^+$.

Step 2

A solution of tert-butyl [4-({[(1S)-1-(5-fluoro-3-methyl-1-benzofuran-2-yl)-2-methylpropyl]carbamoyl}amino)pyrazol-1-yl] formate (50 mg, 0.12 mmol) in HCl/EA (5 mL, 2M) was stirred at 20° C. for 16 h. The reaction mixture was concentrated under reduced pressure to give a residue which was purified by prep-HPLC to give (S)-1-(1-(5-fluoro-3-methylbenzofuran-2-yl)-2-methylpropyl)-3-(1H-pyrazol-4-yl)urea (30 mg, 79%) as white solid. MS (ESI): mass calcd. for $C_{17}H_{19}FN_4O_2$, 330.1, m/z found 331.1 $[M+H]^+$.

$^1$H NMR (400 MHz, DMSO) δ 8.09 (s, 1H), 7.52-7.48 (m, 3H), 7.38-7.35 (m, 1H), 7.11-7.06 (m, 1H), 6.67 (d, J=8.0 Hz, 1H), 4.72 (t, J=8.0 Hz, 1H), 2.18 (s, 3H), 2.11-2.06 (m, 1H), 1.00 (d, J=4.0 Hz, 3H), 0.80 (d, J=4.0 Hz, 3H).

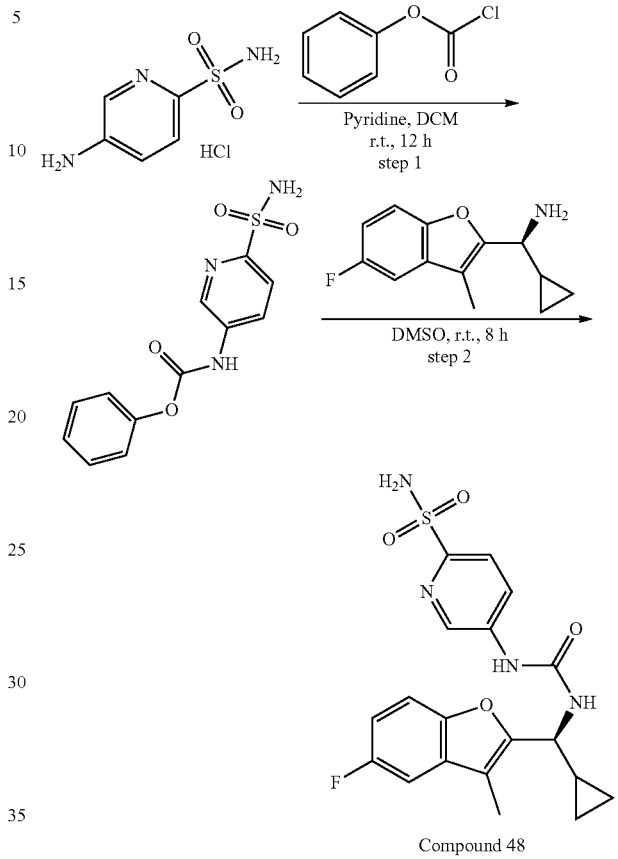

Compound 48

Step 1

To a mixture of 5-aminopyridine-2-sulfonamide (100 mg, 0.476 mmol) and pyridine (75.2 mg, 0.952 mmol) in DCM (10 mL), phenyl carbonochloridate (111.8 mg, 0.714 mmol) was added at 0° C. The reaction mixture was stirred at 25° C. for 1 h under $N_2$. After completion, the reaction was diluted with $H_2O$ (30 mL), extracted with DCM (50 mL×3). The combined organic layers were washed with brine (40 mL), dried over $Na_2SO_4$, concentrated in vacuo to give the crude, which was purified by Prep-TLC (eluent: DCM/MeOH=15/1) to give the phenyl (6-sulfamoylpyridin-3-yl)carbamate (50 mg, yield: 35.8%) as a white solid. MS (ESI): mass calcd. $C_{12}H_{11}N_3O_4S$, 293.05, m/z found 294.1 $[M+H]^+$.

Step 2

To a mixture of phenyl (6-sulfamoylpyridin-3-yl)carbamate (25 mg, 0.085 mmol), (S)-cyclopropyl(5-fluoro-3-methylbenzofuran-2-yl)methanamine (28 mg, 0.128 mmol) in DMSO (3 mL) at room temperature. The reaction mixture was stirred for 8 h under $N_2$. After completion, the reaction was diluted with $H_2O$ (10 mL), extracted with EtOAc (20 mL×3). The combined organic layers were washed with brine (40 mL), dried over $Na_2SO_4$, concentrated in vacuo to give the crude, which was purified by Prep-TLC (eluent: DCM/MeOH=15/1) give the (S)-5-(3-(cyclopropyl(5- fluoro-3-methylbenzofuran-2-yl)methyl)ureido)pyridine-2-sulfonamide (20 mg, yield: 56%) as a white solid. MS (ESI): mass calcd. $C_{19}H_{19}FN_4O_4S$, 418.11, m/z found 419.1 [M+H]$^+$.

$^1$H NMR (400 MHz, DMSO) δ 9.09 (s, 1H), 8.60 (d, J=2.4 Hz, 1H), 8.06-7.99 (m, 1H), 7.78 (d, J=8.6 Hz, 1H), 7.57-7.47 (m, 1H), 7.42-7.35 (m, 1H), 7.31-7.20 (m, 3H), 7.16-7.06 (m, 1H), 4.47 (t, J=8.2 Hz, 1H), 2.20 (s, 3H), 1.40-1.33 (m, 1H), 0.67-0.54 (m, 1H), 0.54-0.42 (m, 2H), 0.37-0.33 (m, 1H).

Example 37: Preparation of Compound 49 and Compound 50

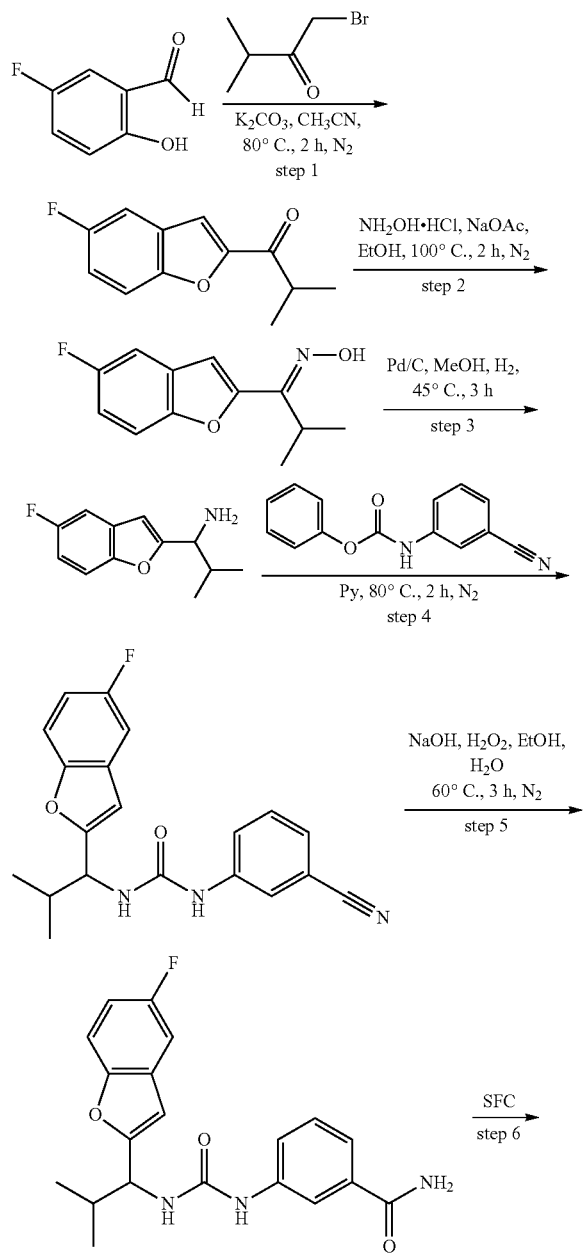

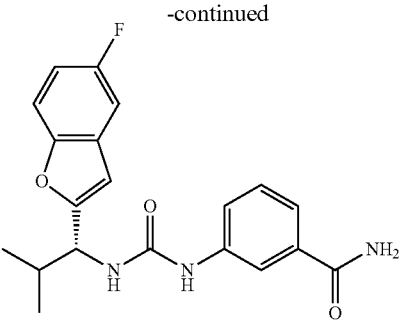

Compound 49

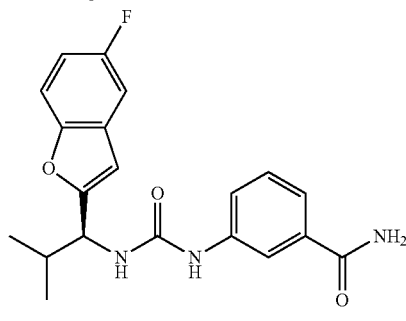

Compound 50

Step 1

To a solution of 5-fluoro-2-hydroxybenzaldehyde (1 g, 7.14 mmol) and 1-bromo-3-methylbutan-2-one (0.87 mL, 7.14 mmol) in CH$_3$CN (20 mL) was added K$_2$Cs$_3$ (2.96 g, 21.41 mmol). The reaction was stirred at 80° C. at N$_2$ atmosphere for 2 h. After completion, the mixture solution was treated with EA and H2E. Collected the organic phase, dried over anhydrous Na$_2$S4, filtrated and concentrated. The residue was by column chromatography (PE:EA=1:1) to get 1-(5-fluorobenzofuran-2-yl)-2-methylpropan-1-one (1.2 g, 81.6%) as white solid. MS (ESI): mass calcd. for $C_{12}H_{11}FO_2$, 206.07, m/z found 207.1 [M+H]$^+$.

Step 2

To a stirred solution of 1-(5-fluorobenzofuran-2-yl)-2-methylpropan-1-one (400 mg, 1.94 mmol), NH$_2$OH·HCl (674 mg, 9.70 mmol), NaOAc (796 mg, 9.70 mmol) in EtOH (10 mL) was stirred at 100° C. at N$_2$ atmosphere for 2 h. After completion, the reaction mixture was concentrated. The residue was treated with H$_2$O and EA. Collected the organic phase, dried over anhydrous Na$_2$SO$_4$, filtrated and concentrated to get (E)-1-(5-fluorobenzofuran-2-yl)-2-methylpropan-1-one oxime (390 mg, 90.9%) as colorless oil without further purification. MS (ESI): mass calcd. for $C_{12}H_{12}FNO_2$, 221.09, m/z found 222.1 [M+H]$^+$.

Step 3

To a stirred solution of (E)-1-(5-fluorobenzofuran-2-yl)-2-methylpropan-1-one oxime (390 mg, 1.76 mmol) and Pd/C (390 mg, 100% w.t.) in MeOH (20 mL) was stirred at 45° C. at H$_2$ atmosphere for 3 h. After completion, the reaction mixture was filtered and concentrated to get 1-(5-fluorobenzofuran-2-yl)-2-methylpropan-1-amine (350 mg, 95.9%) as yellow oil without further purification. MS (ESI): mass calcd. for $C_{12}H_{14}FNO$, 207.11, m/z found 191.1[M+H-17]$^+$.

Step 4

A solution of 1-(5-fluorobenzofuran-2-yl)-2-methylpropan-1-amine (200 mg, 0.965 mmol) and phenyl (3-cyanophenyl)carbamate (230 mg, 0.965 mmol) in pyridine (10 mL) was stirred at 80° C. under $N_2$ atmosphere for 2 h. After completion, the mixture solution was concentrated and treated with $H_2O$ and EA. Collected the organic phase, dried over anhydrous $Na_2SO_4$, filtrated and concentrated. The residue was purified by column chromatography (PE:EA=1:1) to get 1-(3-cyanophenyl)-3-(1-(5-fluorobenzofuran-2-yl)-2-methylpropyl)urea (260 mg, 76.7%) as colorless oil. MS (ESI): mass calcd. for $C_{20}H_{18}FN_3O_2$, 351.14, m/z found 352.1[M+H]$^+$.

Step 5

To a solution of 1-(3-cyanophenyl)-3-(1-(5-fluorobenzofuran-2-yl)-2-methylpropyl)urea (260 mg, 0.740 mmol) and NaOH (41 mg, 1.04 mmol) in EtOH (10 mL) and $H_2O$ (2 mL) was added $H_2O_2$ (30% w.t. in $H_2O$) (252 mg, 2.22 mmol). Then the reaction was stirred at 60° C. at $N_2$ atmosphere for 3 h. After completion, the mixture solution was concentrated and treated with EA and $H_2O$. Collected the organic phase, dried over anhydrous $Na_2SO_4$, filtrated and concentrated. The residue was purified by column chromatography (EA=100%) to get 3-(3-(1-(5-fluorobenzofuran-2-yl)-2-methylpropyl)ureido)benzamide (130 mg, 47.6%) as white solid. MS (ESI): mass calcd. for $C_{20}H_{20}FN_3O_3$, 369.15, m/z found 370.2 [M+H]$^+$.

Step 6

130 mg of racemic (3-(3-(1-(5-fluorobenzofuran-2-yl)-2-methylpropyl)ureido)benzamide) was separated by SFC to give (Compound 49, 34.6 mg) as a white solid and Compound 50, 49.6 mg) as a white solid.

Chiral separation condition: Apparatus: SFC 80; Column: Column: Daicel CHIRALCEL AD, 250 mm×30 mm I.D., 10 µm; Mobile phase: $CO_2$/MeOH [0.2% $NH_3$ (7M Solution in MeOH)]=80/20; Total Flow: 80 g/min.

Compound 49

MS (ESI): mass calcd. for $C_{20}H_{20}FN_3O_3$, 369.15, m/z found 370.2 [M+H]$^+$.
$^1$H NMR (400 MHz, DMSO-$d_6$) δ 8.71 (s, 1H), 7.88 (brs, 1H), 7.81 (t, J=1.6 Hz, 1H), 7.58-7.55 (m, 2H), 7.42-7.39 (m, 2H), 7.31-7.27 (m, 2H), 7.12-7.07 (m, 1H), 6.85 (d, J=8.8 Hz, 1H), 6.74 (s, 1H), 4.84-4.80 (m, 1H), 2.23-2.18 (m, 1H), 0.94-0.91 (m, 6H).

Compound 50

MS (ESI): mass calcd. for $C_{20}H_{20}FN_3O_3$, 369.15, m/z found 370.2 [M+H]$^+$. H NMR (400 MHz, DMSO-$d_6$) δ 8.74 (s, 1H), 7.88 (brs, 1H), 7.81 (t, J=1.6 Hz, 1H), 7.58-7.55 (m, 2H), 7.42-7.39 (m, 2H), 7.31-7.27 (m, 2H), 7.12-7.07 (m, 1H), 6.88 (d, J=9.2 Hz, 1H), 6.74 (s, 1H), 4.84-4.80 (m, 1H), 2.23-2.18 (m, 1H), 0.94-0.92 (m, 6H).

Example 38: Preparation of Compound 51 and Compound 52

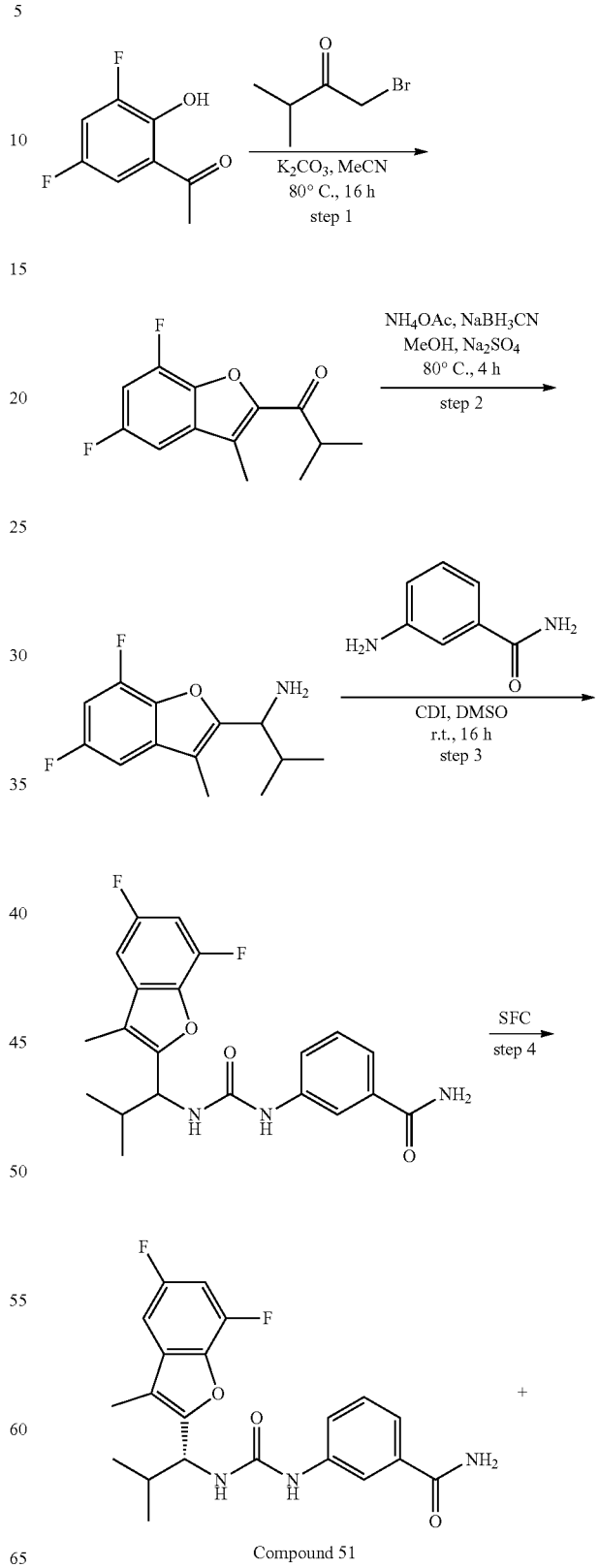

Compound 51

563

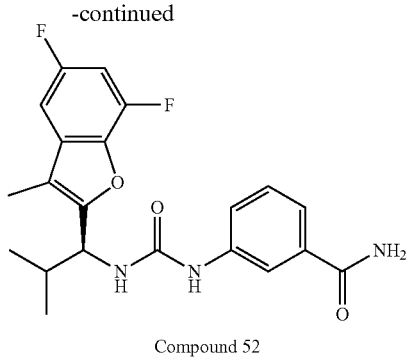

Compound 52

Step 1

To a mixture of 1-(3,5-difluoro-2-hydroxyphenyl)ethan-1-one (1.0 g, 5.8 mmol), 1-bromo-3-methylbutan-2-one (1.05 g, 6.4 mmol), and $K_2CO_3$ (962 mg, 7.0 mmol) in MeCN (25 mL) was stirred at 80° C. for 16 h. After cooled to room temperature, the resulting mixture was diluted with water (50 mL), extracted with EtOAc (50 mL×3). The combined organic layers were washed with brine (60 mL), dried over anhydrous $Na_2SO_4$. After filtration, the filtrate was concentrated under reduced pressure. The residue was purified by flash chromatography (PE/EtOAc from 10 to 50%) to afford 1-(5,7-difluoro-3-methylbenzofuran-2-yl)-2-methylpropan-1-one (650 mg, 47%) as a white solid. MS (ESI): mass calcd. for $C_{13}H_{12}F_2O_2$, 238.08, m/z found 239.1 $[M+H]^+$.

Step 2

To a mixture of 1-(5,7-difluoro-3-methylbenzofuran-2-yl)-2-methylpropan-1-one (300 mg, 1.26 mmol), $NH_4OAc$ (970.6 mg, 12.6 mmol) and $Na_2SO_4$ (54 mg, 0.38 mmol) in MeOH (6 mL) was stirred at room temperature for 30 min. Then the mixture was added $NaBH_3CN$ (83.3 mg, 1.32 mmol) and stirred at 80° C. for 4 h. After completion, the resulting mixture was concentrated under reduced pressure. The residue was purified by flash chromatography (DCM/MeOH from 1 to 5%) to afford 1-(5,7-difluoro-3-methylbenzofuran-2-yl)-2-methylpropan-1-amine (280 mg, 93%) as a white solid. MS (ESI): mass calcd. for $C_{13}H_{15}F_2NO$, 239.11, m/z found 223.11 $[M-NH_2]^+$.

Step 3

A solution of 3-aminobenzamide (100 mg, 0.74 mmol) and CDI (143.9 mg, 0.89 mmol) in DMSO (2 mL) was stirred at room temperature for 15 h. Then a solution of 1-(5,7-difluoro-3-methylbenzofuran-2-yl)-2-methylpropan-1-amine (193.6 mg, 0.81 mmol) in DMSO (1 mL) was added and stirred at room temperature for 1 h. After completion, the resulting mixture was diluted with water (25 mL), extracted with DCM (25 mL×3). The combined organic layers were washed with brine (30 mL), dried over anhydrous $Na_2SO_4$. After filtration, the filtrate was concentrated under reduced pressure. The residue was purified by flash chromatography (DCM/MeOH from 1 to 5%) to afford 3-(3-(1-(5,7-difluoro-3-methylbenzofuran-2-yl)-2-methylpropyl)ureido)benzamide (100 mg, 34%) as a white solid. MS (ESI): mass calcd. for $C_{21}H_{21}F_2N_3O_3$, 401.16, m/z found 402.2 $[M+H]^+$.

564

Step 4

Compound 6 was separated by SFC (Daicel CHIRALPAK IB-N, 250×30 mm I.D., 10 μm 80/20 $CO_2$/MeOH [0.2% $NH_3$ (7M Solution in MeOH)], 70 g/min, 120 bar, 35° C.) to give two enantiomers: (R)-3-(3-(1-(5,7-difluoro-3-methylbenzofuran-2-yl)-2-methylpropyl)ureido)benzamide (Compound 51, 35 mg, 35%) as a white solid and (S)-3-(3-(1-(5,7-difluoro-3-methylbenzofuran-2-yl)-2-methylpropyl)ureido)benzamide (Compound 52, 35 mg, 35%) as a white solid respectively.

Compound 51

MS (ESI): mass calcd. for $C_{21}H_{21}F_2N_3O_3$, 401.16, m/z found 402.1 $[M+H]^+$.
$^1$H NMR (400 MHz, dmso) δ 8.56 (s, 1H), 7.86 (s, 1H), 7.78 (s, 1H), 7.53-7.51 (m, 1H), 7.38 (d, J=7.8 Hz, 1H), 7.33-7.21 (m, 4H), 6.91 (d, J=8.7 Hz, 1H), 4.78 (t, J=8.6 Hz, 1H), 2.23 (s, 3H), 2.18-2.12 (m, 1H), 1.03 (d, J=6.7 Hz, 3H), 0.83 (d, J=6.7 Hz, 3H).

Compound 52

P2: MS (ESI): mass calcd. for $C_{21}H_{21}F_2N_3O_3$, 401.16, m/z found 402.1 $[M+H]^+$.
P2: $^1$H NMR (400 MHz, dmso) δ 8.56 (s, 1H), 7.87 (s, 1H), 7.78 (s, 1H), 7.55-7.48 (m, 1H), 7.38 (d, J=7.8 Hz, 1H), 7.33-7.21 (m, 4H), 6.91 (d, J=8.8 Hz, 1H), 4.78 (t, J=8.6 Hz, 1H), 2.23 (s, 3H), 2.14-2.11 (m, 1H), 1.03 (d, J=6.7 Hz, 3H), 0.84 (d, J=6.7 Hz, 3H).

Example 39: Preparation of Compound 53 and Compound 54

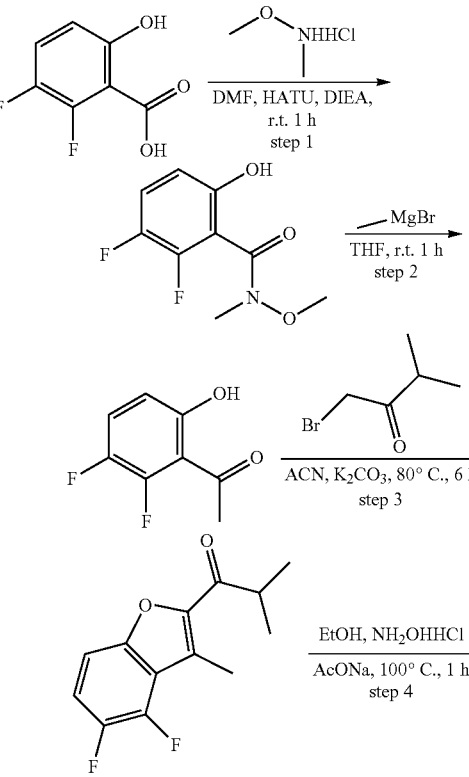

-continued

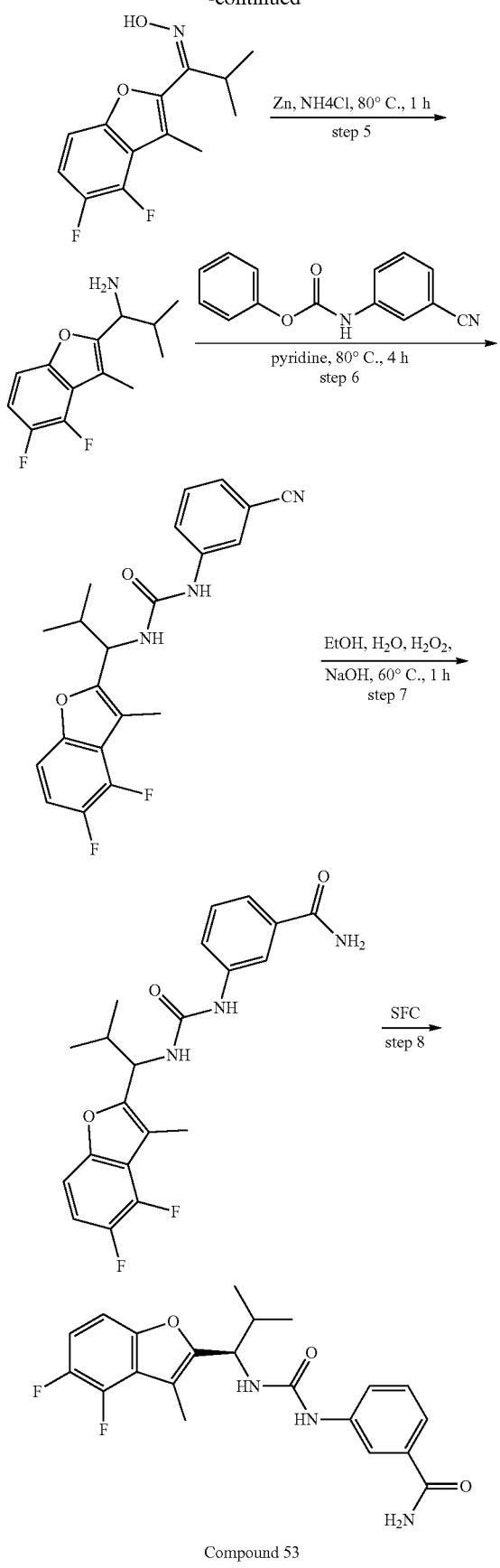

Compound 53

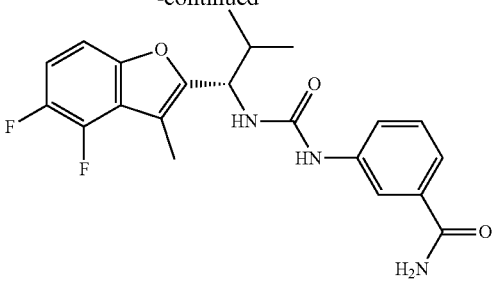

Compound 54

Step 1

To a solution of 2,3-difluoro-6-hydroxybenzoic acid (3.0 g, 17.24 mmol) in DMF (15 mL) was added N,O-Dimethylhydroxylamine hydrochloride (2.02 g, 20.69 mmol), HATU (8.52 g, 22.41 mmol) and DIEA (4.46 g, 34.48 mmol). The mixture was stirred at 25° C. for 1 h. After completion, the mixture was diluted with water, extracted with EA. The organic layer was washed with brine, dried over sodium sulfate, concentrated in vacuum. The residue was purified by column chromatography on silica gel (PE/EA from 10/1 to 5/1) to give 2,3-difluoro-6-hydroxy-N-methoxy-N-methylbenzamide (1.90 g, 50.8%) as white solid. MS (ESI): mass calcd. for $C_9H_9F_2NO_3$, 217.1, m/z found 218.1 $[M+H]^+$.

Step 2

To a solution of 2,3-difluoro-6-hydroxy-N-methoxy-N-methylbenzamide (1.9 g, 8.76 mmol) in THF (20 mL) was added bromo(methyl)magnesium (8.8 mL, 17.51 mmol). The mixture was stirred at 25° C. for 1 h. After completion (the reaction was monitored by TLC), the mixture was added to water, extracted with EA. The organic layer was washed with brine, dried over sodium sulfate, concentrated in vacuum to give 1-(2,3-difluoro-6-hydroxyphenyl)ethan-1-one (600 mg, 39.8%) as yellow solid.

Step 3

To a solution of 1-(2,3-difluoro-6-hydroxyphenyl)ethan-1-one (600 mg, 3.49 mmol) in ACN was added 1-bromo-3-methylbutan-2-one (1.15 g, 6.98 mmol) and $K_2CO_3$ (965 mg, 6.98 mmol). The mixture was stirred at 80° C. for 6 h. After completion, the mixture was added to water, extracted with EA. The organic layer was washed with brine, dried over sodium sulfate, concentrated in vacuum. The residue was purified by column chromatography on silica gel (PE/EA=10/1) to give 1-(4,5-difluoro-3-methylbenzofuran-2-yl)-2-methylpropan-1-one (230 mg, 27.7%) as yellow solid. MS (ESI): mass calcd. for $C_{13}H_{12}F_2O_2$, 238.1, m/z found 239.1 $[M+H]^+$.

Step 4

To a solution of 1-(4,5-difluoro-3-methylbenzofuran-2-yl)-2-methylpropan-1-one (230 mg, 0.97 mmol) in EtOH (5 mL) was added hydroxylamine hydrochloride (674.05 mg, 9.7 mmol) and AcONa (795 mg, 9.7 mmol). The mixture was stirred at 100° C. for 1 h. After completion, the mixture was added to water, extracted with EA. The organic layer was washed with brine, dried over sodium sulfate, concentrated in vacuum to give (Z)-1-(4,5-difluoro-3-methylbenzofuran-2-yl)-2-methylpropan-1-one oxime (203 mg, 82.7%) as white solid. MS (ESI): mass calcd. for $C_{13}H_{13}F_2NO_2$, 253.1, m/z found 254.1 [M+H]$^+$.

Step 5

To a solution of (Z)-1-(4,5-difluoro-3-methylbenzofuran-2-yl)-2-methylpropan-1-one oxime (203 mg, 0.80 mmol) in EtOH (5 mL) was added NH$_4$Cl (aq.) and Zn (523 mg, 8.0 mmol). The mixture was stirred at 80° C. for 1 h. After completion, the mixture was added to water, extracted with EA. The organic layer was washed with brine, dried over sodium sulfate, concentrated in vacuum to give 1-(4,5-difluoro-3-methylbenzofuran-2-yl)-2-methylpropan-1-amine (163 mg, 85.3%) as colorless oil. MS (ESI): mass calcd. for $C_{13}H_{15}F_2NO$, 239.1, m/z found 223.1 [M+H−17]$^+$.

Step 6

To a solution of 3-aminobenzonitrile (83 mg, 0.70 mmol) in pyridine (2 mL) was added phenyl carbonochloridate (109 mg, 0.70 mmol). The mixture was stirred at 25° C. for 1 h. Then 1-(4,5-difluoro-3-methylbenzofuran-2-yl)-2-methylpropan-1-amine (163 mg, 0.68 mmol) was added to the mixture; the mixture was stirred at 80° C. for 4 h. After completion, the mixture was added to water, extracted with EA. The organic layer was washed with brine, dried over sodium sulfate, concentrated in vacuum to give 1-(3-cyanophenyl)-3-(1-(4,5-difluoro-3-methylbenzofuran-2-yl)-2-methylpropyl)urea (182 mg, 70.3%) as yellow solid. MS (ESI): mass calcd. for $C_{21}H_{19}F_2N_3O_2$, 383.1, m/z found 384.1 [M+Na]$^+$.

Step 7

To a solution of 1-(3-cyanophenyl)-3-(1-(4,5-difluoro-3-methylbenzofuran-2-yl)-2-methylpropyl)urea (182 mg, 0.48 mmol) in EtOH (5 mL) was added H$_2$O$_2$ (1 mL) and NaOH (aq.) (3 mL, 4 M). The mixture was stirred at 60° C. for 1 h. After completion, the mixture was added to water, extracted with EA. The organic layer was washed with Na$_2$SO$_3$ (aq.) and brine, dried over sodium sulfate, concentrated in vacuum. The residue was purified by column chromatography on silica gel (DCM/MeOH from 100/1 to 20/1) to give 3-(3-(1-(4,5-difluoro-3-methylbenzofuran-2-yl)-2-methylpropyl)ureido)benzamide (120 mg, 62.3%) as white solid.

Step 8

100 mg of racemic was separated by SFC to give (Compound 53, 42.8 mg) as a white solid and (Compound 54), 45.1 mg) as a white solid.
Chiral separation condition: Apparatus: SFC 150; Column: REGIS (S,S)-Whelk O1, 250 mm×30 mm I.D., 10 μm; Mobile phase: CO$_2$/MeOH[0.2% NH$_3$ (7M Solution in MeOH)]=55/45; Flow rate: 80 g/min; Wavelength: UV 214 nm; Temperature: 35° C.

Compound 53

MS (ESI): mass calcd. for $C_{21}H_{21}F_2N_3O_3$, 401.1, m/z found 402.1 [M+H]$^+$.
$^1$H NMR (400 MHz, DMSO) δ 8.61 (d, J=14 Hz, 1H), 7.86 (s, 1H), 7.80-7.69 (m, 2H), 7.66-7.62 (m, 1H), 7.55-7.47 (m, 1H), 7.37 (d, J=7.6 Hz, 1H), 7.28-7.24 (m, 2H), 6.84 (d, J=8.4 Hz, 1H), 4.73 (t, J=8.4 Hz, 1H), 2.21 (s, 3H), 2.13-2.04 (m, 1H), 1.02 (d, J=6.4 Hz, 3H), 0.82 (d, J=6.8 Hz, 3H).

Compound 54

MS (ESI): mass calcd. for $C_{21}H_{21}F_2N_3O_3$, 401.1, m/z found 402.1 [M+H]$^+$.
$^1$H NMR (400 MHz, DMSO) δ 8.59 (d, J=13.6 Hz, 1H), 7.86 (s, 1H), 7.82-7.71 (m, 2H), 7.66-7.62 (m, 1H), 7.55-7.47 (m, 1H), 7.37 (d, J=7.6 Hz, 1H), 7.28-7.24 (m, 2H), 6.82 (d, J=8.4 Hz, 1H), 4.73 (t, J=8.4 Hz, 1H), 2.21 (s, 3H), 2.15-2.06 (m, 1H), 1.02 (d, J=6.8 Hz, 3H), 0.82 (d, J=6.8 Hz, 3H).

Example 40: Preparation of Compound 55

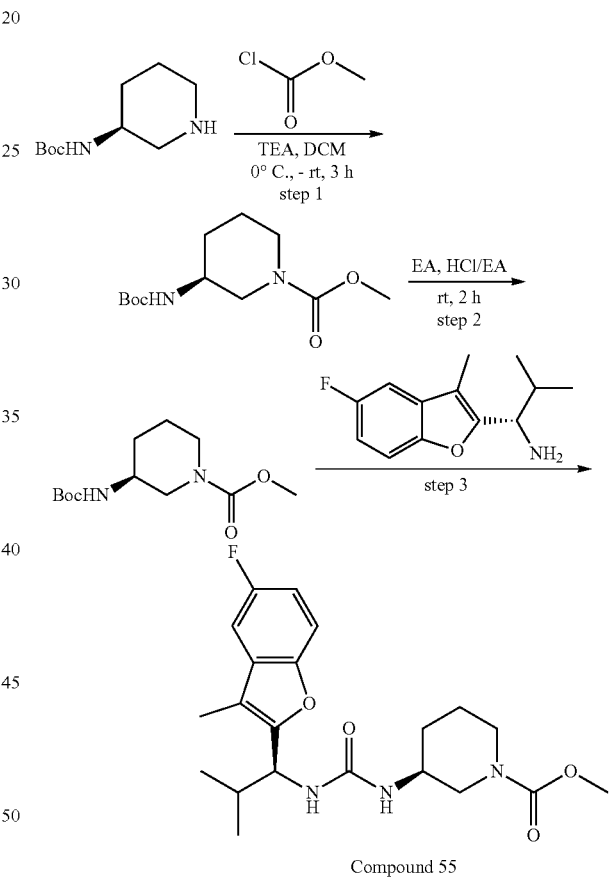

Compound 55

Step 1

To a solution of tert-butyl (S)-piperidin-3-ylcarbamate (5.0 g, 25.0 mmol), TEA (7.6 g, 75.0 mmol) in DCM (100 mL) was added methyl carbonochloridate (4.7 g, 50 mmol) at 0° C. The reaction mixture was stirred at room temperature for 3 h. After reaction, the reaction mixture was quenched with ice water (200 mL) and the organic layer was separated and dried with Na$_2$SO$_4$. The organic layer was concentrated to give a residue which was purified by reverse phase column to give methyl (S)-3-((tert-butoxycarbonyl)amino) piperidine-1-carboxylate (3.5 g, 80%) as white solid.

MS (ESI): mass calcd. for $C_{12}H_{22}N_2O_4$, 258.1, m/z found 281.1 [M+23]+.

Step 2

To a solution of methyl (S)-3-((tert-butoxycarbonyl) amino) piperidine-1-carboxylate (160 mg, 0.62 mmol) in EA (2 mL) was added HCl-EA (6 mL) at room temperature. The reaction mixture was stirred at room temperature for 2 h. The reaction mixture was concentrated to give crude product methyl (S)-3-aminopiperidine-1-carboxylate (100 mg, 100%) as yellow solid. MS (ESI): mass calcd. for $C_7H_{14}N_2O_2$, 158.1, m/z found 159.2 [M+H]+.

Step 3

To a mixture of (S)-1-(5-fluoro-3-methylbenzofuran-2-yl)-2-methylpropan-1-amine (Int-1) (140 mg, 0.63 mmol) and TEA (511 mg, 5.05 mmol) in DCM (10 mL) was added BTC (150 mg, 0.50 mmol) at 0° C. The reaction mixture was stirred for 1 h at room temperature. Methyl (S)-3-aminopiperidine-1-carboxylate (100 mg, 0.63 mmol) was added to the reaction mixture at 0° C. The reaction mixture was stirred for 2 h at room temperature. The reaction mixture was concentrated to give a residue which was purified by Pre-HPLC to give methyl (S)-3-(3-((S)-1-(5-fluoro-3-methyl-benzofuran-2-yl)-2-methylpropyl)ureido)piperidine-1-carboxylate (135.08 mg, 52%) as white solid. MS (ESI): mass calcd. for $C_{21}H_{28}FN_3O_4$, 405.2, m/z found 428.2 [M+Na]+.

$^1$H NMR (400 MHz, DMSO) δ 7.50-7.47 (m, 1H), 7.37-7.34 (m, 1H), 7.10-7.05 (m, 1H), 6.42 (d, J=8.8 Hz, 1H), 5.99 (s, 1H), 4.67 (t, J=8.8 Hz, 1H), 3.76 (s, 1H), 3.58 (s, 3H), 3.49-3.36 (m, 2H), 3.16-3.04 (m, 2H), 2.16 (s, 3H), 2.05-1.98 (m, 1H), 1.70-1.66 (m, 1H), 1.61-1.51 (m, 1H), 1.38-1.33 (m, 2H), 0.96 (d, J=6.8 Hz, 3H), 0.78 (d, J=6.8 Hz, 3H).

Example 41: Preparation of Compound 56

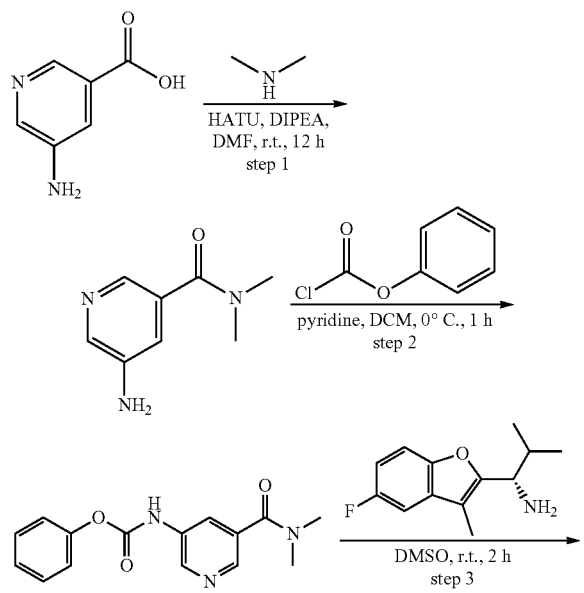

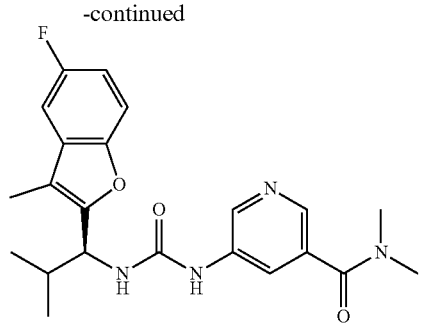

Compound 56

Step 1

To a mixture of 5-aminonicotinic acid (0.77 g, 5.6 mmol), dimethylamine (5.6 mL, 11.2 mmol, 2 M solution THF), and DIPEA (3.6 g, 28.0 mmol) in DMF (35 mL) was added HATU (2.55 g, 6.72 mmol) at room temperature. The reaction mixture was stirred at room temperature for 12 h under $N_2$. After completion, the reaction was diluted with $H_2O$ (30 mL), extracted with EtOAc (50 mL×3). The combined organic layers were washed with brine (40 mL), dried over $Na_2SO_4$, concentrated in vacuo to give the crude, which was purified with silica gel column chromatography, eluting with a gradient of 0-14% of MeOH in DCM to give 5-amino-N,N-dimethylnicotinamide (540 mg, yield: 58.4%) as a yellow solid. MS (ESI): mass calcd. $C_8H_{11}N_3O$, 165.09, m/z found 166.2 [M+H]+.

Step 2

To a mixture of 5-amino-N,N-dimethylnicotinamide (50 mg, 0.3 mmol) and pyridine (47.4 mg, 0.6 mmol) in DCM (5 mL) was added phenyl carbonochloridate (52 mg, 0.33 mmol) at 0° C. The resulting reaction mixture was stirred at 0° C. for 1 h under $N_2$. After completion, the reaction was diluted with $H_2O$ (30 mL), extracted with EtOAc (50 mL×3). The combined organic layers were washed with brine (40 mL), dried over $Na_2SO_4$, concentrated in vacuo to give the crude, which was purified with Prep-TLC (eluent: DCM/MeOH=20/1) to give phenyl (5-(dimethylcarbamoyl) pyridin-3-yl)carbamate (35 mg, yield: 41%) as a white solid. MS (ESI): mass calcd. $C_{15}H_{15}N_3O_3$, 285.11, m/z found 286.2 [M+H]+.

Step 3

A solution of phenyl (5-(dimethylcarbamoyl)pyridin-3-yl)carbamate (35 mg, 0.28 mmol), (R)-1-(5-fluoro-3-methylbenzofuran-2-yl)-2-methylpropan-1-amine (Int-1) (73 mg, 0.33 mmol) in DMSO (5 mL) at room temperature for 2 h. After completion, the reaction was diluted with $H_2O$ (30 mL), extracted with EtOAc (40 mL×3). The combined organic layers were washed with brine (40 mL), dried over $Na_2SO_4$, concentrated in vacuo to give the crude, which was purified with Prep-TLC (eluent: DCM/MeOH=10/1) to give (S)-5-(3-(1-(5-fluoro-3-methylbenzofuran-2-yl)-2-methylpropyl)ureido)-N,N-dimethylnicotinamide (36 mg, yield: 31%) as a white solid. MS (ESI): mass calcd. $C_{22}H_{25}FN_4O_3$, 412.19, m/z found 413.2 [M+H]+.

$^1$H NMR (400 MHz, dmso) δ 8.77 (s, 1H), 8.47 (d, J=2.5 Hz, 1H), 8.13 (d, J=1.9 Hz, 1H), 7.97-7.94 (m, 1H), 7.51 (dd, J=8.9, 4.1 Hz, 1H), 7.38 (dd, J=8.8, 2.7 Hz, 1H), 7.13-7.04 (m, 2H), 4.75 (t, J=8.6 Hz, 1H), 2.98 (s, 3H), 2.89 (s, 3H), 2.20 (s, 3H), 2.16-2.10 (m, 1H), 1.03 (d, J=6.7 Hz, 3H), 0.82 (d, J=6.7 Hz, 3H).

Example 42: Preparation of Compound 57 and Compound 58

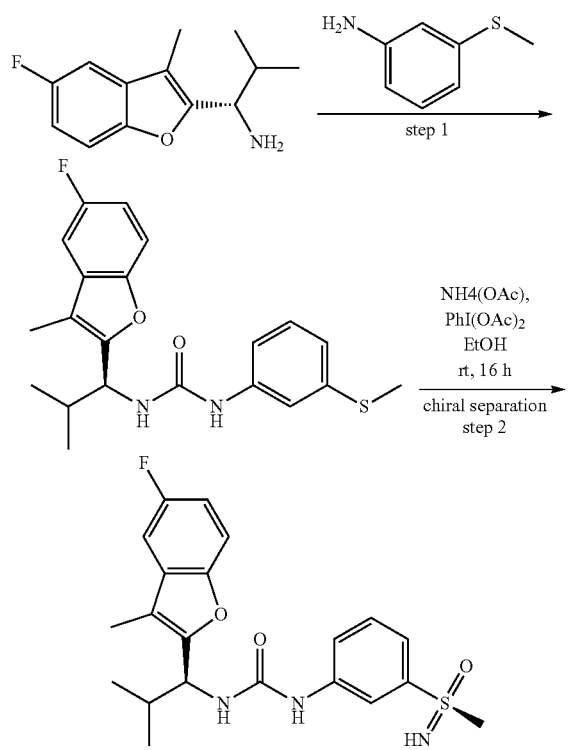

Step 1

To a solution of (S)-1-(5-fluoro-3-methylbenzofuran-2-yl)-2-methylpropan-1-amine (Int-2) (159 mg, 0.72 mmol) and TEA (581 mg, 5.75 mmol) dissolved in DCM (5 mL) was added BTC (171 mg, 0.57 mmol) at 0° C. The reaction mixture was stirred for 30 min at room temperature. 3-(methylthio) aniline (100 mg, 0.72 mmol) was added to the reaction mixture at 0° C. The reaction mixture was stirred at room temperature for 2 h. The reaction mixture was diluted with water and extracted with DCM. The combine organics was concentrated to give a residue which was purified by flash silica gel column chromatography (PE:EA=3:1) to get (S)-1-(1-(5-fluoro-3-methylbenzofuran-2-yl)-2-methylpropyl)-3-(3-(methylthio)phenyl)urea (250 mg, 90%) as yellow solid. MS (ESI): mass calcd. for $C_{21}H_{23}FN_2O_2S$, 386.1, m/z found 387.1 [M+H]$^+$.

Step 2

To a mixture of (S)-1-(1-(5-fluoro-3-methylbenzofuran-2-yl)-2-methylpropyl)-3-(3-(methylthio)phenyl)urea (250 mg, 0.65 mmol) and NH$_4$(OAc) (150 mg, 1.94 mmol) was added PhI(OAc)$_2$ (834 mg, 2.59 mmol) in EtOH (10 mL). The reaction mixture was stirred at room temperature under atmosphere overnight. The reaction mixture was concentrated to dryness in vacuo directly and purified by flash silica gel column chromatography (DCM:MeOH=10:1) to get 1-((S)-1-(5-fluoro-3-methylbenzofuran-2-yl)-2-methylpropyl)-3-(3-(S-methylsulfonimidoyl) phenyl) urea (120 mg, 44%) as a white solid. MS (ESI): mass calcd. for $C_{21}H_{24}FN_3O_3S$, 417.1, m/z found 418.2 [M+H]$^+$.

The product was separated by chiral HPLC separation to give two fractions:

Peak 1 (48.9 mg) and Peak 2 (51.2 mg) were assigned as Compound 57 and Compound 58 respectively.

Compound 57

$^1$H NMR (400 MHz, DMSO) δ 8.82 (s, 1H), 8.05-8.02 (m, 1H), 7.54-7.49 (m, 2H), 7.45-7.41 (m, 2H), 7.39-7.37 (m, 1H), 7.12-7.07 (m, 1H), 6.86 (d, J=8.8 Hz, 1H), 4.76 (t, J=8.8 Hz, 1H), 4.09 (s, 1H), 2.99 (d, J=0.8 Hz, 3H), 2.21 (s, 3H), 2.15-2.10 (m, 1H), 1.03 (d, J=6.8 Hz, 3H), 0.82 (d, J=6.8 Hz, 3H).

Compound 58

$^1$H NMR (400 MHz, DMSO) δ 8.81 (s, 1H), 8.04 (d, J=1.6 Hz, 1H), 7.54-7.49 (m, 2H), 7.45-7.42 (m, 2H), 7.39-7.36 (m, 1H), 7.12-7.07 (m, 1H), 6.86 (d, J=8.8 Hz, 1H), 4.76 (t, J=8.8 Hz, 1H), 4.10 (s, 1H), 3.00 (d, J=0.8 Hz, 3H), 2.21 (s, 3H), 2.15-2.10 (m, 1H), 1.03 (d, J=6.8 Hz, 3H), 0.82 (d, J=6.8 Hz, 3H).

Example 43: Preparation of Compound 59

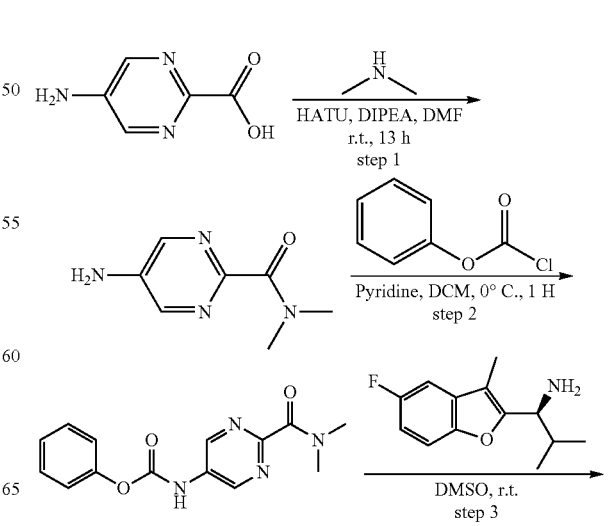

-continued

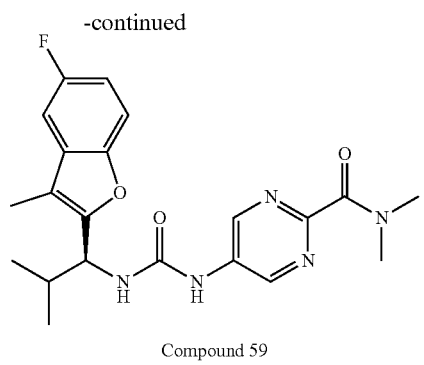

Compound 59

Step 1

A mixture of 5-aminopyrimidine-2-carboxylic acid (500 mg, 3.6 mmol), dimethylamine (9 mL, 18 mmol, 2 M solution in THF), HATU (2.05 g, 5.4 mmol) and DIPEA (1.9 mL, 10.8 mmol) in DMF (30 mL) was stirred at room temperature for 13 h. After completed, the reaction was concentrated in vacuo to give the crude, which was purified with silica gel column chromatography, eluting with a gradient of 0-10% of MeOH in DCM to give 5-amino-N, N-dimethylpyrimidine-2-carboxamide (290 mg, 48.5%) as a yellow oil. MS (ESI): mass calcd. for $C_7H_{10}N_4O$, 166.09, m/z found 167.1 $[M+H]^+$.

Step 2

To a mixture of 5-amino-N, N-dimethylpyrimidine-2-carboxamide (200 mg, 1.2 mmol) and Pyridine (189.6 mg, 2.4 mmol) in DCM (8 mL) was added phenyl carbonochloridate (188.4 mg, 1.2 mmol) at 0° C. The reaction mixture was stirred at 0° C. for 1 h. After completion, the resulting mixture was diluted with water (10 mL), extracted with DCM (10 mL×3). The combined organic layers were washed with brine (30 mL), dried over anhydrous $Na_2SO_4$. After filtration, the filtrate was concentrated under reduced pressure to afford phenyl (2-(dimethylcarbamoyl)pyrimidin-5-yl)carbamate (200 mg, 58%) as a light yellow solid. MS (ESI): mass calcd. for $C_{14}H_{14}N_4O_3$, 286.11, m/z found 286.12$[M+H]^+$.

Step 3

To a mixture of phenyl (2-(dimethylcarbamoyl)pyrimidin-5-yl)carbamate (100 mg, 0.35 mmol) and (S)-1-(5-fluoro-3-methylbenzofuran-2-yl)-2-methylpropan-1-amine (Int-2) (77.3 mg, 0.35 mmol) in DMSO (3 mL) was stirred at room temperature for 4 h. After completion, the resulting mixture was diluted with water (20 mL), extracted with DCM (20 mL×3). The combined organic layers were washed with brine (30 mL), dried over anhydrous $Na_2SO_4$. After filtration, the filtrate was concentrated under reduced pressure. The residue was purified by flash chromatography (DCM/MeOH from 1 to 8%) to afford (S)-5-(3-(1-(5-fluoro-3-methylbenzofuran-2-yl)-2-methylpropyl)ureido)-N,N-dimethylpyrimidine-2-carboxamide (40 mg, 28%) as a white solid. MS (ESI): mass calcd. for $C_{21}H_{24}FN_5O_3$, 413.19, m/z found 414.2 $[M+H]^+$.

$^1$H NMR (400 MHz, dmso) δ 8.89 (s, 1H), 8.86 (s, 2H), 7.51 (dd, J=8.9, 4.1 Hz, 1H), 7.38 (dd, J=8.8, 2.7 Hz, 1H), 7.23 (d, J=8.7 Hz, 1H), 7.13-7.07 (m, 1H), 4.76 (t, J=8.6 Hz, 1H), 2.97 (s, 3H), 2.77 (s, 3H), 2.21 (s, 3H), 2.17-2.10 (m, 1H), 1.03 (d, J=6.7 Hz, 3H), 0.82 (d, J=6.7 Hz, 3H).

Example 44: Preparation of Compound 60

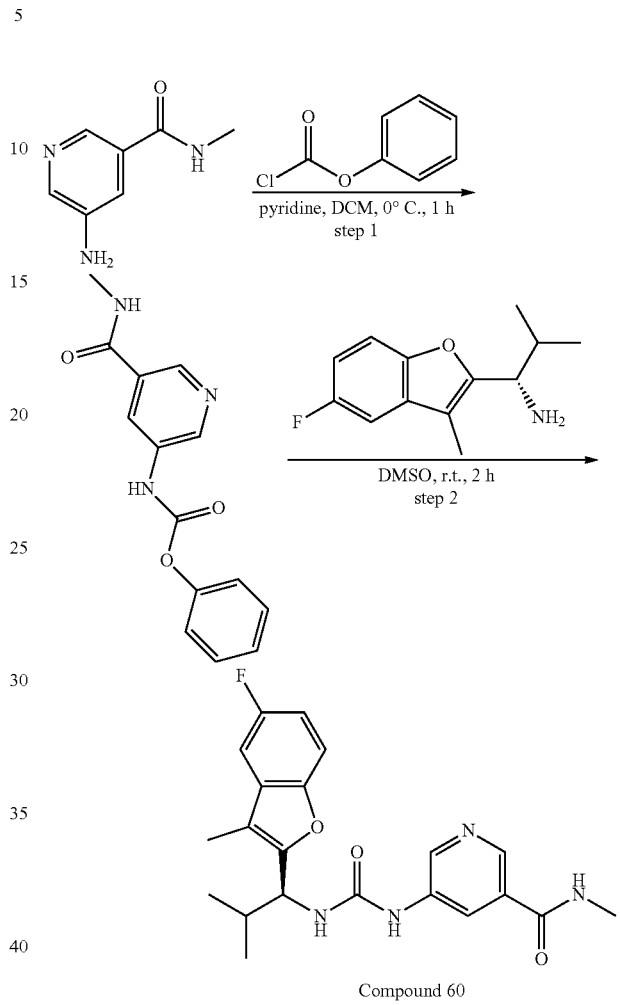

Compound 60

Step 1

To a mixture of 5-amino-N-methylnicotinamide (150 mg, 1 mmol) and pyridine (158 mg, 2 mmol) in DCM (15 mL) was added phenyl carbonochloridate (156 mg, 1 mmol) at 0° C. The resulting reaction mixture was stirred at 0° C. for 1 h under $N_2$. After completion, the reaction was diluted with $H_2O$ (30 mL), extracted with EtOAc (40 mL×3). The combined organic layers were washed with brine (40 mL), dried over $Na_2SO_4$, concentrated in vacuo to give the crude, which was purified with Prep-TLC (eluent: DCM/MeOH=20/1) to give phenyl (5-(methylcarbamoyl)pyridin-3-yl)carbamate (65 mg, yield: 22.8%) as a white solid. MS (ESI): mass calcd. $C_{14}H_{13}N_3O_3$, 271.10, m/z found 272.2 $[M+H]^+$.

Step 2

A solution of phenyl (5-(methylcarbamoyl)pyridin-3-yl) carbamate (40 mg, 0.15 mmol) (S)-1-(5-fluoro-3-methylbenzofuran-2-yl)-2-methylpropan-1-amine (Int-2) (73 mg, 0.33 mmol) in DMSO (5 mL) at room temperature for 5 h. After completion, the reaction was diluted with $H_2O$ (30 mL), extracted with EtOAc (40 mL×3). The combined organic layers were washed with brine (40 mL), dried over Na₂SO₄, concentrated in vacuo to give the crude, which was purified with Prep-TLC (eluent: DCM/MeOH=10/1) to give (S)-5-(3-(1-(5-fluoro-3-methylbenzofuran-2-yl)-2-methylpropyl)ureido)-N-methylnicotinamide (21 mg, yield: 35%) as a white solid. MS (ESI): mass calcd. $C_{21}H_{23}FN_4O_3$, 398.18, m/z found 399.1 $[M+H]^+$.

¹H NMR (400 MHz, dmso) δ 8.83 (s, 1H), 8.50-8.50 (m, 3H), 8.26 (t, J=2.2 Hz, 1H), 7.52 (dd, J=8.9, 4.1 Hz, 1H), 7.38 (dd, J=8.8, 2.7 Hz, 1H), 7.12-7.05 (m, 2H), 4.76 (t, J=8.6 Hz, 1H), 2.77 (d, J=4.5 Hz, 3H), 2.21 (s, 3H), 2.18-2.11 (m, 1H), 1.03 (d, J=6.7 Hz, 3H), 0.82 (d, J=6.7 Hz, 3H).

Example 45: Preparation of Compound 61

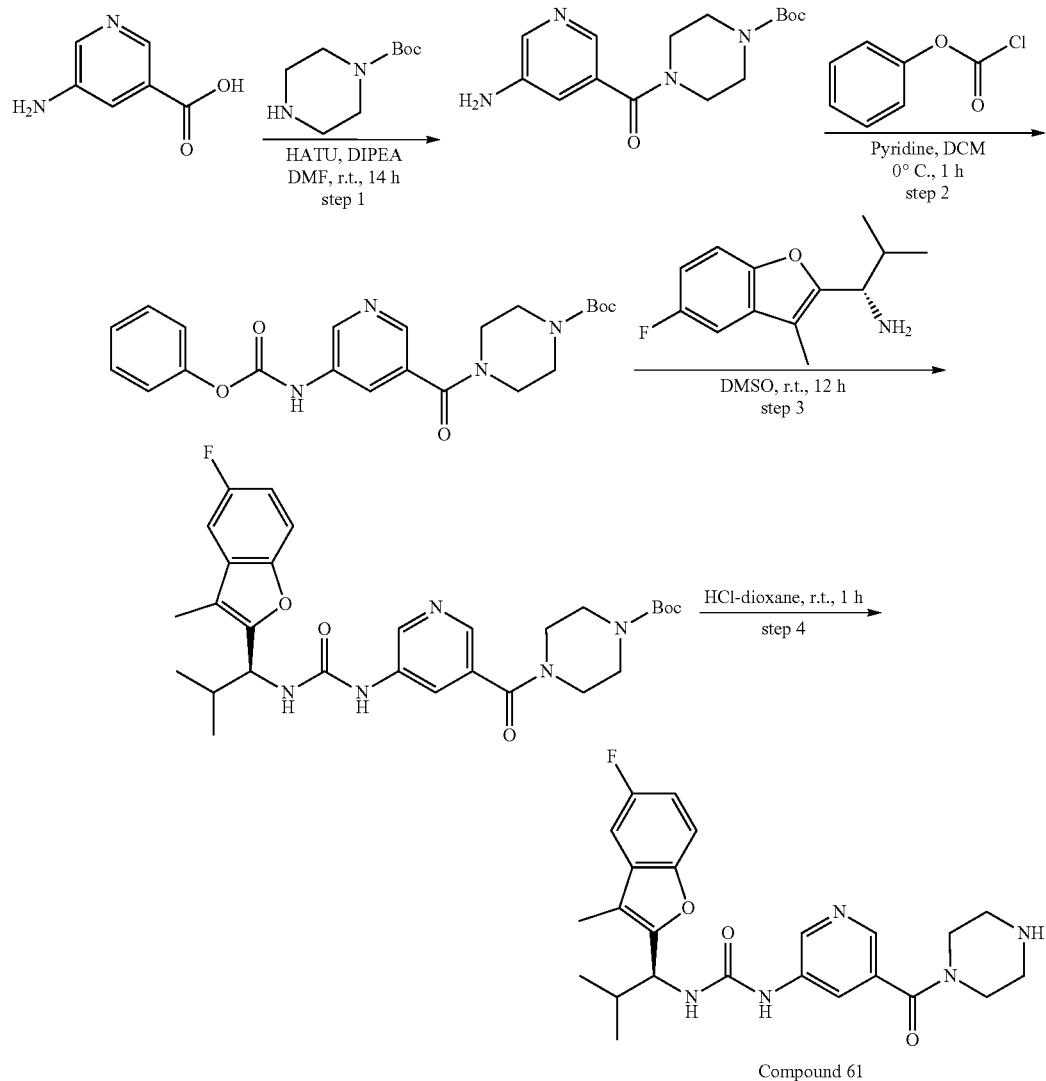

Step 1

To a solution of 5-aminonicotinic acid (500 mg, 3.6 mmol), tert-butyl piperazine-1-carboxylate (1.67 mmol, 9 mmol) and HATU (2.05 g, 5.4 mmol) in DMF (25 mL) was added DIPEA (2.56 mL, 14.4 mmol). The resulting reaction was stirred at room temperature for 14 h. After completed, the reaction was concentrated in vacuo to give the crude, which was purified with silica gel column chromatography, eluting with a gradient of 0-5% MeOH in DCM to give tert-butyl 4-(5-aminonicotinoyl)piperazine-1-carboxylate (380 mg, 34.5%) as yellow oil. MS (ESI): mass calcd. $C_{15}H_{22}N_4O_3$, 306.17, m/z found 306.37 $[M+H]^+$.

Step 2

To a solution of tert-butyl 4-(5-aminonicotinoyl)piperazine-1-carboxylate (200 mg, 0.66 mmol) and pyridine (105 mg, 1.32 mmol) in DCM (7 mL) was added phenyl carbonochloridate (104 mg, 0.66 mmol) was added at 0° C. The reaction mixture was stirred at 0° C. for 1 h under N₂. After completion, the reaction was diluted with H₂O (20 mL), extracted with DCM (30 mL×3). The combined organic layers were washed with brine (30 mL), dried over Na₂SO₄, concentrated in vacuo to give the crude, which was purified by Prep-TLC (eluent: DCM/MeOH=20/1) to give the tert-butyl 4-(5-((phenoxycarbonyl)amino)nicotinoyl)piperazine- 1-carboxylate (150 mg, yield: 53.4%) as a white solid. MS (ESI): mass calcd. $C_{22}H_{26}N_4O_5$, 426.19, m/z found 427.2 $[M+H]^+$.

Step 3

To a mixture of tert-butyl 4-(5-((phenoxycarbonyl)amino) nicotinoyl)piperazine-1-carboxylate (150 mg, 0.35 mmol) in DMSO (3 mL) was added (S)-1-(5-fluoro-3-methylbenzofuran-2-yl)-2-methylpropan-1-amine (Int-2) (117 mg, 0.53 mmol) at room temperature. The reaction mixture was stirred at room temperature for 12 h under $N_2$. After completion, the reaction was diluted with $H_2O$ (25 mL), extracted with EtOAc (30 mL×3). The combined organic layers were washed with brine (30 mL), dried over $Na_2SO_4$, concentrated in vacuo to give the crude, which was purified by Prep-TLC (eluent: DCM/MeOH=15/1) give the tert-butyl (S)-4-(5-(3-(1-(5-fluoro-3-methylbenzofuran-2-yl)-2-methylpropyl)ureido)nicotinoyl)piperazine-1-carboxylate (157 mg, yield: 81%) as a white solid. MS (ESI): mass calcd. $C_{29}H_{36}FN_5O_5$, 553.27, m/z found 554.3 $[M+H]^+$.

Step 4

To a solution of tert-butyl (S)-4-(5-(3-(1-(5-fluoro-3-methylbenzofuran-2-yl)-2-methylpropyl)ureido)nicotinoyl) piperazine-1-carboxylate (157 mg, 0.28 mmol) in MeOH (3 mL) was added HCl (2 mL, 4 M solution in 1,4-dioxane) at 0° C. The reaction mixture was stirred at room temperature for 1 h. After completion, the reaction was concentrated to give the residue, which was neutralized with ammonia (2 mL, 7 M solution in MeOH) and concentrated to give the crude. The crude product was purified by Prep-HPLC to give the (S)-1-(1-(5-fluoro-3-methylbenzofuran-2-yl)-2-methylpropyl)-3-(5-(piperazine-1-carbonyl)pyridin-3-yl)urea (45 mg, yield: 35.4%) as a white solid. MS (ESI): mass calcd. C24H28FN5O3, 453.22, m/z found 454.2 $[M+H]^+$.

$^1$H NMR (400 MHz, DMSO) δ 8.79 (s, 1H), 8.46 (s, 1H), 8.10 (s, 1H), 7.93 (s, 1H), 7.51 (dd, J=8.9, 4.1 Hz, 1H), 7.38 (dd, J=8.8, 4.0 Hz, 1H), 7.19-7.01 (m, 2H), 4.75 (t, J=8.6 Hz, 1H), 3.53 (s, 2H), 3.22 (s, 2H), 2.88-2.57 (m, 4H), 2.33 (s, 3H), 2.16-2.07 (m, 1H), 1.07 (d, J=6.6 Hz, 3H), 0.82 (d, J=6.7 Hz, 3H).

Example 46: Preparation of Compound 62

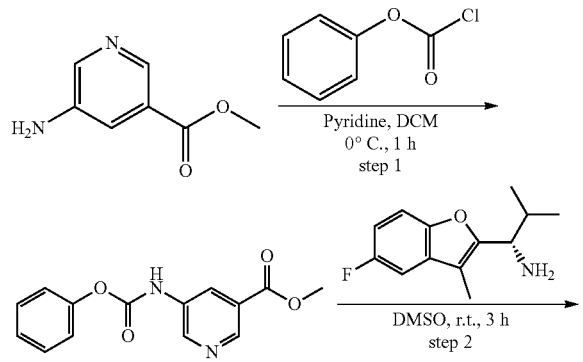

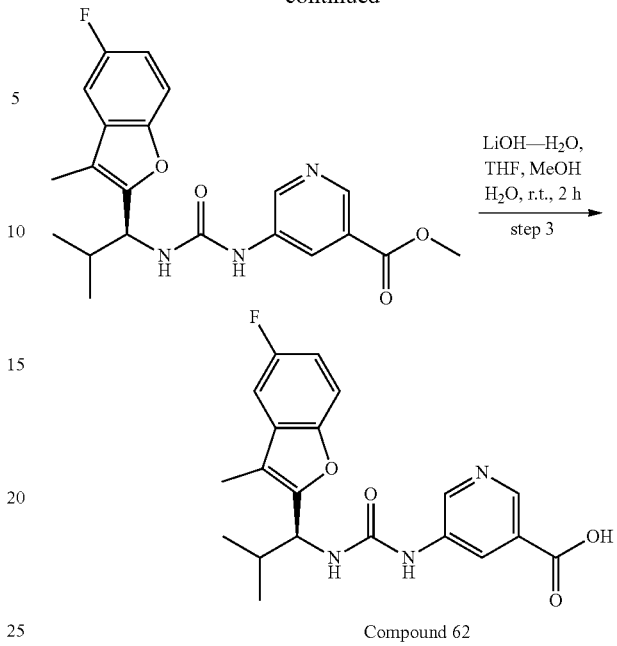

Compound 62

Step 1

To a solution of methyl 5-aminonicotinate (200 mg, 1.3 mmol) and pyridine (206 mg, 2.6 mmol) in DCM (8 mL) was added phenyl carbonochloridate (206 mg, 1.3 mmol) at 0° C. The reaction mixture was stirred at 0° C. for 1 h under $N_2$. After completion, the reaction was diluted with $H_2O$ (30 mL), extracted with DCM (30 mL×3). The combined organic layers were washed with brine (40 mL), dried over $Na_2SO_4$, concentrated in vacuo to give the crude, which was purified by Prep-TLC (eluent: PE/EA=10/1) to give the methyl 5-((phenoxycarbonyl)amino)nicotinate (110 mg, yield: 31.1%) as a white solid. MS (ESI): mass calcd. $C_{14}H_{12}N_2O_4$, 272.08, m/z found 273.1 $[M+H]^+$.

Step 2

A mixture of the methyl 5-((phenoxycarbonyl)amino) nicotinate (110 mg, 0.4 mmol) and (S)-1-(5-fluoro-3-methylbenzofuran-2-yl)-2-methylpropan-1-amine (Int-2) (108 mg, 0.49 mmol) in DMSO (5 mL) was stirred at room temperature for 3 h under $N_2$. The reaction was poured into $H_2O$ (20 mL) and white solid was precipitated. The mixture was filtered and the cake was dried to give methyl (S)-5-(3-(1-(5-fluoro-3-methylbenzofuran-2-yl)-2-methylpropyl) ureido)nicotinate (140 mg, yield: 87.5%) as a white solid. MS (ESI): mass calcd. $C_{21}H_{22}FN_3O_4$, 399.16, m/z found 400.1 $[M+H]^+$.

Step 3

To a mixture of the methyl (S)-5-(3-(1-(5-fluoro-3-methylbenzofuran-2-yl)-2-methylpropyl)ureido)nicotinate (140 mg, 0.35 mmol) in MeOH (2 mL)/THF (2 mL)/$H_2O$ (1 mL) was added LiOH—$H_2O$ (38 mg, 0.91 mmol) at room temperature. The reaction mixture was stirred for 2 h. LCMS indicated starting material consumed and desired product was formed. The reaction mixture was concentrated to give a residue, which was purified by Prep-HPLC to give the (S)-5-(3-(1-(5-fluoro-3-methylbenzofuran-2-yl)-2-methyl-propyl)ureido)nicotinic acid (60 mg, 44.5%) as a white solid. MS (ESI): mass calcd. $C_{20}H_{20}FN_3O_4$, 385.14, m/z found 386.2[M+H]$^+$.

$^1$H NMR (400 MHz, DMSO) δ 8.90 (s, 1H), 8.62-8.60 (m, 2H), 8.47 (s, 1H), 7.55-7.49 (m, 1H), 7.38 (dd, J=8.8, 2.6 Hz, 1H), 7.16-7.04 (m, 2H), 4.76 (t, J=8.2 Hz, 1H), 2.21 (s, 3H), 2.16-2.10 (m, 1H), 1.03 (d, J=6.7 Hz, 3H), 0.82 (d, J=6.7 Hz, 3H).

Example 47: Preparation of Compound 63

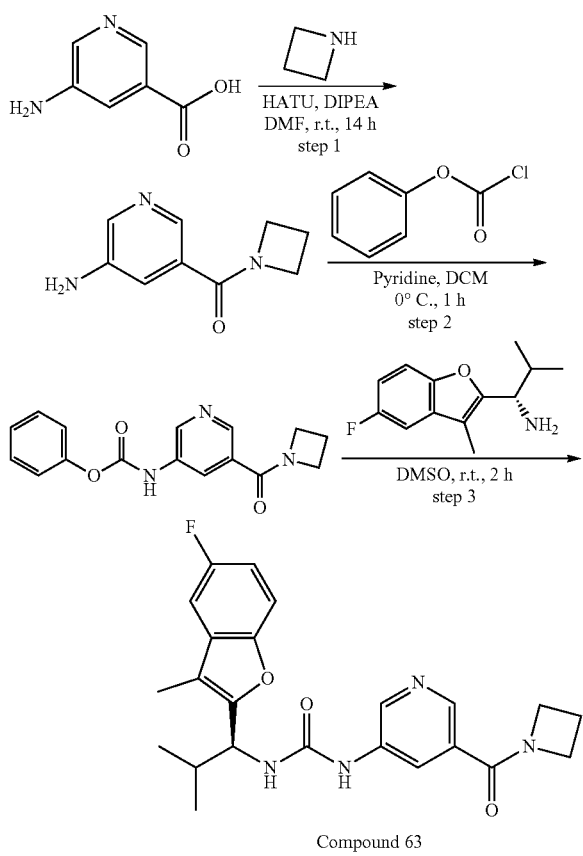

Compound 63

Step 1

To a solution of 5-aminonicotinic acid (690 mg, 5 mmol), azetidine (570 mmol, 10 mmol) and HATU (2.85 g, 7.5 mmol) in DMF (25 mL) was added DIPEA (3.6 mL, 20 mmol). The resulting reaction was stirred at room temperature for 14 h. After completed, the reaction was concentrated in vacuo to give the crude, which was purified with silica gel column chromatography, eluting with a gradient of 0-10% MeOH in DCM to (5-aminopyridin-3-yl)(azetidin-1-yl)methanone (480 mg, 54.2%) as yellow oil. MS (ESI): mass calcd. $C_9H_{11}N_3O$, 177.09, m/z found 178.1 [M+H]$^+$.

Step 2

To a mixture of (5-aminopyridin-3-yl)(azetidin-1-yl)methanone (100 mg, 0.56 mmol) and pyridine (89 mg, 1.12 mmol) in DCM (5 mL) was added phenyl carbonochloridate (88 mg, 0.56 mmol) at 0° C. The resulting reaction mixture was stirred at 0° C. for 1 h under N$_2$. After completion, the reaction was diluted with H$_2$O (25 mL), extracted with DCM (25 mL×3). The combined organic layers were washed with brine (30 mL), dried over Na$_2$SO$_4$, concentrated in vacuo to give the crude, which was purified by Prep-TLC (eluent: DCM/MeOH=15/1) to give the phenyl (5-(azetidine-1-carbonyl)pyridin-3-yl)carbamate (90 mg, yield: 54%) as a white solid. MS (ESI): mass calcd. $C_{12}H_{11}N_3O_4S$, 293.05, m/z found 298.1 [M+H]$^+$.

Step 3

To a mixture of the phenyl (5-(azetidine-1-carbonyl)pyridin-3-yl)carbamate (60 mg, 0.2 mmol) in DMSO (3 mL) was added (S)-1-(5-fluoro-3-methylbenzofuran-2-yl)-2-methylpropan-1-amine (Int-2) (104 mg, 0.66 mmol). The resulting reaction mixture was stirred at room temperature for 2 h under N$_2$. After completion, the reaction was diluted with H$_2$O (20 mL), extracted with EtOAc (30 mL×3). The combined organic layers were washed with brine (40 mL), dried over Na$_2$SO$_4$, concentrated in vacuo to give the crude, which was purified by Prep-TLC (eluent: DCM/MeOH=10/1) give the (S)-1-(5-(azetidine-1-carbonyl)pyridin-3-yl)-3-(1-(5-fluoro-3-methylbenzofuran-2-yl)-2-methylpropyl)urea (40 mg, yield: 47.2%) as a white solid. MS (ESI): mass calcd. $C_{23}H_{25}FN_4O_3$, 424.19, m/z found 425.2 [M+H]$^+$.

$^1$H NMR (400 MHz, DMSO) δ 8.80 (s, 1H), 8.51 (s, J=2.5 Hz, 1H), 8.31 (d, J=1.9 Hz, 1H), 8.18-8.13 (m, 1H), 7.51 (dd, J=8.9, 4.1 Hz, 1H), 7.38 (dd, J=8.8, 2.6 Hz, 1H), 7.13-7.00 (m, 2H), 4.76 (t, J=8.6 Hz, 1H), 4.28 (t, J=7.6 Hz, 2H), 4.04 (t, J=7.7 Hz, 2H), 2.29-2.23 (m, 2H), 2.21 (s, 3H), 2.15-2.11 (m, 1H), 1.03 (d, J=6.7 Hz, 3H), 0.83 (d, J=6.2 Hz, 3H).

Example 48: Preparation of Compound 64

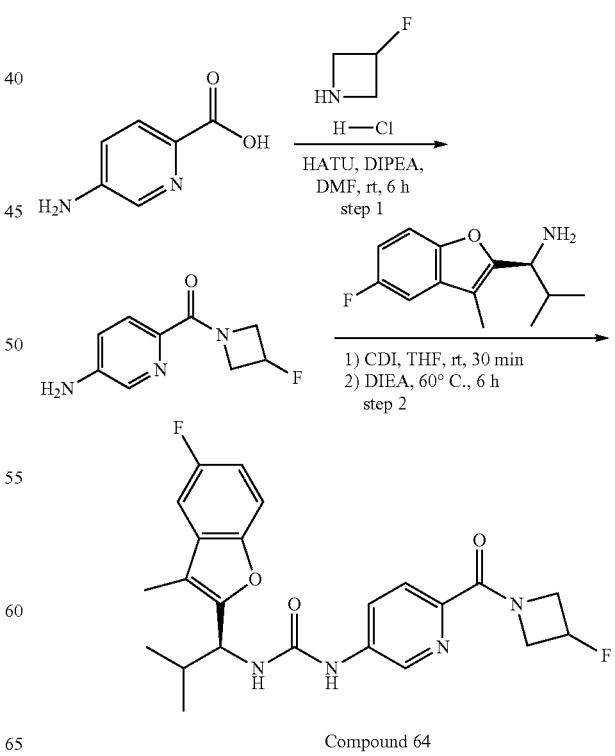

Compound 64

Step 1

To a mixture of 5-aminopyridine-2-carboxylic acid (200 mg, 1.45 mmol), 3-fluoroazetidine hydrochloride (161 mg, 1.45 mmol) and HATU (661 mg, 1.74 mmol) in DMF (10 mL) was added DIEA (561 mg, 4.34 mmol). The reaction mixture was stirred at 20° C. for 16 h. After completion, the mixture was diluted with water and extracted with EA (50 mL×3). The organic layer was dried over anhydrous $Na_2SO_4$ and concentrated under reduced pressure to give a residue which was purified by silica gel Chromatography column (PE/EA from 0~50%) to give (5-aminopyridin-2-yl)(3-fluoroazetidin-1-yl)methanone (100 mg, 32%) as a yellow solid. MS (ESI): mass calcd. for $C_9H_{10}FN_3O$, 195.1, m/z found 196.1 [M+H]$^+$.

Step 2

A mixture of (1S)-1-(5-fluoro-3-methyl-1-benzofuran-2-yl) ethanamine (50 mg, 0.23 mmol), CDI (44 mg, 0.27 mmol) in THF (10 mL) was stirred at 20° C. for 0.5 h. 6-[(3-fluoroazetidin-1-yl) carbonyl] pyridin-3-amine (44 mg, 0.23 mmol) and DIEA (88 mg, 0.68 mmol) were added into the reaction mixture and the mixture was stirred at 60° C. for 2 h. After reaction, the reaction mixture was concentrated under reduced pressure to give a residue which was purified by prep-HPLC to give (S)-1-(1-(5-fluoro-3-methyl-benzofuran-2-yl)-2-methylpropyl)-3-(6-(3-fluoroazetidine-1-carbonyl)pyridin-3-yl)urea (56 mg, 56%) as a white solid. MS (ESI): mass calcd. for $C_{23}H_{24}F_2N_4O_3$, 442.2, m/z found 443.1 [M+H]$^+$.

$^1$H NMR (400 MHz, DMSO) δ 8.92 (s, 1H), 8.53-8.52 (m, 1H), 8.02-7.98 (m, 1H), 7.87-7.85 (m, 1H), 7.53-7.50 (m, 1H), 7.40-7.37 (m, 1H), 7.13-7.07 (m, 2H), 5.51-5.47 (m, 1H), 4.88-4.81 (m, 1H), 4.76 (t, J=8.0 Hz, 1H), 4.62-4.53 (m, 1H), 4.37-4.32 (m, 1H), 4.11-4.01 (m, 1H), 2.21 (s, 3H), 2.17-2.09 (m, 1H), 1.03 (d, J=6.8 Hz, 3H), 0.82 (d, J=6.8 Hz, 3H).

Example 49: Preparation of Compound 65

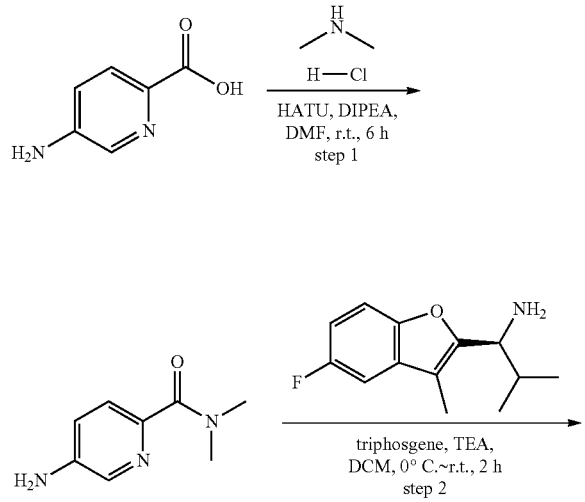

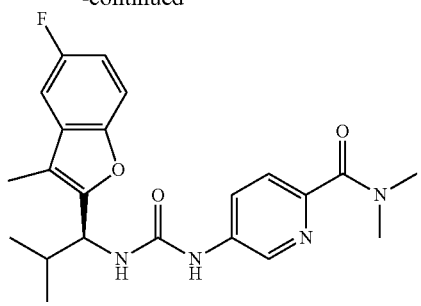

Compound 65

Step 1

To a mixture of 5-aminopyridine-2-carboxylic acid (200 mg, 1.45 mmol), dimethylamine hydrochloride (118 mg, 1.45 mmol) and HATU (661 mg, 1.74 mmol) in DMF (10 mL) was added DIEA (561 mg, 4.34 mmol). The reaction mixture was stirred at 20° C. for 16 h. After completion, the reaction mixture was quenched with water and extracted with EA (50 mL×3). The organic layer was dried over anhydrous $Na_2SO_4$ and concentrated under reduced pressure to give a residue which was purified by silica gel chromatography column (PE/EA from 0~50%) to give 5-amino-N,N-dimethylpicolinamide (100 mg, 38%) as yellow solid. MS (ESI): mass calcd. for $C_8H_{11}N_3O$, 165.1, m/z found 166.1 [M+H]$^+$.

Step 2

To a mixture of (1S)-1-(5-fluoro-3-methyl-1-benzofuran-2-yl)-2-methylpropan-1-amine (50 mg, 0.23 mmol), triethylamine (69 mg, 0.68 mmol) in DCM (5 mL) was added triphosgene (54 mg, 0.18 mmol) at 0° C. and the reaction mixture was stirred at 20° C. for 0.5 h. 5-amino-N,N-dimethylpyridine-2-carboxamide (37.33 mg, 0.226 mmol) was added into the reaction mixture at 0° C. and the mixture was stirred at 20° C. for 2 h. After completion, the reaction mixture was concentrated to give a residue which was purified by prep-HPLC to give (S)-5-(3-(1-(5-fluoro-3-methylbenzofuran-2-yl)-2-methylpropyl)ureido)-N,N-dimethylpicolinamide (42 mg, 45%) as a white solid. MS (ESI): mass calcd. for $C_{22}H_{25}FN_4O_3$, 412.2, m/z found 413.1 [M+H]$^+$.

$^1$H NMR (400 MHz, DMSO) δ 8.87 (s, 1H), 8.53 (s, 1H), 7.97-7.94 (m, 1H), 7.53-7.50 (m, 2H), 7.40-7.37 (m, 1H), 7.13-7.05 (m, 2H), 4.76 (t, J=8.0 Hz, 1H), 2.98 (d, J=8.0 Hz, 6H), 2.21 (s, 3H), 2.16-2.11 (m, 1H), 1.03 (d, J=6.8 Hz, 3H), 0.83 (d, J=6.8 Hz, 3H).

Example 50: Preparation of Compound 66

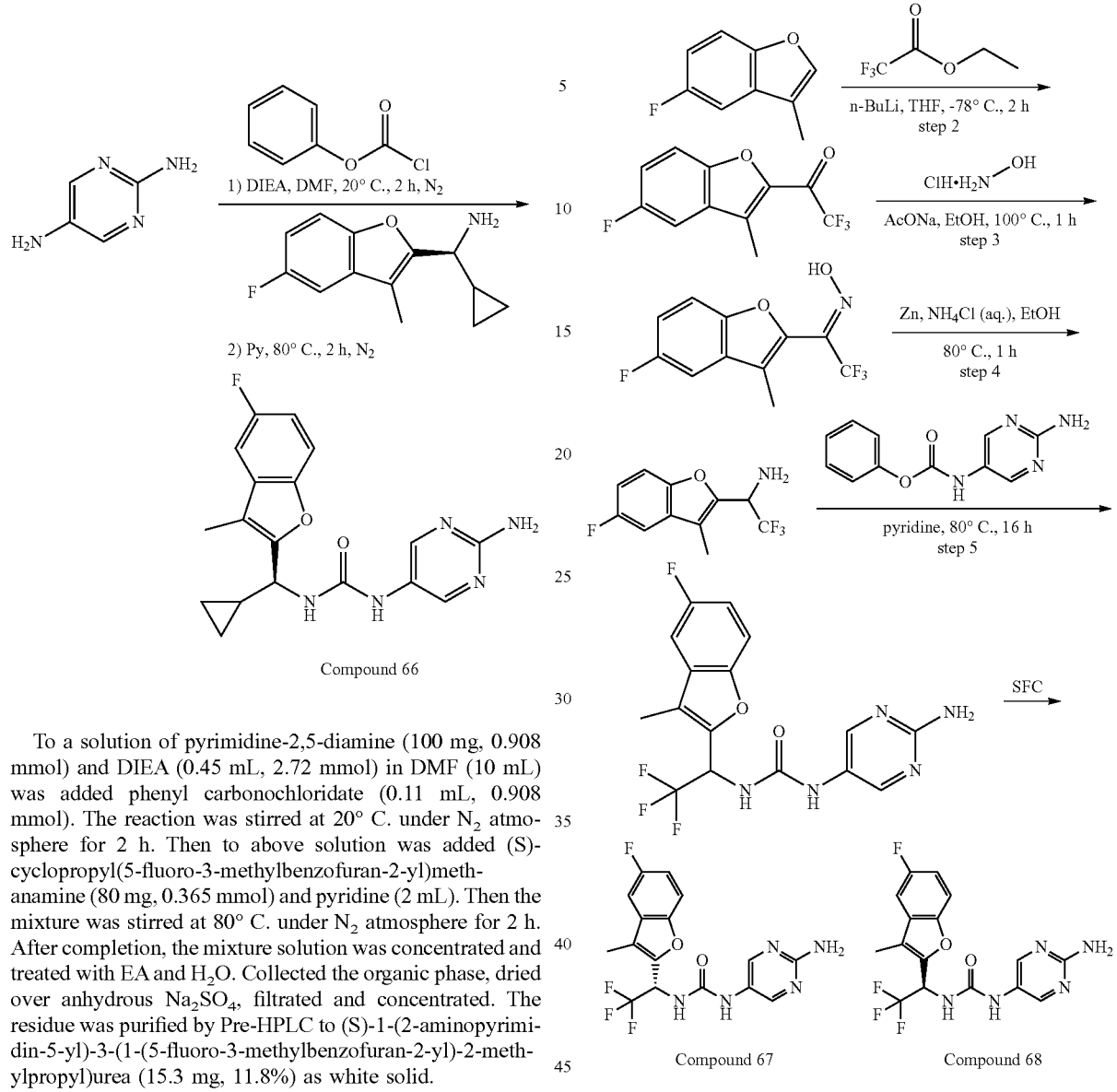

To a solution of pyrimidine-2,5-diamine (100 mg, 0.908 mmol) and DIEA (0.45 mL, 2.72 mmol) in DMF (10 mL) was added phenyl carbonochloridate (0.11 mL, 0.908 mmol). The reaction was stirred at 20° C. under $N_2$ atmosphere for 2 h. Then to above solution was added (S)-cyclopropyl(5-fluoro-3-methylbenzofuran-2-yl)methanamine (80 mg, 0.365 mmol) and pyridine (2 mL). Then the mixture was stirred at 80° C. under $N_2$ atmosphere for 2 h. After completion, the mixture solution was concentrated and treated with EA and $H_2O$. Collected the organic phase, dried over anhydrous $Na_2SO_4$, filtrated and concentrated. The residue was purified by Pre-HPLC to (S)-1-(2-aminopyrimidin-5-yl)-3-(1-(5-fluoro-3-methylbenzofuran-2-yl)-2-methylpropyl)urea (15.3 mg, 11.8%) as white solid.

HPLC condition: Column: Xbridge prep c18 5 um OBD 19*150 mm; Condition: A water (0.1% FA) B (Acetonitrile); 35-45% B in 9 min, hold at 100% B for 1 min, back to 35% B with 1.5 min, stop at 15 min; Flow rate: 25 ml/min; Detector: 214/254. MS (ESI): mass calcd. for $C_{18}H_{18}FN_5O_2$, 355.14, m/z found 356.1 [M+H]⁺.

Example 51: Preparation of Compound 67 and Compound 68

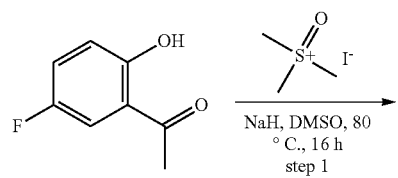

Step 1

To a solution of sodium hydride (7.4 g, 184.9 mmol) in DMSO (400 mL) was added trimethylsulfoxonium iodide (40.7 g, 184.9 mmol). The mixture was stirred at 25° C. for 1 h. Then 1-(5-fluoro-2-hydroxyphenyl)ethanone (19 g, 123.3 mmol) dissolved with DMSO was added to the mixture dropwise. The mixture was stirred at 80° C. for 16 h. After completion, the mixture was quenched with $NH_4Cl$ (aq.), extracted with EA. The organic layer was washed with brine, dried over sodium sulfate, concentrated in vacuum. The residue was purified by column chromatography on silica gel (PE) to give 5-fluoro-3-methylbenzofuran (6.7 g, 36.20%) as colorless oil. MS (ESI): mass calcd. for $C_9H_7FO$, 150.1.

Step 2

To a solution of 5-fluoro-3-methylbenzofuran (6.7 g, 44.7 mmol) in THF (100 mL) was added nBuLi (2.4 M in hexane) (22 mL, 53.6 mmol) dropwise at −78° C. The mixture was stirred at −78° C. for 1 h. Then ethyl 2,2,2-trifluoroacetate (12.7 g, 89.4 mmol) was added to the mixture; the mixture was stirred at −78° C. for 1 h. After completion (TLC monitored the reaction till starting material was consumed fully), the mixture was added to $NH_4Cl$ (aq.), extracted with EA. The organic layer was washed with brine, dried over sodium sulfate, concentrated in vacuum. The residue was purified by column chromatography on silica gel (PE/EA=10/1) to give 2,2,2-trifluoro-1-(5-fluoro-3-methylbenzofuran-2-yl)ethan-1-one (2.4 g, 21.8%) as white solid. MS (ESI): mass calcd. for $C_{11}H_6F_4O_2$, 246.0.

Step 3

To a solution of 2,2,2-trifluoro-1-(5-fluoro-3-methylbenzofuran-2-yl)ethan-1-one (2.4 g, 9.76 mmol) in EtOH (20 mL) was added hydroxylamine hydrochloride (3.4 g, 48.8 mmol) and NaOAc (4.0 g, 48.8 mmol). The mixture was stirred at 100° C. for 1 h. After completion, the mixture was added to water, extracted with EA. The organic layer was washed with brine, dried over sodium sulfate, concentrated in vacuum to give (E)-2,2,2-trifluoro-1-(5-fluoro-3-methylbenzofuran-2-yl)ethan-1-one oxime (2.0 g, 78.5%) as white solid. MS (ESI): mass calcd. for $C_{11}H_7F_4NO_2$, 261.0, m/z found 262.0 $[M+H]^+$.

Step 4

To a solution of (E)-2,2,2-trifluoro-1-(5-fluoro-3-methylbenzofuran-2-yl)ethan-1-one oxime (2.0 g, 7.66 mmol) in EtOH (20 mL) was added $NH_4Cl$ (aq.) and Zn (5.0 g, 76.6 mmol). The mixture was stirred at 80° C. for 1 h. After completion, the mixture was added to water, extracted with EA. The organic layer was washed with brine, dried over sodium sulfate, concentrated in vacuum. The residue was purified by column chromatography on silica gel (PE/EA from 10/1 to 5/1) to give 2,2,2-trifluoro-1-(5-fluoro-3-methylbenzofuran-2-yl)ethan-1-amine (1.6 g, 84.6%) as white solid.
MS (ESI): mass calcd. for $C_{11}H_9F_4NO$, 247.1, m/z found 231.1 $[M+H-17]^+$.

Step 5

Step 5 To a solution of pyrimidine-2,5-diamine (180 mg, 1.64 mmol) in pyridine (5 mL) was added phenyl carbonochloridate (256 mg, 1.64 mmol). The mixture was stirred at 25° C. for 1 h. 2,2,2-trifluoro-1-(5-fluoro-3-methylbenzofuran-2-yl)ethan-1-amine (400 mg, 1.62 mmol) was added to the mixture; the mixture was stirred at 80° C. for 16 h. After completion, the mixture was concentrated in vacuum. The residue was purified by reverse phase (ACN/water from 0~60) to give 1-(2-aminopyrimidin-5-yl)-3-(2,2,2-trifluoro-1-(5-fluoro-3-methylbenzofuran-2-yl)ethyl)urea (280 mg, 44.6%) as white solid. MS (ESI): mass calcd. for $C_{16}H_{13}F_4N_5O_2$, 383.1, m/z found 384.1 $[M+H]^+$.

Step 6

280 mg of racemic was separated by SFC to give (Compound 67, 109.8 mg) as white solid and (Compound 68, 100.7 mg) as white solid.
Chiral separation condition: Apparatus: SFC 80; Column: Daicel CHIRALCEL OD, 250 mm×30 mm I.D., 10 μm; Mobile phase: $CO_2$/MeOH[0.2% $NH_3$ (7M Solution in MeOH)]=60/40;
Flow rate: 70 g/min; Wavelength: UV 214 nm; Temperature: 35° C.

Compound 67

MS (ESI): mass calcd. for $C_{16}H_{13}F_4N_5O_2$, 383.1, m/z found 384.1 $[M+H]^+$.
$^1$H NMR (400 MHz, DMSO) δ 8.21 (s, 3H), 7.72 (d, J=9.2 Hz, 1H), 7.63 (dd, J=8.8, 4.0 Hz, 1H), 7.51 (dd, J=8.4, 2.4 Hz, 1H), 7.24 (td, J=9.6, 2.8 Hz, 1H), 6.39 (s, 2H), 6.05-5.89 (m, 1H), 2.27 (s, 3H).

Compound 68

MS (ESI): mass calcd. for $C_{16}H_{13}F_4N_5O_2$, 383.1, m/z found 384.1 $[M+H]^+$.
$^1$H NMR (400 MHz, DMSO) δ 8.21 (s, 3H), 7.72 (d, J=9.2 Hz, 1H), 7.63 (dd, J=8.8, 4.0 Hz, 1H), 7.51 (dd, J=8.4, 2.4 Hz, 1H), 7.24 (td, J=9.6, 2.8 Hz, 1H), 6.39 (s, 2H), 6.02-5.91 (m, 1H), 2.27 (s, 3H).

Example 52: Preparation of Compound 69 and Compound 70

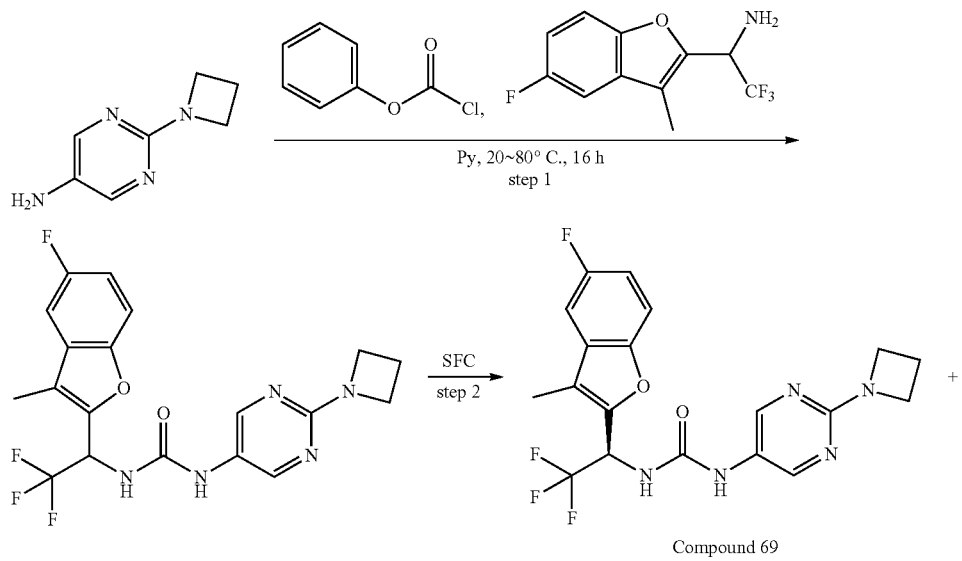

Compound 69

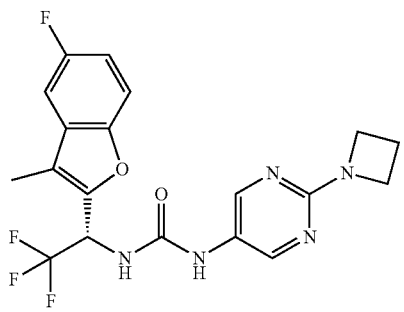

Compound 70

Step 1

To a solution of 2-(azetidin-1-yl)pyrimidin-5-amine (100 mg, 0.67 mmol) in pyridine (5 mL) was added phenyl chloroformate (104 mg, 0.67 mmol). The mixture was stirred at 25° C. for 1 h. 2,2,2-trifluoro-1-(5-fluoro-3-methyl-1-benzofuran-2-yl)ethanamine (166 mg, 0.67 mmol) was added to the mixture and the mixture was stirred at 80° C. for 16 h. After completion, the mixture was concentrated in vacuum. The residue was purified by reverse (ACN/water from 0~70) to give 1-(2-(azetidin-1-yl)pyrimidin-5-yl)-3-(2,2,2-trifluoro-1-(5-fluoro-3-methylbenzofuran-2-yl)ethyl) urea (72 mg, 25.4%) as white solid. MS (ESI): mass calcd. for $C_{19}H_{17}F_4N_5O_2$, 423.1, m/z found 424.1 $[M+H]^+$.

Step 2

70 mg of racemic was separated by SFC to give (Compound 69, 21.6 mg) as white solid and (Compound 70, 18.6 mg) as white solid.

Chiral separation condition: Apparatus: SFC 150; Column: Daicel CHIRALCEL OD, 250 mm×30 mm I.D., 10 μm; Mobile phase: $CO_2$/MeOH[0.2% NH3 (7M Solution in MeOH)]=75/25; Flow rate: 80 g/min; Wavelength: UV 214 nm; Temperature: 35° C.

Compound 69

MS (ESI): mass calcd. for $C_{19}H_{17}F_4N_5O_2$, 423.1, m/z found 424.1 $[M+H]^+$.

$^1$H NMR (400 MHz, DMSO) δ 8.34 (s, 3H), 7.74 (d, J=9.6 Hz, 1H), 7.63 (dd, J=9.2, 4.0 Hz, 1H), 7.51 (dd, J=8.8, 2.8 Hz, 1H), 7.24 (td, J=9.6, 2.8 Hz, 1H), 6.03-5.94 (m, 1H), 3.98 (d, J=7.6 Hz, 4H), 2.37-2.18 (m, 5H).

Compound 70

MS (ESI): mass calcd. for $C_{19}H_{17}F_4N_5O_2$, 423.1, m/z found 424.1 $[M+H]^+$.

$^1$H NMR (400 MHz, DMSO) δ 8.34 (s, 3H), 7.74 (d, J=9.6 Hz, 1H), 7.63 (dd, J=8.8, 4.0 Hz, 1H), 7.51 (dd, J=8.8, 2.8 Hz, 1H), 7.24 (td, J=9.6, 2.8 Hz, 1H), 6.04-5.91 (m, 1H), 4.03-3.92 (m, 4H), 2.35-2.18 (m, 5H).

Example 53: Preparation of Compound 71

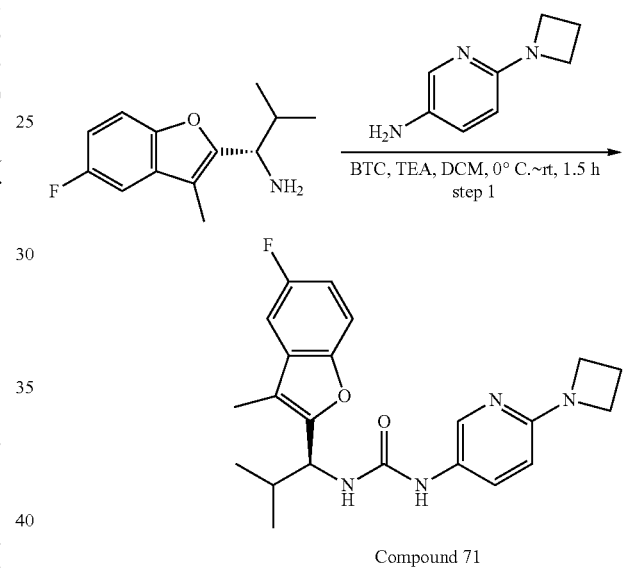

Compound 71

To a stirred solution of (S)-1-(5-fluoro-3-methylbenzofuran-2-yl)-2-methylpropan-1-amine (Int-2) (40 mg, 0.18 mmol) and TEA (128 mg, 1.27 mmol) in DCM (4 mL) was added triphosgene (37 mg, 0.13 mmol) at 0° C. under $N_2$ atmosphere. After stirring at room temperature for 30 min, 6-(azetidin-1-yl) pyridin-3-amine (54 mg, 0.36 mmol) was added into the reaction mixture at 0° C. under $N_2$ atmosphere and the mixture was stirred at room temperature for 1 h. After completion, the reaction mixture was concentrated under reduced pressure to give a residue which was purified by Prep-HPLC to afford —(S)-1-(6-(azetidin-1-yl)pyridin-3-yl)-3-(1-(5-fluoro-3-methylbenzofuran-2-yl)-2-methylpropyl) urea (28 mg, 39%) as white solid. MS (ESI): mass calcd. for $C_{22}H_{25}FN_4O_2$, 396.2, m/z found 397.1 $[M+H]^+$.

$^1$H NMR (400 MHz, DMSO) δ=8.14 (s, 1H), 7.97 (d, J=2.4, 1H), 7.58 (dd, J=8.8, 2.4 Hz, 1H), 7.51 (dd, J=9.2, 4.4, 1H), 7.37 (dd, J=8.8, 2.8 Hz, 1H), 7.09 (m, 1H), 6.70 (d, J=8.8 Hz, 1H), 6.28 (d, J=8.8 Hz, 1H), 4.73 (t, J=8.4 Hz, 1H), 3.83 (t, J=7.2 Hz, 4H), 2.31-2.21 (m, 2H), 2.19 (s, 3H), 2.09 (m, 1H), 1.01 (d, J=6.8 Hz, 3H), 0.82 (d, J=6.8 Hz, 3H).

Example 54: Preparation of Compound 72

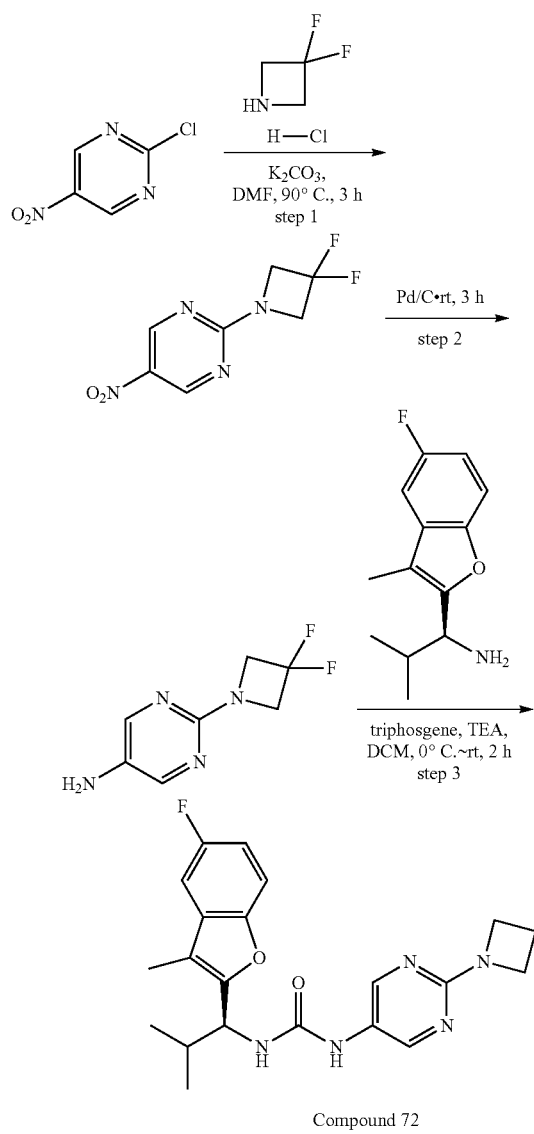

Compound 72

Step 1

To a mixture of 2-chloro-5-nitropyrimidine (1.5 g, 9.4 mmol), 3,3-difluoroazetidine hydrochloride (1.46 g, 11.2 mmol) in DMF (20 mL) was added $K_2CO_3$ (3.9 g, 28.2 mmol). The reaction mixture was stirred at 90° C. for 3 h. After completion, the mixture was quenched with water and extracted with EA (50 mL×3). The organic layer was dried over anhydrous $Na_2SO_4$ and concentrated under reduced pressure to give a residue which was purified by silica gel chromatography column (PE/EA from 0~50%) to give 2-(3, 3-difluoroazetidin-1-yl)-5-nitropyrimidine (0.8 g, 35%) as yellow solid. MS (ESI): mass calcd. for $C_7H_6F_2N_4O_2$, 216.0, m/z found 217.0 $[M+H]^+$.

Step 2

To a solution of 2-(3,3-difluoroazetidin-1-yl)-5-nitropyrimidine (800 mg, 3.70 mmol) in MeOH (10 mL) was added Pd/C (79 mg) and the reaction mixture was stirred under $H_2$ at room temperature for 3 h. After reaction, the reaction mixture was filtered and the filtrate was collected and concentrated to give 2-(3,3-difluoroazetidin-1-yl) pyrimidin-5-amine (650 mg, 85%) as a yellow solid which was used in the next step directly. MS (ESI): mass calcd. for $C_7H_8F_2N_4$, 186.1, m/z found 187.1 $[M+H]^+$.

Step 3

To a mixture of (1S)-1-(5-fluoro-3-methyl-1-benzofuran-2-yl)-2-methylpropan-1-amine (50 mg, 0.23 mmol), triethylamine (69 mg, 0.68 mmol) in DCM (10 mL) was added triphosgene (53.65 mg, 0.1808 mmol) at 0° C. After stirring at 20° C. for 0.5 h, 2-(3,3-difluoroazetidin-1-yl) pyrimidin-5-amine (42 mg, 0.23 mmol) was added at 0° C. and the reaction mixture was stirred at 20° C. for 2 h. After completion, the reaction mixture was concentrated under reduced pressure to give a residue which was purified by prep-HPLC to give (S)-1-(2-(3,3-difluoroazetidin-1-yl)pyrimidin-5-yl)-3-(1-(5-fluoro-3-methylbenzofuran-2-yl)-2-methylpropyl) urea (56 mg, 57%) as white solid.

MS (ESI): mass calcd. for $C_{21}H_{22}F_3N_5O_2$, 433.2, m/z found 434.1 $[M+H]^+$.

$^1$H NMR (400 MHz, DMSO) δ 8.46 (s, 2H), 8.33 (s, 1H), 7.52-7.49 (m, 1H), 7.39-7.36 (m, 1H), 7.12-7.07 (m, 1H), 6.96 (d, J=8.0 Hz, 1H), 4.73 (t, J=8.0 Hz, 1H), 4.42-4.35 (m, 4H), 2.19 (s, 3H), 2.14-2.08 (m, 1H), 1.01 (d, J=8.0 Hz, 3H), 0.81 (d, J=8.0 Hz, 3H).

Example 55: Preparation of Compound 73

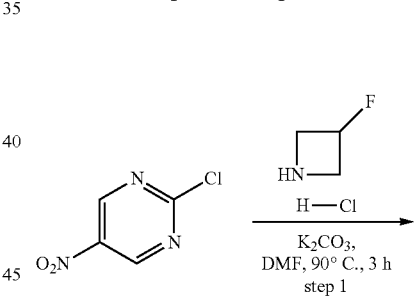

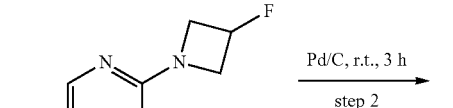

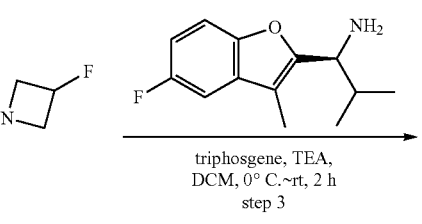

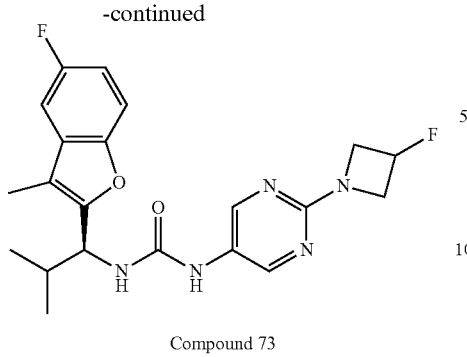

Compound 73

Step 1

To a mixture of 2-chloro-5-nitropyrimidine (1.5 g, 9.4 mmol), 3-fluoroazetidine hydrochloride (1.26 g, 11.2 mmol) in DMF (10 mL) was added $K_2CO_3$ (3.9 g, 28.2 mmol) and the reaction mixture was stirred at 90° C. for 3 h. After completion, the mixture was diluted with water and extracted with EA (50 mL×3). The organic layer was dried over anhydrous $Na_2SO_4$ and concentrated under reduced pressure to give a residue which was purified by silica gel chromatography column (PE/EA from 0~50%) to give 2-(3-fluoroazetidin-1-yl)-5-nitropyrimidine (0.8 g, 38%) as yellow solid. MS (ESI): mass calcd. for $C_7H_7FN_4O_2$, 198.1, m/z found 199.1 $[M+H]^+$.

Step 2

To a solution of 2-(3-fluoroazetidin-1-yl)-5-nitropyrimidine (800 mg, 4.04 mmol) in MeOH (10 mL) was added Pd/C (86 mg) and the reaction was stirred under $H_2$ at room temperature for 3 h. After completion, the reaction solution was filtered and the filtrate was collected and concentrated to give 2-(3-fluoroazetidin-1-yl) pyrimidin-5-amine (650 mg, 86%) as yellow solid which was used in the next step directly. MS (ESI): mass calcd. for $C_7H_9FN_4$, 168.1, m/z found 169.1 $[M+H]^+$.

Step 3

To a mixture of (1S)-1-(5-fluoro-3-methyl-1-benzofuran-2-yl)-2-methylpropan-1-amine (50 mg, 0.23 mmol) and triethylamine (69 mg, 0.68 mmol) in DCM (10 mL) was added triphosgene (54 mg, 0.18 mmol) at 0° C. and the reaction mixture was stirred at 20° C. for 0.5 h. 2-(3-fluoroazetidin-1-yl)pyrimidin-5-amine (38.01 mg, 0.226 mmol) was added into the reaction mixture at 0° C. and the mixture was stirred at 20° C. for 2 h. After reaction, the reaction mixture was concentrated under reduced pressure to give a residue which was purified by prep-HPLC to give (S)-1-(1-(5-fluoro-3-methylbenzofuran-2-yl)-2-methylpropyl)-3-(2-(3-fluoro-azetidin-1-yl)pyrimidin-5-yl)urea (43 mg, 46%) as white solid. MS (ESI): mass calcd. for $C_{21}H_{23}F_2N_5O_2$, 415.2, m/z found 416.1 $[M+H]^+$.

$^1$H NMR (400 MHz, DMSO) δ 8.39 (s, 2H), 8.23 (s, 1H), 7.52-7.49 (m, 1H), 7.39-7.36 (m, 1H), 7.12-7.07 (m, 1H), 6.92 (d, J=8.0 Hz, 1H), 5.55-5.38 (m, 1H), 4.73 (t, J=8.0 Hz, 1H), 4.34-4.24 (m, 2H), 4.06-3.96 (m, 2H), 2.19 (s, 3H), 2.14-2.08 (m, 1H), 1.01 (d, J=8.0 Hz, 3H), 0.81 (d, J=8.0 Hz, 3H).

Example 56: Preparation of Compound 74

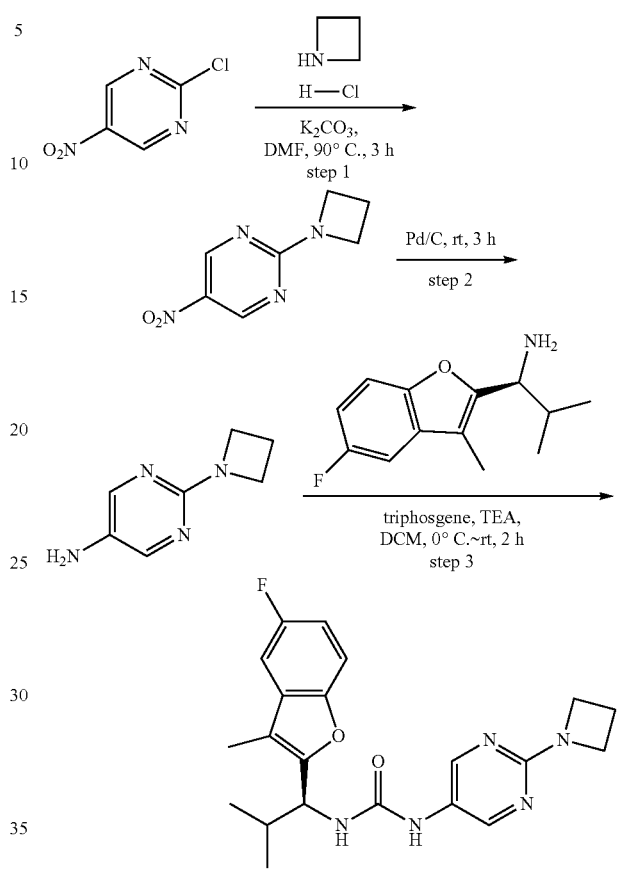

Compound 74

Step 1

To a mixture of 2-chloro-5-nitropyrimidine (2.0 g, 12.5 mol), azetidine hydrochloride (1.4 g, 15.0 mol) in DMF (10 mL) was added $K_2CO_3$ (5.2 g, 37.5 mol) and the reaction mixture was stirred at 90° C. for 3 h. The mixture was diluted with water and extracted with EA (50 mL×3). The organic layer was dried over anhydrous $Na_2SO_4$ and concentrated under reduced pressure to give a residue which was purified by silica gel chromatography column (PE/EA from 0~50%) to give 2-(azetidin-1-yl)-5-nitropyrimidine (1.2 g, 48%) as yellow solid. MS (ESI): mass calcd. for $C_7H_8N_4O_2$, 180.1, m/z found 181.1 $[M+H]^+$.

Step 2

To a solution of 2-(azetidin-1-yl)-5-nitropyrimidine (1.2 g, 6.7 mmol) in MeOH (10 mL) was added Pd/C (0.14 g) and the reaction mixture was stirred under $H_2$ at 20° C. for 3 h. After completion, the reaction mixture was filtered and the filtrate was collected and concentrated to give 2-(azetidin-1-yl) pyrimidin-5-amine (1 g, 90%) as yellow solid which was used in the next step directly. MS (ESI): mass calcd. for $C_7H_{10}N_4$, 150.1, m/z found 151.1 $[M+H]^+$.

Step 3

To a mixture of (1S)-1-(5-fluoro-3-methyl-1-benzofuran-2-yl)-2-methylpropan-1-amine (50 mg, 0.23 mmol) and triethylamine (69 mg, 0.68 mmol) in DCM (10 mL) was added triphosgene (54 mg, 0.18 mmol) at 0° C. After stirring at 20° C. for 0.5 h, 2-(azetidin-1-yl) pyrimidin-5-amine (34 mg, 0.23 mmol) was added at 0° C. and the reaction mixture was stirred at 20° C. for 2 h. After completion, the reaction mixture was concentrated under reduced pressure to give a residue which was purified by prep-HPLC to give S)-1-(2-(azetidin-1-yl)pyrimidin-5-yl)-3-(1-(5-fluoro-3-methylbenzofuran-2-yl)-2-methylpropyl)urea (78 mg, 87%) as white solid. MS (ESI): mass calcd. for $C_{21}H_{24}FN_5O_2$, 397.2, m/z found 398.1 $[M+H]^+$.

$^1$H NMR (400 MHz, DMSO) δ 8.32 (s, 2H), 8.18 (s, 1H), 7.52-7.49 (m, 1H), 7.38-7.36 (m, 1H), 7.12-7.07 (m, 1H), 6.90 (d, J=8.0 Hz, 1H), 4.72 (t, J=8.0 Hz, 1H), 3.97-3.93 (m, 4H), 2.36-2.22 (m, 2H), 2.19 (s, 3H), 2.13-2.08 (m, 1H), 1.01 (d, J=6.8 Hz, 3H), 0.81 (d, J=6.8 Hz, 3H).

Example 57: Preparation of Compound 75 and Compound 76

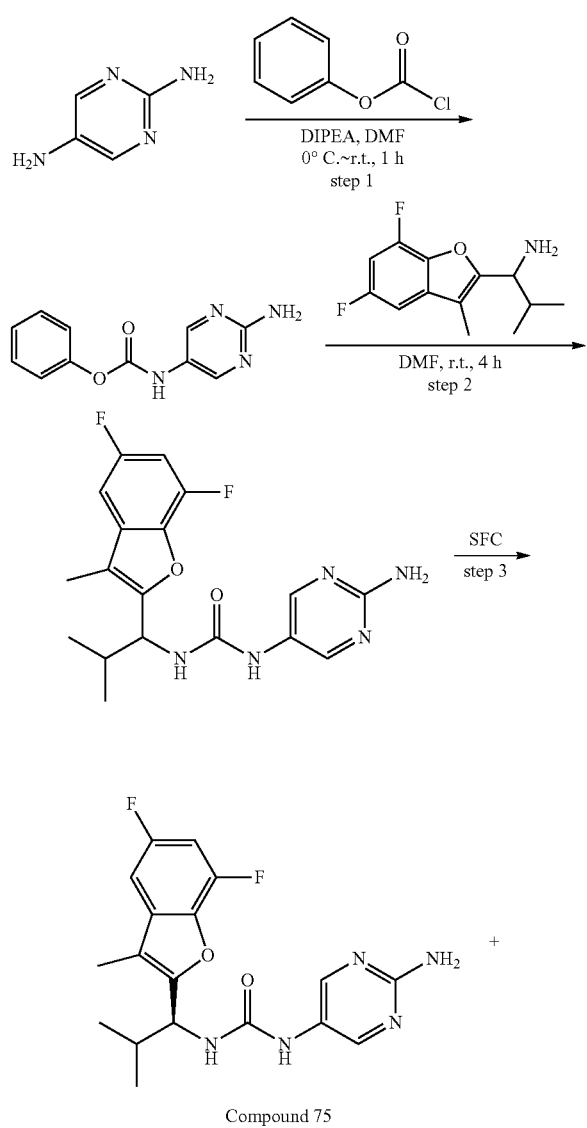

Compound 75

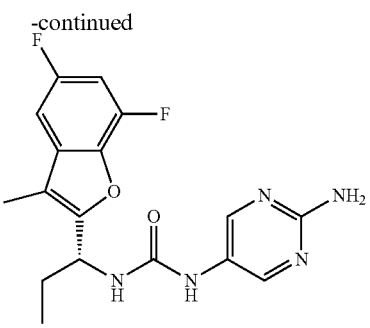

Compound 76

Step 1

To a mixture of pyrimidine-2,5-diamine (300 mg, 2.73 mmol) and DIPEA (1.06 g, 8.19 mmol) in DMF (8 mL) was added phenyl carbonochloridate (428.6 mg, 2.73 mmol) at 0° C. The reaction mixture was stirred at room temperature for 1 h. After completion, the resulting reaction was used into the next step without further any work-up. MS (ESI): mass calcd. for $C_{11}H_{10}N_4O_2$, 230.08, m/z found 231.1 $[M+H]^+$.

Step 2

To the reaction solution from step 1 was added 1-(5,7-difluoro-3-methylbenzofuran-2-yl)-2-methylpropan-1-amine (208 mg, 0.87 mmol) and the reaction mixture was stirred at room temperature for 4 h. After completion, the resulting mixture was diluted with water (30 mL), extracted with EtOAc (30 mL×3). The combined organic layers were washed with brine (40 mL), dried over anhydrous $Na_2SO_4$. After filtration, the filtrate was concentrated under reduced pressure. The residue was purified by flash chromatography (DCM/MeOH from 1 to 8%) to afford 1-(2-aminopyrimidin-5-yl)-3-(1-(5,7-difluoro-3-methylbenzofuran-2-yl)-2-methylpropyl)urea (180 mg, 55% based on the 1-(5,7-difluoro-3-methylbenzofuran-2-yl)-2-methylpropan-1-amine) as a white solid. MS (ESI): mass calcd. for $C_{18}H_{19}F_2N_5O_2$, 375.15, m/z found 376.1 $[M+H]^+$.

Step 3

The product from Step 2 (180 mg) was separated by SFC 80 (Daicel CHIRALCEL IE, 250×30 mm I.D., 10 μm 70/30 $CO_2$/MeOH [0.2% $NH_3$ (7M Solution in MeOH)], 70 g/min, 120 bar, 35° C.) to give two enantiomers: (S)-1-(2-aminopyrimidin-5-yl)-3-(1-(5,7-difluoro-3-methylbenzofuran-2-yl)-2-methylpropyl)urea (Compound 75, 65 mg, 36%) as a white solid and (R)-1-(2-aminopyrimidin-5-yl)-3-(1-(5,7-difluoro-3-methylbenzofuran-2-yl)-2-methylpropyl)urea (Compound 76, 61 mg, 34%) as a white solid respectively.

Compound 75

MS (ESI): mass calcd. for $C_{18}H_{19}F_2N_5O_2$, 375.15, m/z found 376.2 $[M+H]^+$.

$^1$H NMR (400 MHz, DMSO) δ 8.18 (s, 2H), 7.99 (s, 1H), 7.32-7.21 (m, 2H), 6.93 (d, J=8.7 Hz, 1H), 6.27 (s, 2H), 4.73 (t, J=8.6 Hz, 1H), 2.20 (s, 3H), 2.14-2.09 (m, 1H), 1.02 (d, J=6.7 Hz, 3H), 0.81 (d, J=6.7 Hz, 3H).

Compound 76

P2: MS (ESI): mass calcd. for $C_{18}H_{19}F_2N_5O_2$, 375.15, m/z found 376.2 [M+H]+.

P2: 1H NMR (400 MHz, DMSO) δ 8.18 (s, 2H), 7.98 (s, 1H), 7.33-7.20 (m, 2H), 6.92 (d, J=8.7 Hz, 1H), 6.27 (s, 2H), 4.73 (t, J=8.6 Hz, 1H), 2.20 (s, 3H), 2.14-2.09 (m, 1H), 1.02 (d, J=6.7 Hz, 3H), 0.81 (d, J=6.7 Hz, 3H).

Example 58: Preparation of Compound 77

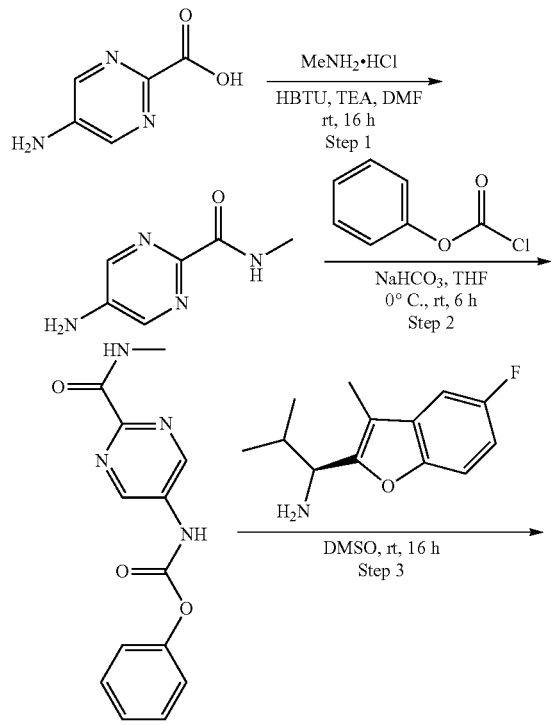

Compound 77

Step 1

To a stirred solution of 5-aminopyrimidine-2-carboxylic acid (250 mg, 1.8 mmol) in anhydrous DMF (10 mL) were added methylamine hydrochloride (128 mg, 1.9 mmol), TEA (547 mg, 5.4 mmol), HBTU (1.02 g, 2.7 mmol). The reaction mixture was stirred at room temperature for 16 h. After completion, the reaction mixture was quenched with water (100 mL) and extracted with EA (100 mL×2). The combined organic phase was washed with brine (300 mL), dried over anhydrous $Na_2SO_4$ and concentrated under reduced pressure to give a residue which was purified by silica gel chromatography column (DCM/MeOH from 0~10%) to give 5-amino-N-methylpyrimidine-2-carboxamide (460 mg) as pale yellow solid. MS (ESI): mass calcd. for $C_6H_8N_4O$, 152.1, m/z found 153.1 [M+H]+.

Step 2

To a stirred solution of 5-amino-N-methylpyrimidine-2-carboxamide (200 mg, 1.3 mmol) in anhydrous THF (50 mL) were added $NaHCO_3$ (555 mg, 6.6 mmol), phenyl chloroformate (310 mg, 2.0 mmol) at 0° C. The reaction mixture was stirred at room temperature for 6 h. After completion, the reaction mixture was concentrated under reduced pressure to obtain a solid which was redissolved with EA. The organic mixture was washed with water and brine, dried over anhydrous $Na_2SO_4$ and concentrated under reduced pressure to give phenyl (2-(methylcarbamoyl)pyrimidin-5-yl) carbamate (300 mg crude) as yellow oil which was used directly in next step.

MS (ESI): mass calcd. for $C_{13}H_{12}N_4O_3$, 272.1, m/z found 273.2 [M+H]+.

Step 3

To a stirred solution of phenyl N-(2-(methylcarbamoyl)pyrimidin-5-yl)carbamate (50 mg, 0.18 mmol) in DMSO (2 mL) was added (1S)-1-(5-fluoro-3-methyl-1-benzofuran-2-yl)-2-methylpropan-1-amine (41 mg, 0.18 mmol). The reaction mixture was stirred at room temperature for 16 h. After completion, the suspension was filtered. The filtered cake was washed with EtOH and Ether to obtain a solid which was dried in vacuum to give (S)-5-(3-(1-(5-fluoro-3-methylbenzofuran-2-yl)-2-methylpropyl) ureido)-N-methylpyrimidine-2-carboxamide (13 mg, 17%) as white solid. MS (ESI): mass calcd. for $C_{20}H_{22}FN_5O_3$, 399.2, m/z found 400.2 [M+H]+.

1H NMR (400 MHz, DMSO) δ 9.02 (s, 1H), 8.91 (s, 2H), 8.70-8.66 (m, 1H), 7.54-7.50 (m, 1H), 7.40-7.37 (m, 1H), 7.27 (d, J=8.8 Hz, 1H), 7.13-7.07 (m, 1H), 4.77 (t, J=8.4 Hz, 1H), 2.78 (d, J=4.8 Hz, 3H), 2.22 (s, 3H), 2.19-2.10 (m, 1H), 1.03 (d, J=6.8 Hz, 3H), 0.83 (d, J=6.8 Hz, 3H).

Example 59: Preparation of Compound 78

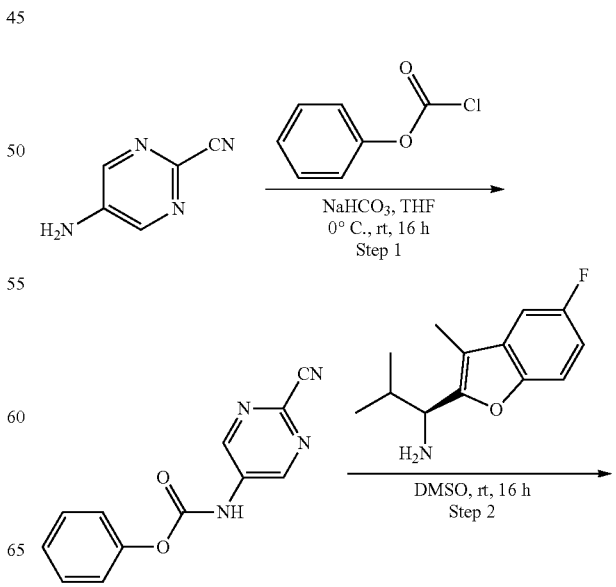

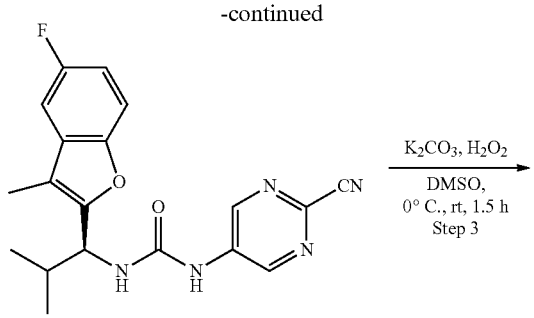

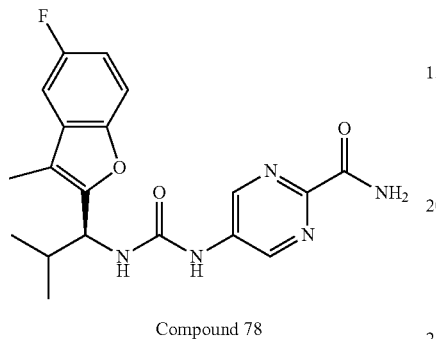

Compound 78

Step 1

To a stirred solution of 5-aminopyrimidine-2-carbonitrile (120 mg, 1.0 mmol) in anhydrous THF (20 mL) were added NaHCO$_3$ (420 mg, 5.0 mmol), phenyl chloroformate (235 mg, 1.5 mmol) at 0° C. The reaction mixture was stirred at room temperature for 16 h. After completion, the reaction mixture was concentrated under reduced pressure. The residue was redissolved with EA, washed with water and brine. The organic phase was dried over anhydrous Na$_2$SO$_4$ and concentrated under reduced pressure to give phenyl (2-cyanopyrimidin-5-yl) carbamate (330 mg, crude) as pale-yellow oil. The crude was used in next step without further purification. MS (ESI): mass calcd. for C$_{12}$H$_8$N$_4$O$_2$, 240.1, m/z found 241.1 [M+H]$^+$.

Step 2

To a stirred solution of phenyl N-(2-cyanopyrimidin-5-yl)carbamate (300 mg, 1.25 mmol) in DMSO (4 mL) was added (1S)-1-(5-fluoro-3-methyl-1-benzofuran-2-yl)-2-methylpropan-1-amine (277 mg, 1.25 mmol). The reaction mixture was stirred at room temperature for 16 h. After completion, the reaction mixture was redissolved with EA, washed with water and brine. The organic phase was dried over anhydrous Na$_2$SO$_4$ and concentrated to give a residue which was purified by silica gel column chromatography (DCM/MeOH from 0~10%) to give (S)-1-(2-cyanopyrimidin-5-yl)-3-(1-(5-fluoro-3-methylbenzofuran-2-yl)-2-methylpropyl)urea (350 mg, 76%) as pale yellow oil. MS (ESI): mass calcd. for C$_{19}$H$_{18}$FN$_5$O$_2$, 367.1, m/z found 368.2 [M+H]$^+$.

Step 3

To a stirred solution of (S)-1-(2-cyanopyrimidin-5-yl)-3-(1-(5-fluoro-3-methylbenzofuran-2-yl)-2-methylpropyl)urea (120 mg, 0.33 mmol) in DMSO (6 mL) were added H$_2$O$_2$ (30%, 1.5 mL), K$_2$CO$_3$ (10 mg, 0.066 mmol) at 0° C. The reaction mixture was stirred at room temperature for 1.5 h. After completion, the reaction mixture was quenched with water and concentrated in vacuum to give a residue which was purified by prep-HPLC to give (S)-5-(3-(1-(5-fluoro-3-methylbenzofuran-2-yl)-2-methylpropyl)ureido)pyrimidine-2-carboxamide (91 mg, 72%) as a white solid. MS (ESI): mass calcd. for C$_{19}$H$_{20}$FN$_5$O$_3$, 385.2, m/z found 386.2 [M+H]$^+$.

$^1$H NMR (400 MHz, DMSO) δ 9.06 (s, 1H), 8.91 (s, 2H), 8.02 (s, 1H), 7.60 (s, 1H), 7.54-7.50 (m, 1H), 7.40-7.37 (m, 1H), 7.29 (d, J=8.4 Hz, 1H), 7.13-7.07 (m, 1H), 4.77 (t, J=8.4 Hz, 1H), 2.22 (s, 3H), 2.20-2.10 (m, 1H), 1.04 (d, J=6.8 Hz, 3H), 0.83 (d, J=6.8 Hz, 3H).

Example 60: Preparation of Compound 79 and Compound 80

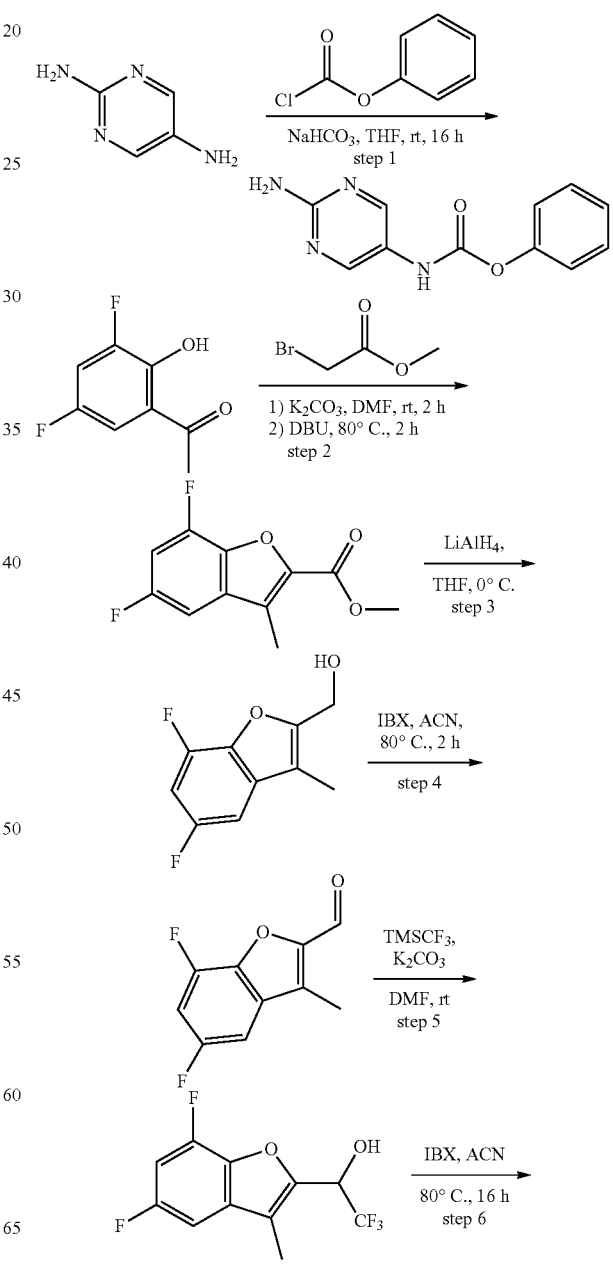

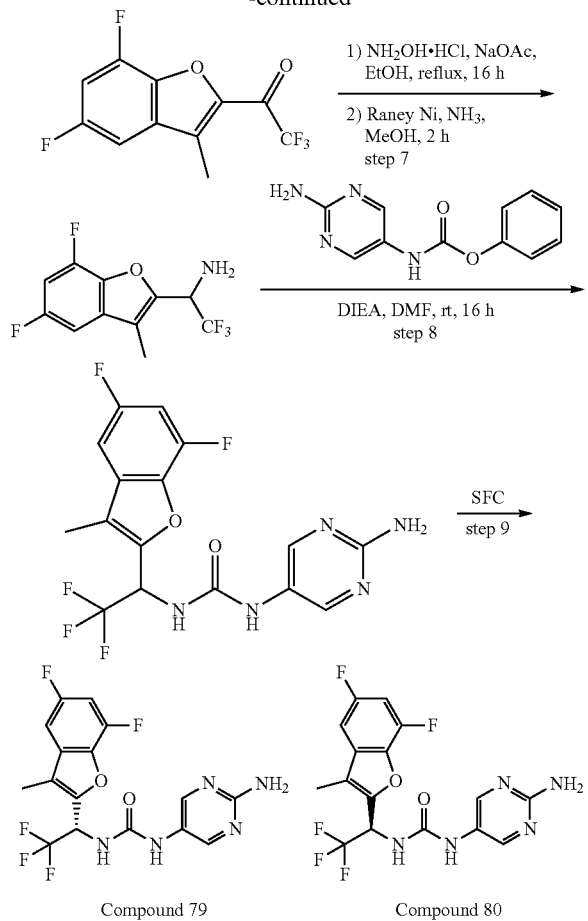

Compound 79      Compound 80

Step 1

To a mixture of pyrimidine-2,5-diamine (3.0 g, 27.2 mmol) and NaHCO₃ (11.4 g, 135.9 mmol) in THF (300 mL) was added phenyl carbonochloridate (4.5 g, 28.5 mmol) dropwise at 0° C. The mixture was stirred at 25° C. for 4 h. After reaction, the reaction mixture was concentrated to give a residue which was purified by silica gel chromatography column (DCM/MeOH from 0~10%) to give phenyl (2-aminopyrimidin-5-yl)carbamate (2.2 g, 34%) as a brown solid. MS (ESI): mass calcd. for $C_{11}H_{10}N_4O_2$, 230.1, m/z found 231.1 $[M+H]^+$.

Step 2

To a solution of 1-(3,5-difluoro-2-hydroxyphenyl)ethan-1-one (20 g, 116.2 mmol) in DMF (200 mL) were added methyl 2-bromoacetate (19.4 g, 127.9 mmol) and K₂CO₃ (24.1 g, 174.4 mmol) at room temperature. The reaction mixture was stirred at room temperature for 2 h. After reaction, the insoluble material was filtered off and DBU (17.7 g, 116.2 mmol) was added into the filtrate which was stirred again at 80° C. for 2 h. After reaction, the reaction mixture was concentrated to give a residue which was purified by silica gel chromatography column (PE/DCM from 0~35%) to give methyl 5,7-difluoro-3-methylbenzo-furan-2-carboxylate (8.4 g, 32%) as off-white solid. MS (ESI): mass calcd. for $C_{11}H_8F_2O_3$, 226.0, m/z found 227.0 $[M+H]^+$.

Step 3

To a solution of 5,7-difluoro-3-methylbenzofuran-2-carboxylate (8.1 g, 35.8 mmol) in THF (160 mL) was added LiAlH₄ (21.5 mL, 21.5 mmol, 1M in THF) at 0° C. The reaction mixture was stirred at 0° C. for 2 h. then slowly quenched with saturated aqueous potassium carbonate (150 mL) and extracted with EA (200 mL×3). The combined organic layer was washed with brine and dried with Na₂SO₄ and concentrated to give a residue which was purified by silica gel chromatography column (PE/EA from 0~30%) to give (5,7-difluoro-3-methylbenzofuran-2-yl)methanol (6.5 g, 91%) as an off-white solid. MS (ESI): mass calcd. for $C_{10}H_8F_2O_2$, 198.0, m/z found 181.0 $[M-H_2O+H]^+$.

Step 4

To a solution of (5,7-difluoro-3-methylbenzofuran-2-yl)methanol (6.5 g, 32.6 mmol) in ACN (65 mL) was added IBX (13.7 g, 49.0 mmol) at room temperature. The reaction mixture was stirred at 80° C. for 2 h. The insoluble material was then filtered off and the filtrate was concentrated to give a residue which was purified by silica gel chromatography column (PE/EA from 0~15%) to give 5,7-difluoro-3-methylbenzofuran-2-carbaldehyde (6.1 g, 95%) as an off-white solid. MS (ESI): mass calcd. for $C_{10}H_6F_2O_2$, 196.0, m/z found 197.1 $[M+H]^+$.

Step 5

To a solution of 5,7-difluoro-3-methylbenzofuran-2-carbaldehyde (6.1 g, 31.1 mmol) in DMF (92 mL) were added trimethyl(trifluoromethyl)silane (8.89 g, 62.2 mmol) and K₂CO₃ (2.1 g, 15.5 mmol) at 0° C. The reaction mixture was stirred at room temperature for 0.5 h and then another batch of K₂CO₃ (4.3 g, 31.0 mmol) was added into the reaction mixture. The mixture was stirred at room temperature for 16 h and then H₂O (2.8 g, 115.5 mmol) was added, and the reaction mixture was further stirred at 0° C. for 1 h. The mixture was quenched with ice water and extracted with EA (200 mL×3). The combined organic layer was washed with brine and dried with Na₂SO₄ and concentrated to give a residue which was purified by silica gel chromatography column (PE/EA from 0~20%) to give 1-(5,7-difluoro-3-methylbenzofuran-2-yl)-2,2,2-trifluoroethan-1-ol (6.5 g, 78%) as light yellow oil. MS (ESI): mass calcd. for $C_{11}H_7F_5O_2$, 266.0, m/z found 249.1 $[M-H_2O+H]^+$.

Step 6

To a solution of 1-(5,7-difluoro-3-methylbenzofuran-2-yl)-2,2,2-trifluoroethan-1-ol (370 mg, 1.39 mmol) in ACN (10 mL) was added IBX (584 mg, 2.08 mmol). The reaction mixture was refluxed for 16 h. After reaction, the mixture was filtered and washed with EA. The filtrate was collected and concentrated to give a residue which was purified by silica gel chromatography column (PE/EA from 0~20%) to 1-(5,7-difluoro-3-methylbenzofuran-2-yl)-2,2,2-trifluoroethan-1-one (320 mg, 87%) as yellow oil. ¹H NMR (400 MHz, DMSO) δ 7.82-7.74 (m, 2H), 2.65 (s, 3H).

Step 7

A mixture of 1-(5,7-difluoro-3-methylbenzofuran-2-yl)-2,2,2-trifluoroethan-1-one (320 mg, 1.21 mmol), hydroxylamine hydrochloride (585 mg, 8.48 mmol) and NaOAc (992 mg, 12.10 mmol) in EtOH (10 mL) was refluxed for 16 h. After reaction, the mixture was concentrated and redissolved in MeOH (10 mL) which was added Raney Ni (50 mg) and one drop of ammonia. The mixture was stirred under $H_2$ at room temperature for 6 h. After reaction, the mixture was filtered and the filtrate was concentrated to give a residue which was purified by silica gel chromatography column (PE/EA from 0~50%) to give 1-(5,7-difluoro-3-methylbenzofuran-2-yl)-2,2,2-trifluoroethan-1-amine (150 mg, 47%) as light yellow oil. MS (ESI): mass calcd. for $C_{11}H_8F_5NO$, 265.0, m/z found 249.1 $[M-NH_3+H]^+$.

Step 8

To a mixture of 1-(5,7-difluoro-3-methylbenzofuran-2-yl)-2,2,2-trifluoroethan-1-amine (150 mg, 0.57 mmol), DIEA (219 mg, 1.70 mmol) in DMF (10 mL) was added phenyl (2-aminopyrimidin-5-yl)carbamate (143 mg, 0.62 mmol) at 0° C. The reaction mixture was then stirred at room temperature for 16 h then quenched with water and extracted with EA (50 mL×3). The combined organic layer was concentrated to give a residue which was purified by silica gel chromatography column (PE/EA from 0~50%) to give (rac)-1-(2-aminopyrimidin-5-yl)-3-(1-(5,7-difluoro-3-methylbenzofuran-2-yl)-2,2,2-trifluoroethyl)urea (150 mg, 66%) as light yellow oil. MS (ESI): mass calcd. for: $C_{16}H_{12}F_5N_5O_2$, 401.1, m/z found 402.1 $[M+H]^+$.

Step 9

(rac)1-(2-aminopyrimidin-5-yl)-3-(1-(5,7-difluoro-3-methylbenzofuran-2-yl)-2,2,2-trifluoroethyl) urea (150 mg) was separated by chiral HPLC to give Compound 79 (peak 1, 61 mg, 41%) and Compound 80 (peak 2, 58 mg, 39%) MS (ESI): mass calcd. for $C_{16}H_{12}F_5N_5O_2$, 401.1, m/z found 402.1 $[M+H]^+$.

Compound 79 (Peak 1)

$^1$H NMR (400 MHz, DMSO-d6) δ 8.21 (s, 2H), 8.20 (s, 1H), 7.81 (d, J=8.0 Hz, 1H), 7.46-7.39 (m, 2H), 6.40 (s, 2H), 6.09-5.98 (m, 1H), 2.29 (s, 3H).

Compound 80 (Peak 2)

$^1$H NMR (400 MHz, DMSO-d6) δ 8.19 (s, 2H), 8.18 (s, 1H), 7.79 (d, J=8.0 Hz, 1H), 7.46-7.34 (m, 2H), 6.37 (s, 2H), 6.03-5.97 (m, 1H), 2.27 (s, 3H).

Example 61: Preparation of Compound 81 and Compound 82

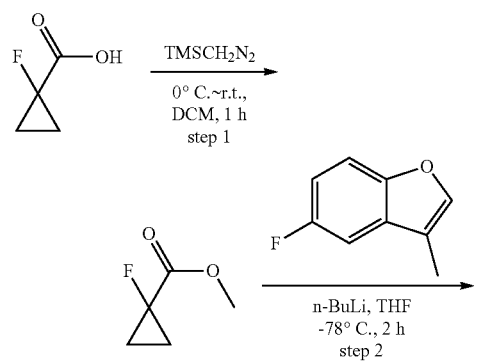

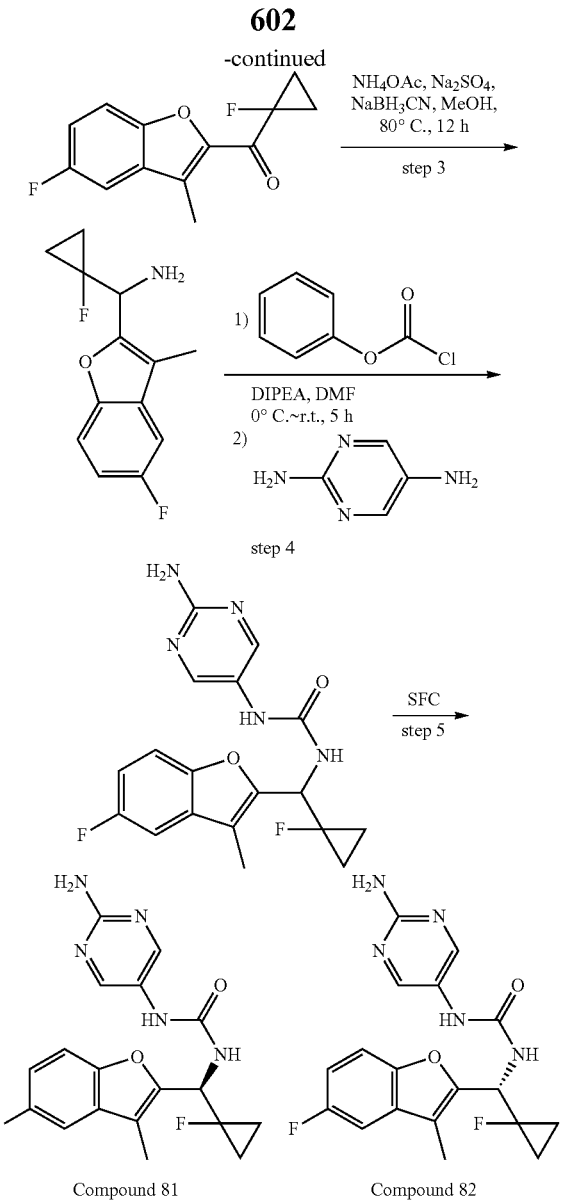

Step 1

To a mixture of 1-fluorocyclopropane-1-carboxylic acid (1.0 g, 9.62 mmol) in DCM (15 mL) was added $TMSCH_2N_2$ (1.1 g, 9.62 mmol) at 0° C. The reaction mixture was stirred at room temperature for 1 h. After completion, the resulting reaction was concentrated to give the crude, which was used into the next step without purification.

Step 2

To a stirred solution of 5-fluoro-3-methylbenzofuran (1.08 g, 7.2 mmol) in THF (16 mL) was slowly added n-BuLi (3.46 mL, 8.64 mmol, 2.5 M solution in hexanes) at −78° C. After 30 min, methyl 1-fluorocyclopropane-1-carboxylate (1.02 g, 8.64 mmol) was added, and the reaction was stirred at −78° C. for another 2 h. The reaction was quenched with $NH_4Cl$ (sat. aq., 50 mL) and extracted with EtOAc (50 mL×3). The organic fractions were washed with brine (50 mL), dried over $Na_2SO_4$, filtered and concentrated to give the crude, which was purified with silica gel chromatography (PE/EtOAc from 1~20%) to give the (5-fluoro-3-methylbenzofuran-2-yl)(1-fluorocyclopropyl)methanone (830 mg, 49%) as a yellow oil. MS (ESI): mass calcd. for $C_{13}H_{10}F_2O_2$, 236.06, m/z found 237.1 [M+H]$^+$.

Step 3

A mixture of (5-fluoro-3-methylbenzofuran-2-yl)(1-fluorocyclopropyl)methanone (830 mg, 3.52 mmol), $NH_4OAc$ (2.71 g, 35.2 mmol) and $Na_2SO_4$ (150 mg, 1.06 mmol) in MeOH (20 mL) was stirred at room temperature for 30 min. Then $NaBH_3CN$ (233 mg, 3.7 mmol) was added and stirred at 80° C. for 12 hours. The reaction was quenched with $NH_4Cl$ (sat. aq., 40 mL) and extracted with EtOAc (50 mL×3). The combined organic layers were washed with brine (60 mL), dried over $Na_2SO_4$, filtered and concentrated to give the crude, which was purified with silica gel chromatography (DCM/MeOH from 1~8%) to give the (5-fluoro-3-methylbenzofuran-2-yl)(1-fluorocyclopropyl)methanamine (580 mg, 70%) as a white solid. MS (ESI): mass calcd. $C_{13}H_{13}F_2NO$, 237.1, m/z found 221.1 [M–NH$_2$]$^+$.

Step 4

To a reaction mixture of pyrimidine-2,5-diamine (200 mg, 1.82 mmol) and DIPEA (704 mg, 5.46 mmol) in DMF (4 mL) was added phenyl carbonochloridate (286 mg, 1.82 mmol) and stirred at room temperature for 1 hour. Then (5-fluoro-3-methylbenzofuran-2-yl)(1-fluorocyclopropyl)methanamine (431 mg, 1.82 mmol) was added and stirred at room temperature for another 4 h. After completed, the reaction was diluted with $H_2O$ (30 mL) and extracted with EtOAc (30 mL×3). The combined organic fractions were washed with brine (40 mL), dried over $Na_2SO_4$, filtered and concentrated to give the crude, which was purified with silica gel column chromatography (DCM/MeOH from 1~8%) to give the 1-(2-aminopyrimidin-5-yl)-3-((5-fluoro-3-methylbenzofuran-2-yl)(1-fluorocyclopropyl)methyl)urea (200 mg, 29%) as a white solid. MS (ESI): mass calcd. $C_{18}H_{17}F_2N_5O_2$, 373.14, m/z found 374.1 [M+H]$^+$.

Step 5

1-(2-aminopyrimidin-5-yl)-3-((5-fluoro-3-methylbenzofuran-2-yl)(1-fluorocyclopropyl)methyl)urea (200 mg) was separated by SFC 80 (Daicel CHIRALCEL OD, 250×30 mm I.D., 10 μm 55/45 CO$_2$/MeOH [0.2% NH3 (7M Solution in MeOH)], 70 g/min, 120 bar, 35° C.) to give two enantiomers: (R)-1-(2-aminopyrimidin-5-yl)-3-((5-fluoro-3-methylbenzofuran-2-yl)(1-fluorocyclopropyl)methyl)urea (Compound 81, 82.4 mg, 41%) as a white solid and (S)-1-(2-aminopyrimidin-5-yl)-3-((5-fluoro-3-methylbenzofuran-2-yl)(1-fluorocyclopropyl)methyl)urea (Compound 82, 81.2 mg, 41%) as a white solid respectively.

Compound 81

MS (ESI): mass calcd. for $C_{18}H_{17}F_2N_5O_2$, 373.14, m/z found 374.1 [M+H]$^+$.
$^1$H NMR (400 MHz, dmso) δ 8.20 (s, 2H), 8.15 (s, 1H), 7.57-7.53 (m, 1H), 7.44-7.41 (m, 1H), 7.27 (d, J=8.8 Hz, 1H), 7.16-7.11 (m, 1H), 6.32 (s, 2H), 5.20-5.12 (m, 1H), 2.22 (s, 3H), 1.13-1.05 (m, 2H), 0.90 (d, J=9.2 Hz, 2H).

Compound 82

MS (ESI): mass calcd. for $C_{18}H_{17}F_2N_5O_2$, 373.14, m/z found 374.1 [M+H]$^+$.
$^1$H NMR (400 MHz, dmso) δ 8.20 (s, 2H), 8.15 (s, 1H), 7.56-7.53 (m, 1H), 7.43-7.40 (m, 1H), 7.26 (d, J=8.7 Hz, 1H), 7.16-7.11 (m, 1H), 6.32 (s, 2H), 5.20-5.12 (m, 1H), 2.22 (s, 3H), 1.13-1.05 (m, 2H), 0.90 (d, J=9.2 Hz, 2H).

Example 62: Preparation of Compound 83 and Compound 84

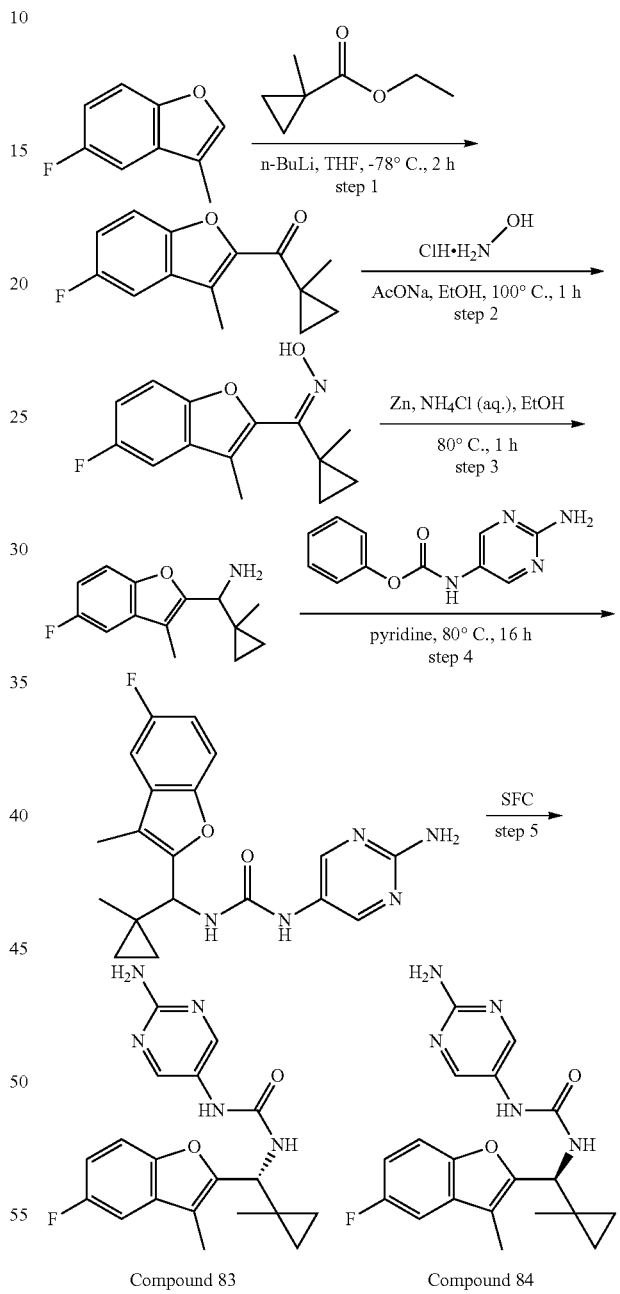

Compound 83    Compound 84

Step 1

To a solution of 5-fluoro-3-methyl-1-benzofuran (1.5 g, 9.99 mmol) in THF (20 mL) was added n-BuLi (2.5 M in hexane) (5.2 mL, 12.99 mmol) dropwise at −78° C. under nitrogen. The mixture was stirred at this temperature for 1 h. Ethyl 1-methylcyclopropane-1-carboxylate (1.9 g, 14.99 mmol) in THF was added to the mixture dropwise at −78° C. The mixture was stirred for 1 h. TLC (PE/EA=20/1) showed the reaction was completed. The mixture was added to water, extracted with EA. The organic layer was washed with brine, dried over sodium sulfate, concentrated in vacuum to give (5-fluoro-3-methylbenzofuran-2-yl)(1-methylcyclopropyl)methanone (1.8 g crude) as brown solid. MS (ESI): mass calcd. for C14H13FO2, 232.1, m/z found 233.1 [M+H]$^+$.

Step 2

To a solution of (5-fluoro-3-methylbenzofuran-2-yl)(1-methylcyclopropyl)methanone (1.8 g crude) in EtOH (15 mL) was added hydroxylamine hydrochloride (3.4 g, 49.95 mmol) and AcONa (4.1 g, 49.95 mmol). The mixture was stirred at 100° C. for 1 h. After completion, the mixture was added to water, extracted with EA. The organic layer was washed with brine, dried over sodium sulfate, concentrated in vacuum. The residue was purified by column chromatography on silica gel (PE/EA from 20/1 to 10/1) to give (Z)-(5-fluoro-3-methylbenzofuran-2-yl)(1-methylcyclopropyl)methanone oxime (125 mg, 5% over two steps). MS (ESI): mass calcd. for C14H14FNO2, 247.1, m/z found 248.1 [M+H]$^+$.

Step 3

To a solution of (Z)-(5-fluoro-3-methylbenzofuran-2-yl)(1-methylcyclopropyl)methanone oxime (125 mg, 0.61 mmol) in EtOH (5 mL) was added NH4Cl (aq.) and Zn (334 mg, 5.1 mmol). The mixture was stirred at 80° C. for 1 h. After completion, the mixture was added to water, extracted with EA. The organic layer was washed with brine, dried over sodium sulfate, concentrated in vacuum to give (5-fluoro-3-methylbenzofuran-2-yl)(1-methylcyclopropyl)methanamine (80 mg, 67%) as white solid. MS (ESI): mass calcd. for C14H16FNO, 233.1, m/z found 217.1 [M+H−17]$^+$.

Step 4

To a solution of pyrimidine-2,5-diamine (37 mg, 0.34 mmol) in pyridine (3 mL) was added phenyl chloroformate (53 mg, 0.34 mmol). The mixture was stirred at 25° C. for 1 h. (5-Fluoro-3-methylbenzofuran-2-yl)(1-methylcyclopropyl)methanamine (80 mg, 0.34 mmol) was added to the mixture and the mixture was stirred at 80° C. for 16 h. After completion, the mixture was concentrated in vacuum. The residue was purified by reverse phase (ACN/water from 0~70%) to give 1-(2-aminopyrimidin-5-yl)-3-((5-fluoro-3-methylbenzofuran-2-yl)(1-methylcyclopropyl)methyl)urea (42 mg, 34%) as white solid. MS (ESI): mass calcd. for C19H20FN5O2, 369.1, m/z found 370.1 [M+H]$^+$.

Step 5

42 mg of 1-(2-aminopyrimidin-5-yl)-3-((5-fluoro-3-methylbenzofuran-2-yl)(1-methylcyclopropyl)methyl)urea was separated by SFC to give (R)-1-(2-aminopyrimidin-5-yl)-3-((5-fluoro-3-methylbenzofuran-2-yl)(1-methylcyclopropyl)methyl)urea Compound 83 (10.6 mg) as white solid and (S)-1-(2-aminopyrimidin-5-yl)-3-((5-fluoro-3-methylbenzofuran-2-yl)(1-methylcyclopropyl)methyl)urea Compound 84 (10.8 mg) as white solid.

Chiral Separation Conditions:

Apparatus: SFC 80

Column: Daicel CHIRALCEL OD, 250 mm×30 mm I.D., 10 μm

Mobile phase: CO2/MeOH [0.2% NH3 (7M Solution in MeOH)]=65/35

Flow rate: 70 g/min

Wavelength: UV 214 nm

Temperature: 35° C.

Compound 83

MS (ESI): mass calcd. for C19H20FN5O2, 369.1, m/z found 370.1 [M+H]$^+$.

$^1$H NMR (400 MHz, DMSO-d$_6$) δ 8.19 (s, 2H), 8.09-8.03 (m, 1H), 7.52 (dd, J=9.2, 4.4 Hz, 1H), 7.38 (dd, J=8.8, 2.8 Hz, 1H), 7.10 (td, J=9.2, 2.8 Hz, 1H), 7.00-6.87 (m, 1H), 6.29 (s, 2H), 4.73 (d, J=8.8 Hz, 1H), 2.18 (s, 3H), 1.09 (s, 3H), 0.59 (s, 2H), 0.39-0.28 (m, 2H).

Compound 84

MS (ESI): mass calcd. for C19H20FN5O2, 369.1, m/z found 370.1 [M+H]$^+$.

$^1$H NMR (400 MHz, DMSO-d$_6$) δ 8.24 (s, 2H), 8.20-8.11 (m, 1H), 7.52 (dd, J=8.8, 4.0 Hz, 1H), 7.38 (dd, J=8.8, 2.8 Hz, 1H), 7.10 (td, J=9.2, 2.8 Hz, 1H), 6.98-6.94 (m, 1H), 6.46 (s, 2H), 4.73 (d, J=8.8 Hz, 1H), 2.19 (s, 3H), 1.09 (s, 3H), 0.59 (s, 2H), 0.45-0.21 (m, 2H).

Example 63: Preparation of Compound 85 and Compound 86

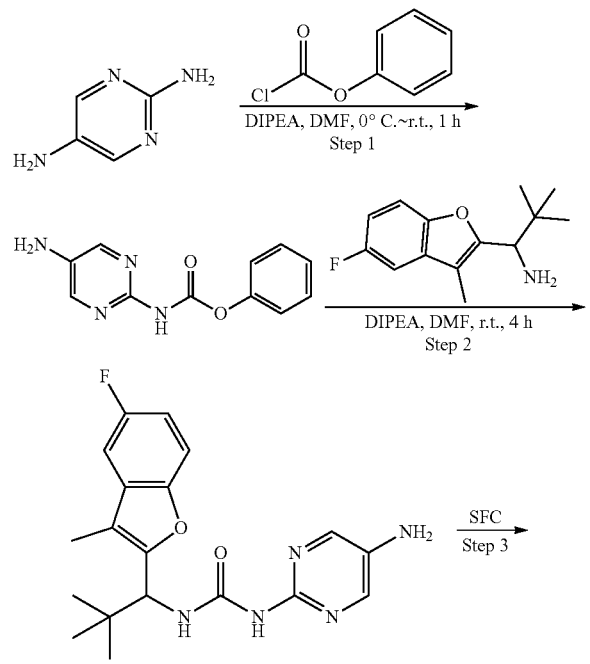

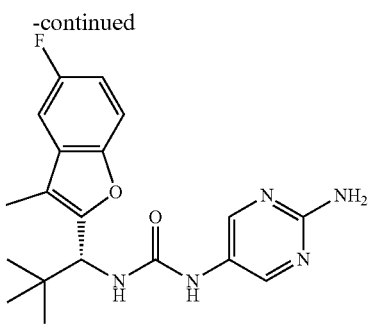

Compound 85

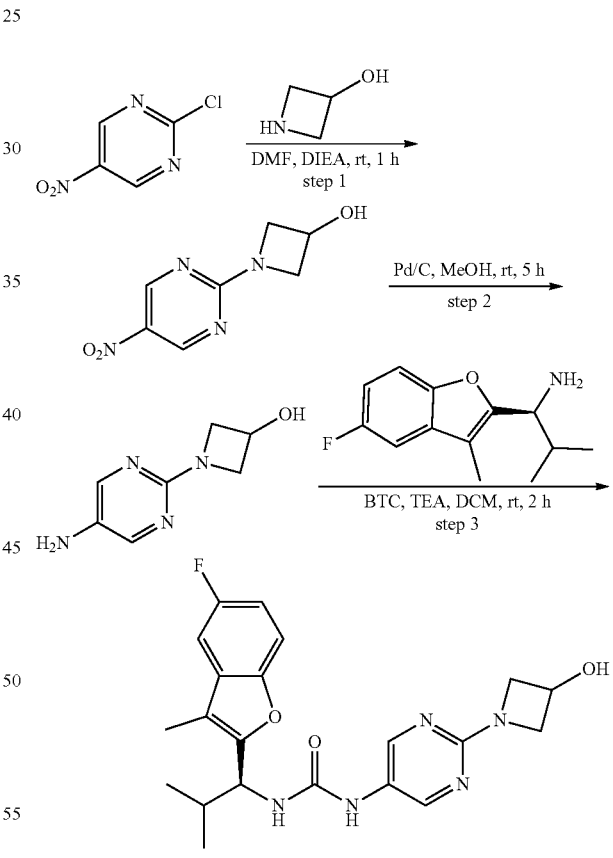

Compound 86

Step 1

To a mixture of pyrimidine-2,5-diamine (200 mg, 1.8 mmol) and DIPEA (697 mg, 5.4 mmol) in DMF (4 mL) was added phenyl carbonochloridate (283 mg, 1.8 mmol) at 0° C. The reaction mixture was stirred at room temperature for 1 h under $N_2$. After completion, the resulting reaction was used into the next step without further any work-up. MS (ESI): mass calcd. for $C_{11}H_{10}N_4O_2$, 230.08, m/z found 231.1 [M+H]$^+$.

Step 2

To the reaction solution from step 1 was added 1-(5-fluoro-3-methylbenzofuran-2-yl)-2,2-dimethylpropan-1-amine (424 mg, 1.8 mmol) and the reaction mixture was stirred at room temperature for 4 h. After completion, the resulting mixture was diluted with water (25 mL), extracted with EtOAc (35 mL×3). The combined organic layers were washed with brine (35 mL), dried over anhydrous $Na_2SO_4$. After filtration, the filtrate was concentrated under reduced pressure. The residue was purified by flash chromatography (DCM/MeOH from 1 to 8%) to afford 1-(5-aminopyrimidin-2-yl)-3-(1-(5-fluoro-3-methylbenzofuran-2-yl)-2,2-dimethylpropyl)urea (120 mg, 18% based on the start material 4) as a white solid. MS (ESI): mass calcd. for $C_{19}H_{22}FN_5O_2$, 371.18, m/z found 372.2 [M+H]$^+$.

Step 3

1-(5-aminopyrimidin-2-yl)-3-(1-(5-fluoro-3-methylbenzofuran-2-yl)-2,2-dimethylpropyl)urea (120 mg) was separated by SFC 80 (Daicel CHIRALCEL OD, 250×30 mm I.D., 10 μm 50/50 CO$_2$/MeOH [0.2% NH3 (7M Solution in MeOH)], 70 g/min, 120 bar, 35° C.) to give two enantiomers:(R)-1-(5-aminopyrimidin-2-yl)-3-(1-(5-fluoro-3-methylbenzofuran-2-yl)-2,2-dimethylpropyl)urea (Compound 85, 60 mg, 9%) as a white solid and (S)-1-(5-aminopyrimidin-2-yl)-3-(1-(5-fluoro-3-methylbenzofuran-2-yl)-2,2-dimethylpropyl)urea (Compound 86, 50 mg, 7%) as a white solid respectively.

Compound 85

MS (ESI): mass calcd. for $C_{19}H_{22}FN_5O_2$, 371.18, m/z found 372.2 [M+H]$^+$.

$^1$H NMR (400 MHz, dmso) δ 8.19 (s, 2H), 8.13 (s, 1H), 7.50 (dd, J=8.9, 4.1 Hz, 1H), 7.38 (dd, J=8.8, 2.6 Hz, 1H), 7.13-7.06 (m, 1H), 6.88 (d, J=9.4 Hz, 1H), 6.27 (s, 2H), 4.83 (d, J=9.4 Hz, 1H), 2.18 (s, 3H), 0.98 (s, 9H).

Compound 86

MS (ESI): mass calcd. for $C_{19}H_{22}FN_5O_2$, 371.18, m/z found 372.2 [M+H]$^+$.

$^1$H NMR (400 MHz, dmso) δ 8.19 (s, 2H), 8.11 (s, 1H), 7.50 (dd, J=8.9, 4.1 Hz, 1H), 7.38 (dd, J=8.8, 2.6 Hz, 1H), 7.13-7.06 (m, 1H), 6.87 (d, J=9.4 Hz, 1H), 6.27 (s, 2H), 4.83 (d, J=9.4 Hz, 1H), 2.18 (s, 3H), 0.98 (s, 9H).

Example 64: Preparation of Compound 87

Step 1

To a mixture of 2-chloro-5-nitropyrimidine (1 g, 6.3 mmol) and DIEA (3.2 g, 25.1 mmol) in DMF (20 mL) was added azetidin-3-ol (1.4 g, 12.6 mmol) at room temperature. The reaction mixture was stirred at room temperature for 1 h. After completion, the reaction mixture was diluted with water and extracted with EA (100 mL×3). The combined organic layer was concentrated to give a residue which was purified by silica gel chromatography column (PE/EA from 0~50%) to give 1-(5-nitropyrimidin-2-yl)azetidin-3-ol (1.2 g, 97%) as yellow solid. MS (ESI): mass calcd. for $C_7H_8FN_4O_3$, 196.1, m/z found 197.1 [M+H]$^+$.

Step 2

To a solution of 1-(5-nitropyrimidin-2-yl) azetidin-3-ol (1.2 g, 6.1 mmol) in MeOH (30 mL) was added Pd/C (240 mg). The reaction mixture was stirred at room temperature under H$_2$ for 5 h. After completion, the mixture was diluted with MeOH and filtered. The filtrate was concentrated to give a residue which was purified by silica gel chromatography column (PE/EA from 0~30%)) to give 1-(5-aminopyrimidin-2-yl)azetidin-3-ol (1.0 g, 98%) as yellow solid. MS (ESI): mass calcd. for $C_7H_{10}N_4O$, 166.1, m/z found 167.2 [M+H]$^+$.

Step 3

To a mixture of (S)-1-(5-fluoro-3-methylbenzofuran-2-yl)-2-methylpropan-1-amine (100 mg, 0.45 mmol) and TEA (365 mg, 3.61 mmol) in DCM (5 mL) was added BTC (107 mg, 0.36 mmol) at 0° C. The reaction mixture was stirred at room temperature for 30 min. 1-(5-aminopyrimidin-2-yl)azetidin-3-ol (75 mg, 0.45 mmol) was added to the reaction mixture at 0° C. and the mixture was stirred at room temperature for 2 h. After completion, the reaction mixture was concentrated to give a residue which was purified by pre-HPLC to give (S)-1-(1-(5-fluoro-3-methylbenzofuran-2-yl)-2-methylpropyl)-3-(2-(3-hydroxyazetidin-1-yl)pyrimidin-5-yl)urea (55 mg, 29%) as white solid. MS (ESI): mass calcd. for $C_{21}H_{24}FN_5O_3$, 413.2, m/z found 414.2 [M+H]$^+$. $^1$H NMR (400 MHz, DMSO) δ 8.35 (s, 2H), 8.26 (s, 1H), 7.52-7.49 (m, 1H), 7.38-7.36 (m, 1H), 7.12-7.07 (m, 1H), 6.93 (d, J=8.8 Hz, 1H), 4.74-4.70 (m, 1H), 4.54-4.50 (m, 1H), 4.20-4.16 (m, 2H), 3.74-3.71 (m, 2H), 2.19 (s, 3H), 2.15-2.06 (m, 1H), 1.01 (d, J=6.8 Hz, 3H), 0.81 (d, J=6.8 Hz, 3H).

Example 65: Preparation of Compound 88 and Compound 89

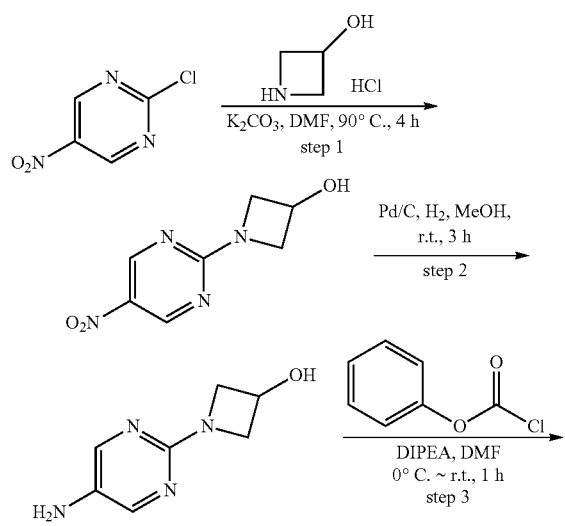

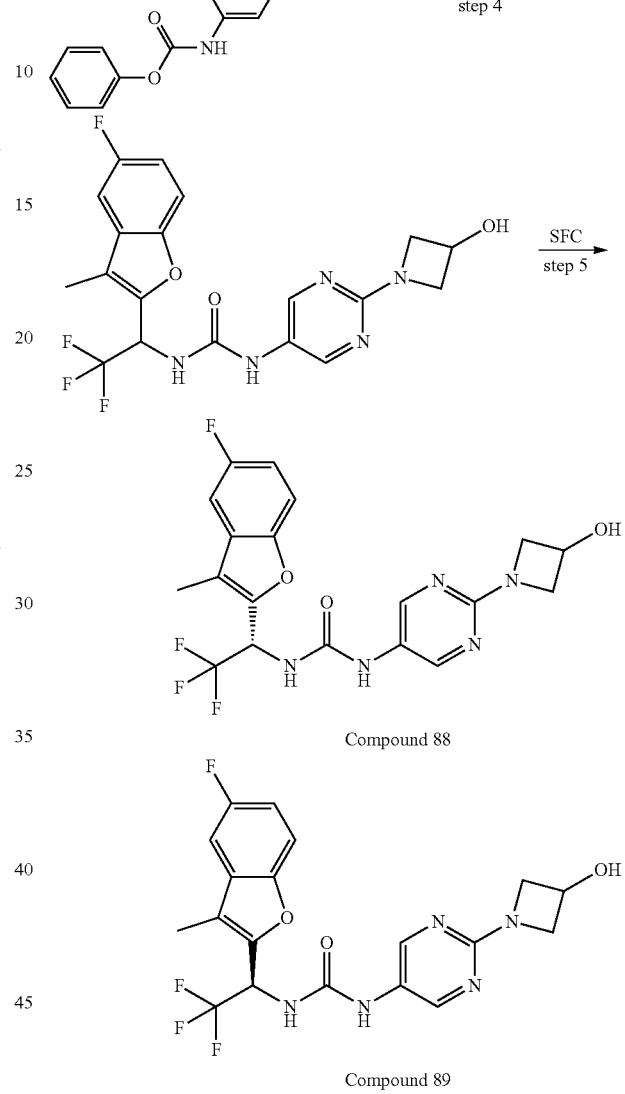

Step 1

To a mixture of 2-chloro-5-nitropyrimidine (400 mg, 2.52 mmol) and azetidin-3-ol hydrochloride (327 mg, 3 mmol) in DMF (15 mL) was added K$_2$CO$_3$ (1.04 g, 7.5 mmol). The reaction mixture was stirred at 90° C. for 4 h under N$_2$. After cooled to room temperature, the resulting mixture was diluted with water (40 mL), extracted with EtOAc (50 mL×3). The combined organic layers were washed with brine (50 mL), dried over anhydrous Na$_2$SO$_4$. After filtration, the filtrate was concentrated under reduced pressure. The residue was purified by flash chromatography (DCM/MeOH from 1 to 5%) to afford 1-(5-nitropyrimidin-2-yl)azetidin-3-ol (422 mg, yield: 85%) as a white solid. MS (ESI): mass calcd. for $C_7H_8N_4O_3$, 196.06, m/z found 197.1 [M+H]$^+$.

Step 2

To a mixture of 1-(5-nitropyrimidin-2-yl)azetidin-3-ol (410 mg, 2.1 mmol) in MeOH (15 mL) was added Pd/C (40 mg). The resulting mixture was stirred at room temperature for 3 h under $H_2$. After filtration, the filtrate was concentrated under reduced pressure. The residue was purified by flash chromatography (DCM/MeOH from 1 to 12%) to give 1-(5-aminopyrimidin-2-yl)-3-methylazetidin-3-ol (309 mg, 88%) as a white solid. MS (ESI): mass calcd. for $C_7H_{10}N_4O$, 166.09, m/z found 167.2 $[M+H]^+$.

Step 3

To a mixture of 1-(5-aminopyrimidin-2-yl)azetidin-3-ol (200 mg, 1.2 mmol) and DIPEA (465 mg, 3.6 mmol) in DMF (5 mL) was added phenyl carbonochloridate (189 mg, 1.2 mmol) at 0° C. The reaction mixture was stirred at room temperature for 1 h. After completion, the resulting reaction was used into the next step without further any work-up. MS (ESI): mass calcd. for $C_{14}H_{14}N_4O_3$, 286.11, m/z found 287.1 $[M+H]^+$.

Step 4

To the reaction solution from step 3 was added 2,2,2-trifluoro-1-(5-fluoro-3-methylbenzofuran-2-yl)ethan-1-amine (247 mg, 1.0 mmol) and the reaction mixture was stirred at room temperature for 4 h. After completion, the resulting mixture was diluted with water (20 mL), extracted with EtOAc (20 mL×3). The combined organic layers were washed with brine (40 mL), dried over anhydrous $Na_2SO_4$. After filtration, the filtrate was concentrated under reduced pressure. The residue was purified by flash chromatography (DCM/MeOH from 1 to 5%) to afford 1-(2-(3-hydroxyazetidin-1-yl)pyrimidin-5-yl)-3-(2,2,2-trifluoro-1-(5-fluoro-3-methylbenzofuran-2-yl)ethyl)urea (100 mg, 23% based on the start material 7) as a white solid. MS (ESI): mass calcd. for $C_{19}H_{17}F_4N_5O_3$, 439.13, m/z found 440.1 $[M+H]^+$.

Step 5

1-(2-(3-hydroxyazetidin-1-yl)pyrimidin-5-yl)-3-(2,2,2-trifluoro-1-(5-fluoro-3-methylbenzofuran-2-yl)ethyl)urea (100 mg) was separated by SFC 80 (Daicel CHIRALCEL OD, 250×30 mm I.D., 10 μm 50/50 $CO_2$/MeOH [0.2% $NH_3$ (7M Solution in MeOH)], 70 g/min, 120 bar, 35° C.) to give two enantiomers: (S)-1-(2-(3-hydroxyazetidin-1-yl)pyrimidin-5-yl)-3-(2,2,2-trifluoro-1-(5-fluoro-3-methylbenzofuran-2-yl)ethyl)urea (Compound 88, 35.3 mg, 35%) as a white solid and (R)-1-(2-(3-hydroxyazetidin-1-yl)pyrimidin-5-yl)-3-(2,2,2-trifluoro-1-(5-fluoro-3-methylbenzofuran-2-yl)ethyl)urea (Compound 89, 35.5 mg, 36%) as a white solid respectively.

Compound 88

MS (ESI): mass calcd. for $C_{19}H_{17}F_4N_5O_3$, 439.13, m/z found 440.1 $[M+H]^+$.

$^1$H NMR (400 MHz, dmso) δ 8.35 (s, 3H), 7.75 (d, J=9.4 Hz, 1H), 7.66-7.61 (m, 1H), 7.53-7.50 (m, 1H), 7.24-7.21 (m, 1H), 6.04-5.93 (m, 1H), 5.65 (d, J=6.5 Hz, 1H), 4.55-4.49 (m, 1H), 4.20-4.14 (m, 2H), 3.73-3.70 (m, 2H), 2.27 (s, 3H).

Compound 89

MS (ESI): mass calcd. for $C_{19}H_{17}F_4N_5O_3$, 439.13, m/z found 440.1 $[M+H]^+$.

$^1$H NMR (400 MHz, dmso) δ 8.35 (s, 3H), 7.75 (d, J=9.4 Hz, 1H), 7.66-7.60 (m, 1H), 7.53-7.49 (m, 1H), 7.24-7.20 (m, 1H), 6.02-5.94 (m, 1H), 5.65 (d, J=6.5 Hz, 1H), 4.56-4.49 (m, 1H), 4.19-4.15 (m, 2H), 3.74-3.70 (m, 2H), 2.27 (s, 3H).

Example 66: Preparation of Compound 90 and Compound 91

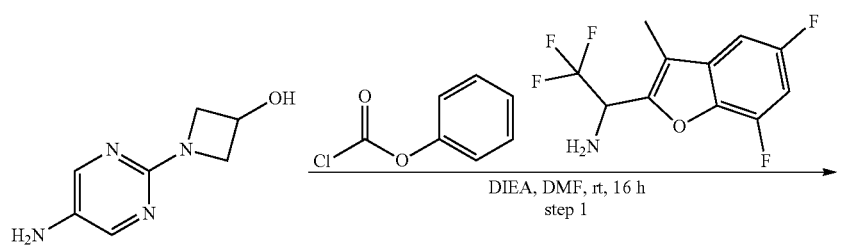

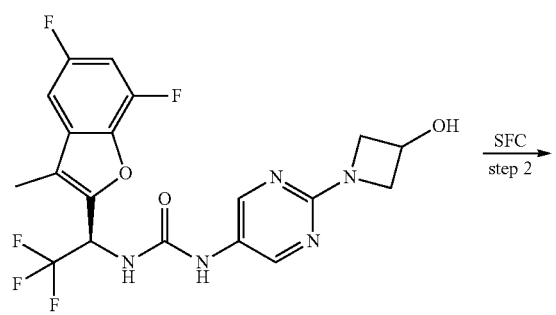

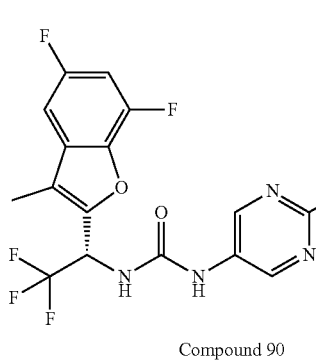

Compound 90

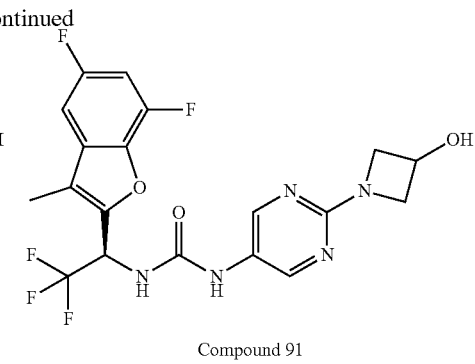

Compound 91

Step 1

To a mixture of 1-(5-aminopyrimidin-2-yl) azetidin-3-ol (260 mg, 1.6 mmol) and DIEA (510 mg, 4.0 mmol) in DMF (10 mL) was added benzoic hypochlorous anhydride (250 mg, 1.6 mmol) at 0° C. and the reaction mixture was stirred at room temperature for 1 h. 1-(5,7-difluoro-3-methylbenzofuran-2-yl)-2,2,2-trifluoroethan-1-amine (350 mg, 1.32 mmol) was added into the above reaction mixture and the mixture was stirred at room temperature for 16. After completion, the reaction mixture was quenched with water and extracted with EA (50 mL×3). The combined organic layer was concentrated to give a residue which was purified by silica gel chromatography column (DCM/MeOH from 0~10%) to get 1-(1-(5,7-difluoro-3-methylbenzofuran-2-yl)-2,2,2-trifluoroethyl)-3-(2-(3-hydroxyazetidin-1-yl)pyrimidin-5-yl)urea (360 mg, 59%) as white solid.

MS (ESI): mass calcd. for $C_{19}H_{16}F_5N_5O_3$, 457.1, m/z found 458.1 $[M+H]^+$.

Step 2

Rac-1-(1-(5,7-difluoro-3-methylbenzofuran-2-yl)-2,2,2-trifluoroethyl)-3-(2-(3-hydroxyazetidin-1-yl) pyrimidin-5-yl) urea (360 mg) was separated by chiral separation to give (S)-1-(1-(5,7-difluoro-3-methylbenzofuran-2-yl)-2,2,2-trifluoroethyl)-3-(2-(3-hydroxyazetidin-1-yl)pyrimidin-5-yl) urea (peak 1, 149 mg, 41%) and (R)-1-(1-(5,7-difluoro-3-methylbenzofuran-2-yl)-2,2,2-trifluoroethyl)-3-(2-(3-hydroxyazetidin-1-yl)pyrimidin-5-yl)urea (peak 2, 150 mg, 42%) as white solids with the following separation conditions.

Separation Conditions
Apparatus: SFC 80
Column: REGIS (S, S)-Whelk O1, 250 mm×30 mm I.D., 10 μm
Mobile phase: $CO_2$/MeOH [0.2% $NH_3$ (7M Solution in MeOH)]=75/25
Flow rate: 70 g/min
Wavelength: UV 214 nm
Temperature: 35° C.

MS (ESI): mass calcd. for $C_{19}H_{16}F_5N_5O_3$, 457.1, m/z found 458.1 $[M+H]^+$.

Compound 90 (peak 1)

$^1$H NMR (400 MHz, DMSO) δ 8.35 (s, 2H), 8.34 (s, 1H), 7.82 (d, J=9.6 Hz, 1H), 7.45-7.38 (m, 2H), 6.08-6.02 (m, 1H), 5.64 (d, J=6.4 Hz, 1H), 4.56-4.50 (m, 1H), 4.19-4.15 (m, 2H), 3.74-3.70 (m, 2H), 2.29 (s, 3H).

Compound 91 (peak 2)

$^1$H NMR (400 MHz, DMSO) δ 8.35 (s, 2H), 8.34 (s, 1H), 7.83 (d, J=9.6 Hz, 1H), 7.45-7.38 (m, 2H), 6.08-6.01 (m, 1H), 5.64 (d, J=6.4 Hz, 1H), 4.56-4.49 (m, 1H), 4.19-4.15 (m, 2H), 3.74-3.70 (m, 2H), 2.30 (s, 3H).

Example 67: Preparation of Compound 92 and Compound 93

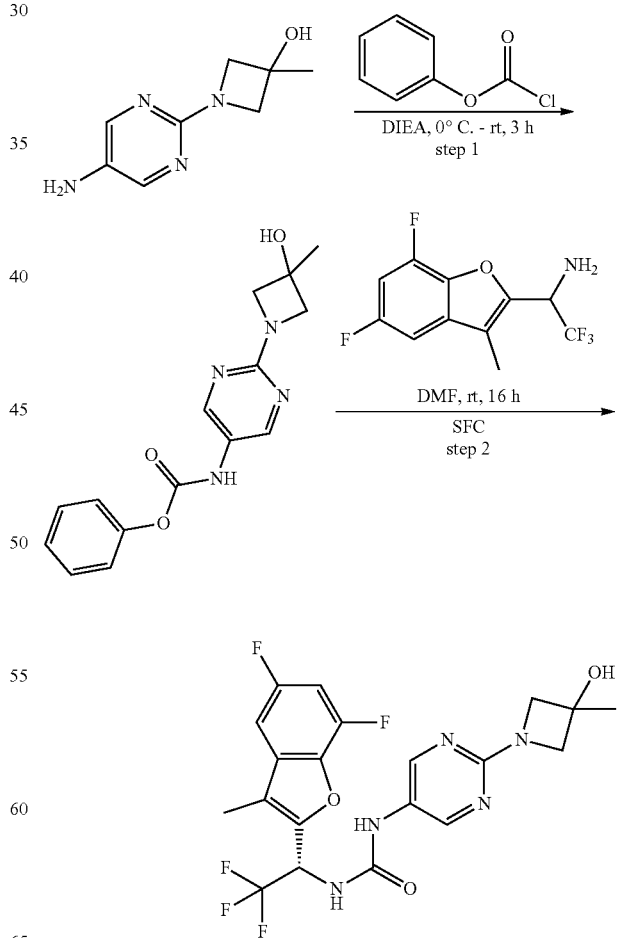

Compound 92

615

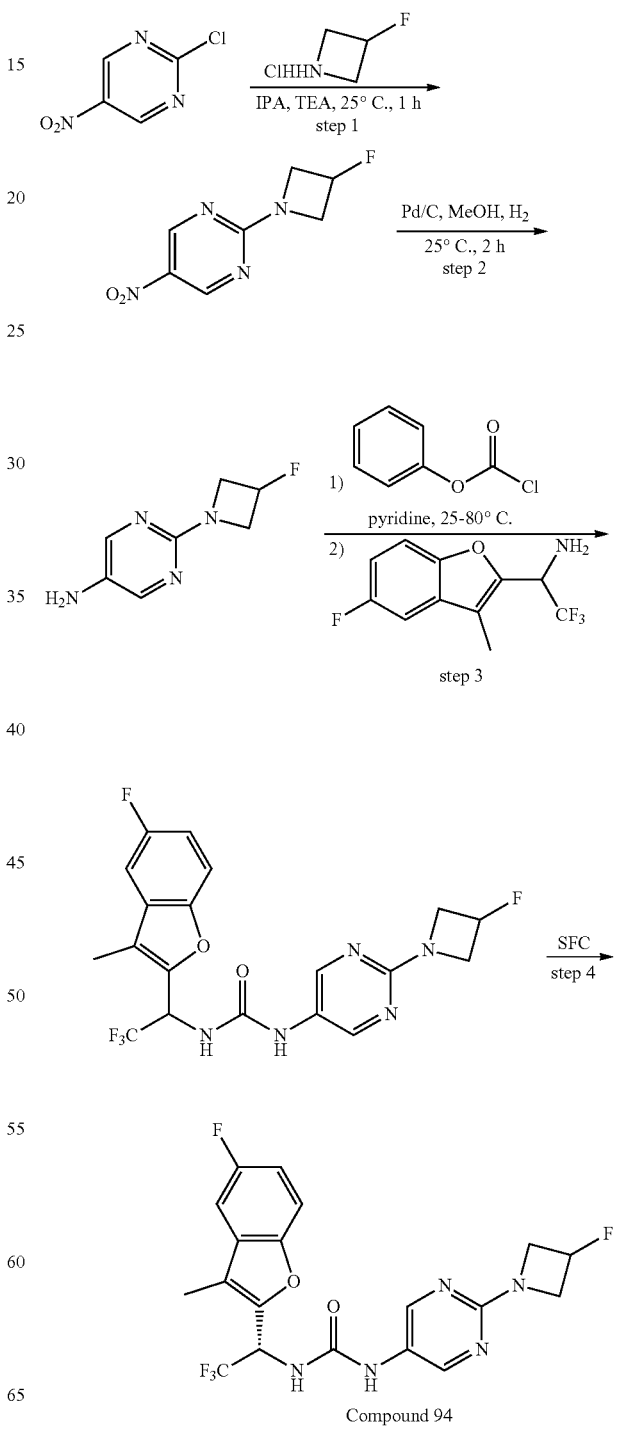

Compound 93

Step 1

To a mixture of 1-(5-aminopyrimidin-2-yl)-3-methylazetidin-3-ol (300 mg, 1.66 mmol), DIEA (645 mg, 4.99 mmol) in DMF (5 mL) was added phenyl chloroformate (261 mg, 1.66 mmol) at 0° C. The reaction mixture was stirred at 25° C. for 3 h. The reaction mixture was concentrated to give phenyl (2-(3-hydroxy-3-methylazetidin-1-yl) pyrimidin-5-yl) carbamate (500 mg, crude) as yellow solid which was used directly in next step. MS (ESI): mass calcd. for $C_{15}H_{16}N_4O_3$, 300.1, m/z found 301.1 [M+H]$^+$.

Step 2

To a solution of phenyl N-[2-(3-hydroxy-3-methylazetidin-1-yl) pyrimidin-5-yl] carbamate (338 mg, 1.13 mmol) in DMF (5 mL) was added (5,7-difluoro-3-methyl-1-benzofuran-2-yl)[(difluoromethyl)-$1^{2}$-fluoranyl]methanamine (250 mg, 0.94 mmol). The reaction mixture was stirred at 25° C. for 16 h. After completion, the reaction mixture was concentrated to give a residue which was purified by silica gel Chromatography column (DCM/MeOH from 0~10%) to get 1-(1-(5,7-difluoro-3-methylbenzofuran-2-yl)-2,2,2-trifluoroethyl)-3-(2-(3-hydroxy-3-methylazetidin-1-yl) pyrimidin-5-yl) urea. The racemic compound was separated by Chiral separation to give (R)-1-(1-(5,7-difluoro-3-methylbenzofuran-2-yl)-2,2,2-trifluoroethyl)-3-(2-(3-hydroxy-3-methylazetidin-1-yl)pyrimidin-5-yl)urea (peak 1, 136 mg, 30%) as a white solid and (S)-1-(1-(5,7-difluoro-3-methylbenzofuran-2-yl)-2,2,2-trifluoroethyl)-3-(2-(3-hydroxy-3-methylazetidin-1-yl)pyrimidin-5-yl)urea (peak 2, 128 mg, 29%) as a white solid with the following separation conditions.

Chiral Separation Conditions:
Apparatus: SFC 80
Column: REGIS (S, S)-Whelk O1, 250 mm×30 mm I.D., 10 μm
Mobile phase: CO$_2$/MeOH [0.2% NH$_3$ (7M Solution in MeOH)]=75/25
Flow rate: 70 g/min
Wavelength: UV 214 nm
Temperature: 35° C.
MS (ESI): mass calcd. for $C_{20}H_{18}F_5N_5O_3$, 471.1, m/z found 472.0 [M+H]$^+$.

Compound 92 Peak 1

$^1$H NMR (400 MHz, DMSO) δ 8.36 (s, 2H), 8.34 (s, 1H), 7.82 (d, J=8.0 Hz, 1H), 7.45-7.38 (m, 2H), 6.07-6.01 (m, 1H), 5.56 (s, 1H), 3.86-3.81 (m, 4H), 2.30 (s, 3H), 1.41 (s, 3H).

616

Compound 93 Peak 2

$^1$H NMR (400 MHz, DMSO) δ 8.36 (s, 3H), 7.83 (d, J=8.0 Hz, 1H), 7.45-7.38 (m, 2H), 6.09-6.01 (m, 1H), 5.56 (s, 1H), 3.86-3.81 (m, 4H), 2.30 (s, 3H), 1.41 (s, 3H).

Example 68: Preparation of Compound 94 and Compound 95

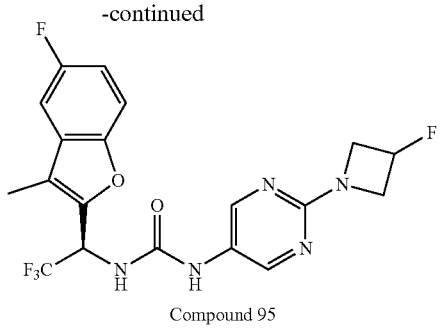

Compound 95

Step 1

To a solution of 2-chloro-5-nitropyrimidine (2.2 g, 13.79 mmol) in IPA (20 mL) was added 3-fluoroazetidine hydrochloride (2.3 g, 20.69 mmol) and TEA (2.8 g, 27.58 mmol). The mixture was stirred at 25° C. for 1 h. TLC (PE/EA=1/1) showed the reaction was completed. The mixture was concentrated in vacuum. The residue was dissolved with EA, washed with water and brine. The organic layer was dried over sodium sulfate, concentrated in vacuum to give 2-(3-fluoroazetidin-1-yl)-5-nitropyrimidine (2.4 g, 88%) as brown solid. MS (ESI): mass calcd. for $C_7H_7FN_4O_2$, 198.1, m/z found 199.1 $[M+H]^+$.

Step 2

To a solution of 2-(3-fluoroazetidin-1-yl)-5-nitropyrimidine (2.4 g, 12.11 mmol) in MeOH (600 mL) was added Pd/C (240 mg). The mixture was stirred at 25° C. for 2 h under hydrogen. After completion, the mixture was filtered, and the filtrate was concentrated in vacuum to give 2-(3-fluoroazetidin-1-yl)pyrimidin-5-amine (2.0 g, 98%) as brown solid. MS (ESI): mass calcd. for $C_7H_9FN_4$, 168.1, m/z found 169.1 $[M+H]^+$.

Step 3

To a solution of 2-(3-fluoroazetidin-1-yl)pyrimidin-5-amine (170 mg, 1.01 mmol) in pyridine (5 mL) was added phenyl chloroformate (158 mg, 1.01 mmol). The mixture was stirred at 25° C. for 1 h. 2,2,2-trifluoro-1-(5-fluoro-3-methylbenzofuran-2-yl)ethan-1-amine (227 mg, 0.92 mmol) was added to the mixture and the mixture was stirred at 80° C. for 16 h. After completion, the mixture was concentrated in vacuum. The residue was purified by reverse (ACN/water from 0~70%) to give 1-(2-(3-fluoroazetidin-1-yl)pyrimidin-5-yl)-3-(2,2,2-trifluoro-1-(5-fluoro-3-methylbenzofuran-2-yl)ethyl)urea (140 mg, 35%) as white solid. MS (ESI): mass calcd. for $C_{19}H_{16}F_5N_5O_2$, 441.1, m/z found 442.1 $[M+H]^+$.

Step 4

140 mg 1-(2-(3-fluoroazetidin-1-yl)pyrimidin-5-yl)-3-(2,2,2-trifluoro-1-(5-fluoro-3-methylbenzofuran-2-yl)ethyl) urea of racemic was separated by SFC to give (S)-1-(2-(3-fluoroazetidin-1-yl)pyrimidin-5-yl)-3-(2,2,2-trifluoro-1-(5-fluoro-3-methylbenzofuran-2-yl)ethyl)urea Compound 94 (35.5 mg) as white solid and (R)-1-(2-(3-fluoroazetidin-1-yl)pyrimidin-5-yl)-3-(2,2,2-trifluoro-1-(5-fluoro-3-methylbenzofuran-2-yl)ethyl)urea Compound 95 (33.3 mg) as white solid.

Chiral Separation Conditions:
Apparatus: SFC 80
Column: Daicel CHIRALCEL OD, 250 mm×30 mm I.D., 10 μm
Mobile phase: $CO_2$/MeOH [0.2% NH3 (7M Solution in MeOH)]=50/50
Flow rate: 70 g/min
Wavelength: UV 214 nm
Temperature: 35° C.

Compound 94

MS (ESI): mass calcd. for $C_{19}H_{16}F_5N_5O_2$, 441.1, m/z found 442.1 $[M+H]^+$.
$^1$H NMR (400 MHz, $CD_3OD$) δ 8.29 (s, 2H), 7.37 (dd, J=8.8, 3.6 Hz, 1H), 7.22 (dd, J=8.4, 2.4 Hz, 1H), 7.02 (td, J=9.2, 2.8 Hz, 1H), 5.83 (q, J=8.0 Hz, 1H), 5.46-5.15 (m, 1H), 4.32-4.23 (m, 2H), 4.07-3.97 (m, 2H), 2.20 (s, 3H).

Compound 95

MS (ESI): mass calcd. for $C_{19}H_{16}F_5N_5O_2$, 441.1, m/z found 442.1 $[M+H]^+$.
$^1$H NMR (400 MHz, $CD_3OD$) δ 8.41 (s, 2H), 7.50 (dd, J=8.8, 3.6 Hz, 1H), 7.34 (dd, J=8.4, 2.4 Hz, 1H), 7.14 (td, J=9.2, 2.8 Hz, 1H), 5.95 (q, J=8.0 Hz, 1H), 5.59-5.30 (m, 1H), 4.44-4.35 (m, 2H), 4.19-4.09 (m, 2H), 2.32 (s, 3H).

Example 69: Preparation of Compound 96

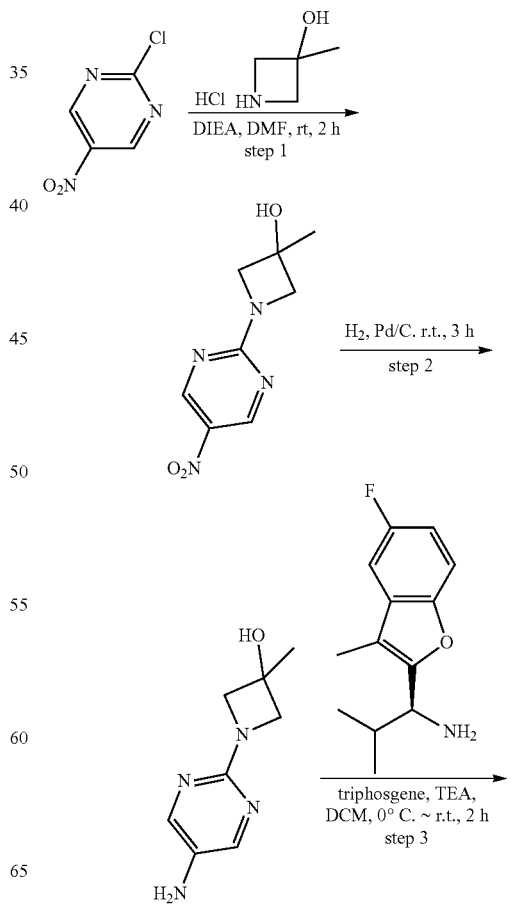

619

-continued

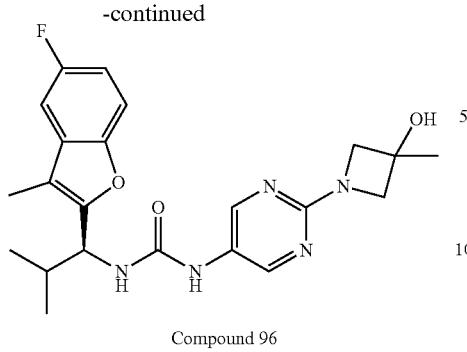

Compound 96

Step 1

To a mixture of 2-chloro-5-nitropyrimidine (500 mg, 3.13 mmol), 3-methylazetidin-3-ol hydrochloride (581 mg, 4.70 mmol) in DMF (10 mL) was added DIEA (1.21 g, 9.40 mmol). The reaction mixture was stirred at 20° C. for 2 h. After completion, the mixture was diluted with water and extracted with EA (50 mL×3). The organic layer was dried over anhydrous $Na_2SO_4$ and concentrated under reduced pressure to give a residue which was purified by silica gel chromatography column (PE/EA from 0~50%) to give 3-methyl-1-(5-nitropyrimidin-2-yl)azetidin-3-ol (500 mg, 68%) as yellow solid. MS (ESI): mass calcd. for $C_8H_{10}N_4O_3$, 210.1, m/z found 211.1 [M+H]$^+$.

Step 2

To a solution of 3-methyl-1-(5-nitropyrimidin-2-yl)azetidin-3-ol (500 mg, 2.38 mmol) in MeOH (20 mL) was added Pd/C (51 mg, 0.48 mmol) and the reaction was stirred under $H_2$ at room temperature for 3 h. After completion, the reaction mixture was filtered and the filtrate was concentrated to give 1-(5-aminopyrimidin-2-yl)-3-methylazetidin-3-ol (400 mg, 84%) as yellow solid which was used directly in next step. MS (ESI): mass calcd. for $C_8H_{12}N_4O$, 180.1, m/z found 181.1 [M+H]$^+$.

Step 3

To a mixture of (1S)-1-(5-fluoro-3-methyl-1-benzofuran-2-yl)-2-methylpropan-1-amine (100 mg, 0.45 mmol) and triethylamine (137 mg, 1.36 mmol) in DCM (10 mL) was added triphosgene (107 mg, 0.36 mmol) at 0° C. and the reaction mixture was stirred at 20° C. for 0.5 h. 1-(5-aminopyrimidin-2-yl)-3-methylazetidin-3-ol (81 mg, 0.45 mmol) was added into the reaction mixture at 0° C. and the mixture was stirred at 20° C. for 2 h. After reaction, the reaction mixture was concentrated under reduced pressure to give a residue which was purified by prep-HPLC to give (S)-1-(1-(5-fluoro-3-methylbenzofuran-2-yl)-2-methylpropyl)-3-(2-(3-hydroxy-3-methylazetidin-1-yl)pyrimidin-5-yl)urea (83 mg, 43%) as white solid. MS (ESI): mass calcd. for $C_{22}H_{26}FN_5O_3$, 427.2, m/z found 428.1 [M+H]$^+$.

$^1$H NMR (400 MHz, DMSO) δ 8.36 (s, 2H), 8.28 (s, 1H), 7.52-7.49 (m, 1H), 7.38-7.36 (m, 1H), 7.12-7.07 (m, 1H), 6.94 (d, J=8.0 Hz, 1H), 4.72 (t, J=8.0 Hz, 1H), 4.01 (s, 1H), 3.86-3.81 (m, 4H), 2.19 (s, 3H), 2.15-2.06 (m, 1H), 1.41 (s, 3H), 1.01 (d, J=8.0 Hz, 3H), 0.81 (d, J=8.0 Hz, 3H).

620

Example 70: Preparation of Compound 97 and Compound 98

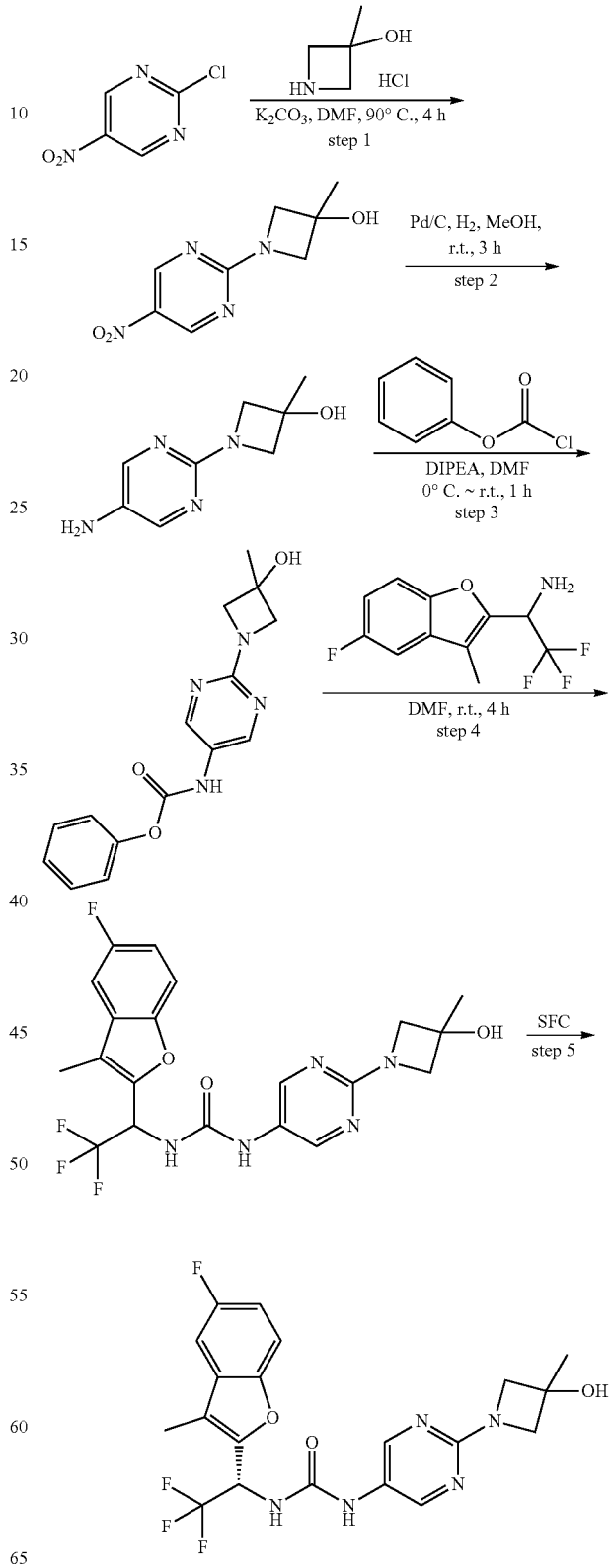

Compound 97

-continued

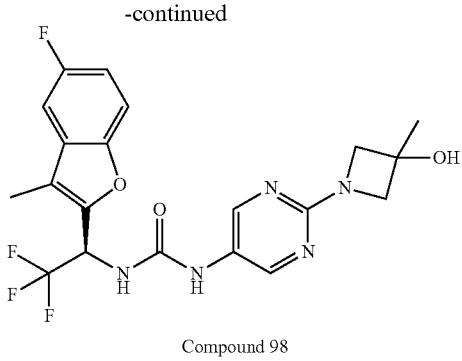

Compound 98

Step 1

To a mixture of 2-chloro-5-nitropyrimidine (100 mg, 0.63 mmol) and 3-methylazetidin-3-ol hydrochloride (92 mg, 0.75 mmol) in DMF (5 mL) was added $K_2CO_3$ (263 mg, 1.9 mmol). The reaction mixture was stirred at 90° C. for 4 h under $N_2$. After cooled to room temperature, the resulting mixture was diluted with water (30 mL), extracted with EtOAc (30 mL×3). The combined organic layers were washed with brine (40 mL), dried over anhydrous $Na_2SO_4$. After filtration, the filtrate was concentrated under reduced pressure. The residue was purified by flash chromatography (DCM/MeOH from 1 to 6%) to afford 3-methyl-1-(5-nitropyrimidin-2-yl)azetidin-3-ol (100 mg, yield: 75%) as a white solid. MS (ESI): mass calcd. for $C_8H_{10}N_4O_3$, 210.08, m/z found 211.1 $[M+H]^+$.

Step 2

To a mixture of 3-methyl-1-(5-nitropyrimidin-2-yl)azetidin-3-ol (100 mg, 0.48 mmol) in MeOH (4 mL) was added Pd/C (20 mg). The resulting mixture was stirred at room temperature for 3 h under $H_2$. After filtration, the filtrate was concentrated under reduced pressure. The residue was purified by flash chromatography (DCM/MeOH from 1 to 10%) to give 1-(5-aminopyrimidin-2-yl)-3-methylazetidin-3-ol (70 mg, 81%) as a white solid. MS (ESI): mass calcd. for $C_8H_{12}N_4O$, 180.10, m/z found 181.2 $[M+H]^+$.

Step 3

To a mixture of 1-(5-aminopyrimidin-2-yl)-3-methylazetidin-3-ol (70 mg, 0.39 mmol) and DIPEA (155 mg, 1.2 mmol) in DMF (3 mL) was added phenyl carbonochloridate (86 mg, 0.39 mmol) at 0° C. The reaction mixture was stirred at room temperature for 1 h under $N_2$. After completion, the resulting reaction was used into the next step without further any work-up. MS (ESI): mass calcd. for $C_{15}H_{16}N_4O_3$, 300.12, m/z found 301.1 $[M+H]^+$.

Step 4

To the reaction solution from step 3 was 2,2,2-trifluoro-1-(5-fluoro-3-methylbenzofuran-2-yl)ethan-1-amine (97 mg, 0.39 mmol) and the reaction mixture was stirred at room temperature for 4 h. After completion, the resulting mixture was diluted with water (25 mL), extracted with EtOAc (25 mL×3). The combined organic layers were washed with brine (20 mL), dried over anhydrous $Na_2SO_4$. After filtration, the filtrate was concentrated under reduced pressure. The residue was purified by flash chromatography (DCM/MeOH from 1 to 5%) to afford 1-(2-(3-hydroxy-3-methylazetidin-1-yl)pyrimidin-5-yl)-3-(2,2,2-trifluoro-1-(5-fluoro-3-methylbenzofuran-2-yl)ethyl)urea (60 mg, 34% based on the start material 7) as a white solid. MS (ESI): mass calcd. for $C_{20}H_{19}F_4N_5O_3$, 453.14, m/z found 454.1 $[M+H]^+$.

Step 5

(rac)-1-(2-(3-hydroxy-3-methylazetidin-1-yl)pyrimidin-5-yl)-3-(2,2,2-trifluoro-1-(5-fluoro-3-methylbenzofuran-2-yl)ethyl)urea (60 mg) was separated by SFC 80 (Daicel CHIRALCEL OD, 250×30 mm I.D., 10 μm 50/50 $CO_2$/MeOH [0.2% NH3 (7M Solution in MeOH)], 70 g/min, 120 bar, 35° C.) to give two enantiomers (S)-1-(2-(3-hydroxy-3-methylazetidin-1-yl)pyrimidin-5-yl)-3-(2,2,2-trifluoro-1-(5-fluoro-3-methylbenzofuran-2-yl)ethyl)urea (Compound 97, 20 mg, 11%) as a white solid and (R)-1-(2-(3-hydroxy-3-methylazetidin-1-yl)pyrimidin-5-yl)-3-(2,2,2-trifluoro-1-(5-fluoro-3-methylbenzofuran-2-yl)ethyl)urea (Compound 98, 25 mg, 14%) as a white solid respectively.

Compound 97

MS (ESI): mass calcd. for $C_{20}H_{19}F_4N_5O_3$, 453.14, m/z found 454.1 $[M+H]^+$.
$^1$H NMR (400 MHz, dmso) δ 8.36 (s, 3H), 7.75 (d, J=9.4 Hz, 1H), 7.63 (dd, J=9.0, 4.0 Hz, 1H), 7.51 (dd, J=8.7, 2.7 Hz, 1H), 7.31-7.16 (m, 1H), 5.97 (dd, J=17.3, 8.3 Hz, 1H), 5.56 (s, 1H), 3.83 (s, 4H), 2.25 (s, 3H), 1.41 (s, 3H).

Compound 98

MS (ESI): mass calcd. for $C_{20}H_{19}F_4N_5O_3$, 453.14, m/z found 454.1 $[M+H]^+$.
$^1$H NMR (400 MHz, dmso) δ 8.35 (s, 3H), 7.75 (d, J=9.4 Hz, 1H), 7.63 (dd, J=9.0, 4.1 Hz, 1H), 7.51 (dd, J=8.7, 2.6 Hz, 1H), 7.31-7.16 (m, 1H), 6.21-5.74 (m, 1H), 3.83 (s, 4H), 2.30 (s, 3H), 1.41 (s, 3H).

Example 71: Preparation of Compound 99 and Compound 100

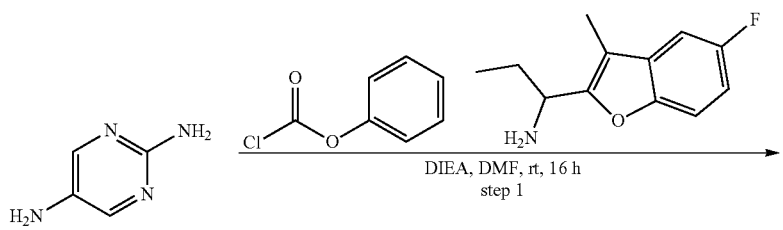

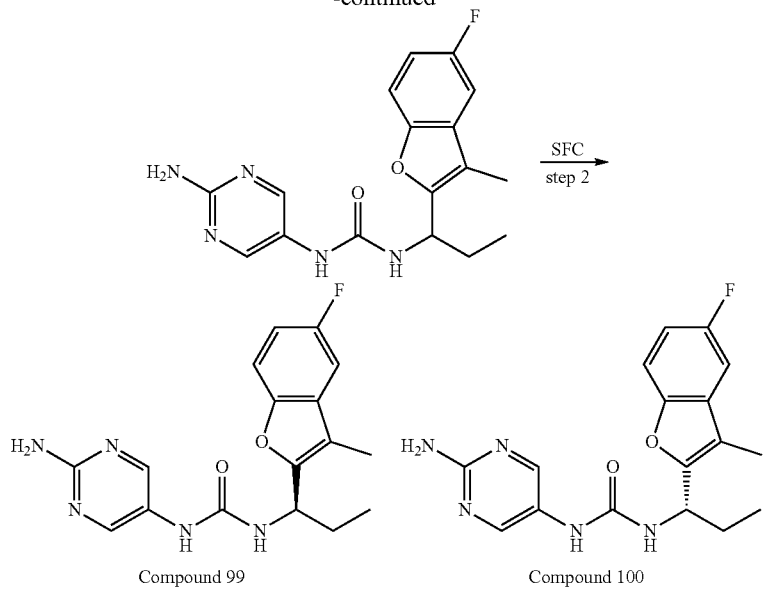

Compound 99

Compound 100

Step 1

To a mixture of pyrimidine-2,5-diamine (150 mg, 1.36 mmol) and DIEA (528 mg, 4.1 mmol) in DMF (10 mL) was added benzoic hypochlorous anhydride (213 mg, 1.36 mmol) at 0° C. The reaction mixture was stirred at room temperature for 1 h. 1-(5-fluoro-3-methylbenzofuran-2-yl)propan-1-amine (282 mg, 1.36 mmol) was added into the above reaction mixture and the mixture was stirred at room temperature for 16. After completion, the mixture was quenched with water and extracted with EA (30 mL×3). The combined organic layer was concentrated to give a residue which was purified by silica gel chromatography column (DCM/MeOH from 0~10%) to get 1-(1-(5,7-difluoro-3-methylbenzofuran-2-yl)-2,2,2-trifluoroethyl)-3-(2-(3-hydroxyazetidin-1-yl)pyrimidin-5-yl)urea (220 mg, 47%) as white solid. MS (ESI): mass calcd. for $C_{17}H_{18}FN_5O_2$, 343.1, m/z found 344.2 [M+H]$^+$.

Step 2

Rac-1-(1-(5,7-difluoro-3-methylbenzofuran-2-yl)-2,2,2-trifluoroethyl)-3-(2-(3-hydroxyazetidin-1-yl)pyrimidin-5-yl)urea (220 mg) was separated by chiral separation to give (R)-1-(2-aminopyrimidin-5-yl)-3-(1-(5-fluoro-3-methylbenzofuran-2-yl)propyl)urea (peak 1, 43 mg, 19%) and (S)-1-(2-aminopyrimidin-5-yl)-3-(1-(5-fluoro-3-methylbenzofuran-2-yl)propyl)urea (peak 2, 52 mg, 23%) as white solid with the following separation conditions. MS (ESI): mass calcd. for $C_{17}H_{18}FN_5O_2$, 343.1, m/z found 344.2 [M+H]$^+$.

Separation Conditions:
Apparatus SFC 150
Column: Daicel CHIRALCEL IE, 250 mm×30 mm I.D., 10 μm
Mobile phase: $CO_2$/MeOH [0.20% NH3 (7M Solution in MeOH)]=70/30
Flow rate: 80 g/min
Wavelength: UV 214 nm
Temperature: 35° C.

Compound 99 (Peak 1)

$^1$H NMR (400 MHz, DMSO) δ 8.28 (s, 2H), 8.18 (s, 1H), 7.53-7.50 (m, 1H), 7.39-7.36 (m, 1H), 7.12-7.07 (m, 1H), 6.94 (d, J=8.0 Hz, 1H), 6.69 (s, 2H), 4.91-4.85 (m, 1H), 2.20 (s, 3H), 1.88-1.78 (m, 2H), 0.85 (t, J=8.0 Hz, 3H).

Compound 100 (Peak 2)

$^1$H NMR (400 MHz, DMSO) δ 8.18 (s, 2H), 7.94 (s, 1H), 7.53-7.50 (m, 1H), 7.39-7.36 (m, 1H), 7.13-7.07 (m, 1H), 6.81 (d, J=8.0 Hz, 1H), 6.28 (s, 2H), 4.91-4.85 (m, 1H), 2.19 (s, 3H), 1.86-1.80 (m, 2H), 0.84 (t, J=8.0 Hz, 3H).

Example 72: Preparation of Compound 101

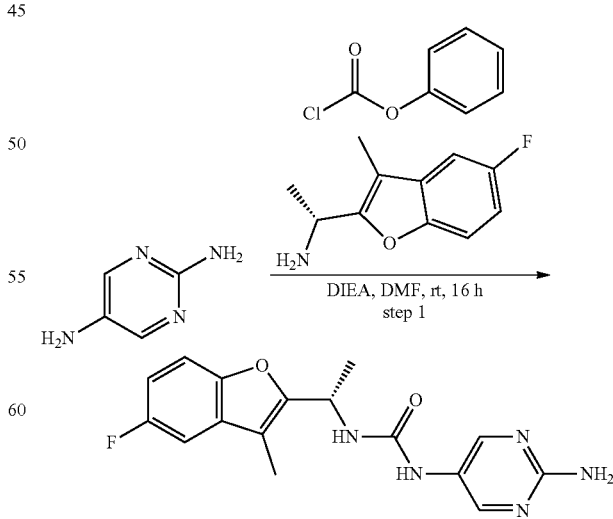

Compound 101

Step 1

To a mixture of pyrimidine-2,5-diamine (100 mg, 0.90 mmol) and DIEA (352 mg, 2.72 mmol) in DMF (10 mL) was added benzoic hypochlorous anhydride (142 mg, 0.90 mmol) at 0° C. The reaction mixture was stirred at room temperature for 1 h. (R)-1-(5-fluoro-3-methylbenzofuran-2-yl) ethan-1-amine (175 mg, 0.90 mmol) was added into the above reaction mixture and the mixture was stirred at room temperature for 16. After completion, the reaction mixture was diluted with water and extracted with EA (50 mL×3). The combine organic layer was concentrated to give a residue which was purified by pre-HPLC to give (S)-1-(2-aminopyrimidin-5-yl)-3-(1-(5-fluoro-3-methylbenzofuran-2-yl)ethyl)urea (55 mg, 18%) as a white solid. MS (ESI): mass calcd. for $C_{16}H_{16}FN_5O_2$, 329.13, m/z found 330.1 $[M+H]^+$.

$^1$H NMR (400 MHz, DMSO) δ 8.17 (s, 2H), 7.93 (s, 1H), 7.53-7.50 (m, 1H), 7.38-7.35 (m, 1H), 7.12-7.07 (m, 1H), 6.83 (d, J=8.0 Hz, 1H), 6.28 (s, 2H), 5.13-5.06 (m, 1H), 2.19 (s, 3H), 1.46 (d, J=8.0 Hz, 3H).

Example 73: Preparation of Compound 102

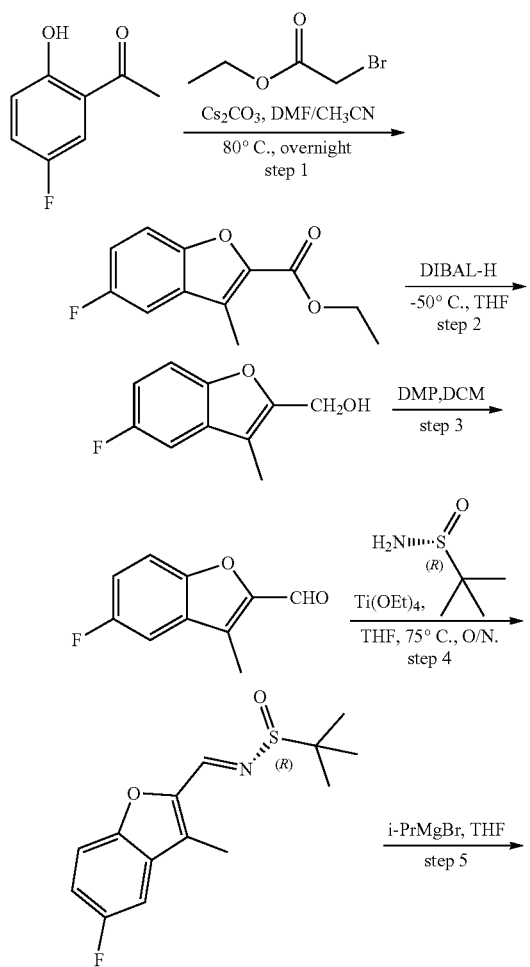

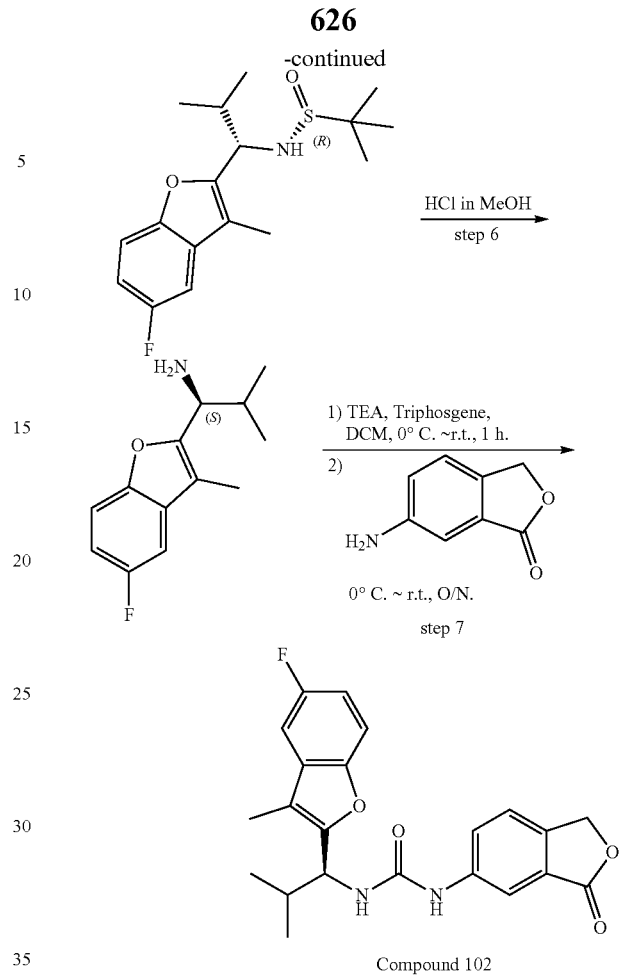

Step 1

To a stirred solution of 1-(5-fluoro-2-hydroxyphenyl)ethanone (100 g, 648.8 mmol) in DMF (450 mL)/ACN (1800 mL) was added ethyl bromoacetate (130 g, 778.5 mmol) and $Cs_2CO_3$ (634.1 g, 1946.3 mmol). The resulting mixture was stirred overnight at 80° C., then cooled down to room temperature and filtered. The filter cake was washed with acetonitrile. The filtrate was concentrated under reduced pressure. The residue was diluted with EtOAc, washed with saturated NaCl 3 times. The organic layer was dried over anhydrous $Na_2SO_4$. After filtration, the filtrate was concentrated under reduced pressure. The residue was purified by silica gel column chromatography, eluted with PE/EtOAc (25:1) to afford ethyl 5-fluoro-3-methyl-1-benzofuran-2-carboxylate (86 g, 59.7%) as a white solid.

Step 2

To a stirred solution of ethyl 5-fluoro-3-methyl-1-benzofuran-2-carboxylate (86 g, 387.4 mmol) in THF (860 mL) was added 1 M DIBAL-H in hexanes (775 mL, 775 mmol) dropwise at −50° C. under nitrogen atmosphere and the resulting solution was stirred for 1 hour under this conditions. Then the solution was poured into ice saturated citric acid, the water phase was extracted with EtOAc 3 times. The combined organic layers were dried by anhydrous $Na_2SO_4$, filtered and then concentrated under reduced pressure to afforded (5-fluoro-3-methyl-1-benzofuran-2-yl) methanol (58.2 g, 83.5%) as an off-white solid.

Step 3

To a stirred solution of (5-fluoro-3-methyl-1-benzofuran-2-yl)methanol (58.2 g, 323.3 mmol) in DCM (580 mL) was added DMP (205.3 g, 484.9 mmol) in portions at 0° C. The reaction solution was stirred at room temperature for 1 hour, then quenched with saturated $Na_2S_2O_3$. The aqueous layer was extracted with DCM 3 times. The combined organic layers were dried by anhydrous $Na_2SO_4$, then filtered and concentrated under reduced pressure. The residue was purified by silica gel column chromatography, eluted with PE/EA (10:1) to afford 5-fluoro-3-methyl-1-benzofuran-2-carbaldehyde (41 g, 71.3%) as a off-white solid.

Step 4

To a stirred solution of 5-fluoro-3-methyl-1-benzofuran-2-carbaldehyde (41 g, 230.1 mmol) and (R)-2-methylpropane-2-sulfinamide (29.3 g, 241.6 mmol) in THF (600 mL) was added tetraethoxytitanium (126 g, 552.3 mmol) at room temperature. The resulting solution was stirred overnight at 75° C. under nitrogen atmosphere, then cooled down to room temperature and diluted with saturated NaCl. The resulting mixture was filtered, the filter cake was washed with EtOAc and MeOH. The filtrate was concentrated under reduced pressure, then diluted with EtOAc, washed with saturated NaCl 2 times. The organic layer was dried over anhydrous $Na_2SO_4$. After filtration, the filtrate was concentrated under reduced pressure to afford (R)-N-[(5-fluoro-3-methyl-1-benzofuran-2-yl)methylidene]-2-methylpropane-2-sulfinamide (41.2 g, 63.6%) as a yellow oil.

Step 5

To a stirred solution of (R)-N-[(5-fluoro-3-methyl-1-benzofuran-2-yl)methylidene]-2-methylpropane-2-sulfinamide (41.2 g, 146.6 mmol) in THF (500 mL) was added bromo(2-methylpropyl) magnesium (660 mL, 660 mmol, 1M in THF) at −40° C. under nitrogen atmosphere. The resulting solution was stirred for 3 hours at room temperature, then quenched with saturated $NH_4Cl$ at 0° C. The organic layer was washed with saturated NaCl twice, dried over anhydrous $Na_2SO_4$ and filtered. The filtrate was concentrated under reduced pressure. The residue was purified by silica gel column chromatography (PE/EtOAc=3:1) to afforded (R)-N-((S)-1-(5-fluoro-3-methylbenzofuran-2-yl)-2-methylpropyl)-2-methylpropane-2-sulfonamide (8.1 g) as a yellow oil.

Step 6

To a stirred solution of (R)-N-((S)-1-(5-fluoro-3-methylbenzofuran-2-yl)-2-methylpropyl)-2-methylpropane-2-sulfonamide (8.1 g, 24.9 mmol) in MeOH (81 mL) was added 4 M HCl (g) in MeOH (15 mL). The resulting solution was stirred for 30 min at room temperature, then diluted with water and adjusted pH to 8-9 with saturated $NaHCO_3$ at 0° C., extracted with DCM 3 times. The combined organic layers were dried over anhydrous $Na_2SO_4$ and filtered. The filtrate was concentrated under reduced pressure to afford (S)-1-(5-fluoro-3-methylbenzofuran-2-yl)-2-methylpropan-1-amine (4.8 g, 87.2%) as a yellow oil.

Step 7

To a stirred solution of (S)-1-(5-fluoro-3-methyl-1-benzofuran-2-yl)-2-methylpropan-1-amine (90 mg, 0.4 mmol) and TEA (329.3 mg, 3.2 mmol) in DCM (3 mL) was added triphosgene (120 mg, 0.4 mmol) at 0° C. The resulting solution was stirred for 1 h at room temperature under nitrogen atmosphere. Then 6-amino-3H-2-benzofuran-1-one (72.8 mg, 0.5 mmol) was added at 0° C. The resulting mixture was stirred overnight at room temperature under nitrogen atmosphere, then quenched with MeOH and concentrated under reduced pressure. The residue was purified by Prep-HPLC to afford 3-[(1S)-1-(5-fluoro-3-methyl-1-benzofuran-2-yl)-2-methylpropyl]-1-(3-oxo-1H-2-benzofuran-5-yl)urea (26.8 mg, 16.6%) as an off-white solid. MS (ESI): mass calcd. for $C_{22}H_{21}FN_2O_4$, 396.15, m/z found 397.15 $[M+H]^+$.

$^1$H NMR (400 MHz, DMSO-d6) δ 8.89-8.77 (s, 1H), 8.08-7.97 (d, J=1.7 Hz, 1H), 7.61-7.47 (m, 3H), 7.44-7.34 (dd, J=2.7, 8.8 Hz, 1H), 7.17-7.06 (td, J=2.7, 9.1 Hz, 1H), 6.99-6.89 (d, J=8.7 Hz, 1H), 5.36-5.28 (s, 2H), 4.86-4.71 (t, J=8.6 Hz, 1H), 2.27-2.20 (s, 3H), 2.18-2.08 (dt, J=7.1, 14.6 Hz, 1H), 1.11-0.97 (d, J=6.7 Hz, 3H), 0.91-0.74 (d, J=6.7 Hz, 3H).

The following compounds were synthesized under analogous conditions for those described in Example 73

Compound 103

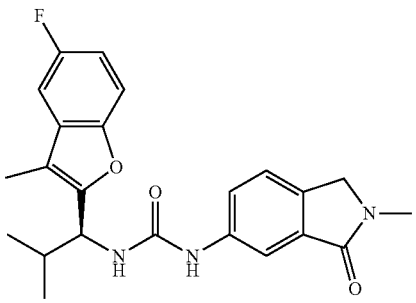

MS (ESI): mass calcd. for $C_{23}H_{24}FN_3O_3$, 409.18, m/z found 408.20 $[M-H]^-$.

$^1$H NMR (400 MHz, DMSO-d$_6$) δ 8.70-8.55 (s, 1H), 7.89-7.77 (s, 1H), 7.67-7.52 (m, 1H), 7.50-7.35 (m, 3H), 7.17-7.02 (t, J=9.0 Hz, 1H), 6.90-6.78 (d, J=8.7 Hz, 1H), 4.85-4.69 (t, J=8.6 Hz, 1H), 4.42-4.29 (s, 2H), 3.12-2.98 (s, 3H), 2.30-2.19 (s, 3H), 2.16-2.03 (m, 1H), 1.08-0.96 (d, J=6.7 Hz, 3H), 0.89-0.78 (d, J=6.7 Hz, 3H).

Compound 104

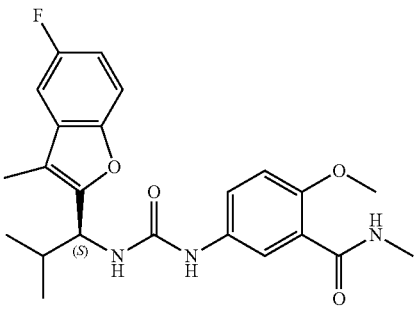

MS (ESI): mass calcd. for $C_{23}H_{26}FN_3O_4$, 427.19, m/z found 428.20 $[M+H]^+$.

$^1$H NMR (400 MHz, DMSO-d6) δ 8.40 (s, 1H), 8.12 (d, J=4.9 Hz, 1H), 7.70 (d, J=2.9 Hz, 1H), 7.50 (m, 2H), 7.38 (dd, J=8.8, 2.7 Hz, 1H), 7.09 (td, J=9.2, 2.7 Hz, 1H), 7.00 (d, J=9.0 Hz, 1H), 6.65 (d, J=8.7 Hz, 1H), 4.75 (t, J=8.6 Hz, 1H), 3.81 (s, 3H), 2.78 (d, J=4.6 Hz, 3H), 2.20 (s, 3H), 2.13-2.00 (m, 1H), 1.02 (d, J=6.7 Hz, 3H), 0.82 (d, J=6.7 Hz, 3H).

Compound 105

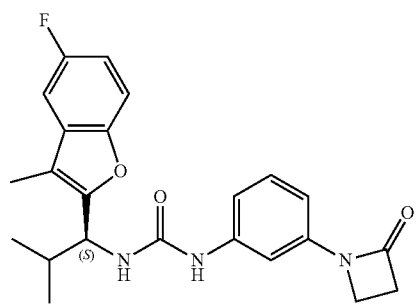

MS (ESI): mass calcd. for $C_{23}H_{24}FN_3O_3$, 409.18, m/z found 410.10 $[M+H]^+$.

$^1$H NMR (400 MHz, DMSO-d6) δ 8.60 (s, 1H), 7.59-7.43 (m, 2H), 7.38 (dd, J=8.9, 2.7 Hz, 1H), 7.18 (t, J=8.1 Hz, 1H), 7.13-7.00 (m, 2H), 6.84 (m, 1H), 6.73 (d, J=8.8 Hz, 1H), 4.76 (t, J=8.5 Hz, 1H), 3.57 (t, J=4.5 Hz, 2H), 3.04 (t, J=4.4 Hz, 2H), 2.21 (s, 3H), 2.16-2.05 (m, 1H), 1.01 (d, J=6.7 Hz, 3H), 0.83 (d, J=6.7 Hz, 3H).

Example 74: Preparation of Compound 106

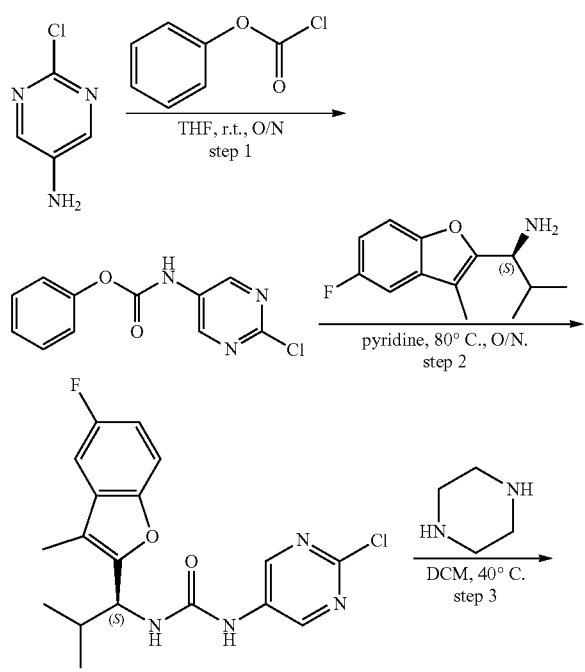

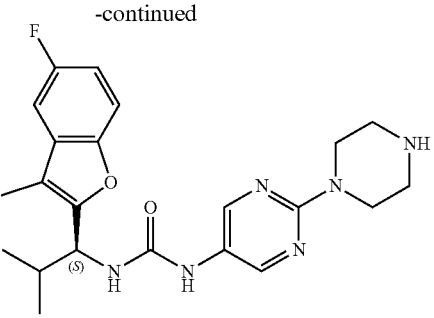

Compound 106

Step 1

A mixture of 2-chloropyrimidin-5-amine (500 mg, 3.8 mmol) and phenyl chloroformate (664.7 mg, 4.2 mmol) in THF (30 mL) was stirred overnight at room temperature under nitrogen atmosphere. The resulting mixture was concentrated under reduced pressure. The residue was purified by silica gel column chromatography, eluted with PE/EA (1:1) to afford phenyl N-(2-chloropyrimidin-5-yl) carbamate (836.7 mg, 86.7%) as an off-white solid.

Step 2

A solution of (S)-1-(5-fluoro-3-methylbenzofuran-2-yl)-2-methylpropan-1-amine (742.6 mg, 3.4 mmol) and phenyl N-(2-chloropyrimidin-5-yl)carbamate (836.7 mg, 3.4 mmol) in pyridine (20 mL) was stirred overnight at 80° C. under nitrogen atmosphere. The resulting solution was concentrated under reduced pressure. The residue was purified by silica gel column chromatography, eluted with PE/EA (10:1) to afford (S)-1-(2-chloropyrimidin-5-yl)-3-(1-(5-fluoro-3-methylbenzofuran-2-yl)-2-methylpropyl)urea (1.1 g, 86.1%) as a yellow oil.

Step 3

A mixture of (S)-1-(2-chloropyrimidin-5-yl)-3-(1-(5-fluoro-3-methylbenzofuran-2-yl)-2-methylpropyl)urea (170 mg, 0.4 mmol) and piperazine (777.2 mg, 9.0 mmol) in DCM (5 mL) was stirred for 3 days at 40° C. The resulting solution was concentrated under reduced pressure. The residue was purified by reverse flash chromatography to afford (S)-1-(1-(5-fluoro-3-methylbenzofuran-2-yl)-2-methylpropyl)-3-(2-(piperazin-1-yl)pyrimidin-5-yl)urea (55.8 mg, 28.7%) as an off-white solid. MS (ESI): mass calcd. for $C_{22}H_{27}FN_6O_2$, 426.22, m/z found 427.10 $[M+H]^+$.

$^1$H NMR (400 MHz, Methanol-d$_4$) δ 8.62-8.26 (s, 2H), 7.44-7.33 (dd, J=4.0, 8.9 Hz, 1H), 7.25-7.15 (dd, J=2.7, 8.6 Hz, 1H), 7.06-6.87 (td, J=2.7, 9.1 Hz, 1H), 4.83-4.78 (d, J=8.8 Hz, 1H), 3.79-3.68 (m, 4H), 2.94-2.83 (m, 4H), 2.26-2.17 (s, 4H), 1.15-1.07 (d, J=6.7 Hz, 3H), 0.89-0.86 (d, J=6.7 Hz, 3H).

The following compound was synthesized under analogous conditions for those described in Example 74

Compound 107

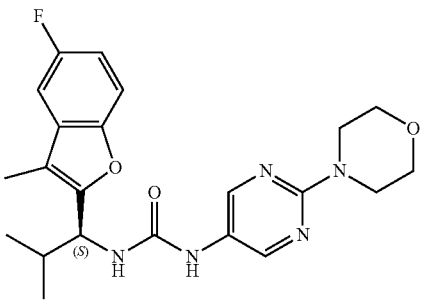

MS (ESI): mass calcd. for C₂₂H₂₆FN₅O₃, 427.20, m/z found 428.10 [M+H]⁺. ¹H NMR (400 MHz, DMSO-d6) δ 8.45-8.35 (s, 2H), 8.25-8.09 (s, 1H), 7.57-7.47 (dd, J=4.1, 8.9 Hz, 1H), 7.43-7.34 (dd, J=2.7, 8.8 Hz, 1H), 7.16-7.04 (td, J=2.7, 9.2 Hz, 1H), 6.99-6.84 (d, J=8.7 Hz, 1H), 4.81-4.68 (t, J=8.6 Hz, 1H), 3.70-3.53 (m, 8H), 2.26-2.16 (s, 3H), 2.15-2.04 (dt, J=7.0, 13.9 Hz, 1H), 1.06-0.93 (d, J=6.6 Hz, 3H), 0.88-0.75 (d, J=6.7 Hz, 3H).

Example 75: Preparation of Compound 108

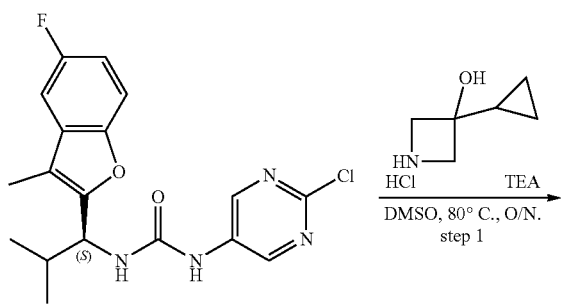

Compound 108

A solution of (S)-1-(2-chloropyrimidin-5-yl)-3-(1-(5-fluoro-3-methylbenzofuran-2-yl)-2-methylpropyl)urea (80 mg, 0.2 mmol), 3-cyclopropyl-3-hydroxyazetidin-1-ium chloride (318 mg, 2.1 mmol) and Et₃N (1 mL) in DMSO (2 mL) was stirred overnight at 80° C. The resulting solution was purified by reverse flash chromatography to afford (S)-1-(2-(3-cyclopropyl-3-hydroxyazetidin-1-yl)pyrimidin-5-yl)-3-(1-(5-fluoro-3-methylbenzofuran-2-yl)-2-methylpropyl)urea (54.7 mg, 56.3%) as a white solid. MS (ESI): mass calcd. for C₂₄H₂₈FN₅O₃, 453.22, m/z found 454.15 [M+H]⁺.

¹H NMR (400 MHz, DMSO-d6) δ 8.33 (s, 2H), 8.14 (s, 1H), 7.51 (dd, J=8.9, 4.1 Hz, 1H), 7.37 (dd, J=8.8, 2.7 Hz, 1H), 7.09 (td, J=9.2, 2.7 Hz, 1H), 6.86 (d, J=8.8 Hz, 1H), 5.51 (s, 1H), 4.72 (t, J=8.6 Hz, 1H), 3.81-3.71 (m, 4H), 2.19 (s, 3H), 2.15-2.04 (m, 1H), 1.18 (ddd, J=13.6, 8.3, 5.3 Hz, 1H), 1.01 (d, J=6.7 Hz, 3H), 0.84-0.73 (m, 3H), 0.44-0.36 (m, 2H), 0.31 (q, J=5.3 Hz, 2H).

The following compound was synthesized under analogous conditions for those described in Example 75.

Compound 109

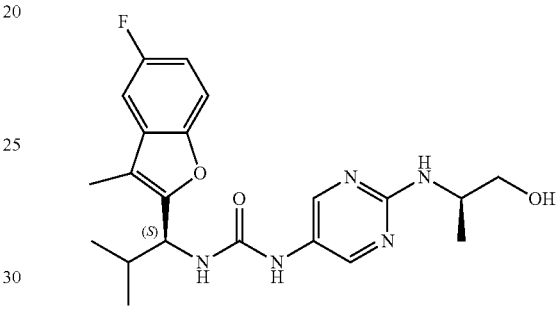

MS (ESI): mass calcd. for C₂₁H₂₆FN₅O₃, 415.20, m/z found 416.15 [M+H]⁺. ¹H NMR (400 MHz, DMSO-d6) δ 8.22 (s, 2H), 7.99 (s, 1H), 7.51 (dd, J=8.9, 4.1 Hz, 1H), 7.37 (dd, J=8.8, 2.7 Hz, 1H), 7.10 (td, J=9.2, 2.7 Hz, 1H), 6.84 (d, J=8.8 Hz, 1H), 6.45 (d, J=8.0 Hz, 1H), 4.73 (t, J=8.6 Hz, 1H), 4.63 (t, J=5.7 Hz, 1H), 3.98-3.79 (m, 1H), 3.44 (dt, J=10.6, 5.4 Hz, 1H), 3.26 (dt, J=10.4, 6.2 Hz, 1H), 2.19 (s, 3H), 2.14-2.03 (m, 1H), 1.09 (d, J=6.6 Hz, 3H), 1.01 (d, J=6.7 Hz, 3H), 0.81 (d, J=6.7 Hz, 3H).

Compound 110

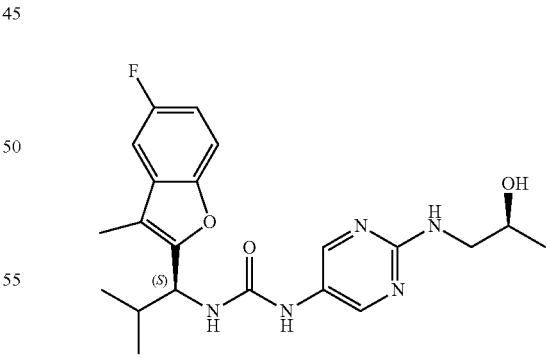

MS (ESI): mass calcd. for C₂₁H₂₆FN₅O₃, 415.20, m/z found 416.25 [M+H]⁺. ¹H NMR (400 MHz, DMSO-d6) δ 8.22 (s, 2H), 8.01 (s, 1H), 7.51 (dd, J=8.9, 4.0 Hz, 1H), 7.37 (dd, J=8.7, 2.7 Hz, 1H), 7.10 (td, J=9.2, 2.7 Hz, 1H), 6.84 (d, J=8.8 Hz, 1H), 6.66 (t, J=5.9 Hz, 1H), 4.73 (t, J=8.6 Hz, 1H), 4.65 (d, J=4.7 Hz, 1H), 3.82-3.66 (m, 1H), 3.16 (t, J=6.0 Hz, 2H), 2.19 (s, 3H), 2.15-2.02 (m, 1H), 1.03 (dd, J=10.4, 6.4 Hz, 6H), 0.81 (d, J=6.7 Hz, 3H).

Compound 111

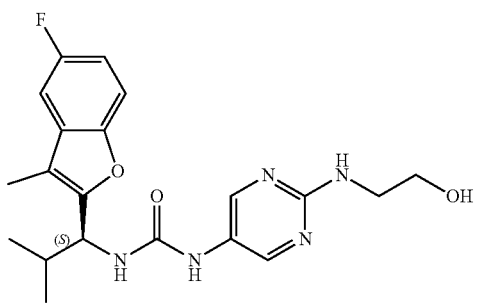

MS (ESI): mass calcd. for $C_{20}H_{24}FN_5O_3$, 401.19, m/z found 402.20 [M+H]$^+$. $^1$H NMR (400 MHz, DMSO-d6) δ 8.23 (s, 2H), 8.01 (s, 1H), 7.51 (dd, J=8.9, 4.1 Hz, 1H), 7.37 (dd, J=8.8, 2.7 Hz, 1H), 7.10 (td, J=9.2, 2.7 Hz, 1H), 6.84 (d, J=8.8 Hz, 1H), 6.68 (t, J=5.8 Hz, 1H), 4.73 (t, J=8.6 Hz, 1H), 4.62 (t, J=5.6 Hz, 1H), 3.48 (m, 2H), 3.35-3.29 (m, 2H), 2.19 (s, 3H), 2.15-2.05 (m, 1H), 1.01 (d, J=6.7 Hz, 3H), 0.81 (d, J=6.7 Hz, 3H).

Compound 112

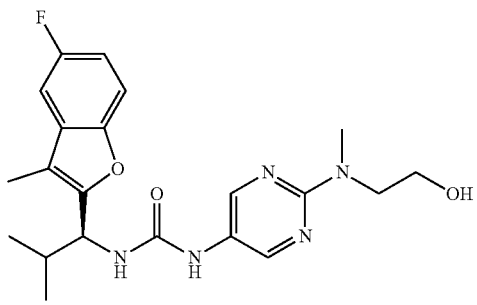 [SMILES: Cc1c([C@@H](NC(=O)Nc2cnc(N(C)CCO)nc2)C(C)C)oc2ccc(F)cc12]

MS (ESI): mass calcd. for $C_{21}H_{26}FN_5O_3$, 415.20, m/z found 416.15 [M+H]$^+$. $^1$H NMR (400 MHz, Methanol-d$_4$) δ 8.34-8.22 (s, 2H), 7.44-7.35 (dd, J=4.0, 8.9 Hz, 1H), 7.26-7.17 (dd, J=2.6, 8.6 Hz, 1H), 7.07-6.97 (td, J=2.7, 9.1 Hz, 1H), 4.84-4.78 (d, J=8.8 Hz, 1H), 3.80-3.65 (d, J=1.8 Hz, 4H), 3.24-3.11 (s, 3H), 2.35-2.11 (m, 4H), 1.17-1.04 (d, J=6.7 Hz, 3H), 0.99-0.84 (d, J=6.7 Hz, 3H).

Compound 113

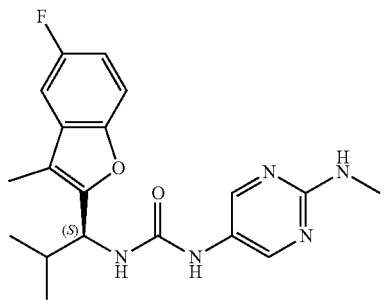

MS (ESI): mass calcd. for $C_{19}H_{22}FN_5O_2$, 371.18, m/z found 372.10 [M+H]$^+$. $^1$H NMR (400 MHz, DMSO-d$_6$) δ 8.29-8.18 (s, 2H), 8.07-7.98 (s, 1H), 7.57-7.47 (dd, J=4.1, 8.9 Hz, 1H), 7.43-7.311 (dd, J=2.7, 8.8 Hz, 1H), 7.17-7.03 (td, J=2.7, 9.2 Hz, 1H), 6.87-6.81 (d, J=8.8 Hz, 1H), 6.79-6.69 (m, 1H) 4.80-4.69 (t, J=8.6 Hz, 1H), 2.82-2.70 (d, J=4.8 Hz, 3H), 2.25-2.16 (s, 3H), 2.16-2.03 (m, 1H), 1.04-0.96 (d, J=6.7 Hz, 3H), 0.85-0.77 (d, J=6.7 Hz, 3H).

Compound 114

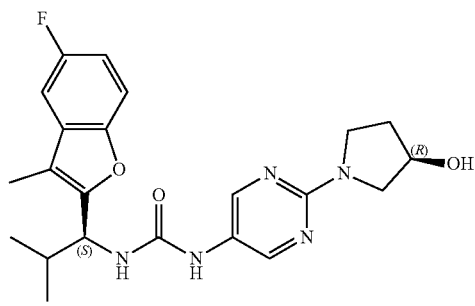

MS (ESI): mass calcd. for $C_{22}H_{26}FN_5O_3$, 427.20, m/z found 428.10 [M+H]$^+$. $^1$H NMR (400 MHz, Methanol-d$_4$) δ 8.34-8.26 (s, 2H), 7.45-7.36 (dd, J=4.0, 8.9 Hz, 1H), 7.27-7.17 (dd, J=2.7, 8.6 Hz, 1H), 7.08-6.95 (td, J=2.7, 9.1 Hz, 1H), 4.86-4.78 (d, J=8.8 Hz, 1H), 4.59-4.46 (tt, J=2.5, 4.8 Hz, 1H), 3.71-3.60 (m, 3H), 3.58-3.51 (dt, J=1.8, 12.0 Hz, 1H), 2.32-2.17 (m, 4H), 2.17-1.98 (m, 2H), 1.19-1.06 (d, J=6.7 Hz, 3H), 0.95-0.83 (d, J=6.7 Hz, 3H).

Compound 115

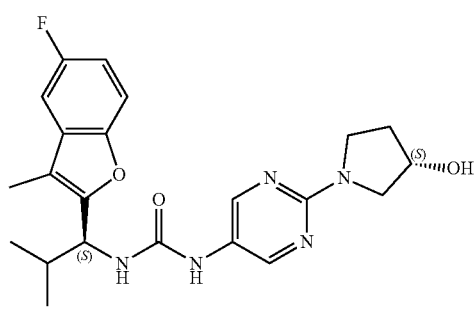

MS (ESI): mass calcd. for $C_{22}H_{26}FN_5O_3$, 427.20, m/z found 428.10 [M+H]$^+$. $^1$H NMR (400 MHz, Methanol-d$_4$) δ 8.37-8.25 (s, 2H), 7.44-7.34 (dd, J=4.0, 8.9 Hz, 1H), 7.26-7.18 (dd, J=2.7, 8.6 Hz, 1H), 7.07-6.96 (td, J=2.7, 9.1 Hz, 1H), 4.85-4.79 (d, J=8.8 Hz, 1H), 4.57-4.47 (dt, J=2.2, 4.4 Hz, 1H), 3.71-3.47 (m, 4H), 2.28-2.21 (m, 4H), 2.18-2.08 (m, 1H), 2.06-1.98 (s, 1H), 1.16-1.08 (d, J=6.7 Hz, 3H), 0.92-0.85 (d, J=6.7 Hz, 3H).

Compound 116

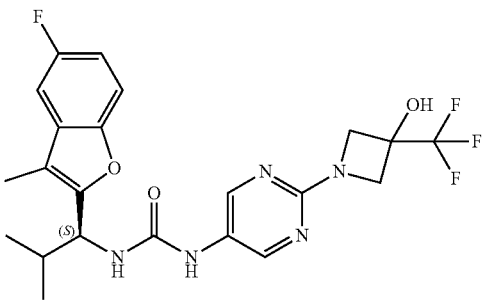

MS (ESI): mass calcd. for C$_{22}$H$_{23}$F$_4$N$_5$O$_3$, 481.17, m/z found 482.10 [M+H]$^+$. $^1$H NMR (400 MHz, DMSO-d6) δ 8.42 (s, 2H), 8.25 (s, 1H), 7.51 (dd, J=8.9, 4.1 Hz, 1H), 7.37 (dd, J=8.8, 2.7 Hz, 1H), 7.10 (td, J=9.2, 2.7 Hz, 1H), 6.92 (d, J=8.7 Hz, 1H), 4.74 (t, J=8.6 Hz, 1H), 4.15-4.24 (m, 2H), 3.99 (d, J=9.6 Hz, 2H), 2.55 (s, 1H), 2.19 (s, 3H), 2.11 (m, 1H), 1.02 (d, J=6.7 Hz, 3H), 0.81 (d, J=6.7 Hz, 3H),

Compound 117

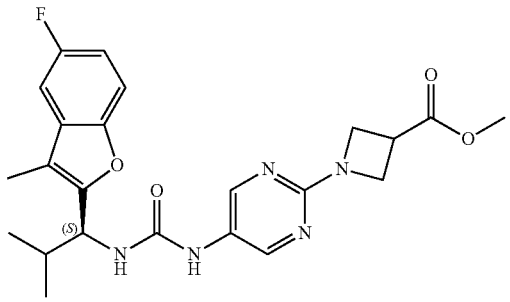

MS (ESI): mass calcd. for C$_{23}$H$_{26}$FN$_5$O$_4$, 455.20, m/z found 456.10 [M+H]$^+$. $^1$H NMR (400 MHz, DMSO-d6) δ 8.38 (s, 2H), 8.21 (s, 1H), 7.51 (dd, J=8.9, 4.1 Hz, 1H), 7.37 (dd, J=8.8, 2.7 Hz, 1H), 7.09 (td, J=9.2, 2.7 Hz, 1H), 6.90 (d, J=8.7 Hz, 1H), 4.73 (t, J=8.6 Hz, 1H), 4.17 (t, J=8.6 Hz, 2H), 4.03 (dd, J=8.4, 5.9 Hz, 2H), 3.67 (s, 3H), 3.62-3.54 (m, 1H), 2.19 (s, 3H), 2.14-2.07 (m, 1H), 1.01 (d, J=6.7 Hz, 3H), 0.81 (d, J=6.7 Hz, 3H).

Compound 118

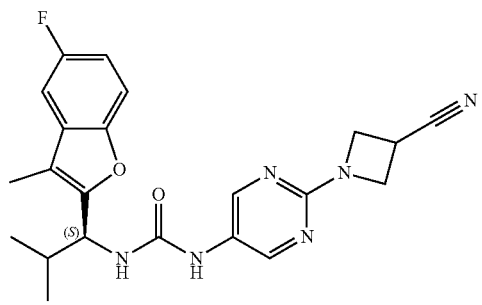

MS (ESI): mass calcd. for C$_{22}$H$_{23}$FN$_6$O$_2$, 422.19, m/z found 423.10 [M+H]$^+$. $^1$H NMR (400 MHz, DMSO-d6) δ 8.41 (s, 2H), 8.25 (s, 1H), 7.51 (dd, J=8.9, 4.1 Hz, 1H), 7.37 (dd, J=8.8, 2.7 Hz, 1H), 7.10 (td, J=9.2, 2.7 Hz, 1H), 6.92 (d, J=8.7 Hz, 1H), 4.73 (t, J=8.6 Hz, 1H), 4.25 (t, J=8.5 Hz, 2H), 4.10 (dd, J=8.3, 5.7 Hz, 2H), 3.83 (tt, J=8.8, 5.7 Hz, 1H), 2.19 (s, 3H), 2.15-2.04 (m, 1H), 1.01 (d, J=6.7 Hz, 3H), 0.81 (d, J=6.7 Hz, 3H).

Example 76: Preparation of Compound 119

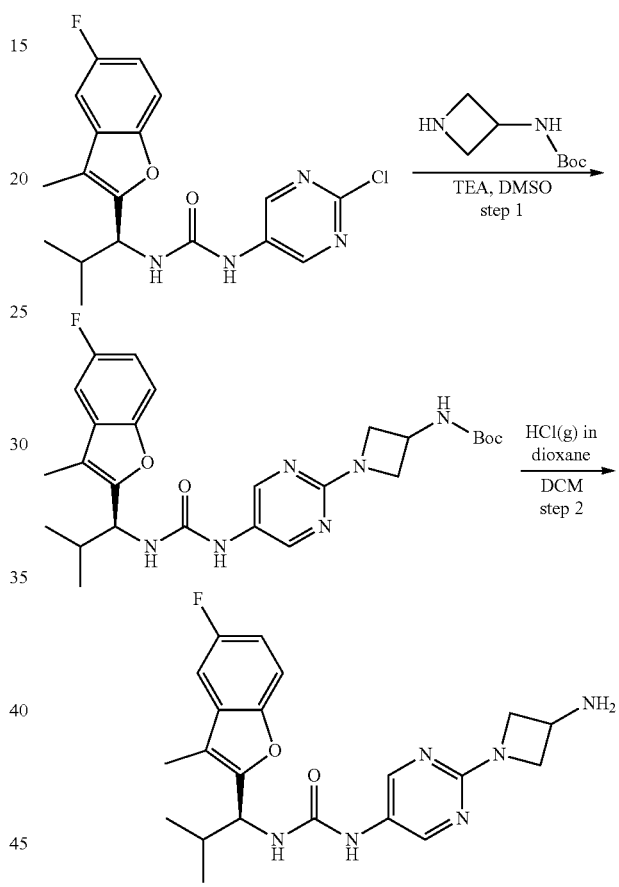

Compound 119

Step 1

A solution of (S)-1-(2-chloropyrimidin-5-yl)-3-(1-(5-fluoro-3-methylbenzofuran-2-yl)-2-methylpropyl)urea (80 mg, 0.2 mmol), tert-butyl N-(azetidin-3-yl)carbamate (365 mg, 2.1 mmol) and TEA (1 mL) in DMSO (2 mL) was stirred overnight at 80° C. The resulting solution was diluted with EtOAc, then washed with saturated NaCl. The organic layer was dried over anhydrous Na$_2$SO$_4$, filtered and concentrated under reduced pressure. The crude product was used in next step directly.

Step 2

To a solution of the crude product in DCM (5 mL) was added 4M HCl (g) in dioxane (1 mL). The resulting solution was stirred for 1 hour at room temperature, then adjusted pH to 8-9 with saturated NaHCO₃. The resulting mixture was extracted with DCM. The combined organic layers were dried over anhydrous Na₂SO₄. After filtration, the filtrate was concentrated under reduced pressure. The residue was purified by Prep-HPLC to afford (S)-1-(2-(3-aminoazetidin-1-yl)pyrimidin-5-yl)-3-(1-(5-fluoro-3-methylbenzofuran-2-yl)-2-methylpropyl)urea (26.2 mg, 29.91% for two steps) as a yellow solid. MS (ESI): mass calcd. for $C_{21}H_{25}FN_6O_2$, 412.20, m/z found 413.10 [M+H]⁺.

¹H NMR (400 MHz, DMSO-d6) δ 8.41 (s, 2H), 8.33 (d, J=7.3 Hz, 3H), 7.51 (dd, J=8.9, 4.1 Hz, 1H), 7.38 (dd, J=8.8, 2.7 Hz, 1H), 7.10 (td, J=9.2, 2.7 Hz, 1H), 6.98 (d, J=8.6 Hz, 1H), 4.72 (t, J=8.6 Hz, 1H), 4.22 (dd, J=9.3, 7.3 Hz, 2H), 4.09 (s, 1H), 3.95 (dd, J=9.5, 4.6 Hz, 2H), 2.19 (s, 3H), 2.12 (dt, J=8.3, 6.6 Hz, 1H), 1.02 (d, J=6.7 Hz, 3H), 0.81 (d, J=6.7 Hz, 3H).

Example 77: Preparation of Compound 120

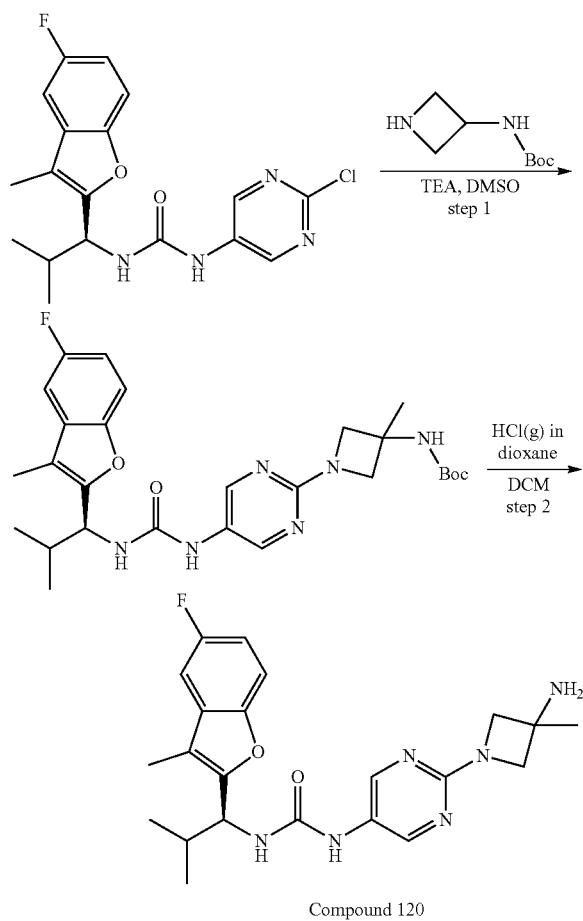

Compound 120

Step 1

A solution of (S)-1-(2-chloropyrimidin-5-yl)-3-(1-(5-fluoro-3-methylbenzofuran-2-yl)-2-methylpropyl)urea (80 mg, 0.2 mmol), tert-butyl N-(3-methylazetidin-3-yl)carbamate (395 mg, 2.1 mmol) and TEA (1 mL) in DMSO (2 mL) was stirred overnight at 80° C. The resulting solution was diluted with EtOAc, then washed with saturated NaCl. The organic layer was dried over anhydrous Na₂SO₄, filtered and concentrated under reduced pressure. The crude product was used in next step directly.

Step 2

To a solution of the crude product in DCM (5 mL) was added 4M HCl (g) in dioxane (1 mL). The resulting solution was stirred for 1 hour at room temperature, then adjusted pH to 8-9 with saturated NaHCO₃. The resulting mixture was extracted with DCM. The combined organic layers were dried over anhydrous Na₂SO₄. After filtration, the filtrate was concentrated under reduced pressure. The residue was purified by Prep-HPLC to afford (S)-1-(2-(3-amino-3-methylazetidin-1-yl)pyrimidin-5-yl)-3-(1-(5-fluoro-3-methylbenzofuran-2-yl)-2-methylpropyl)urea (40.6 mg, 44.81% for two steps) as a yellow solid. MS (ESI): mass calcd. for $C_{22}H_{27}FN_6O_2$, 426.22, m/z found 427.10 [M+H]⁺.

¹H NMR (400 MHz, DMSO-d6) δ 8.42-8.33 (m, 5H), 7.51 (dd, J=8.9, 4.1 Hz, 1H), 7.38 (dd, J=8.8, 2.7 Hz, 1H), 7.10 (td, J=9.2, 2.7 Hz, 1H), 6.98 (d, J=8.6 Hz, 1H), 4.72 (t, J=8.6 Hz, 1H), 4.05 (d, J=9.2 Hz, 2H), 3.92 (d, J=9.2 Hz, 2H), 2.19 (s, 3H), 2.15-2.08 (m, 1H), 1.56 (s, 3H), 1.02 (d, J=6.7 Hz, 3H), 0.81 (d, J=6.7 Hz, 3H).

Example 78: Preparation of Compound 121

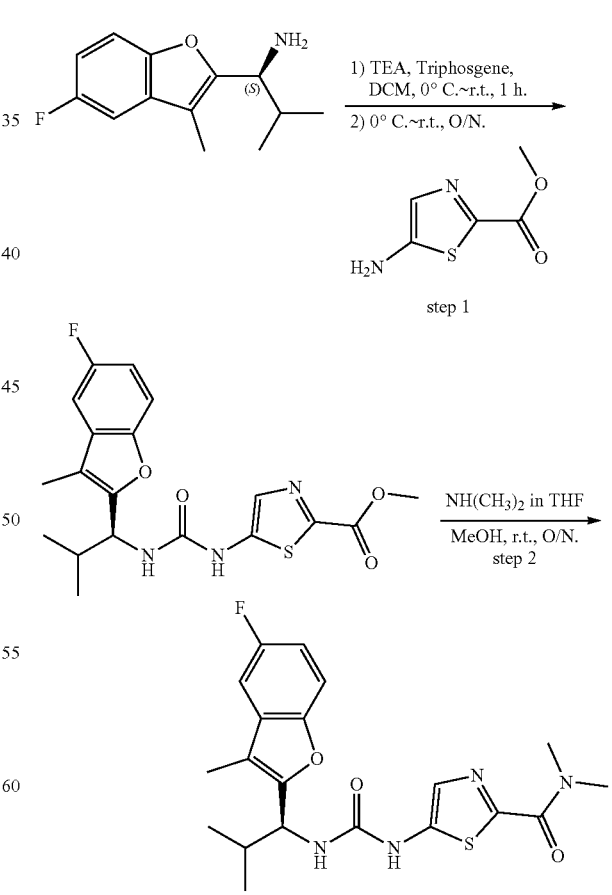

Compound 121

Step 1

To a stirred solution of (S)-1-(5-fluoro-3-methyl-1-benzofuran-2-yl)-2-methylpropan-1-amine (300 mg, 1.3 mmol) and TEA (1.1 mg, 10.9 mmol) in DCM (9 mL) was added triphosgene (400 mg, 1.3 mmol) at 0° C. The resulting solution was stirred for 1 h at room temperature under nitrogen atmosphere. Then methyl 5-aminothiazole-2-carboxylate (252.8 mg, 1.6 mmol) was added at 0° C. The resulting mixture was stirred overnight at room temperature under nitrogen atmosphere, then quenched with MeOH and concentrated under reduced pressure. The residue was purified by reverse flash chromatography to afford methyl (S)-5-(3-(1-(5-fluoro-3-methylbenzofuran-2-yl)-2-methylpropyl)ureido)thiazole-2-carboxylate (310 mg, 56.5%) as an off-white solid.

Step 2

A solution of methyl (S)-5-(3-(1-(5-fluoro-3-methylbenzofuran-2-yl)-2-methylpropyl)ureido) thiazole-2-carboxylate (120 mg, 0.3 mmol) and dimethylamine (1.5 mL, 3 mmol, 2 M in THF) in MeOH (1 mL) was stirred overnight at room temperature, then concentrated under reduced pressure. The residue was purified by Prep-HPLC to afford (S)-5-(3-(1-(5-fluoro-3-methylbenzofuran-2-yl)-2-methylpropyl)ureido)-N,N-dimethylthiazole-2-carboxamide (39.5 mg, 31.6%) as an off-white solid. MS (ESI): mass calcd. for $C_{20}H_{23}FN_4O_3S$, 418.15, m/z found 419.30 [M+H]$^+$.

$^1$H NMR (400 MHz, DMSO-$d_6$) δ 9.99-9.29 (s, 1H), 7.57-7.49 (dd, J=4.1, 8.9 Hz, 1H), 7.48-7.44 (s, 1H), 7.42-7.36 (dd, J=2.7, 8.8 Hz, 1H), 7.28-7.17 (d, J=8.7 Hz, 1H), 7.16-7.06 (td, J=2.7, 9.2 Hz, 1H), 4.80-4.70 (t, J=8.6 Hz, 1H), 3.57-3.43 (s, 3H), 3.06-2.93 (s, 3H), 2.26-2.20 (s, 3H), 2.20-2.08 (m, 1H), 1.08-0.96 (d, J=6.6 Hz, 3H), 0.922-0.74 (d, J=6.7 Hz, 3H).

Example 79: Preparation of Compound 122

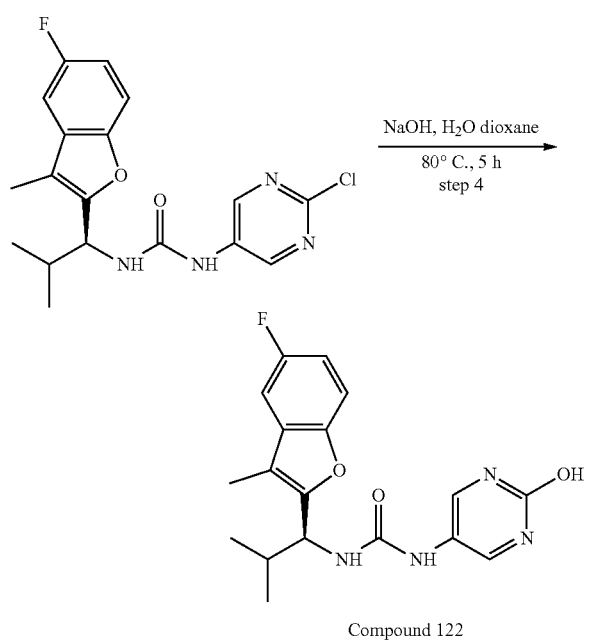

Compound 122

To a solution of sodium (S)-1-(2-chloropyrimidin-5-yl)-3-(1-(5-fluoro-3-methylbenzofuran-2-yl)-2-methylpropyl) urea (100 mg, 0.266 mmol) in dioxane (1.0 mL) and H$_2$O (1.0 mL) was added NaOH (53.2 mg, 1.330 mmol). The mixture was stirred at 80° C. for 5 hours. The combined organic layer was dried over anhydrous sodium sulfate and concentrated under vacuum. The crude product was purified by Prep-HPLC. This resulted in P-106111-0 (27.7 mg, 29.1%) as a white solid. MS (ESI): mass calcd. for $C_{18}H_{19}FN_4O_3$, 358, m/z found 359 [M+H]$^+$.

$^1$H NMR (400 MHz, DMSO) δ $^1$H NMR (400 MHz, DMSO) δ 11.12 (s, 1H), 8.21 (s, 2H), 8.11 (s, 1H), 7.51 (dd, J=4.1, 8.9 Hz, 1H), 7.38 (dd, J=2.7, 8.8 Hz, 1H), 7.10 (td, J=2.8, 9.2, 9.2 Hz, 1H), 7.02 (dd, J=4.2, 8.8 Hz, 1H), 4.70 (t, J=8.6, 8.6 Hz, 1H), 2.19 (s, 3H), 2.10 (dt, J=7.0, 7.0, 14.0 Hz, 1H), 1.01 (d, J=6.6 Hz, 3H), 0.80 (d, J=6.7 Hz, 3H).

Example 80: Preparation of Compound 123

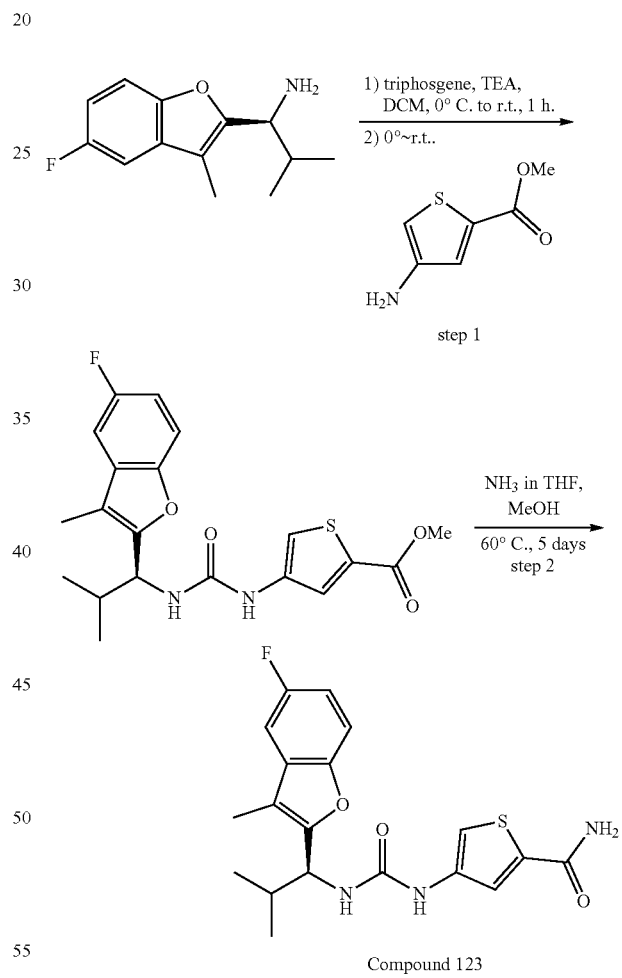

Compound 123

Step 1

To a stirred solution of (S)-1-(5-fluoro-3-methylbenzofuran-2-yl)-2-methylpropan-1-amine (100 mg, 0.4 mmol) and TEA (366 mg, 3.6 mmol) in DCM (3 mL) was added triphosgene (120 mg, 0.4 mmol) at 0° C. The reaction solution was stirred for 1 h at room temperature. Then methyl 4-aminothiophene-2-carboxylate (78 mg, 0.5 mmol) was added at 0° C. The reaction solution was stirred overnight at room temperature, then quenched with MeOH and concentrated under reduced pressure. The residue was purified by reverse flash column chromatography to afford methyl (S)-4-(3-(1-(5-fluoro-3-methylbenzofuran-2-yl)-2-methylpropyl)ureido)thiophene-2-carboxylate (100 mg, 54.94%) as a white solid.

Step 2

A solution of (S)-4-(3-(1-(5-fluoro-3-methylbenzofuran-2-yl)-2-methylpropyl) ureido)thiophene-2-carboxylate (100 mg, 0.2 mmol) and $NH_3$ (1 mL, 1 M in THF) in MeOH (1 mL) was stirred for 5 days. The crude product was purified by Prep-HPLC to afford (S)-4-(3-(1-(5-fluoro-3-methylbenzofuran-2-yl)-2-methylpropyl)ureido)thiophene-2-carboxamide (28.6 mg, 29.54%) as a white solid. MS (ESI): mass calcd. for $C_{19}H_{20}FN_3O_3S$, 389.12, m/z found 390.20 $[M+H]^+$.

$^1$H NMR (400 MHz, DMSO-d6) δ 8.67 (s, 1H), 7.94 (s, 1H), 7.56 (d, J=1.6 Hz, 1H), 7.51 (dd, J=8.9, 4.1 Hz, 1H), 7.38 (dd, J=8.8, 2.7 Hz, 1H), 7.34 (s, 1H), 7.30 (d, J=1.5 Hz, 1H), 7.10 (td, J=9.2, 2.7 Hz, 1H), 6.78 (d, J=8.8 Hz, 1H), 4.74 (t, J=8.6 Hz, 1H), 2.20 (s, 3H), 1.02 (d, J=6.7 Hz, 3H), 0.82 (d, J=6.7 Hz, 3H).

Example 81: Preparation of Compound 124

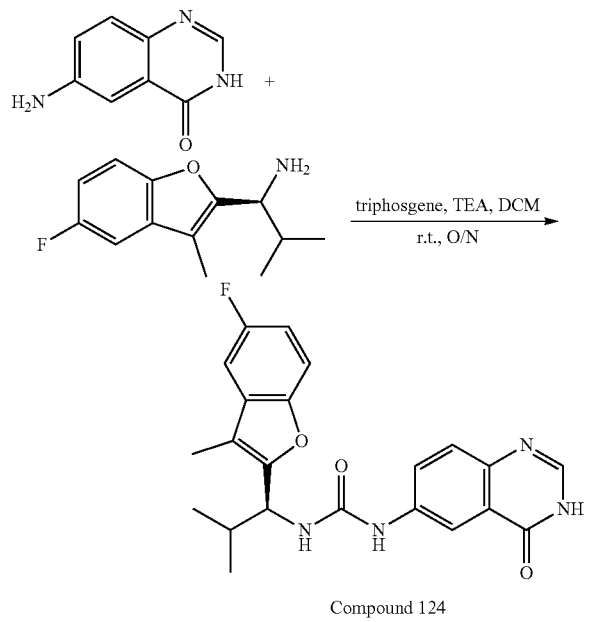

Compound 124

To a stirred solution of (S)-1-(5-fluoro-3-methylbenzofuran-2-yl)-2-methylpropan-1-amine (90 mg, 0.4 mmol) and TEA (329 mg, 3.2 mmol) in DCM (3 mL) was added triphosgene (120 mg, 0.4 mmol) at 0° C. The resulting solution was stirred for 1 hour at room temperature. Then 6-amino-3H-quinazolin-4-one (78 mg, 0.5 mmol) was added at 0° C. The resulting solution was stirred overnight at room temperature, then quenched with MeOH, concentrated under reduced pressure. The residue was purified by reverse flash chromatography to afford (S)-1-(1-(5-fluoro-3-methylbenzofuran-2-yl)-2-methylpropyl)-3-(4-oxo-3,4-dihydroquinazolin-6-yl)urea (10.6 mg, 6.37%) as a off-white solid. MS (ESI): mass calcd. for $C_{22}H_{21}FN_4O_3$, 408.16, m/z found 409.10 $[M+H]^+$.

$^1$H NMR (400 MHz, DMSO-d6) δ 12.08 (s, 1H), 8.86 (s, 1H), 8.24 (d, J=2.6 Hz, 1H), 7.94 (s, 1H), 7.67 (dd, J=8.8, 2.6 Hz, 1H), 7.57-7.48 (m, 2H), 7.39 (dd, J=8.8, 2.7 Hz, 1H), 7.10 (td, J=9.2, 2.7 Hz, 1H), 6.92 (d, J=8.7 Hz, 1H), 4.78 (t, J=8.6 Hz, 1H), 2.23 (s, 3H), 2.14 (m, 1H), 1.05 (d, J=6.6 Hz, 3H), 0.84 (d, J=6.7 Hz, 3H).

Example 82: Preparation of Compound 125

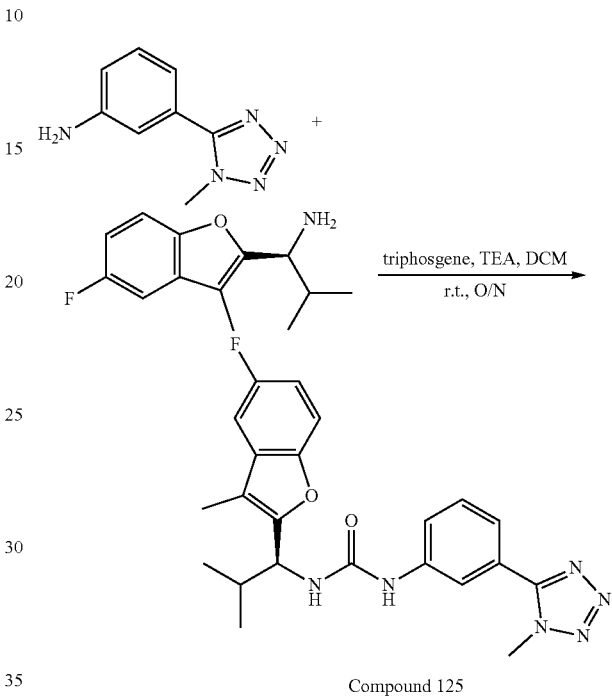

Compound 125

To a stirred solution of (S)-1-(5-fluoro-3-methylbenzofuran-2-yl)-2-methylpropan-1-amine (90 mg, 0.4 mmol) and TEA (329 mg, 3.2 mmol) in DCM (3 mL) was added triphosgene (120 mg, 0.4 mmol) at 0° C. The resulting solution was stirred for 1 hour at room temperature. Then 3-(1-methyl-1,2,3,4-tetrazol-5-yl)aniline (85 mg, 0.5 mmol) was added at 0° C. The resulting solution was stirred overnight at room temperature, then quenched with MeOH, concentrated under reduced pressure. The residue was purified by reverse flash chromatography to afford (S)-1-(1-(5-fluoro-3-methylbenzofuran-2-yl)-2-methylpropyl)-3-(3-(1-methyl-1H-tetrazol-5-yl)phenyl)urea (31.4 mg, 17.54%) as a off-white solid. MS (ESI): mass calcd. for $C_{22}H_{23}FN_6O_2$, 422.19, m/z found 423.10 $[M+H]^+$.

$^1$H NMR (400 MHz, DMSO-d$_6$) δ 8.80 (s, 1H), 7.96 (d, J=2.0 Hz, 1H), 7.58-7.43 (m, 3H), 7.40-7.29 (m, 2H), 7.10 (td, J=9.2, 2.7 Hz, 1H), 6.94 (d, J=8.7 Hz, 1H), 4.78 (t, J=8.5 Hz, 1H), 4.15 (s, 3H), 2.22 (s, 3H), 2.19-2.11 (m, 1H), 1.04 (d, J=6.7 Hz, 3H), 0.83 (d, J=6.7 Hz, 3H).

Example 83: Preparation of Compound 126

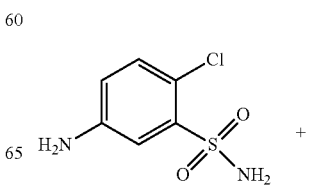

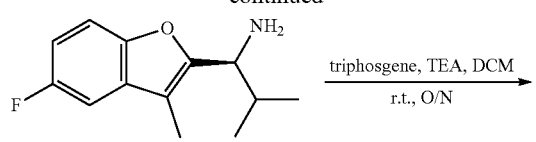

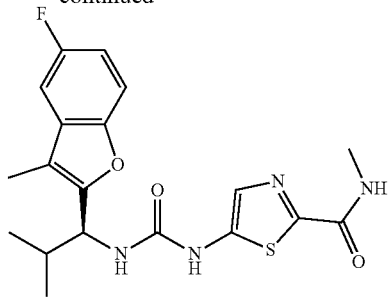

Compound 127

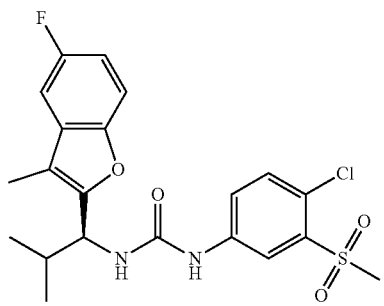

Compound 126

To a stirred solution of (S)-1-(5-fluoro-3-methylbenzofuran-2-yl)-2-methylpropan-1-amine (90 mg, 0.4 mmol) and TEA (329 mg, 3.2 mmol) in DCM (4 mL) was added triphosgene (120 mg, 0.4 mmol) at 0° C. The resulting solution was stirred for 1 hour at room temperature. Then 5-amino-2-chlorobenzenesulfonamide (100 mg, 0.5 mmol) was added at 0° C. The resulting solution was stirred overnight at room temperature, then quenched with MeOH, concentrated under reduced pressure. The residue was purified by reverse flash chromatography to afford (S)-1-(4-chloro-3-(methylsulfonyl)phenyl)-3-(1-(5-fluoro-3-methylbenzofuran-2-yl)-2-methylpropyl)urea (34.4 mg, 17.91%) as a off-white solid. MS (ESI): mass calcd. for $C_{21}H_{22}ClFN_2O_4S$, 452.10, m/z found 453.05 [M+H]$^+$.

$^1$H NMR (400 MHz, DMSO-d$_6$) δ 9.01 (s, 1H), 8.23 (s, 1H), 7.56 (m, 3H), 7.38 (d, J=8.9 Hz, 1H), 7.11 (d, J=9.4 Hz, 1H), 6.92 (d, J=8.7 Hz, 1H), 4.76 (t, J=8.6 Hz, 1H), 3.62-3.21 (s, 3H) 2.32-1.96 (m, 4H), 1.03 (d, J=6.6 Hz, 3H), 0.83 (d, J=6.6 Hz, 3H).

Example 84: Preparation of Compound 127

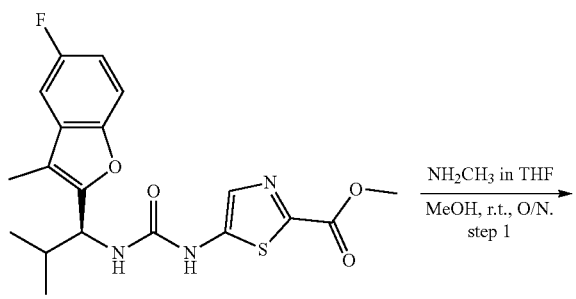

A solution of methyl (S)-5-(3-(1-(5-fluoro-3-methylbenzofuran-2-yl)-2-methylpropyl)ureido) thiazole-2-carboxylate (120 mg, 0.3 mmol) and methylamine (1.5 mL, 3 mmol, 2M in THF) in MeOH (1 mL) was stirred overnight at room temperature, then concentrated under reduced pressure. The residue was purified by reverse flash chromatography to afford (S)-5-(3-(1-(5-fluoro-3-methylbenzofuran-2-yl)-2-methylpropyl)ureido)-N-methylthiazole-2-carboxamide (24.1 mg, 20.1%) as a off-white solid. MS (ESI): mass calcd. for $C_{19}H_{21}FN_4O_3S$, 404.13, m/z found 405.15 [M+H]$^+$.

$^1$H NMR (400 MHz, DMSO-d$_6$) δ 9.90-9.65 (s, 1H), 8.48-8.33 (d, J=4.8 Hz, 1H), 7.55-7.49 (dd, J=4.0, 8.9 Hz, 1H), 7.46-7.35 (m, 2H), 7.32-7.22 (d, J=8.6 Hz, 1H), 7.19-7.03 (td, J=2.7, 9.2 Hz, 1H), 4.81-4.69 (t, J=8.6 Hz, 1H), 2.81-2.63 (d, J=4.8 Hz, 3H), 2.28-2.19 (s, 3H), 2.19-2.06 (dt, J=6.7, 13.4 Hz, 1H), 1.07-0.95 (d, J=6.6 Hz, 3H), 0.93-0.75 (d, J=6.7 Hz, 3H).

Example 85: Preparation of Compound 128

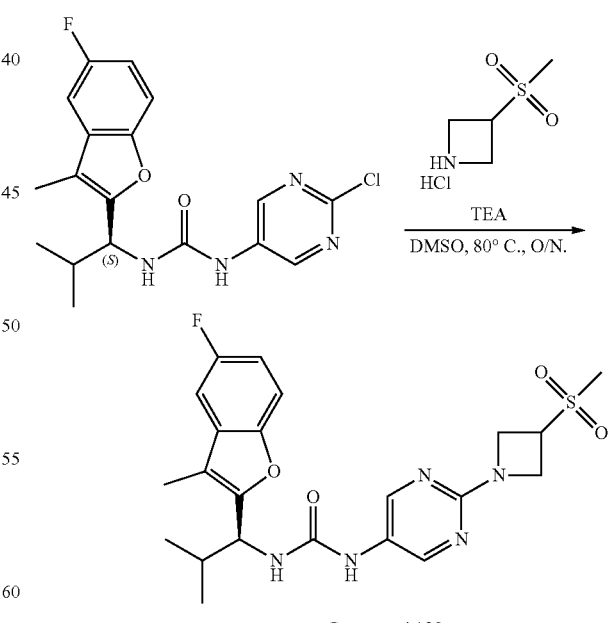

Compound 128

A solution of (S)-1-(2-chloropyrimidin-5-yl)-3-(1-(5-fluoro-3-methylbenzofuran-2-yl)-2-methylpropyl)urea (80 mg, 0.2 mmol), 3-methanesulfonylazetidine hydrochloride (364 mg, 2.1 mmol) and Et$_3$N (1 mL) in DMSO (2 mL) was stirred overnight at 80° C. The resulting solution was purified by Prep-HPLC afford (S)-1-(1-(5-fluoro-3-methylbenzofuran-2-yl)-2-methylpropyl)-3-(2-(3-(methylsulfonyl)azetidin-1-yl)pyrimidin-5-yl)urea (50.0 mg, 49.5%) as a white solid. MS (ESI): mass calcd. for $C_{22}H_{26}FN_5O_4S$, 475.17, m/z found 476.10 [M+H]$^+$. $^1$H NMR (400 MHz, DMSO-d6) δ 8.41 (s, 2H), 8.23 (s, 1H), 7.51 (dd, J=8.8, 4.1 Hz, 1H), 7.37 (dd, J=8.8, 2.7 Hz, 1H), 7.09 (td, J=9.2, 2.7 Hz, 1H), 6.91 (d, J=8.8 Hz, 1H), 4.73 (t, J=8.6 Hz, 1H), 4.41-4.31 (m, 1H), 4.25 (t, J=8.7 Hz, 2H), 4.15 (dd, J=9.6, 5.2 Hz, 2H), 3.03 (s, 3H), 2.19 (s, 3H), 2.16-2.05 (m, 1H), 1.01 (d, J=6.7 Hz, 3H), 0.81 (d, J=6.7 Hz, 3H).

Example 86: Preparation of Compound 129

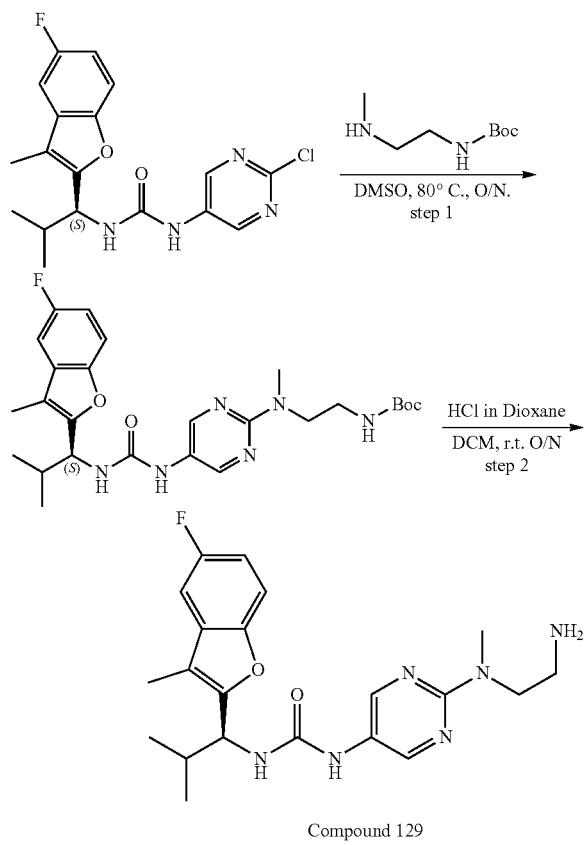

Compound 129

Step 1

A solution of (S)-1-(2-chloropyrimidin-5-yl)-3-(1-(5-fluoro-3-methylbenzofuran-2-yl)-2-methylpropyl)urea (160 mg, 0.4 mmol), tert-butyl N-[2-(methylamino)ethyl]carbamate (370 mg, 2.1 mmol) and TEA (2 mL) in DMSO (6 ml) was stirred overnight at 80° C. The resulting solution was diluted with EA, washed with saturated NaCl. The organic layer was dried over anhydrous Na$_2$SO$_4$, filtered and concentrated under reduced pressure. The residue was purified by silica gel column chromatography to afford tert-butyl (S)-(2-((5-(3-(1-(5-fluoro-3-methylbenzofuran-2-yl)-2-methylpropyl)ureido)pyrimidin-2-yl)(methyl)amino)ethyl)carbamate (100 mg, 45.87%) as a yellow solid.

Step 2

To a stirred solution of tert-butyl (S)-(2-((5-(3-(1-(5-fluoro-3-methylbenzofuran-2-yl)-2-methylpropyl)ureido)pyrimidin-2-yl)(methyl)amino)ethyl)carbamate (100 mg, 0.2 mmol) in DCM (5 ml) was added 4 M HCl (g) in Dioxane (2 ml) at room temperature. The resulting mixture was stirred for 1 hour at room temperature, then basified to pH 8-9 with saturated NaHCO$_3$, extracted with DCM. The combined organic layers were dried over anhydrous Na$_2$SO$_4$, then filtered. The filtrate was concentrated under reduced pressure. The residue was purified by Prep-HPLC to afford (S)-1-(2-((2-aminoethyl)(methyl)amino)pyrimidin-5-yl)-3-(1-(5-fluoro-3-methylbenzofuran-2-yl)-2-methylpropyl)urea (21.0 mg, 26.25%) as a yellow solid. MS (ESI): mass calcd. for $C_{21}H_{27}FN_6O_2$, 414.22, m/z found 415.25 [M+H]$^+$. $^1$H NMR (400 MHz, DMSO-d6) δ 8.91 (s, 1H), 8.43 (s, 1H), 8.38 (s, 2H), 7.54-7.42 (m, 2H), 7.36 (dd, J=8.9, 2.7 Hz, 1H), 7.08 (td, J=9.2, 2.7 Hz, 1H), 4.71 (t, J=8.5 Hz, 1H), 3.67 (t, J=6.5 Hz, 2H), 3.07 (s, 3H), 2.91 (t, J=6.6 Hz, 2H), 2.19 (s, 3H), 2.13 (dt, J=8.2, 6.5 Hz, 1H), 1.02 (d, J=6.6 Hz, 3H), 0.80 (d, J=6.7 Hz, 3H).

Example 87: Preparation of Compound 130

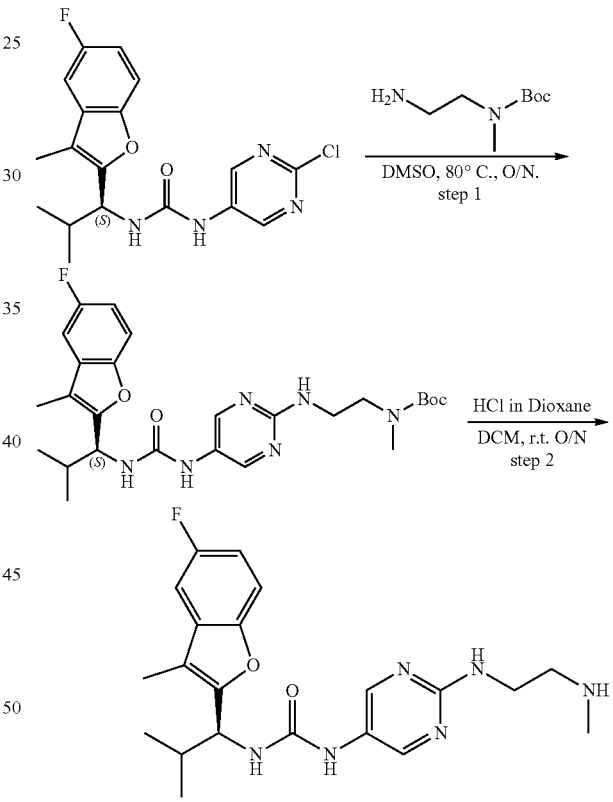

Compound 130

Step 1

A solution of (S)-1-(2-chloropyrimidin-5-yl)-3-(1-(5-fluoro-3-methylbenzofuran-2-yl)-2-methylpropyl)urea (160 mg, 0.4 mmol), tert-butyl (2-aminoethyl)(methyl)carbamate (370 mg, 2.1 mmol) and TEA (2 mL) in DMSO (6 mL) was stirred overnight at 80° C. The resulting solution was diluted with EA, washed with saturated NaCl. The organic layer was dried over anhydrous Na$_2$SO$_4$, filtered and concentrated under reduced pressure The residue was purified by silica gel column chromatography to afford (S)-1-(1-(5-fluoro-3-methylbenzofuran-2-yl)-2-methylpropyl)-3-(2-((2-(methylamino)ethyl)amino)pyrimidin-5-yl)urea (111 mg, 50.91%) as a yellow solid.

Step 2

To a stirred solution of (S)-1-(1-(5-fluoro-3-methylbenzofuran-2-yl)-2-methylpropyl)-3-(2-((2-(methylamino)ethyl)amino)pyrimidin-5-yl)urea (111 mg, 0.2 mmol) in DCM (6 ml) was added 4 M HCl in Dioxane (2 ml) at room temperature. The resulting mixture was stirred for 1 hour at room temperature, then basified to pH 8-9 with saturated NaHCO$_3$, extracted with DCM. The combined organic layers were dried over anhydrous Na$_2$SO$_4$, then filtered. The filtrate was concentrated under reduced pressure. The residue was purified by Prep-HPLC to afford (S)-1-(1-(5-fluoro-3-methylbenzofuran-2-yl)-2-methylpropyl)-3-(2-((2-(methylamino)ethyl)amino)pyrimidin-5-yl)urea (17.4 mg, 19.55%) as a yellow solid. MS (ESI): mass calcd. for C$_{21}$H$_{27}$FN$_6$O$_2$, 414.22, m/z found 415.25 [M+H]$^+$.

$^1$H NMR (400 MHz, DMSO-d6) δ 8.47-8.36 (m, 2H), 8.29 (s, 2H), 7.51 (dd, J=8.9, 4.1 Hz, 1H), 7.37 (dd, J=8.8, 2.7 Hz, 1H), 7.16 (d, J=8.6 Hz, 1H), 7.09 (td, J=9.2, 2.7 Hz, 1H), 6.86 (t, J=5.7 Hz, 1H), 4.71 (t, J=8.6 Hz, 1H), 3.39 (m, Hz, 2H), 2.84 (t, J=6.2 Hz, 2H), 2.42 (s, 3H), 2.19 (s, 3H), 2.12 (m, Hz, 1H), 1.02 (d, J=6.6 Hz, 3H), 0.81 (d, J=6.7 Hz, 3H).

Example 88: Preparation of Compound 131

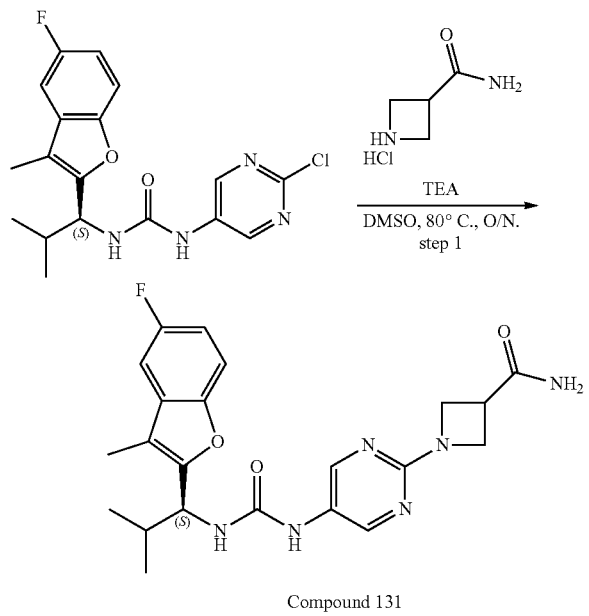

Compound 131

A solution of (S)-1-(2-chloropyrimidin-5-yl)-3-(1-(5-fluoro-3-methylbenzofuran-2-yl)-2-methylpropyl)urea (80 mg, 0.2 mmol), 3-carbamoylazetidin-1-ium chloride (232 mg, 1.7 mmol) and TEA (1 mL) in DMSO (2 mL) was stirred overnight at 80° C. The resulting solution was purified by Prep-HPLC to afford (S)-1-(5-(3-(1-(5-fluoro-3-methylbenzofuran-2-yl)-2-methylpropyl)ureido)pyrimidin-2-yl)azetidine-3-carboxamide (45.5 mg, 48.61%) as a white solid. MS (ESI): mass calcd. for C$_{22}$H$_{25}$FN$_6$O$_3$, 440.20, m/z found 441.10 [M+H]$^+$. $^1$H NMR (400 MHz, DMSO-d6) δ 8.34 (s, 2H), 8.15 (s, 1H), 7.51 (dd, J=8.9, 4.1 Hz, 1H), 7.46 (s, 1H), 7.37 (dd, J=8.9, 2.7 Hz, 1H), 7.09 (td, J=9.2, 2.7 Hz, 1H), 7.00 (s, 1H), 6.87 (d, J=8.7 Hz, 1H), 4.73 (t, J=8.5 Hz, 1H), 4.05 (t, J=8.4 Hz, 2H), 3.96 (dd, J=8.3, 6.1 Hz, 2H), 2.19 (s, 3H), 2.15-2.06 (m, 1H), 1.01 (d, J=6.7 Hz, 3H), 0.81 (d, J=6.7 Hz, 3H).

Example 89: Preparation of Compound 132 and 133

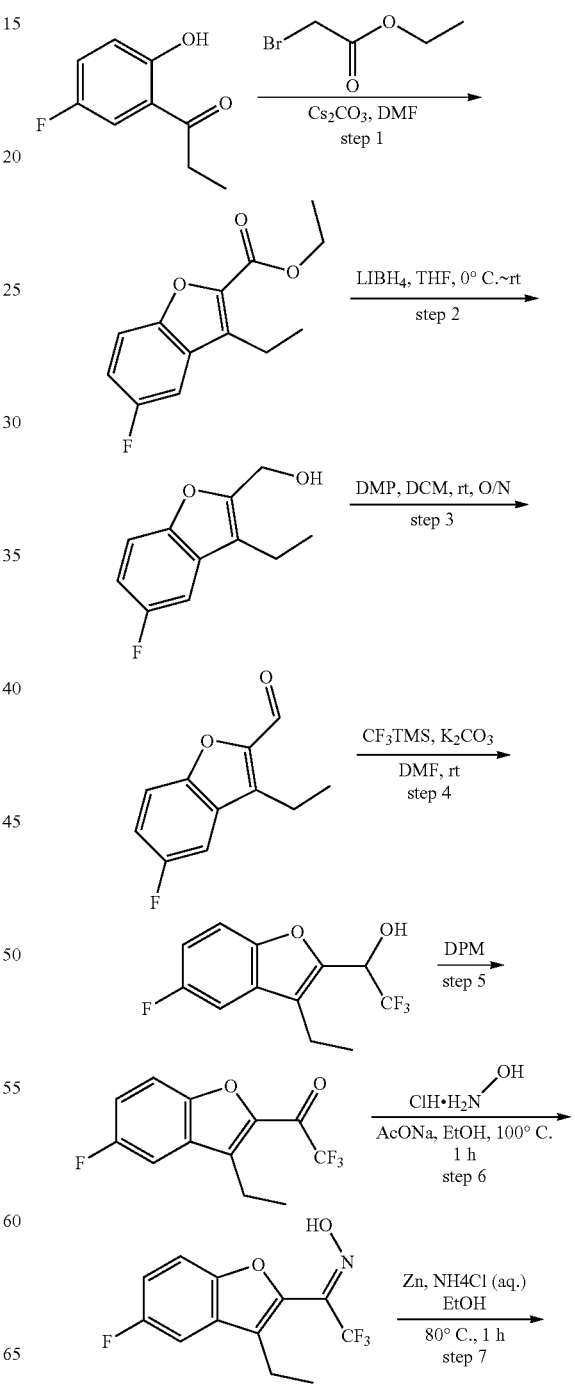

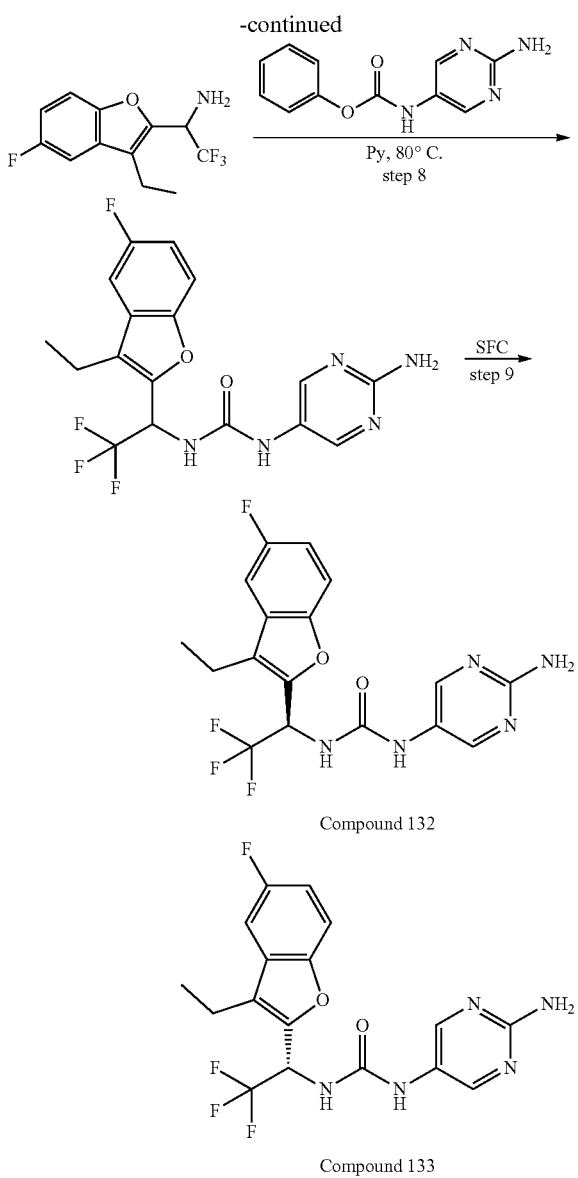

Compound 132

Compound 133

Step 1

To a solution of 1-(5-fluoro-2-hydroxyphenyl)propan-1-one (10 g, 59.465 mmol) and ethyl bromoacetate (19.86 g, 118.930 mmol) in DMF (100 mL) was added $Cs_2CO_3$ (58.12 g, 178.395 mmol). The mixture was stirred at 25° C. for 1 h. The resulting solution was extracted with 3×400 mL of DCM. The organic layers were combined, dried and concentrated under vacuum to afford ethyl 3-ethyl-5-fluoro-1-benzofuran-2-carboxylate (7.3 g, crude) as yellow solid.

Step 2

To a solution of ethyl 3-ethyl-5-fluoro-1-benzofuran-2-carboxylate (5.7 g, 24.128 mmol) in THF (100 mL) was added $LiBH_4$ (2.0 M in THF) (34.14 mL, 68.282 mmol) dropwise for 30 min at 0° C. under nitrogen atmosphere followed. The resulting mixture was stirred for 12 h at room temperature under nitrogen atmosphere. The mixture was stirred at 0° C. The residue was purified by column chromatography on silica gel (PE/EA from 10/1 to 5/1) to give (3-ethyl-5-fluoro-1-benzofuran-2-yl) (4.6 g, 98.2%) as white solid.

Step 3

To a solution of (3-ethyl-5-fluoro-1-benzofuran-2-yl) methanol (4.6 g, 23.686 mmol) in DCM (50 mL) was added DMP (20.09 g, 47.372 mmol). The mixture was stirred at room temperature for 12 h. After completion, the mixture was added to water, extracted with EA. The organic layer was washed with brine, dried over sodium sulfate. After completion, the mixture was concentrated in vacuum. The residue was purified by reverse phase (ACN/water from 0~60) to give 3-ethyl-5-fluoro-1-benzofuran-2-carbaldehyde (3.7 g, 81.3%) as white solid. MS (ESI): mass calcd. for $C_{11}H_9FO_2$, 192.1, m/z found 193.0 $[M+H]^+$.

Step 4

To a solution of 3-ethyl-5-fluoro-1-benzofuran-2-carbaldehyde (3.7 g, 19.252 mmol) and $TMSCF_3$ (5475.08 mg, 38.504 mmol) in DMF (2 mL) were added $K_2CO_3$ (2660.71 mg, 19.252 mmol). The mixture was stirred at room temperature for 12 h. The resulting solution was extracted with 3×400 mL of DCM. The organic layers were combined, dried and concentrated under vacuum to afford ethyl 1-(3-ethyl-5-fluoro-1-benzofuran-2-yl)-2,2,2-trifluoroethanol (3.6 g, crude) as yellow solid.

MS (ESI): mass calcd. for $C_{12}H_{10}F_4O_2$, 262.1, m/z found 263.0 $[M+H]^+$.

Step 5

To a solution of 1-(3-ethyl-5-fluoro-1-benzofuran-2-yl)-2,2,2-trifluoroethanol (3.6 g, 13.730 mmol) in DCM (40 mL) was added DMP (11.65 g, 27.460 mmol). The mixture was stirred at room temperature for 12 h. After completion, the mixture was added to water, extracted with EA. The organic layer was washed with brine, dried over sodium sulfate, concentrated in vacuum to give 1-(3-ethyl-5-fluoro-1-benzofuran-2-yl)-2,2,2-trifluoroethanone (4.0 g, crude) as yellow solid. MS (ESI): mass calcd. for $C_{12}H_8F_4O_2$, 260.1, m/z found 258.9 $[M-H]^-$.

Step 6

To a solution of 1-(3-ethyl-5-fluoro-1-benzofuran-2-yl)-2,2,2-trifluoroethanone (2.0 g, 7.687 mmol) in EtOH (20 mL) was added and hydroxylamine hydrochloride (2.67 g, 38.435 mmol, 5 equiv) and NaOAc (3.15 g, 38.435 mmol). The mixture was stirred at 100° C. for 1 h. The resulting solution was extracted with 3×400 mL of DCM. The organic layers were combined, dried and concentrated under vacuum to afford ethyl (E)-N-[1-(3-ethyl-5-fluoro-1-benzofuran-2-yl)-2,2,2-trifluoroethylidene]hydroxylamine (1.4 g, crude) as white solid. MS (ESI): mass calcd. for $C_{12}H_9F_4NO_2$, 275.1, m/z found 273.9 $[M-H]^-$.

Step 7

To a solution of (E)-N-[1-(3-ethyl-5-fluoro-1-benzofuran-2-yl)-2,2,2-trifluoroethylidene]hydroxylamine (1.4 g, 5.087 mmol) in EtOH (20 mL) was added $NH_4Cl$ (aq.) and Zn (3.33 g, 50.870 mmol). The mixture was stirred at 80° C. for 1 h. The mixture was stirred at room temperature for 12 h. After completion, the mixture was added to water, extracted with EA. The organic layer was washed with brine, dried over sodium sulfate, concentrated in vacuum. The residue was purified by reverse phase (ACN/water from 0~60) to give 1-(3-ethyl-5-fluoro-1-benzofuran-2-yl)-2,2,2-trifluoroethanamine (0.7 g, 52.7%) as white solid. MS (ESI): mass calcd. for $C_{12}H_{11}F_4NO$, 261.1, m/z found 262.0 [M+H]$^+$.

Step 8

To a solution of 1-(3-ethyl-5-fluoro-1-benzofuran-2-yl)-2,2,2-trifluoroethanamine (0.7 g, 2.680 mmol) and phenyl N-(2-aminopyrimidin-5-yl)carbamate (0.62 g, 2.680 mmol) in Pyridine (10 mL). The mixture was stirred at 80° C. for 16 h. After completion, the mixture was concentrated in vacuum. The residue was purified by reverse phase (ACN/water from 0~60) to give 1-(2-aminopyrimidin-5-yl)-3-[1-(3-ethyl-5-fluoro-1-benzofuran-2-yl)-2,2,2-trifluoroethyl] urea (300 mg, 28.2%) as white solid. MS (ESI): mass calcd. for $C_{17}H_{15}F_4N_5O_2$, 397.1, m/z found 398.1 [M+H]$^+$.

Step 9

300 mg of racemic was separated by SFC to give (Compound 132, 120.6 mg) as white solid and (Compound 133, 89.1 mg) as white solid.
Chiral separation conditions: Column: CHIRAL ART Cellulose-SB, 2*25 cm, 5 μm; Mobile Phase A: Hex (0.2% TEA), Mobile Phase B: EtOH; Flow rate: 20 mL/min; Gradient: 50% B to 50% B in 7.5 min; RT1 (min): 3.87; RT2 (min): 5.51.

Compound 132

MS (ESI): mass calcd. for $C_{17}H_{15}F_4N_5O_2$, 397.1, m/z found 398.1 [M+H]$^+$.
$^1$H NMR (400 MHz, DMSO-d$_6$) δ 8.21 (s, 3H), 7.75 (d, J=9.4 Hz, 1H), 7.63 (dd, J=9.0, 4.1 Hz, 1H), 7.56 (dd, J=8.7, 2.7 Hz, 1H), 7.23 (td, J=9.2, 2.7 Hz, 1H), 6.39 (s, 2H), 5.96 (p, J=8.4 Hz, 1H), 2.75 (qd, J=7.3, 3.4 Hz, 2H), 1.19 (t, J=7.5 Hz, 3H).

Compound 133

MS (ESI): mass calcd. for $C_{17}H_{15}F_4N_5O_2$, 397.1, m/z found 398.1 [M+H]$^+$.
$^1$H NMR (400 MHz, DMSO-d$_6$) δ 8.20 (d, J=2.8 Hz, 3H), 7.75 (d, J=9.4 Hz, 1H), 7.63 (dd, J=9.0, 4.1 Hz, 1H), 7.57 (dd, J=8.8, 2.7 Hz, 1H), 7.23 (td, J=9.2, 2.7 Hz, 1H), 6.39 (s, 2H), 5.96 (p, J=8.4 Hz, 1H), 2.76 (qd, J=7.3, 3.5 Hz, 2H), 1.19 (t, J=7.5 Hz, 3H).

Example 90: Preparation of Compound 134

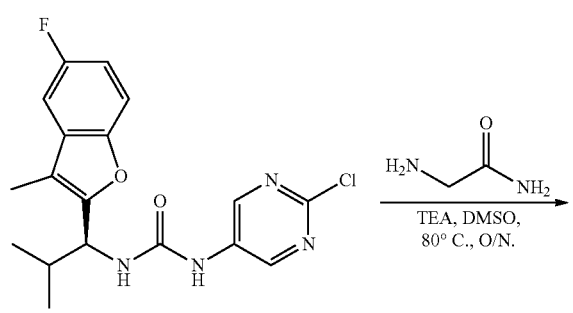

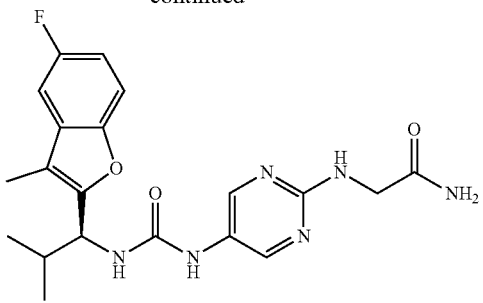

Compound 134

A solution of (S)-1-(2-chloropyrimidin-5-yl)-3-(1-(5-fluoro-3-methylbenzofuran-2-yl)-2-methylpropyl)urea (100 mg, 0.27 mmol) and glycinamide (197 mg, 2.65 mmol) in DMSO (2.5 mL)/TEA (1.3 mL) was stirred overnight at 80° C. The reaction was concentrated under reduced pressure. The residue was purified by Prep-HPLC to afford (S)-2-((5-(3-(1-(5-fluoro-3-methylbenzofuran-2-yl)-2-methylpropyl) ureido)pyrimidin-2-yl)amino)acetamide (17.4 mg, 15.7%) as an off-white solid. MS (ESI): mass calcd. for $C_{20}H_{23}FN_6O_3$, 414.2, m/z found 415.15 [M+H]$^+$.
$^1$H NMR (400 MHz, DMSO-d$_6$) δ 8.33-8.22 (s, 2H), 8.11-8.03 (s, 1H), 7.57-7.44 (dd, J=9.0, 4.0 Hz, 1H), 7.44-7.33 (dd, J=8.7, 2.7 Hz, 1H), 7.28-7.18 (s, 1H), 7.18-7.03 (td, J=9.1, 2.7 Hz, 1H), 7.01-6.91 (s, 1H), 6.89-6.80 (m, 2H), 4.78-4.68 (t, J=8.6 Hz, 1H), 3.81-3.66 (d, J=6.1 Hz, 2H), 2.24-2.17 (s, 3H), 2.16-2.04 (m, 1H), 1.04-0.98 (d, J=6.6 Hz, 3H), 0.86-0.77 (d, J=6.7 Hz, 3H).

Example 91: Preparation of Compound 135

Compound 135

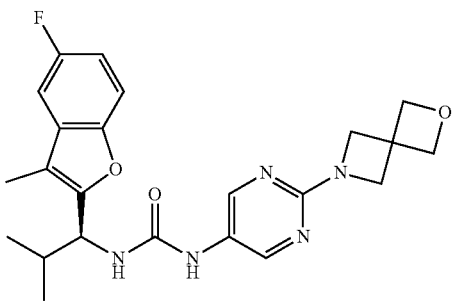

Prepared using the same procedure as Compound 134 using the appropriate amine. MS (ESI): mass calcd. for $C_{23}H_{26}FN_5O_3$, 439.2, m/z found 440.15 [M+H]$^+$.
$^1$H NMR (400 MHz, DMSO-d6) δ 8.34 (s, 2H), 8.16 (s, 1H), 7.51 (dd, J=8.9, 4.1 Hz, 1H), 7.37 (dd, J=8.8, 2.7 Hz, 1H), 7.10 (td, J=9.2, 2.8 Hz, 1H), 6.87 (d, J=8.7 Hz, 1H), 4.70 (s, 5H), 4.12 (s, 4H), 2.19 (s, 3H), 2.17-2.00 (m, 1H), 1.01 (d, J=6.7 Hz, 3H), 0.81 (d, J=6.7 Hz, 3H).

Example 92: Preparation of Compound 136

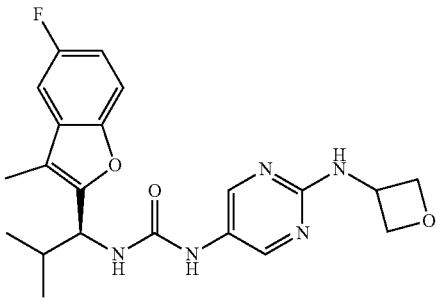

Compound 136

Prepared using the same procedure as Compound 134 using the appropriate amine. MS (ESI): mass calcd. for $C_{21}H_{24}FN_5O_3$, 413.2, m/z found 414.10 [M+H]$^+$.

$^1$H NMR (400 MHz, DMSO-d6) δ 8.33-8.22 (d, J=3.0 Hz, 2H), 8.14-8.01 (d, J=3.2 Hz, 1H), 7.66-7.57 (d, J=6.0 Hz, 1H), 7.57-7.46 (dd, J=8.9, 4.0 Hz, 1H), 7.43-7.33 (dd, J=8.8, 2.8 Hz, 1H), 7.16-7.04 (td, J=9.2, 2.8 Hz, 1H), 6.95-6.82 (d, J=8.7 Hz, 1H), 4.90-4.79 (m, 1H), 4.79-4.63 (td, J=8.6, 7.5, 4.8 Hz, 3H), 4.53-4.39 (t, J=6.1 Hz, 2H), 2.25-2.15 (d, J=2.9 Hz, 3H), 2.15-2.03 (m, 1H), 1.06-0.95 (dd, J=6.7, 3.0 Hz, 3H), 0.88-0.74 (dd, J=6.7, 3.0 Hz, 3H).

Example 93: Preparation of Compound 137

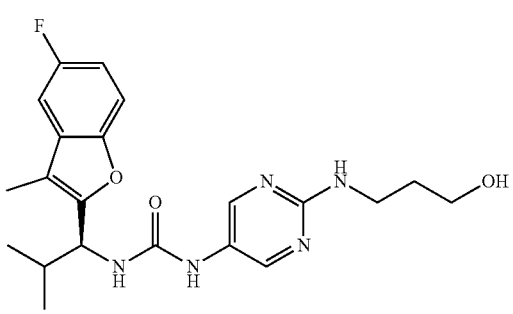

Compound 137

Prepared using the same procedure as Compound 134 using the appropriate amine. MS (ESI): mass calcd. for $C_{21}H_{26}FN_5O_3$, 415.2, m/z found 416.15 [M+H]$^+$.

$^1$H NMR (400 MHz, DMSO-d6) δ 8.22 (s, 2H), 7.99 (s, 1H), 7.51 (dd, J=8.9, 4.1 Hz, 1H), 7.37 (dd, J=8.8, 2.7 Hz, 1H), 7.18-7.02 (m, 1H), 6.86-6.77 (m, 2H), 4.72 (t, J=8.6 Hz, 1H), 4.43 (t, J=5.2 Hz, 1H), 3.45 (td, J=6.3, 5.2 Hz, 2H), 3.25 (m, 2H), 2.19 (s, 3H), 2.13-2.06 (m, 1H), 1.64 (m, 2H), 1.01 (d, J=6.7 Hz, 3H), 0.81 (d, J=6.7 Hz, 3H).

Example 94: Preparation of Compound 138

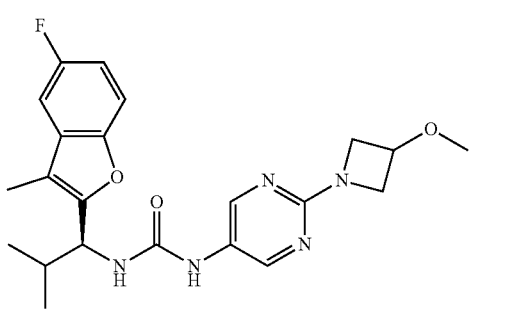

Compound 138

Prepared using the same procedure as Compound 134 using the appropriate amine. MS (ESI): mass calcd. for $C_{22}H_{26}FN_5O_3$, 427.2, m/z found 428.20 [M+H]$^+$.

$^1$H NMR (400 MHz, DMSO-d$_6$) δ 8.35 (s, 2H), 8.30 (s, 1H), 7.50 (dd, J=8.9, 4.1 Hz, 1H), 7.36 (dd, J=8.8, 2.7 Hz, 1H), 7.09 (td, J=9.2, 2.7 Hz, 1H), 6.98 (d, J=8.7 Hz, 1H), 4.73 (t, J=8.6 Hz, 1H), 4.27 (tt, J=6.0, 4.0 Hz, 1H), 4.14 (m, 2H), 3.81-3.68 (m, 2H), 3.23 (s, 3H), 2.19 (s, 3H), 2.17-1.93 (m, 1H), 1.01 (d, J=6.7 Hz, 3H), 0.81 (d, J=6.7 Hz, 3H).

Example 95: Preparation of Compound 139

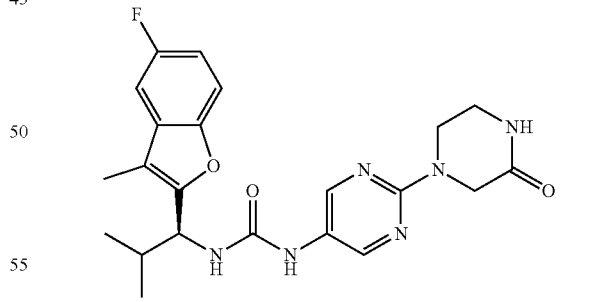

Compound 139

Prepared using the same procedure as Compound 134 using the appropriate amine. MS (ESI): mass calcd. for $C_{22}H_{25}FN_6O_3$, 440.2, m/z found 441.15 [M+H]$^+$.

$^1$H NMR (400 MHz, DMSO-d6) δ 8.42 (s, 2H), 8.24 (s, 1H), 8.05 (s, 1H), 7.51 (dd, J=9.0, 4.1 Hz, 1H), 7.38 (d, J=8.4 Hz, 1H), 7.10 (t, J=9.3 Hz, 1H), 6.94 (d, J=8.7 Hz, 1H), 4.74 (t, J=8.5 Hz, 1H), 4.09 (s, 2H), 3.82 (t, J=5.5 Hz, 2H), 3.25 (s, 2H), 2.20 (m, 4H), 1.02 (d, J=6.7 Hz, 3H), 0.81 (d, J=6.7 Hz, 3H).

Example 96: Preparation of Compound 140

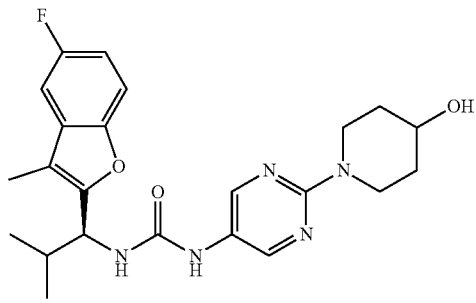

Compound 140

Prepared using the same procedure as Compound 134 using the appropriate amine. MS (ESI): mass calcd. for $C_{23}H_{28}FN_5O_3$, 441.2, m/z found 442.15 [M+H]$^+$.

$^1$H NMR (400 MHz, DMSO-d$_6$) δ 8.41-8.26 (s, 2H), 8.16-8.05 (s, 1H), 7.57-7.45 (dd, J=8.9, 4.1 Hz, 1H), 7.45-7.30 (dd, J=8.8, 2.7 Hz, 1H), 7.17-7.03 (td, J=9.2, 2.7 Hz, 1H), 6.93-6.79 (d, J=8.7 Hz, 1H), 4.82-4.61 (m, 2H), 4.26-4.10 (dt, J=13.6, 4.4 Hz, 2H), 3.77-3.63 (m, 1H), 3.24-3.08 (m, 2H), 2.26-2.17 (s, 3H), 2.16-2.04 (m, 1H), 1.81-1.66 (dd, J=13.5, 3.7 Hz, 2H), 1.36-1.20 (m, 2H), 1.08-0.93 (d, J=6.7 Hz, 3H), 0.86-0.76 (d, J=6.7 Hz, 3H).

Example 97: Preparation of Compound 141

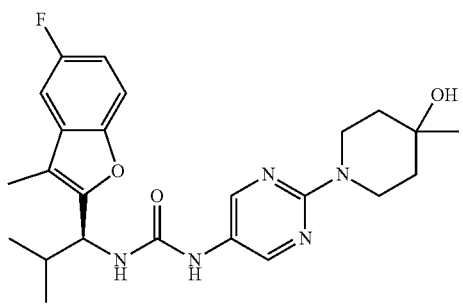

Compound 141

Prepared using the same procedure as Compound 134 using the appropriate amine. MS (ESI): mass calcd. for $C_{24}H_{30}FN_5O_3$, 455.2, m/z found 456.15 [M+H]$^+$.

$^1$H NMR (400 MHz, DMSO-d6) δ 8.37-8.26 (s, 2H), 8.12-8.04 (s, 1H), 7.55-7.46 (dd, J=8.9, 4.1 Hz, 1H), 7.42-7.33 (dd, J=8.8, 2.7 Hz, 1H), 7.16-7.04 (td, J=9.2, 2.7 Hz, 1H), 6.92-6.79 (d, J=8.8 Hz, 1H), 4.81-4.66 (t, J=8.6 Hz, 1H), 4.37-4.25 (s, 1H), 4.10-3.96 (dt, J=13.3, 4.4 Hz, 2H), 3.45-3.35 (td, J=10.2, 5.2 Hz, 2H), 2.24-2.16 (s, 3H), 2.16-2.03 (m, 1H), 1.53-1.32 (m, 4H), 1.18-1.09 (s, 3H), 1.07-0.94 (d, J=6.6 Hz, 3H), 0.90-0.76 (d, J=6.7 Hz, 3H).

Example 98: Preparation of Compound 142

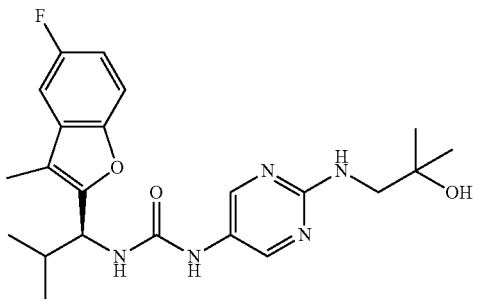

Compound 142

Prepared using the same procedure as Compound 134 using the appropriate amine. MS (ESI): mass calcd. for $C_{22}H_{28}FN_5O_3$, 429.2, m/z found 430.40 [M+H]$^+$.

$^1$H NMR (400 MHz, DMSO-d6) δ 8.23 (s, 2H), 8.06 (s, 1H), 7.51 (dd, J=8.9, 4.1 Hz, 1H), 7.37 (dd, J=8.9, 2.7 Hz, 1H), 7.10 (td, J=9.2, 2.7 Hz, 1H), 6.89 (d, J=8.8 Hz, 1H), 6.47 (t, J=6.1 Hz, 1H), 4.72 (t, J=8.6 Hz, 1H), 4.55 (s, 1H), 3.23 (d, J=6.1 Hz, 2H), 2.19 (s, 3H), 2.11-1.97 (m, 1H), 1.08 (s, 6H), 1.01 (d, J=6.7 Hz, 3H), 0.81 (d, J=6.7 Hz, 3H).

Example 99: Preparation of Compound 143

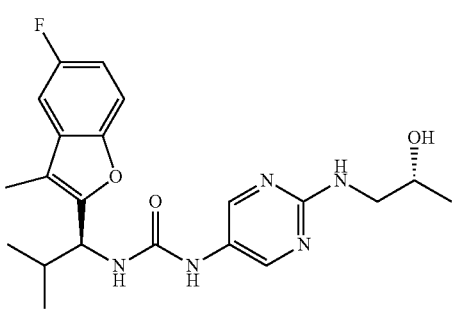

Compound 143

Prepared using the same procedure as Compound 134 using the appropriate amine. MS (ESI): mass calcd. for $C_{21}H_{26}FN_5O_3$, 415.2, m/z found 416.20 [M+H]$^+$.

$^1$H NMR (400 MHz, DMSO-d$_6$) δ 8.33-8.14 (s, 2H), 8.09-7.92 (s, 1H), 7.60-7.44 (dd, J=8.9, 4.1 Hz, 1H), 7.45-7.32 (dd, J=8.8, 2.7 Hz, 1H), 7.18-7.03 (dt, J=10.6, 5.4 Hz, 1H), 6.94-6.80 (d, J=8.7 Hz, 1H), 6.74-6.60 (t, J=5.9 Hz, 1H), 4.81-4.70 (t, J=8.5 Hz, 1H), 4.69-4.59 (d, J=4.6 Hz, 1H), 3.84-3.66 (m, 1H), 3.25-3.08 (t, J=5.9 Hz, 2H), 2.27-2.16 (s, 3H), 2.16-2.03 (m, 1H), 1.12-0.94 (dd, J=10.1, 6.4 Hz, 6H), 0.89-0.77 (d, J=6.6 Hz, 3H).

Example 100: Preparation of Compound 144

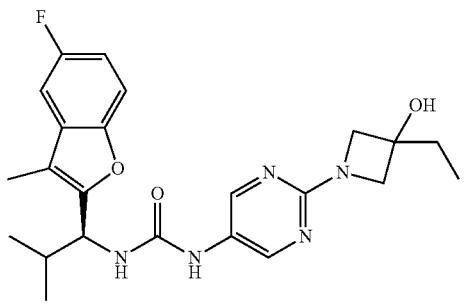

Compound 144

Prepared using the same procedure as Compound 134 using the appropriate amine. MS (ESI): mass calcd. for $C_{23}H_{28}FN_5O_3$, 441.2, m/z found 442.15 [M+H]$^+$.

$^1$H NMR (400 MHz, DMSO-d$_6$) δ 8.39-8.28 (s, 2H), 8.20-8.11 (s, 1H), 7.57-7.46 (dd, J=9.0, 4.1 Hz, 1H), 7.43-7.33 (dd, J=8.9, 2.6 Hz, 1H), 7.16-7.03 (m, 1H), 6.93-6.83 (d, J=8.7 Hz, 1H), 5.52-5.42 (s, 1H), 4.79-4.69 (t, J=8.6 Hz, 1H), 3.91-3.83 (d, J=8.7 Hz, 2H), 3.81-3.70 (d, J=8.7 Hz, 2H), 2.24-2.16 (s, 3H), 2.15-2.05 (m, 1H), 1.71-1.62 (m, 2H), 1.06-0.97 (d, J=6.6 Hz, 3H), 0.94-0.86 (t, J=7.3 Hz, 3H), 0.85-0.77 (d, J=6.6 Hz, 3H).

Example 101: Preparation of Compound 145

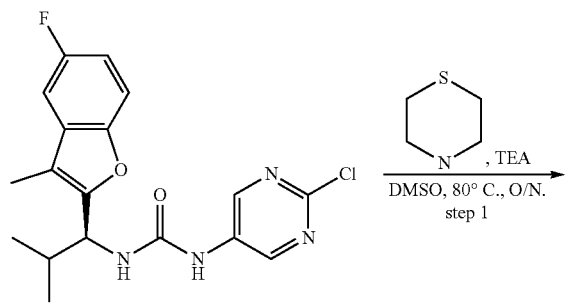

Compound 145

1-(2-chloropyrimidin-5-yl)-3-[(1S)-1-(5-fluoro-3-methyl-1-benzofuran-2-yl)-2-methylpropyl]urea (80 mg, 0.212 mmol, 1 equiv), thiomorpholine (131.43 mg, 1.272 mmol, 6 equiv) and Et$_3$N (1 mL, 7.194 mmol, 33.89 equiv) were dissolved in DMSO (2 mL), stirred at 80° C. overnight. The resulting mixture was diluted with 30 mL EA, washed with 3×10 mL of brine. The organic phase was dried with anhydrous sodium sulfate, concentrated under vacuum. The crude product was purified by Prep-HPLC to afford 3-[(1S)-1-(5-fluoro-3-methyl-1-benzofuran-2-yl)-2-methylpropyl]-1-[2-(thiomorpholin-4-yl)pyrimidin-5-yl]urea (28.4 mg, 30.04%) as a white solid. MS (ESI): mass calcd. for $C_9H_7FO$, 443.1, m/z found 444.0 [M+H]$^+$.

$^1$H NMR (400 MHz, DMSO-d6) δ 8.37 (s, 2H), 8.15 (s, 1H), 7.51 (dd, J=8.9, 4.1 Hz, 1H), 7.38 (dd, J=8.8, 2.7 Hz, 1H), 7.10 (td, J=9.2, 2.7 Hz, 1H), 6.89 (d, J=8.7 Hz, 1H), 4.73 (t, J=8.6 Hz, 1H), 4.02-3.95 (m, 4H), 2.60-2.53 (m, 4H), 2.19 (s, 3H), 2.18-2.05 (m, 1H), 1.02 (d, J=6.6 Hz, 3H), 0.81 (d, J=6.7 Hz, 3H).

Example 102: Preparation of Compound 146

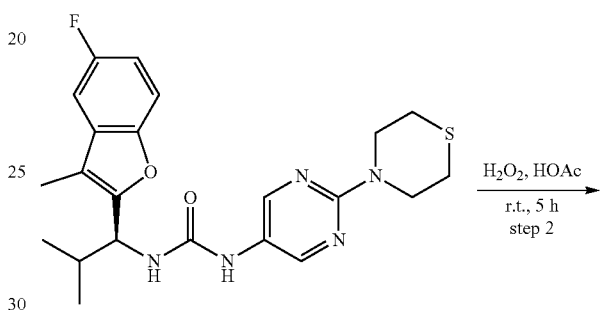

Compound 145

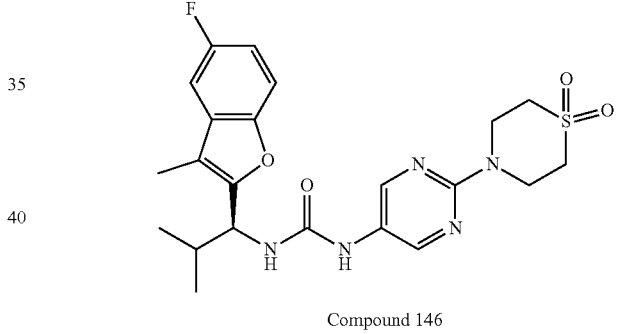

Compound 146

3-[(1S)-1-(5-fluoro-3-methyl-1-benzofuran-2-yl)-2-methylpropyl]-1-[2-(thiomorpholin-4-yl)pyrimidin-5-yl]urea (60 mg, 0.135 mmol, 1 equiv) and H$_2$O$_2$ (23.01 mg, 0.675 mmol, 5 equiv) were mixed in CH$_3$COOH (1.5 mL), stirred for 5 h. The reaction was quenched with sat. sodium hyposulfite (aq.) at 0° C. The aqueous layer was extracted with EtOAc (3×5 mL). The resulting organic phase was dried with anhydrous sodium sulfate, concentrated under vacuum. The crude product (80 mg) was purified by Prep-HPLC to afford 1-[2-(1,1-dioxo-1lambda6-thiomorpholin-4-yl)pyrimidin-5-yl]-3-[(1S)-1-(5-fluoro-3-methyl-1-benzofuran-2-yl)-2-methylpropyl]urea (13 mg, 20.15%) as a white solid. MS (ESI): mass calcd. for $C_{11}H_6F_4O_2$, 475.1, m/z found 476.0 [M+H]$^+$.

$^1$H NMR (400 MHz, DMSO-d$_6$) δ 8.45 (s, 2H), 8.27 (s, 1H), 7.52 (dd, J=8.9, 4.1 Hz, 1H), 7.38 (dd, J=8.8, 2.7 Hz, 1H), 7.10 (td, J=9.2, 2.7 Hz, 1H), 6.93 (d, J=8.8 Hz, 1H), 4.74 (t, J=8.6 Hz, 1H), 4.14 (s, 3H), 3.10 (t, J=5.2 Hz, 4H), 2.20 (s, 3H), 2.11 (dt, J=14.0, 6.9 Hz, 1H), 1.24 (s, 1H), 1.02 (d, J=6.6 Hz, 3H), 0.81 (d, J=6.7 Hz, 3H).

Example 103: Preparation of Compound 147

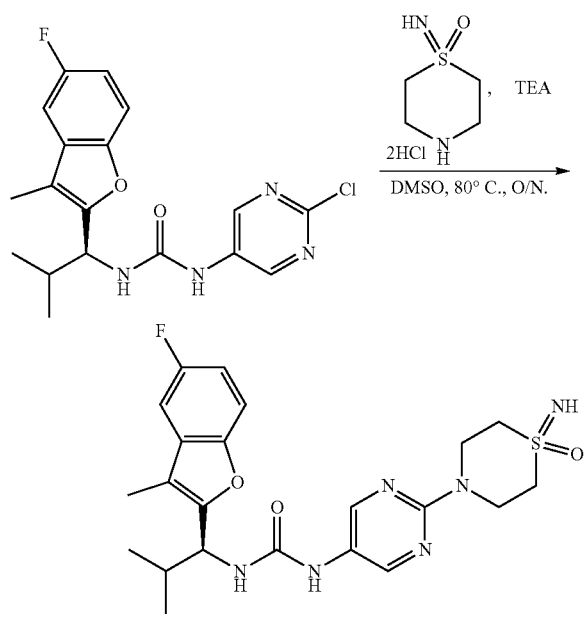

Compound 147

1-(2-chloropyrimidin-5-yl)-3-[(1S)-1-(5-fluoro-3-methyl-1-benzofuran-2-yl)-2-methylpropyl]urea (80 mg, 0.212 mmol, 1 equiv), 1-imino-1lambda6-thiomorpholin-1-one (284.91 mg, 2.120 mmol, 10 equiv) and Et₃N (1 mL) were mixed in DMSO (2 mL), stirred at 80° C. overnight. The resulting mixture was concentrated under vacuum. The crude product (80 mg) was purified by Prep-HPLC to afford 3-[(1S)-1-(5-fluoro-3-methyl-1-benzofuran-2-yl)-2-methylpropyl]-1-[2-(1-imino-1-oxo-1lambda6-thiomorpholin-4-yl)pyrimidin-5-yl]urea (20.0 mg, 18.90%) as a white solid. MS (ESI): mass calcd. for $C_{11}H_7F_4NO_2$, 474.1, m/z found 475.3 [M+H]⁺.

¹H NMR (400 MHz, DMSO-d₆) δ 8.43 (s, 2H), 8.25 (s, 1H), 7.51 (dd, J=8.9, 4.1 Hz, 1H), 7.38 (dd, J=8.8, 2.7 Hz, 1H), 7.10 (td, J=9.2, 2.7 Hz, 1H), 6.92 (d, J=8.7 Hz, 1H), 4.74 (t, J=8.6 Hz, 1H), 4.30 (d, J=14.8 Hz, 2H), 3.88 (dd, J=12.6, 8.4 Hz, 2H), 3.79 (s, 1H), 2.97 (s, 3H), 2.92 (d, J=13.3 Hz, 1H), 2.20 (s, 3H), 2.17-2.07 (m, 1H), 1.02 (d, J=6.7 Hz, 3H), 0.81 (d, J=6.7 Hz, 3H).

Example 104: Preparation of Compound 148 and 149

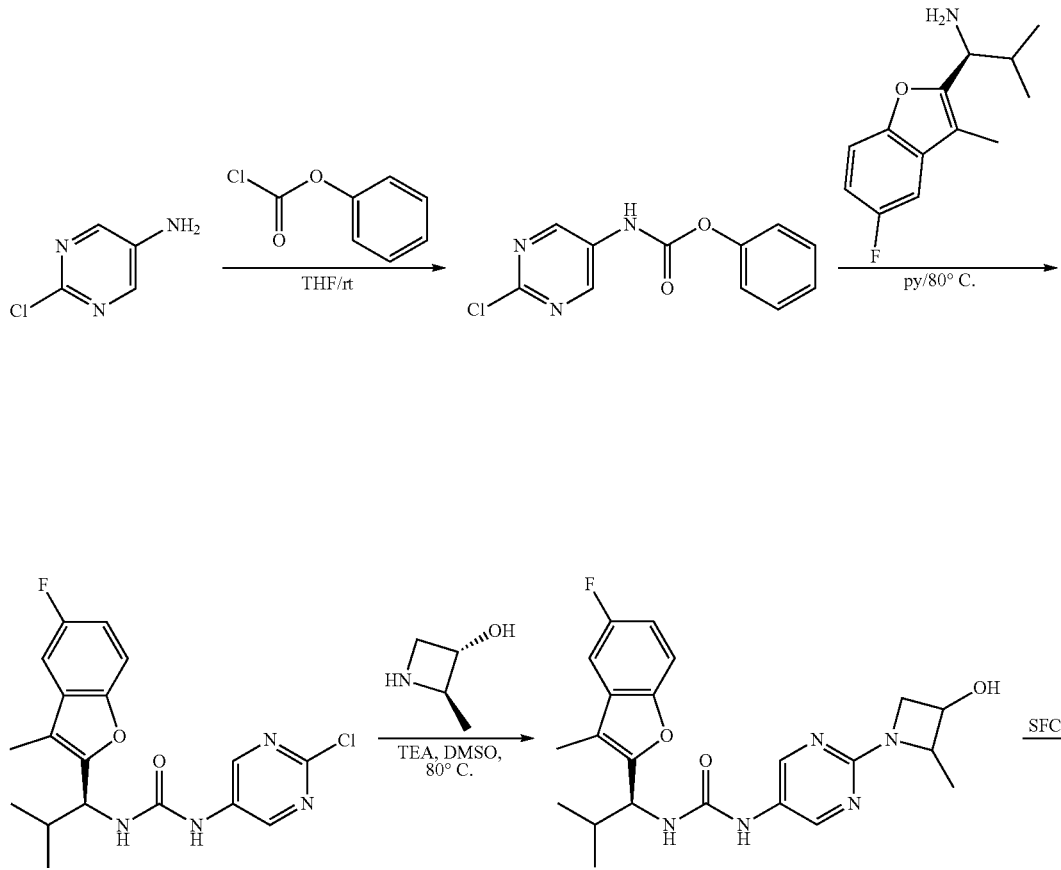

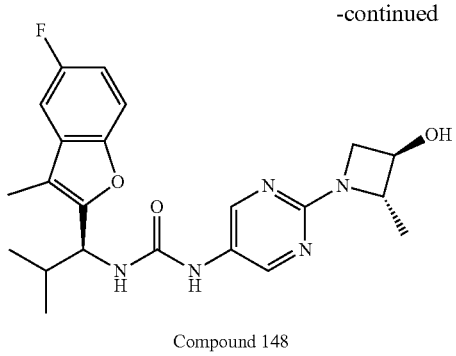

Compound 148

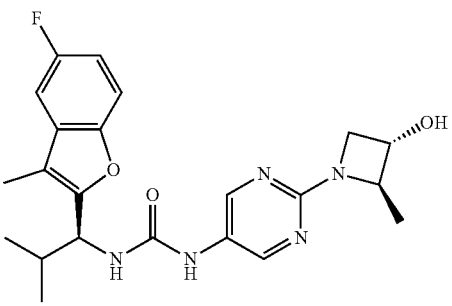

Compound 149

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 $[M+H]^+$.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl] urea (7 g, 82.21%) as a yellow oil. MS (ESI): mass calcd. for $C_{18}H_{18}ClFN_4O_2$, 376.1, m/z found 377.3 $[M+H]^+$.

Step 3

To a stirred solution of 1-(2-chloropyrimidin-5-yl)-3-[(1S)-1-(5-fluoro-3-methyl-1-benzofuran-2-yl)-2-methylpropyl]urea (100 mg, 0.265 mmol, 1 equiv) and (2R*, 3R**)-2-methylazetidin-3-ol (46.24 mg, 0.530 mmol, 2 equiv) in DMSO (3 mL) was added TEA (80.56 mg, 0.795 mmol, 3 equiv) dropwise at room temperature under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The crude product (150 mg) was purified by Prep-HPLC with the following conditions (Column: XBridge Shield RP18 OBD Column, 30*150 mm, 5 μm; Mobile Phase A: Water (10 mmol/L $NH_4HCO_3$+0.1% $NH^3·H^2O$), Mobile Phase B: ACN; Flow rate: 60 mL/min; Gradient: 31% B to 56% B in 8 min, 56% B; Wave Length: 220 nm; RT1 (min): 7.77; Number Of Runs: 0) to afford 3-[(1S)-1-(5-fluoro-3-methyl-1-benzofuran-2-yl)-2-methylpropyl]-1-{2-[(2R*,3R**)-3-hydroxy-2-methylazetidin-1-yl]pyrimidin-5-yl}urea as a white solid. MS (ESI): mass calcd. for $C_{22}H_{26}FN_5O_3$, 427.2, m/z found 428.1 $[M+H]^+$.

Step 4

110 mg of racemic was separated by SFC to give (Compound 148, 35.5 mg) as white solid and (Compound 149, 34.7 mg) as white solid.

Chiral Separation Conditions:

Apparatus: SFC 80

Column: DZ-CHIRALPAK IC-3, 4.6*50 mm, 3.0 μm

Mobile phase: A: Hex (0.2% DEA):EtOH=90:10

Flow rate: 1 mL/min

Gradient: 0% B to 0% B

Injection Volume: 5 mL.

Compound 148

MS (ESI): mass calcd. for $C_{22}H_{26}FN_5O_3$, 427.2, m/z found 428.1 $[M+H]^+$.

$^1$H NMR (400 MHz, DMSO-d6) δ 8.34 (s, 2H), 8.15 (s, 1H), 7.51 (dd, J=8.9, 4.1 Hz, 1H), 7.38 (dd, J=8.8, 2.6 Hz, 1H), 7.10 (td, J=9.2, 2.7 Hz, 1H), 6.88 (d, J=8.8 Hz, 1H), 5.55 (d, J=6.4 Hz, 1H), 4.73 (t, J=8.6 Hz, 1H), 4.11-3.99 (m, 2H), 3.95-3.89 (m, 1H), 3.53-3.48 (m, 1H), 2.19 (s, 3H), 2.11 (dt, J=8.3, 6.7 Hz, 1H), 1.39 (d, J=6.3 Hz, 3H), 1.01 (d, J=6.7 Hz, 3H), 0.81 (d, J=6.7 Hz, 3H).

Compound 149

MS (ESI): mass calcd. for $C_{22}H_{26}FN_5O_3$, 427.2, m/z found 428.1 $[M+H]^+$.

$^1$H NMR (400 MHz, DMSO-d6) δ 8.34 (s, 2H), 8.15 (s, 1H), 7.51 (dd, J=8.9, 4.1 Hz, 1H), 7.38 (dd, J=8.8, 2.7 Hz, 1H), 7.10 (td, J=9.2, 2.7 Hz, 1H), 6.88 (d, J=8.8 Hz, 1H), 5.55 (d, J=6.3 Hz, 1H), 4.73 (t, J=8.6 Hz, 1H), 4.10-4.00 (m, 2H), 3.95-3.89 (m, 1H), 3.53-3.48 (m, 1H), 2.19 (s, 3H), 2.11 (dt, J=8.5, 6.7 Hz, 1H), 1.39 (d, J=6.3 Hz, 3H), 1.01 (d, J=6.7 Hz, 3H), 0.81 (d, J=6.7 Hz, 3H).

Example 105: Preparation of Compound 150

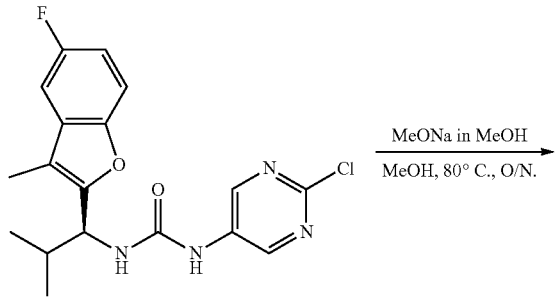

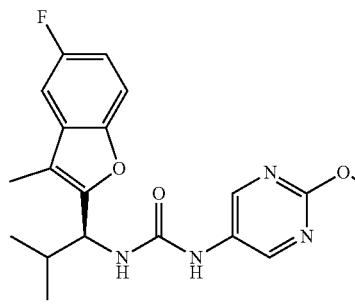

Compound 150

A solution of (S)-1-(2-chloropyrimidin-5-yl)-3-(1-(5-fluoro-3-methylbenzofuran-2-yl)-2-methylpropyl)urea (100 mg, 0.27 mmol) and sodium methoxide (1 mL, 2.5 mmol) in MeOH (1 mL) was stirred for 2 h at 60° C. The reaction was quenched with water, then purified by Prep-HPLC to afford (S)-1-(1-(5-fluoro-3-methylbenzofuran-2-yl)-2-methylpropyl)-3-(2-methoxypyrimidin-5-yl)urea (28.6 mg, 28.6%) as a off-white solid. MS (ESI): mass calcd. for $C_{19}H_{21}FN_4O_3$, 372.2, m/z found 373.10 $[M+H]^+$.

$^1$H NMR (400 MHz, DMSO-d6) δ 8.66-8.54 (d, J=1.0 Hz, 2H), 8.54-8.43 (s, 1H), 7.58-7.46 (dd, J=8.8, 4.1 Hz, 1H), 7.46-7.34 (m, 1H), 7.19-7.00 (m, 2H), 4.84-4.70 (t, J=8.7 Hz, 1H), 3.92-3.80 (t, J=1.9 Hz, 3H), 2.30-2.18 (d, J=1.2 Hz, 3H), 2.18-2.05 (m, 1H), 1.11-0.94 (d, J=6.6 Hz, 3H), 0.92-0.75 (d, J=6.6 Hz, 3H).

Example 106: Preparation of Compound 151

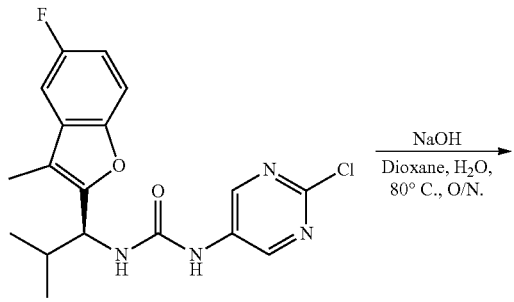

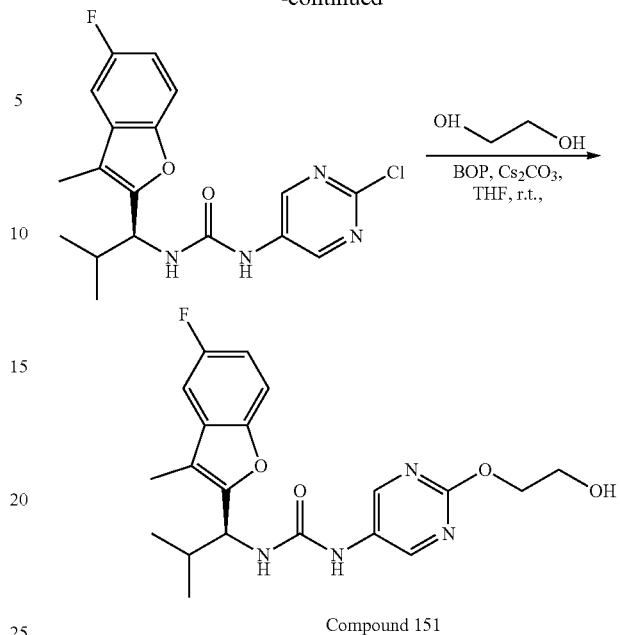

Compound 151

Step 1

A solution of (S)-1-(2-chloropyrimidin-5-yl)-3-(1-(5-fluoro-3-methylbenzofuran-2-yl)-2-methylpropyl)urea (450 mg, 1.19 mmol) and NaOH (573 mg, 14.33 mmol) in 1,4-dioxane (12 mL)/H$_2$O (4 mL) was stirred overnight at 80° C. The resulting mixture was diluted with water and adjusted pH to 5-6 with HCl (aq), then extracted with DCM 3 times. The combined organic layers were dried over anhydrous Na$_2$SO$_4$. After filtration, the filtrate was concentrated under reduced pressure. The residue was purified by reverse flash chromatography to afford (S)-1-(1-(5-fluoro-3-methylbenzofuran-2-yl)-2-methylpropyl)-3-(2-hydroxypyrimidin-5-yl)urea (200 mg, 46.7%) as a yellow solid. MS (ESI): mass calcd. for $C_{18}H_{19}FN_4O_3$, 358.1, m/z found 359.2 $[M+H]^+$.

Step 2

A solution of (S)-1-(1-(5-fluoro-3-methylbenzofuran-2-yl)-2-methylpropyl)-3-(2-hydroxypyrimidin-5-yl)urea (70 mg, 0.20 mmol), BOP (172 mg, 0.39 mmol) and Cs$_2$CO$_3$ (127 mg, 0.39 mmol) in THF (2 mL) was stirred for 1 h at room temperature under nitrogen atmosphere. Then ethylene glycol (2 mL) was added. The reaction was stirred overnight at 60° C. under nitrogen atmosphere. The resulting mixture was diluted with water, extracted with DCM 3 times. The combined organic layers were dried over anhydrous Na$_2$SO$_4$. After filtration, the filtrate was concentrated under reduced pressure. The residue was purified by Prep-HPLC to afford (S)-1-(1-(5-fluoro-3-methylbenzofuran-2-yl)-2-methylpropyl)-3-(2-(2-hydroxyethoxy)pyrimidin-5-yl)urea (16.2 mg, 20.3%) as a off-white solid. MS (ESI): mass calcd. for $C_{20}H_{23}FN_4O_4$, 402.2, m/z found 403.2 $[M+H]^+$.

$^1$H NMR (400 MHz, DMSO-d$_6$) δ 8.65-8.54 (d, J=1.3 Hz, 2H), 8.53-8.44 (s, 1H), 7.58-7.47 (dd, J=9.0, 4.0 Hz, 1H), 7.44-7.33 (dd, J=9.1, 2.7 Hz, 1H), 7.19-7.00 (m, 2H), 4.93-4.82 (t, J=5.7 Hz, 1H), 4.81-4.69 (t, J=8.6 Hz, 1H), 4.30-4.18 (t, J=5.2 Hz, 2H), 3.75-3.62 (m, 2H), 2.29-2.18 (m, 3H), 2.18-2.06 (m, 1H), 1.10-0.95 (d, J=6.5 Hz, 3H), 0.89-0.77 (d, J=6.5 Hz, 3H).

Example 107: Preparation of Compound 152

Compound 152

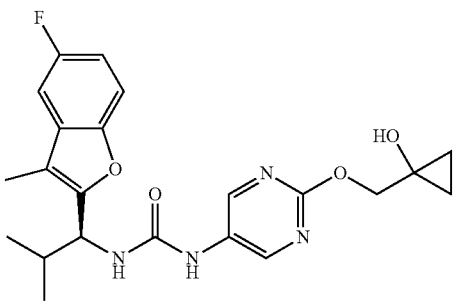

Prepared using the same procedure as Compound 151 using the appropriate alcohol. MS (ESI): mass calcd. for $C_{22}H_{25}FN_4O_4$, 428.2, m/z found 429.35 $[M+H]^+$.

$^1$H NMR (400 MHz, DMSO-d$_6$) δ 8.61-8.55 (s, 2H), 8.55-8.49 (s, 1H), 7.57-7.47 (dd, J=8.9, 4.1 Hz, 1H), 7.42-7.34 (dd, J=8.8, 2.7 Hz, 1H), 7.15-7.03 (m, 2H), 5.65-5.58 (s, 1H), 4.79-4.70 (t, J=8.6 Hz, 1H), 4.26-4.19 (s, 2H), 2.24-2.19 (s, 3H), 2.18-2.07 (m, 1H), 1.07-0.98 (d, J=6.6 Hz, 3H), 0.87-0.78 (d, J=6.7 Hz, 3H), 0.70-0.58 (m, 4H).

Example 108: Preparation of Compound 153 and 154

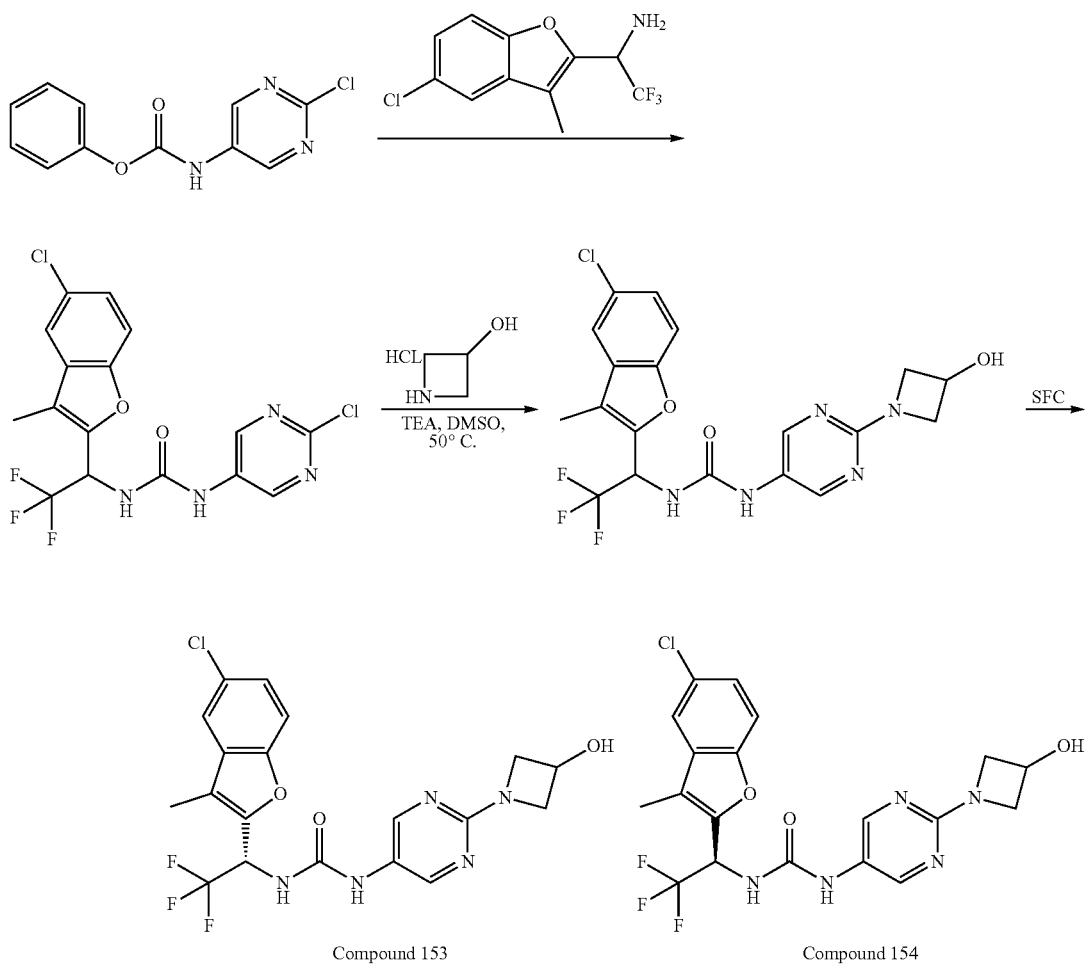

Compound 153      Compound 154

Step 1

To a solution of 1-(5-chloro-3-methyl-1-benzofuran-2-yl)-2,2,2-trifluoroethanamine (300 mg, 1.138 mmol) and phenyl N-(2-chloropyrimidin-5-yl)carbamate (284.08 mg, 1.138 mmol) in Pyridine (10 mL). The mixture was stirred at 80° C. for 16 h. After completion, the mixture was concentrated in vacuum. The residue was purified by reverse phase (ACN/water from 0~60) to give 3-[1-(5-chloro-3- methyl-1-benzofuran-2-yl)-2,2,2-trifluoroethyl]-1-(2-chloropyrimidin-5-yl)urea (270 mg, 56.6%) as white solid. MS (ESI): mass calcd. for $C_{16}H_{11}Cl_2F_3N_4O_2$, 418.0, m/z found 419.1 [M+H]$^+$.

Step 2

A solution of 3-[1-(5-chloro-3-methyl-1-benzofuran-2-yl)-2,2,2-trifluoroethyl]-1-(2-chloropyrimidin-5-yl)urea (235 mg, 0.561 mmol) in DMSO (4 mL) was added TEA (2 mL) and azetidin-3-ol hydrochloride (92.13 mg, 0.842 mmol) at 80° C. for 16 h. The reaction mixture was purified using flash chromatography with the following conditions (Mobile Phase A: Water, Mobile Phase B: ACN; Flow rate: 50 mL/min; Gradient: 0% B to 100% B in 40 min; 254; 220 nm). This resulted 3-[1-(5-chloro-3-methyl-1-benzofuran-2-yl)-2,2,2-trifluoroethyl]-1-[2-(3-hydroxyazetidin-1-yl)pyrimidin-5-yl]urea (190 mg, 74.35%) as a yellow solid. MS (ESI): mass calcd. for $C_{19}H_{17}ClF_3N_5O_3$, 455.1, m/z found 456.2 [M+H]$^+$.

Step 3

160 mg of racemic was separated by SFC to give (Compound 153, 47.5 mg) as white solid and (Compound 154, 46.5 mg) as white solid.

Chiral Separation Conditions:
Column: CHIRALPAK IG, 2*25 cm, 5 μm; Mobile Phase A: Hex (0.5% 2M NH$_3$-MeOH), Mobile Phase B: EtOH; Flow rate: 20 mL/min; Gradient: 20% B to 20% B in 12 min; RT1 (min): 7.00; RT2 (min): 8.82;

Compound 153

MS (ESI): mass calcd. for $C_{19}H_{17}ClF_3N_5O_3$, 455.1, m/z found 456.2 [M+H]$^+$.

$^1$H NMR (400 MHz, DMSO-d$_6$) δ 8.35 (d, J=2.2 Hz, 3H), 7.81-7.73 (m, 2H), 7.65 (d, J=8.8 Hz, 1H), 7.42 (dd, J=8.8, 2.2 Hz, 1H), 6.00 (p, J=8.1 Hz, 1H), 5.65 (d, J=6.5 Hz, 1H), 4.52 (ddd, J=11.2, 6.5, 4.6 Hz, 1H), 4.18 (dd, J=9.1, 6.5 Hz, 2H), 3.73 (dd, J=9.3, 4.6 Hz, 2H), 2.29 (s, 3H).

Compound 154

MS (ESI): mass calcd. for $C_{19}H_{17}ClF_3N_5O_3$, 455.1, m/z found 456.2 [M+H]$^+$. H NMR (400 MHz, DMSO-d$_6$) δ 8.36 (s, 3H), 7.81-7.73 (m, 2H), 7.65 (d, J=8.8 Hz, 1H), 7.42 (dd, J=8.8, 2.2 Hz, 1H), 5.99 (q, J=8.5 Hz, 1H), 5.65 (d, J=6.5 Hz, 1H), 4.57-4.47 (m, 1H), 4.18 (dd, J=9.0, 6.6 Hz, 2H), 3.73 (dd, J=9.3, 4.6 Hz, 2H), 2.29 (s, 3H).

Example 109: Preparation of Compound 155 and 156

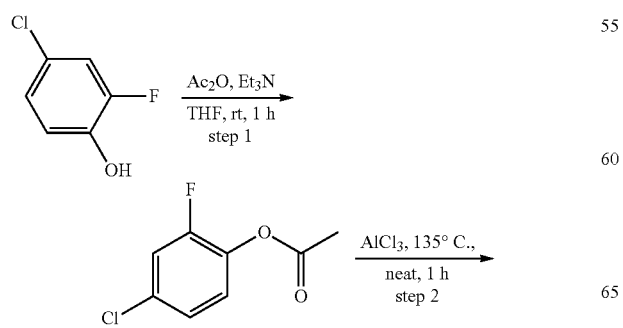

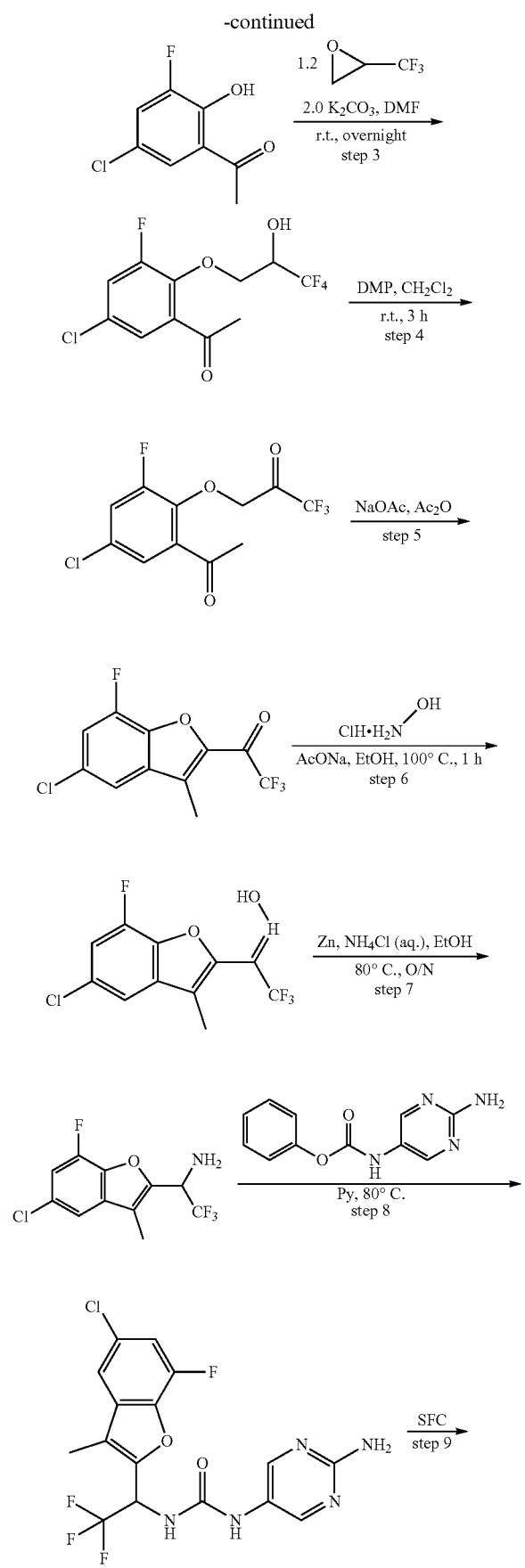

-continued

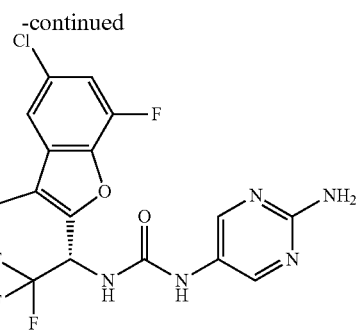

Compound 155

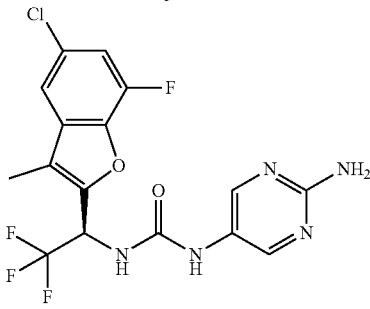

Compound 156

Step 1

A solution of 4-chloro-2-fluorophenol (2.9 g, 19.79 mmol, 1 equiv), Ac$_2$O (3.03 g, 29.68 mmol, 1.5 equiv) and Et$_3$N (3.20 g, 31.66 mmol, 1.6 equiv) in THF (30 mL) was stirred for 1 h at room temperature under air atmosphere. After the reaction was completed, the mixture was quenched with saturated NaHCO$_3$, extracted with EA. Then the organic phase was combined, washed with the brine, dried over anhydrous Na$_2$SO$_4$ to get 4-chloro-2-fluorophenyl acetate (3.7 g, 99.15%) yellow oil as product.

Step 2

A mixture of 4-chloro-2-fluorophenyl acetate (3.7 g, 19.62 mmol, 1 equiv) and AlCl$_3$ (3.92 g, 29.43 mmol, 1.5 equiv) was stirred for 1 h at 135° C. Then 500 ml 1M HCl solution was added into the mixture slowly. The solution was stirred for 3 h. Solid was created, the solid was filtrated and dried to get 1-(5-chloro-3-fluoro-2-hydroxyphenyl)ethanone (3.7 g, crude) light-brown solid as product.

Step 3

A solution of 1-(5-chloro-3-fluoro-2-hydroxyphenyl)ethanone (1.88 g, 9.97 mmol, 1 equiv), 2-(trifluoromethyl)oxirane (1.01 g, 8.97 mmol, 0.9 equiv) and K$_2$CO$_3$ (2.76 g, 19.94 mmol, 2 equiv) in DMF (25 mL) was stirred for overnight at room temperature. After the reaction was completed, the mixture was diluted with 500 ml water, extracted with EA, washed with the brine, dried with anhydrous Na$_2$SO$_4$ to afford 1-[5-chloro-3-fluoro-2-(3,3,3-trifluoro-2-hydroxypropoxy) phenyl]ethanone (2.99 g, crude) yellow semi-solid as product. MS (ESI): mass calcd. for C$_{11}$H$_9$ClF$_4$O$_3$, 300.0. m/z. found 300.9 [M+H]$^+$.

Step 4

A solution of 1-[5-chloro-3-fluoro-2-(3,3,3-trifluoro-2-hydroxypropoxy) phenyl] ethanone (3 g, 9.98 mmol, 1 equiv) and DMP (6.35 g, 14.97 mmol, 1.5 equiv) in DCM (25 mL) was stirred for overnight at room temperature. The mixture was quenched with saturated NaHCO$_3$ and filtrated, the filtrate was extracted with DCM, the organic phase was combined, washed with the brine, dried over anhydrous Na$_2$SO$_4$ to get the crude. Finally, the crude was purified by reserved-flash to get 3-(2-acetyl-4-chloro-6-fluorophenoxy)-1,1,1-trifluoropropan-2-one (464 mg, 15.57%) yellow solid as product.

Step 5

A solution of 3-(2-acetyl-4-chloro-6-fluorophenoxy)-1,1,1-trifluoropropan-2-one (928 mg, 3.11 mmol, 1 equiv) and Ac$_2$O (793.14 mg, 7.77 mmol, 2.5 equiv) in NaOAc (10 mL) was stirred for 30 min at 110° C. After the reaction was completed, the mixture was quenched with saturated NaHCO$_3$ until no bubble appeared, extracted with EA. The organic phase was combined and washed with the brine, dried over anhydrous Na$_2$SO$_4$ to the crude. The residue was purified by reserved-flash to get 1-(5-chloro-7-fluoro-3-methyl-1-benzofuran-2-yl)-2,2,2-trifluoroethanone (345 mg, 39.56%) yellow solid as product. MS (ESI): mass calcd. for C$_{11}$H$_5$ClF$_4$O$_2$, 280.6, m/z found 282.1 [M+H]$^+$.

Step 6

A solution of 1-(5-chloro-7-fluoro-3-methyl-1-benzofuran-2-yl)-2,2,2-trifluoroethanone (345 mg, 1.23 mmol, 1 equiv), NaOAc (504.31 mg, 6.150 mmol, 5 equiv) and hydroxylamine hydrochloride (427.20 mg, 6.15 mmol, 5 equiv) in EtOH (10 mL) was stirred for 1 h at 100° C. After the reaction was completed, the mixture was purified by reserved-flash to get (E)-N-[1-(5-chloro-7-fluoro-3-methyl-1-benzofuran-2-yl)-2,2,2-trifluoroethylidene] hydroxylamine (90 mg, 24.76%) yellow solid as product. MS (ESI): mass calcd. for C$_{11}$H$_6$ClF$_4$NO$_2$, 295, m/z found 296.3 [M+H]$^+$.

Step 7

A solution of (E)-N-[1-(5-chloro-7-fluoro-3-methyl-1-benzofuran-2-yl)-2,2,2-trifluoroethylidene]hydroxylamine (88 mg, 0.30 mmol, 1 equiv),1-(5-chloro-7-fluoro-3-methyl-1-benzofuran-2-yl)-2,2,2-trifluoroethanamine (60 mg) and Zn (194.62 mg, 2.98 mmol, 10 equiv) in EtOH (3 mL) and H$_2$O (3 mL) was stirred for 1 h at 80° C. After the reaction was completed, the solid was filtrated, the solution was condensed to get 1-(5-chloro-7-fluoro-3-methyl-1-benzofuran-2-yl)-2,2,2-trifluoroethanamine (60 mg, 71.57%) as yellow solid. MS (ESI): mass calcd. for C$_{11}$H$_8$ClF$_4$NO, 281.0, m/z found 282.3 [M+H]$^+$.

Step 8

A solution of 1-(5-chloro-7-fluoro-3-methyl-1-benzofuran-2-yl)-2,2,2-trifluoroethanamine (60 mg, 0.21 mmol, 1 equiv) and phenyl N-(2-aminopyrimidin-5-yl) carbamate (49.05 mg, 0.21 mmol, 1 equiv) in Pyridine (3 mL) was stirred for overnight at 80° C. After the reaction was completed, the solvent was condensed to get the crude product. The crude was purified by reserved-flash to get 1-(2-aminopyrimidin-5-yl)-3-[1-(5-chloro-7-fluoro-3-methyl-1-benzofuran-2-yl)-2,2,2-trifluoroethyl]urea (50 mg, 56.18%) yellow solid as product. MS (ESI): mass calcd. for C$_{16}$H$_{12}$ClF$_4$N$_5$O$_2$, 417.1, m/z found 417.95 [M+H]$^+$.

Step 9

40 mg of racemic was separated by SFC to give (Compound 155, 8.1 mg) as white solid and (Compound 156, 7.4 mg) as white solid.
Chiral Separation Conditions:
Apparatus: Prep-HPLC
Column: CHIRALPAK IG, 2*25 cm, 5 μm; Mobile Phase A: Hex (0.2% TEA)-HPLC, Mobile Phase B: EtOH-HPLC; Flow rate: 20 mL/min; Gradient: 20% B to 20% B in 9 min; Wave Length: 220/254 nm; RT1 (min): 5.90; RT2 (min): 8.13; Sample Solvent: EtOH-HPLC; Injection Volume: 0.85 mL Compound 155

MS (ESI): mass calcd. for $C_{16}H_{12}ClF_4N_5O_2$, 417.1, m/z found 417.95 [M+H]$^+$. 1H NMR (400 MHz, DMSO) δ 8.22 (d, J=4 Hz, 3H), 7.83 (d, J=5.2 Hz, 1H), 7.68 (d, J=2.0 Hz, 1H), 7.56 (dd, J=10.8, 2.0 Hz, 1H), 6.41 (s, 2H), 6.07-6.02 (m, 1H), 2.31 (s, 3H).

Compound 156

MS (ESI): mass calcd. for $C_{16}H_{12}ClF_4N_5O_2$, 417.1, m/z found 417.95 [M+H]$^+$.

1H NMR (400 MHz, DMSO) δ 8.22 (d, J=4 Hz, 3H), 7.83 (d, J=5.2 Hz, 1H), 7.68 (d, J=2.0 Hz, 1H), 7.56 (dd, J=10.8, 2.0 Hz, 1H), 6.41 (s, 2H), 6.07-6.02 (m, 1H), 2.31 (s, 3H).

Example 110: Preparation of Compound 157 and 158

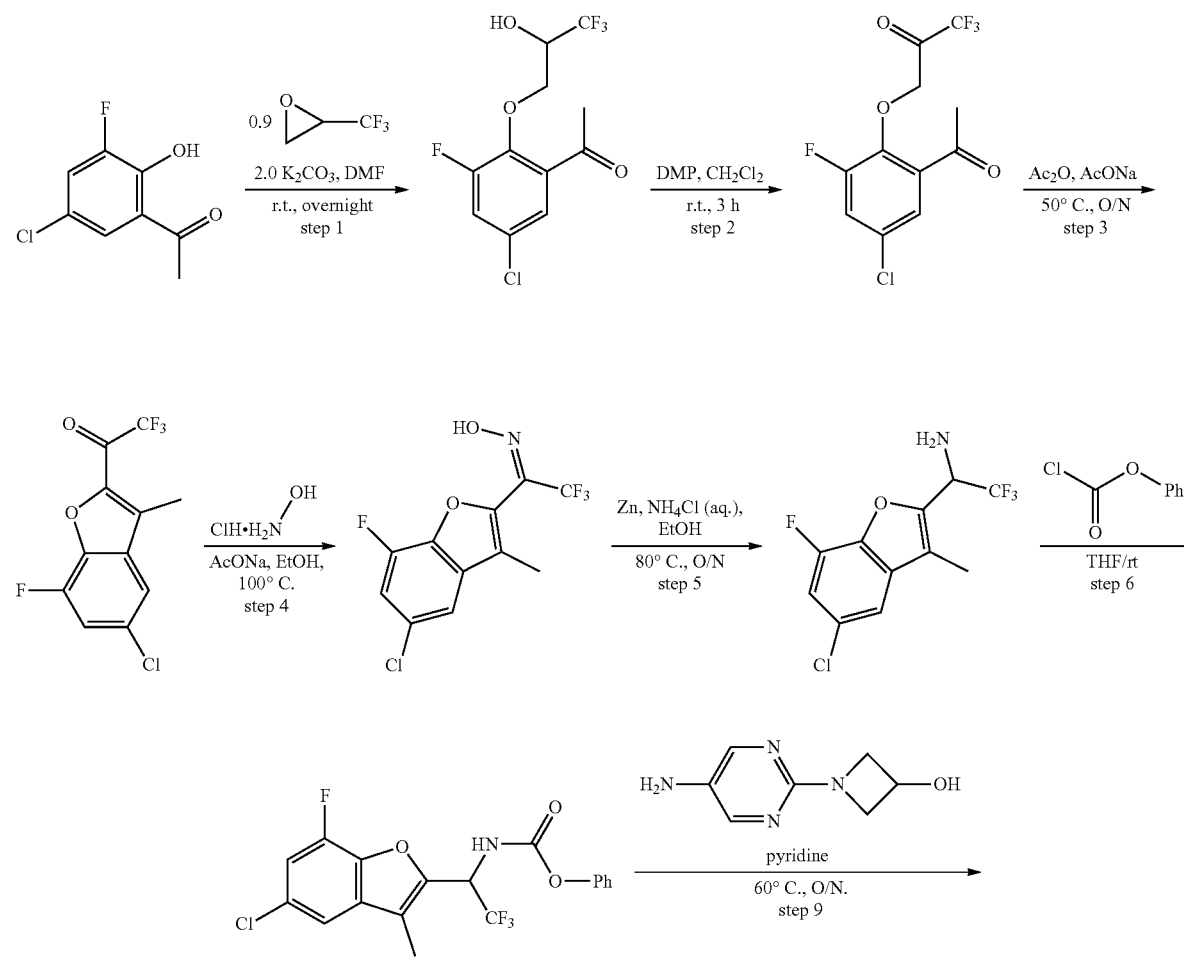

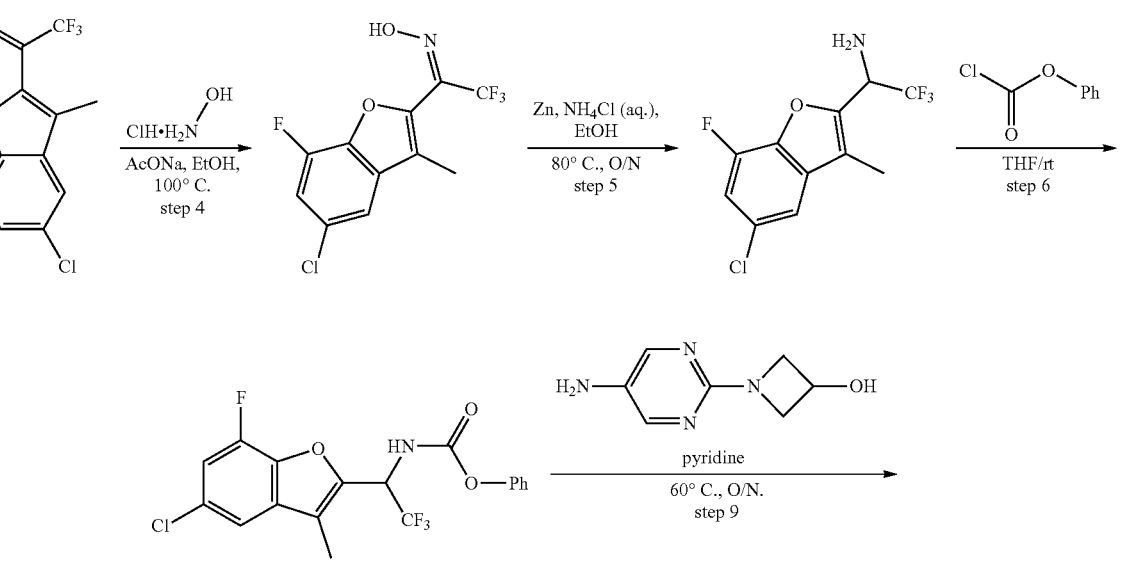

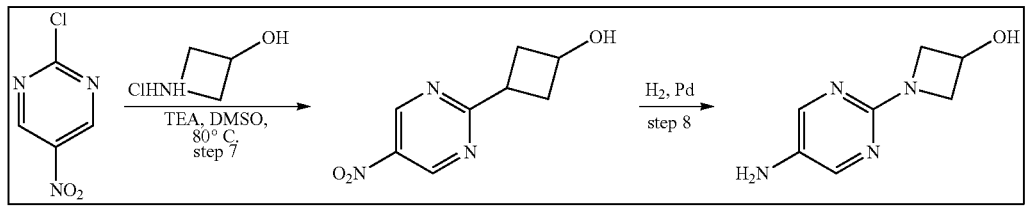

-continued

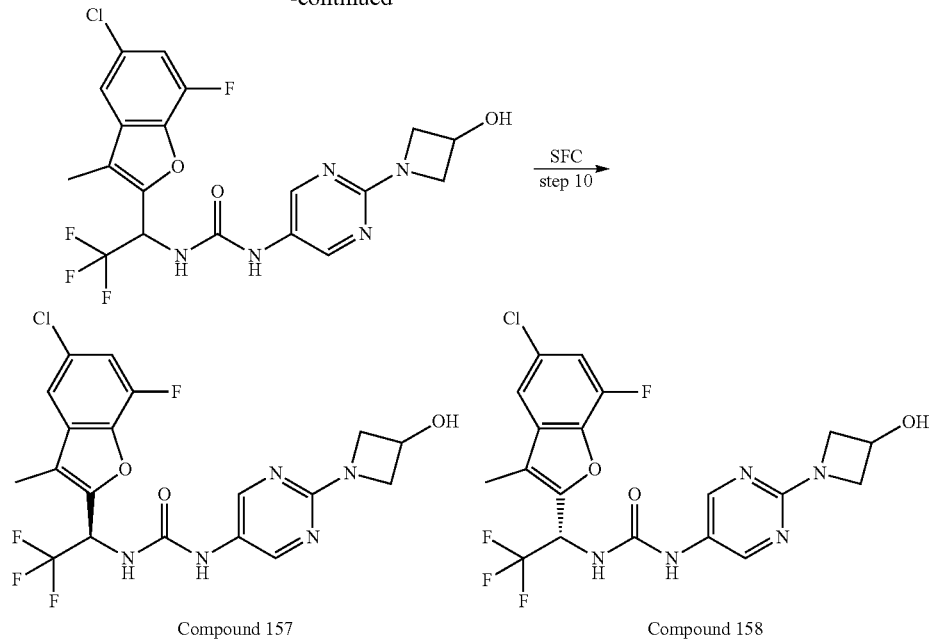

Compound 157

Compound 158

Step 1

A solution of 1-(5-chloro-3-fluoro-2-hydroxyphenyl)ethanone (3.4 g, 18.03 mmol, 1 equiv), 2-(trifluoromethyl)oxirane (1.82 g, 16.23 mmol, 0.9 equiv) and $K_2CO_3$ (4.99 g, 36.06 mmol, 2 equiv) in DMF (50 mL) was stirred for overnight at room temperature. After the reaction was completed, the mixture was diluted with 500 ml water, extracted with EA, washed with the brine, dried with anhydrous $Na_2SO_4$ to afford 1-[5-chloro-3-fluoro-2-(3,3,3-trifluoro-2-hydroxypropoxy)phenyl]ethanone (5.272 g, 97.27%) yellow semi-solid as product.

Step 2

A solution of 1-[5-chloro-3-fluoro-2-(3,3,3-trifluoro-2-hydroxypropoxy) phenyl] ethanone (5.272 g, 17.54 mmol, 1 equiv) and DMP (11.16 g, 26.31 mmol, 1.50 equiv) in DCM (50 mL) was stirred for overnight at room temperature. The mixture was quenched with saturated $NaHCO_3$ and filtrated, the filtrate was extracted with DCM, the organic phase was combined, washed with the brine, dried over anhydrous $Na_2SO_4$ to get the crude. Finally, the crude was purified by reserved-flash to get 3-(2-acetyl-4-chloro-6-fluorophenoxy)-1,1,1-trifluoropropan-2-one (1.6 g, 30.55%) yellow solid as product.

Step 3

A solution of 3-(2-acetyl-4-chloro-6-fluorophenoxy)-1,1,1-trifluoropropan-2-one (1.6 g, 5.36 mmol, 1 equiv) and NaOAc (0.82 g, 8.04 mmol, 1.5 equiv) in $Ac_2O$ (16 mL) was stirred for 30 min at 110° C. After the reaction was completed, the mixture was quenched with saturated $NaHCO_3$ until no bubble appeared, extracted with EA. The organic phase was combined and washed with the brine, dried over anhydrous $Na_2SO_4$ to the crude. In the end, the residue was purified by reserved-flash to get 1-(5-chloro-7-fluoro-3-methyl-1-benzofuran-2-yl)-2,2,2-trifluoroethanone (510 mg, 33.92%) yellow solid as product.

Step 4

A solution of 1-(5-chloro-7-fluoro-3-methyl-1-benzofuran-2-yl)-2,2,2-trifluoroethanone (345 mg, 1.23 mmol, 1 equiv), NaOAc (745.50 mg, 9.09 mmol, 5 equiv) and hydroxylamine hydrochloride (427.20 mg, 6.15 mmol, 5 equiv) in EtOH (15 mL) was stirred for 1 h at 100° C. After the reaction was completed, the mixture was purified by reserved-flash to get (E)-N-[1-(5-chloro-7-fluoro-3-methyl-1-benzofuran-2-yl)-2,2,2-trifluoroethylidene]hydroxylamine (602 mg, 112.04%) yellow semi-solid as product. MS (ESI): mass calcd. for $C_{11}H_6ClF_4NO_2$, 295.0, m/z found 293.9 [M−H]⁻.

Step 5

A solution of (E)-N-[1-(5-chloro-7-fluoro-3-methyl-1-benzofuran-2-yl)-2,2,2-trifluoroethylidene]hydroxylamine (602 mg, 2.07 mmol, 1 equiv) and Zn (1331.40 mg, 20.36 mmol, 10 equiv) in EtOH (12 mL) and $H_2O$ (8 mL) was stirred for 1 h at 80° C. After the reaction was completed, the solid was filtrated, the solution was condensed to get 1-(5-chloro-7-fluoro-3-methyl-1-benzofuran-2-yl)-2,2,2-trifluoroethanamine (197.7 mg, 34.47%) as yellow solid. MS (ESI): mass calcd. for $C_{11}H_8ClF_4NO$, 281.0, m/z found 282.0 [M+H]⁺.

Step 6

A solution of 1-(5-chloro-7-fluoro-3-methyl-1-benzofuran-2-yl)-2,2,2-trifluoroethanamine (300 mg, 1.07 mmol, 1 equiv), phenyl chloroformate (166.78 mg, 1.07 mmol, 1 equiv) and TEA (161.69 mg, 1.60 mmol, 1.5 equiv) in THF (5 mL) was stirred for 3 h at room temperature. After the reaction was completed, the solution was concentrated under vacuum to get the crude. The product was purified to afford phenyl N-[1-(5-chloro-7-fluoro-3-methyl-1-benzofuran-2-yl)-2,2,2-trifluoroethyl]carbamate (299 mg, 69.87%) color-less semi-solid as product.

Step 7

A solution of 2-chloro-5-nitropyrimidine (954 mg, 5.980 mmol, 1 equiv), azetidin-3-ol hydrochloride (986 mg, 8.970 mmol, 1.5 equiv) and TEA (907.71 mg, 8.970 mmol, 1.5 equiv) in DMSO (3 mL) was stirred for overnight at 80° C. The mixture was purified by reserved-flash to get 1-(5-nitropyrimidin-2-yl) azetidin-3-ol (752 mg, 64.10%) light-pink solid.

Step 8

A solution of 1-(5-nitropyrimidin-2-yl) azetidin-3-ol (332 mg, 1.69 mmol, 1 equiv) and Pd/C (100 mg, 0.94 mmol, 0.56 equiv) in MeOH (20 mL) was stirred for 3 h at room temperature. After the reaction was completed, the solid as filtrated. The solution was concentrated under reduced pressure to get the crude product. The residue was purified by reserved-flash to get 1-(5-aminopyrimidin-2-yl) azetidin-3-ol (272 mg, 96.71%) yellow solid as product.

Step 9

A solution of phenyl N-[1-(5-chloro-7-fluoro-3-methyl-1-benzofuran-2-yl)-2,2,2-trifluoroethyl]carbamate (299 mg, 0.74 mmol, 1 equiv) and 1-(5-aminopyrimidin-2-yl)azetidin-3-ol (123.68 mg, 0.74 mmol, 1 equiv) in pyridine (5 mL) was stirred for 3 h at 60° C. After the reaction was completed, the mixture was purified by reserved-flash to get 3-[1-(5-chloro-7-fluoro-3-methyl-1-benzofuran-2-yl)-2,2,2-trifluoroethyl]-1-[2-(3-hydroxyazetidin-1-yl)pyrimidin-5-yl]urea (83.2 mg, 23.59%) yellow solid as product. MS (ESI): mass calcd. for $C_{19}H_{16}ClF_4N_5O_3$, 473.1, m/z found 474.2 [M+H]$^+$.

Step 10

83.2 mg of racemic was separated by SFC to give (Compound 157, 24 mg) as white solid and (Compound 158, 25.2 mg) as white solid.
Chiral Separation Conditions:
Apparatus: Prep-Chiral-HPLC
Column: DZ-CHIRALPAK ID-3, 4.6*50 mm, 3.0 μm;
Mobile Phase A: Hex (0.2% DEA):
EtOH=85: 15; Flow rate: 1 mL/min; Gradient: 0% B to 0% B; Injection Volume: 5 mL.

Compound 157

MS (ESI): mass calcd. for $C_{19}H_{16}ClF_4N_5O_3$, 473.1, m/z found 474.2 [M+H]$^+$.
$^1$H NMR (400 MHz, DMSO) δ 8.35 (d, J=4.8 Hz, 3H), 7.84 (d, J=9.2 Hz, 1H), 7.68 (d, J=2.0 Hz, 1H), 7.56 (dd, J=10.8, 8.8 Hz, 1H), 6.07-6.02 (m, 1H), 5.65 (d, J=2.0 Hz, 1H), 4.52 (m, 1H), 4.20-4.16 (m, 2H), 3.74-3.71 (m, 2H), 2.31 (s, 3H).

Compound 158

MS (ESI): mass calcd. for $C_{19}H_{16}ClF_4N_5O_3$, 473.1, m/z found 474.2 [M+H]$^+$.
$^1$H NMR (400 MHz, DMSO) δ 8.35 (d, J=4.8 Hz, 3H), 7.84 (d, J=9.2 Hz, 1H), 7.68 (d, J=2.0 Hz, 1H), 7.56 (dd, J=10.8, 8.8 Hz, 1H), 6.07-6.02 (m, 1H), 5.65 (d, J=2.0 Hz, 1H), 4.52 (m, 1H), 4.20-4.16 (m, 2H), 3.74-3.71 (m, 2H), 2.31 (s, 3H).

Example 111: Preparation of Compound 159

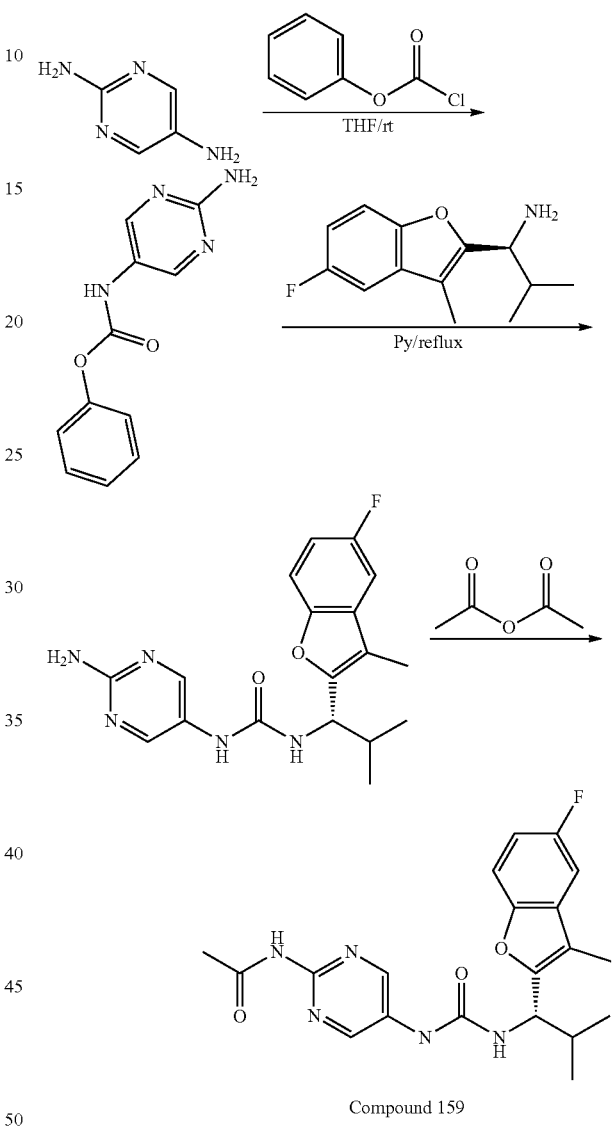

Compound 159

Step 1

A solution of pyrimidine-2,5-diamine (1 g, 9.081 mmol, 1 equiv) and phenyl chloroformate (1.42 g, 9.081 mmol, 1 equiv) in THF (10 mL) was stirred for 2 h at room temperature. The resulting mixture was concentrated under reduced pressure. This resulted in phenyl N-(2-aminopyrimidin-5-yl)carbamate (600 mg, 28.70%) as a light yellow oil. MS (ESI): mass calcd. for $C_{11}H_{10}N_4O_2$, 230.1, m/z found 231.1 [M+H].

Step 2

A solution of phenyl N-(2-aminopyrimidin-5-yl)carbamate (1 g, 4.344 mmol, 1 equiv) and (1S)-1-(5-fluoro-3- methyl-1-benzofuran-2-yl)-2-methylpropan-1-amine (0.96 g, 4.344 mmol, 1 equiv) in Pyridine (10 mL) was stirred for 3 h at 80° C. under nitrogen atmosphere. The resulting mixture was concentrated under reduced pressure. This resulted in 1-(2-aminopyrimidin-5-yl)-3-[(1S)-1-(5-fluoro-3-methyl-1-benzofuran-2-yl)-2-methylpropyl]urea (600 mg, 38.65%) as a yellow oil.

MS (ESI): mass calcd. for $C_{11}H_6FN_5O_2$, 357.2, m/z found 358.2 [M+H]+.

Step 3

A solution of 1-(2-aminopyrimidin-5-yl)-3-[(1S)-1-(5-fluoro-3-methyl-1-benzofuran-2-yl)-2-methylpropyl] urea (100 mg, 0.280 mmol, 1 equiv) and acetic anhydride (28.57 mg, 0.280 mmol, 1 equiv) in Pyridine (2 mL) was stirred for 1 h at 80° C. under nitrogen atmosphere. The resulting mixture was concentrated under reduced pressure. The residue was purified by Prep-HPLC with the following conditions: Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 25% B to 55% B in 8 min; Wave Length: 220 nm; RT1 (min): 7.65. MS (ESI): mass calcd. for $C_{20}H_{22}FN_5O_3$, 399.2, m/z found 400.1 [M+H]+.

$^1$H NMR (400 MHz, DMSO-d6) δ 10.37 (s, 1H), 8.62 (d, J=21.5 Hz, 3H), 7.52 (dd, J=8.9, 4.1 Hz, 1H), 7.38 (dd, J=8.8, 2.7 Hz, 1H), 7.16-7.01 (m, 2H), 4.75 (t, J=8.6 Hz, 1H), 2.21 (s, 3H), 2.10 (s, 4H), 1.03 (d, J=6.7 Hz, 3H), 0.82 (d, J=6.7 Hz, 3H).

Example 112: Preparation of Compound 160

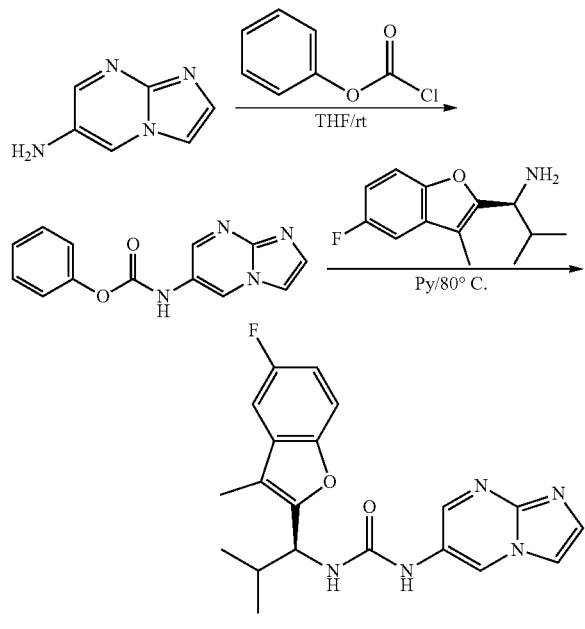

Compound 160

Step 1

A mixture of imidazo[1,2-a]pyrimidin-6-amine (200 mg, 1.491 mmol, 1 equiv), phenyl chloroformate (250 mg, 1.597 mmol, 1.07 equiv) in THF (5 mL) was stirred for 0.5 h at rt. The resulting mixture was concentrated under reduced pressure to give phenyl imidazo[1,2-a]pyrimidin-6-ylcarbamate (250 mg, 65.95%) as a yellow solid.

Step 2

A mixture of phenyl imidazo[1,2-a]pyrimidin-6-ylcarbamate (200 mg, 0.787 mmol, 1 equiv), (S)-1-(5-fluoro-3-methylbenzofuran-2-yl)-2-methylpropan-1-amine (174.06 mg, 0.787 mmol, 1 equiv) in Pyridine (2 mL) was stirred for 16 h at 80° C. The resulting mixture was concentrated under reduced pressure. The residue was purified by reverse flash chromatography to give (S)-1-(1-(5-fluoro-3-methylbenzofuran-2-yl)-2-methylpropyl)-3-(imidazo[1,2-a]pyrimidin-6-yl)urea (92.4 mg, 30.80%) as a white solid. MS (ESI): mass calcd. for $C_{20}H_{20}FN_5O_2$, 381.2, m/z found 382.1 [M+H]+.

$^1$H NMR (400 MHz, DMSO-d6) δ 9.34 (d, J=2.4 Hz, 1H), 8.88 (s, 1H), 8.42 (d, J=2.8 Hz, 1H), 7.98 (s, 1H), 7.76 (s, 1H), 7.52 (dd, J=8.8, 4.0 Hz, 1H), 7.39 (dd, J=8.8, 2.4 Hz, 1H), 7.20 (d, J=8.8 Hz, 1H), 7.10 (td, J=9.2, 2.8 Hz, 1H), 4.75 (t, J=8.8 Hz, 1H), 2.22 (s, 3H), 2.21-0.11 (m, 1H), 1.05 (d, J=6.8 Hz, 3H), 0.83 (d, J=6.7 Hz, 3H).

Example 113: Preparation of Compound 161

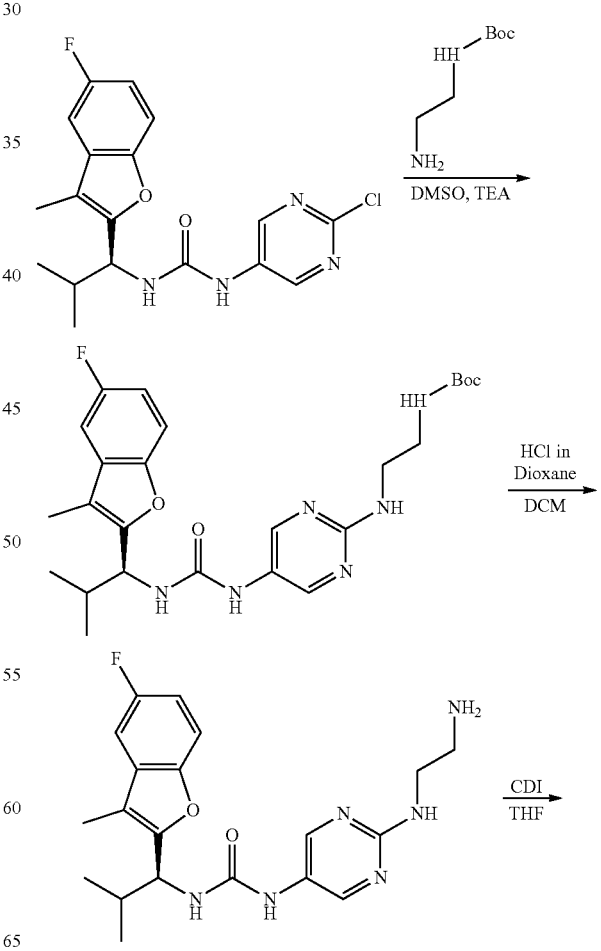

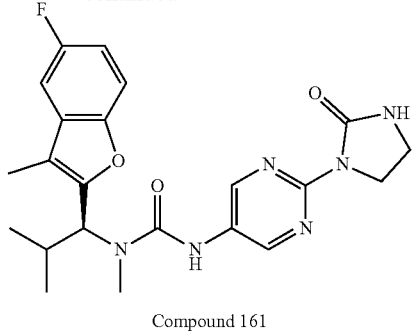

Compound 161

Step 1

A solution of (S)-1-(2-chloropyrimidin-5-yl)-3-(1-(5-fluoro-3-methylbenzofuran-2-yl)-2-methylpropyl)urea (200 mg, 0.53 mmol) and tert-butyl N-(2-aminoethyl)carbamate (255 mg, 1.59 mmol) in DMSO (4 mL)/TEA (2 mL) was stirred for 2 days at 80° C. The resulting mixture concentrated under reduced pressure. The residue was purified by Prep-TLC (EA) to afford tert-butyl (S)-(2-((5-(3-(1-(5-fluoro-3-methylbenzofuran-2-yl)-2-methylpropyl)ureido)pyrimidin-2-yl) amino)ethyl)carbamate (157.8 mg, 57.0%) as a yellow solid. MS (ESI): mass calcd. for $C_{25}H_{33}FN_6O_4$, 500.3, m/z found 501.4 $[M+H]^+$.

Step 2

To a stirred solution of tert-butyl (S)-(2-((5-(3-(1-(5-fluoro-3-methylbenzofuran-2-yl)-2-methylpropyl)ureido)pyrimidin-2-yl)amino)ethyl)carbamate (157.8 mg, 0.32 mmol) in DCM (10 mL) was added HCl in 1,4-dioxane (2 mL, 8 mmol). The resulting mixture was stirred for 1 hour at room temperature, then quenched with saturated $NaHCO_3$ and extracted with DCM 3 times. The combined organic layers were dried over anhydrous $Na_2SO_4$. After filtration, the filtrate was concentrated under reduced pressure to afforded (S)-1-(2-((2-aminoethyl)amino)pyrimidin-5-yl)-3-(1-(5-fluoro-3-methylbenzofuran-2-yl)-2-methylpropyl)urea (100 mg) as a yellow oil. MS (ESI): mass calcd. for $C_{20}H_{25}FN_6O_2$, 400.2, m/z found 401.3 $[M+H]^+$.

Step 3

A solution of (S)-1-(2-((2-aminoethyl)amino)pyrimidin-5-yl)-3-(1-(5-fluoro-3-methylbenzofuran-2-yl)-2-methylpropyl)urea (100 mg, 0.25 mmol) and CDI (121 mg, 0.75 mmol) in THF (3 mL) was stirred overnight at room temperature. The reaction was diluted with water and then extracted with DCM 3 times. The combined organic layers were dried over anhydrous $Na_2SO_4$. After filtration, the filtrate was concentrated under reduced pressure. The residue was purified by reverse flash chromatography to afforded 3-[(1S)-1-(5-fluoro-3-methyl-1-benzofuran-2-yl)-2-methylpropyl]-1-[2-(2-oxoimidazolidin-1-yl)pyrimidin-5-yl]urea (23.3 mg, 21.2%) as a white solid. MS (ESI): mass calcd. for $C_{21}H_{23}FN_6O_3$, 426.2, m/z found 427.05 $[M+H]^+$.

$^1$H NMR (400 MHz, DMSO-d6) δ 8.62 (s, 2H), 8.53 (s, 1H), 7.52 (dd, J=8.9, 4.1 Hz, 1H), 7.38 (dd, J=8.8, 2.7 Hz, 1H), 7.10 (td, J=9.2, 2.7 Hz, 1H), 6.96-7.06 (m, 2H), 4.76 (t, J=8.5 Hz, 1H), 3.93 (dd, J=8.7, 7.1 Hz, 2H), 3.36 (d, J=8.1 Hz, 2H), 2.21 (s, 3H), 2.11 (dd, J=15.1, 7.9 Hz, 1H), 1.03 (d, J=6.7 Hz, 3H), 0.83 (d, J=6.7 Hz, 3H).

Example 114: Preparation of Compound 162

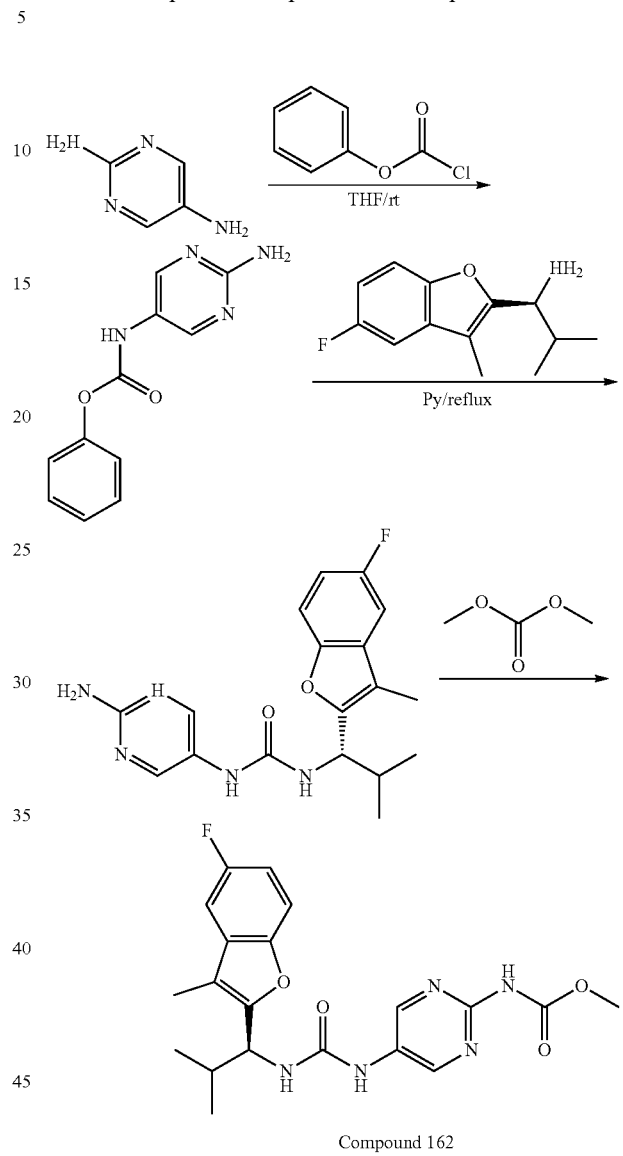

Compound 162

Step 1

A solution of pyrimidine-2,5-diamine (1 g, 9.081 mmol, 1 equiv) and phenyl chloroformate (1.42 g, 9.081 mmol, 1 equiv) in THF (10 mL) was stirred for 2 h at room temperature. The resulting mixture was concentrated under reduced pressure. This resulted in phenyl N-(2-aminopyrimidin-5-yl)carbamate (600 mg, 28.70%) as a light yellow oil. MS (ESI): mass calcd. for $C_{11}H_{10}N_4O_2$, 230.1, m/z found 231.1 $[M+H]^+$.

Step 2

A solution of phenyl N-(2-aminopyrimidin-5-yl)carbamate (1 g, 4.344 mmol, 1 equiv) and (1 S)-1-(5-fluoro-3-methyl-1-benzofuran-2-yl)-2-methylpropan-1-amine (0.96 g, 4.344 mmol, 1 equiv) in Pyridine (10 mL) was stirred for 3 h at 80° C. under nitrogen atmosphere. The resulting mixture was concentrated under reduced pressure. This resulted in 1-(2-aminopyrimidin-5-yl)-3-[(1S)-1-(5-fluoro-3-methyl-1-benzofuran-2-yl)-2-methylpropyl]urea (600 mg, 38.65%) as a yellow oil.

MS (ESI): mass calcd. for $C_{18}H_{20}FN_5O_2$, 357.2. m/z found 358.1 [M+H]⁺.

Step 3

A solution of 1-(2-aminopyrimidin-5-yl)-3-[(1S)-1-(5-fluoro-3-methyl-1-benzofuran-2-yl)-2-methyl propyl]urea (60 mg, 0.168 mmol, 1 equiv) and dimethyl dicarbonate (45.02 mg, 0.336 mmol, 2 equiv) in Pyridine (2 mL) was stirred for 1 h at room temperature under nitrogen atmosphere. The resulting mixture was concentrated under reduced pressure. The residue was purified by reverse flash chromatography to afford methyl N-[5-({[(1S)-1-(5-fluoro-3-methyl-1-benzofuran-2-yl)-2-methyl propyl] carbamoyl} amino)pyrimidin-2-yl]carbamate (20.3 mg, 29.11%) as a off-white solid. MS (ESI): mass calcd. for $C_{20}H_{22}FN_5O_4$, 415.2, m/z found 416.1 [M+H]⁺. Column: XBridge Shield RP18 OBD Column, 30*150 mm, 5 µm; Mobile phase; A: Water (10 mmol/L $NH_4HCO_3$+0.1% $NH_3·H_2O$), Mobile Phase B: CAN; Flow rate: 60 mL/min; Gradient: 32% B to 57% B in 8 min; Wavelength: UV 254 nm; RT1 (min): 7.43; Temperature: 35° C.

¹H NMR (400 MHz, DMSO-d6) δ 10.20 (s, 1H), 8.76-8.43 (m, 3H), 7.45 (d, J=50.3 Hz, 2H), 7.10 (s, 2H), 4.79 (d, J=24.1 Hz, 1H), 3.62 (d, J=11.1 Hz, 3H), 2.21 (s, 4H), 1.06 (d, J=23.8 Hz, 3H), 0.84 (s, 3H).

Example 115: Preparation of Compound 163

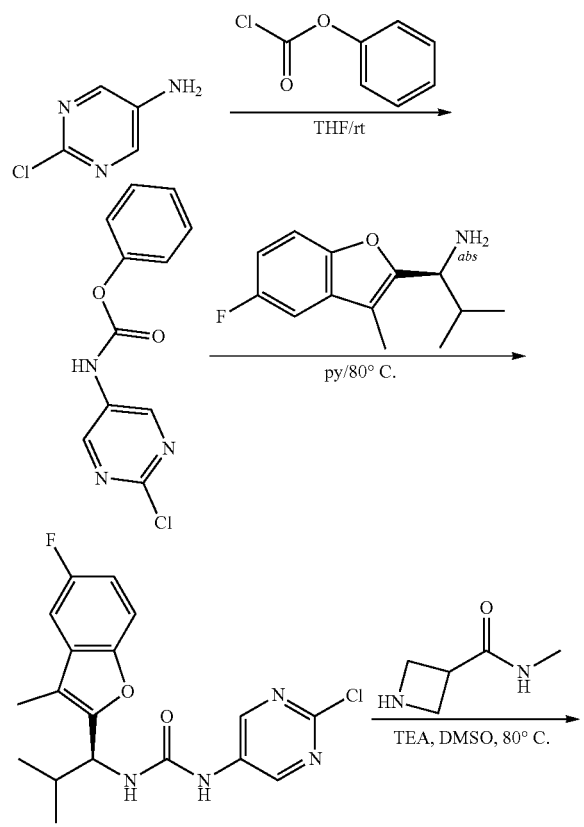

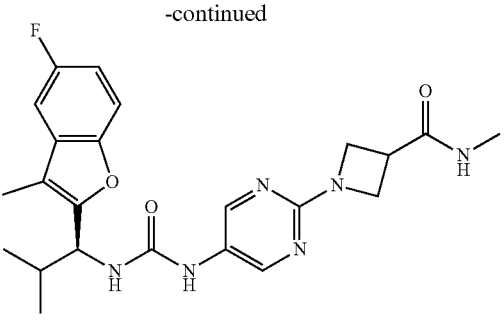

Compound 163

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2[M+H]⁺.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl] urea (7 g, 82.21%) as a yellow oil.

MS (ESI): mass calcd. for $C_{18}H_{18}ClFN_4O_2$, 376.1, m/z found 377.3 [M+H]⁺.

Step 3

To a stirred solution of 1-(2-chloropyrimidin-5-yl)-3-[(1S)-1-(5-fluoro-3-methyl-1-benzofuran-2-yl)-2-methylpropyl]urea (100 mg, 0.265 mmol, 1 equiv) and N-methylazetidine-3-carboxamide (60.63 mg, 0.530 mmol, 2 equiv) in DMSO (5 mL) was added TEA (80.56 mg, 0.795 mmol, 3 equiv) dropwise s at room temperature under nitrogen atmosphere. The resulting mixture was stirred for overnight at 80° C. under nitrogen atmosphere. The mixture was allowed to cool down to room temperature. The resulting mixture was extracted with EtOAc (2×50 mL). The combined organic layers were washed with brine (2×1 100 mL), dried over anhydrous $Na_2SO_4$. After filtration, the filtrate was concentrated under reduced pressure. The crude product (80 mg) was purified by Prep-HPLC with the following conditions (Column: XBridge Shield RP18 OBD Column, 30*150 mm, 5 µm; Mobile Phase A: Water (10 mmol/L $NH_4HCO_3$), Mobile Phase B: ACN; Flow rate: 60 mL/min; Gradient: 27% B to 52% B in 8 min, 52% B; Wave Length: 254 nm; RT1 (min): 7.67; Number Of Runs: 0) to afford 1-[5-({[(1S)-1-(5-fluoro-3-methyl-1-benzofuran-2-yl)-2-methylpropyl]carbamoyl}amino)pyrimidin-2-yl]-N-methyl-azetidine-3-carboxamide (30.1 mg, 24.96%) as a white solid. MS (ESI): mass calcd. for $C_{23}H_{27}FN_6O_3$, 454.2, m/z found 455.1 [M+H]$^+$. MS (ESI): mass calcd. for $C_{23}H_{27}FN_6O_3$, 454.2, m/z found 455.1 [M+H]$^+$.

$^1$H NMR (400 MHz, DMSO-d6) δ 8.35 (s, 2H), 8.16 (s, 1H), 7.95 (d, J=4.8 Hz, 1H), 7.51 (dd, J=8.8, 4.1 Hz, 1H), 7.38 (dd, J=8.8, 2.7 Hz, 1H), 7.10 (td, J=9.2, 2.7 Hz, 1H), 6.87 (d, J=8.8 Hz, 1H), 4.73 (t, J=8.6 Hz, 1H), 4.05 (t, J=8.4 Hz, 2H), 3.96 (dd, J=8.2, 6.1 Hz, 2H), 3.44-3.35 (m, 1H), 2.60 (d, J=4.6 Hz, 3H), 2.19 (s, 3H), 2.12 (dt, J=14.8, 6.8 Hz, 1H), 1.01 (d, J=6.8 Hz, 3H), 0.81 (d, J=6.8 Hz, 3H).

Example 116: Preparation of Compound 164

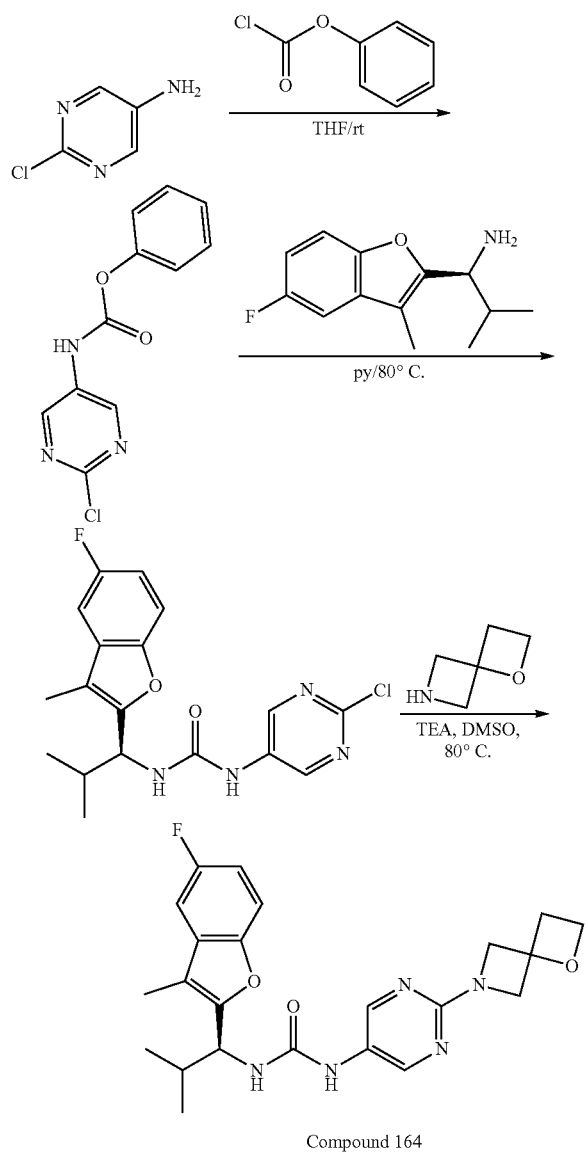

Compound 164

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 [M+H]$^+$.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous Na2SO4. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl] urea (7 g, 82.21%) as a yellow oil. MS (ESI): mass calcd. for $C_{18}H_{18}ClFN_4O_2$, 376.1, m/z found 377.3 [M+H]$^+$.

Step 3

To a stirred solution of 1-(2-chloropyrimidin-5-yl)-3-[(1S)-1-(5-fluoro-3-methyl-1-benzofuran-2-yl)-2-methyl-propyl]urea (100 mg, 0.265 mmol, 1 equiv) and 1-oxa-6-azaspiro[3.3]heptane (52.62 mg, 0.530 mmol, 2 equiv) in DMSO (5 mL) was added TEA (80.56 mg, 0.795 mmol, 3 equiv) dropwise at room temperature under nitrogen atmosphere. The resulting mixture was stirred for overnight at 80° C. under nitrogen atmosphere. The mixture was allowed to cool down to room temperature. The resulting mixture was extracted with EtOAc (2×50 mL). The combined organic layers were washed with brine (2×1 100 mL), dried over anhydrous Na$_2$SO$_4$. After filtration, the filtrate was concentrated under reduced pressure. The crude product (80 mg) was purified by Prep-HPLC with the following conditions (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 29% B to 59% B in 8 min, 59% B; Wave Length: 220 nm; RT1 (min): 7.63; Number Of Runs: 0) to afford 3-[(1S)-1-(5-fluoro-3-methyl-1-benzofuran-2-yl)-2-methylpropyl]-1-(2-{1-oxa-6-azaspiro[3.3]heptan-6-yl}pyrimidin-5-yl)urea (26.7 mg, 22.89%) as a white solid.

MS (ESI): mass calcd. for $C_{23}H_{26}FN_5O_3$, 439.2, m/z found 440.2 [M+H]$^+$.

$^1$H NMR (400 MHz, DMSO-d6) δ 8.35 (s, 2H), 8.17 (s, 1H), 7.51 (dd, J=8.9, 4.1 Hz, 1H), 7.37 (dd, J=8.8, 2.7 Hz, 1H), 7.10 (td, J=9.2, 2.7 Hz, 1H), 6.88 (d, J=8.8 Hz, 1H), 4.73 (t, J=8.6 Hz, 1H), 4.43 (t, J=7.5 Hz, 2H), 4.20 (dd, J=10.1, 1.5 Hz, 2H), 4.03 (dd, J=10.0, 1.5 Hz, 2H), 2.85 (t, J=7.5 Hz, 2H), 2.19 (s, 3H), 2.16-2.05 (m, 1H), 1.01 (d, J=6.7 Hz, 3H), 0.81 (d, J=6.7 Hz, 3H).

Example 117: Preparation of Compound 165

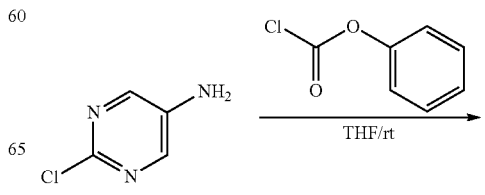

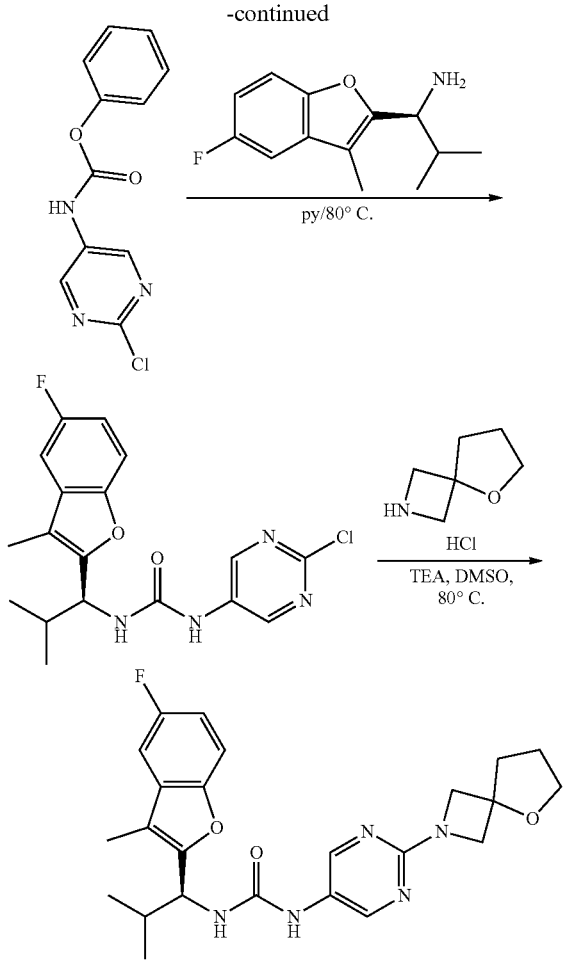

urea (7 g, 82.21%) as a yellow oil. MS (ESI): mass calcd. for C₁₈H₁₈ClFN₄O₂, 376.1, m/z found 377.3 [M+H]⁺.

Step 3

To a stirred solution of 1-(2-chloropyrimidin-5-yl)-3-[(1S)-1-(5-fluoro-3-methyl-1-benzofuran-2-yl)-2-methylpropyl] urea (100 mg, 0.265 mmol, 1 equiv) and 5-oxa-2-azaspiro[3.4]octane (60.06 mg, 0.530 mmol, 2 equiv) in DMSO (5 mL) was added TEA (80.56 mg, 0.795 mmol, 3 equiv) dropwise at room temperature under air atmosphere. The mixture was allowed to cool down to room temperature. The resulting mixture was extracted with EtOAc (2×20 mL). The combined organic layers were washed with brine (4×1 40 mL), dried over anhydrous Na₂SO₄. After filtration, the filtrate was concentrated under reduced pressure. The crude product was purified by Prep-HPLC with the following conditions (Column: XBridge Shield RP18 OBD Column, 30*150 mm, 5 µm; Mobile Phase A: Water (10 mmol/L NH4HCO3+0.1% NH3·H2O), Mobile Phase B: ACN; Flow rate: 60 mL/min; Gradient: 37% B to 62% B in 8 min, 62% B; Wave Length: 220 nm; RT1 (min): 7.48; Number Of Runs: 0) to afford 3-[(1S)-1-(5-fluoro-3-methyl-1-benzofuran-2-yl)-2-methylpropyl]-1-(2-{5-oxa-2-azaspiro[3.4]octan-2-yl}pyrimidin-5-yl)urea (37.2 mg, 30.66%) as a white solid. MS (ESI): mass calcd. for C₂₄H₂₈FN₅O₃, 453.2, m/z found 454.4 [M+H]⁺.

¹H NMR (400 MHz, DMSO-d6) δ 8.35 (s, 2H), 8.16 (s, 1H), 7.51 (dd, J=8.9, 4.1 Hz, 1H), 7.38 (dd, J=8.8, 2.6 Hz, 1H), 7.10 (td, J=9.2, 2.7 Hz, 1H), 6.87 (d, J=8.8 Hz, 1H), 4.73 (t, J=8.6 Hz, 1H), 4.02-3.94 (m, 2H), 3.94-3.86 (m, 2H), 3.76 (t, J=6.8 Hz, 2H), 2.19 (s, 3H), 2.15-2.02 (m, 3H), 1.92-1.81 (m, 2H), 1.01 (d, J=6.7 Hz, 3H), 0.81 (d, J=6.6 Hz, 3H).

Example 118: Preparation of Compound 166

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for C₁₁H₈ClN₃O₂, 249.0, m/z found 250.2 [M+H]⁺.

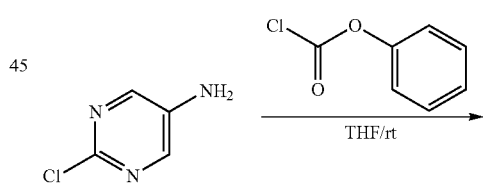

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous Na₂SO₄. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl]

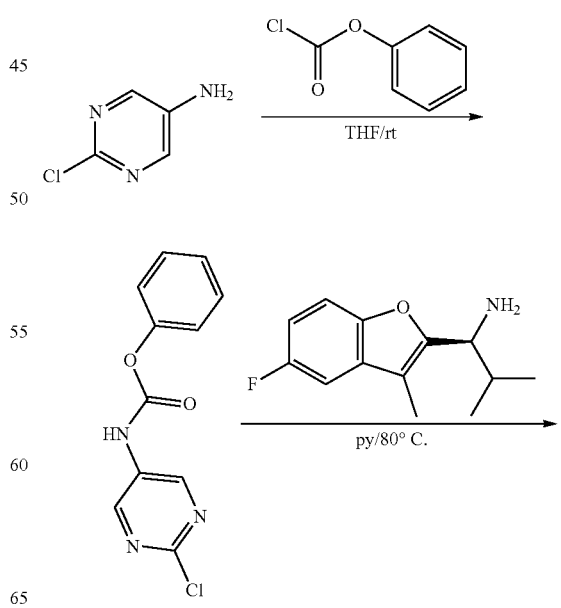

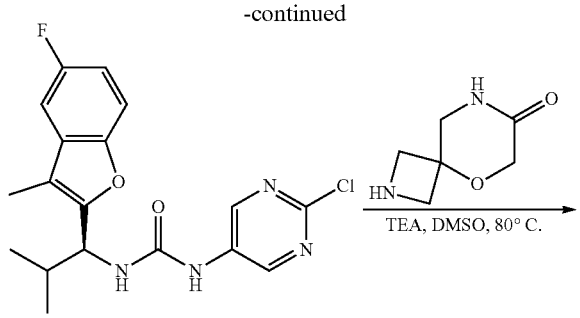

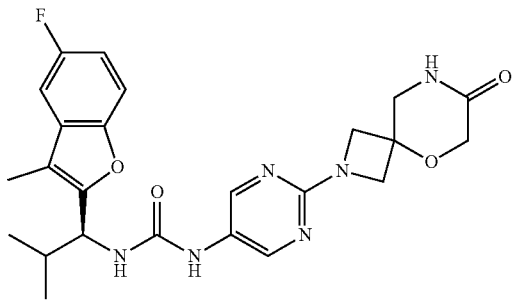

Compound 166

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 [M+H]⁺.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl]urea (7 g, 82.21%) as a yellow oil. MS (ESI): mass calcd. for $C_{18}H_{18}ClFN_4O_2$, 376.1, m/z found 377.3 [M+H]⁺.

Step 3

To a stirred solution of 1-(2-chloropyrimidin-5-yl)-3-[(1S)-1-(5-fluoro-3-methyl-1-benzofuran-2-yl)-2-methylpropyl]urea (100 mg, 0.265 mmol, 1 equiv) and 5-oxa-2,8-diazaspiro[3.5]nonan-7-one (75.45 mg, 0.530 mmol, 2 equiv) in DMSO (10 mL) was added TEA (80.56 mg, 0.795 mmol, 3 equiv) dropwise at room temperature under nitrogen atmosphere. The resulting mixture was stirred for 4 h at 80° C. under nitrogen atmosphere. The crude product (100 mg) was purified by Prep-HPLC with the following conditions (Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 25% B to 53% B in 8 min, 53% B; Wave Length: 220 nm; RT1 (min): 7.97; Number Of Runs: 0) to afford 3-[(1S)-1-(5-fluoro-3-methyl-1-benzofuran-2-yl)-2-methylpropyl]-1-(2-{7-oxo-5-oxa-2,8-diazaspiro[3.5]nonan-2-yl}pyrimidin-5-yl)urea (48.2 mg, 37.64%) as a white solid. MS (ESI): mass calcd. for $C_{24}H_{27}FN_6O_4$, 482.2, m/z found 483.1 [M+H]⁺.

¹H NMR (400 MHz, DMSO-d6) δ 8.38 (s, 2H), 8.20 (s, 1H), 8.09 (t, J=2.4 Hz, 1H), 7.51 (dd, J=8.9, 4.1 Hz, 1H), 7.38 (dd, J=8.8, 2.7 Hz, 1H), 7.14-7.04 (m, 1H), 6.89 (d, J=8.7 Hz, 1H), 4.73 (t, J=8.6 Hz, 1H), 4.13 (s, 2H), 4.03-3.91 (m, 4H), 3.48 (d, J=2.4 Hz, 2H), 2.19 (s, 3H), 2.13-2.04 (m, 1H), 1.01 (d, J=6.7 Hz, 3H), 0.81 (d, J=6.7 Hz, 3H).

Example 119: Preparation of Compound 167

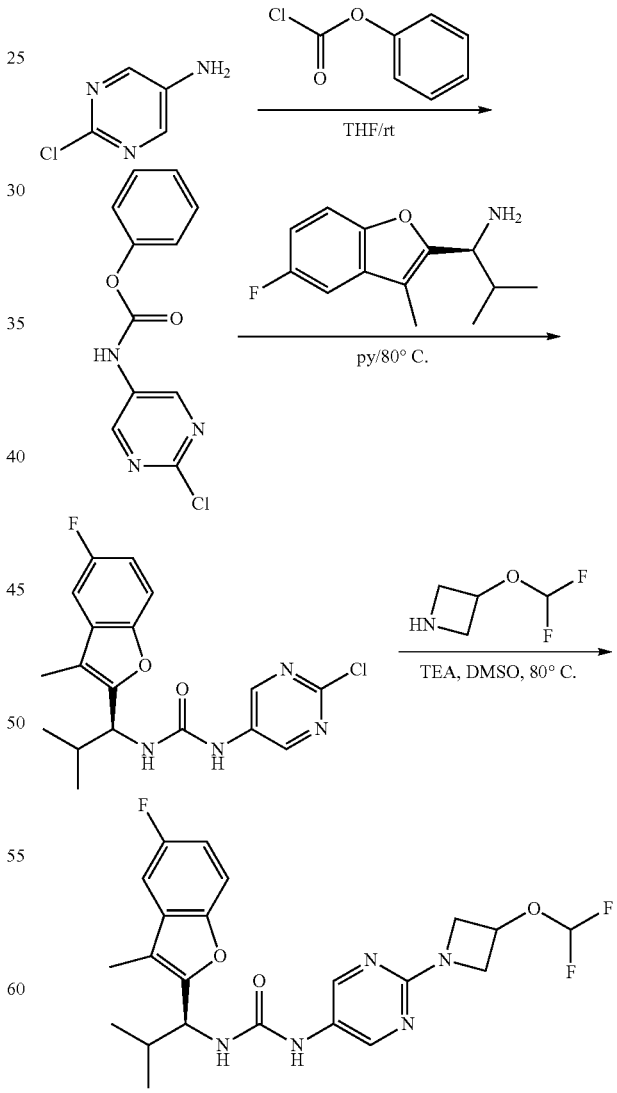

Compound 167

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 $[M+H]^+$.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl] urea (7 g, 82.21%) as a yellow oil. MS (ESI): mass calcd. for $C_{18}H_{18}ClFN_4O_2$, 376.1, m/z found 377.3 $[M+H]^+$.

Step 3

To a stirred solution of 1-(2-chloropyrimidin-5-yl)-3-[(1S)-1-(5-fluoro-3-methyl-1-benzofuran-2-yl)-2-methyl-propyl]urea (100 mg, 0.265 mmol, 1 equiv) and 3-(difluoromethoxy)azetidine (65.34 mg, 0.531 mmol, 2.00 equiv) in DMSO (1 mL) was added TEA (80.56 mg, 0.795 mmol, 3 equiv) dropwise at room temperature under nitrogen atmosphere. The resulting mixture was stirred for overnight at 80° C. under nitrogen atmosphere. The mixture was allowed to cool down to room temperature. The resulting mixture was extracted with EtOAc (2×50 mL). The combined organic layers were washed with brine (2×2 100 mL), dried over anhydrous $Na_2SO_4$. After filtration, the filtrate was concentrated under reduced pressure. The crude product (100 mg) was purified by Prep-HPLC with the following conditions (Column: XBridge Prep OBD C18 Column, 30*150 mm, 5 µm; Mobile Phase A: Water (10 mmol/L $NH_4HCO_3$), Mobile Phase B: ACN; Flow rate: 60 mL/min; Gradient: 37% B to 67% B in 8 min, 67% B; Wave Length: 220 nm; RT1 (min): 7.72; Number Of Runs: 0) to afford 1-{2-[3-(difluoromethoxy) azetidin-1-yl]pyrimidin-5-yl}-3-[(1S)-1-(5-fluoro-3-methyl-1-benzofuran-2-yl)-2-methyl-propyl]urea (24.5 mg, 19.92%) as a white solid.

MS (ESI): mass calcd. for $C_{22}H_{24}F_3N_5O_3$, 463.2, m/z found 464.1 $[M+H]^+$.

$^1$H NMR (400 MHz, DMSO-d6) δ 8.38 (s, 2H), 8.21 (s, 1H), 7.51 (dd, J=8.9, 4.1 Hz, 1H), 7.38 (dd, J=8.8, 2.7 Hz, 1H), 7.10 (td, J=9.2, 2.7 Hz, 1H), 6.99-6.56 (m, 2H), 5.04 (tt, J=6.5, 4.1 Hz, 1H), 4.73 (t, J=8.6 Hz, 1H), 4.30 (ddd, J=9.7, 6.6, 1.2 Hz, 2H), 3.92 (ddd, J=9.7, 4.0, 1.2 Hz, 2H), 2.19 (s, 3H), 2.16-2.05 (m, 1H), 1.01 (d, J=6.7 Hz, 3H), 0.81 (d, J=6.7 Hz, 3H).

Example 120: Preparation of Compound 168

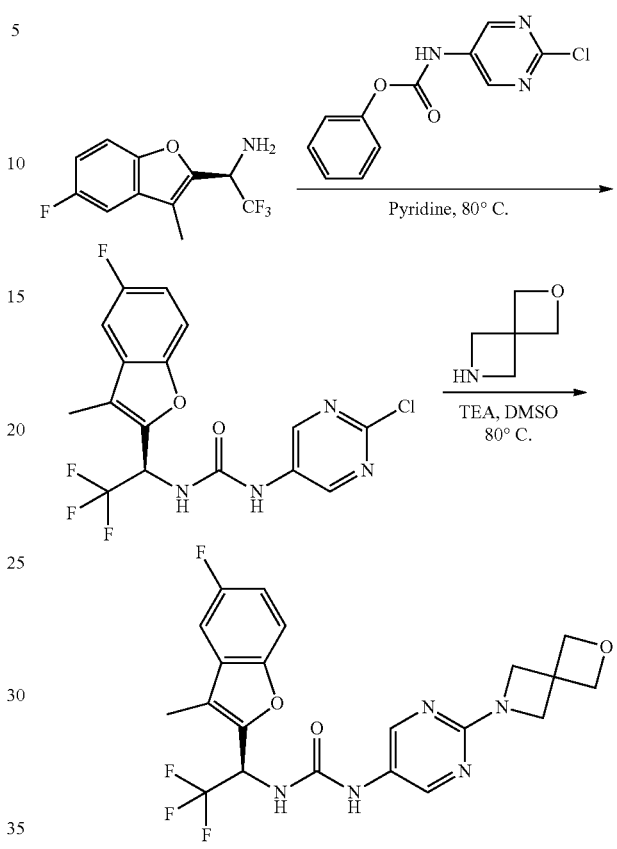

Compound 168

Step 1

A solution of phenyl N-(2-chloropyrimidin-5-yl)carbamate (1.51 g, 6.07 mmol) and (R)-2,2,2-trifluoro-1-(5-fluoro-3-methylbenzofuran-2-yl)ethan-1-amine (1 g, 4.05 mmol) in Pyridine (20 mL) was stirred overnight at 80° C. The resulting solution was concentrated under reduced pressure. The residue was purified by reverse flash chromatography to afford (R)-1-(2-chloropyrimidin-5-yl)-3-(2,2,2-trifluoro-1-(5-fluoro-3-methylbenzofuran-2-yl)ethyl)urea (1.4 g, 85.9%) as a yellow solid. MS (ESI): mass calcd. for $C_{16}H_{11}ClF_4N_4O_2$, 402.1, m/z found 402.95 $[M+H]^+$.

Step 2

A solution of (R)-1-(2-chloropyrimidin-5-yl)-3-(2,2,2-trifluoro-1-(5-fluoro-3-methylbenzofuran-2-yl)ethyl)urea (200 mg, 0.50 mmol) and 2-oxa-6-azaspiro[3.3]heptane (123 mg, 1.24 mmol) in DMSO (2 mL)/TEA (1 mL) was stirred overnight at 80° C. The reaction was concentrated under reduced pressure. The residue was purified by Prep-HPLC to afford (R)-1-(2-(2-oxa-6-azaspiro[3.3]heptan-6-yl)pyrimidin-5-yl)-3-(2,2,2-trifluoro-1-(5-fluoro-3-methylbenzofuran-2-yl) ethyl)urea (136.6 mg, 58.9%) as a off-white solid. MS (ESI): mass calcd. for $C_{21}H_{19}F_4N_5O_3$, 465.1, m/z found 466.15 $[M+H]^+$.

$^1$H NMR (400 MHz, DMSO-d$_6$) δ 8.43-8.32 (s, 3H), 7.80-7.71 (d, J=9.4 Hz, 1H), 7.68-7.59 (dd, J=9.0, 4.0 Hz,

1H), 7.56-7.44 (dd, J=8.7, 2.7 Hz, 1H), 7.30-7.18 (td, J=9.2, 2.7 Hz, 1H), 6.06-5.90 (m, 1H), 4.78-4.63 (s, 4H), 4.20-4.07 (s, 4H), 2.35-2.20 (s, 3H).

Example 121: Preparation of Compound 169

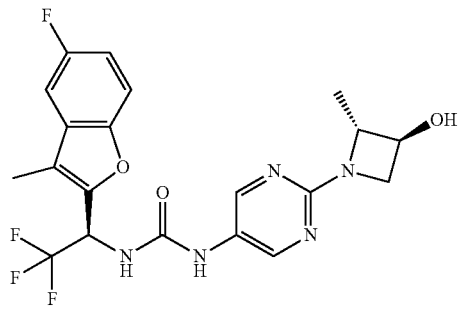

Compound 169

Prepared using the same procedure as Compound 168 using the appropriate amine. MS (ESI): mass calcd. for $C_{20}H_{19}F_4N_5O_3$, 453.1, m/z found 454.10 [M+H]$^+$.

$^1$H NMR (400 MHz, DMSO-d$_6$) δ 8.42-8.32 (s, 3H), 7.81-7.71 (d, J=9.4 Hz, 1H), 7.68-7.60 (dd, J=9.0, 4.0 Hz, 1H), 7.55-7.48 (dd, J=8.6, 2.7 Hz, 1H), 7.30-7.20 (td, J=9.2, 2.7 Hz, 1H), 6.06-5.93 (m, 1H), 5.62-5.53 (d, J=6.6 Hz, 1H), 4.15-4.01 (m, 2H), 4.00-3.91 (m, 1H), 3.59-3.49 (dd, J=8.3, 5.0 Hz, 1H), 2.33-2.23 (s, 3H), 1.46-1.33 (d, J=6.3 Hz, 3H).

Example 122: Preparation of Compound 170

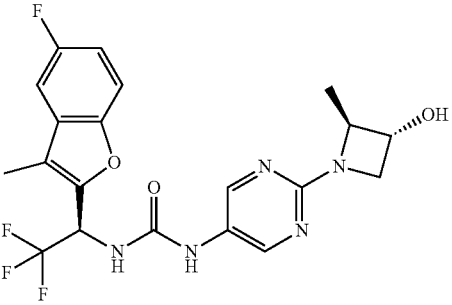

Compound 170

Prepared using the same procedure as Compound 168 using the appropriate amine. MS (ESI): mass calcd. for $C_{20}H_{19}F_4N_5O_3$, 453.1, m/z found 454.15 [M+H]$^+$.

$^1$H NMR (400 MHz, DMSO-d$_6$) δ 8.50-8.27 (d, J=3.6 Hz, 3H), 7.81-7.70 (d, J=9.4 Hz, 1H), 7.68-7.59 (dd, J=9.3, 3.8 Hz, 1H), 7.57-7.44 (dd, J=8.7, 2.5 Hz, 1H), 7.31-7.15 (td, J=9.2, 2.5 Hz, 1H), 6.08-5.91 (t, J=8.5 Hz, 1H), 5.62-5.52 (d, J=6.4 Hz, 1H), 4.18-4.01 (dt, J=21.3, 6.6 Hz, 2H), 4.02-3.89 (t, J=5.9 Hz, 1H), 3.59-3.47 (dd, J=8.3, 5.1 Hz, 1H), 2.37-2.16 (d, J=2.2 Hz, 3H), 1.49-1.27 (d, J=6.2 Hz, 3H).

Example 123: Preparation of Compound 171 and 172

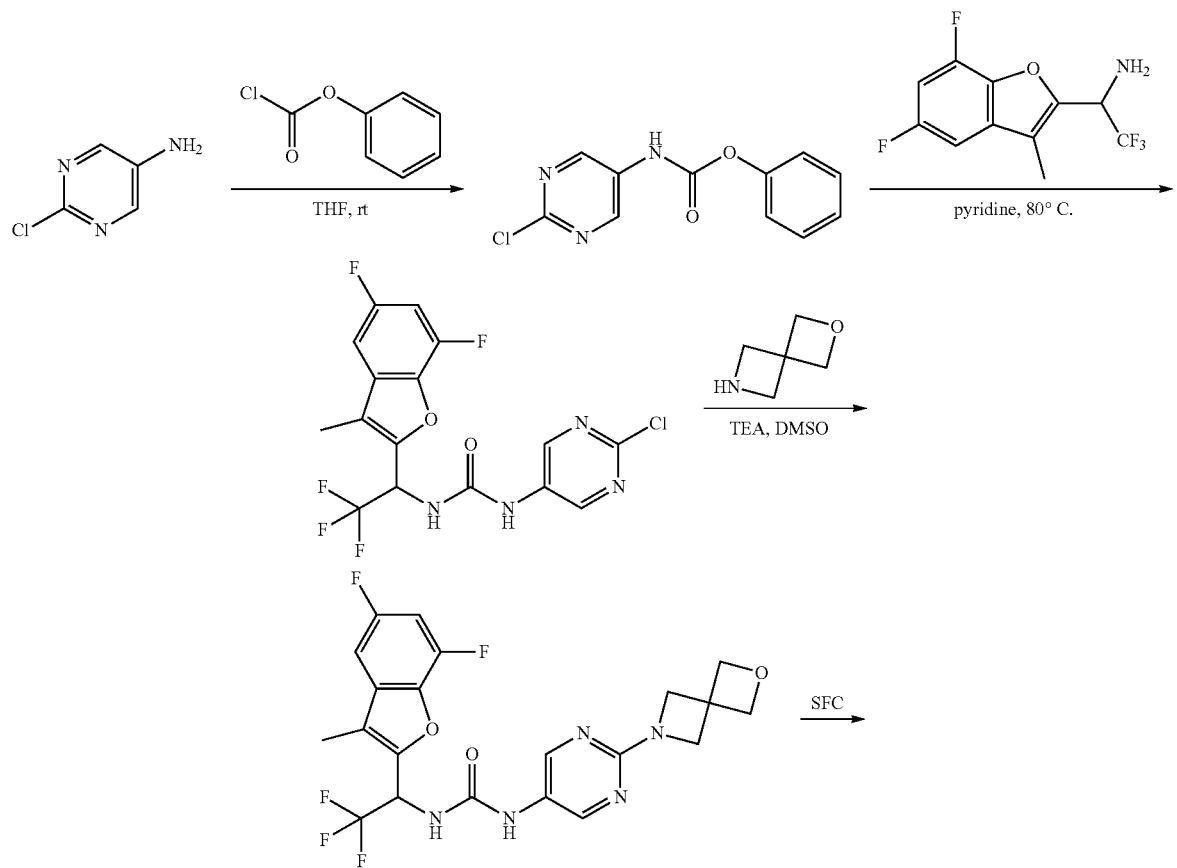

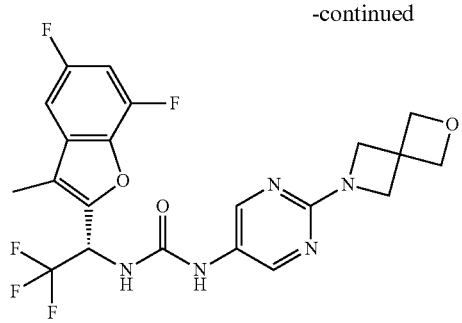

Compound 171

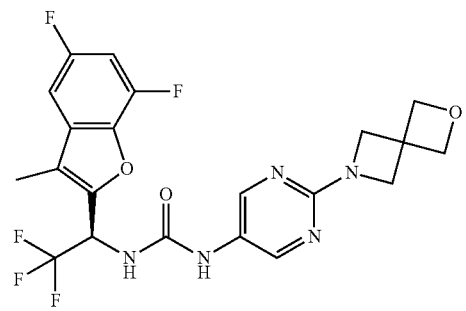

Compound 172

Step 1

A solution of 2-chloropyrimidin-5-amine (2 g, 0.02 mol) in THF (20 mL) was added phenyl carbonochloridate (2.4 g, 0.02 mol) at room temperature. The mixture was stirred at room temperature for 1 hour. The resulting solution was extracted with 3×400 mL of DCM. The organic layers were combined, dried and concentrated under vacuum to afford phenyl (2-chloropyrimidin-5-yl)carbamate (2.7 g, crude) as yellow solid. MS (ESI): mass calcd. for $C_{11}H_8ClN_3O_2$, 249.03, m/z found 250.0 [M+H]$^+$.

Step 2

A solution of 1-(5,7-difluoro-3-methylbenzofuran-2-yl)-2,2,2-trifluoroethan-1-amine (2 g, 0.01 mol) in pyridine (20 mL) was added phenyl (2-chloropyrimidin-5-yl)carbamate (2.3 g, 0.01 mol) at room temperature. The mixture was stirred at 80° C. for overnight. The reaction mixture concentrated under vacuum. The crude product was soluble in the ACN and purified using flash chromatography with the following conditions (Mobile Phase A: Water, Mobile Phase B: ACN; Flow rate: 55 mL/min; Gradient: 0% B to 100% B in 30 min; 254; 220 nm). This resulted in 1-(2-chloropyrimidin-5-yl)-3-(1-(5,7-difluoro-3-methylbenzofuran-2-yl)-2,2,2-trifluoroethyl)urea (2.3 g, 72.6%) as a yellow solid. MS (ESI): mass calcd. for $C_{16}H_{10}ClF_5N_4O_2$, 420.04, m/z found 421.0 [M+H]$^+$.

Step 3

A solution of (1-(5,7-difluoro-3-methylbenzofuran-2-yl)-2,2,2-trifluoroethyl)urea (400 mg, 0.95 mmol) in DMSO (3 mL) was added TEA (1.5 mL) and 2-oxa-6-azaspiro[3.3]heptane (142 mg, 1.43 mmol) at room temperature. The mixture was stirred at room temperature for overnight. The reaction mixture was purified using flash chromatography with the following conditions (Mobile Phase A: Water, Mobile Phase B: ACN; Flow rate: 50 mL/min; Gradient: 0% B to 100% B in 40 min; 254; 220 nm). This resulted in 1-(2-(2-oxa-6-azaspiro[3.3]heptan-6-yl)pyrimidin-5-yl)-3-(1-(5,7-difluoro-3-methylbenzofuran-2-yl)-2,2,2-trifluoroethyl)urea (360 mg, 78.3%) as a yellow solid. MS (ESI): mass calcd. for $C_{21}H_{18}F_5N_5O_3$, 483.13, m/z found 484.2 [M+H]$^+$.

Step 4

360 mg of racemic was separated by SFC to give (Compound 171, 129.7 mg) as white solid and (Compound 172, 107.9 mg) as white solid.

Chiral separation conditions: Column: CHIRALPAK IG, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 30% B to 30% B in 13 min; Wave Length: 220/254 nm; RT1 (min): 7.9; RT2 (min): 9.8; Sample Solvent: EtOH-HPLC; Injection Volume: 0.2 mL; Number Of Runs: 21

Compound 171

MS (ESI): mass calcd. for $C_{21}H_{18}F_5N_5O_3$, 483.13, m/z found 484.2 [M+H]$^+$. $^1$H NMR (400 MHz, DMSO) δ 8.38 (s, 3H), 7.85 (d, J=9.4 Hz, 1H), 7.51-7.35 (m, 2H), 6.06 (p, J=8.3, 8.3, 8.5, 8.5 Hz, 1H), 4.71 (s, 4H), 4.15 (s, 4H), 2.30 (s, 3H)

Compound 172

MS (ESI): mass calcd. for $C_{21}H_{18}F_5N_5O_3$, 483.13, m/z found 484.2 [M+H]$^+$.

1H NMR (400 MHz, DMSO) δ 1H NMR (400 MHz, DMSO) δ 8.38 (d, J=1.8 Hz, 3H), 7.85 (d, J=9.4 Hz, 1H), 7.53-7.32 (m, 2H), 6.21-5.88 (m, 1H), 4.71 (s, 4H), 4.15 (s, 4H), 2.30 (s, 3H).

Example 124: Preparation of Compound 173 and 174

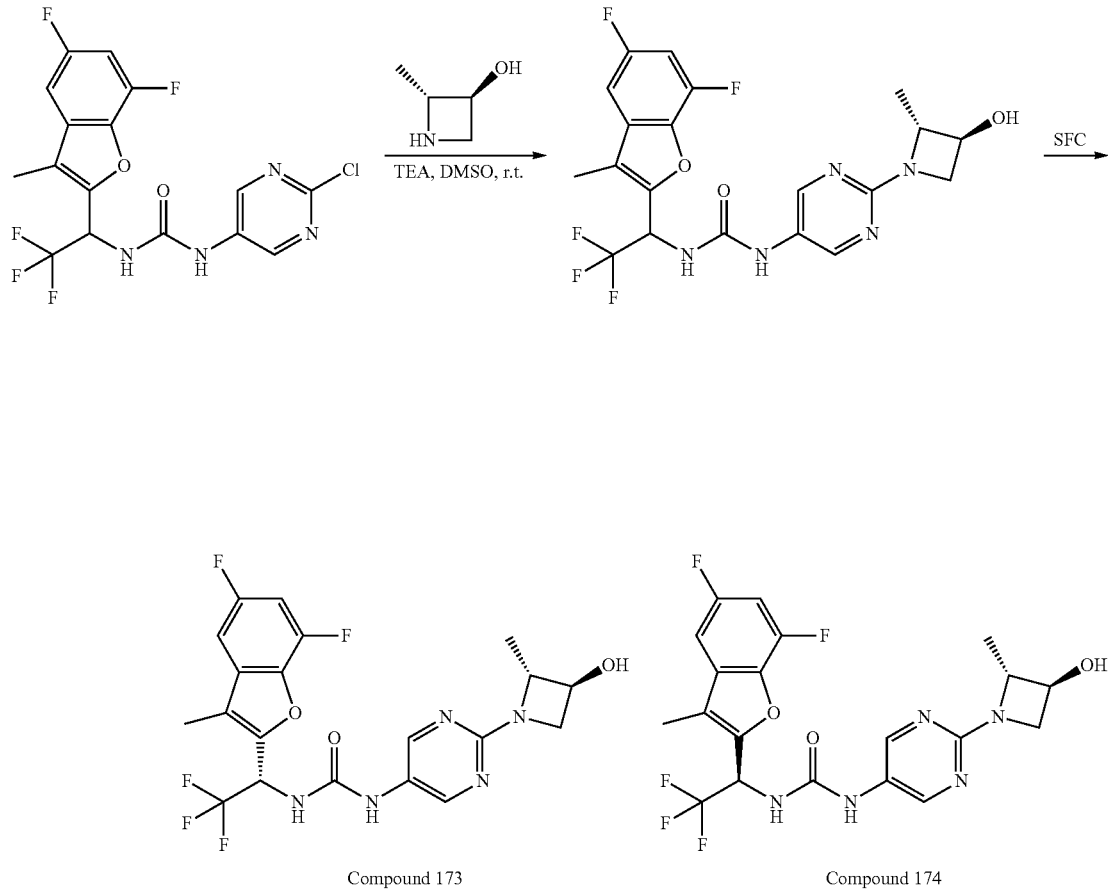

Compound 173

Compound 174

Step 1

A solution of 1-(2-chloropyrimidin-5-yl)-3-[1-(5,7-difluoro-3-methyl-1-benzofuran-2-yl)-2,2,2-trifluoroethyl]urea (400 mg, 0.951 mmol) in DMSO (3 mL) was added TEA (1.5 mL) and (2R,3S)-2-methylazetidin-3-ol (99.40 mg, 1.141 mmol) at room temperature. The mixture was stirred at room temperature for 48 hours. The reaction mixture was purified using flash chromatography with the following conditions (Mobile Phase A: Water, Mobile Phase B: ACN; Flow rate: 50 mL/min; Gradient: 0% B to 100% B in 40 min; 254; 220 nm). This resulted in 3-[1-(5,7-difluoro-1-benzofuran-2-yl)-2,2,2-trifluoroethyl]-1-{2-[(2R,3S)-3-hydroxy-2-methylazetidin-1-yl]pyrimidin-5-yl}urea (350 mg, 78.1%) as a yellow solid. MS (ESI): mass calcd. for $C_{20}H_{18}F_5N_5O_3$, 471.13, m/z found 472.2 [M+H]$^+$.

Step 2

350 mg of racemic was separated by SFC to give (Compound 173, 103.3 mg) as white solid and (Compound 174, 111.1 mg) as white solid.
Chiral Separation Conditions:
Column: CHIRALPAK IC, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 10% B to 10% B in 13 min; Wave Length: 220/254 nm; RT1 (min): 7.62; RT2 (min): 10.79; Sample Solvent: EtOH-HPLC; Injection Volume: 0.5 mL.

Compound 173

MS (ESI): mass calcd. for $C_{20}H_{18}F_5N_5O_3$, 471.13, m/z found 472.2 [M+H]$^+$.

$^1$H NMR (400 MHz, DMSO-d$_6$) δ 8.37 (d, J=2.1 Hz, 3H), 7.84 (d, J=9.5 Hz, 1H), 7.48-7.37 (m, 2H), 6.07 (q, J=8.4 Hz, 1H), 5.58 (d, J=6.6 Hz, 1H), 4.14-3.91 (m, 2H), 3.54 (dd, J=8.3, 5.0 Hz, 1H), 2.30 (s, 3H), 1.40 (d, J=6.3 Hz, 3H).

Compound 174

MS (ESI): mass calcd. for $C_{20}H_{18}F_5N_5O_3$, 471.13, m/z found 472.2 [M+H]$^+$.

$^1$H NMR (400 MHz, DMSO-d6) δ 8.37 (d, J=2.4 Hz, 3H), 7.84 (d, J=9.4 Hz, 1H), 7.48-7.38 (m, 2H), 6.06 (t, J=8.6 Hz, 1H), 5.58 (d, J=6.6 Hz, 1H), 4.14-3.99 (m, 2H), 3.99-3.91 (m, 1H), 3.54 (dd, J=8.3, 4.9 Hz, 1H), 2.30 (s, 3H), 1.40 (d, J=6.3 Hz, 3H).

Example 125: Preparation of Compound 175 and 176

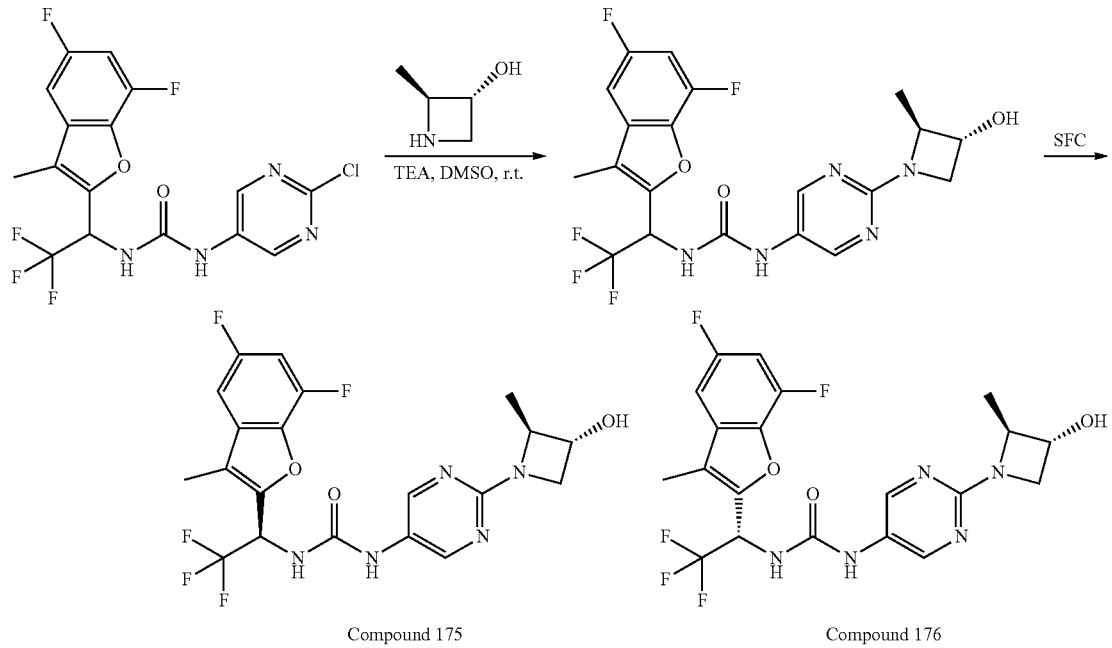

Compound 175

Compound 176

Step 1

A solution of (1-(5,7-difluoro-3-methylbenzofuran-2-yl)-2,2,2-trifluoroethyl)urea (400 mg, 0.95 mmol) in DMSO (3 mL) was added TEA (1.5 mL) and (2S,3R)-2-Methylazetidin-3-ol hydrochloride (177 mg, 1.43 mmol) at room temperature. the mixture was stirred at room temperature for 48 hours. The reaction mixture was purified using flash chromatography with the following conditions (Mobile Phase A: Water, Mobile Phase B: ACN; Flow rate: 50 mL/min; Gradient: 0% B to 100% B in 40 min; 254; 220 nm). This resulted in 1-(1-(5,7-difluoro-3-methylbenzofuran-2-yl)-2,2,2-trifluoroethyl)-3-(2-((2S,3R)-3-hydroxy-2-methylazetidin-1-yl)pyrimidin-5-yl)urea (310 mg, 69.1%) as a yellow solid. MS (ESI): mass calcd. for $C_{20}H_{18}F_5N_5O_3$, 471.13, m/z found 472.0 [M+H]$^+$.

Step 2

310 mg of racemic was separated by SFC to give (Compound 175, 106.3 mg) as white solid and (Compound 176, 103.9 mg) as white solid.

Chiral Separation Conditions:
Column: CHIRALPAK IC, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 10% B to 10% B in 15 min; Wave Length: 220/254 nm; RT1 (min): 10.39; RT2 (min): 12.49; Sample Solvent: EtOH-HPLC; Injection Volume: 0.2 mL; Number Of Runs: 13.

Compound 175

MS (ESI): mass calcd. for $C_{20}H_{18}F_5N_5O_3$, 471.13, m/z found 472.0 [M+H]$^+$.
$^1$H NMR (400 MHz, DMSO) δ 8.37 (d, J=2.3 Hz, 3H), 7.84 (d, J=9.4 Hz, 1H), 7.60-7.34 (m, 2H), 6.06 (p, J=8.3, 8.3, 8.4, 8.4 Hz, 1H), 5.58 (d, J=6.5 Hz, 1H), 4.20-4.02 (m, 2H), 3.98-3.90 (m, 1H), 3.54 (dd, J=5.0, 8.4 Hz, 1H), 2.30 (s, 3H), 1.40 (d, J=6.3 Hz, 3H).

Compound 176

MS (ESI): mass calcd. for $C_{20}H_{18}F_5N_5O_3$, 471.13, m/z found 472.0 [M+H]$^+$.
$^1$H NMR (400 MHz, DMSO) δ 8.37 (s, 3H), 7.84 (d, J=9.4 Hz, 1H), 7.52-7.27 (m, 2H), 6.06 (p, J=8.3, 8.3, 8.5, 8.5 Hz, 1H), 5.58 (d, J=6.5 Hz, 1H), 4.23-4.04 (m, 2H), 3.98-3.89 (m, 1H), 3.54 (dd, J=5.0, 8.3 Hz, 1H), 2.30 (s, 3H), 1.40 (d, J=6.3 Hz, 3H).

Example 126: Preparation of Compound 177 and 178

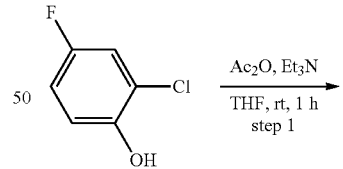

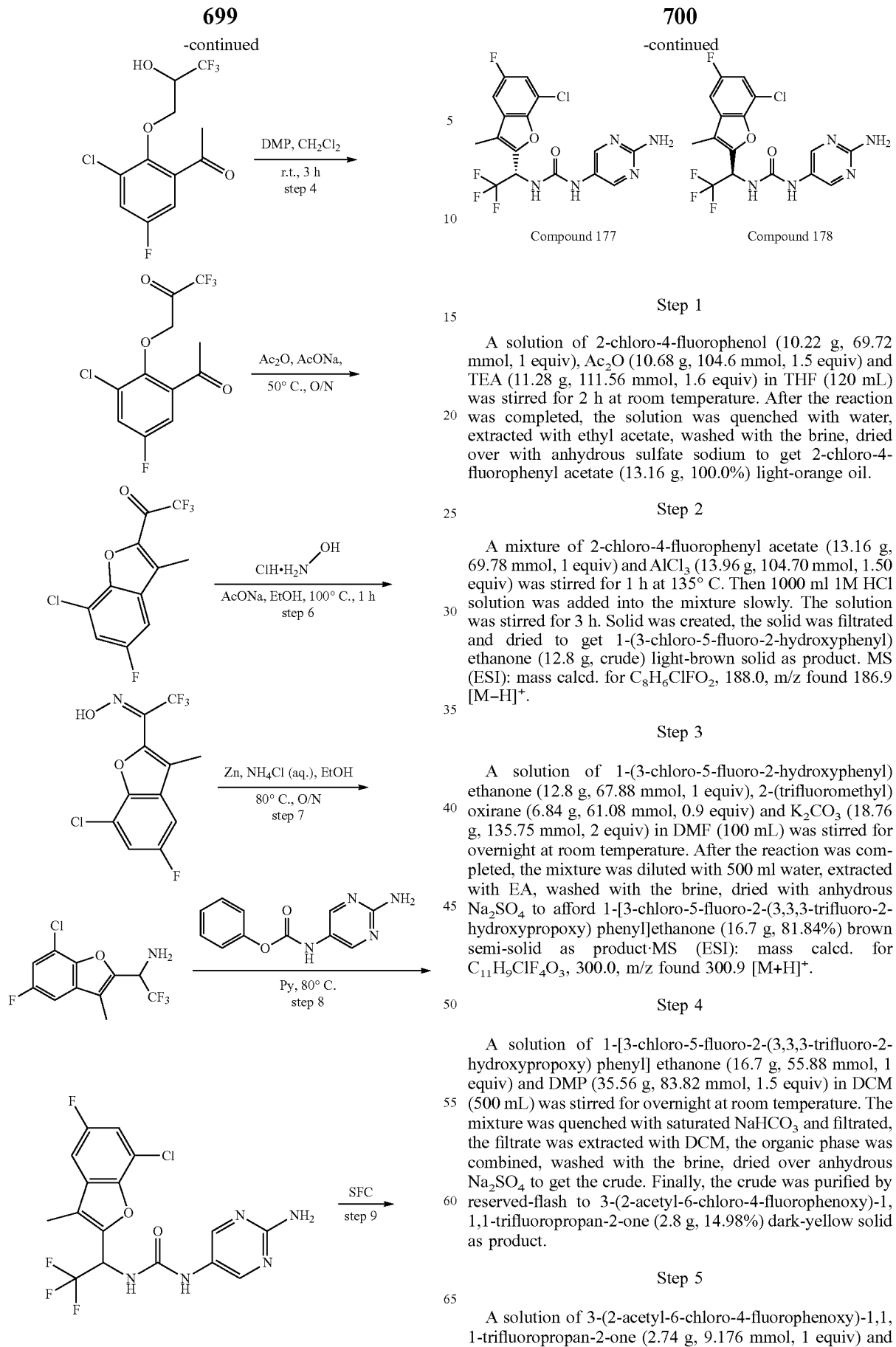

Compound 177      Compound 178

Step 1

A solution of 2-chloro-4-fluorophenol (10.22 g, 69.72 mmol, 1 equiv), Ac$_2$O (10.68 g, 104.6 mmol, 1.5 equiv) and TEA (11.28 g, 111.56 mmol, 1.6 equiv) in THF (120 mL) was stirred for 2 h at room temperature. After the reaction was completed, the solution was quenched with water, extracted with ethyl acetate, washed with the brine, dried over with anhydrous sulfate sodium to get 2-chloro-4-fluorophenyl acetate (13.16 g, 100.0%) light-orange oil.

Step 2

A mixture of 2-chloro-4-fluorophenyl acetate (13.16 g, 69.78 mmol, 1 equiv) and AlCl$_3$ (13.96 g, 104.70 mmol, 1.50 equiv) was stirred for 1 h at 135° C. Then 1000 ml 1M HCl solution was added into the mixture slowly. The solution was stirred for 3 h. Solid was created, the solid was filtrated and dried to get 1-(3-chloro-5-fluoro-2-hydroxyphenyl) ethanone (12.8 g, crude) light-brown solid as product. MS (ESI): mass calcd. for C$_8$H$_6$ClFO$_2$, 188.0, m/z found 186.9 [M−H]$^+$.

Step 3

A solution of 1-(3-chloro-5-fluoro-2-hydroxyphenyl) ethanone (12.8 g, 67.88 mmol, 1 equiv), 2-(trifluoromethyl) oxirane (6.84 g, 61.08 mmol, 0.9 equiv) and K$_2$CO$_3$ (18.76 g, 135.75 mmol, 2 equiv) in DMF (100 mL) was stirred for overnight at room temperature. After the reaction was completed, the mixture was diluted with 500 ml water, extracted with EA, washed with the brine, dried with anhydrous Na$_2$SO$_4$ to afford 1-[3-chloro-5-fluoro-2-(3,3,3-trifluoro-2-hydroxypropoxy) phenyl]ethanone (16.7 g, 81.84%) brown semi-solid as product·MS (ESI): mass calcd. for C$_{11}$H$_9$ClF$_4$O$_3$, 300.0, m/z found 300.9 [M+H]$^+$.

Step 4

A solution of 1-[3-chloro-5-fluoro-2-(3,3,3-trifluoro-2-hydroxypropoxy) phenyl] ethanone (16.7 g, 55.88 mmol, 1 equiv) and DMP (35.56 g, 83.82 mmol, 1.5 equiv) in DCM (500 mL) was stirred for overnight at room temperature. The mixture was quenched with saturated NaHCO$_3$ and filtrated, the filtrate was extracted with DCM, the organic phase was combined, washed with the brine, dried over anhydrous Na$_2$SO$_4$ to get the crude. Finally, the crude was purified by reserved-flash to 3-(2-acetyl-6-chloro-4-fluorophenoxy)-1,1,1-trifluoropropan-2-one (2.8 g, 14.98%) dark-yellow solid as product.

Step 5

A solution of 3-(2-acetyl-6-chloro-4-fluorophenoxy)-1,1,1-trifluoropropan-2-one (2.74 g, 9.176 mmol, 1 equiv) and NaOAc (1.12 g, 14.57 mmol, 1.5 equiv) in Ac$_2$O (26 mL) was stirred for 30 min at 110° C. After the reaction was completed, the mixture was quenched with saturated NaHCO$_3$ until no bubble appeared, extracted with EA. The organic phase was combined and washed with the brine, dried over anhydrous Na$_2$SO$_4$ to the crude. In the end, the residue was purified by reserved-flash to get 1-(7-chloro-5-fluoro-3-methyl-1-benzofuran-2-yl)-2,2,2-trifluoroethanone (2.4 g, 93.22%) yellow solid as product.

Step 6

A solution of 1-(5-chloro-7-fluoro-3-methyl-1-benzofuran-2-yl)-2,2,2-trifluoroethanone (2.2 g, 7.84 mmol, 1 equiv), NaOAc (3.216 g, 39.20 mmol, 5.00 equiv) and hydroxylamine hydrochloride (854.4 mg, 12.30 mmol, 5 equiv) in EtOH (30 mL) was stirred for 1 h at 100° C. After the reaction was completed, the mixture was purified by reserved-flash to get (E)-N-[1-(5-chloro-7-fluoro-3-methyl-1-benzofuran-2-yl)-2,2,2-trifluoroethylidene]hydroxylamine (1.7 g, 81.98%) yellow semi-solid as product. MS (ESI): mass calcd. for C$_{11}$H$_6$ClF$_4$NO$_2$, 295.0, m/z found 293.9 [M−H]$^+$.

Step 7

A solution of (E)-N-[1-(7-chloro-5-fluoro-3-methyl-1-benzofuran-2-yl)-2,2,2-trifluoroethylidene]hydroxylamine (1.7 g, 3.214 mmol, 1 equiv) Zn (1.799 g, 32.14 mmol, 5 equiv) and NH$_4$Cl (1.719 g, 32.14 mmol, 5 equiv) in EtOH (4 mL) and H$_2$O (4 mL) was stirred for overnight at 80° C. After the reaction was completed, the mixture was purified by reserved-flash to 1-(7-chloro-5-fluoro-3-methyl-1-benzofuran-2-yl)-2,2,2-trifluoroethanamine (1.036 g, 57.23%) light-yellow solid as product.

Step 8

A solution of 1-(7-chloro-5-fluoro-3-methyl-1-benzofuran-2-yl)-2,2,2-trifluoroethanamine (562 mg, 2.00 mmol, 1 equiv) and phenyl N-(2-aminopyrimidin-5-yl) carbamate (551.31 mg, 2.40 mmol, 1.2 equiv) in pyridine (10 mL) was stirred for overnight at 80° C. After the reaction was completed, the mixture was purified by reserved-flash to get 1-(2-aminopyrimidin-5-yl)-3-[1-(7-chloro-5-fluoro-3-methyl-1-benzofuran-2-yl)-2,2,2-trifluoroethyl] urea (760 mg) yellow solid as product MS (ESI): mass calcd. for C$_{16}$H$_{12}$ClF$_4$N$_5$O$_2$, 417.1. m/z found 418.0 [M+H]$^+$.

Step 9

83.2 mg of racemic was separated by SFC to give (Compound 177, 148.7 mg) as white solid and (Compound 178, 156.9 mg) as white solid.
Chiral Separation Conditions:
Apparatus: Prep-Chiral-HPLC
Column: CHIRALPAK IC, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 10% B to 10% B in 15 min; Wave Length: 220/254 nm; RT$_1$ (min): 9.564; RT$_2$ (min): 11.568; Sample Solvent: EtOH:DCM=1:1-HPLC; Injection Volume: 0.6 mL; Number Of Runs: 27.

Compound 177

MS (ESI): mass calcd. for C$_{16}$H$_{12}$ClF$_4$N$_5$O$_2$, 417.1, m/z found 418.0 [M+H]$^+$.
$^1$H NMR (400 MHz, DMSO) δ 8.24 (d, J=14.4 Hz, 3H), 7.74 (d, J=9.6 Hz, 1H), 7.57 (s, 2H), 6.40 (s, 2H), 6.04 (s, 1H), 2.30 (s, 3H).

Compound 178

MS (ESI): mass calcd. for C$_{16}$H$_{12}$ClF$_4$N$_5$O$_2$, 417.1, m/z found 418.0 [M+H]$^+$.
$^1$H NMR (400 MHz, DMSO) δ 8.24 (d, J=14.4 Hz, 3H), 7.75 (d, J=9.6 Hz, 1H), 7.60-7.54 (m, 2H), 6.40 (s, 2H), 6.04 (t, J=8.8 Hz, 1H) 2.30 (s, 3H).

Example 127: Preparation of Compound 179 and 180

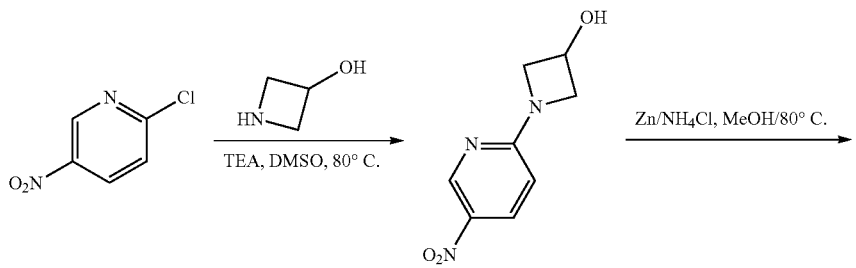

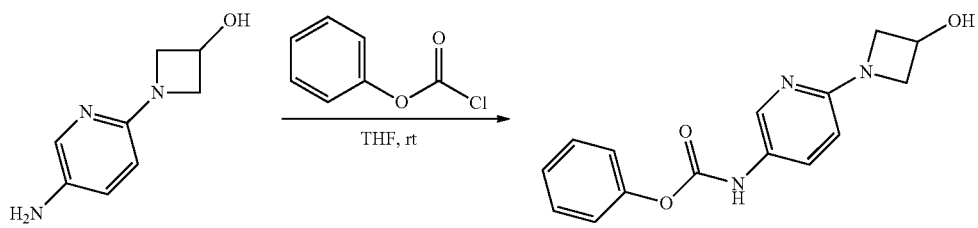

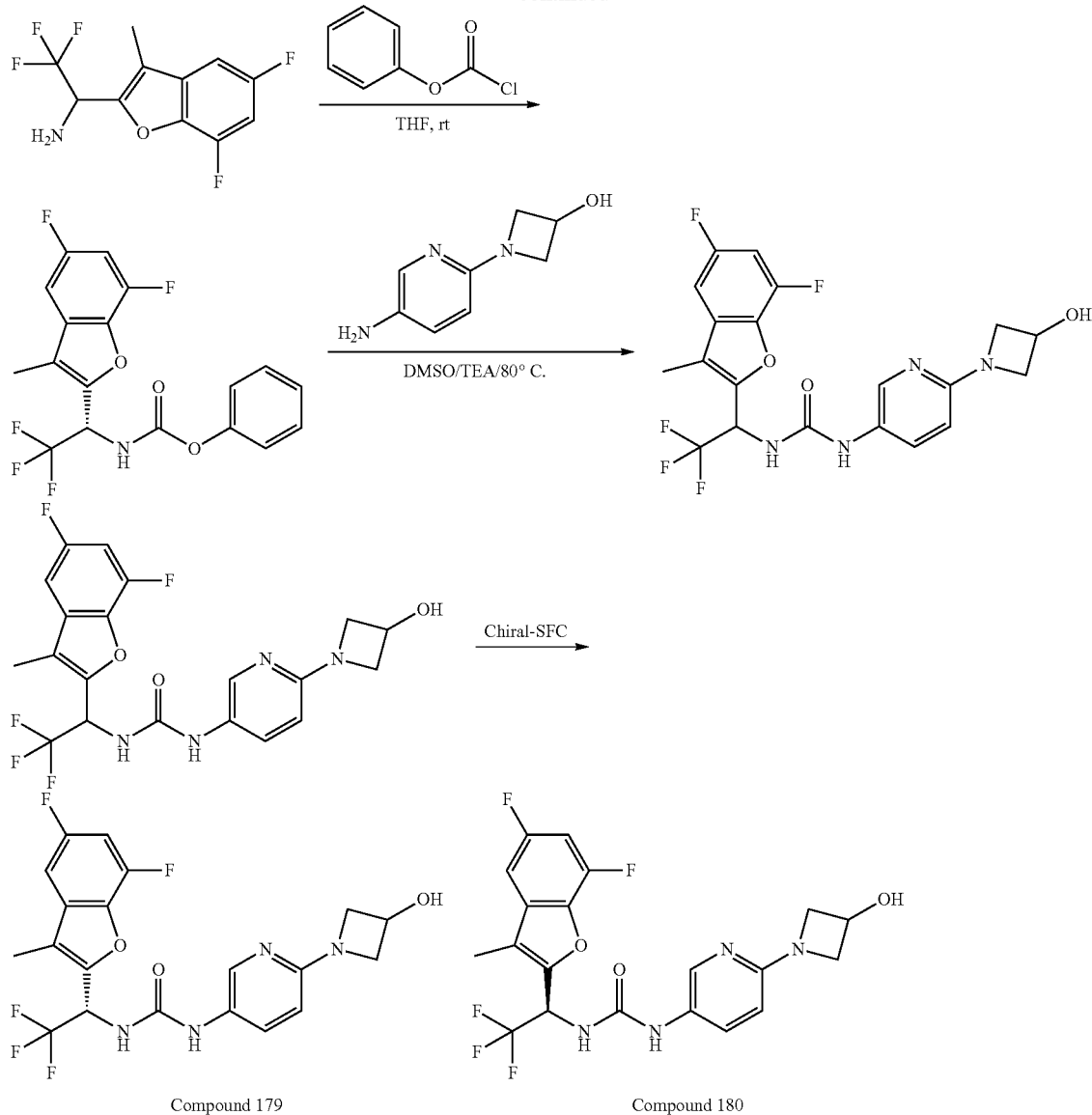

Compound 179          Compound 180

Step 1

To a stirred solution/mixture of pyridine, 2-chloro-5-nitro-pyridine (1 g, 6.308 mmol, 1 equiv) and TEA (1.91 g, 18.924 mmol, 3 equiv) in DMSO was added azetidin-3-ol hydrochloride (0.73 g, 6.623 mmol, 1.05 equiv) dropwise at 80° C. under air atmosphere. The aqueous layer was extracted with CH2Cl2. The resulting liquid was dried under vacuum. This resulted in 1-(5-nitropyridin-2-yl)azetidin-3-ol (1.6709 g, 135.72%) as a Brown yellow solid. MS (ESI): mass calcd. for $C_8H_9N_3O_3$, 195.1, m/z found 196.0 [M+H]$^+$.

Step 2

A solution of Zn (1.34 g, 20.495 mmol, 5 equiv) in EtOH was treated with NH$_4$Cl (1.10 g, 20.495 mmol, 5 equiv) for 2 h at room temperature followed by the addition of 1-(5-nitropyridin-2-yl)azetidin-3-ol (800 mg, 4.099 mmol, 1 equiv) dropwise/in portions at 80° C. The precipitated solids were collected by filtration and washed with MeOH. The crude product/resulting mixture was used in the next step directly without further purification. MS (ESI): mass calcd. for $C_8H_{11}N_3O$, 165.1. m/z. found 166.0 [M+H]$^+$.

Step 3

A solution/mixture of 1-(5,7-difluoro-3-methyl-1-benzofuran-2-yl)-2,2,2-trifluoroethanamine (10 mg, 0.038 mmol, 1 equiv) and phenyl chloroformate (5.90 mg, 0.038 mmol, 1 equiv) in THF was stirred for 1 h at room temperature under air atmosphere. The aqueous layer was extracted with CH$_2$Cl$_2$. This resulted in phenyl N-[1-(5,7-difluoro-3-methyl-1-benzofuran-2-yl)-2,2,2-trifluoroethyl]carbamate (12 mg, 82.59%) as an off-white liquid.

Step 4

A solution/mixture of phenyl N-[1-(5,7-difluoro-3-methyl-1-benzofuran-2-yl)-2,2-difluoroethyl]carbamate (10 mg, 0.027 mmol, 1 equiv) and 1-(5-aminopyridin-2-yl)

azetidin-3-ol (4.50 mg, 0.027 mmol, 1 equiv) and TEA (183.77 mg, 1.815 mmol, 3 equiv) in DMSO was stirred for 1 h at 80° C. under air atmosphere. The resulting liquid was dried under vacuum. The residue was purified by reverse flash chromatography with the following conditions: column, C18 silica gel; mobile phase, MeOH in water, 10% to 50% gradient in 10 min; detector, UV 254 nm. This resulted in 3-[1-(5,7-difluoro-3-methyl-1-benzofuran-2-yl)-2,2,2-trifluoroethyl]-1-[6-(3-hydroxyazetidin-1-yl)pyridin-3-yl]urea (130.5 mg, 47.24%) as an off-white solid. It was make Chiral-SFC to give 3-[(1S)-1-(5,7-difluoro-3-methyl-1-benzofuran-2-yl)-2,2,2-trifluoroethyl]-1-[6-(3-hydroxyazetidin-1-yl)pyridin-3-yl]urea 28.5 mg. MS (ESI): mass calcd. for $C_{20}H_{17}F_5N_4O_3$, 456.1, m/z found 457.0 $[M+H]^+$.

Step 5

120 mg of racemic was separated by SFC to give (Compound 179, 29.6 mg) as white solid and (Compound 180, 32.3 mg) as white solid.
Chiral Separation Conditions:
Apparatus: SFC 80
Column: DZ-CHIRALPAK IC-3, 4.6*50 mm, 3.0 µm;
Mobile Phase A: Hex (0.2% DEA):EtOH=85:15;
Flow rate: 1 mL/min; Gradient: 0% B to 0% B;
Injection Volume: 5 mL
Temperature: 35° C.

Compound 179

MS (ESI): mass calcd. for $C_{20}H_{17}F_5N_4O_3$, 456.1, m/z found 457.0 $[M+H]^+$.
$^1$H NMR (400 MHz, DMSO-d6) δ 8.36 (s, 1H), 8.02 (d, J=2.6 Hz, 1H), 7.71-7.55 (m, 2H), 7.48-7.37 (m, 1H), 6.35 (d, J=8.8 Hz, 1H), 6.03 (q, J=8.4 Hz, 2H), 5.58 (d, J=6.6 Hz, 1H), 4.54 (h, J=6.2 Hz, 1H), 4.08 (dd, J=8.1, 6.7 Hz, 2H), 3.59 (dd, J=8.7, 4.8 Hz, 2H), 2.30 (s, 3H).

Compound 180

MS (ESI): mass calcd. for $C_{20}H_{17}F_5N_4O_3$, 456.1, m/z found 457.0 $[M+H]^+$.
$^1$H NMR (400 MHz, DMSO-d6) δ 8.37 (s, 1H), 8.03 (d, J=2.7 Hz, 1H), 7.70-7.53 (m, 2H), 7.49-7.32 (m, 2H), 6.36 (d, J=8.9 Hz, 1H), 6.03 (q, J=8.4 Hz, 1H), 5.59 (d, J=6.2 Hz, 1H), 4.54 (d, J=6.3 Hz, 1H), 4.09 (t, J=7.5 Hz, 2H), 3.67-3.51 (m, 2H), 2.30 (s, 3H).

Example 128: Preparation of Compound 181 and 182

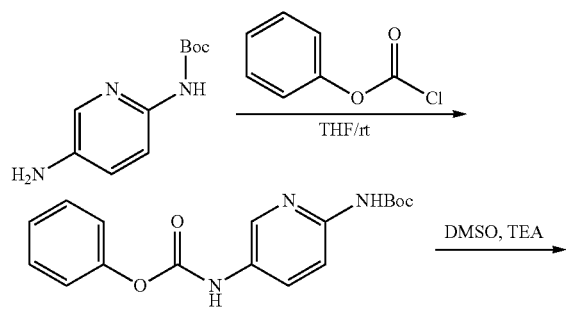

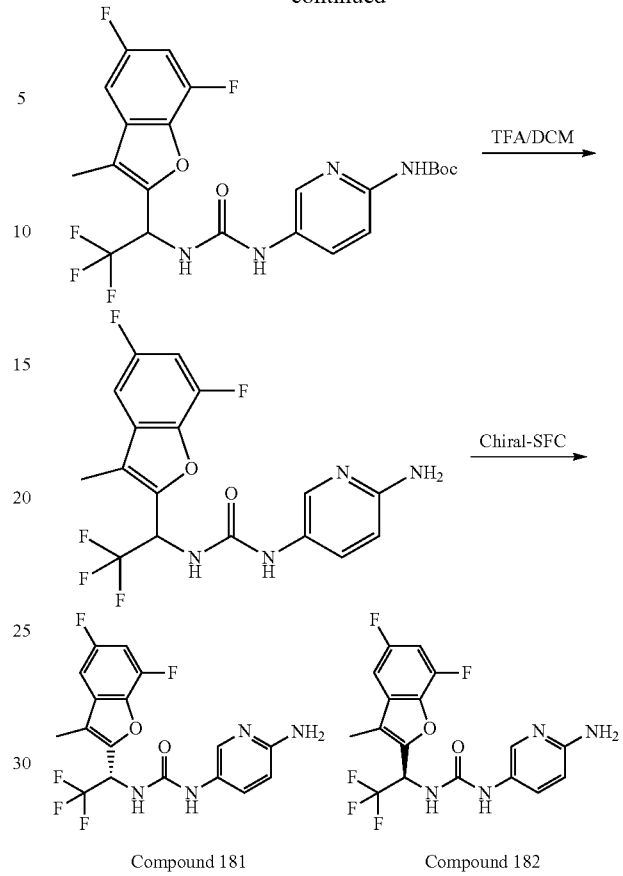

Step 1

A solution of tert-butyl N-(5-aminopyridin-2-yl)carbamate (500 mg, 2.389 mmol, 1 equiv) and phenyl chloroformate (374.12 mg, 2.389 mmol, 1 equiv) in THF (2 mL) was stirred for 2 h at room temperature under nitrogen atmosphere. The resulting mixture was concentrated under reduced pressure. This resulted in phenyl N-{6-[(tert-butoxycarbonyl)amino]pyridin-3-yl}carbamate (700 mg, 88.95%) as a off-white solid. MS (ESI): mass calcd. for $C_{17}H_{29}N_3O_4$, 329.1, m/z found 330.1 $[M+H]^+$.

Step 2

A solution of phenyl N-{6-[(tert-butoxycarbonyl)amino]pyridin-3-yl}carbamate (300 mg, 0.911 mmol, 1 equiv), Et3N (276.52 mg, 2.733 mmol, 3 equiv) and 1-(5,7-difluoro-3-methyl-1-benzofuran-2-yl)-2,2,2-trifluoroethanamine (241.55 mg, 0.911 mmol, 1 equiv) in DMSO (3 mL) was stirred for 2 h at 80° C. under nitrogen atmosphere. The residue was purified by reverse flash chromatography with the following conditions: column, silica gel; mobile phase, MeCN in water, 70% to 75% gradient in 10 min; detector, UV 254/220 nm. This resulted in tert-butyl N-[5-({[1-(5,7-difluoro-3-methyl-1-benzofuran-2-yl)-2,2,2-trifluoroethyl]carbamoyl}amino)pyridin-2-yl]carbamate (220 mg, 48.26%) as a light yellow solid. MS (ESI): mass calcd. for $C_{22}H_{21}F_5N_4O_4$, 500.1, m/z found 501.3$[M+H]^+$.

Step 3

A solution of tert-butyl N-[5-({[1-(5,7-difluoro-3-methyl-1-benzofuran-2-yl)-2,2,2-trifluoroethyl]carbamoyl}amino)

pyridin-2-yl]carbamate (220 mg, 0.440 mmol, 1 equiv) in DCM (5 mL) was treated with HCl (gas) in 1,4-dioxane (1 mL). The resulting mixture was stirred for 30 min at room temperature under nitrogen atmosphere. MS (ESI): mass calcd. for $C_{17}H_{13}F_5N_4O_2$, 400.1, m/z found 401.1 [M+H]$^+$.

Step 4

70 mg of racemic was separated by SFC to give (Compound 181, 26.7 mg) as white solid and (Compound 182, 26.1 mg) as white solid.
Chiral Separation Conditions:
Apparatus: SFC 80
Column: DZ-CHIRALPAK IG-3, 4.6*50 mm, 3.0 μm;
Mobile Phase A: Hex (0.2% DEA):EtOH=90:10;
Flow rate: 1 mL/min; Gradient: 0% B to 0% B;
Injection Volume: 5 mL
Temperature: 35° C.

Compound 181

MS (ESI): mass calcd. for $C_{17}H_{13}F_5N_4O_2$, 400.1, m/z found 401.1 [M+H]$^+$.
1H NMR (400 MHz, DMSO-d6) δ 8.21 (s, 1H), 7.88 (d, J=2.6 Hz, 1H), 7.61 (d, J=9.5 Hz, 1H), 7.51-7.33 (m, 3H), 6.40 (d, J=8.7 Hz, 1H), 6.03 (p, J=8.5 Hz, 1H), 5.68 (s, 2H), 2.30 (s, 3H).

Compound 182

MS (ESI): mass calcd. for $C_{17}H_{13}F_5N_4O_2$, 400.1, m/z found 401.1 [M+H]$^+$.
1H NMR (400 MHz, DMSO-d6) δ 8.21 (s, 1H), 7.88 (d, J=2.7 Hz, 1H), 7.61 (d, J=9.5 Hz, 1H), 7.54-7.33 (m, 3H), 6.40 (d, J=8.7 Hz, 1H), 6.02 (q, J=8.5 Hz, 1H), 5.67 (s, 2H), 2.30 (s, 3H).

Example 129: Preparation of Compound 183 and 184

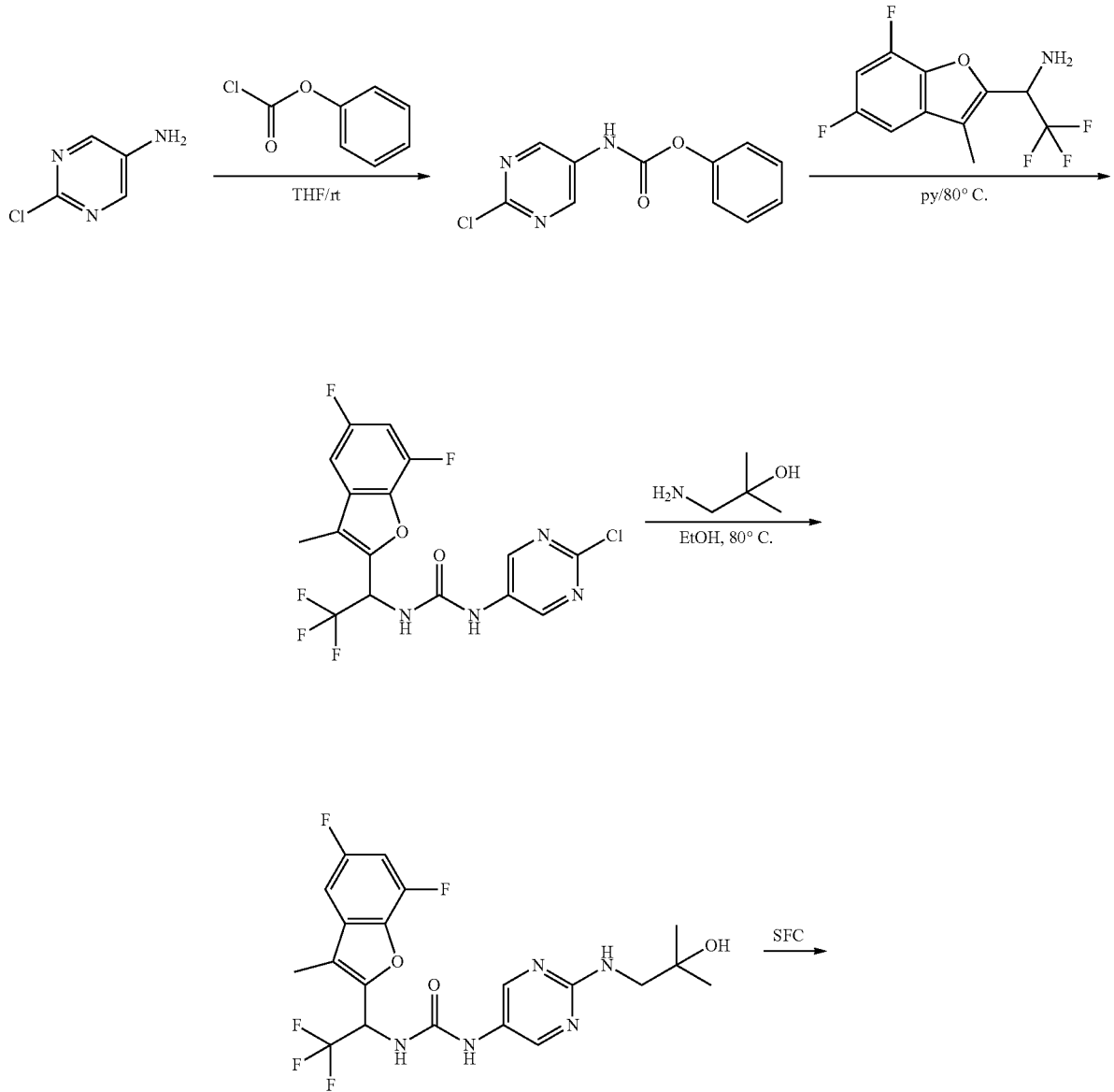

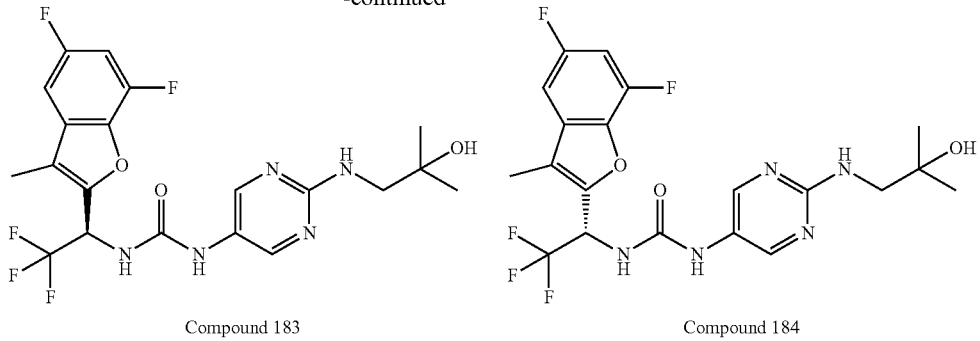

Compound 183         Compound 184

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 $[M+H]^+$.

Step 2

A solution of phenyl N-(2-chloropyrimidin-5-yl) carbamate (5.51 g, 22.054 mmol, 1.22 equiv) and (1S)-1-(5-fluoro-3-methyl-1-benzofuran-2-yl)-2-methylpropan-1-amine (4 g, 18.077 mmol, 1.00 equiv) in Pyridine (10 mL) was stirred for 4 h at 80° C. under nitrogen atmosphere. The resulting mixture was extracted with EtOAc (2×20 mL). The combined organic layers were washed with brine (4×1 40 mL), dried over anhydrous $Na_2SO_4$. After filtration, the filtrate was concentrated under reduced pressure. The residue was purified by silica gel column chromatography, eluted with PE/EA (10:1) to afford 1-(2-chloropyrimidin-5-yl)-3-[(1S)-1-(5-fluoro-3-methyl-1-benzofuran-2-yl)-2-methylpropyl]urea (7 g, 82.21%) as a yellow oil. MS (ESI): mass calcd. for $C_{16}H_{10}ClF_5N_4O_2$, 420.0, m/z found 421.0 $[M+H]^+$.

Step 3

A solution of rel-1-(2-chloropyrimidin-5-yl)-3-[(1R)-1-(5,7-difluoro-3-methyl-1-benzofuran-2-yl)-2,2,2-trifluoroethyl]urea (200 mg, 0.475 mmol, 1 equiv) and 1-amino-2-methylpropan-2-ol (169.50 mg, 1.900 mmol, 4 equiv) in EtOH) was stirred for overnight at 80° C. under nitrogen atmosphere. The mixture was allowed to cool down to room temperature. The resulting mixture was concentrated under reduced pressure to afford 100 mg crude product. MS (ESI): mass calcd. for $C_{20}H_{20}F_5N_5O_3$, 473.1, m/z found 474.2 $[M+H]^+$.

Step 4

100 mg of racemic was separated by SFC to give (Compound 183) and (Compound 184) as a white solid.
Chiral Separation Conditions:
Apparatus: SFC 80
Column: DZ-CHIRALPAK IF-3, 4.6*50 mm, 3.0 μm
Mobile Phase A: Hex (0.2% DEA):EtOH=80:20
Flow rate: 1 mL/min
Gradient: 0% B to 0% B
Injection Volume: 5 mL.

Compound 183

MS (ESI): mass calcd. for $C_{20}H_{20}F_5N_5O_3$, 473.1, m/z found 474.2 $[M+H]^+$.
$^1$H NMR (400 MHz, DMSO-d6) δ 8.24 (d, J=13.3 Hz, 3H), 7.82 (d, J=9.5 Hz, 1H), 7.46-7.38 (m, 2H), 6.59 (t, J=6.0 Hz, 1H), 6.04 (t, J=8.3 Hz, 1H), 4.52 (s, 1H), 3.25 (d, J=6.1 Hz, 2H), 2.30 (s, 3H), 1.09 (s, 6H).

Compound 184

MS (ESI): mass calcd. for $C_{20}H_{20}F_5N_5O_3$, 473.1, m/z found 474.2 $[M+H]^+$.
$^1$H NMR (400 MHz, DMSO-d6) δ 8.24 (d, J=12.7 Hz, 3H), 7.82 (d, J=9.4 Hz, 1H), 7.49-7.35 (m, 2H), 6.59 (t, J=6.1 Hz, 1H), 6.03 (q, J=8.5 Hz, 1H), 4.52 (s, 1H), 3.25 (d, J=6.1 Hz, 2H), 2.30 (s, 3H), 1.09 (s, 6H).

Example 130: Preparation of Compound 185 and 186

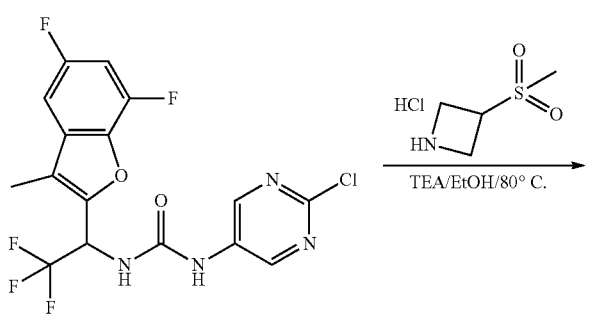

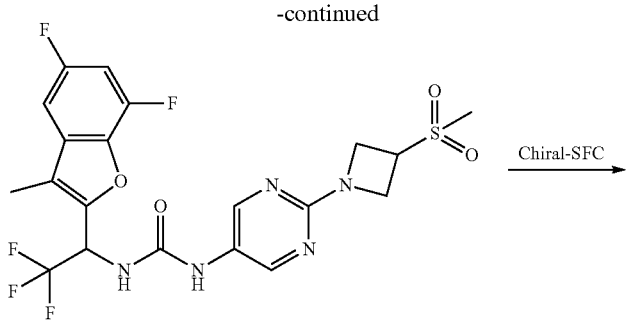

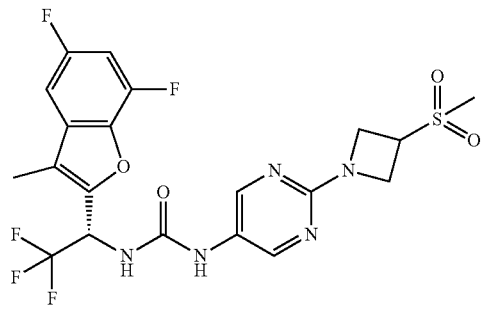

Compound 185

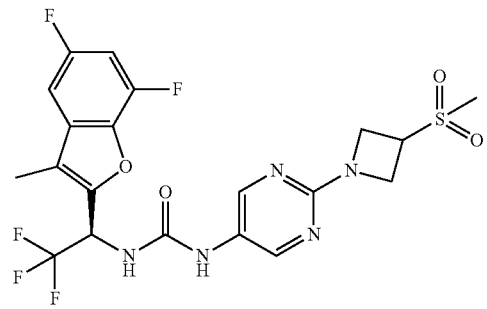

Compound 186

Step 1

The resulting mixture of 1-(2-chloropyrimidin-5-yl)-3-(1-(5,7-difluoro-3-methylbenzofuran-2-yl)-2,2,2-trifluoroethyl)urea (100 mg, 0.238 mmol, 1 equiv), 3-(methylsulfonyl)azetidine hydrochloride (160 mg, 0.932 mmol, 3.92 equiv), TEA (120 mg, 1.186 mmol, 4.99 equiv) in EtOH (5 mL) was stirred for 16 h at 80° C. under nitrogen atmosphere. The resulting mixture was concentrated under reduced pressure to give 150 mg (crude). The residue was purified by Prep-TLC to afford 1-(1-(5,7-difluoro-3-methylbenzofuran-2-yl)-2,2,2-trifluoroethyl)-3-(2-(3-(methylsulfonyl) azetidin-1-yl)pyrimidin-5-yl)urea (70 mg, 56.70%) as an off-white solid. MS (ESI): mass calcd. for $C_{20}H_{18}F_5N_5O_4S$, 519.1, m/z found 520.0 [M+H]$^+$.

Step 2

70 mg of racemic was separated by Chiral-HPLC to give (Compound 185, 17.1 mg) as white solid and (Compound 186, 14.3 mg) as white solid.

Chiral Separation Conditions:
Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 33% B to 58% B in 8 min, 58% B; Wave Length: 254 nm; RT1 (min): 7.27; Number Of Runs: 0.

Compound 185

MS (ESI): mass calcd. for $C_{16}H_{13}F_4N_5O_2$, 519.1, m/z found 520.0 [M+H]$^+$. $^1$H NMR (400 MHz, DMSO-d6) δ 8.44 (s, 3H), 7.88 (d, J=9.2 Hz, 1H), 7.56-7.38 (m, 2H), 6.06 (t, J=8.8 Hz, 1H), 4.47-4.32 (m, 1H), 4.29 (t, J=8.8 Hz, 2H), 4.18 (dd, J=9.2, 4.8 Hz, 2H), 3.05 (s, 3H), 2.30 (s, 3H).

Compound 186

MS (ESI): mass calcd. for $C_{16}H_{13}F_4N_5O_2$, 519.1, m/z found 520.0 [M+H]$^+$. $^1$H NMR (400 MHz, DMSO-d6) δ 8.44 (s, 3H), 7.88 (d, J=9.2 Hz, 1H), 7.56-7.38 (m, 2H), 6.06 (t, J=8.8 Hz, 1H), 4.47-4.32 (m, 1H), 4.29 (t, J=8.8 Hz, 2H), 4.18 (dd, J=9.2, 4.8 Hz, 2H), 3.05 (s, 3H), 2.30 (s, 3H).

Example 131: Preparation of Compound 187 and 188

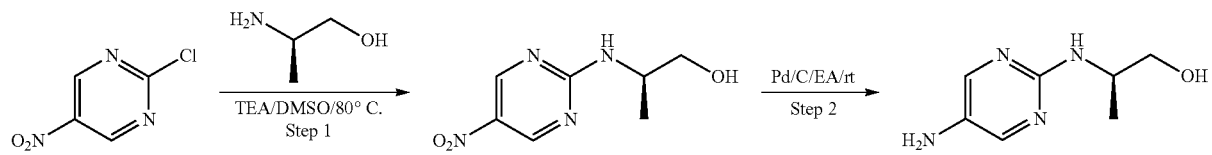

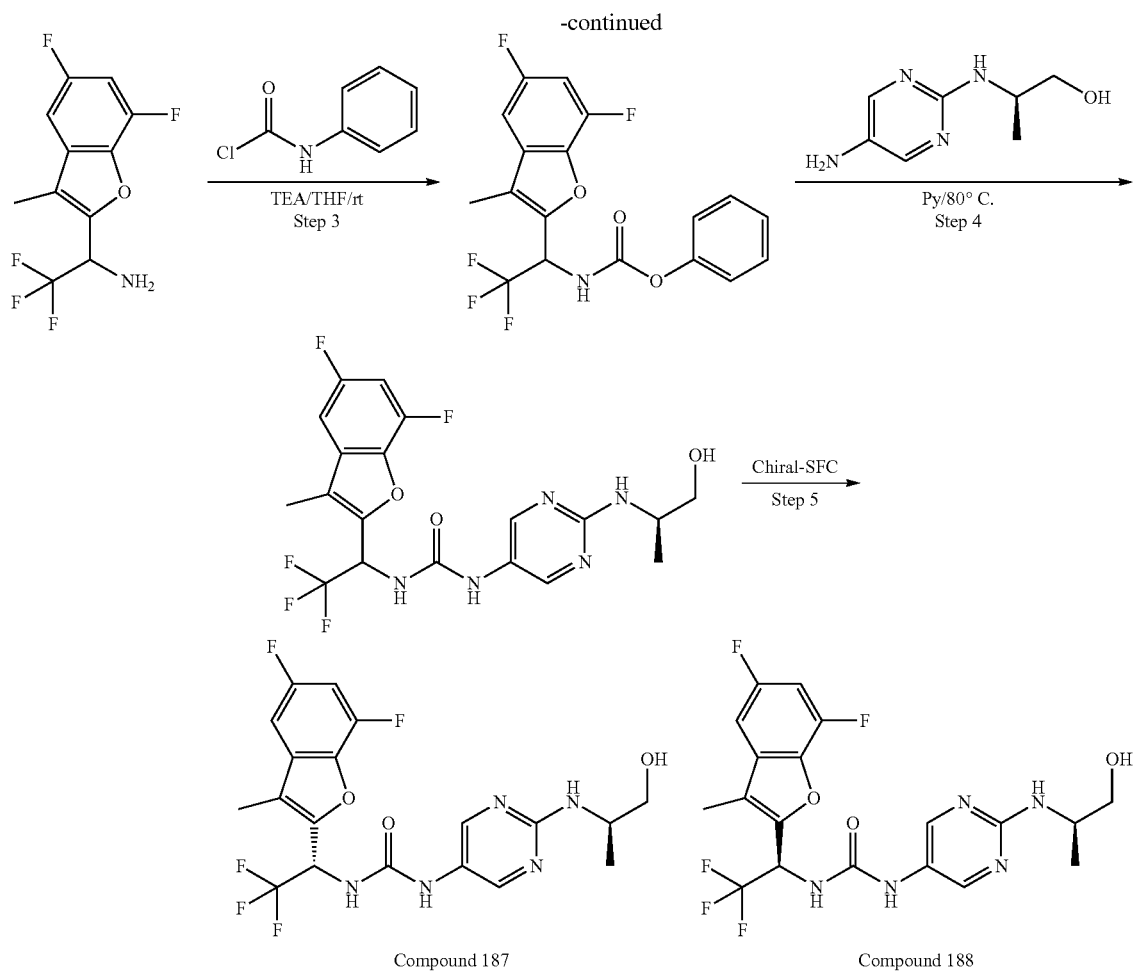

Compound 187          Compound 188

Step 1

The resulting mixture of 2-chloro-5-nitropyrimidine (200 mg, 1.254 mmol, 1 equiv), (R)-2-aminopropan-1-ol (110 mg, 1.464 mmol, 1.17 equiv), TEA (380 mg, 3.755 mmol, 3.00 equiv) in DMSO (3 mL) was stirred for 16 h at 80° C. under nitrogen atmosphere. The resulting mixture was diluted with water. The resulting mixture was extracted with EtOAc. The combined organic layers were washed with brine, dried over anhydrous Na$_2$SO$_4$. After filtration, the filtrate was concentrated under reduced pressure. The residue was purified by Prep-TLC (PE/EA 3:1) to afford (R)-2-((5-nitropyrimidin-2-yl)amino)propan-1-ol (150 mg, 60.37%) as a yellow solid.

Step 2

The resulting mixture of (R)-2-((5-nitropyrimidin-2-yl)amino)propan-1-ol (130 mg, 0.656 mmol, 1 equiv), Pd/C (30 mg, 0.282 mmol, 0.43 equiv) in EtOAc (6 mL) was stirred for 16 h at room temperature under hydrogen atmosphere. The resulting mixture was filtered, the filter cake was washed with EtOAc. The filtrate was concentrated under reduced pressure to give (R)-2-((5-aminopyrimidin-2-yl)amino)propan-1-ol (100 mg, 90.63%) as a brown oil.

Step 3

The resulting mixture of 1-(5,7-difluoro-3-methylbenzofuran-2-yl)-2,2,2-trifluoroethan-1-amine (150 mg, 0.566 mmol, 1 equiv), phenyl chloroformate (90 mg, 0.575 mmol, 1.02 equiv), TEA (110 mg, 1.087 mmol, 1.92 equiv) in THF (5 mL) was stirred for 1 h at room temperature under nitrogen atmosphere. The resulting mixture was concentrated under reduced pressure to give phenyl (1-(5,7-difluoro-3-methylbenzofuran-2-yl)-2,2,2-trifluoroethyl)carbamate (200 mg, crude) as a colorless semi-solid.

Step 4

The resulting mixture of phenyl (1-(5,7-difluoro-3-methylbenzofuran-2-yl)-2,2,2-trifluoroethyl) carbamate (150 mg, 0.389 mmol, 1 equiv), (R)-2-((5-aminopyrimidin-2-yl)amino)propan-1-ol (65 mg, 0.386 mmol, 0.99 equiv) in Pyridine (3 mL) was stirred for 16 h at 80° C. under nitrogen atmosphere. The resulting mixture was concentrated under reduced pressure. The resulting mixture was diluted with water. The resulting mixture was extracted with EtOAc (3×20 mL). The combined organic layers were washed with brine, dried over anhydrous Na$_2$SO$_4$. After filtration, the filtrate was concentrated under reduced pressure. The residue was purified by Prep-TLC (CH$_2$Cl$_2$/MeOH 20:1) to afford 1-(1-(5,7-difluoro-3-methylbenzofuran-2-yl)-2,2,2-trifluoroethyl)-3-(2-(((R)-1-hydroxypropan-2-yl)amino)pyrimidin-5-yl)urea (100 mg, 55.78%) as a white solid.

Step 5

100 mg of racemic was separated by SFC to give (Compound 188, 41.4 mg) as white solid and (Compound 188, 36.2 mg) as white solid. Chiral separation conditions:

Column: CHIRALPAK IF, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 20% B to 20% B in 11 min; Wave Length: 220/254 nm; RT1 (min): 5.361; RT2 (min): 7.624; Sample Solvent: EtOH:DCM=1:1-HPLC; Injection Volume: 1.5 mL; Number Of Runs: 4.

Compound 187

MS (ESI): mass calcd. for $C_{19}H_{18}F_5N_5O_3$, 459.1, m/z found 460.2 [M+H]$^+$. $^1$H NMR (400 MHz, DMSO-d$_6$) δ 8.32-8.12 (m, 3H), 7.80 (d, J=9.2 Hz, 1H), 7.57-7.35 (m, 2H), 6.59 (d, J=8.0 Hz, 1H), 6.16-6.00 (m, 1H), 4.64 (br s, 1H), 3.99-3.790 (m, 1H), 2.30 (s, 3H), 1.10 (d, J=6.8 Hz, 3H).

Compound 188

MS (ESI): mass calcd. for $C_{19}H_{18}F_5N_5O_3$, 459.1, m/z found 460.1 [M+H]$^+$. $^1$H NMR (400 MHz, DMSO-d$_6$) δ 8.32-8.12 (m, 3H), 7.80 (d, J=9.2 Hz, 1H), 7.57-7.35 (m, 2H), 6.59 (d, J=8.0 Hz, 1H), 6.16-6.00 (m, 1H), 4.64 (br s, 1H), 3.99-3.790 (m, 1H), 2.30 (s, 3H), 1.10 (d, J=6.8 Hz, 3H).

Example 132: Preparation of Compound 189 and 190

Step 1

The resulting mixture of 1-(2-chloropyrimidin-5-yl)-3-(1-(5,7-difluoro-3-methylbenzofuran-2-yl)-2,2,2-trifluoroethyl)urea (150 mg, 0.357 mmol, 1 equiv), piperazin-2-one (140 mg, 1.398 mmol, 3.92 equiv), TEA (180 mg, 1.779 mmol, 4.99 equiv) in EtOH (5 mL) was stirred for 24 h at 80° C. under nitrogen atmosphere. The resulting mixture was concentrated under reduced pressure. The resulting mixture was diluted with water (10 mL). The resulting mixture was extracted with EtOAc (3×20 mL). The combined organic layers were washed with brine (1×5 mL), dried over anhydrous Na$_2$SO$_4$. After filtration, the filtrate was concentrated under reduced pressure. The residue was purified by Prep-TLC (CH$_2$Cl$_2$/MeOH 10:1) to afford 1-(1-(5,7-difluoro-3-methylbenzofuran-2-yl)-2,2,2-trifluoroethyl)-3-(2-(3-oxopiperazin-1-yl)pyrimidin-5-yl)urea (90 mg, 52.2%) as an off-white solid. MS (ESI): mass calcd. for $C_{20}H_{17}F_5N_6O_3$, 484.1, m/z found 485.1 [M+H]$^+$.

Step 2

90 mg of racemic was separated by Chiral-HPLC to give (Compound 189, 38.5 mg) and (Compound 190, 39.5 mg) as a white solid.

Chiral Separation Conditions:

Column: CHIRALPAK IF, 2*25 cm, 5 μm; Mobile Phase A: Hex (0.5% 2M N13-MeOH)-HPLC, Mobile Phase B: EtOH-HPLC; Flow rate: 20 mL/min; Gradient: 20% B to 20% B in 11 min; Wave Length: 220/254 nm; RT1 (min): 12.706; RT2 (min): 17.897; Sample Solvent: EtOH:DCM=1:1-HPLC; Injection Volume: 3.5 mL; Number Of Runs: 3.

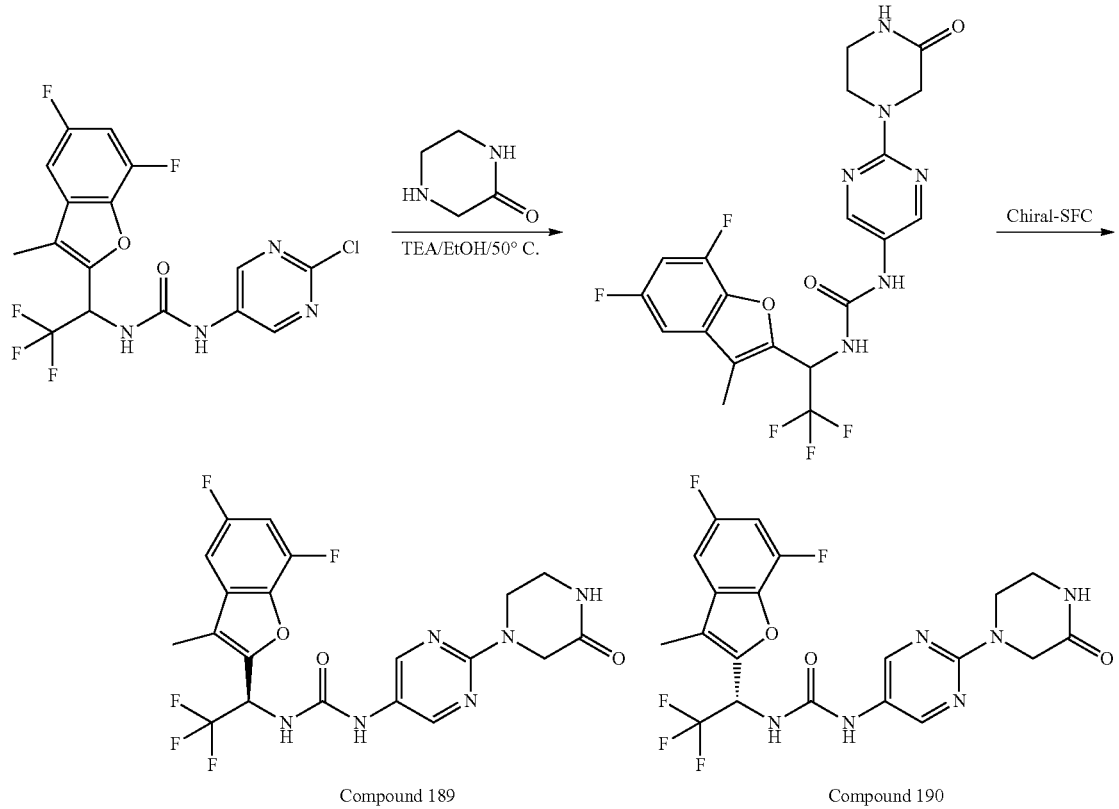

Compound 189

Compound 190

Compound 189

MS (ESI): mass calcd. for $C_{20}H_{17}F_5N_6O_3$, 484.1, m/z found 485.1 [M+H]$^+$. $^1$H NMR (400 MHz, DMSO-d$_6$) δ 8.47-8.39 (m, 3H), 8.07 (s, 1H), 7.87 (d, J=9.2 Hz, 1H), 7.48-7.31 (m, 2H), 6.14-5.98 (m, 1H), 4.11 (s, 2H), 3.90-3.77 (m, 2H), 3.28-3.25 (m, 2H), 2.30 (s, 3H).

Compound 190

MS (ESI): mass calcd. for $C_{20}H_{17}F_5N_6O_3$, 484.1, m/z found 485.1 [M+H]$^+$. $^1$H NMR (400 MHz, DMSO-d$_6$) δ 8.47-8.39 (m, 3H), 8.07 (s, 1H), 7.87 (d, J=9.2 Hz, 1H), 7.48-7.31 (m, 2H), 6.14-5.98 (m, 1H), 4.11 (s, 2H), 3.90-3.77 (m, 2H), 3.28-3.25 (m, 2H), 2.30 (s, 3H).

Example 133: Preparation of Compound 191 and 192

Step 1

A solution of 2-chloropyrimidin-5-amine (3 g, 23.157 mmol, 1 equiv) and phenyl chloroformate (3.63 g, 23.157 mmol, 1 equiv) in THF (15 mL) was stirred for 4 h at room temperature under nitrogen atmosphere. Desired product could be detected by LCMS. The resulting mixture was concentrated under reduced pressure to afford phenyl N-(2-chloropyrimidin-5-yl) carbamate (6.7 g, 81.13%) as a yellow solid. MS (ESI): mass calcd. for $C_{11}H_8ClN_3O_2$, 249.0, m/z found 250.2 [M+H]$^+$.

Step 2

A solution of phenyl N-(2-chloropyrimidin-5-yl)carbamate (1.4 g, 5.608 mmol, 1 equiv) and 1-(5,7-difluoro-3-methyl-1-benzofuran-2-yl)-2,2,2-trifluoroethanamine (1.64 g, 6.169 mmol, 1.1 equiv) in Pyridine (15 mL) was stirred for 5 h at 80° C. under nitrogen atmosphere. The mixture

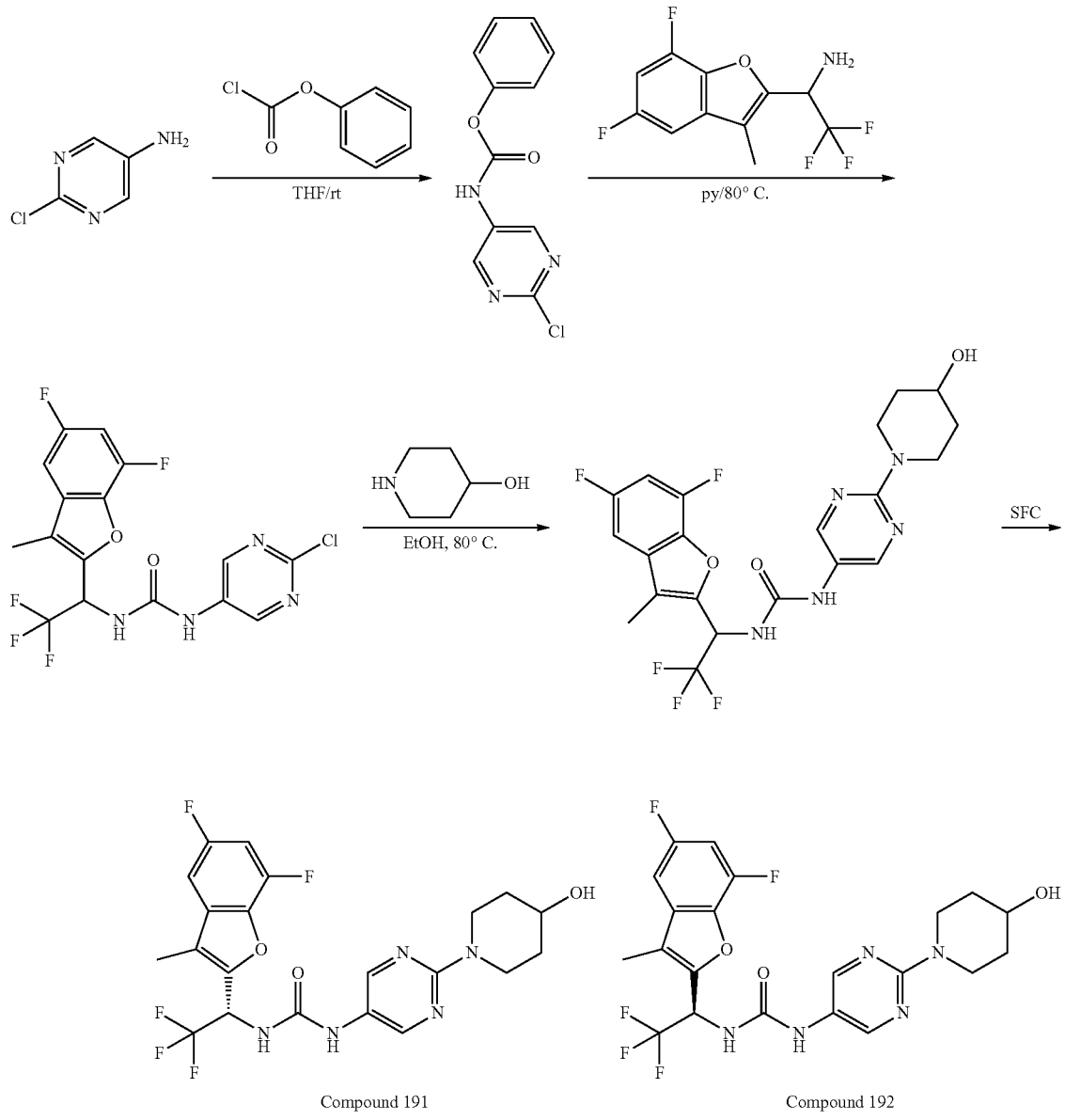

Compound 191      Compound 192 was allowed to cool down to room temperature. The resulting mixture was extracted with EtOAc (2×200 mL). The combined organic layers were washed with brine (4×1 200 mL), dried over anhydrous Na2SO4. After filtration, the filtrate was concentrated under reduced pressure. The residue was purified by silica gel column chromatography, eluted with PE/EA (5:1) to afford 1-(2-chloropyrimidin-5-yl)-3-[1-(5,7-difluoro-3-methyl-1-benzofuran-2-yl)-2,2,2-trifluoroethyl]urea (1.7 g, 72.05%) as a off-white solid. MS (ESI): mass calcd. for $C_{16}H_{10}ClF_5N_4O_2$, 420.0, m/z found 421.0[M+H]$^+$.

Step 3

A solution of rel-1-(2-chloropyrimidin-5-yl)-3-[(1R)-1-(5,7-difluoro-3-methyl-1-benzofuran-2-yl)-2,2,2-trifluoroethyl] urea (200 mg, 0.475 mmol, 1 equiv) and piperidin-4-ol (200.03 mg, 1.976 mmol, 4.16 equiv) in EtOH (10 mL) was stirred for 3 h at 80° C. under nitrogen atmosphere. The mixture was allowed to cool down to room temperature. The resulting mixture was concentrated under reduced pressure. to afford rel-3-[(1R)-1-(5,7-difluoro-3-methyl-1-benzofuran-2-yl)-2,2,2-trifluoroethyl]-1-[2-(4-hydroxypiperidin-1-yl) pyrimidin-5-yl] urea (200 mg) as a white solid. MS (ESI): mass calcd. for $C_{21}H_{20}F_5N_5O_3$, 485.1, m/z found 486.0 [M+H]$^+$.

Step 4

200 mg of racemic was separated by SFC to give (Compound 191, 56.2 mg) as white solid and (Compound 192, 56.2 mg) as white solid.

(Column: DZ-CHIRALPAK IF-3, 4.6*50 mm, 3.0 μm; Mobile Phase A: Hex (0.2% DEA):EtOH=80:20; Flow rate: 1 mL/min; Gradient: 0% B to 0% B; Injection Volume: 5 mL)

Compound 191

$^1$H NMR (400 MHz, DMSO-d6) δ 8.33 (d, J=12.1 Hz, 3H), 7.82 (d, J=9.4 Hz, 1H), 7.50-7.33 (m, 2H), 6.05 (d, J=961.6 Hz, 1H), 4.69 (d, J=4.2 Hz, 1H), 4.27-4.13 (m, 2H), 3.77-3.62 (m, 1H), 3.19 (ddd, J=13.3, 10.0, 3.2 Hz, 2H), 2.30 (s, 3H), 1.81-1.66 (m, 2H), 1.37-1.20 (m, 2H).

Compound 192

$^1$H NMR (400 MHz, DMSO-d6) δ 8.33 (d, J=10.7 Hz, 3H), 7.83 (d, J=9.5 Hz, 1H), 7.49-7.33 (m, 2H), 6.11-5.98 (m, 1H), 4.69 (d, J=4.2 Hz, 1H), 4.20 (dt, J=13.3, 4.5 Hz, 2H), 3.78-3.64 (m, 1H), 3.19 (ddd, J=13.2, 10.0, 3.1 Hz, 2H), 2.30 (s, 3H), 1.84-1.62 (m, 2H), 1.37-1.21 (m, 2H).

Example 134: Preparation of Compound 193 and 194

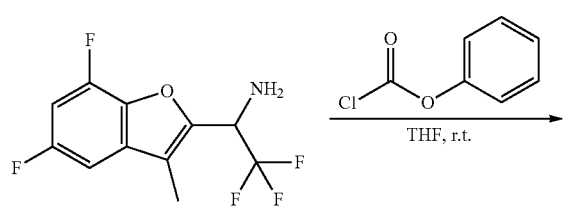

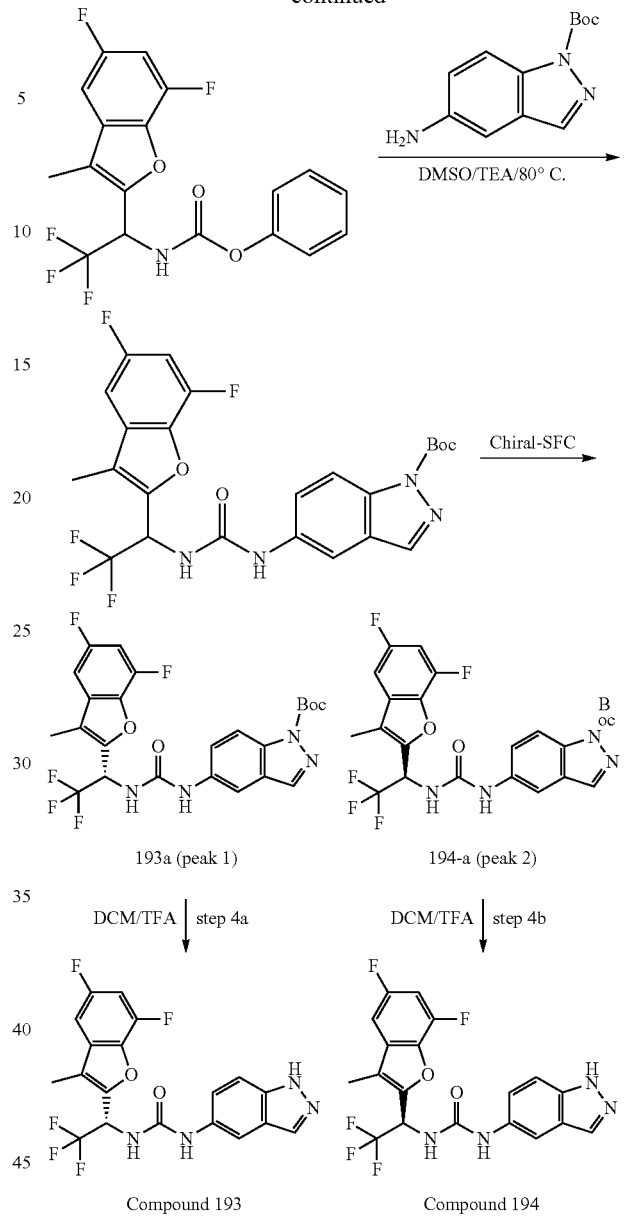

Step 1

To a stirred solution of 1-(5,7-difluoro-3-methyl-1-benzofuran-2-yl)-2,2,2-trifluoroethanamine (150 mg, 0.566 mmol, 1 equiv) in THF (20 mL) were added phenyl chloroformate (88.56 mg, 0.566 mmol, 1 equiv) dropwise at room temperature. The resulting mixture was concentrated under reduced pressure. The crude mixture was used in the next step directly without further purification.

Step 2

A solution/mixture of phenyl N-[1-(5,7-difluoro-3-methyl-1-benzofuran-2-yl)-2,2,2-trifluoroethyl]carbamate (200 mg, 0.519 mmol, 1 equiv) and tert-butyl 5-aminoindazole-1-carboxylate (145.31 mg, 0.623 mmol, 1.2 equiv), TEA (157.58 mg, 1.557 mmol, 3 equiv) in DMSO was stirred for 1 h at 80° C. under air atmosphere. The residue was purified by reverse flash chromatography with the following conditions: column, C18 silica gel; mobile phase, MeCN in Water (0.1% TFA), 10% to 50% gradient in 10 min; detector, UV 254 nm. Desired product could be detected by LCMS/MS (ESI): mass calcd. for $C_{24}H_{21}F_5N_4O_4$, 524.1, m/z found 525.1 $[M+H]^+$.

Step 3

130 mg of racemic was separated by SFC to give (193-a, 40 mg) as white solid and (194-a, 40 mg) as white solid. Chiral separation conditions: Apparatus: SFC 80; Column: CHIRALPAK IG, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 15% B to 15% B in 14 min;
Wave Length: 220/254 nm; RT1 (min): 7.457; RT2 (min): 10.885;
Sample Solvent: EtOH-HPLC; Injection Volume: 1 mL; Number Of Runs: 2
Temperature: 35° C. MS (ESI): mass calcd. for $C_{24}H_{21}F_5N_4O_4$, 524.1, m/z found 525.1 $[M+H]^+$.

Step 4a

A solution of 193-a (40 mg, 0.076 mmol, 1 equiv) and TFA (34.79 mg, 0.304 mmol, 4 equiv) in DCM was stirred for 0.5 h at room temperature under air atmosphere. The crude product (mg) was purified by Prep-HPLC to afford 3-[(1S)-1-(5,7-difluoro-3-methyl-1-benzofuran-2-yl)-2,2,2-trifluoroethyl]-1-(1H-indazol-5-yl)urea (4 mg, 12.36%) as an off-white solid. MS (ESI): mass calcd. for $C_{19}H_{13}F_5N_4O_2$, 424.1, m/z found 425.1 $[M+H]^+$.

$^1$H NMR (400 MHz, DMSO-d6) δ 12.93 (s, 1H), 8.65 (s, 1H), 7.97 (t, J=1.3 Hz, 1H), 7.86 (d, J=1.9 Hz, 1H), 7.65 (d, J=9.4 Hz, 1H), 7.50-7.37 (m, 3H), 7.25 (dd, J=8.9, 2.0 Hz, 1H), 6.15-6.02 (m, 1H), 2.32 (s, 3H). Column: DZ-CHIRALPAK IG-3, 4.6*50 mm, 3.0 μm;
Mobile Phase A: Hex (0.2% DEA):EtOH=90:10; Flow rate: 1 mL/min; Gradient: 0% B to 0% B; Injection Volume: 5 mL.

Step 4b

A solution of 194-a (40 mg, 0.076 mmol, 1 equiv) and TFA (34.79 mg, 0.304 mmol, 4 equiv) in DCM was stirred for 0.5 h at room temperature under air atmosphere. The crude product was purified by Prep-HPLC to afford 3-[(1R)-1-(5,7-difluoro-3-methyl-1-benzofuran-2-yl)-2,2,2-trifluoroethyl]-1-(1H-indazol-5-yl)urea (10.1 mg, 31.21%) as an off-white solid. Desired product could be detected by LCMS.

MS (ESI): mass calcd. for $C_{19}H_{13}F_5N_4O_2$, 424.1, m/z found 425.1 $[M+H]^+$.

$^1$H NMR (400 MHz, DMSO-d6) δ 12.93 (s, 1H), 8.65 (s, 1H), 7.97 (s, 1H), 7.90-7.82 (m, 1H), 7.65 (d, J=9.5 Hz, 1H), 7.50-7.35 (m, 3H), 7.25 (dd, J=8.9, 2.0 Hz, 1H), 6.08 (p, J=8.3 Hz, 1H), 2.32 (s, 3H). Column: DZ-CHIRALPAK IG-3, 4.6*50 mm, 3.0 μm; Mobile Phase A: Hex (0.2% DEA):EtOH=90:10; Flow rate: 1 mL/min; Gradient: 0% B to 0% B; Injection Volume: 5 mL Example 135: Preparation of Compound 195 and 196

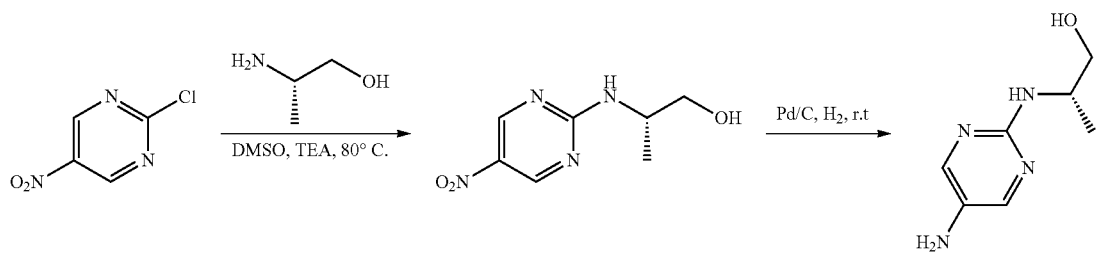

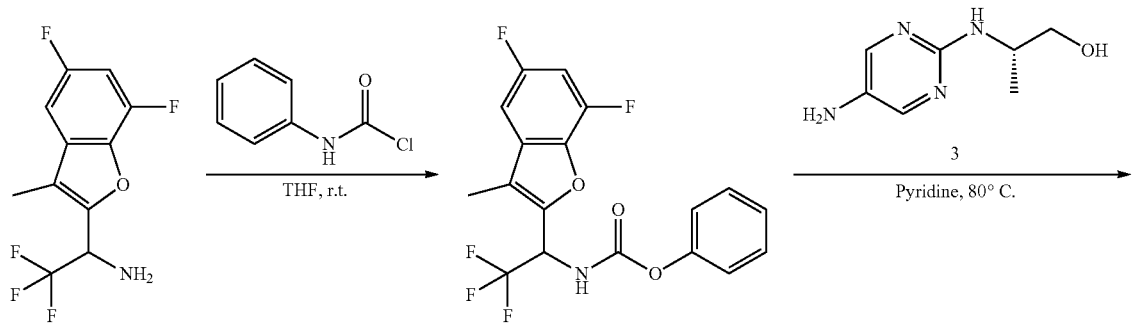

-continued

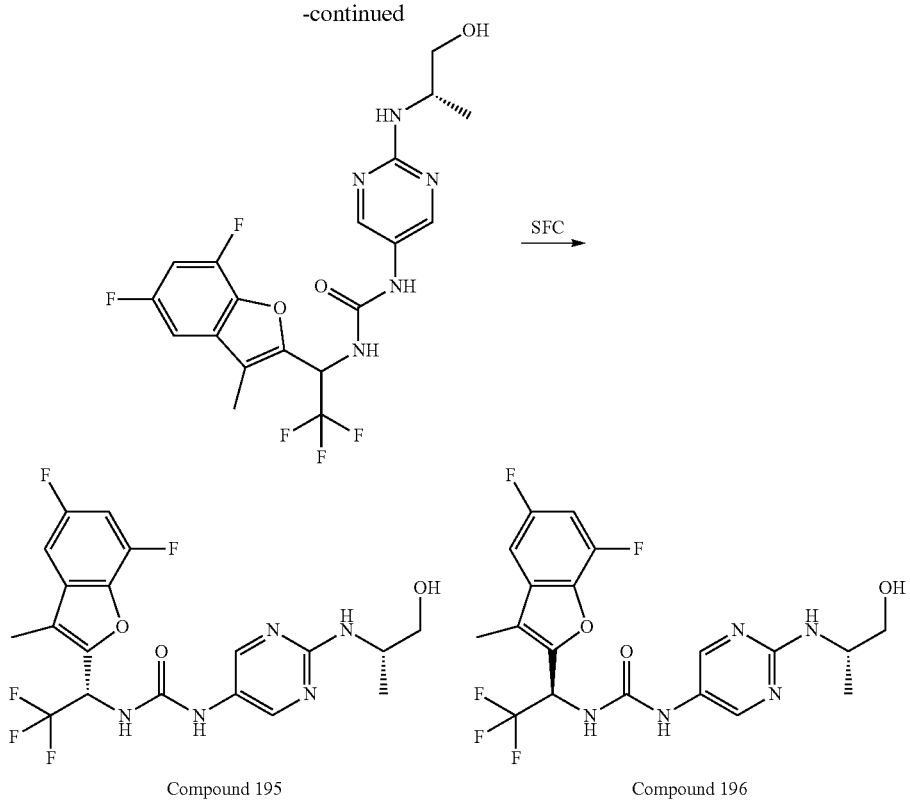

Step 1

To a stirred solution of 2-chloro-5-nitropyrimidine (200 mg, 1.254 mmol, 1 equiv) and (2S)-2-aminopropan-1-ol (141.25 mg, 1.881 mmol, 1.5 equiv) in DMSO (4 mL) was added TEA (380.59 mg, 3.762 mmol, 3 equiv) dropwise at room temperature under air atmosphere. The resulting mixture was stirred for 2 h at 80° C. under nitrogen atmosphere. The resulting mixture was extracted with EtOAc (2×10 mL). The combined organic layers were washed with brine (4×1 20 mL), dried over anhydrous $Na_2SO_4$. After filtration, the filtrate was concentrated under reduced pressure. The residue was purified by Prep-TLC (PE/EA 1:1). The resulting mixture was concentrated under reduced pressure to afford (2S)-2-[(5-nitropyrimidin-2-yl) amino] propan-1-ol (160 mg, 64.40%) as a light yellow solid. MS (ESI): mass calcd. for $C_7H_{10}N_4O_3$, 198.1, m/z found 199.2 $[M+H]^+$.

Step 2

To a solution of (2S)-2-[(5-nitropyrimidin-2-yl) amino] propan-1-ol (100 mg, 0.505 mmol, 1 equiv) in 5 mL EtOAc was added Pd/C (10%, 0.01 g) under nitrogen atmosphere in a 50 mL round-bottom flask. The mixture was hydrogenated at room temperature for 3 h under hydrogen atmosphere using a hydrogen balloon, filtered through a Celite pad and concentrated under reduced pressure to afford (2S)-2-[(5-aminopyrimidin-2-yl) amino] propan-1-ol (90 mg, 84.83%) as a yellow oil.

MS (ESI): mass calcd. for $C_7H_{12}N_4O$, 168.1, m/z found 169.3 $[M+H]^+$.

Step 3

A solution of 1-(5,7-difluoro-3-methyl-1-benzofuran-2-yl)-2,2,2-trifluoroethanamine (150 mg, 0.566 mmol, 1 equiv) and phenyl chloroformate (97.42 mg, 0.623 mmol, 1.1 equiv) in THF (5 mL, 61.714 mmol) was stirred for 1 h at room temperature under nitrogen atmosphere. The resulting mixture was concentrated under reduced pressure to afford phenyl N-[1-(5,7-difluoro-3-methyl-1-benzofuran-2-yl)-2,2,2-trifluoroethyl] carbamate as a Brown yellow solid. MS (ESI): mass calcd. for $C_{18}H_{12}F_5NO_3$, 385.1, m/z found 386.2 $[M+H]^+$.

Step 4

A solution of phenyl N-[1-(5,7-difluoro-3-methyl-1-benzofuran-2-yl)-2,2,2-trifluoroethyl]carbamate (160 mg, 0.415 mmol, 1 equiv) and (2S)-2-[(5-aminopyrimidin-2-yl)amino] propan-1-ol (76.83 mg, 0.457 mmol, 1.1 equiv) in Pyridine (10 mL) was stirred for 3 h at 80° C. under nitrogen atmosphere. The resulting mixture was extracted with EtOAc (2×20 mL). The combined organic layers were washed with brine (5×1 40 mL), dried over anhydrous $Na_2SO_4$. After filtration, the filtrate was concentrated under reduced pressure. The residue was purified by reverse flash chromatography with the following conditions: column, silica gel; mobile phase, MeCN in water, 10% to 50% gradient in 10 min; detector, UV 254 nm. The resulting mixture was concentrated under reduced pressure to afford 1-(1-(5,7-difluoro-3-methylbenzofuran-2-yl)-2,2,2-trifluoroethyl)-3-(2-(((S)-1-hydroxypropan-2-yl)amino)pyrimidin-5-yl)urea (110 mg) as a pink oil. MS (ESI): mass calcd. for $C_{19}H_{18}F_5N_5O_3$, 459.1, m/z found 460.1 $[M+H]^+$.

Step 5

110 mg of racemic was separated by SFC to give (Compound 195, 36.7 mg) as white solid and (Compound 196, 31.0 mg) as white solid. Chiral separation conditions: Apparatus: SFC 80; Column: DZ-CHIRALPAK IC-3, 4.6*50 mm, 3.0 μm; Mobile Phase A: Hex (0.2% DEA):EtOH=90:10; Flow rate: 1 mL/min; Gradient: 0% B to 0% B; Injection Volume: 5 mL.

Compound 195

MS (ESI): mass calcd. for $C_{19}H_{18}F_5N_5O_3$, 459.1, m/z found 460.1 [M+H]$^+$.

$^1$H NMR (400 MHz, DMSO-d6) δ 8.23 (d, J=16.8 Hz, 3H), 7.81 (d, J=9.4 Hz, 1H), 7.47-7.37 (m, 2H), 6.59 (d, J=8.0 Hz, 1H), 6.07-6.01 (m, 1H), 4.64 (s, 1H), 3.88 (dt, J=13.3, 6.6 Hz, 1H), 2.30 (s, 3H), 1.10 (d, J=6.6 Hz, 3H).

Compound 196

MS (ESI): mass calcd. for $C_{19}H_{18}F_5N_5O_3$, 459.1, m/z found 460.1 [M+H]$^+$.

$^1$H NMR (400 MHz, DMSO-d6) δ 8.23 (d, J=16.5 Hz, 3H), 7.81 (d, J=9.5 Hz, 1H), 7.47-7.40 (m, 2H), 6.59 (d, J=8.1 Hz, 1H), 6.04 (p, J=8.2 Hz, 2H), 4.64 (s, 1H), 3.88 (dt, J=13.2, 6.5 Hz, 1H), 2.30 (s, 3H), 1.10 (d, J=6.6 Hz, 3H).

Example 136: Preparation of Compound 197 and 198

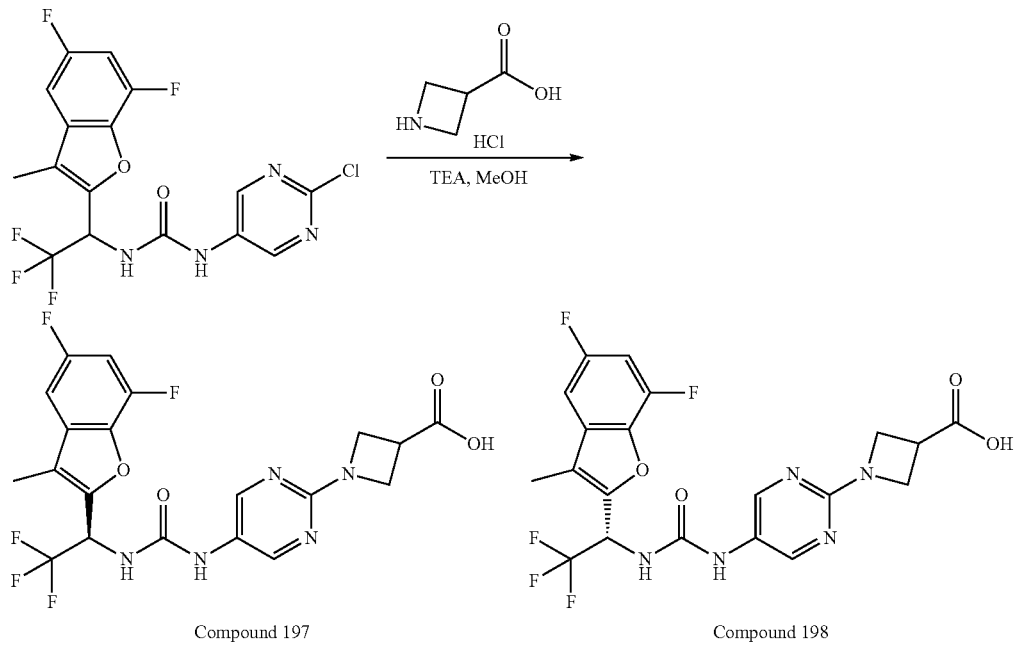

Compound 197

Compound 198

To a stirred solution of 1-(2-chloropyrimidin-5-yl)-3-[1-(5,7-difluoro-3-methyl-1-benzofuran-2-yl)-2,2,2-trifluoroethyl]urea (200 mg, 0.5 mmol) and methyl azetidine-3-carboxylate hydrochloride (144 mg, 1.0 mmol) in MeOH (4 mL) was added TEA (2 mL) dropwise at room temperature under nitrogen atmosphere. The resulting mixture was stirred for overnight at 60° C. under nitrogen atmosphere. The resulting mixture was concentrated under reduced pressure. The residue was purified by reverse flash chromatography with the following conditions: mobile phase, MeCN in water, 10% to 50% gradient in 30 min; detector, UV 254 nm to afford methyl 1-[5-({[1-(5,7-difluoro-3-methyl-1-benzofuran-2-yl)-2,2,2-trifluoroethyl]carbamoyl}amino)pyrimidin-2-yl]azetidine-3-carboxylate (100 mg, 42.1%) as a white solid and 1-[5-({[1-(5,7-difluoro-3-methyl-1-benzofuran-2-yl)-2,2,2-trifluoroethyl]carbamoyl}amino)pyrimidin-2-yl]azetidine-3-carboxylic acid (70 mg, 60.7%) as a white solid. 70 mg of racemic was separated by CHIRAL-HPLC to give (Compound 197, 29.4 mg) as white solid and (Compound 198, 26.9 mg) as white solid.

Chiral Separation Conditions:
Apparatus: Prep-HPLC-072
Column: (R, R)-WHELK-O1-Kromasil, 2.12*25 cm, 5 μm
Mobile phase: Hex (0.1% TFA):(EtOH:DCM=1:1)=80:20
Flow rate: 20 mL/min
Wavelength: UV 254 nm
Temperature: 25° C.

Compound 197

MS (ESI): mass calcd. for $C_{20}H_{16}F_5N_5O_4$, 485.11, m/z found 486.05 [M+H]$^+$.

$^1$H NMR (400 MHz, DMSO-d$_6$) δ 12.58 (brs, 1H), 8.40 (s, 3H), 7.86 (d, J=9.4 Hz, 1H), 7.53-7.36 (m, 2H), 6.06 (p, J=8.3 Hz, 1H), 4.17 (t, J=8.6 Hz, 2H), 4.03 (dd, J=8.5, 5.8 Hz, 2H), 3.52-3.45 (m, 1H), 2.30 (s, 3H).

Compound 198

MS (ESI): mass calcd. for $C_{20}H_{16}F_5N_5O_4$, 485.11, m/z found 486.00 [M+H]$^+$.

$^1$H NMR (400 MHz, DMSO-d6) δ 12.61 (brs, 1H), 8.40 (s, 3H), 7.85 (d, J=9.4 Hz, 1H), 7.51-7.36 (m, 2H), 6.06 (p, J=8.3 Hz, 1H), 4.17 (t, J=8.6 Hz, 2H), 4.03 (dd, J=8.4, 5.8 Hz, 2H), 3.53-3.45 (m, 1H), 2.30 (s, 3H).

Example 137: Preparation of Compound 199 and 200

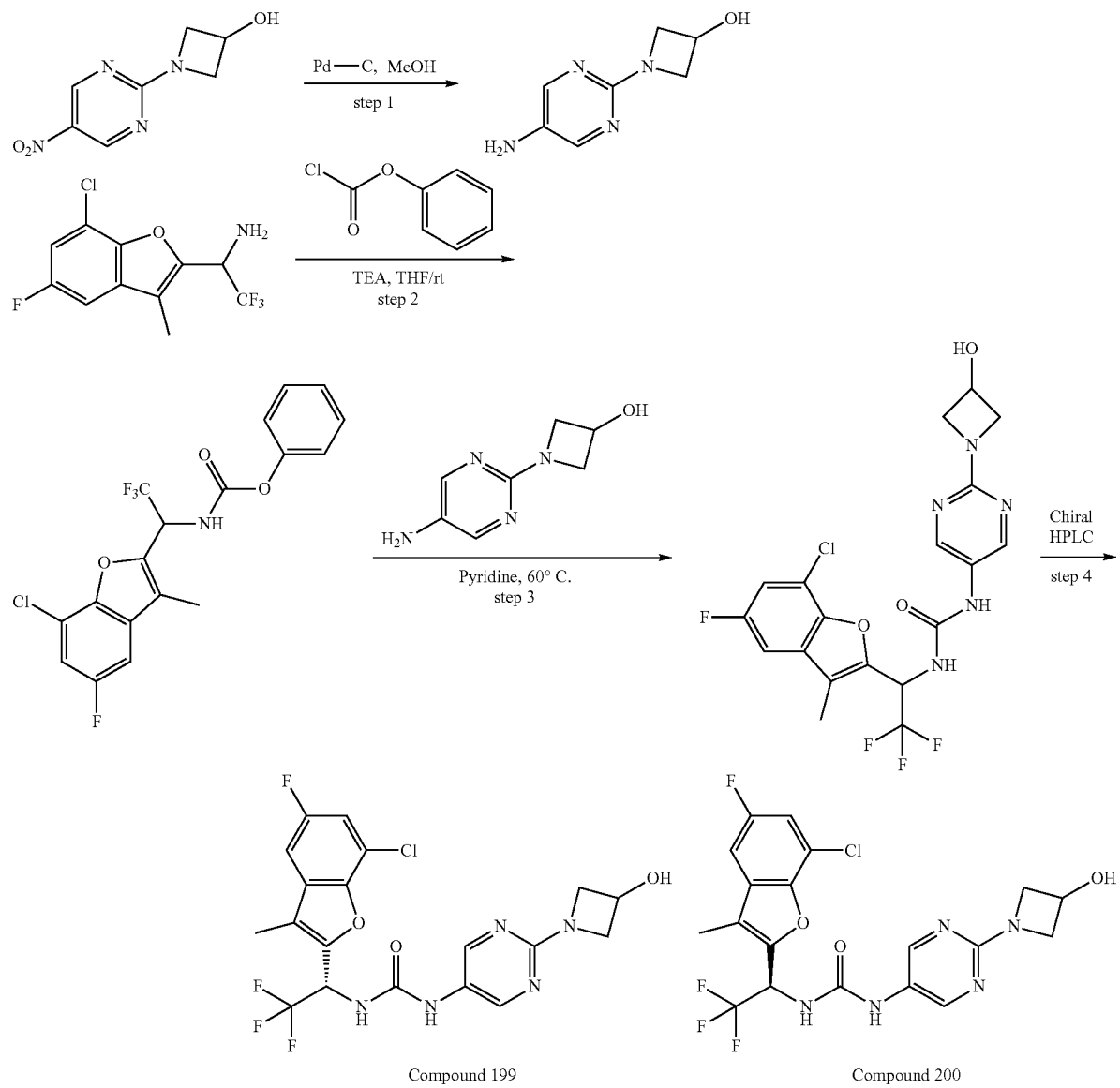

Step 1

A solution of 1-(5-nitropyrimidin-2-yl) azetidin-3-ol (170 mg, 0.87 mmol, 1 equiv) and Pd/C (51.65 mg, 0.49 mmol, 0.56 equiv) in MeOH (6 mL) was stirred for 3 h at room temperature. After the reaction was completed, the solid as filtrated. The solution was concentrated under reduced pressure to get the crude product. The residue was purified by reserved-flash to get 1-(5-aminopyrimidin-2-yl) azetidin-3-ol (138 mg, 95.82%) yellow solid as product.

Step 2

A solution of 1-(7-chloro-5-fluoro-3-methyl-1-benzofuran-2-yl)-2,2,2-trifluoroethanamine (200 mg, 0.71 mmol, 1 equiv), phenyl chloroformate (111.19 mg, 0.71 mmol, 1 equiv) and TEA (107.79 mg, 1.07 mmol, 1.5 equiv) in THF (5 mL) was stirred for 3 h at room temperature. After the reaction was completed, the mixture was concentrated under vacuum to get the crude. The residue was purified by reserved-flash to get phenyl N-[1-(7-chloro-5-fluoro-3-methyl-1-benzofuran-2-yl)-2,2,2-trifluoroethyl]carbamate (157 mg, 55.03%) colorless semi-solid as product.

Step 3

A solution of phenyl N-[1-(7-chloro-5-fluoro-3-methyl-1-benzofuran-2-yl)-2,2,2-trifluoroethyl]carbamate (157 mg, 0.39 mmol, 1 equiv) and 1-(5-aminopyrimidin-2-yl) azetidin-3-ol (97.42 mg, 0.59 mmol, 1.5 equiv) in pyridine (5 mL) was stirred for 3 h at 60° C. After the reaction was completed, the solvent was concentrated. The mixture was purified by reserved-flash to get 3-[1-(7-chloro-5-fluoro-3-methyl-1-benzofuran-2-yl)-2,2,2-trifluoroethyl]-1-[2-(3-hy droxyazetidin-1-yl) pyrimidin-5-yl] urea (50 mg, 27.00%) yellow solid as product. MS (ESI): mass calcd. for $C_{19}H_{16}ClF_4N_5O_3$, 473.1, m/z found 474.2 [M+H]$^+$.

Step 4

50 mg of racemic was separated by SFC to give (Compound 199, 17.2 mg) as a white solid and (Compound 200, 15.6 mg) as a white solid.

Chiral Separation Conditions:

Apparatus: Prep-Chiral-HPLC

Column: CHIRALPAK IC, 2*25 cm, 5 μm; Mobile Phase A: Hex (0.5% 2M NH$_3$-MeOH)-HPLC, Mobile Phase B: EtOH-HPLC; Flow rate: 20 mL/min; Gradient: 15% B to 15% B in 13 min; Wave Length: 220/254 nm; RT1 (min): 7.973; RT2 (min): 10.255; Sample Solvent: EtOH:DCM=1: 1-HPLC; Injection Volume: 0.6 mL; Number Of Runs: 3.

Compound 199

MS (ESI): mass calcd. for $C_{19}H_{16}ClF_4N_5O_3$, 473.1, m/z found 474.2 [M+H]$^+$. 1H NMR (400 MHz, DMSO) δ 8.38 (d, J=16 Hz, 3H), 7.77 (d, J=9.6 Hz, 1H), 7.60-7.54 (m, 2H), 6.06 (t, J=8.4 Hz, 1H), 5.65 (d, J=6.4 Hz, 1H), 4.56-4.51 (m, 1H), 4.20-4.16 (m, 2H), 3.75-3.71 (m, 2H), 2.50 (s, 3H).

Compound 200

MS (ESI): mass calcd. for $C_{19}H_{16}ClF_4N_5O_3$, 473.1, m/z found 474.2 [M+H]$^+$. 1H NMR (400 MHz, DMSO) δ 8.38 (d, J=16 Hz, 3H), 7.77 (d, J=9.6 Hz, 1H), 7.60-7.54 (m, 2H), 6.06 (t, J=8.4 Hz, 1H), 5.65 (d, J=6.4 Hz, 1H), 4.56-4.51 (m, 1H), 4.20-4.16 (m, 2H), 3.75-3.71 (m, 2H), 2.50 (s, 3H).

Example 138: Preparation of Compound 201 and 202

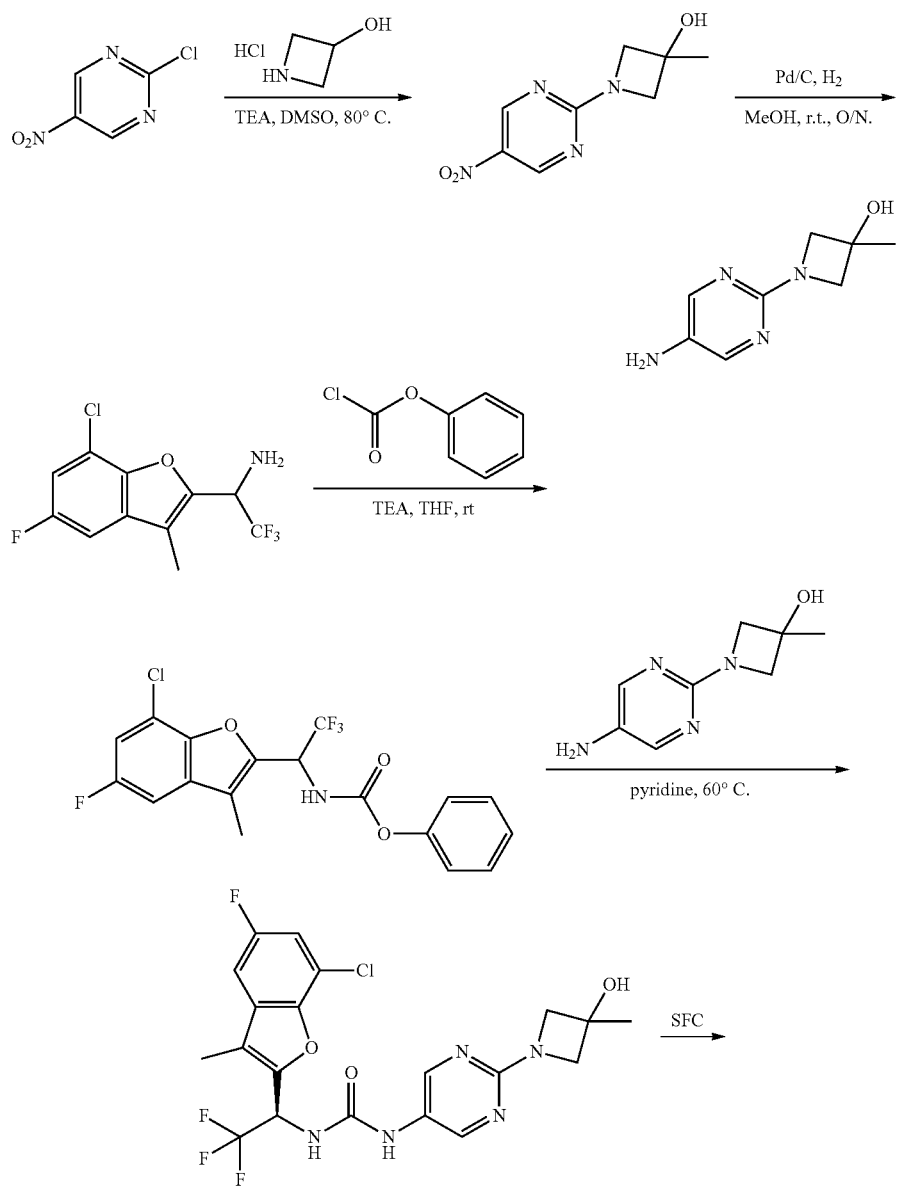

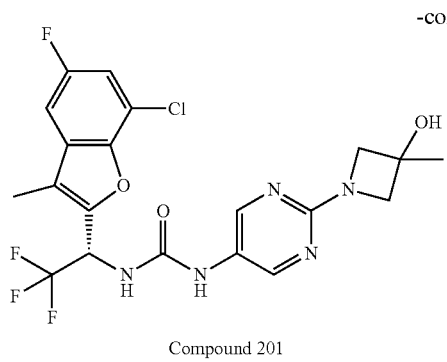

Compound 201

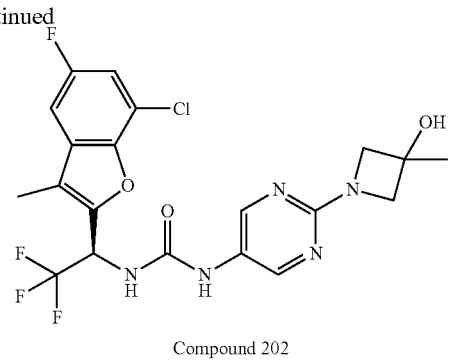

Compound 202

Step 1

A solution of 2-chloro-5-nitropyrimidine (470 mg, 2.96 mmol) in DMSO (4 mL) was added TEA (2 mL) and 3-methylazetidin-3-ol hydrochloride (550 mg, 4.43 mmol) at room temperature. The mixture was stirred at 80° C. for 2 hours. The reaction mixture was purified using flash chromatography with the following conditions (Mobile Phase A: Water, Mobile Phase B: ACN; Flow rate: 50 mL/min; Gradient: 0% B to 100% B in 40 min; 254; 220 nm). This resulted in 3-methyl-1-(5-nitropyrimidin-2-yl)azetidin-3-ol (600 mg, 96.7%) as a yellow solid. MS (ESI): mass calcd. for $C_8H_{10}N_4O_3$, 210.08, m/z found 211.1 $[M+H]^+$.

Step 2

To a solution of 3-methyl-1-(5-nitropyrimidin-2-yl)azetidin-3-ol (600 mg, 2.86 mmol) in MeOH (7 mL). The flask was evacuated and flushed three times with nitrogen. Then added Pd/C (600 mg) at room temperature. The solution was evacuated and flushed three times with nitrogen, followed by flushing with hydrogen. The mixture was stirred overnight at room temperature under an atmosphere of hydrogen (balloon). After the reaction, the solid was filtered out. The filtrate was concentrated under vacuum to afford 1-(5-aminopyrimidin-2-yl)-3-methylazetidin-3-ol (490 mg, crude) as a yellow oil. MS (ESI): mass calcd. for $C_8H_{12}N_4O$, 180.10, m/z found 181.0 $[M+H]^+$.

Step 3

A solution of 1-(7-chloro-5-fluoro-3-methylbenzofuran-2-yl)-2,2,2-trifluoroethan-1-amine (200 mg, 0.71 mmol) in THF (4 mL) was added phenyl carbonochloridate (156 mg, 0.85 mmol) and TEA (144 mg, 1.42 mmol) at room temperature. the mixture was stirred at room temperature for 1 hour. The resulting solution was extracted with 3×50 mL of DCM. The organic layers were combined, dried, and concentrated under vacuum to afford phenyl (1-(7-chloro-5-fluoro-3-methylbenzofuran-2-yl)-2,2,2-trifluoroethyl)carbamate (185 mg, crude) as yellow solid. MS (ESI): mass calcd. for $C_{18}H_{12}ClF_4NO_3$, 401.04, m/z found 402.0 $[M+H]^+$.

Step 4

A solution of phenyl (1-(7-chloro-5-fluoro-3-methylbenzofuran-2-yl)-2,2,2-trifluoroethyl)carbamate (185 mg, 0.46 mol) in pyridine (3 mL) was added 1-(5-aminopyrimidin-2-yl)-3-methylazetidin-3-ol (84 mg, 0.46 mmol) at room temperature. The mixture was stirred at 60° C. overnight. The reaction mixture concentrated under vacuum. The crude product was soluble in the ACN and purified using flash chromatography with the following conditions (Mobile Phase A: Water, Mobile Phase B: ACN; Flow rate: 55 mL/min; Gradient: 0% B to 100% B in 30 min; 254; 220 nm). This resulted in 1-(1-(7-chloro-5-fluoro-3-methylbenzofuran-2-yl)-2,2,2-trifluoroethyl)-3-(2-(3-hydroxy-3-methylazetidin-1-yl)pyrimidin-5-yl)urea (72 mg, 31.7%) as a yellow solid. MS (ESI): mass calcd. for $C_{20}H_{18}ClF_4N_5O_3$, 487.10, m/z found 488.1 $[M+H]^+$.

Step 5

72 mg of racemic was separated by SFC to give (Compound 201, 20.0 mg) as white solid and (Compound 202, 21.6 mg) as white solid.

Chiral Separation Conditions:

Column: CHIRALPAK IC, 2*25 cm, 5 μm; Mobile Phase A: Hex (0.5% 2M $NH_3$-MeOH), Mobile Phase B: EtOH; Flow rate: 20 mL/min; Gradient: 15% B to 15% B in 9 min; Wave Length: 220/254 nm; RT1 (min): 6.323; RT2 (min): 8.471.

Compound 201

MS (ESI): mass calcd. for $C_{20}H_{18}ClF_4N_5O_3$, 487.10, m/z found 488.1 $[M+H]^+$.

$^1$H NMR (400 MHz, DMSO) δ 8.39 (d, J=16.7 Hz, 3H), 7.77 (d, J=9.4 Hz, 1H), 7.66-7.48 (m, 2H), 6.06 (p, J=8.3, 8.3, 8.5, 8.5 Hz, 1H), 5.56 (s, 1H), 3.96-3.73 (m, 4H), 2.30 (s, 3H), 1.42 (s, 3H).

Compound 202

MS (ESI): mass calcd. for $C_{20}H_{18}ClF_4N_5O_3$, 487.10, m/z found 488.1 $[M+H]^+$.

$^1$H NMR (400 MHz, DMSO) δ 8.39 (d, J=19.2 Hz, 3H), 7.77 (d, J=9.4 Hz, 1H), 7.57 (ddd, J=2.5, 8.7, 11.6 Hz, 2H), 6.06 (p, J=8.3, 8.3, 8.5, 8.5 Hz, 1H), 5.56 (s, 1H), 3.84 (d, J=1.9 Hz, 4H), 2.30 (s, 3H), 1.42 (s, 3H).

Example 139: Preparation of Compound 203 and 204

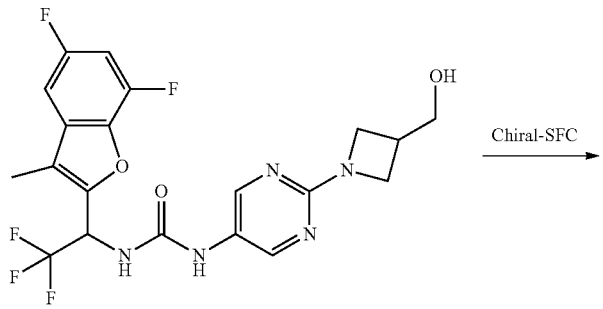

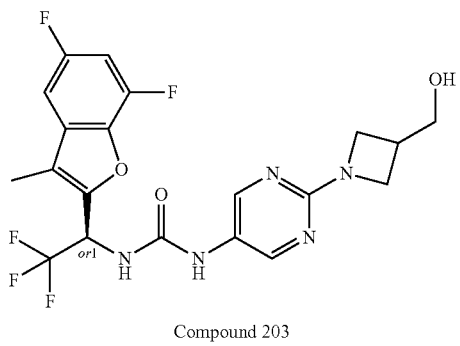

Compound 203

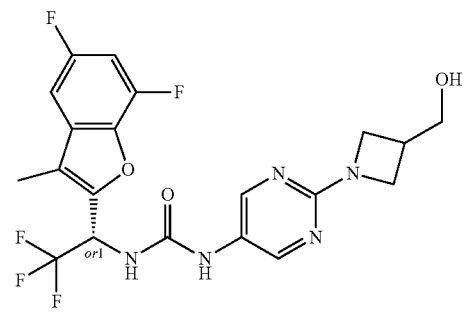

Compound 204

84 mg of racemic was separated by SFC to give (Compound 203, 21.6 mg) as white solid and (Compound 204, 23.8 mg) as white solid.

Chiral Separation Conditions:
Apparatus: Prep-HPLC-072
Column: CHIRALPAK ID, 2*25 cm, 5 μm
Mobile phase: Hex (0.2% DEA):EtOH=80:20
Flow rate: 20 mL/min
Wavelength: UV 220/254 nm
Temperature: 25° C.

Compound 203

MS (ESI): mass calcd. for $C_{20}H_{18}F_5N_5O_3$, 471.13, m/z found 472.05 [M+H]$^+$.

$^1$H NMR (400 MHz, DMSO-d6) δ 8.35 (s, 3H), 7.83 (d, J=9.4 Hz, 1H), 7.50-7.37 (m, 2H), 6.12-5.97 (m, 1H), 3.99 (t, J=8.3 Hz, 2H), 3.76-3.67 (m, 2H), 3.56 (d, J=6.2 Hz, 2H), 2.82-2.65 (m, 1H), 2.30 (s, 3H).

Compound 204

MS (ESI): mass calcd. for $C_{20}H_{18}F_5N_5O_3$, 471.13, m/z found 472.05 [M+H]$^+$.

$^1$H NMR (400 MHz, DMSO-d$_6$) δ 8.34 (s, 3H), 7.83 (d, J=9.4 Hz, 1H), 7.52-7.36 (m, 2H), 6.14-5.99 (m, 1H), 4.75 (s, 1H), 3.98 (t, J=8.3 Hz, 2H), 3.78-3.67 (m, 2H), 3.56 (d, J=6.3 Hz, 2H), 2.80-2.69 (m, 1H), 2.30 (s, 3H).

Example 140: Preparation of Compound 205 and 206

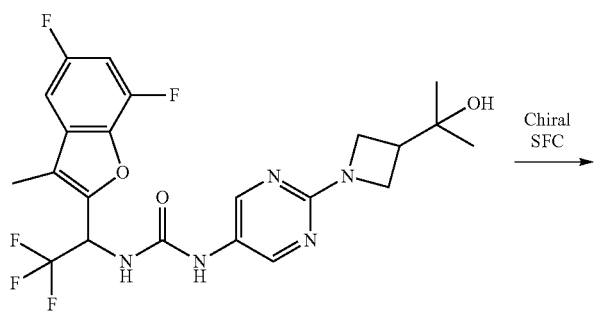

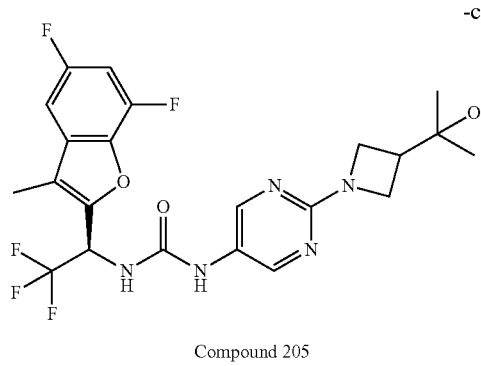

Compound 205

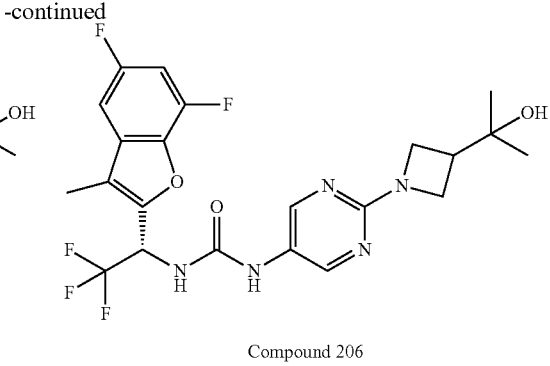

Compound 206

100 mg of racemic was separated by CHIRAL-HPLC to give (Compound 205, 44.5 mg) as white solid and (Compound 206, 44.7 mg) as white solid.
Chiral Separation Conditions:
Apparatus: Prep-HPLC-072
Column: CHIRALPAK ID, 2*25 cm, 5 μm
Mobile phase: Hex (0.2% DEA):EtOH=80:20
Flow rate: 20 mL/min
Wavelength: UV 254 nm
Temperature: 25° C.

Compound 205

MS (ESI): mass calcd. for $C_{22}H_{22}F_5N_5O_3$, 499.16, m/z found 500.10 [M+H]$^+$. H NMR (400 MHz, DMSO-d$_6$) δ 8.33 (s, 2H), 8.31 (s, 1H), 7.82 (d, J=9.4 Hz, 1H), 7.48-7.37 (m, 2H), 6.12-5.99 (m, 1H), 4.44 (s, 1H), 3.92-3.83 (m, 4H), 2.70-2.58 (m, 1H), 2.30 (s, 3H), 1.05 (s, 6H).

Compound 206

MS (ESI): mass calcd. for $C_{22}H_{22}F_5N_5O_3$, 499.16, m/z found 500.15 [M+H]$^+$. H NMR (400 MHz, DMSO-d6) δ 8.33 (s, 2H), 8.31 (s, 1H), 7.82 (d, J=9.4 Hz, 1H), 7.52-7.34 (m, 2H), 6.17-5.95 (m, 1H), 4.44 (s, 1H), 3.94-3.83 (m, 4H), 2.71-2.56 (m, 1H), 2.30 (s, 3H), 1.05 (s, 6H).

Example 141: Preparation of Compound 207 and 208

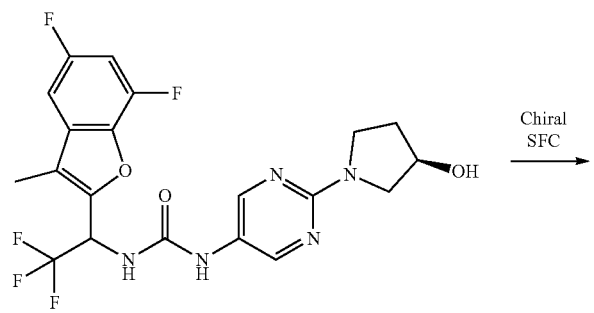

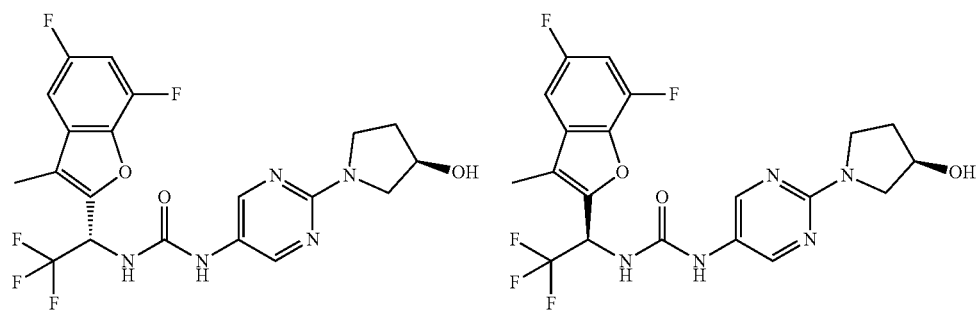

Compound 207

Compound 208

50 mg of racemic was separated by CHIRAL-HPLC to give (Compound 207, 20.5 mg) as white solid and (Compound 208, 19.3 mg) as white solid.
Chiral Separation Conditions:
Apparatus: Prep-HPLC-037
Column: CHIRALPAK IC, 2*25 cm, 5 μm
Mobile phase: Mobile Phase A: Hex (0.5% 2M NH$_3$-MeOH)-HPLC, Mobile Phase B: EtOH:DCM=1:1-HPLC
Flow rate: 20 mL/min
Wavelength: UV 220/254 nm
Temperature: 25° C.

Compound 207

MS (ESI): mass calcd. for $C_{20}H_{18}F_5N_5O_3$, 471.13, m/z found 472.05 [M+H]$^+$.
$^1$H NMR (400 MHz, DMSO-d6) δ 8.33 (s, 2H), 8.26 (s, 1H), 7.79 (d, J=9.5 Hz, 1H), 7.48-7.35 (m, 2H), 6.05 (p, J=8.4 Hz, 1H), 4.92 (d, J=3.6 Hz, 1H), 4.35 (s, 1H), 3.59-3.44 (m, 3H), 3.39-3.36 (m, 1H), 2.30 (s, 3H), 2.03-1.94 (m, 1H), 1.88-1.87 (m, 1H).

Compound 208

MS (ESI): mass calcd. for $C_{20}H_{18}F_5N_5O_3$, 471.13, m/z found 472.05 [M+H]$^+$.
$^1$H NMR (400 MHz, DMSO-d6) δ 8.33 (s, 2H), 8.27 (s, 1H), 7.79 (d, J=9.4 Hz, 1H), 7.49-7.37 (m, 2H), 6.04 (q, J=8.4 Hz, 1H), 4.93 (d, J=3.6 Hz, 1H), 4.36 (s, 1H), 3.57-3.43 (m, 3H), 3.39-3.32 (m, 1H), 2.30 (s, 3H), 2.07-1.91 (m, 1H), 1.88-1.87 (m, 1H).

Example 142: Preparation of Compound 209 and 210

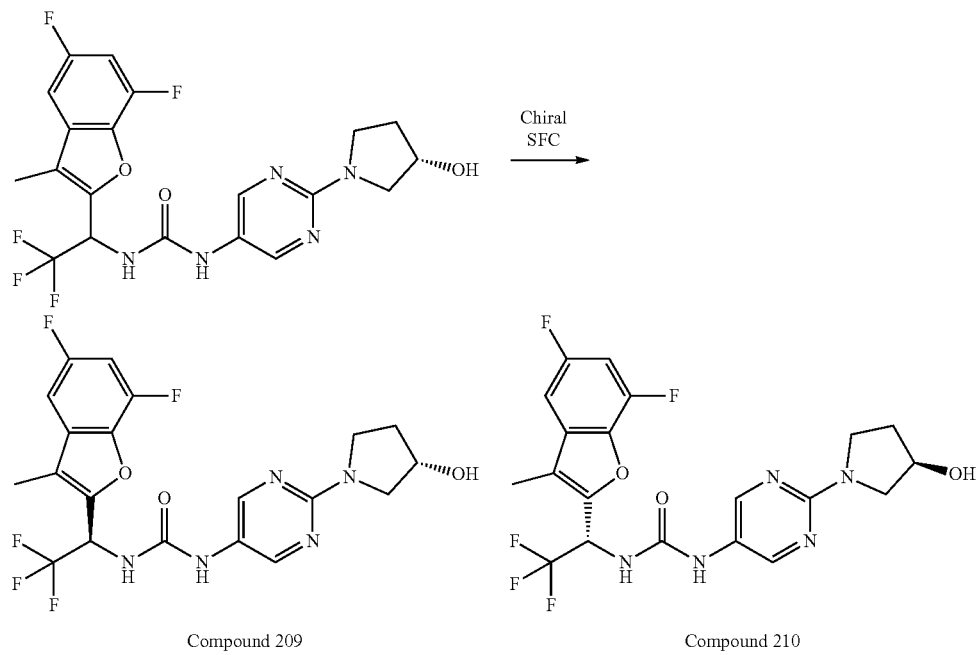

Compound 209

Compound 210

59 mg of racemic was separated by CHIRAL-HPLC to give (Compound 209, 23.2 mg) as white solid and (Compound 210, 26.4 mg) as white solid.
Chiral Separation Conditions:
Apparatus: Prep-HPLC-037
Column: CHIRALPAK IG, 2*25 cm, 5 μm
Mobile phase: Mobile Phase A: Hex (0.5% 2M NH$_3$-MeOH), Mobile Phase B: EtOH;
Flow rate: 20 mL/min
Wavelength: UV 254 nm
Temperature: 25° C.

Compound 209

MS (ESI): mass calcd. for $C_{20}H_{18}F_5N_5O_3$, 471.13, m/z found 472.15 [M+H]$^+$.
$^1$H NMR (400 MHz, DMSO-d$_6$) δ 8.33 (s, 2H), 8.26 (s, 1H), 7.79 (d, J=9.2 Hz, 1H), 7.46-7.39 (m, 2H), 6.08-6.03 (m, 1H), 4.93 (d, J=3.6 Hz, 1H), 4.38-4.34 (m, 1H), 3.54-3.47 (m, 3H), 3.40-3.37 (m, 1H), 2.30 (s, 3H), 2.01-1.95 (m, 1H), 1.89-1.88 (m, 1H).

Compound 210

MS (ESI): mass calcd. for $C_{20}H_{18}F_5N_5O_3$, 471.13, m/z found 472.15 [M+H]$^+$.

Example 143: Preparation of Compound 211 and 212

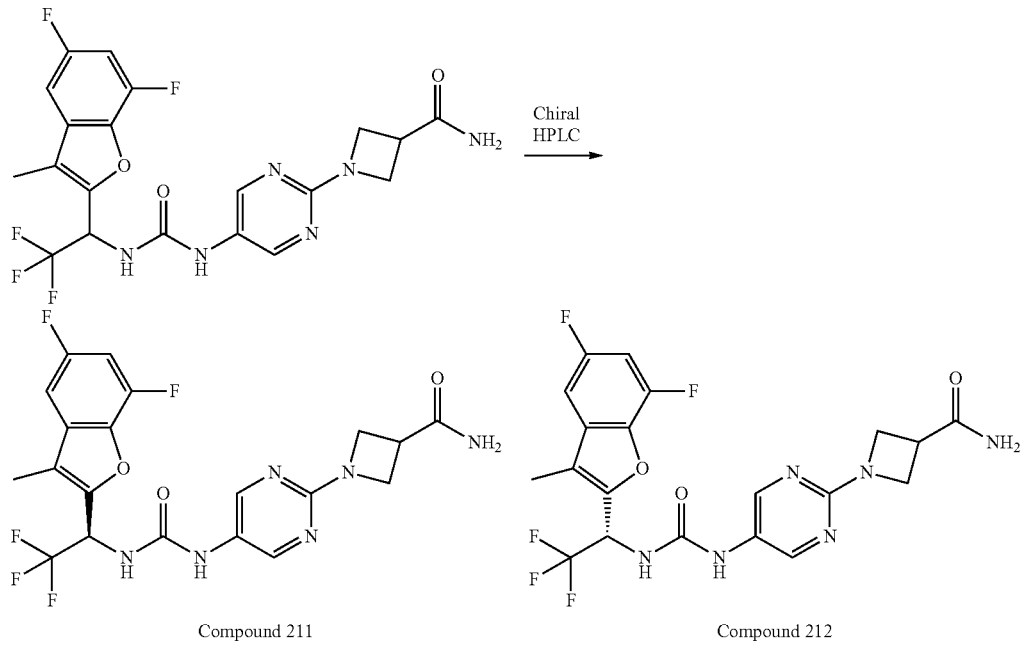

Compound 211                Compound 212

75 mg of racemic was separated by CHIRAL-HPLC to give (Compound 211, 24.5 mg) as white solid and (Compound 212, 21.2 mg) as white solid.

Chiral Separation Conditions:

Apparatus: Prep-HPLC-072

Column: CHIRALPAK IG, 2*25 cm, 5 μm

Mobile phase: Mobile Phase A: Hex (0.5% 2M $NH_3$-MeOH), Mobile Phase B: EtOH

Flow rate: 20 mL/min

Wavelength: UV 254 nm

Temperature: 25° C.

Compound 211

MS (ESI): mass calcd. for $C_{20}H_{17}F_5N_6O_3$, 484.13, m/z found 485.15 [M+H]$^+$. H NMR (400 MHz, DMSO-$d_6$) δ 8.38 (s, 3H), 7.84 (d, J=9.5 Hz, 1H), 7.54-7.36 (m, 3H), 7.02 (s, 1H), 6.06 (p, J=8.3 Hz, 1H), 4.08 (t, J=8.5 Hz, 2H), 3.99 (dd, J=8.3, 6.0 Hz, 2H), 3.44-3.36 (m, 1H), 2.30 (s, 3H).

Compound 212

MS (ESI): mass calcd. for $C_{20}H_{17}F_5N_6O_3$, 484.13, m/z found 485.15 [M+H]$^+$.

$^1$H NMR (400 MHz, DMSO-$d_6$) δ 8.38 (s, 3H), 7.84 (d, J=9.4 Hz, 1H), 7.53-7.36 (m, 3H), 7.02 (s, 1H), 6.06 (p, J=8.3 Hz, 1H), 4.08 (t, J=8.4 Hz, 2H), 3.99 (dd, J=8.3, 6.0 Hz, 2H), 3.44-3.36 (m, 1H), 2.30 (s, 3H).

Example 144: Preparation of Compound 213 and 214

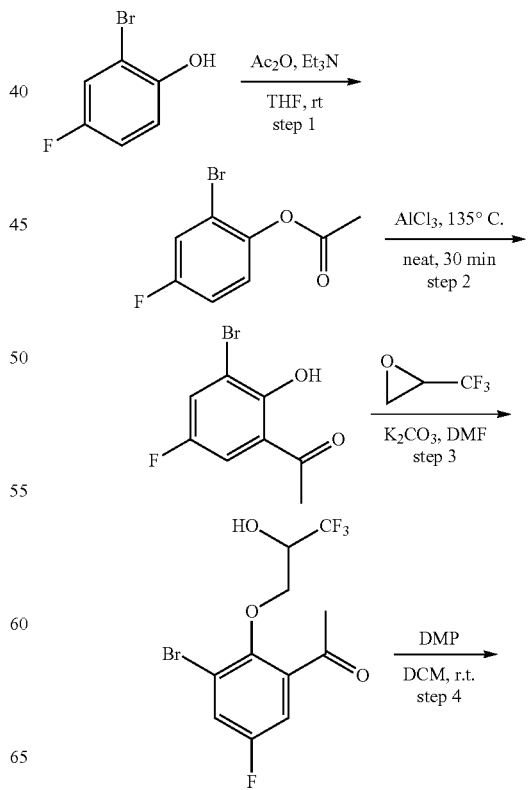

741
-continued

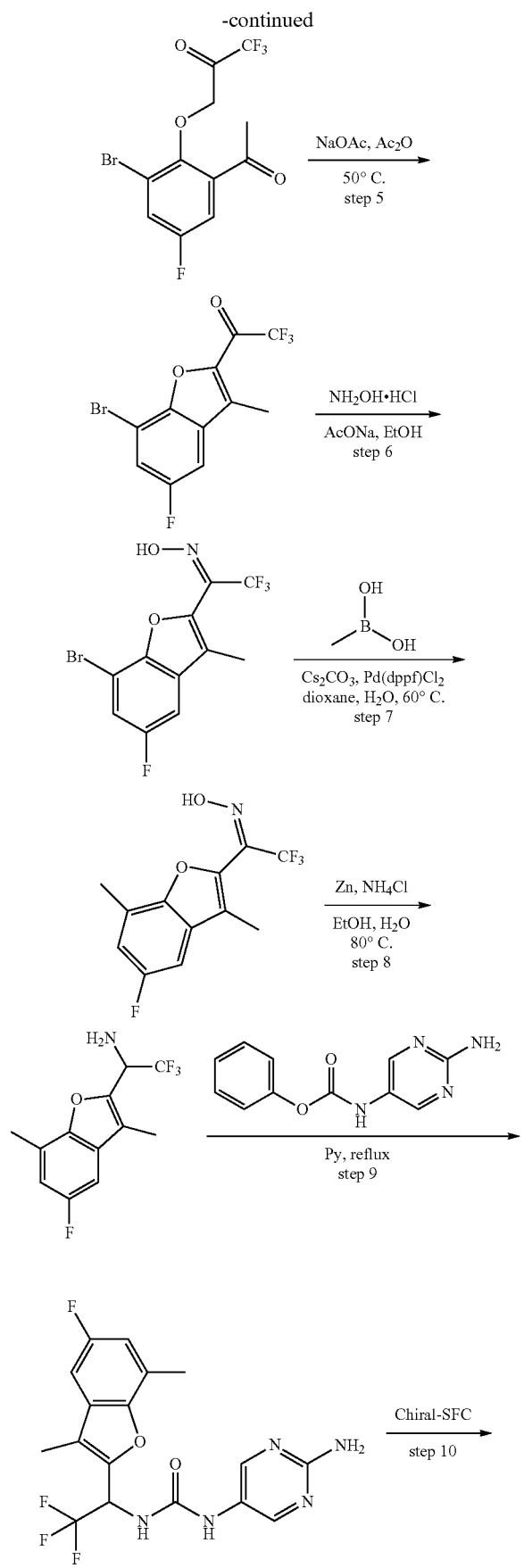

742
-continued

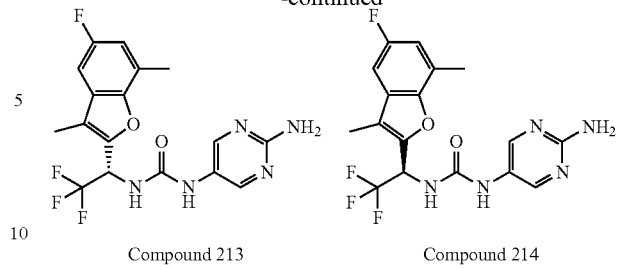

Compound 213          Compound 214

Step 1

To a stirred mixture of 2-bromo-4-fluorophenol (50 g, 261.7 mmol) and Et₃N (42.4 g, 418.9 mmol) in THF (500 mL) was added Ac₂O (40.1 g, 392.7 mmol) in portions at room temperature under nitrogen atmosphere. The resulting mixture was stirred for 1 h at room temperature under nitrogen atmosphere. The reaction was monitored by TLC. The reaction was quenched by the addition of Water (100 mL) at room temperature. The resulting mixture was extracted with EtOAc (3×200 mL). The combined organic layers were washed with brine (1×200 mL), dried over anhydrous Na₂SO₄. After filtration, the filtrate was concentrated under reduced pressure. The resulting mixture was concentrated under vacuum. This resulted in 2-bromo-4-fluorophenyl acetate (64 g, crude) as a yellow oil. The crude resulting mixture was used in the next step directly without further purification.

Step 2

Into a 100 mL round-bottom flask were added 2-bromo-4-fluorophenyl acetate (10.0 g, 42.9 mmol) and AlCl₃ (8.6 g, 64.4 mmol) at 0° C. The resulting mixture was stirred for 0.5 h at 135° C. The reaction was quenched with ice containing HCl (1M, 200 mL) at 0° C. The resulting mixture was extracted with EtOAc (3×200 mL). The combined organic layers were washed with brine (1×100 mL), dried over anhydrous Na₂SO₄. After filtration, the filtrate was concentrated under reduced pressure. The residue was purified by silica gel column chromatography, eluted with PE/EA (15:1) to afford 1-(3-bromo-5-fluoro-2-hydroxyphenyl)ethanone (8.0 g, 64.0%) as a yellow solid.

MS (ESI): mass calcd. for C₈H₆BrFO₂, 232.0, 234.0, m/z found 231.0, 232.80 [M−H]⁻.

Step 3

A solution of 1-(3-bromo-5-fluoro-2-hydroxyphenyl)ethanone (1.0 g, 4.3 mmol) and 2-(trifluoromethyl)oxirane (960 mg, 8.6 mmol) and K₂CO₃ (1.2 g, 8.6 mmol) in ACN (15 mL) was stirred for 2 h at 80° C. use sealed tube. The resulting mixture was filtered, the filter cake was washed with EtOAc (3×50 mL). The filtrate was concentrated under reduced pressure. The residue was purified by silica gel column chromatography, eluted with PE/EA (15:1) to afford 1-[3-bromo-5-fluoro-2-(3,3,3-trifluoro-2-hydroxypropoxy)phenyl]ethanone (740 mg, 49.9%) as a yellow oil. MS (ESI): mass calcd. for C₁₁H₉BrF₄O₃, 344.0, 346.0, m/z found 345.0, 346.75 [M+H]⁺.

Step 4

To a stirred solution of 1-[3-bromo-5-fluoro-2-(3,3,3-trifluoro-2-hydroxypropoxy)phenyl]ethanone (1.3 g, 3.7 mmol) in DCM (13 mL) was added DMP (1.9 g, 4.4 mmol) in portions at 0° C. under nitrogen atmosphere. The resulting mixture was stirred for overnight at room temperature under nitrogen atmosphere. The reaction was monitored by LCMS. The resulting mixture was diluted with DCM (10 mL). The residue was washed with sat. $Na_2S_2O_3$ (1×10 mL) and sat. $NaHCO_3$ (3×10 mL). The resulting mixture was concentrated under vacuum. The residue was purified by silica gel column chromatography, eluted with PE/EA (10:1) to afford 3-(2-acetyl-6-bromo-4-fluorophenoxy)-1,1,1-trifluoropropan-2-one (1.11 g, 88.1%) as a yellow oil. MS (ESI): mass calcd. for $C_{11}H_7BrF_4O_3$, 343, m/z found 344 $[M+H]^+$.

Step 5

To a stirred solution of 3-(2-acetyl-6-bromo-4-fluorophenoxy)-1,1,1-trifluoropropan-2-one (1.1 g, 3.2 mmol) in $Ac_2O$ (11 mL) was added NaOAc (398 mg, 4.9 mmol) in portions at room temperature under air atmosphere. The resulting mixture was stirred for 3 h at 50° C. under nitrogen atmosphere. The reaction was monitored by LCMS. The mixture was basified to pH 7 with saturated $NaHCO_3$ (aq.). The aqueous layer was extracted with $CH_2Cl_2$ (3×10 mL). The resulting mixture was concentrated under vacuum. The residue was purified by silica gel column chromatography, eluted with PE to afford 1-(7-bromo-5-fluoro-3-methyl-1-benzofuran-2-yl)-2,2,2-trifluoroethanone (640 mg, 60.9%) as a white solid. MS (ESI): mass calcd. for $C_{11}H_5BrF_4O_2$, 324, m/z found 323 $[M-H]^-$.

Step 6

To a stirred solution of 1-(7-bromo-5-fluoro-3-methyl-1-benzofuran-2-yl)-2,2,2-trifluoroethanone (640 mg, 2.0 mmol) and hydroxylamine hydrochloride (274 mg, 3.9 mmol) in EtOH (10 mL) was added AcONa (323 mg, 3.9 mmol) in portions at room temperature under nitrogen atmosphere. The resulting mixture was stirred for overnight at 80° C. under nitrogen atmosphere. The resulting mixture was filtered, the filter cake was washed with DCM (3×10 mL). The filtrate was concentrated under reduced pressure. The residue was purified by silica gel column chromatography, eluted with PE/DCM (1:1) to afford (E/Z)-N-[1-(7-bromo-5-fluoro-3-methyl-1-benzofuran-2-yl)-2,2,2-trifluoroethylidene]hydroxylamine (560 mg, 83.6%) as a white solid. MS (ESI): mass calcd. for $C_{11}H_6BrF_4NO_2$, 339, m/z found 338 $[M-H]^-$.

Step 7

To a stirred solution of (E)-N-[1-(7-bromo-5-fluoro-3-methyl-1-benzofuran-2-yl)-2,2,2-trifluoroethylidene]hydroxylamine (500 mg, 1.5 mmol) and methylboronic acid (265 mg, 4.4 mmol) in dioxane (10 mL) and $H_2O$ (2 mL) was added $Cs_2CO_3$ (1.4 g, 4.4 mmol) and Pd(dppf)$Cl_2 \cdot CH_2Cl_2$ (120 mg, 0.15 mmol) at room temperature under nitrogen atmosphere. The resulting mixture was stirred for overnight at 60° C. under nitrogen atmosphere. The resulting mixture was extracted with EtOAc (3×20 mL). The combined organic layers dried over anhydrous $Na_2SO_4$. After filtration, the filtrate was concentrated under reduced pressure and purified by silica gel column chromatography, eluted with DCM/PE (35:65) to afford (E/Z)-N-[2,2,2-trifluoro-1-(5-fluoro-3,7-dimethyl-1-benzofuran-2-yl)ethylidene]hydroxylamine (300 mg, 74.1%) as a white solid. MS (ESI): mass calcd. for $C_{12}H_9F_4NO_2$, 275, m/z found 274 $[M+H]^-$.

Step 8

To a stirred solution of (E/Z)-N-[2,2,2-trifluoro-1-(5-fluoro-3,7-dimethyl-1-benzofuran-2-yl) ethylidene]hydroxylamine (280 mg, 1.0 mmol) and Zn (665 mg, 10.2 mmol) and $NH_4Cl$ (544 mg, 10.2 mmol) in EtOH (5 mL) and $H_2O$ (1 mL) at room temperature under nitrogen atmosphere. The resulting mixture was stirred for overnight at 80° C. under nitrogen atmosphere. The resulting mixture was extracted with $CH_2Cl_2$ (3×20 mL). The combined organic layers were dried over anhydrous $Na_2SO_4$. After filtration, the filtrate was concentrated under reduced pressure. The residue was purified by silica gel column chromatography, eluted with $CH_2Cl_2$ to afford 2,2,2-trifluoro-1-(5-fluoro-3,7-dimethyl-1-benzofuran-2-yl)ethanamine (210 mg, 79.0%) as a colorless oil. MS (ESI): mass calcd. for $C_{12}H_{11}F_4NO$, 261, m/z found 262 $[M+H]^+$.

Step 9

To a stirred solution of 2,2,2-trifluoro-1-(5-fluoro-3,7-dimethyl-1-benzofuran-2-yl)ethanamine (190 mg, 0.7 mmol) and phenyl N-(2-aminopyrimidin-5-yl)carbamate (168 mg, 0.7 mmol) in Pyridine (7 mL) at room temperature under nitrogen atmosphere. The resulting mixture was stirred for overnight at 80° C. under nitrogen atmosphere. The resulting mixture was extracted with EtOAc (3×20 mL). The combined organic layers were dried over anhydrous $Na_2SO_4$. After filtration, the filtrate was concentrated under reduced pressure. The residue was purified by reverse flash chromatography with the following conditions: column, C18 spherical column; mobile phase, MeCN in water, 0% to 100% gradient in 30 min; detector, UV 254 nm to afford 1-(2-aminopyrimidin-5-yl)-3-[2,2,2-trifluoro-1-(5-fluoro-3,7-dimethyl-1-benzofuran-2-yl)ethyl]urea (130 mg, 45.0%) as an off-white solid. MS (ESI): mass calcd. for $C_{17}H_{15}F_4N_5O_2$, 397, m/z found 398 $[M+H]^+$.

Step 10

130 mg of racemic was separated by CHIRAL-HPLC to give (Compound 213, 32.3 mg) as white solid and (Compound 214, 34.8 mg) as white solid.
Chiral Separation Conditions:
Apparatus: Prep-HPLC-072
Column: CHIRALPAK IC, 2*25 cm, 5 μm
Mobile phase: Mobile Phase A: Hex (0.5% 2M $NH_3$-MeOH)-HPLC, Mobile Phase B: EtOH:DCM=1:1-HPLC
Flow rate: 20 mL/min
Wavelength: UV 220/254 nm
Temperature: 25° C.

Compound 213

MS (ESI): mass calcd. for $C_{17}H_{15}F_4N_5O_2$, 397.12, m/z found 398.00 $[M+H]^+$.
$^1$H NMR (400 MHz, DMSO-$d_6$) δ 8.25 (s, 1H), 8.22 (s, 1H), 7.66 (d, J=9.4 Hz, 1H), 7.31 (dd, J=8.7, 2.7 Hz, 1H), 7.13-7.09 (m, 1H), 6.40 (s, 2H), 5.97 (p, J=8.4 Hz, 1H), 2.49 (s, 3H), 2.26 (s, 3H).

Compound 214

MS (ESI): mass calcd. for $C_{17}H_{15}F_4N_5O_2$, 397.12, m/z found 398.00 $[M+H]^+$.

¹H NMR (400 MHz, DMSO-d₆) δ 8.25 (s, 1H), 8.22 (s, 1H), 7.66 (d, J=9.4 Hz, 1H), 7.31 (dd, J=8.5, 2.6 Hz, 1H), 7.13-7.09 (m, 1H), 6.40 (s, 2H), 5.97 (p, J=8.3 Hz, 1H), 2.49 (s, 3H), 2.26 (s, 3H).

Example 145: Preparation of Compound 215 and 216

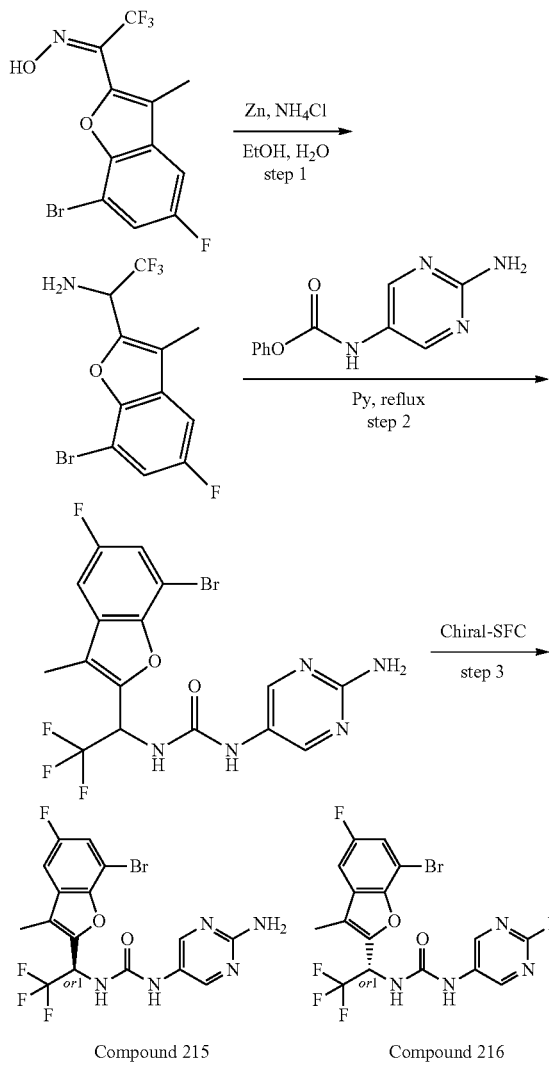

Step 1

A mixture of (E/Z)-N-[1-(7-bromo-5-fluoro-3-methyl-1-benzofuran-2-yl)-2,2,2-trifluoroethylidene] hydroxylamine (1.0 g, 2.9 mmol) and Zn (1.9 g, 29.4 mmol) and NH₄Cl (1.6 g, 29.4 mmol) in EtOH (25 mL) and H₂O (5 mL) was stirred for 2 h at 80° C. under nitrogen atmosphere. The reaction was monitored by LCMS. The resulting mixture was filtered, the filter cake was washed with DCM (3×5 mL). The filtrate was concentrated under reduced pressure. The residue was purified by silica gel column chromatography, eluted with CH₂Cl₂/PE (1:1) to afford 1-(7-bromo-5-fluoro-3-methyl-1-benzofuran-2-yl)-2,2,2-trifluoroethanamine (760 mg, 79.3%) as a colorless oil. MS (ESI): mass calcd. for C₁₁H₈BrF₄NO, 325, m/z found 309[M-NH₂]⁺.

Step 2

A solution of 1-(7-bromo-5-fluoro-3-methyl-1-benzofuran-2-yl)-2,2,2-trifluoroethanamine (740 mg, 2.3 mmol) and phenyl N-(2-aminopyrimidin-5-yl)carbamate (522 mg, 2.3 mmol) in Pyridine (7.4 mL) was stirred for 5 h at 80° C. under nitrogen atmosphere. The reaction was monitored by LCMS. The resulting mixture was diluted with water (5 mL). The resulting mixture was extracted with EtOAc (3×20 mL). The combined organic layers were dried over anhydrous Na₂SO₄. After filtration, the filtrate was concentrated under reduced pressure. The residue was purified by silica gel column chromatography, eluted with PE/EA (3:1) to afford 1-(2-aminopyrimidin-5-yl)-3-[1-(7-bromo-5-fluoro-3-methyl-1-benzofuran-2-yl)-2,2,2-trifluoroethyl]urea (458 mg, 43.7%) as a light yellow solid. MS (ESI): mass calcd. for C₁₆H₁₂BrF₄N₅O₂, 461, m/z found 462[M+H]⁺.

Step 3

130 mg of racemic was separated by CHIRAL-HPLC to give (Compound 215, 25.2 mg) as white solid and (Compound 216, 21.7 mg) as white solid.
Chiral Separation Conditions:
Apparatus: Prep-HPLC-072
Column: CHIRALPAK IC, 2*25 cm, 5 μm
Mobile phase: Mobile Phase A: Hex (0.5% 2M NH₃-MeOH)-HPLC, Mobile Phase B: EtOH-HPLC
Flow rate: 20 mL/min
Wavelength: UV 220/254 nm
Temperature: 25° C.

Compound 215

MS (ESI): mass calcd. for C₁₆H₁₂BrF₄N₅O₂, 461.01, m/z found 462.05 [M+H]⁺.
¹H NMR (400 MHz, DMSO-d₆) δ 8.36 (s, 1H), 8.22 (s, 2H), 7.78 (d, J=9.4 Hz, 1H), 7.66-7.59 (m, 2H), 6.40 (s, 2H), 6.04 (p, J=8.3 Hz, 1H), 2.29 (s, 3H).

Compound 216

MS (ESI): mass calcd. for C₁₆H₁₂BrF₄N₅O₂, 461.01, m/z found 462.05[M+H]⁺.
¹H NMR (400 MHz, DMSO-d₆) δ 8.30 (s, 1H), 8.22 (s, 2H), 7.74 (d, J=9.4 Hz, 1H), 7.63 (ddd, J=16.4, 8.6, 2.5 Hz, 2H), 6.41 (s, 2H), 6.04 (p, J=8.3 Hz, 1H), 2.29 (s, 3H).

Example 146: Preparation of Compound 217 and 218

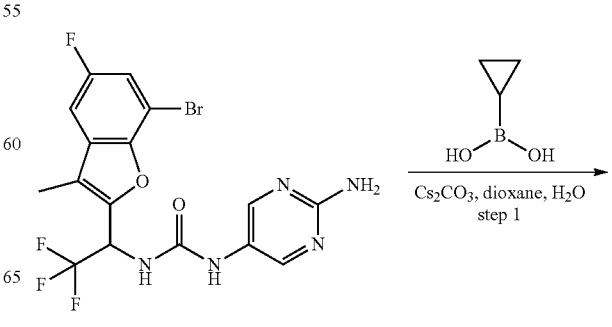

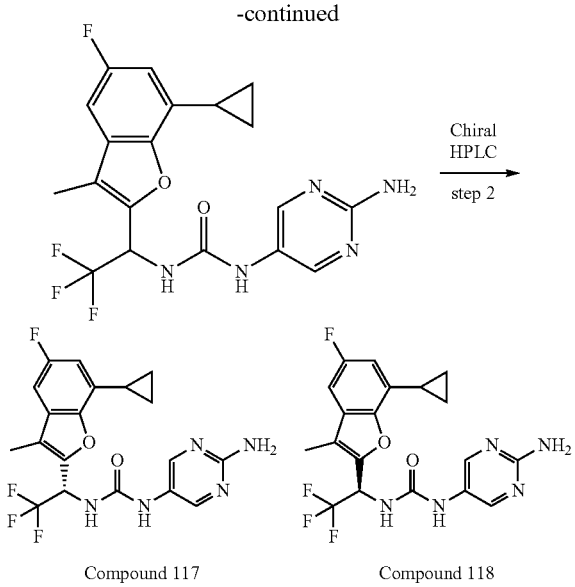

Compound 117　　　　Compound 118

Step 1

To a stirred solution of 1-(2-aminopyrimidin-5-yl)-3-[1-(7-bromo-5-fluoro-3-methyl-1-benzofuran-2-yl)-2,2,2-trifluoroethyl]urea (100 mg, 0.2 mmol) and cyclopropylboronic acid (56 mg, 0.6 mmol) in dioxane (2 mL) and $H_2O$ (0.4 mL) were added $Cs_2CO_3$ (2.1 g, 0.6 mmol) and Pd(dppf)$Cl_2CH_2Cl_2$ (36 mg, 0.04 mmol) in portions at room temperature under nitrogen atmosphere. The resulting mixture was stirred for overnight at 60° C. under nitrogen atmosphere. The resulting mixture was extracted with EtOAc (3×20 mL). The combined organic layers were dried over anhydrous $Na_2SO_4$. After filtration, the filtrate was concentrated under reduced pressure. The residue was purified by reverse flash chromatography with the following conditions: column, C18 spherical column; mobile phase, MeCN in water, 10% to 50% gradient in 10 min; detector, UV 254 nm to afford 1-(2-aminopyrimidin-5-yl)-3-[1-(7-cyclopropyl-5-fluoro-3-methyl-1-benzofuran-2-yl)-2,2,2-trifluoroethyl]urea (55 mg, 60.0%) as a off-white solid. MS (ESI): mass calcd. for $C_{19}H_{17}F_4N_5O_2$, 423, m/z found 424[M+H]$^+$.

Step 2

55 mg of racemic was separated by CHIRAL-HPLC to give (Compound 117, 16.3 mg) as white solid and (Compound 118, 16.2 mg) as white solid.

Chiral Separation Conditions:
Apparatus: Prep-HPLC-072
Column: CHIRALPAK IC, 2*25 cm, 5 μm
Mobile phase: Mobile Phase A: Hex (0.5% 2M $NH_3$-MeOH)-HPLC, Mobile Phase B: EtOH-HPLC
Flow rate: 20 mL/min
Wavelength: UV 220/254 nm
Temperature: 25° C.

Compound 117

MS (ESI): mass calcd. for $C_{19}H_{17}F_4N_5O_2$, 423.13, m/z found 424.05 [M+H]$^+$.

$^1$H NMR (400 MHz, DMSO-$d_6$) δ 8.27 (s, 1H), 8.23 (s, 2H), 7.62 (d, J=9.4 Hz, 1H), 7.23 (dd, J=8.4, 2.6 Hz, 1H), 6.84 (dd, J=10.7, 2.6 Hz, 1H), 6.39 (s, 2H), 5.97 (p, J=8.4 Hz, 1H), 2.34-2.24 (m, 4H), 1.19-1.06 (m, 2H), 1.04-0.87 (m, 2H).

Compound 118

MS (ESI): mass calcd. for $C_{19}H_{17}F_4N_5O_2$, 423.13, m/z found 424.00 [M+H]$^+$.

$^1$H NMR (400 MHz, DMSO-$d_6$) δ8.27 (s, 1H), 8.23 (s, 2H), 7.62 (d, J=9.4 Hz, 1H), 7.23 (dd, J=8.4, 2.6 Hz, 1H), 6.84 (dd, J=10.7, 2.6 Hz, 1H), 6.39 (s, 2H), 5.97 (p, J=8.4 Hz, 1H), 2.34-2.24 (m, 4H), 1.19-1.06 (m, 2H), 1.04-0.87 (m, 2H).

Example 147: Preparation of Compound 219 and 220

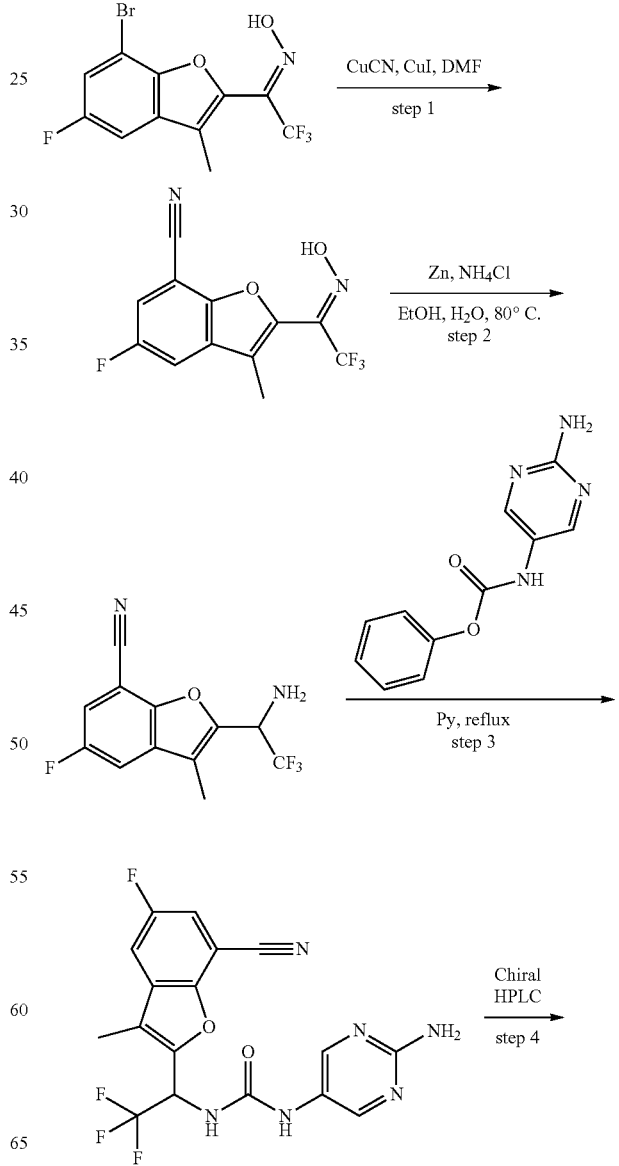

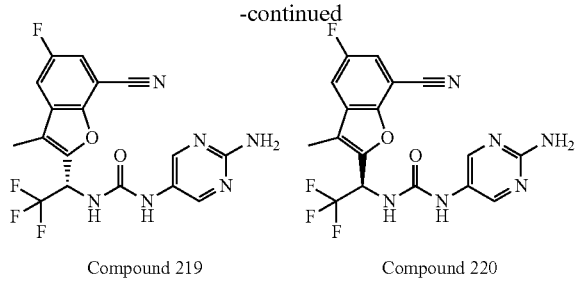

Compound 219                Compound 220

Step 1

Into a 5 mL vial were added (E/Z)-N-[1-(7-bromo-5-fluoro-3-methyl-1-benzofuran-2-yl)-2,2,2-trifluoroethylidene]hydroxylamine (500 mg, 1.5 mmol) and CuCN (395 mg, 4.4 mmol) and CuI (560 mg, 2.9 mmol) and DMF (10 mL) at room temperature. The resulting mixture was stirred for 1 h at 110° C. under nitrogen atmosphere. The reaction was monitored by LCMS. The residue was purified by reverse flash chromatography with the following conditions: column, C18 spherical column; mobile phase, MeCN in water, 0% to 100% gradient in 30 min; detector, UV 254 nm to afford 5-fluoro-3-methyl-2-[(1E/Z)-2,2,2-trifluoro-1-(hydroxyimino)ethyl]-1-benzofuran-7-carbonitrile (130 mg, 30.9%) as a yellow green solid. MS (ESI): mass calcd. for $C_{12}H_6F_4N_2O_2$, 286, m/z found 285[M−H]⁻.

Step 2

A solution of 5-fluoro-3-methyl-2-[(1E/Z)-2,2,2-trifluoro-1-(hydroxyimino)ethyl]-1-benzofuran-7-carbonitrile (130 mg, 0.45 mmol, 1.00 equiv) and Zn (297 mg, 4.54 mmol, 10.00 equiv) and NH₄Cl (243 mg, 4.54 mmol, 10.00 equiv) in EtOH (2 mL) and H₂O (0.4 mL) was stirred for 2 h at 80° C. under nitrogen atmosphere. The reaction was monitored by LCMS. The resulting mixture was filtered, the filter cake was washed with EtOH (3×5 mL). The resulting mixture was concentrated under reduced pressure. The residue was purified by silica gel column chromatography, eluted with PE/EA (10:1) to afford 2-(1-amino-2,2,2-trifluoroethyl)-5-fluoro-3-methyl-1-benzofuran-7-carbonitrile (77 mg, 62.3%) as a yellow oil. MS (ESI): mass calcd. for $C_{12}H_8F_4N_2O$, 272, m/z found 256[M−NH₂]⁺.

Step 3

A solution of 2-(1-amino-2,2,2-trifluoroethyl)-5-fluoro-3-methyl-1-benzofuran-7-carbonitrile (77 mg, 0.3 mmol) and phenyl N-(2-aminopyrimidin-5-yl)carbamate (65 mg, 0.3 mmol) in Pyridine (1 mL) was stirred for overnight at 80° C. under nitrogen atmosphere. The reaction was monitored by LCMS. The resulting mixture was concentrated under reduced pressure. The residue was purified by Prep-TLC (CH₂Cl₂/MeOH 12:1) to afford 1-(2-aminopyrimidin-5-yl)-3-[1-(7-cyano-5-fluoro-3-methyl-1-benzofuran-2-yl)-2,2,2-trifluoroethyl]urea (60 mg, 51.9%) as a light yellow solid. MS (ESI): mass calcd. for $C_{17}H_{12}F_4N_6O_2$, 408, m/z found 409[M+H]⁺.

Step 4

60 mg of racemic was separated by CHIRAL-HPLC to give (Compound 219, 18.2 mg) as white solid and (Compound 220, 17.3 mg) as white solid.

Chiral Separation Conditions:
Apparatus: Prep-HPLC-072
Column: CHIRALPAK IC, 2*25 cm, 5 μm
Mobile phase: Mobile Phase A: Hex (0.5% 2M NH₃-MeOH)-HPLC, Mobile Phase B: EtOH-HPLC
Flow rate: 20 mL/min
Wavelength: UV 220/254 nm
Temperature: 25° C.

Compound 219

MS (ESI): mass calcd. for $C_{17}H_{12}F_4N_6O_2$, 408, m/z found 409.00[M+H]⁺.
¹H NMR (400 MHz, DMSO-d6) δ 8.26 (s, 1H), 8.22 (s, 2H), 8.06-7.94 (m, 2H), 7.80 (d, J=9.4 Hz, 1H), 6.39 (s, 2H), 6.19-5.99 (m, 1H), 2.33 (s, 3H)

Compound 220

MS (ESI): mass calcd. for $C_{17}H_{12}F_4N_6O_2$, 408, m/z found 409.00[M+H]⁺.
¹H NMR (400 MHz, DMSO-d6) δ 8.26 (s, 1H), 8.22 (s, 2H), 8.06-7.93 (m, 2H), 7.80 (d, J=9.4 Hz, 1H), 6.39 (s, 2H), 6.17-6.02 (m, 1H), 2.33 (s, 3H).

Example 148: Preparation of Compound 221 and 222

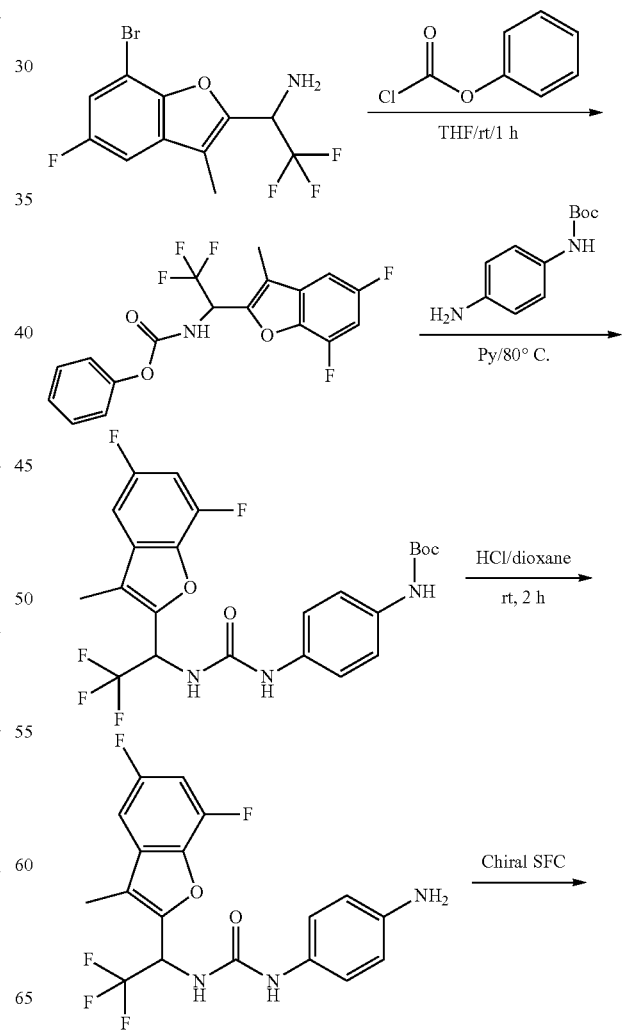

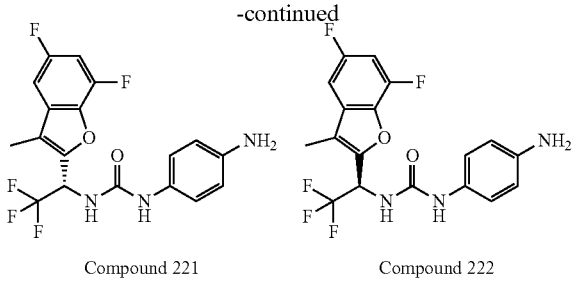

Compound 221    Compound 222

Step 1

The resulting mixture of 1-(5,7-difluoro-3-methylbenzofuran-2-yl)-2,2,2-trifluoroethan-1-amine (100 mg, 0.377 mmol, 1 equiv), phenyl chloroformate (60 mg, 0.383 mmol, 1.02 equiv), TEA (75 mg, 0.741 mmol, 1.97 equiv) in THF (6 mL) was stirred for 1 h at room temperature under nitrogen atmosphere. The resulting mixture was concentrated under reduced pressure to give phenyl (1-(5,7-difluoro-3-methylbenzofuran-2-yl)-2,2,2-trifluoroethyl)carbamate (130 mg, crude) as a colorless semi-solid.

Step 2

The resulting mixture of phenyl (1-(5,7-difluoro-3-methylbenzofuran-2-yl)-2,2,2-trifluoroethyl) carbamate (130 mg, 0.337 mmol, 1 equiv), tert-butyl N-(4-aminophenyl)carbamate (65 mg, 0.312 mmol, 0.93 equiv) in Pyridine (3 mL) was stirred for 16 h at 80° C. under nitrogen atmosphere. The resulting mixture was concentrated under reduced pressure. The resulting mixture was diluted with water. The resulting mixture was extracted with EtOAc. The combined organic layers were washed with brine, dried over anhydrous $Na_2SO_4$. After filtration, the filtrate was concentrated under reduced pressure. The residue was purified by Prep-TLC ($CH_2Cl_2$/MeOH 10:1) to afford tert-butyl(4-(3-(1-(5,7-difluoro-3-methylbenzofuran-2-yl)-2,2,2-trifluoroethyl)ureido)phenyl)carbamate (120 mg, 71.21%) as a yellow solid.

Step 3

The resulting mixture of tert-butyl (4-(3-(1-(5,7-difluoro-3-methylbenzofuran-2-yl)-2,2,2-trifluoroethyl)ureido)phenyl)carbamate (100 mg, 0.200 mmol, 1 equiv) in HCl (gas) in 1,4-dioxane (3 mL) was stirred for 2 h at rt. The resulting mixture was concentrated under reduced pressure. The resulting mixture was extracted with DCM. The combined organic layers were washed with brine, dried over anhydrous $Na_2SO_4$. After filtration, the filtrate was concentrated under reduced pressure. The residue was purified by Prep-TLC to afford 1-(4-aminophenyl)-3-(1-(5,7-difluoro-3-methylbenzofuran-2-yl)-2,2,2-trifluoroethyl)urea (50 mg, 62.54%) as a yellow solid.

Step 4

50 mg of racemic was separated by SFC to give (Compound 222, 11.5 mg) as white solid and (Compound 221, 8.8 mg) as white solid.
Chiral Separation Conditions:
Column: CHIRALPAK IG, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 10% B to 10% B in 10 min; Wave Length: 220/254 nm; RT1 (min): 7.186; RT2 (min): 10.545; Sample Solvent: EtOH:DCM=1:1-HPLC; Injection Volume: 2.3 mL; Number Of Runs: 3.

Compound 221

MS (ESI): mass calcd. for $C_{18}H_{14}F_5N_3O_2$, 399.1, m/z found 400.0 [M+H]$^+$. $^1$H NMR (400 MHz, DMSO-d$_6$) δ 8.17 (s, 1H), 7.56-7.37 (m, 3H), 7.01 (d, J=8.8 Hz, 2H), 6.48 (d, J=8.8 Hz, 2H), 6.05-5.98 (m, 1H), 4.78 (s, 2H), 2.30 (s, 3H).

Compound 222

MS (ESI): mass calcd. for $C_{18}H_{14}F_5N_3O_2$, 399.1, m/z found 400.0 [M+H]$^+$. $^1$H NMR (400 MHz, DMSO-d6) δ 8.17 (s, 1H), 7.56-7.37 (m, 3H), 7.01 (d, J=8.8 Hz, 2H), 6.48 (d, J=8.8 Hz, 2H), 6.05-5.98 (m, 1H), 4.78 (br s, 2H), 2.30 (s, 3H).

Example 149: Preparation of Compound 223 and 224

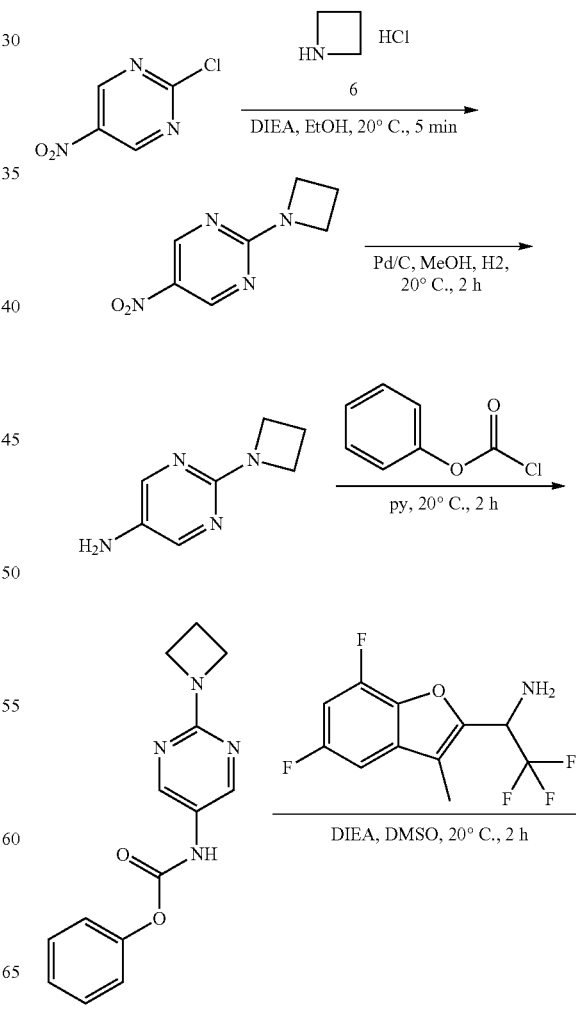

-continued

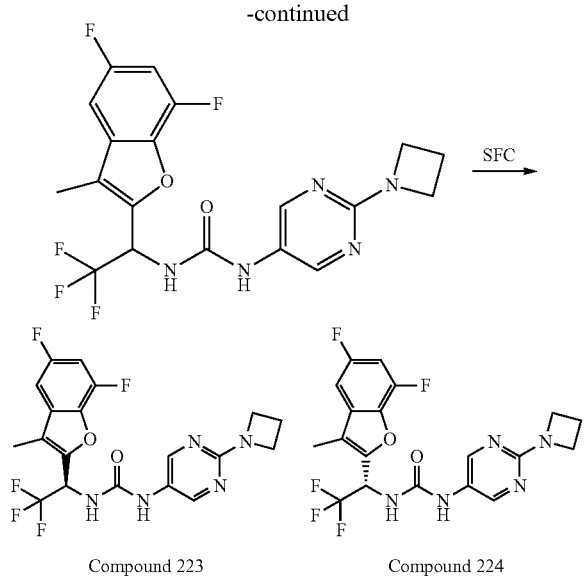

Compound 223     Compound 224

Step 1

To a solution of 2-chloro-5-nitropyrimidine (2.6 g, 16.30 mmol) and DIEA (8.1 mL, 48.89 mmol) in EtOH (20 mL) was added azetidine hydrochloride (1.5 g, 16.30 mmol) at 20° C. The reaction was stirred at 20° C. at $N_2$ atmosphere for 5 min. After completion, the mixture solution was concentrated and treated with EA and $H_2O$. Collected the organic phase, dried over anhydrous $Na_2SO_4$, filtrated and concentrated to get 2-(azetidin-1-yl)-5-nitropyrimidine (2.8 g, 96% yield) as red solid without further purification. MS (ESI): mass calcd. for $C_7H_8N_4O_2$, 180.06, m/z found 181.1 $[M+H]^+$.

Step 2

To a solution of 2-(azetidin-1-yl)-5-nitropyrimidine (2.8 g, 15.54 mmol) Pd/C (280 mg, 10% wt.) in MeOH (20 mL) was stirred at 20° C. at $H_2$ atmosphere for 2 h. After completion, the mixture solution was filtrated. The filtrated was concentrated to get 2-(azetidin-1-yl) pyrimidin-5-amine (2.0 g, 86% yield) as black solid without further purification. MS (ESI): mass calcd. for $C_7H_{10}N_4$, 150.09, m/z found 151.1 $[M+H]^+$.

Step 3

To a solution of 2-(azetidin-1-yl) pyrimidin-5-amine (850 mg, 5.66 mmol) in pyridine (30 mL) was added phenyl carbonochloridate (0.69 mL, 5.66 mmol). The mixture solution was stirred at 20° C. at $N_2$ atmosphere for 2 h. After completion, the mixture solution was concentrated and purified by column chromatography (PE:EA=2:1) to get phenyl (2-(azetidin-1-yl)pyrimidin-5-yl)carbamate (320 mg, 20.9%) as white solid. MS (ESI): mass calcd. for $C_{14}H_{14}N_4O_2$, 270.11, m/z found 271.1 $[M+H]^+$.

Step 4

To a solution of phenyl (2-(azetidin-1-yl)pyrimidin-5-yl) carbamate (310 mg, 1.15 mmol) and DIEA (0.57 mL, 3.44 mmol) in DMSO (20 mL) was added 1-(5,7-difluoro-3-methylbenzofuran-2-yl)-2,2,2-trifluoroethan-1-amine (305 mg, 1.15 mmol). The mixture solution was stirred at 20° C. at $N_2$ atmosphere for 2 h. After completion, the reaction mixture was treated with EA and $H_2O$. Collected the organic phase, dried over anhydrous $Na_2SO_4$, filtrated and concentrated. The residue was purified with column (PE:EA=2:1) to get 1-(2-(azetidin-1-yl)pyrimidin-5-yl)-3-(1-(5,7-difluoro-3-methylbenzofuran-2-yl)-2,2,2-trifluoroethyl)urea (360 mg, 71% yield) as yellow solid.

MS (ESI): mass calcd. for $C_{19}H_{16}F_5N_5O_2$, 441.12, m/z found 442.1 $[M+H]^+$.

Step 5

360 mg of racemic 1-(2-(azetidin-1-yl)pyrimidin-5-yl)-3-(1-(5,7-difluoro-3-methylbenzofuran-2-yl)-2,2,2-trifluoroethyl)urea was separated by SFC to give (Compound 223, 156.1 mg, 43% yield) as yellow solid and give (Compound 224, 152.4 mg, 42% yield) as yellow solid.

Chiral Separation Conditions:
Apparatus: SFC 80
Column: Daicel CHIRALCEL IG, 250 mm×30 mm I.D., 10 μm
Mobile phase: $CO_2$/MeOH [0.20% NH3 (7M Solution in MeOH)]=80/20
Flow rate: 70 g/min
Wavelength: UV 214 nm
Temperature: 35° C.

Compound 223

MS (ESI): mass calcd. for $C_{19}H_{16}F_5N_5O_2$, 441.12, m/z found 442.1 $[M+H]^+$.
$^1$H NMR (400 MHz, DMSO-d6) δ 8.35-8.34 (m, 3H), 7.82 (d, J=9.6 Hz, 1H), 7.45-7.38 (m, 2H), 6.09-6.01 (m, 1H), 3.98 (t, J=7.2 Hz, 4H), 2.31-2.24 (m, 5H).

Compound 224

MS (ESI): mass calcd. for $C_{19}H_{16}F_5N_5O_2$, 441.12, m/z found 442.1 $[M+H]^+$.
$^1$H NMR (400 MHz, DMSO-$d_6$) δ 8.35 (s, 3H), 7.83 (d, J=9.2 Hz, 1H), 7.45-7.38 (m, 2H), 6.09-6.01 (m, 1H), 3.98 (t, J=7.6 Hz, 4H), 2.31-2.24 (m, 5H).

Example 150: Preparation of Compound 225 and 226

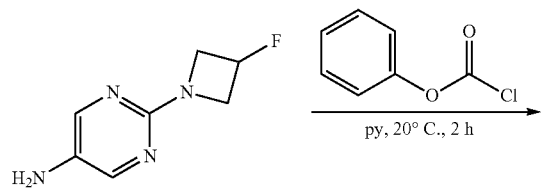

-continued

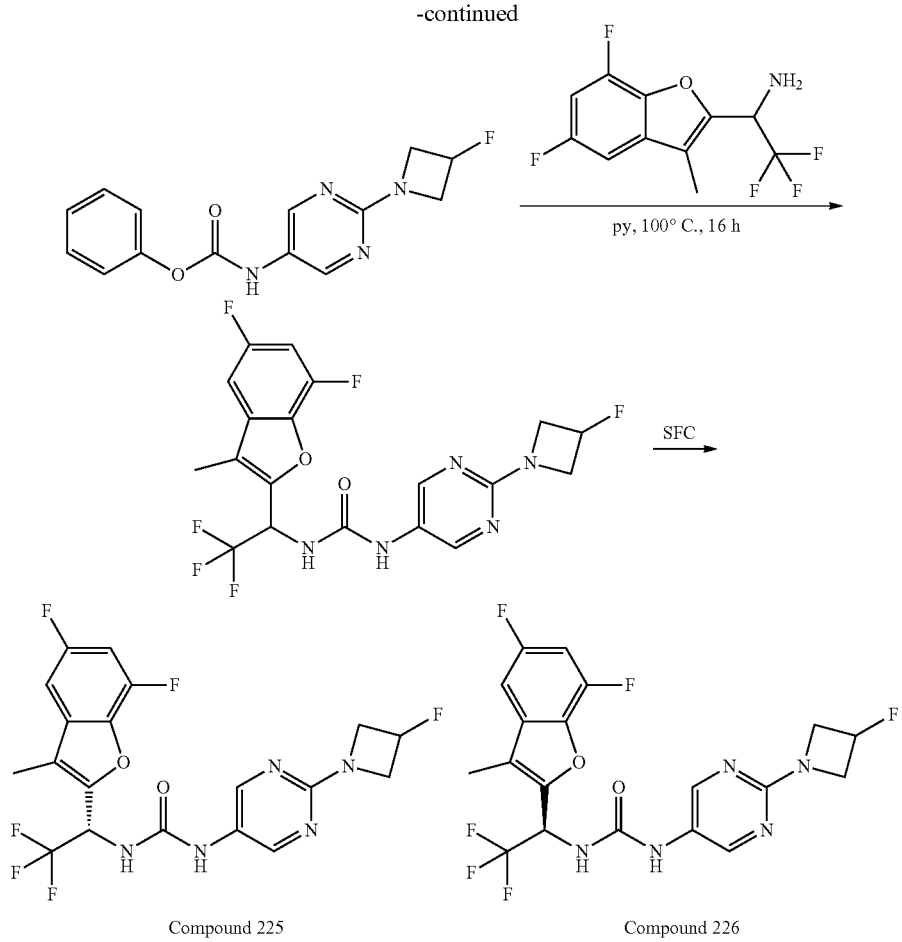

Compound 225

Compound 226

Step 1

To a solution of 2-(3-fluoroazetidin-1-yl)pyrimidin-5-amine (900 mg, 5.35 mmol) in pyridine (50 mL) was added phenyl carbonochloridate (0.67 mL, 5.35 mmol). The mixture solution was stirred at 20° C. at $N_2$ atmosphere for 2 h. After completion, the mixture solution was used in the next step directly. MS (ESI): mass calcd. for $C_{14}H_{13}FN_4O_2$, 288.10, m/z found 289.1 $[M+H]^+$.

Step 2

To the mixture solution was added 1-(5,7-difluoro-3-methylbenzofuran-2-yl)-2,2,2-trifluoroethan-1-amine (709 mg, 2.68 mmol). The reaction mixture was stirred at 100° C. at $N_2$ atmosphere for 16 h. After completion, the reaction mixture was concentrated and purified by column chromatography (PE:EA=1:1) to get 1-(1-(5,7-difluoro-3-methylbenzofuran-2-yl)-2,2,2-trifluoroethyl)-3-(2-(3-fluoroazetidin-1-yl)pyrimidin-5-yl)urea (380 mg, 30.9% yield) as brown solid. MS (ESI): mass calcd. for $C_{19}H_{15}F_6N_5O_2$, 459.11, m/z found 460.1 $[M+H]^+$.

Step 3

380 mg of 1-(1-(5,7-difluoro-3-methylbenzofuran-2-yl)-2,2,2-trifluoroethyl)-3-(2-(3-fluoroazetidin-1-yl)pyrimidin-5-yl)urea was separated by SFC to give (Compound 225, 159.7 mg) as yellow solid and (Compound 226, 146.3 mg) as yellow solid.

Chiral Separation Conditions:
Apparatus: SFC 150
Column: REGIS (S,S)-Whelk O1, 250 mm×30 mm I.D., 10 μm
Mobile phase: $CO_2$/MeOH[0.2% $NH_3$ (7M Solution in MeOH)]=65/35
Flow rate: 80 g/min
Wavelength: UV 214 nm
Temperature: 35° C.

Compound 225

MS (ESI): mass calcd. for $C_{19}H_{15}F_6N_5O_2$, 459.11, m/z found 460.1 $[M+H]^+$.

$^1$H NMR (400 MHz, DMSO-$d_6$) δ 8.44 (s, 1H), 8.41 (s, 2H), 7.87 (d, J=9.2 Hz, 1H), 7.45-7.38 (m, 2H), 6.10-6.01 (m, 1H), 5.57-5.38 (m, 1H), 4.37-4.27 (m, 2H), 4.08-3.99 (m, 2H), 2.30 (s, 3H).

Compound 226

MS (ESI): mass calcd. for $C_{19}H_{15}F_6N_5O_2$, 459.11, m/z found 460.1 $[M+H]^+$.

$^1$H NMR (400 MHz, DMSO-$d_6$) δ 8.59 (s, 1H), 8.42 (s, 2H), 7.92 (d, J=9.6 Hz, 1H), 7.44-7.39 (m, 2H), 6.10-6.01 (m, 1H), 5.55-5.40 (m, 1H), 4.37-4.27 (m, 2H), 4.08-3.99 (m, 2H), 2.30 (s, 3H).

Example 151: Preparation of Compound 227

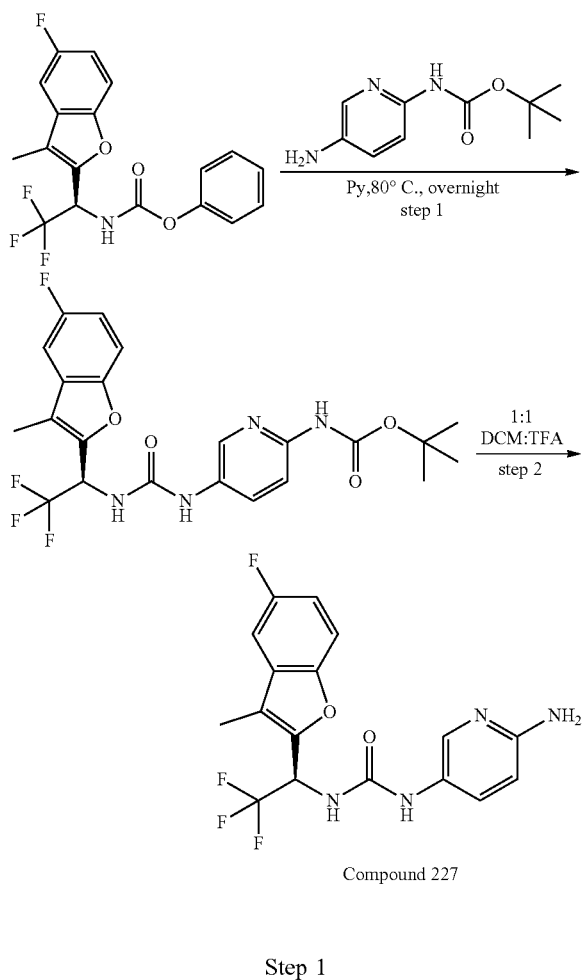

Compound 227

Step 1

A solution of phenyl N-[(1R)-2,2,2-trifluoro-1-(5-fluoro-3-methyl-1-benzofuran-2-yl)ethyl]carbamate (100 mg, 0.272 mmol, 1.2 equiv) in pyridine was treated with tert-butyl N-(5-aminopyridin-2-yl)carbamate (47.47 mg, 0.227 mmol, 1 equiv) overnight at 80° C. under a nitrogen atmosphere. After the reaction was complete, the mixture was diluted with water, extracted with EA, washed with brine, dried over anhydrous $Na_2SO_4$, and concentrated to afford the crude product. The residue was purified by reverse flash chromatography with the following conditions: column, C18 silica gel; mobile phase, MeCN in water (0.1% TFA), 0% to 100% gradient in 30 min; detector, UV 254 nm. This resulted in tert-butyl N-[5-({[(1R)-2,2,2-trifluoro-1-(5-fluoro-3-methyl-1-benzofuran-2-yl)ethyl]carbamoyl}amino)pyridin-2-yl]carbamate (90 mg, 82.23%) as a light yellow solid. MS (ESI): mass calcd. for $C_{22}H_{22}F_4N_4O_4$, 482.44, m/z found 483.25 $[M+H]^+$.

Step 2

A solution of tert-butyl N-[5-({[(1R)-2,2,2-trifluoro-1-(5-fluoro-3-methyl-1-benzofuran-2-yl)ethyl]carbamoyl}amino)pyridin-2-yl]carbamate (90 mg, 0.187 mmol, 1 equiv) in DCM was treated with TFA (3 mL, 21.583 mmol) for 1 h at room temperature under nitrogen atmosphere. After the reaction was complete the mixture was diluted with water, extracted with EA, washed with brine, dried over anhydrous $Na_2SO_4$, concentrated to afford the crude product. The residue was purified by reverse flash chromatography with the following conditions: column, C18 silica gel; mobile phase, MeCN in water (0.1% FA), 0% to 100% gradient in 30 min; detector, UV 254 nm. This resulted in 1-(6-aminopyridin-3-yl)-3-[(1R)-2,2,2-trifluoro-1-(5-fluoro-3-methyl-1-benzofuran-2-yl)ethyl]urea (31.9 mg, 44.73%) as a white solid. MS (ESI): mass calcd. for $C_{17}H_{14}F_4N_4O_2$, 382.32, m/z found 383.05 $[M+H]^+$.

$^1$H NMR (400 MHz, DMSO-$d_6$) δ 8.21 (s, 1H), 7.87 (d, J=2.7 Hz, 1H), 7.64 (dd, J=9.0, 4.0 Hz, 1H), 7.57-7.49 (m, 2H), 7.41 (dd, J=8.8, 2.7 Hz, 1H), 7.25 (td, J=9.2, 2.7 Hz, 1H), 6.39 (d, J=8.8 Hz, 1H), 5.97 (p, J=8.4 Hz, 1H), 5.65 (s, 2H), 2.28 (s, 3H).

Example 152: Preparation of Compound 228

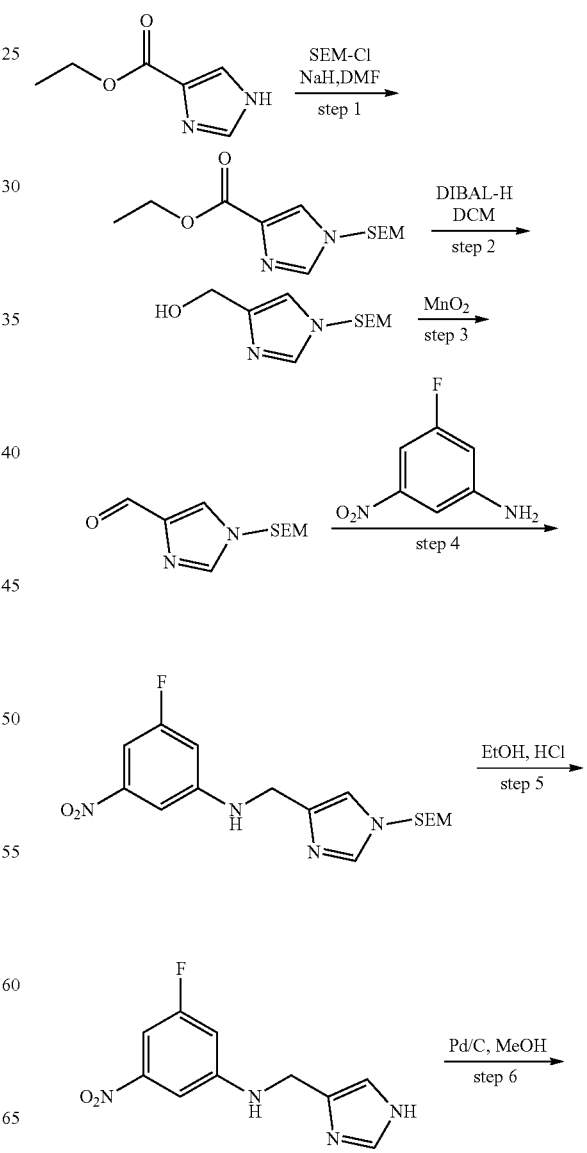

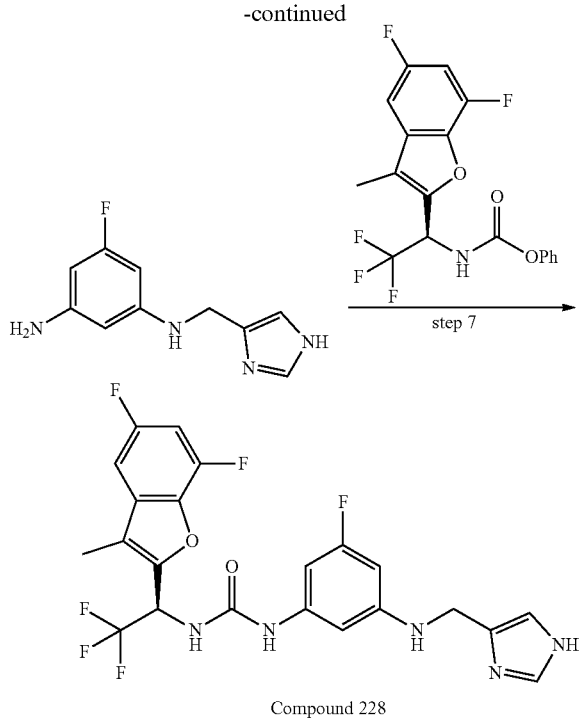

Compound 228

Step 1

To a solution of ethyl 1H-imidazole-4-carboxylate (1.00 g, 7.14 mmol) in DMF (15 mL) was added NaH (430 mg, 10.70 mmol, 60% in oil) at 0° C. The mixture was stirred for 15 min. SEM-Cl (1.31 g, 7.85 mmol) was added and the mixture was allowed to warm to RT and stirred overnight. The reaction mixture was quenched with water and extracted with DCM (3*25 mL). The residue was purified by silica gel column chromatography, eluting with PE/EA (1:1) to afford ethyl 1-{[2-(trimethylsilyl)ethoxy]methyl}imidazole-4-carboxylate (810 mg, 41.98%) as a colorless oil.

MS (ESI): mass calcd. for $C_{12}H_{22}N_2O_3Si$, 270.14, m/z found 271.00 [M+H]$^+$.

Step 2

To a solution of ethyl 1-{[2-(trimethylsilyl)ethoxy]methyl}imidazole-4-carboxylate (760 mg, 2.81 mmol) in DCM (30 mL) was added DIBAL-H (7.03 mL, 7.03 mmol) at −50° C. under nitrogen atmosphere. The resulting mixture was stirred for 2 h at room temperature under nitrogen atmosphere. The reaction was quenched by the addition of MeOH (5 mL) and aqueous NaOAc (30 ml) at 0° C. The resulting mixture was extracted with $CH_2Cl_2$ (3×50 mL). The combined organic layers were washed with brine (3×100 mL), dried over anhydrous $Na_2SO_4$. After filtration, the filtrate was concentrated under reduced pressure to afford (1-{[2-(trimethylsilyl)ethoxy]methyl}imidazol-4-yl)methanol (560 mg, 87.3%) as a white solid.

Step 3

To a stirred solution of (1-{[2-(trimethylsilyl)ethoxy]methyl}imidazol-4-yl)methanol (490 mg, 2.15 mmol) in DCM (5 mL) was added manganese dioxide (1.87 g, 21.460 mmol) in portions at room temperature under nitrogen atmosphere for 1 h. The resulting mixture was filtered, the filter cake was washed with DCM (3×50 mL). The filtrate was concentrated under reduced pressure to afford 1-{[2-(trimethylsilyl)ethoxy]methyl}imidazole-4-carbaldehyde (450 mg, 92.65%) as a colorless oil. MS (ESI): mass calcd. for $C_{10}H_{18}N_2O_2Si$, 226.11, m/z found 227.00 [M+H]$^+$.

Step 4

To a stirred solution of 1-{[2-(trimethylsilyl)ethoxy]methyl}imidazole-4-carbaldehyde (540 mg, 2.39 mmol) and 3-fluoro-5-nitroaniline (372 mg, 2.39 mmol) in MeOH (10 mL) was added HOAc (1.43 g, 23.86 mmol) dropwise at room temperature under nitrogen atmosphere. The resulting mixture was stirred for 1 h at room temperature under nitrogen atmosphere. To the above mixture was added NaBH$_3$CN (300 mg, 4.77 mmol) in portions at room temperature. The resulting mixture was stirred overnight at room temperature under nitrogen atmosphere. The resulting mixture was extracted with EtOAc (2×50 mL). The combined organic layers were dried over anhydrous $Na_2SO_4$. After filtration, the filtrate was concentrated under reduced pressure. The residue was purified by silica gel column chromatography, eluted with $CH_2Cl_2$/MeOH (98:2) to afford 3-fluoro-5-nitro-N-[(1-{[2-(trimethylsilyl)ethoxy]methyl}imidazol-4-yl)methyl]aniline (800 mg, 91.50%) as a yellow oil. MS (ESI): mass calcd. for $C_{16}H_{23}FN_4O_3Si$, 366.15, m/z found 367.20 [M+H]$^+$.

Step 5

To a stirred solution of 3-fluoro-5-nitro-N-[(1-{[2-(trimethylsilyl)ethoxy]methyl}imidazol-4-yl)methyl]aniline (350 mg, 0.95 mmol) in EtOH (3 mL) was added HCl (3 mL) (1 M) at room temperature under nitrogen atmosphere. The resulting mixture was stirred overnight at 90° C. under nitrogen atmosphere. The mixture was neutralized to pH 7 with NaOH (1M). The resulting mixture was extracted with $CH_2Cl_2$/MeOH=10/1 (3×20 mL). The combined organic layers were dried over anhydrous $Na_2SO_4$. After filtration, the filtrate was concentrated under reduced pressure to afford 3-fluoro-N-(1H-imidazol-4-ylmethyl)-5-nitroaniline (190 mg, 84.22%) as a yellow solid. MS (ESI): mass calcd. for $C_{10}H_9FN_4O_2$, 236.07, m/z found 236.95 [M+H]$^+$.

Step 6

To a solution of 3-fluoro-N-(1H-imidazol-4-ylmethyl)-5-nitroaniline (160 mg, 0.68 mmol) in 5 mL MeOH was added Pd/C (107 mg, 67% w/w) under nitrogen atmosphere. The mixture was hydrogenated at room temperature for 1 h under hydrogen atmosphere. And using a hydrogen balloon, filtered through a Celite pad and concentrated under reduced pressure. The residue was purified by silica gel column chromatography, eluted with $CH_2Cl_2$/MeOH (10:1) to afford 5-fluoro-N1-(1H-imidazol-4-ylmethyl)benzene-1,3-diamine (100 mg, 71.59%) as a light yellow solid. MS (ESI): mass calcd. for $C_{10}H_{11}FN_4$, 206.10, m/z found 207.10 [M+H]$^+$.

Step 7

A solution of 5-fluoro-N1-(1H-imidazol-4-ylmethyl)benzene-1,3-diamine (52 mg, 0.25 mmol) and phenyl N-[(1R)-1-(5,7-difluoro-3-methyl-1-benzofuran-2-yl)-2,2,2-trifluoroethyl]carbamate (88 mg, 0.23 mmol) in pyridine (2 mL) was stirred for 2 h at 80° C. under nitrogen atmosphere. The resulting mixture was concentrated under reduced pressure.

The residue was purified by reverse flash chromatography with the following conditions: column, C18 silica gel; mobile phase, MeCN in water (10 mmol/L NH$_4$HCO$_3$), 10% to 50% gradient in 20 min; detector, UV 254 nm to afford 3-[(1R)-1-(5,7-difluoro-3-methyl-1-benzofuran-2-yl)-2,2,2-trifluoroethyl]-1-{3-fluoro-5-[(1H-imidazol-4-ylmethyl)amino]phenyl}urea (73 mg, 64.26%) as a off-white solid. MS (ESI): mass calcd. for C$_{22}$H$_{17}$F$_6$N$_5$O$_2$, 497.13, m/z found 498.00 [M+H]$^+$.

$^1$H NMR (400 MHz, DMSO-d$_6$) δ 11.88 (brs, 1H), 8.63 (s, 1H), 7.62 (d, J=9.4 Hz, 1H), 7.57 (d, J=1.2 Hz, 1H), 7.47-7.35 (m, 2H), 6.98-6.87 (m, 1H), 6.61-6.58 (m, 1H), 6.33 (t, J=2.0 Hz, 1H), 6.20 (t, J=5.6 Hz, 1H), 6.10-5.97 (m, 2H), 4.08 (d, J=5.3 Hz, 2H), 2.31 (s, 3H).

Example 153: Preparation of Compound 229

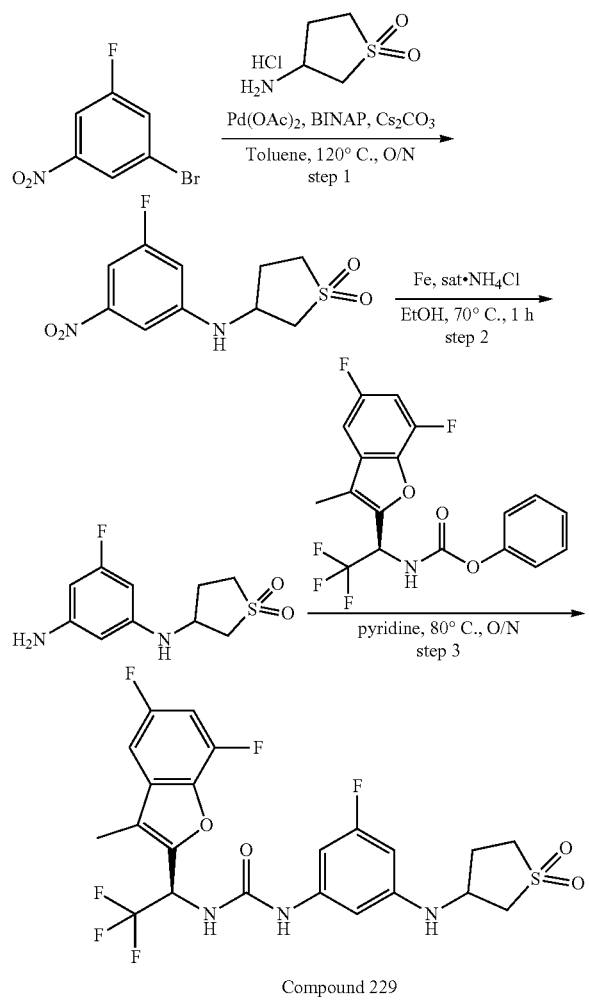

Compound 229

Step 1

A mixture of 1-bromo-3-fluoro-5-nitrobenzene (500 mg, 2.27 mmol), 3-aminotetrahydrothiophene 1,1-dioxide hydrogen chloride (388.6 mg, 2.27 mmol), BINAP (113.2 mg, 0.18 mmol), Cs$_2$CO$_3$ (2.2 g, 6.82 mmol) and Pd(OAc)$_2$ (25.5 mg, 0.11 mmol) in toluene (10 mL) was added stirred overnight at 120° C. under nitrogen atmosphere. The precipitate was filtered and the filtrate was concentrated under reduced pressure to provide a residue. The residue was purified by reverse flash chromatography to afford 3-((3-fluoro-5-nitrophenyl)amino)tetrahydrothiophene 1,1-dioxide (30 mg, 4.81%) as a light yellow solid. MS (ESI): mass calcd. for C$_{10}$H$_{11}$FN$_2$O$_4$S, 274.04, m/z found 275.00 [M+H]$^+$.

Step 2

A mixture of 3-((3-fluoro-5-nitrophenyl)amino)tetrahydrothiophene 1,1-dioxide (30 mg, 0.11 mmol) and Fe (48.8 mg, 0.87 mmol) in EtOH (2 mL)/sat. NH$_4$Cl (1 mL) stirred for 1 h at 70° C., then filtered and the filter cake was washed with EtOH. The filtrate was diluted with water and extracted with DCM (3×10 mL). The combined organic layers were dried over anhydrous Na$_2$SO$_4$. After filtration, the filtrate was concentrated under reduced pressure to afford 3-((3-amino-5-fluorophenyl)amino)tetrahydrothiophene 1,1-dioxide (33 mg) as a brown solid. MS (ESI): mass calcd. for C$_{10}$H$_{13}$FN$_2$O$_2$S, 244.07, m/z found 244.95 [M+H]$^+$.

Step 3

A solution of phenyl N-[(1R)-1-(5,7-difluoro-3-methyl-1-benzofuran-2-yl)-2,2,2-trifluoroethyl]carbamate (52 mg, 0.14 mmol) and 3-((3-amino-5-fluorophenyl)amino)tetrahydrothiophene 1,1-dioxide (33 mg) in pyridine (2 mL) was stirred overnight at 80° C. The resulting solution was concentrated under reduced pressure. The residue was purified by Prep-HPLC to afford 1-((R)-1-(5,7-difluoro-3-methylbenzofuran-2-yl)-2,2,2-trifluoroethyl)-3-(3-((1,1-dioxidotetrahydrothiophen-3-yl)amino)-5-fluorophenyl)urea (18.9 mg, 26.13%) as a white solid.

MS (ESI): mass calcd. for C$_{22}$H$_{19}$F$_6$N$_3$O$_4$S, 535.10, m/z found 536.20 [M+H]$^+$.

$^1$H NMR (400 MHz, Chloroform-d) δ 7.05-6.98 (m, 1H), 6.94-6.84 (m, 2H), 6.60 (d, J=10.1 Hz, 1H), 6.52 (s, 1H), 6.08 (d, J=11.6 Hz, 2H), 5.94 (m, 1H), 4.30 (d, J=6.1 Hz, 1H), 3.55 (dd, J=13.7, 6.8 Hz, 1H), 3.40-3.32 (m, 1H), 3.20 (dt, J=14.2, 8.0 Hz, 1H), 3.01 (d, J=13.2 Hz, 1H), 2.62 (dd, J=13.6, 7.1 Hz, 1H), 2.30 (s, 4H).

The following compounds were synthesized under analogous conditions to those described in Example 153.

Compound 230

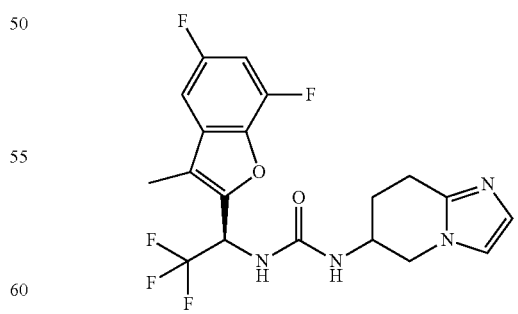

MS (ESI): mass calcd. for C$_{19}$H$_{17}$F$_5$N$_4$O$_2$, 428.13, m/z found 429.05 [M+H]$^+$.

$^1$H NMR (400 MHz, DMSO-d$_6$) δ 7.47-7.31 (m, 3H), 7.04-6.90 (d, J=28.9 Hz, 1H), 6.87-6.77 (d, J=11.9 Hz, 1H), 6.66-6.56 (dd, J=4.6, 7.2 Hz, 1H), 6.03-5.90 (m, 1H), 4.18-4.03 (m, 2H), 3.88-3.71 (m, 1H), 2.90-2.67 (m, 2H), 2.36-2.20 (d, J=2.2 Hz, 3H), 2.07-1.78 (m, 2H).
Compound 231
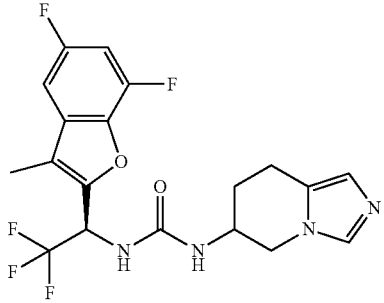 [SMILES: Cc1c([C@@H](NC(=O)NC2CCc3cncn3C2)C(F)(F)F)oc2c(F)cc(F)cc12]
MS (ESI): mass calcd. for $C_{19}H_{17}F_5N_4O_2$, 428.13, m/z found 429.05 [M+H]$^+$.
$^1$H NMR (400 MHz, DMSO-d6) δ 7.54-7.32 (m, 4H), 6.64 (d, J=1.1 Hz, 1H), 6.57 (dd, J=7.2, 3.6 Hz, 1H), 5.96 (m, 1H), 4.24-3.95 (m, 2H), 3.92-3.68 (m, 1H), 2.84-2.64 (m, 2H), 2.28 (d, J=1.0 Hz, 3H), 1.83 (m, 2H).
Compound 232
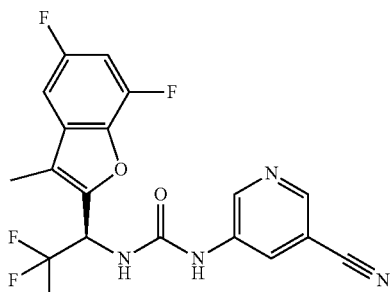
MS (ESI): mass calcd. For $C_{18}H_{11}F_5N_4O_2$, 410.3, m/z found 411.3 [M+H]$^+$.
$^1$H NMR (400 MHz, DMSO-d$_6$) δ 9.16 (s, 1H), 8.79 (d, J=2.6 Hz, 1H), 8.63 (d, J=1.8 Hz, 1H), 8.35 (t, J=2.2 Hz, 1H), 8.16 (d, J=9.3 Hz, 1H), 7.49-7.37 (m, 2H), 6.12 (p, J=8.2 Hz, 1H), 2.32 (s, 3H).
Example 154: Preparation of Compound 233
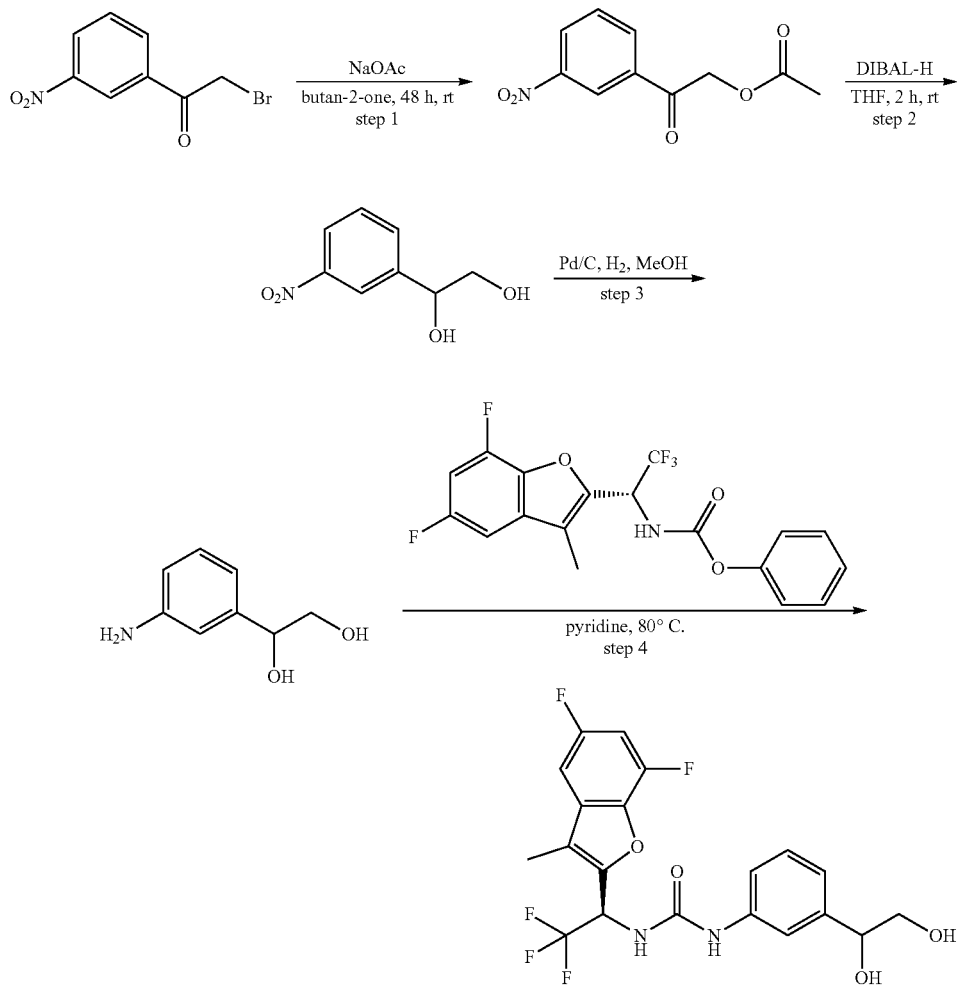
Compound 233

Step 1

To a stirred solution of 2-bromo-1-(3-nitrophenyl)ethan-1-one (2 g, 8.23 mmol) in butan-2-one (60 mL) was added NaOAc (1.02 g, 12.35 mmol). The resulting mixture was stirred at room temperature for 48 hours. The reaction mixture was partitioned between $CH_2Cl_2$ and water. The aqueous layer was extracted again with $CH_2Cl_2$. The combined organic layer was dried over anhydrous sodium sulfate and concentrated under vacuum. This resulted in 2-(3-nitrophenyl)-2-oxoethyl acetate (2.1 g, crude) as an off-white solid. MS (ESI): mass calcd. for $C_{10}H_9NO_5$, 223.05, m/z found 222 [M–H]$^+$.

Step 2

To a stirred solution 2-(3-nitrophenyl)-2-oxoethyl acetate (300 mg, 1.35 mmol) in THF (25 mL) were added DIBAL-H (1M in DCM, 4.5 mL) at 0° C. The resulting mixture was stirred at room temperature for 2 hours. Then the reaction was then quenched by the addition of 10 mL of water at 0° C. The solid was filtered out, the filtrate was partitioned between $CH_2Cl_2$ and water. The aqueous layer was extracted again with $CH_2Cl_2$. The combined organic layer was dried over anhydrous sodium sulfate and concentrated under vacuum. This resulted in 1-(3-nitrophenyl)ethane-1,2-diol (250 mg, crude) as a white solid. MS (ESI): mass calcd. for $C_8H_9NO_4$, 183.05, m/z found no mass [M+H]$^+$.

Step 3

To a solution of 1-(3-nitrophenyl)ethane-1,2-diol (250 mg, 2.67 mmol) in MeOH (5 mL). The flask was evacuated and flushed three times with nitrogen. Then Pd/C (80 mg) was added at room temperature. The solution was evacuated and flushed three times with nitrogen, followed by flushing with hydrogen. The mixture was stirred overnight at room temperature under an atmosphere of hydrogen (balloon). After the reaction, the solid was filtered out. The filtrate was concentrated under vacuum to afford 1-(3-aminophenyl)ethane-1,2-diol (171 mg, crude) as a yellow oil. MS (ESI): mass calcd. for $C_8H_{11}NO_2$, 153.08, m/z found 154 [M+H]$^+$.

Step 4

To a solution of phenyl N-[(1S)-1-(5,7-difluoro-3-methyl-1-benzofuran-2-yl)-2,2,2-trifluoroethyl]carbamate (270 mg, 0.701 mmol) in pyridine (3 mL) was added 1-(3-aminophenyl)ethane-1,2-diol (107.34 mg, 0.701 mmol) at room temperature. The mixture was stirred at 80° C. overnight. The reaction mixture was concentrated under vacuum. The crude product was dissolved in ACN and purified using prep-HPLC. This resulted in 3-[(1R)-1-(5,7-difluoro-3-methyl-1-benzofuran-2-yl)-2,2,2-trifluoroethyl]-1-[3-(1,2-dihydroxyethyl)phenyl]urea (38.5 mg, 12.4%) as a white solid. MS (ESI): mass calcd. for $C_{20}H_{17}F_5N_2O_4$, 444.11, m/z found 445 [M+H]$^+$.

$^1$H NMR (400 MHz, DMSO) δ 8.67 (s, 1H), 7.64 (d, J=9.4 Hz, 1H), 7.44-7.32 (m, 3H), 7.34-7.21 (m, 1H), 7.19 (t, J=7.8, 7.8 Hz, 1H), 6.94 (d, J=7.5 Hz, 1H), 6.07 (p, J=8.3, 8.3, 8.4, 8.4 Hz, 1H), 5.21 (d, J=4.1 Hz, 1H), 4.70 (t, J=5.8, 5.8 Hz, 1H), 4.47 (q, J=5.7, 5.7, 5.9 Hz, 1H), 3.47-3.33 (m, 2H), 2.32 (s, 3H).

Example 155: Preparation of Compound 234

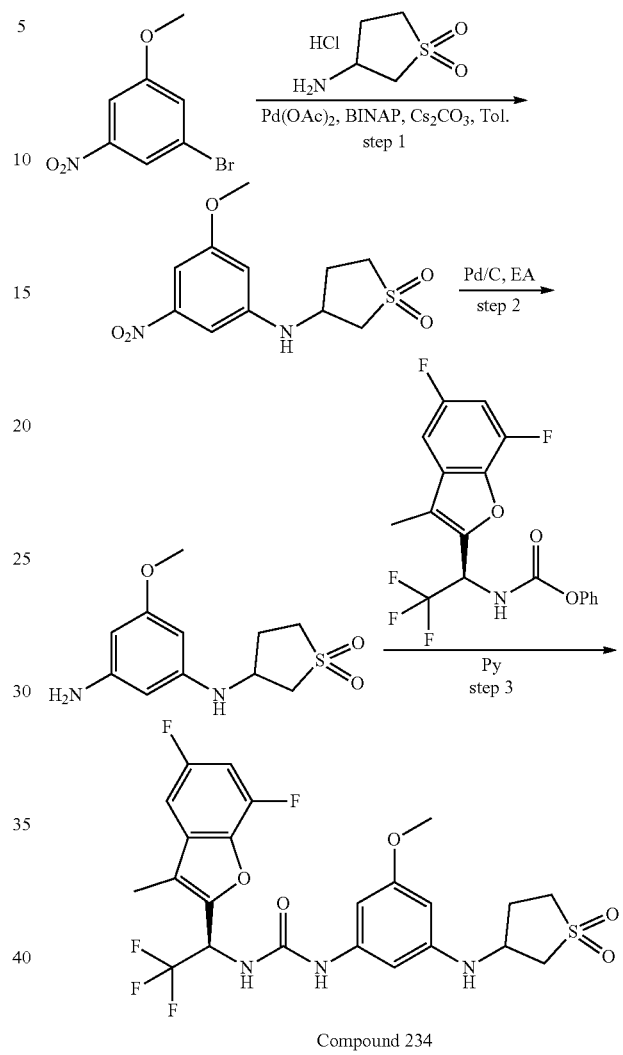

Compound 234

Step 1

To a solution of 3-aminotetrahydrothiophene 1,1-dioxide (1.0 g, 5.8 mmol) and 1-bromo-3-methoxy-5-nitrobenzene (1.4 g, 5.8 mmol) in toluene (10 mL) were added BINAP (0.29 g, 0.5 mmol), Pd(OAc)$_2$ (0.13 g, 0.6 mmol), and Cs$_2$CO$_3$ (5.7 g, 17.5 mmol). The resulting mixture was stirred overnight at 80° C. under nitrogen atmosphere. The resulting mixture was allowed to cool down to room temperature. The mixture was extracted with EtOAc (3×100 mL). The combined organic layers were washed with water (3×50 mL) and dried over anhydrous Na$_2$SO$_4$. After filtration, the filtrate was concentrated under reduced pressure. The residue was purified by silica gel column chromatography eluting with $CH_2Cl_2$/MeOH (20:1) to afford 3-((3-methoxy-5-nitrophenyl)amino)tetrahydrothiophene 1,1-dioxide (760 mg, 45.6%) as a yellow solid. MS (ESI): mass calcd. for $C_{11}H_{14}N_2O_5S$, 286.10, m/z found 287.00 [M+H]$^+$.

Step 2

A solution of 3-((3-methoxy-5-nitrophenyl)amino)tetrahydrothiophene 1,1-dioxide (100 mg, 0.3 mmol) and Pd/C (50 mg, 50% w/w) in EtOAc (2 mL) was stirred for 5 h at room temperature under hydrogen atmosphere. The resulting mixture was filtered and the filter cake was washed with EtOAc (3×30 mL). The filtrate was concentrated under reduced pressure. The resulting residue was purified by Prep-TLC (CH$_2$Cl$_2$/MeOH 10:1) to afford 3-((3-amino-5-methoxyphenyl)amino)tetrahydrothiophene 1,1-dioxide (70 mg, 41.44%) as a brown solid. MS (ESI): mass calcd. for C$_{11}$H$_{16}$N$_2$O$_3$S, 256.10, m/z found 256.95 [M+H]$^+$.

Step 3

A solution of phenyl N-[(1R)-1-(5,7-difluoro-3-methyl-1-benzofuran-2-yl)-2,2,2-trifluoroethyl]carbamate (105 mg, 0.3 mmol) and 3-((3-amino-5-methoxyphenyl)amino)tetrahydrothiophene 1,1-dioxide (70 mg, 0.3 mmol) in pyridine (1 mL) was stirred overnight at 80° C. The residue product was purified by reverse phase flash with the following conditions (column, C18 silica gel; mobile phase, MeCN in water (0.1% FA), 10% to 50% gradient in 30 min; detector, UV 254 nm) to afford 1-((R)-1-(5,7-difluoro-3-methylbenzofuran-2-yl)-2,2,2-trifluoroethyl)-3-(3-((1,1-dioxidotetrahydrothiophen-3-yl)amino)-5-methoxyphenyl)urea as a yellow solid. The crude product (120 mg) was purified by Prep-HPLC with the following conditions (Column: YMC-Actus Triart C18 ExRS, 30*150 mm, 5 µm; Mobile Phase A: water (10 mmol/L NH$_4$HCO$_3$), Mobile Phase B: ACN; Flow rate: 60 mL/min; Gradient: 45% B to 65% B in 8 min, 65% B; Wave Length: 220 nm; RT1 (min): 8; Number Of Runs: 0) to afford 1-((R)-1-(5,7-difluoro-3-methylbenzofuran-2-yl)-2,2,2-trifluoroethyl)-3-(3-((1,1-dioxidotetrahydrothiophen-3-yl)amino)-5-methoxyphenyl)urea (76.3 mg, 50.93%) as a white solid.

MS (ESI): mass calcd. for C$_{23}$H$_{22}$F$_5$N$_3$O$_5$S, 547.10, m/z found 548.05 [M+H]$^+$.

$^1$H NMR (400 MHz, DMSO-d$_6$) δ 8.51 (s, 1H), 7.59 (d, J=9.4 Hz, 1H), 7.48-7.33 (m, 2H), 6.34 (t, J=2.0 Hz, 1H), 6.28 (t, J=1.9 Hz, 1H), 6.05-6.02 (m, 2H), 5.83 (t, J=2.1 Hz, 1H), 4.21-4.16 (m, 1H), 3.66 (s, 3H), 3.55-3.49 (m, 1H), 3.31 (t, J=3.5 Hz, 1H), 3.18-3.11 (m, 1H), 2.82-2.77 (m, 1H), 2.50-2.45 (m, 1H), 2.31 (s, 3H), 2.11-1.99 (m, 1H).

Example 156: Preparation of Compound 235

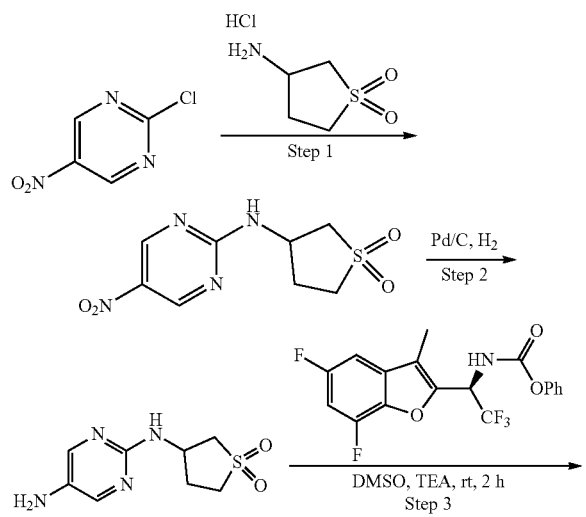

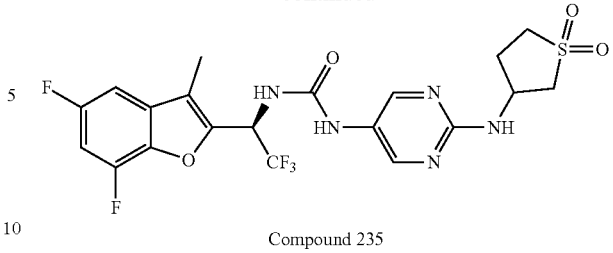

Compound 235

Step 1

A solution of 2-chloropyrimidin-5-amine (1 g, 7.719 mmol, 1 equiv) in DMSO was treated with 3-aminotetrahydrothiophene 1,1-dioxide hydrochloride (1.59 g, 9.263 mmol, 1.2 equiv) for 2 h at room temperature under nitrogen atmosphere followed by the addition of TEA (3.22 mL, 23.157 mmol, 3 equiv) dropwise at room temperature. After the reaction was complete the mixture was diluted with water, extracted with EA, washed with brine, dried over anhydrous Na$_2$SO$_4$, and concentrated to afford the crude product. The residue was purified by reverse flash chromatography with the following conditions: column, C18 silica gel; mobile phase, MeCN in water (0.1% FA), 0% to 100% gradient in 10 min; detector, UV 254 nm. Desired product could be detected by LCMS. This resulted in 3-((5-nitropyrimidin-2-yl)amino)tetrahydrothiophene 1,1-dioxide (900 mg, 51.08%) as a yellow solid. MS (ESI): mass calcd. for C$_8$H$_{12}$N$_4$O$_2$S, 258.25, m/z found 259.05 [M+H]$^+$.

Step 2

To a solution of 3-((5-nitropyrimidin-2-yl)amino)tetrahydrothiophene 1,1-dioxide (400 mg, 1.549 mmol, 1 equiv) in 10 mL MeOH was added Pd/C (10%, 1 g) in a pressure tank. The mixture was hydrogenated at room temperature under 30 psi of hydrogen pressure for 2 h, filtered through a Celite pad and concentrated under reduced pressure. The precipitated solids were collected by filtration and washed with DCM. The resulting mixture was concentrated under vacuum. The crude product was used in the next step directly without further purification. This resulted in 3-((5-aminopyrimidin-2-yl)amino)tetrahydrothiophene 1,1-dioxide (240 mg, 67.88%) as a white solid.

MS (ESI): mass calcd. for C$_8$H$_{12}$N$_4$O$_2$S, 228.27, m/z found 229.05 [M+H]$^+$.

Step 3

A solution of phenyl N-[(1R)-1-(5,7-difluoro-3-methyl-1-benzofuran-2-yl)-2,2,2-trifluoroethyl]carbamate (150 mg, 0.389 mmol, 1 equiv) in DMSO was treated with 3-((5-aminopyrimidin-2-yl)amino)tetrahydrothiophene 1,1-dioxide (106.64 mg, 0.467 mmol, 1.2 equiv) for 2 h at room temperature. The residue was purified by reverse flash chromatography with the following conditions: column, C18 silica gel; mobile phase, MeCN in water (0.1% FA), 0% to 100% gradient in 30 min; detector, UV 254 nm. This resulted in (R)-1-(2-aminopyrimidin-5-yl)-3-(1-(5,7-difluoro-3-methylbenzofuran-2-yl)-2,2,2-trifluoroethyl)urea (73 mg, 36.10%) as a white solid.

MS (ESI): mass calcd. for C$_{20}$H$_{18}$F$_5$N$_5$O$_4$S, 519.45, m/z found 520.15 [M+H]$^+$.

$^1$H NMR (400 MHz, DMSO-d6) δ 8.34 (d, J=11.6 Hz, 3H), 7.59-7.27 (m, 3H), 6.05 (p, J=8.5 Hz, 1H), 4.55 (h, J=7.4 Hz, 1H), 3.49 (dd, J=13.3, 7.4 Hz, 1H), 3.40-3.36 (m, 1H), 3.17 (dt, J=13.3, 8.4 Hz, 1H), 2.96 (dd, J=13.3, 7.6 Hz, 1H), 2.43 (dd, J=12.9, 6.9 Hz, 1H), 2.30 (s, 3H), 2.22-2.11 (m, 1H).

Example 157: Preparation of Compound 236

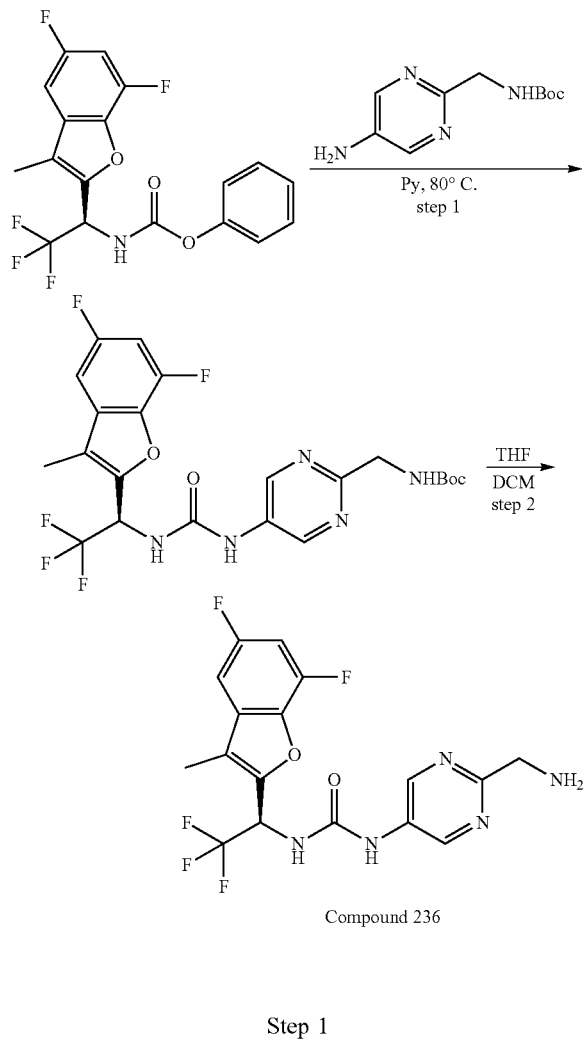

Compound 236

Step 1

To a stirred solution of phenyl N-[(1R)-1-(5,7-difluoro-3-methyl-1-benzofuran-2-yl)-2,2,2-trifluoroethyl]carbamate (283.47 mg, 0.736 mmol, 1.1 equiv) in pyridine (2 mL) was added tert-butyl N-[(5-aminopyrimidin-2-yl)methyl]carbamate (150 mg, 0.669 mmol, 1.00 equiv) in dropwise portions. The resulting mixture was stirred overnight at 80° C. under air atmosphere. The reaction was monitored by LCMS. The residue was purified by reverse flash chromatography with the following conditions: column, C18 silica gel; mobile phase, MeCN in water (0.1% NH$_3$·H$_2$O), 0% to 100% gradient in 30 min; detector, UV 254 nm. This resulted in tert-butyl N-{[5-({[(1R)-1-(5,7-difluoro-3-methyl-1-benzofuran-2-yl)-2,2,2-trifluoroethyl]carbamoyl}amino)pyrimidin-2-yl]methyl}carbamate (100 mg, 27.56%) as an off-white solid.

Step 2

To a stirred solution of tert-butyl N-{[5-({[(1R)-1-(5,7-difluoro-3-methyl-1-benzofuran-2-yl)-2,2,2-trifluoroethyl]carbamoyl}amino)pyrimidin-2-yl]methyl}carbamate (100 mg, 0.194 mmol, 1 equiv) in DCM (2 mL) was added TFA (2 mL). The resulting mixture was stirred for 1 h at room temperature under air atmosphere. The reaction was monitored by LCMS. The crude product was purified by reverse phase flash with the following conditions: column, C18 silica gel; mobile phase, MeCN in water (0.1% NH$_3$·H$_2$O), 0% to 100% gradient in 30 min; detector, UV 254 nm to afford Compound 236 (74.5 mg, 92.09%) as a white solid. MS (ESI): mass calcd. for C$_{17}$H$_{14}$F$_5$N$_5$O$_2$, 415.1, m/z found 416.1 [M+H]$^+$.

$^1$H NMR (400 MHz, DMSO-d$_6$) δ 8.99 (s, 1H), 8.81 (s, 2H), 8.14 (s, 1H), 7.48-7.37 (m, 2H), 6.10 (t, J=8.2 Hz, 1H), 3.83 (s, 2H), 2.68 (s, 2H), 2.32 (s, 3H).

Example 158: Preparation of Compound 237

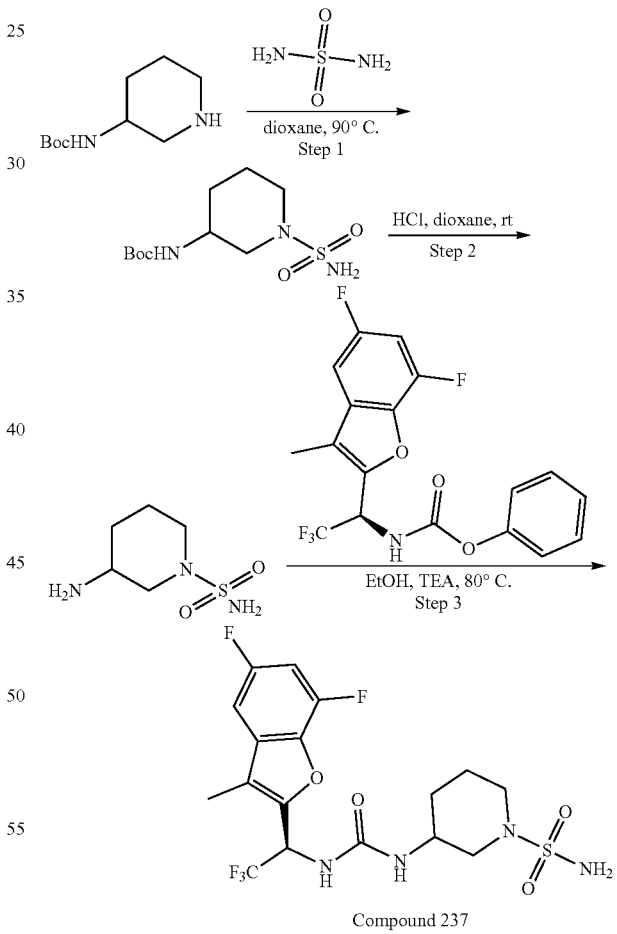

Compound 237

Step 1

The resulting mixture of tert-butyl piperidin-3-ylcarbamate (200 mg, 0.999 mmol, 1 equiv), sulfamide (200 mg, 2.081 mmol, 2.08 equiv) in dioxane (6 mL) was stirred for 16 h at 90° C. under nitrogen atmosphere. The resulting mixture was diluted with water. The resulting mixture was extracted with EA. The combined organic layers were washed with brine and dried over anhydrous $Na_2SO_4$. After filtration, the filtrate was concentrated under reduced pressure to provide tert-butyl (1-sulfamoylpiperidin-3-yl)carbamate (170 mg, 60.94%) was obtained as colorless oil. MS (ESI): mass calcd. for $C_{10}H_{21}N_3O_4S$, 279.1, m/z found 280.0 $[M+H]^+$.

Step 2

The resulting mixture of tert-butyl (1-sulfamoylpiperidin-3-yl)carbamate (150 mg, 0.537 mmol, 1 equiv) and HCl (gas) in 1,4-dioxane (6 mL) was stirred for 2 h at room temperature under nitrogen atmosphere. The resulting mixture was concentrated under reduced pressure to give 3-aminopiperidine-1-sulfonamide (100 mg, crude) as a yellow solid. MS (ESI): mass calcd. For $C_5H_{13}N_3O_2S$, 179.1

Step 3

A mixture of phenyl (R)-(1-(5,7-difluoro-3-methylbenzofuran-2-yl)-2,2,2-trifluoroethyl)carbamate (100 mg, 0.260 mmol, 1 equiv), 3-aminopiperidine-1-sulfonamide (100 mg, 0.558 mmol, 2.15 equiv), TEA (100 mg, 0.988 mmol, 3.81 equiv) in EtOH (5 mL) was stirred for 16 h at 80° C. under nitrogen atmosphere. The resulting mixture was diluted with water. The resulting mixture was extracted with DCM. The combined organic layers were washed with brine, dried over anhydrous $Na_2SO_4$. After filtration, the filtrate was concentrated under reduced pressure. The residue was purified by Prep-TLC ($CH_2Cl_2$/MeOH 10:1) to afford 3-(3-((R)-1-(5,7-difluoro-3-methylbenzofuran-2-yl)-2,2,2-trifluoroethyl)ureido)piperidine-1-sulfonamide (26.9 mg, 22.03%) as a white solid. MS (ESI): mass calcd. for $C_{17}H_{19}F_5N_4O_4S$, 470.1, m/z found 471.0 $[M+H]^+$.

$^1$H NMR (400 MHz, DMSO-$d_6$) δ 7.60-7.35 (m, 3H), 6.76 (s, 1H), 6.71 (s, 1H), 6.45 (t, J=7.2 Hz, 1H), 6.08-5.87 (m, 1H), 3.88-3.59 (m, 1H), 3.25-3.14 (m, 1H), 3.08-2.93 (m, 3H), 2.85-2.71 (m, 1H), 2.60-2.52 (m, 1H), 2.27 (s, 3H), 1.79-1.41 (m, 3H), 1.40-1.18 (s, 2H).

Example 159: Preparation of Compound 238

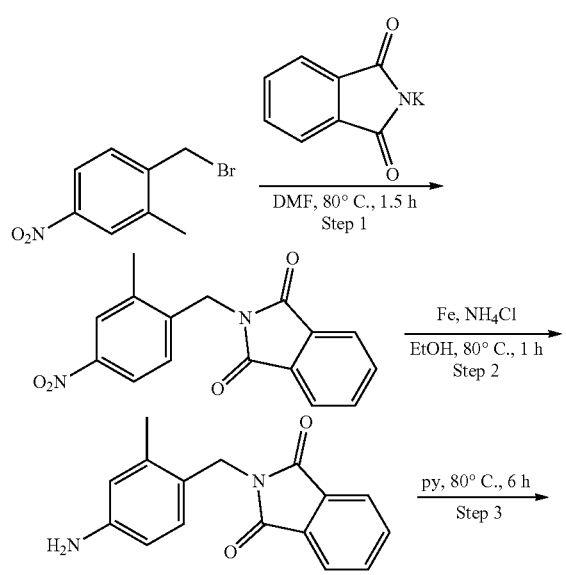

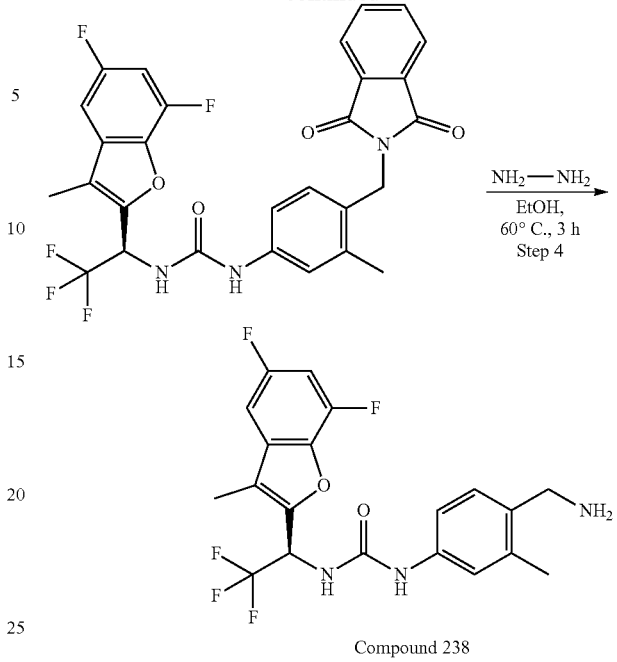

Compound 238

Step 1

A solution of 1-(bromomethyl)-2-methyl-4-nitrobenzene (300 mg, 1.304 mmol, 1 equiv) and 2-potassioisoindole-1,3-dione (362.30 mg, 1.956 mmol, 1.5 equiv) in DMF (5 mL) was stirred for 1.5 h at 80° C. under nitrogen atmosphere. Desired product could be detected by LCMS. The resulting mixture was concentrated under reduced pressure. The resulting mixture was extracted with EtOAc (2×10 mL). The combined organic layers were washed with brine (4×1 20 mL) and dried over anhydrous $Na_2SO_4$. After filtration, the filtrate was concentrated under reduced pressure to afford 2-[(2-methyl-4-nitrophenyl)methyl]isoindole-1,3-dione (350 mg, 90.59%) as a yellow solid.

MS (ESI): mass calcd. for $C_{16}H_{12}N_2O_4$, 296.1, m/z found 296.9 $[M+H]^+$.

Step 2

To a stirred solution of 2-[(2-methyl-4-nitrophenyl)methyl]isoindole-1,3-dione (300 mg, 1.013 mmol, 1 equiv) and Fe (282.73 mg, 5.065 mmol, 5 equiv) in EtOH (5 mL) were added $NH_4Cl$ (270.81 mg, 5.065 mmol, 5 equiv) and AcOH (1 mL, 17.452 mmol) at room temperature under air atmosphere. The resulting mixture was stirred for 1 h at 80° C. under air atmosphere. Desired product could be detected by LCMS. The resulting mixture was extracted with EtOAc (2×5 mL). The combined organic layers were washed with brine (4×1 10 mL) and dried over anhydrous $Na_2SO_4$. After filtration, the filtrate was concentrated under reduced pressure to afford 2-[(4-amino-2-methylphenyl)methyl]isoindole-1,3-dione (200 mg, 74.17%) as a brown oil. MS (ESI): mass calcd. for $C_{16}H_{14}N_2O_2$, 266.1, m/z found 267.0 $[M+H]^+$.

Step 3

A solution of 2-[(4-amino-2-methylphenyl)methyl]isoindole-1,3-dione (170 mg, 0.638 mmol, 1 equiv) and phenyl N-[(1R)-1-(5,7-difluoro-3-methyl-1-benzofuran-2-yl)-2,2,2-trifluoroethyl]carbamate (245.96 mg, 0.638 mmol, 1 equiv) in pyridine (5 mL, 0.063 mmol) was stirred for 5 h at 80° C. under nitrogen atmosphere. Desired product could be detected by LCMS. The resulting mixture was extracted with EtOAc (2×10 mL). The combined organic layers were washed with brine (4×1 10 mL), dried over anhydrous Na$_2$SO$_4$. After filtration, the filtrate was concentrated under reduced pressure. The residue was purified by reverse flash chromatography with the following conditions: column, C18 silica gel; mobile phase, MeCN in water (0.1% FA), 10% to 50% gradient in 10 min; detector, UV 254 nm. The resulting mixture was concentrated under reduced pressure to afford 3-[(1R)-1-(5,7-difluoro-3-methyl-1-benzofuran-2-yl)-2,2,2-trifluoroethyl]-1-{4-[(1,3-dioxoisoindol-2-yl)methyl]-3-methylphenyl}urea (250 mg, 70.25%) as a light brown solid. MS (ESI): mass calcd. for C$_{28}$H$_{20}$F$_5$N$_3$O$_4$, 227.1, m/z found 580.2 [M+Na]$^+$.

Step 4

A solution of 3-[(1R)-1-(5,7-difluoro-3-methyl-1-benzofuran-2-yl)-2,2,2-trifluoroethyl]-1-{4-[(1,3-dioxoisoindol-2-yl)methyl]-3-methylphenyl}urea (160 mg, 0.287 mmol, 1 equiv) and hydrazine (45.99 mg, 1.435 mmol, 5 equiv) in EtOH (5 mL) was stirred for 1 h at 60° C. under nitrogen atmosphere. Desired product could be detected by LCMS. The resulting mixture was concentrated under reduced pressure. The crude product (100 mg) was purified by Prep-HPLC with the following conditions (Column: YMC-Actus Triart C18 ExRS, 30*150 mm, 5 μm; Mobile Phase A: water (50 mmol/L NH$_4$HCO$_3$), Mobile Phase B: ACN; Flow rate: 60 mL/min; Gradient: 35% B to 62% B in 7.5 min, 62% B; Wave Length: 220 nm; RT1 (min): 6.25; Number Of Runs: 0) to afford 1-[4-(aminomethyl)-3-methylphenyl]-3-[(1R)-1-(5,7-difluoro-3-methyl-1-benzofuran-2-yl)-2,2,2-trifluoroethyl]urea (34.5 mg, 28.13%) as a white solid. MS (ESI): mass calcd. for C$_{20}$H$_{18}$F$_5$N$_3$O$_2$, 427.1, m/z found 855.2 [2M+H]$^+$.

$^1$H NMR (400 MHz, DMSO-d6) δ 8.59 (d, J=9.3 Hz, 1H), 7.68 (d, J=9.4 Hz, 1H), 7.50-7.36 (m, 2H), 7.27-6.94 (m, 3H), 6.05 (p, J=8.3 Hz, 1H), 3.63 (s, 2H), 2.31 (s, 3H), 2.22 (s, 3H).

Example 160: Preparation of Compound 239

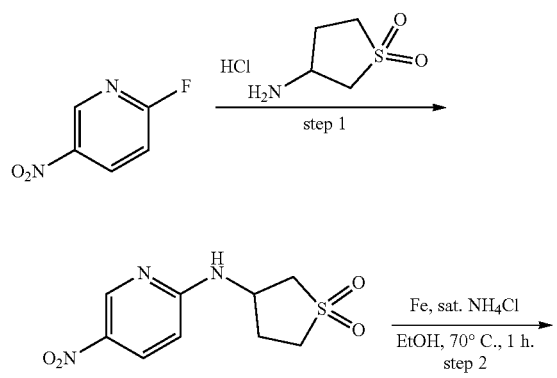

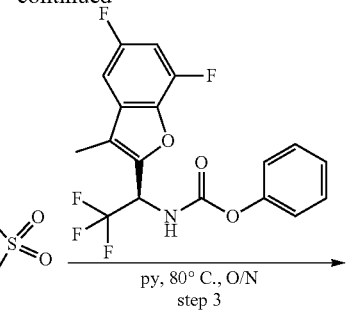

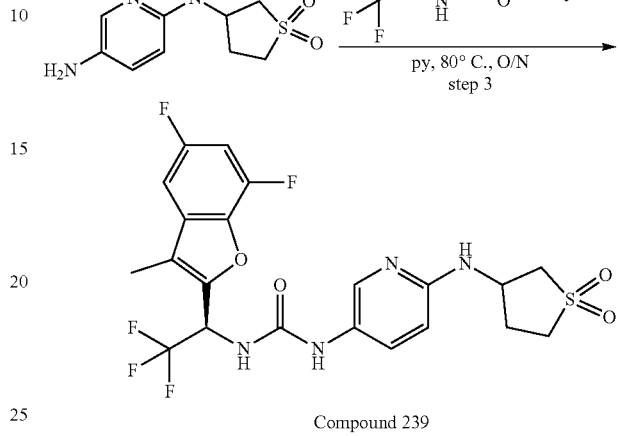

Compound 239

Step 1

A mixture of 2-fluoro-5-nitropyridine (500 mg, 3.52 mmol), 3-aminotetrahydrothiophene 1,1-dioxide hydrochloride (1.2 g, 7.04 mmol) and TEA (2 mL) in DMSO (6 mL) was stirred overnight at 100° C. The resulting mixture was concentrated under reduced pressure. The residue was purified by reverse flash chromatography to afford 3-((5-nitropyridin-2-yl)amino) tetrahydrothiophene 1,1-dioxide (900 mg, 99.42%) as a red solid. MS (ESI): mass calcd. for C$_9$H$_{11}$N$_3$O$_4$S, 257.05, m/z found 258.20 [M+H]$^+$.

Step 2

A mixture of 3-((5-nitropyridin-2-yl)amino)tetrahydrothiophene 1,1-dioxide (500 mg, 1.94 mmol), and Fe (1.08 g, 19.44 mmol) in EtOH (4 mL) and sat. NH$_4$Cl (4 mL) was stirred for 1 h at 70° C. The resulting mixture was filtered and the filter cake was washed with EtOH. The filtrate was diluted with water and extracted with DCM (3×50 mL). The combined organic layers were dried over anhydrous Na$_2$SO$_4$. After filtration, the filtrate was concentrated under reduced pressure to afford 3-((5-aminopyridin-2-yl)amino) tetrahydrothiophene 1,1-dioxide (371 mg, 84.13%) as a yellow oil.

MS (ESI): mass calcd. for C$_9$H$_{13}$N$_3$O$_2$S, 227.07, m/z found 228.00 [M+H]$^+$.

Step 3

A solution of 3-((5-aminopyridin-2-yl)amino)tetrahydrothiophene 1,1-dioxide (141.5 mg, 0.62 mmol) and phenyl N-[(1R)-1-(5,7-difluoro-3-methyl-1-benzofuran-2-yl)-2,2,2-trifluoroethyl]carbamate (80 mg, 0.21 mmol) in pyridine (2 mL) was stirred overnight at 80° C., then concentrated under reduced pressure. The residue was purified by Prep-HPLC to afford 1-((R)-1-(5,7-difluoro-3-methylbenzofuran-2-yl)-2,2,2-trifluoroethyl)-3-(6-((1,1-dioxidotetrahydrothiophen-3-yl)amino)pyridine-3-yl)urea (46 mg, 42.99%) as a white solid. MS (ESI): mass calcd. for $C_{21}H_{19}F_5N_4O_4S$, 518.10, m/z found 519.20 [M+H]$^+$.

$^1$H NMR (400 MHz, DMSO-d6) δ 8.33 (s, 1H), 7.99 (d, J=2.7 Hz, 1H), 7.66 (d, J=9.5 Hz, 1H), 7.51 (dd, J=8.8, 2.7 Hz, 1H), 7.48-7.37 (m, 2H), 6.76 (d, J=6.8 Hz, 1H), 6.49 (d, J=8.9 Hz, 1H), 6.03 (m, 1H), 4.54 (m, 1H), 3.51 (dd, J=13.3, 7.3 Hz, 1H), 3.33 (t, J=13.3 Hz, 1H), 3.16 (dt, J=13.3, 8.0 Hz, 1H), 2.85 (dd, J=13.3, 7.1 Hz, 1H), 2.44 (dt, J=12.7, 6.4 Hz, 1H), 2.30 (s, 3H), 2.17-2.03 (m, 1H).

Example 161: Preparation of Compound 240

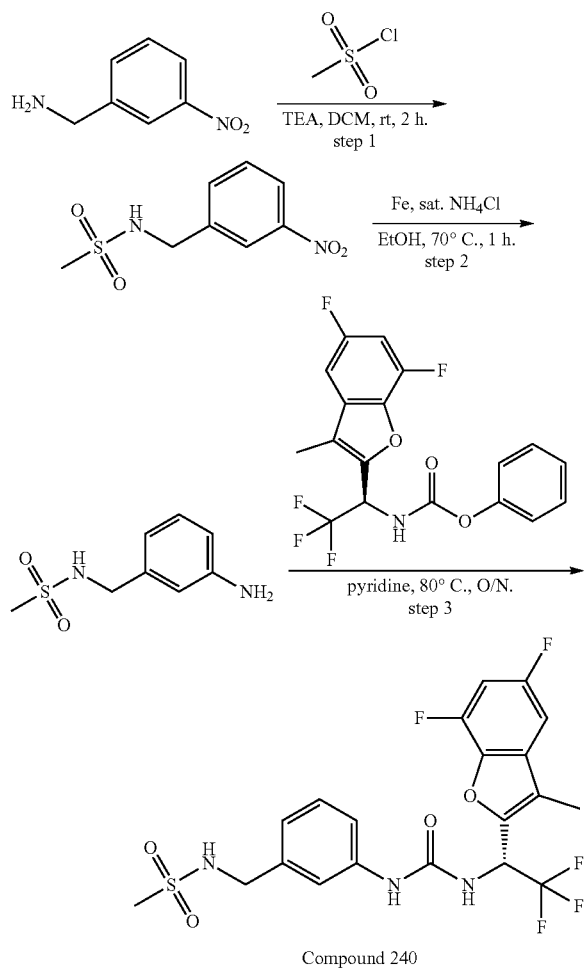

Compound 240

Step 1

To a stirred solution of 1-(3-nitrophenyl) methanamine (1 g, 6.57 mmol) and TEA (1.99 g, 19.74 mmol) in DCM (10 mL) was added methanesulfonyl chloride (0.90 g, 7.89 mmol) at 0° C. The resulting solution was stirred for 2 h at room temperature, then diluted with sat. NaHCO$_3$. The resulting mixture was extracted with DCM (3×50 mL). The combined organic layers were dried over anhydrous Na$_2$SO$_4$. After filtration, the filtrate was concentrated under reduced pressure to afford N-[(3-nitrophenyl) methyl] methanesulfonamide (1.5 g, 99.13%) as a light yellow solid.

MS (ESI): mass calcd. for $C_8H_{10}N_2O_4S$, 230.04, m/z found 248.25 [M+18]$^+$.

Step 2

A mixture of N-[(3-nitrophenyl) methyl] methanesulfonamide (500 mg, 2.17 mmol) and Fe (1.21 g, 21.72 mmol) in EtOH (4 mL) and sat. NH$_4$Cl (4 mL) was stirred for 1 h at 70° C. The resulting mixture was filtered and the filter cake was washed with EtOH. The filtrate was diluted with water, then extracted with DCM (3×50 mL). The combined organic layers were dried over anhydrous Na$_2$SO$_4$. After filtration, the filtrate was concentrated under reduced pressure to afford N-(3-aminobenzyl)methanesulfonamide (400 mg, 92.17%) as a yellow oil. MS (ESI): mass calcd. for $C_8H_{12}N_2O_2S$, 200.06. m/z found 200.95 [M+1]$^+$.

Step 3

A solution of N-[(3-aminophenyl) methyl] methanesulfonamide (124.7 mg, 0.62 mmol) and phenyl N-[(1R)-1-(5,7-difluoro-3-methyl-1-benzofuran-2-yl)-2,2,2-trifluoroethyl] carbamate (80 mg, 0.21 mmol) in pyridine (3 mL) was stirred overnight at 80° C. The resulting solution was concentrated under reduced pressure. The residue was purified by Prep-HPLC to afford 3-[(1R)-1-(5,7-difluoro-3-methyl-1-benzofuran-2-yl)-2,2,2-trifluoroethyl]-1-[3-(methanesulfonamidomethyl)phenyl]urea (41.4 mg, 40.57%) as a white powder. MS (ESI): mass calcd. for $C_{20}H_{18}F_5N_3O_4S$, 491.09, m/z found 492.15 [M+H]$^+$.

$^1$H NMR (400 MHz, DMSO-d6) δ 8.75 (s, 1H), 7.68 (d, J=9.5 Hz, 1H), 7.56 (s, 1H), 7.49-7.37 (m, 3H), 7.35-7.28 (m, 1H), 7.24 (t, J=7.8 Hz, 1H), 6.95 (d, J=7.2 Hz, 1H), 6.09 (m, 1H), 4.11 (d, J=5.5 Hz, 2H), 2.86 (s, 3H), 2.32 (s, 3H).

Example 162: Preparation of Compound 241

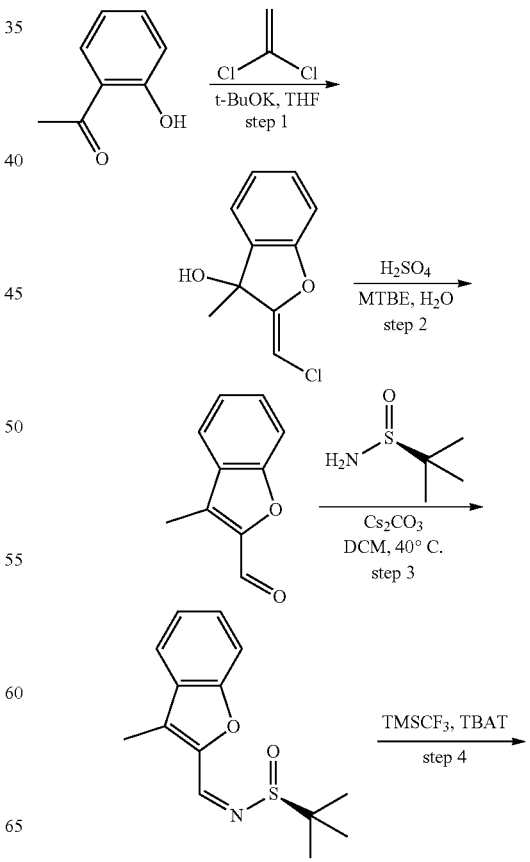

-continued

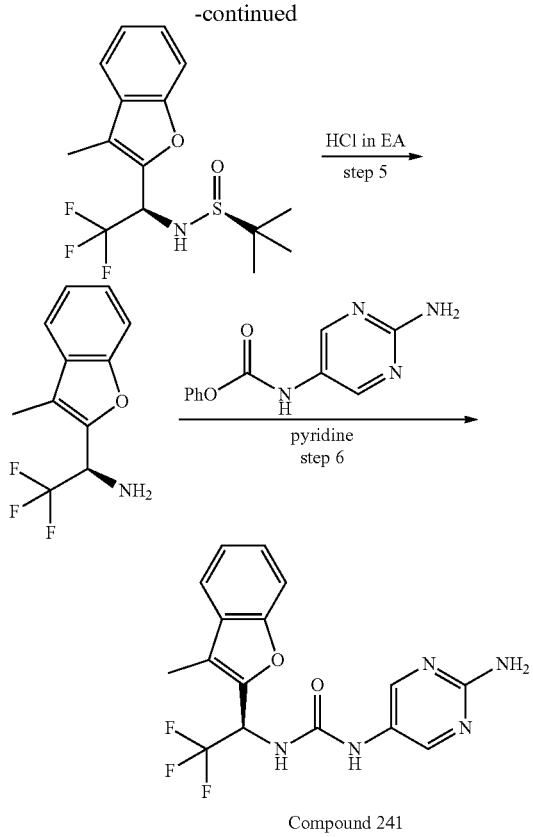

Compound 241

Step 1

A 250 mL three-neck flask was equipped with an overhead stirrer, addition funnel, and thermometer. THF (50 mL) was added to the flask. O-acetylphenol (5 g, 36.72 mmol) was added to the flask at 25° C. in one portion. Vinylidene chloride (4.11 mL, 51.42 mmol) was carefully added under nitrogen atmosphere. The mixture turned light yellow, then was stirred at 0° C. for 20 min and t-BuOK (15.66 g, 139.55 mmol) was added slowly to the reaction mixture under $N_2$. After addition, the mixture turned white. The resulting mixture was stirred at 25° C. for 3 hr. To the resulting mixture was added water, then was extracted with MTBE (3×100 mL). The combined organic layers were washed with brine (2×50 mL) and dried over anhydrous $Na_2SO_4$. After filtration, the filtrate was concentrated under reduced pressure. This resulted in (2Z)-2-(chloromethylidene)-3-methyl-1-benzofuran-3-ol (8 g) as a light yellow oil. The crude product was used in the next step directly without further purification.

Step 2

To a solution of (2Z)-2-(chloromethylidene)-3-methyl-1-benzofuran-3-ol (8 g, 40.69 mmol) in MTBE (20 mL) was added $H_2SO_4$ (20.00 mL, 80.15 mmol, 4M). The resulting mixture was stirred overnight at room temperature under nitrogen atmosphere. The reaction mixture was quenched by addition of $H_2O$ (50 mL) and extracted with EA (100 mL). The combined organic layers were dried over $Na_2SO_4$, filtered, and concentrated under reduced pressure to give a residue. The residue was purified by silica gel column chromatography and eluted with PE/EA (5:1) to afford 3-methyl-1-benzofuran-2-carbaldehyde (5.63 g, 86.39%) as a yellow solid.

Step 3

To a solution of 3-methyl-1-benzofuran-2-carbaldehyde (5 g, 31.22 mmol) in DCM (50 mL) was added $Cs_2CO_3$ (10.37 g, 31.83 mmol) at 25° C. The reaction mixture was stirred at 25° C. for 10 min, then (S)-2-methylpropane-2-sulfinamide (4.28 g, 35.27 mmol) was added to the reaction mixture. The mixture was stirred at room temperature for 1 hr. The resulting mixture was filtered, the filter cake was washed with DCM (3×10 mL). The filtrate was concentrated under reduced pressure. The residue was purified by silica gel column chromatography, eluted with PE/EA (10:1) to afford (S)-2-methyl-N-[(1Z)-(3-methyl-1-benzofuran-2-yl)methylidene]propane-2-sulfinamide (8.6 g, 93.40%) as a yellow solid. MS (ESI): mass calcd. For $C_{14}H_{17}NO_2S$, 263.10, m/z found 264.00 $[M+H]^+$.

Step 4

To a solution of (S)-2-methyl-N-[(1Z)-(3-methyl-1-benzofuran-2-yl)methylidene]propane-2-sulfinamide (1 g, 3.79 mmol) in THF (10 mL) at −60° C. was added tetrabutylammonium difluorotriphenylsilicate difluorotriphenyl-1^[5]-silane (2.05 g, 3.79 mmol). The mixture was stirred at −60° C. for 1 hr. Then $TMSCF_3$ (2.16 g, 15.19 mmol) in THF (2 mL) was added at −60° C. The mixture was stirred at −30° C. for 30 min. The reaction was quenched by the addition of sat. $NH_4Cl$ (aq.) (20 mL) at −30° C. The resulting mixture was extracted with EtOAc (3×20 mL). The combined organic layers were washed with brine (1×20 mL), dried over anhydrous $Na_2SO_4$. After filtration, the filtrate was concentrated under reduced pressure. The residue was purified by reverse flash chromatography with mobile phase, EA in PE, 0% to 50% gradient in 25 min; detector, UV 254 nm. This resulted in (S)-2-methyl-N-[(1R)-2,2,2-trifluoro-1-(3-methyl-1-benzofuran-2-yl)ethyl]propane-2-sulfinamide (1.15 g, 90.85%) as a yellow oil. MS (ESI): mass calcd. For $C_{15}H_{18}F_3NO_2S$, 333.10, m/z found 334.10 $[M+H]^+$.

Step 5

A solution of (S)-2-methyl-N-[(1R)-2,2,2-trifluoro-1-(3-methyl-1-benzofuran-2-yl)ethyl]propane-2-sulfinamide (1 g, 3.00 mmol) in EA (10 mL) was added HCl (g) in EA (10 mL, 4M) dropwise at 0° C. The resulting mixture was stirred overnight at room temperature under nitrogen atmosphere. The mixture was neutralized to pH 7 with saturated $NaHCO_3$ (aq.). The resulting mixture was extracted with EtOAc (3×20 mL). The combined organic layers were washed with brine (2×20 mL) and dried over anhydrous $Na_2SO_4$. After filtration, the filtrate was concentrated under reduced pressure to afford (1R)-2,2,2-trifluoro-1-(3-methyl-1-benzofuran-2-yl)ethanamine (500 mg, 72.72%) as a light yellow oil. MS (ESI): mass calcd. for $C_{11}H_{10}F_3NO$, 229.07, m/z found 230.00 $[M+H]^+$.

Step 6

A solution of (1R)-2,2,2-trifluoro-1-(3-methyl-1-benzofuran-2-yl)ethanamine (100 mg, 0.44 mmol) and phenyl N-(2-aminopyrimidin-5-yl)carbamate (90.40 mg, 0.39 mmol) in pyridine (1 mL) was stirred overnight at 80° C. under nitrogen atmosphere. The resulting mixture was concentrated under reduced pressure. The residue was purified by reverse flash chromatography with the following conditions: column, C18 silica gel; mobile phase, MeCN in water (0.1% FA), 10% to 50% gradient in 30 min; detector, UV 254 nm to afford 1-(2-aminopyrimidin-5-yl)-3-[(1R)-2,2,2-trifluoro-1-(3-methyl-1-benzofuran-2-yl)ethyl]urea (36 mg, 22.6%) as a yellow solid. The product was separated by CHIRAL_HPLC: Column: (R, R)-WHELK-O1-Kromasi, 5*25 cm, 5 μm; Mobile Phase A: Hex (0.5% 2M NH$_3$-MeOH)-HPLC, Mobile Phase B: EtOH-HPLC; Flow rate: 20 mL/min; Gradient: 20% B to 20% B in 20 min; Wave Length: 220/254 nm; RT1 (min): 9.65; RT2 (min): 15.82; Sample Solvent: EtOH-HPLC; Injection Volume: 2.3 mL; Number Of Runs: 1 to give 1-(2-aminopyrimidin-5-yl)-3-[(1R)-2,2,2-trifluoro-1-(3-methyl-1-benzofuran-2-yl)ethyl]urea (24.3 mg, 67.16%) as a white solid. MS (ESI): mass calcd. for $C_{16}H_{14}F_3N_5O_2$, 365.11, m/z found 366.00 $[M+H]^+$.

$^1$H NMR (400 MHz, DMSO-d6) δ 8.21 (s, 3H), 7.72 (d, J=9.4 Hz, 1H), 7.67 (dd, J=7.7, 1.3 Hz, 1H), 7.63-7.57 (m, 1H), 7.42-7.32 (m, 2H), 6.40 (s, 2H), 5.96 (p, J=8.5 Hz, 1H), 2.30 (s, 3H).

Example 163: Preparation of Compound 242 and 243

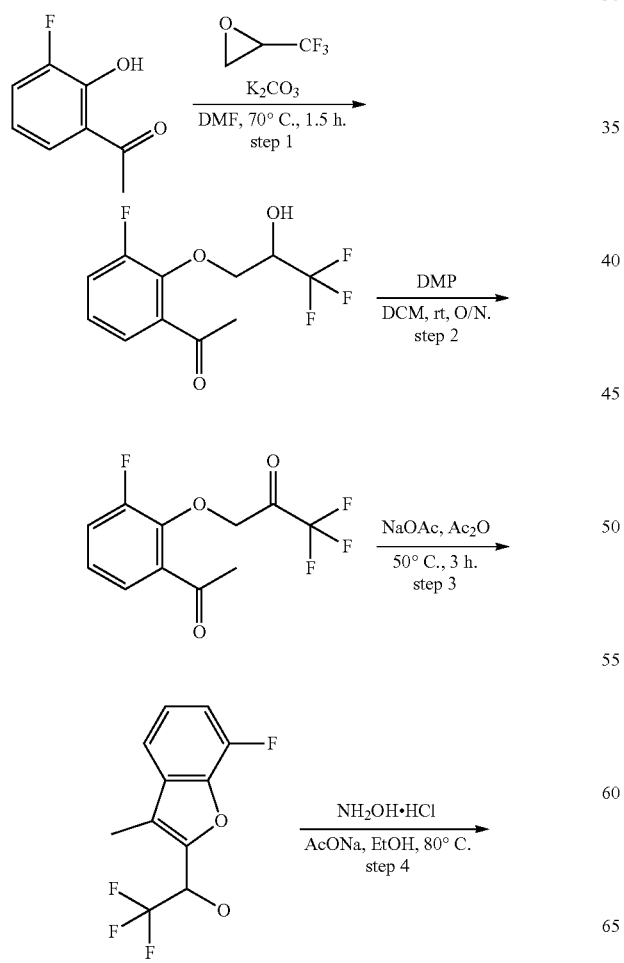

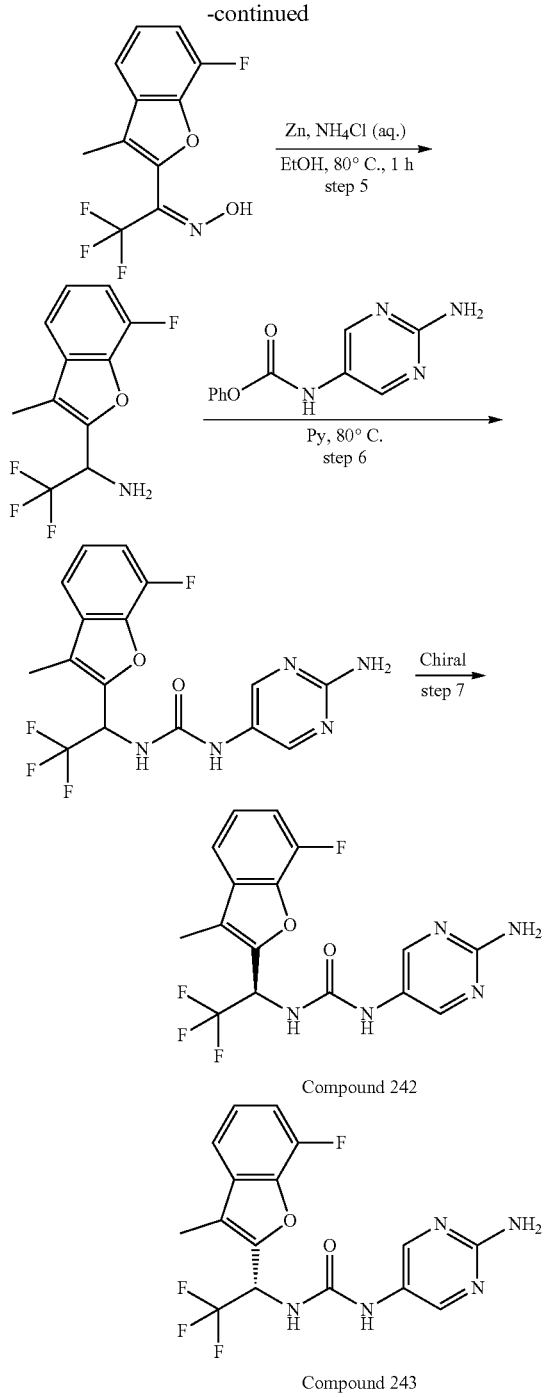

Compound 242

Compound 243

Step 1

To a stirred mixture of 1-(3-fluoro-2-hydroxyphenyl)ethanone (1 g, 6.49 mmol) and 2-(trifluoromethyl)oxirane (1.09 g, 9.73 mmol) in DMF (10 mL) was added K$_2$CO$_3$ (1.34 g, 9.73 mmol) in portions at room temperature under nitrogen atmosphere. The resulting mixture was stirred for 4 h at 70° C. under nitrogen atmosphere. The resulting mixture was extracted with EtOAc (2×30 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with PE/EA (8:1) to afford 1-[3-fluoro-2-(3,3,3-trifluoro-2-hydroxypropoxy)phenyl]ethanone (1.5 g, 86.86%) as a yellow oil.

MS (ESI): mass calcd. For $C_{11}H_{10}F_4O_3$, 266.06, m/z found 266.95 $[M+H]^+$.

Step 2

To a stirred solution of 1-[3-fluoro-2-(3,3,3-trifluoro-2-hydroxypropoxy)phenyl]ethanone (1 g, 3.78 mmol) in DCM (10 mL) was added DMP (1.91 g, 4.51 mmol) in portions at room temperature. The resulting mixture was stirred overnight at room temperature under nitrogen atmosphere. The reaction was quenched by the addition of sat. sodium hyposulfite (aq.) (20 mL) at 0° C. The resulting mixture was extracted with $CH_2Cl_2$ (2×30 mL). The combined organic layers were washed with sat. $NaHCO_3$ (aq.) (3×50 mL), dried over anhydrous $Na_2SO_4$. After filtration, the filtrate was concentrated under reduced pressure. The residue was purified by silica gel column chromatography, eluted with PE/EA (3:1) to afford 3-(2-acetyl-6-fluorophenoxy)-1,1,1-trifluoropropan-2-one (950 mg, 95.72%) as a yellow oil. MS (ESI): mass calcd. For $C_{11}H_8F_4O_3$, 264.04, m/z found 264.95 $[M+H]^+$.

Step 3

A mixture of 3-(2-acetyl-6-fluorophenoxy)-1,1,1-trifluoropropan-2-one (1 g, 3.79 mmol) and NaOAc (0.47 g, 5.68 mmol) in $Ac_2O$ (10 mL) was stirred for 2 h at room temperature under nitrogen atmosphere. The mixture was basified to pH 7 with NaOH (aq.). The resulting mixture was extracted with EtOAc (2×30 mL). The combined organic layers were dried over anhydrous $Na_2SO_4$. After filtration, the filtrate was concentrated under reduced pressure to afford 2,2,2-trifluoro-1-(7-fluoro-3-methyl-1-benzofuran-2-yl)ethanone (930 mg, 99.81%) as a white solid.

MS (ESI): mass calcd. For $C_{11}H_6F_4O_2$, 246.03, m/z found 244.90 $[M-H]^+$.

Step 4

To a stirred solution of 2,2,2-trifluoro-1-(7-fluoro-3-methyl-1-benzofuran-2-yl)ethanone (900 mg, 3.66 mmol) and $NH_2OH·HCl$ (636 mg, 9.14 mmol) in EtOH (10 mL) was added AcONa (600 mg, 7.31 mmol) in portions at room temperature under nitrogen atmosphere. The resulting mixture was stirred overnight at 80° C. under nitrogen atmosphere. The resulting mixture was filtered, the filter cake was washed with EtOH (3×20 mL). The filtrate was concentrated under reduced pressure. The residue was purified by silica gel column chromatography, eluted with PE/EA (5:1) to afford (E)-N-[2,2,2-trifluoro-1-(7-fluoro-3-methyl-1-benzofuran-2-yl)ethylidene]hydroxylamine (870 mg, 91.11%) as a white solid. MS (ESI): mass calcd. For $C_{11}H_7F_4NO_2$, 261.04, m/z found 261.95 $[M+H]^+$.

Step 5

To a stirred mixture of (E)-N-[2,2,2-trifluoro-1-(7-fluoro-3-methyl-1-benzofuran-2-yl)ethylidene]hydroxylamine (200 mg, 0.77 mmol) in EtOH (4 mL) and $H_2O$ (0.8 mL) was added Zn (501 mg, 7.66 mmol) and $NH_4Cl$ (410 mg, 7.66 mmol) in portions at room temperature under nitrogen atmosphere. The resulting mixture was stirred overnight at 80° C. under nitrogen atmosphere. The resulting mixture was filtered, the filter cake was washed with EtOH (3×20 mL). The filtrate was concentrated under reduced pressure. The residue was purified by silica gel column chromatography, eluted with PE/EA (5:1) to afford 2,2,2-trifluoro-1-(7-fluoro-3-methyl-1-benzofuran-2-yl)ethanamine (100 mg, 52.83%) as a colorless oil. MS (ESI): mass calcd. for $C_{11}H_9F_4NO$, 247.06, m/z found 248.00 $[M+H]^+$.

Step 6

A mixture of 2,2,2-trifluoro-1-(7-fluoro-3-methyl-1-benzofuran-2-yl)ethanamine (90 mg, 0.36 mmol) and phenyl N-(2-aminopyrimidin-5-yl)carbamate (84 mg, 0.36 mmol) in pyridine (2 mL) was stirred overnight at 80° C. under nitrogen atmosphere. The resulting mixture was concentrated under reduced pressure. The residue was purified by reverse flash chromatography with the following conditions: column, C18 silica gel; mobile phase, MeCN in water (0.1% FA), 10% to 50% gradient in 30 min; detector, UV 254 nm to afford 1-(2-aminopyrimidin-5-yl)-3-[2,2,2-trifluoro-1-(7-fluoro-3-methyl-1-benzofuran-2-yl)ethyl]urea (70 mg, 50.16%) as a yellow solid.

MS (ESI): mass calcd. for $C_{16}H_{13}F_4N_5O_2$, 383.10, m/z found 384.10 $[M+H]^+$.

Step 7

190 mg of racemic was separated by CHIRAL-HPLC to give (Compound 242, 34.6 mg) as white solid and (Compound 243, 31.8 mg) as white solid.

Chiral Separation Condition:
Apparatus: Prep-HPLC-072
Column: (R, R)-WHELK-O1-Kromasi, 5*25 cm, 5 μm
Mobile phase: Mobile Phase A: Hex (0.5% 2M $NH_3$-MeOH)-HPLC, Mobile Phase B: EtOH-HPLC
Flow rate: 20 mL/min
Wavelength: UV 220/254 nm
Temperature: 25° C.

Compound 242

MS (ESI): mass calcd. For $C_{16}H_{13}F_4N_5O_2$, 383.10, m/z found 384.10 $[M+H]^+$.

$^1$H NMR (400 MHz, DMSO-$d_6$) δ 8.22 (s, 3H), 7.81 (d, J=9.4 Hz, 1H), 7.51 (dd, J=5.6, 3.2 Hz, 1H), 7.37-7.27 (m, 2H), 6.40 (s, 2H), 6.03 (p, J=8.4 Hz, 1H), 2.32 (s, 3H).

Example 164: Preparation of Compound 244

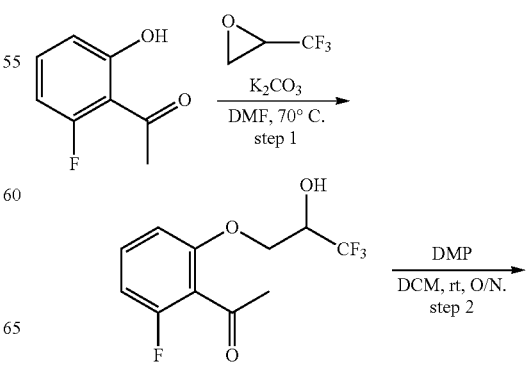

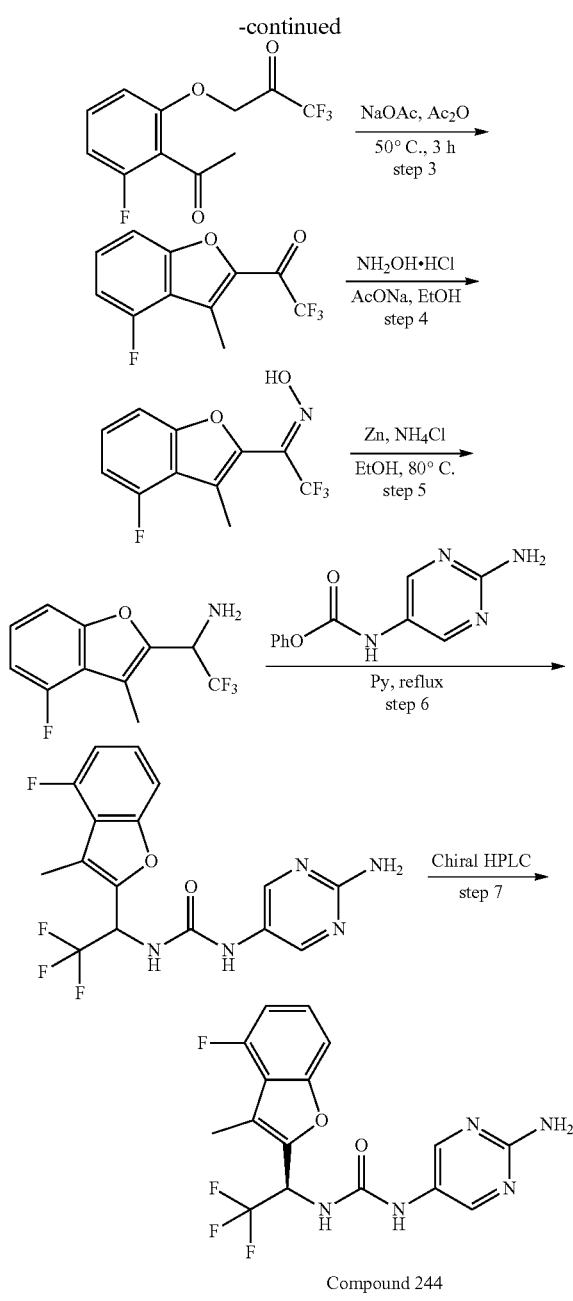

Compound 244

Step 1

A solution of 1-(2-fluoro-6-hydroxyphenyl)ethanone (1.2 g, 7.79 mmol) and 2-(trifluoromethyl)oxirane (0.87 g, 7.77 mmol) and $K_2CO_3$ (1.61 g, 11.69 mmol) in DMF (10 mL) was stirred for 2 h at 70° C. under nitrogen atmosphere. The mixture was allowed to cool down to room temperature. The resulting mixture was diluted with water (60 mL). The resulting mixture was extracted with EtOAc (3×50 mL). The combined organic layers were washed with water (3×50 mL) and dried over anhydrous $Na_2SO_4$. After filtration, the filtrate was concentrated under reduced pressure. The residue was purified by silica gel column chromatography, eluted with PE/EA (10:1) to afford 1-[2-fluoro-6-(3,3,3-trifluoro-2-hydroxypropoxy)phenyl]ethanone (1.4 g, 67.56%) as a yellow oil. MS (ESI): mass calcd. for $C_{11}H_{10}F_4O_3$, 266.06, m/z found 266.90 [M+H]$^+$.

Step 2

To a stirred solution of 1-[2-fluoro-6-(3,3,3-trifluoro-2-hydroxypropoxy)phenyl]ethanone (1.3 g, 4.89 mmol) in DCM (10 mL) was added DMP (2.49 g, 5.86 mmol) in portions at 0° C. under nitrogen atmosphere. The resulting mixture was stirred for 8 h at room temperature under nitrogen atmosphere. The reaction was quenched by the addition of sat. sodium hyposulfite (aq.) (20 mL) at 0° C. The resulting mixture was extracted with $CH_2Cl_2$ (3×50 mL). The combined organic layers were washed with sat. $NaHCO_3$ (aq.) (1×50 mL), dried over anhydrous $Na_2SO_4$. After filtration, the filtrate was concentrated under reduced pressure. The residue was purified by silica gel column chromatography and eluted with PE/EA (5:1) to afford 3-(2-acetyl-3-fluorophenoxy)-1,1,1-trifluoropropan-2-one (1.1 g, 63.09%) as a yellow oil. MS (ESI): mass calcd. for $C_{11}H_8F_4O_3$, 264.04, m/z found 262.90 [M−H]$^-$.

Step 3

A mixture of 3-(2-acetyl-3-fluorophenoxy)-1,1,1-trifluoropropan-2-one (1.14 g, 4.32 mmol) and NaOAc (530 mg, 6.47 mmol) in $Ac_2O$ (10 mL) was stirred for 2 h at 50° C. under a nitrogen atmosphere. The mixture was basified to pH 7 with $Na_2CO_3$ (aq.). To the reaction was added water, and the resulting mixture was extracted with EtOAc (2×100 mL). The combined organic layers were dried over anhydrous $Na_2SO_4$ and concentrated under vacuum. The residue was purified by silica gel column chromatography, eluted with PE to afford 2,2,2-trifluoro-1-(4-fluoro-3-methyl-1-benzofuran-2-yl)ethanone (590 mg, 55.54%) as a white solid. MS (ESI): mass calcd. for $C_{11}H_6F_4O_2$, 246.03, m/z found 244.90 [M−H]$^-$.

Step 4

To a stirred solution of 2,2,2-trifluoro-1-(4-fluoro-3-methyl-1-benzofuran-2-yl)ethanone (590 mg, 2.40 mmol) and $NH_2OH$ HCl (333 mg, 4.79 mmol) in EtOH (2 mL) was added AcONa (393 mg, 4.79 mmol) in portions at room temperature under nitrogen atmosphere. The resulting mixture was stirred overnight at 80° C. under nitrogen atmosphere. The resulting mixture was filtered, the filter cake was washed with EtOH (3×50 mL). The filtrate was concentrated under reduced pressure. The residue was purified by silica gel column chromatography, eluting with PE/EA (5:1) to afford (E)-N-[2,2,2-trifluoro-1-(4-fluoro-3-methyl-1-benzofuran-2-yl)ethylidene]hydroxylamine (611 mg, 97.62%) as a white solid. MS (ESI): mass calcd. for $C_{11}H_7F_4NO_2$, 261.04, m/z found 259.95 [M−H]$^+$.

Step 5

To a stirred mixture of (E)-N-[2,2,2-trifluoro-1-(4-fluoro-3-methyl-1-benzofuran-2-yl)ethylidene]hydroxylamine (630 mg, 2.41 mmol) in EtOH (5 mL) and $H_2O$ (1 mL) was added Zn (1.58 g, 24.12 mmol) and $NH_4Cl$ (1.29 g, 24.12 mmol) in portions at room temperature under a nitrogen atmosphere. The resulting mixture was stirred for 3 h at 80° C. under nitrogen atmosphere. The resulting mixture was filtered, the filter cake was washed with EtOH (3×50 mL). The filtrate was concentrated under reduced pressure. The residue was purified by silica gel column chromatography, eluting with CH₂Cl₂ to afford 2,2,2-trifluoro-1-(4-fluoro-3-methyl-1-benzofuran-2-yl)ethanamine (420 mg, 70.44%) as a yellow oil. MS (ESI): mass calcd. for $C_{11}H_9F_4NO$, 247.06, m/z found 230.95 $[M-NH_3+H]^+$.

Step 6

A mixture of 2,2,2-trifluoro-1-(4-fluoro-3-methyl-1-benzofuran-2-yl)ethanamine (100 mg, 0.41 mmol) and phenyl N-(2-aminopyrimidin-5-yl)carbamate (112 mg, 0.49 mmol) in pyridine (1 mL) was stirred for 24 h at 80° C. under nitrogen atmosphere. The resulting mixture was concentrated under reduced pressure. The residue was purified by Prep-TLC (CH₂Cl₂/MeOH 10:1) to afford 1-(2-aminopyrimidin-5-yl)-3-[2,2,2-trifluoro-1-(4-fluoro-3-methyl-1-benzofuran-2-yl)ethyl]urea (50 mg, 32.24%) as a yellow solid. MS (ESI): mass calcd. for $C_{16}H_{13}F_4N_5O_2$, 383.10, m/z found 384.05 $[M+H]^+$.

Step 7

50 mg of racemic was separated by CHIRAL-HPLC to give (Compound 244, 19.6 mg) as a white solid.
Chiral Separation Condition:
Apparatus: Prep-HPLC-072
Column: (R, R)-WHELK-O1-Kromasi, 5*25 cm, 5 μm
Mobile phase: Mobile Phase A: Hex (0.5% 2M NH₃-MeOH)-HPLC, Mobile Phase B: EtOH:DCM=1:1-HPLC
Flow rate: 20 mL/min
Wavelength: UV 220/254 nm
Temperature: 25° C.
MS (ESI): mass calcd. For $C_{16}H_{13}F_4N_5O_2$, 383.10, m/z found 384.10 $[M+H]^+$.
¹H NMR (400 MHz, DMSO-d₆) δ 8.22-8.21 (m, 3H), 7.75 (d, J=9.4 Hz, 1H), 7.48 (d, J=8.3 Hz, 1H), 7.47-7.38 (m, 1H), 7.15-7.10 (m, 1H), 6.40 (s, 2H), 5.99 (p, J=8.3 Hz, 1H), 2.40 (s, 3H).

Example 165: Preparation of Compound 245

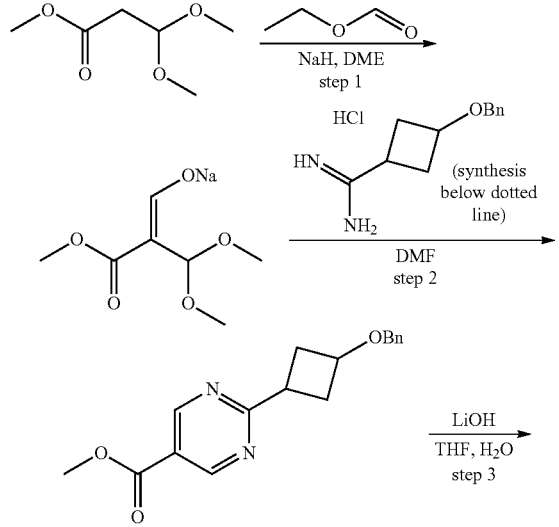

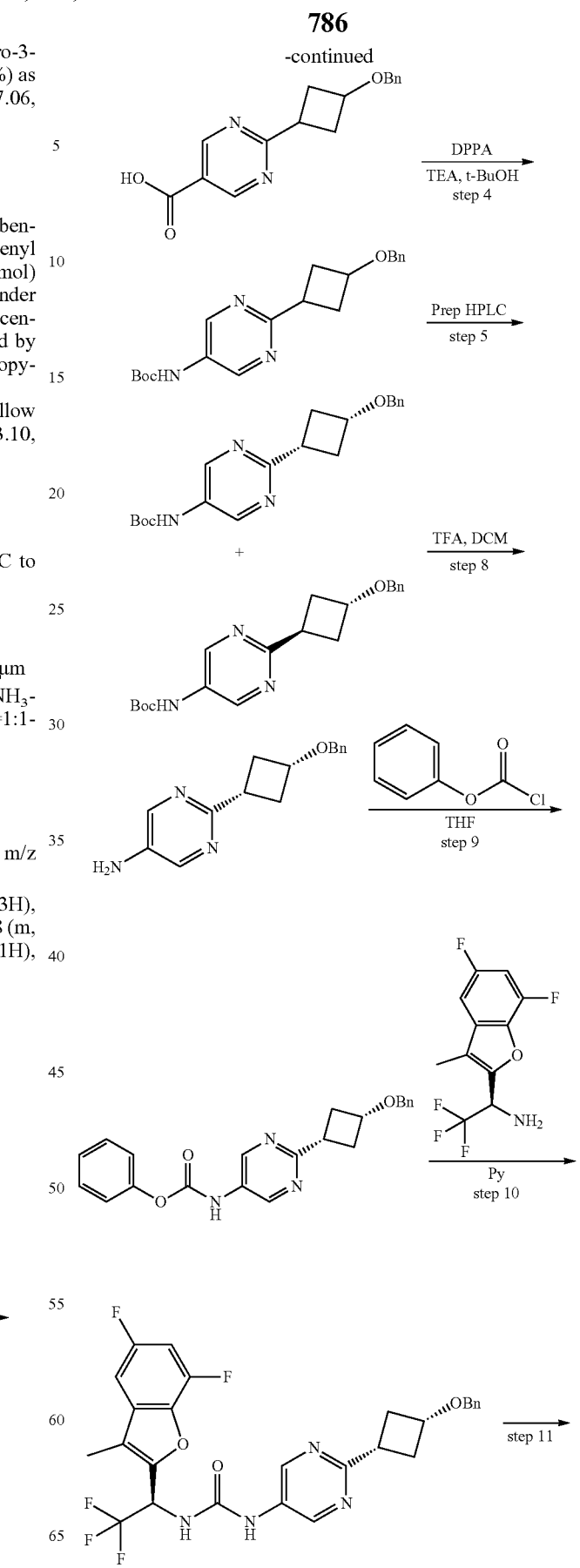

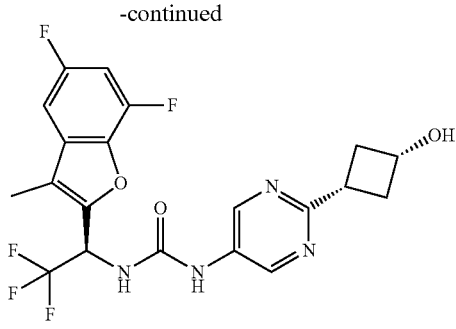

Compound 245

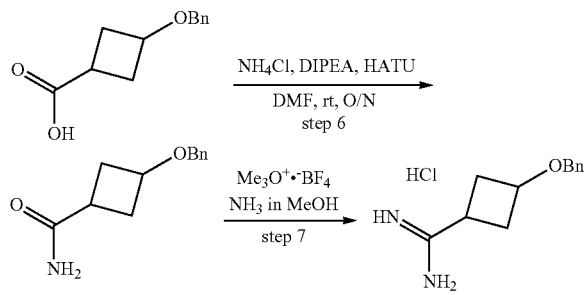

Step 1

To a stirred solution of methyl 3,3-dimethoxypropanoate (5.00 g, 33.75 mmol) in DME (24 mL) was added ethyl formate (6.25 g, 84.37 mmol) and NaH (1.75 g, 43.87 mmol, 60% in oil) in portions at room temperature under nitrogen atmosphere. The resulting mixture was stirred for 10 min at 45° C. under nitrogen atmosphere. The mixture was warmed to room temperature and stirred overnight at room temperature. The resulting mixture was concentrated under reduced pressure. The residue was dissolved in Et$_2$O (20 mL). The precipitated solids were collected by filtration and washed with Et$_2$O (3×10 mL) to afford methyl (2E)-2-(dimethoxymethyl)-3-(sodiooxy)prop-2-enoate (3.8 g, 56.83%) as a yellow solid.

Step 2

A mixture of methyl (2E)-2-(dimethoxymethyl)-3-(sodiooxy)prop-2-enoate (2.00 g, 10.09 mmol) and 3-(benzyloxy)cyclobutane-1-carboximidamide hydrochloride (2.19 g, 9.08 mmol) in DMF (20 mL) was stirred for 2 h at 100° C. under nitrogen atmosphere. The resulting mixture was extracted with EtOAc (3×50 mL). The combined organic layers were washed with brine (3×100 mL) and dried over anhydrous Na$_2$SO$_4$. After filtration, the filtrate was concentrated under reduced pressure. The residue was purified by silica gel column chromatography, eluting with PE/EA (85:15) to afford methyl 2-[3-(benzyloxy)cyclobutyl]pyrimidine-5-carboxylate (1.6 g, 53.13%) as a colorless oil. MS (ESI): mass calcd. for C$_{17}$H$_{18}$N$_2$O$_3$, 298.13, m/z found 299.10 [M+H]$^+$.

Step 3

To a stirred solution of methyl 2-[3-(benzyloxy)cyclobutyl]pyrimidine-5-carboxylate (1.40 g, 4.69 mmol) in THF (14 mL) was added LiOH (562 mg, 23.46 mmol) in H$_2$O (5 mL) in portions at room temperature under nitrogen atmosphere. The resulting mixture was stirred overnight at room temperature under nitrogen atmosphere. The resulting mixture was concentrated under reduced pressure. The mixture was acidified to pH 1 with 2 M HCl (aq.). The resulting mixture was extracted with EtOAc (3×50 mL). The combined organic layers were dried over anhydrous Na$_2$SO$_4$. After filtration, the filtrate was concentrated under reduced pressure to afford 2-[3-(benzyloxy)cyclobutyl]pyrimidine-5-carboxylic acid (1.3 g, 97.44%) as a white solid. MS (ESI): mass calcd. for C$_{16}$H$_{16}$N$_2$O$_3$, 284.12, m/z found 285.00 [M+H]$^+$.

Step 4

To a stirred solution of 2-[3-(benzyloxy)cyclobutyl]pyrimidine-5-carboxylic acid (1.30 g, 4.57 mmol) in t-BuOH (13 mL) was added DPPA (1.26 g, 4.57 mmol) and TEA (463 mg, 4.57 mmol) in portions at room temperature under nitrogen atmosphere. The resulting mixture was stirred for 3 h at 85° C. under nitrogen atmosphere. The resulting mixture was concentrated under reduced pressure. The residue was purified by silica gel column chromatography, eluting with PE/EA (2:1) to afford tert-butyl N-{2-[3-(benzyloxy)cyclobutyl]pyrimidin-5-yl}carbamate (1.3 g, 79.99%) as a white solid. MS (ESI): mass calcd. for C$_{20}$H$_{25}$N$_3$O$_3$, 355.19, m/z found 356.50 [M+H]$^+$.

Step 5

The tert-butyl (2-(3-(benzyloxy)cyclobutyl)pyrimidin-5-yl)carbamate (1.3 g) was dissolved in DMSO and was purified by Prep-HPLC with the following conditions (Column: Xselect CSH C18 OBD Column 50*250 mm 10 μm, n; Mobile Phase A: Water (0.1% NH$_4$HCO$_3$), Mobile Phase B: ACN; Flow rate: 60 mL/min; Gradient: 30% B to 60% B in 10 min, 60% B; Wave Length: 254; 220 nm; RT1 (min): 6.42; Number Of Runs: 0) to give (tert-butyl (2-((1s,3s)-3-(benzyloxy)cyclobutyl)pyrimidin-5-yl)carbamate, 760 mg) as white solid and (tert-butyl (2-((1R,3R)-3-(benzyloxy)cyclobutyl)pyrimidin-5-yl)carbamate, 200 mg) as white solid.

Step 6

To a stirred solution of 3-(benzyloxy)cyclobutane-1-carboxylic acid (3.00 g, 14.55 mmol) and NH$_4$Cl (1.17 g, 21.82 mmol) in DMF (30 ml) were added DIEA (5.64 g, 43.64 mmol) and HATU (6.64 g, 17.46 mmol) in portions at room temperature under nitrogen atmosphere. The resulting mixture was stirred for additional overnight at room temperature. The crude product was purified by reverse phase flash with the following conditions (MeCN in water, 10% to 50% gradient in 30 min; detector, UV 254 nm) to afford 3-(benzyloxy)cyclobutane-1-carboxamide (2.88 g, 96.4%) as a off-white solid. MS (ESI): mass calcd. for C$_{12}$H$_{15}$NO$_2$, 205.11, m/z found 206.10 [M+H]$^+$.

Step 7

A solution of 3-(benzyloxy)cyclobutane-1-carboxamide (1.60 g, 7.80 mmol) and trimethyloxonium tetrafluoroborate (1.27 g, 8.58 mmol) in THF (32 mL) was stirred for 1 h at room temperature under nitrogen atmosphere. The solvent was removed and the residue dissolved in methanol (35 mL). Ammonia (7M in methanol) (55 mL) was added while cooling the reaction mixture in a cold water bath. Once the addition was complete the reaction was allowed to warm to room temperature. The resulting mixture was stirred for additional 15 min at room temperature. The resulting suspension was concentrated to a thick mixture, diluted with EA and filtered through celite. The filtrate was cooled to ~10° C. and HCl (4M in dioxane) (35 mL) added dropwise. The resulting mixture was washed with 3×100 mL of DCM:MeOH=10:1. The aqueous layer was concentrated under reduced pressure to afford 3-(benzyloxy)cyclobutane-1-carboximidamide hydrochloride (2.2 g) as a white crude oil.

Step 8

To a stirred solution of tert-butyl N-{2-[(1S,3S)-3-(benzyloxy)cyclobutyl]pyrimidin-5-yl}carbamate (200 mg, 0.56 mmol) in DCM (3 mL) was added TFA (1 mL) dropwise at room temperature under nitrogen atmosphere. The resulting mixture was stirred for 1 h at room temperature under nitrogen atmosphere. The resulting mixture was concentrated under reduced pressure. The mixture was basified to pH 7 with saturated NaHCO$_3$ (aq.). The resulting mixture was extracted with EtOAc (3×10 mL). The combined organic layers were dried over anhydrous Na$_2$SO$_4$. After filtration, the filtrate was concentrated under reduced pressure to afford 2-[(1s,3s)-3-(benzyloxy)cyclobutyl]pyrimidin-5-amine (150 mg, 99.19%) as a yellow oil. MS (ESI): mass calcd. for C$_{15}$H$_{17}$N$_3$O, 255.14, m/z found 256.20 [M+H]$^+$.

Step 9

To a stirred solution of 2-[(1S,3S)-3-(benzyloxy)cyclobutyl]pyrimidin-5-amine (130 mg, 0.51 mmol) in tetrahydrofuran (3 mL) was added phenyl chloroformate (80 mg, 0.51 mmol) dropwise at room temperature under nitrogen atmosphere. The resulting mixture was stirred for 1 h at room temperature under nitrogen atmosphere. The resulting mixture was concentrated under reduced pressure to afford phenyl N-{2-[3-(benzyloxy)cyclobutyl]pyrimidin-5-yl}carbamate (210 mg, crude) as a yellow solid. MS (ESI): mass calcd. for C$_{22}$H$_{21}$N$_3$O$_3$, 375.16, m/z found 376.15 [M+H]$^+$.

Step 10

To a stirred solution of phenyl N-{2-[3-(benzyloxy)cyclobutyl]pyrimidin-5-yl}carbamate (78 mg, 0.21 mmol) and (1R)-1-(5,7-difluoro-3-methyl-1-benzofuran-2-yl)-2,2,2-trifluoroethanamine (50 mg, 0.19 mmol) in pyridine (2 mL). The reaction was stirred overnight at 80° C. under nitrogen atmosphere. The resulting mixture was concentrated under vacuum. The residue was purified by silica gel column chromatography, eluted with PE/EA (2:1) to afford 3-[(1R)-1-(5,7-difluoro-3-methyl-1-benzofuran-2-yl)-2,2,2-trifluoroethyl]-1-{2-[(1s,3s)-3-(benzyloxy)cyclobutyl]pyrimidin-5-yl}urea (90 mg, 87.34%) as a yellow solid. MS (ESI): mass calcd. for C$_{27}$H$_{23}$F$_5$N$_4$O$_3$, 546.17, m/z found 547.40 [M+H]$^+$.

Step 11

To a solution of 3-[(1R)-1-(5,7-difluoro-3-methyl-1-benzofuran-2-yl)-2,2,2-trifluoroethyl]-1-{2-[(1s,3s)-3-(benzyloxy)cyclobutyl]pyrimidin-5-yl}urea (55 mg, 0.10 mmol) in DCM (2 mL) was added boron trichloride (0.30 mL, 0.30 mmol) at −78° C. under nitrogen atmosphere. The resulting mixture was stirred for 1 h at room temperature under nitrogen atmosphere. The reaction was quenched with water at 0° C. The resulting mixture was extracted with CH$_2$Cl$_2$/MeOH (3×10 mL). The combined organic layers were dried over anhydrous Na$_2$SO$_4$. After filtration, the filtrate was concentrated under reduced pressure. The residue was purified by silica gel column chromatography, eluted with CH$_2$Cl$_2$/MeOH (15:1) to afford 3-[(1R)-1-(5,7-difluoro-3-methyl-1-benzofuran-2-yl)-2,2,2-trifluoroethyl]-1-{2-[(1S,3S)-3-hydroxycyclobutyl]pyrimidin-5-yl}urea (30.5 mg, 66.41%) as a white solid. MS (ESI): mass calcd. for C$_{20}$H$_{17}$F$_5$N$_4$O$_3$, 456.12, m/z found 457.05 [M+H]$^+$.

$^1$H NMR (400 MHz, Chloroform-d) δ 8.91 (s, 2H), 8.04 (s, 1H), 7.06-6.95 (m, 1H), 6.85-3.83 (m, 1H), 6.82-6.70 (m, 1H), 5.96-5.88 (m, 1H), 4.44 (p, J=6.8 Hz, 1H), 3.40 (p, J=8.1 Hz, 1H), 2.92-2.81 (m, 2H), 2.39-2.36 (m, 2H), 2.29 (s, 3H).

Example 166: Preparation of Compound 246

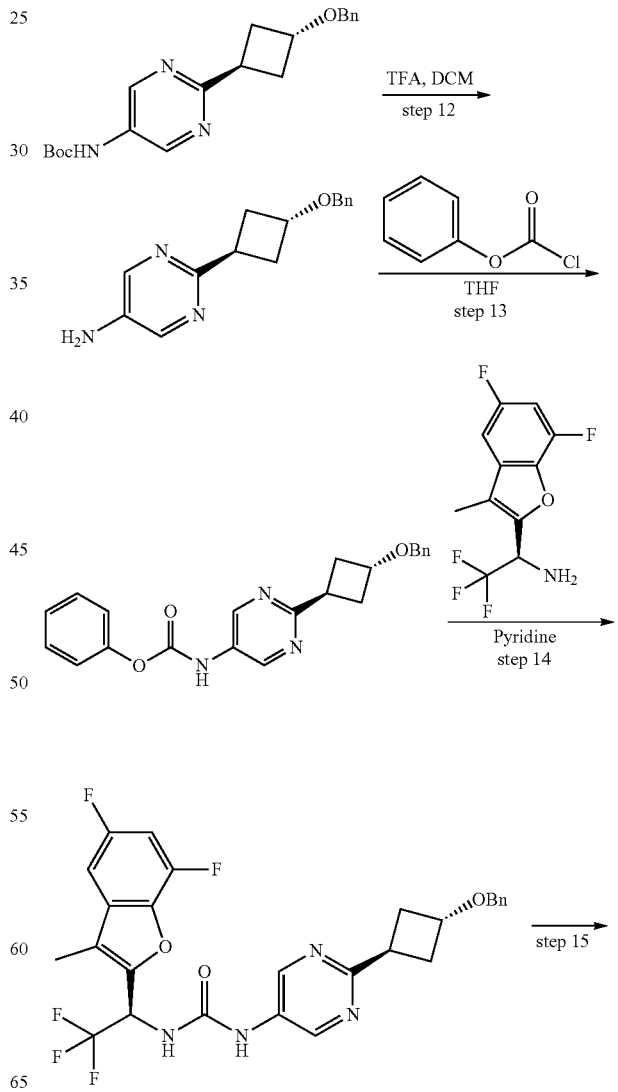

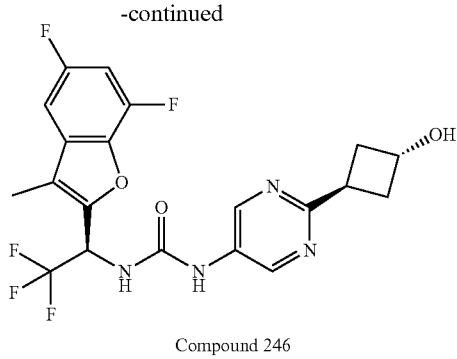

Compound 246

Step 12

To a solution of tert-butyl N-{2-[(1R,3R)-3-(benzyloxy)cyclobutyl]pyrimidin-5-yl}carbamate (100 mg, 0.3 mmol) in DCM (1.5 mL) were added TFA (0.5 mL) at room temperature. The resulting mixture was stirred for 1 h at 30° C. The reaction was monitored by TLC. The resulting mixture was concentrated under vacuum. The residue was basified to pH=8 with saturated NaHCO₃ (aq.). The resulting mixture was extracted with EA (3×20 mL). The combined organic layers were washed with brine (50 mL) and dried over anhydrous Na₂SO₄. After filtration, the filtrate was concentrated under reduced pressure to give 2-[(1R,3R)-3-(benzyloxy)cyclobutyl]pyrimidin-5-amine (62 mg, 86.3%) as light yellow solid. MS (ESI): mass calcd. for $C_{15}H_{17}N_3O$, 255.14, m/z found 256.20 [M+H]$^+$.

Step 13

To a stirred solution of 2-[(1R,3R)-3-(benzyloxy)cyclobutyl]pyrimidin-5-amine (65 mg, 0.3 mmol) in THF (1 mL) was added phenyl chloroformate (40 mg, 0.3 mmol) dropwise at room temperature under nitrogen atmosphere. The resulting mixture was stirred for 3 h at room temperature under nitrogen atmosphere. The reaction was monitored by LCMS. The solution was concentrated in vacuum to give phenyl N-{2-[3-(benzyloxy)cyclobutyl]pyrimidin-5-yl}carbamate (107 mg, crude) as off-white solid. MS (ESI): mass calcd. for $C_{22}H_{21}N_3O_3$, 375.16, m/z found 376.15 [M+H]$^+$.

Step 14

To a stirred solution of phenyl N-{2-[3-(benzyloxy)cyclobutyl]pyrimidin-5-yl}carbamate (117 mg, 0.3 mmol) in pyridine (1 mL) was added (1R)-1-(5,7-difluoro-3-methyl-1-benzofuran-2-yl)-2,2,2-trifluoroethanamine (75 mg, 0.3 mmol) at room temperature. The resulting mixture was stirred overnight at 80° C. The reaction was monitored by LCMS. The solution was concentrated in vacuum. The residue was purified by silica gel column chromatography, eluted with PE/EA (2:1) to afford 3-[(1R)-1-(5,7-difluoro-3-methyl-1-benzofuran-2-yl)-2,2,2-trifluoroethyl]-1-{2-[(1R,3R)-3-(benzyloxy)cyclobutyl]pyrimidin-5-yl}urea (100 mg, 64.7%) as a brown solid. MS (ESI): mass calcd. for $C_{27}H_{23}F_5N_4O_3$, 546.17, m/z found 547.40 [M+H]$^+$.

Step 15

To a solution of 3-[(1R)-1-(5,7-difluoro-3-methyl-1-benzofuran-2-yl)-2,2,2-trifluoroethyl]-1-{2-[(1R,3R)-3-(benzyloxy)cyclobutyl]pyrimidin-5-yl}urea (80 mg, 0.15 mmol) mL in DCM (1 mL) were added boron trichloride (51 mg, 0.4 mmol) at −78° C. The resulting mixture was stirred for 1 h at room temperature. The reaction was monitored by LCMS. The reaction was quenched by the addition of water (10 mL) at 0° C. The resulting mixture was extracted with CH₂Cl₂:MeOH (10:1) (3×20 mL). The combined organic layers were washed with brine (30 mL) and dried over anhydrous Na₂SO₄. After filtration, the filtrate was concentrated under reduced pressure. The residue was purified by reverse flash chromatography with the following conditions: column, C18 spherical column; mobile phase, MeCN in water (10 mmol/L NH₄HCO₃), 0% to 55% gradient in 20 min; detector, UV 254 nm to give a 3-[(1R)-1-(5,7-difluoro-3-methyl-1-benzofuran-2-yl)-2,2,2-trifluoroethyl]-1-{2-[(1R,3R)-3-hydroxycyclobutyl]pyrimidin-5-yl}urea (24.0 mg, 35.6%) as white solid. MS (ESI): mass calcd. for $C_{20}H_{17}F_5N_4O_3$, 456.12, m/z found 457.05 [M+H]$^+$.

$^1$H NMR (400 MHz, DMSO-d₆) δ 8.86 (s, 1H), 8.77 (s, 2H), 8.02 (d, J=9.6 Hz, 1H), 7.46-7.42 (m, 2H), 6.14-6.06 (m, 1H), 5.06 (d, J=6.4 Hz, 1H), 4.40-4.38 (m, 1H), 3.53 (t, J=4.4 Hz, 1H), 2.51-2.50 (m, 2H), 2.32 (s, 3H), 2.28-2.23 (m, 2H).

Example 167: Preparation of Compound 247

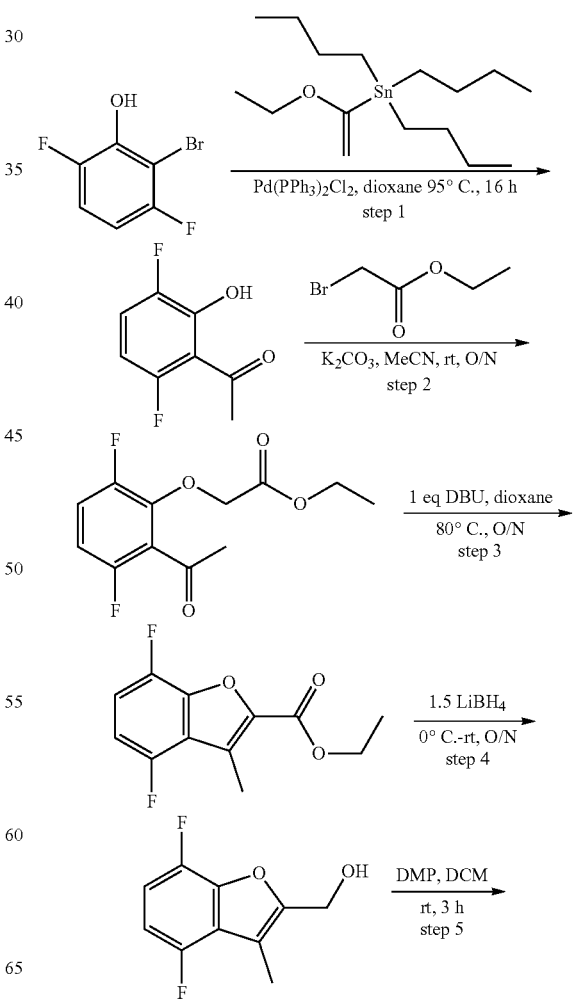

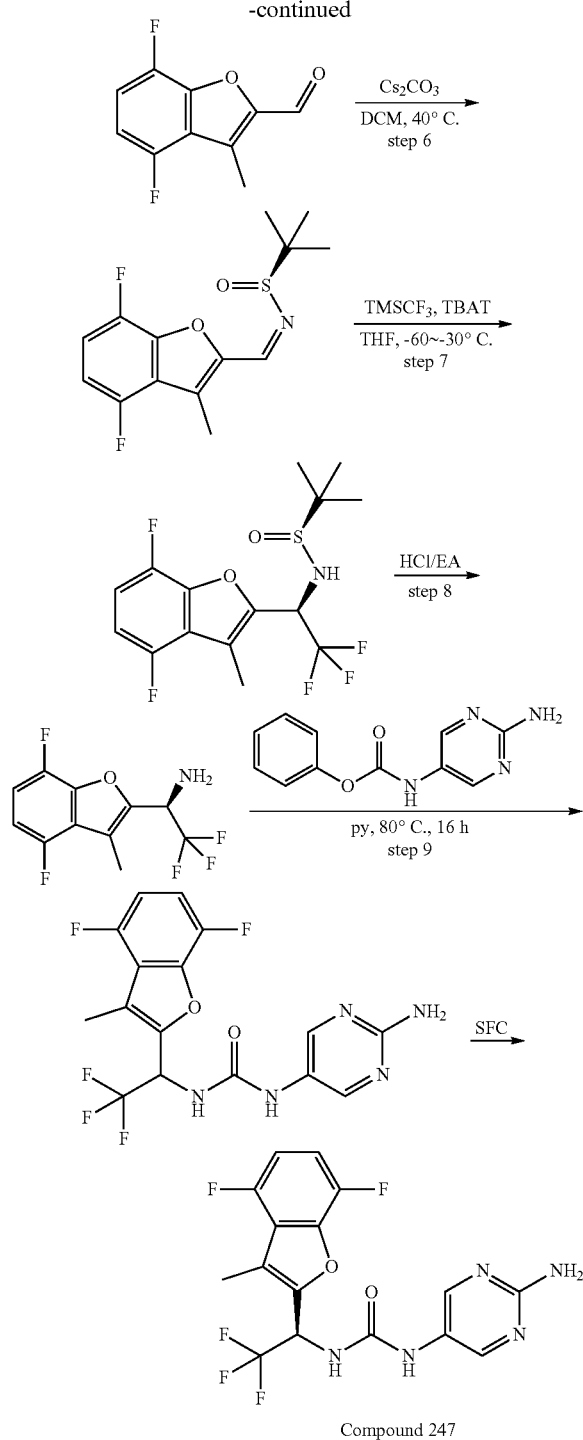

Compound 247

Step 1

A mixture of 2-bromo-3,6-difluorophenol (7.0 g, 0.033 mol), tributyl(1-ethoxyvinyl)stannane (14.6 g, 0.041 mol) and Pd(PPh$_3$)$_2$Cl$_2$ (2.3 g, 0.003 mol) in dioxane (100.00 mL) was stirred for 16 h at 95° C. under nitrogen atmosphere. The reaction was quenched with water at room temperature. The resulting mixture was extracted with EtOAc (3×30 mL). The combined organic layers were washed with brine (3×30 mL) and dried over anhydrous Na$_2$SO$_4$. After filtration, the filtrate was concentrated under reduced pressure. This resulted in 1-(3,6-difluoro-2-hydroxyphenyl)ethan-1-one (5.4 g, crude) as a black solid. MS (ESI): mass calcd. for C$_8$H$_6$F$_2$O$_2$, 172.03, m/z found 173 [M+H]$^+$.

Step 2

A solution of 1-(3,6-difluoro-2-hydroxyphenyl)ethan-1-one (5.4 g, 0.031 mol) and ethyl 2-bromoacetate (5.8 g, 0.034 mol) in ACN (60 mL) was added K$_2$CO$_3$ (6.5 g, 0047 mol). The reaction mixture was stirred at room temperature overnight. The reaction was quenched with water at room temperature. The resulting mixture was extracted with EtOAc (3×30 mL). The combined organic layers were washed with brine (3×30 mL) and dried over anhydrous Na$_2$SO$_4$. After filtration, the filtrate was concentrated under reduced pressure. The mixture was purified using flash chromatography with the following conditions (Mobile Phase A: Water, Mobile Phase B: ACN; Flow rate: 65 mL/min; Gradient: 0% B to 100% B in 40 min; 254; 220 nm). This resulted in ethyl 2-(2-acetyl-3,6-difluorophenoxy)acetate (1.8 g) as an off-white solid. MS (ESI): mass calcd. for C$_{12}$H$_{12}$F$_2$O$_4$, 258.07, m/z found 259 [M+H]$^+$.

Step 3

A solution of ethyl 2-(2-acetyl-3,6-difluorophenoxy)acetate (1.8 g, 0.007 mol) in dioxane (12 mL) was added DBU (1.1 g, 0.007 mol). The reaction mixture was stirred at 80° C. overnight. The reaction was quenched with water at room temperature. The resulting mixture was extracted with EtOAc (3×30 mL). The combined organic layers were washed with brine (3×30 mL) and dried over anhydrous Na$_2$SO$_4$. After filtration, the filtrate was concentrated under reduced pressure. The reaction mixture was purified using flash chromatography with the following conditions (Mobile Phase A: Water, Mobile Phase B: ACN; Flow rate: 55 mL/min; Gradient: 0% B to 100% B in 40 min; 254; 220 nm). This resulted in ethyl 4,7-difluoro-3-methylbenzofuran-2-carboxylate (800 mg) as an off-white solid. MS (ESI): mass calcd. for C$_{12}$H$_{10}$F$_2$O$_3$, 240.06, m/z found 241 [M+H]$^+$.

Step 4

To a stirred solution ethyl 4,7-difluoro-3-methylbenzofuran-2-carboxylate (800 mg, 3.33 mmol) in THF (8 mL) was added LiBH$_4$ (2M in THF, 3.5 mL) at 0° C. The resulting mixture was stirred at room temperature overnight. Then the reaction was quenched by the addition of 10 mL of water at 0° C. The mixture was partitioned between CH$_2$Cl$_2$ and water. The aqueous layer was extracted again with CH$_2$Cl$_2$. The combined organic layer was dried over anhydrous sodium sulfate and concentrated under vacuum. This resulted in (4,7-difluoro-3-methylbenzofuran-2-yl)methanol (520 mg, crude) as a white solid. MS (ESI): mass calcd. for C$_{10}$H$_8$F$_2$O$_2$, 198.05, m/z found no mass [M+H]$^+$.

Step 5

To a solution of (4,7-difluoro-3-methylbenzofuran-2-yl)methanol (500 mg, 2.53 mmol) in DCM (7 mL) was added DMP (1.61 g, 3.79 mmol) at 0° C. The reaction mixture was stirred at room temperature for 3 hours. After reaction, the mixture was quenched by the addition of 500 mL of saturated sodium bicarbonate. The filtrate was extracted with 3×400 mL of DCM. The organic layers were combined, washed with sodium sodium bicarbonate, dried and concentrated under vacuum to give 4,7-difluoro-3-methylbenzofuran-2-carbaldehyde (480 mg, crude) as an off-white solid. MS (ESI): mass calcd. for $C_{10}H_6F_2O_2$, 196.03, m/z found 197 $[M+H]^+$.

Step 6

To a solution of 4,7-difluoro-3-methylbenzofuran-2-carbaldehyde (431 mg, 2.19 mmol) in DCM (6 mL) was added $Cs_2CO_3$ (559 mg, 2.24 mmol) at 25° C. And the reaction was stirred at 25° C. for 10 min. (S)-2-methylpropane-2-sulfinamide (301 mg, 2.48 mmol) was added to the reaction mixture. The mixture was stirred at 40° C. for 12 hr. And then filtered. The filtrate was extracted with 3×20 mL of DCM. The organic layers were combined, washed with sodium sodium bicarbonate, dried, and concentrated under vacuum to give (S,Z)-N-((4,7-difluoro-3-methylbenzofuran-2-yl)methylene)-2-methylpropane-2-sulfinamide (550 mg, crude) as a yellow solid. MS (ESI): mass calcd. for $C_{14}H_{15}F_2NO_2S$, 299.08, m/z found 300 $[M+H]^+$.

Step 7

To a solution of (S,Z)-N-((4,7-difluoro-3-methylbenzofuran-2-yl)methylene)-2-methylpropane-2-sulfinamide (500 mg, 1.67 mmol) in THF (6 mL) at −60° C. was added TBAT (903 mg, 1.67 mmol). The mixture was stirred at −60° C. for 1 hour. Then $TMSCF_3$ (969 mg, 6.82 mol, 500 mL) in THE (5 mL) was added at −60° C. The mixture was stirred at −30° C. for 30 min. and then quenched by addition of saturated aq. $NH_4Cl$ (5 mL) at 0° C., and then extracted with EA (50 mL*3). The combined organic layers were dried over $Na_2SO_4$, filtered and concentrated under reduced pressure to give a residue. This resulted in (S)-N-((R)-1-(4,7-difluoro-3-methylbenzofuran-2-yl)-2,2,2-trifluoroethyl)-2-methylpropane-2-sulfinamide (200 mg, crude) as a yellow solid. MS (ESI): mass calcd. for $C_{15}H_{16}F_5NO_2S$, 369.08, m/z found 370 $[M+H]^+$.

Step 8

To a solution of (S)-N-((R)-1-(4,7-difluoro-3-methylbenzofuran-2-yl)-2,2,2-trifluoroethyl)-2-methylpropane-2-sulfinamide (200 mg, 0.54 mmol) in EA (6 mL) was added HCl/dioxane (4 M, 3 mL) at 0° C. The mixture was stirred at 25° C. for 12 hours. The reaction mixture was concentrated under vacuum. This resulted in (R)-1-(4,7-difluoro-3-methylbenzofuran-2-yl)-2,2,2-trifluoroethan-1-amine (100 mg, crude) as a yellow solid. MS (ESI): mass calcd. for $C_{11}H_8F_5NO$, 265.05, m/z found 266 $[M+H]^+$.

Step 9

To a solution of (R)-1-(4,7-difluoro-3-methylbenzofuran-2-yl)-2,2,2-trifluoroethan-1-amine (100 mg, 0.38 mmol) in pyridine (3 mL) was added phenyl (2-aminopyrimidin-5-yl) carbamate (86.8 mg, 0.38 mmol) at room temperature. The mixture was stirred at 80° C. for 16 hours. The reaction mixture was concentrated under vacuum. The crude product was dissolved in ACN and purified using flash chromatography with the following conditions (Mobile Phase A: Water, Mobile Phase B: ACN; Flow rate: 55 mL/min; Gradient: 0% B to 100% B in 30 min; 254; 220 nm). This resulted in 1-(2-aminopyrimidin-5-yl)-3-(1-(4,7-difluoro-3-methylbenzofuran-2-yl)-2,2,2-trifluoroethyl)urea (35 mg) as a yellow solid. MS (ESI): mass calcd. for $C_{16}H_{12}F_5N_5O_2$, 401.09, m/z found 402 $[M+H]^+$.

Step 10

35 mg of racemic was separated by SFC to give (Compound 247, 10.5 mg) as white solid
Chiral Separation Condition:
Column: CHIRALPAK IE, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 15% B to 15% B in 12 min; Wave Length: 220/254 nm; RT1 (min): 8.67; RT2 (min): 10.33; Sample Solvent: EtOH-HPLC; Injection Volume: 0.9 mL; Number Of Runs: 4. MS (ESI): mass calcd. for $C_{16}H_{12}F_5N_5O_2$, 401.09, m/z found 402 $[M+H]^+$.
$^1H$ NMR (400 MHz, DMSO) δ 8.24 (d, J=3.1 Hz, 3H), 7.87 (d, J=9.3 Hz, 1H), 7.43-7.26 (m, 1H), 7.14 (td, J=2.9, 9.1, 9.2 Hz, 1H), 6.49 (s, 1H), 6.06 (p, J=8.5, 8.5, 8.6, 8.6 Hz, 1H), 2.40 (s, 3H).

Example 168: Preparation of Compound 248

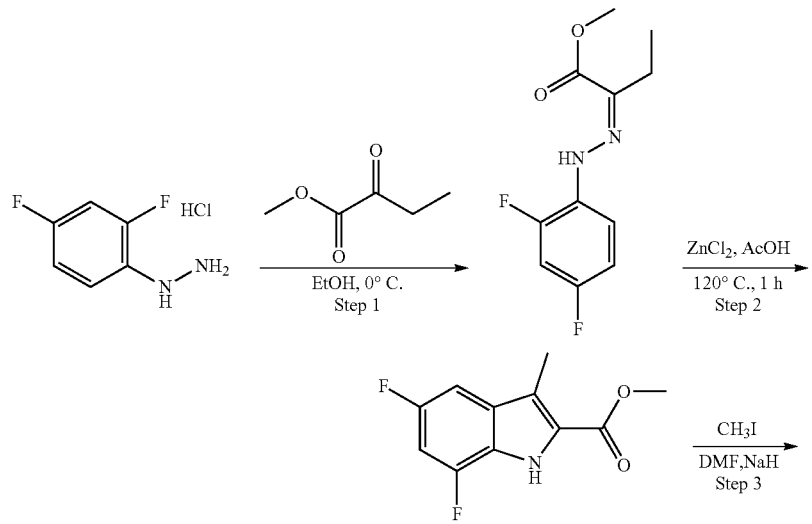

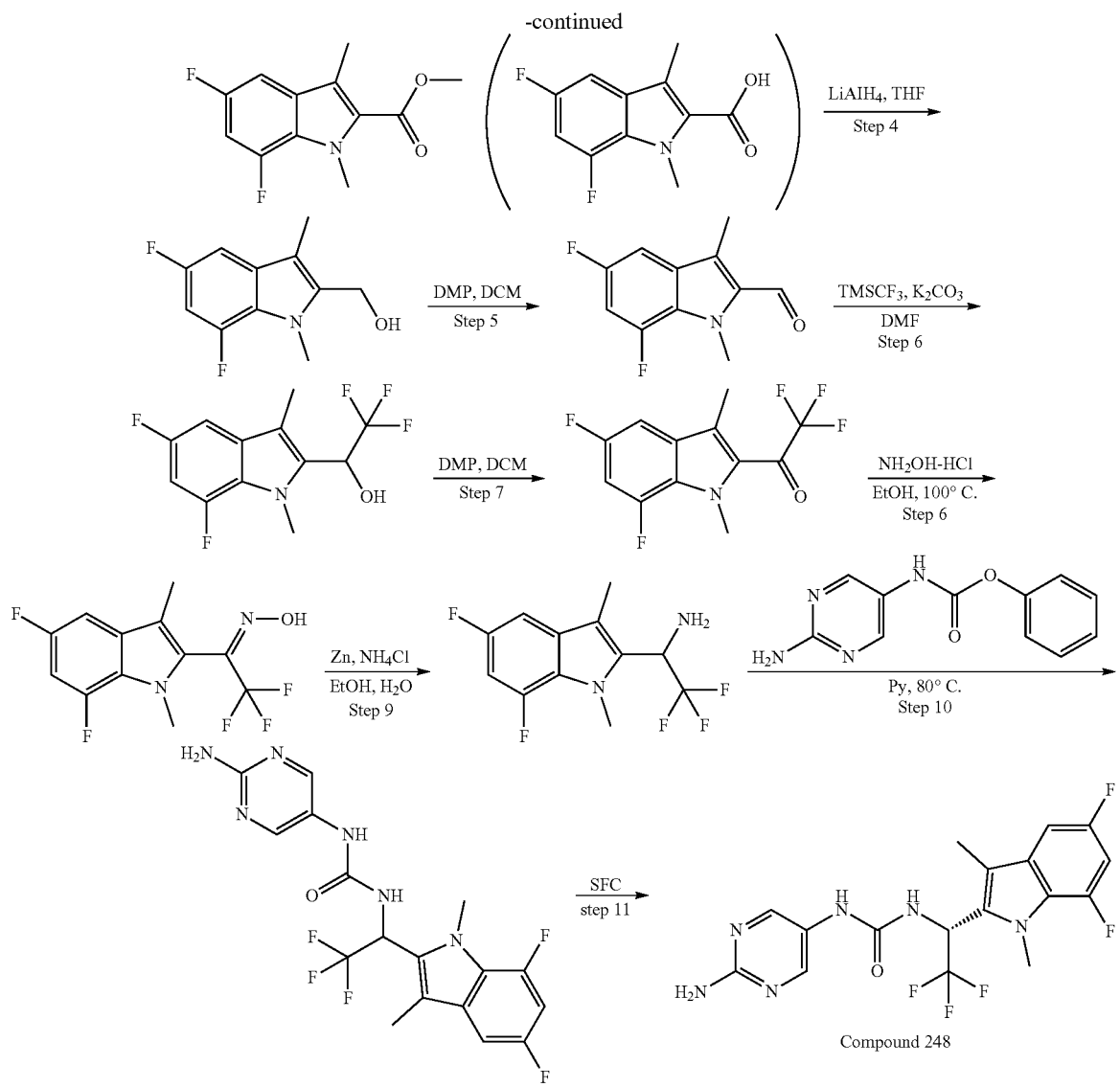

Compound 248

Step 1

A solution of (2,4-difluorophenyl)hydrazine (1.8 g, 12.49 mmol, 1 equiv) and dimethylpyruvic acid (1.89 g, 16.28 mmol, 1.30 equiv) in EtOH (60 mL) was stirred for 3 h at room temperature. After the reaction was complete the solvent was evaporated to get methyl (2Z)-2-[2-(2,4-difluorophenyl)hydrazin-1-ylidene]butanoate (2.43 g, 80.33%) yellow semi-solid as product MS (ESI): mass calcd. for $C_{11}H_{12}F_2N_2O_2$, 242.2, m/z found 243.10 [M+H]$^+$.

Step 2

A solution of methyl (2Z)-2-[2-(2,4-difluorophenyl)hydrazin-1-ylidene]butanoate (2.43 g, 10.00 mmol, 1 equiv) and ZnCl2 (50.6 g, 371.6 mmol, 5 equiv) in AcOH was stirred for 1 h at 120° C. After the reaction was complete the pH of the solution was adjusted with NaHCO₃ to 8, extracted with EA, washed with the brine, dried over anhydrous Na₂SO₄ to get methyl 5,7-difluoro-3-methyl-1H-indole-2-carboxylate (5 g, 29.88%) yellow solid as product.

MS (ESI): mass calcd. for $C_{11}H_9F_2NO_2$, 225.1, m/z found 224.00 [M–H]$^-$.

Step 3

A solution of methyl 5,7-difluoro-3-methyl-1H-indole-2-carboxylate (1.55 g, 6.88 mmol, 1 equiv), CH₃I (4.88 g, 34.38 mmol, 5.00 equiv) and Cs₂CO₃ (5.61 g, 17.21 mmol, 2.5 equiv) in DMF (50 mL) was stirred overnight at room temperature. After the reaction was complete the mixture was quenched with water, extracted with EA, washed with the brine, and dried over anhydrous Na₂SO₄ to yield the crude product. The residue was purified by reverse phase flash chromatography to provide methyl 5,7-difluoro-1,3-dimethylindole-2-carboxylate (1.325 g, 80.47%) yellow solid as product.

MS (ESI): mass calcd. for $C_{12}H_{11}F_2NO_2$, 239.2. m/z found 240.0 [M+H]$^+$.

Step 4

A solution of methyl 5,7-difluoro-1,3-dimethylindole-2-carboxylate (1.3 g, 5.43 mmol, 1 equiv) and LiAlH₄ (412.46 mg, 10.87 mmol, 2 equiv) in THF (15 mL) was stirred for 2 h from 0° C. to room temperature. After the reaction was complete the solution was quenched with NH$_4$Cl, extracted with ethyl acetate, washed with brine, and dried over anhydrous Na$_2$SO$_4$ to get (5,7-difluoro-1,3-dimethylindol-2-yl)methanol (1.1 g, 95.84%) as a yellow solid.

MS (ESI): mass calcd. for C$_{11}$H$_{11}$F$_2$NO, 211.2, m/z found 212.10 [M+H]$^+$.

Step 5

A solution of (5,7-difluoro-1,3-dimethylindol-2-yl)methanol (1.05 g, 4.97 mmol, 1 equiv) and Dess-Martin periodinane (3.16 g, 7.46 mmol, 1.5 equiv) in DCM (50 mL) was stirred for 3 h at room temperature. After the reaction was complete the solution was quenched with saturated NaHCO$_3$ solution and filtrated. The filtrate was extracted with DCM, washed with the brine, dried over anhydrous Na$_2$SO$_4$ to get the crude product. The residue was purified by reverse phase flash chromatography to get 5,7-difluoro-1,3-dimethylindole-2-carbaldehyde (600 mg, 57.69%) yellow solid as product. MS (ESI): mass calcd. for C$_{11}$H$_9$F$_2$NO, 209.2, m/z found 210.1 [M+H]$^+$.

Step 6

A solution of 5,7-difluoro-1,3-dimethylindole-2-carbaldehyde (607 mg, 2.90 mmol, 1 equiv), K$_2$CO$_3$ (802.03 mg, 5.80 mmol, 2 equiv) and TMSCF$_3$ (825.19 mg, 5.80 mmol, 2 equiv) in DMF (10 mL) was stirred overnight at room temperature. After the reaction was complete the mixture was quenched with water, extracted with water, washed with brine, dried over anhydrous Na$_2$SO$_4$ and concentrated under reduced pressure to get 1-(5,7-difluoro-1,3-dimethylindol-2-yl)-2,2,2-trifluoroethanol (580 mg, 71.59%) light-yellow solid as product. MS (ESI): mass calcd. for C$_{12}$H$_{10}$F$_5$NO, 279.2, m/z found 280.00 [M+H]$^+$.

Step 7

A solution of 1-(5,7-difluoro-1,3-dimethylindol-2-yl)-2,2,2-trifluoroethanol (2.1 g, 7.52 mmol, 1 equiv) and DMP (4.79 g, 11.28 mmol, 1.5 equiv) in DCM (70 mL) was stirred for 4 h at room temperature. After the reaction was complete the solution was quenched with saturated NaHCO$_3$ solution and filtered. The filtrate was extracted with DCM, washed with brine, and dried over anhydrous Na$_2$SO$_4$ to get the crude product. The residue was purified by reverse phase flash chromatography to get 1-(5,7-difluoro-1,3-dimethylindol-2-yl)-2,2,2-trifluoroethanone (1.8 g, 86.34%) yellow solid as product. MS (ESI): mass calcd. for C$_{12}$H$_8$F$_5$NO, 277.2, m/z found 278.10 [M+H]$^+$.

Step 8

A solution of 1-(5,7-difluoro-1,3-dimethylindol-2-yl)-2,2,2-trifluoroethanone (831 mg, 3.00 mmol, 1 equiv), NH$_2$OH·HCl (1041.62 mg, 14.99 mmol, 5 equiv) and NaOAc (1229.65 mg, 14.99 mmol, 5 equiv) in EtOH (30 mL) was stirred overnight at 80° C. After the reaction was complete the mixture was purified by reverse phase flash chromatography to provide (Z)-N-[1-(5,7-difluoro-1,3-dimethylindol-2-yl)-2,2,2-trifluoroethylidene] hydroxylamine (720 mg, 82.19%) yellow solid as product. MS (ESI): mass calcd. for C$_{12}$H$_9$F$_5$N$_2$O, 292.2, m/z found 293.0 [M+H]$^+$.

Step 9

A solution of (Z)-N-[1-(5,7-difluoro-1,3-dimethylindol-2-yl)-2,2,2 trifluoroethylidene] hydroxyl-amine (643.3 mg, 2.20 mmol, 1 equiv), Zn (1439.34 mg, 22.02 mmol, 10 equiv) and NH$_4$Cl (588.79 mg, 11.01 mmol, 5 equiv) in EtOH (30 mL) and H$_2$O (10 mL) was stirred overnight at 80° C. After the reaction was complete the mixture was purified by reverse phase flash chromatography to get 1-(5,7-difluoro-1,3-dimethylindol-2-yl)-2,2,2-trifluoroethanamine (252 mg, 41.14%) yellow solid. MS (ESI): mass calcd. for C$_{12}$H$_{11}$F$_5$N$_2$, 278.2, m/z found 262.20[M-NH$_2$]$^+$.

Step 10

A solution of (1R)-1-(5,7-difluoro-1,3-dimethylindol-2-yl)-2,2,2-trifluoroethanamine (132 mg, 0.47 mmol, 1 equiv) in phenyl N-(2-aminopyrimidin-5-yl) carbamate (3 mL) was stirred overnight at 80° C. After the reaction was complete the mixture was concentrated under reduced pressure, purified by reverse phase flash chromatography to get the crude product. The crude product was purified by Prep-HPLC to get 35 mg racemate. Finally, the racemate was purified by Prep-Chiral-HPLC to get 1-(2-aminopyrimidin-5-yl)-3-[(1R)-1-(5,7-difluoro-1,3-dimethylindol-2-yl)-2,2,2-trifluoroethyl]urea (19.8 mg, 10.04%) off-white solid as product. MS (ESI): mass calcd. for C$_{17}$H$_{15}$F$_5$N$_6$O, 414.3, m/z found 415.2 [M+H]$^+$.

$^1$H NMR (400 MHz, DMSO) δ8.35 (s, 1H), 8.22 (s, 1H), 7.63 (d, J=8.8 Hz, 1H), 7.24 (dd, J=2.4, 8.2 Hz, 1H), 7.09-7.03 (m, 1H), 6.39 (s, 2H), 6.06 (d, J=8.8 Hz, 1H), 3.96 (s, 3H), 2.33 (s, 3H).

Example 169: Preparation of Compound 249 and 250

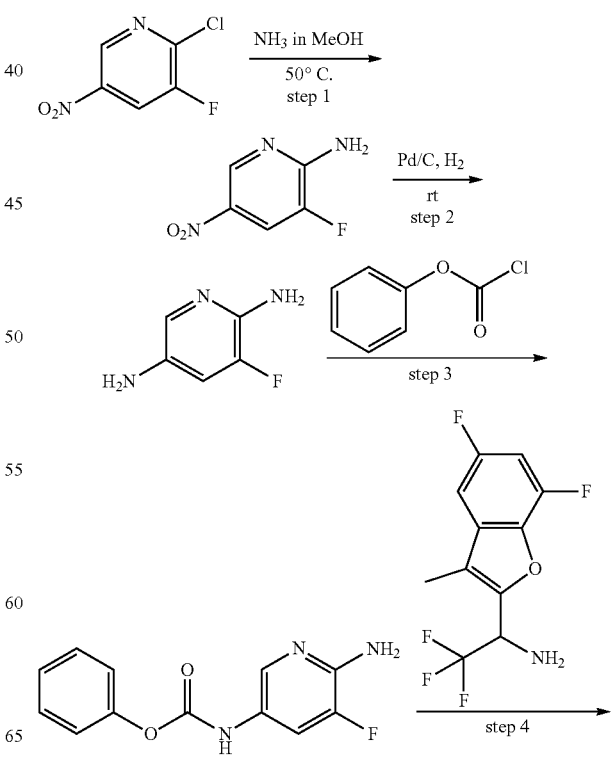

801

-continued

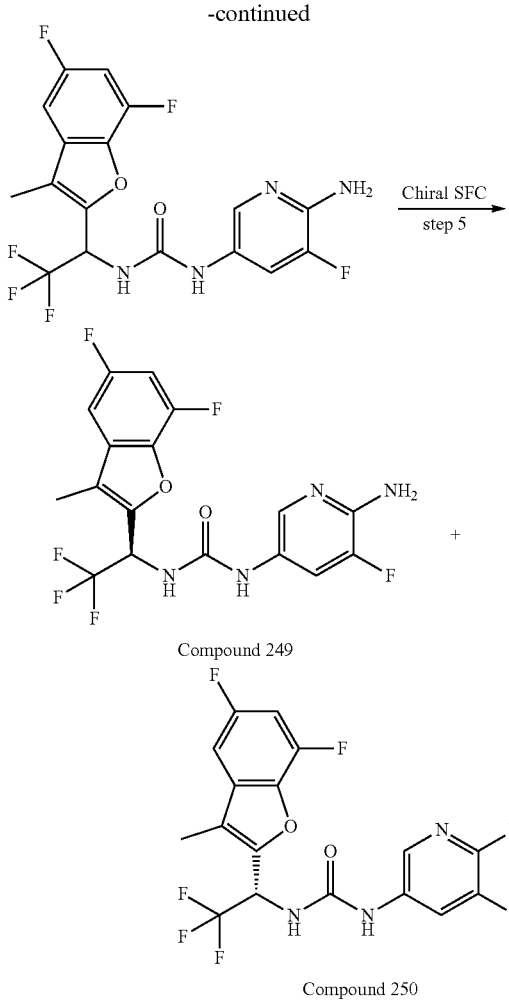

Compound 249

Compound 250

Step 1

A solution of 2-chloro-3-fluoro-5-nitropyridine (400 mg, 2.266 mmol, 1 equiv) in $NH_3$ (g) in MeOH (10 mL) was stirred overnight at 50° C. under air atmosphere. The mixture was allowed to cool down to room temperature. The resulting mixture was concentrated under reduced pressure to afford 3-fluoro-5-nitropyridin-2-amine (320 mg, 89.89%) as a white solid.

Step 2

A solution of 3-fluoro-5-nitropyridin-2-amine (260 mg, 1.655 mmol, 1 equiv) and Pd/C (44.03 mg, 0.414 mmol, 0.25 equiv) in EA (2 mL) was stirred for 2 h at room temperature under hydrogen atmosphere. The resulting mixture was concentrated under reduced pressure. The crude product was used in the next step directly without further purification to afford 3-fluoropyridine-2,5-diamine (220 mg, 83.66%) as a yellow oil. MS (ESI): mass calcd. for $C_5H_6FN_3$, 127.1. m/z found 128.1 [M+H]$^+$.

Step 3

A solution of 3-fluoropyridine-2,5-diamine (200 mg, 1.573 mmol, 1 equiv) and phenyl chloroformate (344.86 mg,

802

2.202 mmol, 1.4 equiv) in THF (5 mL) was stirred for 1 h at room temperature under nitrogen atmosphere. The resulting mixture was concentrated under reduced pressure. The crude product was used in the next step directly without further purification to afford phenyl N-(6-amino-5-fluoropyridin-3-yl)carbamate as a white solid. MS (ESI): mass calcd. for $C_{12}H_{10}FN_3O_2$, 247.2. m/z found 248.2[M+H]$^+$.

Step 4

A solution of phenyl N-(6-amino-5-fluoropyridin-3-yl) carbamate (150 mg, 0.607 mmol, 1 equiv) and 1-(5,7-difluoro-3-methyl-1-benzofuran-2-yl)-2,2,2-trifluoroethanamine (160.89 mg, 0.607 mmol, 1 equiv) in pyridine (5 mL) was stirred for 2 h at 80° C. under nitrogen atmosphere. The mixture was allowed to cool down to room temperature. The resulting mixture was extracted with EtOAc (2×50 mL). The combined organic layers were washed with brine (4×1 80 mL), dried over anhydrous $Na_2SO_4$. After filtration, the filtrate was concentrated under reduced pressure. The crude product (120 mg) was purified by Prep-HPLC with the following conditions (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 65% B in 7 min, 65% B; Wave Length: 220 nm; RT1 (min): 7.85; Number Of Runs: 0) to afford 1-(6-amino-5-fluoropyridin-3-yl)-3-[(1R)-1-(5,7-difluoro-3-methyl-1-benzofuran-2-yl)-2,2,2-trifluoroethyl]urea (100 mg, 39.40%) as a white solid. MS (ESI): mass calcd. for $C_{17}H_{12}F_6N_4O_2$, 418.3. m/z found 419.2[M+H]$^+$.

Step 5

100 mg of racemic was separated by SFC to give (Compound 249, 25.7 mg) as white solid and (Compound 250, 22.5 mg) as white solid.

(Column: CHIRAL ART Cellulose-SB, 2*25 cm, 5 cm; Mobile Phase A: Hex (0.5% 2M NH3-MeOH)-HPLC, Mobile Phase B: EtOH-HPLC; Flow rate: 20 mL/min; Gradient: 25% B to 25% B in 8 min; Wave Length: 220/254 nm; RT1 (min): 4.64; RT2 (min): 6.29; Sample Solvent: EtOH-HPLC; Injection Volume: 0.7 mL; Number Of Runs: 5.

Compound 249

$^1$H NMR (400 MHz, DMSO-d6) δ 8.43 (s, 1H), 7.72 (dd, J=5.9, 3.7 Hz, 2H), 7.54 (dd, J=12.7, 2.2 Hz, 1H), 7.47-7.35 (m, 2H), 6.04 (p, J=8.3 Hz, 1H), 5.87 (s, 2H), 2.30 (s, 3H).

Compound 250

$^1$H NMR (400 MHz, DMSO-d6) δ 8.43 (s, 1H), 7.77-7.67 (m, 2H), 7.54 (dd, J=12.8, 2.2 Hz, 1H), 7.48-7.37 (m, 2H), 6.04 (p, J=8.2 Hz, 1H), 5.87 (s, 2H), 2.30 (s, 3H).

Example 170: Preparation of Compound 251

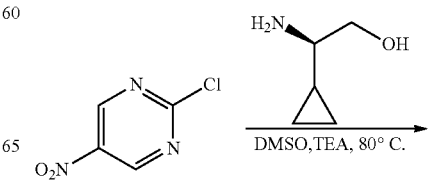

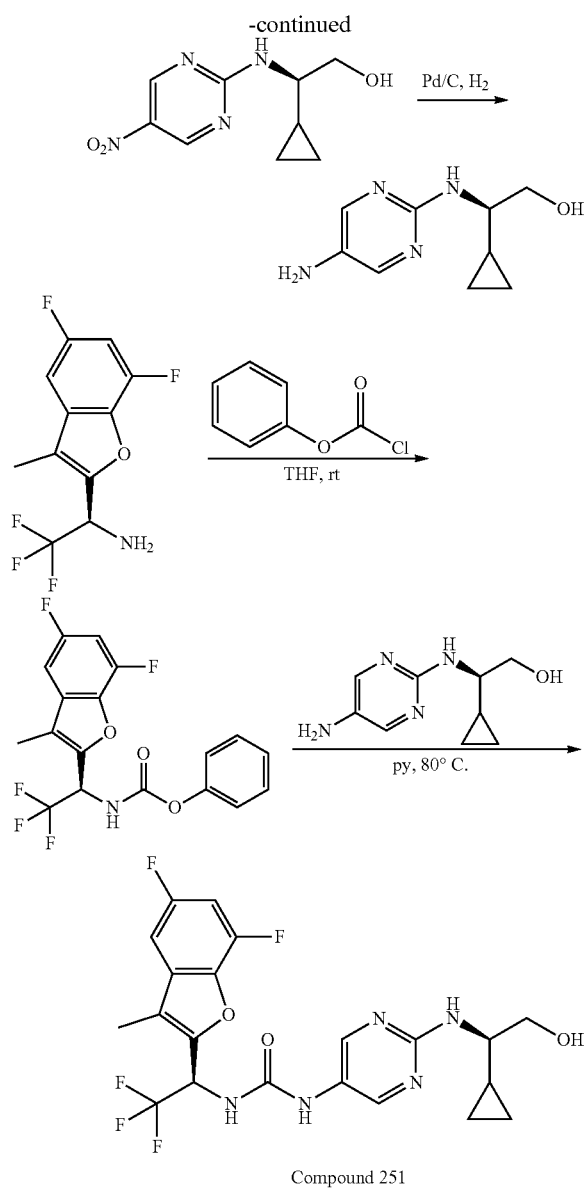

Compound 251

Step 1

To a stirred solution of 2-chloro-5-nitropyrimidine (150 mg, 0.940 mmol, 1 equiv) and TEA (285.44 mg, 2.820 mmol, 3 equiv) in DMSO (10 mL) was added (R)-2-amino-2-cyclopropylethanol HCl (194.08 mg, 1.410 mmol, 1.5 equiv) dropwise at room temperature under air atmosphere. The resulting mixture was stirred for 3 h at 80° C. under nitrogen atmosphere. Desired product could be detected by LCMS. The resulting mixture was extracted with EtOAc (2×5 mL). The combined organic layers were washed with brine (4×1 10 mL) and dried over anhydrous $Na_2SO_4$. After filtration, the filtrate was concentrated under reduced pressure to afford (2R)-2-cyclopropyl-2-[(5-nitropyrimidin-2-yl)amino]ethanol (200 mg, 94.87%) as a yellow oil.

MS (ESI): mass calcd. for $C_9H_{12}N_4O_3$, 224.1, m/z found 225.3 $[M+H]^+$.

Step 2

To a solution of (2R)-2-cyclopropyl-2-[(5-nitropyrimidin-2-yl)amino]ethanol (200 mg, 0.892 mmol, 1 equiv) in 5 mL EtOAc was added Pd/C (10%, 0.1 g) under nitrogen atmosphere in a 50 mL round-bottom flask. The mixture was hydrogenated at room temperature for 24 h under hydrogen atmosphere using a hydrogen balloon, filtered through a Celite pad, and concentrated under reduced pressure to afford (2R)-2-[(5-aminopyrimidin-2-yl)amino]-2-cyclopropylethanol (170 mg, 98.12%) as a yellow oil. MS (ESI): mass calcd. for $C_9H_{14}N_4O$, 194.1, m/z found 195.3 $[M+H]^+$.

Step 3

A solution of (1R)-1-(5,7-difluoro-3-methyl-1-benzofuran-2-yl)-2,2,2-trifluoroethanamine (800 mg, 3.017 mmol, 1 equiv) and phenyl chloroformate (519.57 mg, 3.319 mmol, 1.1 equiv) in THF (20 mL) was stirred for 1 h at room temperature under nitrogen atmosphere. Desired product could be detected by LCMS. The resulting mixture was concentrated under reduced pressure to afford phenyl N-[(1R)-1-(5,7-difluoro-3-methyl-1-benzofuran-2-yl)-2,2,2-trifluoroethyl]carbamate (1100 mg, 94.64%) as an off-white solid. MS (ESI): mass calcd. for $C_{18}H_{12}F_5NO_3$, 385.1, m/z found 386.3 $[M+H]^+$.

Step 4

A solution of phenyl N-[(1R)-1-(5,7-difluoro-3-methyl-1-benzofuran-2-yl)-2,2,2-trifluoroethyl]carbamate (250 mg, 0.649 mmol, 1 equiv) and (2R)-2-[(5-aminopyrimidin-2-yl)amino]-2-cyclopropylethanol (138.64 mg, 0.714 mmol, 1.1 equiv) in pyridine (10 mL) was stirred for 3 h at 80° C. under nitrogen atmosphere. The resulting mixture was concentrated under reduced pressure. The crude product was purified by Prep-HPLC with the following conditions (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 37% B to 56% B in 8 min, 56% B; Wave Length: 254 nm; RT1 (min): 7.62; Number Of Runs: 0) to afford 1-(2-{[(1R)-1-cyclopropyl-2-hydroxyethyl]amino}pyrimidin-5-yl)-3-[(1R)-1-(5,7-difluoro-3-methyl-1-benzofuran-2-yl)-2,2,2-trifluoroethyl]urea (90.5 mg, 28.04%) as a off-white solid. MS (ESI): mass calcd. for $C_{21}H_{20}F_5N_5O_3$, 485.2, m/z found 486.1 $[M+H-17]^+$.

$^1$H NMR (400 MHz, DMSO-d6) δ 8.20 (d, J=11.1 Hz, 3H), 7.80 (d, J=9.4 Hz, 1H), 7.46-7.37 (m, 2H), 6.60 (d, J=7.9 Hz, 1H), 6.04 (p, J=8.3 Hz, 1H), 4.57 (t, J=5.4 Hz, 1H), 3.49 (pd, J=7.0, 6.4, 4.2 Hz, 3H), 2.30 (s, 3H), 0.97 (ddt, J=9.9, 5.1, 2.3 Hz, 1H), 0.43-0.34 (m, 1H), 0.33-0.24 (m, 2H), 0.17 (ddt, J=8.8, 5.3, 2.5 Hz, 1H).

Example 171: Preparation of Compound 252

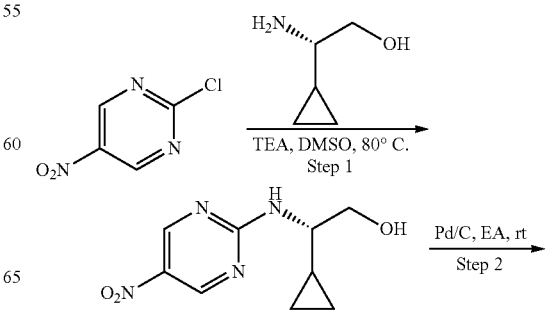

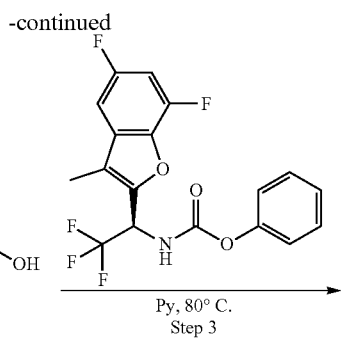

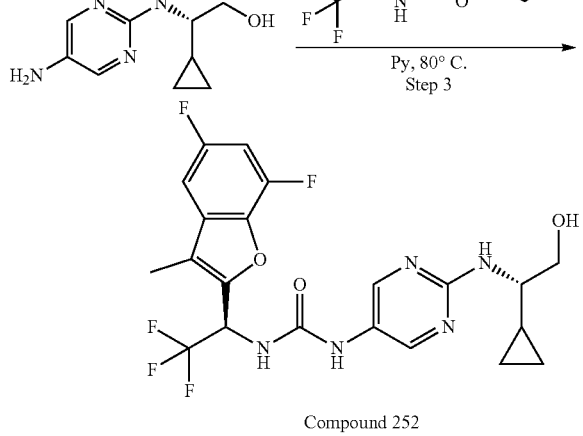

Compound 252

Step 1

A mixture of 2-chloro-5-nitropyrimidine (200 mg, 1.254 mmol, 1 equiv), (S)-2-amino-2-cyclopropylethan-1-ol (140 mg, 1.384 mmol, 1.10 equiv), and TEA (254 mg, 2.510 mmol, 2.00 equiv) in DMSO (2.5 mL) was stirred overnight at 80° C. under nitrogen atmosphere. The mixture was allowed to cool down to room temperature. The residue was dissolved in water (15 mL). The resulting mixture was extracted with EtOAc (3×15 mL). The combined organic layers were washed with brine (1×15 mL) and dried over anhydrous $Na_2SO_4$. After filtration, the filtrate was concentrated under reduced pressure. The residue was purified by Prep-TLC (PE/EA 5:1) to afford (S)-2-cyclopropyl-2-((5-nitropyrimidin-2-yl)amino)ethan-1-ol (80 mg, 28.46%) as a white solid. MS (ESI): mass calcd. for $C_9H_{12}N_4O_3$, 224.1, m/z found 225.1 $[M+H]^+$.

Step 2

To a solution of (S)-2-cyclopropyl-2-((5-nitropyrimidin-2-yl)amino)ethan-1-ol (70 mg, 0.312 mmol, 1 equiv) in 2 mL EA was added Pd/C (10%, 7 mg) under a nitrogen atmosphere in a 100 mL round-bottom flask. The mixture was hydrogenated at room temperature for overnight under hydrogen atmosphere using a hydrogen balloon, filtered through a Celite pad, and concentrated under reduced pressure. The residue was purified by Prep-TLC (DCM/MeOH 12:1) to afford (S)-2-((5-aminopyrimidin-2-yl)amino)-2-cyclopropylethan-1-ol (50 mg, 82.45%) as an off-white solid.

MS (ESI): mass calcd. for $C_9H_{14}N_4O$, 194.1, m/z found 195.1 $[M+H]^+$.

Step 3

A mixture of (S)-2-((5-aminopyrimidin-2-yl)amino)-2-cyclopropylethan-1-ol (50 mg, 0.257 mmol, 1 equiv) and phenyl (R)-(1-(5,7-difluoro-3-methylbenzofuran-2-yl)-2,2,2-trifluoroethyl)carbamate (100 mg, 0.260 mmol, 1.01 equiv) in pyridine (3 mL) was stirred overnight at 80° C. under nitrogen atmosphere. The resulting mixture was concentrated under vacuum. The residue was dissolved in water (10 mL). The resulting mixture was extracted with EtOAc (3×10 mL). The combined organic layers were washed with brine (1×10 mL), dried over anhydrous $Na_2SO_4$. After filtration, the filtrate was concentrated under reduced pressure. The residue was purified by Prep-TLC (DCM/MeOH 10:1) and Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 60% B in 7 min, 60% B; Wave Length: 220 nm; RT1 (min): 6.73; Number Of Runs: 0) to afford 1-(2-(((S)-1-cyclopropyl-2-hydroxyethyl)amino)pyrimidin-5-yl)-3-((R)-1-(5,7-difluoro-3-methylbenzofuran-2-yl)-2,2,2-trifluoroethyl)urea (23.2 mg, 18.57%) as a white solid. MS (ESI): mass calcd. for $C_{21}H_{20}F_5N_5O_3$, 485.1, m/z found 486.1 $[M+H]^+$.

$^1$H NMR (400 MHz, DMSO-d6) δ 8.20 (d, J=11.6 Hz, 3H), 7.80 (d, J=9.2 Hz, 1H), 7.51-7.27 (m, 2H), 6.60 (d, J=8.0 Hz, 1H), 6.03 (q, J=8.8 Hz, 1H), 4.57 (d, J=5.6 Hz, 1H), 3.55-3.41 (m, 3H), 2.30 (s, 3H), 0.97 (d, J=6.4 Hz, 1H), 0.44-0.34 (m, 1H), 0.33-0.27 (m, 2H), 0.22-0.11 (m, 1H).

Example 172: Preparation of Compound 253

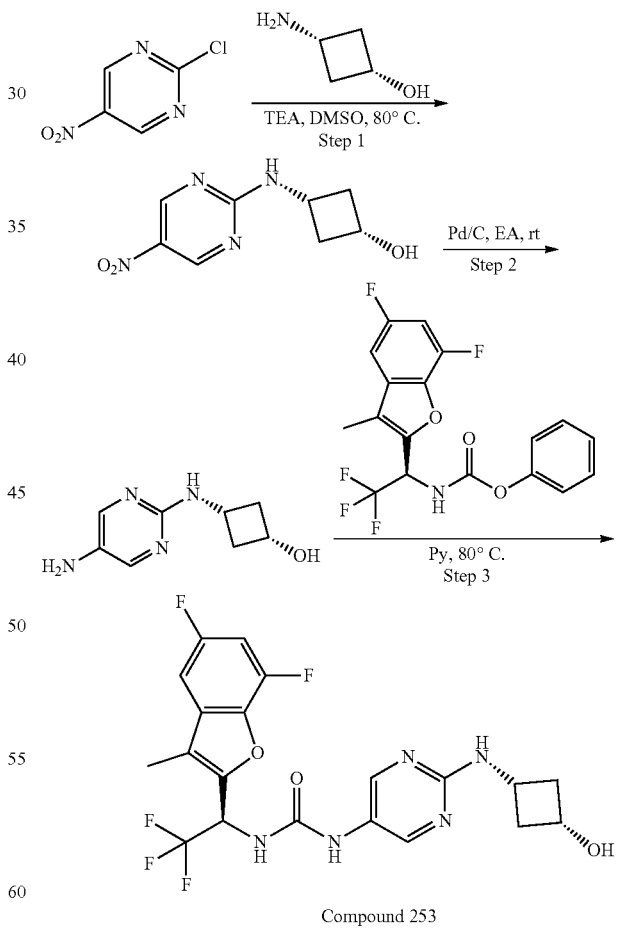

Compound 253

Step 1

A mixture of 2-chloro-5-nitropyrimidine (200 mg, 1.254 mmol, 1 equiv), (1S,3S)-3-aminocyclobutan-1-ol (219 mg, 2.514 mmol, 2.01 equiv) and TEA (380 mg, 3.755 mmol, 3.00 equiv) in DMSO (4 mL) was stirred overnight at 80° C. under nitrogen atmosphere. The mixture was allowed to cool down to room temperature. The residue was dissolved in water (8 mL). The resulting mixture was extracted with EtOAc (3×13 mL). The combined organic layers were washed with brine (1×7 mL) and dried over anhydrous $Na_2SO_4$. After filtration, the filtrate was concentrated under reduced pressure. The residue was purified by Prep-TLC (PE/EA 10:1) to afford (1S,3S)-3-((5-nitropyrimidin-2-yl)amino)cyclobutan-1-ol (100 mg, 37.95%) as an off-white solid. MS (ESI): mass calcd. for $C_8H_{10}N_4O_3$, 210.1, m/z found 211.0 [M+H]$^+$.

Step 2

To a solution of (1S,3S)-3-((5-nitropyrimidin-2-yl)amino)cyclobutan-1-ol (70 mg, 0.333 mmol, 1 equiv) in 3 mL EA was added Pd/C (10%, 7 mg) under nitrogen atmosphere in a 25 mL round-bottom flask. The mixture was hydrogenated at room temperature overnight under a hydrogen atmosphere using a hydrogen balloon, filtered through a Celite pad, and concentrated under reduced pressure. The residue was purified by Prep-TLC (PE/EA 1:1) to afford (1S,3S)-3-((5-aminopyrimidin-2-yl)amino)cyclobutan-1-ol (60 mg, 99.97%) as a yellow oil. MS (ESI): mass calcd. for $C_8H_{12}N_4O$, 180.1, m/z found 181.0 [M+H]$^+$.

Step 3

A mixture of (1S,3S)-3-((5-aminopyrimidin-2-yl)amino)cyclobutan-1-ol (60 mg, 0.333 mmol, 1 equiv) and phenyl (R)-(1-(5,7-difluoro-3-methylbenzofuran-2-yl)-2,2,2-trifluoroethyl)carbamate (90 mg, 0.234 mmol, 0.70 equiv) in pyridine (3 mL) was stirred overnight at 80° C. under nitrogen atmosphere. The resulting mixture was concentrated under vacuum. The residue was dissolved in water (10 mL). The resulting mixture was extracted with EtOAc (3×10 mL). The combined organic layers were washed with brine (1×10 mL) and dried over anhydrous $Na_2SO_4$. After filtration, the filtrate was concentrated under reduced pressure. The residue was purified by Prep-TLC ($CH_2Cl_2$/MeOH 10:1) and Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 32% B to 52% B in 8 min, 52% B; Wave Length: 254 nm; RT1 (min): 7.67; Number Of Runs: 0) to afford 1-((R)-1-(5,7-difluoro-3-methylbenzofuran-2-yl)-2,2,2-trifluoroethyl)-3-(2-(((1s,3S)-3-hydroxycyclobutyl)amino) pyrimidin-5-yl)urea (13.6 mg, 8.67%) as a white solid. MS (ESI): mass calcd. for $C_{20}H_{18}F_5N_5O_3$, 471.1, m/z found 472.1 [M+H]$^+$.

$^1$H NMR (400 MHz, DMSO-d6) δ 8.23 (d, J=12.0 Hz, 3H), 7.80 (d, J=9.2 Hz, 1H), 7.57-7.30 (m, 2H), 7.18 (d, J=7.2 Hz, 1H), 6.18-5.82 (m, 1H), 5.00 (d, J=6.0 Hz, 1H), 3.87-3.60 (m, 2H), 2.58-2.56 (m, 1H), 2.30 (s, 3H), 1.77 (q, J=8.4 Hz, 2H).

Example 173: Preparation of Compound 254

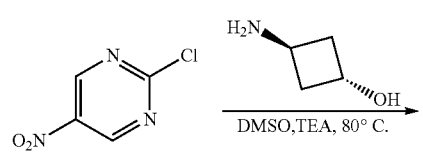

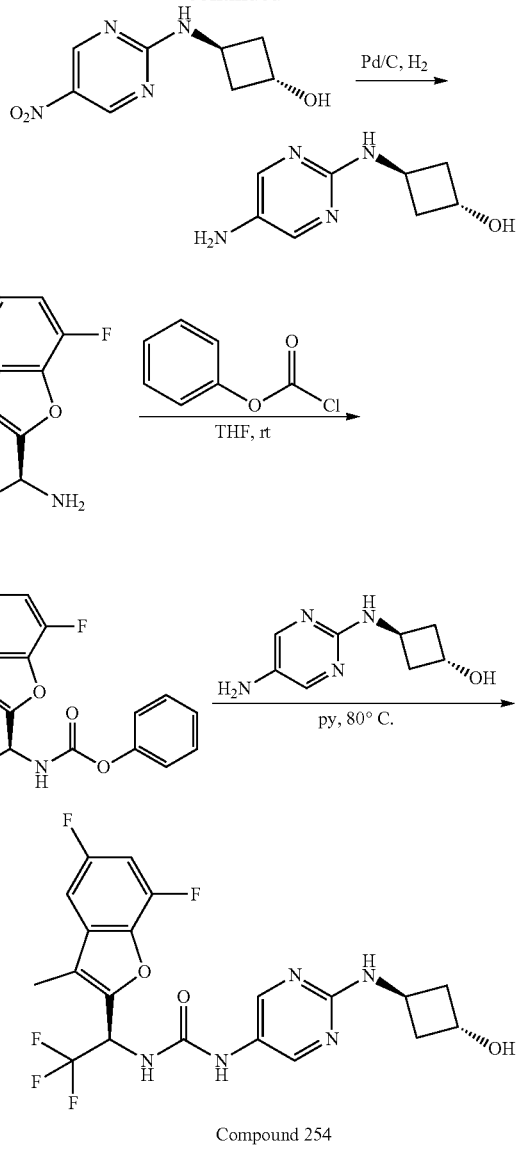

Compound 254

Step 1

To a stirred solution of 2-chloro-5-nitropyrimidine (150 mg, 0.940 mmol, 1 equiv) and TEA (285.44 mg, 2.820 mmol, 3 equiv) in DMSO (10 mL) was added (1R,3R)-3-aminocyclobutan-1-ol (122.88 mg, 1.410 mmol, 1.5 equiv) dropwise at room temperature under an air atmosphere. The resulting mixture was stirred for 3 h at 80° C. under nitrogen atmosphere. Desired product could be detected by LCMS. The resulting mixture was extracted with EtOAc (2×5 mL). The combined organic layers were washed with brine (4×1 10 mL), dried over anhydrous $Na_2SO_4$. After filtration, the filtrate was concentrated under reduced pressure to afford (1r,3r)-3-[(5-nitropyrimidin-2-yl)amino]cyclobutan-1-ol (180 mg, 91.08%) as a light yellow solid. MS (ESI): mass calcd. for $C_8H_{10}N_4O_3$, 210.1, m/z found 211.3 [M+H]$^+$.

Step 2

To a solution of (1R,3R)-3-[(5-nitropyrimidin-2-yl)amino]cyclobutan-1-ol (180 mg, 0.856 mmol, 1 equiv) in 5 mL EtOAc was added Pd/C (10%, 1 g) under nitrogen atmosphere in a 50 mL round-bottom flask. The mixture was hydrogenated at room temperature for 2 h under hydrogen atmosphere using a hydrogen balloon, filtered through a Celite pad, and concentrated under reduced pressure to afford (1R,3R)-3-[(5-aminopyrimidin-2-yl)amino]cyclobutan-1-ol (150 mg, 97.20%) as a light yellow solid. MS (ESI): mass calcd. for $C_8H_{12}N_4O$, 180.1, m/z found 181.2 $[M+H]^+$.

Step 3

A solution of (1R)-1-(5,7-difluoro-3-methyl-1-benzofuran-2-yl)-2,2,2-trifluoroethanamine (800 mg, 3.017 mmol, 1 equiv) and phenyl chloroformate (519.57 mg, 3.319 mmol, 1.1 equiv) in THF (20 mL) was stirred for 1 h at room temperature under nitrogen atmosphere. Desired product could be detected by LCMS. The resulting mixture was concentrated under reduced pressure to afford phenyl N-[(1R)-1-(5,7-difluoro-3-methyl-1-benzofuran-2-yl)-2,2,2-trifluoroethyl]carbamate (1100 mg, 94.64%) as an off-white solid. MS (ESI): mass calcd. for $C_{18}H_{12}F_5NO_3$, 385.1, m/z found 386.3 $[M+H]^+$.

Step 4

A solution of phenyl N-[(1R)-1-(5,7-difluoro-3-methyl-1-benzofuran-2-yl)-2,2,2-trifluoroethyl]carbamate (200 mg, 0.519 mmol, 1 equiv) and (1R,3R)-3-[(5-aminopyrimidin-2-yl)amino]cyclobutan-1-ol (102.90 mg, 0.571 mmol, 1.1 equiv) in pyridine (10 mL) was stirred for 3 h at 80° C. under nitrogen atmosphere. The resulting mixture was concentrated under reduced pressure. The crude product was purified by Prep-HPLC with the following conditions (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 25% B to 55% B in 7 min, 55% B; Wave Length: 220 nm; RT1 (min): 8.03; Number Of Runs: 0) to afford 3-[(1R)-1-(5,7-difluoro-3-methyl-1-benzofuran-2-yl)-2,2,2-trifluoroethyl]-1-(2-{[(1R,3R)-3-hydroxycyclobutyl]amino}pyrimidin-5-yl)urea (41.3 mg, 16.51%) as a white solid. MS (ESI): mass calcd. for $C_{20}H_{18}F_5N_5O_3$, 471.1, m/z found 472.0 $[M+H-17]^+$.

$^1$H NMR (400 MHz, DMSO-d6) δ 8.23 (d, J=17.4 Hz, 3H), 7.80 (d, J=9.4 Hz, 1H), 7.47-7.37 (m, 2H), 7.25 (d, J=6.6 Hz, 1H), 6.04 (p, J=8.3 Hz, 1H), 4.94 (d, J=5.4 Hz, 1H), 4.25 (tt, J=13.1, 6.2 Hz, 2H), 2.30 (s, 3H), 2.14 (qt, J=11.2, 5.8 Hz, 4H).

Example 174: Preparation of Compound 255

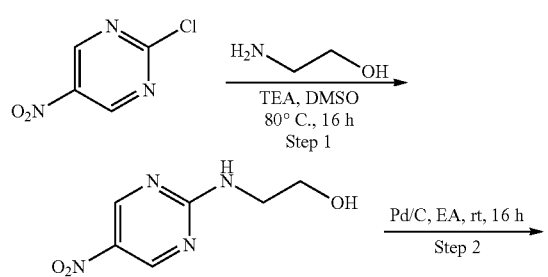

Compound 255

Step 1

A mixture of 2-chloro-5-nitropyrimidine (200 mg, 1.254 mmol, 1 equiv), 2-aminoethan-1-ol (100 mg, 1.637 mmol, 1.31 equiv), and TEA (400 mg, 3.953 mmol, 3.15 equiv) in DMSO (3 mL) was stirred for 16 h at 80° C. under nitrogen atmosphere. The resulting mixture was diluted with water. The resulting mixture was extracted with EA. The combined organic layers were washed with brine and dried over anhydrous $Na_2SO_4$. After filtration, the filtrate was concentrated under reduced pressure. The residue was purified by Prep-TLC (PE/EA 1:1) to afford 2-((5-nitropyrimidin-2-yl)amino)ethan-1-ol (100 mg, 43.31%) as a yellow solid. MS (ESI): mass calcd. for $C_6H_8N_4O_3$, 184.1. m/z found 185.1 $[M+H]^+$.

Step 2

The resulting mixture of 2-((5-nitropyrimidin-2-yl)amino)ethan-1-ol (90 mg, 0.489 mmol, 1 equiv), Pd/C (20 mg, 0.188 mmol, 0.38 equiv) in EA (5 mL) was stirred for 16 h at room temperature under nitrogen atmosphere. The resulting mixture was filtered and the filter cake was washed with EA. The filtrate was concentrated under reduced pressure. The residue was purified by Prep-TLC ($CH_2Cl_2$/MeOH 10:1) to afford 2-((5-aminopyrimidin-2-yl)amino)ethan-1-ol (53 mg, 70.34%) as a yellow solid. MS (ESI): mass calcd. for $C_6H_{10}N_4O$, 154.1. m/z found 155.1 $[M+H]^+$.

Step 3

A mixture of 2-((5-aminopyrimidin-2-yl)amino)ethan-1-ol (48 mg, 0.311 mmol, 1 equiv) and phenyl (R)-(1-(5,7-difluoro-3-methylbenzofuran-2-yl)-2,2,2-trifluoroethyl)carbamate (120 mg, 0.311 mmol, 1.00 equiv) in pyridine (3 mL) was stirred for 16 h at room temperature under nitrogen atmosphere. The resulting mixture was concentrated under reduced pressure. The residue was purified by Prep-TLC and Prep-HPLC: Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 25% B to 60% B in 7 min, 60% B; Wave Length: 220 nm; RT1 (min): 7.42; Number Of Runs: 0 to afford (R)-1-(1-(5,7-difluoro-3-methylbenzofuran-2-yl)-2,2,2-trifluoroethyl)-3-(2-((2-hydroxyethyl)amino)pyrimidin-5-yl) urea (7.6 mg, 5.48%) as a white solid.

MS (ESI): mass calcd. for $C_{18}H_{16}F_5N_5O_3$, 445.1, m/z found 446.1 [M+H]⁺.

¹H NMR (400 MHz, DMSO-d₆) δ 8.25-8.22 (m, 3H), 7.81 (d, J=9.2 Hz, 1H), 7.50-7.30 (m, 2H), 6.83 (t, J=5.6 Hz, 1H), 6.06 (q, J=8.4 Hz, 1H), 4.64 (t, J=5.6 Hz, 1H), 3.48 (q, J=6.0 Hz, 2H), 3.32-3.25 (m, 2H), 2.30 (s, 3H).

Example 175: Preparation of Compound 256

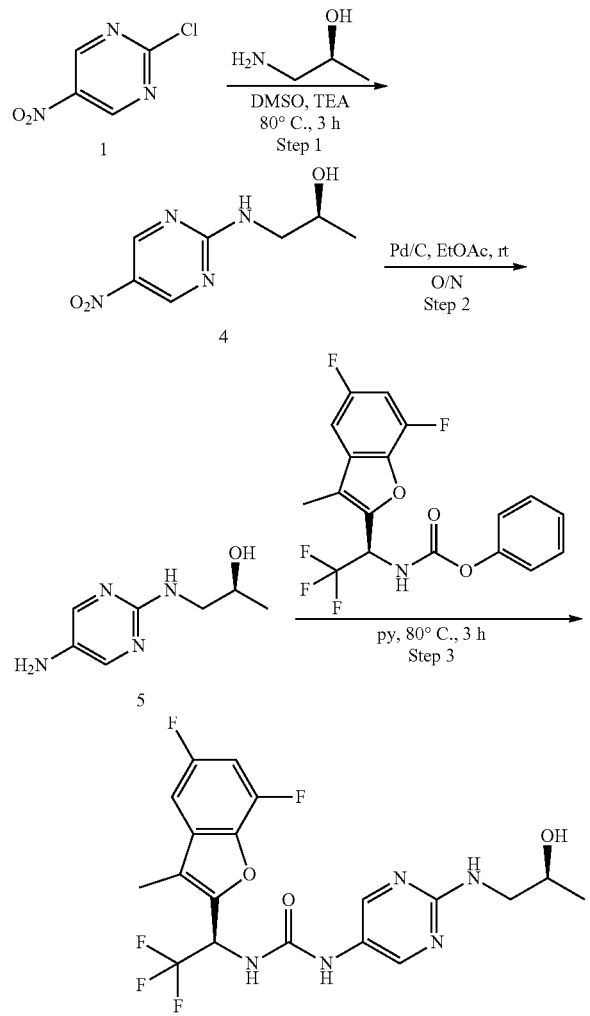

Compound 256

Step 1

To a stirred solution of 2-chloro-5-nitropyrimidine (200 mg, 1.254 mmol, 1 equiv) and (2S)-1-aminopropan-2-ol (141.25 mg, 1.881 mmol, 1.5 equiv) in DMSO (5 mL) was added TEA (380.59 mg, 3.762 mmol, 3 equiv) dropwise at 80° C. under nitrogen atmosphere. The resulting mixture was stirred for 2 h at 80° C. under a nitrogen atmosphere. The mixture was allowed to cool down to room temperature. The resulting mixture was extracted with EtOAc (2×80 mL). The combined organic layers were washed with brine (2×1 mL) and dried over anhydrous Na₂SO₄. After filtration, the filtrate was concentrated under reduced pressure. The crude product was used in the next step directly without further purification. MS (ESI): mass calcd. for $C_7H_{10}N_4O_3$, 198.1 m/z found 199.3[M+H]⁺.

Step 2

A solution of (2S)-1-[(5-nitropyrimidin-2-yl)amino]propan-2-ol (230 mg, 1.161 mmol, 1 equiv) and Pd/C (20 mg, 0.188 mmol, 0.16 equiv) in EtOAc (30 mL) was stirred overnight at room temperature under hydrogen atmosphere. The resulting mixture was concentrated under reduced pressure. The resulting mixture was used in the next step directly without further purification. to afford (2S)-1-[(5-aminopyrimidin-2-yl)amino]propan-2-ol (110 mg, 56.35%) as a yellow oil. MS (ESI): mass calcd. for $C_7H_{12}N_4O$, 168.1. m/z found 169.0 [M+H]⁺.

Step 3

A solution of (2S)-1-[(5-aminopyrimidin-2-yl) amino] propan-2-ol (98.22 mg, 0.584 mmol, 1.5 equiv) and phenyl N-[(1R)-1-(5,7-difluoro-3-methyl-1-benzofuran-2-yl)-2,2, 2-trifluoroethyl]carbamate (150 mg, 0.389 mmol, 1.00 equiv) in pyridine (3 mL) was stirred for 3 h at 80° C. under nitrogen atmosphere. Desired product could be detected by LCMS. The mixture was allowed to cool down to room temperature. The resulting mixture was extracted with EtOAc (2×50 mL). The combined organic layers were washed with brine (5×180 mL) and dried over anhydrous Na₂SO₄. After filtration, the filtrate was concentrated under reduced pressure. The crude product (100 mg) was purified by Prep-HPLC with the following conditions (Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 25% B to 60% B in 7 min, 60% B; Wave Length: 220 nm; RT1 (min): 7.73; Number Of Runs: 0) to afford 3-[(1R)-1-(5,7-difluoro-3-methyl-1-benzofuran-2-yl)-2,2,2-trifluoroethyl]-1-(2-{[(2S)-2-hydroxypropyl]amino}pyrimidin-5-yl)urea (34.8 mg, 19.46%) as a white solid. MS (ESI): mass calcd. for $C_{19}H_{18}F_5N_5O_3$, 459.4, m/z found 460.1 [M+H]⁺.

¹H NMR (400 MHz, DMSO-d6) δ 8.24 (d, J=13.2 Hz, 3H), 7.82 (d, J=9.4 Hz, 1H), 7.50-7.34 (m, 2H), 6.80 (t, J=5.9 Hz, 1H), 6.04 (p, J=8.3 Hz, 1H), 4.67 (d, J=4.8 Hz, 1H), 3.76 (qd, J=6.3, 4.8 Hz, 1H), 3.17 (t, J=6.0 Hz, 2H), 2.30 (s, 3H), 1.05 (d, J=6.2 Hz, 3H).

Example 176: Preparation of Compound 257

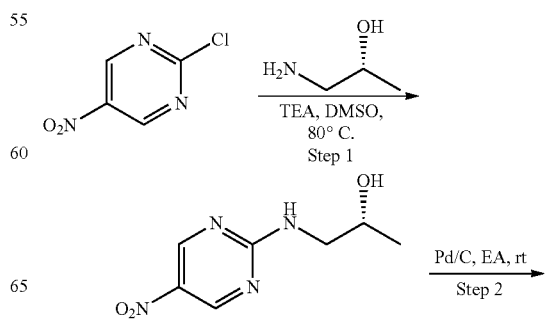

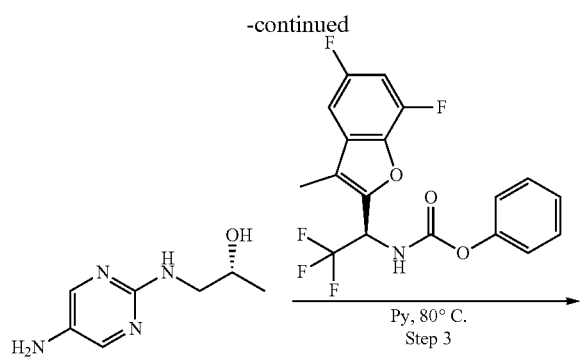

amino)propan-2-ol (150 mg, 60.37%) as a white solid. MS (ESI): mass calcd. for $C_7H_{10}N_4O_3$, 198.1, m/z found 199.0 [M+H]$^+$.

Step 2

A mixture of (R)-1-((5-nitropyrimidin-2-yl)amino)propan-2-ol (150 mg, 0.757 mmol, 1 equiv) and Pd/C (10 mg, 0.094 mmol, 0.12 equiv) in EtOAc (5 mL) was stirred overnight at room temperature under a hydrogen atmosphere. The resulting mixture was filtered and the filter cake was washed with EtOAc (2×10 mL). The filtrate was concentrated under reduced pressure to give (R)-1-((5-aminopyrimidin-2-yl)amino)propan-2-ol (70 mg, 54.95%) as a brown oil. MS (ESI): mass calcd. for $C_7H_{12}N_4O$, 168.1, m/z found 169.1 [M+H]$^+$.

Step 3

A mixture of (R)-1-((5-aminopyrimidin-2-yl)amino)propan-2-ol (70 mg, 0.416 mmol, 1 equiv) and phenyl (R)-(1-(5,7-difluoro-3-methylbenzofuran-2-yl)-2,2,2-trifluoroethyl)carbamate (161 mg, 0.418 mmol, 1.00 equiv) in pyridine (4 mL) was stirred overnight at 80° C. under a nitrogen atmosphere. The mixture was allowed to cool down to room temperature. The resulting mixture was concentrated under reduced pressure. The residue was dissolved in water (8 mL). The resulting mixture was extracted with EtOAc (3×10 mL). The combined organic layers were washed with brine (1×10 mL) and dried over anhydrous $Na_2SO_4$. After filtration, the filtrate was concentrated under reduced pressure. The residue was purified by silica gel column chromatography, eluting with DCM/MeOH (10:1) and Prep-HPLC: Column: XBridge Shield RP18 OBD Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 33% B to 53% B in 8 min, 53% B; Wave Length: 220 nm; RT1 (min): 7.73; Number Of Runs: 0 to afford 1-((R)-1-(5,7-difluoro-3-methylbenzofuran-2-yl)-2,2,2-trifluoroethyl)-3-(2-(((R)-2-hydroxypropyl)amino)pyrimidin-5-yl)urea (53.6 mg, 27.73%) as a white solid. MS (ESI): mass calcd. for $C_{19}H_{18}F_5N_5O_3$, 459.1, m/z found 460.2 [M+H]$^+$.

$^1$H NMR (400 MHz, DMSO-$d_6$) δ 8.23 (d, J=14.4 Hz, 3H), 7.81 (d, J=9.2 Hz, 1H), 7.52-7.37 (m, 2H), 6.80 (t, J=6.0 Hz, 1H), 6.03 (q, J=8.4 Hz, 1H), 4.66 (d, J=4.8 Hz, 1H), 3.84-3.67 (m, 1H), 3.17 (t, J=6.0 Hz, 2H), 2.30 (s, 3H), 1.05 (d, J=6.4 Hz, 3H).

Example 177: Preparation of Compound 258

Compound 257

Step 1

The resulting mixture of 2-chloro-5-nitropyrimidine (200 mg, 1.254 mmol, 1 equiv), (R)-1-aminopropan-2-ol (100 mg, 1.331 mmol, 1.06 equiv), TEA (255 mg, 2.520 mmol, 2.01 equiv) in DMSO (5 mL) was stirred overnight at 80° C. under nitrogen atmosphere. The residue was dissolved in water (15 mL). The resulting mixture was extracted with EtOAc (3×8 mL). The combined organic layers were washed with brine (1×15 mL) and dried over anhydrous $Na_2SO_4$. After filtration, the filtrate was concentrated under reduced pressure. The residue was purified by Prep-TLC (DCM/MeOH 10:1) to afford (R)-1-((5-nitropyrimidin-2-yl)

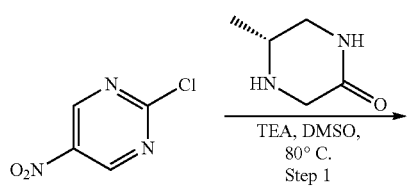

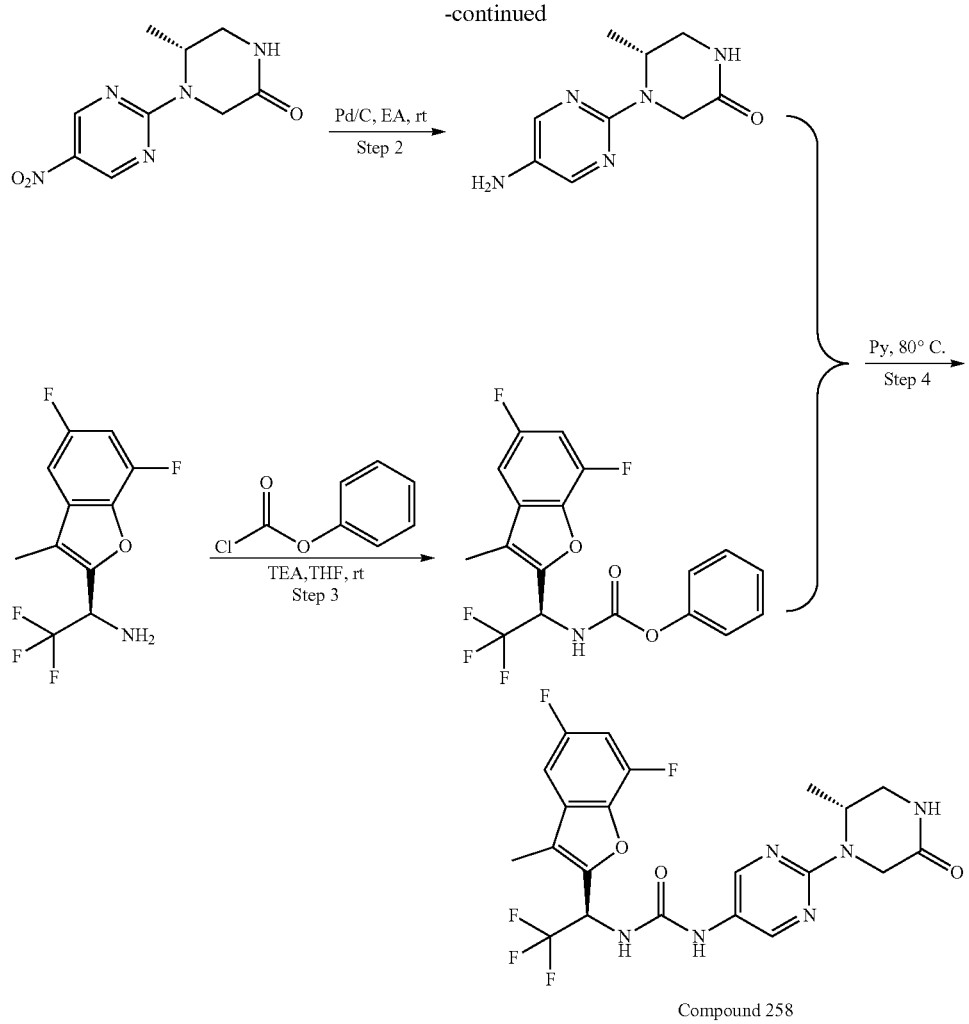

Compound 258

Step 1

2-chloro-5-nitropyrimidine (200 mg, 1.254 mmol, 1 equiv), (5R)-5-methylpiperazin-2-one (172 mg, 1.507 mmol, 1.20 equiv), and TEA (380 mg, 3.755 mmol, 3.00 equiv) were stirred in DMSO (4 mL) overnight at 80° C. under nitrogen atmosphere. The mixture was allowed to cool down to room temperature and diluted with water (10 mL). The resulting mixture was extracted with EtOAc (3×10 mL). The combined organic layers were washed with brine (1×8 mL) and dried over anhydrous $Na_2SO_4$. After filtration, the filtrate was concentrated under reduced pressure. The residue was purified by Prep-TLC (PE/EA 5:1) to afford (5R)-5-methyl-4-(5-nitropyrimidin-2-yl)piperazin-2-one (150 mg, 50.44%) as a white solid. MS (ESI): mass calcd. for $C_9H_{11}N_5O_3$, 237.1, m/z found 238.1 $[M+H]^+$.

Step 2

To a solution of (5R)-5-methyl-4-(5-nitropyrimidin-2-yl)piperazin-2-one (140 mg, 0.590 mmol, 1 equiv) in 3 mL EA was added Pd/C (10%, 6.4 mg) under a hydrogen atmosphere in a 100 mL round-bottom flask. The mixture was hydrogenated at room temperature overnight under hydrogen atmosphere using a hydrogen balloon, filtered through a Celite pad, and concentrated under reduced pressure to afford (5R)-4-(5-aminopyrimidin-2-yl)-5-methylpiperazin-2-one (90 mg, 73.59%) as a white solid. The crude product mixture was used in the next step directly without further purification. MS (ESI): mass calcd. for $C_9H_{13}N_5O$, 207.1, m/z found 208.1 $[M+H]^+$.

Step 3

A mixture of (1R)-1-(5,7-difluoro-3-methyl-1-benzofuran-2-yl)-2,2,2-trifluoroethanamine (80 mg, 0.302 mmol, 1 equiv), phenyl chloroformate (52 mg, 0.332 mmol, 1.10 equiv), and TEA (60 mg, 0.593 mmol, 1.97 equiv) in THF (2 mL) was stirred for 1.5 h at room temperature under nitrogen atmosphere. The resulting mixture was concentrated under reduced pressure, yielding phenyl N-[(1R)-1-(5,7-difluoro-3-methyl-1-benzofuran-2-yl)-2,2,2-trifluoroethyl]carbamate (100 mg, 86.03%) as a yellow solid. The crude product was used in the next step directly without further purification. MS (ESI): mass calcd. for $C_{18}H_{14}F_5N_3O_2$, 385.1, m/z found 386.10 $[M+H]^+$.

Step 4

A mixture of (5R)-4-(5-aminopyrimidin-2-yl)-5-methylpiperazin-2-one (90 mg, 0.434 mmol, 1 equiv), and phenyl N-[(1R)-1-(5,7-difluoro-3-methyl-1-benzofuran-2-yl)-2,2,2-trifluoroethyl]carbamate (130 mg, 0.337 mmol, 0.78 equiv) in pyridine (3 mL) was stirred overnight at 80° C. under nitrogen atmosphere. The resulting mixture was concentrated under reduced pressure. The residue was dissolved in water (5 mL). The resulting mixture was extracted with EtOAc (3×10 mL). The combined organic layers were washed with brine (1×5 mL) and dried over anhydrous Na$_2$SO$_4$. After filtration, the filtrate was concentrated under reduced pressure. The residue was purified by Prep-TLC (DCM/MeOH 10:1) and Prep-HPLC: Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 35% B to 56% B in 8 min, 56% B; Wave Length: 254 nm; RT1 (min): 7.47; Number Of Runs: 0 to afford 3-[(1R)-1-(5,7-difluoro-3-methyl-1-benzofuran-2-yl)-2,2,2-trifluoroethyl]-1-{2-[(2R)-2-methyl-5-oxopiperazin-1-yl]pyrimidin-5-yl}urea (42.1 mg, 19.45%) as a white solid. MS (ESI): mass calcd. for C$_{18}$H$_{14}$F$_5$N$_3$O$_2$, 498.1, m/z found 499.1 [M+H]$^+$.

$^1$H NMR (400 MHz, DMSO-d$_6$) δ 8.44 (s, 2H), 8.38 (s, 1H), 8.04 (s, 1H), 7.86 (d, J=9.2 Hz, 1H), 7.48-7.35 (m, 2H), 6.18-5.92 (m, 1H), 4.91-4.78 (m 1H), 4.33 (d, J=18.4 Hz, 1H), 3.68 (d, J=18.4 Hz, 1H), 3.50-3.43 (m, 1H), 3.11-3.05 (m, 1H), 2.30 (s, 3H), 1.15 (d, J=6.8 Hz, 3H).

Example 178: Preparation of Compound 259

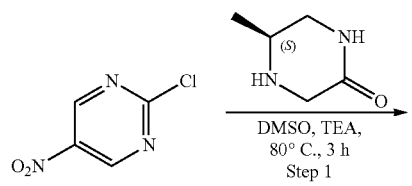

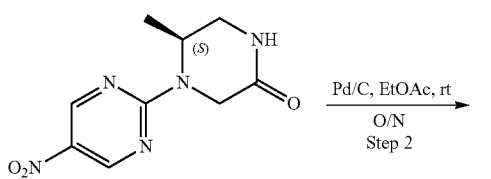

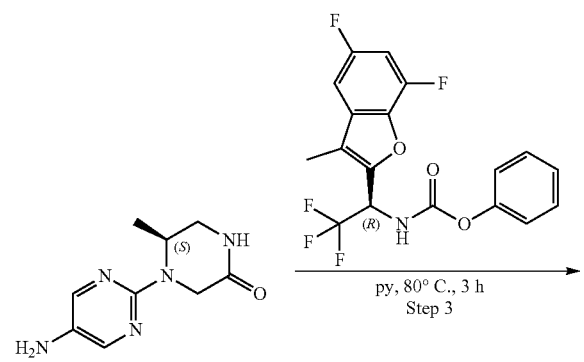

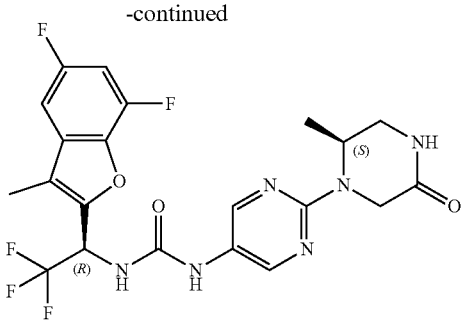

Compound 259

Step 1

To a stirred solution of 2-chloro-5-nitropyrimidine (150 mg, 0.940 mmol, 1 equiv) and (5S)-5-methylpiperazin-2-one (160.99 mg, 1.410 mmol, 1.5 equiv) in DMSO (5 mL) was added TEA (285.44 mg, 2.820 mmol, 3 equiv) in portions at 80° C. under nitrogen atmosphere. The resulting mixture was stirred for 3 h at 80° C. under nitrogen atmosphere. The mixture was allowed to cool down to room temperature. The resulting mixture was extracted with EtOAc (2×100 mL). The combined organic layers were washed with brine (2×1100 mL) and dried over anhydrous Na$_2$SO$_4$. After filtration, the filtrate was concentrated under reduced pressure. The crude product was used in the next step directly without further purification. MS (ESI): mass calcd. for C$_9$H$_{11}$N$_5$O$_3$, 237.2. m/z found 238.2 [M+H]$^+$.

Step 2

A solution of (5S)-5-methyl-4-(5-nitropyrimidin-2-yl)piperazin-2-one (200 mg, 0.843 mmol, 1 equiv) and Pd/C (20 mg, 0.188 mmol, 0.22 equiv) in EtOAc (5 mL) was stirred overnight at room temperature under hydrogen atmosphere. The resulting mixture was filtered and the filter cake was washed with EtOAc (2×1300 mL). The filtrate was concentrated under reduced pressure. to afford (5S)-4-(5-aminopyrimidin-2-yl)-5-methylpiperazin-2-one (150 mg, 85.85%) as a yellow oil.

MS (ESI): mass calcd. for C$_9$H$_{13}$N$_5$O, 207.1 [M+H]$^+$, m/z found 207.10[M+H]$^+$.

Step 3

A solution of (5S)-4-(5-aminopyrimidin-2-yl)-5-methylpiperazin-2-one (104.89 mg, 0.506 mmol, 1.30 equiv) and phenyl N-[(1R)-1-(5,7-difluoro-3-methyl-1-benzofuran-2-yl)-2,2,2-trifluoroethyl]carbamate (150 mg, 0.389 mmol, 1.00 equiv) in pyridine (3 mL) was stirred for 3 h at 80° C. under nitrogen atmosphere. The mixture was allowed to cool down to room temperature. The resulting mixture was extracted with EtOAc (2×50 mL). The combined organic layers were washed with brine (5×180 mL) and dried over anhydrous Na$_2$SO$_4$. After filtration, the filtrate was concentrated under reduced pressure. The crude product (100 mg) was purified by Prep-HPLC with the following conditions (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 30% B to 60% B in 7 min, 60% B; Wave Length: 220 nm; RT1 (min): 7.70; Number Of Runs: 0) to afford 3-[(1R)-1-(5,7-difluoro-3-methyl-1-benzofuran-2-yl)-2,2,2-trifluoroethyl]-1-{2-

[(2S)-2-methyl-5-oxopiperazin-1-yl]pyrimidin-5-yl}urea (39.4 mg, 20.30%) as a white solid.

MS (ESI): mass calcd. for $C_{21}H_{19}F_5N_6O_3$, 498.4, m/z found 499.2 $[M+H]^+$.

$^1$H NMR (400 MHz, DMSO-d6) δ 8.41 (d, J=21.9 Hz, 3H), 8.05 (d, J=4.8 Hz, 1H), 7.87 (d, J=9.4 Hz, 1H), 7.48-7.36 (m, 2H), 6.06 (p, J=8.3 Hz, 1H), 4.84 (dtd, J=6.8, 5.1, 4.6, 2.8 Hz, 1H), 4.33 (d, J=18.4 Hz, 1H), 3.68 (d, J=18.3 Hz, 1H), 3.47 (dd, J=12.6, 4.4 Hz, 1H), 3.09 (ddd, J=12.5, 5.0, 2.1 Hz, 1H), 2.30 (s, 3H), 1.15 (d, J=6.6 Hz, 3H).

Example 179: Preparation of Compound 260

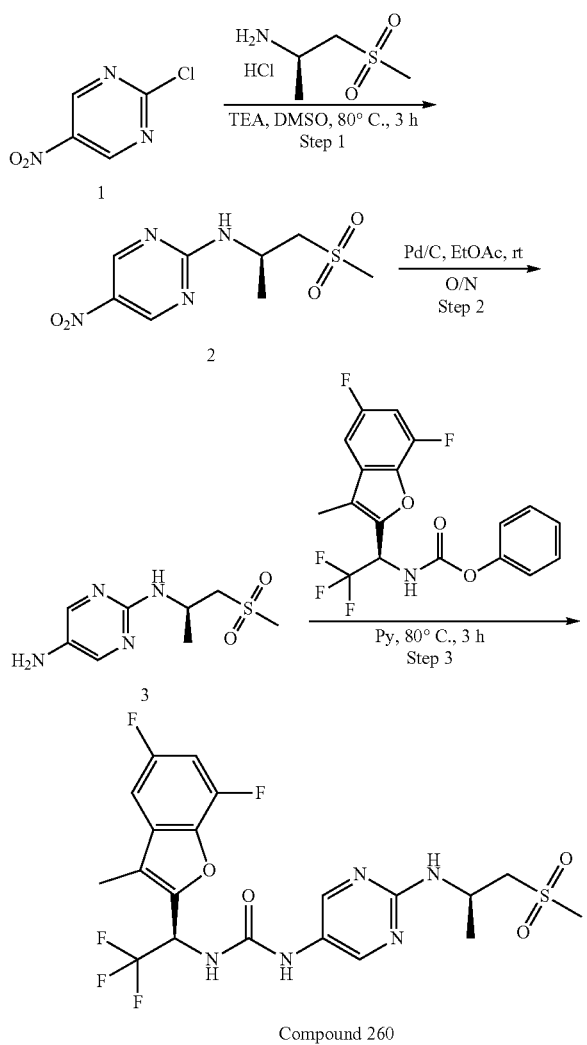

Compound 260

Step 1

To a stirred solution of 2-chloro-5-nitropyrimidine (150 mg, 0.940 mmol, 1 equiv) and (2R)-1-methanesulfonylpropan-2-amine (193.51 mg, 1.410 mmol, 1.5 equiv) in DMSO (5 mL) was added TEA (190.30 mg, 1.880 mmol, 2 equiv) dropwise at room temperature under a nitrogen atmosphere. The resulting mixture was stirred for 3 h at 80° C. under nitrogen atmosphere. The mixture was allowed to cool down to room temperature. The resulting mixture was extracted with EtOAc (2×80 mL). The combined organic layers were washed with brine (2×1100 mL) and dried over anhydrous $Na_2SO_4$. After filtration, the filtrate was concentrated under reduced pressure. The crude product was used in the next step directly without further purification. to afford N-[(2S)-1-methanesulfonylpropan-2-yl]-5-nitropyrimidin-2-amine (200 mg, 81.73%) as a white solid. MS (ESI): mass calcd. for $C_8H_{12}N_4O_4S$, 206.3 $[M+H]^+$.

Step 2

A solution of N-[(2R)-1-methanesulfonylpropan-2-yl]-5-nitropyrimidin-2-amine (200 mg, 0.768 mmol, 1 equiv) and Pd/C (10 mg, 0.094 mmol, 0.12 equiv) in EtOAc (20 mL) was stirred overnight at room temperature under hydrogen atmosphere. The resulting mixture was concentrated under reduced pressure. The crude product was used in the next step directly without further purification to afford N2-[(2R)-1-methanesulfonylpropan-2-yl]pyrimidine-2,5-diamine (160 mg, 90.41%) as a yellow oil. MS (ESI): mass calcd. for $C_8H_{14}N_4O_2S$, 230.3. m/z found 231.2 $[M+H]^+$.

Step 3

A solution of N2-[(2R)-1-methanesulfonylpropan-2-yl]pyrimidine-2,5-diamine (89.66 mg, 0.389 mmol, 1.50 equiv) and phenyl N-[(1R)-1-(5,7-difluoro-3-methyl-1-benzofuran-2-yl)-2,2,2-trifluoroethyl]carbamate (100 mg, 0.260 mmol, 1.00 equiv) in pyridine (5 mL) was stirred for 2 h at 80° C. under nitrogen atmosphere. The mixture was allowed to cool down to room temperature. The resulting mixture was extracted with EtOAc (2×50 mL). The combined organic layers were washed with brine (5×1 80 mL) and dried over anhydrous $Na_2SO_4$. After filtration, the filtrate was concentrated under reduced pressure. The crude product (100 mg) was purified by Prep-HPLC with the following conditions (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 60% B in 7 min, 60% B; Wave Length: 220 nm; RT1 (min): 7.98; Number Of Runs: 0) to afford 3-[(1R)-1-(5,7-difluoro-3-methyl-1-benzofuran-2-yl)-2,2,2-trifluoroethyl]-1-(2-{[(2R)-1-methanesulfonylpropan-2-yl]amino}pyrimidin-5-yl)urea (36.2 mg, 26.75%) as a white solid. MS (ESI): mass calcd. for $C_{20}H_{20}F_5N_5O_4S$, 521.4, m/z found 522.1 $[M+H]^+$.

$^1$H NMR (400 MHz, DMSO-d6) δ 8.30 (d, J=14.4 Hz, 3H), 7.84 (d, J=9.4 Hz, 1H), 7.52-7.31 (m, 2H), 7.07 (d, J=8.5 Hz, 1H), 6.05 (p, J=8.3 Hz, 1H), 4.43 (p, J=6.7 Hz, 1H), 3.46 (dd, J=14.3, 6.8 Hz, 1H), 3.18 (dd, J=14.3, 5.9 Hz, 1H), 2.97 (s, 3H), 2.30 (s, 3H), 1.27 (d, J=6.6 Hz, 3H).

Example 180: Preparation of Compound 261

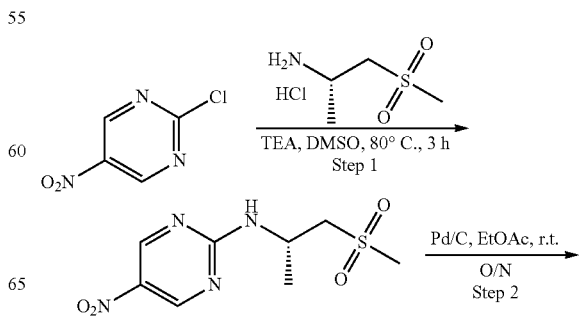

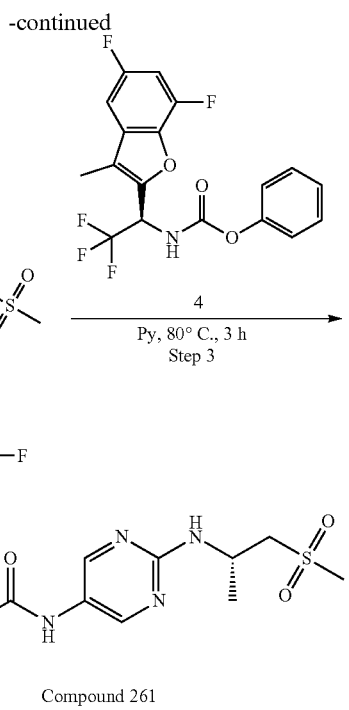

Compound 261

Step 1

To a stirred solution of 2-chloro-5-nitropyrimidine (150 mg, 0.940 mmol, 1 equiv) and (2S)-1-methanesulfonylpropan-2-amine (193.51 mg, 1.410 mmol, 1.5 equiv) in DMSO (5 mL) was added TEA (285.44 mg, 2.820 mmol, 3 equiv) dropwise at room temperature under nitrogen atmosphere. The resulting mixture was stirred for 3 h at 80° C. under nitrogen atmosphere. The mixture was allowed to cool down to room temperature. The resulting mixture was extracted with EtOAc (2×50 mL). The combined organic layers were washed with brine (3×180 mL) and dried over anhydrous $Na_2SO_4$. After filtration, the filtrate was concentrated under reduced pressure. The crude product was used in the next step directly without further purification to afford N-[(2S)-1-methanesulfonylpropan-2-yl]-5-nitropyrimidin-2-amine (180 mg, 73.55%) as a yellow oil. MS (ESI): mass calcd. for $C_8H_{12}N_4O_4S$, 260.2. no MS signal $[M+H]^+$.

Step 2

A solution of N-[(2S)-1-methanesulfonylpropan-2-yl]-5-nitropyrimidin-2-amine (200 mg, 0.768 mmol, 1 equiv) and Pd/C (16.36 mg, 0.154 mmol, 0.2 equiv) in EtOAc (20 mL) was stirred overnight at room temperature under hydrogen atmosphere. The resulting mixture was concentrated under reduced pressure to afford N2-[(2S)-1-methanesulfonylpropan-2-yl]pyrimidine-2,5-diamine (180 mg, 81.37%) as a yellow oil. MS (ESI): mass calcd. for $C_{18}H_{18}ClFN_4O_2$, 230.1. m/z found 231.3 $[M+H]^+$.

Step 3

A solution of N2-[(2S)-1-methanesulfonylpropan-2-yl]pyrimidine-2,5-diamine (149.79 mg, 0.650 mmol, 1.79 equiv) and phenyl N-[(1R)-1-(5,7-difluoro-3-methyl-1-benzofuran-2-yl)-2,2,2-trifluoroethyl]carbamate (140 mg, 0.363 mmol, 1.00 equiv) in pyridine (1 mL) was stirred for 3 h at 80° C. under nitrogen atmosphere. The mixture was allowed to cool down to room temperature. The resulting mixture was extracted with EtOAc (2×50 mL). The combined organic layers were washed with brine (4×180 mL) and dried over anhydrous $Na_2SO_4$. After filtration, the filtrate was concentrated under reduced pressure. The crude product (100 mg) was purified by Prep-HPLC with the following conditions (Column: XSelect CSH Fluoro Phenyl, 30*150 mm, 5 μm; Mobile Phase A: Water (10 mmol/L $NH_4HCO_3$), Mobile Phase B: ACN; Flow rate: 60 mL/min; Gradient: 33% B to 48% B in 8 min, 48% B; Wave Length: 254 nm; RT1 (min): 7.48; Number Of Runs: 0) to afford 3-[(1R)-1-(5,7-difluoro-3-methyl-1-benzofuran-2-yl)-2,2,2-trifluoroethyl]-1-(2-{[(2S)-1-methanesulfonylpropan-2-yl]amino}pyrimidin-5-yl)urea (51.9 mg, 27.39%) as a white solid.

MS (ESI): mass calcd. for $C_{23}H_{27}FN_6O_3$, 521.5, m/z found 522.1 $[M+H]^+$.

$^1$H NMR (400 MHz, DMSO-d6) δ 8.29 (d, J=16.2 Hz, 3H), 7.84 (d, J=9.5 Hz, 1H), 7.47-7.34 (m, 2H), 7.06 (d, J=8.6 Hz, 1H), 6.10-5.98 (m, 1H), 4.50-4.37 (m, 1H), 3.46 (dd, J=14.3, 6.8 Hz, 1H), 3.18 (dd, J=14.5, 5.9 Hz, 1H), 2.97 (s, 3H), 2.30 (s, 3H), 1.27 (d, J=6.6 Hz, 3H).

Example 181: Preparation of Compound 262

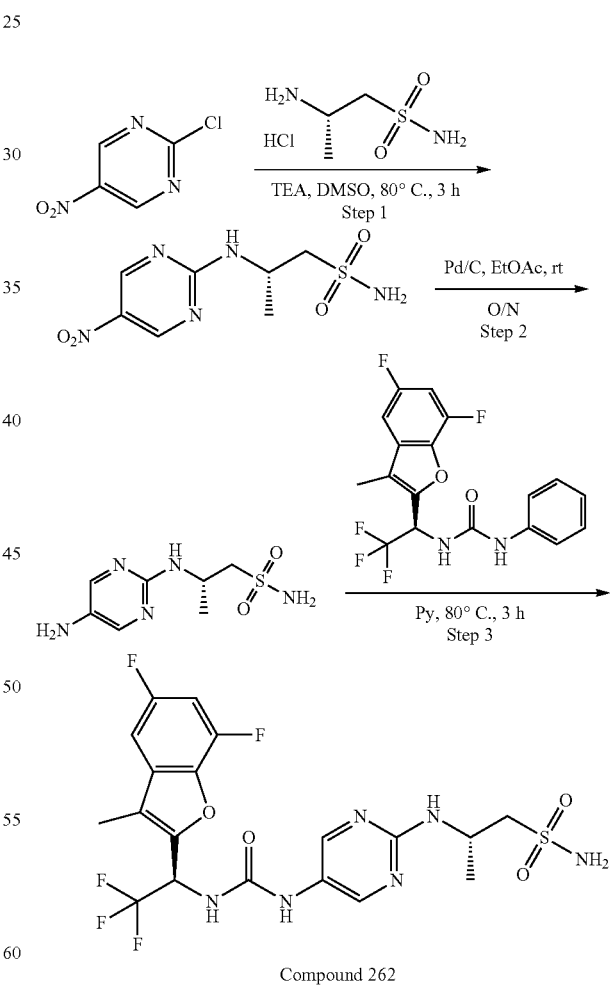

Compound 262

Step 1

A solution of 2-chloro-5-nitropyrimidine (150 mg, 0.940 mmol, 1 equiv) and (2S)-2-aminopropane-1-sulfonamide (155.92 mg, 1.128 mmol, 1.2 equiv) in DMSO (4 mL) was stirred for 3 h at 80° C. under nitrogen atmosphere. The resulting mixture was stirred for 4 h at 80° C. under nitrogen atmosphere. The mixture was allowed to cool down to room temperature. The resulting mixture was extracted with EtOAc (2×80 mL). The combined organic layers were washed with brine (2×1100 mL) and dried over anhydrous Na$_2$SO$_4$. After filtration, the filtrate was concentrated under reduced pressure. The crude product was used in the next step directly without further purification to afford (2S)-2-[(5-nitropyrimidin-2-yl)amino]propane-1-sulfonamide (180 mg, 73.27%) as a yellow oil. MS (ESI): mass calcd. for C$_7$H$_{11}$N$_5$O$_4$S, 261.3. m/z found 262.1. [M+H]$^+$.

Step 2

A solution of (2S)-2-[(5-nitropyrimidin-2-yl)amino]propane-1-sulfonamide (180 mg, 0.689 mmol, 1 equiv) and Pd/C (14.66 mg, 0.138 mmol, 0.2 equiv) in EA (5 mL) was stirred overnight at room temperature under a hydrogen atmosphere. The resulting mixture was stirred overnight at room temperature under hydrogen atmosphere. The resulting mixture was concentrated under reduced pressure. The resulting mixture was used in the next step directly without further purification to afford (2S)-2-[(5-aminopyrimidin-2-yl)amino]propane-1-sulfonamide (120 mg, 75.31%) as a yellow oil. MS (ESI): mass calcd. for C$_7$H$_{13}$N$_5$O$_2$S, 231.3, m/z found 232.10 [M+H]$^+$.

Step 3

A solution of (2S)-2-[(5-aminopyrimidin-2-yl)amino]propane-1-sulfonamide (78.03 mg, 0.338 mmol, 1.3 equiv) and phenyl N-[(1R)-1-(5,7-difluoro-3-methyl-1-benzofuran-2-yl)-2,2,2-trifluoroethyl]carbamate (100 mg, 0.260 mmol, 1.00 equiv) in pyridine (2 mL) was stirred for 3 h at 80° C. under nitrogen atmosphere. The mixture was allowed to cool down to room temperature. The resulting mixture was extracted with EtOAc (2×50 mL). The combined organic layers were washed with brine (5×180 mL) and dried over anhydrous Na$_2$SO$_4$. After filtration, the filtrate was concentrated under reduced pressure. The crude product (100 mg) was purified by Prep-HPLC with the following conditions (Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 32% B to 57% B in 8 min, 57% B; Wave Length: 220 nm; RT1 (min): 7.43; Number Of Runs: 0) to afford 3-[(1R)-1-(5,7-difluoro-3-methyl-1-benzofuran-2-yl)-2,2,2-trifluoroethyl]-1-(2-{[(2S)-1-sulfamoylpropan-2-yl]amino}pyrimidin-5-yl)urea (23.4 mg, 17.26%) as a white solid MS (ESI): mass calcd. for C$_{19}$H$_{19}$F$_5$N$_6$O$_4$S, 522.5, m/z found 523.1 [M+H]$^+$.

$^1$H NMR (400 MHz, DMSO-d6) δ 8.28 (d, J=13.9 Hz, 3H), 7.83 (d, J=9.5 Hz, 1H), 7.48-7.28 (m, 2H), 6.97 (d, J=8.3 Hz, 1H), 6.86 (s, 2H), 6.05 (p, J=8.3 Hz, 1H), 4.35 (p, J=7.4 Hz, 1H), 3.07 (dd, J=13.8, 7.8 Hz, 1H), 2.30 (s, 3H), 1.30 (d, J=6.6 Hz, 3H).

Example 182: Preparation of Compound 263

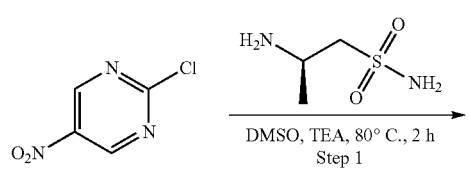

DMSO, TEA, 80° C., 2 h
Step 1

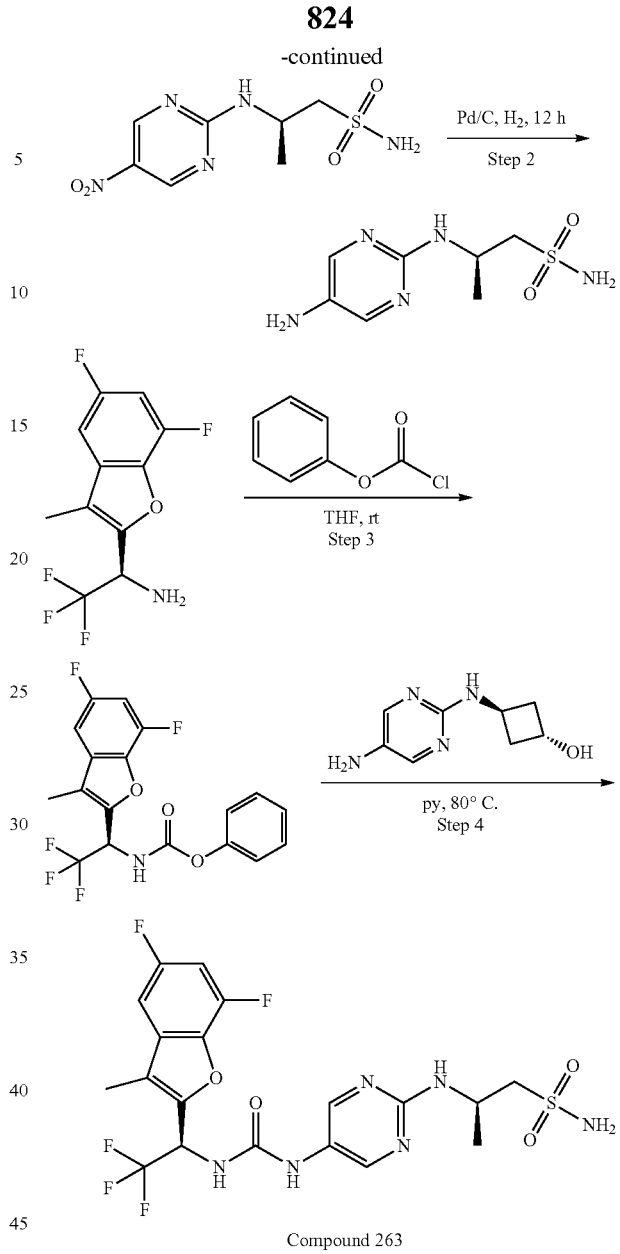

Compound 263

Step 1

To a stirred solution of 2-chloro-5-nitropyrimidine (100 mg, 0.627 mmol, 1 equiv) and (2R)-2-aminopropane-1-sulfonamide (129.93 mg, 0.941 mmol, 1.5 equiv) in DMSO (5 mL) was added TEA (190.30 mg, 1.881 mmol, 3 equiv) dropwise at room temperature under air atmosphere. The resulting mixture was stirred for 3 h at 80° C. under nitrogen atmosphere. Desired product could be detected by LCMS. The resulting mixture was extracted with EtOAc (2×5 mL). The combined organic layers were washed with brine (4×110 mL), dried over anhydrous Na$_2$SO$_4$. After filtration, the filtrate was concentrated under reduced pressure to afford (2R)-2-[(5-nitropyrimidin-2-yl)amino]propane-1-sulfonamide (150 mg, 91.59%) as a light yellow solid. MS (ESI): mass calcd. for C$_7$H$_{11}$N$_5$O$_4$S, 261.0, m/z found 262.2 [M+H]$^+$.

Step 2

To a solution of (2R)-2-[(5-nitropyrimidin-2-yl)amino]propane-1-sulfonamide (150 mg, 0.574 mmol, 1 equiv) in 5 mL EtOAc was added Pd/C (10%, 0.1 g) under nitrogen atmosphere in a 50 mL round-bottom flask. The mixture was hydrogenated at room temperature for 12 h under hydrogen atmosphere using a hydrogen balloon, filtered through a Celite pad, and concentrated under reduced pressure to afford (2R)-2-[(5-aminopyrimidin-2-yl)amino]propane-1-sulfonamide (100 mg, 75.31%) as a yellow oil. MS (ESI): mass calcd. for $C_7H_{13}N_5O_2S$, 231.1, m/z found 232.1 [M+H]$^+$.

Step 3

A solution of (1R)-1-(5,7-difluoro-3-methyl-1-benzofuran-2-yl)-2,2,2-trifluoroethanamine (800 mg, 3.017 mmol, 1 equiv) and phenyl chloroformate (519.57 mg, 3.319 mmol, 1.1 equiv) in THF (20 mL) was stirred for 1 h at room temperature under nitrogen atmosphere. Desired product could be detected by LCMS. The resulting mixture was concentrated under reduced pressure to afford phenyl N-[(1R)-1-(5,7-difluoro-3-methyl-1-benzofuran-2-yl)-2,2,2-trifluoroethyl]carbamate (1100 mg, 94.64%) as a off-white solid. MS (ESI): mass calcd. for $C_{18}H_{12}F_5NO_3$, 385.1, m/z found 386.3 [M+H]$^+$.

Step 4

A solution of (2R)-2-[(5-aminopyrimidin-2-yl)amino]propane-1-sulfonamide (79.23 mg, 0.342 mmol, 1.1 equiv) and phenyl N-[(1R)-1-(5,7-difluoro-3-methyl-1-benzofuran-2-yl)-2,2,2-trifluoroethyl]carbamate (120 mg, 0.311 mmol, 1 equiv) in pyridine (10 mL) was stirred for 2 h at 80° C. under nitrogen atmosphere. Desired product was detected by LCMS. The resulting mixture was extracted with EtOAc (2×10 mL). The combined organic layers were washed with brine (5×1 20 mL) and dried over anhydrous Na$_2$SO$_4$. After filtration, the filtrate was concentrated under reduced pressure to afford 3-[(1R)-1-(5,7-difluoro-3-methyl-1-benzofuran-2-yl)-2,2,2-trifluoroethyl]-1-(2-{[(2R)-1-sulfamoylpropan-2-yl]amino}pyrimidin-5-yl)urea (45.2 mg, 27.78%) as a yellow oil. The crude product (200 mg) was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 30% B to 60% B in 7 min, 60% B; Wave Length: 220 nm; RT1 (min): 7.63; Number Of Runs: 0) to afford 3-[(1R)-1-(5,7-difluoro-3-methyl-1-benzofuran-2-yl)-2,2,2-trifluoroethyl]-1-(2-{[(2R)-1-sulfamoylpropan-2-yl]amino}pyrimidin-5-yl)urea (45.2 mg, 27.78%) as a white solid. MS (ESI): mass calcd. for $C_{19}H_{19}F_5N_6O_4S$, 522.1, m/z found 523.1 [M+H−17]$^+$.

$^1$H NMR (400 MHz, DMSO-d6) δ 8.28 (d, J=14.3 Hz, 3H), 7.83 (d, J=9.5 Hz, 1H), 7.47-7.37 (m, 2H), 6.96 (d, J=8.3 Hz, 1H), 6.86 (s, 2H), 6.04 (q, J=8.5 Hz, 1H), 4.36 (p, J=7.0 Hz, 1H), 3.34 (s, 1H), 3.08 (dd, J=13.8, 7.8 Hz, 1H), 2.30 (s, 3H), 1.30 (d, J=6.6 Hz, 3H).

Example 183: Preparation of Compound 264

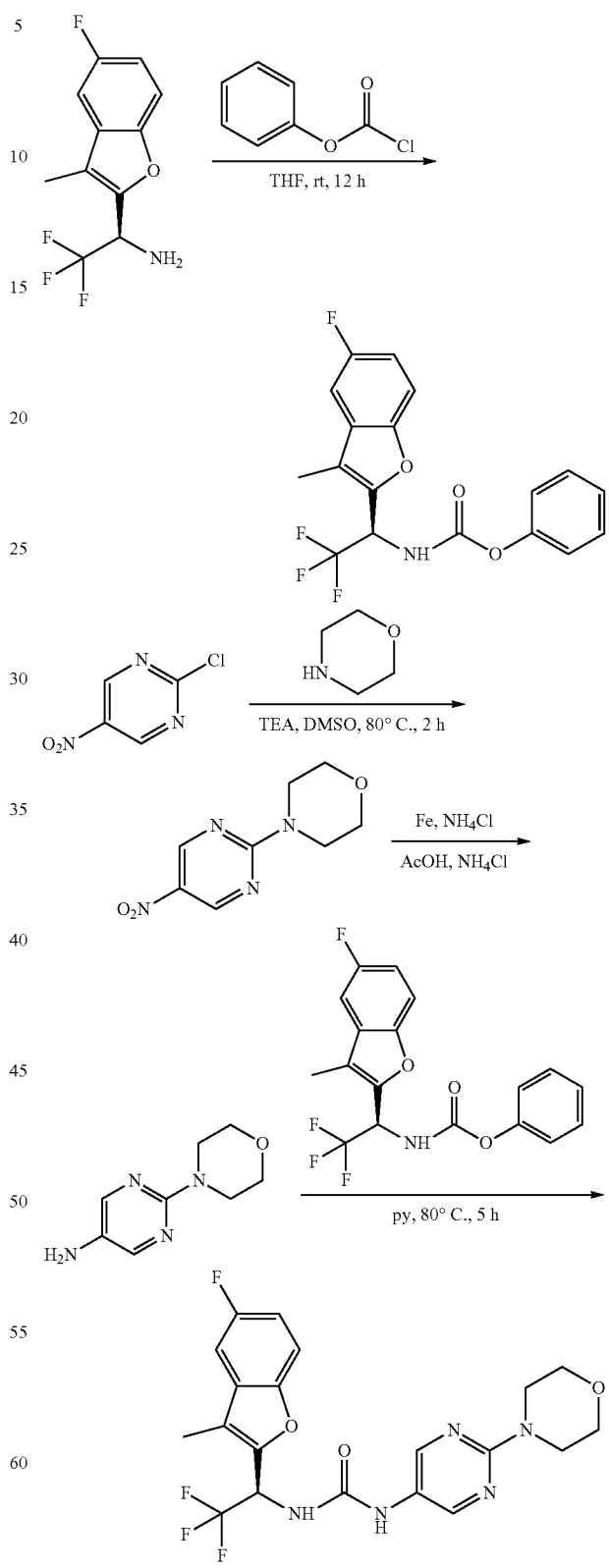

Compound 264

Step 1

A solution of (1R)-2,2,2-trifluoro-1-(5-fluoro-3-methyl-1-benzofuran-2-yl)ethanamine (3 g, 12.136 mmol, 1 equiv) and phenyl chloroformate (2.28 g, 14.563 mmol, 1.2 equiv) in THF (1 mL) was stirred for 7 h at room temperature under air atmosphere. Desired product could be detected by LCMS. The resulting mixture was concentrated under reduced pressure to afford phenyl N-[(1R)-2,2,2-trifluoro-1-(5-fluoro-3-methyl-1-benzofuran-2-yl)ethyl]carbamate (4.2 g, 94.22%) as a off-white solid. MS (ESI): mass calcd. for $C_{18}H_{14}F_4NO_3$, 367.1, m/z found 368.2 $[M+H]^+$.

Step 2

To a stirred solution of 2-chloro-5-nitropyrimidine (500 mg, 3.134 mmol, 1 equiv) and morpholine (409.58 mg, 4.701 mmol, 1.5 equiv) was added TEA (951.48 mg, 9.402 mmol, 3 equiv) at room temperature under air atmosphere. The resulting mixture was stirred for 1.5 h at 80° C. under nitrogen atmosphere. Desired product could be detected by LCMS. The resulting mixture was extracted with EtOAc (2×10 mL). The combined organic layers were washed with brine (4×1 20 mL), dried over anhydrous $Na_2SO_4$. After filtration, the filtrate was concentrated under reduced pressure to afford 4-(5-nitropyrimidin-2-yl)morpholine (600 mg, 91.08%) as a yellow solid. MS (ESI): mass calcd. for $C_8H_{10}N_4O_3$, 210.1, m/z found 210.9 $[M+H]^+$.

Step 3

To a stirred solution of 4-(5-nitropyrimidin-2-yl)morpholine (500 mg, 2.379 mmol, 1 equiv) and Fe (26.57 mg, 0.475 mmol, 5 equiv) in EtOH (10 mL, 17.213 mmol) were added $NH_4Cl$ (636.20 mg, 11.895 mmol, 5 equiv) and AcOH (1 mL, 17.452 mmol) at room temperature under air atmosphere. The resulting mixture was stirred for 1 h at 80° C. under air atmosphere. Desired product could be detected by LCMS. The resulting mixture was extracted with EtOAc (2×20 mL). The combined organic layers were washed with brine (4×110 mL), dried over anhydrous $Na_2SO_4$. After filtration, the filtrate was concentrated under reduced pressure to afford 2-(morpholin-4-yl)pyrimidin-5-amine (290 mg, 67.65%) as a brown oil. MS (ESI): mass calcd. for $C_8H_{12}N_4O$, 180.1, m/z found 181.0 $[M+H]^+$.

Step 4

A solution of phenyl N-[(1R)-2,2,2-trifluoro-1-(5-fluoro-3-methyl-1-benzofuran-2-yl)ethyl]carbamate (200 mg, 0.545 mmol, 1 equiv) and 2-(morpholin-4-yl)pyrimidin-5-amine (98.13 mg, 0.545 mmol, 1 equiv) in pyridine (5 mL) was stirred for 2 h at 80° C. under nitrogen atmosphere. Desired product could be detected by LCMS. The resulting mixture was extracted with EtOAc (2×10 mL). The combined organic layers were washed with brine (5×120 mL) and dried over anhydrous $Na_2SO_4$. After filtration, the filtrate was concentrated under reduced pressure. The residue was purified by reverse flash chromatography with the following conditions: column, C18 silica gel; mobile phase, MeCN in Water (0.1% FA), 10% to 50% gradient in 10 min; detector, UV 254 nm. The crude product (100 mg) was purified by Prep-HPLC with the following conditions (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 20% B to 50% B in 7 min, 50% B; Wave Length: 220 nm; RT1 (min): 7.00; Number Of Runs: 0) to afford 1-[2-(morpholin-4-yl)pyrimidin-5-yl]-3-[(1R)-2,2,2-trifluoro-1-(5-fluoro-3-methyl-1-benzofuran-2-yl)ethyl]urea (41 mg, 16.61%) as a white solid. MS (ESI): mass calcd. for $C_{20}H_{19}F_4N_5O_3$, 453.1, m/z found 454.1 $[M+H]^+$.

$^1$H NMR (400 MHz, DMSO-d6) δ 8.41 (d, J=5.8 Hz, 3H), 7.78 (d, J=9.3 Hz, 1H), 7.64 (dd, J=9.0, 4.0 Hz, 1H), 7.52 (dd, J=8.6, 2.7 Hz, 1H), 7.27-7.20 (m, 1H), 5.98 (q, J=8.4 Hz, 1H), 3.68-3.56 (m, 8H), 2.28 (s, 3H).

Example 184: Preparation of Compound 265

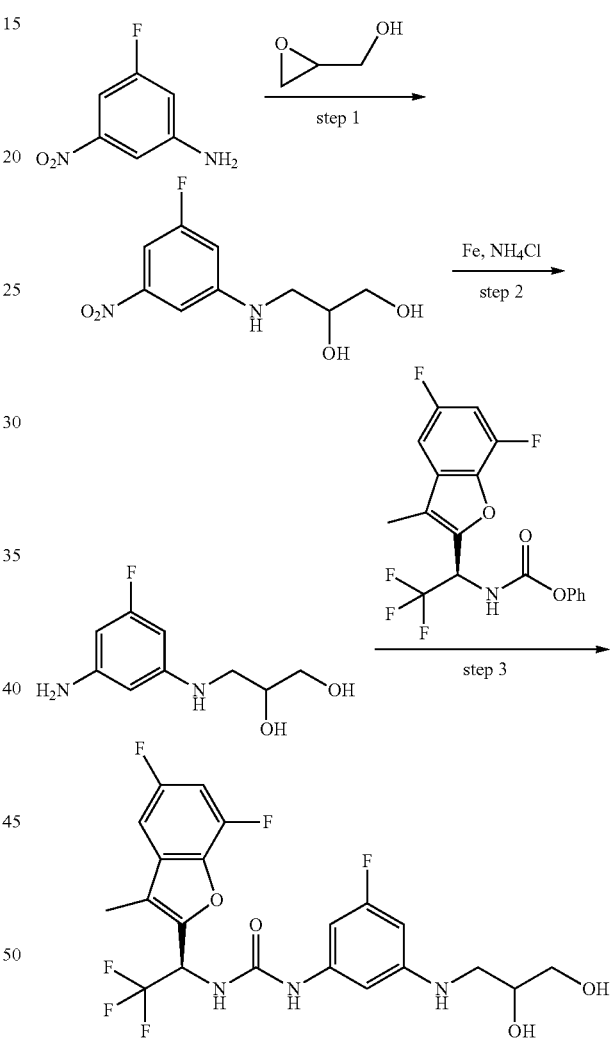

Compound 265

Step 1

To a stirred solution of 3-fluoro-5-nitroaniline (300 mg, 1.92 mmol) in MeOH (3 mL) was added (+/−)-glycidol (285 mg, 3.84 mmol) dropwise at room temperature under nitrogen atmosphere. The resulting mixture was stirred overnight at 80° C. under nitrogen atmosphere use sealed tube. The resulting mixture was concentrated under reduced pressure. The residue was purified by silica gel column chromatography, eluted with EA to afford 3-[(3-fluoro-5-nitrophenyl)

amino]propane-1,2-diol (340 mg, 76.86%) as a yellow solid. MS (ESI): mass calcd. for $C_9H_{11}FN_2O_4$, 230.07, m/z found 230.95 $[M+H]^+$.

Step 2

To a stirred mixture of 3-[(3-fluoro-5-nitrophenyl)amino]propane-1,2-diol (100 mg, 0.43 mmol) in EtOH (2 mL) and $H_2O$ (0.4 mL) were added Fe (243 mg, 4.34 mmol) and $NH_4Cl$ (232 mg, 4.34 mmol) in portions at room temperature. The resulting mixture was stirred for 0.5 h at 80° C. The resulting mixture was filtered and the filter cake was washed with MeOH (3×10 mL). The filtrate was concentrated under reduced pressure. The residue was purified by silica gel column chromatography, eluted with $CH_2Cl_2$/MeOH (10:1) to afford 3-[(3-amino-5-fluorophenyl)amino]propane-1,2-diol (85 mg, 97.73%) as a yellow oil. MS (ESI): mass calcd. for $C_9H_{13}FN_2O_2$, 200.10, m/z found 201.05 $[M+H]^+$.

Step 3

A mixture of 3-[(3-amino-5-fluorophenyl)amino]propane-1,2-diol (29 mg, 0.14 mmol) and phenyl N-[(1R)-1-(5,7-difluoro-3-methyl-1-benzofuran-2-yl)-2,2,2-trifluoroethyl]carbamate (50 mg, 0.13 mmol) in pyridine (1 mL) was stirred overnight at 80° C. under nitrogen atmosphere. The resulting mixture was diluted with EtOAc (5 mL). The residue was washed with 1M HCl (3×10 mL). The resulting mixture was concentrated under vacuum and dissolved in DMSO. The crude product (75 mg) was purified by Prep-HPLC with the following conditions (Column: Sunfire prep C18 column, 30*150 mm, 5 μm; Mobile Phase A: Water (0.1% FA), Mobile Phase B: ACN; Flow rate: 60 mL/min; Gradient: 46% B to 50% B in 7 min, 50% B; Wave Length: 254; 220 nm; RT1 (min): 6.4; Number Of Runs: 0) to afford 3-[(1R)-1-(5,7-difluoro-3-methyl-1-benzofuran-2-yl)-2,2,2-trifluoroethyl]-1-{3-[(2,3-dihydroxypropyl)amino]-5-fluorophenyl}urea (28.8 mg, 45.16%) as a white solid. MS (ESI): mass calcd. for $C_{21}H_{19}F_6N_3O_4$, 491.13, m/z found 492.05 $[M+H]^+$.

$^1$H NMR (400 MHz, DMSO-$d_6$) δ 8.63 (s, 1H), 7.64 (d, J=9.4 Hz, 1H), 7.48-7.37 (m, 2H), 6.56-6.52 (m, 1H), 6.33 (t, J=2.0 Hz, 1H), 6.11-5.98 (m, 2H), 5.86 (t, J=5.9 Hz, 1H), 4.77 (d, J=5.0 Hz, 1H), 4.60 (t, J=5.6 Hz, 1H), 3.63-3.56 (m, 1H), 3.37-3.34 (m, 2H), 3.13-3.07 (m, 1H), 2.88-2.82 (m, 1H), 2.31 (s, 3H).

Example 185: Preparation of Compound 266

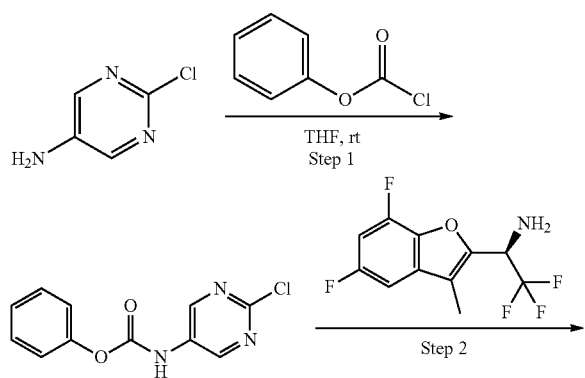

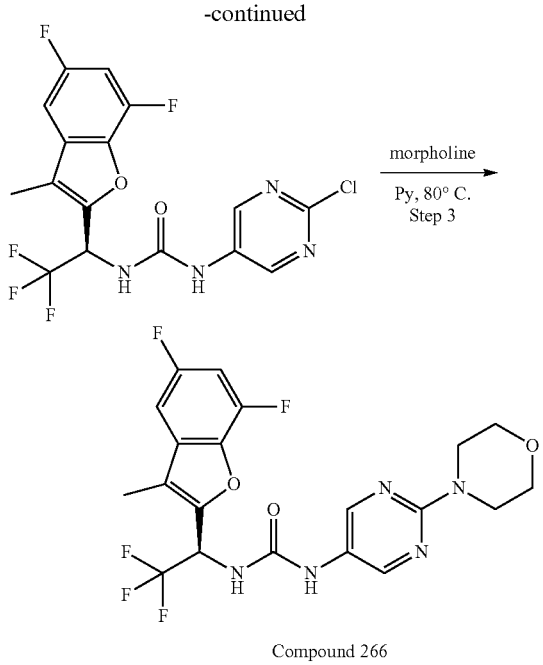

Compound 266

Step 1

A solution of 2-chloropyrimidin-5-amine (5 g, 38.595 mmol, 1 equiv) and phenyl chloroformate (7.86 g, 50.173 mmol, 1.3 equiv) in THF (50 mL) was stirred for 1 h at room temperature under nitrogen atmosphere. The resulting mixture was concentrated under reduced pressure. The crude product mixture was used in the next step directly without further purification. This resulted in phenyl N-(2-chloropyrimidin-5-yl)carbamate (8 g, 83.03%) as a light yellow solid.

MS (ESI): mass calcd. for $C_{11}H_8ClN_3O_2$, 249.0, m/z found 250.10 $[M+H]^+$.

Step 2

A solution of phenyl N-(2-chloropyrimidin-5-yl)carbamate (3 g, 12.017 mmol, 1.68 equiv) and 1-(5,7-difluoro-3-methyl-1-benzofuran-2-yl)-2,2,2-trifluoroethanamine (1.9 g, 7.165 mmol, 1.00 equiv) in pyridine (19 mL) was stirred overnight at 80° C. The resulting mixture was concentrated under reduced pressure. The residue was purified by reverse flash chromatography with the following conditions (column, C18 silica gel; mobile phase, MeOH in water, 0% to 100% gradient in 25 min; detector, UV 254 nm) to afford 1-(2-chloropyrimidin-5-yl)-3-[1-(5,7-difluoro-3-methyl-1-benzofuran-2-yl)-2,2,2-trifluoroethyl]urea (2.9 g, 96.20%) as a yellow solid. MS (ESI): mass calcd. for $C_{16}H_{10}ClF_5N_4O_3$, 420.0. m/z found 421.0 $[M+H]^+$.

Step 3

A solution/mixture of 1-(2-chloropyrimidin-5-yl)-3-[(1R)-1-(5,7-difluoro-3-methyl-1-benzofuran-2-yl)-2,2,2-trifluoroethyl]urea (100 mg, 0.238 mmol, 1 equiv) and morpholine (20.71 mg, 0.238 mmol, 1 equiv) in pyridine was stirred for 2 h at 80° C. under air atmosphere. The residue was purified by Prep-TLC ($CH_3CN$/H2O 1:1) to afford 3-[(1R)-1-(5,7-difluoro-3-methyl-1-benzofuran-2- yl)-2,2,2-trifluoroethyl]-1-[2-(morpholin-4-yl)pyrimidin-5-yl]urea (38.5 mg, 34.36%) as an off-white solid.

Column: XBridge Shield RP18 OBD Column, 30*150 mm, 5 μm;
Mobile Phase A: Water (10 mmol/L NH$_4$HCO$_3$+0.1% NH$_3$·H$_2$O), Mobile Phase B: ACN;
Flow rate: 60 mL/min;
Gradient: 42% B to 67% B in 8 min, 67% B;
Wave Length: 254 nm;
RT1 (min): 7.55;
Number Of Runs: 0
Temperature: 35° C.
MS (ESI): mass calcd. for C$_{20}$H$_{18}$F$_5$N$_5$O$_3$, 471.1. m/z found 472.2[M+H]$^+$.
$^1$H NMR (400 MHz, Chloroform-d) δ 8.38 (s, 2H), 7.05-6.98 (m, 1H), 6.89 (ddd, J=11.4, 9.3, 2.3 Hz, 1H), 6.66 (s, 1H), 6.01-5.89 (m, 1H), 5.89 (s, 1H), 3.82 (h, J=3.7 Hz, 8H), 2.30 (s, 3H).

Example 186: Preparation of Compound 267

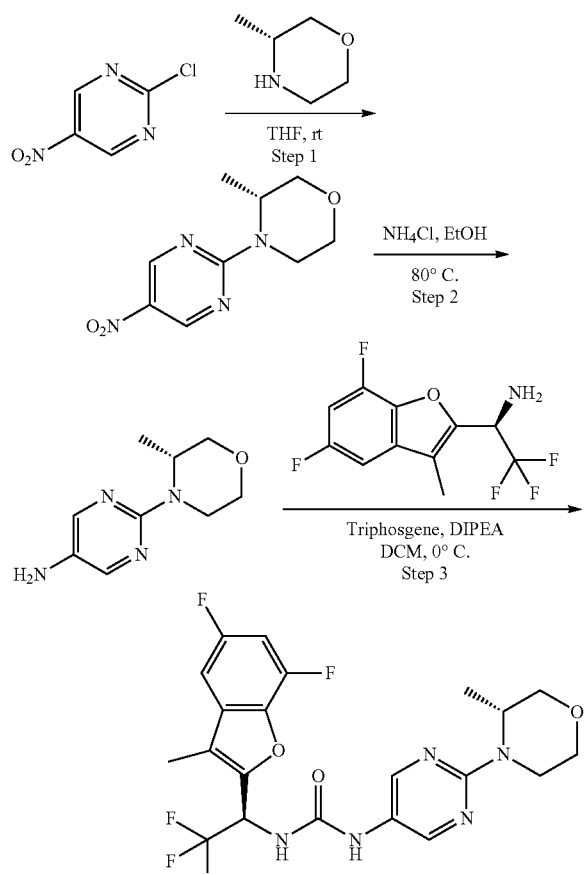

Compound 267

Step 1

A solution of 2-chloro-5-nitropyrimidine (500 mg, 3.134 mmol, 1 equiv) and TEA (951.48 mg, 9.402 mmol, 3 equiv) in DMSO (5 mL) was stirred for 1 h at 80° C. The residue was purified by reverse flash chromatography with the following conditions: column, C18 silica gel; mobile phase, MeCN in water, 40% to 50% gradient in 10 min; detector, UV 254 nm. This resulted in (3R)-3-methyl-4-(5-nitropyrimidin-2-yl) morpholine (650 mg, 92.49%) as a light yellow solid. MS (ESI): mass calcd. for C$_9$H$_{12}$N$_4$O$_3$, 224.1. m/z found 225.0 [M+H]$^+$.

Step 2

A solution of (3R)-3-methyl-4-(5-nitropyrimidin-2-yl) morpholine (650 mg, 2.899 mmol, 1 equiv) and NH$_4$Cl (1550.64 mg, 28.989 mmol, 10.00 equiv) in EtOH (20 mL) was stirred for h at 80° C. The resulting mixture was filtered and the filter cake was washed with CH$_2$Cl$_2$ (3×10 mL). The filtrate was concentrated under reduced pressure. The residue was purified by reverse flash chromatography with the following conditions: column, C18 silica gel; mobile phase, MeCN in water, 45% to 50% gradient in 10 min; detector, UV 254 nm. This resulted in 2-[(3R)-3-methylmorpholin-4-yl]pyrimidin-5-amine (370 mg, 65.71%) as a red oil. MS (ESI): mass calcd. for C$_9$H$_{14}$N$_4$O, 194.1, m/z found 195.0 [M+H]$^+$.

Step 3

A solution of (1R)-1-(5,7-difluoro-3-methyl-1-benzofuran-2-yl)-2,2,2-trifluoroethanamine (100 mg, 0.377 mmol, 1 equiv) and DIPEA (146.22 mg, 1.131 mmol, 3 equiv) in DCM (2 mL). To the above mixture was added triphosgene (55.95 mg, 0.189 mmol, 0.5 equiv) dropwise over 1 min at 0° C. The resulting mixture was stirred for additional 30 min at 0° C. To the above mixture was added 2-[(3R)-3-methylmorpholin-4-yl] pyrimidin-5-amine (73.25 mg, 0.377 mmol, 1 equiv) dropwise over 1 min at 0° C. The resulting mixture was stirred for additional 30 min at 0° C. The resulting mixture was concentrated under reduced pressure. The residue was purified by reverse flash chromatography. This resulted in 3-[(1R)-1-(5,7-difluoro-3-methyl-1-benzofuran-2-yl)-2,2,2-trifluoroethyl]-1-{2-[(3R)-3-methylmorpholin-4-yl]pyrimidin-5-yl}urea (41.4 mg, 22.62%) as a light yellow solid. MS (ESI): mass calcd. for C$_{21}$H$_{20}$F$_5$N$_5$O$_3$, 485.1, m/z found 486.1 [M+H]$^+$.

Column: XBridge Prep OBD C18 Column, 30*150 mm, 5 μm
Mobile phase: Water (10 mmol/L NH$_4$HCO$_3$), Mobile Phase B: ACN
Flow rate: 60 mL/min
Gradient: 45% B to 65% B in 8 min
Wavelength: UV 220 nm
RT1 (min): 7.52
Temperature: 35° C.
$^1$H NMR (400 MHz, DMSO-d$_6$) δ 8.38 (d, J=21.2 Hz, 3H), 7.84 (d, J=9.4 Hz, 1H), 7.50-7.38 (m, 2H), 6.06 (p, J=8.3 Hz, 1H), 4.59-4.43 (m, 1H), 4.16-4.07 (m, 1H), 3.90 (dd, J=11.3, 3.7 Hz, 1H), 3.69 (d, J=11.2 Hz, 1H), 3.57 (dd, J=11.3, 3.2 Hz, 1H), 3.49-3.40 (m, 1H), 3.10 (ddd, J=13.5, 12.3, 3.8 Hz, 1H), 2.30 (s, 3H), 1.14 (d, J=6.7 Hz, 3H).

Example 187: Preparation of Compound 268

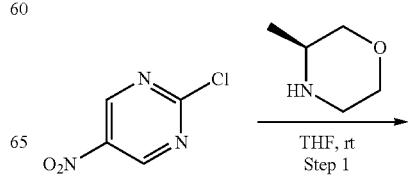

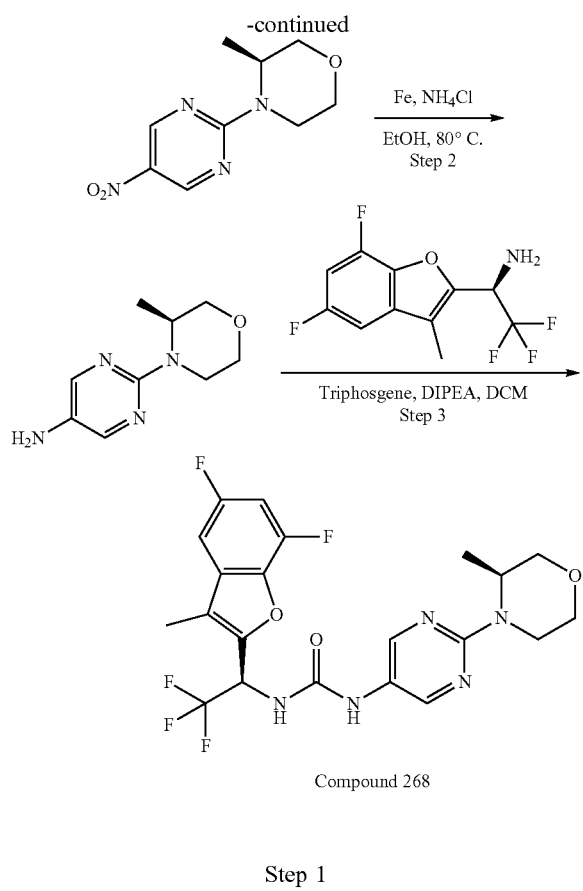

Compound 268

Step 1

A solution/mixture of 2-chloro-5-nitropyrimidine (500 mg, 3.134 mmol, 1 equiv) and (3R)-3-methylmorpholine (412.13 mg, 4.074 mmol, 1.3 equiv) and TEA (951.48 mg, 9.402 mmol, 3 equiv) in DMSO was stirred for 1 h at 80° C. under air atmosphere. The resulting liquid was dried under vacuum. This resulted in (3R)-3-methyl-4-(5-nitropyrimidin-2-yl)morpholine (650 mg, 92.49%) as an off-white solid. MS (ESI): mass calcd. for $C_9H_{12}N_4O_3$, 224.1. m/z found 225.0 [M+H]$^+$.

Step 2

A mixture of (3R)-3-methyl-4-(5-nitropyrimidin-2-yl)morpholine (650 mg, 2.899 mmol, 1 equiv) and Fe (2.49 mg, 0.045 mmol, 1 equiv) in EtOH was stirred for 1 h at 80° C. under an air atmosphere. The residue was purified by silica gel column chromatography eluting with PE/EA to afford 2-[(3R)-3-methylmorpholin-4-yl]pyrimidin-5-amine (370 mg, 65.71%) as a light yellow oil. MS (ESI): mass calcd. for $C_9H_{14}N_4O$, 194.1 m/z found 195.1[M+H]$^+$.

Step 3

A solution of 2-[(3S)-3-methylmorpholin-4-yl]pyrimidin-5-amine (150 mg, 0.772 mmol, 1 equiv) in DCM was treated with (1R)-1-(5,7-difluoro-3-methyl-1-benzofuran-2-yl)-2,2,2-trifluoroethanamine (225.27 mg, 0.849 mmol, 1.1 equiv) for 30 min at room temperature under a nitrogen atmosphere followed by the addition of triphosgene (252.06 mg, 0.849 mmol, 1.1 equiv) in portions at room temperature. The crude product was purified by Prep-HPLC to afford 3-[(1R)-1-(5,7-difluoro-3-methyl-1-benzofuran-2-yl)-2,2,2-trifluoroethyl]-1-{2-[(3S)-3-methylmorpholin-4-yl]pyrimidin-5-yl}urea (23.8 mg, 6.35%) as an off-white solid.

Column: XBridge Prep OBD C18 Column, 30*150 mm, 5 μm;

Mobile Phase A: Water (10 mmol/L NH4HCO3), Mobile Phase B: ACN; Flow rate: 60 mL/min;

Gradient: 45% B to 70% B in 8 min, 70% B; Wave Length: 220 nm;

RT1 (min): 6.95;

Temperature: 35° C.

MS (ESI): mass calcd. for $C_{21}H_{20}F_5N_5O_3$, 485.1. m/z found 486.1 [M+H]$^+$.

1H NMR (400 MHz, DMSO-d6) δ 8.41 (s, 2H), 8.36 (s, 1H), 7.84 (d, J=9.4 Hz, 1H), 7.48-7.37 (m, 2H), 6.06 (p, J=8.4 Hz, 1H), 4.51 (dd, J=7.0, 3.0 Hz, 1H), 4.12 (dd, J=13.6, 2.8 Hz, 1H), 3.90 (dd, J=11.2, 3.7 Hz, 1H), 3.70 (d, J=11.4 Hz, 1H), 3.64-3.53 (m, 1H), 3.47-3.37 (m, 1H), 3.16-3.04 (m, 1H), 2.29 (d, J=9.1 Hz, 3H), 1.14 (d, J=6.7 Hz, 3H).

Example 188: Preparation of Compound 269

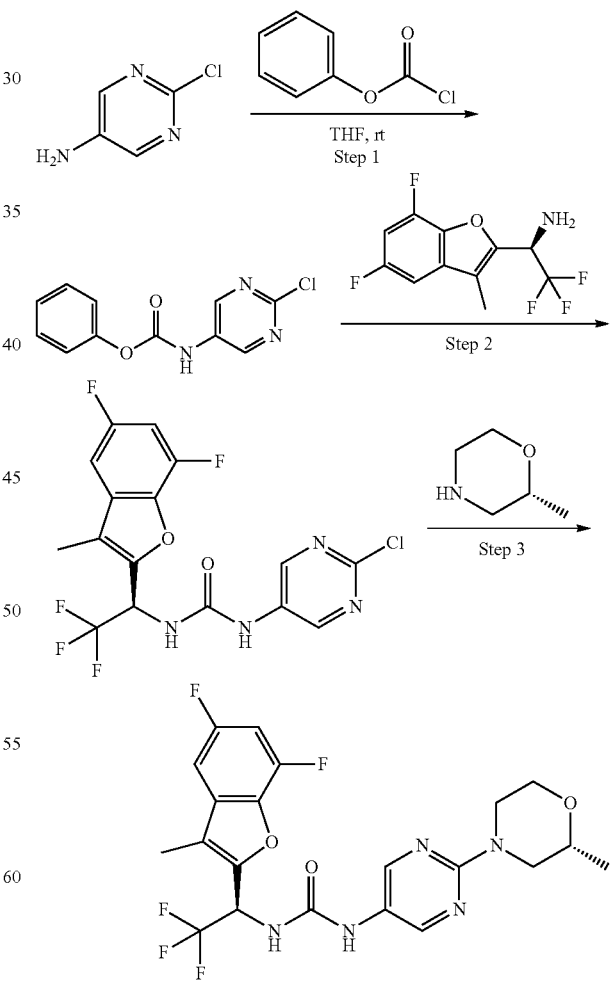

Compound 269

Step 1

A solution of 2-chloropyrimidin-5-amine (5 g, 38.595 mmol, 1 equiv) and phenyl chloroformate (7.86 g, 50.173 mmol, 1.3 equiv) in THF (50 mL) was stirred for 1 h at room temperature under nitrogen atmosphere. The resulting mixture was concentrated under reduced pressure. The crude phenyl N-(2-chloropyrimidin-5-yl)carbamate (8 g, 83.03%) was obtained as a light yellow solid and was used in the next step directly without further purification. MS (ESI): mass calcd. for $C_{11}H_8ClN_3O_2$, 249.0, m/z found 250.10 $[M+H]^+$.

Step 2

A solution of phenyl N-(2-chloropyrimidin-5-yl)carbamate (3 g, 12.017 mmol, 1.68 equiv) and 1-(5,7-difluoro-3-methyl-1-benzofuran-2-yl)-2,2,2-trifluoroethanamine (1.9 g, 7.165 mmol, 1.00 equiv) in pyridine (19 mL) was stirred overnight at 80° C. The resulting mixture was concentrated under reduced pressure. The residue was purified by reverse flash chromatography with the following conditions (column, C18 silica gel; mobile phase, MeOH in water, 0% to 100% gradient in 25 min; detector, UV 254 nm) to afford 1-(2-chloropyrimidin-5-yl)-3-[1-(5,7-difluoro-3-methyl-1-benzofuran-2-yl)-2,2,2-trifluoroethyl]urea (2.9 g, 96.20%) as a yellow solid.

MS (ESI): mass calcd. for $C_{16}H_{10}ClF_5N_4O_3$, 420.0. m/z found 421.0 $[M+H]^+$.

Step 3

A solution/mixture of 1-(2-chloropyrimidin-5-yl)-3-[(1R)-1-(5,7-difluoro-3-methyl-1-benzofuran-2-yl)-2,2,2-trifluoroethyl]urea (100 mg, 0.238 mmol, 1 equiv) and (2R)-2-methylmorpholine (24.04 mg, 0.238 mmol, 1 equiv) in pyridine was stirred for 1 h at 80° C. under air atmosphere. The crude product was purified by reverse phase flash to afford 3-[(1R)-1-(5,7-difluoro-3-methyl-1-benzofuran-2-yl)-2,2,2-trifluoroethyl]-1-{2-[(2S)-2-methylmorpholin-4-yl]pyrimidin-5-yl}urea (10.8 mg, 9.36%) as a off-white solid.

Column: XBridge Prep OBD C18 Column, 30*150 mm, 5 μm;
Mobile Phase A: Water (10 mmol/L NH4HCO3), Mobile Phase B: ACN;
Flow rate: 60 mL/min; Gradient: 48% B to 60% B in 8 min, 60% B;
Wave Length: 254 nm;
RT1 (min): 10.02; Number Of Runs: 0
Temperature: 35° C.

MS (ESI): mass calcd. for $C_{21}H_{20}F_5N_5O_3$, 485.1. m/z found 486.2$[M+H]^+$.

$^1$H NMR (400 MHz, Chloroform-d) δ 8.39 (s, 2H), 7.01 (dd, J=7.8, 2.3 Hz, 1H), 6.89 (ddd, J=10.4, 9.2, 2.3 Hz, 1H), 6.80 (s, 1H), 5.94 (s, 2H), 4.58-4.45 (m, 2H), 4.06-3.98 (m, 1H), 3.68 (dd, J=11.8, 2.8 Hz, 1H), 3.63 (tt, J=6.1, 3.0 Hz, 1H), 3.11 (td, J=12.6, 3.6 Hz, 1H), 2.76 (dd, J=13.1, 10.4 Hz, 1H), 2.30 (s, 3H), 1.28 (d, J=6.2 Hz, 3H).

Example 189: Preparation of Compound 270

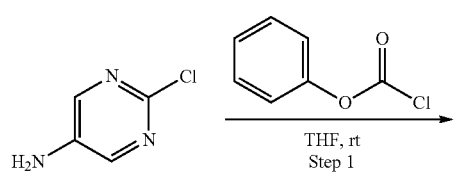

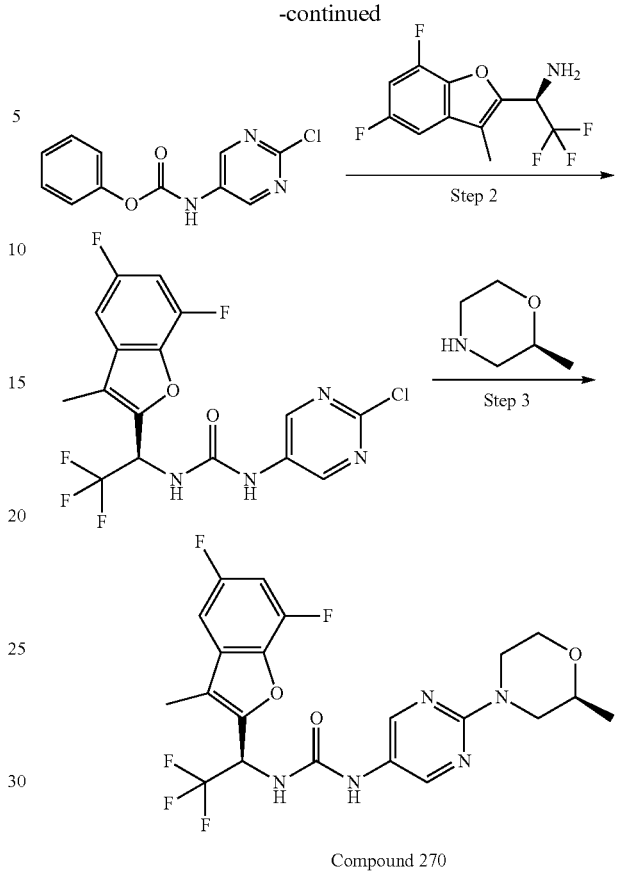

Compound 270

Step 1

A solution of 2-chloropyrimidin-5-amine (5 g, 38.595 mmol, 1 equiv) and phenyl chloroformate (7.86 g, 50.173 mmol, 1.3 equiv) in THF (50 mL) was stirred for 1 h at room temperature under nitrogen atmosphere. The resulting mixture was concentrated under reduced pressure. The crude product mixture was used in the next step directly without further purification. This resulted in phenyl N-(2-chloropyrimidin-5-yl)carbamate (8 g, 83.03%) as a light yellow solid. MS (ESI): mass calcd. for $C_{11}H_8ClN_3O_2$, 249.0, m/z found 250.10 $[M+H]^+$.

Step 2

A solution of phenyl N-(2-chloropyrimidin-5-yl)carbamate (3 g, 12.017 mmol, 1.68 equiv) and 1-(5,7-difluoro-3-methyl-1-benzofuran-2-yl)-2,2,2-trifluoroethanamine (1.9 g, 7.165 mmol, 1.00 equiv) in pyridine (19 mL) was stirred overnight at 80° C. The resulting mixture was concentrated under reduced pressure. The residue was purified by reverse flash chromatography with the following conditions (column, C18 silica gel; mobile phase, MeOH in water, 0% to 100% gradient in 25 min; detector, UV 254 nm) to afford 1-(2-chloropyrimidin-5-yl)-3-[1-(5,7-difluoro-3-methyl-1-benzofuran-2-yl)-2,2,2-trifluoroethyl]urea (2.9 g, 96.20%) as a yellow solid. MS (ESI): mass calcd. for $C_{16}H_{10}ClF_5N_4O_3$, 420.0. m/z found 421.0 $[M+H]^+$.

Step 3

A solution/mixture of 1-(2-chloropyrimidin-5-yl)-3-[(1R)-1-(5,7-difluoro-3-methyl-1-benzofuran-2-yl)-2,2,2- trifluoroethyl]urea (200 mg, 0.475 mmol, 1 equiv) and (2S)-2-methylmorpholine (50 mg, 0.494 mmol, 1.04 equiv) in pyridine was stirred for 2 h at 80° C. under air atmosphere. The residue was purified by reverse flash chromatography with the following conditions: column, C18 silica gel; mobile phase, MeCN in water (0.1% TFA), 10% to 50% gradient in 10 min; detector, UV 254 nm. Desired product could be detected by LCMS. This resulted in 3-[(1R)-1-(5,7-difluoro-3-methyl-1-benzofuran-2-yl)-2,2,2-trifluoroethyl]-1-{2-[(2S)-2-methylmorpholin-4-yl]pyrimidin-5-yl}urea (33.4 mg, 14.47%) as an off-white solid.

Column: XBridge Prep OBD C18 Column, 30*150 mm, 5 μm;

Mobile Phase A: Water (10 mmol/L NH₄HCO₃), Mobile Phase B: ACN;

Flow rate: 25 mL/min;

Gradient: 48% B to 60% B in 8 min, 60% B;

Wave Length: 254 nm;

RT1 (min): 10.45;

Temperature: 35° C.

MS (ESI): mass calcd. for $C_{21}H_{20}F_5N_5O_3$, 485.1. m/z found 486.2[M+H]⁺.

¹H NMR (400 MHz, Chloroform-d) δ 8.31 (s, 2H), 7.04-6.97 (m, 1H), 6.87 (ddd, J=10.5, 9.2, 2.4 Hz, 1H), 6.80 (s, 1H), 6.19 (d, J=9.5 Hz, 1H), 5.94 (dq, J=9.5, 7.5 Hz, 1H), 4.53-4.40 (m, 2H), 4.00 (ddd, J=11.6, 3.6, 1.4 Hz, 1H), 3.66 (dd, J=11.8, 2.9 Hz, 1H), 3.65-3.56 (m, 1H), 3.05 (ddd, J=13.2, 11.9, 3.6 Hz, 1H), 2.71 (dd, J=13.1, 10.5 Hz, 1H), 2.28 (s, 3H), 1.27 (d, J=6.2 Hz, 3H).

Example 190: Preparation of Compound 271

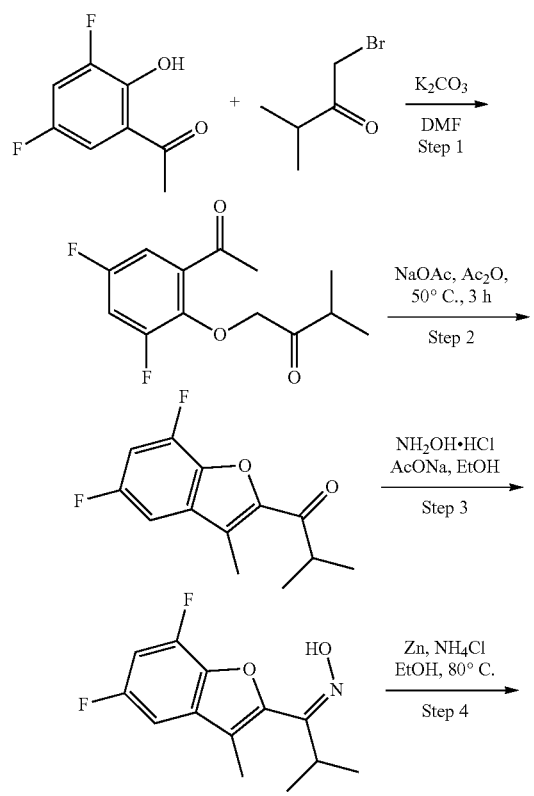

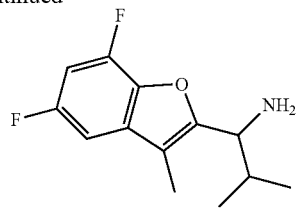

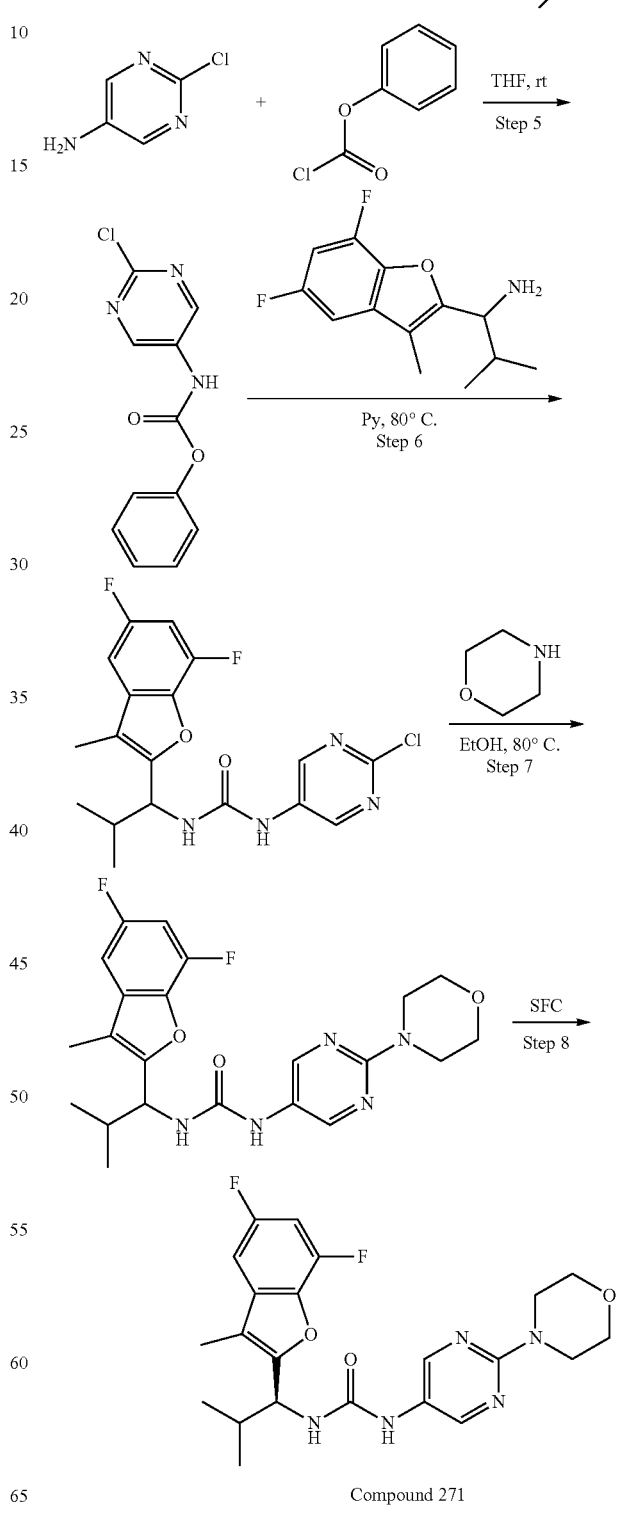

Compound 271

Step 1

A mixture of 1-(3,5-difluoro-2-hydroxyphenyl) ethanone (6.5 g, 37.762 mmol, 1 equiv), $K_2CO_3$ (15.66 g, 113.286 mmol, 3.0 equiv), and 1-bromo-2-butanone (6.27 g, 41.538 mmol, 1.1 equiv) in DMF was stirred overnight at room temperature. The resulting mixture was extracted with ethyl acetate (3×100 mL). The combined organic layers were washed with water (3×100 mL) and dried over anhydrous $Na_2SO_4$. After filtration, the filtrate was concentrated under reduced pressure. Desired product could be detected by LCMS. MS (ESI): mass calc. for $C_{13}H_{14}F_2O_3$, 256.09, m/z found 257.05 $[M+H]^+$.

Step 2

A mixture of 1-(2-acetyl-4,6-difluorophenoxy)-3-methylbutan-2-one (5.2 g, 20.293 mmol, 1 equiv) and NaOAc in $Ac_2O$ was stirred overnight. The reaction was quenched with $NaHCO_3$ solution at 10° C. The aqueous layer was extracted with EtOAc (3×150 mL). The combined organic layers were washed with deionized water (3×200 mL) and dried over anhydrous $Na_2SO_4$. After filtration, the filtrate was concentrated under reduced pressure. The residue was purified by silica gel column chromatography, eluting with $CH_2Cl_2$/PE (1:1) to afford 1-(5,7-difluoro-3-methyl-1-benzofuran-2-yl)-2-methylpropan-1-one as a white solid.

Step 3

To a stirred solution of 1-(5,7-difluoro-3-methyl-1-benzofuran-2-yl)-2-methylpropan-1-one (350 mg, 1.469 mmol, 1 equiv) and AcONa (602.60 mg, 7.345 mmol, 5 equiv) in ethanol was added hydroxylamine hydrochloride (510.46 mg, 7.345 mmol, 5 equiv) at room temperature. The reaction solution was heated at 100° C. overnight. The reaction was monitored by TLC and LCMS. The resulting mixture was concentrated, and was washed with deionized water (3×20 mL). The organic phase was concentrated under reduced pressure. MS (ESI): mass calc. for $C_{13}H_{13}F_2NO_2$, 253.09, m/z found 254.05 $[M+H]^+$.

Step 4

A solution of (Z)-N-[1-(5,7-difluoro-3-methyl-1-benzofuran-2-yl)-2-methylpropylidene]hydroxylamine (350 mg, 1.382 mmol, 1 equiv) in EtOH and $NH_4Cl$ solution was treated with Zn powder for 2 h at 80° C. under nitrogen atmosphere. Desired product could be detected by LCMS. After completion, the mixture was added to water and extracted with EA. The organic layer was washed with brine, dried over sodium sulfate, and concentrated under vacuum. The residue was purified by column chromatography on silica gel (PE/EA from 10/1 to 5/1) to give the desired product as a white solid. MS (ESI): mass calc. for $C_{13}H_{15}F_2NO$, 239.11, m/z found 223.05 $[M+H-17]^+$.

Step 5

To a stirred solution of 2-chloropyrimidin-5-amine (0.5 g, 3.860 mmol, 1 equiv) in THF was added phenyl chloroformate (0.60 g, 3.860 mmol, 1 equiv) dropwise at room temperature overnight. The reaction was monitored by TLC and LCMS. After the reaction is completed, it was concentrated to remove the solvent to afford 1.2 g crude product as yellow solid, which is used in next step without further purification. MS (ESI): mass calc. for $C_{11}H_8ClN_3O_2$, 249.03, m/z found 250.00 $[M+H]^+$.

Step 6

To a stirred solution of 1-(5,7-difluoro-3-methyl-1-benzofuran-2-yl)-2-methylpropan-1-amine (475 mg, 1.985 mmol, 1.00 equiv) in pyridine was added phenyl N-(2-chloropyrimidin-5-yl) carbamate (520.40 mg, 2.084 mmol, 1.05 equiv) at room temperature. The resulting mixture was stirred overnight at 80° C. The reaction was monitored by LCMS. Desired product could be detected by LCMS. The resulting mixture was concentrated under vacuum. The residue was purified by reverse flash chromatography. MS (ESI): mass calc. for $C_{18}H_{17}ClF_2N_4O_2$, 394.10, m/z found 395.05 $[M+H]^+$.

Step 7

A solution of 1-(2-chloropyrimidin-5-yl)-3-[1-(5,7-difluoro-3-methyl-1-benzofuran-2-yl)-2-methylpropyl] urea (350 mg, 0.887 mmol, 1 equiv) and morpholine (386.17 mg, 4.435 mmol, 5 equiv) in EtOH was stirred overnight at 80° C. under nitrogen atmosphere. Desired product could be detected by LCMS. The resulting mixture was concentrated under vacuum. The crude product (400 mg) was purified by Prep-HPLC to afford 3-[1-(5,7-difluoro-3-methyl-1-benzofuran-2-yl)-2-methylpropyl]-1-[2-(morpholin-4-yl) pyrimidin-5-yl] urea) as a white powder (210 mg).
MS (ESI): mass calc. for $C_{22}H_{25}F_2N_5O_3$, 445.19, m/z found 446.10 $[M+H]^+$.

Step 8

210 mg of racemate was separated by SFC to give (PH-SCO-P-127418, 38.7 mg) as white solid.
Chiral Separation Condition:
Apparatus: SFC 80
Column: CHIRALPAK IC-3 4.6*50 mm, 3.0 μm
Mobile phase: Hex (0.2% DEA):EtOH=80:20
Flow rate: 1.0 mL/min
Wavelength: UV 254 nm
Temperature: 25° C.
MS (ESI): mass calc. for $C_{22}H_{25}F_2N_5O_3$, 445.19, m/z found 446.15 $[M+H]^+$.
1H NMR (400 MHz, DMSO-d6) δ 8.38 (s, 2H), 8.15 (s, 1H), 7.37-7.17 (m, 2H), 6.96 (d, J=8.7 Hz, 1H), 4.75 (t, J=8.6 Hz, 1H), 3.63 (dd, J=5.8, 3.8 Hz, 4H), 3.58 (dd, J=6.1, 4.0 Hz, 4H), 2.20 (s, 3H), 2.17-2.07 (m, 1H), 1.02 (d, J=6.6 Hz, 3H), 0.82 (d, J=6.7 Hz, 3H).

Example 191: Preparation of Compound 272

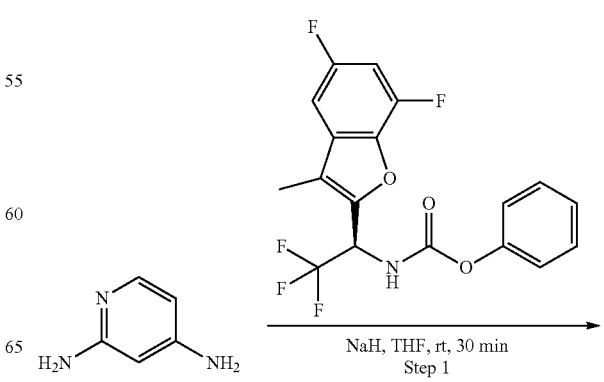

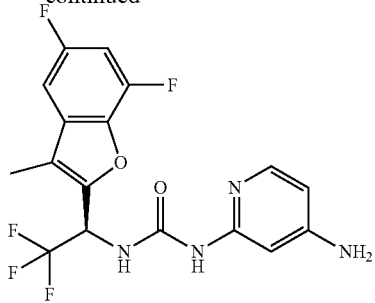

Compound 272

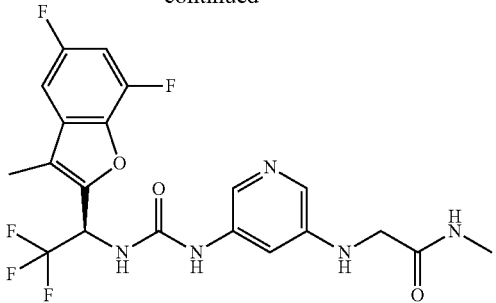

Compound 273

Step 1

2,4-diaminopyridine (50 mg, 0.458 mmol, 1.18 equiv) and NaH (12 mg, 0.500 mmol, 1.28 equiv) in THF (5 mL) was stirred for 0.5 h at 0° C. under nitrogen atmosphere. Phenyl N-[(1R)-1-(5,7-difluoro-3-methyl-1-benzofuran-2-yl)-2,2,2-trifluoroethyl]carbamate (150 mg, 0.389 mmol, 1 equiv) was added at 0° C. The resulting mixture was stirred for 16 h at rt under nitrogen atmosphere. The resulting mixture was diluted with water. The resulting mixture was extracted with EtOAc (3×10 mL). The combined organic layers were washed with brine and dried over anhydrous $Na_2SO_4$. After filtration, the filtrate was concentrated under reduced pressure. The residue was purified by Prep-TLC ($CH_2Cl_2$/MeOH 10:1) and Prep-HPLC to afford 1-(4-aminopyridin-2-yl)-3-[(1R)-1-(5,7-difluoro-3-methyl-1-benzofuran-2-yl)-2,2,2-trifluoroethyl]urea (44.1 mg, 28.30%) as an off-white solid. MS (ESI): mass calcd. for $C_{17}H_{13}F_5N_4O$, 400.1, m/z found 401.3 $[M+H]^+$.

$^1$H NMR (400 MHz, DMSO-$d_6$) δ 10.56 (br s, 1H), 9.31 (s, 1H), 7.69 (d, J=5.6 Hz, 1H), 7.58-7.29 (m, 2H), 6.30 (br s, 1H), 6.21-6.01 (m, 4H), 2.32 (s, 3H).

Example 192: Preparation of Compound 273

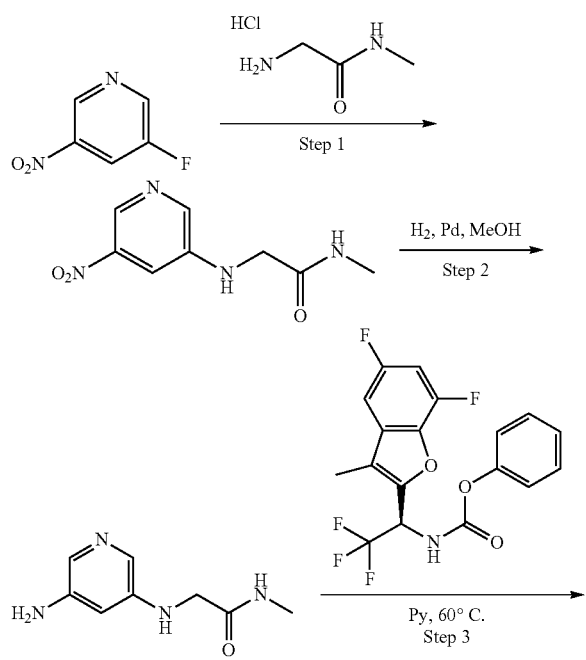

Step 1

A solution of 3-fluoro-5-nitropyridine (568 mg, 3.997 mmol, 1 equiv), 2-amino-N-methylacetamide (352.22 mg, 3.997 mmol, 1 equiv) and DIPEA (1033.33 mg, 7.994 mmol, 2 equiv) in DMSO (10 mL, 140.791 mmol, 35.22 equiv) was stirred for 2.5 h at 160° C. in a microwave reactor. (170 W) After the reaction was complete the mixture was diluted with water, extracted with EA, washed with brine, dried over anhydrous $Na_2SO_4$, concentrated to afford N-methyl-2-[(5-nitropyridin-3-yl)amino]acetamide (862.3 mg, crude) as orange solid. MS (ESI): mass calcd. for $C_8H_{10}N_4O_3$, 210.2. m/z found 211.1 $[M+H]^+$.

Step 2

A solution of N-methyl-2-[(5-nitropyridin-3-yl)amino]acetamide (862.3 mg, 4.102 mmol, 1 equiv), Zn (2682.16 mg, 41.020 mmol, 10 equiv), and $NH_4Cl$ (1097.19 mg, 20.510 mmol, 5 equiv) in $H_2O$ (10 mL, 555.093 mmol, 135.31 equiv) and EtOH (10 mL, 172.133 mmol, 41.96 equiv) was stirred overnight at 80° C. After the reaction was complete the mixture was filtered, the filtrate was concentrated to the crude. Then the residue was purified by reverse phase flash chromatography to get 2-[(5-aminopyridin-3-yl)amino]-N-methylacetamide (800 mg, 108.21%) brown solid. MS (ESI): mass calcd. for $C_8H_{12}N_4O$, 180.1. m/z found 181.2 $[M+H]^+$.

Step 3

A solution of 2-[(5-aminopyridin-3-yl)amino]-N-methylacetamide (200 mg, 1.110 mmol, 1 equiv) and phenyl N-[(1R)-1-(5,7-difluoro-3-methyl-1-benzofuran-2-yl)-2,2,2-trifluoroethyl]carbamate (427.60 mg, 1.110 mmol, 1 equiv) in pyridine (6 mL) was stirred overnight at 60° C. After the reaction was complete the solvent was concentrated to provide a residue. The residue was purified by reverse phase flash chromatography to get the crude product. Finally, the crude was repurified by Prep-HPLC (Column: Xselect CSH C18 OBD Column 30*150 mm 5 m, n; Mobile Phase A: Water (0.1% FA), Mobile Phase B: ACN; Flow rate: 60 mL/min; Gradient: 23% B to 35% B in 7 min, 35% B; Wave Length: 254; 220 nm; RT1 (min): 6.07; Number Of Runs: 0) to afford bis(2-{[5-({[(1R)-1-(5,7-difluoro-3-methyl-1-benzofuran-2-yl)-2,2,2-trifluoroethyl]carbamoyl}amino)pyridin-3-yl]amino}-N-methylacetamide) (33.8 mg, 3.16%) white solid as product. MS (ESI): mass calcd. for $C_{40}H_{36}F_{10}N_{10}O_6$, 471.4. m/z found 472.2 $[M+H]^+$. 1H NMR (400 MHz, DMSO) δ8.67 (s, 1H), 7.88 (d, J=3.2 Hz, 1H), 7.86 (s, 1H), 7.79 (s, 1H), 7.72 (s, 2H), 7.69-7.40 (m, 2H), 7.05 (t, J=2.4 Hz, 1H), 6.23 (t, J=6.0 Hz, 1H), 6.11-6.02 (m, 1H), 3.61 (d, J=5.6 Hz, 2H), 2.68 (s, 3H), 2.31 (s, 3H).

Example 193: Preparation of Compound 274

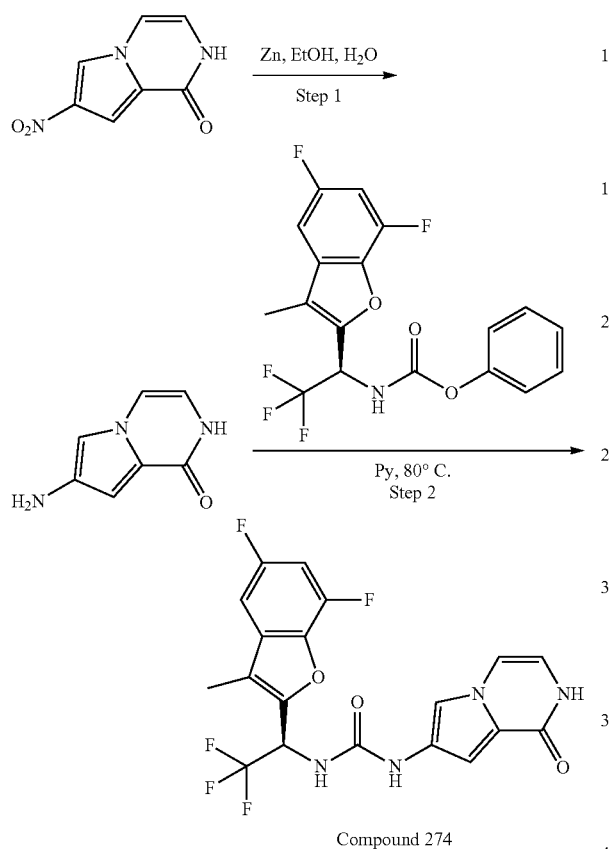

Compound 274

Step 1

A solution of 7-nitro-2H-pyrrolo[1,2-a]pyrazin-1-one (107.4 mg, 0.600 mmol, 1 equiv) and Zn (391.98 mg, 6.000 mmol, 10 equiv) in EtOH (3.5 mL) and H$_2$O (3.5 mL) was stirred for 1 h at 60° C. After the reaction was complete the solid was filtered and concentrated to provide 7-amino-2H-pyrrolo[1,2-a]pyrazin-1-one (100 mg, crude) grey solid as product.

MS (ESI): mass calcd. for C$_7$H$_7$N$_3$O, 210.2. m/z found 211.1 [M+H]$^+$.

Step 2

A solution of 7-amino-2H-pyrrolo[1,2-a]pyrazin-1-one (91 mg, 0.610 mmol, 1 equiv) and phenyl N-[(1R)-1-(5,7-difluoro-3-methyl-1-benzofuran-2-yl)-2,2,2-trifluoroethyl] carbamate (164.55 mg, 0.427 mmol, 0.7 equiv) in pyridine (5 mL) was stirred overnight at 80° C. After the reaction was complete the mixture was purified by reverse phase chromatography then re-purified by prep-HPLC to get 3-[(1R)-1-(5,7-difluoro-3-methyl-1-benzofuran-2-yl)-2,2,2-trifluoroethyl]-1-{1-oxo-2H-pyrrolo[1,2-a]pyrazin-7-yl}urea (43.9 mg, 16.29%) as a light-yellow solid. MS (ESI): mass calcd. for C$_{19}$H$_{13}$F$_5$N$_4$O$_3$, 440.3. m/z found 441.05[M+H]$^+$.

$^1$H NMR (400 MHz, DMSO) δ10.44 (d, J=5.2 Hz, 1H), 8.67 (s, 1H), 7.70 (d, J=9.6 Hz, 1H), 7.58 (s, 1H), 7.47-7.40 (m, 2H), 7.28 (d, J=2.0 Hz, 1H), 6.65 (s, 1H), 6.54 (t, J=5.6 Hz, 1H), 6.12-6.03 (m, 1H), 2.09 (s, 3H).

Example 194: Preparation of Compound 275

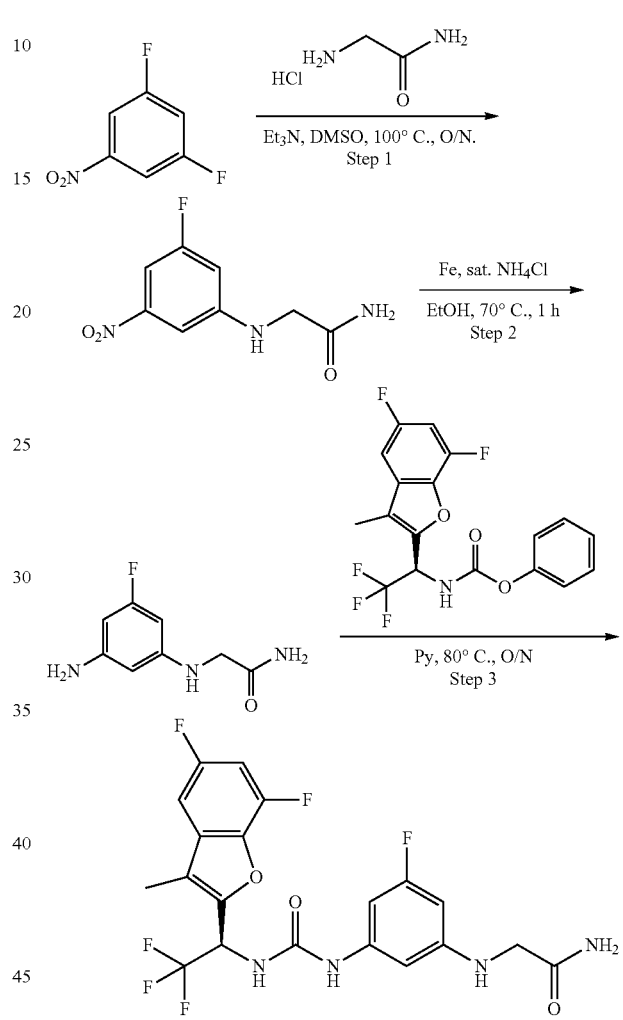

Compound 275

Step 1

A mixture of 1,3-difluoro-5-nitrobenzene (1 g, 6.29 mmol) and 2-aminoacetamide hydrochloride (0.83 g, 7.54 mmol) in Et$_3$N (5 mL) and DMSO (10 mL) was stirred overnight at 80° C. The resulting mixture was concentrated under reduced pressure. The residue was purified by reverse phase flash chromatography to afford 2-[(3-fluoro-5-nitrophenyl)amino]acetamide (450 mg, 33.58%) as a yellow solid. MS (ESI): mass calcd. for C$_8$H$_8$FN$_3$O$_3$, 213.05, m/z found 214.05 [M+H]$^+$.

Step 2

A mixture of 2-[(3-fluoro-5-nitrophenyl)amino]acetamide (400 mg, 1.88 mmol) and Fe (524 mg, 9.38 mmol) in EtOH (3 mL) and sat. NH$_4$Cl (3 mL) was stirred for 1 h at 70° C.

845

The resulting mixture was filtered and the filter cake was washed with EtOH. The filtrate was diluted with water (20 mL) and extracted with DCM (3×20 mL). The combined organic layers were dried over anhydrous $Na_2SO_4$. After filtration, the filtrate was concentrated under reduced pressure to afford 2-[(3-amino-5-fluorophenyl)amino]acetamide (300 mg, 87.46%) as a yellow solid.

MS (ESI): mass calcd. for $C_8H_{10}FN_3O$, 183.08, m/z found 184.05 $[M+H]^+$.

Step 3

A mixture of 2-[(3-amino-5-fluorophenyl)amino]acetamide (120 mg, 0.66 mmol) and phenyl N-[(1R)-1-(5,7-difluoro-3-methyl-1-benzofuran-2-yl)-2,2,2-trifluoroethyl]carbamate (80 mg, 0.21 mmol) in pyridine (2 mL) was stirred overnight at 80° C. The resulting solution was concentrated under reduced pressure. The residue was purified by reverse phase flash chromatography to afford 2-{[3-({[(1R)-1-(5,7-difluoro-3-methyl-1-benzofuran-2-yl)-2,2,2-trifluoroethyl]carbamoyl}amino)-5-fluorophenyl]amino}acetamide (60 mg, 19.31%) as a white solid. MS (ESI): mass calcd. for $C_{20}H_{16}F_6N_4O_3$, 474.11, m/z found 475.10 $[M+H]^+$.

$^1$H NMR (400 MHz, DMSO-$d_6$) δ 8.69 (s, 1H), 7.63 (d, J=9.4 Hz, 1H), 7.50-7.31 (m, 3H), 7.10 (s, 1H), 6.62 (dt, J=11.4, 2.1 Hz, 1H), 6.34-6.17 (m, 2H), 6.09-5.92 (m, 2H), 3.55 (d, J=5.8 Hz, 2H), 2.31 (s, 3H),

Example 195: Preparation of Compound 276

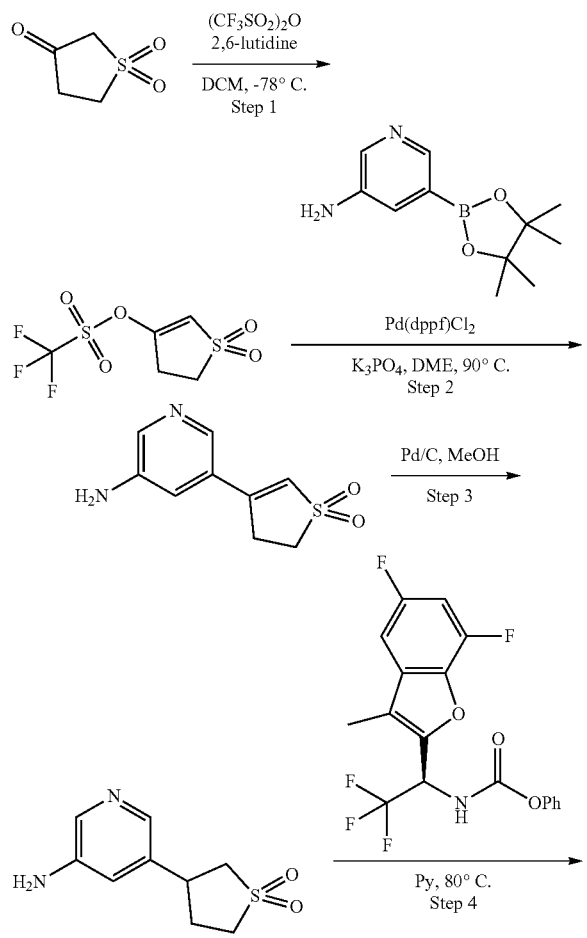

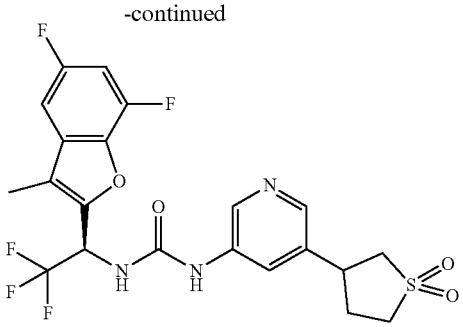

Compound 276

Step 1

To a stirred solution of dihydrothiophen-3(2H)-one 1,1-dioxide (300 mg, 2.24 mmol, 1.00 equiv) in DCM (15 mL) was added 2,6-lutidine (0.39 mL, 3.35 mmol, 1.50 equiv) and (trifluoromethane)sulfonyl trifluoromethanesulfonate (0.45 mL, 2.68 mmol, 1.20 equiv) dropwise at −78° C. under nitrogen atmosphere. The resulting mixture was stirred for 0.5 h at −78° C. under nitrogen atmosphere before warming to rt for 1 h. The reaction was monitored by TLC. The mixture was washed with 1 N HCl (10 ml), then with a dilute aqueous solution of $NaHCO_3$ (5 ml). The organic layer was dried over $Na_2SO_4$ and concentrated to afford 1,1-dioxido-4,5-dihydrothiophen-3-yl trifluoromethanesulfonate (550 mg, 92.39%) as a brown solid.

Step 2

To a stirred mixture of 1,1-dioxido-4,5-dihydrothiophen-3-yl trifluoromethanesulfonate (200 mg, 0.75 mmol, 1.00 equiv) and 5-(4,4,5,5-tetramethyl-1,3,2-dioxaborolan-2-yl)pyridin-3-amine (331 mg, 1.50 mmol, 2.00 equiv) in DME (5 mL) were added $Pd(dppf)Cl_2 \cdot CH_2Cl_2$ (306 mg, 0.38 mmol, 0.50 equiv) and $K_3PO_4$ (479 mg, 2.25 mmol, 3.00 equiv) at room temperature under argon. The resulting mixture was stirred for 3 h at 60° C. under argon. The resulting mixture was filtered and the filter cake was washed with DCM (3×20 mL). The filtrate was concentrated under reduced pressure. The residue was purified by silica gel column chromatography, eluting with $CH_2Cl_2$/MeOH (10:1) to afford 4-(5-aminopyridin-3-yl)-2,3-dihydrothiophene 1,1-dioxide (150 mg, 94.99%) as a yellow solid.

MS (ESI): mass calcd. for $C_9H_{10}N_2O_2S$, 210.05, m/z found 210.95 $[M+H]^+$.

Step 3

To a solution of 4-(5-aminopyridin-3-yl)-2,3-dihydrothiophene 1,1-dioxide (150 mg, 0.71 mmol, 1.00 equiv) in MeOH (5 mL) was added Pd/C (150 mg, 100% w/w) under a nitrogen atmosphere. The mixture was hydrogenated at room temperature for 2 h under hydrogen atmosphere using a hydrogen balloon. The resulting mixture was filtered and concentrated under reduced pressure. The residue was purified by silica gel column chromatography, eluting with $CH_2Cl_2$/MeOH (10:1) to afford 3-(5-aminopyridin-3-yl)tetrahydrothiophene 1,1-dioxide (70 mg, 46.22%) as a yellow solid. MS (ESI): mass calcd. for $C_9H_{12}N_2O_2S$, 212.06, m/z found 213.00 $[M+H]^+$.

Step 4

A mixture of 3-(5-aminopyridin-3-yl)tetrahydrothiophene 1,1-dioxide (70 mg, 0.33 mmol, 1.00 equiv) and phenyl N-[(1R)-1-(5,7-difluoro-3-methyl-1-benzofuran-2-yl)-2,2,2-trifluoroethyl]carbamate (127 mg, 0.33 mmol, 1.00 equiv) in pyridine (2 mL) was stirred for 2 h at 80° C. under nitrogen atmosphere. The resulting mixture was diluted with EtOAc (5 mL). The residue was washed with HCl (1 M) (3×10 mL). The resulting mixture was concentrated under vacuum and dissolved in DMSO. The crude product (100 mg) was purified by Prep-HPLC with the following conditions (Column: Sunfire prep C18 column, 30*150 mm, 5 μm; Mobile Phase A: Water (0.1% FA), Mobile Phase B: ACN; Flow rate: 60 mL/min; Gradient: 40% B to 50% B in 7 min, 50% B; Wave Length: 254; 220 nm; RT1 (min): 6.98; Number Of Runs: 0) to afford 1-((R)-1-(5,7-difluoro-3-methylbenzofuran-2-yl)-2,2,2-trifluoroethyl)-3-(5-(1,1-dioxidotetrahydrothiophen-3-yl)pyridin-3-yl)urea (71.8 mg, 43.25%) as a off-white solid. MS (ESI): mass calcd. for $C_{21}H_{18}F_5N_3O_4S$, 503.09, m/z found 504.25 $[M+H]^+$.

$^1$H NMR (400 MHz, DMSO-$d_6$) δ 8.86 (s, 1H), 8.48 (d, J=2.4 Hz, 1H), 8.23 (d, J=2.0 Hz, 1H), 7.94 (d, J=9.4 Hz, 1H), 7.87 (t, J=2.2 Hz, 1H), 7.49-7.38 (m, 2H), 6.09 (p, J=8.2 Hz, 1H), 3.71-3.53 (m, 2H), 3.43-3.36 (m, 1H), 3.25-3.09 (m, 2H), 2.49-2.43 (m, 1H), 2.32 (s, 3H), 2.24-2.06 (m, 1H).

Assays

Surface Plasmon Resonance (SPR)

SPR experiments were performed on a Biacore 8K instrument. A biotinylated recombinant PI3Kα H1047R protein was used in this study. The protein contained a full-length p110-α subunit harboring the H1047R mutation with an N-terminal AviTag, complexed with a truncated p85-α subunit (amino acid residues 322-694). The protein was first incubated with 1 μM wortmannin for 30 min at RT to covalently block the ATP binding site, then immobilized onto a streptavidin sensor chip by flowing the protein through the sensor chip at typically 20 μg/mL concentration and 2 μL/min flow rate for 1200 seconds. Compound binding affinities were measured in the multi-cycle kinetics mode, at 90 μL/min flow rate with 90 seconds association time and 240 seconds dissociation time. The running buffer contained 50 mM Tris, pH 7.5, 150 mM NaCl, 0.01% Brij35, 1 mM DTT, 1 mM $MgCl_2$, 0.05% Tween-20 and 2% DMSO. Temperature was maintained at 25° C. during experiments. See Table 3.

Homogenous Time-Resolved Fluorescence (HTRF)—pAKT-T47D

Compounds were assayed using homogeneous time-resolved fluorescence (HTRF). See Table 3.

Materials, Reagents, and Equipment

Gibco RPMI 1640 Medium, no phenol red; Gibco RPMI 1640 Medium; Gibco Trypsin-EDTA (0.5%), no phenol red; Gibco DPBS; Trypan blue solution 0.4% (Corning); Avantor Seradigm Premium Grade Fetal Bovine Serum (FBS); Greiner 784080-384 well TC treated white plates; pAKT (Ser473) HTRF; Gibco Insulin, human recombinant, zinc solution; Gibco Recovery Cell Culture Freezing Medium; Countess II FL Automated Cell Counter (ThermoFisher); Countess II Slides (ThermoFisher); Microscope; and PHERAstar FSX Microplate Reader (BMG LABTECH, Inc.).

Procedure

The scinamic cell line ID was T47D.1, the HTRF detection was pAKT (S473), a PI3Kα H1047R mutation was present, the seeding density was 5000, the timepoint was 1 hour, and the medium used was RPMI+10% FBS (no phenol red)+0.2 units/ml bovine insulin.

Cell Culture Maintenance:

The cell density was not permitted to reach 100% confluence. The cells were split 1:5 when they reached ~80% confluence.

Cells were split twice a week (Mon and Fri).

Cells over passage 18 were not used (~2 months of maintenance).

Antibiotics were not used for tissue culture maintenance or assays.

For Freezing Cells:
1. Trypsinized cells were collected and counted. Cells were pelleted at 1000 rpm, 5 minutes and supernatant was aspirated.
2. Pelleted cells were gently resuspended at 3e6 cells/1 mL of freezing medium (Gibco Freezing Medium). For example, if there were 9e6 total cells, cell pellet was resuspended in 3 mL of freezing medium.
3. Measured aliquot of 1 mL of resuspended cells/cryovial. Cells were frozen in appropriate cell freezing container (i.e. Mr. Frosty or Corning CoolCell Freezing System) at −80° C.
4. Cells were transferred to Liquid Nitrogen Cryotank for long term storage.

For Thawing Cells:
1. Cells were removed from liquid nitrogen tank. Cryovials were thawed in 37° C. waterbath until small "ice pellet" remained. This was then sprayed down with 70% ethanol before moving to TC/BSC hood.
2. Added 9 ml of fresh media to a 15 mL conical tube. Added 10 mL of fresh media to a T75 TC treated flask.
3. Gently transferred 1 mL of cells in freezing medium from cryovial to 15 mL conical tube containing media.
4. Centrifuged at 1000 rpm, 5 mins to pellet cells.
5. Aspirated media/freezing media.
6. Gently resuspended cell pellet in 5 mL fresh media and transferred to T75 flask with 10 mLs of fresh media. Place flasks in 37° C. incubator, 5% $CO_2$.

Protocol

Day 1

The procedure was as follows:
1. Prepared ARP:
   a. Stamped 12.5 nL from 10 mM source plate to destination plate using Echo. Sealed plate immediately and froze at −20° C. if it was not used on the same day.
   b. If a frozen ARP was used, the plate was thawed and spun at 1000 rpm×1 min.
2. Preparation of Cells (Adherent):
   a. Aspirated media from cells. Washed cells with sterile 1×PBS. Aspirated PBS and added appropriate amount of Trypsin.
   b. Once cells were fully trypsinized, added appropriate media to resuspend cells. Transferred cells to a 15 mL or 50 mL conical tube.
   c. Counted cells on the Countess II Cell Counter.
3. Plating of Cells:
   a. Prepared cells at appropriate plating density. Dispensed 12 μL of diluted cells per well of a Greiner 784080-384 well TC treated white plate using a Multidrop Combi to columns 1-23. Added 12 uL of appropriate phenol free media only to column 24.
   b. Placed plates in 37° C. tissue culture incubator for appropriate treatment time (refer to "Assay" table).
4. Prepared HTRF Lysis Buffer
   a. Calculate the amount of HTRF lysis buffer master mix needed to perform the desired experiments plus any extra dead volume required for dispensing (4 μL required per well). Dilute the Blocking Reagent into 4× Lysis Buffer at a ratio of 1:25 (i.e. 0.1 mL Blocking Reagent Solution plus 2.4 mL 4× Lysis Buffer).
b. Add 4 uL Lysis buffer master mix to all wells with sample or DMSO. Centrifuge the plates for 1 minute at 1000 rpm.
c. Incubate at room temperature for 30 minutes.
5. Prepared HTRF Antibody
a. Calculated the amount of HTRF antibody master mix needed to perform the desired experiments plus any extra dead volume required for dispensing (4 mL required per well). Eu Cryptate antibody and d2 antibody were added to detection buffer each at a ratio of 1:40 (i.e. 100 μL Eu Cryptate+100 μL d2 Cryptate+ 3800 μL detection buffer).
b. 4 μL of antibody master mix was added to each well including the media only column 24.
c. Centrifuged the plates for 1 minute at 1000 rpm. Placed lid on and created a "humidity chamber" by placing the plates into a ziplock bag with wet paper towels or something similar and incubated overnight at room temperature, keeping away from light.

Day 2
6. Measured on the PHERAstar/Envision Using the HTRF Protocol.

When plates were read, all wells were read.

The biological activity of certain compounds using the assays described above is shown in Table 2. The $K_D$ ranges are as follows: for PI3$\alpha^{H1047R}$+wortmannin $K_D$ (nM), A denotes <100 nM; B denotes 100 nM≤$K_D$<250 nM; C denotes 250 nM≤$K_D$<500 nM; D denotes $K_D$≥500 nM. For T47D pAKT IC$_{50}$ (nM), A denotes <1,000 nM; B denotes 1,000 nM≤IC$_{50}$<5,000 nM; C denotes ≥5,000 nM. ND denotes value not determined with that assay for the specified compound.

TABLE 3

| SPR and HTRF Data | | |
|---|---|---|
| Compound No. | PI3Kα &H1047R + wortmannin $K_D$ (nM) | T47D pAKT IC$^{50}$ (nM) |
| 1 | C | B |
| 3 | D | C |
| 4 | D | — |
| 6 | C | — |
| 7 | D | — |
| 9 | C | — |
| 11 | B | — |
| 12 | D | B |
| 13 | D | C |
| 14 | D | — |
| 16 | D | — |
| 17 | C | — |
| 19 | D | — |
| 20 | B | B |
| 21 | B | — |
| 22 | A | B |
| 23 | C | B |
| 24 | A | A |
| 25 | D | — |
| 26 | D | — |
| 27 | A | A |
| 28 | B | — |
| 31 | C | C |
| 32 | B | C |
| 33 | A | A |
| 34 | A | B |
| 35 | C | B |
| 36 | D | C |
| 37 | D | C |

TABLE 3-continued

| SPR and HTRF Data | | |
|---|---|---|
| Compound No. | PI3Kα &H1047R + wortmannin $K_D$ (nM) | T47D pAKT IC$^{50}$ (nM) |
| 38 | B | A |
| 39 | A | A |
| 40 | C | B |
| 41 | A | A |
| 42 | D | — |
| 43 | B | B |
| 44 | C | B |
| 45 | B | B |
| 46 | D | — |
| 47 | B | B |
| 48 | B | B |
| 50 | B | C |
| 52 | A | A |
| 54 | B | C |
| 55 | D | — |
| 56 | A | A |
| 29 | B | B |
| 30 | B | B |
| 59 | B | A |
| 60 | B | B |
| 61 | B | B |
| 62 | A | C |
| 63 | A | A |
| 64 | A | B |
| 65 | B | B |
| 66 | A | B |
| 68 | A | A |
| 69 | A | A |
| 71 | A | A |
| 72 | A | A |
| 73 | A | A |
| 74 | A | A |
| 75 | A | A |
| 77 | — | B |
| 78 | — | B |
| 80 | — | A |
| 81 | — | A |
| 84 | — | A |
| 86 | — | A |
| 87 | — | A |
| 89 | — | A |
| 91 | — | A |
| 93 | — | A |
| 95 | — | A |
| 96 | — | A |
| 98 | — | A |
| 100 | — | A |
| 101 | — | B |
| 102 | — | B |
| 103 | — | B |
| 104 | — | A |
| 105 | — | B |
| 106 | — | B |
| 107 | — | A |
| 121 | — | B |
| 123 | — | B |
| 124 | — | B |
| 125 | — | B |
| 126 | — | B |
| 128 | — | B |
| 129 | — | — |
| 130 | — | — |
| 131 | — | — |
| 132 | — | A |
| 133 | — | C |
| 134 | — | A |
| 135 | — | A |
| 136 | — | A |
| 137 | — | A |
| 138 | — | A |
| 139 | — | A |
| 140 | — | A |
| 141 | — | A |
| 142 | — | A |
| 143 | — | A |

TABLE 3-continued

SPR and HTRF Data

| Compound No. | PI3Kα &H1047R + wortmannin $K_D$ (nM) | T47D pAKT $IC^{50}$ (nM) |
|---|---|---|
| 144 | — | A |
| 145 | — | A |
| 146 | — | A |
| 147 | — | A |
| 148 | — | A |
| 149 | — | A |
| 150 | — | A |
| 151 | — | A |
| 152 | — | A |
| 153 | — | C |
| 154 | — | A |
| 155 | — | C |
| 156 | — | A |
| 157 | — | A |
| 158 | — | C |
| 159 | — | A |
| 160 | — | A |
| 161 | — | A |
| 162 | — | A |
| 163 | — | A |
| 164 | — | A |
| 165 | — | A |
| 166 | — | A |
| 167 | — | A |
| 168 | — | A |
| 169 | — | A |
| 170 | — | A |
| 171 | — | C |
| 172 | — | A |
| 173 | — | C |
| 174 | — | A |
| 175 | — | A |
| 176 | — | C |
| 177 | — | C |
| 178 | — | A |
| 179 | — | C |
| 180 | — | A |
| 181 | — | C |
| 182 | — | A |
| 183 | — | A |
| 184 | — | C |
| 185 | — | B |
| 186 | — | A |
| 187 | — | C |
| 188 | — | A |
| 189 | — | A |
| 190 | — | C |
| 191 | — | B |
| 192 | — | A |
| 193 | — | C |
| 194 | — | A |
| 195 | — | C |
| 196 | — | A |
| 197 | — | A |
| 198 | — | C |
| 199 | — | C |
| 200 | — | A |
| 201 | — | C |
| 202 | — | A |
| 203 | — | A |
| 204 | — | C |
| 205 | — | A |
| 206 | — | C |
| 207 | — | C |
| 208 | — | A |
| 209 | — | A |
| 210 | — | C |
| 211 | — | A |
| 212 | — | C |
| 213 | — | C |
| 214 | — | A |
| 215 | — | B |
| 216 | — | A |
| 217 | — | C |
| 218 | — | A |
| 219 | — | B |
| 220 | — | A |
| 221 | — | B |
| 222 | — | A |
| 223 | — | A |
| 224 | — | B |
| 225 | — | B |
| 226 | — | A |

What is claimed is:

1. A compound which is 1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

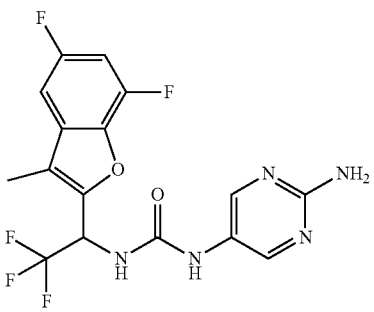 [SMILES: Cc1c(C(NC(=O)Nc2cnc(N)nc2)C(F)(F)F)oc2c(F)cc(F)cc12]

or a pharmaceutically acceptable salt thereof.

2. The compound of claim 1, wherein the compound is (S)-1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

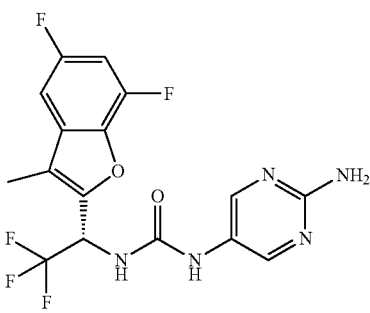 [SMILES: Cc1c([C@H](NC(=O)Nc2cnc(N)nc2)C(F)(F)F)oc2c(F)cc(F)cc12]

or a pharmaceutically acceptable salt thereof.

3. The compound of claim 1, wherein the compound is (R)-1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

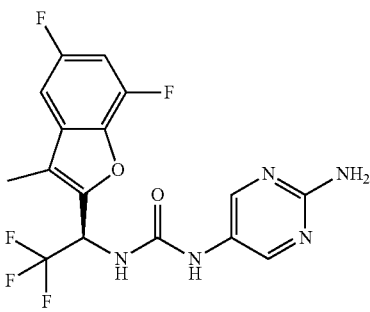 [SMILES: Cc1c([C@@H](NC(=O)Nc2cnc(N)nc2)C(F)(F)F)oc2c(F)cc(F)cc12]

or a pharmaceutically acceptable salt thereof.

4. The compound of claim 1, wherein the compound is 1-(2-aminopyrimidin-5-yl)-3-(1-(5,7-difluoro-3-methylbenzofuran-2-yl)-2,2,2-trifluoroethyl)urea.

5. The compound of claim 4, wherein the compound is (S)-1-(2-aminopyrimidin-5-yl)-3-(1-(5,7-difluoro-3-methylbenzofuran-2-yl)-2,2,2-trifluoroethyl)urea.

6. The compound of claim 4, wherein the compound is (R)-1-(2-aminopyrimidin-5-yl)-3-(1-(5,7-difluoro-3-methylbenzofuran-2-yl)-2,2,2-trifluoroethyl)urea.

7. A pharmaceutical composition comprising a compound which is 1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

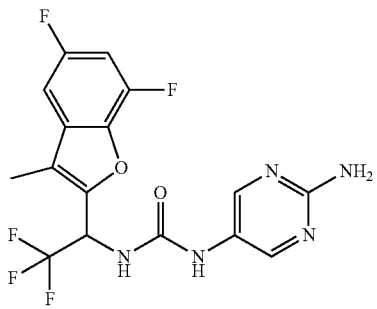 [SMILES: Cc1c(C(NC(=O)Nc2cnc(N)nc2)C(F)(F)F)oc2c(F)cc(F)cc12]

or a pharmaceutically acceptable salt thereof.

8. The pharmaceutical composition of claim 7, wherein the compound is (S)-1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

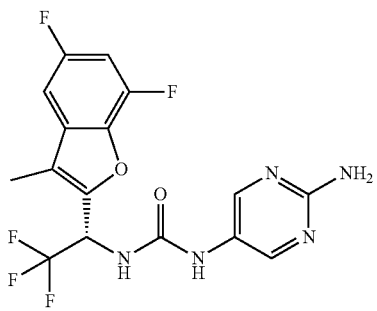 [SMILES: Cc1c([C@H](NC(=O)Nc2cnc(N)nc2)C(F)(F)F)oc2c(F)cc(F)cc12]

or a pharmaceutically acceptable salt thereof.

9. The pharmaceutical composition of claim 7, wherein the compound is (R)-1-(2-aminopyrimidin-5-yl)-3-(1-(5,7-difluoro-3-methylbenzofuran-2-yl)-2,2,2-trifluoroethyl)urea, or a pharmaceutically acceptable salt thereof, having the structure:

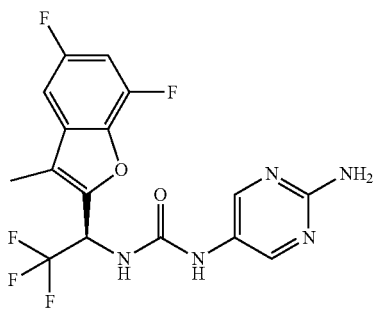 [SMILES: Cc1c([C@@H](NC(=O)Nc2cnc(N)nc2)C(F)(F)F)oc2c(F)cc(F)cc12]

or a pharmaceutically acceptable salt thereof.

10. The pharmaceutical composition of claim 7, wherein the compound is 1-(2-aminopyrimidin-5-yl)-3-(1-(5,7-difluoro-3-methylbenzofuran-2-yl)-2,2,2-trifluoroethyl)urea.

11. The pharmaceutical composition of claim 10, wherein the compound is (S)-1-(2-aminopyrimidin-5-yl)-3-(1-(5,7-difluoro-3-methylbenzofuran-2-yl)-2,2,2-trifluoroethyl) urea.

12. The pharmaceutical composition of claim 10, wherein the compound is (R)-1-(2-aminopyrimidin-5-yl)-3-(1-(5,7-difluoro-3-methylbenzofuran-2-yl)-2,2,2-trifluoroethyl) urea.

\* \* \* \* \*

SEQUENCE LISTING

```
Sequence total quantity: 1
SEQ ID NO: 1             moltype = AA  length = 1068
FEATURE                  Location/Qualifiers
source                   1..1068
                         mol_type = protein
                         organism = Homo sapiens
SEQUENCE: 1
MPPRPSSGEL WGIHLMPPRI LVECLLPNGM IVTLECLREA TLITIKHELF KEARKYPLHQ  60
LLQDESSYIF VSVTQEAERE EFFDETRRLC DLRLFQPFLK VIEPVGNREE KILNREIGFA  120
IGMPVCEFDM VKDPEVQDFR RNILNVCKEA VDLRDLNSPH SRAMYVYPPN VESSPELPKH  180
IYNKLDKGQI IVVIWVIVSP NNDKQKYTLK INHDCVPEQV IAEAIRKKTR SMLLSSEQLK  240
LCVLEYQGKY ILKVCGCDEY FLEKYPLSQY KYIRSCIMLG RMPNLMLMAK ESLYSQLPMD  300
CFTMPSYSRR ISTATPYMNG ETSTKSLWVI NSALRIKILC ATYVNVNIRD IDKIYVRTGI  360
YHGGEPLCDN VNTQRVPCSN PRWNEWLNYD IYIPDLPRAA RLCLSICSVK GRKGAKEEHC  420
PLAWGNINLF DYTDTLVSGK MALNLWPVPH GLEDLLNPIG VTGSNPNKET PCLELEFDWF  480
SSVVKFPDMS VIEEHANWSV SREAGFSYSH AGLSNRLARD NELRENDKEQ LKAISTRDPL  540
SEITEQEKDF LWSHRHYCVT IPEILPKLLL SVKWNSRDEV AQMYCLVKDW PPIKPEQAME  600
LLDCNYPDPM VRGFAVRCLE KYLTDDKLSQ YLIQLVQVLK YEQYLDNLLV RFLLKKALTN  660
QRIGHFFFWH LKSEMHNKTV SQRFGLLLES YCRACGMYLK HLNRQVEAME KLINLTDILK  720
QEKKDETQKV QMKFLVEQMR RPDFMDALQG FLSPLNPAHQ LGNLRLEECR IMSSAKRPLW  780
LNWENPDIMS ELLFQNNEII FKNGDDLRQD MLTLQIIRIM ENIWQNQGLD LRMLPYGCLS  840
IGDCVGLIEV VRNSHTIMQI QCKGGLKGAL QFNSHTLHQW LKDKNKGEIY DAAIDLFTRS  900
CAGYCVATFI LGIGDRHNSN IMVKDDGQLF HIDFGHFLDH KKKKFGYKRE RVPFVLTQDF  960
LIVISKGAQE CTKTREFERF QEMCYKAYLA IRQHANLFIN LFSMMLGSGM PELQSFDDIA  1020
YIRKTLALDK TEQEALEYFM KQMNDAHHGG WTTKMDWIFH TIKQHALN              1068
```